United States Patent
Guerin et al.

(10) Patent No.: US 12,162,888 B2
(45) Date of Patent: *Dec. 10, 2024

(54) CARBOXAMIDES AS UBIQUITIN-SPECIFIC PROTEASE INHIBITORS

(71) Applicant: Valo Early Discovery, Inc., Boston, MA (US)

(72) Inventors: David J. Guerin, Natick, MA (US); Pui Yee Ng, Lexington, MA (US); Zhongguo Wang, Lexington, MA (US); Tatiana Shelekhin, Ridgefield, CT (US); Justin Caravella, Cambridge, MA (US); Mary-Margaret Zablocki, Revere, MA (US); Jennifer R. Downing, Clinton, MA (US); Hongbin Li, Madison, CT (US); Stephanos Ioannidis, Natick, MA (US)

(73) Assignee: Valo Health, Inc., Boston, MA (US)

(*) Notice: Subject to any disclaimer, the term of this patent is extended or adjusted under 35 U.S.C. 154(b) by 654 days.

This patent is subject to a terminal disclaimer.

(21) Appl. No.: 17/266,026

(22) PCT Filed: Aug. 8, 2019

(86) PCT No.: PCT/US2019/045732
§ 371 (c)(1),
(2) Date: Feb. 4, 2021

(87) PCT Pub. No.: WO2020/033707
PCT Pub. Date: Feb. 13, 2020

(65) Prior Publication Data
US 2021/0323975 A1    Oct. 21, 2021

Related U.S. Application Data

(60) Provisional application No. 62/716,744, filed on Aug. 9, 2018, provisional application No. 62/788,204, filed on Jan. 4, 2019, provisional application No. 62/805,118, filed on Feb. 13, 2019.

(30) Foreign Application Priority Data

Aug. 9, 2018    (WO) ................ PCT/US2018/046061

(51) Int. Cl.
*C07D 495/04* (2006.01)
*C07D 513/04* (2006.01)
*C07D 519/00* (2006.01)

(52) U.S. Cl.
CPC ......... *C07D 495/04* (2013.01); *C07D 513/04* (2013.01); *C07D 519/00* (2013.01)

(58) Field of Classification Search
None
See application file for complete search history.

(56) References Cited

U.S. PATENT DOCUMENTS

| 10,889,592 B2 | 1/2021 | Guerin et al. |
| 10,913,753 B2 | 2/2021 | Guerin et al. |
| 11,524,966 B1 * | 12/2022 | Guerin ................ C07D 471/04 |
| 2015/0031670 A1 | 1/2015 | Heinrich et al. |
| 2017/0073343 A1 | 3/2017 | Galatsis et al. |
| 2017/0088520 A1 | 3/2017 | Lai et al. |
| 2017/0145012 A1 | 5/2017 | Buckmelter et al. |
| 2021/0047343 A1 | 2/2021 | Guerin et al. |

FOREIGN PATENT DOCUMENTS

| CN | 101128470 A | 2/2008 |
| CN | 108137586 A | 6/2018 |
| WO | WO 2000/078934 | 12/2000 |
| WO | WO 2005/037845 | 4/2004 |
| WO | WO 2006/068618 | 6/2006 |
| WO | WO 2010/092153 | 8/2010 |
| WO | WO 2010/099166 | 9/2010 |
| WO | WO 2012/040527 | 3/2012 |
| WO | WO 2014/105952 | 7/2014 |
| WO | WO 2014/116859 | 7/2014 |
| WO | WO 2017/139778 | 8/2017 |
| WO | WO 2017/139779 | 8/2017 |
| WO | WO 2019/032863 | 2/2019 |
| WO | WO 2020/033709 | 2/2020 |
| WO | 2013149704 A1 | 10/2023 |

OTHER PUBLICATIONS

Cas Registry No. 1197807-87-6 (Year: 2009).*
Beroukhim et al., "The landscape of somatic copy-number alteration across human cancers," Nature vol. 463, doi.10.1038/nature08822, pp. 899-905, (2010).
Bradley et al., "Tumor necrosis factor receptor-associated factors (TRAFs)," Oncogene Nature 20, pp. 6482-6491, (2001).
Brockman et al., "Small Molecule Inhibitors of Aurora-A Induce Proteasomal Degradation of N-Myc in Childhood Neuroblastoma" Cancer Cell., 24(1), Doi:10.1016/.ccr.2013.05.005, pp. 75-89, (2013).
Colland et al., "Small-molecule inhibitor of USP7/HAUSP ubiquitin protease stabilizes and activates p53 in cells," Molecular Cancer Therapeutics, DOI: 10.1158-1535-7163.MCT-09-0097, pp. 2286-2295, (2009).
Colombo et al., "Synthesis and biological evaluation of 9-oxo-9H-indeno[1,2-b]pyrazine-2,3-dicarbonitrile Analogues as Potential Inhibitors of Deubiquitinating Enzymes," ChemMedChem DOI: 10.1002/cmdc.200900409, pp. 552-558. (2010).
Conacci-Sorrell et al., "An Overview of MYC and Its Interactome," Cold Spring Harb Perspect Med 2014;4:a014357, pp. 1-24 (2014).

(Continued)

*Primary Examiner* — Matthew P Coughlin
*Assistant Examiner* — Meghan C Heasley
(74) *Attorney, Agent, or Firm* — Barnes & Thornburg LLP; Aisha R. Hasan

(57) ABSTRACT

The present disclosure relates to modulators, such as inhibitors, of at least one pathway chosen from USP28 and USP25, pharmaceutical compositions comprising the inhibitors, and methods of using the inhibitors. The modulators, such as inhibitors, of at least one pathway chosen from USP28 and USP25 can be useful in the treatment of cancers, among other ailments.

15 Claims, 18 Drawing Sheets

(56) References Cited

OTHER PUBLICATIONS

Cremona et al., "Fbw7 and Its Counteracting Forces in Stem Cells and Cancer: Oncoproteins in the Balance," Semin Cancer Biol., 36:52-61, Feb. 2016.
Cui et al., "Mechanisms and pathways of innate immune activation and regulation in health and cancer," Human Vaccines & Immunotherapeutics 10:11, pp. 3270-3285, (2014).
D'Arcy et al., "Deubiquitinase inhibition as a cancer therapeutic strategy," Pharmacology & Therapeutics 147, http://dx.doi.org/10.1016/j.pharmthera.2014.11.002, pp. 32-54, (2015).
Diefenbacher et al., "The deubiquitinase USP28 controls intestinal homeostasis and promotes colorectal cancer," The Journal of Clinical Investigation, vol. 124, No. 8 doi:10.1172/JCI73733, pp. 3407-3418 (2014).
Diefenbacher et al., "Usp28 Counteracts Fbw7 in Intestinal Homeostasis and Cancer," Cancer Res., 75(7):1181-6, Apr. 1, 2015. (Epub Feb. 25, 2015.).
Examination Report issued in European Patent Application No. 17708031.4, dated Jun. 13, 2019.
Farshi et al., "Deubiquitinases (DUBs) and DUB inhibitors: a patent review," Expert Opin Ther Pat., 25(10):1191-1208, 2015.
Flugel et al., "GSK-3B regulates cell growth, migration, and angiogenesis via Fbw7 and USP28-dependent degradation of HIF-1a," Vascular Biology, Blood, vol. 119, No. 5, pp. 1292-1301, (2012).
Gabay et al., "MYC Activation is a Hallmark of Cancer Initiation and Maintenance," Cold Spring Harb Perspect Med 2014;4:a014241, pp. 1-13 (2014).
Gersch et al., "Distinct USP25 and USP28 Oligomerization States Regulate Deubiquitinating Activity," Mol. Cell 74:436-451. May 2, 2019.
Guo et al., "USP28 is a potential prognostic marker for bladder cancer," Tumor Biology DOI 10.1007/513277-013-1525-1, pp. 4017-4022 (2013).
Huang et al., "Neuroblastoma and MYCN," Cold Spring Harb Perspect Med 2013;3:a014415; pp. 1-22, (2013).
International Search Report and Written Opinion for International Application No. PCT/US2017/017690, pp. 1-11, Apr. 19, 2017.
International Search Report and Written Opinion for International Application No. PCT/US2017/017691, pp. 1-6, Mar. 29, 2017.
International Search Report issued in Application No. PCT/US2018/046061, dated Oct. 25, 2018.
International Search Report issued in Application No. PCT/US2019/045732, dated Oct. 23, 2019.
International Search Report issued in Application No. PCT/US2019/045734, dated Jan. 2, 2020.
Iwakura et al., "Functional Specialization of Interleukin-17 Family Members," Immunity 34, pp. 149-162 (2011).
Kapuria et al., "Deubiquitinase Inhibition by Small-Molecule WP1130 Triggers Aggresome Formation and Tumor Cell Apoptosis," Cancer Research Therapeutics, Targets, and Chemical Biology DOI: 10.1158/0008-5472.CAN-10-1530, pp. 9265-9276, (2010).
Knobel et al., "USP28 Is Recruited to Sites of DNA Damage by the Tandem BRCT Domains of 53BP1 but Plays a Minor Role in Double-Strand Break Metabolism," Molecular and Cellular Biology, vol. 34, No. 11, pp. 2062-2074 (2014).
Komander et al., "Breaking the chains: structure and function of the deubiquitinases," Nature, vol. 10, pp. 550-563 (2009).
Le et al., "Discovery of a selective M4 positive allosteric modulator based on the 3-amino-thieno[2,3-b]pyridine-2-carboxamide scaffold: development of ML253, a potent and brain penetrant compound that is active in a preclinical model of schizophrenia," Bioorg Med Chem Lett. doi:10.1016/j.bmcl.2012.10.073, pp. 346-350 (2013).
Lee et al., "Enhancement of proteasome activity by a small-molecule inhibitor of USP14," Nature 467 doi:10.1038/nature09299, pp. 179-184 (2010).
Li et al., "miRNA-200c inhibits invasion and metastasis of human non-small cell lung cancer by directly targeting ubiquitin specific peptidase 25," Molecular Cancer, vol. 13, pp. 1-14 (2014).

Liang et al., "A selective USP1-UAF1 inhibitor links deubiquitination to DNA damage responses," Nat. Chem. Biol. DOI: 10.1038/NCHEMBIO.1455, pp. 298-304 (2014).
Lorenzin et al., "Different promoter affinities account for specificity in MYC-dependent gene regulation," eLife 2016;5:e15161, pp. 1-35 (2016).
Meng et al., "γ-Secretase Inhibitors Abrogate Oxaliplatin-Induced Activation of the Notch-1 Signaling Pathway in Colon Cancer Cells Resulting in Enhanced Chemosensitivity," Cancer Research 69(2), pp. 573-582 (2009).
Metzger et al., "LSD1 demethylates repressive histone marks to promote androgen-receptor-dependent transcription," Nature doi:10.1038/nature04020, vol. 437, pp. 436-439 (2005).
Meyer et al. "Reflecting on 25 years with MYC," Nature Perspectives, vol. 8, pp. 976-990 (2008).
Nijman et al., "A Genomic and Functional Inventory of Deubiquitinating Enzymes," Cell 123, pp. 773-786 (2005).
Periz et al., "Regulation of Protein Quality Control by UBE4B and LSD1 through p53-Mediated Transcription," PLOS Biology DOI:10.1371/journal.pbio.1002114, pp. 1-29 (2015).
Popov et al., "The ubiquitin-specific protease USP28 is required for MYC stability," Nature Cell Biology, vol. 9, No. 7, pp. 765-774 (2007).
Popov et al., "Fbw7 and Usp28 Regulate Myc Protein Stability in Response to DNA Damage," Cell Cycle, 6:19, 2327-2331, Oct. 2, 2007.
Prieto-Garcia et al., "The USP28-ΔNp63 axis is a vulnerability of squamous tumours," bioRxiv preprint, Jun. 27, 2019.
Reverdy et al., "Discovery of Specific Inhibitors of Human USP7/HAUSP Deubiquitinating Enzyme," Chemistry & Biology 19, pp. 467-477 + Supplemental Information, (2012).
Roussel et al., "Role of MYC in Medulloblastoma," Cold Spring Harb Perspect Med 2013;3:a014308; pp. 1-15, (2013).
Sacco et al., "Emerging Roles of Deubiquitinases in Cancer-Associated Pathways," Life 62(2):140-157, Feb. 2010.
Sankar et al., "Reversible LSD1 Inhibition Interferes with Global EWS/ETS Transcriptional Activity and Impedes Ewing Sarcoma Tumor Growth," Clinical Cancer Research, DOI: 10.1158/1078-0432.CCR-14-0072, pp. 4584-4597 (2014).
Sauer et al., "Differential Oligomerization of the Deubiquitinases USP25 and USP28 Regulates Their Activities," Mol. Cell 74(3):421-435, May 2, 2019.
Schenk et al., "Inhibition of the LSD1 (KDM1A) demethylase reactivates the all-trans-retinoic acid differentiation pathway in acute myeloid leukemia," Nature Medicine, vol. 18, No. 4, pp. 605-611 (2012).
Schmitz et al., "Oncogenic Mechanisms in Burkitt Lymphoma," Cold Spring Harb Perspect Med 2014;4:a014282, pp. 1-13 (2014).
Schulein-Volk et al., "Dual Regulation of Fbw7 Function and Oncogenic Transformation b Usp28," Cell Reports 9, 1099-1109, Nov. 6, 2014.
Sheridan, C., "Drug makers target ubiquitin proteasome pathway anew," Nature Biotechnology, vol. 33, No. 11, pp. 1115-1117 (2015); corrected version (2016).
Stoeck et al., "Discovery of Biomarkers Predictive of GSI Response in Triple-Negative Breast Cancer and Adenoid Cystic Carcinoma," American Association for Cancer Research, Cancer Discovery DOI: 10.1158/2159-8290.CD-13-0830, pp. 1155-1167 (2014).
Toffolo et al., "Phosphorylation of neuronal Lysine-Specific Demethylase 1LSD1/KDM1A impairs transcriptional repression by regulating interaction with CoREST and histone deacetylases HDAC1/2," Journal of Neurochemistry, vol. 128, doi: 10.1111/jnc.12457, pp. 603-616 (2014).
Walsh et al., "Tumor necrosis factor receptor-associated factor 6 (TRAF6) regulation of development, function, and homeostasis of the immune system," John Wiley & Sons Ltd, Immunological Reviews 0105-2896, vol. 266, pp. 72-92 (2015).
Walz et al., "Activation and repression by oncogenic MYC shape tumour-specific gene expression profiles," Nature, doi:10.1038/nature13473, pp. 1-17 (2014).
Wang et al., "Ubiquitin-specific protease 28 is overexpressed in human glioblastomas and contributes to glioma tumorigenicity by

(56) References Cited

OTHER PUBLICATIONS regulating MYC expression," Experimental Biology and Medicine, DOI: 10.1177/1535370215595468, pp. 255-264 (2015).

Weng et al., "Activating Mutations of NOTCH1 in Human T Cell Acute Lymphoblastic Leukemia," Science, vol. 306, pp. 269-271 (2004).

Wrigley et al., "Enzymatic characterisation of USP7 deubiquitinating activity and inhibition," Cell Biochem. Biophys., vol. 60, DOI 10.1007/512013-01-9186-4, pp. 99-111 (2011).

Wrigley et al., "Identification and Characterization of Dual Inhibitors of the USP25/28 Deubiquitinating Enzyme Subfamily" ACS Chem. Biol. 12, pp. 3113-3125 (2017).

Wrigley et al., "Identification and Characterization of Dual Inhibitors of the USP25/28 Deubiquitinating Enzyme Subfamily," Peer-reviewed (pre-print) version, published Nov. 13, 2017.

Wu et al., "The Deubiquitinase USP28 Stabilizes LSD1 and Confers Stem-Cell-like Traits to Breast Cancer Cells," Cell Press Reports, vol. 5, pp. 224-236 (2013)

Zhang et al., "A Role for the Deubiquitinating EnzymeUSP28 in Control of the DNA-Damage Response," Cell 126, pp. 529-542 (2006).

Zhang et al., "Overexpression of deubiquitinating enzyme USP28 promoted non-small cell lung cancer growth," J. Cell Mol. Med., pp. 1-7 , doi: 10.1111/jcmm.12426 (2015).

Zhong et al., "Negative regulation of IL-17-mediated signaling and inflammation by the ubiquitin-specific protease USP25," Nature Immunology, vol. 13, No. 11, pp. 1110-1117 (2012).

Zhong et al., "Ubiquitin-Specific Protease 25 Regulates TLR4-Dependent Innate Immune Responses Through Deubiquitination of the Adaptor Protein TRAF3," Science Signaling, vol. 6, Issue 275 ra35, pp. 1-10 (2013).

Zhong et al., "Ubiquitin-Specific Proteases 25 Negatively Regulates Virus-Induced Type I Interferon Signaling," PLOS One, vol. 8, Issue 11, pp. 1-14 (2013).

Prakash Srinivasan et al., "Disrupting Malaria Parasite AMA1-RON2 Interaciton With a Small Molecure Prevents Erythrocyte Invasion", Nature Communications, Aug. 2, 2013, pp. 1-9.

Xiaoqiang Guo, et al., "Tumor Suppressor Function and Mechanism of Ubiquitin Ligase FBW7", Chinese Journal of Biochemistry and Molecular Biology, Nov. 30, 2011, pp. 998-1006, vol. 27, No. 11 and Abstract.

Official Action and Search Report issued in Chinese Application No. 2019800668841, Oct. 28, 2023, 9 pages.

\* cited by examiner

TABLE C

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

TABLE C (continued)

CARBOXAMIDES AS UBIQUITIN-SPECIFIC PROTEASE INHIBITORS

CROSS REFERENCE TO RELATED APPLICATIONS

This application claims priority to PCT International Application No. PCT/US2018/046061, filed on Aug. 9, 2018; to U.S. Provisional Application No. 62/716,744, filed on Aug. 9, 2018; to U.S. Provisional Application No. 62/788,204, filed on Jan. 4, 2019; and to U.S. Provisional Application No. 62/805,118, filed on Feb. 13, 2019; the contents of each of which are incorporated by reference in their entirety.

TECHNICAL FIELD

The present disclosure is directed to modulators of at least one pathway chosen from ubiquitin-specific protease 28 (USP28) and/or ubiquitin-specific protease 25 (USP25) useful in the treatment of diseases or disorders associated with at least one pathway chosen from USP28 and USP25 enzymes. Specifically, the disclosure is concerned with chemical entities and compositions inhibiting at least one pathway chosen from USP28 and USP25, methods of treating diseases or disorders associated with at least one pathway chosen from USP28 and USP25, and methods of synthesis of these compounds.

BACKGROUND

USP28 and USP25 are cysteine isopeptidases of the USP sub-family of DUBs containing three distinct domains: an N-terminal UBA-like domain; a pair of ubiquitin-interacting motifs (UIM) and a USP domain that is predicted to have the conserved fold of the USP sub-family (Nijman et al., *Cell* 2005, 123, 773-786; Komander et al., *Mol. Cell Bio.* 2009, 10, 550-563). USP28 and USP25 exert their function through regulating the stability of a plethora of cellular proteins. USP28 has been characterized as a tumor-promoting factor and has been found to stabilize many oncoproteins. USP25 has been characterized as a tumor-promoting factor and as a regulator of cellular responses related to autoimmune disease, inflammation, and infectious diseases (such as viruses and bacteria).

Amplification, deletions and mutations of USP28 have been identified in multiple cancer types, including breast cancer, AML, ovarian cancer, and colorectal cancer. (cbioportal; http://www.cbioportal.org; Diefenbacher et al., *J. of Clin. Investi.* 2014,124, 3407-3418; Popov et al., *Nat. Cell. Biol.* 2007, 9, 729-731). Furthermore, USP28 overexpression has been correlated with poor prognosis in patients with glioblastoma, non-small cell lung carcinoma and bladder cancers suggesting that USP28 plays an important role in tumorigenesis of these tumor types. (Wang et al. *Exp. Biol. Med.* 2016, 255-264; Zhang et al. *J. Cell. Mol. Med.* 2015, 19, 799-805; Guo et al., *Tumor Bio.* 2014, 35, 4017-4022).

A large-scale shRNA screen has also identified a role of USP28 in the control of the stability of MYC protein. (Popov, *Nat. Cell. Biol.,* 765-774). MYC is a master regulator of the transcription of genes involved in cell growth, proliferation and apoptosis and is essential for tumor initiation and maintenance in many tumor types. (Meyer et al., *Nat. Rev. Cancer* 2006, 8, 976-990; Conacci-Sorrell et al., *Cold Spring Harb. Perspect. Med* 2014, 4, 1-24; Huang et al., *Cold Spring Harb. Perspect. Med* 2013; Roussel et al., *Cold Spring Harb. Perspect. Med.* 2013; Gabay et al., *Cold Spring Harb. Perspect. Med.* 2014; Schmitz et al., *Cold Spring Harb. Perspect. Med* 2014). In addition, MYC is the most frequently amplified oncogene in human cancer, with alterations in many tumor types including breast, lung and prostate. (Beroukhim et al., *Nature* 2010, 463, 899-905). Knockdown of the USP28 gene has been shown to lead to a decrease of MYC protein and an associated inhibition of growth in a panel of human cancer cell lines in vitro. (Popov, *Nat. Cell Biol.,* 765-774).

USP28 has also been reported to be required to impart stability on the LSD1 (lysine-specific demethylase 1) protein. (Wu et al., *Cell Rep.* 2013, 5, 224-236). LSD1 is a histone demethylase that complexes with many partner proteins to control cellular pluripotency and differentiation. (Metzger et al. *Nature* 2005,437, 436-439; Toffolo et al, *J. Neurochem.* 2014 128, 603-616, 2014; Periz et al., *PloSBiology* 2015). Knockdown of USP28 in tumor cells has been shown to lead to the destabilization of LSD1 protein, the suppression of cancer stem cell (CSC)-like characteristics in vitro, and the inhibition of tumor growth in vivo. (Wu, *Cell Rep.,* 224-236). Small molecule inhibitors of LSD1 have shown antitumor activity in models of AML and Ewing sarcoma. (Sankar et al., "Reversible LSD1 inhibition interferes with global EWS/ETS transcriptional activity and impedes Ewing sarcoma tumor growth" *Clin Cancer Res.* 2014 4584-4597; Schenk et al., *Nat. Med* 2012, 18, 605-611). Thus, USP28 inhibition represents an alternate approach to targeting LSD1 in these tumor types.

USP28 inhibition has also been shown to reduce NICD1-Levels and to lead to inhibition of the NOTCH pathway activity. (Diefenbacher et al.). NOTCH signaling controls diverse cellular differentiation decisions and drives tumorigenesis in certain tumor types. NOTCH1 is a potent T-cell oncogene, with >50% of T-cell acute lymphoblastic leukemia (T-ALL) cases carrying activating mutations in NOTCH1. (Weng et al. *Science* 2004, 306, 269-271). Increased NOTCH1 protein levels have also been associated with disease progression in colon cancer. (Meng et al., *Cancer Res.* 2009, 69, 573-582). NOTCH1 rearrangements lead to constitutive pathway activation and drive tumorigenesis in many cancer types, including triple-negative breast cancer. (Stoeck et al., *Cancer Discov.* 2014, 4, 1154-1167).

Other reported substrates of USP28 include c-Jun, Cyclin E, HIF-1α, Claspin, 53BP1, and Mdc1, many of which play important roles in tumorigenesis in humans. (Diefenbacher et al.; Flügel et al. *Blood* 2012, 119, 1292-1301; Zhang et al., "A role for the deubiquitinating enzyme USP28 in control of the DNA-damage response" *Cell* 2006, 126, 529-542). Interestingly, many USP28 substrates are recognized by FBW7, the substrate recognition subunit of SCF (FBW7) E3 ubiquitin ligase. (Diefenbacher et al.). FBW7 recognizes USP28 substrates in a phosphorylation-dependent manner and targets them for ubiquitination ultimately leading to their proteasomal degradation. The antagonizing roles of USP28 and FBW7 on their shared oncoprotein substrates indicate the intricate nature of protein stability control and may provide additional therapeutic opportunities for cancer treatment.

Mice with a germline knockout of USP28 have been shown to be viable and fertile, confirming that USP28 activity is not required for normal development and reproductive function. (Knobel et al., *Molecular and Cellular Biology* 2014, 34, 2062-2074). Conditional knockout of USP28 in mouse intestine led to the reduction of oncoproteins including c-Myc, active NOTCH (NICD1) and c-JUN which was associated with decreased intestinal cell proliferation and enhanced differentiation. More importantly, intestinal tumorigenesis induced by APC mutation was effectively blocked with acute USP28 depiction suggesting that USP28 could be an appealing target to reduce tumor burden and improve survival for intestinal cancers. (Diefenbacher et al.).

In summary, USP28 and USP25 play important roles in promoting tumorigenesis in cells and modulating immune responses. Its major role being in the deubiquitination and stabilization of diverse oncoproteins and epigenetic drivers and immunomodulatory proteins among other cellular factors, which are necessary for immune responses and tumor initiation and growth in humans. Inhibition of USP28 and/or USP25 with small molecule inhibitors therefore can be developed for medical use, such as for the treatment for cancer such as lung cancer. For this reason, there remains a considerable need for novel and potent small molecule inhibitors of USP28 and/or USP25.

SUMMARY

The present disclosure provides compounds of Formula (I):

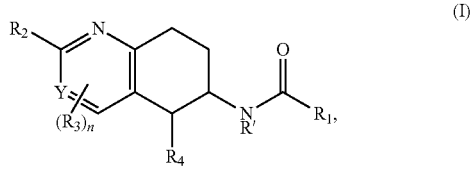

or a pharmaceutically acceptable form thereof, wherein
Y is chosen from $C(R_3)$ and N;
R' is chosen from H and $CH_3$;
$R_1$ is chosen from 6-11 membered heteroaryls optionally substituted with one or more substituent chosen from $R_5$ and/or $R_6$;
$R_2$ is chosen from N-linked 4-12 membered heterocyclyls and C-linked 4-12 membered heterocyclyls, wherein the heterocyclyls are optionally substituted with one or more $R_5$, and further wherein any $R_2$ group containing hydrogen can have one or more hydrogen replaced with deuterium;
each $R_3$ (if present) is independently chosen from H, deuterium, $(C_1-C_6)$ alkyl, $(C_1-C_6)$ alkoxy, $(C_1-C_6)$ haloalkyl, $(C_1-C_6)$ haloalkoxy, halogen, —OH, —CN, wherein each of $(C_1-C_6)$ alkyl, $(C_1-C_6)$ alkoxy, $(C_1-C_6)$ haloalkyl, $(C_1-C_6)$ haloalkoxy, $(C_3-C_1)$ cycloalkyl, heterocycloalkyl, aryl, and heteroaryl groups are optionally substituted with one or more $R_7$;
each $R_4$ is chosen from H, deuterium, $(C_1-C_6)$ alkyl, halogen, —OH, —CN, and further wherein any $R_4$ group containing hydrogen can have one or more hydrogen replaced with deuterium;
each $R_5$ (if present) is independently chosen from —OH, —NH$_2$, NHC(O)CH$_3$, —C(O)NHCH$_3$, $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, and —C(O)-heterocycloalkyl groups, wherein each of —NH$_2$, —NHC(O)CH$_3$, —C(O)NHCH$_3$, $(C_1-C_6)$ alkyl, $(C_1-C_6)$ alkoxy, $(C_1-C_6)$ haloalkyl, $(C_1-C_6)$ haloalkoxy, cycloalkyl, heterocycloalkyl, and —C(O)-heterocycloalkyl are optionally substituted with one or more substituent independently chosen from $(C_1-C_6)$ alkoxy, —NH$_2$, and —OH, and wherein any $R_5$ group containing hydrogen can have one or more hydrogen replaced with deuterium;
each $R_6$ (if present) is chosen from —NH$(C_1-C_6)$alkyl-aryls, —NH$(C_1-C_6)$alkyl-heteroaryls, —NH$(C_1-C_6)$alkyl-cyclyl groups, and —NH$(C_1-C_6)$alkyl-heterocyclyl groups, wherein each of the $R_6$ groups are optionally substituted with one or more substituent chosen from —OH, —NH, halogens, $(C_1-C_6)$ alkyl, $(C_1-C_6)$ alkoxy, and $(C_1-C_6)$ haloalkyl groups, and further wherein any $R_6$ group containing hydrogen can have one or more hydrogen replaced with deuterium;
each $R_7$ (if present) is independently chosen from —OH, —NH$_2$, $(C_1-C_6)$ alkyl, $(C_1-C_6)$ alkoxy, $(C_1-C_6)$ haloalkyl, $(C_1-C_6)$ haloalkoxy, halogen, cycloalkyl, —C(O)-cycloalkyl, heterocycloalkyl, and —C(O)-heterocycloalkyl groups, wherein each of —NH$_2$, $(C_1-C_6)$ alkyl, $(C_1-C_6)$ alkoxy, $(C_1-C_6)$ haloalkyl, $(C_1-C_6)$ haloalkoxy, halogen, cycloalkyl, —C(O)-cycloalkyl, heterocycloalkyl, and —C(O)-heterocycloalkyl are optionally substituted with one or more substituent independently chosen from $(C_1-C_6)$ alkyl, $(C_1-C_6)$ alkoxy, and —OH; and
n is 0, 1, 2, or 3,
provided that the compound is not present in Table C of FIG. 1.

The compounds of Formula (I) can be a compound, or pharmaceutically acceptable forms thereof, wherein:
Y is chosen from $C(R_3)$ and N;
R' is chosen from H and $CH_3$;
$R_1$ is chosen from 8-11 membered heteroaryls optionally substituted with one or more substituent chosen from $R_5$ and $R_6$;
$R_2$ is chosen from N-linked 4-12 membered heterocyclyls optionally substituted with one or more $R_5$; $R_3$ is independently chosen from H, deuterium, $(C_1-C_6)$ alkyl, $(C_1-C_6)$ alkoxy, $(C_1-C_6)$ haloalkyl, halogen, —OH, —CN, wherein each of $(C_1-C_6)$ alkyl, $(C_1-C_6)$ alkoxy, and $(C_1-C_6)$ haloalkyl are optionally substituted with one or more substituent independently chosen from deuterium, halogen, $(C_1-C_6)$ alkoxy, —NH$_2$, and —OH;
$R_4$ is chosen from H, deuterium, $(C_1-C_4)$ alkyl, halogen, —OH, —CN, and further wherein any $R_4$ group containing hydrogen can have one or more hydrogen replaced with deuterium;
each $R_5$ (if present) is independently chosen from —OH, —NH$_2$, NHC(O)CH$_3$, $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, and —C(O)-heterocycloalkyl groups, wherein each of —NH$_2$, NHC(O)CHs, $(C_1-C_6)$ alkyl, $(C_1-C_6)$ alkoxy, $(C_1-C_6)$ haloalkyl, $(C_1-C_6)$ haloalkoxy, cycloalkyl, heterocycloalkyl, and —C(O)-heterocycloalkyl are optionally substituted with one or more substituent independently chosen from halogen, $(C_1-C_6)$ alkoxy, —NH$_2$, and —OH, and wherein any $R_5$ group containing hydrogen can have one or more hydrogen replaced with deuterium;
each $R_6$ (if present) is chosen from —N$(C_1-C_6)$alkyl-aryls, —N$(C_1-C_6)$alkyl-heteroaryls, and —N$(C_1-C_6)$alkyl-heterocyclyl groups, wherein the groups are optionally substituted with one or more substituent chosen from —OH, —NH, halogen, $(C_1-C_6)$ alkyl, $(C_1-C_6)$ alkoxy, and $(C_1-C_6)$ haloalkyl groups, and further wherein any $R_6$ group containing hydrogen can have one or more hydrogen replaced with deuterium; and n is 0, 1, 2, or 3, provided that the compound is not present in Table C of FIG. 1.

In another aspect, the compound can be a compound of Formula (VI)

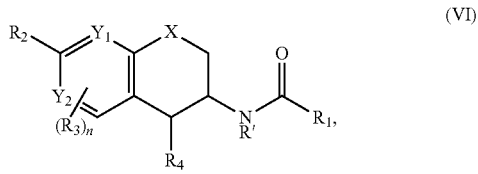

or a pharmaceutically
wherein:
- X is chosen from C(R)(R") and O;
- each of $Y_1$, $Y_2$, and $Y_3$ is independently chosen from $C(R_3)$ and N;
- R' is chosen from H, deuterium, and —CH$_3$;
- each of R and R" is independently chosen from H, halogen, —OH, —CN, $C_1$-$C_6$ alkyl optionally substituted with one or more Ri, R and R" together with the carbon they are attached form a spirocyclic cyclopropyl optionally substituted with one or more Ri, wherein any R, R", or Ri group being or containing hydrogen can independently have one or more hydrogen replaced with deuterium;
- each Ri is independently chosen from halogen, —OH, and CH$_3$;
- $R_1$ is chosen from 6-12 membered fused and nonfused heteroaryls optionally substituted with one or more substituent chosen from $R_5$ and/or $R_6$, and further wherein any $R_1$ group containing hydrogen can have one or more hydrogen replaced with deuterium;
- $R_2$ is chosen from N-linked 4-12 membered heterocyclyls, C-linked 4-12 membered heterocyclyls, and an —O-linked 4-12 membered heterocyclyl, wherein the 4-12 membered heterocyclyls are optionally substituted with one or more $R_5$ (which can be the same or different from the one or more $R_5$ of $R_1$), and further wherein any hydrogen in a $R_2$ group can have one or more hydrogen replaced with deuterium;
- each $R_3$ is independently chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, ($C_3$-$C_8$) cycloalkyl, heterocycloalkyl, aryl, and heteroaryl groups, wherein each of ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, aryl, and heteroaryl groups are optionally substituted with one or more $R_7$;
- $R_4$ is chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, ($C_3$-$C_8$) cycloalkyl, heterocycloalkyl, aryl, and heteroaryl groups, wherein each of ($C_1$-$C_6$) alkyl, ($C_1$-$C_6$) alkoxy, ($C_1$-$C_6$) haloalkyl, ($C_1$-$C_6$) haloalkoxy, ($C_2$-$C_8$) cycloalkyl, heterocycloalkyl, aryl, and heteroaryl are optionally substituted with one or more $R_5$, and further wherein any $R_4$ group containing hydrogen can have one or more hydrogen replaced with deuterium;
- each $R_5$ is independently chosen from —OH, —NH$_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)— heterocycloalkyl groups, wherein each of —NH$_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, —NH$_2$, and —OH, and wherein any $R_5$ group containing hydrogen can have one or more hydrogen replaced with deuterium;
- each $R_6$ is independently chosen from -amino alkyl-aryls, -amino alkyl-heteroaryls, -amino alkyl-cyclyl, and -amino alkyl-heterocyclyl groups, wherein each of the $R_6$ groups are optionally substituted with one or more substituent chosen from —OH, —NH, halogen, ($C_1$-$C_6$) alkyl, ($C_1$-$C_6$) alkoxy, and ($C_1$-$C_6$) haloalkyl groups, and further wherein any $R_6$ group containing hydrogen can have one or more hydrogen replaced with deuterium;
- each $R_7$ is independently chosen from —OH, —NH$_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl groups, wherein each of —NH$_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, and —OH; and
- n is 0, 1, 2, or 3, provided that the compound is not present in Table C.

In another aspect, the compound can be a compound of Formula (II):

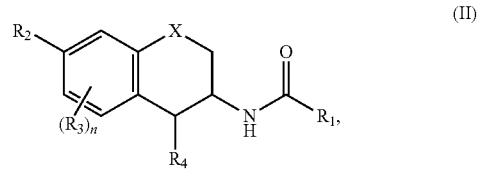

or a pharmaceutically acceptable salt thereof, wherein
- each of X, $R_1$, $R_2$, $R_3$, $R_7$ and n are as defined in Formula (VI); $R_4$ is chosen from H, ($C_1$-$C_6$) alkyl, halogen, and —OH;
- each $R_5$ is independently chosen from —OH, —NH$_2$, —NHC(O)CH$_3$, —C(O)NHCH$_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)—heterocycloalkyl groups, wherein each of —NH$_2$, —NHC(O)CH$_3$, —C(O)NHCH$_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, —NH$_2$, and —OH; and
- each $R_6$ is independently chosen from —NH($C_1$-$C_6$)alkyl-aryls, —NH($C_1$-$C_6$)alkyl-heteroaryls, —NH($C_1$-$C_6$)alkyl-cyclyl, and —NH($C_1$-$C_6$)alkyl-heterocyclyl groups, wherein each of the $R_6$ groups are optionally substituted with one or more substituent chosen from —OH, —NH, halogens, ($C_1$-$C_6$) alkyl, ($C_1$-$C_6$) alkoxy, and ($C_1$-$C_6$) haloalkyl groups, provided that the compound is not present in Table C.

In another aspect, the compound can be a compound of Formula (II):

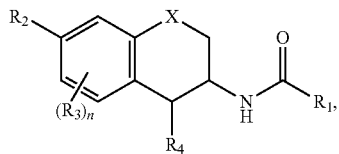

(II)

or a pharmaceutically acceptable salt thereof, wherein
each of X, $R_1$, $R_2$, $R_3$, $R_7$ and n are as defined in Formula (VI);
$R_4$ is chosen from H. ($C_1$-$C_6$) alkyl, halogen, and —OH;
each $R_5$ is independently chosen from —OH, —$NH_2$, —NHC(O)$CH_3$, —C(O)NH$CH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)—heterocycloalkyl groups, wherein each of —$NH_2$, —NHC(O)$CH_3$, —C(O)NH$CH_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, —$NH_2$, and —OH; and
each $R_6$ is independently chosen from —NH($C_1$-$C_6$)alkyl-aryls, —NH($C_1$-$C_6$)alkyl-heteroaryls, —NH($C_1$-$C_6$)alkyl-cyclyl, and —NH($C_1$-$C_6$)alkyl-heterocyclyl groups, wherein each of the $R_6$ groups are optionally substituted with one or more substituent chosen from —OH, —NH, halogen, ($C_1$-$C_6$) alkyl, ($C_1$-$C_6$) alkoxy, and ($C_1$-$C_6$) haloalkyl groups,
wherein the compound is not present in Table C.

In another aspect, the compound can be a compound of Formula (IIaa)

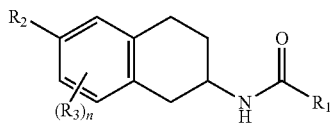

(IIaa)

or a pharmaceutically acceptable salt thereof, wherein
$R_1$ is chosen from 8-9-membered heteroaryls substituted with one or more substituent chosen from $R_5$ and $R_6$, wherein each $R_5$ and $R_6$ are independently as defined in Formula (II); $R_2$ is chosen from N-linked 6-12 membered heterocyclyls or C-linked 6-12 membered heterocyclyls optionally substituted with one or more $R_5$, wherein $R_5$ is as defined in Formula (II); and
$R_3$ is independently chosen from H, ($C_1$-$C_6$) alkyl, halogen, and —CN, wherein the ($C_1$-$C_6$) alkyl groups are optionally substituted with $R_7$ wherein each $R_7$ is independently as defined in Formula (VI),
wherein the compound is not present in Table C of FIG. 1.

In another aspect the compound can be a compound of Formula (IIb'):

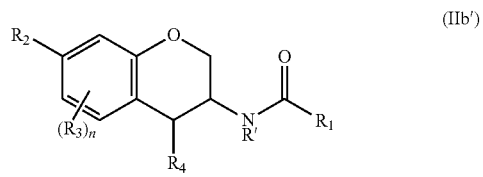

(IIb')

or a pharmaceutically acceptable salt thereof, wherein
R' is chosen from H and $CH_3$;
$R_1$ is chosen from 8-9 membered heteroaryls substituted with one or more substituent chosen from $R_5$ and $R_6$, wherein each $R_5$ and/or $R_6$ (if present) are independently as defined in Formula (VI);
$R_2$ is chosen from N-linked 6-12 membered heterocyclyls or C-linked 6-12 membered heterocyclyls optionally substituted with one or more $R_5$, wherein each $R_5$ is independently as defined in Formula (VI); and $R_3$ is independently chosen from H, ($C_1$-$C_6$) alkyl, halogen, and —CN, wherein the ($C_1$-$C_6$) alkyl groups are optionally substituted with $R_7$ wherein each $R_7$ is independently as defined in Formula (VI), and
wherein the compound is not present in Table C.

In another aspect, the compound can be a compound of any one of Formula (VI), (II), (IIaa), and (IIb'), wherein Ri, optionally substituted with $R_5$ and/or $R_6$, is chosen from Table A, wherein the compound is not present in Table C.

In another aspect, the compound can be a compound of any one of Formula (VI), (II), (IIaa), and (IIb'), wherein $R_2$, optionally substituted with $R_5$, is chosen from Table B, wherein the compound is not present in Table C.

In another aspect, the compound can be a compound of Example 2-38, 3-17, 3-18, 10-15, 10-16, 14-15, 14-16, 14-17, 14-18, 14-19, 14-20, 14-21, 14-22, 14-23, 14-24, 22-5, 22-6, 23-1, 23-2, 24-1, 24-2, 25, 26-1, 26-2; 27-1, 27-2, 28-1, 28-2, 29-1, 29-2, 30-1, 30-2, 31-1, 31-2, 31-3, 31-4, 32-1, 32-2, 33-3, 33-4, 34, 35, Table 21, and Table 25, provided that the compound is not present in Table C.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

DRAWINGS

In order that the disclosure may be well understood, there will now be described various forms thereof, given by way of example, reference being made to the accompanying drawings, in which.

DESCRIPTION OF THE EMBODIMENTS

Figure 1:
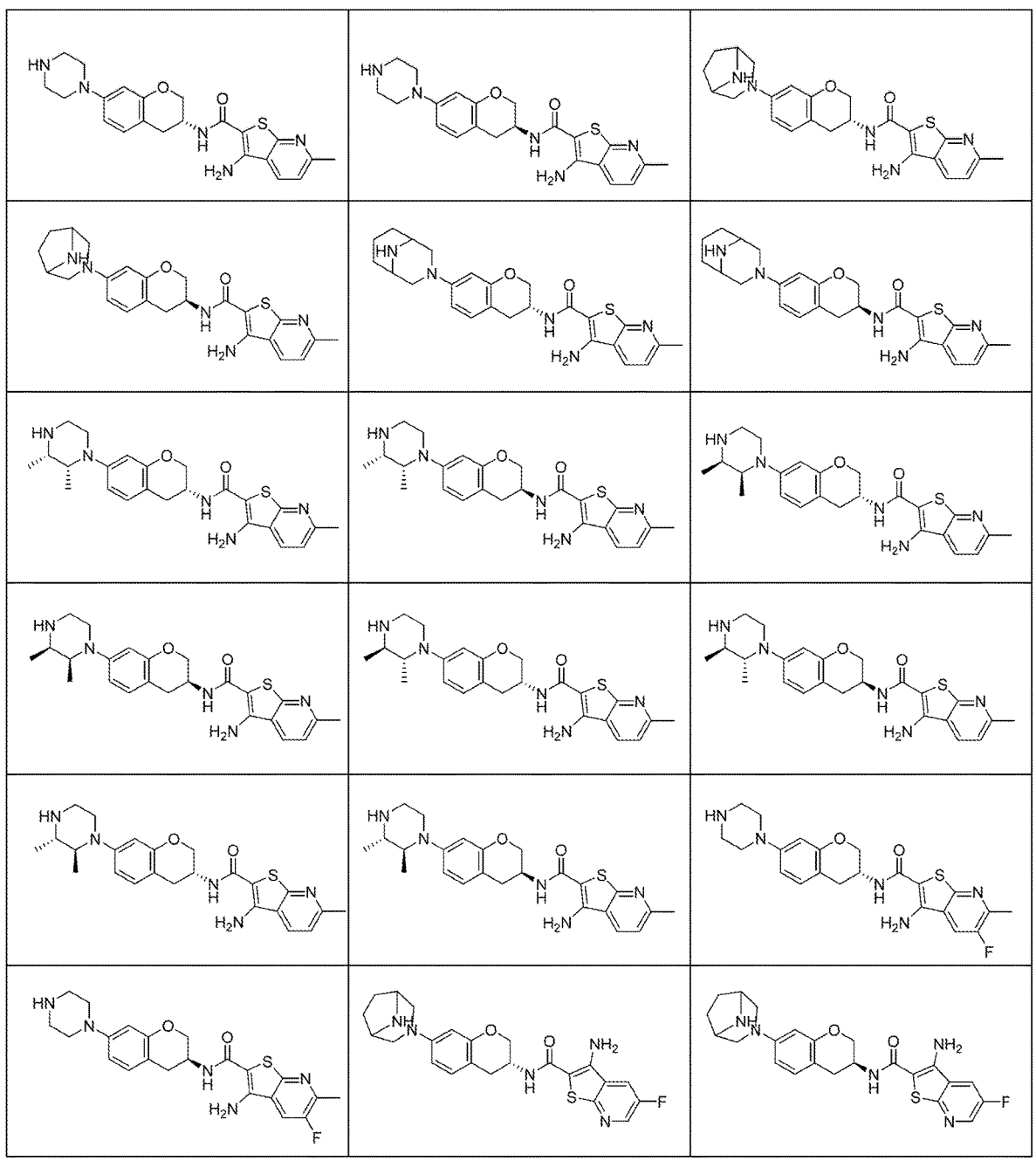
FIG. 1 is Table C, which depicts the structures of a number of compounds.
Figure 1:
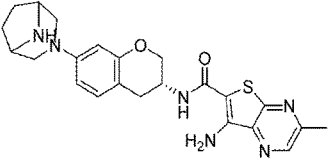
Figure 1:
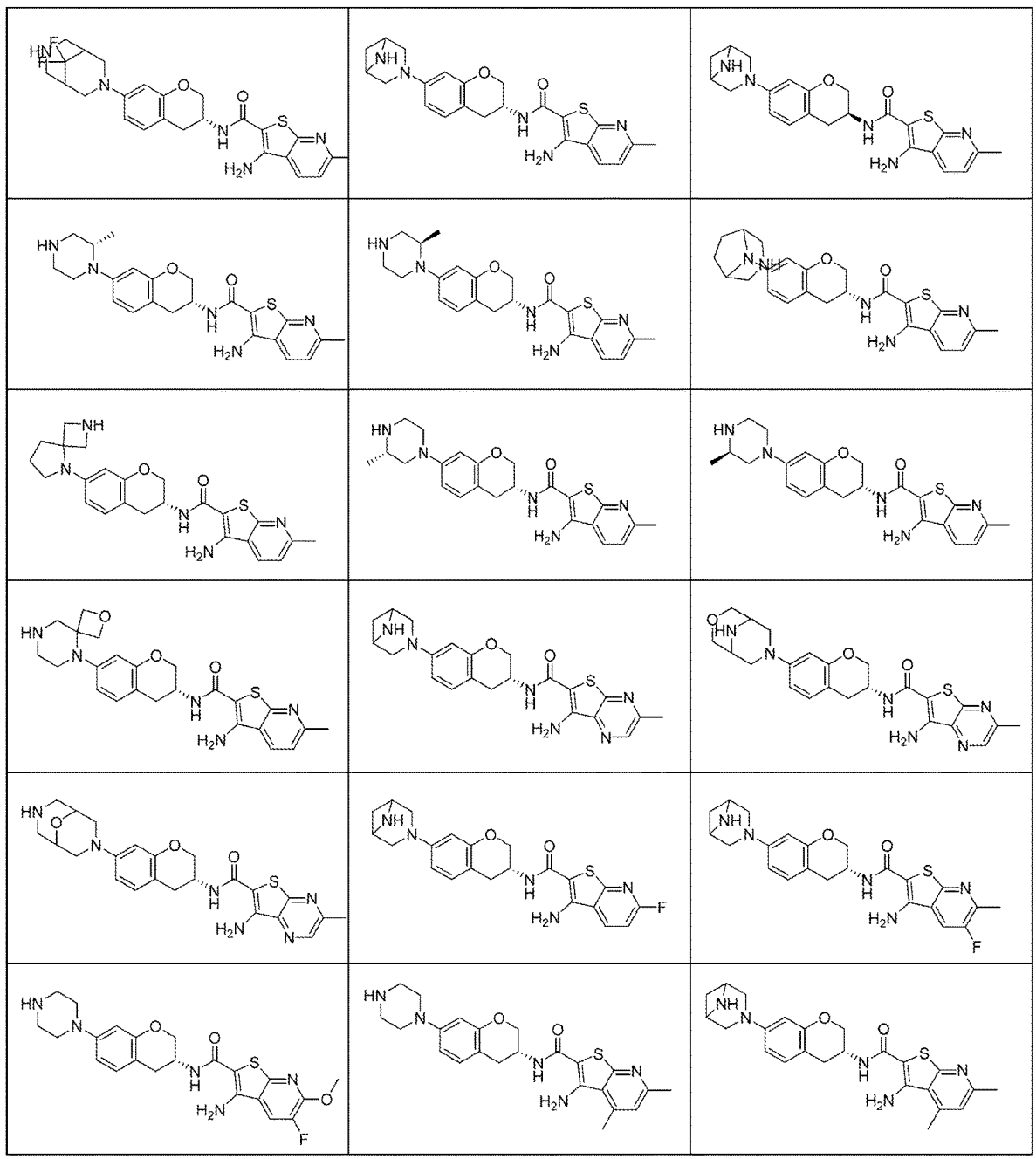
Figure 1:
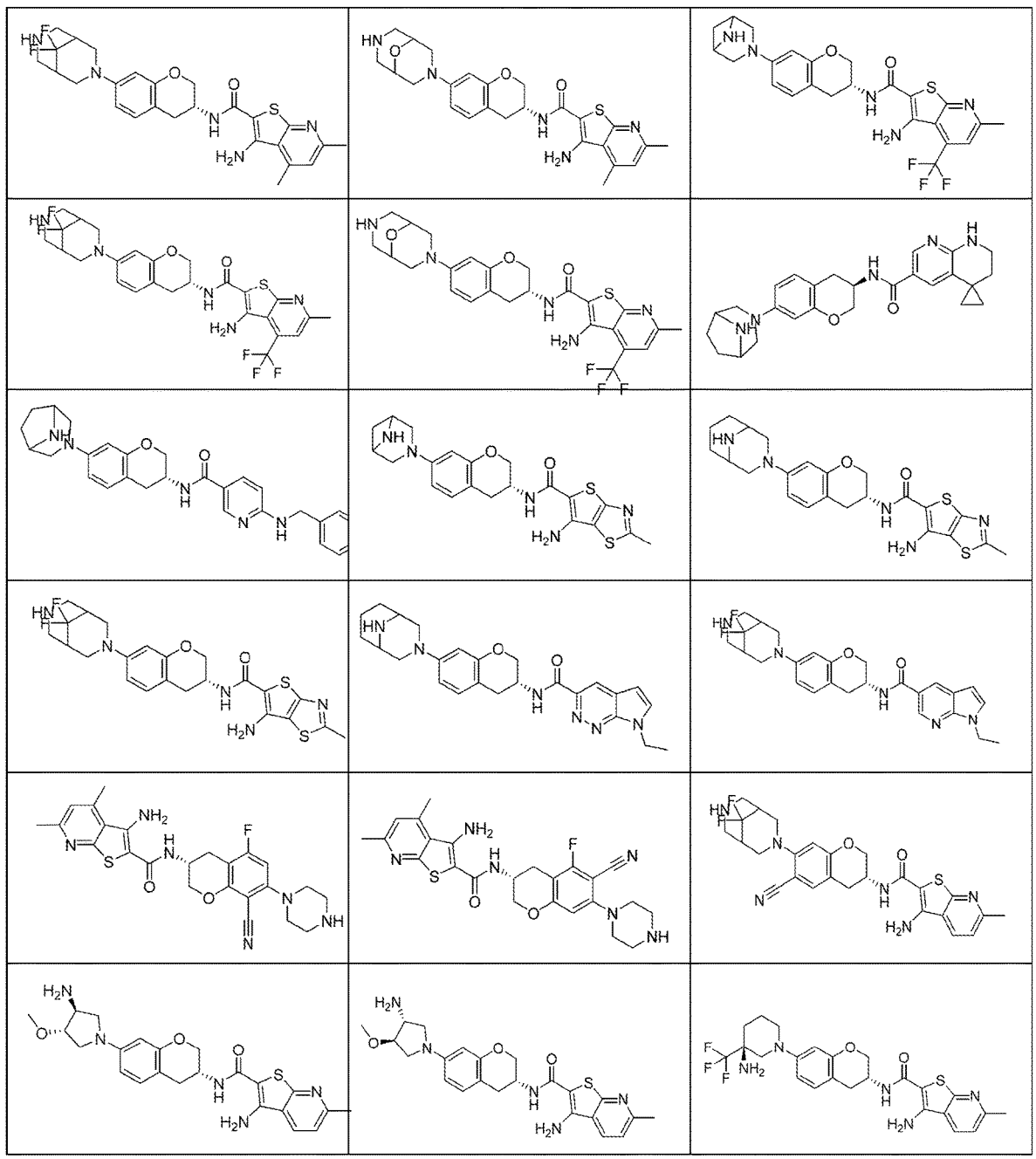
Figure 1:
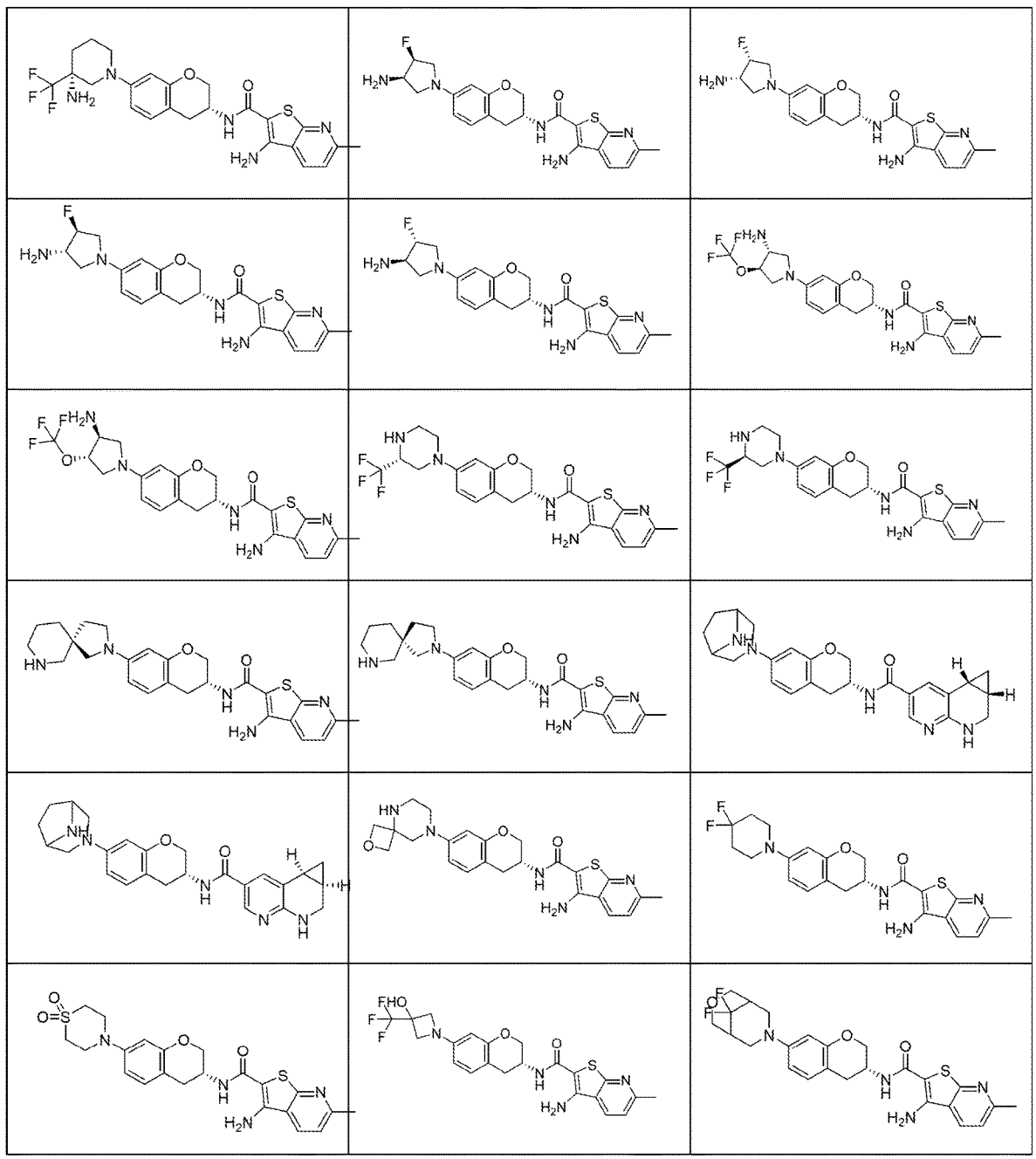
Figure 1:
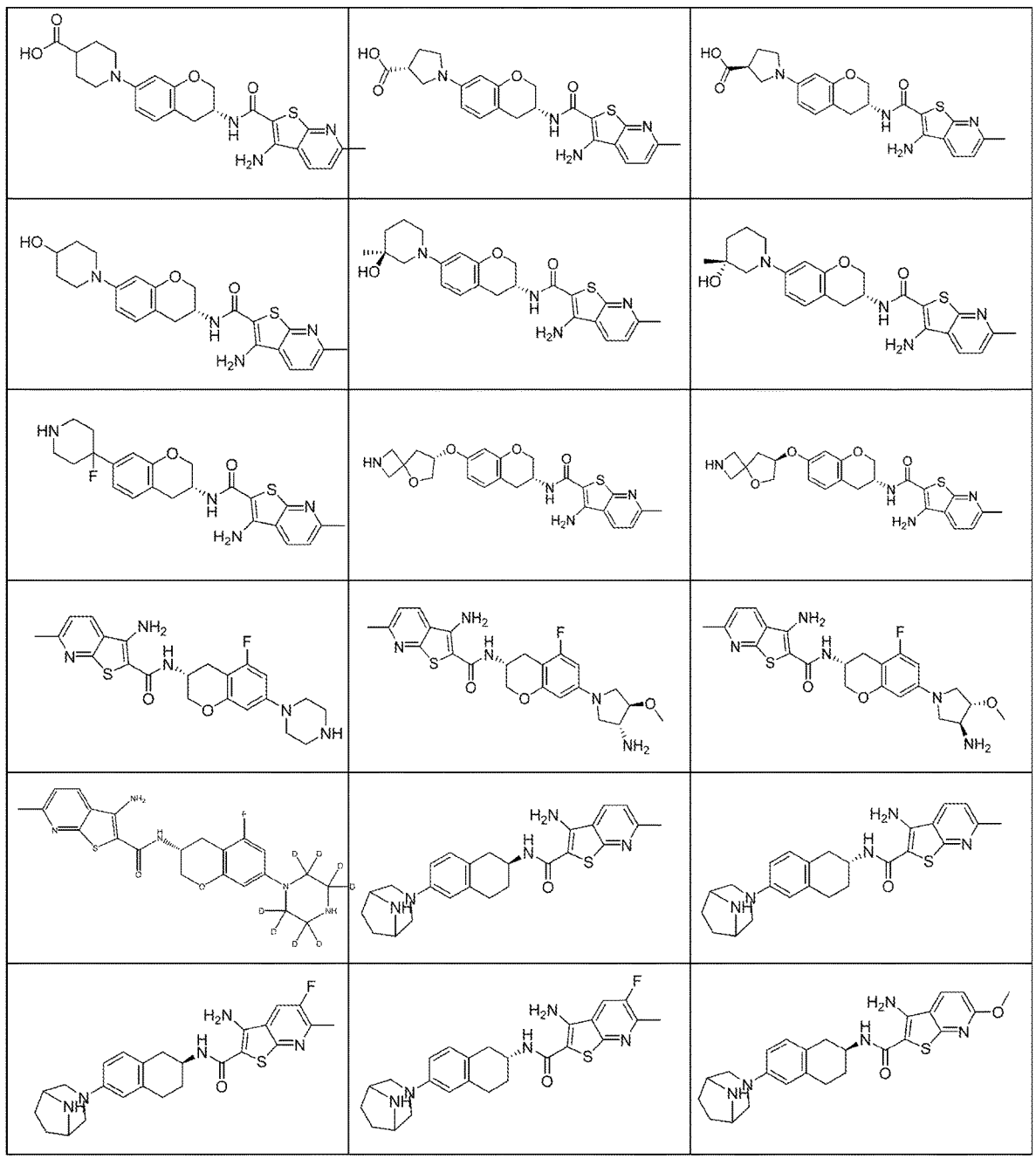
Figure 1:
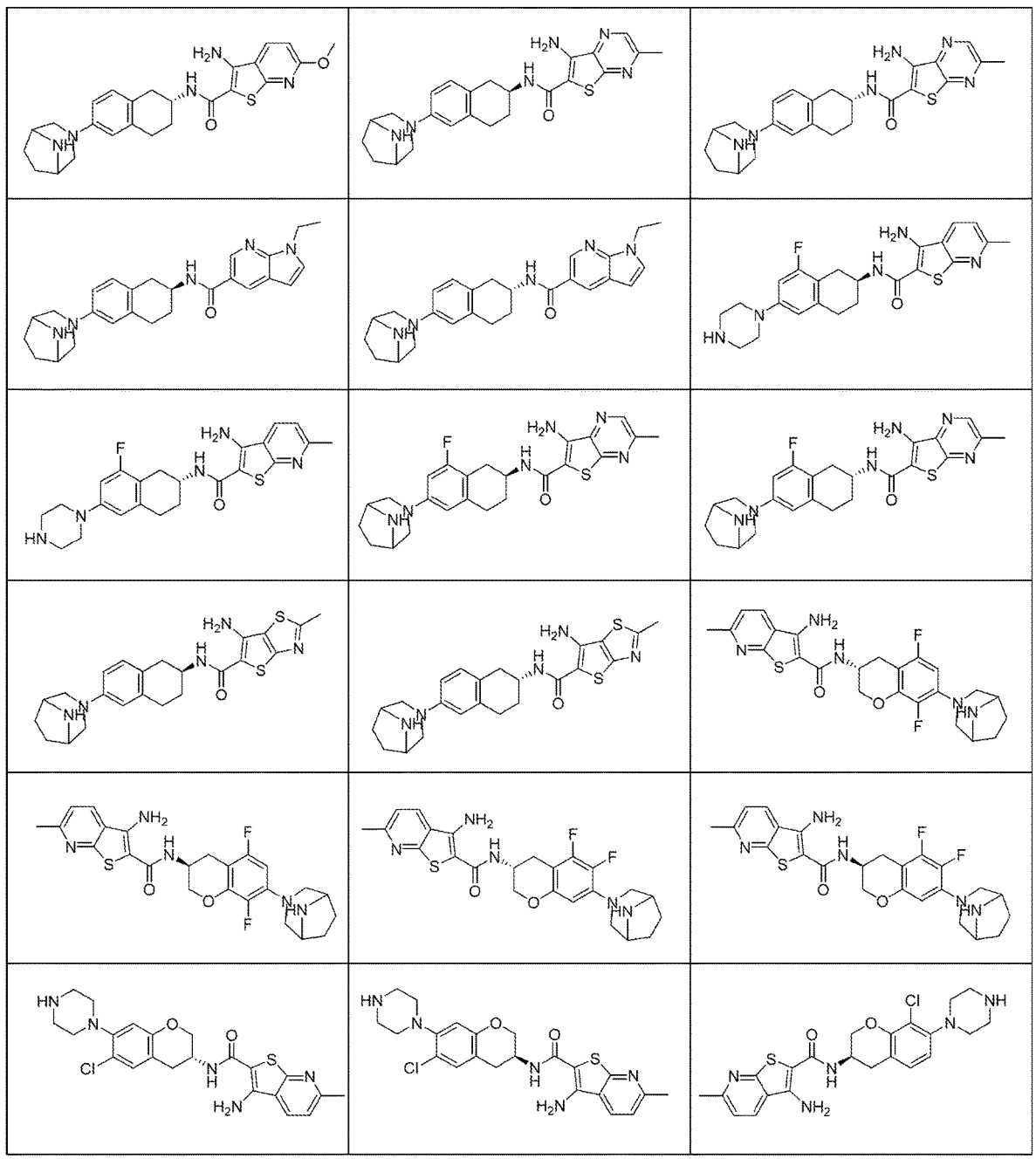
Figure 1:
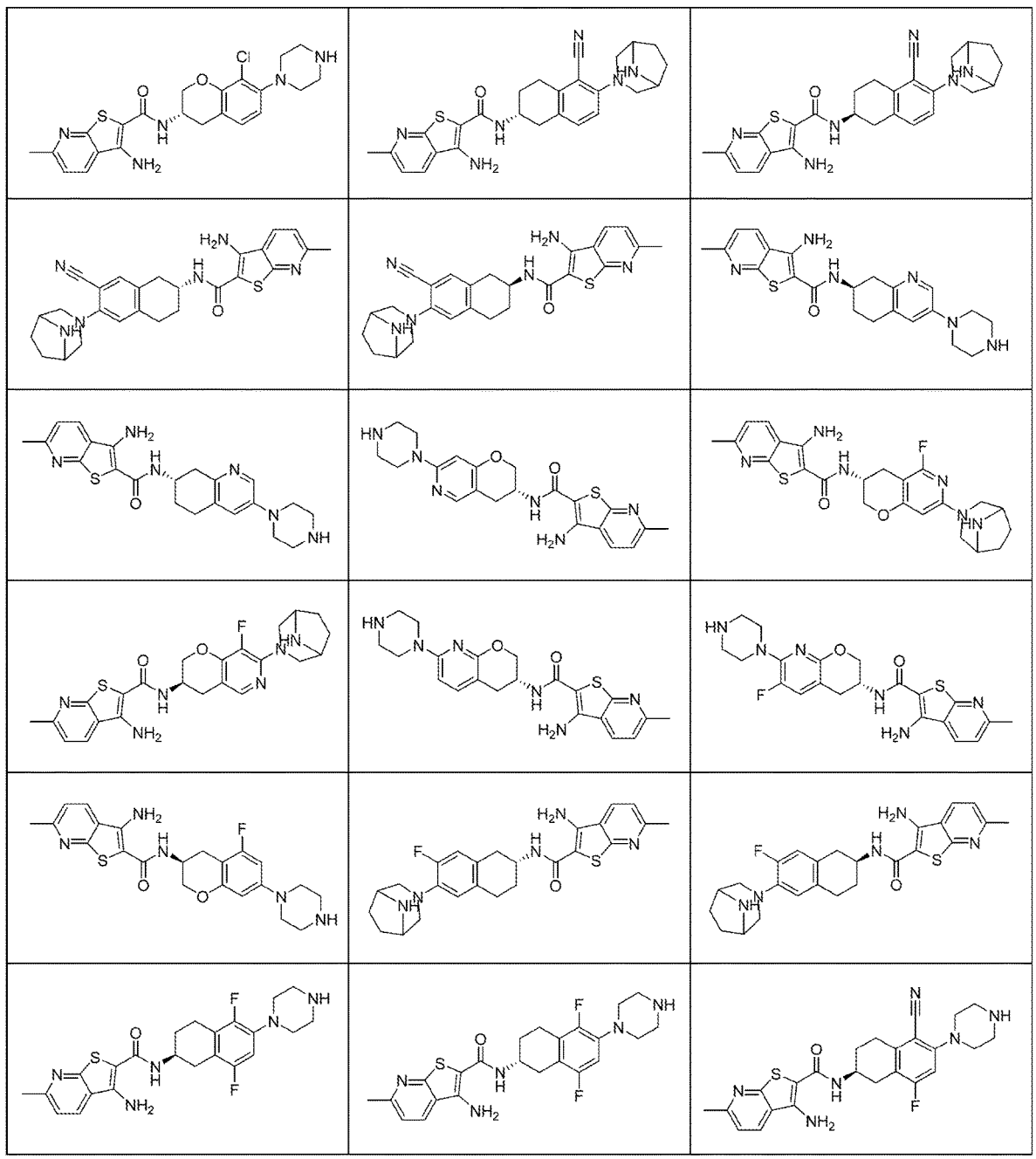
Figure 1:
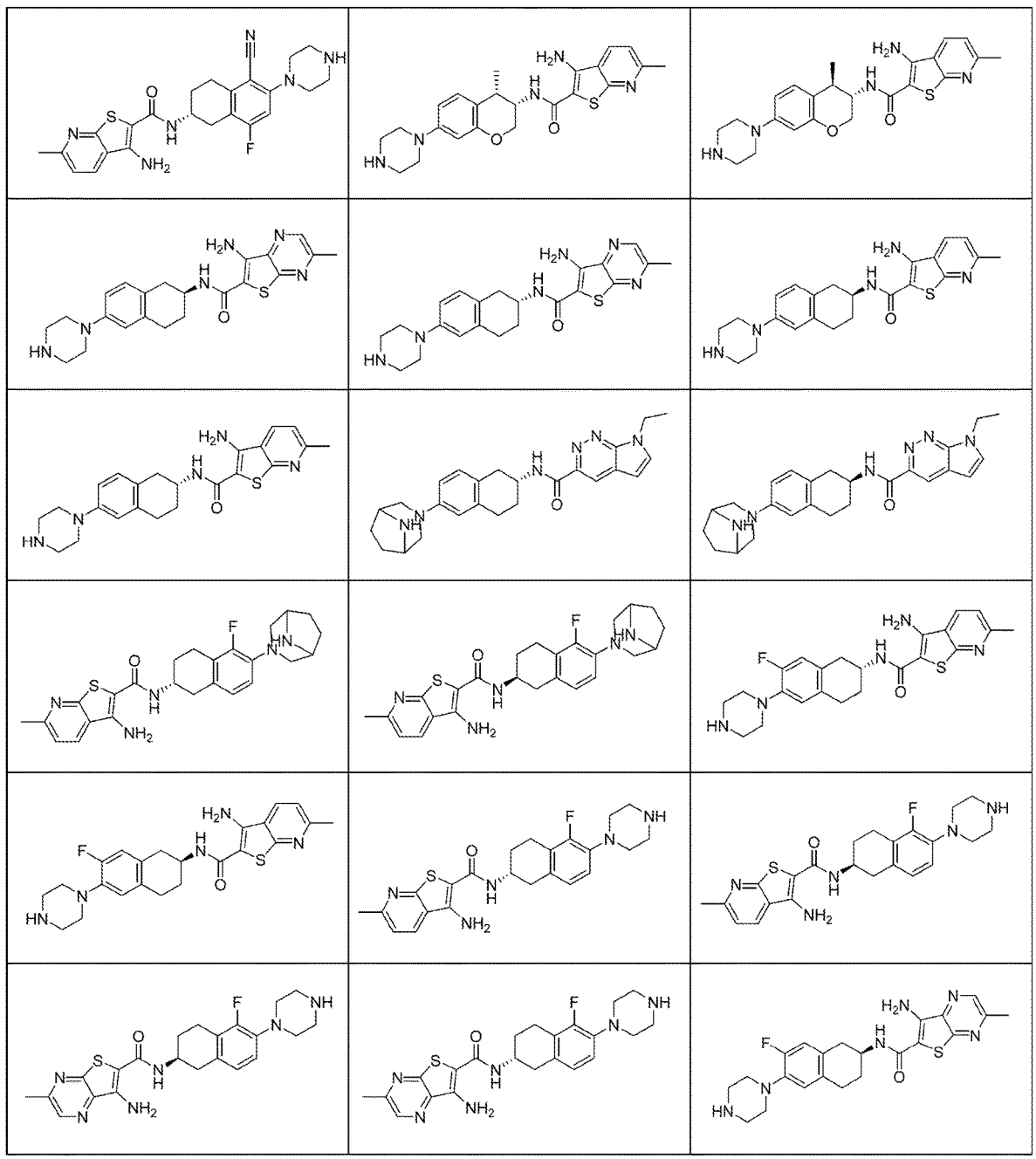
Figure 1:
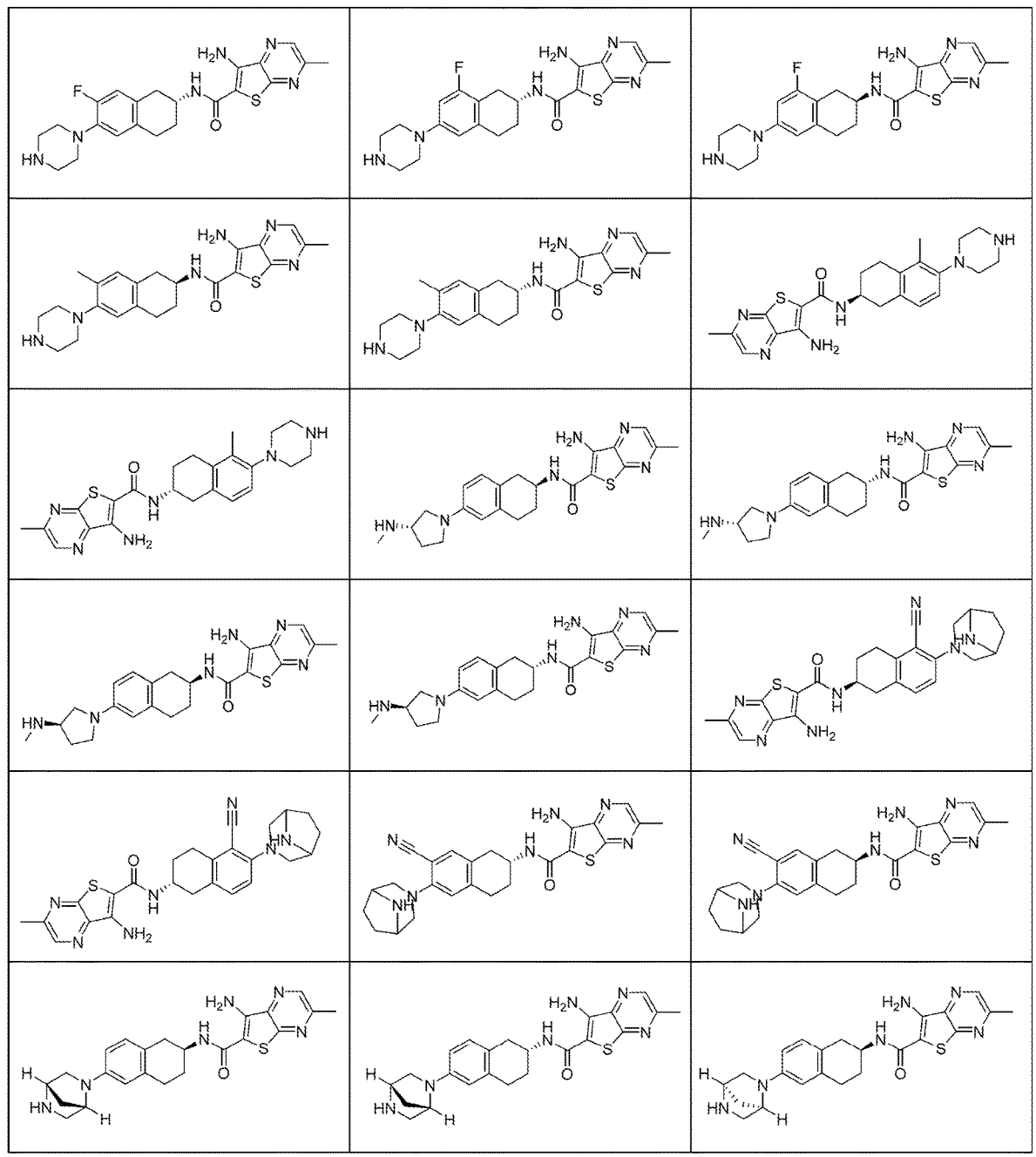
Figure 1:
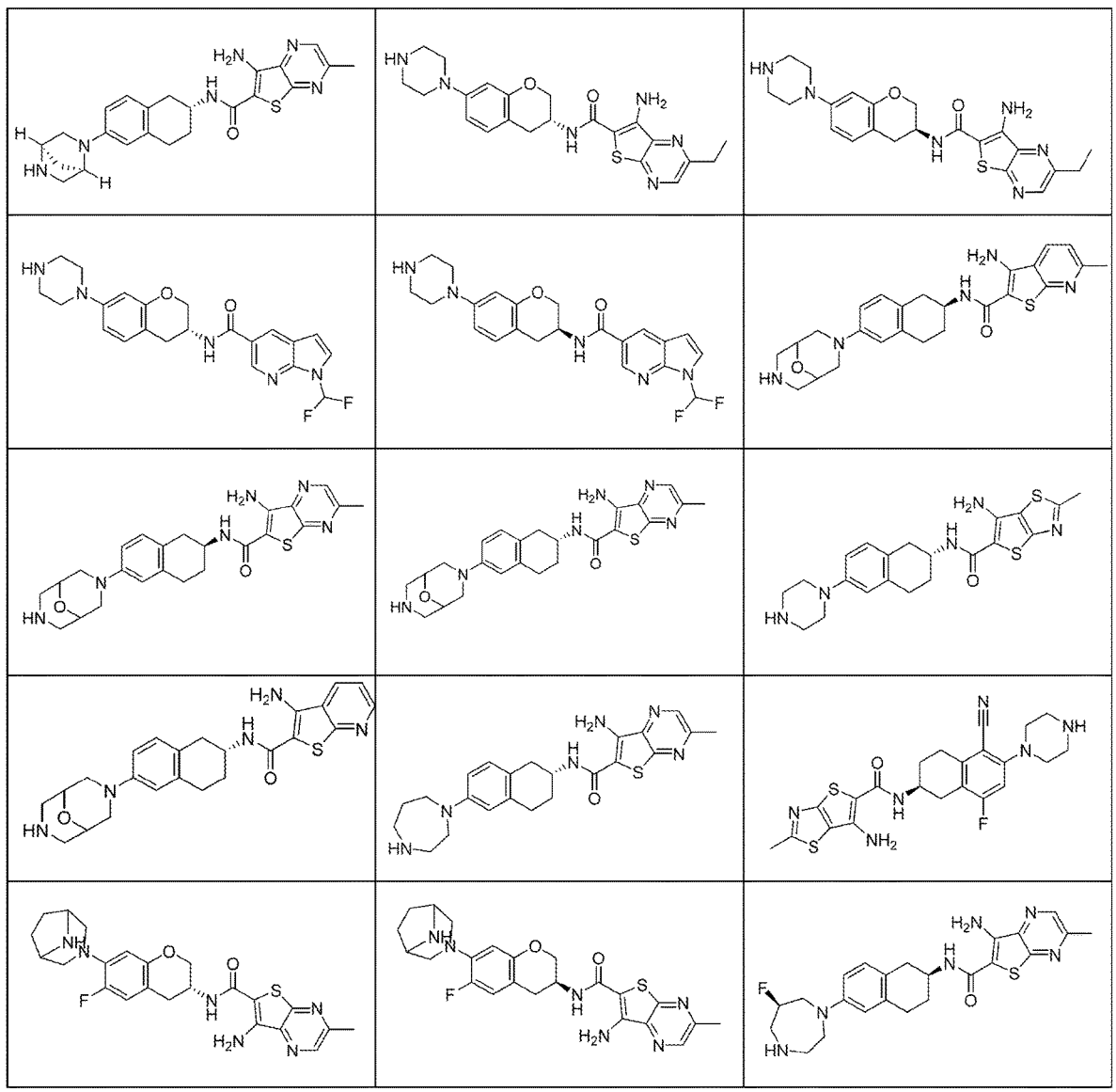
Figure 1:
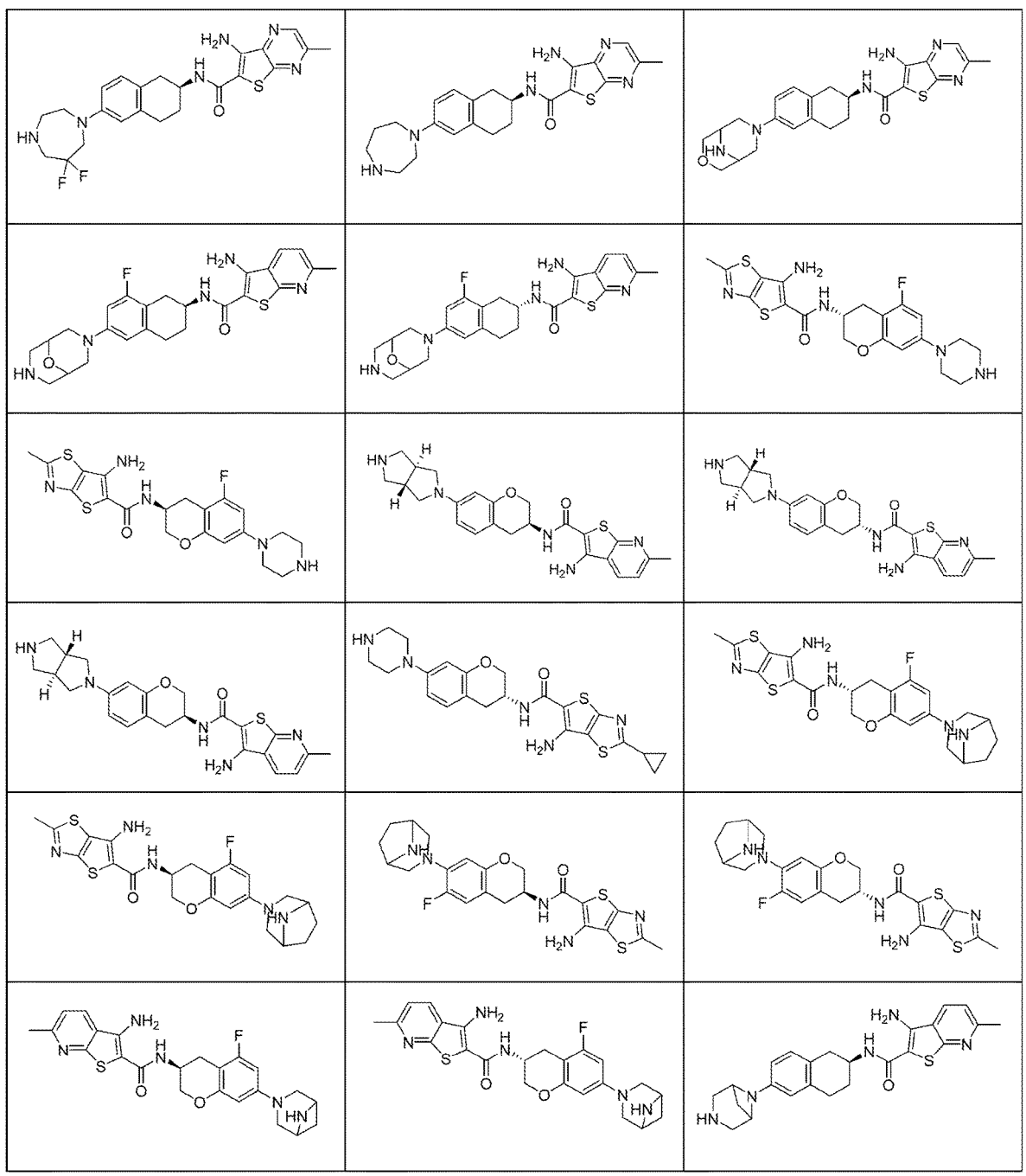
Figure 1:
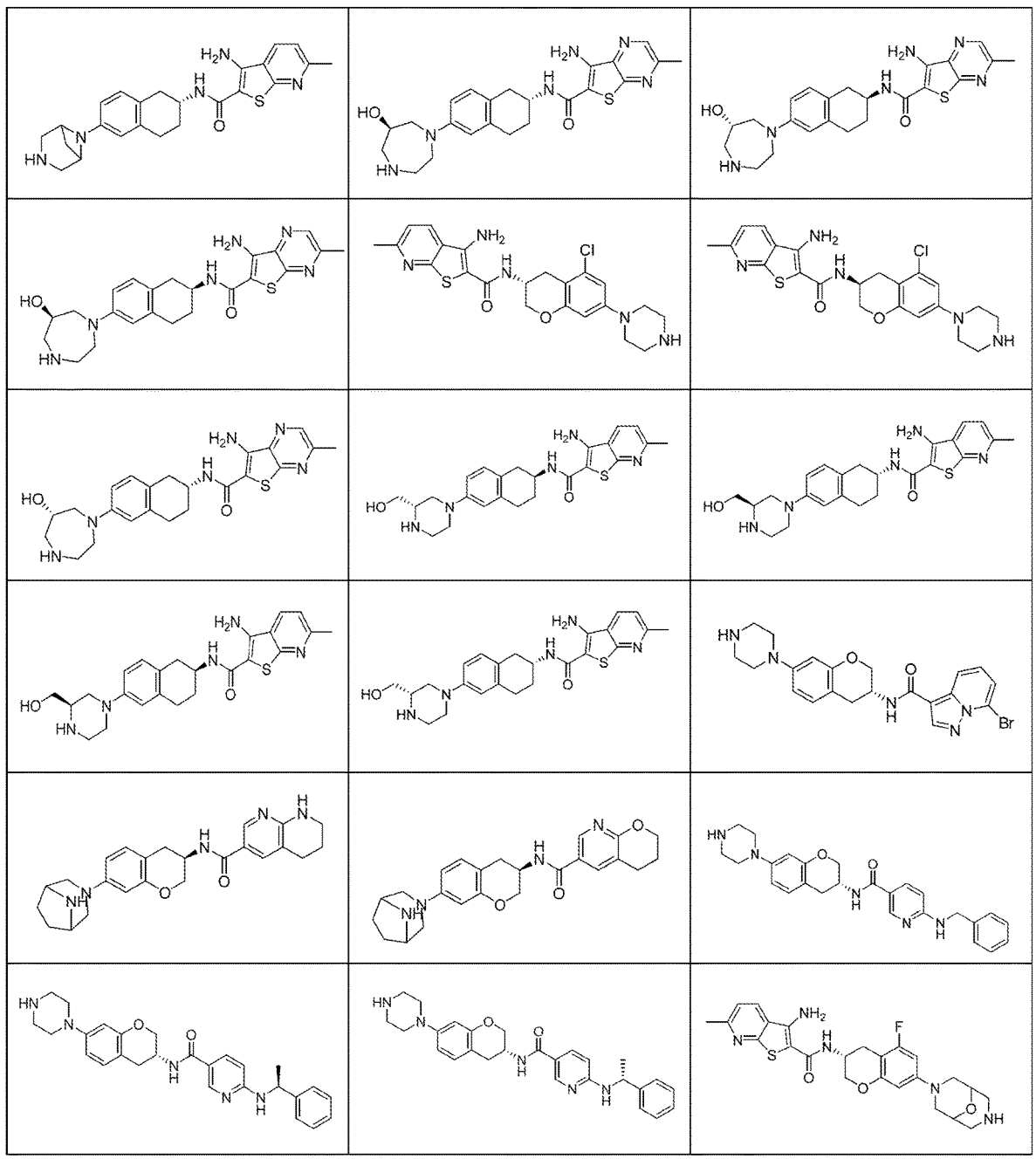
Figure 1:
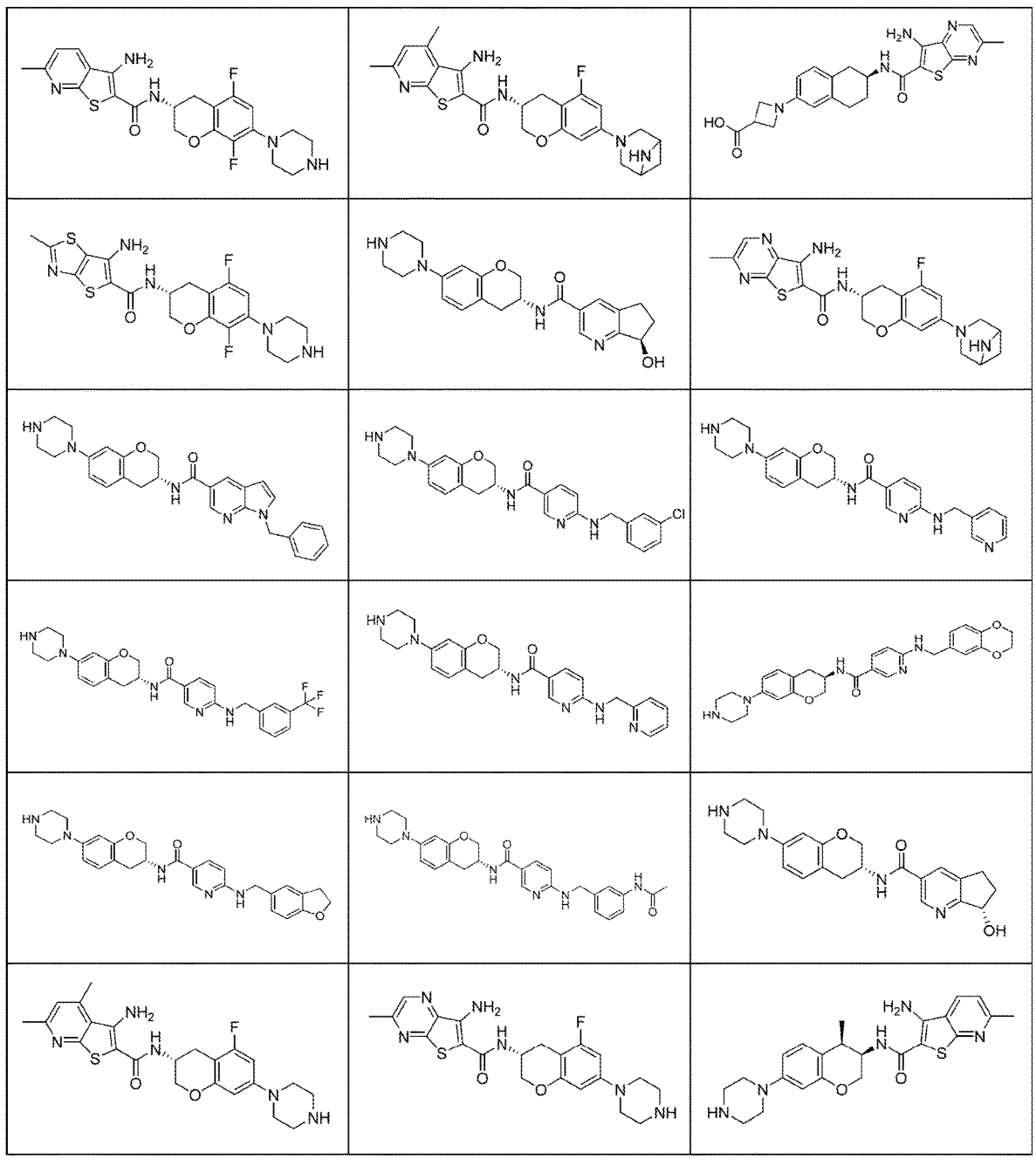
Figure 1:
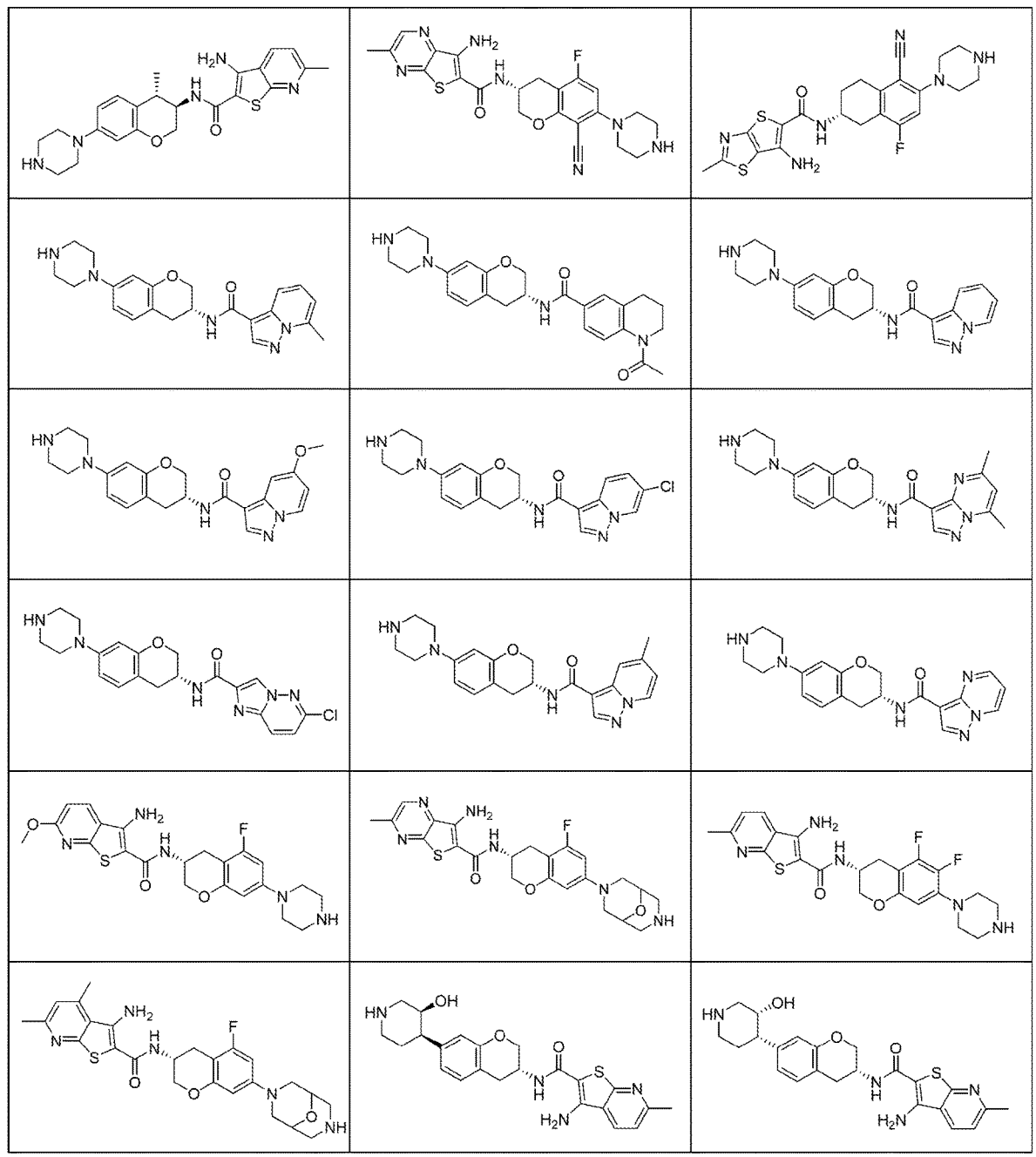
Figure 1:
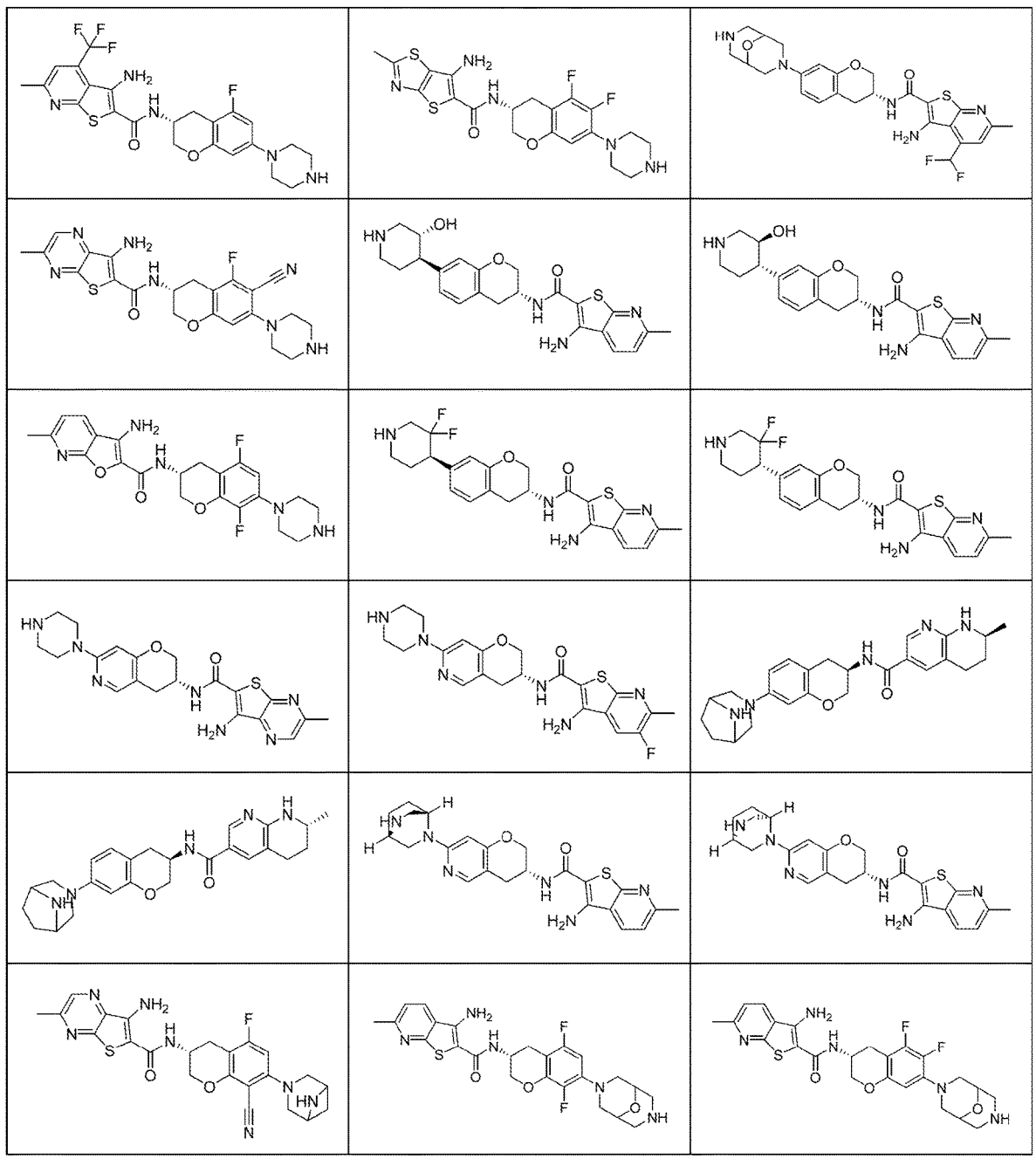
Figure 1:
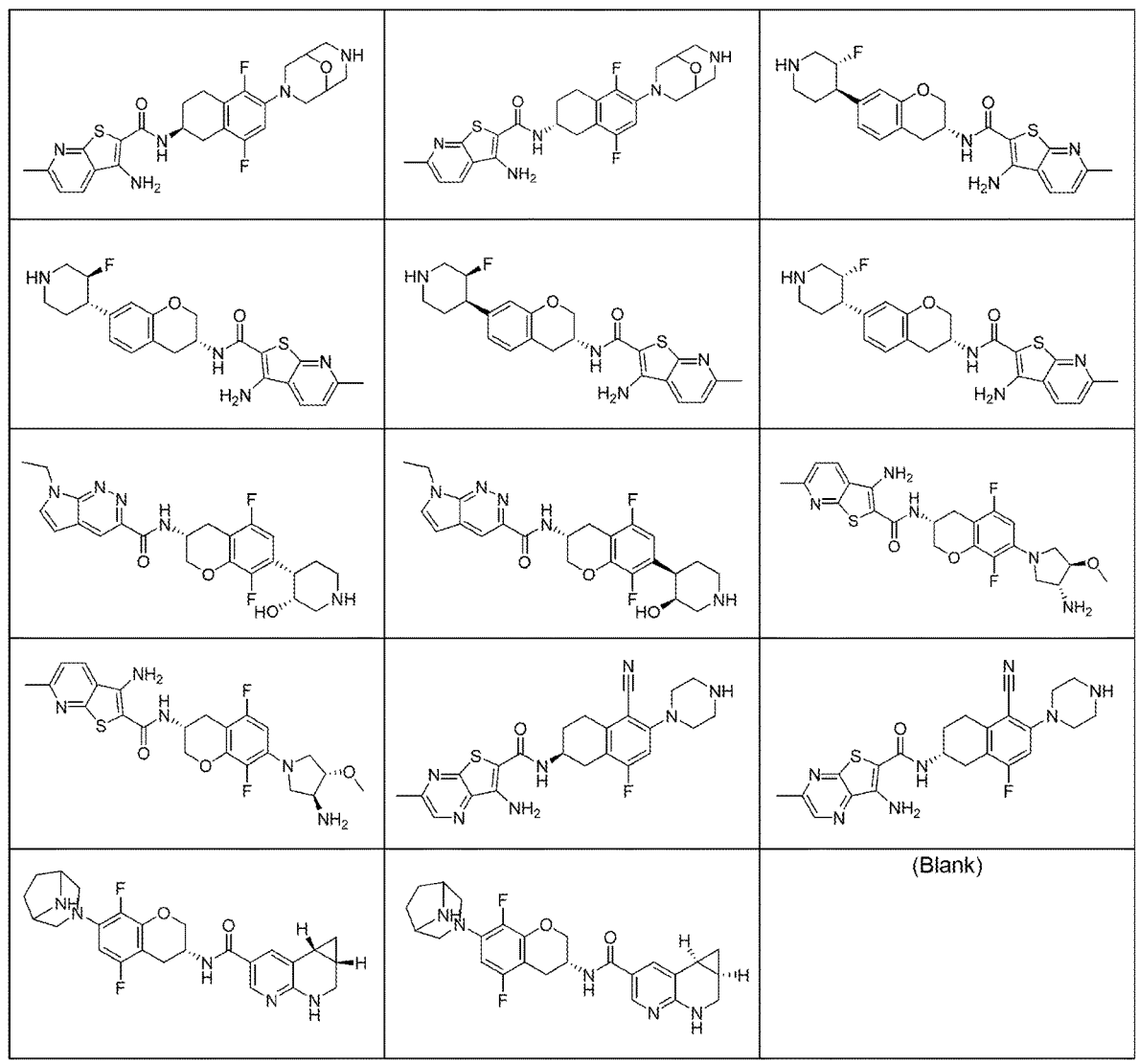

Compounds useful for inhibiting USP28 and/or USP25 are disclosed herein, including USP25 Inhibitor compounds, USP28 Inhibitor compounds and USP28/25 Inhibitor compounds as defined herein. The USP28/25 Inhibitor, USP28 Inhibitor and/or USP25 Inhibitor compounds can be a compound disclosed herein, including a compound of Formula (I), a compound of Formula (II), a compound of Formula (III), a compound of Formula (IV), a compound of Formula (V), a compound of Formula (VI), and/or a compound of Formula (VII). These chemical entities may not include the compounds illustrated in Table C.

The term "USP28 Inhibitor" compound as used herein refers to a compound disclosed herein (e.g., a compound of Formula (I), a compound of Formula (II), a compound of Formula (III), a compound of Formula (IV), a compound of Formula (V), a compound of Formula (VI), and/or a compound of Formula (VII)) having an $IC_{50}$ of 2 micromolar or less in the Ubiquitin-Rhodamine 110 Assay for USP28 as described in Example A-1(a) and/or the Ubiquitin-Rhodamine 110 Assay for USP28 as described in Example A-1(b) herein. For example, the USP28 Inhibitor can be a compound of a formula disclosed herein having an $IC_{50}$ value of up to 2 micromolar using the Ubiquitin-Rhodamine 110 Assay for USP28 as described in Example A-1(a), including $IC_{50}$ values ranging from 0.001-2 micromolar, preferably 0.001-0.2 micromolar, and more preferably 0.001-0.05 micromolar. The USP28 Inhibitor can be a compound of a formula disclosed herein having an $IC_{50}$ value of up to 2 micromolar using the Ubiquitin-Rhodamine 110 Assay for USP28 as described in Example A-1(b), including $IC_{50}$ values ranging from 0.001-2 micromolar, preferably 0.001-0.2 micromolar, more preferably from 0.001-0.05 micromolar. The USP28 Inhibitor can be a compound of a formula disclosed herein having an $IC_{50}$ values of up to 2 micromolar using both the Ubiquitin-Rhodamine 110 Assay for USP28 as described in Example A-1(a) and the Ubiquitin-Rhodamine 110 Assay for USP28 as described in Example A-1(b), including $IC_{50}$ values of 0.001-2 micromolar, preferably 0.001-0.2 micromolar, more preferably 0.001-0.05 micromolar for both assays.

The term "USP25 Inhibitor" as used herein refers to a compound disclosed herein (e.g., a compound of Formula (I), a compound of Formula (II), a compound of Formula (III), a compound of Formula (IV), a compound of Formula (V), a compound of Formula (VI), and/or a compound of Formula (VII)) having an $IC_{50}$ of 2 micromolar or less in the Ubiquitin-Rhodamine 110 Assay for USP25 as described in Example A-2 herein. For example, the USP25 Inhibitor can be a compound of a formula disclosed herein having an $IC_{50}$ value of up to 2 micromolar using the Ubiquitin-Rhodamine 110 Assay for USP25 as described in Example A-2, including $IC_{50}$ values ranging from 0.001-2 micromolar, preferably 0.001-0.2 micromolar, more preferably 0.001-0.05 micromolar. The USP25 Inhibitor can be a compound of a formula disclosed herein having an $IC_{50}$ value of up to 2 micromolar using the Ubiquitin-Rhodamine 110 Assay for USP25 as described in Example A-2, including $IC_{50}$ values ranging from 0.001-2 micromolar, preferably 0.001-0.2 micromolar, more preferably 0.001-0.05 micromolar. The USP25 Inhibitor can be a compound of a formula disclosed herein having an $IC_{50}$ values of up to 2 micromolar using both the Ubiquitin-Rhodamine 110 Assay for USP25 as described in Example A-2 and the Ubiquitin-Rhodamine 110 Assay for USP25 as described in Example A-2, including $IC_{50}$ values ranging from 0.001-2 micromolar, preferably 0.001-0.2 micromolar, more preferably 0.001-0.05 micromolar for both assays.

The term "USP28/25 Inhibitor" as used herein refers to a compound disclosed herein (e.g., a compound of Formula (I), a compound of Formula (II), a compound of Formula (III), a compound of Formula (IV), a compound of Formula (V), a compound of Formula (VI), and/or a compound of Formula (VII)) that is a USP28 Inhibitor or a USP25 Inhibitor or both a USP28 Inhibitor and USP25 Inhibitor, as defined herein.

Optionally, any one or more hydrogen atoms in a compound of Formula (I), Formula (II), a compound of Formula (III), a compound of Formula (IV), a compound of Formula (V), a compound of Formula (VI), and/or a compound of Formula (VII)) can independently be replaced with deuterium or other hydrogen isotope.

In a first aspect of the disclosure, the chemical entities are chosen from compounds of Formula (I):

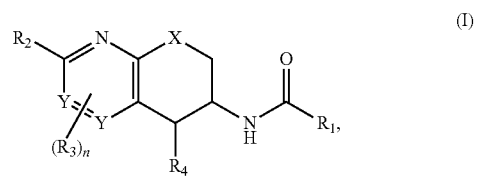

and pharmaceutically acceptable salts, solvates, prodrugs, stereoisomers, and tautomers thereof, are described wherein X, Y, $R_1$, $R_2$, $R_3$, $R_4$, and n are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-

$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and —S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, and S, the remaining ring atoms being C. Heteroaryl as herein defined also means a bicyclic heteroaromatic group wherein the heteroatom is selected from N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, thieno[2,3-d]thiazole, 1a,2,3,7b-tetrahydro-1H-cyclopropa[c][1,8]naphthyridine, 3H-indolyl, and derivatives thereof. Furthermore the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, isoindolyl and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_0$-$C_6$ alkylene. An alkylene may further be a $C_0$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" or "carbocyclyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" monocyclic or polycyclic rings containing carbon and heteroatoms taken from oxygen, nitrogen, or sulfur and wherein there is not delocalized π electrons (aromaticity) shared among the entire ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. As used herein, "heterocyclyl" and "heterocycloalkyl" also includes bridged and spirocyclic ring systems where at least one atom is a heteroatom. A heterocyclic ring as a substituent may attach via a ring heteroatom (e.g. "N-linked") or via a ring carbon (e.g. "C-linked").

The term "hydroxyalkyl" means an alkyl group as defined above, where the alkyl group is substituted with one or more OH groups. Examples of hydroxyalkyl groups include HO—$CH_2$—, HO—$CH_2$—$CH_2$—and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, e.g., C≡N.

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "cancer" includes, but is not limited to, the following cancers: bladder cancer, breast cancer (e.g., ductal carcinoma), cervical cancer (e.g., squamous cell carcinoma), colorectal cancer (e.g., adenocarcinoma), esophageal cancer (e.g., squamous cell carcinoma), gastric cancer (e.g.: adenocarcinoma, medulloblastoma, colon cancer, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hypereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian (e.g., adenocarcinoma), pancreatic cancer (e.g., ductal carcinoma), prostate cancer (e.g., adenocarcinoma), renal cancer (e.g., renal cell carcinoma, clear cell renal carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer.

The present disclosure relates to chemical entities chosen from compounds and pharmaceutically acceptable salts, solvates, prodrugs, stereoisomers, and tautomers thereof, capable of inhibiting at least one pathway chosen from USP28 and USP25, which are useful for the treatment of diseases and disorders associated with modulation of at least one pathway chosen from USP28 and USP25. The disclosure further relates to chemical entities chosen from compounds and pharmaceutically acceptable salts, solvates, prodrugs, stereoisomers, and tautomers thereof, which are useful for inhibiting at least one pathway chosen from USP28 and USP25.

In any of the embodiments as disclosed herein, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

The present disclosure relates to chemical entities chosen from compounds and pharmaceutically acceptable salts, solvates, prodrugs, stereoisomers, and tautomers thereof, capable of inhibiting at least one pathway chosen from USP28 and USP25, which are useful for the treatment of diseases and disorders associated with modulation of at least one pathway chosen from USP28 and/or USP25 enzyme. The present disclosure further relates to chemical entities chosen from compounds and pharmaceutically acceptable salts, solvates, prodrugs, stereoisomers, and tautomers thereof, which are useful for inhibiting at least one pathway chosen from USP28 and USP25.

In one embodiment, the chemical entities are chosen from compounds of Formula (II):

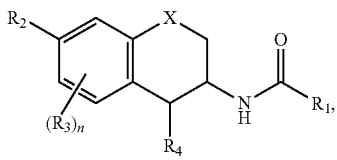

(II)

wherein X, Y, $R_1$, $R_2$, $R_3$, $R_4$, and n are as described herein above, and pharmaceutically acceptable salts, solvates, prodrugs, stereoisomers, and tautomers thereof.

In another embodiment, the chemical entities are chosen from compounds of Formula (III):

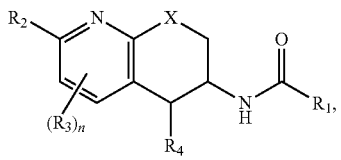

(III)

wherein X, Y, $R_1$, $R_2$, $R_3$, $R_4$, and n are as described herein above, and pharmaceutically acceptable salts, hydrates, solvates, prodrugs, stereoisomers, and tautomers thereof.

In another embodiment, the chemical entities are chosen from compounds of Formula (IV):

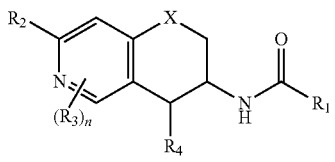

(IV)

wherein X, Y, $R_1$, $R_2$, $R_3$, $R_4$, and n are as described herein above and pharmaceutically acceptable salts, hydrates, solvates, prodrugs, stereoisomers, and tautomers thereof.

In another embodiment, the chemical entities are chosen from compounds of Formula (V):

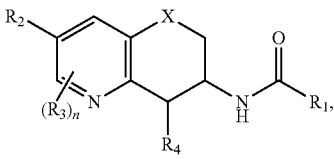

(V)

wherein X, Y, $R_1$, $R_2$, $R_3$, $R_4$, and n are as described herein above and pharmaceutically acceptable salts, hydrates, solvates, prodrugs, stereoisomers, and tautomers thereof.

In some embodiments, the chemical entities are chosen from compounds of Formula (VI):

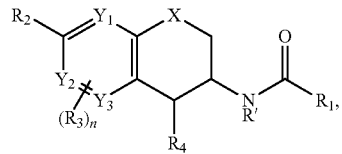

(VI)

or a pharmaceutically acceptable salt thereof,
wherein:
X is chosen from C(R)(R") and O;
each of $Y_1$, $Y_2$, and $Y_3$ is independently chosen from $C(R_3)$ and N;
R' is chosen from H, deuterium, and $CH_3$;
each of R and R" is independently chosen from H, halogen, —OH, —CN, $C_1$-$C_6$ alkyl optionally substituted with one or more Ri,
or R and R" together with the carbon they are attached form a spirocyclic cyclopropyl optionally substituted with one or more Ri, wherein any R, R", or Ri group being or containing hydrogen can independently have one or more hydrogen replaced with deuterium;
each Ri is independently chosen from halogen, —OH, and $CH_3$;
$R_1$ is chosen from 6-12 membered fused and nonfused heteroaryls optionally substituted with one or more substituent chosen from $R_5$ and/or $R_6$, and further wherein any $R_1$ group containing hydrogen can have one or more hydrogen replaced with deuterium;
$R_2$ is chosen from N-linked 4-12 membered heterocyclyls, C-linked 4-12 membered heterocyclyls, and an O linker attached to a 4-12 membered heterocyclyl, wherein the 4-12 membered heterocyclyls are optionally substituted with one or more $R_5$ (which can be the same or different from the one or more $R_5$ of $R_1$), and further wherein any hydrogen in a $R_2$ group can have one or more hydrogen replaced with deuterium;
each $R_3$ is independently chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, ($C_3$-$C_5$) cycloalkyl, heterocycloalkyl, aryl, and heteroaryl groups, wherein each of ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, aryl, and heteroaryl groups are optionally substituted with one or more $R_7$;
$R_4$ is chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, ($C_3$-$C_5$) cycloalkyl, heterocycloalkyl, aryl, and heteroaryl groups, wherein each of ($C_1$-$C_6$) alkyl, ($C_1$-$C_6$) alkoxy, ($C_1$-$C_6$) haloalkyl, ($C_1$-$C_6$) haloalkoxy, ($C_3$-$C_5$) cycloalkyl, heterocycloalkyl, aryl, and heteroaryl are optionally substituted with one or more $R_5$, and further wherein any $R_4$ group containing hydrogen can have one or more hydrogen replaced with deuterium;
each $R_5$ is independently chosen from —OH, —$NH_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)— heterocycloalkyl groups, wherein each of —$NH_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, —$NH_2$, and —OH, and wherein any $R_5$ group containing hydrogen can have one or more hydrogen replaced with deuterium;

each $R_6$ is independently chosen from -amino alkyl-aryls, -amino alkyl-heteroaryls, -amino alkyl-cyclyl, and -amino alkyl-heterocyclyl groups, wherein each of the $R_6$ groups are optionally substituted with one or more substituent chosen from —OH, —NH, halogen, ($C_1$-$C_6$) alkyl, ($C_1$-$C_6$) alkoxy, and ($C_1$-$C_6$) haloalkyl groups, and further wherein any $R_6$ group containing hydrogen can have one or more hydrogen replaced with deuterium;

each $R_7$ is independently chosen from —OH, —NH$_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl groups, wherein each of —NH$_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, and —OH; and n is 0, 1, 2, or 3.

The compound of Formula (VI) or a pharmaceutically acceptable salt thereof, wherein:

X is chosen from C(R)(R") and O;

each of $Y_1$, $Y_2$, and $Y_3$ is independently chosen from C($R_3$) and N; R' is chosen from H, and CH$_3$;

each of R and R" is independently chosen from H, halogens, —OH, —CN, $C_1$-$C_6$ alkyl optionally substituted with one or more Ri, or R and R" together with the carbon they are attached form a spirocyclic cycloalkyl (e.g., spirocyclic cyclopropyl) optionally substituted with one or more Ri, wherein any R, R";

each Ri is independently chosen from halogen, —OH, and CH$_3$;

$R_1$ is chosen from a fused or nonfused heteroaryls (e.g., 6-12 membered fused or nonfused heteroaryls) optionally substituted with one or more substituent chosen from $R_5$ and/or $R_6$ (e.g., a 6-membered nonfused heteroaryl optionally substituted with one or more $R_6$);

$R_2$ is chosen from N-linked-heterocyclyls (e.g., 4-12 membered heterocyclyls), C-linked-heterocyclyls (e.g., 4-12 membered heterocyclyls), and O-linker-heterocyclyls (e.g., 4-12 membered heterocyclyls such as

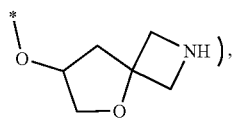

wherein any of the —N-linked-, —C-linked or —O-linked (e.g., 4-12 membered) heterocyclyls is optionally substituted with one or more $R_5$ (which can be the same or different from the one or more $R_5$ of $R_1$);

each $R_3$ is independently chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, ($C_3$-$C_5$) cycloalkyl, heterocycloalkyl, aryl, and heteroaryl groups, wherein each of ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, aryl, and heteroaryl groups are optionally substituted with one or more $R_7$;

$R_4$ is chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, ($C_3$-$C_8$) cycloalkyl, heterocycloalkyl, aryl, and heteroaryl groups, wherein each of ($C_1$-$C_6$) alkyl, ($C_1$-$C_6$) alkoxy, ($C_1$-$C_6$) haloalkyl, ($C_1$-$C_6$) haloalkoxy, ($C_3$-$C_5$) cycloalkyl, heterocycloalkyl, aryl, and heteroaryl are optionally substituted with one or more $R_5$;

each $R_5$ is independently chosen from —OH, —NH$_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)— heterocycloalkyl groups, wherein each of —NH$_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, —NH$_2$, and —OH;

each $R_6$ is independently chosen from -amino alkyl-aryls, -amino alkyl-heteroaryls, -amino alkyl-cyclyl, and -amino alkyl-heterocyclyl groups, wherein each of the $R_6$ groups are optionally substituted with one or more substituent chosen from —OH, —NH, halogen, ($C_1$-$C_6$) alkyl, ($C_1$-$C_6$) alkoxy, and ($C_1$-$C_6$) haloalkyl groups;

each $R_7$ is independently chosen from —OH, —NH$_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl groups, wherein each of —NH$_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, and —OH; and n is 0, 1, 2, or 3.

In some embodiments, a compound of Formula (I), Formula (II), Formula (III), Formula (IV), Formula (V) and/or Formula (VI) above includes X (if present) as CH$_2$ (e.g., R and R" are both hydrogen in Formula (VI)). In other embodiments, a compound of Formula (I), Formula (II), Formula (III), Formula (IV), Formula (V) and/or Formula (VI) above includes X (if present) as O.

In another embodiment, the chemical entities are chosen from compounds of Formula (VI) and pharmaceutically acceptable salts thereof, wherein:

X is chosen from C(R)(R") and O;

each of $Y_1$, $Y_2$, and $Y_3$ is independently chosen from C($R_3$) and N;

R' is chosen from H and CH$_3$;

each of R and R" is independently chosen from H, halogen, —OH, —CN, $C_1$-$C_6$ alkyl optionally substituted with one or more Ri;

each Ri is independently chosen from halogen, —OH, and CH$_3$;

$R_1$ is chosen from 6-12 membered fused and nonfused heteroaryls optionally substituted with one or more $R_5$, wherein a 6-membered nonfused heteroaryl is substituted with one or more $R_6$;

$R_2$ is chosen from N-linked and C-linked 4-12 membered heterocyclyls, wherein the 4-12 membered heterocyclyls are optionally substituted with one or more $R_5$ (which can be the same or different from the one or more $R_5$ of $R_1$);

each $R_3$ is independently chosen from H, ($C_1$-$C_6$) alkyl, ($C_1$-$C_6$) alkoxy, ($C_1$-$C_6$) haloalkyl, ($C_1$-$C_6$) haloalkoxy, halogen, —OH, and —CN, wherein each of ($C_1$-$C_6$)

alkyl, ($C_1$-$C_6$) alkoxy, ($C_1$-$C_6$) haloalkyl, and ($C_1$-$C_6$) haloalkoxy groups are optionally substituted with one or more $R_7$;

$R_4$ is chosen from H, ($C_1$-$C_6$) alkyl, halogen, —OH, and —CN, wherein the ($C_1$-$C_6$) alkyls are optionally substituted with one or more substituent independently chosen from ($C_1$-$C_6$) alkoxy and —OH;

each $R_5$ is independently chosen from —OH, —$NH_2$, —NHC(O)$CH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)-heterocycloalkyl groups, wherein alkyls are optionally substituted with one or more substituent independently chosen from ($C_1$-$C_6$) alkoxy, —$NH_2$, and —OH;

each $R_6$ is independently chosen from —NH($C_1$-$C_6$)alkyl-aryls, —NH($C_1$-$C_6$)alkyl-heteroaryls, —NH($C_1$-$C_6$)alkyl-cyclyl and —NH($C_1$-$C_6$)alkyl-heterocyclyl groups, wherein each of the $R_6$ groups are optionally substituted with one or more substituent chosen from —OH, —NH, halogens, ($C_1$-$C_6$) alkyl, ($C_1$-$C_6$) alkoxy, and ($C_1$-$C_6$) haloalkyl groups;

each $R_7$ is independently chosen from —OH, —$NH_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl groups, wherein the ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl groups are optionally substituted with one or more substituent independently chosen from ($C_1$-$C_6$) alkoxy and —OH; and n is 0, 1, 2, or 3.

In another embodiment, the chemical entities are chosen from compound of Formula (VII):

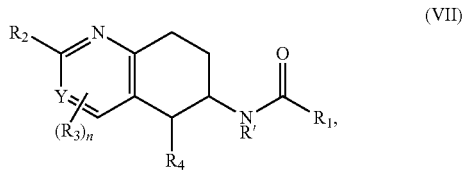

(VII)

or a pharmaceutically acceptable salt thereof, wherein
Y is chosen from C($R_3$) and N;
R' is chosen from H, deuterium, and $CH_3$;
$R_1$ is chosen from 6-11 membered heteroaryls optionally substituted with one or more substituent chosen from $R_5$ and/or $R_6$;
$R_2$ is chosen from N-linked 4-12 membered heterocyclyls and C-linked 4-12 membered heterocyclyls, wherein the heterocyclyls are optionally substituted with one or more $R_5$, and further wherein any $R_2$ group containing hydrogen can have one or more hydrogen replaced with deuterium;
each $R_3$ (if present) is independently chosen from H, deuterium, ($C_1$-$C_6$) alkyl, ($C_1$-$C_6$) alkoxy, ($C_1$-$C_6$) haloalkyl, ($C_1$-$C_6$) haloalkoxy, halogen, —OH, —CN, wherein each of ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, aryl, and heteroaryl groups are optionally substituted with one or more $R_7$;
each $R_4$ is chosen from H, deuterium, ($C_1$-$C_6$) alkyl, halogen, —OH, —CN, and further wherein any $R_4$ group containing hydrogen can have one or more hydrogen replaced with deuterium;

each $R_5$ (if present) is independently chosen from —OH, —$NH_2$, —NHC(O)$CH_3$, —C(O)NH$CH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)-heterocycloalkyl groups, wherein each of —$NH_2$, —NHC(O)$CH_3$, —C(O)NH$CH_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkoxy, —$NH_2$, and —OH, and wherein any $R_5$ group containing hydrogen can have one or more hydrogen replaced with deuterium;

each $R_6$ (if present) is chosen from —NH($C_1$-$C_6$)alkyl-aryls, —NH($C_1$-$C_6$)alkyl-heteroaryls, —NH($C_1$-$C_6$)alkyl-heterocyclyl groups, and —NH($C_1$-$C_6$)alkyl-heterocyclyl groups, wherein each of the $R_6$ groups are optionally substituted with one or more substituent chosen from —OH, —NH, halogens, ($C_1$-$C_6$) alkyl, ($C_1$-$C_6$) alkoxy, and ($C_1$-$C_6$) haloalkyl groups, and further wherein any $R_6$ group containing hydrogen can have one or more hydrogen replaced with deuterium;

each $R_7$ (if present) is independently chosen from —OH, —$NH_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)— heterocycloalkyl groups, wherein each of —$NH_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, and —OH; and n is 0, 1, 2, or 3.

In some embodiments, the compounds of Formula (VII) are chosen from compounds of Formula (VII'):

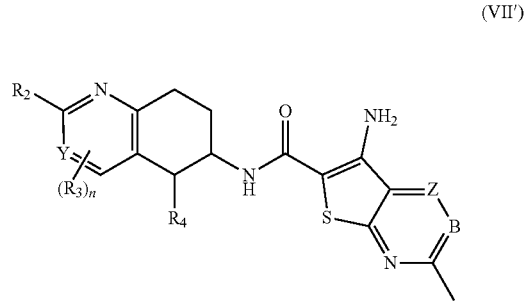

(VII')

wherein Y is chosen from C($R_3$) and N; $R_3$ is independently chosen from hydrogen and halogen; $R_4$ is chosen from H, deuterium, ($C_1$-$C_6$) alkyl, halogen, —OH, —CN, and further wherein any $R_4$ group containing hydrogen can have one or more hydrogen replaced with deuterium; B is chosen from a bond, N, or C($R^{b'}$); Z is chosen from N, S, C(R''); wherein $R^{b'}$ and $R^{z''}$ are each independently chosen from H and $R_{5'}$; $R_{5'}$ is each independently chosen from —$NH_2$, ($C_1$-$C_6$) alkyl, ($C_1$-$C_6$) haloalkyl, and halogen groups, $R_2$ is chosen from N-linked 5-8 membered mono- or bi-cyclic heterocyclyls substituted with one to three $R_5$; each $R_5$ is independently chosen from —OH, —$NH_2$, ($C_1$-$C_6$) alkyl, ($C_1$-$C_6$) alkoxy, ($C_1$-$C_6$) haloalkyl, N(CO)$CH_3$, ($C_1$-$C_6$) haloalkoxy, halogen, cycloalkyl, heterocycloalkyl, and —C(O)-heterocycloalkyl groups, wherein each of —NH$_2$, (C$_1$-C$_6$) alkyl, (C$_1$-C$_6$) alkoxy, (C$_1$-C$_6$) haloalkyl, N(CO)CH$_3$, (C$_1$-C$_6$) haloalkoxy, cycloalkyl, heterocycloalkyl, and —C(O)-heterocycloalkyl alkyls are optionally substituted with one or more substituent independently chosen from (C$_1$-C$_6$) alkoxy —NH$_2$, and —OH, and wherein any R$_5$ group containing hydrogen can have one or more hydrogens replaced with deuterium; and n is chosen from 0, 1, or 2.

In some embodiments, the compounds of Formula (VII), chosen from compounds of Formula (VII"):

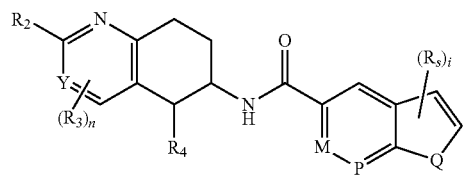

(VII")

wherein

Y is chosen from C(R$_3$) and N; R$_3$ is independently chosen from hydrogen and halogen; R$_4$ is chosen from H, deuterium, (C$_1$-C$_6$) alkyl, halogen, —OH, —CN, and further wherein any R$_4$ group containing hydrogen can have one or more hydrogen replaced with deuterium; M is chosen from N and C(R$_m$); P is chosen from N and C(R$_p$); Q is chosen from N(R$_q$"), S, or C(R$_q$); wherein R$_m$, R$_p$, and R$_q$, and R$_q$ are each independently chosen from hydrogen and R$_5$; each R$_5$, which, when present, can be attached at any portion of the fused ring system, is independently chosen from —NH$_2$, (C$_1$-C$_6$) alkyl, (C$_1$-C$_6$) haloalkyl, and halogen; s is chosen from 0, 1, 2, 3, 4, 5, or 6; R$_2$ is chosen from N-linked 5-8 membered mono- or bi-cyclic heterocyclyls substituted with one to three R$_5$; each R$_5$ is independently chosen from —OH, —NH$_2$, (C$_1$-C$_6$) alkyl, (C$_1$-C$_6$) alkoxy, (C$_1$-C$_6$) haloalkyl, —N(CO)CH$_3$, (C$_1$-C$_6$) haloalkoxy, halogen, cycloalkyl, heterocycloalkyl, and —C(O)— heterocycloalkyl groups, wherein each of —NH$_2$, (C$_1$-C$_6$) alkyl, (C$_1$-C$_6$) alkoxy, (C$_1$-C$_6$) haloalkyl, —N(CO)CH$_3$, —(C$_1$-C$_6$) haloalkoxy, cycloalkyl, heterocycloalkyl, and —C(O)-heterocycloalkyl alkyls are optionally substituted with one or more substituent independently chosen from (C$_1$-C$_6$) alkoxy —NH$_2$, and —OH, and wherein any R$_5$ group containing hydrogen can have one or more hydrogens replaced with deuterium; and n is chosen from 0, 1, or 2.

The present disclosure also provides compounds of Formula (VII'''):

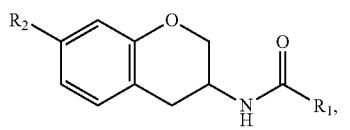

(VII''')

or a pharmaceutically acceptable form thereof, wherein R$_1$ is

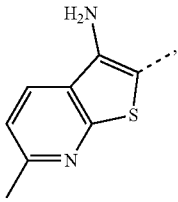

and R$_2$, is chosen from

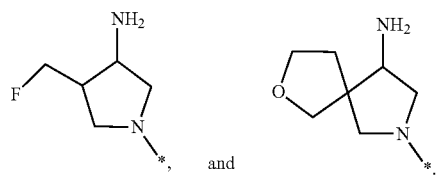

In some embodiments, the present disclosure provides compounds of Formula (VIII):

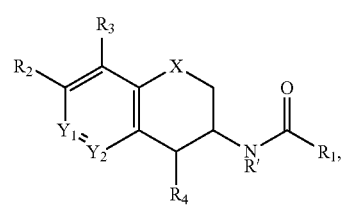

(VIII)

or pharmaceutically acceptable forms thereof, wherein: X is chosen from C(R)(R") and O; Y$_1$ is chosen from C(R$_3$·) and N; Y$_2$ is chosen from C(R$_3$·) and N; wherein Y$_1$ is C(Rr) when Y$_2$ is N, or Y$_2$ is C(R$_3$·) when Y$_1$ is N; each of R, R' and R" is chosen from H, and deuterium; R$_1$ is preferably chosen from a 8-10 membered fused heteroaryls comprising one or more N atoms and optionally substituted with one or more substituent chosen from halogen (preferably F or Cl), (C$_1$-C$_4$) alkyl (preferably methyl, or ethyl), (C$_3$) cycloalkyl (cyclopropyl or fused cyclopropyl), or an amine selected from the group —NH$_2$, —NHR$_{10}$ or NR$_{10}$R$_{10'}$, where R$_{10}$ and R$_{10'}$ are each independently (C$_1$-C$_4$) alkyl (preferably methyl); R$_2$ is preferably chosen from 5-8 member monocyclic or bicyclic N-linked-heterocycloalkyl moiety optionally bridged, and optionally substituted with one or more R$_5$, and optionally substituted with one or more an amine selected from the group NH$_2$, NHR$_{11}$ or NR$_{11}$R$_{11'}$, where R$_{11}$ and R$_{11'}$ are each independently (C$_1$-C$_4$) alkyl (preferably methyl), and wherein the R$_2$ 5-8 member monocyclic or bicyclic N-linked-heterocycloalkyl moiety preferably comprises at least 2 nitrogen heteroatoms or 1 nitrogen heteroatom and at least one amine substitution; R$_3$, R$_3$·, and R$_3$· are each independently chosen from H, (C$_1$-C$_6$) alkyl (preferably methyl), halogen (preferably —F or —Cl), and —CN; R$_4$ is chosen from H, (C$_1$-C$_6$) alkyl (preferably methyl), halogen, and further wherein any R$_4$ group containing hydrogen can have one or more hydrogen replaced with deuterium;

each $R_5$ is independently chosen from —OH, —NH$_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)— heterocycloalkyl groups, wherein each of —NH$_2$, amido-($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkyl, ($C_1$-$C_6$) alkoxy, —NH$_2$, and —OH, and wherein any $R_5$ group containing hydrogen can have one or more hydrogen replaced with deuterium;

each $R_6$ is independently chosen from -amino alkyl-aryls, -amino alkyl-heteroaryls, -amino alkyl-cyclyl, and -amino alkyl-heterocyclyl groups, wherein each of the R groups are optionally substituted with one or more substituent chosen from —OH, —NH, halogens, ($C_1$-$C_6$) alkyl, ($C_1$-$C_6$) alkoxy, and ($C_1$-$C_6$) haloalkyl groups, and further wherein any $R_6$ group containing hydrogen can have one or more hydrogen replaced with deuterium;

provided that the compounds of Formula (VIII) are not chosen from the compounds of Table C found in FIG. 1.

In some embodiments, the substituents of Formula (VIII) are defined as in Formula (VI).

In some embodiments, the $R_1$ and $R_2$ groups of Formula (VIII) are selected from Tables A and B, respectively.

In some embodiments of Formula (VIII), the compounds can be chosen from compounds of Formula (I'):

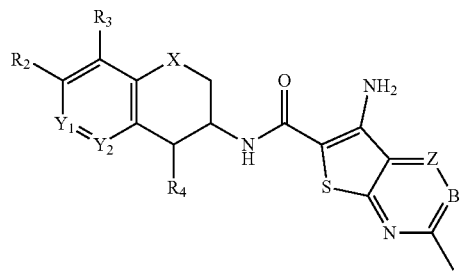

(VIII')

and pharmaceutically acceptable forms thereof, wherein
X is chosen from C(R)(R") and O; each of R and R" is independently chosen from H, halogen, —OH, —CN, $C_1$-$C_6$ alkyl optionally substituted with one or more Ri; each Ri is independently chosen from halogen, —OH, and —CH$_3$; $Y_1$ is chosen from C($R_3$') and N; $Y_2$ is chosen from C($R_3$") and N; $R_3$, $R_3$', and $R_3$" are each independently chosen from H, ($C_1$-$C_6$) alkyl, ($C_1$-$C_6$) haloalkyl, halogen, —OH, —CN, wherein each of ($C_1$-$C_6$) alkyl and ($C_1$-$C_6$) haloalkyl groups are optionally substituted with one or more $R_7$; $R_4$ is chosen from H, deuterium, ($C_1$-$C_6$) alkyl, halogen, —OH, —CN, and further wherein any $R_4$ group containing hydrogen can have one or more hydrogen replaced with deuterium, B is chosen from a bond, N, or C(R'); Z is chosen from N, S, C($R^{z'}$),wherein $R^{b'}$ and $R^{z''}$ are each independently chosen from H and $R_5$;

$R_{5'}$ is each independently chosen from —NH$_2$, ($C_1$-$C_6$) alkyl, ($C_1$-$C_6$) haloalkyl, and halogen, $R_2$ is chosen from N-linked 5-8 membered mono- or bi-cyclic heterocyclyls substituted with one to three $R_5$;

each $R_5$ is independently chosen from —OH, —NH$_2$, ($C_1$-$C_6$) alkyl, ($C_1$-$C_6$) alkoxy, ($C_1$-$C_6$) haloalkyl, N(CO)CH$_3$, ($C_1$-$C_6$) haloalkoxy, halogen, cycloalkyl, heterocycloalkyl, and —C(O)-heterocycloalkyl groups, wherein each of —NH$_2$, ($C_1$-$C_6$) alkyl, ($C_1$-$C_6$) alkoxy, ($C_1$-$C_6$) haloalkyl, N(CO)CH$_3$, ($C_1$-$C_6$) haloalkoxy, cycloalkyl, heterocycloalkyl, and —C(O)-heterocycloalkyl alkyls are optionally substituted with one or more substituent independently chosen from ($C_1$-$C_6$) alkoxy —NH$_2$, and —OH, and wherein any $R_5$ group containing hydrogen can have one or more hydrogens replaced with deuterium; and provided that the compounds of Formula (VII') are not chosen from the compounds of Table C found in FIG. 1.

Preferably, $R_2$ in Formula (VIII') is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —NH$_2$, —NHR$_{11}$ or —NR$_{11}$R$_{11'}$, where $R_{11}$ and $R_{11'}$ are each independently ($C_1$-$C_4$) alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of Formula (VIII), the compounds can be chosen from compounds of Formula (VIII"

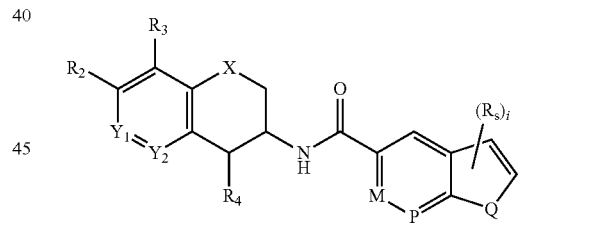

(VIII")

and pharmaceutically acceptable forms thereof, wherein
X is chosen from C(R)(R") and O;
each of R and R" is independently chosen from H, halogen, —OH, —CN, $C_1$-$C_6$ alkyl optionally substituted with one or more Ri; each Ri is independently chosen from halogen, —OH, and CH$_3$; $Y_1$ is chosen from C($R_3$) and N; $Y_2$ is chosen from C($R_3$") and N;

$R_3$, $R_3$', and $R_3$" are each independently chosen from H, ($C_1$-$C_6$) alkyl, ($C_1$-$C_6$) haloalkyl, halogen, —OH, —CN, wherein each of ($C_1$-$C_6$) alkyl and ($C_1$-$C_6$) haloalkyl groups are optionally substituted with one or more $R_7$;

$R_4$ is chosen from H, deuterium, ($C_1$-$C_6$) alkyl, halogen, —OH, —CN, and further wherein any $R_4$ group containing hydrogen can have one or more hydrogen replaced with deuterium, M is chosen from N and C($R_m$); P is chosen from N and C($R_p$); Q is chosen from N($R_q$'), S, or C($R_q$);

wherein $R_m$, $R_p$, and $R_q'$, and $R_q$ are each independently chosen from hydrogen and $R_6$;

each $R_s$, which, when present, can be attached at any portion of the fused ring system, is independently chosen from —NH$_2$, (C$_1$-C$_6$) alkyl, (C$_1$-C$_6$) haloalkyl, and halogen;

i is chosen from 0, 1, 2, 3, 4, 5, or 6;

$R_2$ is chosen from N-linked 5-8 membered mono- or bi-cyclic heterocyclyls substituted with one to three $R_5$;

each $R_5$ is independently chosen from —OH, —NH$_2$, (C$_1$-C$_6$) alkyl, (C$_1$-C$_6$) alkoxy, (C$_1$-C$_6$) haloalkyl, N(CO)CH$_3$, (C$_1$-C$_6$) haloalkoxy, halogen, cycloalkyl, heterocycloalkyl, and —C(O)-heterocycloalkyl groups, wherein each of —NH$_2$, (C$_1$-C$_6$) alkyl, (C$_1$-C$_6$) alkoxy, (C$_1$-C$_6$) haloalkyl, N(CO)CH$_3$, (C$_1$-C$_6$) haloalkoxy, cycloalkyl, heterocycloalkyl, and —C(O)-heterocycloalkyl alkyls are optionally substituted with one or more substituent independently chosen from (C$_1$-C$_6$) alkoxy —NH$_2$, and —OH, and wherein any $R_5$ group containing hydrogen can have one or more hydrogens replaced with deuterium;

provided that the compounds of Formula (VIII") are not chosen from the compounds of Table C found in FIG. 1.

Preferably, $R_2$ in Formula (VIIII") is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —NH$_2$, —NHR$_{11}$ or —NR$_{11}$R$_{11'}$, where $R_{11}$ and $R_{11'}$ are each independently (C$_1$-C$_4$) alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments, the compounds of Formula (VIII) can be chosen from compounds of Formula (IX):

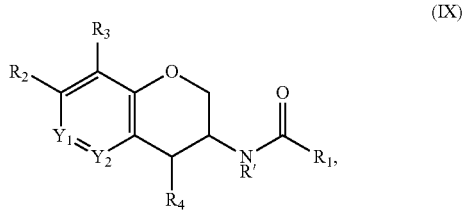

(IX)

and pharmaceutically acceptable forms thereof, wherein $Y_1$, $Y_2$, R', $R_1$, $R_2$, $R_3$, $R_{3'}$, $R_{3''}$, $R_4$, $R_5$, $R_6$, and $R_7$ are all as defined for Formula (VIII), and provided that the compounds of Formula (II) are not chosen from the compounds of Table C found in FIG. 1.

In some embodiments of Formula (IX), $Y_1$ is chosen from C(R$_{3'}$) and N; $Y_2$ is chosen from C(R$_{3'}$) and N; R' is chosen from H and deuterium; $R_1$ is chosen from 6-11 membered heteroaryls optionally substituted with one or more substituent chosen from $R_5$ and/or $R_6$; $R_2$ is chosen from N-linked 4-12 membered heterocyclyls and C-linked 4-12 membered heterocyclyls, wherein the heterocyclyls are optionally substituted with one or more $R_5$, and further wherein any $R_2$ group containing hydrogen can have one or more hydrogen replaced with deuterium; $R_3$, $R_3'$, and $R_3''$ are each independently chosen from H, deuterium, (C$_1$-C$_6$) alkyl, (C$_1$-C$_6$) haloalkyl, halogen, —OH, —CN, wherein each of (C$_1$-C$_6$) alkyl, and (C$_1$-C$_6$) haloalkyl groups are optionally substituted with one or more $R_7$; each $R_4$ is chosen from H and deuterium; each $R_5$ (if present) is independently chosen from —OH, —NH$_2$, NHC(O)CH$_3$, —C(O)NHCH$_3$, (C$_1$-C$_6$) alkyl, (C$_1$-C$_6$) alkoxy, (C$_1$-C$_6$) haloalkyl, (C$_1$-C$_6$) haloalkoxy, halogen, cycloalkyl, heterocycloalkyl, and —C(O)-heterocycloalkyl groups, wherein each of —NH$_2$, —NHC(O)CH$_3$, —C(O)NHCH$_3$, (C$_1$-C$_6$) alkyl, (C$_1$-C$_6$) alkoxy, (C$_1$-C$_6$) haloalkyl, (C$_1$-C$_6$) haloalkoxy, cycloalkyl, heterocycloalkyl, and —C(O)-heterocycloalkyl are optionally substituted with one or more substituent independently chosen from (C$_1$-C$_6$) alkoxy, —NH$_2$, and —OH, and wherein any $R_5$ group containing hydrogen can have one or more hydrogen replaced with deuterium; each $R_6$ (if present) is independently chosen from —NH(C$_1$-C$_6$)alkyl-aryls, —NH(C$_1$-C$_6$)alkyl-heteroaryls, —NH(C$_1$-C$_6$)alkyl-heterocyclyl groups, and —NH(C$_1$-C$_6$)alkyl-heterocyclyl groups, wherein each of the $R_6$ groups are optionally substituted with one or more substituent chosen from —OH, —NH, halogen, (C$_1$-C$_6$) alkyl, (C$_1$-C$_6$) alkoxy, and (C$_1$-C$_6$) haloalkyl groups, and further wherein any $R_6$ group containing hydrogen can have one or more hydrogen replaced with deuterium; and each $R_7$ (if present) is independently chosen from —OH, —NH$_2$, (C$_1$-C$_6$) alkyl, (C$_1$-C$_6$) alkoxy, (C$_1$-C$_6$) haloalkyl, (C$_1$-C$_6$) haloalkoxy, halogen, cycloalkyl, —C(O)-cycloalkyl, heterocycloalkyl, and —C(O)-heterocycloalkyl groups, wherein each of —NH$_2$, (C$_1$-C$_6$) alkyl, (C$_1$-C$_6$) alkoxy, (C$_1$-C$_6$) haloalkyl, (C$_1$-C$_6$) haloalkoxy, halogen, cycloalkyl, —C(O)-cycloalkyl, heterocycloalkyl, and —C(O)-heterocycloalkyl are optionally substituted with one or more substituent independently chosen from (C$_1$-C$_6$) alkyl, (C$_1$-C$_6$) alkoxy, and —OH.

In some embodiments of Formula (IX), $Y_1$ is chosen from C(R$_{3'}$); $Y_2$ is chosen from C(R$_{3''}$); R' is chosen from H and deuterium; $R_1$ is chosen from the groups of Table A; $R_2$ is chosen from the groups of Table B; $R_3$ is chosen from H, deuterium, (C$_1$-C$_6$) alkyl, (C$_1$-C$_6$) haloalkyl, halogen, and —CN, wherein each of the (C$_1$-C$_6$) alkyl, and (C$_1$-C$_6$) haloalkyl groups are optionally substituted with one or more $R_7$; $R_3'$ is chosen from H, deuterium, and halogen; Rr is chosen from H, deuterium, (C$_1$-C$_6$) alkyl, (C$_1$-C$_6$) haloalkyl, halogen, and —CN, wherein each of the (C$_1$-C$_6$) alkyl, and (C$_1$-C$_6$) haloalkyl groups are optionally substituted with one or more $R_7$; $R_1$ is hydrogen.

Preferably, $R_1$ in Formula (IX) is a 8-, 9- or 10-member fused bicyclic heteroaryl group containing at least one nitrogen atom and one or more additional heteroatoms selected from nitrogen, sulfur and oxygen, and optionally substituted with (C$_1$-C$_4$) alkyl, halogen (preferably Cl or F) or an amine (e.g., —NH$_2$, or a secondary or tertiary amine substituted with one or more alkyl or haloalkyl moieties). Preferably, $R_1$ is selected from the group consisting of:

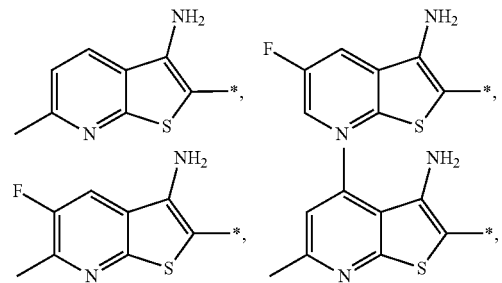

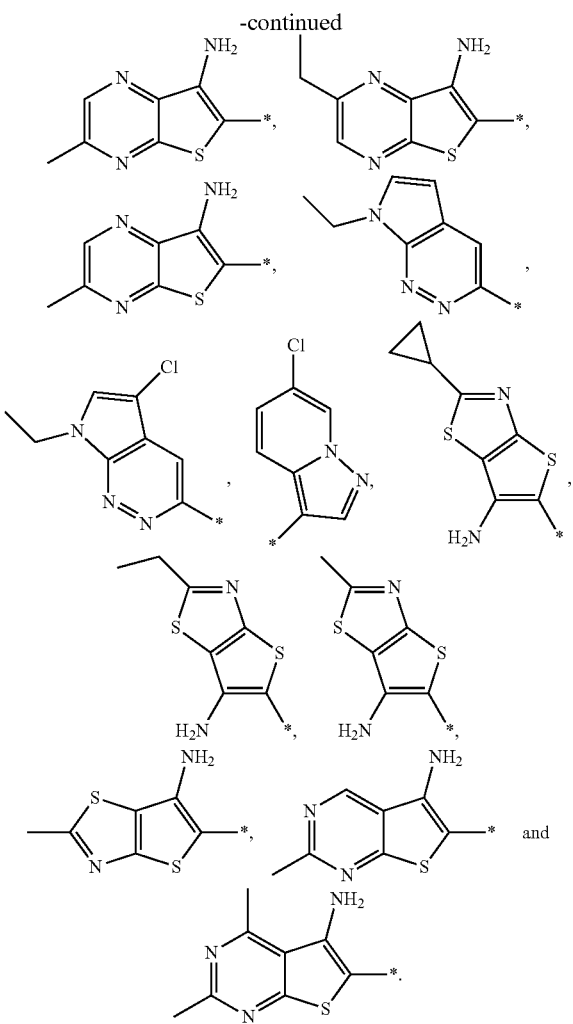

Alternatively, $R_1$ in Formula (IX) can be a 5-6 member heteroaryl group fused to a 3-6 member heterocycloalkyl or cycloalkyl group, which may itself be substituted to a fused or spirocyclic 3-6 member heterocycloalkyl or cycloalkyl group (e.g., preferably a 6 member heteroaryl group fused to a 6 member heterocycloalkyl moiety that is optionally substituted with a spirocyclic or fused cyclobutyl moiety). In some embodiments, $R_1$ is selected from the group consisting of:

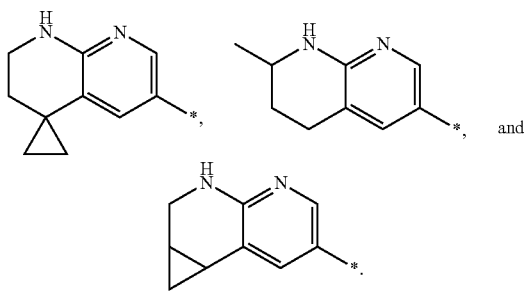

Preferably, $R_2$ in Formula (IX) is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group $NH_2$, $NHR_{11}$ or $NR_{11}R_{11'}$, where $R_{11}$ and $R_{11'}$ are each independently ($C_1$-$C_4$) alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of Formula (IX), the compounds can be chosen from compounds of Formula (IX'):

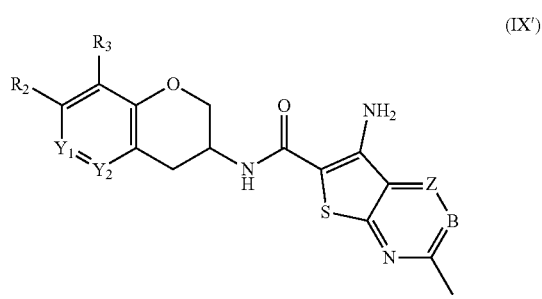

(IX')

and pharmaceutically acceptable forms thereof, wherein $Y_1$ is chosen from $C(R_3')$ and N; $Y_2$ is chosen from $C(R_3'')$ and N; $R_3$, $R_3'$, and $R_3'''$ are each independently chosen from H, ($C_1$-$C_6$) alkyl, ($C_1$-$C_6$) haloalkyl, halogen, —OH, —CN, wherein each of ($C_1$-$C_6$) alkyl and ($C_1$-$C_6$) haloalkyl groups are optionally substituted with one or more $R_7$, B is chosen from a bond, N, or $C(R_b')$; Z is chosen from N, S, $C(R_z')$ wherein $R_b'$ and $R_z'$ are each independently chosen from H and $R_5'$; $R_5'$ is each independently chosen from —$NH_2$, ($C_1$-$C_6$) alkyl, ($C_1$-$C_6$) haloalkyl, and halogen groups; $R_2$ is chosen from N-linked 5-8 membered mono- or bi-cyclic heterocyclyls substituted with one to three $R_5$; each $R_5$ is independently chosen from —OH, —$NH_2$, ($C_1$-$C_6$) alkyl, ($C_1$-$C_6$) alkoxy, ($C_1$-$C_6$) haloalkyl, —N(CO)$CH_3$, ($C_1$-$C_6$) haloalkoxy, halogen, cycloalkyl, heterocycloalkyl, and —C(O)-heterocycloalkyl groups, wherein each of —$NH_2$, ($C_1$-$C_6$) alkyl, ($C_1$-$C_6$) alkoxy, ($C_1$-$C_6$) haloalkyl, N(CO)$CH_3$, ($C_1$-$C_6$) haloalkoxy, cycloalkyl, heterocycloalkyl, and —C(O)-heterocycloalkyl alkyls are optionally substituted with one or more substituent independently chosen from ($C_1$-$C_6$) alkoxy-$NH_2$, and —OH, and wherein any $R_5$ group containing hydrogen can have one or more hydrogens replaced with deuterium; and provided that the compounds of Formula (IX') are not chosen from the compounds of Table C found in FIG. 1.

Preferably, $R_2$ in Formula (IX') is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —$NH_2$, —$NHR_{11}$ or —$NR_{11}R_{11'}$, where $R_{11}$ and $R_{11'}$ are each independently ($C_1$-$C_4$) alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of Formula (II), the compounds can be chosen from compounds of Formula (IX"):

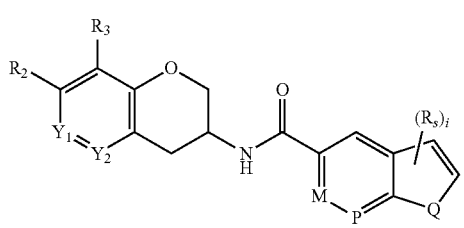

(IX")

and pharmaceutically acceptable forms thereof, wherein $Y_1$ is chosen from $C(R_3')$ and N; $Y_2$ is chosen from $C(R_3")$ and N; $R_3$, $R_3'$, and $R_3"$ are each independently chosen from H, $(C_1-C_6)$ alkyl, $(C_1-C_6)$ haloalkyl, halogen, —OH, —CN, wherein each of $(C_1-C_6)$ alkyl and $(C_1-C_6)$ haloalkyl groups are optionally substituted with one or more $R_7$; M is chosen from N and $C(R_m)$; P is chosen from N and $C(R_p)$; Q is chosen from $N(R_q')$, S, or $C(R_q)$; wherein $R_m$, $R_p$, and $R_q'$, and $R_q$ are each independently chosen from hydrogen and $R_s$; each $R_s$, which, when present, can be attached at any portion of the fused ring system, is independently chosen from —$NH_2$, $(C_1-C_6)$ alkyl, $(C_1-C_6)$ haloalkyl, and halogen; i is chosen from 0, 1, 2, 3, 4, 5, or 6; $R_2$ is chosen from N-linked 5-8 membered mono- or bi-cyclic heterocyclyls substituted with one to three $R_5$; each $R_5$ is independently chosen from —OH, —$NH_2$, $(C_1-C_6)$ alkyl, $(C_1-C_6)$ alkoxy, $(C_1-C_6)$ haloalkyl, —N(CO)$CH_3$, $(C_1-C_6)$ haloalkoxy, halogen, cycloalkyl, heterocycloalkyl, and —C(O)-heterocycloalkyl groups, wherein each of —$NH_2$, $(C_1-C_6)$ alkyl, $(C_1-C_6)$ alkoxy, $(C_1-C_6)$ haloalkyl, —N(CO)$CH_3$, $(C_1-C_6)$ haloalkoxy, cycloalkyl, heterocycloalkyl, and —C(O)-heterocycloalkyl alkyls are optionally substituted with one or more substituent independently chosen from $(C_1-C_6)$ alkoxy —$NH_2$, and —OH, and wherein any $R_5$ group containing hydrogen can have one or more hydrogens replaced with deuterium; and provided that the compounds of Formula (IX") are not chosen from the compounds of Table C found in FIG. 1.

Preferably, $R_2$ in Formula (IX") is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —$NH_2$, —$NHR_{11}$ or —$NR_{11}R_{11'}$, where $R_{11}$ and $R_{11'}$ are each independently $(C_1-C_4)$ alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of Formula (IX), the compounds can be chosen from compounds of Formula (IX'''):

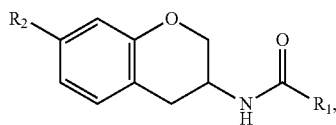

(IX''')

or a pharmaceutically acceptable form thereof, wherein $R_1$ is,

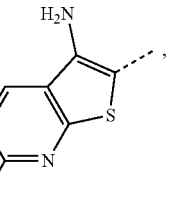

and $R_2$ is chosen from

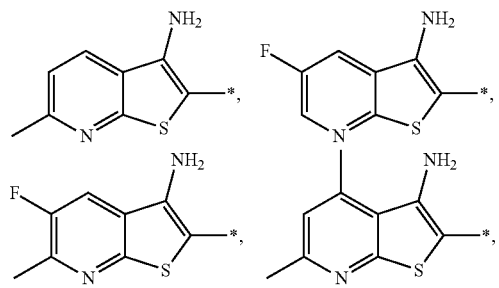

*, and *.

In some embodiments, the compounds of Formula (VIII) can be chosen from compounds of Formula (X):

(X)

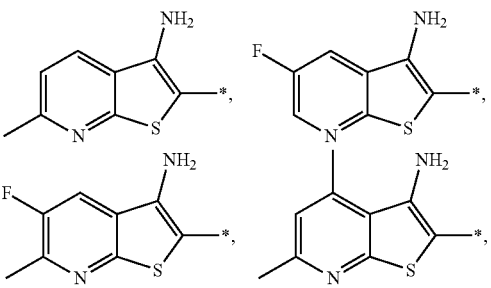

or a pharmaceutically acceptable form thereof, wherein $Y_1$, $Y_2$, R', $R_1$, $R_2$, $R_3$, $R_3$, $R_3$, $R_4$, $R_5$, $R_6$, and R; are all as defined for Formula (VIII), and provided that the compounds of Formula (X) are not a compound from Table C of FIG. 1.

Preferably, $R_1$ in Formula (X) is a 8-, 9- or 10-member fused bicyclic heteroaryl group containing at least one nitrogen atom and one or more additional heteroatoms selected from nitrogen, sulfur and oxygen, and optionally substituted with $(C_1-C_4)$ alkyl, halogen (preferably Cl or F) or an amine (e.g., $NH_2$, or a secondary or tertiary amine substituted with one or more alkyl or haloalkyl moieties). Preferably, $R_1$ in Formula (III) is selected from the group consisting of:

-continued

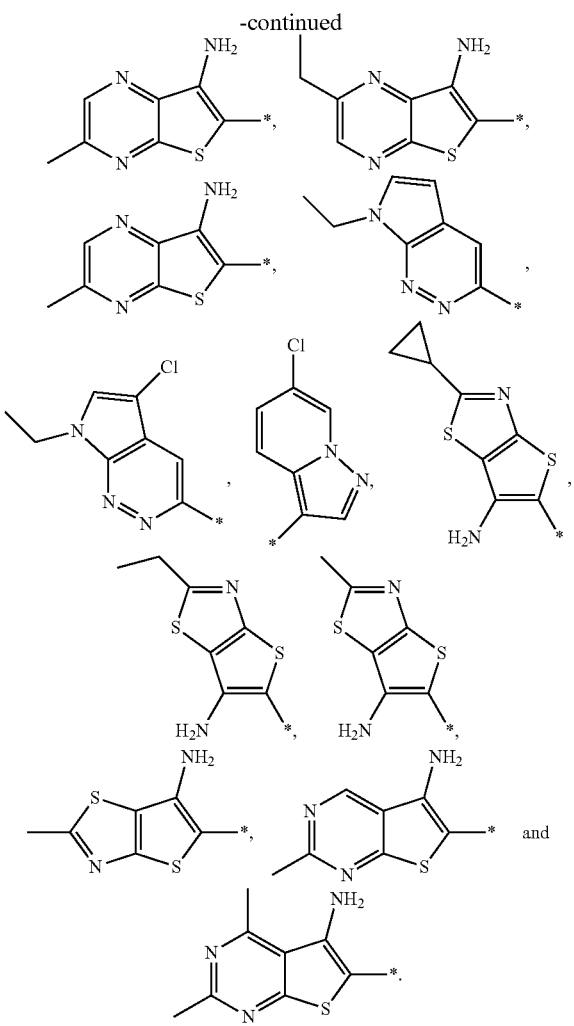

Alternatively, $R_1$ in Formula (X) can be a 5-6 member heteroaryl group fused to a 3-6 member heterocycloalkyl or cycloalkyl group, which may itself be substituted to a fused or spirocyclic 3-6 member heterocycloalkyl or cycloalkyl group (e.g., preferably a 6 member heteroaryl group fused to a 6 member heterocycloalkyl moiety that is optionally substituted with a spirocyclic or fused cyclobutyl moiety). In some embodiments, $R_1$ is selected from the group consisting of:

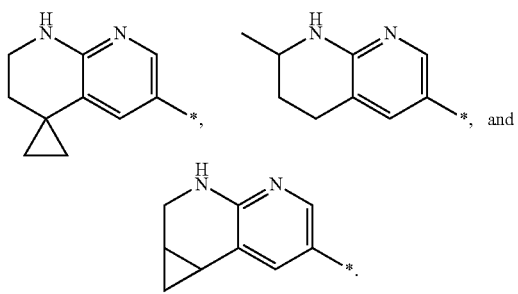

Preferably, $R_2$ in Formula (X) is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —$NH_2$, —$NHR_{11}$ or —$NR_{11}R_{11'}$, where $R_{11}$ and $R_{11'}$ are each independently ($C_1$-$C_4$) alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of Formula (X), $Y_1$ is chosen from $C(R_{3'})$ and N; $Y_2$ is chosen from $C(R_{3''})$ and N; R' is chosen from H and deuterium; $R_1$ is chosen from 6-11 membered heteroaryls optionally substituted with one or more substituent chosen from $R_5$ and/or $R_6$; $R_2$ is chosen from N-linked 4-12 membered heterocyclyls and C-linked 4-12 membered heterocyclyls, wherein the heterocyclyls are optionally substituted with one or more $R_5$, and further wherein any $R_2$ group containing hydrogen can have one or more hydrogen replaced with deuterium; $R_3$, $R_{3'}$, and $R_{3''}$ are each independently chosen from H, deuterium, ($C_1$-$C_6$) alkyl, ($C_1$-$C_6$) haloalkyl, halogen, —OH, —CN, wherein each of ($C_1$-$C_6$) alkyl, and ($C_1$-$C_6$) haloalkyl groups are optionally substituted with one or more $R_7$; $R_4$ is chosen from H and deuterium; each $R_5$ (if present) is independently chosen from —OH, —$NH_2$, —$NHC(O)CH_3$, —$C(O)NHCH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)-heterocycloalkyl groups, wherein each of —$NH_2$, —$NHC(O)CH_3$, —$C(O)NHCH_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkoxy, —$NH_2$, and —OH, and wherein any $R_5$ group containing hydrogen can have one or more hydrogen replaced with deuterium; each $R_6$ (if present) is independently chosen from —NH($C_1$-$C_6$)alkyl-aryls, —NH($C_1$-$C_6$)alkyl-heteroaryls, —NH($C_1$-$C_6$)alkyl-heterocyclyl groups, and —NH($C_1$-$C_6$)alkyl-heterocyclyl groups, wherein each of the $R_6$ groups are optionally substituted with one or more substituent chosen from —OH, —NH, halogen, ($C_1$-$C_6$) alkyl, ($C_1$-$C_6$) alkoxy, and ($C_1$-$C_6$) haloalkyl groups, and further wherein any $R_6$ group containing hydrogen can have one or more hydrogen replaced with deuterium; each $R_7$ (if present) is independently chosen from —OH, —$NH_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)-heterocycloalkyl groups, wherein each of —$NH_2$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, —C(O)-cycloalkyl, heterocycloalkyl, and —C(O)— heterocycloalkyl are optionally substituted with one or more substituent independently chosen from ($C_1$-$C_6$) alkyl, ($C_1$-$C_6$) alkoxy, and —OH; and provided that the compounds of Formula (X) are not chosen from the compounds of Table C found in FIG. 1.

In some embodiments of Formula (X), $Y_1$ is chosen from $C(R_3)$; $Y_2$ is chosen from $C(R_3)$; R' is chosen from H and deuterium; $R_1$ is chosen from the groups of Table A; $R_2$ is chosen from the groups of Table B; $R_3$ is chosen from H, deuterium, ($C_1$-$C_6$) alkyl, ($C_1$-$C_6$) haloalkyl, halogen, and —CN, wherein each of the ($C_1$-$C_6$) alkyl, and ($C_1$-$C_6$) haloalkyl groups are optionally substituted with one or more $R_7$; $R_{3'}$ is chosen from H, deuterium, and halogen; $R_3$, is chosen from H, deuterium, ($C_1$-$C_6$) alkyl, ($C_1$-$C_6$) haloalkyl, halogen, and —CN, wherein each of the ($C_1$-$C_6$) alkyl, and $(C_1-C_6)$ haloalkyl groups are optionally substituted with one or more $R_7$; $R_4$ is hydrogen; and provided that the compounds of Formula (X) are not chosen from the compounds of Table C found in FIG. 1.

In some embodiments of Formula (X), the compounds can be chosen from compounds of Formula (X'):

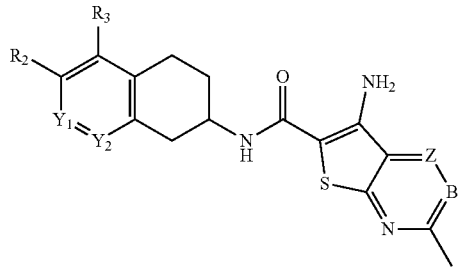

(X')

and pharmaceutically acceptable forms thereof, wherein
$Y_1$ is chosen from $C(R_3)$ and N; $Y_2$ is chosen from $C(Rr)$ and N;
$R_3$, $R_{3'}$, and $R_{3''}$ are each independently chosen from H, $(C_1-C_6)$ alkyl, $(C_1-C_6)$ haloalkyl, halogen, —OH, —CN, wherein each of $(C_1-C_6)$ alkyl and $(C_1-C_6)$ haloalkyl groups are optionally substituted with one or more $R_7$;
B is chosen from a bond, N, or $C(R^{b'})$; Z is chosen from N, S, $C(R^{z'})$ wherein $R^{b'}$ and $R^{z'}$ are each independently chosen from H and $R_5$;
$R_5$ is each independently chosen from —$NH_2$, $(C_1-C_6)$ alkyl, $(C_1-C_6)$ haloalkyl, and halogen groups;
$R_2$ is chosen from N-linked 5-8 membered mono- or bi-cyclic heterocyclyls substituted with one to three $R_5$;
each $R_5$ is independently chosen from —OH, —$NH_2$, $(C_1-C_6)$ alkyl, $(C_1-C_6)$ alkoxy, $(C_1-C_6)$ haloalkyl, $N(CO)CH_3$, $(C_1-C_6)$ haloalkoxy, halogen, cycloalkyl, heterocycloalkyl, and —C(O)-heterocycloalkyl groups, wherein each of —$NH_2$, $(C_1-C_6)$ alkyl, $(C_1-C_6)$ alkoxy, $(C_1-C_6)$ haloalkyl, —$N(CO)CH_3$, —$(C_1-C_6)$ haloalkoxy, cycloalkyl, heterocycloalkyl, and —C(O)-heterocycloalkyl alkyls are optionally substituted with one or more substituent independently chosen from $(C_1-C_6)$ alkoxy —$NH_2$, and —OH, and wherein any $R_5$ group containing hydrogen can have one or more hydrogens replaced with deuterium; and
provided that the compounds of Formula (X') are not chosen from the compounds of Table C found in FIG. 1.

Preferably, $R_2$ in Formula (X') is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —$NH_2$, —$NHR_{11}$ or —$NR_{11}R_{11'}$, where $R_{11}$ and $R_{11'}$ are each independently $(C_1-C_4)$ alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of Formula (X), the compounds can be chosen from compounds of Formula (X''):

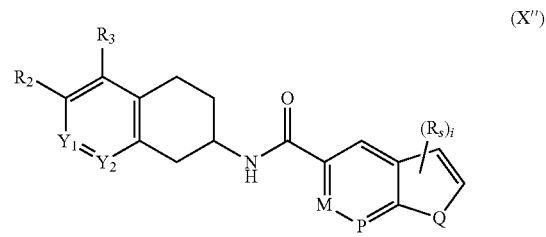

(X'')

an pharmaceutically acceptable forms thereof, wherein
$Y_1$ is chosen from $C(Ry)$; $Y_2$ is chosen from $C(R_{3''})$;
$R_3$, $R_{3'}$, and $R_{3''}$ are each independently chosen from H, $(C_1-C_6)$ alkyl, $(C_1-C_6)$ haloalkyl, halogen, —OH, —CN, wherein each of $(C_1-C_6)$ alkyl and $(C_1-C_6)$ haloalkyl groups are optionally substituted with one or more $R_7$;
M is chosen from N and $C(R_m)$;
P is chosen from N and $C(R_p)$;
Q is chosen from $N(R_{q'})$, S, or $C(R_q)$;
wherein $R_m$, $R_p$, and $R_{q'}$, and $R_q$ are each independently chosen from hydrogen and $R_s$;
each Rs, which, when present, can be attached at any portion of the fused ring system, is independently chosen from —$NH_2$, $(C_1-C_6)$ alkyl, $(C_1-C_6)$ haloalkyl, and halogen;
i is chosen from 0, 1, 2, 3, 4, 5, or 6;
$R_2$ is chosen from N-linked 5-8 membered mono- or bi-cyclic heterocyclyls substituted with one to three $R_5$;
each $R_5$ is independently chosen from —OH, —$NH_2$, $(C_1-C_6)$ alkyl, $(C_1-C_6)$ alkoxy, $(C_1-C_6)$ haloalkyl, —$N(CO)CH_3$, —$(C_1-C_6)$ haloalkoxy, halogen, cycloalkyl, heterocycloalkyl, and —C(O)-heterocycloalkyl groups, wherein each of —$NH_2$, $(C_1-C_6)$ alkyl, $(C_1-C_6)$ alkoxy, $(C_1-C_6)$ haloalkyl, —$N(CO)CH_3$, $(C_1-C_6)$ haloalkoxy, cycloalkyl, heterocycloalkyl, and —C(O)-heterocycloalkyl alkyls are optionally substituted with one or more substituent independently chosen from $(C_1-C_6)$ alkoxy —$NH_2$, and —OH, and wherein any $R_5$ group containing hydrogen can have one or more hydrogens replaced with deuterium;
provided that the compounds of Formula (X'') are not chosen from the compounds of Table C found in FIG. 1.

Preferably, $R_2$ in Formula (X'') is a 5-8 member monocyclic or bicyclic N-linked heterocycloalkyl, heteroaryl or fused heterocycloalkyl-heteroaryl moiety that either contains a second nitrogen heteroatom or is substituted with an amine moiety selected from the group —$NH_2$, $NHR_{11}$ or $NR_{11}R_{11'}$, where $R_{11}$ and $R_{11'}$ are each independently $(C_1-C_4)$ alkyl (preferably methyl). The $R_2$ moiety preferably comprises at least 2 nitrogen heteroatoms or 1 nitrogen heteroatom and at least one amine substitution. $R_2$ can be a monocyclic or bicyclic (e.g., bridged, fused or spirocyclic) cycloheteroalkyl structure. $R_2$ can be a N-linked 5-, 6-, or 7-member monocyclic N-linked-heterocycloalkyl moiety that contains at least two nitrogen atoms. In any case, $R_2$ can be further optionally substituted with additional moieties, as indicated above.

In some embodiments of the Formulae above, X is $CH_2$. In another embodiments, X is O.

In some embodiments of the Formulae above, $R_1$ is chosen from 6-12 membered heteroaryls optionally substituted with one or more $R_5$. In some embodiments of the Formulae above, $R_1$ is chosen from 6 membered heteroaryls substituted with one or more $R_6$. In some embodiments of the Formulae above, any $R_1$ group or optional substituent containing hydrogen can have one or more hydrogen replaced with deuterium.

In some embodiments of the Formulae above, $R_2$ is chosen from N-linked 4-10 membered heterocyclyls optionally substituted with one or more $R_5$, and wherein a sulfur member of the heterocyclyls can be S(O) or S(O)$_2$. In some embodiments of the Formulae above $R_2$ is chosen from C-linked 4-10 membered heterocyclyls optionally substituted with one or more $R_5$, and wherein a sulfur member of the heterocyclyls can be S(O) or S(O)$_2$. In some embodiments of the Formulae above $R_2$ is chosen from O linked to a heterocyclic entity that is optionally substituted with one or more $R_5$, and wherein a sulfur member of the heterocyclyls can be S(O) or S(O)$_2$. In some embodiments of the Formulae above, any $R_2$ group or optional substituent containing hydrogen can have one or more hydrogen replaced with deuterium.

In some embodiments of the Formulae above, $R_3$ is independently chosen from H, (C$_1$-C$_6$) alkyl, (C$_1$-C$_6$) haloalkoxy, halogen, and —CN.

In some embodiments of the Formulae above, $R_4$ is chosen from H and (C$_1$-C$_6$) alkyls. In some embodiments of the Formulae above, one or more hydrogen of $R_4$ can be replaced with deuterium.

In some embodiments of the Formulae above, n is 0, 1, or 2. In another embodiment, n is 0 or 1. In yet another embodiment, n is 1, 2, or 3. In another embodiment, n is 1 or 2. In another embodiment, n is 2 or 3. In another embodiment, n is 0. In another embodiment, n is 1. In another embodiment, n is 2. In another embodiment, n is 3.

In some embodiments of the Formulae above, $R_1$, optionally substituted with $R_5$ and/or $R_6$, is chosen from the groups of Table A and/or Table A-2. Preferably, a compound of Formula (I), Formula (II), Formula (III). Formula (IV), Formula (V), Formula (VI) and/or Formula (VII) comprises $R_1$ (alone or as substituted with one of more $R_5$ and/or $R_6$) that is selected from the groups in Table A and/or Table A-2 below.

TABLE A

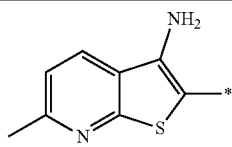

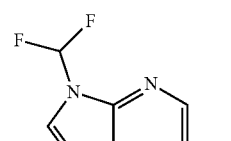

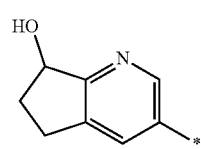

TABLE A-continued

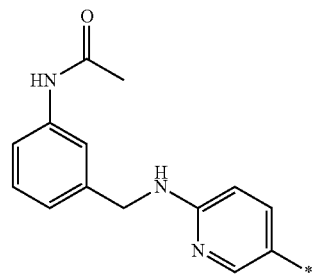 [SMILES: *c1ccc(NCc2cccc(NC(C)=O)c2)nc1]

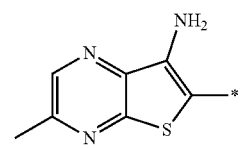 [SMILES: *c1sc2nc(C)cnc2c1N]

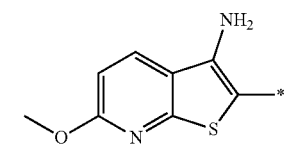 [SMILES: *c1sc2nc(OC)ccc2c1N]

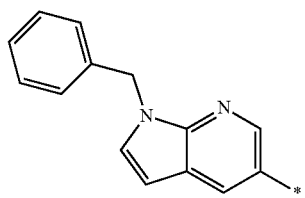 [SMILES: *c1cnc2c(ccn2Cc2ccccc2)c1]

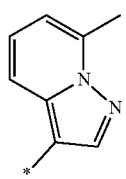 [SMILES: *c1cnn2c(C)cccc12]

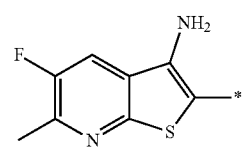 [SMILES: *c1sc2nc(C)c(F)cc2c1N]

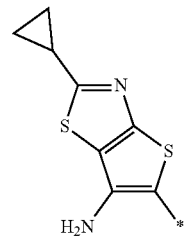 [SMILES: *c1sc2nc(C3CC3)sc2c1N]

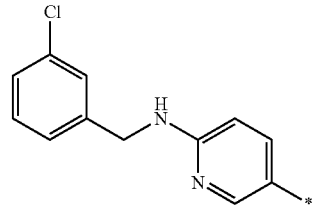 [SMILES: *c1ccc(NCc2cccc(Cl)c2)nc1]

TABLE A-continued
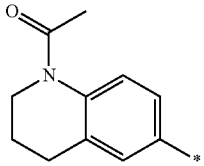 [SMILES: *c1ccc2c(c1)CCCN2C(C)=O]
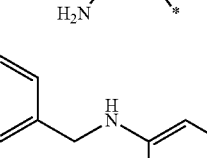
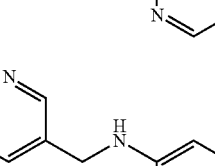
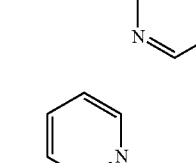
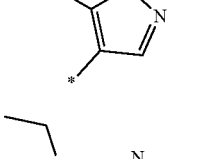
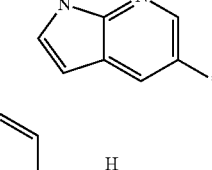
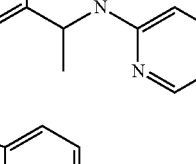
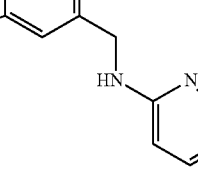
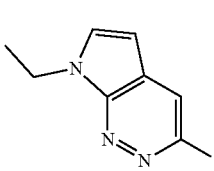
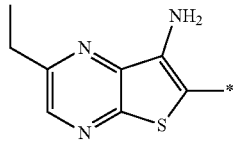 [SMILES: *c1sc2ncc(CC)nc2c1N]
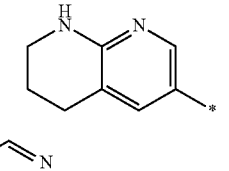
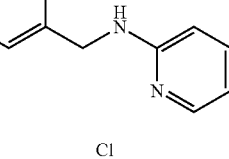
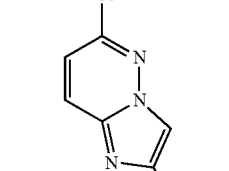
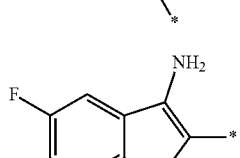
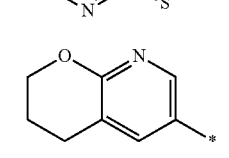
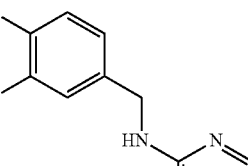
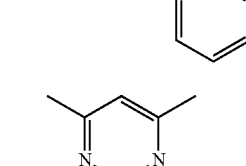
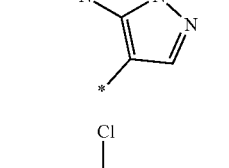
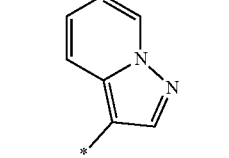

TABLE A-continued
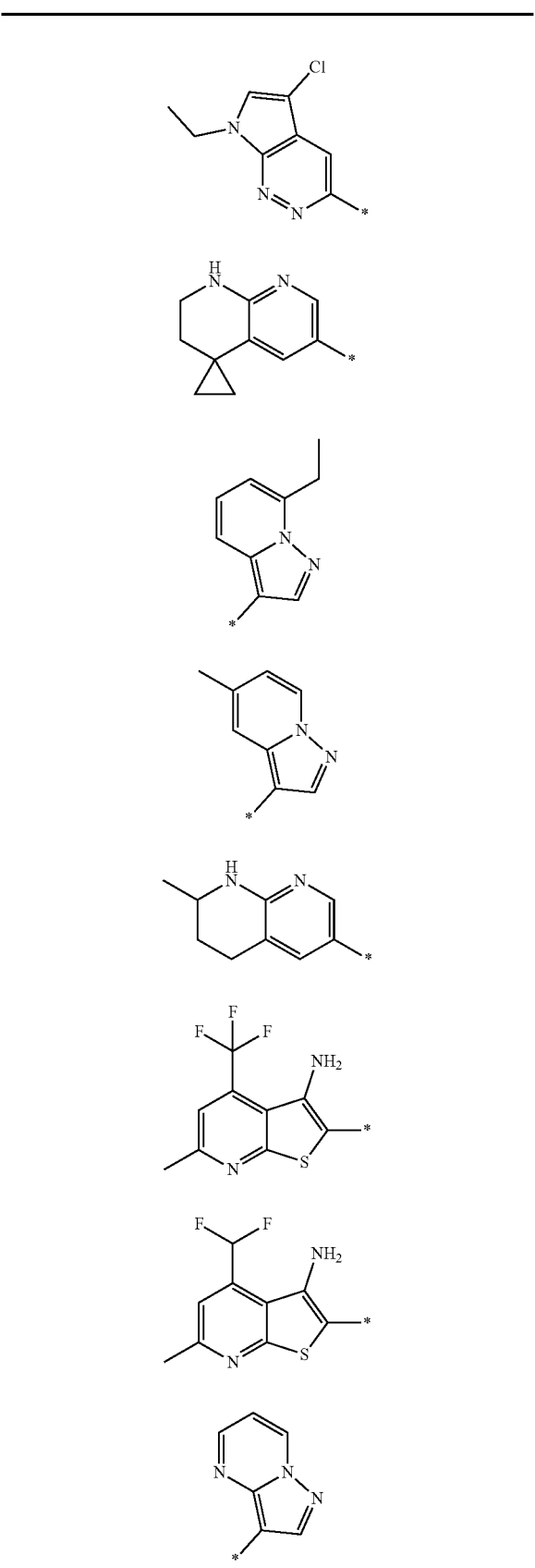
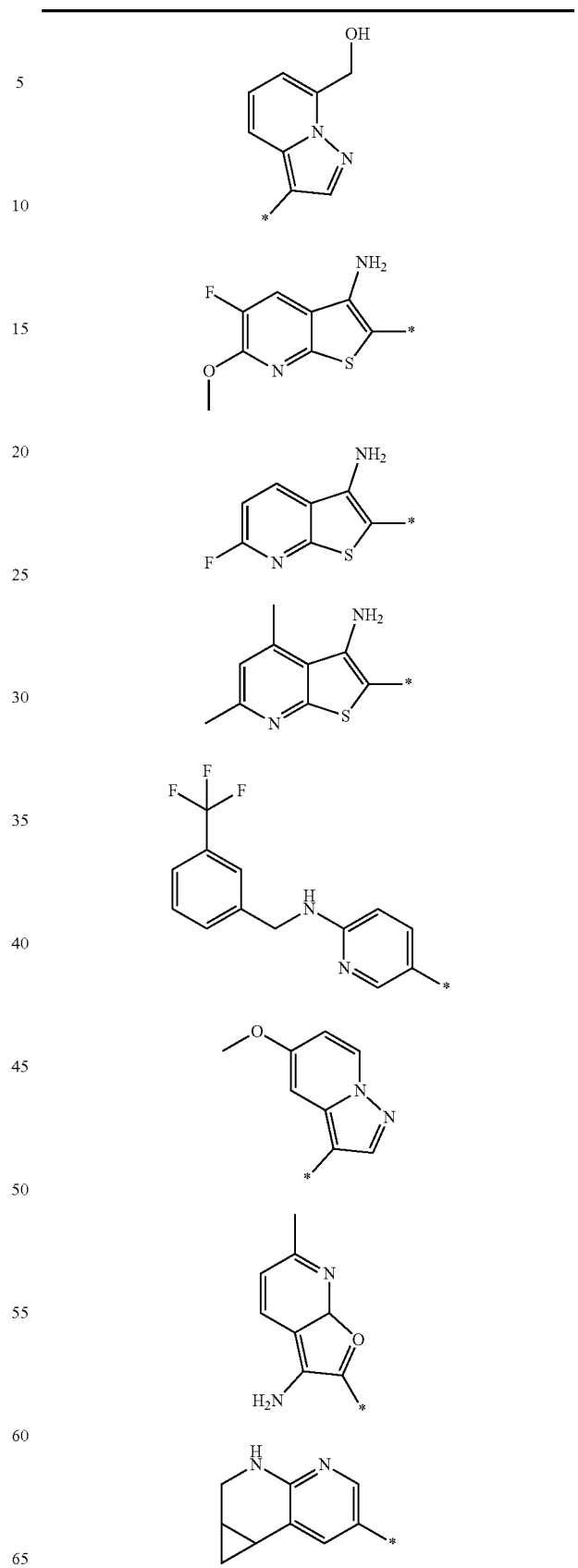

TABLE A-continued

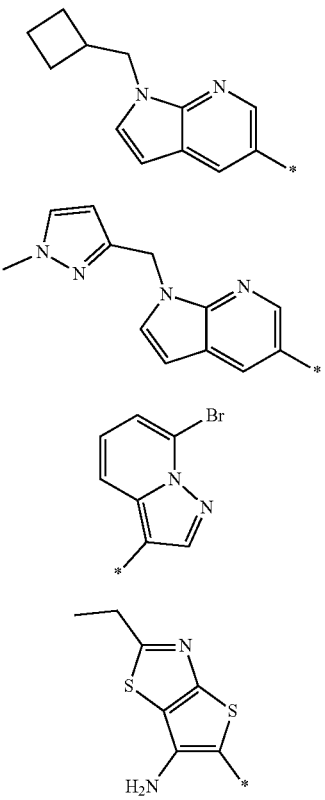

TABLE A-2

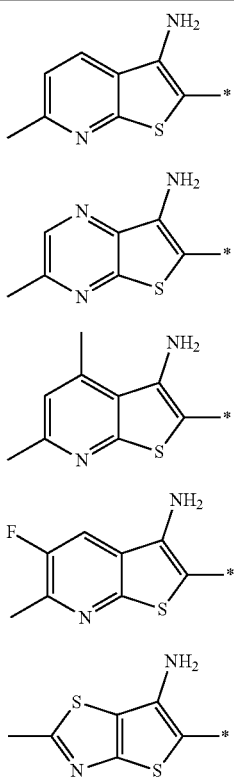

TABLE A-2-continued

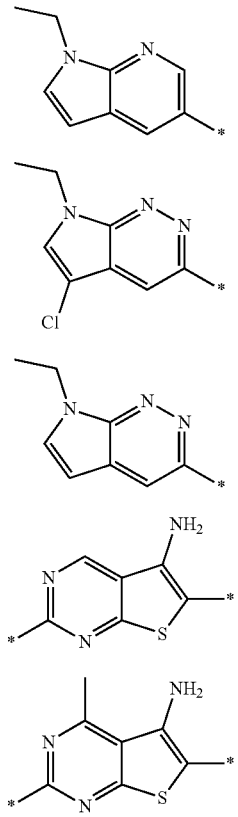

In some embodiments of the Formulae above, $R_2$, optionally substituted with $R_5$, is chosen from the groups of Table B and/or Table B-2 below. Preferably, a compound of Formula (I), Formula (II), Formula (III), Formula (IV), Formula (V), Formula (VI) and/or Formula (VII) can comprises $R_2$ (alone or as substituted with one of more $R_5$ and/or $R_6$, which can be the same or different) that is selected from the groups in Table B and/or Table B-2 below.

TABLE B

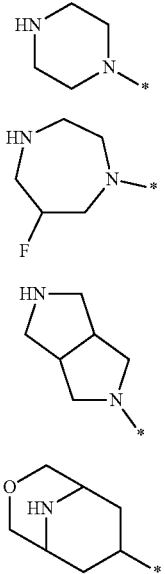

TABLE B-continued
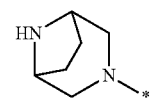
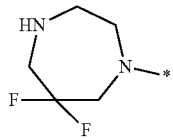
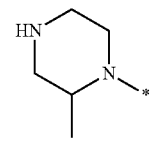 [SMILES: *N1CCNCC1C]
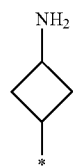
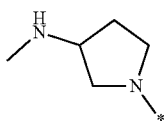
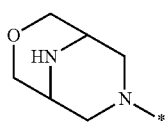 [SMILES: *N1CC2COCC(C1)N2]
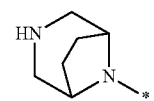
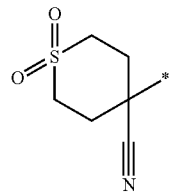 [SMILES: *C1(C#N)CCS(=O)(=O)CC1]
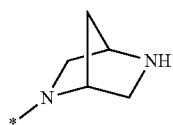
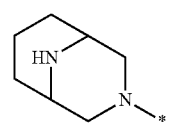 [SMILES: *N1CC2CCCC(C1)N2]
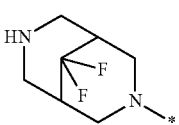 [SMILES: *N1CC2CNCC(C1)C2(F)F]
TABLE B-continued
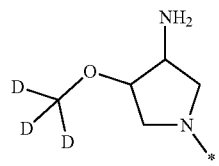 [SMILES: *N1CC(N)C(OC([2H])([2H])[2H])C1]
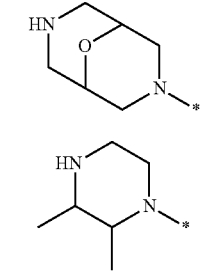
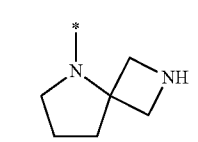 [SMILES: *N1CCCC12CNC2]
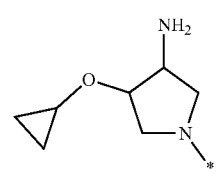
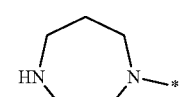
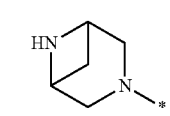
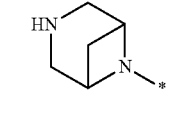 [SMILES: *N1C2CNCC1C2]
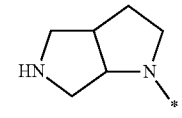
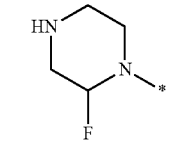 [SMILES: *N1CCNCC1F]
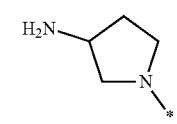

TABLE B-continued

TABLE B-continued

TABLE B-continued
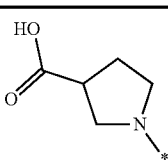
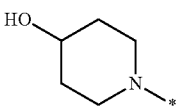
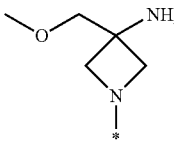
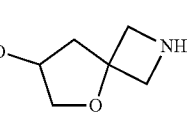
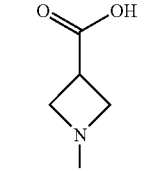
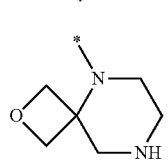
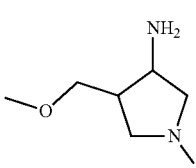
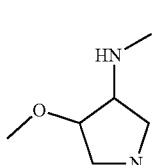
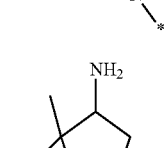
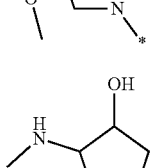
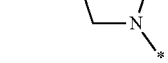
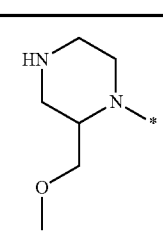
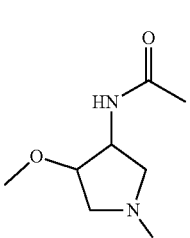
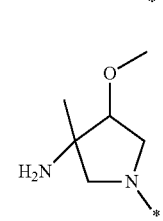
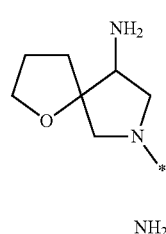
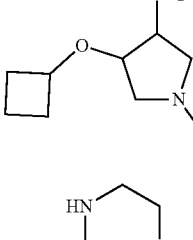
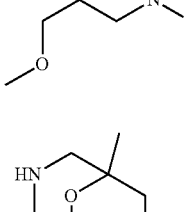
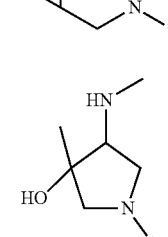

TABLE B-continued
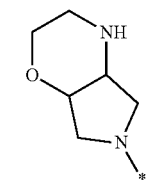
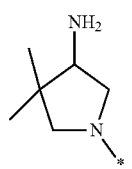
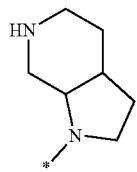
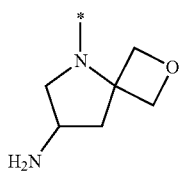
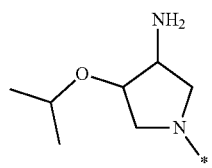
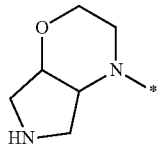
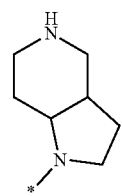 [SMILES: *N1CCC2CNCCC21]
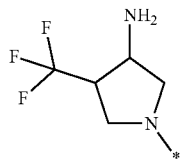
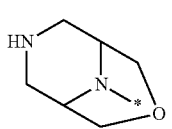
TABLE B-continued
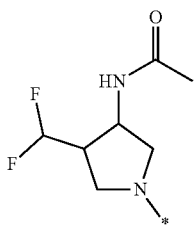 [SMILES: *N1CC(NC(C)=O)C(C(F)F)C1]
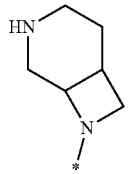
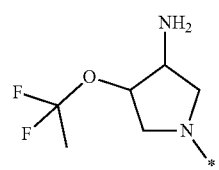 [SMILES: *N1CC(N)C(OC(C)(F)F)C1]
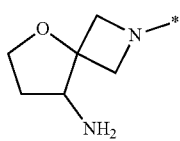
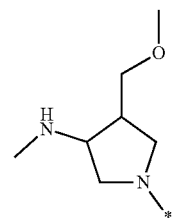 [SMILES: *N1CC(COC)C(NC)C1]
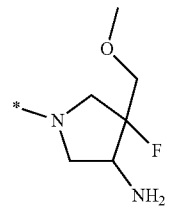
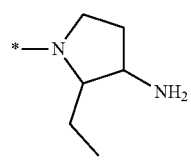 [SMILES: *N1CCC(N)C1CC]
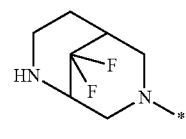
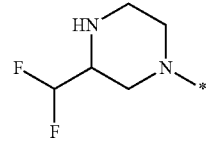 [SMILES: *N1CCNC(C(F)F)C1]

TABLE B-continued
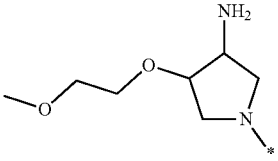 [SMILES: *N1CC(N)C(OCCOC)C1]
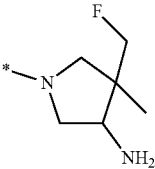
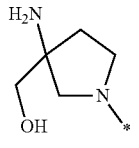 [SMILES: *N1CCC(N)(CO)C1]
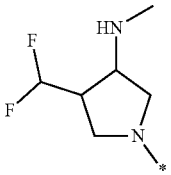
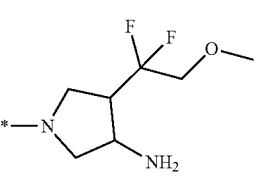 [SMILES: *N1CC(N)C(C(F)(F)COC)C1]
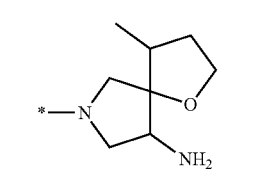 [SMILES: *N1CC(N)C2(C1)OCCC2C]
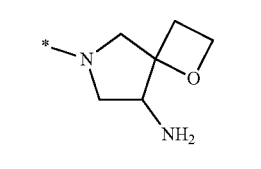 [SMILES: *N1CC(N)C2(CCO2)C1]
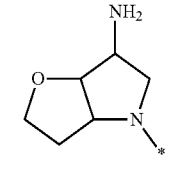 [SMILES: *N1CC(N)C2OCCC21]
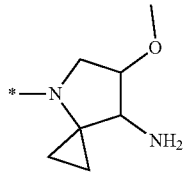 [SMILES: *N1CC(OC)C(N)C12CC2]
TABLE B-continued
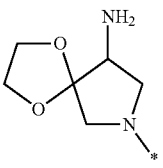
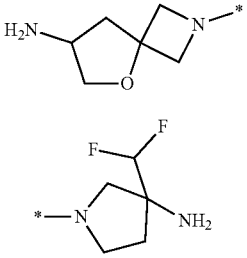
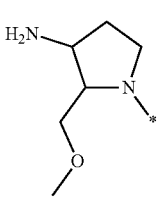 [SMILES: *N1CCC(N)C1COC]
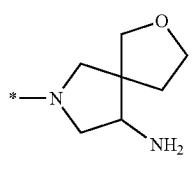
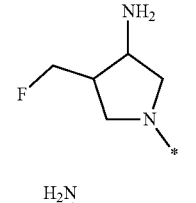
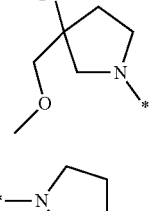
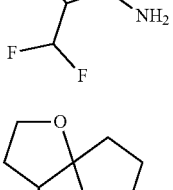
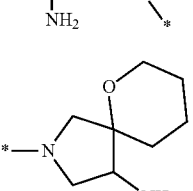

TABLE B-continued
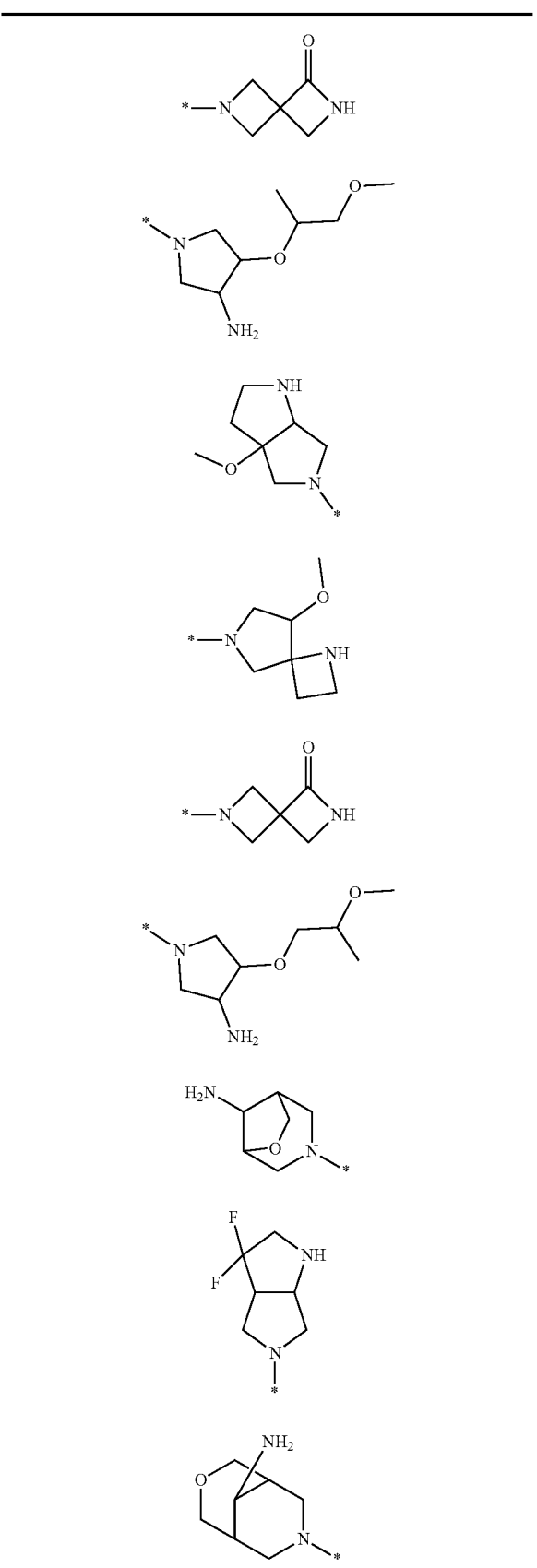
TABLE B-continued
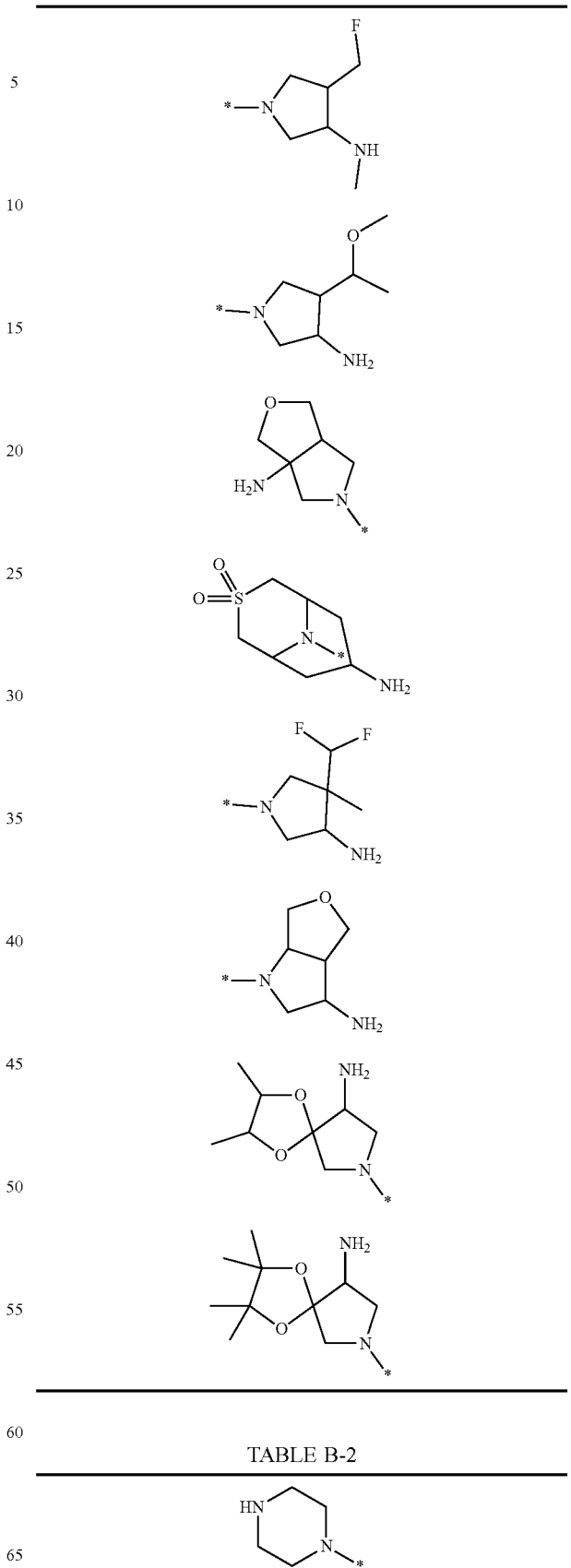
TABLE B-2
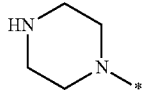

TABLE B-2-continued

TABLE B-2-continued
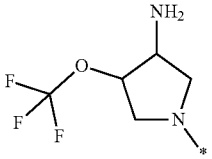 [SMILES: *N1CC(N)C(OC(F)(F)F)C1]
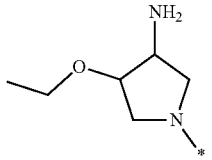 [SMILES: *N1CC(N)C(OCC)C1]
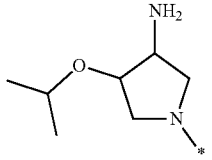 [SMILES: *N1CC(N)C(OC(C)C)C1]
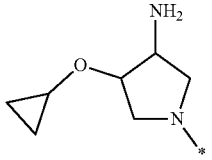 [SMILES: *N1CC(N)C(OC2CC2)C1]
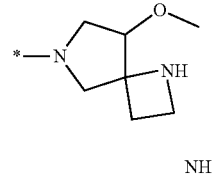
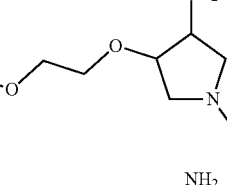
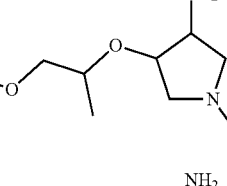
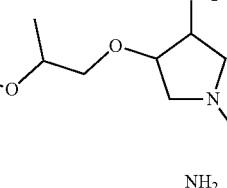
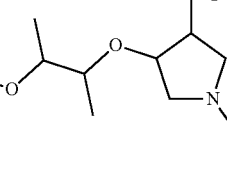
TABLE B-2-continued
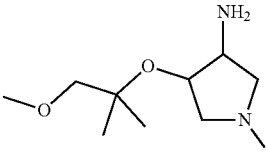
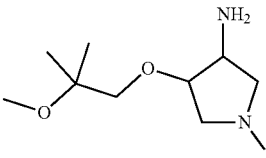
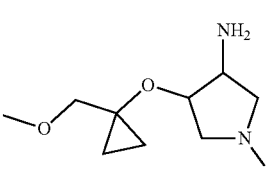
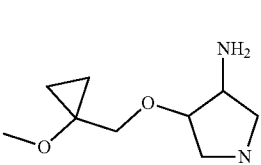
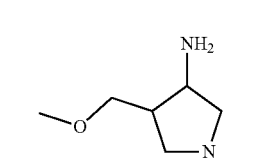
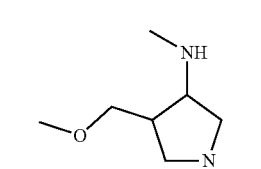
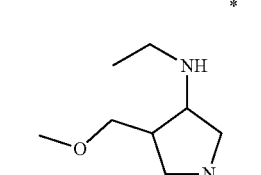
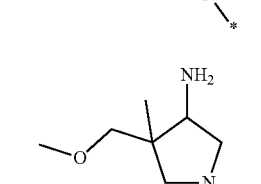
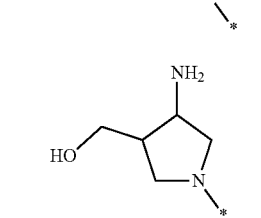

TABLE B-2-continued
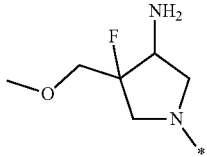 [SMILES: *N1CC(N)C(F)(COC)C1]
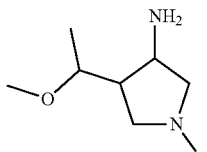
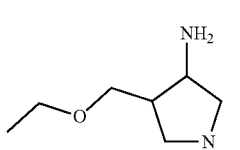
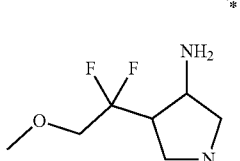
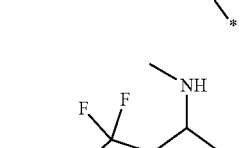
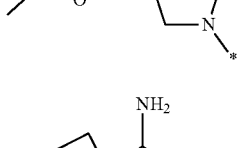
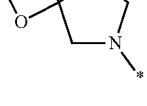
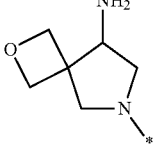
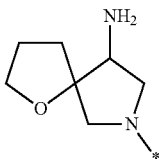
TABLE B-2-continued
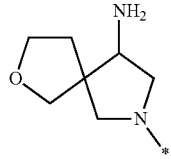 [SMILES: *N1CC(N)C2(CCOC2)C1]
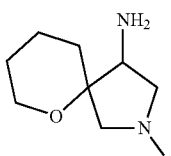
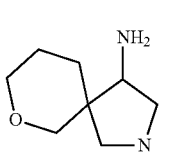
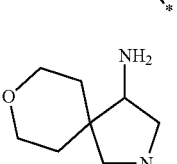
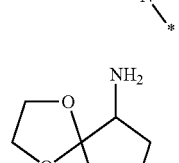
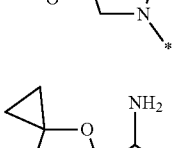
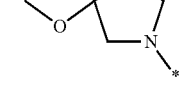
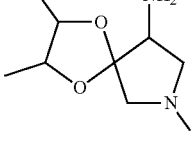
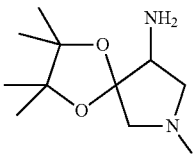

TABLE B-2-continued

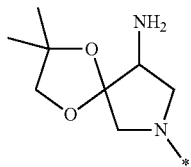 [SMILES: *N1CC(N)C2(C1)OCC(C)(C)O2]

Preferably, a compound of Formula (I), Formula (I'), Formula (I"), Formula (I'''), Formula (II), Formula (III), Formula (IV), Formula (V), Formula (VI) and/or Formula (VII) can comprises both $R_1$ (alone or as substituted with one of more $R_5$ and/or $R_6$, which can be the same or different) that is selected from the groups in Table A and/or Table A-2 above, and $R_2$ (alone or as substituted with one of more $R_5$ and/or $R_6$, which can be the same or different) that is selected from the groups in Table B and/or Table B-2 above.

In some embodiments, the chemical entities are chosen from compounds of Formula (IIa):

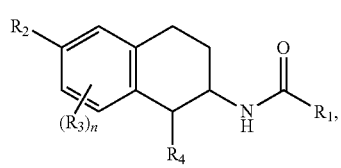

or a pharmaceutically acceptable salt thereof, wherein $R_1$, $R_2$, $R_3$, $R_4$, $R_5$, $R_6$, $R_7$ and n are as defined in Formula (I), and/or from compounds of Formula (IIaa):

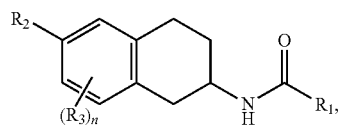

or a pharmaceutically acceptable salt thereof, wherein $R_1$, $R_2$, $R_3$, $R_5$, $R_6$, $R_7$ and n are as defined in Formula (I).

In some embodiments, the chemical entities are chosen from compounds of Formula (IIb)

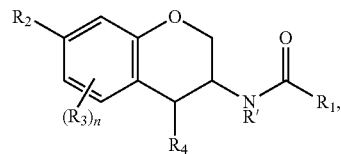

or a pharmaceutically acceptable salt thereof,
wherein R', $R_1$, $R_2$, $R_3$, $R_4$, $R_5$, $R_6$, $R_7$ and n are each independently as defined Formula (VI).

In some embodiments, the chemical entities are chosen from compounds of Formula (IIaa):

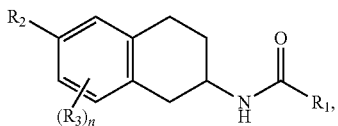

or a pharmaceutically acceptable salt thereof,
wherein
$R_1$ is chosen from 8-9-membered heteroaryls substituted with one or more substituent chosen from $R_5$ and $R_6$;
$R_2$ is chosen from N-linked 6-12 membered heterocyclyls or C-linked 6-12 membered heterocyclyls, wherein the 6-12 membered heterocyclyls are optionally substituted with one or more $R_5$;
$R_3$ is independently chosen from H, ($C_1$-$C_6$) alkyl, halogen, and —CN; and
wherein $R_5$, $R_6$, $R_7$ and n are each independently as defined in Formula (I).

In preferred embodiments of Formula (IIaa), Ri, optionally substituted with $R_5$ and/or $R_6$, is chosen from

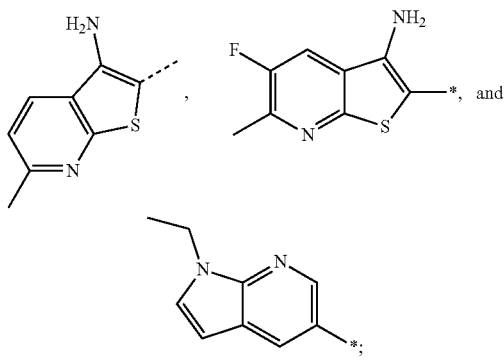

and $R_2$, optionally substituted with $R_5$, is chosen from

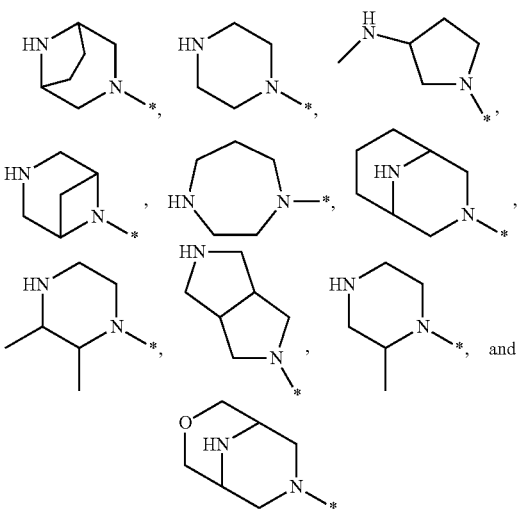

In some embodiments, the chemical entities are chosen from compounds of Formula (IIb'):

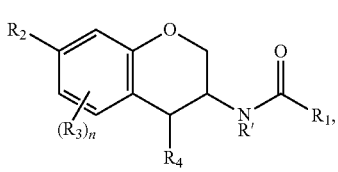

or a pharmaceutically acceptable salt thereof,
wherein R' is chosen from H and CH$_3$;
R$_1$ is chosen from 8-9 membered heteroaryls substituted with one or more substituent chosen from R$_5$ and R$_6$;
R$_2$ is chosen from N-linked 6-12 membered heterocyclyls or C-linked 6-12 membered heterocyclyls, wherein the 6-12 membered heterocyclyls are optionally substituted with one or more R$_5$;
R$_3$ is independently chosen from H and halogen; and
R$_5$, R$_6$, R$_7$ and n are each independently as defined in Formula (VI).

In preferred embodiments of Formula (IIb'), R$_1$, optionally substituted with R$_5$ and/or R$_6$, is chosen from

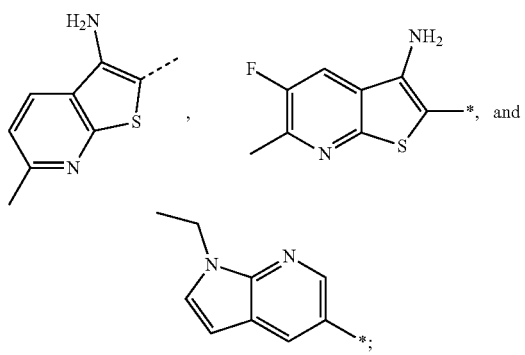

and
R$_2$, optionally substituted with R$_5$, is chosen from

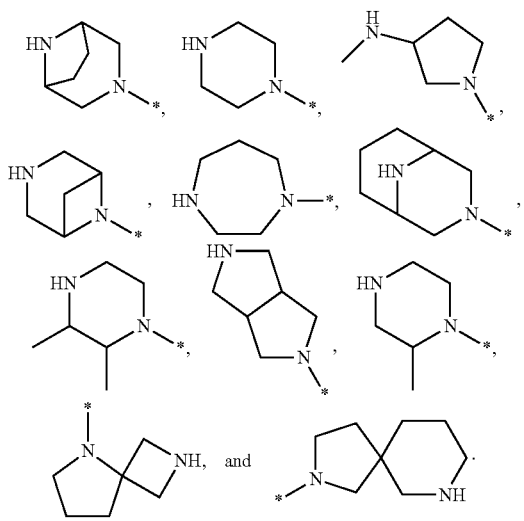

In some embodiments, the chemical entities are chosen from compounds of Formula (IIIa):

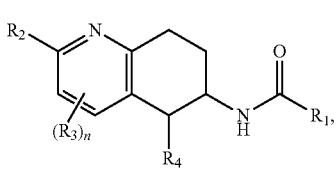

or a pharmaceutically acceptable salt thereof,
wherein R$_1$, R$_2$, R$_3$, R$_4$, R$_5$, R$_6$, R$_7$ and n are each independently as defined Formula (I); and/or from compounds Formula (IIIb):

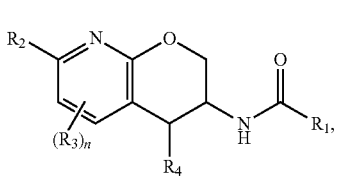

or a pharmaceutically acceptable salt thereof,
wherein R$_1$, R$_2$, R$_3$, R$_4$, R$_5$, R$_6$, R$_7$ and n are each independently as defined Formula (I).

In some embodiments, the chemical entities are chosen from compounds of Formula (IIIaa):

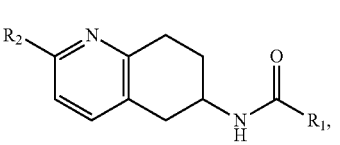

or a pharmaceutically acceptable salt thereof, wherein
  R$_1$ is chosen from 8-11 membered heteroaryls optionally substituted with one or more R$_5$;
  R$_2$ is chosen from N-linked 4-12 membered heterocyclyls and C-linked 4-12 membered heterocyclyls, optionally substituted with one or more R$_5$;
  each R$_5$ (if present) is independently chosen from —OH, —NH$_2$, NHC(O)CH$_3$, (C$_1$-C$_6$) alkyl, (C$_1$-C$_6$) alkoxy, (C$_1$-C$_6$) haloalkyl, (C$_1$-C$_6$) haloalkoxy, halogen, cycloalkyl, heterocycloalkyl, and —C(O)— heterocycloalkyl groups, wherein each of —NH$_2$, —NHC(O)CH$_3$, (C$_1$-C$_6$) alkyl, (C$_1$-C$_6$) alkoxy, (C$_1$-C$_6$) haloalkyl, (C$_1$-C$_6$) haloalkoxy, cycloalkyl, heterocycloalkyl, and —C(O)-heterocycloalkyl are optionally substituted with one or more substituent independently chosen from (C$_1$-C$_6$) alkoxy, —NH$_2$, and —OH; and
  n is 0, 1, 2, or 3.

In preferred embodiments of Formula (IIIaa), R$_1$ is chosen from

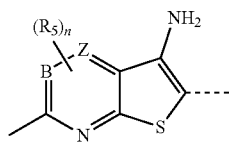

wherein B is chosen from a bond or C;
Z is chosen from N, S, C(Rii);
Rii is chosen from H, CH$_3$ and R$_5$;

$R_2$ is chosen from N-linked 5-8 membered heterocyclyls substituted with one to three $R_5$;

each $R_5$ (if present) is independently chosen from —OH, —$NH_2$, $NHC(O)CH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)—heterocycloalkyl groups, wherein each of —$NH_2$, —$NHC(O)CH_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkoxy, —$NH_2$, and —OH; and n is 0, 1, 2, or 3.

In further preferred embodiments of Formula (IIIaa), $R_1$, optionally substituted with $R_5$, is chosen from

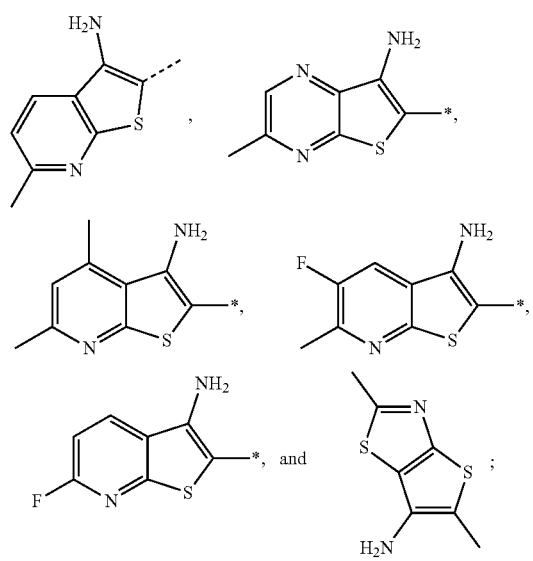

and $R_2$, optionally substituted with $R_5$, is chosen from

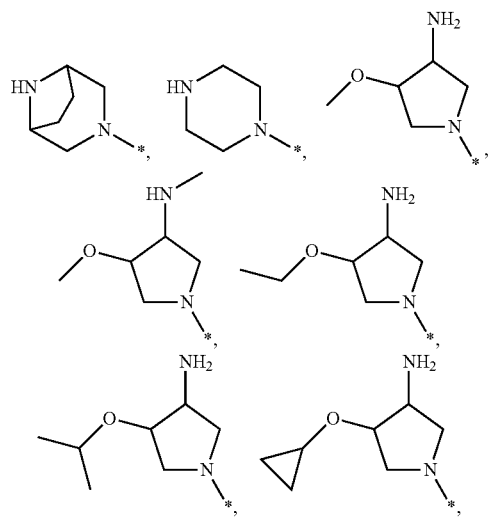

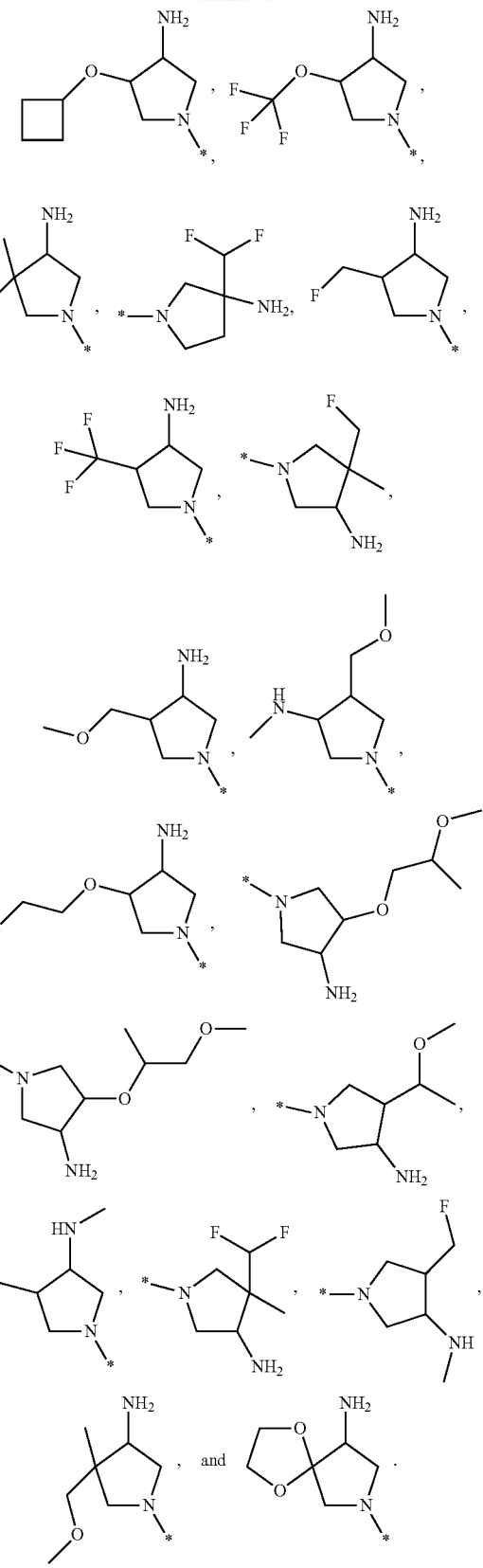

In some embodiments, the chemical entities are chosen from compounds of Formula (IVa):

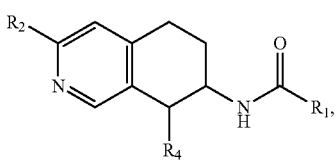
(IVa)

or a pharmaceutically acceptable salt thereof
wherein $R_1$, $R_2$, $R_4$, $R_5$, $R_6$, $R_7$ and n are each independently as defined Formula (I).

In some embodiments, the chemical entities are chosen from compounds of Formula (Va):

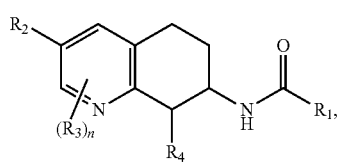
(Va)

or a pharmaceutically acceptable salt thereof,
wherein $R_1$, $R_2$, $R_3$, $R_4$, $R_5$, $R_6$, $R_7$ and n are each independently as defined Formula (I).

In some embodiments, the chemical entity is chosen from compounds of Formula (Vaa):

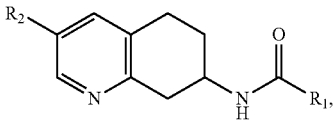
(Vaa)

or a pharmaceutically acceptable salt thereof,
wherein $R_1$ is chosen from 8-membered heteroaryls substituted with one or more substituent chosen from $R_5$ and $R_6$; $R_2$ is chosen from N-linked 5-membered heterocyclyls; and $R_5$, $R_6$, $R_7$ and n are each independently as defined Formula (I).

In further preferred embodiments of Formula (Vaa), $R_1$ substituted with $R_5$ is chosen from

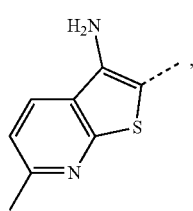

and $R_2$ is chosen from

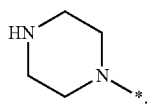

In some embodiments, the chemical entities are chosen from compounds of Formula (VIIa'):

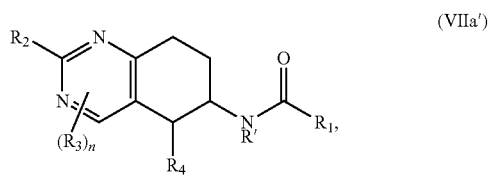
(VIIa')

or a pharmaceutically acceptable salt thereof,
wherein R', $R_1$, $R_2$, $R_3$, $R_4$, $R_5$, $R_6$, $R_7$ and n are each independently as defined Formula (VI).

In at least one embodiment, the chemical entities are chosen from compounds of Formula (VIIaa):

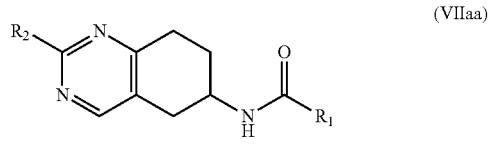
(VIIaa)

or a pharmaceutically acceptable salt thereof, wherein
$R_1$ is chosen from 8-9 membered heteroaryls optionally substituted with one or more $R_5$;
$R_2$ is chosen from N-linked 4-12 membered heterocyclyls optionally substituted with one or more $R_5$;
each $R_5$ (if present) is independently chosen from —OH, —$NH_2$, NHC(O)$CH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)— heterocycloalkyl groups, wherein each of —$NH_2$, —NHC(O)$CH_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkoxy, —$NH_2$, and —OH; and
n is 0, 1, 2, or 3.

In preferred embodiments of Formula (VIIaa), $R_1$ is chosen from

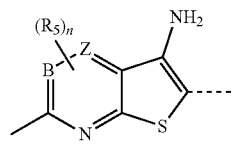

wherein B is chosen from a bond or C;
Z is chosen from N, S, C(Rii);
Rii is chosen from H, $CH_3$ and $R_5$;
$R_2$ is chosen from N-linked 5-8 membered heterocyclyls substituted with one to three $R_5$;
each $R_5$ (if present) is independently chosen from —OH, —$NH_2$, NHC(O)$CH_3$, ($C_1$-$C_6$) alkyl, ($C_1$-$C_6$) alkoxy, ($C_1$-$C_6$) haloalkyl, ($C_1$-$C_6$) haloalkoxy, halogen, cycloalkyl, heterocycloalkyl, and —C(O)— heterocycloalkyl groups, wherein each of —$NH_2$, —NHC(O)$CH_3$, ($C_1$-$C_6$) alkyl, ($C_1$-$C_6$) alkoxy, ($C_1$-$C_6$) haloalkyl, ($C_1$-$C_6$) haloalkoxy, cycloalkyl, heterocycloalkyl, and —C(O)-heterocycloalkyl are optionally substituted with one or more substituent independently chosen from ($C_1$-$C_6$) alkoxy, —$NH_2$, and —OH; and n is 0, 1, 2, or 3.

In further preferred embodiments of Formula (VIIaa), R₁, optionally substituted with R₅, is chosen from

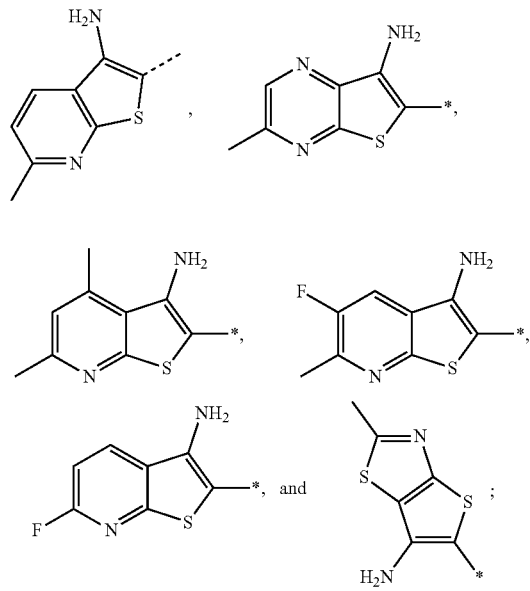

and

R₂, optionally substituted with R₅, is chosen from IDC

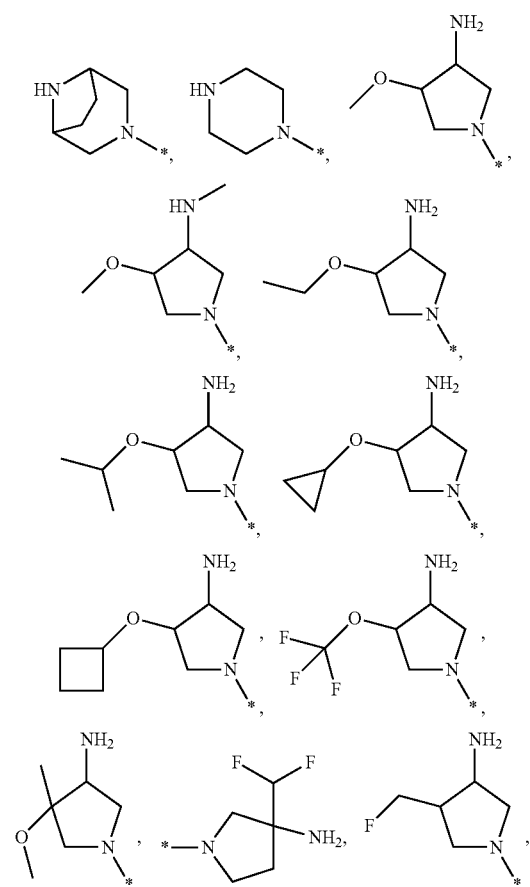

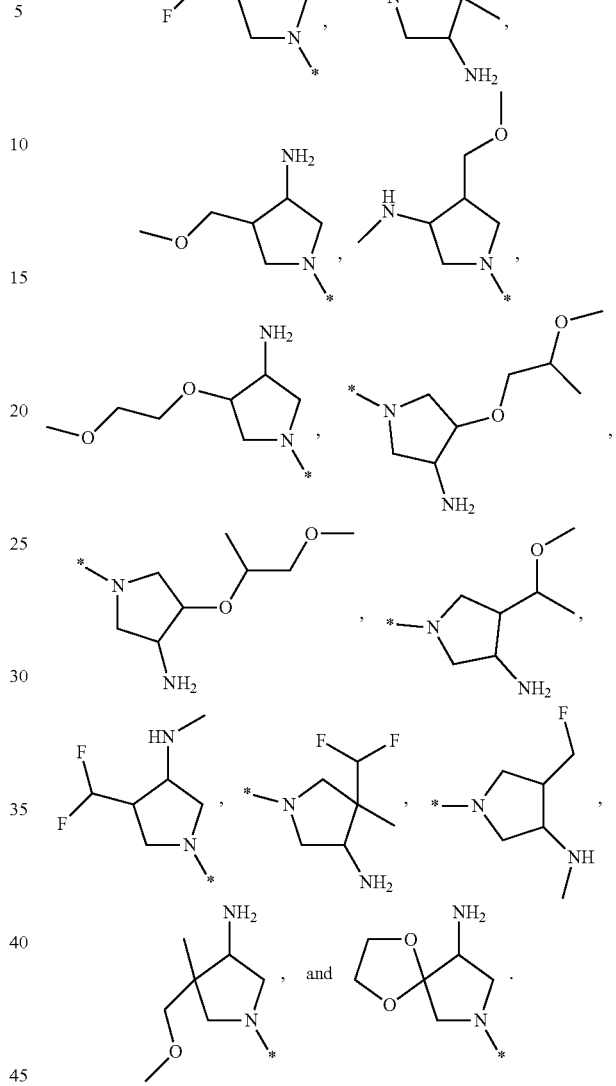

Preferably, the compound is a compound of Formula (I), (II), (III), (IV), (V), (VI), (VII), (IIa), (IIaa), (IIb'), (IIIa), (IIIb), (IIIaa), (IVa), (Va), (Vaa), (VIIa') or Formula (VIIaa) that is USP28 Inhibitor, a USP25 Inhibitor and/or a USP 28/25 Inhibitor as defined herein.

In another embodiment of the disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds of the disclosure may contain asymmetric or chiral centers, and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the compounds disclosed herein.

The compounds disclosed herein may form salts which are also within the scope of this disclosure.

The present disclosure relates to compounds which are modulators of at least one pathway chosen from USP28 and USP25. In one embodiment, the compounds of the present disclosure are inhibitors of at least one pathway chosen from USP28 and USP25.

The present disclosure is directed to chemical entities chosen from compounds as described herein and pharmaceutically acceptable salts, solvates, prodrugs, stereoisomers, and tautomers thereof, and pharmaceutical compositions comprising at least one chemical entity chosen from compounds as described herein, and pharmaceutically acceptable salts, hydrates, solvates, prodrugs, stereoisomers, and tautomers thereof.

Another aspect of the disclosure relates to a method of treating, preventing, inhibiting, or eliminating a disease or disorder associated with modulation of USP28. The method comprises administering to a patient in need of a treatment for diseases or disorders associated with modulation of USP28 an effective amount the compositions and chemical entities of Formula (I). In one embodiment, the disease or disorder is cancer.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP28 an effective amount the compositions and chemical entities of Formula (I). In one embodiment, the disease or disorder is cancer.

In another aspect, the present disclosure is directed to a method of inhibiting USP28. The method involves administering to a patient in need thereof an effective amount of a chemical entity of Formula (I).

Another aspect of the disclosure relates to a method of treating, preventing, inhibiting, or eliminating a disease or disorder associated with modulation of USP25. The method comprises administering to a patient in need of a treatment for diseases or disorders associated with modulation of USP25 an effective amount the compositions and chemical entities of Formula (I). In one embodiment, the disease or disorder is cancer.

In another aspect, the present disclosure is directed to a method of treating, preventing, inhibiting, or eliminating a disease or disorder associated with inhibition of USP25. The method comprises administering to a patient in need of a treatment for diseases or disorders associated with modulation of USP25 an effective amount the compositions and chemical entities of Formula (I). In one embodiment, the disease or disorder is cancer.

In another aspect, the present disclosure is directed to a method of inhibiting USP25. The method involves administering to a patient in need thereof an effective amount of a chemical entity of Formula (I).

Another aspect of the disclosure relates to a method of treating, preventing, inhibiting, or eliminating a disease or disorder associated with modulation of USP28. The method comprises administering to a patient in need of a treatment for diseases or disorders associated with modulation of USP28 an effective amount the compositions and chemical entities of Formula (I). In one embodiment, the disease or disorder is cancer. In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP28 an effective amount the compositions and chemical entities of Formula (I). In one embodiment, the disease or disorder is cancer. The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein. In another aspect, the present disclosure is directed to a method of inhibiting at least one pathway chosen from USP28 and USP25. The method involves administering to a patient in need thereof an effective amount of a chemical entity of Formula (I). The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein.

Another aspect of the present disclosure relates to a method of treating, preventing, inhibiting, or eliminating a disease or disorder in a patient associated with the inhibition of USP28, the method comprising administering to a patient in need thereof an effective amount of a chemical entity of Formula (I). In one embodiment, the disease or disorder is cancer. The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein.

Another aspect of the present disclosure relates to a method of treating, preventing, inhibiting, or eliminating a disease or disorder in a patient associated with the inhibition of USP25, the method comprising administering to a patient in need thereof an effective amount of a chemical entity of Formula (I). In one embodiment, the disease or disorder is cancer. The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein.

Another aspect of the present disclosure relates to a method of treating, preventing, inhibiting, or eliminating a disease or disorder in a patient associated with the inhibition of at least one pathway chosen from USP28 and USP25, the method comprising administering to a patient in need thereof an effective amount of a chemical entity of Formula (I). In one embodiment, the disease or disorder is cancer. The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein.

In another aspect, the present disclosure relates to a method of treating, preventing, inhibiting, or eliminating cancer. The method comprises administering to a patient in need of a treatment for cancer an effective amount of a chemical entity chosen from compounds of Formula (I), and pharmaceutically acceptable salts, solvates, prodrugs, stereoisomers, and tautomers thereof. The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein.

Another aspect of the present disclosure relates to a chemical entity chosen from compounds of Formula (I), and pharmaceutically acceptable salts, solvates, prodrugs, stereoisomers, and tautomers thereof, for use in a method of treating, preventing, inhibiting, or eliminating a disease or disorder associated with inhibiting USP28. In one embodiment, the disease or disorder is cancer. The method can comprise administering to a patient in need of a treatment for diseases or disorders associated with modulation of USP28 and/or USP25 an effective amount of a pharmaceutical composition comprising a USP28 Inhibitor, USP25 Inhibitor, and/or USP28/25 Inhibitor as disclosed herein.

In another aspect, the present disclosure relates to a chemical entity chosen from compounds of Formula (I), and pharmaceutically acceptable salts, solvates, prodrugs, stereoisomers, and tautomers thereof, for use in a method of treating, preventing, inhibiting, or eliminating a disease or disorder associated with inhibiting USP25. In one embodiment, the disease or disorder is cancer.

Another aspect of the present disclosure relates to a chemical entity chosen from compounds of Formula (I), and pharmaceutically acceptable salts, solvates, prodrugs, stereoisomers, and tautomers thereof, for use in a method of treating, preventing, inhibiting, or eliminating a disease or disorder associated with inhibiting at least one pathway chosen from USP28 and USP25. In one embodiment, the disease or disorder is cancer.

In another aspect, the present disclosure relates to a chemical entity chosen from compounds of Formula (I), and pharmaceutically acceptable salts, solvates, prodrugs, stereoisomers, and tautomers thereof, for use in a method for treating, preventing, inhibiting, or eliminating cancer.

Another aspect of the present disclosure relates to the use of a chemical entity chosen from compounds of Formula (I), and pharmaceutically acceptable salts, solvates, prodrugs, stereoisomers, and tautomers thereof, in the manufacture of a medicament for treating, preventing, inhibiting, or eliminating a disease or disorder associated with inhibiting USP28. In one embodiment, the disease or disorder is cancer.

Another aspect of the present disclosure relates to the use of a chemical entity chosen from compounds of Formula (I), and pharmaceutically acceptable salts, solvates, prodrugs, stereoisomers, and tautomers thereof, in the manufacture of a medicament for treating, preventing, inhibiting, or eliminating a disease or disorder associated with inhibiting at least one pathway chosen from USP28 and USP25. In one embodiment, the disease or disorder is cancer.

In another aspect, the present disclosure relates to the use of a chemical entity chosen from compounds of Formula (I), and pharmaceutically acceptable salts, solvates, prodrugs, stereoisomers, and tautomers thereof, in the manufacture of a medicament for treating, preventing, inhibiting, or eliminating cancer.

In other embodiments, the present disclosure relates to the use of an inhibitor of USP28 for the preparation of a medicament used in the treatment, prevention, inhibition or elimination of a disease or disorder associated with cancer.

The present disclosure also relates to the use of an inhibitor of USP28 for the preparation of a medicament used in the treatment, prevention, inhibition, or elimination of a disease or condition mediated by USP28, wherein the medicament comprises a chemical entity chosen from compounds of Formula (I), and pharmaceutically acceptable salts, solvates, prodrugs, stereoisomers, and tautomers thereof. The present disclosure also relates to the use of an inhibitor of USP28 for the preparation of a medicament used in the treatment, prevention, inhibition, or elimination of a disease or condition mediated by USP28, wherein the medicament comprises a chemical entity chosen from compounds of Formulae (II), (III), (IV), (V), (VI), (VII), (IIa), (IIaa), (IIb'), (IIIa), (IIIb), (IIIaa), (IVa), (Va), (Vaa), (VIIa') or Formula (VIIaa) that is USP28 Inhibitor, a USP25 Inhibitor and/or a USP 28/25 Inhibitor as defined herein.

The present disclosure also relates to the use of an inhibitor of USP25 for the preparation of a medicament used in the treatment, prevention, inhibition, or elimination of a disease or condition mediated by USP25, wherein the medicament comprises a chemical entity chosen from compounds of Formula (I), and pharmaceutically acceptable salts, solvates, prodrugs, stereoisomers, and tautomers thereof. The present disclosure also relates to the use of an inhibitor of USP25 for the preparation of a medicament used in the treatment, prevention, inhibition, or elimination of a disease or condition mediated by USP25, wherein the medicament comprises a chemical entity chosen from compounds of Formulae (II), (III), (IV), (V), (VI), (VII), (IIa), (IIaa), (IIb'), (IIa), (IIIb), (IIIaa), (IVa), (Va), (Vaa), (VIIa') or Formula (VIIaa) that is USP28 Inhibitor, a USP25 Inhibitor and/or a USP 28/25 Inhibitor as defined herein.

In another aspect, the present disclosure relates to a method for the manufacture of a medicament for treating, preventing, inhibiting, or eliminating a disease or condition mediated by at least one pathway chosen from USP28 and USP25, wherein the medicament comprises a chemical entity chosen from compounds of Formula (I), and pharmaceutically acceptable salts, solvates, prodrugs, stereoisomers, and tautomers thereof. These mechanisms have been shown to be useful in treating cancer such as lung cancer and brain cancer.

In some embodiments, the patient is selected for treatment based on gene amplification and/or elevated tumor expression of USP28, MYC, LSD1, NICD1, and/or reduced expression of FBXW7 relative to tissue-matched expression.

In some embodiments, the patient is selected for treatment based on gene amplification and/or elevated tumor expression of USP28, USP25, MYC, LSD1, NICD1, and/or reduced expression of FBXW7 relative to tissue-matched expression.

In some embodiments, administration of a compound of Formula (I) or a pharmaceutical composition comprising a compound of the present disclosure and a pharmaceutically acceptable carrier induces a change in the cell cycle, cell viability, cell apoptosis, or differentiation.

For example, the change in the cell cycle or cell viability or differentiation may be indicated by decreased tumor levels of MYC, LSD1, NICD1, PIM1, CDK1, POLA2, HEY1, and/or CCND1, and/or increased levels of CD86, p21, LGALS4, and/or DLL1.

Another aspect of the disclosure is directed to pharmaceutical compositions comprising a chemical entity chosen from compounds of Formula (I), and pharmaceutically acceptable salts, solvates, prodrugs, stereoisomers, and tautomers thereof and a pharmaceutically acceptable carrier. The pharmaceutical acceptable carrier may further include an excipient, diluent, or surfactant. Another aspect of the disclosure is directed to pharmaceutical compositions comprising a chemical entity chosen from compounds of Formulae (II), (III), (IV), (V), (VI), (VII), (IIa), (IIaa), (IIb'), (IIIa), (IIIb), (IIIaa), (IVa), (Va), (Vaa), (VIIa') or Formula (VIIaa) that is USP28 Inhibitor, a USP25 Inhibitor and/or a USP 28/25 Inhibitor as defined herein.

In one embodiment, are provided methods of treating a disease or disorder associated with modulation of USP28 including cancer comprising administering to a patient suffering from at least one of said diseases or disorder a chemical entity of Formula (I). The methods of treating a disease or disorder associated with modulation of USP28 including cancer can comprise administering to a patient suffering from at least one of said diseases or disorder a chemical entity of Formulae (II), (III), (IV), (V), (VI), (VII), (IIa), (IIaa), (IIb'), (IIIa), (IIIb), (IIIaa), (IVa), (Va), (Vaa), (VIIa') or Formula (VIIaa) that is USP28 Inhibitor, a USP25 Inhibitor and/or a USP 28/25 Inhibitor as defined herein.

In another embodiment, are provided methods of treating a disease or disorder associated with modulation of USP25 including cancer, comprising administering to a patient suffering from at least one of said diseases or disorder a chemical entity of Formula (I). The methods of treating a disease or disorder associated with modulation of USP25 including cancer, can comprise administering to a patient suffering from at least one of said diseases or disorder a chemical entity of Formulae (II), (III), (IV), (V), (VI), (VII), (IIa), (IIaa), (IIb'), (IIIa), (IIIb), (IIIaa), (IVa), (Va), (Vaa), (VIIa') or Formula (VIIaa) that is USP28 Inhibitor, a USP25 Inhibitor and/or a USP 28/25 Inhibitor as defined herein.

In another embodiment, are provided methods of treating a disease or disorder associated with modulation of at least one pathway chosen from USP28 and USP25 including cancer, comprising administering to a patient suffering from at least one of said diseases or disorder a chemical entity of Formula (I). The methods of treating a disease or disorder associated with modulation of at least one pathway chosen from USP28 and USP25 including cancer, can also comprise administering to a patient suffering from at least one of said diseases or disorder a chemical entity of Formulae (II), (III), (IV), (V), (VI), (VII), (IIa), (IIaa), (IIb'), (IIIa), (IIIb), (IIIaa), (IVa), (Va), (Vaa), (VIIa') or Formula (VIIIaa) that is USP28 Inhibitor, a USP25 Inhibitor and/or a USP 28/25 Inhibitor as defined herein.

One therapeutic use of the compounds or compositions of the present disclosure which inhibit USP28 is to provide treatment to patients or subjects suffering from cancer.

Another therapeutic use of the compounds or compositions of the present disclosure which inhibit USP25 is to provide treatment to patients or subjects suffering from cancer.

Another therapeutic use of the compounds or compositions of the present disclosure which inhibit at least one pathway chosen from USP28 and USP25 is to provide treatment to patients or subjects suffering from cancer.

The compounds of the disclosure can be administered in effective amounts to treat or prevent a disorder and/or prevent the development thereof in subjects.

Administration of the disclosed compounds can be accomplished via any mode of administration for therapeutic agents.

Another aspect of the disclosure is directed to pharmaceutical compositions comprising a chemical entity chosen from compounds of Formula (I), and pharmaceutically acceptable salts, solvates, prodrugs, stereoisomers, and tautomers thereof and a pharmaceutically acceptable carrier. The pharmaceutical acceptable carrier may further include an excipient, diluent, or surfactant.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Non-limiting examples of compounds according to Formulae (I)-(VII) of the disclosure include those of Tables 9-25 below.

Method of Synthesizing the Compounds

The compounds of the present disclosure can be prepared in a number of ways known to those skilled in the art of organic synthesis. The compounds of the present disclosure may be made by a variety of methods, including standard chemistry. Suitable synthetic routes are depicted in the Schemes provided herein. The compounds disclosed herein may be prepared by methods known in the art of organic synthesis as set forth in part by the following synthetic schemes. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds disclosed herein (including, e.g., compounds of Formula (I)).

The compounds described herein may be made from commercially available starting materials or synthesized using known organic, inorganic, and/or enzymatic processes. Those skilled in the art will recognize if a stereocenter exists in the compounds disclosed herein. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

By way of example, compounds of the present disclosure can be synthesized using the methods described below, together with synthetic methods known in the art of synthetic organic chemistry, or variations thereof as appreciated by those skilled in the art. Preferred methods include but are not limited to those methods described below. General procedures to prepare compounds of the instant invention are described in General Scheme 1. An appropriately substituted and protected bicyclic intermediate 1 can be reacted with an appropriately substituted protected amine intermediate 2 under palladium-catalyzed carbon-nitrogen coupling protocols using an appropriate palladium complex, ligand, and base (such as but not limited to: RuPhos $3^{rd}$ generation palladium precatalyst and cesium carbonate) in a suitable solvent such as toluene at an appropriate temperature (such as 100° C.) to afford intermediate 3. The protecting group 1 (PGj; typically a Cbz group) can be removed under suitable deprotection conditions (such as but not limited to: hydrogen (gas), with palladium on carbon in an appropriate solvent such as methanol, ethanol, or ethyl acetate) to afford amine intermediate 4. The suitably substituted amine intermediate 4 can be reacted with a suitably substituted carboxylic acid under amide coupling conditions (such as but not limited to: the coupling reagents EDC and HOBt with an appropriate base such as $Et_3N$ or DIEA in a solvent such as DMF or DMA) to afford the penultimate amide intermediate 5. The protecting group 2 ($PG_2$; typically a boc group) can be removed under appropriate conditions such as TFA in a solvent such as DCM or HCl in a solvent such as MeOH or dioxane to afford the final compounds 6. The final compounds can be typically purified by preparative HPLC and isolated as the free base. In the case where mixtures of enantiomers and/or diastereomers are formed, the individual stereoisomers can be purified at an appropriate stage, in many cases by chiral HPLC.

General Scheme 1

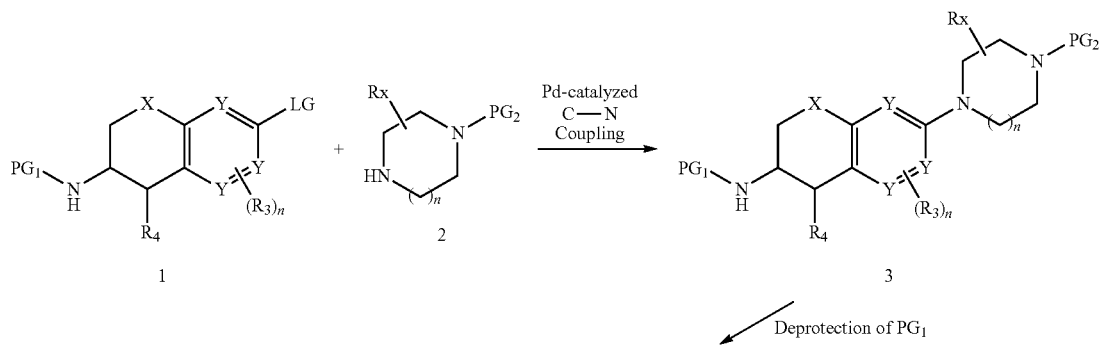

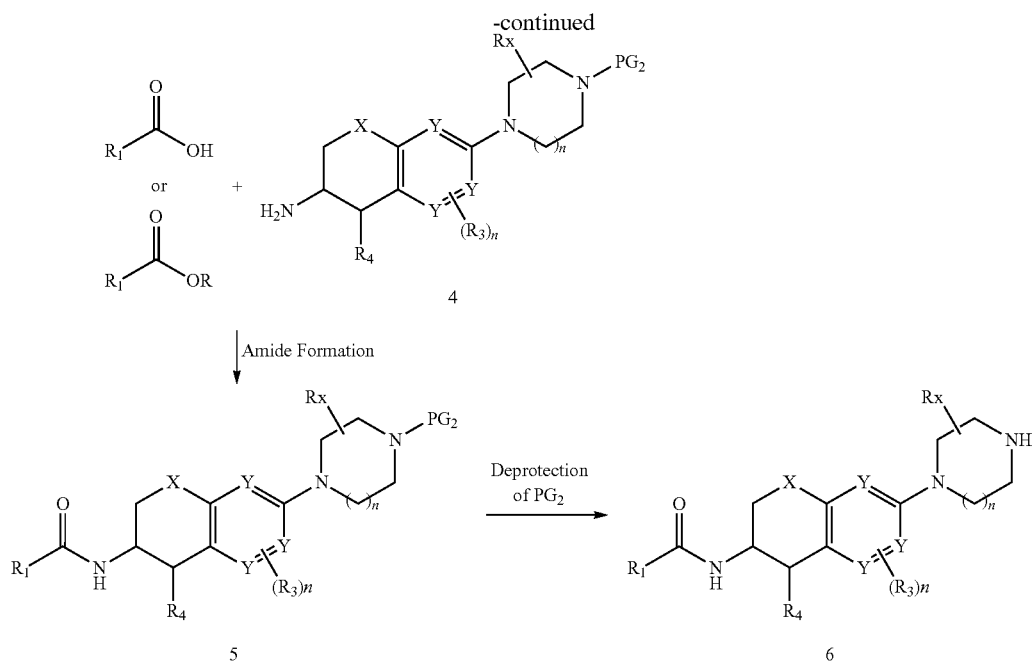

General Methods for the Preparation of Selected Intermediates

General procedures to prepare intermediates of the instant invention are described in Intermediate General Scheme 1. An appropriately substituted leaving group containing starting material 1 (LG$_1$; typically a bromide) can be reacted with the lithiated chiral auxiliary 2 (formed by reacting 2 with a strong base such as nBuLi) in an appropriate solvent such as THF at low temperature (typically −78° C.) to afford intermediate 3. Hydrolysis to remove the auxiliary under conditions such as aqueous HCl in a solvent such as acetonitrile, followed by reduction (typically using NaBH$_4$ in a solvent such as MeOH) can afford amino alcohol 4. Amino alcohol 4 can be cyclized using a strong base such as NaH in a solvent such as DMSO at low temperature (typically −70° C.) to afford Intermediate 4. Addition of an appropriate protecting group (PG$_1$; typically a CBz group) to the corresponding intermediate can result in an appropriately substituted bicyclic intermediate 5.

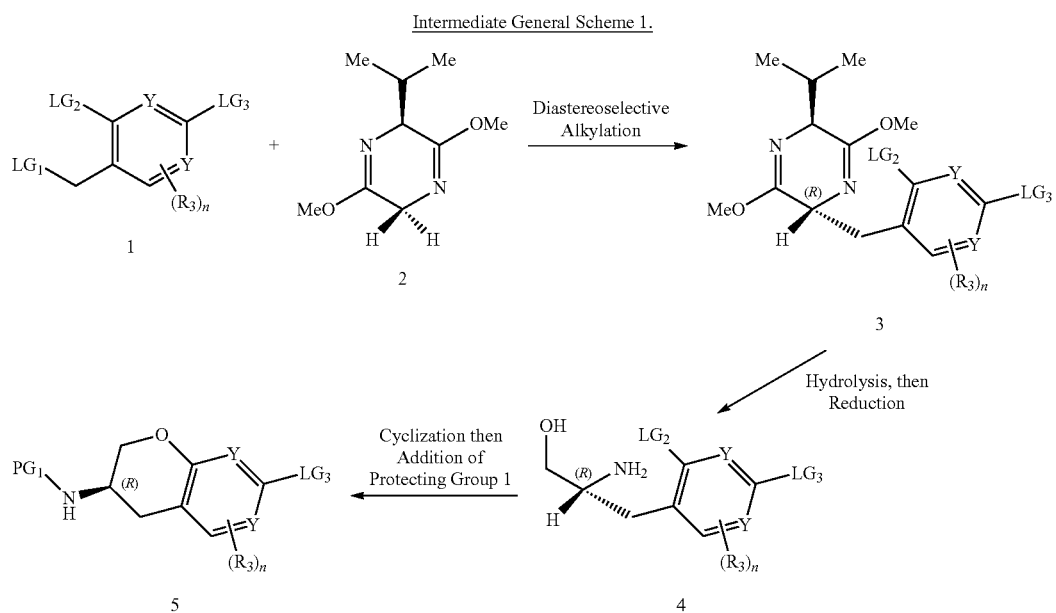

Intermediate General Scheme 1.

General procedures to prepare intermediates of the instant invention are described in Intermediate General Scheme 2. An appropriately substituted ketone 1 can be reacted under reductive amination conditions (typically with ammonium acetate as the amine source, NaBH$_3$CN as the reductant, and a solvent such as MeOH) to afford the amine intermediate 2. Amine 2 is then protected (PG$_1$; typically a CBz group) to afford the appropriately substituted intermediate 3.

Intermediate General Scheme 2.

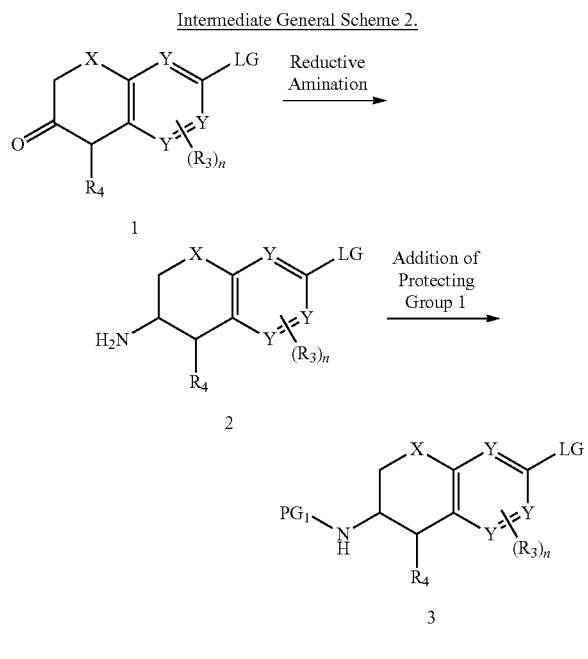

General procedures to prepare intermediates of the instant invention are described in Intermediate General Scheme 3. Acid chloride 1 can be reacted under a lewis acid promoted ethylene addition (typically using AlCl$_3$ and ethylene gas in a solvent such as DCM) to afford ketone 2. Ketone 2 can then either be converted to an oxime then reduced (using O-Methylhydroxylamine hydrochloride, pyridine and EtOH to form the oxime; reduction using hydrogen gas, Raney Ni in EtOH solvent) or reacted under reductive amination conditions (typically with ammonium acetate as the amine source, NaBH$_3$CN as the reductant, and a solvent such as MeOH) to afford amine 3. Amine 3 can be then protected (PG$_1$; typically a CBz group) to afford the appropriately substituted intermediate 4.

General procedures to prepare intermediates of the instant invention are described in Intermediate General Scheme 4. 2-Pyridone 2 can be obtained by the Michael addition of enamino ketone (typically generated in situ by treatment of a mono-protected cyclohexane-1,4-dione such as 1 with ammonia in methanol) with propynoic ester. Pyridone 2 can be converted to incorporate a leaving group (LG; typically a triflate group which can be obtained by treatment with triflic anhydride in the presence of a base, such as triethylamine). Following removal of the ketone protecting group, ketone 4 can then be reacted under reductive amination conditions (typically with ammonium acetate as the amine source, NaBH$_3$CN as the reductant, and a solvent such as MeOH) to afford amine 5. Amine 5 can be then protected (PG$_1$; typically a Cbz group) to afford the appropriately substituted intermediate 6.

Intermediate General Scheme 4.

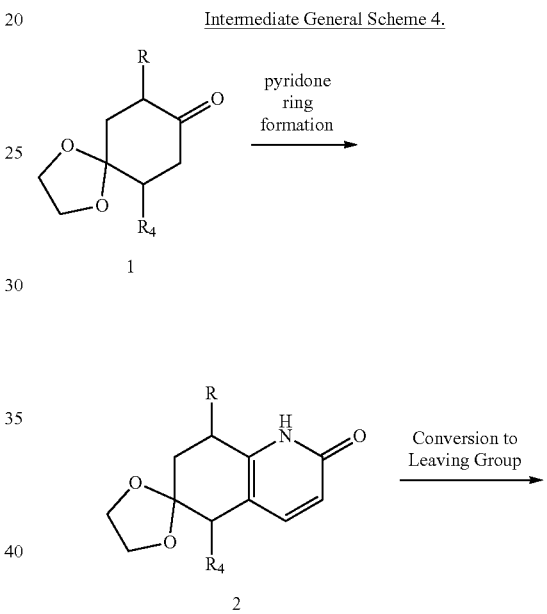

Intermediate General Scheme 3.

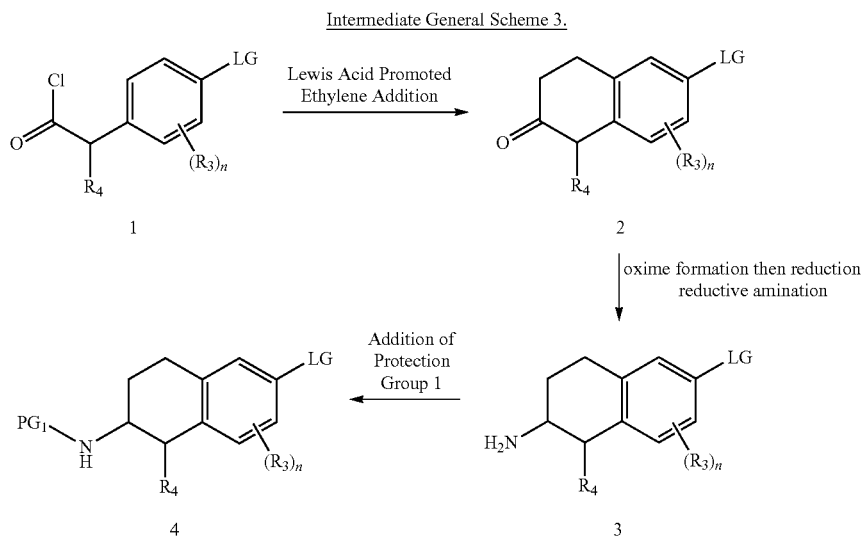

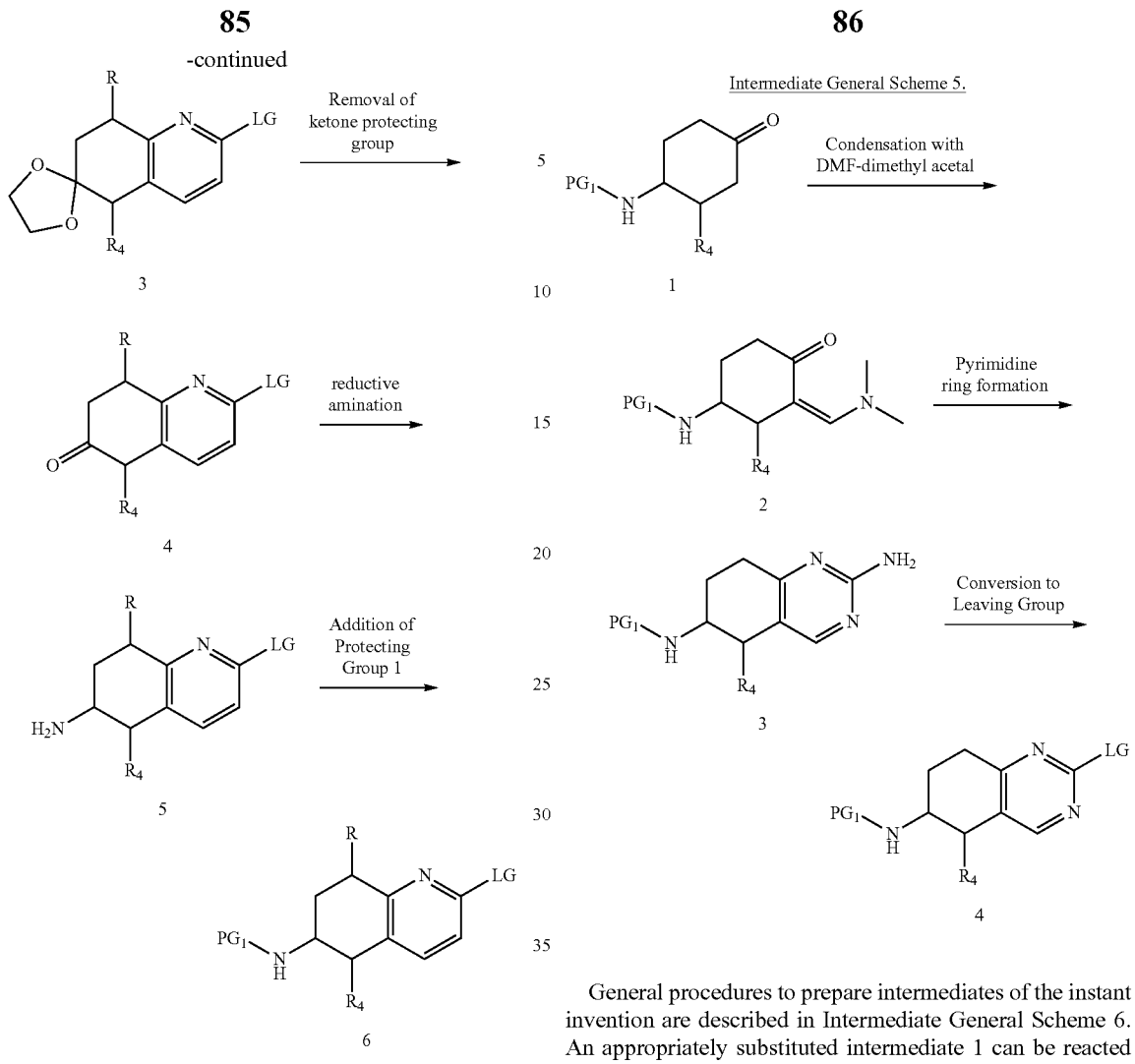

General procedures to prepare intermediates of the instant invention are described in Intermediate General Scheme 5. Ketone 1 can be condensed with dimethyl-formamide dimethyl acetal in a solvent (such as toluene) to provide enamino ketone 2. Ketone 2 can be treated with quinidine and a base (such as sodium ethoxide) to provide pyrimidin-2-amine 3. Pyrimidin-2-amine 3 can be converted to incorporate a leaving group (LG; typically a chloride group which can be obtained by treatment with CuCl$_2$ and tert-butyl nitrite) to afford the appropriately substituted intermediate 4.

General procedures to prepare intermediates of the instant invention are described in Intermediate General Scheme 6. An appropriately substituted intermediate 1 can be reacted with an appropriately substituted boronic ester 2 (or boronic acid) under palladium catalyzed carbon-carbon bond forming conditions (using an appropriate palladium catalyst such as Pd(dppf)Cl$_2$ dichloromethane complex) in a solvent such as 1,4-dioxane/water mixture, and a base such as potassium carbonate at a temperature such as 100° C.) to afford the coupled intermediate 3. The olefin double bond present in intermediate 3 can then be functionalized using standard methods such as but not limited to: olefin reduction and epoxidation followed by reduction of the resultant epoxide to afford an appropriately substituted intermediate 4.

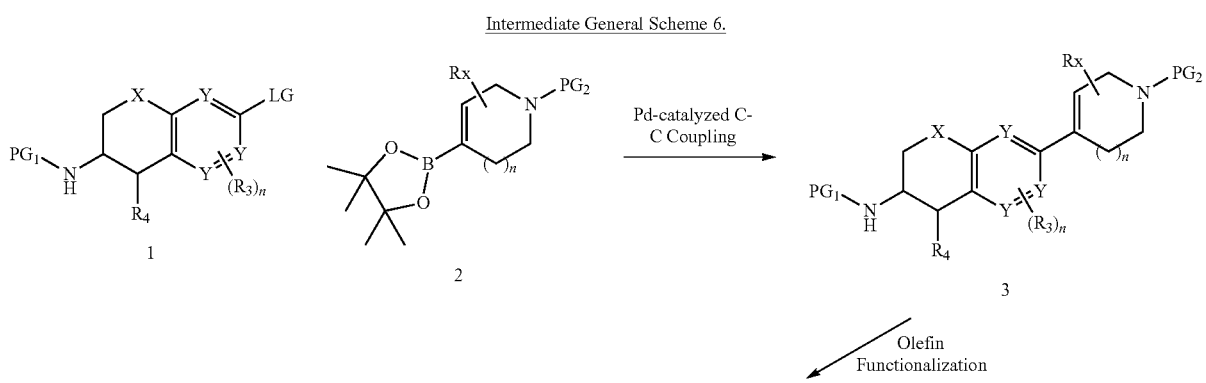

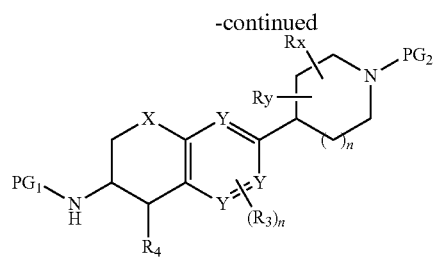

General procedures to prepare intermediates of the instant invention are described in Intermediate General Scheme 7. An appropriately substituted intermediate 1 can be reacted under palladium-catalyzed boronic ester forming conditions (using a palladium catalyst such as Pd(dppf)Cl$_2$—CH$_2$Cl$_2$ complex and a boronic ester source such as Bis(pinacolato) diboron in a solvent such as dioxane at a temperature such as 80° C.) to afford the boronic ester 2. Boronic ester 2 can be reacted in the presence of a suitable oxidant (such as urea-hydrogen peroxide complex in a solvent such as MeOH) to afford the phenol intermediate 3. The phenol intermediate can then be alkylated with a suitable electrophile (for example by using Mitsonobu-type conditions: such as DIAD with PPh$_3$) to afford the appropriately substituted intermediate 4.

those skilled in the art without departing from the spirit of the present disclosure and/or scope of the appended claims.

Analytical Methods, Materials, and Instrumentation

Unless otherwise noted, reagents and solvents were used as received from commercial suppliers. Unless otherwise noted, reactions were conducted under an inert atmosphere of nitrogen. Proton nuclear magnetic resonance (NMR) spectra were obtained on either Bruker or Varian spectrometers at 300 or 400 MHz. Spectra are given in ppm (δ) and coupling constants, J, are reported in Hertz. Tetramethylsilane (TMS) was used as an internal standard. Purity and mass spectral data were measured using one of the two following methods. Method 1: Waters Acquity i-class ultra-performance liquid chromatography (UPLC) system with Acquity Photo Diode Array Detector, Acquity Evaporative

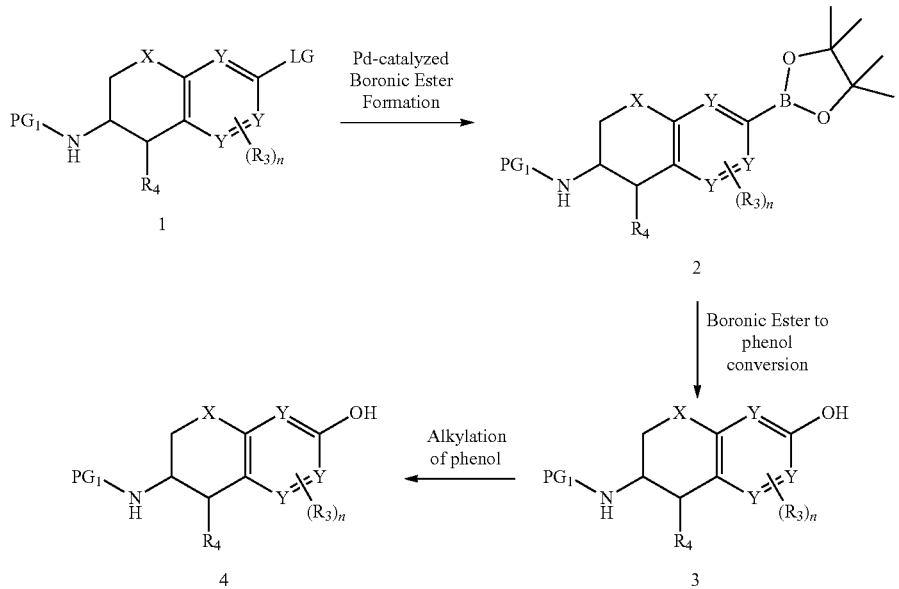

Intermediate General Scheme 7.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 m 2.1×50 mm; Flow Rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 min and 5% B at 2.21 min). Method 2: SHIMADZU LCMS consisting of an UFLC 20-AD and LCMS 2020 MS detector. (Column: Shim-pack XR-ODS, 2.2 m, 3.0×50 mm; Solvent: (acetonitrile/water, containing 0.05% $NH_4HCO_3$)). Preparatory HPLC purifications were conducted as designated below with a Flow Rate of 20 mL/min and detection by UV wavelength 220 nm and 254 nm, unless otherwise noted. The absolute configuration of the separated enantiomers of the compounds in the examples described herein was occasionally determined. In all other cases the absolute configuration of the separated enantiomers was not determined and in those instances the configuration of the resolved materials were arbitrarily assigned as R or S in each case.

Abbreviations Used in the Following Examples and Elsewhere Herein are

| Abbr | Name |
| --- | --- |
| ACN | acetonitrile |
| atm | atmospheres |
| Boc | t-butoxycarbonyl |
| BOP | (benzotriazol-1-yloxy)tris(dimethylamino)-phosphonium hexafluorophosphate |
| CbzCl | benzyl chloroformate |
| $CDCl_3$ | deuterated chloroform |
| $CH_2Cl_2$ | methylene chloride, dichloromethane |
| CO (g) | carbon monoxide gas |
| $Cs_2CO_3$ | cesium carbonate |
| DAST | diethylaminosulfur trifluoride |
| DBU | 1,8-diazabicyclo[5.4.0]undec-7-ene |
| DCM | methylene chloride, dichloromethane |
| DIEA | diisopropylethylamine |
| DMA | N,N-dimethylacetamide |
| DMF | N,N-dimethylformamide |
| DMSO | dimethylsulfoxide |
| DPPA | diphenylphosphoryl azide |
| EDCI | 1-ethyl-3-(3-dimethylaminopropyl)carbodiimide |
| ESI | electrospray ionization |
| $Et_2O$ | diethyl ether |
| $Et_3N$ | triethylamine |
| EtOAc | ethyl acetate |
| EtOH | ethanol |
| h | hours |
| $H_2O$ | water |
| HATU | 1-[bis(dimethylamino)methylene]-1H-1,2,3-triazolo[4,5-b]pyridinium 3-oxid hexafluorophosphate |
| HBTU | N,N,N',N'-tetramethyl-O-(1H-benzotriazol-1-yl)uronium hexafluorophosphate |
| HCl | hydrochloric acid |
| HMTA | hexamethylenetetramine |
| HOBt | hydroxybenzotriazole |
| IPA | isopropanol |
| $K_2CO_3$ | potassium carbonate |
| LDA | lithium diisopropylamide |
| m-CPBA | 3-chloroperbenzoic acid |
| MeOH | methanol |
| $MgSO_4$ | magnesium sulfate |
| min | minutes |
| MS | mass spectrometry |
| MsCl | methanesulfonyl chloride |
| MTBE | methyl tert-butyl ether |
| $Na_2CO_3$ | sodium carbonate |
| $Na_2SO_4$ | sodium sulfate |
| NaH | sodium hydride |
| $NaHCO_3$ | sodium bicarbonate |
| NaOH | sodium hydroxide |
| NBS | N-bromosuccinimide |
| $NH_2OH \cdot HCl$ | hydroxylamine hydrochloride |
| $NH_4Cl$ | ammonium chloride |
| $NH_4HCO_3$ | ammonium bicarbonate |
| $NH_4OH$ | ammonium hydroxide |
| NMP | N-methyl-2-pyrrolidone |
| NMR | nuclear magnetic resonance |
| $Pd_2(dba)_3$ | tris(dibenzylideneacetone)dipalladium(0) |

-continued

| Abbr | Name |
| --- | --- |
| $Pd(dppf)Cl_2$ | [1,1'-bis(diphenylphosphino)ferrocene]-dichloropalladium(II) |
| $Pd(dppf)Cl_2$-$CH_2Cl_2$ | [1,1'-bis(diphenylphosphino)ferrocene]-dichloropalladium(II)-DCM adduct |
| Pd/C | palladium on carbon |
| $Pd(OAc)_2$ | palladium(II) acetate |
| pet. ether | petroleum ether |
| prep-HPLC | preparatory high pressure liquid chromatography |
| prep-TLC | preparatory thin layer chromatography |
| PTSA | p-Toluenesulfonic acid |
| RT | retention time |
| RuPhos | 2-dicyclohexylphosphino-2',6'-diisopropoxybiphenyl |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| SFC | supercritical fluid chromatography |
| TBS | tert-butyl(dimethyl)silyl |
| t-BuOH | tert-butanol |
| t-BuOK | potassium tert-butoxide |
| t-BuXPhos | methanesulfonato(2-di-t-butylphosphino-2',4',6'-tri-i-propyl-1,1'-biphenyl)(2'-methylamino-1,1'-biphenyl-2-yl)palladium(II) |
| Pd G4 | DCM adduct |
| TEDA | triethylenediamine |
| TFA | trifluoroacetic acid |
| TFAA | trifluoroacetic anhydride |
| THF | THF |
| XPhos Pd G3 | (2-dicyclohexylphosphino-2',4',6'-triisopropyl-1,1'-biphenyl)[2-(2'-amino-1,1'-biphenyl)]palladium(II) methanesulfonate |

Preparation of Intermediates

Intermediates 1, 2, and 3. Benzyl (7-bromochroman-3-yl)carbamate, Benzyl (R)-(7-bromochroman-3-yl)carbamate, and Benzyl (S)-(7-bromochroman-3-yl)carbamate

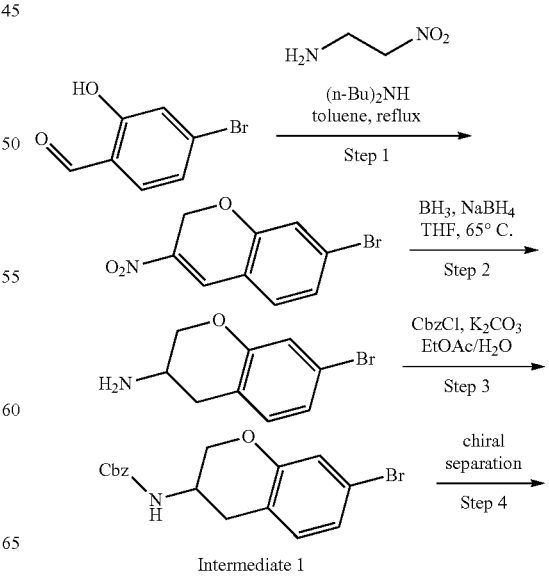

Intermediate 1

-continued

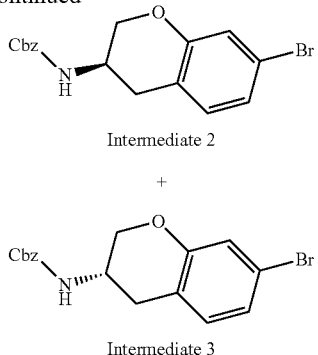

Step 1. 7-Bromo-3-nitro-2H-chromene

A mixture of 4-bromo-2-hydroxybenzaldehyde (21.6 g, 108 mmol), 1,3-dihydro-2-benzofuran-1,3-dione (32 g, 216 mmol) and dibutylamine (7.0 g, 54 mmol) in toluene (800 mL) was heated to reflux under an atmosphere of $N_2$. 2-Nitroethan-1-amine (50 g, 550 mmol) was added in portions over 2 h. The mixture was stirred at reflux overnight using a Dean-Stark apparatus. After cooling to room temperature, the solids were filtered out. Eight batches were thus run in parallel and the filtrate from the eight batches were combined and concentrated under vacuum. The residue was diluted with EtOAc (2 L) and washed with 1N NaOH (2 L). The organic layer was dried over anhydrous $Na_2SO_4$, filtered, and concentrated under vacuum. Purification by silica gel chromatography (eluting with 1:6 EtOAc/pet. ether) afforded 7-bromo-3-nitro-2H-chromene as a yellow solid. MS: (ESI, m/z): 256, 258 [M+H]$^+$.

Step 2. 7-Bromochroman-3-amine

To a solution of 7-bromo-3-nitro-2H-chromene (27 g, 106 mmol) in THF (300 mL) were added $BH_3$ (1M in THF, 600 mL, 600 mmol) and $NaBH_4$ (201 mg, 5.3 mmol). The mixture was stirred overnight at 65° C. After cooling to room temperature, the reaction was then quenched by the addition of 600 mL of MeOH and stirred for 8 h at 80° C. After cooling to room temperature, the mixture was concentrated under vacuum. The residue was purified by reverse phase chromatography (Column: C18 silica gel; Mobile phase A: water (10 mM $NH_4HCO_3$), B: ACN; Gradient: 0% to 50% B over 40 min) to afford 7-bromochroman-3-amine as a white solid. MS: (ESI, m/z): 228, 230 [M+H]$^-$.

Step 3. Benzyl (7-bromochroman-3-yl)carbamate (Intermediate 1)

A solution of $K_2CO_3$ (19.3 g, 140 mmol) in water (150 mL) was added to a solution of 7-bromochroman-3-amine (16.0 g, 70.1 mmol) in EtOAc (300 mL). Benzyl chloroformate (17.8 g, 104 mmol) was added at −10° C. and the reaction mixture was stirred for 30 min at room temperature. The mixture was diluted with EtOAc (200 mL). The organic layer was collected, dried over anhydrous $Na_2SO_4$, filtered, and concentrated under vacuum. The residue was washed with 1:1 EtOAc/pet. ether (200 mL) to give benzyl-(7-bromochroman-3-yl)carbamate as a white solid. MS: (ESI, m/z): 362, 364 [M+H]$^+$.

Step 4. Benzyl (R)-(7-bromochroman-3-yl)carbamate (Intermediate 2) and Benzyl (S)-(7-bromochroman-3-yl)carbamate (Intermediate 3)

The racemate benzyl (7-bromochroman-3-yl)carbamate (12.5 g, 34.6 mmol) was separated by SFC (Column: ChiralArt Amylose-SA, 2×25 cm, 5 μm; Mobile phase A: $CO_2$, 80%, B: EtOH, 20%; Flow rate: 40 mL/min) to afford the title compounds as follows: benzyl (R)-(7-bromochroman-3-yl)carbamate (first eluting isomer, RT=7.98 min) as a white solid and benzyl (S)-(7-bromochroman-3-yl)carbamate (second eluting isomer, RT=9.21 min) as a white solid.

First eluting isomer: $^1$H NMR (CDCl$_3$, 400 MHz) δ (ppm): 7.35-7.32 (m, 5H), 7.03-7.01 (m, 2H), 6.90 (d, J=8.8 Hz, 1H), 5.22-5.10 (m, 3H), 4.25 (s, 1H), 4.17-4.09 (m, 2H), 3.04 (dd, J=16.8 Hz, 4.8 Hz, 1H), 2.73 (d, J=16.8 Hz, 1H). MS: (ESI, m/z): 362, 364 [M+H]$^+$.

Second eluting isomer: $^1$H NMR (CDCl$_3$, 400 MHz) δ(ppm): 7.35-7.32 (m, 5H), 7.03-7.01 (m, 2H), 6.90 (d, J=8.8 Hz, 1H), 5.22-5.07 (m, 3H), 4.25 (s, 1H), 4.18-4.09 (m, 2H), 3.04 (dd, J=16.8 Hz, 4.8 Hz, 1H), 2.73 (d, J=16.80 Hz, 1H). MS: (ESI, m/z): 362, 364 [M+H]$^-$.

Intermediate 4-1. tert-Butyl 4-(3-amino-8-fluoro-chroman-7-yl)piperazine-1-carboxylate

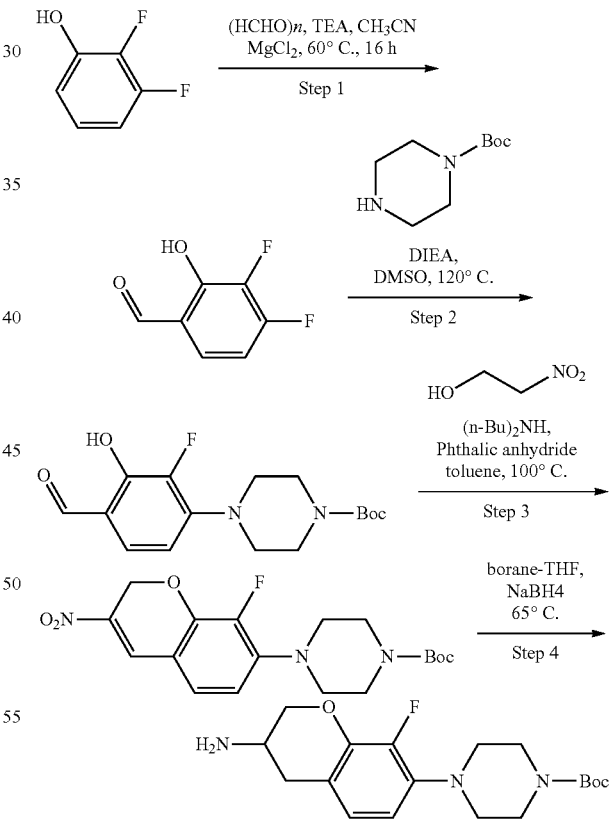

Step 1. 3,4-Difluoro-2-hydroxybenzaldehyde

Into a 500-mL round-bottom flask purged and maintained with an inert atmosphere of nitrogen was added a 2,3-difluorophenol (10.0 g, 75.33 mmol), ACN (200 mL), HCHO (23.06 g, 738 mmol), Et$_3$N (21.0 mL, 146 mmol), and $MgCl_2$ (14.6 g, 150.28 mmol). The resulting solution was stirred for 16 h at 60° C. The reaction mixture was cooled to 26° C., then was diluted with 200 mL of water. The resulting solution was extracted with ethyl acetate (3×100 mL). The organic layers were combined, dried over anhydrous sodium sulfate, filtered, and concentrated under vacuum to afford a residue that was purified by silica gel chromatography with ethyl acetate/pet. ether (1:4) to afford 3,4-difluoro-2-hydroxybenzaldehyde as light yellow oil.

Step 2. tert-Butyl 4-(2-fluoro-4-formyl-3-hydroxyphenyl)piperazine-1-carboxylate Into a 250-mL round-bottom flask was added 3,4-difluoro-2-hydroxybenzaldehyde (5 g, 31.63 mmol), tert-butyl piperazine-1-carboxylate (5.9 g, 31.68 mmol), DMSO (100 mL), and DIEA (6.1 g, 47.20 mmol). The resulting solution was stirred for 6 h at 120° C. After cooling to room temperature, the reaction was then quenched by the addition of 100 mL of water. The resulting solution was extracted with ethyl acetate (3×100 mL). The organic layers were combined, dried over anhydrous sodium sulfate, filtered, and concentrated under vacuum to afford a residue that was purified by silica gel chromatography with ethyl acetate/pet. ether (0-30%) to afford tert-butyl 4-(2-fluoro-4-formyl-3-hydroxyphenyl)piperazine-1-carboxylate as yellow oil.

Step 3. tert-Butyl 4-(8-fluoro-3-nitro-2H-chromen-7-yl)piperazine-1-carboxylate Into a 100-mL round-bottom flask was added tert-butyl 4-(2-fluoro-4-formyl-3-hydroxyphenyl)piperazine-1-carboxylate (185 mg, 0.48 mmol), 1,3-dihydro-2-benzofuran-1,3-dione (166 mg, 1.06 mmol, 95%), 2-nitroethan-1-ol (104 mg, 1.08 mmol), dibutylamine (37 mg, 0.27 mmol), and toluene (10 mL). The resulting solution was stirred for 8 h at 100° C. in an oil bath. The reaction mixture was cooled to room temperature, then was quenched by addition of 5 mL water, and extracted with DCM (3×10 mL). The organic layers were combined, washed with brine (3×10 mL), dried over anhydrous sodium sulfate, filtered, and concentrated under vacuum to afford a residue that was purified by a silica gel chromatography with ethyl acetate/pet. ether (1:3) to afford tert-butyl 4-(8-fluoro-3-nitro-2H-chromen-7-yl)piperazine-1-carboxylate as a red solid.

Step 4. tert-Butyl 4-(3-amino-8-fluorochroman-7-yl)piperazine-1-carboxylate

Into a 100-mL 3-necked round-bottom flask purged and maintained with an inert atmosphere of nitrogen, was added tert-butyl 4-(8-fluoro-3-nitro-2H-chromen-7-yl)piperazine-1-carboxylate (150 mg, 0.39 mmol), and THF (20 mL). Borane-THF complex (4 mL, 4 mmol) was added dropwise with stirring at 0° C. To this reaction mixture was added $NaBH_4$ (73 mg, 1.93 mmol). The resulting solution was stirred for 12 h at 65° C., then was quenched by the addition of methanol (20 mL), and concentrated under vacuum to afford a residue that was purified by silica gel chromatography with ethyl acetate/pet. ether (0-100%) to afford tert-butyl 4-(3-amino-8-fluoro-3,4-dihydro-2H-1-benzopyran-7-yl)piperazine-1-carboxylate as yellow oil.

The following intermediate in Table 1 was prepared using standard chemical manipulations and procedures similar to those used for the preparation of Intermediate 4-1.

TABLE 1

| Intermediate Number | Structure and Compound Name | LRMS m/z [M + H]+ |
|---|---|---|
| 4-2[1] | 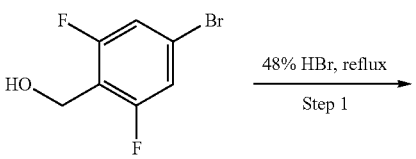<br>tert-Butyl 4-(3-amino-6-fluorochroman-7-yl)piperazine-1-carboxylate | 352 |

[1]Notes on procedures:
Step 1 was not necessary.

Intermediate 5-1. Benzyl (R)-(7-bromo-5-fluorochroman-3-yl)carbamate

Method 1

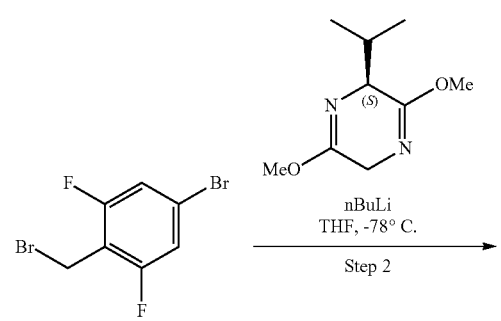

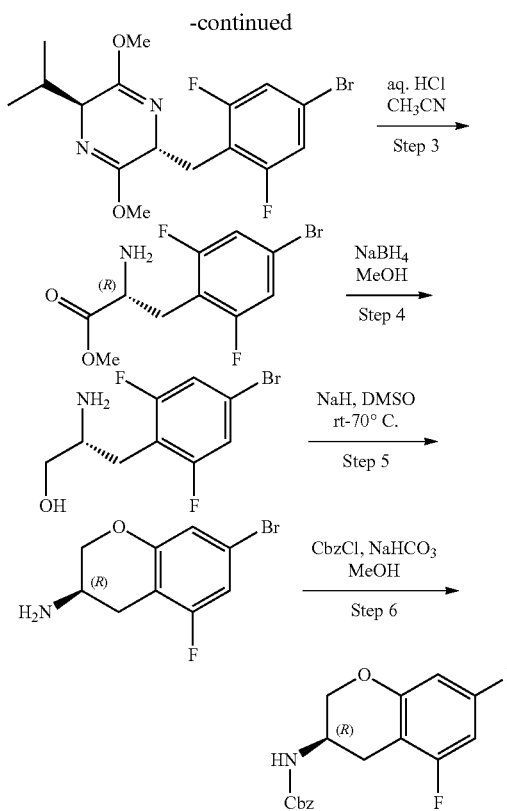

Step 1.
5-Bromo-2-(bromomethyl)-1,3-difluorobenzene

A mixture of 48% HBr (130 mL, 1149 mmol) and (4-bromo-2,6-difluorophenyl)methanol (40 g, 179 mmol) was heated to reflux overnight. After cooling to room temperature, the reaction mixture was poured into 80 mL of water and was extracted with hexanes (2×300 mL). The combined organic layers were washed with sodium bicarbonate solution, dried over MgSO$_4$, filtered, and concentrated to afford 5-bromo-2-(bromomethyl)-1,3-difluorobenzene. $^1$H NMR (CDCl$_3$, 300 MHz) δ(ppm): 6.94-7.22 (m, 2H), 4.46 (s, 2H).

Step 2. (2R,5S)-2-(4-bromo-2,6-difluorobenzyl)-5-isopropyl-3,6-dimethoxy-2,5-dihydropyrazine A solution of nBuLi (6.78 mL, 10.86 mmol, 1.6 M) in hexanes was added dropwise to a solution of (S)-2-isopropyl-3,6-dimethoxy-2,5-dihydropyrazine (2.0 g, 10.86 mmol) in 20 mL of THF at −78° C. After stirring for 30 min at −78° C., a solution of 5-bromo-2-(bromomethyl)-1,3-difluorobenzene (3.10 g, 10.86 mmol) in 10 mL of THF was added and the reaction mixture was stirred at −78° C. for 3 h. Then 20 mL of saturated NH$_4$Cl solution was added. After the reaction mixture was warmed to room temperature, 150 mL of water was added and the mixture was extracted with EtOAc three times. The combined organic layers were dried over MgSO$_4$, filtered, and concentrated. Purification by silica gel chromatography (eluting with 0 to 15% EtOAc/Hexanes) afforded (2R,5S)-2-(4-bromo-2,6-difluorobenzyl)-5-isopropyl-3,6-dimethoxy-2,5-dihydropyrazine. $^1$H NMR (CDCl$_3$, 300 MHz) δ(ppm): 7.03 (d, J=7.04 Hz, 2H), 4.14-4.32 (m, 1H), 3.71 (s, 3H), 3.58 (s, 3H), 3.13-3.33 (m, 1H), 2.79-2.93 (m, 1H), 2.13-2.33 (m, 1H), 1.00 (d, J=7.04 Hz, 3H), 0.64 (d, J=7.04 Hz, 3H). MS: (ESI, m/z): 389, 391 [M+H]$^+$.

Step 3. Methyl (R)-2-amino-3-(4-bromo-2,6-difluorophenyl)propanoate

A solution of (2R,5S)-2-(4-bromo-2,6-difluorobenzyl)-5-isopropyl-3,6-dimethoxy-2,5-dihydropyrazine (3.1 g, 8.02 mmol) in acetonitrile (60 mL) was treated with HCl (53.5 ml, 16.04 mmol, 0.3 N). The reaction mixture was stirred at room temperature for 60 min. The reaction was made basic with sat. aq. NaHCO$_3$ solution and the mixture was extracted with CH$_2$Cl$_2$ three times. The combined organic layers were dried over MgSO$_4$, filtered, and concentrated. Purification by silica gel chromatography (eluting with 0 to 100% EtOAc/Hexanes) afforded methyl (R)-2-amino-3-(4-bromo-2,6-difluorophenyl)propanoate. $^1$H NMR (CDCl$_3$, 300 MHz) δ(ppm): 7.07 (d, J=6.74 Hz, 2H), 3.54-3.80 (m, 4H), 3.01-3.24 (m, 1H), 2.93 (s, 1H), 1.62 (br s, 2H). MS: (ESI, m/z): 294, 296 [M+H]$^-$.

Step 4. (R)-2-amino-3-(4-bromo-2,6-difluorophenyl)propan-1-ol

To a solution of methyl (R)-2-amino-3-(4-bromo-2,6-difluorophenyl)propanoate (2.3 g, 7.85 mmol) in MeOH (70 mL) at room temperature was added NaBH$_4$ (1.043 g, 27.57 mmol) in portions. The mixture was stirred at room temperature overnight. Water was added and the MeOH was removed under reduced pressure. The aqueous mixture was extracted with chloroform three times. The combined organic layers were dried over Na$_2$SO$_4$, filtered, and concentrated to afford (R)-2-amino-3-(4-bromo-2,6-difluorophenyl)propan-1-ol. $^1$H NMR (CDCl$_3$, 300 MHz) δ(ppm): 7.08 (d, J=6.74 Hz, 2H), 3.54-3.72 (m, 1H), 3.36 (dd, J=10.55, 7.62 Hz, 1H), 3.09 (br s, 1H), 2.51-2.86 (m, 2H), 1.74 (br s, 3H). MS: (ESI, m/z): 266, 268 [M+H]$^-$.

Step 5. (R)-7-bromo-5-fluorochroman-3-amine

To a solution of (R)-2-amino-3-(4-bromo-2,6-difluorophenyl)propan-1-ol (500 mg, 1.88 mmol) in DMSO (3 mL) at room temperature was added NaH (113 mg, 2.82 mmol). The mixture was stirred at room temperature for 30 min, then at 70° C. for 30 min, and kept stirring at 50° C. overnight. After cooling to room temperature, 30 mL of water, and the mixture was extracted with EtOAc three times. The combined organic layers were washed with water, dried over Na$_2$SO$_4$, filtered, and concentrated to afford crude (R)-7-bromo-5-fluorochroman-3-amine. $^1$H NMR (CDCl$_3$, 300 MHz) δ(ppm): 6.61-6.92 (m, 2H), 4.01-4.32 (m, 1H), 3.67-3.88 (m, 1H), 3.35 (ddt, J=7.00, 3.19, 1.80, 1.80 Hz, 1H), 2.79-3.03 (m, 1H), 2.46 (br d, J=6.74 Hz, 1H), 1.40-1.89 (m, 2H). MS: (ESI, m/z): 246, 248 [M+H]$^-$.

Step 6. Benzyl (R)-(7-bromo-5-fluorochroman-3-yl)carbamate

To a solution of (R)-7-bromo-5-fluorochroman-3-amine (467 mg, 1.90 mmol) and saturated solution of sodium hydrogen carbonate (10 mL) in MeOH (20 mL) at 0° C. was added benzyl chloroformate (0.405 mL, 2.85 mmol) dropwise. The mixture was stirred overnight, allowing the temperature to warm to room temperature. 20 mL of water was added and the mixture was extracted with EtOAc three times. The combined organic layers were washed with water, dried over Na$_2$SO$_4$, filtered, and concentrated. Purification by silica gel chromatography (eluting with 7% to 60% EtOAc/Hexanes) afforded benzyl (R)-(7-bromo-5-fluorochroman-3-yl)carbamate. $^1$H NMR (CDCl$_3$, 300 MHz) δ(ppm): 7.34 (s, 5H), 6.65-6.97 (m, 2H), 5.10 (s, 2H), 4.90-5.08 (m, 1H), 4.26 (br s, 1H), 3.97-4.21 (m, 3H), 2.89 (m, 1H), 2.78 (m, 1H). MS: (ESI, m/z): 380, 382 [M+H]$^-$.

Intermediate 5-1. Benzyl (R)-(7-bromo-5-fluorochroman-3-yl)carbamate

Method 2

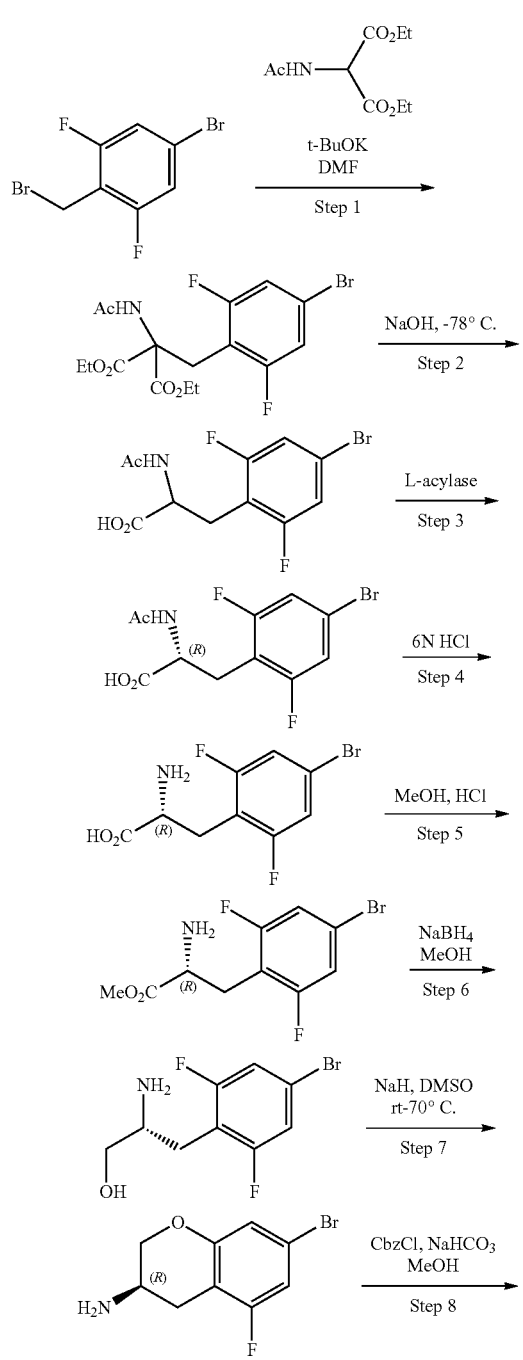

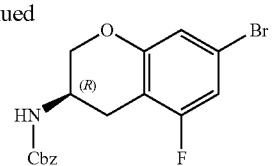

Step 1. Diethyl 2-acetamido-2-(4-bromo-2,6-difluorobenzyl)malonate

To a stirred solution of diethyl 2-acetamidomalonate (59.2 g, 0.273 mol) in DMF (500 mL) was added t-BuOK (33.1 g, 0.295 mol) in portions at room temperature. The mixture was stirred at room temperature for 1 h and 5-bromo-2-(bromomethyl)-1,3-difluorobenzene (65.0 g, 0.227 mol) was added. The reaction mixture was stirred at room temperature for 3 h. Water (2000 mL) was added slowly and the mixture was stirred for 1 h. The resulting precipitate was collected by filtration, washed with water (3×250 mL) and dried under vacuum to give diethyl 2-acetamido-2-(4-bromo-2,6-difluorobenzyl)malonate as an off-white solid.

Step 2. 2-Acetamido-3-(4-bromo-2,6-difluorophenyl)propanoic acid

To a stirred solution of diethyl 2-acetamido-2-(4-bromo-2,6-difluorobenzyl)malonate (80 g, 0.189 mol) in ethanol (500 mL) was added a solution of NaOH (30 g, 0.758 mol) in water (500 mL). The reaction mixture was heated at reflux for 5 h and then cooled to room temperature. The mixture was adjusted to pH=5-6 with 2N aqueous HCl and heated at reflux overnight. The mixture was cooled to room temperature and adjusted to pH=8-9 with 10% aqueous NaOH. The resulting mixture was washed with MTBE (300 mL) and the aqueous phase was adjusted to pH 2-3 with 2N aqueous HCl and then extracted with EtOAc (500 mL×2). The combined extracts were washed with brine (300 mL), dried over anhydrous Na$_2$SO$_4$, filtered, and concentrated to dryness. The residue was treated with a mixture of EtOAc (100 mL) and pet. ether (150 mL) under stirring for 1 h. The resulting precipitate was collected by filtration, washed with pet. ether and dried under vacuum to give 2-acetamido-3-(4-bromo-2,6-difluorophenyl)propanoic acid as a white solid. H NMR (DMSO-d$_6$, 400 MHz) δ(ppm): 12.86 (br s, 1H), 8.31 (br s, 1H), 7.43 (d, J=6.8 Hz, 2H), 4.43 (m, 1H), 3.08-2.87 (m, 2H), 1.77 (s, 3H). MS: (ESI, m/z): 322, 324 [M+H]$^+$.

Step 3. (R)-2-Acetamido-3-(4-bromo-2,6-difluorophenyl)propanoic acid

To a suspension of 2-acetamido-3-(4-bromo-2,6-difluorophenyl)propanoic acid (55 g, 0.171 mol) in distilled water (1.1 L) was added 10% aqueous NaOH dropwise to adjust pH to 8.5. The mixture was heated to 35-38° C. and L-acylase (11.0 g) was added. The reaction mixture was stirred at this temperature for 48 h while keeping the pH at 8.5 with 10% aqueous NaOH. The mixture was adjusted to pH 4-5 with 2N aqueous HCl and activated carbon (2 g) was added. The mixture was heated at 60° C. for 2 h and then cooled to room temperature. The mixture was adjusted to pH 9.5-10 with 10% aqueous NaOH and filtered. The filtrate was adjusted to pH 2-3 with 2N aqueous HCl and then extracted with EtOAc (400 mL×2). The combined extracts were washed with 0.5N aqueous HCl (200 mL×2) and brine (200 mL), dried over anhydrous Na$_2$SO$_4$, filtered, and concentrated to dryness. The residue was treated with a mixture of EtOAc (60 mL) and pet. ether (80 mL) under stirring for 1 h. The resulting precipitate was collected by filtration, washed with pet. ether and dried under vacuum to give (R)-2-acetamido-3-(4-bromo-2,6-difluorophenyl)propanoic acid as a white solid.

Step 4. (R)-2-Amino-3-(4-bromo-2,6-difluorophenyl)propanoic acid hydrochloride A mixture of (R)-2-acetamido-3-(4-bromo-2,6-difluorophenyl)propanoic acid (26 g, 80.7 mmol) in 6N aqueous HCl (260 mL) was heated under reflux for 5 h. The mixture was concentrated and the residue was dried under vacuum at 50° C. to provide crude (R)-2-amino-3-(4-bromo-2,6-difluorophenyl)propanoic acid hydrochloride as a white solid.

Step 5. (R)-Methyl 2-amino-3-(4-bromo-2,6-difluorophenyl)propanoate

To a solution of (R)-2-amino-3-(4-bromo-2,6-difluorophenyl)propanoic acid hydrochloride (25.4 g, 80.7 mmol) in MeOH (125 mL) was added MeOH/HCl (8M, 125 mL). The reaction mixture was stirred at room temperature overnight and concentrated to dryness. The residue was suspended in 5% aqueous Na$_2$CO$_3$ (250 mL) and then extracted with EtOAc (250 mL×2). The combined extracts were washed with brine, dried over anhydrous Na$_2$SO$_4$, filtered, and concentrated to give (R)-methyl 2-amino-3-(4-bromo-2,6-difluorophenyl)propanoate as an oil. $^1$H NMR (CDCl$_3$, 400 MHz) δ(ppm): 7.08 (m, 2H), 3.73 (s, 3H), 3.70 (m, 1H), 3.09-2.87 (m, 2H), 1.55 (br s, 2H). MS: (ESI, m/z): 294, 296 [M+H]$^+$.

Step 6. (R)-2-Amino-3-(4-bromo-2,6-difluorophenyl)propan-1-ol

To a stirred solution of (R)-methyl 2-amino-3-(4-bromo-2,6-difluorophenyl)propanoate (23.5 g, 79.9 mmol) in MeOH (500 mL) was added NaBH$_4$ (6.08 g, 159.9 mmol) portionwise. The reaction mixture was stirred at room temperature for 3 h and NaBH$_4$ (1.52 g, 39.9 mmol) was added. The reaction mixture was stirred at room temperature overnight. Water (500 mL) was added and MeOH was removed by evaporation under vacuum. The resulting mixture was extracted with CH$_2$Cl$_2$ (250 mL×3) and the combined extracts were dried over anhydrous Na$_2$SO$_4$, filtered, and concentrated to afford crude (R)-2-amino-3-(4-bromo-2,6-difluorophenyl)propan-1-ol as a white solid. MS: (ESI, m/z): 266, 268 [M+H]$^+$.

Step 7. (R)-7-Bromo-5-fluorochroman-3-amine

To a stirred solution of (R)-2-amino-3-(4-bromo-2,6-difluorophenyl)propan-1-ol (18.5 g, 69.5 mmol) in DMSO (100 mL) was added NaH (60% in mineral oil, 4.17 g) at room temperature. The reaction mixture was stirred at 35° C. for 3 h and ice-water (500 mL) was added carefully to quench the reaction. The resulting mixture was extracted with EtOAc (300 mL×3) and the combined extracts were washed with brine (200 mL), dried over anhydrous Na$_2$SO$_4$, filtered, and concentrated to give crude (R)-7-bromo-5-fluorochroman-3-amine. MS: (ESI, m/z): 246, 248 [M+H]$^+$.

Step 8. Benzyl (R)-(7-bromo-5-fluorochroman-3-yl)carbamate

To a stirred mixture of crude (R)-7-bromo-5-fluorochroman-3-amine (17 g, 69.5 mmol) and saturated aqueous NaHCO$_3$ (200 mL) in MeOH (400 mL) was added benzyl chloroformate (17.7 g, 104.2 mmol) dropwise. The reaction mixture was stirred at room temperature overnight and then diluted with water (500 mL). The resulting mixture was extracted with EtOAc (300 mL×2) and the combined extracts were washed with water (200 mL), dried over anhydrous Na$_2$SO$_4$, filtered, and concentrated. The residue was purified by silica gel chromatography to give benzyl (R)-(7-bromo-5-fluorochroman-3-yl)carbamate. MS: (ESI, m/z): 380, 382 [M+H]$^+$.

The following intermediate in Table 2 may be prepared using standard chemical manipulations and procedures similar to Method 2 of Intermediate 5-1.

TABLE 2

| Intermediate Number | Structure and Compound Name | LRMS m/z [M + H]$^+$ |
|---|---|---|
| 5-2[1] | 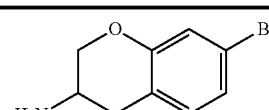<br>7-bromo-5-fluorochroman-4,4-d2-3-amine | 248, 250 |

[1]Notes on procedures:
Step 3 and Step 8 were not performed. In Step 1, 5-bromo-2-(bromomethyl-d2)-1,3-difluorobenzene was prepared from methyl 4-bromo-2,6-difluorobenzoate in two steps: Methanol (0.806 ml, 19.92 mmol) was carefully added dropwise to a stirring solution of methyl 4-bromo-2,6-difluorobenzoate (5 g, 19.92 mmol), sodium tetrahydroborate-d4 (0.834 g, 19.92 mmol) in THF (15 mL). The reaction was then allowed to stir at 70° C. for 2 h. The reaction was cooled to room temperature and 10 mL sat. aq. NH$_4$Cl was added. The reaction was allowed to stir at room temperature for 2 h. The organic layer was separated. The aqueous layer was extracted with 2 × 15 mL DCM. The organic layers were combined, dried over Na$_2$SO$_4$, filtered, and concentrated under vacuum to afford (4-bromo-2,6-difluorophenyl)methan-d2-ol.

A solution of (4-bromo-2,6-difluorophenyl)methan-d2-ol (3.00 g, 13.33 mmol) and PBr$_3$ (14.21 mL, 14.21 mmol) in DCM (30 mL) was stirred at 40° C. for 30 min. After cooling to room temperature, the reaction was quenched by the addition of water (7.5 mL). The resulting mixture was extracted with DCM (3×10 mL) and the organic layers were combined, dried over Na$_2$SO$_4$, filtered, and concentrated to afford a crude pale yellow oil. The oil was purified by normal phase chromatography using Biotage (KP-SIL 50 g, 2% EtOAc/hexanes up to 25% EtOAc/hexanes. Desired fractions were combined and concentrated to afford 5-bromo-2-(bromomethyl-d2)-1,3-difluorobenzene. $^1$H NMR (CDC$_3$, 300 MHz) δ(ppm): 1.54 (s, 1H) 4.46 (br d, J=3.8 Hz, 1H) 7.05-7.21 (m, 2H).

Intermediate 6. tert-Butyl (R)-4-(3-amino-8-bromo-5-fluorochroman-7-yl)piperazine-1-carboxylate and Intermediate 7-1. tert-Butyl (R)-4-(3-amino-6-cyano-5-fluorochroman-7-yl)piperazine-1-carboxylate

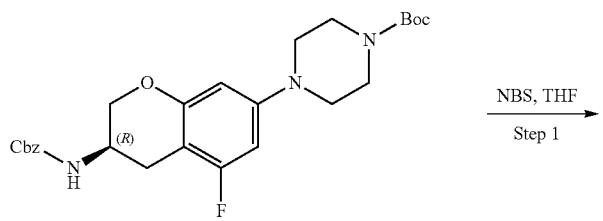

These regioisomers were separated by chromatography and carried on independently to the final compounds (only one representative is shown here)

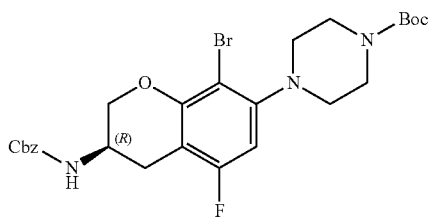

first eluting isomer
Intermediate 6

+

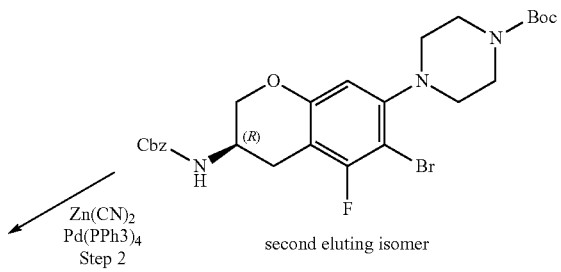

second eluting isomer

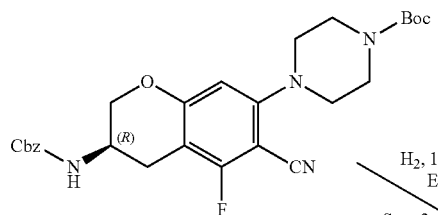

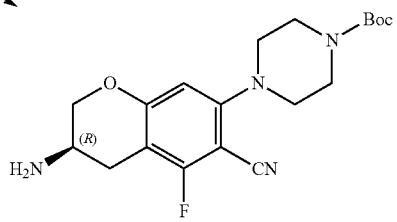

Intermediate 7-1

Step 1: tert-Butyl (R)-4-(3-(((benzyloxy)carbonyl)amino)-8-bromo-5-fluorochroman-7-yl)piperazine-1-carboxylate and tert-butyl (R)-4-(3-(((benzyloxy)carbonyl)amino)-6-bromo-5-fluorochroman-7-yl)piperazine-1-carboxylate Into a 20-mL vial, was added tert-butyl 4-[(3R)-3-[[(benzyloxy)carbonyl]amino]-5-fluoro-3,4-dihydro-2H-1-benzopyran-7-yl]piperazine-1-carboxylate (570 mg, 1.17 mmol), THF (10 mL), and NBS (314 mg, 1.76 mmol). The resulting solution was stirred for 2 h at 25° C., then was quenched by the addition of water (30 mL). The resulting mixture was extracted with ethyl acetate (3×30 mL). The organic layers were combined, dried over anhydrous sodium sulfate, filtered and concentrated under vacuum. The residue was purified by prep-HPLC (Column: XSelect CSH Prep C18 OBD, 5 μm, 19×150 mm; Mobile phase A: water (0.05% TFA), B: ACN; Gradient: 45% B increasing to 70% B within 15 min). The collected fraction was concentrated under vacuum to afford tert-butyl 4-[(3R)-3-[[(benzyloxy)carbonyl]amino]-8-bromo-5-fluoro-3,4-dihydro-2H-1-benzopyran-7-yl]piperazine-1-carboxylate (peak 1) (Intermediate 6) as an off-white solid and tert-butyl 4-[(3R)-3-[[(benzyloxy)carbonyl]amino]-6-bromo-5-fluoro-3,4-dihydro-2H-1-benzopyran-7-yl]piperazine-1-carboxylate (peak 2) as off-white solid. MS (ESI, m/z): 564, 566 [M+H]⁻. These two compounds were carried on independently into subsequent synthetic steps.

Step 2: tert-Butyl 4-[(3R)-3-[[(benzyloxy)carbonyl]amino]-6-cyano-5-fluoro-3,4-dihydro-2H-1-benzopyran-7-yl]piperazine-1-carboxylate Into a 10-mL sealed tube purged and maintained with an inert atmosphere of nitrogen, was added tert-butyl 4-[(3R)-3-[[(benzyloxy)carbonyl]amino]-6-bromo-5-fluoro-3,4-dihydro-2H-1-benzopyran-7-yl]piperazine-1-carboxylate (80 mg, 0.14 mmol), Zn(CN)$_2$ (13 mg, 0.11 mmol), Pd(PPh$_3$)$_4$ (8 mg, 0.01 mmol), PPh$_3$ (7 mg, 0.03 mmol), and NMP (5 mL). The resulting solution was stirred for 1 h at 120° C. After cooling to 25° C., the reaction was quenched by the addition of 10 mL of water. The resulting mixture was extracted with 3×20 mL of ethyl acetate. The organic layers were combined, dried over anhydrous sodium sulfate, filtered and concentrated under vacuum to afford a residue that was purified via reverse phase chromatography (Column: C18 silica gel; Mobile phase A: 0.1% TFA in H$_2$O, B: ACN; Flow rate: 50 mL/min; Gradient: 0% B increasing to 80% B within 30 min). The collected fractions were concentrated under vacuum to afford tert-butyl 4-[(3R)-3-[[(benzyloxy)carbonyl]amino]-6-cyano-5-fluoro-3,4-dihydro-2H-1-benzopyran-7-yl]piperazine-1-carboxylate as an off-white solid. MS (ESI, m/z): 511 [M+H]$^+$.

Step 3: tert-Butyl 4-[(3R)-3-amino-6-cyano-5-fluoro-3,4-dihydro-2H-1-benzopyran-7-yl]piperazine-1-carboxylate Into a 25-mL round-bottom flask purged and maintained with nitrogen, was placed tert-butyl 4-[(3R)-3-[[(benzyloxy) carbonyl]amino]-6-cyano-5-fluoro-3,4-dihydro-2H-1-benzopyran-7-yl]piperazine-1-carboxylate (40 mg, 0.08 mmol), ethyl acetate (4 mL), and 10% Palladium on carbon (40 mg,). The resulting mixture was stirred for 2 h at 25° C. under hydrogen atmosphere. The solids were removed by filtration through Celite and the filtrate was concentrated under vacuum to afford tert-butyl 4-[(3R)-3-amino-6-cyano-5-fluoro-3,4-dihydro-2H-1-benzopyran-7-yl]piperazine-1-carboxylate (Intermediate 7-1) as yellow oil. MS (ESI, m/z): 377 [M+H]$^+$.

The following intermediate in Table 3 may be prepared using standard chemical manipulations and procedures similar to those used for the preparation of Intermediate 7-1.

TABLE 3

| Intermediate Number | Structure and Compound Name | LRMS m/z [M + H]$^+$ |
|---|---|---|
| 7-2 | ![structure] tert-butyl (R)-4-(3-amino-8-cyano-5-fluorochroman-7-yl)piperazine-1-carboxylate | 377 |

Intermediate 8. Benzyl (6-bromo-1,2,3,4-tetrahydronaphthalen-2-yl)carbamate

Intermediate 9. Benzyl (S)-(6-bromo-1,2,3,4-tetrahydronaphthalen-2-yl)carbamate and Intermediate 10. Benzyl (R)-(6-bromo-1,2,3,4-tetrahydronaphthalen-2-yl)carbamate

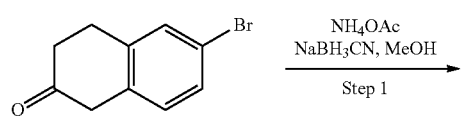

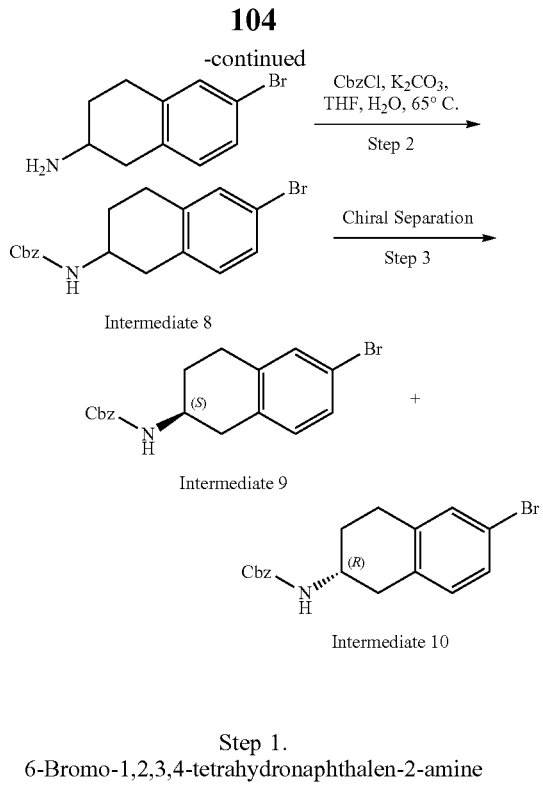

Step 1.
6-Bromo-1,2,3,4-tetrahydronaphthalen-2-amine

A solution of 6-bromo-3,4-dihydronaphthalen-2(1H)-one (5 g, 22.21 mmol), NH$_4$OAc (13.8 g, 179 mmol), and NaBH$_3$CN (1.68 g, 26.67 mmol) in MeOH (250 mL) was stirred for 1 h at room temperature. The reaction mixture was acidified with 2N HCl solution to pH 4-5 and was concentrated under vacuum. The residual solution was washed with CH$_2$Cl$_2$ (200 mL×2). The aqueous layer was basified with 1N NaOH solution to pH 10, then extracted with CH$_2$Cl$_2$ (200 mL×2). The combined organic layer was dried over Na$_2$SO$_4$, filtered, and concentrated under vacuum to afford 6-bromo-1,2,3,4-tetrahydronaphthalen-2-amine as a yellow oil. MS: (ESI, m/z): 226, 228 [M+H]$^+$.

Step 2. Benzyl (6-bromo-1,2,3,4-tetrahydronaphtha-len-2-yl)carbamate (Intermediate 8)

A solution of 6-bromo-1,2,3,4-tetrahydronaphthalen-2-amine (1.8 g, 7.96 mmol), benzyl chloroformate (1.6 g, 9.55 mmol), and Cs$_2$CO$_3$ (3 g, 21.71 mmol) in THF (20 mL) and water (20 mL) was stirred at 60° C. overnight. After cooling to room temperature, the reaction mixture was extracted with EtOAc (30 mL×3). The combined organic layer was dried over Na$_2$SO$_4$, filtered, and concentrated under vacuum. Purification by silica gel chromatography (eluting with gradient 1:100 to 1:3 EtOAc/pet. ether) afforded benzyl (6-bromo-1,2,3,4-tetrahydronaphthalen-2-yl)carbamate (Intermediate 8) as a solid. MS: (ESI, m/z): 360, 362 [M+H]$^-$.

Step 3. Benzyl (S)-(6-bromo-1,2,3,4-tetrahydronaphthalen-2-yl)carbamate (Intermediate 9) and Benzyl (R)-(6-bromo-1,2,3,4-tetrahydronaphthalen-2-yl)carbamate (Intermediate 10)

The racemate benzyl (6-bromo-1,2,3,4-tetrahydronaphthalen-2-yl)carbamate was separated by SFC (Column: Chiralpak IA-SFC-03, 5×25 cm, 5 μm; Mobile phase A: CO$_2$, B: MeOH; Flow rate: 170 mL/min) to afford the title compounds as follows: benzyl (S)-(6-bromo-1,2,3,4-tetrahydronaphthalen-2-yl)carbamate (first eluting isomer, RT=6.54 min) as a white solid and benzyl (R)-(6-bromo-1,2,3,4-tetrahydronaphthalen-2-yl)carbamate (second eluting isomer, RT=9.06 min) as a white solid. First eluting isomer: $^1$H NMR (CDCl$_3$, 400 MHz) δ(ppm): 7.30-7.21 (m, 5H), 7.17-7.13 (m, 2H), 6.85-6.83 (d, J=8.00 Hz, 1H), 5.02 (s, 2H), 4.70 (br, 1H), 3.95 (m, 1H), 3.01-2.96 (dd, J=4.00 Hz, 16.00 Hz, 2H), 2.79-2.75 (m, 2H), 2.53-2.47 (m, 1H), 2.00-1.97 (m, 1H), 1.68-1.66 (m, 1H). MS: (ESI, m/z): 360, 362 [M+H]$^+$. Second eluting isomer: $^1$H NMR (CDCl$_3$, 400 MHz) δ(ppm): 7.30-7.23 (m, 5H), 7.17-7.13 (m, 2H), 6.84-6.82 (d, J=8.00 Hz, 1H), 5.02 (s, 2H), 4.70 (br, 1H), 4.06-3.95 (m, 1H), 3.01-2.96 (dd, J=4.00 Hz, 16.0 Hz, 2H), 2.79-2.75 (m, 2H), 2.51-2.47 (m, 1H), 2.00-1.96 (m, 1H), 1.68-1.66 (m, 1H). MS: (ESI, m/z): 360, 362 [M+H]$^+$.

Intermediate 11-1. Benzyl (6-bromo-8-fluoro-1,2,3,4-tetrahydronaphthalen-2-yl)carbamate

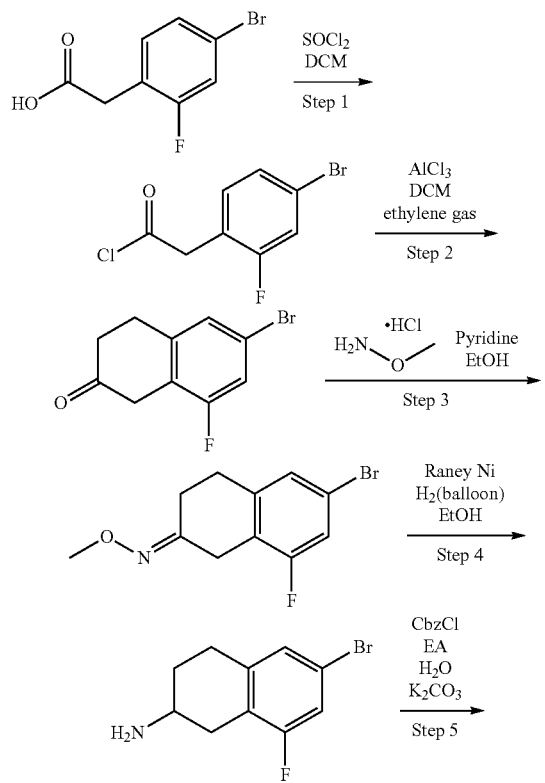

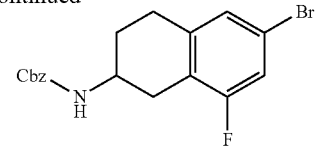

Step 1. 2-(4-Bromo-2-fluorophenyl)acetyl chloride

A 250-mL round-bottom flask was charged with 2-(4-bromo-2-fluorophenyl)acetic acid (10 g, 42.05 mmol), DCM (50 mL), and thionyl chloride (6.3 mL, 85.11 mmol). The resulting solution was stirred for 16 h at 40° C. After cooling to 25° C., the reaction mixture was concentrated under vacuum to afford 2-(4-bromo-2-fluorophenyl)acetyl chloride as brown oil.

Step 2. 6-Bromo-8-fluoro-3,4-dihydronaphthalen-2(1H)-one

A 500-mL round-bottom flask was charged with 2-(4-bromo-2-fluorophenyl)acetyl chloride (5.0 g, 18.49 mmol) and DCM (100 mL). AlCl$_3$ (7.15 g, 53.09 mmol) was then added in portions at 0° C. The resulting mixture was stirred for 10 min at 0° C., then a gentle stream of ethylene gas was bubble into the reaction mixture for 5 h at 0° C. The reaction mixture was poured into ice and concentrated hydrochloric acid (5 mL) was added. The resulting solution was extracted with DCM (3×50 mL), the organic layers combined, dried over anhydrous sodium sulfate and concentrated under vacuum to afford a crude residue that was purified by column chromatography eluting with ethyl acetate/pet. ether (1:2) to afford 6-bromo-8-fluoro-3,4-dihydronaphthalen-2(1H)-one as a brown solid. $^1$H NMR (400 MHz, DMSO-d$_6$) δ(ppm): 2.49 (t, J=8.0 Hz, 2H), 3.08 (t, J=8.0 Hz, 2H), 3.49 (s, 2H), 7.40-7.42 (m, 2H).

Step 3. (2E)-6-Bromo-8-fluoro-N-methoxy-1,2,3,4-tetrahydronaphthalen-2-imine

A 250-mL round-bottom flask was charged with 6-bromo-8-fluoro-3,4-dihydronaphthalen-2(1H)-one (4.2 g, 16.07 mmol), the HCl salt of O-methylhydroxylamine (2.16 g, 25.60 mmol), ethanol (50 mL) and pyridine (5 mL, 61.50 mmol). The resulting mixture was stirred for 16 h at 80° C. in an oil bath, then was cooled to 25° C. After cooling, the resulting mixture was concentrated under vacuum to afford a residue that was purified by column chromatography eluting with ethyl acetate/pet. ether (1:2) to afford (2E)-6-bromo-8-fluoro-N-methoxy-1,2,3,4-tetrahydronaphthalen-2-imine as a brown solid. MS: (ESI, m/z) 272, 274 [M+H]$^+$.

Step 4. 6-Bromo-8-fluoro-1,2,3,4-tetrahydronaphthalen-2-amine

A 250-mL round-bottom flask that was purged with nitrogen was charged with (2E)-6-bromo-8-fluoro-N-methoxy-1,2,3,4-tetrahydronaphthalen-2-imine (3.5 g, 11.58 mmol, 90%), ethanol (50 mL) and Raney Ni (2.0 g, 23.11 mmol). To this hydrogen (g) was introduced in. The resulting mixture was stirred for 48 h at 25° C. The solids were removed by filtration over Celite. The filtrate was concentrated under vacuum to afford a residue that was purified by column chromatography eluting with DCM/methanol (10:1)

to afford 6-bromo-8-fluoro-1,2,3,4-tetrahydronaphthalen-2-amine as a brown solid. MS: (ESI, m/z): 244, 246 [M+H]+.

Step 5. Benzyl (6-bromo-8-fluoro-1,2,3,4-tetrahydronaphthalen-2-yl)carbamate

A 100-mL round-bottom flask was charged with 6-bromo-8-fluoro-1,2,3,4-tetrahydronaphthalen-2-amine (930 mg, 3.43 mmol), ethyl acetate (15 mL), water (15 mL), potassium carbonate (1.58 g, 11.32 mmol), and benzyl chloroformate (780 mg, 4.53 mmol). The resulting mixture was stirred for 16 h at 60° C. in an oil bath. After cooling to 25° C., the reaction was diluted with water (30 mL). The resulting solution was extracted with ethyl acetate (3×40 mL), the organic layers combined, dried over anhydrous sodium sulfate, filtered, and concentrated under vacuum to afford a residue that was purified by column chromatography eluting with ethyl acetate/pet. ether (1:5) to afford benzyl (6-bromo-8-fluoro-1,2,3,4-tetrahydronaphthalen-2-yl)carbamate as an off-white solid. MS: (ESI, m/z): 378, 380 [M+H]+.

The following intermediates in Table 4 were prepared using standard chemical manipulations and procedures similar to those used for the preparation of Intermediate 11-1.

TABLE 4

| Intermediate Number | Structure and Compound Name | LRMS m/z [M + H]+ |
|---|---|---|
| 11-2[1] | benzyl (S)-(6-bromo-7-methyl-1,2,3,4-tetrahydronaphthalen-2-yl)carbamate | 374, 376 |
| 11-3[1] | benzyl (R)-(6-bromo-7-methyl-1,2,3,4-tetrahydronaphthalen-2-yl)carbamate | 374, 376 |
| 11-4[1] | benzyl (S)-(6-bromo-5-methyl-1,2,3,4-tetrahydronaphthalen-2-yl)carbamate | 374, 376 |

TABLE 4-continued

| Intermediate Number | Structure and Compound Name | LRMS m/z [M + H]+ |
|---|---|---|
| 11-5[1] | benzyl (R)-(6-bromo-5-methyl-1,2,3,4-tetrahydronaphthalen-2-yl)carbamate | 374, 376 |

[1]Notes on procedures:
In Step 2, a mixture of regioisomers 6-bromo-7-methyl-3,4-dihydronaphthalen-2(1H)-one and 6-bromo-5-methyl-3,4-dihydronaphthalen-2(1H)-one (3:1, respectively) were generated. The mixture was carried through Step 5. The regioisomers and enantiomers were separated by SFC using the chiral column Phenomenex Lux 5 μm Cellulose-3 and mobile phase 50% CO2/IPA (2 mM NH3—MeOH) to provide Intermediate 11-4 as the first eluting isomer, Intermediate 11-2 as the second eluting isomer, Intermediate 11-5 as the third eluting isomer, and Intermediate 11-3 as the fourth eluting isomer. Stereochemistry of the separated enantiomers were arbitrarily assigned.

Intermediate 12. tert-Butyl 4-(3-aminochroman-7-yl)piperazine-1-carboxylate

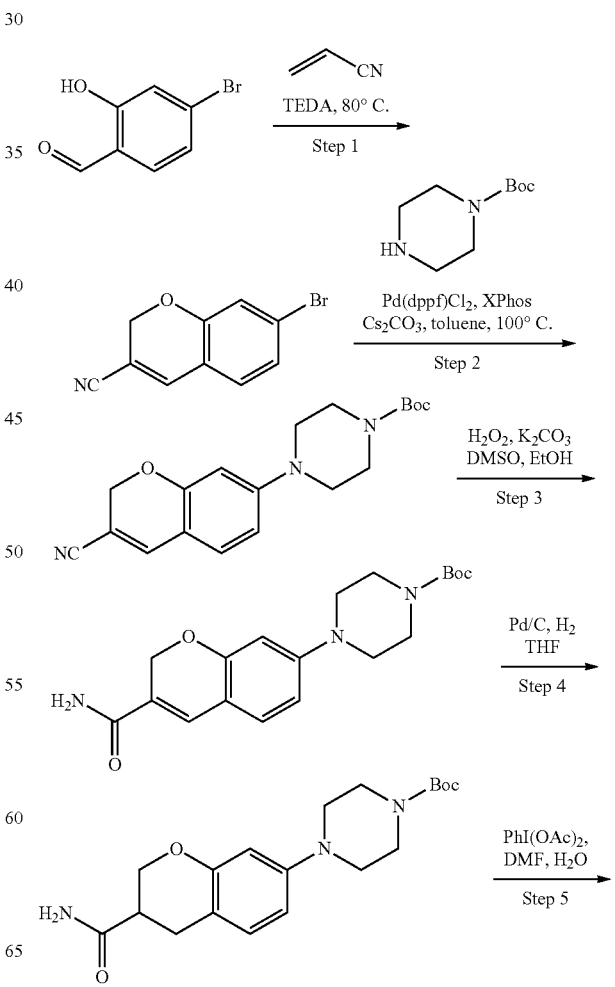

-continued

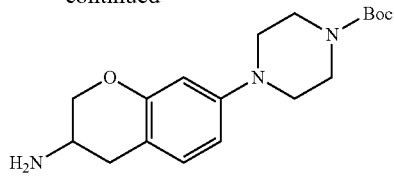

Step 1. 7-Bromo-2H-chromene-3-carbonitrile

A solution of 4-bromo-2-hydroxybenzaldehyde (10 g, 47.26 mmol) and triethylenediamine (1.12 g, 9.49 mmol) in acrylonitrile (16 mL) was stirred for 24 h at 80° C. After cooling to room temperature, the reaction was quenched with 1N NaOH (400 mL). The resulting solution was extracted with EtOAc (300 mL×3). The organic layers were combined, dried over anhydrous $Na_2SO_4$, filtered, and concentrated under vacuum. The residue was purified by silica gel chromatography (eluting with 20:1-9:1 pet. ether/EtOAc) to give 7-bromo-2H-chromene-3-carbonitrile as a yellow solid. MS: (ESI, m/z): 236, 238 $[M+H]^+$.

Step 2. tert-Butyl 4-(3-cyano-2H-chromen-7-yl)piperazine-1-carboxylate

A mixture of 7-bromo-2H-chromene-3-carbonitrile (1 g, 3.81 mmol), tert-butyl piperazine-1-carboxylate (950 mg, 4.85 mmol), $Pd(dppf)Cl_2$ (327 mg, 0.42 mmol), XPhos (191 mg, 0.38 mmol) and $Cs_2CO_3$ (3.9 g, 11.37 mmol) in toluene (20 mL) was stirred for 18 h at 100° C. After cooling to room temperature, the reaction was quenched by the addition of 30 mL of water. The resulting mixture was extracted with EtOAc (30 mL×3). The organic layers were combined, dried over anhydrous $Na_2SO_4$, filtered, and concentrated under vacuum. The residue was purified by silica gel chromatography (eluting with 9:1-4:1 pet. ether/EtOAc) to give 0.7 g of tert-butyl 4-(3-cyano-2H-chromen-7-yl)piperazine-1-carboxylate as a yellow solid. MS: (ESI, m/z): 342 $[M+H]^+$.

Step 3. tert-Butyl 4-(3-carbamoyl-2H-chromen-7-yl)piperazine-1-carboxylate

A solution of tert-butyl 4-(3-cyano-2H-chromen-7-yl)piperazine-1-carboxylate (500 mg, 1.32 mmol), 30% hydrogen peroxide (0.2 mL, 2.58 mmol), and potassium carbonate (304 mg, 2.09 mmol) in a mixture of DMSO (2 mL) and ethanol (10 mL) was stirred for 3 h at room temperature. The reaction was quenched by the addition of 50 mL of water. The resulting mixture was extracted with EtOAc (50 mL×3). The organic layers were combined, dried over anhydrous $Na_2SO_4$, filtered, and concentrated under vacuum. The residue was purified by silica gel chromatography (eluting with 10:1-3:1 pet. ether/EtOAc) to give tert-butyl 4-(3-carbamoyl-2H-chromen-7-yl)piperazine-1-carboxylate as a yellow solid. MS: (ESI, m/z): 360 $[M+H]^+$.

Step 4. tert-Butyl 4-(3-carbamoylchroman-7-yl)piperazine-1-carboxylate

A mixture of tert-butyl 4-(3-carbamoyl-2H-chromen-7-yl)piperazine-1-carboxylate (700 mg. 1.95 mmol) and Pd/C (100 mg, 10%) in THF (50 mL) was stirred for 18 h at room temperature under an atmosphere of hydrogen. The solids were filtered away and the filtrate was concentrated under vacuum. The residue was purified by silica gel chromatography (eluting with EtOAc) to give tert-butyl 4-(3-carbamoylchroman-7-yl)piperazine-1-carboxylate as a light yellow solid. MS: (ESI, m/z): 362 $[M+H]^+$.

Step 5. tert-Butyl 4-(3-aminochroman-7-yl)piperazine-1-carboxylate

To a stirring solution of (diacetoxyiodo)benzene (468 mg, 1.45 mmol) in a mixture of DMF (3.88 mL) and water (3.88 mL) was added tert-butyl 4-(3-carbamoylchroman-7-yl)piperazine-1-carboxylate (350 mg, 0.97 mmol). The resulting solution was stirred for 18 h at room temperature. Additional (diacetoxyiodo)benzene (936 mg, 2.90 mmol) was added in two portions over 24 h. The resulting solution was diluted with 20 mL of water and was extracted with EtOAc (50 mL). The aqueous layer was concentrated under vacuum. The residue was purified by prep-HPLC (Column: SunFire Prep C18, 19×150 mm; Mobile phase A: water (0.05% $NH_4HCO_3$), B: ACN; Gradient: 15% B to 70% B in 15 min) to afford tert-butyl 4-(3-aminochroman-7-yl)piperazine-1-carboxylate as a light yellow solid. MS: (ESI, m/z): 334 $[M+H]^-$.

Intermediate 13. tert-Butyl 3-(3-aminochroman-7-yl)-3,8-diazabicyclo[3.2.1]octane-8-carboxylate

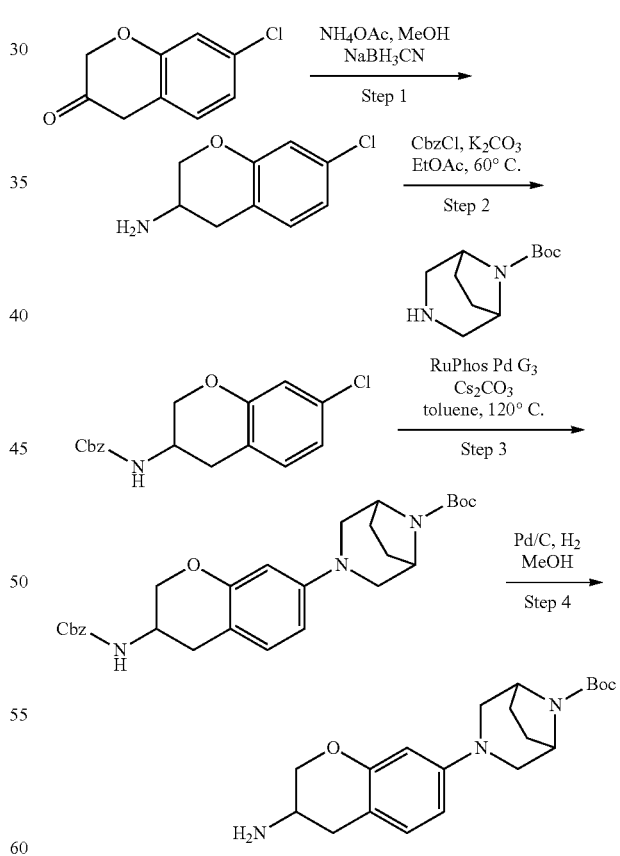

Step 1. 7-Chlorochroman-3-amine

A solution of 7-chlorochroman-3-one (700 mg, 3.83 mmol) and $NH_4OAc$ (2.37 g, 30.75 mmol) in MeOH (35 mL) was stirred for 4 h at room temperature. To this was added NaBH₃CN (364 mg, 5.79 mmol). The resulting mixture was stirred for 14 h at room temperature and then concentrated under vacuum. The residue was diluted with 50 mL of water. The pH value of the mixture was adjusted to 5 with 1N HCl. The resulting mixture was extracted with CH₂Cl₂ (20 mL×2). The pH value of the aqueous layer was adjusted to 10 with 1M NaOH solution. The resulting solution was extracted with CH₂Cl₂ (30 mL×3). The organic layers were combined, dried over anhydrous Na₂SO₄, filtered, and concentrated under vacuum to afford 7-chlorochroman-3-amine as a light yellow oil. MS: (ESI, m/z): 184 [M+H]⁺.

Step 2. Benzyl (7-chlorochroman-3-yl)carbamate

A mixture of 7-chlorochroman-3-amine (350 mg, 1.91 mmol), potassium carbonate (786.6 mg, 5.69 mmol), and benzyl chloroformate (390 mg, 2.29 mmol) in a mixture of EtOAc (15 mL) and water (15 mL) was stirred for 3 h at 60° C. After cooling to room temperature, the reaction mixture was poured into 10 mL of water and was extracted with EtOAc (10 mL×3). The organic layers were combined, dried over anhydrous Na₂SO₄, filtered, and concentrated under vacuum. The residue was purified by silica gel chromatography (eluting with 7:1 pet. ether/EtOAc) to afford benzyl (7-chlorochroman-3-yl)carbamate as a white solid. MS: (ESI, m/z): 318 [M+H]⁻.

Step 3. tert-Butyl 3-(3-(((benzyloxy)carbonyl) amino)chroman-7-yl)-3,8-diazabicyclo[3.2.1]octane-8-carboxylate Into a 20-mL sealed tube purged and maintained with an inert atmosphere of nitrogen was placed benzyl (7-chlorochroman-3-yl)carbamate (95 mg, 0.26 mmol), tert-butyl 3,8-diazabicyclo[3.2.1]octane-8-carboxylate (70 mg, 0.33 mmol), Cs₂CO₃ (294 mg, 0.90 mmol), toluene (5 mL) and RuPhos Pd G3 (25.1 mg, 0.03 mmol). The reaction mixture was treated with microwave radiation for 5 h at 120° C. After cooling to room temperature, the reaction mixture was then poured into 10 mL of water. The resulting mixture was extracted with CH₂Cl₂ (10 mL×3). The organic layers were combined, dried over anhydrous Na₂SO₄, filtered, and concentrated under vacuum. The residue was purified by silica gel chromatography (eluting with 2:1 pet. ether/EtOAc) to afford tert-butyl 3-(3-(((benzyloxy)carbonyl)amino)chroman-7-yl)-3,8-diazabicyclo[3.2.1]octane-8-carboxylate as light yellow oil. MS: (ESI, m/z): 494 [M+H]⁻.

Step 4. tert-Butyl 3-(3-aminochroman-7-yl)-3,8-diazabicyclo[3.2.1]octane-8-carboxylate A mixture of tert-butyl 3-(3-(((benzyloxy)carbonyl) amino)chroman-7-yl)-3,8-diazabicyclo[3.2.1]octane-8-carboxylate (300 mg, 0.60 mmol) and Pd/C (60 mg, 10%) in MeOH (25 mL) was stirred for 2 h at room temperature under an atmosphere of hydrogen. The solids were filtered away and the filtrate was concentrated to give tert-butyl 3-(3-aminochroman-7-yl)-3,8-diazabicyclo[3.2.1]octane-8-carboxylate as a yellow oil. MS: (ESI, m/z): 360 [M+H]⁺.

Intermediate 14-1. tert-Butyl 3-(3-aminochroman-7-yl)-3,9-diazabicyclo[3.3.1]nonane-9-carboxylate

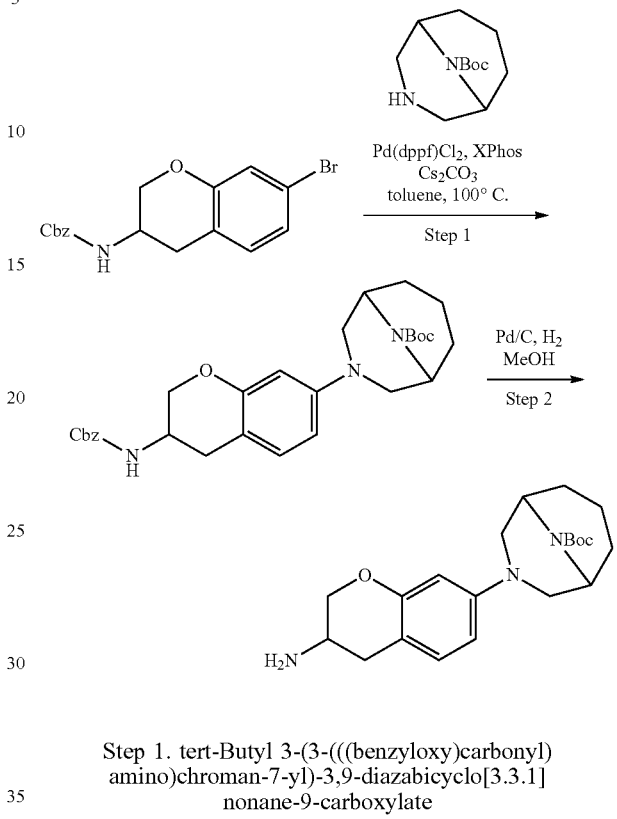

Step 1. tert-Butyl 3-(3-(((benzyloxy)carbonyl) amino)chroman-7-yl)-3,9-diazabicyclo[3.3.1] nonane-9-carboxylate A mixture of benzyl-(7-bromochroman-3-yl)carbamate, Intermediate 1, (400 mg, 1.07 mmol), tert-butyl 3,9-diazabicyclo[3.3.1]nonane-9-carboxylate (300 mg, 1.31 mmol), Pd(dppf)Cl₂—CH₂Cl₂ (90 mg, 0.11 mmol), Xphos (52 mg, 0.11 mmol), and Cs₂CO₃ (722 mg, 2.22 mmol) in toluene (6 mL) was stirred at 100° C. for 14 h. After cooling to room temperature, water was added and the reaction mixture was extracted with EtOAc (70 mL×2). The combined organic layers were dried over sodium sulfate, filtered, and concentrated. Purification by prep-TLC (eluting with 1:3 EtOAc/ pet. ether) afforded tert-butyl 3-(3-(((benzyloxy)carbonyl) amino)chroman-7-yl)-3,9-diazabicyclo[3.3.1]nonane-9-carboxylate as a pale yellow solid. MS: (ESI, m/z): 508 [M+H]⁺.

Step 2. tert-Butyl 3-(3-(((benzyloxy)carbonyl) amino)chroman-7-yl)-3,9-diazabicyclo[3.3.1] nonane-9-carboxylate A mixture of tert-butyl 3-(3-(((benzyloxy)carbonyl) amino)chroman-7-yl)-3,9-diazabicyclol[3.3.1]nonane-9-carboxylate (120 mg, 0.22 mmol) and Pd/C (60 mg, 10%) in MeOH (5 mL) was stirred for 1 h at room temperature under an atmosphere of hydrogen. The solids were filtered away and the filtrate was concentrated under vacuum to afford tert-butyl 3-(3-(((benzyloxy)carbonyl)amino)chroman-7-yl)-3,9-diazabicyclo[3.3.1]nonane-9-carboxylate as colorless oil. MS: (ESI, m/z): 374 [M+H]⁺.

The following intermediate in Table 5 was prepared using standard chemical manipulations and procedures similar to those used for the preparation of Intermediate 14-1.

TABLE 5

| Intermediate Number | Structure and Name | LRMS m/z [M + H]+ |
|---|---|---|
| 14-2 | 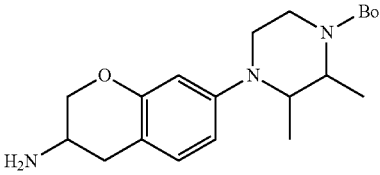<br>tert-butyl 4-(3-aminochroman-7-yl)-2,3-dimethylpiperazine-1-carboxylate | 362 |

[1]Notes on Procedures:
In Step 1, RuPhos Pd G3/RuPhos was used as the catalyst/ligand system.

Intermediate 15-1. tert-Butyl 3-(3-amino-5-fluoro-chroman-7-yl)-3,8-diazabicyclo[3.2.1]octane-8-carboxylate

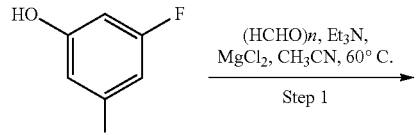

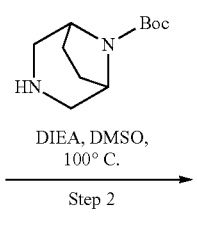

Step 1. 2,4-Difluoro-6-hydroxybenzaldehyde

A solution of 3,5-difluorophenol (10 g, 73 mmol), paraformaldehyde (23 g, 728 mmol), Et$_3$N (21 mL), and MgCl$_2$ (14.6 g, 153.34 mmol) in ACN (200 mL) was stirred for 14 h at 60° C. After cooling to room temperature, the reaction was quenched by the addition of water (100 mL). The resulting mixture was extracted with DCM (2×200 mL). The combined organic layers were dried over anhydrous sodium sulfate, filtered and concentrated under vacuum. Purification by silica gel chromatography (eluting with gradient 1:10 to 1:1 EtOAc/pet. ether) afforded 2,4-difluoro-6-hydroxybenzaldehyde as a pale yellow solid. MS: (ESI, m/z): 159 [M+H]$^-$.

Step 2. tert-Butyl 3-(3-fluoro-4-formyl-5-hydroxyphenyl)-3,8-diazabicyclo[3.2.1]octane-8-carboxylate A solution of 2,4-difluoro-6-hydroxybenzaldehyde (600 mg, 3.80 mmol), tert-butyl 3,8-diazabicyclo[3.2.1]octane-8-carboxylate (800 mg, 3.75 mmol), and DIEA (700 mg, 5.42 mmol) in DMSO (10 mL) was stirred for 2 h at 100° C. After cooling to room temperature the reaction was quenched by the addition of water (10 mL). The resulting mixture was extracted with DCM (2×20 mL). The combined organic layers were dried over anhydrous sodium sulfate, filtered, and concentrated under vacuum. Purification by silica gel chromatography (eluting with 1:4 EtOAc/pet. ether) afforded tert-butyl 3-(3-fluoro-4-formyl-5-hydroxyphenyl)-3,8-diazabicyclo[3.2.1]octane-8-carboxylate as a yellow solid. MS: (ESI, m/z): 351 [M+H]+.

Step 3. tert-Butyl 3-(3-(allyloxy)-5-fluoro-4-formylphenyl)-3,8-diazabicyclo[3.2.1]octane-8-carboxylate A solution of tert-butyl 3-(3-fluoro-4-formyl-5-hydroxyphenyl)-3,8-diazabicyclo[3.2.1]octane-8-carboxylate (1.4 g, 3.60 mmol), potassium carbonate (3 g, 21.71 mmol), and allylbromide (500 mg, 4.13 mmol) in DMF (20 mL) was stirred for 2 h at 100° C. After cooling to room temperature the reaction was quenched by the addition of water (20 mL). The resulting mixture was extracted with DCM (2×50 mL). The combined organic layers were dried over anhydrous sodium sulfate, filtered, and concentrated under vacuum. Purification by silica gel chromatography (eluting with 1:5 EtOAc/pet. ether) afforded tert-butyl 3-(3-(allyloxy)-5-fluoro-4-formylphenyl)-3,8-diazabicyclo[3.2.1]octane-8-carboxylate as a yellow solid. MS: (ESI, m/z): 392 [M+H]+.

Step 4. tert-Butyl 3-(3-(allyloxy)-5-fluoro-4-vinylphenyl)-3,8-diazabicyclo[3.2.1]octane-8-carboxylate To a solution of methyltriphenylphosphonium bromide (3.3 g, 8.86 mmol) in THF (25 mL) was added sodium hydride (178 mg, 4.45 mmol, 60% dispersion in oil) in portions at 0° C. The reaction mixture was stirred for 4 h at room temperature. This was followed by the dropwise addition of a solution of tert-Butyl 3-(3-(allyloxy)-5-fluoro-4-formylphenyl)-3,8-diazabicyclo[3.2.1]octane-8-carboxylate (1.2 g, 2.77 mmol) in THF (20 mL) and stirring continued for 3 h at 30° C. The reaction was quenched by the addition of water (60 mL). The resulting mixture was extracted with EtOAc (3×50 mL). The combined organic layers were washed with brine (50 mL), dried over anhydrous sodium sulfate, filtered, and concentrated under vacuum. Purification by silica gel chromatography (eluting with gradient 1:6 to 1:1 EtOAc/pet. ether) afforded tert-butyl 3-(3-(allyloxy)-5-fluoro-4-vinylphenyl)-3,8-diazabicyclo[3.2.1]octane-8-carboxylate as a colorless oil. MS: (ESI, m/z): 389 [M+H]+.

Step 5. tert-Butyl 3-(5-fluoro-2H-chromen-7-yl)-3,8-diazabicyclo[3.2.1]octane-8-carboxylate A solution of tert-butyl 3-(3-(allyloxy)-5-fluoro-4-vinylphenyl)-3,8-diazabicyclo[3.2.1]octane-8-carboxylate (800 mg, 2.06 mmol) and Grubbs Catalyst™ 2$^{nd}$ Gen (48 mg, 0.05 mmol) in DCM (10 mL) was stirred for 1 h at room temperature. The mixture was concentrated under vacuum. Purification by silica gel chromatography (eluting with 1:3 EtOAc/pet. ether) afforded tert-butyl 3-(5-fluoro-2H-chromen-7-yl)-3,8-diazabicyclo[3.2.1]octane-8-carboxylate as a colorless oil. MS: (ESI, m/z): 361 [M+H]−.

Step 6. tert-Butyl 3-(5-fluoro-3-nitro-2H-chromen-7-yl)-3,8-diazabicyclo[3.2.1]octane-8-carboxylate A solution of KNO$_2$ (945 mg, 11.10 mmol) and 18-crown-6 (2.2 g, 8.32 mmol) in THF (20 mL) was stirred for 1 h at room temperature. Then I$_2$ (2.3 g, 9.06 mmol) was added and stirring was continued for 1 h. Finally, a solution of tert-butyl. 3-(5-fluoro-2H-chromen-7-yl)-3,8-diazabicyclo[3.2.1]octane-8-carboxylate (1 g, 2.77 mmol) and pyridine (110 mg, 1.39 mmol) in THF (10 mL) was added to the solution and stirring was continued for 14 h. The reaction was quenched by the addition of water (20 mL). The resulting mixture was extracted with DCM (2×50 mL). The combined organic layers were dried over anhydrous sodium sulfate, filtered, and concentrated under vacuum. Purification by silica gel chromatography (eluting with 1:6 EtOAc/pet. ether) afforded tert-butyl 3-(5-fluoro-3-nitro-2H-chromen-7-yl)-3,8-diazabicyclo[3.2.1]octane-8-carboxylate as a yellow solid. MS: (ESI, m/z): 406 [M+H]+.

Step 7. tert-Butyl 3-(3-amino-5-fluorochroman-7-yl)-3,8-diazabicyclo[3.2.1]octane-8-carboxylate A solution of tert-butyl 3-(5-fluoro-3-nitro-2H-chromen-7-yl)-3,8-diazabicyclo[3.2.1]octane-8-carboxylate (120 mg, 0.30 mmol), BH$_3$-THF (1 M, 20 mL, 20.0 mmol), and NaBH$_4$ (116 mg, 3.07 mmol) in THF (20 mL) was stirred for 14 h at 65° C. Then methanol (20 mL) was added and stirring was continued for 4 h at 85° C. The mixture was concentrated under vacuum. Purification by reverse phase chromatography (Column: C18 silica gel; Mobile phase A: water with 10 mM NH$_4$HCO$_3$, B: ACN; Flow rate: 50 mL/min; Gradient: 0% to 50% B over 40 min) gave tert-butyl 3-(3-amino-5-fluorochroman-7-yl)-3,8-diazabicyclo[3.2.1]octane-8-carboxylate as a colorless oil. MS: (ESI, m/z): 378 [M+H]−.

The following intermediates in Table 6 were prepared using standard chemical manipulations and procedures similar to those used for the preparation of Intermediate 15-1.

TABLE 6

| Intermediate Number | Structure and Name | LRMS m/z [M + H]+ |
|---|---|---|
| 15-2[1] | tert-butyl 4-(3-amino-6-(trifluoromethoxy)chroman-7-yl)piperazine-1-carboxylate | 418 |
| 15-3 | tert-butyl 4-(3-amino-5-fluorochroman-7-yl)piperazine-1-carboxylate | 352 |

TABLE 6-continued

| Intermediate Number | Structure and Name | LRMS m/z [M + H]+ |
|---|---|---|
| 15-4 | tert-butyl 3-(3-amino-5-fluorochroman-7-yl)-3,6-diazabicyclo[3.1.1]heptane-6-carboxylate | 364 |

[1]Notes on procedures:
Step 6: nitration was conducted by sonicating a solution of tert-butyl 4-[6-(trifluoromethoxy)-2H-chromen-7-yl]piperazine-1-carboxylate (800 mg, 2.00 mmol), ACN (2.2 g, 4.00 mmol), NaNO₂ (1.4 g, 20.29 mmol) and acetic acid (1.44 g, 23.98 mmol) in chloroform (40 mL) for 6 h at 50° C. The reaction was quenched with sat. aq. NaHCO₃ solution (40 mL) and an extractive work up was performed with EtOAc.

Intermediate 16. 3-Amino-5-fluoro-6-methylthieno[2,3-b]pyridine-2-carboxylic acid

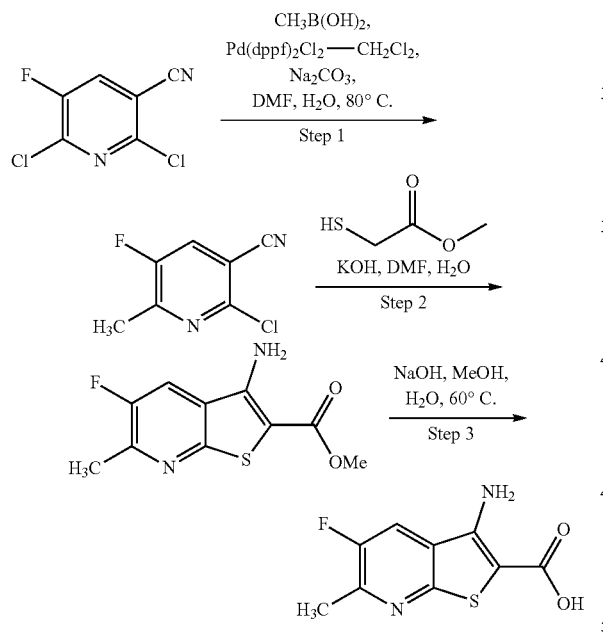

Step 1. 2-Chloro-5-fluoro-6-methylnicotinonitrile

A mixture of 2,6-dichloro-5-fluoropyridine-3-carbonitrile (5 g, 26.18 mmol), methylboronic acid (1.58 g, 26.36 mmol), Na₂CO₃ (8.33 g, 78.54 mmol), and Pd(dppf)Cl₂—CH₂Cl₂ (958 mg, 1.31 mmol) in DMF (40 mL) and water (20 mL) was stirred for 3 h at 80° C. After cooling to room temperature, the reaction mixture was diluted with 50 mL of water. The resulting mixture was extracted with EtOAc (3×100 mL). The combined organic layers were dried over anhydrous sodium sulfate, filtered, and concentrated under vacuum. Purification by silica gel chromatography (eluting with 1:5 EtOAc/pet. ether) afforded 2-chloro-5-fluoro-6-methylnicotinonitrile as a pink solid. MS: (ESI, m/z): 171 [M+H]+.

Step 2. Methyl 3-amino-5-fluoro-6-methylthieno[2,3-b]pyridine-2-carboxylate

A solution of 2-chloro-5-fluoro-6-methylnicotinonitrile (1.40 g, 8.21 mmol), KOH (1.38 g, 24.63 mmol), and methyl 2-mercaptoacetate (1.74 g, 16.42 mmol) in DMF (20 mL) and water (20 mL) was stirred for 3 h at room temperature. The pH value of the solution was adjusted to 5 with 1N HCl solution. The solids were collected by filtration to afford methyl 3-amino-5-fluoro-6-methylthieno[2,3-b]pyridine-2-carboxylate as a yellow solid. MS: (ESI, m/z): 241 [M+H]+.

Step 3. 3-Amino-5-fluoro-6-methylthieno[2,3-b]pyridine-2-carboxylic acid

A solution of methyl 3-amino-5-fluoro-6-methylthieno[2,3-b]pyridine-2-carboxylate (200 mg, 0.83 mmol) and NaOH (66 mg, 1.66 mmol) in MeOH (2 mL) and water (1 mL) was stirred for 1 h at 60° C. After cooling to room temperature, the resulting mixture was concentrated under vacuum. The residue was diluted with 20 mL of water. The pH value of the mixture was adjusted to 5 with 1N HCl solution. The solids were collected by filtration to give 3-amino-5-fluoro-6-methylthieno[2,3-b]pyridine-2-carboxylic acid as a yellow solid. MS: (ESI, m/z): 227 [M+H]+.

Intermediate 17. 3-amino-5-fluorothieno[2,3-b]pyridine-2-carboxylic acid

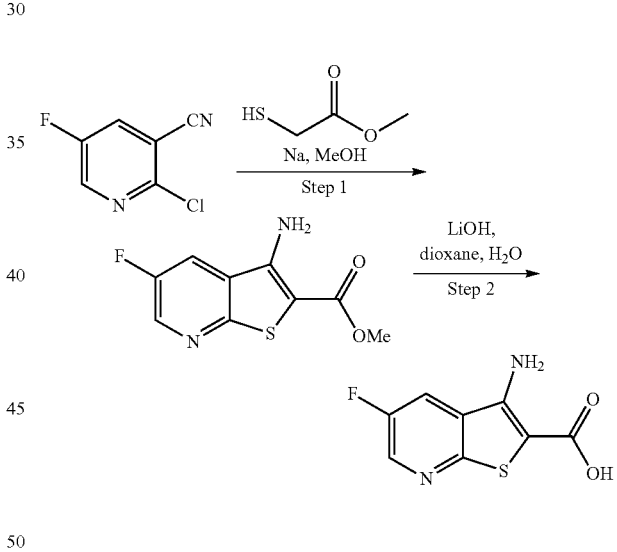

Step 1. Methyl 3-amino-5-fluorothieno[2,3-b]pyridine-2-carboxylate

Sodium (230 mg, 10.00 mmol) was added to MeOH (20 mL) at 0° C. and the resulting mixture was stirred for 30 min at 0° C. until the sodium was consumed. To the reaction mixture was added 2-chloro-5-fluoronicotinonitrile (900 mg, 5.75 mmol) and methyl 2-mercaptoacetate (1.8 mL, 14.98 mmol). The resulting solution was stirred for 16 h at room temperature. The reaction was quenched by the addition of 50 mL of water and was extracted with DCM (3×50 mL). The organic layers were combined, dried over anhydrous sodium sulfate, filtered, and concentrated under vacuum. Purification by silica gel chromatography (eluting with 1:1 EtOAc/pet. ether) afforded methyl 3-amino-5-fluorothieno[2,3-b]pyridine-2-carboxylate as a yellow solid. MS: (ESI, m/z): 227 [M+H]+.

Step 2. 3-Amino-5-fluorothieno[2,3-b]pyridine-2-carboxylic acid

A solution of methyl 3-amino-5-fluorothieno[2,3-b]pyridine-2-carboxylate (1 g, 3.76 mmol) and LiOH (100 mg, 3.97 mmol) in water (10 mL) and dioxane (10 mL) was stirred for 1 h at room temperature. The reaction was diluted with 20 mL of water and was extracted with EtOAc (3×30 mL). The pH value of the aqueous layer was adjusted to 6 with 6N HCl solution. The solids were collected by filtration to afford 3-amino-5-fluorothieno[2,3-b]pyridine-2-carboxylic acid as a yellow solid. MS: (ESI, m/z): 213 [M+H]$^+$.

Intermediate 18. 3-Amino-6-fluorothieno[2,3-b]pyridine-2-carboxylic acid

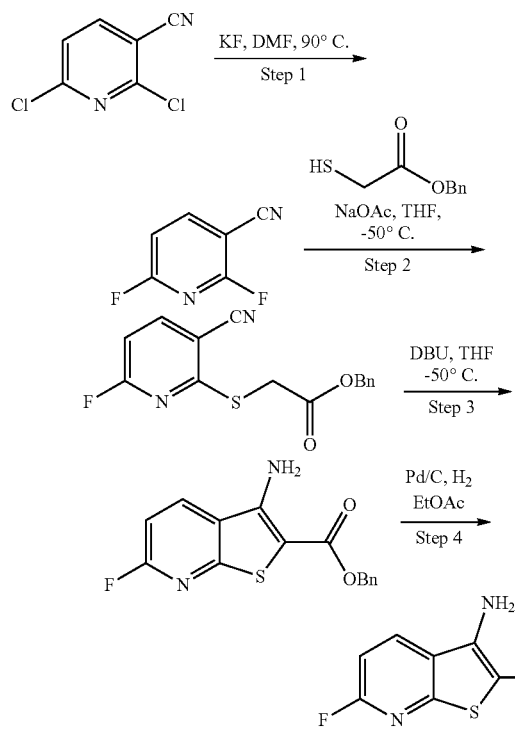

Step 1. 2,6-Difluoronicotinonitrile

A mixture of 2,6-dichloronicotinonitrile (6.92 g, 40.00 mmol) and KF (6.98 g, 120.14 mmol) in DMF (30 mL) was stirred overnight at 90° C. After cooling to room temperature, the reaction was quenched by the addition of 100 mL of water. The resulting mixture was extracted with EtOAc (3×100 mL). The combined organic layers were dried over anhydrous sodium sulfate, filtered and concentrated under vacuum. Purification by silica gel chromatography (eluting with 1:3 EtOAc/pet. ether) afforded 2,6-difluoronicotinonitrile as a white solid. MS: (ESI, m/z): 141 [M+H]$^+$.

Step 2. Benzyl 2-((3-cyano-6-fluoropyridin-2-yl)thio)acetate

To a mixture of 2,6-difluoronicotinonitrile (1 g, 6.42 mmol) and NaOAc (878 mg, 10.70 mmol) in THF (20 mL) was added benzyl 2-mercaptoacetate (1.17 g, 6.42 mmol) at −70° C. The resulting solution was warmed to room temperature slowly and then stirred for 30 min. The reaction was quenched by the addition of 20 mL of water. The resulting mixture was extracted with DCM (3×30 mL). The combined organic layers were dried over anhydrous sodium sulfate, filtered and concentrated under vacuum. Purification by silica gel chromatography (eluting with 2:25 EtOAc/pet. ether) afforded benzyl 2-((3-cyano-6-fluoropyridin-2-yl)thio)acetate as a white solid. MS: (ESI, m/z): 303[M+H]$^+$.

Step 3. Benzyl 3-amino-6-fluorothieno[2,3-b]pyridine-2-carboxylate

A solution of benzyl 2-((3-cyano-6-fluoropyridin-2-yl)thio)acetate (120 mg, 0.40 mmol) in THF (2 mL) was added dropwise at −50° C. to a solution of DBU (120 mg, 0.79 mmol) in THF (3 mL). The mixture was then warmed to room temperature and stirred overnight. The resulting solution was concentrated under vacuum. Purification by silica gel chromatography (eluting with 1:1 EtOAc/pet. ether) afforded benzyl 3-amino-6-fluorothieno[2,3-b]pyridine-2-carboxylate as an off-white solid. MS: (ESI, m/z): 303 [M+H]$^+$.

Step 4. 3-Amino-6-fluorothieno[2,3-b]pyridine-2-carboxylic acid

A mixture of benzyl 3-amino-6-fluorothieno[2,3-b]pyridine-2-carboxylate (89 mg, 0.29 mmol) and Pd/C (20 mg, 10%) in EtOAc (15 mL) was stirred for 1 h at room temperature. The solids were filtered out. The filtrate was concentrated under vacuum to give 3-amino-6-fluorothieno[2,3-b]pyridine-2-carboxylic acid as a light yellow solid. MS: (ESI, m/z): 213 [M+H]$^+$.

Intermediate 19. 3-Amino-6-methoxythieno[2,3-b]pyridine-2-carboxylic acid

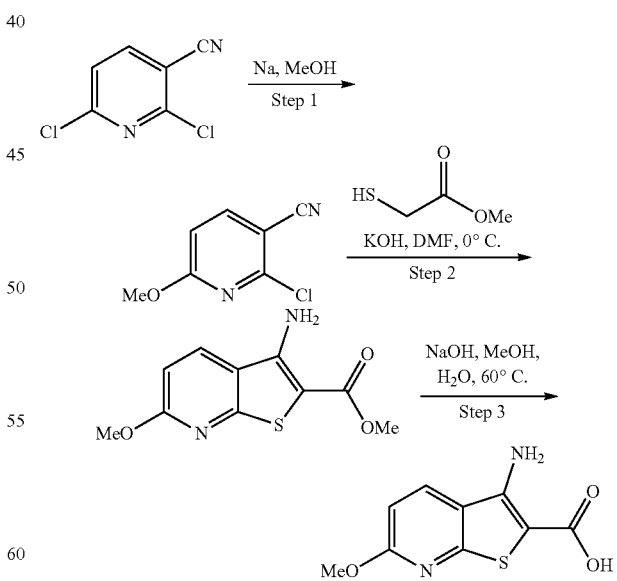

Step 1. 2-Chloro-6-methoxynicotinonitrile

Sodium (1.5 g, 65.22 mmol) was added to MeOH (25 mL) at 0° C. and the resulting mixture was stirred for 30 min at room temperature until the sodium was consumed. To the reaction mixture was added 2,6-dichloronicotinonitrile (5 g, 28.90 mmol) over 5 min, maintaining reaction temperature below 10° C. The resulting solution was stirred overnight at room temperature. The solids were filtered away and the filtrate was concentrated under vacuum. Purification by silica gel chromatography (eluting with 1:3 EtOAc/hexanes) afforded 2-chloro-6-methoxynicotinonitrile as a white solid. MS: (ESI, m/z): 169 [M+H]$^+$.

Step 2. Methyl 3-amino-6-methoxythieno[2,3-b]pyridine-2-carboxylate

To a solution of 2-chloro-6-methoxynicotinonitrile (3.9 g, 23.13 mmol) in DMF (10 mL) was added KOH (5.2 g) at 0° C. over 5 min, followed by the addition of methyl 2-mercaptoacetate (2.46 g, 23.18 mmol). The resulting solution was stirred for 1 h at 0° C. The reaction was quenched by the addition of 20 mL of water. The resulting mixture was extracted with EtOAc (3×30 mL). The combined organic layers were washed with water (50 mL) and brine (50 mL), dried over anhydrous sodium sulfate, filtered and concentrated under vacuum. Purification by silica gel chromatography (eluting with 1:10 to 1:1 EtOAc/hexanes) afforded methyl 3-amino-6-methoxythieno[2,3-b]pyridine-2-carboxylate as a light yellow solid. $^1$H NMR (DMSO-d$_6$, 300 MHz) δ(ppm): 8.40 (d, J=8.7 Hz, 1H), 7.24 (br, 2H), 6.89 (d, J=9.0 Hz, 1H), 3.93 (s, 3H), 3.77 (s, 3H). MS: (ESI, m/z): 239 [M+H]$^+$.

Step 3. 3-Amino-6-methoxythieno[2,3-b]pyridine-2-carboxylic acid

A solution of methyl 3-amino-6-methoxythieno[2,3-b]pyridine-2-carboxylate (110 mg, 0.46 mmol) and LiOH (100 mg, 4.18 mmol) in THF (4 mL) and water (1.5 mL) was stirred for 2 h at 60° C. After cooling to room temperature, the resulting mixture was concentrated under vacuum. The residue was diluted with 2 mL of water. The pH value of the solution was adjusted to 7 with 1N HCl. The solids were collected by filtration to afford 3-amino-6-methoxythieno[2,3-b]pyridine-2-carboxylic acid as a yellow solid. MS: (ESI, m/z): 225 [M+H]$^+$.

Intermediate 20. 3-Amino-5-fluoro-6-methoxythieno[2,3-b]pyridine-2-carboxylic acid

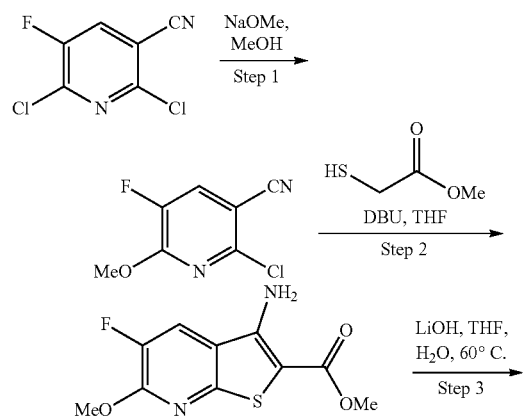

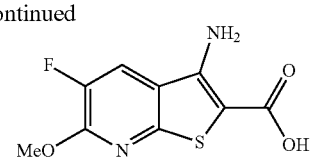

Step 1. 2-Chloro-5-fluoro-6-methoxynicotinonitrile

A mixture of 2,6-dichloro-5-fluoropyridine-3-carbonitrile (3.0 g, 15.71 mmol) and MeONa (1.28 g, 23.70 mmol) in MeOH (30 mL) was stirred for 5 h at room temperature. The resulting mixture was concentrated under vacuum. Purification by silica gel chromatography (eluting with 1:3 EtOAc/pet. ether) afforded 2-chloro-5-fluoro-6-methoxynicotinonitrile as a yellow solid. MS: (ESI, m/z): 187, 189 [M+H]$^-$.

Step 2. Methyl 3-amino-5-fluoro-6-methoxythieno[2,3-b]pyridine-2-carboxylate

A solution of 2-chloro-5-fluoro-6-methoxynicotinonitrile (1.90 g, 10.22 mmol) methyl 2-mercaptoacetate (1.3 g, 12.26 mmol), and DBU (7.2 g, 47.29 mmol) in THF (30 mL) was stirred overnight at room temperature. The reaction was quenched by the addition of 50 mL of water and was extracted with EtOAc (3×50 mL). The organic layers were combined, dried over anhydrous sodium sulfate, filtered and concentrated under vacuum. Purification by silica gel chromatography (eluting with 1:3 EtOAc/pet. ether) afforded methyl 3-amino-5-fluoro-6-methoxythieno[2,3-b]pyridine-2-carboxylate as a yellow solid. MS: (ESI, m/z): 257 [M+H]$^+$.

Step 3. 3-Amino-5-fluoro-6-methoxythieno[2,3-b]pyridine-2-carboxylic acid

A mixture of methyl 3-amino-5-fluoro-6-methoxythieno[2,3-b]pyridine-2-carboxylate (500 mg, 1.95 mmol) and LiOH (236 mg, 9.85 mmol) in THF (8 mL) and water (8 mL) was stirred overnight at 60° C. After cooling to room temperature, the solvent was removed under vacuum. The pH value of the residue was adjusted to 7 with 3N HCl. The solids were collected by filtration to afford 3-amino-5-fluoro-6-methoxythieno[2,3-b]pyridine-2-carboxylic acid as a yellow solid. MS: (ESI, m/z): 243 [M+H]$^+$.

Intermediate 21. 3-Amino-4,6-dimethylthieno[2,3-b]pyridine-2-carboxylic

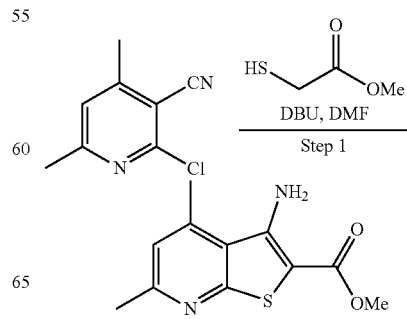

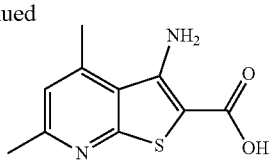

Step 1. Methyl 3-amino-4,6-dimethylthieno[2,3-b]pyridine-2-carboxylate

To a solution of 2-chloro-4,6-dimethylnicotinonitrile (2.000 g, 12.00 mmol) and DBU (5.00 g, 32.84 mmol) in DMF (20 mL) was added methyl 2-sulfanylacetate (1.019 g, 9.60 mmol) dropwise with stirring at −50° C. The resulting solution was stirred overnight at room temperature. The mixture was poured into water (50 mL) and the solids were collected by filtration to give methyl 3-amino-4,6-dimethylthieno[2,3-b]pyridine-2-carboxylate as a light yellow solid. MS: (ESI, m/z): 237 [M+H]$^+$.

Step 2. 3-Amino-4,6-dimethylthieno[2,3-b]pyridine-2-carboxylic acid

To a solution of methyl 3-amino-4,6-dimethylthieno[2,3-b]pyridine-2-carboxylate (300 mg, 1.27 mmol) in MeOH (5 mL) was added a solution of NaOH (254 mg, 6.35 mmol) in water (5 mL). The resulting solution was stirred for 3 h at 70° C. After cooling to room temperature, the solvent was removed under vacuum. The pH value of the residue was adjusted to 6 with 3N HCl. The solids were collected by filtration to afford 3-amino-4,6-dimethylthieno[2,3-b]pyridine-2-carboxylic acid as a yellow solid. MS: (ESI, m/z): 223 [M+H]$^+$.

Intermediate 22. 3-Amino-6-methyl-4-(trifluoromethyl)thieno[2,3-b]pyridine-2-carboxylic acid

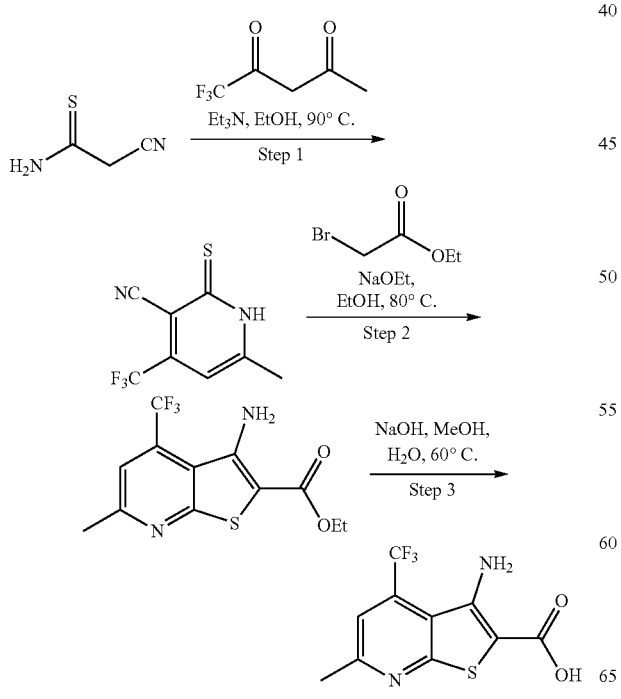

Step 1. 6-Methyl-2-thioxo-4-(trifluoromethyl)-1,2-dihydropyridine-3-carbonitrile A solution of 2-cyanoethanethioamide (2 g, 19.97 mmo) 1,1,1-trifluoropentane-2,4-dione (3 g, 19.47 mmol), and triethylamine (0.1 mL) in in ethanol (20 mL) was stirred for 1 h at 90° C. After cooling to room temperature, the solids were collected by filtration and dried in an oven under reduced pressure to afford 6-methyl-2-thioxo-4-(trifluoromethyl)-1,2-dihydropyridine-3-carbonitrile as a yellow solid. MS: (ESI, m/z): 219 [M+H]$^-$.

Step 2. Ethyl 3-amino-6-methyl-4-(trifluoromethyl)thieno[2,3-b]pyridine-2-carboxylate A solution of 6-methyl-2-thioxo-4-(trifluoromethyl)-1,2-dihydropyridine-3-carbonitrile (800 mg, 3.67 mmol), ethyl 2-bromoacetate (609 mg, 3.65 mmol), and NaOEt (297 mg, 4.37 mmol) in ethanol (20 mL) was stirred overnight at 80° C. The solvent was removed under vacuum. The residue was diluted with 30 mL of water and was extracted with ethyl acetate (3×30 mL). The organic layers were combined, dried over anhydrous sodium sulfate, filtered and concentrated under vacuum. Purification by silica gel chromatography (eluting with 1:10 to 1:1 EtOAc/pet. ether) afforded ethyl 3-amino-6-methyl-4-(trifluoromethyl)thieno[2,3-b]pyridine-2-carboxylate as a yellow solid. MS: (ESI, m/z): 305 [M+H]$^+$.

Step 3. 3-Amino-6-methyl-4-(trifluoromethyl)thieno[2,3-b]pyridine-2-carboxylic acid A solution of ethyl 3-amino-6-methyl-4-(trifluoromethyl)thieno[2,3-b]pyridine-2-carboxylate (1.0 g, 3.29 mmol) and sodium hydroxide (470 mg, 11.75 mmol) in water (2 mL) and methanol (10 mL) was stirred for 2 h at 60° C. The resulting mixture was concentrated under vacuum. The residue was diluted with 10 mL of water. The pH value of the solution was adjusted to 3 with 3N HCl. The solids were collected by filtration to give 3-amino-6-methyl-4-(trifluoromethyl)thieno[2,3-b]pyridine-2-carboxylic acid as a yellow solid. MS: (ESI, m/z): 277 [M+H]$^+$.

Intermediate 23. Methyl 6-amino-2-methylthieno[2,3-d]thiazole-5-carboxylate and

Intermediate 24. 6-Amino-2-methylthieno[2,3-d]thiazole-5-carboxylic acid

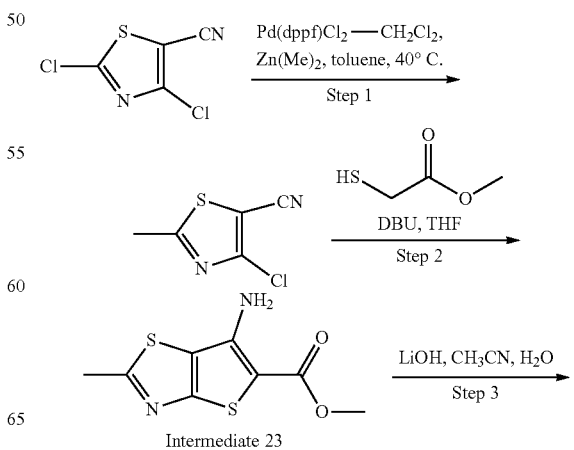

-continued

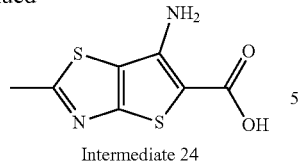
Intermediate 24

Step 1. 4-Chloro-2-methylthiazole-5-carbonitrile

A mixture of 2,4-dichlorothiazole-5-carbonitrile (1.00 g, 5.59 mmol), dimethylzinc (1M in Et$_2$O) (8.8 mL, 8.80 mmol), and Pd(dppf)Cl$_2$-CH$_2$Cl$_2$ (911 mg, 1.12 mmol) in toluene (30 mL) was stirred for 4 h at 40° C. The reaction was quenched by the addition of 20 mL of water. The resulting mixture was extracted with EtOAc (3×20 mL). The organic layers were combined, dried over anhydrous sodium sulfate, filtered, and concentrated under vacuum. Purification by silica gel chromatography (eluting with 1:5 EtOAc/pet. ether) afforded 4-chloro-2-methylthiazole-5-carbonitrile as a light yellow solid. MS: (ESI, m/z): 159 [M+H]$^+$.

Step 2. Methyl 6-amino-2-methylthieno[2,3-d]thiazole-5-carboxylate

To a solution of 4-chloro-2-methylthiazole-5-carbonitrile (550 mg, 3.47 mmol) and DBU (1.06 g, 6.94 mmol) in THF (20 mL) was added a solution of methyl 2-mercaptoacetate (443 mg, 4.17 mmol) in THF (2 mL) dropwise with stirring at −40° C. The resulting solution allowed to warm to room temperature while stirring overnight. The reaction was quenched with 20 mL of water. The resulting mixture was extracted with EtOAc (3×20 mL). The combined organic layers were dried over anhydrous sodium sulfate, filtered, and concentrated under vacuum. Purification by silica gel chromatography (eluting with 1:7 EtOAc/pet. ether) afforded methyl 6-amino-2-methylthieno[2,3-d]thiazole-5-carboxylate as a light yellow solid. MS: (ESI, m/z): 229 [M+H]$^+$.

Step 3. 6-Amino-2-methylthieno[2,3-d]thiazole-5-carboxylic acid

To a solution of methyl 6-amino-2-methylthieno[2,3-d]thiazole-5-carboxylate (174 mg, 0.76 mmol) in ACN (11 mL) was added a solution of LiOH (100 mg, 4.18 mmol) in water (5 mL). The resulting solution was stirred overnight at 30° C., then was concentrated under vacuum. The residue was diluted with 1 mL of water. The pH value of the residue was adjusted to 7 with 1N HCl solution. The solids were collected by filtration to give 6-amino-2-methylthieno[2,3-d]thiazole-5-carboxylic acid as an off-white solid. MS: (ESI, m/z): 214 [M+H]$^+$.

Intermediate 25. 1-Ethyl-1H-pyrrolo[2,3-b]pyridine-5-carboxylic acid

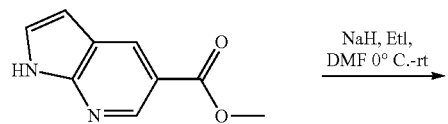

-continued

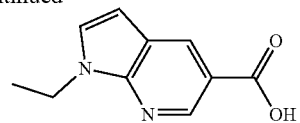

To a solution of methyl $^1$H-pyrrolo[2,3-b]pyridine-5-carboxylate (3 g, 17.03 mmol) in DMF (80 mL) was added sodium hydride (2.04 g, 51.09 mmol, 60% dispersion in oil) in portions at 0° C. The reaction mixture was stirred for 1 h at 0° C. Then iodoethane (5.32 g, 34.06 mmol) was added at 0° C. The resulting solution was stirred for 10 h at room temperature. The reaction was quenched with 10 mL of water. After stirred for 30 min, the pH value of the solution was adjusted to 7-8 with 3N HCl. The resulting mixture was extracted with EtOAc (6×50 mL). The combined organic layers were washed with brine (50 mL), dried over anhydrous sodium sulfate, filtered, and concentrated under vacuum to give of 1-ethyl-1H-pyrrolo[2,3-b]pyridine-5-carboxylic acid as a yellow solid (crude, 90% purity). MS: (ESI, m/z): 191 [M+H]$^-$.

Intermediate 26. 7-Ethyl-7H-pyrrolo[2,3-c]pyridazine-3-carboxylic acid

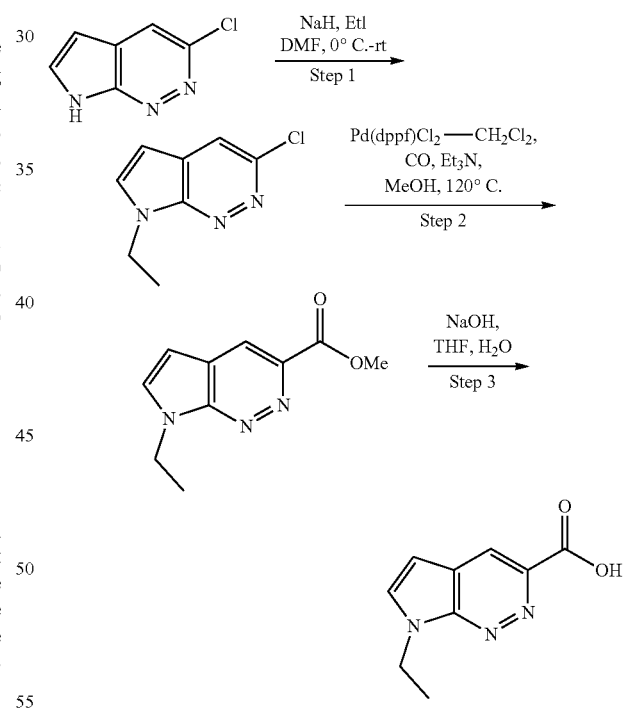

Step 1. 3-Chloro-7-ethyl-7H-pyrrolo[2,3-c]pyridazine

To a solution of 3-chloro-7H-pyrrolo[2,3-c]pyridazine (700 mg, 4.56 mmol) in DMF (17 mL) was added NaH (365 mg, 9.12 mmol, 60% dispersion in oil) in portions at 0° C. The reaction mixture was stirred for 30 min at 0° C. Then iodoethane (856 mg, 5.49 mmol) was added at 0° C. and the reaction mixture was stirred for 2 h at room temperature. The reaction was quenched by the addition of 40 mL of water.

The resulting mixture was extracted with EtOAc (3×20 mL). The organic layers were combined, dried over anhydrous sodium sulfate, filtered and concentrated under vacuum. Purification by prep-TLC (eluting with 1:1 EtOAc/pet. ether) afforded 3-chloro-7-ethyl-7H-pyrrolo[2,3-c]pyridazine as yellow oil. MS: (ESI, m/z): 182, 183 [M+H]⁻.

Step 2. Methyl 7-ethyl-7H-pyrrolo[2,3-c]pyridazine-3-carboxylate

In a 30-mL pressure tank reactor, a solution of 3-chloro-7-ethyl-7H-pyrrolo[2,3-c]pyridazine (300 mg, 1.65 mmol), Pd(dppf)Cl$_2$·CH$_2$Cl$_2$ (121 mg, 0.15 mmol), and Et$_3$N (0.69 mL, 4.96 mmol) in MeOH (15 mL) was stirred for 48 h at 120° C. under 50 atm of CO (g). After cooling to room temperature, the resulting mixture was concentrated under vacuum. The residue was diluted with 20 mL of water. The resulting mixture was extracted with EtOAc (3×20 mL). The organic layers were combined, dried over anhydrous sodium sulfate, filtered and concentrated under vacuum. Purification by prep-TLC (eluting with 1:1 EtOAc/pet. ether) afforded methyl 7-ethyl-7H-pyrrolo[2,3-c]pyridazine-3-carboxylate as a yellow solid. MS: (ESI, m/z): 206 [M+H]⁺.

Step 3. 7-Ethyl-7H-pyrrolo[2,3-c]pyridazine-3-carboxylic acid

A mixture of methyl 7-ethyl-7H-pyrrolo[2,3-c]pyridazine-3-carboxylate (238 mg, 1.04 mmol), and sodium hydroxide (206 mg, 5.20 mmol) in THF (10 mL) and water (10 mL was stirred for 18 h at room temperature. The resulting mixture was concentrated under vacuum. The residue was diluted with 10 mL of water. The pH value of the mixture was adjusted to 5 with 2N HCl. The resulting mixture was extracted with EtOAc (3×30 mL). The organic layers were combined, dried over anhydrous sodium sulfate, filtered and concentrated under vacuum to give 7-ethyl-7H-pyrrolo[2,3-c]pyridazine-3-carboxylic acid as a light yellow solid (crude). MS: (ESI, m/z): 192 [M+H]⁺.

Intermediate 27. 3-Amino-6-methylfuro[2,3-b]pyridine-2-carboxylic acid

Step 1. Ethyl 3-amino-6-methylfuro[2,3-b]pyridine-2-carboxylate

A solution of 2-chloro-6-methylnicotinonitrile (5 g, 32.77 mmol), ethyl 2-hydroxyacetate (3.36 g, 32.28 mmol), and Cs$_2$CO$_3$ (32.2 g, 98.83 mmol) in NMP (80 mL) was stirred overnight at 75° C. After cooling to room temperature, the mixture was poured into 100 mL of water. The resulting mixture was extracted with ethyl acetate (3×100 mL). The combined organic layers were washed with brine (100 mL), dried over anhydrous sodium sulfate, filtered and concentrated under vacuum. Purification by silica gel chromatography (eluting with 1:3 ethyl acetate/pet. ether) afforded ethyl 3-amino-6-methylfuro[2,3-b]pyridine-2-carboxylate as a pink solid. MS: (ESI, m/z): 221 [M+H]⁺.

Step 2. 3-Amino-6-methylfuro[2,3-b]pyridine-2-carboxylic acid

To a solution of ethyl 3-amino-6-methylfuro[2,3-b]pyridine-2-carboxylate (110 mg, 0.53 mmol) in methanol (1 mL) and THF (1 mL) was added a solution of LiOH (24 mg, 1.00 mmol) in water (0.5 mL) dropwise with stirring. The resulting solution was stirred overnight at room temperature. The pH value of the solution was adjusted to 8 with 1N HCl. The resulting mixture was extracted with ethyl acetate (3×20 mL). The combined organic layers were dried over anhydrous sodium sulfate, filtered, and concentrated under vacuum. Purification by reverse phase chromatography (Column: C18 silica gel; Mobile phase A: water (0.1% formic acid), B: ACN; Flow rate: 50 mL/min; Gradient: 0% B to 100% B in 30 min) afforded 3-amino-6-methylfuro[2,3-b]pyridine-2-carboxylic acid as a light yellow solid. MS: (ESI, m/z): 193 [M+H]⁺.

Intermediate 28. 8-(tert-Butoxycarbonyl)-5,6,7,8-tetrahydro-1,8-naphthyridine-3-carboxylic acid

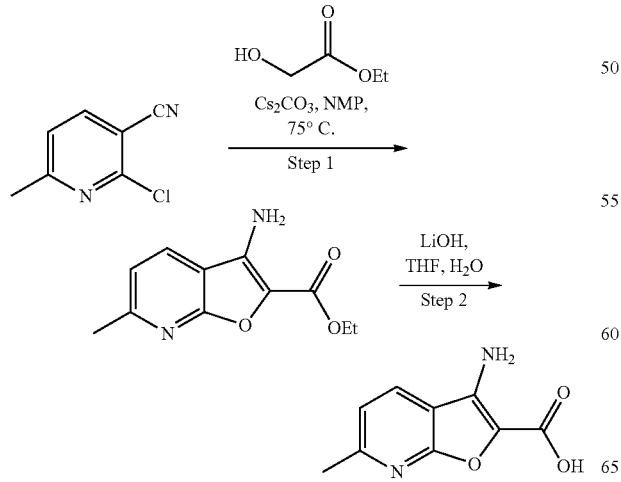

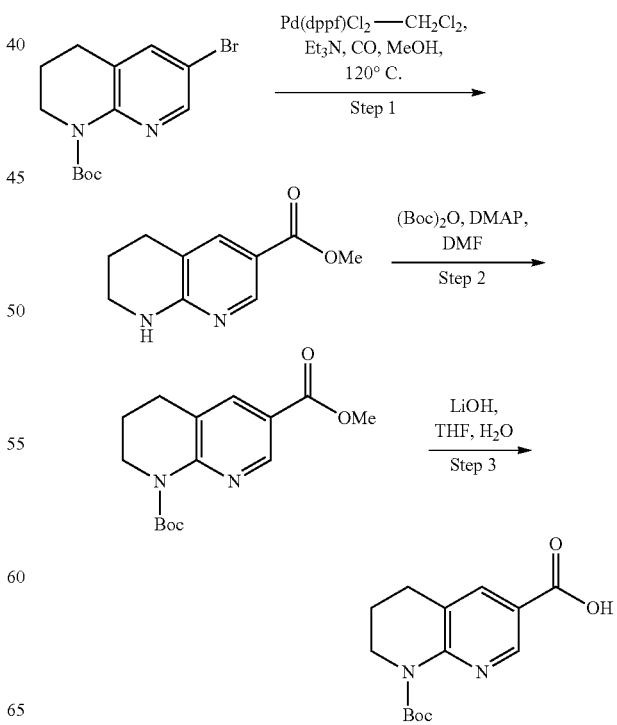

Step 1. Methyl 5,6,7,8-tetrahydro-1,8-naphthyridine-3-carboxylate

In a 30-mL pressure tank reactor, a mixture of tert-butyl 6-bromo-3,4-dihydro-1,8-naphthyridine-1(2H)-carboxylate (300 mg, 0.86 mmol), Pd(dppf)Cl$_2$—CH$_2$Cl$_2$ (90 mg, 0.11 mmol), and Et$_3$N (1 mL) in MeOH (5 mL) was stirred for 48 h at 120° C. under 5 atm of CO (g). After cooling to room temperature, the solvent was removed under vacuum. The residue was diluted with water (10 mL) and was extracted with EtOAc (3×10 mL). The combined organic layers were dried over Na$_2$SO$_4$, filtered, and concentrated under vacuum. The residue was purified by silica gel chromatography (eluting with 1:5 EtOAc/pet. ether) to afford 0.15 g of methyl 5,6,7,8-tetrahydro-1,8-naphthyridine-3-carboxylate as a white solid. MS: (ESI, m/z): 193 [M+H]$^+$.

Step 2. 1-(tert-Butyl) 6-methyl 3,4-dihydro-1,8-naphthyridine-1,6(2H)-dicarboxylate A solution of methyl 5,6,7,8-tetrahydro-1,8-naphthyridine-3-carboxylate (110 mg, 0.52 mmol), DMAP (126 mg, 1.03 mmol), and (Boc)$_2$O (227 mg, 1.04 mmol) in DMF (5 mL) was stirred for 1 h at room temperature. The reaction was quenched by the addition of 5 mL of water. The resulting mixture was extracted with ethyl acetate (3×10 mL). The combined organic layers were dried over Na$_2$SO$_4$, filtered, and concentrated under vacuum. The residue was purified by silica gel chromatography (eluting with 1:8 EtOAc/pet. ether) to afford 1-(tert-butyl) 6-methyl 3,4-dihydro-1,8-naphthyridine-1,6(2H)-dicarboxylate as a white solid. MS: (ESI, m/z): 293 [M+H]$^-$.

Step 3. 8-(tert-Butoxycarbonyl)-5,6,7,8-tetrahydro-1,8-naphthyridine-3-carboxylic acid A solution of 1-(tert-butyl) 6-methyl 3,4-dihydro-1,8-naphthyridine-1,6(2H)-dicarboxylate (280 mg, 0.86 mmol) and LiOH (81 mg, 3.38 mmol) in THF (5 mL) and water (5 mL) was stirred for 3 h at room temperature. The resulting mixture was concentrated under vacuum. The residue was purified by reverse phase chromatography (Column: C18 silica gel; Mobile phase A: water (0.05% formic acid), B: ACN; Gradient: 0% B to 60% B in 40 min) to afford 8-(tert-butoxycarbonyl)-5,6,7,8-tetrahydro-1,8-naphthyridine-3-carboxylic acid as a white solid. MS: (ESI, m/z): 279 [M+H]$^+$.

Intermediate 29. 2',3'-Dihydro-1'H-spiro[cyclopropane-1,4'-[1,8]naphthyridine]-6'-carboxylic acid

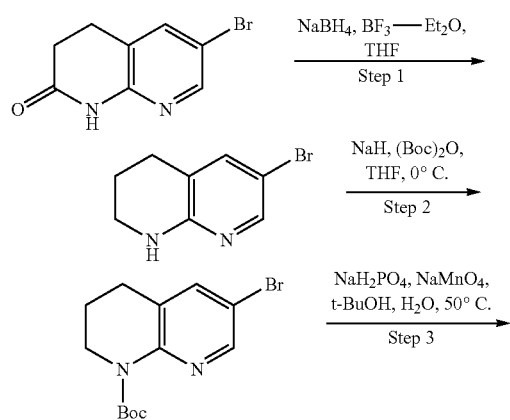

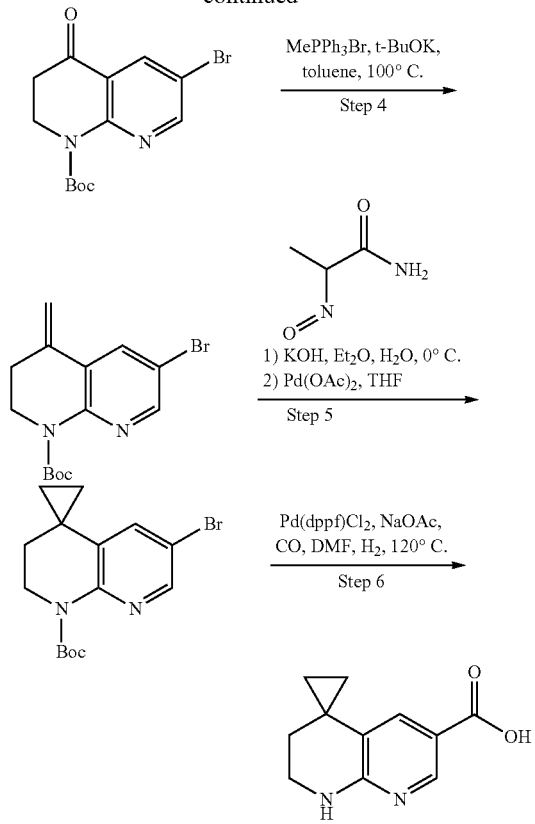

Step 1. 6-Bromo-1,2,3,4-tetrahydro-1,8-naphthyridine

To a solution of 6-bromo-3,4-dihydro-1,8-naphthyridin-2(1H)-one (5.0 g, 21.80 mmol) and NaBH$_4$ (4.18 g, 110.49 mmol) in THF (140 mL) was added BF$_3$-Et$_2$O (20 mL, 157.83 mmol) dropwise at 0° C. The reaction mixture was stirred for 16 h at room temperature. 1N HCl solution (100 mL) was added and the reaction mixture was stirred for an additional 16 h at room temperature. The pH value of the mixture was then adjusted to 8 with aq. sat. NaHCO$_3$ solution. The resulting mixture was extracted with ethyl acetate (3×150 mL) and the combined organic layers were dried over anhydrous sodium sulfate, filtered and concentrated under vacuum to give 6-bromo-1,2,3,4-tetrahydro-1,8-naphthyridine as a white solid. MS: (ESI, m/z): 213, 215 [M+H]$^-$.

Step 2. tert-Butyl 6-bromo-3,4-dihydro-1,8-naphthyridine-1(2H)-carboxylate

To a mixture of sodium hydride (1.41 g, 58.76 mmol, 60% dispersion in oil) in THF (100 mL) was added a solution of 6-bromo-1,2,3,4-tetrahydro-1,8-naphthyridine (5.0 g, 22.53 mmol) in THF (100 mL) at 0° C. The reaction mixture was stirred for 30 min at 0° C. To the mixture was then added a solution of (Boc)$_2$O (10.15 g, 46.51 mmol) in THF (50 mL). The resulting mixture was heated at reflux for 16 h. After cooling to room temperature, the reaction was quenched by the addition of water (150 mL). The resulting mixture was extracted with ethyl acetate (3×150 mL) and the combined organic layers were dried over anhydrous sodium sulfate, filtered and concentrated under vacuum. Purification by silica gel chromatography (eluting with 1:3 EtOAc/pet. ether) afforded tert-butyl 6-bromo-3,4-dihydro-1,8-naphthyridine-1(2H)-carboxylate as a light yellow solid. MS: (ESI, m/z): 313, 315 [M+H]+.

Step 3. tert-Butyl 6-bromo-4-oxo-3,4-dihydro-1,8-naphthyridine-1(2H)-carboxylate To a solution of tert-butyl 6-bromo-3,4-dihydro-1,8-naphthyridine-1(2H)-carboxylate (2.0 g, 6.13 mmol) and NaH$_2$PO$_4$ (1.92 g, 16.00 mmol) in tert-butanol (20 mL) and water (15 mL) was added a solution of NaMnO$_4$—H$_2$O (6.13 g, 38.31 mmol) in water (5 mL) dropwise at 50° C. The reaction mixture was stirred for 3 h at 50° C. After cooling to room temperature, Na$_2$SO$_3$ was added and the mixture was stirred for 30 min at room temperature. The solids were filtered away and the filtrate was diluted with 50 mL of water. The resulting mixture was extracted with ethyl acetate (3×50 mL) and the combined organic layers were dried over anhydrous sodium sulfate, filtered and concentrated under vacuum. Purification by silica gel chromatography (eluting with 1:3 EtOAc/pet. ether) afforded tert-butyl 6-bromo-4-oxo-3,4-dihydro-1,8-naphthyridine-1(2H)-carboxylate as a white solid. MS: (ESI, m/z): 327, 329 [M+H]+.

Step 4. tert-Butyl 6-bromo-4-methylene-3,4-dihydro-1,8-naphthyridine-1(2H)-carboxylate A solution of methyltriphenylphosphonium bromide (3.29 g, 9.21 mmol) and t-BuOK (1M in THF) (9.2 mL, 9.02 mmol) in toluene (30 mL) was stirred for 1 h at 100° C. To the reaction mixture was added a solution of tert-butyl 6-bromo-4-oxo-3,4-dihydro-1,8-naphthyridine-1(2H)-carboxylate (1.5 g, 4.40 mmol) in toluene (5 mL). The resulting solution was for 1 h at 100° C. After cooling to room temperature, the reaction was quenched by the addition of water (50 mL). The resulting mixture was extracted with ethyl acetate (3×50 mL) and the combined organic layers were dried over anhydrous sodium sulfate, filtered and concentrated under vacuum. Purification by silica gel chromatography (eluting with gradient 1:100 to 1:3 EtOAc/pet. ether) afforded tert-butyl 6-bromo-4-methylene-3,4-dihydro-1,8-naphthyridine-1(2H)-carboxylate as a white solid. MS: (ESI, m/z): 325, 327 [M+I-]*.

Step 5. tert-Butyl 6'-bromo-2',3'-dihydro-1'H-spiro[cyclopropane-1,4'-[1,8]naphthyridine]-1'-carboxylate To a solution of potassium hydroxide (4.8 g, 85.55 mmol) in water (7.2 mL) was added a solution of 2-nitrosopropanamide (3.76 g, 36.83 mmol) in Et$_2$O (30 mL) was added. The resulting solution was stirred for 1 h at 0° C. The organic phase was separated to obtain the solution of diazomethane in Et$_2$O. To a solution of tert-butyl 6-bromo-4-methylene-3,4-dihydro-1,8-naphthyridine-1(2H)-carboxylate (400 mg, 1.18 mmol) in THE (30 mL) was added the solution of diazomethane at 0° C., followed by the addition of a mixture of Pd(OAc)$_2$ (28 mg, 0.12 mmol) in THF (3 mL). The reaction mixture was stirred for an additional 3 h at room temperature. The solids were filtered away and the filtrate was concentrated under vacuum. Purification by silica gel chromatography (eluting with 1:3 EtOAc/pet. ether) afforded tert-butyl 6'-bromo-2',3'-dihydro-1'H-spiro[cyclopropane-1,4'-[1,8]naphthyridine]-1'-carboxylate as a light yellow solid. MS: (ESI, m/z): 339, 341 [M+H]+.

Step 6. 2',3'-Dihydro-1'H-spiro[cyclopropane-1,4'-[1,8]naphthyridine]-6'-carboxylic acid Into a 30-mL pressure tank reactor fitted with a magnetic stir bar, was placed a mixture of tert-butyl 6'-bromo-2',3'-dihydro-1'H-spiro[cyclopropane-1,4'-[1,8]naphthyridine]-1'-carboxylate (140 mg, 0.40 mmol), sodium acetate trihydrate (167 mg, 1.23 mmol), and Pd(dppf)Cl$_2$—CH$_2$Cl$_2$ (65 mg, 0.08 mmol) in DMF (6 mL) and water (2 mL). The reaction mixture was stirred for 16 h at 120° C. under an atmosphere of carbon monoxide at 50 atm. After cooling to room temperature, the reaction was quenched by the addition of 20 mL of water. The resulting solution was extracted with ethyl acetate (3×20 mL). The combined organic layers were dried over anhydrous sodium sulfate, filtered and concentrated under vacuum. Purification by reverse phase chromatography (Column: C18 silica gel; Mobile phase A: water, B: ACN; Gradient: 0% B to 10% B in 10 min) afforded 2',3'-dihydro-1'H-spiro[cyclopropane-1,4'-[1,8]naphthyridine]-6'-carboxylic acid as an off-white solid. MS: (ESI, m/z): 205 [M+H]+.

Intermediate 30. 3-(tert-Butoxycarbonyl)-1a,2,3,7b-tetrahydro-1H-cyclopropa[c][1,8]naphthyridine-6-carboxylic acid

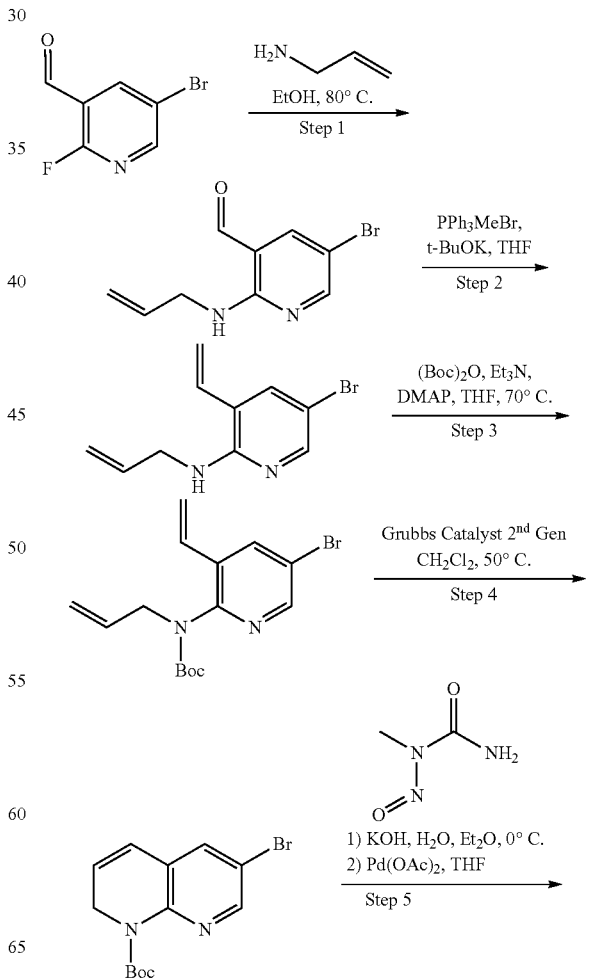

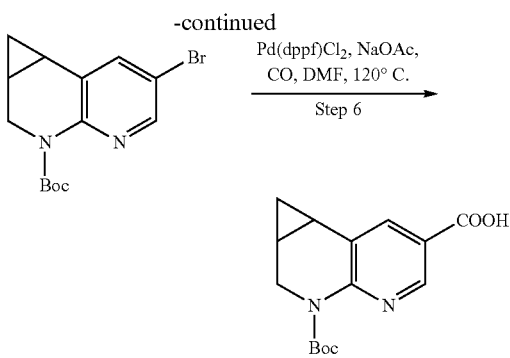

Step 1. 2-(Allylamino)-5-bromonicotinaldehyde

Into two parallel 30 ml sealed tubes, each was placed 5-bromo-2-fluoronicotinaldehyde (1.83 g, 9.0 mmol), allylamine (1.03 g, 18.0 mmol) and ethanol (15 mL). The resulting solution was stirred for 3 h at 80° C. After cooling room temperature, the resulting solution was poured into 30 mL of hydrochloric acid (1N) and the resulting mixture was stirred for 10 min and then extracted with ethyl acetate (3×30 mL). The combined organic layers were dried over anhydrous sodium sulfate, filtered and concentrated under vacuum. Purification by silica gel chromatography (eluting with 1:10 EtOAc/pet. ether) afforded 2-(allylamino)-5-bromonicotinaldehyde as a light yellow solid. MS: (ESI, m/z): 241, 243 [M+H]⁻.

Step 2. N-Allyl-5-bromo-3-vinylpyridin-2-amine

A solution of methyltriphenylphosphonium bromide (6.22 g, 17.42 mmol) and potassium tert butoxide (1.96 g, 17.42 mmol) in THF (30 mL) was stirred for 1 h at room temperature. Then a solution of 2-(allylamino)-5-bromonicotinaldehyde (2.10 g, 87.1 mmol) in THF (5 mL) was added dropwise at room temperature and the reaction mixture was stirred overnight at room temperature. The reaction was quenched by the addition of 20 mL of water and was extracted with DCM (3×40). The combined organic layers were dried over anhydrous sodium sulfate, filtered and concentrated under vacuum. Purification by silica gel chromatography (eluting with 1:20 EtOAc/pet. ether) afforded N-allyl-5-bromo-3-vinylpyridin-2-amine as a light yellow liquid. MS: (ESI, m/z): 239, 241 [M+H]⁺.

Step 3. tert-Butyl allyl(5-bromo-3-vinylpyridin-2-yl)carbamate

A solution of N-allyl-5-bromo-3-vinylpyridin-2-amine (590 mg, 2.47 mmol), di-tert-butyl dicarbonate (1.62 g, 7.40 mmol), triethylamine (749 mg, 7.40 mmol) and 4-dimethylaminopyridine (90 mg, 0.74 mmol) in THF (15 mL) was stirred overnight at 70° C. After cooling to room temperature, the reaction was quenched by the addition of 50 mL of water. The resulting mixture was extracted with ethyl acetate (3×40 mL). The combined organic layers were dried over anhydrous sodium sulfate, filtered and concentrated under vacuum. Purification by silica gel chromatography (eluting with 1:30 EtOAc/pet. ether) afforded tert-butyl allyl(5-bromo-3-vinylpyridin-2-yl)carbamate as an off-white solid. MS: (ESI, m/z): 339, 341 [M+H]⁺.

Step 4. tert-Butyl 6-bromo-1,8-naphthyridine-1(2H)-carboxylate

A solution of tert-butyl allyl(5-bromo-3-vinylpyridin-2-yl)carbamate (600 mg, 1.77 mmol) and dichloro[1,3-bis(2,4,6-trimethylphenyl)-2-imidazolidinylidene](benzylidene)(tricyclohexylphosphine)ruthenium(II) (Grubbs Catalyst™ 2$^{nd}$ Gen) (75 mg, 0.09 mmol) in DCM (10 mL) was stirred overnight at 50° C. After cooling to room temperature, the resulting mixture was concentrated under vacuum. Purification by silica gel chromatography (eluting with 1:20 EtOAc/pet. ether) afforded tert-butyl 6-bromo-1,8-naphthyridine-1(2H)-carboxylate as an off-white solid. MS: (ESI, m/z): 311, 313 [M+H]⁺.

Step 5. tert-Butyl 6-bromo-1,1a,2,7b-tetrahydro-3H-cyclopropa[c][1,8]naphthyridine-3-carboxylate To a solution of potassium hydroxide (5.68 g, 101.24 mmol) in water (8 mL) was added a solution of 1-methyl-1-nitrosourea (2.98 g, 28.92 mmol) in Et₂O (40 mL) dropwise at 0° C. The reaction mixture was stirred for 1 h at 0° C. Then the organic phase was separated to obtain the solution of diazomethane in Et₂O. To a solution of tert-butyl 6-bromo-1,8-naphthyridine-1(2H)-carboxylate (450 mg, 1.45 mmol) in THF (15 mL) was added the solution of diazomethane in Et₂O (40 mL), followed by the addition of a solution of Pd(OAc)₂ (32 mg, 0.14 mmol) in THF (7 mL). The resulting solution was stirred overnight at room temperature. The solids were filtered away and the filtrate was concentrated under vacuum. Purification by silica gel chromatography (eluting with gradient 1:50 to 1:20 EtOAc/pet. ether) afforded tert-butyl 6-bromo-1,1a,2,7b-tetrahydro-3H-cyclopropa[c][1,8]naphthyridine-3-carboxylate as an off-white solid. MS: (ESI, m/z): 325, 327 [M+H]⁺.

Step 6. 3-(tert-Butoxycarbonyl)-1a,2,3,7b-tetrahydro-1H-cyclopropa[c][1,8]naphthyridine-6-carboxylic acid Into a 30-mL pressure tank reactor, was placed tert-butyl 6-bromo-1,1a,2,7b-tetrahydro-3H-cyclopropa[c][1,8]naphthyridine-3-carboxylate (200 mg, 0.62 mmol), Pd(dppf)Cl₂ (90 mg, 0.12 mmol), NaOAc (151 mg, 1.85 mmol), DMF (4.5 mL) and water (1.5 mL). The reaction mixture was stirred for 18 h at 120° C. under 50 atm of CO (g). After cooling to room temperature, the reaction mixture was diluted with 10 mL of water. The resulting mixture was extracted with ethyl acetate (3×10 mL). The combined organic layers were dried over anhydrous sodium sulfate, filtered and concentrated under vacuum. Purification by reverse phase chromatography (Column: C18 silica gel; Mobile phase A: water (0.1% formic acid), B: ACN; Flow rate: 50 mL/min; Gradient: 0% B to 100% B in 30 min) afforded 3-(tert-butoxycarbonyl)-1a,2,3,7b-tetrahydro-1H-cyclopropa[c][1,8]naphthyridine-6-carboxylic acid as a light yellow solid. MS: (ESI, m/z): 291 [M+H]⁻.

Intermediate 31. 6-(Benzylamino)nicotinic acid

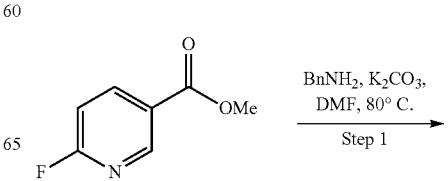

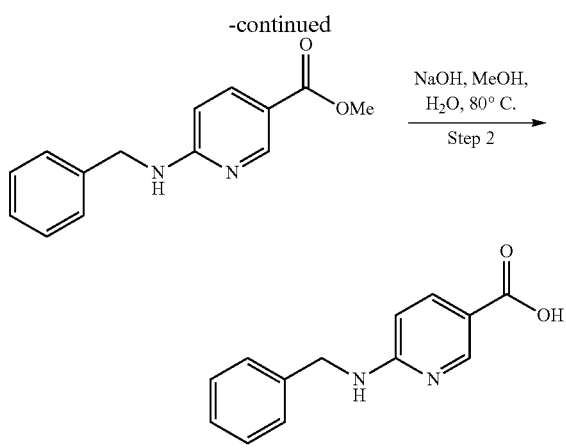

Step 1. Methyl 6-(benzylamino)nicotinate

A mixture of methyl 6-fluoropyridine-3-carboxylate (1 g, 6.12 mmol), phenylmethanamine (1.38 g, 12.88 mmol), and potassium carbonate (2.67 g, 19.32 mmol) in DMF (10 mL) was stirred for 2 h at 80° C. After cooling to room temperature, the reaction was quenched by the addition of 20 mL of water. The resulting mixture was extracted with ethyl acetate (3×20 mL). The combined organic layers were dried over anhydrous sodium sulfate, filtered and concentrated under vacuum. Purification by silica gel chromatography (eluting with 3:10 EtOAc:pet. ether) afforded methyl 6-(benzylamino)nicotinate as a white solid. MS: (ESI, m/z): 243 [M+H]$^+$.

Step 2. 6-(Benzylamino)nicotinic acid

A mixture of methyl 6-(benzylamino)nicotinate (500 mg, 1.86 mmol), methanol (20 mL), water (2 mL), and NaOH (165 mg, 4.13 mmol) was stirred for 3 h at 80° C. After cooling to room temperature, the resulting mixture was concentrated under vacuum. The residue was dissolved in 10 mL of water. The pH value of the solution was adjusted to 6 with hydrochloric acid (6 N). The solids were collected by filtration to afford 6-(benzylamino)nicotinic acid as a white solid. MS: (ESI, m/z): 229 [M+H]$^+$.

Intermediate 32. tert-Butyl 9,9-difluoro-3,7-diazabicyclo[3.3.1]nonane-3-carboxylate

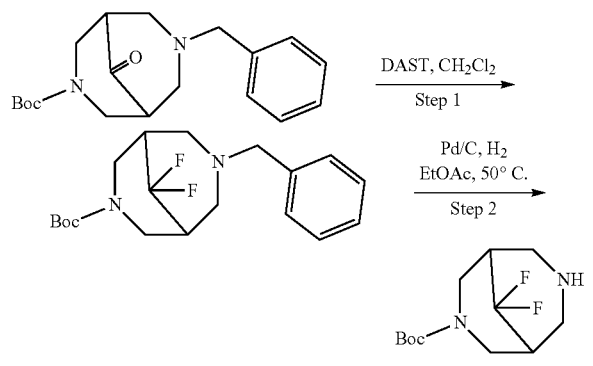

Step 1: tert-Butyl 7-benzyl-9,9-difluoro-3,7-diazabicyclo[3.3.1]nonane-3-carboxylate A solution of tert-butyl 7-benzyl-9-oxo-3,7-diazabicyclo[3.3.1]nonane-3-carboxylate (5 g, 14.94 mmol) and DAST (12.2 g, 75.69 mmol) in CH$_2$Cl$_2$ (80 mL) was stirred for 16 h at room temperature. The reaction was then quenched by the addition of 50 mL of saturated aqueous NaHCO$_3$ solution. The resulting mixture was extracted with CH$_2$Cl$_2$ (100 mL×3). The combined organic layers were dried over anhydrous sodium sulfate, filtered, and concentrated under vacuum. Purification by silica gel chromatography (eluting with 5:1 pet. ether/EtOAc) afforded 700 μmg of tert-butyl 7-benzyl-9,9-difluoro-3,7-diazabicyclo[3.3.1]nonane-3-carboxylate as a yellow solid. MS: (ESI, m/z): 353 [M+H]$^-$.

Step 2: tert-Butyl 9,9-difluoro-3,7-diazabicyclo[3.3.1]nonane-3-carboxylate

A mixture of tert-butyl 7-benzyl-9,9-difluoro-3,7-diazabicyclo[3.3.1]nonane-3-carboxylate (460 mg, 1.24 mmol) and Pd/C (50 mg, 10%) in EtOAc (20 mL) was stirred at 50° C. for 2 h under an atmosphere of hydrogen. After cooling to room temperature, the solids were filtered away and the filtrate was concentrated under vacuum. The residue was purified by pre-HPLC (Column: XBridge Prep C18 OBD, 19×250 mm; Mobile phase A: water (10 mM NH$_4$HCO$_3$), B: ACN; Gradient: 20% B to 45% B in 7 min) to afford tert-butyl 9,9-difluoro-3,7-diazabicyclo[3.3.1]nonane-3-carboxylate as a light yellow solid. MS: (ESI, m/z): 263 [M+H]$^+$.

Intermediate 33. 5-Benzyl-2-oxa-5,8-diazaspiro[3.5]nonane

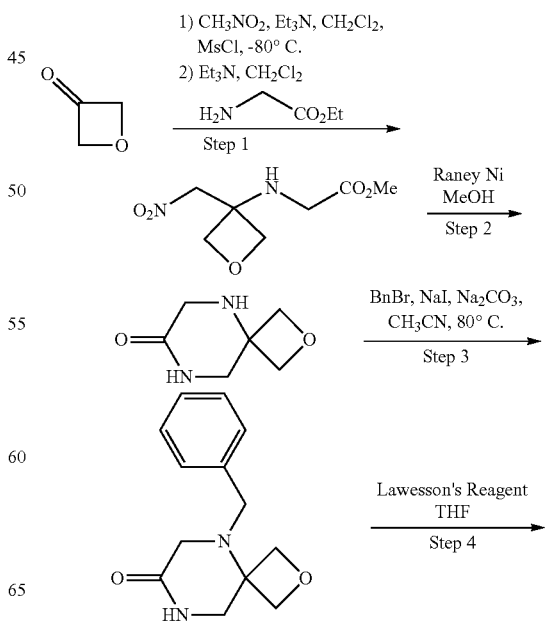

-continued

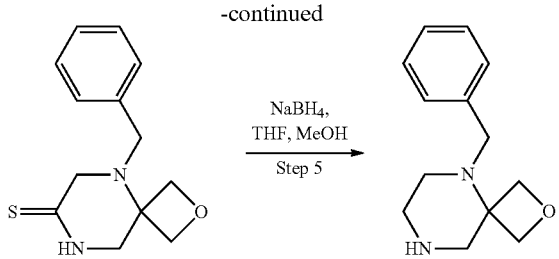

Step 1. Methyl 2-(3-(nitromethyl)oxetan-3-ylamino)acetate

To a solution of oxetan-3-one (5 g, 69.38 mmol), nitromethane (5.93 g, 97.15 mmol), and Et$_3$N (2.1 g, 13.28 mmol) in DCM (70 mL) was added a solution of MsCl (10 g, 87.30 mmol) in DCM (70 mL) at −80° C. Stirring continued at −80° C. for an additional 90 min. Separately, a solution of glycine ethyl ester hydrochloride (19.4 g, 139 mmol) and Et$_3$N (21 g, 139 mmol) in DCM (300 mL) was allowed to react, with stirring, for 10 min at room temperature. The resulting solution was added into the first reaction mixture at −80° C. in portions. After addition, the reaction mixture was stirred for 16 h at room temperature. The reaction was quenched by the addition of 100 mL of water and was extracted with 2×300 mL of DCM. The combined organic layers were dried over anhydrous sodium sulfate, filtered, and concentrated under vacuum. Purification by prep-HPLC (Column: XBridge Prep C18 OBD, 19×150 mm, 5 μm; Mobile phase A: water (10 mM NH$_4$HCO$_3$), B: ACN; Gradient: 10% B to 50% B in 30 min) afforded methyl 2-(3-(nitromethyl)oxetan-3-ylamino)acetate as a yellow oil. MS: (ESI, m/z): 205 [M+H]$^+$.

Step 2. 2-Oxa-5,8-diazaspiro[3.5]nonan-7-one

A suspension of methyl 2-(3-(nitromethyl)oxetan-3-ylamino)acetate (8.5 g, 41.63 mmol) and Raney Ni (2 g) in MeOH (50 mL) was stirred for 16 h at room temperature under an atmosphere of hydrogen. The solids were filtered away and the filtrate was concentrated under vacuum. Purification by prep-HPLC (Column: XBridge Prep C18 OBD, 19×150 mm, 5 μm; Mobile phase A: water (10 mM NH$_4$HCO$_3$), B: ACN; Gradient: 10% B to 80% B in 30 min) afforded 2-oxa-5,8-diazaspiro[3.5]nonan-7-one as a red solid. MS: (ESI, m/z): 143 [M+H]$^+$.

Step 3. 5-Benzyl-2-oxa-5,8-diazaspiro[3.5]nonan-7-one

A mixture of 2-oxa-5,8-diazaspiro[3.5]nonan-7-one (4 g, 28.14 mmol), (bromomethyl)benzene (12 g, 70.16 mmol), Na$_2$CO$_3$ (20.9 g, 197.18 mmol), and NaI (10.5 g, 70.05 mmol) in acetonitrile (200 mL) was stirred for 3 h at 80° C. After cooling to room temperature, the solvent was removed under vacuum. The residue was diluted with water (200 mL). The resulting mixture was extracted with DCM (2×300 mL). The combined organic layers were dried over anhydrous sodium sulfate, filtered, and concentrated under vacuum. Purification by silica gel chromatography (eluting with 1:10 MeOH/CH$_2$Cl$_2$) afforded 5-benzyl-2-oxa-5,8-diazaspiro[3.5]nonan-7-one as a yellow solid. MS: (ESI, m/z): 233 [M+H]$^+$.

Step 4. 5-Benzyl-2-oxa-5,8-diazaspiro[3.5]nonane-7-thione

A solution of 5-benzyl-2-oxa-5,8-diazaspiro [3.5]nonan-7-one (2.9 g, 11.86 mmol) and 2,4-bis(4-methoxyphenyl)-2,4-dithioxo-1,3,2,4-dithiadiphosphetane (Lawesson reagent) (2.44 g, 6.03 mmol) in THF (150 mL) was stirred for 16 h at room temperature and then stirred for an additional 3 h at 65° C. The reaction mixture was then poured into water (100 mL) and was extracted with DCM (2×150 mL). The combined organic layers were dried over anhydrous sodium sulfate, filtered, and concentrated under vacuum. Purification by silica gel chromatography (eluting with 1:3 EtOAc/pet. ether) afforded 5-benzyl-2-oxa-5,8-diazaspiro[3.5]nonane-7-thione as a white solid. MS: (ESI, m/z): 249 [M+H]$^+$.

Step 5. 5-Benzyl-2-oxa-5,8-diazaspiro[3.5]nonane

A solution of 5-benzyl-2-oxa-5,8-diazaspiro [30.5]nonane-7-thione (300 mg, 1.15 mmol) and sodium borohydride (412 mg, 11.19 mmol) in THF (15 mL) and MeOH (30 mL) was stirred for 2 h at room temperature. The reaction was quenched with water (15 mL) and was stirred for an additional 14 h at room temperature. The resulting mixture was extracted with DCM (2×50 mL). The combined organic layers were dried over anhydrous sodium sulfate, filtered, and concentrated under vacuum. Purification by prep-HPLC (Column: XBridge Prep C18 OBD, 19×150 mm, 5 μm; Mobile phase A: water (10 mM NH$_4$HCO$_3$), B: ACN; Gradient: 10% B to 75% B in 30 min) afforded 5-benzyl-2-oxa-5,8-diazaspiro[3.5]nonane as a white solid. MS: (ESI, m/z): 219 [M+H]$^+$.

Intermediate 34. tert-Butyl 2-oxa-5,8-diazaspiro[3.5]nonane-8-carboxylate

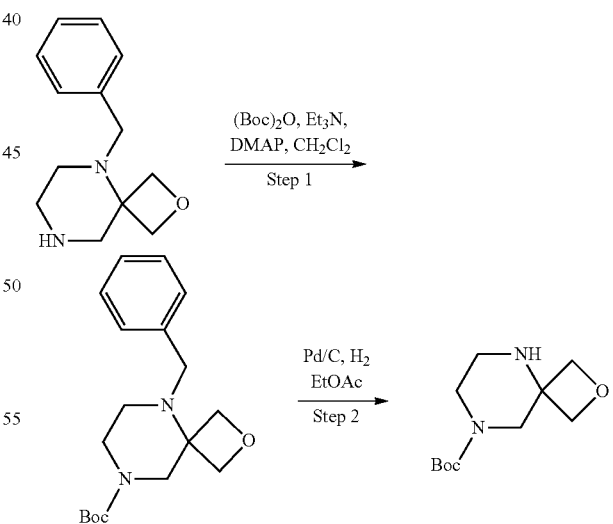

Step 1. tert-Butyl 5-benzyl-2-oxa-5,8-diazaspiro[3.5]nonane-8-carboxylate

A solution of 5-benzyl-2-oxa-5,8-diazaspiro[3.5]nonane, Intermediate 31, (200 mg, 0.82 mmol), (Boc)$_2$O (200 mg, 0.92 mmol), Et$_3$N (185 mg, 1.83 mmol), and 4-dimethylaminopyridine (11 mg, 0.09 mmol) in DCM (4 mL) was stirred for 2.5 h at room temperature. The reaction was quenched by the addition of water (20 mL) and was extracted with EtOAc (3×20 mL). The combined organic layers were dried over anhydrous sodium sulfate, filtered, and concentrated under vacuum. Purification by silica gel chromatography (eluting with 1:4 EtOAc/pet. ether) afforded of tert-butyl 5-benzyl-2-oxa-5,8-diazaspiro[3.5]nonane-8-carboxylate as a yellow oil. MS: (ESI, m/z): 319 [M+H]$^+$.

Step 2 tert-Butyl 2-oxa-5,8-diazaspiro[3.5]nonane-8-carboxylate

A mixture of tert-butyl 5-benzyl-2-oxa-5,8-diazaspiro[3.5]nonane-8-carboxylate (190 mg, 0.60 mmol) and Pd/C (20 mg, 10%) in EtOAc (10 mL) was stirred for 1 h at room temperature. The solids were filtered away and the filtrate was concentrated under vacuum to afford tert-butyl 2-oxa-5,8-diazaspiro[3.5]nonane-8-carboxylate as a yellow oil. MS: (ESI, m/z): 229 [M+H]$^+$.

Intermediate 35. tert-Butyl N-(4-methoxypyrrolidin-3-yl)carbamate

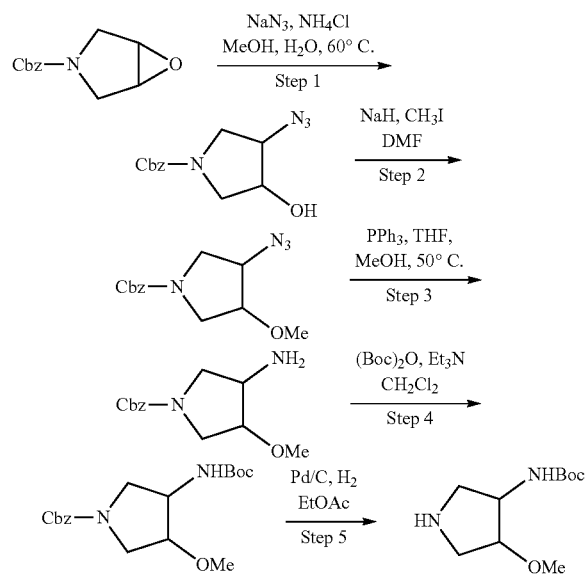

Step 1. Benzyl 3-azido-4-hydroxypyrrolidine-1-carboxylate

A solution of benzyl 6-oxa-3-azabicyclo[3.1.0]hexane-3-carboxylate (5 g, 22.81 mmol), NaN$_3$ (3 g, 46.15 mmol), NH$_4$Cl (1.23 g, 22.99 mmol) in MeOH (60 mL) and water (10 mL) was stirred for 16 h at 65° C. After cooling to room temperature, the pH value was adjusted to 7-8 with aq. 0.5N NaOH. The resulting mixture was extracted with DCM (2×150 mL). The combined organic layers were dried over anhydrous sodium sulfate, filtered, and concentrated under vacuum to give benzyl 3-azido-4-hydroxypyrrolidine-1-carboxylate as light-yellow solid. MS: (ESI, m/z): 263 [M+H]$^+$.

Step 2. Benzyl 3-azido-4-methoxypyrrolidine-1-carboxylate

To a solution of benzyl 3-azido-4-hydroxypyrrolidine-1-carboxylate (4 g, 15.25 mmol) in DMF (40 mL) was added NaH (1.2 g, 60% dispersion in oil) at <10° C. The resulting solution was stirred for 1 h at room temperature. Iodomethane (2.8 mL, 44.98 mmol) was added and stirring was continued for another 1 h. The reaction was quenched by the addition of water (50 mL). The resulting mixture was extracted with Et$_2$O (2×50 mL). The organic layers were combined, dried over anhydrous sodium sulfate, filtered, and concentrated under vacuum. Purification by silica gel chromatography (eluting with 1:1 EtOAc/pet. ether) afforded benzyl 3-azido-4-methoxypyrrolidine-1-carboxylate as a colorless oil. MS: (ESI, m/z): 277 [M+H]$^+$.

Step 3. Benzyl 3-amino-4-methoxypyrrolidine-1-carboxylate

A solution of benzyl 3-azido-4-methoxypyrrolidine-1-carboxylate (2 g, 7.24 mmol) and PPh$_3$ (2.1 g, 8.01 mmol) in THF (50 mL) and water (5 mL) was stirred for 1 h at room temperature, then for an additional 5 h at 50° C. After cooling to room temperature, the reaction was concentrated under vacuum. Purification by prep-HPLC (Column: XBridge Prep C18 OBD, 19×50 mm, 5 μm; Mobile phase A: water (10 mM NH$_4$HCO$_3$), B: ACN; Gradient: 10% B to 80% B in 30 min) afforded benzyl 3-amino-4-methoxypyrrolidine-1-carboxylate as a colorless oil. MS: (ESI, m/z): 251 [M+H]$^-$.

Step 4. Benzyl 3-((tert-butoxycarbonyl)amino)-4-methoxypyrrolidine-1-carboxylate A solution of benzyl 3-amino-4-methoxypyrrolidine-1-carboxylate (600 mg, 2.40 mmol), Et$_3$N (457 mg, 4.52 mmol), and (Boc)$_2$O (786 mg, 3.60 mmol) in THF (12 mL) and water (12 mL) was stirred for 30 min at room temperature. The resulting mixture was extracted with DCM (2×30 mL). The combined organic layers were dried over anhydrous sodium sulfate, filtered, and concentrated under vacuum. The residue was purified by silica gel chromatography (eluting with 1:1 EtOAc/pet. ether) to give benzyl 3-((tert-butoxycarbonyl)amino)-4-methoxypyrrolidine-1-carboxylate as a white solid. MS: (ESI, m/z): 351 [M+H]$^+$.

Step 5. tert-Butyl N-(4-methoxypyrrolidin-3-yl)carbamate

A mixture of benzyl 3-((tert-butoxycarbonyl)amino)-4-methoxypyrrolidine-1-carboxylate (200 mg, 0.57 mmol) and Pd/C (200 mg, 10%) in EtOAc (10 mL) was stirred for 3 h at room temperature under an atmosphere of hydrogen. The solids were filtered out and washed with EtOAc (3×10 mL). The filtrate was concentrated under vacuum to give tert-butyl N-(4-methoxypyrrolidin-3-yl)carbamate as a white solid. MS: (ESI, m/z): 217 [M+H]$^+$.

Intermediate 36. tert-butyl ((3S,4S)-4-methoxypyrrolidin-3-yl)carbamate

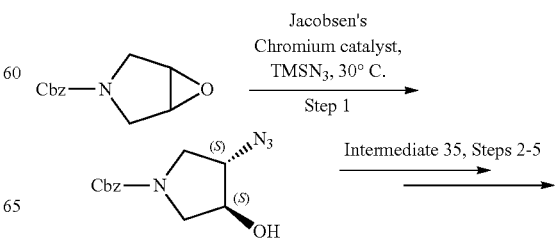

-continued

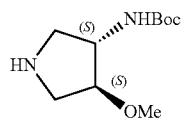

Step 1. Benzyl (3S,4S)-3-azido-4-hydroxypyrrolidine-1-carboxylate

To a mixture of benzyl 6-oxa-3-azabicyclo[3.1.0]hexane-3-carboxylate (10 g, 44.70 mmol) and (1R,2R)-(−)-[1,2-cyclohexanediamino-N N'-bis(3,5-di-t-butylsalicylidene)] chromium (III) chloride (Jacobsen's Chromium catalyst) (682 mg, 1.08 mmol) was added azidotrimethylsilane (6.52 g, 56.59 mmol) at 30° C. The reaction mixture was stirred for 16 h at 30° C. Methanol (30 mL) and trifluoroacetic acid (0.5 mL) were added. The resulting solution was stirred at 30° C. for 3 h, then concentrated under vacuum. The residue was diluted with 100 mL of water and was extracted with ethyl acetate (3×100 mL). The combined organic layers were dried over anhydrous sodium sulfate, filtered, and concentrated under vacuum. Purification by silica gel chromatography (eluting with 1:2 EtOAc/pet.ether) afforded benzyl (3S,4S)-3-azido-4-hydroxypyrrolidine-1-carboxylate as a light yellow oil. MS: (ESI, m/z): 263 [M+H]⁻.

Step 2. Benzyl (3S,4S)-3-azido-4-methoxypyrrolidine-1-carboxylate

The title compound was prepared according to the procedures of Intermediate 35, Step 2, starting from benzyl (3S,4S)-3-azido-4-hydroxypyrrolidine-1-carboxylate. MS: (ESI, m/z): 277 [M+H]⁺.

Step 3. Benzyl (3S,4S)-3-amino-4-methoxypyrrolidine-1-carboxylate

The title compound was prepared according to the procedures of Intermediate 35, Step 3, starting from benzyl (3S,4S)-3-azido-4-methoxypyrrolidine-1-carboxylate. MS: (ESI, m/z): 251 [M+H]⁺.

Step 4. Benzyl (3S,4S)-3-((tert-butoxycarbonyl)amino)-4-methoxypyrrolidine-1-carboxylate The title compound was prepared according to the procedures of Intermediate 35, Step 4, starting from benzyl (3S,4S)-3-amino-4-methoxypyrrolidine-1-carboxylate. MS: (ESI, m/z): 351 [M+H]⁺.

Step 5. tert-butyl ((3S,4S)-4-methoxypyrrolidin-3-yl)carbamate

The title compound was prepared according to the procedures of Intermediate 35, Step 5, starting from benzyl (3S,4S)-3-((tert-butoxycarbonyl)amino)-4-methoxypyrrolidine-1-carboxylate. MS: (ESI, m/z): 217 [M+H]⁻.

Intermediate 37. tert-Butyl 3-(trifluoromethyl)piperidin-3-ylcarbamate

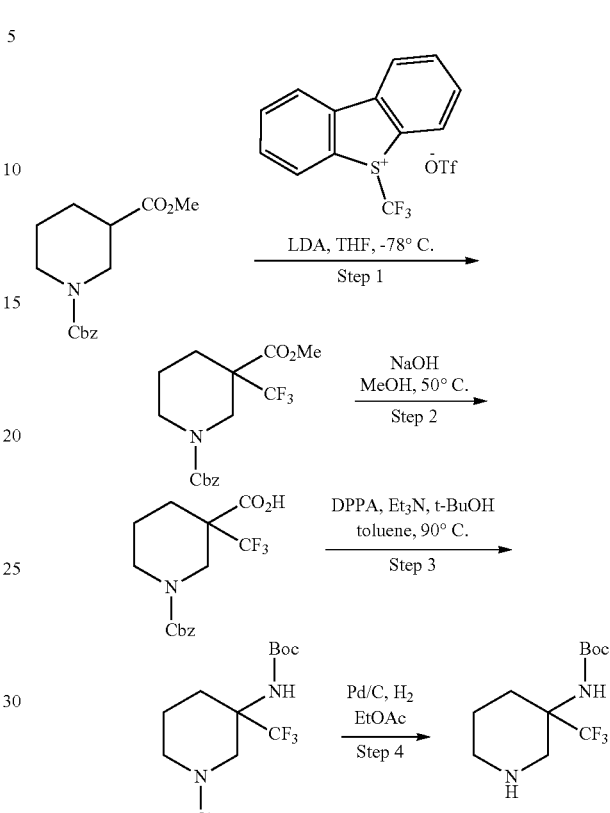

Step 1. 1-Benzyl 3-methyl 3-(trifluoromethyl)piperidine-1,3-dicarboxylate

To a solution of 1-benzyl 3-methyl piperidine-1,3-dicarboxylate (2.0 g, 7.14 mmol) in THF (60 mL) was added LDA (2.0 M in THF) (10.8 mL, 21.66 mmol) dropwise at −78° C. After the solution was stirred for 30 min at −78° C., S-(trifluoromethyl)dibenzothiophenium trifluoromethanesulfonate (4.35 g, 10.81 mmol) was added. After addition, the resulting solution was allowed to react, with stirring, for an additional 2 h at −40° C. The reaction was then quenched by the addition of 30 mL of a saturated aqueous solution of NH₄Cl. The resulting mixture was extracted with EtOAc (3×70 mL). The combined organic layers were dried over anhydrous sodium sulfate, filtered, and concentrated under vacuum. Purification by silica gel chromatography (eluting with 1:4 EtOAc/pet. ether) afforded 1-benzyl 3-methyl 3-(trifluoromethyl)piperidine-1,3-dicarboxylate as a yellow oil. MS: (ESI, m/z): 346 [M+H]⁻.

Step 2. 1-((Benzyloxy)carbonyl)-3-(trifluoromethyl)piperidine-3-carboxylic acid A solution of 1-benzyl 3-methyl 3-(trifluoromethyl)piperidine-1,3-dicarboxylate (310 mg, 0.83 mmol) in MeOH (10 mL) and aq. 1N NaOH (2.7 mL, 2.70 mmol) was stirred for 2 h at 50° C. and then concentrated under vacuum. The residue was diluted with 5 mL of water. The pH value of the solution was adjusted to 3-4 with 6N HCl. The solids were collected by filtration to give of 1-((benzyloxy)carbonyl)-3-

(trifluoromethyl)piperidine-3-carboxylic acid as a yellow solid. MS: (ESI, m/z): 332 [M+H]⁻.

Step 3. Benzyl 3-((tert-butoxycarbonyl)amino)-3-(trifluoromethyl)piperidine-1-carboxylate A solution of 1-((benzyloxy)carbonyl)-3-(trifluoromethyl)piperidine-3-carboxylic acid (250 mg, 0.76 mmol), Et₃N (229 mg, 2.26 mmol), and DPPA (415 mg, 1.51 mmol) in toluene (8 mL) was stirred for 2 h at 90° C. tert-Butanol (279 mg, 3.76 mmol) was added and the reaction mixture was stirred for an additional 16 h at 90° C. After cooling to room temperature, the reaction was quenched by the addition of water (20 mL) and was extracted with EtOAc (20 mL×3). The combined organic layers were dried over anhydrous sodium sulfate, filtered, and concentrated under vacuum. Purification by silica gel chromatography (eluting with 1:10 to 1:3 EtOAc/pet. ether) afforded benzyl 3-((tert-butoxycarbonyl)amino)-3-(trifluoromethyl)piperidine-1-carboxylate as a yellow solid. MS: (ESI, m/z): 403 [M+H]⁺.

Step 4. tert-Butyl (3-(trifluoromethyl)piperidin-3-yl)carbamate

A mixture of benzyl 3-((tert-butoxycarbonyl)amino)-3-(trifluoromethyl)piperidine-1-carboxylate (90 mg, 0.21 mmol) and Pd/C (10 mg, 10%) in EtOAc (5 mL) was stirred for 1 h at room temperature under an atmosphere of hydrogen. The solids were filtered away and the filtrate was concentrated under vacuum to give tert-butyl (3-(trifluoromethyl)piperidin-3-yl)carbamate as yellow oil. MS: (ESI, m/z): 269 [M+H]⁻.

Intermediate 38. tert-Butyl (4-(trifluoromethoxy)pyrrolidin-3-yl)carbamate

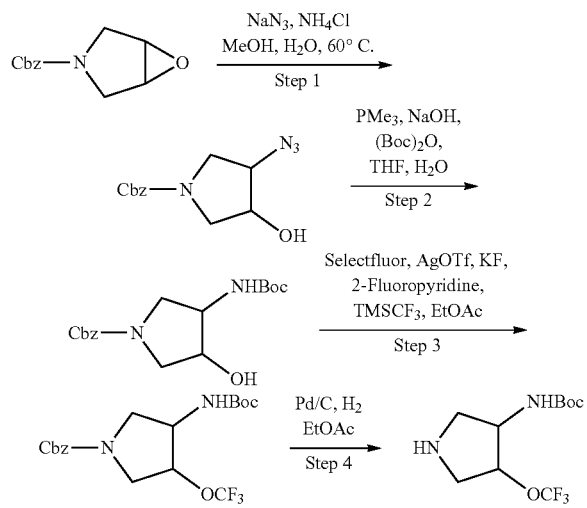

Step 1. Benzyl 3-azido-4-hydroxypyrrolidine-1-carboxylate

A solution of benzyl 6-oxa-3-azabicyclo[3.1.0]hexane-3-carboxylate (5 g, 22.81 mmol), NaN₃ (3 g, 46.15 mmol), NH₄Cl (1.23 g, 22.99 mmol) in MeOH (60 mL) and water (10 mL) was stirred for 16 h at 65° C. After cooling to room temperature, the pH value was adjusted to 7-8 with aq. 0.5N NaOH. The resulting mixture was extracted with DCM (2×150 mL). The combined organic layers were dried over anhydrous sodium sulfate, filtered, and concentrated under vacuum to give benzyl 3-azido-4-hydroxypyrrolidine-1-carboxylate as light-yellow solid. MS: (ESI, m/z): 263 [M+H]⁺.

Step 2. Benzyl 3-((tert-butoxycarbonyl)amino)-4-hydroxypyrrolidine-1-carboxylate A solution of benzyl 3-azido-4-hydroxypyrrolidine-1-carboxylate (6 g, 22.88 mmol), aq. 1 N NaOH (46 mL, 46 mmol), PMe₃ (1M in THF) (70 mL, 70 mmol), and (Boc)₂O (15.0 g, 68.73 mmol) in THF (228 mL) was stirred for 3 h at room temperature. The reaction mixture was diluted with 50 mL of water and was extracted with CH₂Cl₂ (3×200 mL). The combined organic layers were dried over anhydrous Na₂SO₄, filtered, and concentrated under vacuum. Purification by reverse phase chromatography (Column: C18 silica gel; Mobile phase A: water (10 mM NH₄HCO₃), B: ACN; Flow rate: 50 mL/min; Gradient: 0% B to 70% B in 40 min) afforded benzyl 3-((tert-butoxycarbonyl)amino)-4-hydroxypyrrolidine-1-carboxylate as a white solid. MS: (ESI, m/z): 337 [M+H]⁺.

Step 3. Benzyl 3-((tert-butoxycarbonyl)amino)-4-(trifluoromethoxy)pyrrolidine-1-carboxylate A solution of benzyl 3-((tert-butoxycarbonyl)amino)-4-hydroxypyrrolidine-1-carboxylate (1 g, 2.97 mmol), Selectfluor® (5.26 g, 14.85 mmol), AgOTf (7.6 g, 29.7 mmol), KF (1.72 g, 29.61 mmol), 2-fluoropyridine (2.88 g, 29.66 mmol) and TMS-CF₃ (4.22 g, 29.68 mmol) in EtOAc (14 mL) was stirred overnight at room temperature. The solids were filtered out and washed with CH₂Cl₂ (3×50 mL). The combined filtrate was concentrated under vacuum and purified by reverse phase chromatography (Column: C18 silica gel; Mobile phase A: water (10 mM NH₄HCO₃), B: ACN; Flow rate: 50 mL/min; Gradient: 0% B to 80% B in 40 min) to give benzyl 3-((tert-butoxycarbonyl)amino)-4-(trifluoromethoxy)pyrrolidine-1-carboxylate as yellow oil. MS: (ESI, m/z): 405 [M+H]⁻.

Step 4. tert-Butyl (4-(trifluoromethoxy)pyrrolidin-3-yl)carbamate

A mixture of benzyl 3-((tert-butoxycarbonyl)amino)-4-(trifluoromethoxy)pyrrolidine-1-carboxylate (190 mg, 0.47 mmol) and Pd/C (20 mg, 10%) in EtOAc (10 mL) was stirred for 2 h at room temperature under an atmosphere of hydrogen. The solids were filtered away and the filtrate was concentrated under vacuum to give tert-butyl (4-(trifluoromethoxy)pyrrolidin-3-yl)carbamate as a yellow oil. MS: (ESI, m/z): 271 [M+H]⁺.

Intermediate 39. 4-(tert-butyldimethylsilyloxy)piperidine

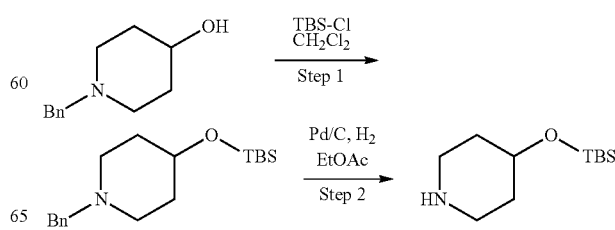

Step 1. 1-Benzyl-4-(tert-butyldimethylsilyloxy)piperidine

A solution of 1-benzylpiperidin-4-ol (1 g, 5.23 mmol), imidazole (712 mg, 10.46 mmol), and tert-butyldimethylsilyl chloride (867 mg, 5.75 mmol) in DCM (20 mL) was stirred for 3 h at room temperature and then diluted with 20 mL of water. The resulting mixture was extracted with DCM (3×20 mL). The combined organic layers were dried over anhydrous sodium sulfate, filtered, and concentrated under vacuum. Purification by silica gel chromatography (eluting with 1:3 EtOAc/pet. ether) afforded 1-benzyl-4-(tert-butyldimethylsilyloxy)piperidine as colorless oil. MS: (ESI, m/z): 306 [M+H]$^+$.

Step 2. 4-(tert-Butyldimethylsilyloxy)piperidine

A mixture of 1-benzyl-4-(tert-butyldimethylsilyloxy)piperidine (500 mg, 1.64 mmol) and Pd/C (50 mg, 10%) in EtOAc (20 mL) was stirred for 2 h at room temperature under an atmosphere of hydrogen. The solids were filtered out and the filtrate was concentrated under vacuum to give 4-(tert-butyldimethylsilyloxy)piperidine as colorless oil. MS: (ESI, m/z): 216 [M+H]$^+$.

Intermediate 40. 3-((tert-butyldimethylsilyl)oxy)-3-methylpiperidine

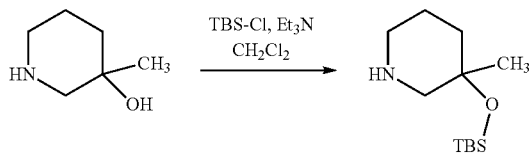

A solution of 3-methylpiperidin-3-ol (500 mg, 3.91 mmol), tert-butyldimethylsilyl chloride (497 mg, 3.30 mmol), and Et$_3$N (837 mg. 8.27 mmol) in DCM (20 mL) was stirred for 24 h at room temperature. The reaction was quenched by the addition of 50 mL of water. The resulting mixture was extracted with DCM (3×40 mL). The combined organic layers were dried over anhydrous sodium sulfate, filtered, and concentrated under vacuum. Purification by silica gel chromatography (eluting with gradient 1:20 to 1:5 EtOAc/pet.ether) afforded 3-((tert-butyldimethylsilyl)oxy)-3-methylpiperidine as colorless oil. MS: (ESI, m/z): 230 [M+H]$^+$.

Intermediate 41. tert-Butyl 7-hydroxy-5-oxa-2-azaspiro[3.4]octane-2-carboxylate

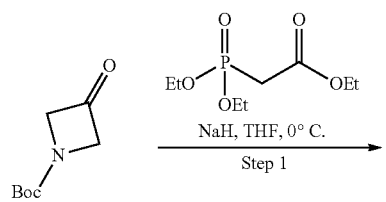

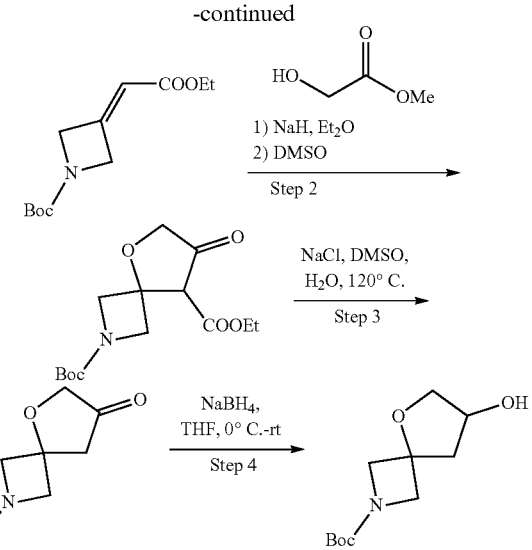

Step 1. tert-Butyl 3-(2-ethoxy-2-oxoethylidene)azetidine-1-carboxylate

To a solution of ethyl 2-(diethoxyphosphoryl)acetate (26.2 g, 116.86 mmol) in THF (60 mL) was added NaH (4.68 g, 117.01 mmol, 60% dispersion in oil) in portions at 0° C. The resulting solution was stirred for 30 min at room temperature. To the reaction mixture was added tert-butyl 3-oxoazetidine-1-carboxylate (10 g, 58.41 mmol) with stirring at 0° C. The resulting solution was stirred for an additional 30 min at room temperature. The reaction was then quenched by the addition of 30 mL of a water/ice mixture. The resulting solution was extracted with DCM (3×40 mL). The combined organic layers were dried over anhydrous Na$_2$SO$_4$, filtered and concentrated under vacuum. Purification by silica gel chromatography (eluting with 1:5 EtOAc/pet. ether) afforded tert-butyl 3-(2-ethoxy-2-oxoethylidene)azetidine-1-carboxylate as yellow oil. MS: (ESI, m/z): 242 [M+H]$^+$.

Step 2: 2-(tert-Butyl) 8-ethyl 7-oxo-5-oxa-2-azaspiro[3.4]octane-2,8-dicarboxylate To a solution of NaH (1.2 g, 30.00 mmol, 60% dispersion in oil) in Et$_2$O (20 mL) was added methyl 2-hydroxyacetate (2.69 g, 29.86 mmol) at 0° C. The resulting solution was stirred for 30 min at room temperature and then concentrated under vacuum. The residue was diluted with 20 mL of DMSO and tert-butyl 3-(2-ethoxy-2-oxoethylidene)azetidine-1-carboxylate (6 g, 24.87 mmol) was added. The resulting solution was stirred overnight at room temperature. The pH value of the solution was adjusted to 4-5 with hydrochloric acid (1N). The resulting mixture was extracted with Et$_2$O (4×20 mL). The combined organic layers were dried over anhydrous Na$_2$SO$_4$, filtered and concentrated under vacuum. Purification by silica gel chromatography (eluting with gradient 1:10 to 1:5 EtOAc/pet. ether) afforded 2-(tert-butyl) 8-ethyl 7-oxo-5-oxa-2-azaspiro[3.4]octane-2,8-dicarboxylate as a light yellow solid. MS: (ESI, m/z): 300 [M+H]$^+$.

Step 3. tert-Butyl 7-oxo-5-oxa-2-azaspiro[3.4]octane-2-carboxylate

A solution of 2-(tert-butyl) 8-ethyl 7-oxo-5-oxa-2-azaspiro[3.4]octane-2,8-dicarboxylate (4 g, 13.4 mmol) and NaCl (1.33 g, 22.76 mmol) in DMSO/water (10:1, 20 mL) was stirred for 2 h at 120° C. After cooling to room temperature, the reaction was quenched with 20 mL of water. The resulting mixture was extracted with Et$_2$O (4×20 mL). The combined organic layers were dried over anhydrous Na$_2$SO$_4$, filtered and concentrated under vacuum. Purification by silica gel chromatography (eluting with 1:3 EtOAc/pet. ether) afforded tert-butyl 7-oxo-5-oxa-2-azaspiro[3.4]octane-2-carboxylate as a white solid. MS: (ESI, m/z): 228 [M+H]$^+$.

Step 4. tert-Butyl 7-hydroxy-5-oxa-2-azaspiro[3.4]octane-2-carboxylate

To a solution of tert-butyl 7-oxo-5-oxa-2-azaspiro[3.4]octane-2-carboxylate (1.1 g, 4.84 mmol) in THF (8 mL) was added NaH (276 mg, 7.49 mmol) in portions at 0° C. The resulting mixture was stirred for 30 min at room temperature. The reaction was quenched with 50 mL of a water/ice mixture. The resulting mixture was extracted with ethyl acetate (3×50 mL). The combined organic layers were dried over anhydrous Na$_2$SO$_4$, filtered and concentrated under vacuum. Purification by reverse phase chromatography (Column: C18 silica gel; Mobile phase A: water (0.5% TFA), B: ACN; Gradient: 0% to 50% B over 35 min) afforded tert-butyl 7-hydroxy-5-oxa-2-azaspiro[3.4]octane-2-carboxylate as yellow oil. MS: (ESI, m/z): 230 [M+H]$^+$.

Intermediate 42. Benzyl (R)-(7-chloro-3,4-dihydro-2H-pyrano[3,2-c]pyridin-3-yl)carbamate

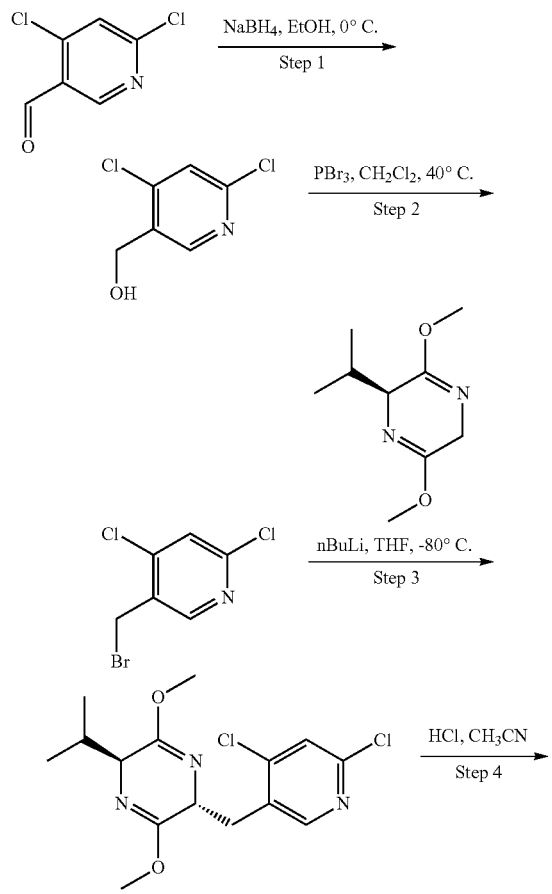

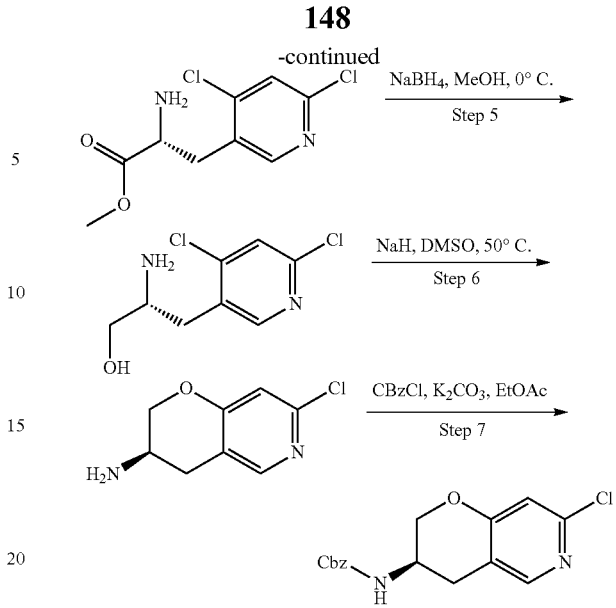

Step 1. (4,6-Dichloropyridin-3-yl)methanol

Into a 500-mL 3-necked round-bottom flask purged and maintained with an inert atmosphere of nitrogen, was placed 4,6-dichloronicotinaldehyde (8 g, 43.18 mmol) and ethanol (200 mL). NaBH$_4$ (5.2 g, 141.21 mmol) was added in portions at 0° C. Then the resulting solution was stirred for 2 h at 25° C. The reaction was then quenched by the addition of water (200 mL). The resulting mixture was extracted with DCM (3×300 mL) and the organic layers were combined, dried over anhydrous sodium sulfate, filtered and concentrated under vacuum. The residue was purified by silica gel chromatography (eluting with 1:10 ethyl acetate/pet. ether) to give of ((4,6-dichloropyridin-3-yl)methanol as a colorless oil. MS: (ESI, m/z): 178,180 [M+H]$^+$.

Step 2. 5-(Bromomethyl)-2,4-dichloropyridine

Into a 250-mL 3-necked round-bottom flask purged and maintained with an inert atmosphere of nitrogen, was placed (4,6-dichloropyridin-3-yl)methanol (5 g, 26.68 mmol), DCM (100 mL) and PBr$_3$ (7.7 g, 28.45 mmol). The resulting solution was stirred for 30 min at 40° C. in an oil bath. After cooling to 25° C., the reaction was then quenched by the addition of water (120 mL). The resulting mixture was extracted with DCM (2×150 mL) and the organic layers were combined, dried over anhydrous sodium sulfate, filtered and concentrated under vacuum. The residue was purified by silica gel chromatography (eluting with 1:30 ethyl acetate/pet. ether) to give 5-(bromomethyl)-2,4-dichloropyridine as a colorless oil. MS: (ESI, m/z): 240, 242, 244 [M+H]$^-$.

Step 3. (2R,5S)-2-((4,6-Dichloropyridin-3-yl)methyl)-5-isopropyl-3,6-dimethoxy-2,5-dihydropyrazine Into a 500-mL 3-necked round-bottom flask purged and maintained with an inert atmosphere of nitrogen, was placed (2S)-3,6-dimethoxy-2-(propan-2-yl)-2,5-dihydropyrazine (3 g, 15.47 mmol) and THF (200 mL). A solution of n-BuLi in n-hexane (2.5 M) (9.8 mL, 24.5 mmol) was added at −80° C. in a liquid nitrogen bath. The resulting solution was stirred for 30 min at −80° C. in a liquid nitrogen bath. Then a solution of 5-(bromomethyl)-2,4-dichloropyridine (4.7 g, 18.53 mmol) in THF (10 mL) was added. The resulting solution was allowed to react, with stirring, for an additional 1 h while the temperature was maintained at −80° C. in a liquid nitrogen bath. The reaction was then quenched by the addition of 120 mL of ammonium chloride (sat. aq.). The resulting mixture was extracted with DCM (2×150 mL) and the organic layers were combined, dried over anhydrous sodium sulfate, filtered and concentrated under vacuum. The residue was purified by silica gel chromatography (eluting with 1:10 ethyl acetate/pet. ether) to afford (2R,5S)-2-[(4,6-dichloropyridin-3-yl)methyl]-3,6-dimethoxy-5-(propan-2-yl)-2,5-dihydropyrazine as a white solid. MS: (ESI, m/z): 344, 346 [M+H]+.

Step 4. Methyl (2R)-2-amino-3-(4,6-dichloropyridin-3-yl)propanoate

Into a 250-mL round-bottom flask, was placed (2R,5S)-2-[(4,6-dichloropyridin-3-yl)methyl]-3,6-dimethoxy-5-(propan-2-yl)-2,5-dihydropyrazine (3.5 g, 9.66 mmol), hydrochloride acid (0.3M) (70 mL) and ACN (80 mL). The resulting solution was stirred for 2 h at 25° C. The reaction was then quenched by the addition of 100 mL of sodium bicarbonate (sat. aq.). The resulting mixture was extracted with 2×150 mL of DCM and the organic layers were combined, dried over anhydrous sodium sulfate, filtered and concentrated under vacuum to give methyl (2R)-2-amino-3-(4,6-dichloropyridin-3-yl)propanoate as colorless oil. MS: (ESI, m/z): 249, 251 [M+H]+.

Step 5. (2R)-2-Amino-3-(4,6-dichloropyridin-3-yl)propan-1-ol

Into a 250-mL round-bottom flask, was placed methyl (2R)-2-amino-3-(4,6-dichloropyridin-3-yl)propanoate (1.5 g, 5.72 mmol) and methanol (50 mL). NaBH4 (690 mg, 18.24 mmol) was added in portion at 0° C. The resulting solution was stirred for 3 h at 25° C. The reaction was then quenched by the addition of water (20 mL). The resulting mixture was extracted with DCM (2×50 mL) and the organic layers were combined, dried over anhydrous sodium sulfate, filtered and concentrated under vacuum. The residue was purified by silica gel chromatography (eluting with 1:10 methanol/DCM) to afford (2R)-2-amino-3-(4,6-dichloropyridin-3-yl)propan-1-ol as a white solid. MS: (ESI, m/z): 221, 223 [M+H]+.

Step 6. (R)-7-Chloro-3,4-dihydro-2H-pyrano[3,2-c]pyridin-3-amine

Into a 50-mL round-bottom flask purged and maintained with an inert atmosphere of nitrogen, was placed (2R)-2-amino-3-(4,6-dichloropyridin-3-yl)propan-1-ol (1 g, 4.30 mmo), sodium hydride (271 mg, 6.78 mmol, 60%) and DMSO (10 mL). The resulting solution was stirred for 16 h at 50° C. in an oil bath. After cooling to 25° C., the reaction was then quenched by the addition of water (20 mL). The resulting mixture was extracted with DCM (2×30 mL) and the organic layers were combined, dried over anhydrous sodium sulfate, filtered and concentrated under vacuum. The residue was purified by reverse phase chromatography (Column: C18 silica gel; Mobile phase A: water (0.1% formic acid), B: ACN; Flow rate: 50 mL/min; Gradient: 0% B to 30% B in 30 min). The collected fraction was concentrated under vacuum to give (R)-7-chloro-3,4-dihydro-2H-pyrano[3,2-c]pyridin-3-amine as a white solid. MS: (ESI, m/z): 185, 187 [M+H]+.

Step 7. Benzyl (R)-(7-chloro-3,4-dihydro-2H-pyrano[3,2-c]pyridin-3-yl)carbamate

Into a 50-mL round-bottom flask, was placed (R)-7-chloro-3,4-dihydro-2H-pyrano[3,2-c]pyridin-3-amine (500 mg, 2.57 mmol, ethyl acetate (15 mL, 153.23 mmol), water (15 mL), benzyl chloroformate (558 mg, 3.27 mmol) and potassium carbonate (751 mg, 5.43 mmol). The resulting mixture was stirred for 30 min at 25° C. The resulting mixture was extracted with 3×20 mL of ethyl acetate. The organic layers were combined, dried over anhydrous sodium sulfate, filtered and concentrated under vacuum. The residue was purified by silica gel chromatography (eluting with 1:1 ethyl acetate/pet. ether) to afford benzyl (R)-(7-chloro-3,4-dihydro-2H-pyrano[3,2-c]pyridin-3-yl)carbamate as a white solid. MS: (ESI, m/z): 319,321 [M+H]−.

Intermediate 43. Benzyl (R)-(7-chloro-3,4-dihydro-2H-pyrano[2,3-b]pyridin-3-yl)carbamate

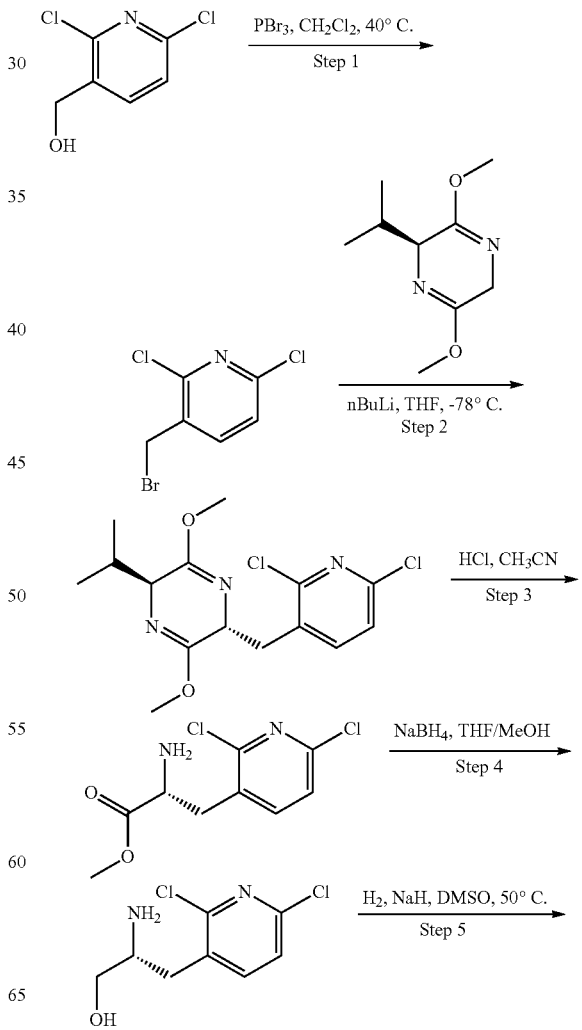

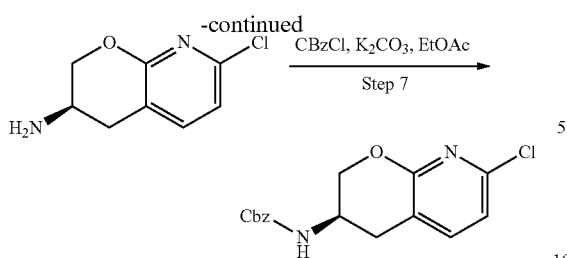

Step 1. 3-(Bromomethyl)-2,6-dichloropyridine

Into a 500-mL 3-necked round-bottom flask purged and maintained with an inert atmosphere of nitrogen, was placed (2,6-dichloropyridin-3-yl)methanol (10 g, 56.17 mmol), DCM (200 mL) and PBr$_3$ (15.3 g, 56.52 mmol). The resulting solution was stirred for 30 min at 40° C. in an oil bath. The pH value of the solution was adjusted to 7 with NH$_4$HCO$_3$ (sat. aq.). The resulting mixture was extracted with 3×200 mL of DCM. The organic layers combined, dried over anhydrous sodium sulfate, filtered and concentrated under vacuum. The residue was purified by silica gel chromatography (eluting with 1:10 to 1:5 ethyl acetate/pet. ether) to give 3-(bromomethyl)-2,6-dichloropyridine as an off-white solid. MS: (ESI, m/z): 240, 242, 244 [M+H]$^+$.

Step 2. (2R,5S)-2-((2,6-Dichloropyridin-3-yl)methyl)-5-isopropyl-3,6-dimethoxy-2,5-dihydropyrazine Into two 250-mL 3-necked round-bottom flask purged and maintained with an inert atmosphere of nitrogen, was placed (2S)-3,6-dimethoxy-2-(propan-2-yl)-2,5-dihydropyrazine (2 g, 10.86 mmol) and THF (15 mL). This was followed by the addition of butyllithium (2.5 M) (6.5 mL, 16.25 mmol) at −78° C. The resulting solution was stirred for 30 min. To this was added 3-(bromomethyl)-2,6-dichloropyridine (2.62 g, 10.88 mmol). The resulting solution was stirred for an additional 1 h at −78° C. The reaction was then quenched by the addition of 5 mL of NH$_4$HCO$_3$ (saturated) and the mixture was diluted with 10 mL of H$_2$O. The resulting mixture of two batches was combined and extracted with 3×50 mL of ethyl acetate. The organic layers were combined, dried over anhydrous sodium sulfate, filtered and concentrated under vacuum. The residue was purified by silica gel chromatography (eluting with 1/5 ethyl acetate/pet. ether) to afford (2R,5S)-2-((2,6-dichloropyridin-3-yl)methyl)-5-isopropyl-3,6-dimethoxy-2,5-dihydropyrazine as a colorless oil. MS: (ESI, m/z): 344, 346 [M+H]$^+$.

Step 3. Methyl (R)-2-amino-3-(2,6-dichloropyridin-3-yl)propanoate

Into a 500-mL round-bottom flask, was placed (2R,5S)-2-((2,6-dichloropyridin-3-yl)methyl)-5-isopropyl-3,6-dimethoxy-2,5-dihydropyrazine (5.4 g, 16.35 mmol), acetonitrile (100 mL) and hydrochloric acid (0.3 N) (157 mL). The resulting solution was stirred for 1 hour at 24° C. The solvent was removed under vacuum and the residue was extracted with 3×100 mL of DCM. The organic layers were combined, dried over anhydrous sodium sulfate, filtered and concentrated under vacuum. The residue was purified by silica gel chromatography (eluting with 1:5 to 1:1 ethyl acetate/pet. ether) to afford to give methyl (R)-2-amino-3-(2,6-dichloropyridin-3-yl)propanoate as an off-white solid. MS: (ESI, m/z): 249, 251 [M+H]$^-$.

Step 4. (R)-2-Amino-3-(2,6-dichloropyridin-3-yl)propan-1-ol

Into a 250-mL round-bottom flask, was placed methyl (R)-2-amino-3-(2,6-dichloropyridin-3-yl)propanoate (3.2 g, 12.85 mmol), methanol (15 mL), THF (60 mL) and NaBH$_4$ (1.46 g, 39.65 mmol). The resulting solution was stirred for 2 h at 24° C. The reaction was then quenched by the addition of 5 mL of water. The solvent was removed under vacuum. The residue was diluted with 50 mL of water. The resulting mixture was extracted with 3×50 mL of ethyl acetate. The organic layers were combined, dried over anhydrous sodium sulfate, filtered and concentrated under vacuum. The residue was purified by silica gel chromatography (eluting with 1:20 methanol/DCM) to afford (R)-2-amino-3-(2,6-dichloropyridin-3-yl)propan-1-ol as an off-white solid. MS: (ESI, m/z): 221, 223 [M+H]$^+$.

Step 5. (R)-7-Chloro-3,4-dihydro-2H-pyrano[2,3-b]pyridin-3-amine

Into a 250-mL round-bottom flask fitted with a hydrogen balloon, was placed (R)-2-amino-3-(2,6-dichloropyridin-3-yl)propan-1-ol (2.6 g, 11.76 mmol) and DMSO (30 mL). This was followed by the addition of sodium hydride (706 mg, 29.42 mmol, 60%) at 0° C. The resulting solution was stirred at 24° C. for 30 min and then stirred overnight at 50° C. After cooling to 25° C., the reaction was then quenched by the addition of 60 mL of water. The resulting mixture was extracted with 3×60 mL of ethyl acetate. The organic layers combined, dried over anhydrous sodium sulfate, filtered and concentrated under vacuum. The residue was purified by reverse phase chromatography (Column: C18 silica gel; Mobile phase A: water (10 mM NH$_4$HCO$_3$), B: ACN; Flow rate: 50 mL/min; Gradient: 0% B to 30% B in 30 min). The collected fraction was concentrated under vacuum to give (R)-7-chloro-3,4-dihydro-2H-pyrano[2,3-b]pyridin-3-amine as an off-white solid. MS: (ESI, m/z): 185, 187 [M+H]$^+$.

Step 6. Benzyl (R)-(7-chloro-3,4-dihydro-2H-pyrano[2,3-b]pyridin-3-yl)carbamate Into a 100-mL round-bottom flask, was placed (R)-7-chloro-3,4-dihydro-2H-pyrano[2,3-b]pyridin-3-amine (1.3 g, 6.34 mmol), ethyl acetate (15 mL), water (10 mL), potassium carbonate (1.95 g, 14.11 mmol) and benzyl chloroformate (1.44 g, 8.44 mmol). The resulting solution was stirred for 2 h at 25° C. The reaction was then quenched by the addition of 30 mL of water. The resulting mixture was extracted with 3×30 mL of ethyl acetate and the organic layers combined, dried over anhydrous sodium sulfate, filtered and concentrated under vacuum. The residue was purified by re-crystallization from pet. ether. The solids were collected by filtration to give benzyl (R)-(7-chloro-3,4-dihydro-2H-pyrano[2,3-b]pyridin-3-yl)carbamate as a white solid. MS: (ESI, m/z): 319, 321 [M+H]$^+$.

Intermediate 44. tert-Butyl 4-[(3R)-3-[[(benzyloxy)carbonyl]amino]-3,4-dihydro-2H-1-benzopyran-7-yl]-4-fluoropiperidine-1-carboxylate

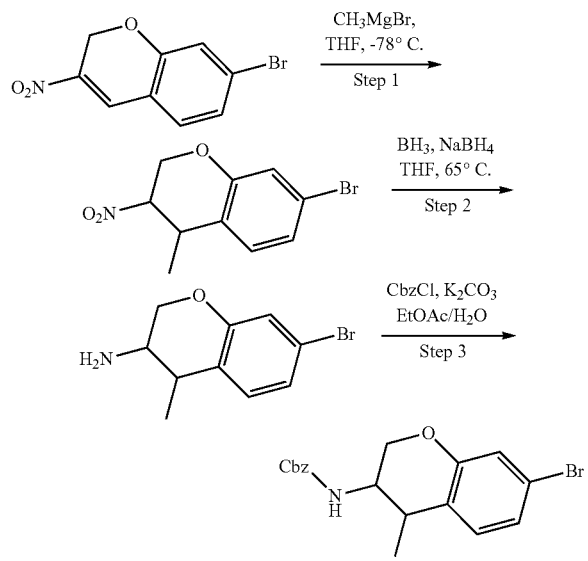

Step 1. 7-Bromo-4-methyl-3-nitro-3,4-dihydro-2H-1-benzopyran

To a solution of 7-bromo-3-nitro-2H-chromene (2.2 g, 8.59 mmol) in THF (30 mL) was added CH$_3$MgBr (1 M in THF) (13 mL, 13.00 mmol) at −78° C. The resulting solution was stirred for 20 min at −78° C. The reaction was then quenched by the addition of 20 mL of saturated aqueous NH$_4$Cl solution. The resulting mixture was extracted with 3×50 mL of ethyl acetate. The organic layers were combined, dried over anhydrous sodium sulfate, filtered and concentrated under vacuum. The residue was purified by silica gel chromatography (eluting with 3:1 pet. ether/ethyl acetate) to afford 7-bromo-4-methyl-3-nitro-3,4-dihydro-2H-1-benzopyran as yellow oil. GCMS: (ESI, m/z): 271, 273 [M+H]$^-$.

Step 2. 7-Bromo-4-methyl-3,4-dihydro-2H-1-benzopyran-3-amine

To a solution of BH$_3$-THF (1M) (40 mL, 40.00 mmol) and NaBH$_4$ (1.26 g, 33.30 mmol) in THF (40 mL) was added 7-bromo-4-methyl-3-nitro-3,4-dihydro-2H-1-benzopyran (900 mg, 3.31 mmol). The resulting mixture was stirred in a sealed tube for 16 h at 75° C. Then methanol (40 mL) was added and the reaction mixture was stirred for 6 h at 80° C. After cooling to 25° C., the solvent was removed under vacuum. The residue was diluted with 50 mL of ice/water. The resulting mixture was extracted with 3×50 of ethyl acetate. The organic layers were combined, dried over anhydrous sodium sulfate, filtered and concentrated under vacuum. The residue was purified by reverse phase chromatography (Column: C18 silica gel; Mobile phase A: water (0.05% TFA), B: ACN; Gradient: 0% B to 40% over 45 min) to afford 7-bromo-4-methyl-3,4-dihydro-2H-1-benzopyran-3-amine as a white solid. MS: (ESI, m/z): 242, 244 [M+H]$^+$.

Step 3. Benzyl N-(7-bromo-4-methyl-3,4-dihydro-2H-1-benzopyran-3-yl) carbamate A solution of 7-bromo-4-methyl-3,4-dihydro-2H-1-benzopyran-3-amine (500 mg, 2.07 mmol) and CbzCl (423 mg, 2.48 mmol) in ethyl acetate (8 mL) and a solution of potassium carbonate (567 mg, 4.10 mmol) in water (8 mL) was stirred for 1 h at 25° C. The resulting solution was diluted with 20 mL of water. The resulting mixture was extracted with 3×20 mL of ethyl acetate. The organic layers were combined, dried over anhydrous sodium sulfate, filtered and concentrated under vacuum. The residue was purified by silica gel chromatography (eluting with 3:1 pet. ether/ethyl acetate) to afford benzyl N-(7-bromo-4-methyl-3,4-dihydro-2H-1-benzopyran-3-yl)carbamate as a white solid. MS: (ESI, m/z): 376, 378 [M+H]$^+$.

Intermediate 45. tert-Butyl 6-((tert-butyldimethylsilyl)oxy)-1,4-diazepane-1-carboxylate

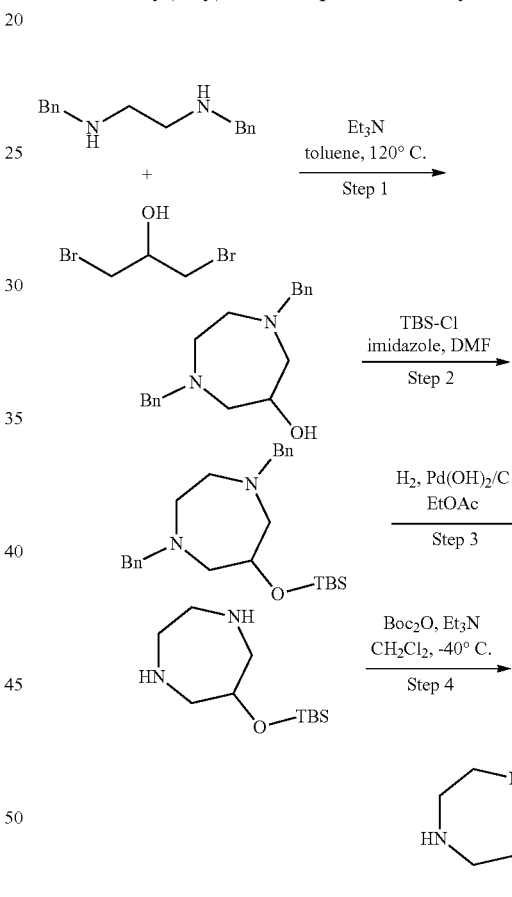

Step 1. 1,4-Dibenzyl-1,4-diazepan-6-ol

A solution of 1,3-dibromopropan-2-ol (12.37 µg, 56.77 µmmol), benzyl(2-(benzylamino)ethyl)amine (13.56 g, 56.42 mmol), and Et$_3$N (17.17 g, 169.68 mmol) in toluene (50 mL) was stirred for 48 h at 120° C. After cooling to 25° C., the reaction was then quenched by the addition of 100 mL of water. The resulting mixture was extracted with 2×100 mL of ethyl acetate and the organic layers were combined, dried over anhydrous sodium sulfate, filtered and concentrated under vacuum. The residue was purified by silica gel chromatography (eluting with 1:2 ethyl acetate/pet.

ether) to afford 1,4-dibenzyl-1,4-diazepan-6-ol as yellow oil. MS: (ESI, m/z): 297 [M+H]⁺.

Step 2. 1,4-Dibenzyl-6-((tert-butyldimethylsilyl)oxy)-1,4-diazepane

A solution of 1,4-dibenzyl-1,4-diazepan-6-ol (2.0 g, 6.61 mmol), imidazole (900 mg, 13.22 mmol) and TBS-Cl (1.2 g, 7.96 mmol) in DMF (10 mL) was stirred for 16 h at 25° C. The reaction was then quenched by the addition of 50 mL of water. The resulting mixture was extracted with 2×50 mL of ethyl acetate and the organic layers were combined, dried over anhydrous sodium sulfate, filtered and concentrated under vacuum. The residue was purified by silica gel chromatography (eluting with 1:5 ethyl acetate/pet. ether) to afford 1,4-dibenzyl-6-((tert-butyldimethylsilyl)oxy)-1,4-diazepane as yellow oil. MS: (ESI, m/z): 411 [M+H]⁻.

Step 3. 6-((tert-Butyldimethylsilyl)oxy)-1,4-diazepane

A mixture of 1,4-dibenzyl-6-((tert-butyldimethylsilyl)oxy)-1,4-diazepane (1.5 g, 3.47 mmol) and Pd(OH)₂ on carbon (20 mg, 10%) in ethyl acetate (10 mL) was stirred under an atmosphere of hydrogen for 28 h at 20° C. The solids were filtered out. The filtrate was concentrated under vacuum to afford 6-((tert-butyldimethylsilyl)oxy)-1,4-diazepane as colorless oil. MS: (ESI, m/z): 231 [M+H]⁺.

Step 4. tert-Butyl 6-((tert-butyldimethylsilyl)oxy)-1,4-diazepane-1-carboxylate

A solution of 6-((tert-butyldimethylsilyl)oxy)-1,4-diazepane (1.2 g, 4.95 mmol), Boc₂O (700 mg, 3.21 mmol), and triethylamine (500 mg, 4.94 mmol) in DCM (20 mL) was stirred for 2 h at –40° C. in a dry ice/ethanol bath and stirred for an additional 1 h at 20° C. The reaction was then quenched by the addition of 40 mL of water. The resulting mixture was extracted with 2×40 mL of ethyl acetate and the organic layers were combined, dried over anhydrous sodium sulfate, filtered and concentrated under vacuum. The residue was purified by silica gel chromatography (eluting with 1:10 methanol/DCM) to afford tert-butyl 6-((tert-butyldimethylsilyl)oxy)-1,4-diazepane-1-carboxylate as colorless oil. MS: (ESI, m/z): 331 [M+H]⁺.

Intermediate 46. tert-Butyl 6-((tert-butyldimethylsilyl)oxy)-1,4-diazepane-1-carboxylate

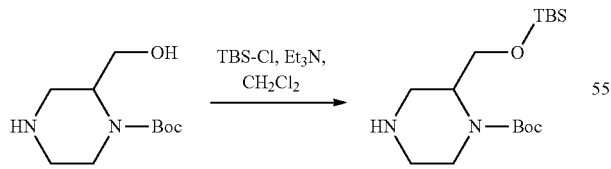

To a solution of tert-butyl 2-(hydroxymethyl)piperazine-1-carboxylate (1 g, 4.39 mmol) and triethylamine (1.53 mL, 10.98 mmol) in DCM (20 mL) was added tert-butyl(chloro)dimethylsilane (693 mg, 4.60 mmol). The resulting solution was stirred overnight at 20° C. The reaction was then quenched by the addition of 20 mL of water. The resulting mixture was extracted with 3×20 mL of DCM. The organic layers were combined, dried over anhydrous sodium sulfate, filtered and concentrated under vacuum. The residue was purified by silica gel chromatography (eluting with 20:1 ethyl DCM/methanol) to afford tert-butyl 6-((tert-butyldimethylsilyl)oxy)-1,4-diazepane-1-carboxylate as an off-colorless oil. MS: (ESI, m/z): 331 [M+H]⁺.

Intermediate 47-1. Benzyl N-[2-[(trifluoromethane)sulfonyloxy]-5,6,7,8-tetrahydroquinolin-6-yl]carbamate Intermediate 47-2. Benzyl N-[(6S)-2-(trifluoromethanesulfonyloxy)-5,6,7,8-tetrahydroquinolin-6-yl]carbamate Intermediate 47-3. Benzyl N-[(6R)-2-(trifluoromethanesulfonyloxy)-5,6,7,8-tetrahydroquinolin-6-yl]carbamate Method 1. Chiral Separation

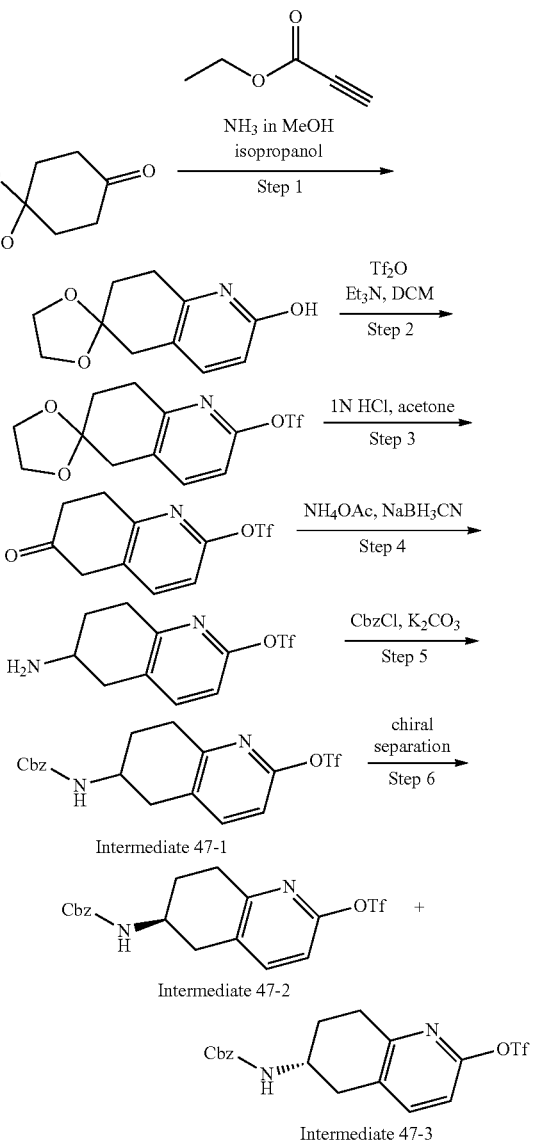

Step 1. 7',8'-Dihydro-5'H-spiro[1,3-dioxolane-2,6'-quinoline]-2'-ol

A solution of 1,4-dioxaspiro[4.5]decan-8-one (50.0 g, 320 mmol), ethyl prop-2-ynoate (68 mL, 672 mmol) and a solution of NH$_3$ in MeOH (230 mL, 7M) in isopropanol (1.3 L) was stirred for 14 h at 130° C. The reaction mixture was cooled to 20° C. The solvent was removed under vacuum. The solids were collected by filtration. The cake was washed with 2×30 mL of pet. ether and dried under vacuum to give 7',8'-dihydro-5'H-spiro[1,3-dioxolane-2,6'-quinoline]-2'-ol as an off-white solid. MS (ESI, m/z): 208 [M+H]$^+$.

Step 2. 7',8'-Dihydro-5'H-spiro[1,3-dioxolane-2,6'-quinoline]-2'-yl trifluoromethanesulfonate To a solution of 7',8'-dihydro-5'H-spiro[1,3-dioxolane-2,6'-quinoline]-2'-ol (24.0 g, 116 mmol) and triethylamine (64.4 mL, 464 mmol) in DCM (500 mL) was added a solution of trifluoromethanesulfonic anhydride (58.4 mL, 347 mmol) in DCM (100 mL) at 10° C. The resulting solution was stirred for 1 h at 20° C. The mixture was concentrated under vacuum. The residue was purified by silica gel chromatography (eluting with 3:1 ethyl acetate/pet. ether) to afford 7',8'-dihydro-5'H-spiro[1,3-dioxolane-2,6'-quinoline]-2'-yl trifluoromethanesulfonate as a yellow oil. MS (ESI, m/z): 340 [M+H]$^+$.

Step 3. 6-Oxo-5,6,7,8-tetrahydroquinolin-2-yl trifluoromethanesulfonate

A solution of 7',8'-dihydro-5'H-spiro[1,3-dioxolane-2,6'-quinoline]-2'-yl trifluoromethanesulfonate (35.0 g, 103 mmol) and hydrochloric acid (206 mL, 1N) in acetone (300 mL) was stirred for 1 h at 75° C. The mixture was cooled to 20° C. The acetone was concentrated under vacuum. The pH value of the residue was adjusted to 7-8 with NaHCO$_3$ (sat., aq.). The resulting mixture was extracted with 3×100 mL of DCM. The organic layers were combined, dried over anhydrous sodium sulfate, filtered and concentrated under vacuum. The residue was purified by recrystallization with 100 mL of the mixture solvent of ethyl acetate and pet. ether (10:1) to give 6-oxo-5,6,7,8-tetrahydroquinolin-2-yl trifluoromethanesulfonate as an off-white solid. MS (ESI, m/z): 296 [M+H]$^-$.

Step 4. 6-Amino-5,6,7,8-tetrahydroquinolin-2-yl trifluoromethanesulfonate

A mixture of 6-oxo-5,6,7,8-tetrahydroquinolin-2-yl trifluoromethanesulfonate (16.0 g, 54.2 mmol) and NH$_4$OAc (50.1 g, 650 mmol) in methanol (250 mL) was stirred for 1 h at 20° C. NaBH$_3$CN (4.10 g, 65.2 mmol) was added in portions at 10° C. The resulting mixture was allowed to react for 13 h at 20° C. The reaction was then quenched by the addition of 50 mL of water/ice. The solvent was concentrated under vacuum. The residue was diluted with 100 mL of hydrochloric acid (1N). The resulting mixture was extracted with 2×100 mL of DCM. The pH value of aqueous phase was adjusted to 10 with Na$_2$CO$_3$ (sat., aq.). The aqueous phase was extracted with 4×100 mL of DCM. The organic layers were combined, dried over anhydrous sodium sulfate, filtered and concentrated under vacuum to give 6-amino-5,6,7,8-tetrahydroquinolin-2-yl trifluoromethanesulfonate as a yellow oil. MS (ESI, m/z): 297 [M+H]$^-$.

Step 5. Benzyl N-[2-[(trifluoromethane)sulfonyloxy]-5,6,7,8-tetrahydroquinolin-6-yl]carbamate A mixture of 6-amino-5,6,7,8-tetrahydroquinolin-2-yl trifluoromethanesulfonate (12.0 g, 40.5 mmol), potassium carbonate (14.0 g, 101 mmol) and CbzCl (7.4 mL, 52.8 mmol) in ethyl acetate (100 mL) was stirred for 2 h at 20° C. The reaction was then quenched by the addition of 100 mL of water/ice. The mixture was extracted with 3×100 mL of ethyl acetate. The organic layers were combined, dried over anhydrous sodium sulfate, filtered and concentrated under vacuum. The residue was purified by recrystallization with 80 mL of the mixture solvent of ethyl acetate and pet. ether (10:1) to give benzyl N-[2-[(trifluoromethane)sulfonyloxy]-5,6,7,8-tetrahydroquinolin-6-yl]carbamate as an off-white solid. MS (ESI, m/z): 431 [M+H]$^+$.

Step 6. Benzyl N-[(6S)-2-(trifluoromethanesulfonyloxy)-5,6,7,8-tetrahydroquinolin-6-yl]carbamate and benzyl N-[(6R)-2-(trifluoromethanesulfonyloxy)-5,6,7,8-tetrahydroquinolin-6-yl]carbamate The racemate benzyl N-[2-(trifluoromethanesulfonyloxy)-5,6,7,8-tetrahydroquinolin-6-yl]carbamate (Intermediate 47-1) (7.00 g, 16.3 mmol,) was separated by SFC (Column: Chiralpak AD-H SFC, 5×25 cm, 5 µm; Mobile Phase, A: CO$_2$: 55% and B: MeOH: 45%; Flow rate: 150 mL/min). The first eluting isomer (RT=4.23 min) was collected and concentrated under vacuum to give benzyl N-[(6S)-2-(trifluoromethanesulfonyloxy)-5,6,7,8-tetrahydroquinolin-6-yl]carbamate (Intermediate 47-2) as an off-white solid. And the second eluting isomer (RT=5.16 min) was collected and concentrated under vacuum to give benzyl N-[(6R)-2-(trifluoromethanesulfonyloxy)-5,6,7,8-tetrahydroquinolin-6-yl]carbamate (Intermediate 47-3) as an off-white solid. MS (ESI, m/z) for both isomers: 431 [M+H]$^+$.

Intermediate 47-2. Benzyl N-[(6S)-2-(trifluoromethanesulfonyloxy)-5,6,7,8-tetrahydroquinolin-6-yl]carbamate Method 2. Chiral Resolution

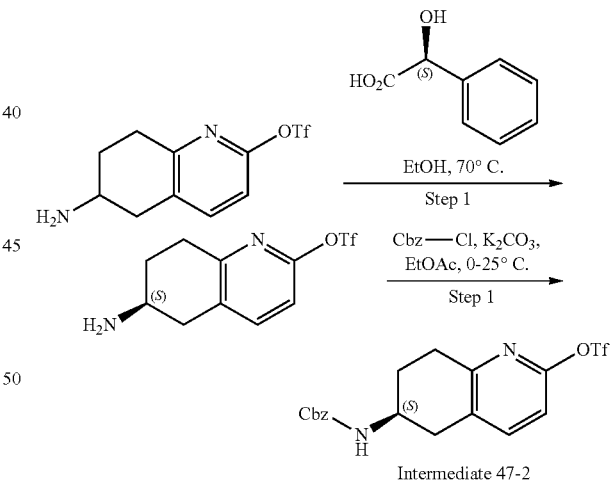

Step 1. (S)-6-Amino-5,6,7,8-tetrahydroquinolin-2-yl trifluoromethanesulfonate A solution of 6-amino-5,6,7,8-tetrahydroquinolin-2-yl trifluoromethanesulfonate (183 g, 525.65 mmol) and L-(−)-mandelic acid (39.99 g, 262.83 mmol) in EtOH (1830 mL) was stirred at 70° C. for 2 h. The mixture was allowed to cool down to 25° C. slowly and stirred for overnight. The precipitate that was formed was collected by filtration and dried under vacuum to afford the chiral salt as a white solid. The salt was dissolved in H$_2$O (350 mL) and the pH value of aqueous phase was adjusted to 12-14 with NaOH (1 N, aq). The aqueous phase was extracted with EtOAc (500 mL). The organic layer was dried over $Na_2SO_4$, filtered and concentrated under vacuum to afford the free base of the chiral amine (S)-6-amino-5,6,7,8-tetrahydroquinolin-2-yl trifluoromethanesulfonate as a yellow oil. MS (ESI, m/z): 297 $[M+H]^+$. $^1$H NMR (DMSO-$d_6$, 400 mHz) δ(ppm): 7.79 (d, J=8.0 Hz, 1H), 7.25 (d, J=8.4 Hz, 1H), 3.14-3.11 (m, 1H), 2.97-2.81 (m, 3H), 2.54-2.52 (m, 1H), 2.61-2.58 (m, 2H), 1.64-1.59 (m, 1H).

Step 2. Benzyl N-[(6S)-2-(trifluoromethanesulfonyloxy)-5,6,7,8-tetrahydroquinolin-6-yl]carbamate To a solution of (S)-6-amino-5,6,7,8-tetrahydroquinolin-2-yl trifluoromethanesulfonate (48.0 g, 162.02 mmol) and $K_2CO_3$ (55.98 g, 405.04 mmol) in EtOAc (480 mL) was added drop-wise CbzCl (35.93 g, 210.62 mmol, 29.94 mL) at 0° C. The mixture was stirred at 20° C. for 30 min. The reaction was then quenched by water/ice (150 mL). The mixture was extracted with ethyl acetate (350 mL). The organic layer was dried over anhydrous sodium sulfate, filtered and concentrated under vacuum. The crude was triturated with pet. ether (200 mL) at 20° C. The resulting precipitate was collected by filtration and dried under vacuum to afford benzyl N-[(6S)-2-(trifluoromethanesulfonyloxy)-5,6,7,8-tetrahydroquinolin-6-yl]carbamate as a pale pink solid. MS (ESI, m/z): 431 $[M+H]^+$. $^1$H NMR (DMSO-$d_6$, 400 mHz) δ(ppm): 7.82 (d, J=8.0 Hz, 1H), 7.49 (m, 1H), 7.37-7.28 (m, 6H), 5.04 (s, 2H), 3.82 (m, 1H), 3.08 (dd, J=16.8 Hz, 4.8 Hz, 1H), 2.91-2.88 (m, 2H), 2.76-2.72 (m, 1H), 2.02-2.00 (m, 1H), 1.83-1.75 (m, 1H).

The following intermediate in Table 7 was prepared using standard chemical manipulations and procedures similar to those used for the preparation of Intermediate 47-1.

TABLE 7

| Intermediate Number | Structure and Name | LRMS m/z $[M + H]^+$ |
|---|---|---|
| 47-4[1] | 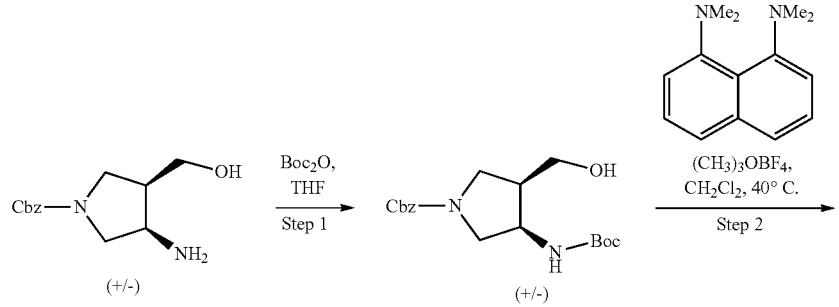<br>benzyl N-[2'-(trifluoromethanesulfonyloxy)-6',7'-dihydro-5'H-spiro[cyclopropane-1,8'-quinolin]-6'-yl]carbamate | 457 |

[1]Notes on procedures:
In Step 1, the ketone used was 6,9-dioxadispiro [2.1.4$^5$.3$^3$]dodecan-12-one, which was prepared by the following method: (2-chloroethyl)dimethylsulfonium iodide (88.0 g, 347 mmol) was slowly added to a solution of 1,4-dioxaspiro[4.5]decan-8-one (60.0 g, 384 mmol) and t-BuOK (88.0 g, 784 mmol) in t-BuOH (1.50 L) over 4 h. The resulting solution was stirred for 1 h at 25° C. The solids were filtered. The filtrate was concentrated under vacuum. The residue was diluted with water (400 mL). The resulting mixture was extracted with DCM (3 × 400 mL). The organic layers were combined, dried over anhydrous sodium sulfate, filtered and concentrated under vacuum. The residue was purified via reverse phase chromatography to afford 6,9-dioxadispiro[2.1.4$^5$.3$^3$] dodecan-12-one as a pale yellow oil. MS (ESI, m/z): 183 $[M + H]^+$.

Intermediate 48-1. cis-tert-Butyl N-[4-(methoxymethyl)pyrrolidin-3-yl]carbamate

Intermediate 48-2. tert-Butyl N-[(3R,4R)-4-(methoxymethyl)pyrrolidin-3-yl]carbamate and Intermediate 48-3. Benzyl (3R,4R)-3-[[(tert-butoxy)carbonyl]amino]-4-(methoxymethyl)pyrrolidine-1-carboxylate

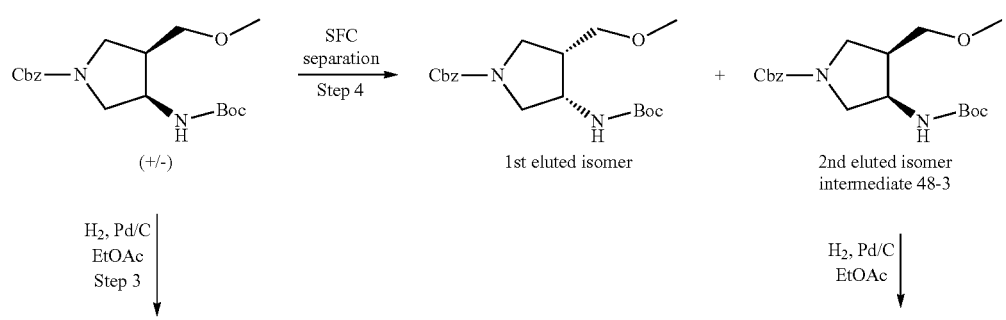

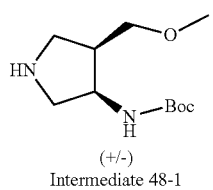

(+/-)
Intermediate 48-1

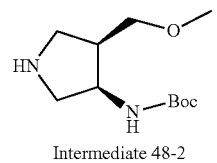

Intermediate 48-2

Step 1. cis-Benzyl 3-[[(tert-butoxy)carbonyl]amino]-4-(hydroxymethyl)pyrrolidine-1-carboxylate A solution of cis-benzyl 3-amino-4-(hydroxymethyl)pyrrolidine-1-carboxylate (2.00 g, 7.99 mmol), Et₃N (2.13 mL, 23.7 mmol) and (Boc)₂O (2.20 g, 10.1 mmol) in THF (40 mL) and water (20 mL) was stirred for 2 h at 20° C. The solvent was removed under vacuum. The residue was diluted with water (20 mL). The resulting mixture was extracted with ethyl acetate (3×20 mL), dried over anhydrous sodium sulfate, filtered and concentrated under vacuum. The residue was purified by a silica gel chromatography (eluting with 1:3 ethyl acetate/pet. ether) to give cis-benzyl 3-[[(tert-butoxy)carbonyl]amino]-4-(hydroxymethyl)pyrrolidine-1-carboxylate as an off-white solid. MS (ESI, m/z): 351 [M+H]⁺.

Step 2. cis-Benzyl 3-[[(tert-butoxy)carbonyl]amino]-4-(methoxymethyl)pyrrolidine-1-carboxylate A solution of trimethyloxoniumtetrafluoroborate (1.50 g, 10.4 mmol) in DCM (20 mL) was added to a stirring solution of 1,8-bis(dimethylamino)naphthalene (2.20 g, 10.3 mmol) and cis-benzyl 3-[[(tert-butoxy)carbonyl]amino]-4-(hydroxymethyl)pyrrolidine-1-carboxylate (2.20 g, 6.09 mmol) in DCM (100 mL). The resulting mixture was stirred for 3 h at 40° C. The pH of the mixture was adjusted to 4-6 with HCl (3N, aq.). The resulting mixture was extracted with ethyl acetate (3×100 mL), dried over anhydrous sodium sulfate, filtered and concentrated under vacuum. The residue was purified by silica gel chromatography (eluting with 1:1 ethyl acetate/pet. ether) to afford cis-benzyl 3-[[(tert-butoxy)carbonyl]amino]-4-(methoxymethyl)pyrrolidine-1-carboxylate as white solid. MS (ESI, m/z): 365 [M+H]⁺.

Step 3. cis-tert-Butyl N-[4-(methoxymethyl)pyrrolidin-3-yl]carbamate

A mixture of cis-benzyl 3-[[(tert-butoxy)carbonyl]amino]-4-(methoxymethyl)pyrrolidine-1-carboxylate (1.00 g, 2.74 mmol) and palladium on carbon (1.00 g, 10%) in ethyl acetate (50 mL) was stirred for 1 h at 20° C. under a hydrogen atmosphere (balloon). The solids were filtered out. The filtrate was concentrated under vacuum to give cis-tert-butyl N-[4-(methoxymethyl)pyrrolidin-3-yl]carbamate (Intermediate 48-1) as yellow oil (crude). MS (ESI, m/z): 231 [M+H]⁺.

Step 4. tert-Butyl N-[(3R,4R)-4-(methoxymethyl)pyrrolidin-3-yl]carbamate

The racemate cis-benzyl 3-[[(tert-butoxy)carbonyl]amino]-4-(methoxymethyl)pyrrolidine-1-carboxylate was separated into its enantiomers by SFC (Column: Chiralpak IA-SFC, 5×25 cm, 5 μm; Mobile Phase, A: CO₂: 70% and B: MeOH (containing 2 mM NH₃ in MeOH): 30%; Flow rate: 150 mL/min). The first eluting isomer (RT=3.91 min) was collected and concentrated under vacuum to give benzyl (3S,4S)-3-[[(tert-butoxy)carbonyl]amino]-4-(methoxymethyl)pyrrolidine-1-carboxylate as a yellow solid. The second eluting isomer (RT=5.04 min) was collected and concentrated under vacuum to give benzyl (3R,4R)-3-[[(tert-butoxy)carbonyl]amino]-4-(methoxymethyl)pyrrolidine-1-carboxylate (Intermediate 48-3) as a yellow solid. MS (ESI, m/z): 365 [M+H]⁻.

A mixture of benzyl (3R,4R)-3-[[(tert-butoxy)carbonyl]amino]-4-(methoxymethyl)pyrrolidine-1-carboxylate (Intermediate 48-3) (0.800 g, 2.20 mmol) and palladium on carbon (0.800 g, 10%) in ethyl acetate (30 mL) was stirred for 1 h at 25° C. under a hydrogen atmosphere (balloon). The solids were filtered out. The filtrate was concentrated under vacuum to give tert-butyl N-[(3R,4R)-4-(methoxymethyl)pyrrolidin-3-yl]carbamate (Intermediate 48-2) as a yellow oil (crude). MS (ESI, m/z): 231 [M+H]⁺.

Intermediate 48-3. Benzyl (3R,4R)-3-[[(tert-butoxy)carbonyl]amino]-4-(methoxymethyl)pyrrolidine-1-carboxylate Method 2

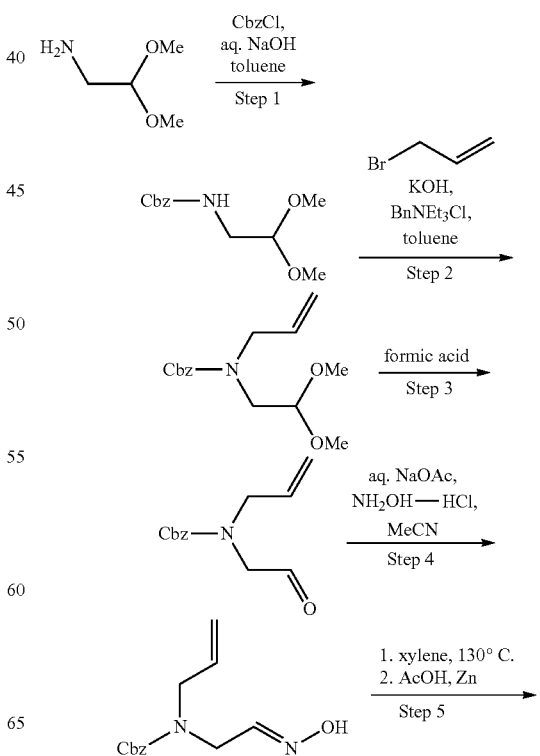

-continued

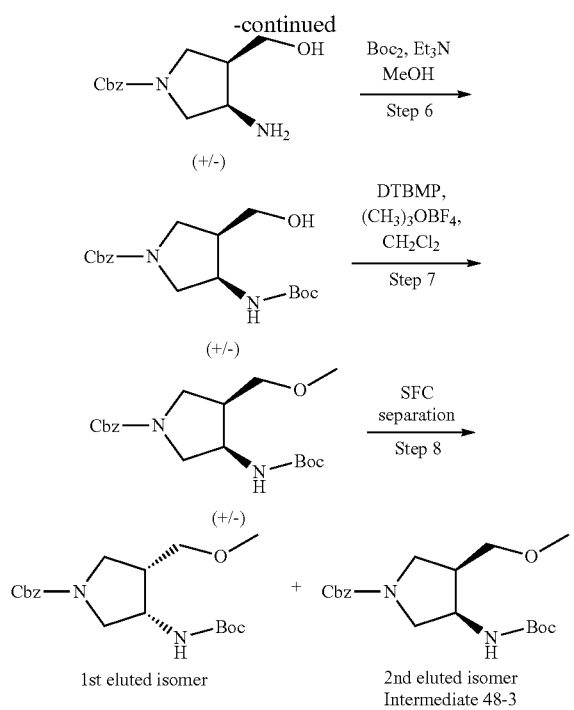

(+/−)    Boc₂, Et₃N
         MeOH
         ──────→
         Step 6

(+/−)    DTBMP,
         (CH₃)₃OBF₄,
         CH₂Cl₂
         ──────→
         Step 7

(+/−)    SFC
         separation
         ──────→
         Step 8

1st eluted isomer    +    2nd eluted isomer
                          Intermediate 48-3

Step 1. Benzyl N-(2,2-dimethoxyethyl)carbamate

A solution of 2,2-dimethoxyethan-1-amine (1600 g, 15.22 mol) in toluene (8 L), was added a solution of NaOH (858 g, 21.45 mol) in water (4.42 L). This was followed by the addition of CbzCl (2598 g, 15.23 mol) dropwise with stirring at <20° C. The resulting solution was stirred for 4 h at room temperature. The organic layer was separated and washed with 3×5 L of brine. The organic layer was dried over anhydrous sodium sulfate and concentrated under vacuum to afford benzyl N-(2,2-dimethoxyethyl)carbamate as a white solid.

Step 2. Benzyl N-(2,2-dimethoxyethyl)-N-(prop-2-en-1-yl)carbamate

To a solution of benzyl N-(2,2-dimethoxyethyl)carbamate (1700 g, 7.10 mol), KOH (1755 g, 31.28 mol) and bezyltriethylammonium chloride (32.37 g, 142.1 mmol) in toluene (7.82 L) was added 3-bromoprop-1-ene (1117.4 g, 9.24 mol) dropwise with stirring at room temperature. The resulting solution was stirred for 24 h at room temperature. Two batches were thus run in parallel. The reaction was then quenched by the addition of 10 L of water. The resulting solution was extracted with 2×7 L of toluene and the organic layers combined. The organic phase was washed with 2×10 L of brine. The mixture was dried over anhydrous sodium sulfate and concentrated under vacuum to afford benzyl N-(2,2-dimethoxyethyl)-N-(prop-2-en-1-yl)carbamate as pale yellow oil.

Step 3. Benzyl N-(2-oxoethyl)-N-(prop-2-en-1-yl)carbamate

A solution of benzyl N-(2,2-dimethoxyethyl)-N-(prop-2-en-1-yl)carbamate (3900 g, 13.96 mol) in 88% formic acid (5460 mL) was stirred overnight at room temperature. The resulting mixture was concentrated under vacuum. The residue was diluted with 20 L of ethyl acetate, washed with 4×10 L of brine. The organic phase was dried over anhydrous sodium sulfate and concentrated under vacuum to afford benzyl N-(2-oxoethyl)-N-(prop-2-en-1-yl)carbamate as brown oil.

Step 4. Benzyl N-[2-(hydroxyimino)ethyl]-N-(prop-2-en-1-yl)carbamate

To a solution of benzyl N-(2-oxoethyl)-N-(prop-2-en-1-yl)carbamate (1700 g, 7.29 mol) and $NH_2OH \cdot HCl$ (638 g, 9.18 mol) in ACN (9.52 L) was added a solution of NaOAc (669 g, 8.16 mol) in $H_2O$ (4.96 L). The resulting solution was stirred for 20 h at room temperature. Two batches were thus run in parallel. The resulting mixture was concentrated under vacuum and extracted with 3×10 L of ethyl acetate and the organic layers combined. The organic phase was washed with 3×5 L of brine, dried over anhydrous sodium sulfate and concentrated under vacuum. The crude product was purified by silica gel chromatography (eluting with 1:9 EtOAc/pet. ether) to afford benzyl N-[2-(hydroxyimino)ethyl]-N-(prop-2-en-1-yl)carbamate as colorless oil.

Step 5. cis-Benzyl 3-amino-4-(hydroxymethyl)pyrrolidine-1-carboxylate

A solution of benzyl N-[2-(hydroxyimino)ethyl]-N-(prop-2-en-1-yl)carbamate (1200 g, 4.83 mol) and xylene (6 L) was stirred overnight at 130° C. The mixture was cooled to room temperature. HOAc (6 L) was added to the mixture. Then Zn (1200 g, 18.35 mol) was added into the mixture at 15° C. The resulting solution was stirred overnight at room temperature in a water bath. Two batches were thus run in parallel. The batches were combined and filtered. The filtered cake was washed with xylene. The combined filtrate was diluted with 20 L of water. The mixture was extracted with xylene (4×5 L). The aqueous phase was concentrated under vacuum. The pH value of the residue was adjusted to 9-10 with saturated sodium carbonate. The solids were filtered out. The filtrate was concentrated under vacuum. The residue was extracted with 5 L of THF and concentrated under vacuum to afford cis-benzyl 3-amino-4-(hydroxymethyl)pyrrolidine-1-carboxylate as brown oil.

Step 6. cis-Benzyl 3-[[(tert-butoxy)carbonyl]amino]-4-(hydroxymethyl)pyrrolidine-1-carboxylate To a solution of cis-benzyl 3-amino-4-(hydroxymethyl)pyrrolidine-1-carboxylate (900 g, 3.60 mol) and triethylamine (728 g, 7.19 mol) in methanol (9 L) was added di-tert-butyl dicarbonate (863 g, 3.95 mol) dropwise with stirring at room temperature. The resulting solution was stirred overnight at room temperature. The resulting mixture was concentrated under vacuum. The crude product was purified by silica gel chromatography (eluting with 2:3 EtOAc/pet. ether) to afford cis-benzyl 3-[[(tert-butoxy)carbonyl]amino]-4-(hydroxymethyl)pyrrolidine-1-carboxylate as a white solid.

Step 7. cis-Benzyl 3-[[(tert-butoxy)carbonyl]amino]-4-(methoxymethyl)pyrrolidine-1-carboxylate To a mixture of cis-benzyl 3-[[(tert-butoxy)carbonyl]amino]-4-(hydroxymethyl)pyrrolidine-1-carboxylate (600 g, 1.71 mol) and 2,6-di-tert-butyl-4-methylpyridine (1406 g, 6.85 mol) in DCM (12 L) was added trimethyloxonium tetrafluoroborate (506.5 g, 3.42 mol). The reaction was stirred overnight at room temperature. The resulting solution was concentrated under vacuum. The crude product was purified by silica gel chromatography (eluting with 3:7 EtOAc/pet. ether) to afford cis-benzyl 3-[[(tert-butoxy)carbonyl]amino]-4-(methoxymethyl)pyrrolidine-1-carboxylate as a white solid.

Step 8. Benzyl (3R,4R)-3-[[(tert-butoxy)carbonyl]amino]-4-(methoxymethyl)pyrrolidine-1-carboxylate The racemate cis-benzyl 3-[[(tert-butoxy)carbonyl]amino]-4-(methoxymethyl)pyrrolidine-1-carboxylate was separated into its enantiomers by SFC (Column: Lux 5 μm Amylose-1, 5×25 cm, 5 μm; Mobile Phase A: $CO_2$: 50%, and B: MeOH: 50%; Flow rate: 160 mL/min). The first eluting isomer (RT=4.2 min) was collected and concentrated under vacuum to give benzyl (3S,4S)-3-[[(tert-butoxy)carbonyl]amino]-4-(methoxymethyl)pyrrolidine-1-carboxylate as a white solid. MS (ESI, m/z): 387 [M+Na]~. $^1$H NMR (CDCl$_3$, 300 MHz) δ(ppm): 7.31-7.44 (m, 5H), 5.14-5.36 (m, 3H), 4.28 (s, 1H), 3.46-3.70 (m, 4H), 3.32-3.46 (m, 5H), 2.54 (s, 1H), 1.47 (s, 9H).

The second eluting isomer (RT=5.7 min) was collected and concentrated under vacuum to give benzyl (3R,4R)-3-[[(tert-butoxy)carbonyl]amino]-4-(methoxymethyl)pyrrolidine-1-carboxylate (Intermediate 48-3) as a white solid. MS (ESI, m/z): 387 [M+Na]+. $^1$H NMR (CDCl$_3$, 300 MHz) δ(ppm): 7.33-7.40 (m, 5H), 5.09-5.40 (m, 3H), 4.28 (s, 1H), 3.46-3.73 (m, 4H), 3.32-3.46 (m, 5H), 2.53-5.55 (m, 1H), 1.46 (s, 9H).

Intermediate 49. tert-Butyl ((3S,4S)-4-(methoxy-d3)pyrrolidin-3-yl)carbamate

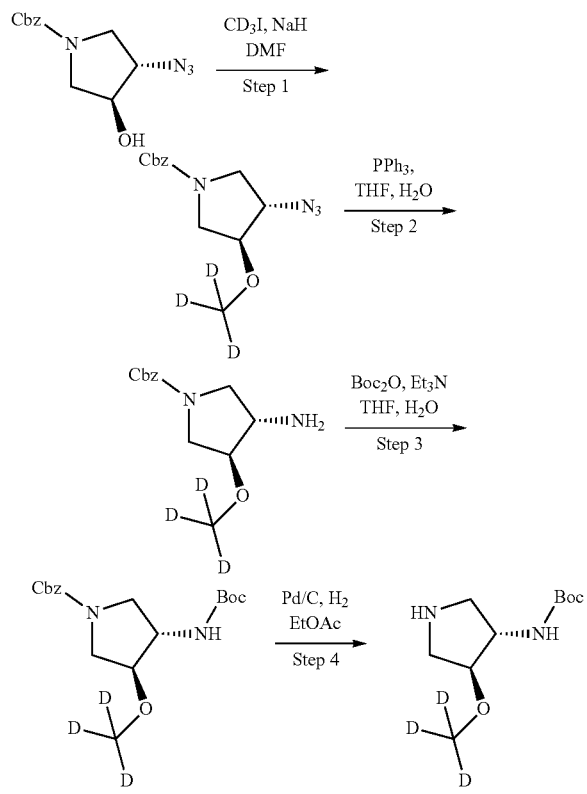

Step 1. Benzyl (3S,4S)-3-azido-4-(methoxy-d3)pyrrolidine-1-carboxylate

To a solution of benzyl (3S,4S)-3-azido-4-hydroxypyrrolidine-1-carboxylate (202.7 mg, 0.773 mmol) in anhydrous DMF (5 mL) was added NaH (60% dispersion in mineral oil, 37.1 mg, 0.927 mmol). The reaction was allowed to stir at room temperature for 1 h. Then, iodomethane-d3 (0.058 ml, 0.927 mmol) was added and the reaction was stirred at 22° C. for 6 h. The reaction was diluted with 5 mL of EtOAc and washed with 2×3 mL of $H_2O$. The organic layer was separated, dried over anhydrous $Na_2SO_4$, filtered, and concentrated to afford crude benzyl (3S,4S)-3-azido-4-(methoxy-d3)pyrrolidine-1-carboxylate as a yellow oil. MS: (ESI, m/z): 280 [M+H]$^+$.

Step 2. Benzyl (3S,4S)-3-amino-4-(methoxy-d3)pyrrolidine-1-carboxylate

A solution of benzyl (3S,4S)-3-azido-4-(methoxy-d3)pyrrolidine-1-carboxylate (215.8 mg, 0.773 mmol) and triphenylphosphine (223 mg, 0.850 mmol) in THF (1.405 mL) and water (0.14 mL) was stirred for 1 h at room temperature. The reaction was then heated at 50° C. for 5 h. After cooling to room temperature, the reaction was concentrated under vacuum. The residue was purified by prep-HPLC (Column: Waters XBridge Prep C18 OBD 5 m, 19×50 mm; Mobile Phase gradient 0% to 35% ACN, 0.1% formic acid over 8 min; Flow rate: 23 mL/min) to afford benzyl (3S,4S)-3-amino-4-(methoxy-d3)pyrrolidine-1-carboxylate as a colorless oil. MS: (ESI, m/z): 254 [M+H]$^-$.

Step 3. Benzyl (3S,4S)-3-((tert-butoxycarbonyl)amino)-4-(methoxy-d3)pyrrolidine-1-carboxylate A solution of benzyl (3S,4S)-3-amino-4-(methoxy-d3)pyrrolidine-1-carboxylate (217 mg, 0.858 mmol), Et$_3$N (225 μl, 1.61 mmol), and Boc$_2$O (0.299 mL, 1.29 mmol) in THF (1.43 mL) and water (1.43 mL) was stirred for 30 min at room temperature. The resulting mixture was extracted with 2×30 mL of DCM. The combined organic layers were dried over anhydrous $Na_2SO_4$, filtered, and concentrated under vacuum to afford benzyl (3S,4S)-3-((tert-butoxycarbonyl)amino)-4-(methoxy-d3)pyrrolidine-1-carboxylate as a colorless oil. MS: (ESI, m/z): 354 [M+H]$^+$.

Step 4. tert-Butyl ((3S,4S)-4-(methoxy-d3)pyrrolidin-3-yl)carbamate

A mixture of benzyl 3-((tert-butoxycarbonyl)amino)-4-methoxypyrrolidine-1-carboxylate (200 mg, 0.57 mmol) and Pd/C (200 mg, 10%) in EtOAc (10 mL) was stirred for 3 h at room temperature under an atmosphere of hydrogen. The solids were filtered out and washed with 3×10 mL of EtOAc. The filtrate was concentrated under vacuum to afford tert-butyl N-(4-methoxypyrrolidin-3-yl)carbamate as a colorless oil. MS: (ESI, m/z): 220 [M+H]$^+$. $^1$HNMR(CDCl$_3$, 300 MHz) δ(ppm): 8.04-8.26 (m, 1H), 4.41-4.86 (m, 1H), 3.93-4.22 (m, 1H), 3.09-3.92 (m, 3H), 1.46 (s, 9H).

Intermediate 50. Benzyl N-(7-chloro-6,8-difluoro-3,4-dihydro-2H-1-benzopyran-3-yl)carbamate

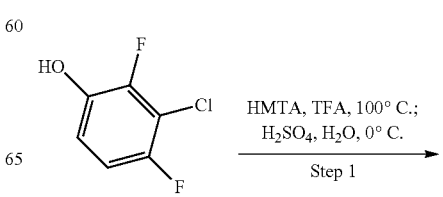

Step 1. 4-Chloro-3,5-difluoro-2-hydroxybenzaldehyde

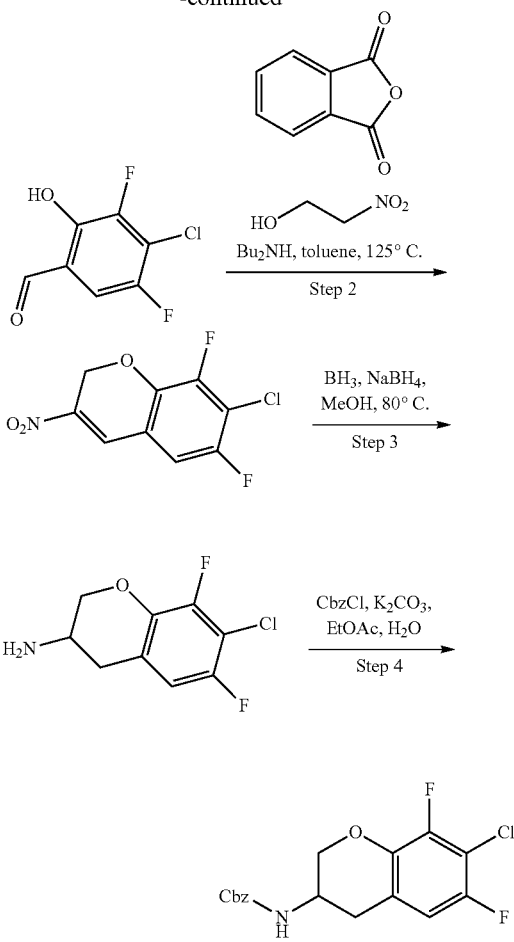

A solution of 3-chloro-2,4-difluorophenol (4.00 g, 23.6 mmol) and HMTA (6.60 g, 47.2 mmol) in TFA (60 mL) was stirred for 3 h at 100° C. After cooling to 0° C., conc. H₂SO₄(10 mL) and H₂O (50 mL) were added into the mixture at 0° C. The mixture was stirred for 2 h at 20° C. and then diluted with H₂O (40 mL). The pH value of the mixture was adjusted to 7-8 with dibutylamine. The resulting mixture was extracted with ethyl acetate (3×100 mL). The organic layers were combined, dried over anhydrous sodium sulfate, filtered and concentrated under vacuum. The residue was purified by silica gel chromatography (eluting with 1:5 ethyl acetate/pet. ether) to afford 4-chloro-3,5-difluoro-2-hydroxybenzaldehyde as an off-white solid. GCMS (ESI, m/z): 192,194 [M+H]⁺.

Step 2. 7-Chloro-6,8-difluoro-3-nitro-2H-chromene

2-Nitroethan-1-ol (3.72 mL, 51.9 mmol) was added to a stirring solution of 4-chloro-3,5-difluoro-2-hydroxybenzaldehyde (1.50 g, 7.77 mmol), dibutylamine (0.659 mL, 3.89 mmol) and phthalic anhydride (2.20 g, 14.8 mmol) in toluene (80 mL) via an injection pump with the flowrate of 0.5 mL/h at 125° C. The resulting solution was refluxed for 16 h at 125° C. After cooling to 20° C., the resulting mixture was concentrated under vacuum. The residue was purified by silica gel chromatography (eluting with 1:10 ethyl acetate/pet. ether) to give 7-chloro-6,8-difluoro-3-nitro-2H-chromene as a yellow solid. MS (ESI, m/z): 248, 250 [M+H]⁻.

Step 3. 7-Chloro-8-fluoro-3,4-dihydro-2H-1-benzopyran-3-amine

A mixture of 7-chloro-6,8-difluoro-3-nitro-2H-chromene (1.30 g, 5.25 mmol), BH₃ (40 mL, LM in THF), and NaBH₄ (399 mg, 10.5 mmol) was stirred for 16 h at 65° C. MeOH (80 mL) was added into the mixture slowly at <10° C. The resulting solution was stirred for 8 h at 80° C. After cooling to 20° C., the resulting mixture was concentrated under vacuum. The residue was purified via reverse phase chromatography (Column: C18 silica gel; Mobile phase, A: water (10 mM NH₄HCO₃) and B: ACN (5% to 75% in 20 min)) to afford 7-chloro-8-fluoro-3,4-dihydro-2H-1-benzopyran-3-amine as an off-white solid. MS (ESI, m/z): 220, 222 [M+H]⁺.

Step 4. Benzyl N-(7-chloro-6,8-difluoro-3,4-dihydro-2H-1-benzopyran-3-yl)carbamate CbzCl (0.500 mL, 3.55 mmol) was added to a mixture of 7-chloro-6,8-difluoro-3,4-dihydro-2H-1-benzopyran-3-amine (650 mg, 2.96 mmol) and potassium carbonate (822 mg, 5.92 mmol) in ethyl acetate (20 mL) and water (20 mL) at <10° C. The resulting solution was then stirred for 1 h at 25° C. and diluted with water (30 mL). The resulting mixture was extracted with ethyl acetate (3×30 mL). The organic layers were combined, dried over anhydrous sodium sulfate, filtered and concentrated under vacuum. The residue was purified by silica gel chromatography (eluting with 1:5 ethyl acetate/pet. ether) to afford benzyl N-(7-chloro-6,8-difluoro-3,4-dihydro-2H-1-benzopyran-3-yl)carbamate as an off-white solid. MS (ESI, m/z): 354, 356 [M+H]⁺.

Intermediate 51-1. tert-Butyl N-[(3R,4S)-4-(difluoromethyl)pyrrolidin-3-yl]carbamate Intermediate 51-2. tert-Butyl N-[(3S,4R)-4-(difluoromethyl)pyrrolidin-3-yl]carbamate

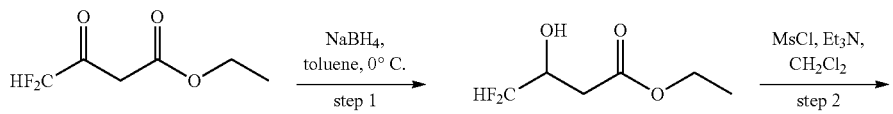

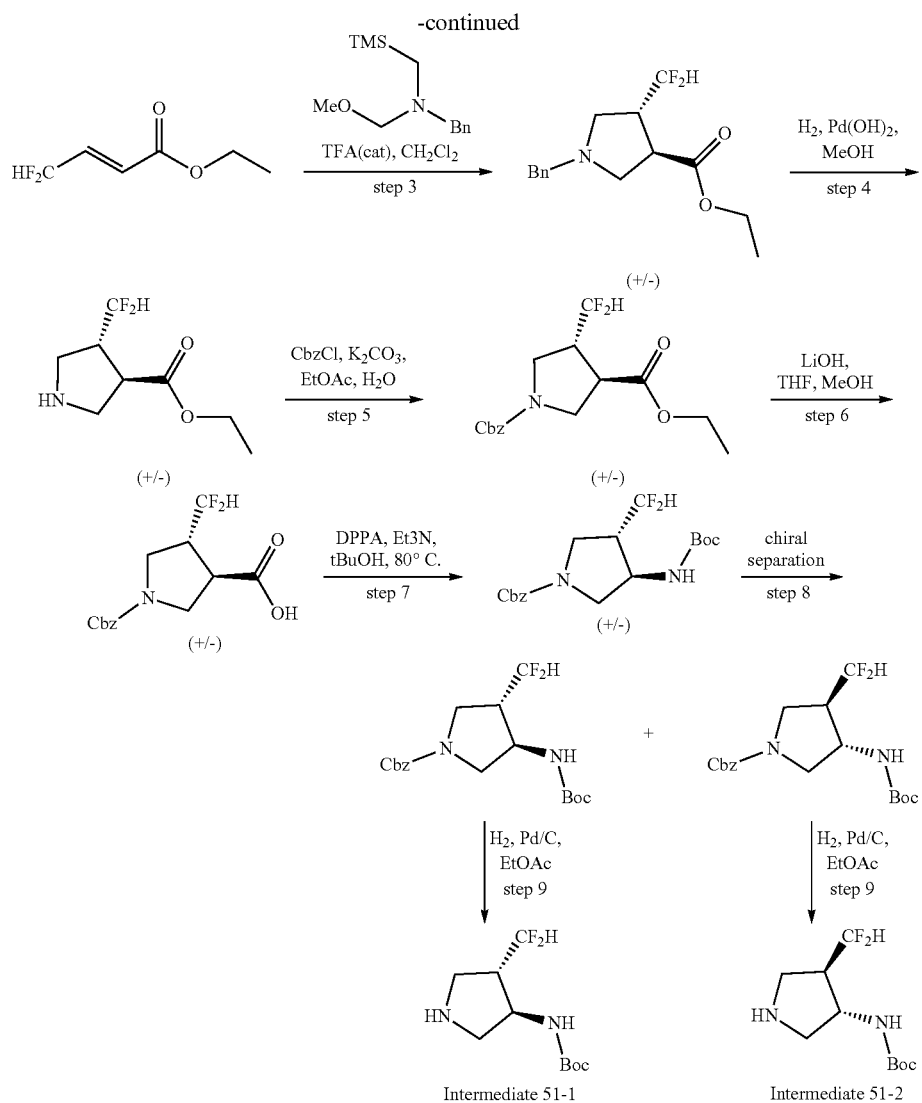

Step 1. Ethyl 4,4-difluoro-3-hydroxybutanoate

NaBH$_4$ (34.2 g, 902 mmol) was added into a stirring solution of ethyl 4,4-difluoro-3-oxobutanoate (100 g, 602 mmol) in toluene (1 L) at 0° C. The resulting mixture was stirred for 2 h at 0° C., and then warmed up to 25° C. and stirred for 16 h. The reaction was quenched with water (400 mL). The resulting mixture was extracted with ethyl acetate (2×1 L). The organic layers were combined, dried over anhydrous sodium sulfate, filtered and concentrated under vacuum to afford ethyl 4,4-difluoro-3-hydroxybutanoate as a light yellow oil. GCMS (ESI, m/z): 168 [M+H]$^+$.

Step 2. Ethyl (2E)-4,4-difluorobut-2-enoate

To a solution of ethyl 4,4-difluoro-3-hydroxybutanoate (40.0 g, 238 mmol) and Et$_3$N (99.0 mL, 712 mmol) in DCM (300 mL) was added MsCl (28.0 mL, 244 mmol) dropwise at 0° C. The resulting mixture was warmed to 25° C. and stirred for 16 h. The reaction was quenched with water (500 mL). The resulting mixture was extracted with DCM (2×500 mL). The organic layers were combined, washed with brine (500 mL), dried over anhydrous sodium sulfate, filtered and concentrated under vacuum. The residue was purified by silica gel chromatography (eluting with 1:10 ethyl acetate/pet. ether) to afford ethyl (2E)-4,4-difluorobut-2-enoate as a yellow green oil. GCMS (ESI, m/z): 150 [M+H]$^+$.

Step 3. trans-Ethyl 1-benzyl-4-(difluoromethyl)pyrrolidine-3-carboxylate

To a stirring solution of ethyl (2E)-4,4-difluorobut-2-enoate (12.0 g, 79.9 mmol) and benzyl(methoxymethyl)[(trimethylsilyl)methyl]amine (30.7 mL, 120 mmol) in DCM (250 mL) was added a solution of TFA (0.59 mL, 5.21 mmol) in DCM(20 mL) dropwise over 2 min at 0° C. The resulting mixture was warm to 25° C. and was stirred for 14 h. The reaction was quenched by the addition of water (500 mL). The resulting mixture was extracted with DCM (2×300 mL). The organic layers were combined, washed with sodium bicarbonate solution (sat., 300 mL), dried over anhydrous sodium sulfate, filtered and concentrated under vacuum. The residue was purified by silica gel chromatography (eluting with 1:10 to 1:5 ethyl acetate/pet. ether). The collected fraction was concentrated under vacuum to afford trans-ethyl 1-benzyl-4-(difluoromethyl)pyrrolidine-3-carboxylate as a yellow oil. MS (ESI, m/z): 284 [M+H]+.

Step 4. trans-Ethyl 4-(difluoromethyl)pyrrolidine-3-carboxylate

A mixture of trans-ethyl-1-benzyl-4-(difluoromethyl)pyrrolidine-3-carboxylate (5.50 g, 19.4 mmol) and Pd(OH)$_2$/C (2.00 g, 10%) in MeOH (30 mL) was stirred for 2 h at 25° C. under hydrogen atmosphere (balloon). The solids were filtered out and the filter cake was washed with MeOH (3×10 mL). The filtrate was concentrated under reduced pressure to afford trans-ethyl 4-(difluoromethyl)pyrrolidine-3-carboxylate as a white solid. MS (ESI, m/z): 194 [M+H]+.

Step 5. trans-Benzyl 3-(difluoromethyl)-4-[ethoxy(hydroxy)methyl]pyrrolidine-1-carboxylate CbzCl (4.05 g, 23.741 mmol) was added into a stirring solution of trans-ethyl 4-(difluoromethyl)pyrrolidine-3-carboxylate (3.90 g, 19.8 mmol) and K$_2$CO$_3$ (8.20 g, 59.3 mmol) in H$_2$O (20 mL) and ethyl acetate (40 mL) at 0° C. The resulting mixture was stirred for 1 h at 25° C. The reaction was quenched by the addition of water (100 mL). The resulting mixture was extracted with DCM (2×200 mL). The organic layers were combined, dried over anhydrous sodium sulfate, filtered and concentrated under vacuum. The residue was purified by reverse phase chromatography (column, C18 silica gel; Mobile phase, A: water (containing 0.1% TFA) and B: ACN (0% to 60% in 30 min)) to afford trans-benzyl 3-(difluoromethyl)-4-[ethoxy(hydroxy)methyl]pyrrolidine-1-carboxylate as a yellow oil. MS (ESI, m/z): 328 [M+H]+.

Step 6. trans-1-[(Benzyloxy)carbonyl]-4-(difluoromethyl)pyrrolidine-3-carboxylic acid To a stirring solution of trans-benzyl 3-(difluoromethyl)-4-[ethoxy(hydroxy)methyl]pyrrolidine-1-carboxylate (6.00 g, 18.0 mmol) in THF (80 mL) and MeOH (20 mL) was added a solution of LiOH (4.30 g, 180 mmol) in water (10 mL). The resulting mixture was stirred for 1 h at 25° C. The solvent was removed under vacuum. pH value of the residue was adjusted to 5-6 with NH$_4$Cl (sat. aq.). The resulting mixture was extracted with DCM (3×50 mL). The organic layers were combined, washed with sodium bicarbonate solution (sat., 50 mL), dried over anhydrous sodium sulfate, filtered and concentrated under vacuum. The residue was purified by reverse phase chromatography (column: C18 silica gel; Mobile phase, A: water (containing 0.1% TFA) and B: ACN (0% to 60% in 30 min)) to afford trans-1-[(benzyloxy)carbonyl]-4-(difluoromethyl)pyrrolidine-3-carboxylic acid as a colorless oil. MS (ESI, m/z): 300 [M+H]+.

Step 7. trans-Benzyl 3-[[(tert-butoxy)carbonyl]amino]-4-(difluoromethyl)pyrrolidine-1-carboxylate To a stirring solution of trans-1-[(benzyloxy)carbonyl]-4-(difluoromethyl)pyrrolidine-3-carboxylic acid (4.00 g, 13.1 mmol) in t-BuOH (100 mL) were added Et$_3$N (2.73 mL, 19.6 mmol) and DPPA (4.33 g, 15.7 mmol) dropwise at 0° C. After addition, the resulting mixture was stirred for 2 h at 80° C. The mixture was allowed to cool down to 25° C. and then concentrated under vacuum. The residue was purified by reverse flash chromatography (column, C18 silica gel; Mobile phase, A: water (containing 0.1% TFA) and B: ACN (0% to 100% in 40 min)) to afford desired product. It was further purified by silica gel chromatography (eluting with 2:5 THF/pet. ether) to afford trans-benzyl 3-[[(tert-butoxy)carbonyl]amino]-4-(difluoromethyl)pyrrolidine-1-carboxylate as a colorless oil. MS (ESI, m/z): 371 [M+H]+.

Step 8. tert-Butyl N-[(3S,4R)-4-(difluoromethyl)pyrrolidin-3-yl]carbamate and tert-butyl N-[(3R,4S)-4-(difluoromethyl)pyrrolidin-3-yl]carbamate trans-Benzyl 3-[[(tert-butoxy)carbonyl]amino]-4-(difluoromethyl)pyrrolidine-1-carboxylate (1.70 g, 4.58 mmol) was separated by SFC (Column: Chiralpak AD-H SFC, 5×25 cm, 5 μm; Mobile Phase, A: CO$_2$:70% and B: MeOH (containing 2 mM NH$_3$-MeOH): 30%; Flow rate: 180 mL/min) to afford the first eluted isomer (RT=4.23 min) as a white solid, the stereochemistry arbitrarily assigned as tert-butyl N-[(3R,4S)-4-(difluoromethyl)pyrrolidin-3-yl]carbamate; and the second eluted isomer (RT=6.14 min) as a white solid, the stereochemistry arbitrarily assigned as tert-butyl N-[(3S,4R)-4-(difluoromethyl)pyrrolidin-3-yl]carbamate. MS (ESI, m/z): 371 [M+H]+.

Step 9. tert-Butyl N-[(3S,4R)-4-(difluoromethyl)pyrrolidin-3-yl]carbamate and tert-Butyl N-[(3R,4S)-4-(difluoromethyl)pyrrolidin-3-yl]carbamate A mixture of benzyl (3S,4R)-3-[[(tert-butoxy)carbonyl]amino]-4-(difluoromethyl)pyrrolidine-1-carboxylate (650 mg, 1.76 mmol) and Pd/C (450 mg, 10%) in ethyl acetate (14 mL) was stirred for 3 h at 25° C. under an atmosphere of hydrogen (balloon). The solids were filtered out. The filtrate was concentrated under vacuum to give tert-butyl N-[(3S,4R)-4-(difluoromethyl)pyrrolidin-3-yl]carbamate as a colorless oil. MS (ESI, m/z): 237 [M+H]+.

tert-Butyl N-[(3R,4S)-4-(difluoromethyl)pyrrolidin-3-yl]carbamate was similarly obtained from benzyl (3R,4S)-3-[[(tert-butoxy)carbonyl]amino]-4-(difluoromethyl)pyrrolidine-1-carboxylate. MS (ESI, m/z): 237 [M+H]+.

Intermediate 52-1. tert-Butyl 4-[(6S)-6-amino-4-fluoro-5,6,7,8-tetrahydroquinolin-2-yl]piperazine-1-carboxylate

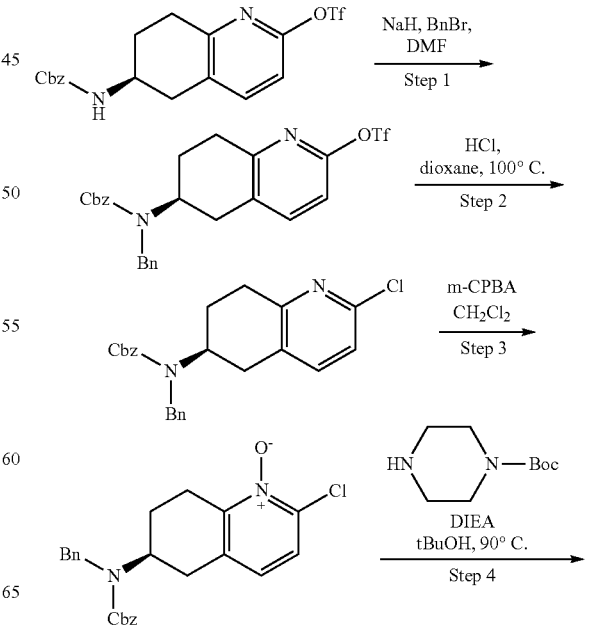

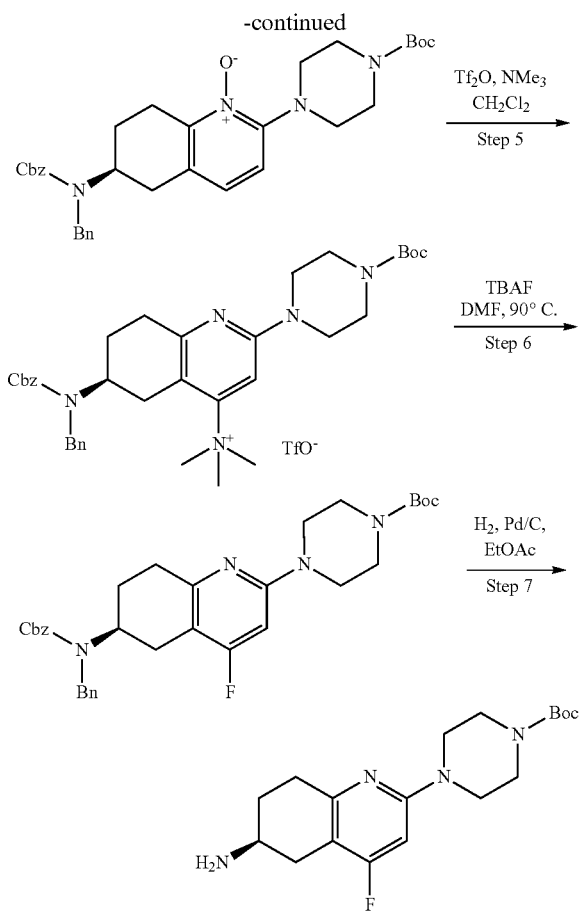

Step 1. Benzyl N-benzyl-N-[(6S)-2-(trifluoromethanesulfonyloxy)-5,6,7,8-tetrahydroquinolin-6-yl]carbamate NaH (260 mg, 6.50 mmol, 60%) was added into a stirring solution of benzyl N-[(6S)-2-(trifluoromethanesulfonyloxy)-5,6,7,8-tetrahydroquinolin-6-yl]carbamate (Intermediate 47-2) (1.00 g, 2.23 mmol) in DMF (5 mL) in portions at 0° C. The resulting mixture was stirred for 30 min at 0° C. To the above mixture was added benzyl bromide (795 mg, 4.56 mmol) dropwise over 30 min at 0° C. The resulting mixture was stirred at 26° C. for 1 h. The reaction was quenched by the addition of water (30 mL) at 0° C. The resulting mixture was extracted with ethyl acetate (3×30 mL). The organic layers were combined, dried over anhydrous sodium sulfate, filtered and concentrated under vacuum. The residue was purified by reversed phase chromatography (Column: C18 silica gel; Mobile phase, A: water (containing 10 mmol/L $NH_4HCO_3$) and B: ACN (5% to 80% in 30 min)). The collected fraction was concentrated to give benzyl N-benzyl-N-[(6S)-2-(trifluoromethanesulfonyloxy)-5,6,7,8-tetrahydroquinolin-6-yl]carbamate as a brown solid. MS (ESI, m/z): 521 [M+H]$^+$.

Step 2. Benzyl N-benzyl-N-[(6S)-2-chloro-5,6,7,8-tetrahydroquinolin-6-yl]carbamate A solution of benzyl N-benzyl-N-[(6S)-2-(trifluoromethanesulfonyloxy)-5,6,7,8-tetrahydroquinolin-6-yl]carbamate (925 mg, 1.69 mmol) and a solution of HCl (1 mL, 4M in dioxane) in dioxane (3 mL) was stirred for 15 min at 100° C. The mixture was allowed to cool to 25° C. and concentrated under vacuum. The residue was purified by reverse phase chromatography (Column: C18 silica gel; Mobile phase, A: water (containing 10 mmol/L $NH_4HCO_3$) and B: ACN (5% to 80% in 30 min)). The collected fraction was concentrated to give benzyl N-benzyl-N-[(6S)-2-chloro-5,6,7,8-tetrahydroquinolin-6-yl]carbamate as a brown oil. MS (ESI, m/z): 407, 409 [M+H]$^+$.

Step 3. (6S)-6-[Benzyl[(benzyloxy)carbonyl]amino]-2-chloro-5,6,7,8-tetrahydroquinolin-1-ium-1-olate A solution of benzyl N-benzyl-N-[(6S)-2-chloro-5,6,7,8-tetrahydroquinolin-6-yl]carbamate (632 mg, 1.49 mmol) and m-CPBA (1.31 g, 7.46 mmol) in DCM (20 mL) was stirred for 16 h at 25° C. The reaction was quenched by the addition of $Na_2SO_3$ (sat. aq., 30 mL) and $NaHCO_3$ (sat. aq., 30 mL). The resulting mixture was extracted with ethyl acetate (3×50 mL). The organic layers were combined, dried over anhydrous sodium sulfate, filtered and concentrated under vacuum. The residue was purified by silica gel chromatography (eluting with 1:3 ethyl acetate/pet. ether) to afford (6S)-6-[benzyl[(benzyloxy)carbonyl]amino]-2-chloro-5,6,7,8-tetrahydroquinolin-1-ium-1-olate as a white solid. MS (ESI, m/z): 423, 425 [M+H]$^+$.

Step 4. (6S)-6-[Benzyl[(benzyloxy)carbonyl]amino]-2-[4-[(tert-butoxy)carbonyl]piperazin-1-yl]-5,6,7,8-tetrahydroquinolin-1-ium-1-olate A solution of (6S)-6-[benzyl[(benzyloxy)carbonyl]amino]-2-chloro-5,6,7,8-tetrahydroquinolin-1-ium-1-olate (470 mg, 1.06 mmol), tert-butyl piperazine-1-carboxylate (1.04 g, 5.58 mmol) and DIEA (0.990 mL, 5.57 mmol) in t-BuOH (5 mL) was stirred for 10 h at 90° C. The resulting mixture was concentrated under vacuum. The residue was purified by reverse phase chromatography (C18 silica gel; Mobile phase, A: water (containing 10 mmol/L $NH_4HCO_3$) and B: ACN (5% to 80% in 30 min)). The collected fraction was concentrated to give (6S)-6-[benzyl[(benzyloxy)carbonyl]amino]-2-[4-[(tert-butoxy)carbonyl]piperazin-1-yl]-5,6,7,8-tetrahydroquinolin-1-ium-1-olate as a yellow solid. MS (ESI, m/z): 573 [M+H]$^+$.

Step 5. TFA salt of (6S)-6-[benzyl[(benzyloxy)carbonyl]amino]-2-[4-[(tert-butoxy)carbonyl]piperazin-1-yl]-N,N,N-trimethyl-5,6,7,8-tetrahydroquinolin-4-aminium A solution of (6S)-6-[benzyl[(benzyloxy)carbonyl]amino]-2-[4-[(tert-butoxy)carbonyl]piperazin-1-yl]-5,6,7,8-tetrahydroquinolin-1-ium-1-olate (460 mg, 0.760 mmol) in DCM (9 mL) was treated with a solution of trimethylamine (3.63 mL, 1M in THF) at 0° C., followed by the addition of $Tf_2O$ (0.365 mL, 2.13 mmol) dropwise at 0° C. The resulting mixture was stirred for 1 h at 25° C. and then concentrated under vacuum. The residue was purified by reverse phase chromatography (Column: C18 silica gel; Mobile phase, A: water (containing 10 mmol/L $NH_4HCO_3$) and B: ACN (5% to 80% in 30 min)). The collected fraction was concentrated to afford the TFA salt of (6S)-6-[benzyl[(benzyloxy)carbonyl]amino]-2-[4-[(tert-butoxy)carbonyl]piperazin-1-yl]-N,N,N-trimethyl-5,6,7,8-tetrahydroquinolin-4-aminium as a light brown solid. MS (ESI, m/z): 615 [M+H]$^+$.

Step 6. tert-Butyl 4-[(6S)-6-[benzyl[(benzyloxy) carbonyl]amino]-4-fluoro-5,6,7,8-tetrahydroquinolin-2-yl]piperazine-1-carboxylate A solution of the TFA salt of (6S)-6-[benzyl[(benzyloxy) carbonyl]amino]-2-[4-[(tert-butoxy)carbonyl]piperazin-1-yl]-N,N,N-trimethyl-5,6,7,8-tetrahydroquinolin-4-aminium (230 mg, 0.300 mmol) and a solution of TBAF (3.30 mL, 1M in THF) in DMF (5 mL) was stirred for 2 h at 90° C. The mixture was purified by reverse phase chromatography (Column: C18 silica gel; Mobile phase, A: water (containing 10 mmol/L NH4HCO3) and B: ACN (5% to 80% in 30 min)). The collected fraction was concentrated to give tert-butyl 4-[(6S)-6-[benzyl[(benzyloxy)carbonyl]amino]-4-fluoro-5,6,7,8-tetrahydroquinolin-2-yl]piperazine-1-carboxylate as a white solid. MS (ESI, m/z): 575 [M+H]$^+$.

Step 7. tert-Butyl 4-[(6S)-6-amino-4-fluoro-5,6,7,8-tetrahydroquinolin-2-yl]piperazine-1-carboxylate A mixture of tert-butyl 4-[(6S)-6-[benzyl[(benzyloxy)carbonyl]amino]-4-fluoro-5,6,7,8-tetrahydroquinolin-2-yl]piperazine-1-carboxylate (100 mg, 0.170 mmol) and palladium on carbon (100 mg, 10%) in ethyl acetate (5 mL) was stirred for 3 h at 25° C. under hydrogen atmosphere. The solids were filtered out and the filter cake was washed with ethyl acetate (3×10 mL). The filtrate was concentrated under reduced pressure to afford tert-butyl 4-[(6S)-6-amino-4-fluoro-5,6,7,8-tetrahydroquinolin-2-yl]piperazine-1-carboxylate as a light brown solid. MS (ESI, m/z): 351 [M+H]$^-$.

The following intermediate in Table 8 was prepared using standard chemical manipulations and procedures similar to those used for the preparation of Intermediate 52-1.

TABLE 8

| Intermediate Number | Structure and Compound Name | LRMS m/z [M + H]$^+$ |
|---|---|---|
| 52-2 | tert-butyl 3-[(6S)-6-amino-4-fluoro-5,6,7,8-tetrahydroquinolin-2-yl]-3,8-diazabicyclo[3.2.1]octane-8-carboxylate | 377 |

Intermediate 53. trans-tert-Butyl N-[4-(methoxymethyl)pyrrolidin-3-yl]-N-methylcarbamate

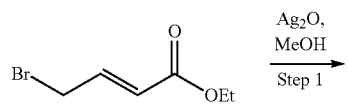

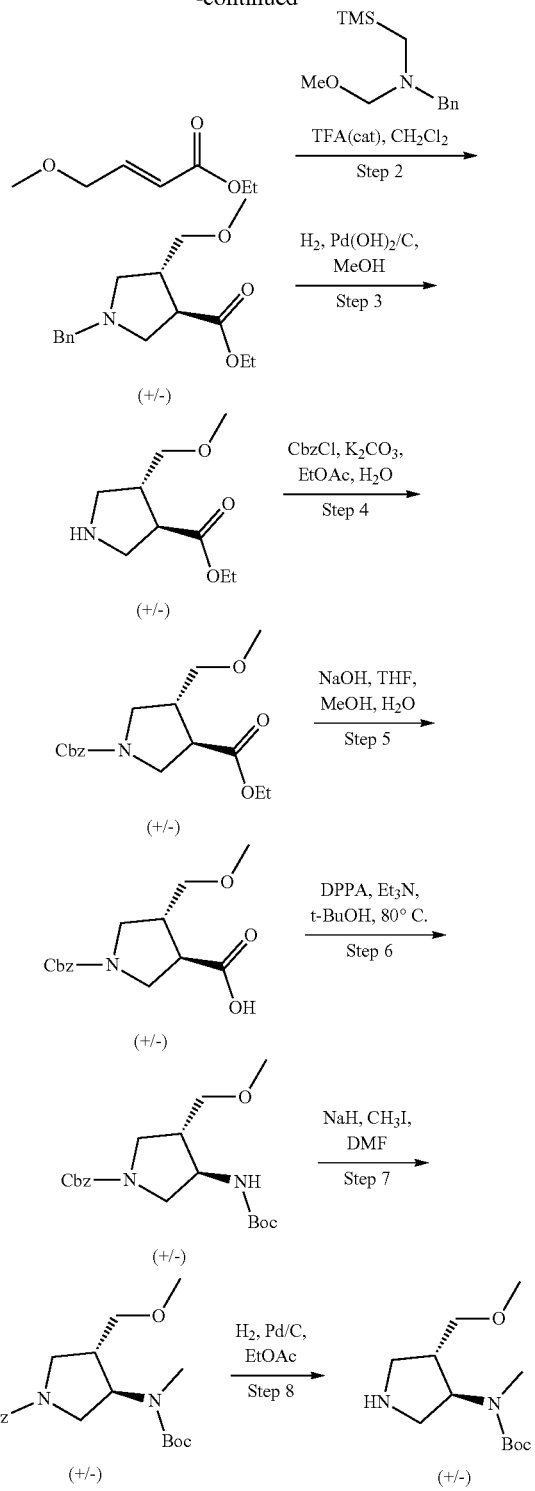

Step 1. Ethyl (2E)-4-methoxybut-2-enoate

A mixture of ethyl (2E)-4-bromobut-2-enoate (33.0 g, 171 mmol), Ag$_2$O (39.6 g, 171 mmol) and MeOH (100 mL) was stirred for 12 h at 25° C. without light. The solids were filtered out. The filtrate was concentrated under vacuum. The residue was purified via reverse phase chromatography (Column: C18 silica gel; Mobile phase, A: water (containing 0.05% TFA) and B: ACN (5% to 75% in 20 min)). The collected fraction was concentrated under vacuum to give ethyl (2E)-4-methoxybut-2-enoate as yellow oil. MS (ESI, m/z): 145 [M+H]+.

Step 2. trans-Ethyl 1-benzyl-4-(methoxymethyl)pyrrolidine-3-carboxylate

A solution of TFA (0.480 mL, 4.20 mmol) in DCM (2 mL) was added to a stirring solution of ethyl (2E)-4-methoxybut-2-enoate (9.30 μg, 64.5 μmmol) and benzyl(methoxymethyl)[(trimethylsilyl)methyl]amine (22.9 g, 96.7 mmol) in DCM (400 mL) at <10° C. The resulting mixture was stirred for 2 h at 25° C. The reaction was quenched by the addition of $NH_4HCO_3$ (sat. aq., 150 mL). The resulting mixture was extracted with DCM (3×100 mL). The organic layers were combined, dried over anhydrous $Na_2SO_4$, filtered and concentrated under reduced pressure. The residue was purified by silica gel chromatography (eluting with 1:5 ethyl acetate/pet. ether) to afford trans-ethyl 1-benzyl-4-(methoxymethyl)pyrrolidine-3-carboxylate as a yellow oil. MS (ESI, m/z): 278 [M+H]−.

Step 3. trans-Ethyl 4-(methoxymethyl)pyrrolidine-3-carboxylate

A mixture of trans-ethyl 1-benzyl-4-(methoxymethyl)pyrrolidine-3-carboxylate (14.0 g, 50.4 mmol), $Pd(OH)_2$/C (8.43 g, 10%) and MeOH (200 mL) was stirred for 1 h at 25° C. under hydrogen atmosphere (balloon). The solids were filtered out. The filtrate was concentrated under vacuum to give trans-ethyl 4-(methoxymethyl)pyrrolidine-3-carboxylate as a yellow oil. MS (ESI, m/z): 188 [M+H]+.

Step 4. trans-1-Benzyl 3-ethyl 4-(methoxymethyl)pyrrolidine-1,3-dicarboxylate

CbzCl (9.01 mL, 64.0 μmmol) was added into a mixture of trans-ethyl 4-(methoxymethyl)pyrrolidine-3-carboxylate (8.00 g, 42.7 mmol) and $K_2CO_3$ (14.7 g, 106 mmol) in ethyl acetate (100 mL) and $H_2O$ (100 mL) at 0° C. The mixture was stirred for 1 h at 25° C. The mixture was extracted with ethyl acetate (3×50 mL). The organic layers were combined, dried over anhydrous sodium sulfate, filtered and concentrated under vacuum. The residue was purified by silica gel chromatography (eluting with 1:3 ethyl acetate/pet. ether) to afford trans-1-benzyl 3-ethyl 4-(methoxymethyl)pyrrolidine-1,3-dicarboxylate as a yellow oil. MS (ESI, m/z): 322 [M+H]+.

Step 5. trans-1-[(Benzyloxy)carbonyl]-4-(methoxymethyl)pyrrolidine-3-carboxylic acid A solution of trans-1-benzyl 3-ethyl 4-(methoxymethyl)pyrrolidine-1,3-dicarboxylate (5.00 g, 15.6 mmol) and NaOH (3.11 g, 77.7 mmol) in $H_2O$ (40 mL), THF (40 mL) and MeOH (40 mL) was stirred for 2 h at 25° C. The solvent was removed under vacuum. The pH value of the residue was adjusted to pH 6 with hydrochloric acid (3N). The resulting mixture was extracted with ethyl acetate (3×25 mL). The organic layers were combined, dried over anhydrous sodium sulfate, filtered and concentrated under vacuum to give trans-1-[(benzyloxy)carbonyl]-4-(methoxymethyl)pyrrolidine-3-carboxylic acid as yellow oil. MS (ESI, miz): 294 [M+H]+.

Step 6. trans-Benzyl 3-[[(tert-butoxy)carbonyl]amino]-4-(methoxymethyl)pyrrolidine-1-carboxylate A solution of trans-1-[(benzyloxy)carbonyl]-4-(methoxymethyl)pyrrolidine-3-carboxylic acid (3.00 g, 10.2 mmol), DPPA (3.38 g, 12.3 mmol), and $Et_3N$ (4.25 mL, 30.6 mmol) in t-BuOH (60 mL) was stirred for 3 h at 80° C. The mixture was cooled to 25° C. and concentrated under vacuum. The residue was purified via reverse phase chromatography (Column: C18 silica gel; Mobile phase, A: water (containing 0.05% TFA) and B: ACN (5% to 75% in 20 min)). The collected fraction was concentrated under vacuum to give a crude product. The crude product was purified by silica gel chromatography (eluting with 1:3 THF/pet. ether) to afford trans-benzyl 3-[[(tert-butoxy)carbonyl]amino]-4-(methoxymethyl)pyrrolidine-1-carboxylate as a colorless oil. MS (ESI, m/z): 365 [M+H]+.

Step 7. trans-tert-Butyl N-[1-benzyl-4-(methoxymethyl)pyrrolidin-3-yl]-N-methylcarbamate NaH (59.0 mg, 1.48 mmol, 60%) was added to a solution of trans-tert-butyl N-[1-benzyl-4-(methoxymethyl)pyrrolidin-3-yl]carbamate (350 mg, 0.983 mmol) in DMF (4 mL) at 0° C. The resulting solution was stirred for 30 min at 0° C. Then $CH_3I$ (0.018 mL, 0.281 mmol) was added at 0° C. The resulting mixture was stirred for additional 2 h at 25° C. The reaction was quenched with water (50 mL). The resulting mixture was extracted with ethyl acetate (3×50 mL). The organic layers were combined, dried over anhydrous $Na_2SO_4$, filtered and concentrated under reduced pressure. The residue was purified by silica gel chromatography (eluting with 1:3 ethyl acetate/pet. ether) to afford trans-tert-butyl N-[1-benzyl-4-(methoxymethyl)pyrrolidin-3-yl]-N-methylcarbamate as a white solid. MS (ESI, m/z): 379 [M+H]+.

Step 8. trans-tert-Butyl N-[4-(methoxymethyl)pyrrolidin-3-yl]-N-methylcarbamate

A mixture of trans-tert-butyl N-[1-benzyl-4-(methoxymethyl)pyrrolidin-3-yl]-N-methylcarbamate (330 mg, 0.828 mmol) and palladium on carbon (300 mg, 10%) in ethyl acetate (10 mL) was stirred for 3 h at 25° C. under hydrogen atmosphere (balloon). The resulting mixture was filtered. The filtrate was concentrated under reduced pressure to afford trans-tert-butyl N-[4-(methoxymethyl)pyrrolidin-3-yl]-N-methylcarbamate as a colorless oil. MS (ESI, m/z): 245 [M+H]+.

Intermediate 54. cis-tert-Butyl N-[4-(fluoromethyl)pyrrolidin-3-yl]carbamate

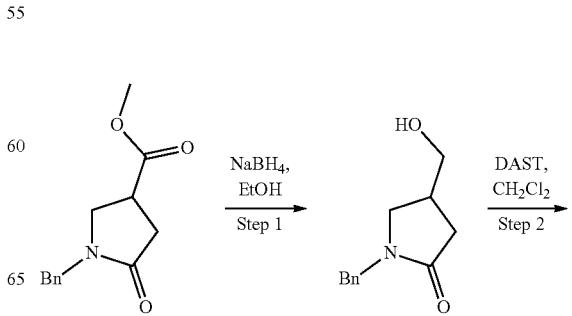

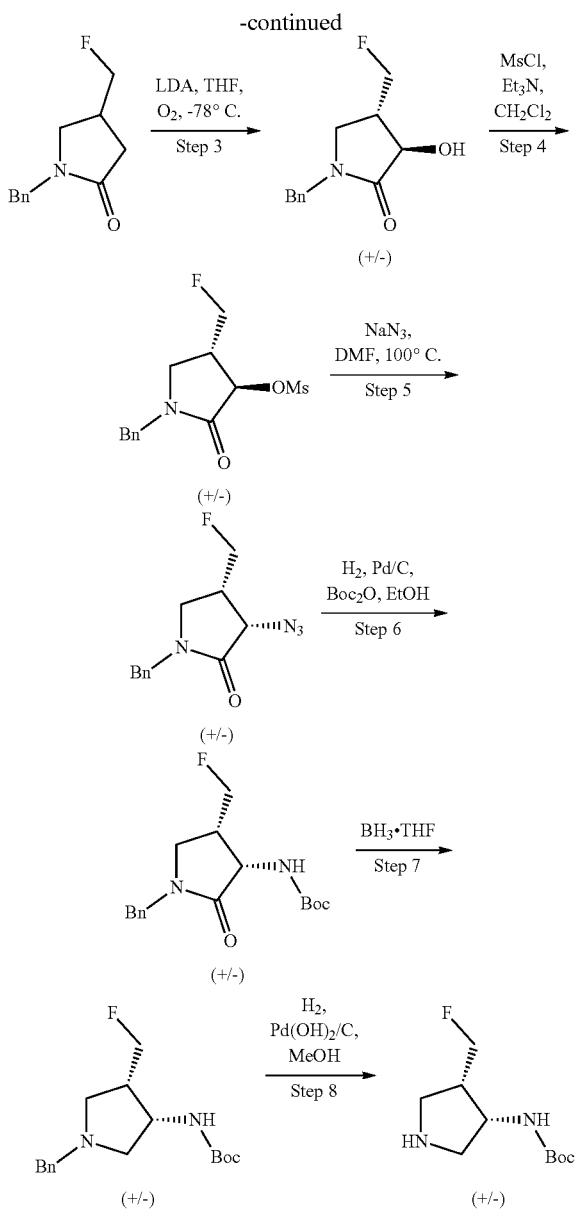

Step 1. 1-Benzyl-4-(hydroxymethyl)pyrrolidin-2-one

NaBH$_4$ (24.0 g, 634 mmol) was added to a solution of methyl 1-benzyl-5-oxopyrrolidine-3-carboxylate (50.0 g, 214 mmol) in ethanol (800 mL) at 0° C. The resulting solution was stirred for 4 h at 25° C. The reaction was quenched with water (50 mL). The mixture was concentrated under vacuum. The residue was diluted with water (200 mL). The resulting mixture was extracted with DCM (3×500 mL). The organic layers were combined, dried over anhydrous sodium sulfate, filtered and concentrated under vacuum. The residue was purified by silica gel chromatography (eluting with 10:1 dicholoromethane/methanol) to give 1-benzyl-4-(hydroxymethyl)pyrrolidin-2-one as colorless oil. MS (ESI, m/z): 206 [M+H]$^+$.

Step 2. 1-Benzyl-4-(fluoromethyl)pyrrolidin-2-one

DAST (32.2 mL, 244 mmol) was added to a solution of 1-benzyl-4-(hydroxymethyl)pyrrolidin-2-one (20.0 g, 97.5 mmol) in DCM (300 mL) at −78° C. The resulting solution was stirred for 16 h at 25° C. The reaction was poured into ice-water (200 mL). The resulting mixture was extracted with DCM (3×200 mL). The organic layers were combined, dried over anhydrous sodium sulfate, filtered and concentrated under vacuum. The residue was purified via reverse phase chromatography (Column: C18 column; Mobile phase, A: water (containing 10 mmol/L NH$_4$HCO$_3$) and B: ACN (0% to 50% in 45 min)) to give 1-benzyl-4-(fluoromethyl)pyrrolidin-2-one as yellow oil. MS (ESI, m/z): 208 [M+H]+.

Step 3. trans-1-Benzyl-4-(fluoromethyl)-3-hydroxypyrrolidin-2-one

A solution of LDA (24.0 mL, 2M in THF) was added to a solution of 1-benzyl-4-(fluoromethyl)pyrrolidin-2-one (5.00 g, 23.6 mmol) in THF (100 mL) at −78° C. The resulting solution was stirred for 1 h at −78° C. Then O$_2$ was introduced in. The resulting solution was stirred for 3 h at −78° C. The reaction was quenched by the addition of water (50 mL). The solvent was removed under vacuum. The residue was extracted with DCM (3×100 mL). The organic layers were combined, dried over anhydrous Na$_2$SO$_4$, filtered and concentrated under reduced pressure. The residue was purified by reverse phase chromatography (Column: C18 silica gel; Mobile phase, A: water (containing 0.1% TFA) and B: ACN (0% to 60% in 30 min)) to afford trans-1-benzyl-4-(fluoromethyl)-3-hydroxypyrrolidin-2-one as a brown oil. MS (ESI, m/z): 224 [M+H]$^+$.

Step 4. trans-1-Benzyl-4-(fluoromethyl)-2-oxopyrrolidin-3-yl methanesulfonate MsCl (2.75 mL, 35.5 mmol) was added to a stirring solution of trans-1-benzyl-4-(fluoromethyl)-3-hydroxypyrrolidin-2-one (5.40 g, 23.7 mmol) and Et$_3$N (6.59 mL, 47.4 mmol) in DCM (70 mL) at 0° C. The resulting mixture was stirred for 2 h at 25° C. The reaction was quenched by the addition of water (50 mL) at 0° C. The resulting mixture was extracted with DCM (3×50 mL). The organic layers were combined, dried over anhydrous Na$_2$SO$_4$, filtered concentrated under reduced pressure to afford trans-1-benzyl-4-(fluoromethyl)-2-oxopyrrolidin-3-yl methanesulfonate as a brown oil. MS (ESI, m/z): 302 [M+H]$^+$.

Step 5. cis-3-Azido-1-benzyl-4-(fluoromethyl)pyrrolidin-2-one

A mixture of trans-1-benzyl-4-(fluoromethyl)-2-oxopyrrolidin-3-yl methanesulfonate (6.00 g, 19.5 mmol) and NaN$_3$ (3.81 g, 58.6 mmol) in DMF (150 mL) was stirred for 1 h at 100° C. The mixture was allowed to cool down to 25° C. The reaction was quenched by the addition of water (500 mL) at 25° C. The resulting mixture was extracted with ethyl acetate (3×200 mL). The combined organic layers were washed with brine (300 mL), dried over anhydrous Na$_2$SO$_4$, filtered and concentrated under reduced pressure. The residue was purified by silica gel chromatography (eluting with 1:1 ethyl acetate/pet. ether) to afford cis-3-azido-1-benzyl-4-(fluoromethyl)pyrrolidin-2-one as a yellow oil. MS (ESI, m/z): 249 [M+H]$^+$.

Step 6. cis-tert-Butyl N-[1-benzyl-4-(fluoromethyl)-2-oxopyrrolidin-3-yl]carbamate A mixture of 3-azido-1-benzyl-4-(fluoromethyl)pyrrolidin-2-one (4.00 g, 15.8 mmol), Palladium on carbon (4.00 g, 10%) and di-tert-butyl dicarbonate (6.89 g, 31.6 mmol) in EtOH (100 mL) was stirred for 3 h at 25° C. under hydrogen atmosphere (balloon). The solids were filtered out. The filtrate was concentrated under vacuum. The residue was purified by silica gel chromatography (eluting with 1:1 ethyl acetate/pet. ether) to afford cis-tert-butyl N-[1-benzyl-4-(fluoromethyl)-2-oxopyrrolidin-3-yl]carbamate as a white solid. MS (ESI, m/z): 323 [M+H]$^+$.

Step 7. cis-tert-Butyl N-[1-benzyl-4-(fluoromethyl) pyrrolidin-3-yl]carbamate

A solution of BH$_3$ (30 mL, 1M in THF) was added to a stirring solution of cis-tert-butyl N-[1-benzyl-4-(fluoromethyl)-2-oxopyrrolidin-3-yl]carbamate (2.40 g, 7.30 mmol) in THF (60 mL) at 0° C. The resulting mixture was stirred for 16 h at 25° C. The resulting mixture was concentrated under vacuum. Then EtOH (60 mL), H$_2$O (15 mL) and Et$_3$N (15 mL) were added. The resulting mixture was stirred for 2 h at 80° C. The resulting mixture was cooled to 25° C. and concentrated under vacuum. The residue was purified by reverse phase chromatography (Column: C18 Column; Mobile phase, A: water (containing 10 mmol/L NH$_4$HCO$_3$) and B: ACN (0% to 100% in 30 min)) to afford cis-tert-butyl N-[1-benzyl-4-(fluoromethyl)pyrrolidin-3-yl]carbamate as a white solid. MS (ESI, m/z): 309 [M+H]$^+$.

Step 8. cis-tert-Butyl N-[4-(fluoromethyl)pyrrolidin-3-yl]carbamate

A mixture of tert-butyl N-[1-benzyl-4-(fluoromethyl)pyrrolidin-3-yl]carbamate (450 mg, 1.43 mmol) and Pd(OH)$_2$/C (450 mg, 10%) in ethyl acetate (10 mL) was stirred for 2 h at 25° C. under hydrogen atmosphere (balloon). The resulting mixture filtered. The filtrate was concentrated under reduced pressure to afford cis-tert-butyl N-[4-(fluoromethyl)pyrrolidin-3-yl]carbamate as a brown oil. MS (ESI, m/z): 219 [M+H]$^+$.

Intermediate 55. trans-tert-Butyl N-[4-(2-methoxyethoxy)pyrrolidin-3-yl]carbamate

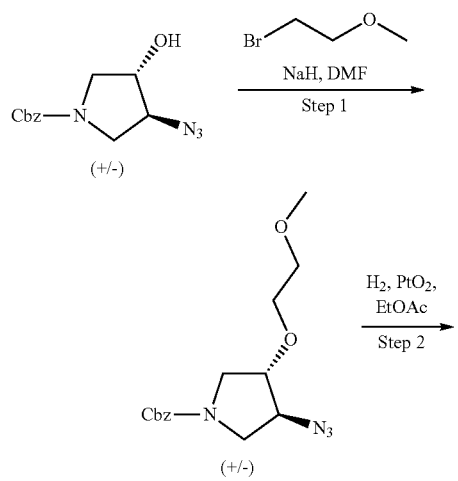

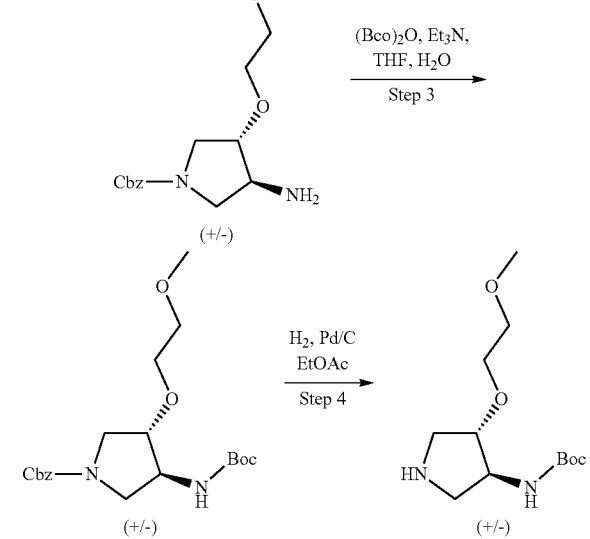

Step 1. trans-Benzyl 3-azido-4-(2-methoxyethoxy) pyrrolidine-1-carboxylate

NaH (1.91 g, 47.7 mmol, 60%) was added into a stirring solution of trans-benzyl 3-azido-4-hydroxypyrrolidine-1-carboxylate (5.00 g, 19.1 mmol) in DMF (70 mL) at <10° C. The resulting solution was stirred for 30 min at <10° C. Then 1-bromo-2-methoxyethane (7.95 g, 57.2 mmol) was added to the mixture at <10° C. The resulting mixture was stirred for 3 h at 26° C. The reaction was then quenched by the addition of water/ice (70 mL). The resulting mixture was extracted with ethyl acetate (3×100 mL). The organic layers were combined, dried over anhydrous sodium sulfate, filtered and the filtrate concentrated under vacuum. The residue was purified via reverse phase chromatography (Column: C18 silica gel; Mobile phase, A: water (containing 0.05% TFA) and B: ACN (10% to 75% in 25 min)). The collected fraction was concentrated under vacuum to give trans-benzyl 3-azido-4-(2-methoxyethoxy)pyrrolidine-1-carboxylate as yellow oil. MS (ESI, m/z): 321 [M+H]$^+$.

Step 2. trans-Benzyl 3-amino-4-(2-methoxyethoxy) pyrrolidine-1-carboxylate

A mixture of trans-benzyl 3-azido-4-(2-methoxyethoxy) pyrrolidine-1-carboxylate (5.60 g, 17.4 mmol) and PtO$_2$ (2.00 g, 8.80 mmol) in ethyl acetate (100 mL) was stirred for 1 h at 26° C. under hydrogen atmosphere (balloon). The solids were filtered out. The filtrate was concentrated under vacuum to give trans-benzyl 3-amino-4-(2-methoxyethoxy) pyrrolidine-1-carboxylate as a black oil. MS (ESI, m/z): 295 [M+H]$^+$.

Step 3. trans-Benzyl 3-[[(tert-butoxy)carbonyl] amino]-4-(2-methoxyethoxy)pyrrolidine-1-carboxylate (Boc)$_2$O (5.45 g, 25.0 mmol) was added into a solution of trans-benzyl 3-amino-4-(2-methoxyethoxy)pyrrolidine-1-carboxylate (5.00 g, 17.0 mmol) and Et$_3$N (7.08 mL, 70.0 mmol) in THF (70 mL) and H$_2$O (70 mL). The resulting solution was stirred for 3 h at 26° C. THF was removed under vacuum. The residue was extracted with ethyl acetate (3×100 mL). The organic layers were combined, dried over anhydrous sodium sulfate, filtered and the filtrate concentrated under vacuum. The residue was purified by silica gel chromatography (eluting with 1:3 ethyl acetate/pet. ether) to afford trans-benzyl 3-[[(tert-butoxy)carbonyl]amino]-4-(2-methoxyethoxy)pyrrolidine-1-carboxylate as yellow oil. MS (ESI, m/z): 395 [M+H]+.

Step 4. trans-tert-Butyl N-[4-(2-methoxyethoxy)pyrrolidin-3-yl]carbamate

A mixture of trans-benzyl 3-[[(tert-butoxy)carbonyl]amino]-4-(2-methoxyethoxy)pyrrolidine-1-carboxylate (1.60 g, 4.06 mmol) and palladium on carbon (1.60 g, 10%) in ethyl acetate (30 mL) was stirred for 2 h at 26° C. under hydrogen atmosphere (balloon). The solids were filtered out. The filtrate was concentrated under vacuum to give trans-tert-butyl N-[4-(2-methoxyethoxy)pyrrolidin-3-yl]carbamate as light yellow oil. MS (ESI, m/z): 261 [M+H]+.

Intermediate 56. tert-Butyl N-[(3S,4S)-4-(propan-2-yloxy)pyrrolidin-3-yl]carbamate

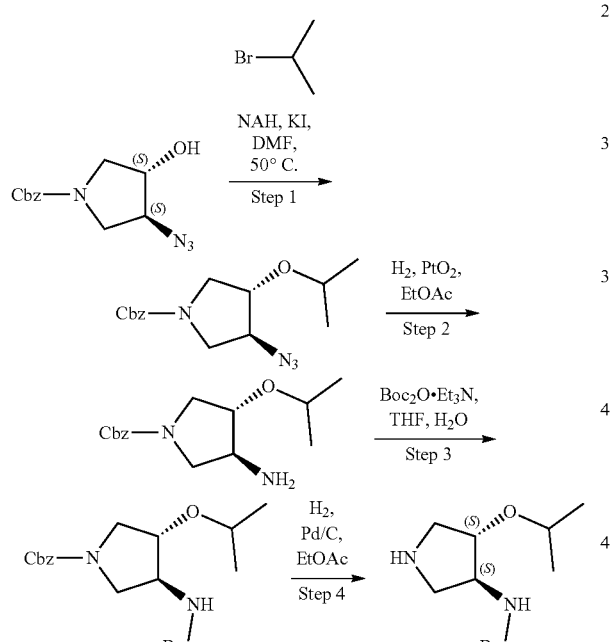

Step 2. Benzyl (3S,4S)-3-amino-4-(propan-2-yloxy)pyrrolidine-1-carboxylate

A mixture of benzyl (3S,4S)-3-azido-4-(propan-2-yloxy)pyrrolidine-1-carboxylate (220 mg, 0.72 mmol) and PtO2 (33.0 mg, 0.150 mmol) in ethyl acetate (10 mL) was stirred for 2 h at 25° C. under hydrogen atmosphere (balloon). The solids were filtered out. The filtrate was concentrated under vacuum to give benzyl (3S,4S)-3-amino-4-(propan-2-yloxy)pyrrolidine-1-carboxylate as brown oil. MS (ESI, m/z): 279 [M+H]+.

Step 3. Benzyl (3S,4S)-3-[[(tert-butoxy)carbonyl]amino]-4-(propan-2-yloxy)pyrrolidine-1-carboxylate A solution of benzyl (3S,4S)-3-amino-4-(propan-2-yloxy)pyrrolidine-1-carboxylate (200 mg, 0.720 mmol), Et3N (0.190 mL, 1.35 mmol) and (Boc)2O (236 mg, 1.08 mmol) in THF (5 mL) and water (5 mL) was stirred for 30 min at 25° C. The solvent was removed under vacuum. The residue was diluted with water (10 mL). The resulting mixture was extracted with ethyl acetate (3×20 mL), dried over anhydrous sodium sulfate, filtered and concentrated under vacuum. The residue was purified by a silica gel chromatography (eluting with 1:5 ethyl acetate/pet. ether) to give benzyl (3S,4S)-3-[[(tert-butoxy)carbonyl]amino]-4-(propan-2-yloxy)pyrrolidine-1-carboxylate as colorless oil. MS (ESI, m/z): 379 [M+H]+.

Step 4. tert-Butyl N-[(3S,4S)-4-(propan-2-yloxy)pyrrolidin-3-yl]carbamate

A mixture of benzyl (3S,4S)-3-[[(tert-butoxy)carbonyl]amino]-4-(propan-2-yloxy)pyrrolidine-1-carboxylate (250 mg, 0.660 mmol) and Palladium on carbon (250 mg, 10%) in ethyl acetate (5 mL) was stirred for 2 h at 25° C. under hydrogen atmosphere (balloon). The solids were filtered out. The filtered was concentrated under vacuum to give tert-butyl N-[(3S,4S)-4-(propan-2-yloxy)pyrrolidin-3-yl]carbamate as a brown solid. MS (ESI, m/z): 245 [M+H]+.

Intermediate 57. Benzyl N-(2-chloro-5,6,7,8-tetrahydroquinazolin-6-yl)carbamate

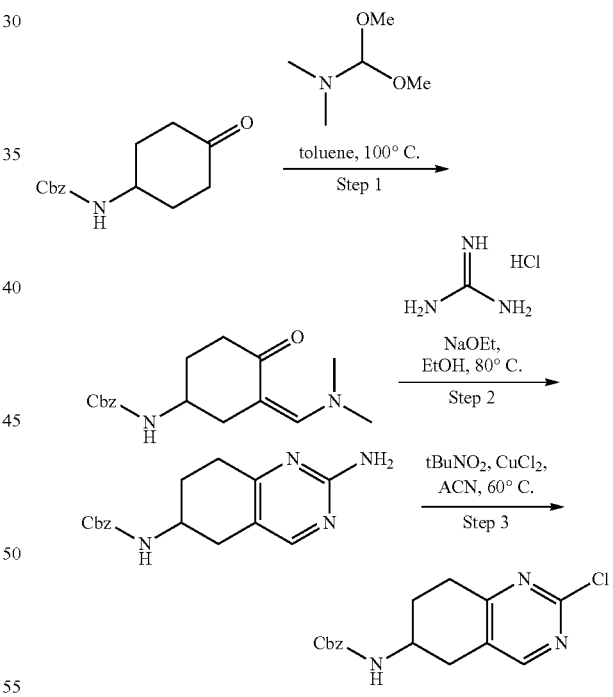

Step 1. Benzyl N-[(3Z)-3-[(dimethylamino)methylidene]-4-oxocyclohexyl]carbamate

A solution of benzyl N-(4-oxocyclohexyl)carbamate (10.0 µg, 40.4 µmmol) and (dimethoxymethyl)dimethylamine (4.80 g, 40.4 mmol) in toluene (20 mL) was stirred for 16 h at 100° C. The resulting mixture was concentrated under vacuum to give benzyl N-[(3Z)-3-[(dimethylamino)methylidene]-4-oxocyclohexyl]carbamate as yellow oil. MS (ESI, m/z): 303 [M+H]+.

Step 2. Benzyl N-(2-amino-5,6,7,8-tetrahydroquinazolin-6-yl)carbamate

A solution of guanidine hydrochloride (3.45 g, 36.1 mmol) and sodium ethoxide (2.47 g, 36.3 mmol) in ethanol (150 mL) was stirred for 30 min at 23° C. Benzyl N-[(3Z)-3-[(dimethylamino)methylidene]-4-oxocyclohexyl]carbamate (11 g, 21.8 mmol, purity: 60%) was then added. The resulting solution was stirred for overnight at 80° C. The resulting mixture was concentrated under vacuum. The residue was purified by a silica gel chromatography (eluting with 1:10 MeOH/DCM) to give benzyl N-(2-amino-5,6,7,8-tetrahydroquinazolin-6-yl)carbamate as a white solid. S (ESI, m/z): 299 [M+H]⁻.

Step 3. Benzyl N-(2-chloro-5,6,7,8-tetrahydroquinazolin-6-yl)carbamate

A mixture of benzyl N-(2-amino-5,6,7,8-tetrahydroquinazolin-6-yl)carbamate (1.85 g, 6.20 mmol), t-BuNO$_2$ (3.72 mL, 31.0 mmol) and CuCl$_2$ (4.14 g, 30.8 mmol) in ACN (40 mL) was stirred for 20 min at 60° C. The reaction mixture was cooled to 25° C. and diethyl ether (20 mL) was added. The solids were filtered out. The filtrate was concentrated under vacuum. The residue was purified by reversed phase chromatography (Column: C18 silica gel; Mobile phase, A: water (containing 0.05% NH$_4$HCO$_3$) and B: ACN (5% to 80% in 30 min)) to afford benzyl N-(2-chloro-5,6,7,8-tetrahydroquinazolin-6-yl)carbamate as a white solid. MS (ESI, m/z): 318, 320 [M+H]⁺.

Intermediate 58. tert-Butyl 4-(7-amino-5,6,7,8-tetrahydroisoquinolin-3-yl)piperazine-1-carboxylate

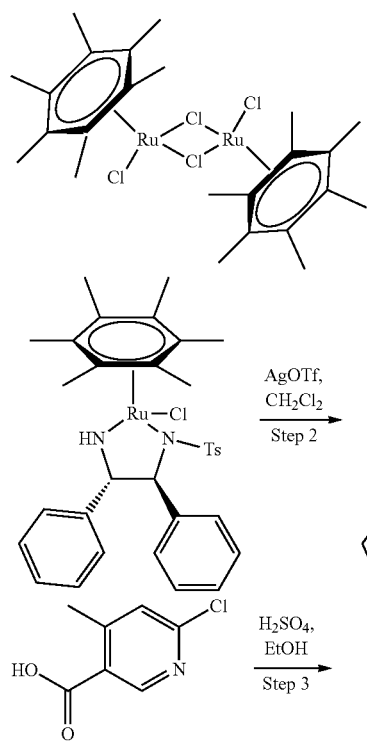

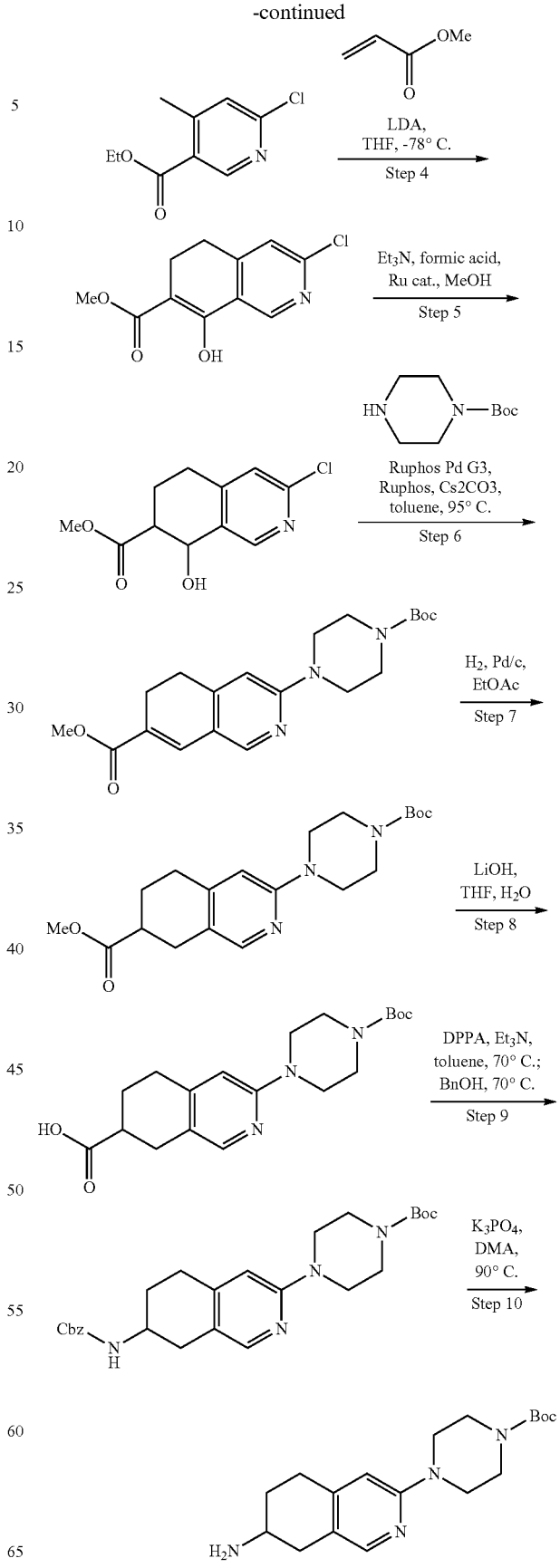

Step 1. RuCl-(S,S)-Ts-DPEN(hexamethylbenzene)

A solution of N-[(1S,2S)-2-amino-1,2-diphenylethyl]-4-methylbenzene-1-sulfonamide (S,S-Ts-DPEN) (1.09 g, 3.00 mmol), Et$_3$N (0.90 mL, 6.47 mmol), and [RuCl$_2$(hexamethylbenzene)]$_2$ (1.00 g, 1.50 mmol) in DCM (40 mL) was stirred for 5 h at 25° C. The resulting mixture was concentrated under vacuum. The residue was purified by silica gel chromatography (eluting with 1:10 MeOH/DCM) to afford RuCl-(S,S)-Ts-DPEN(hexamethylbenzene) as a red solid.

Step 2
RuCl-(S,S)-Ts-DPEN-OTf(hexamethylbenzene)

A solution of RuCl-(S,S)-Ts-DPEN(hexamethylbenzene) (1.95 g, 2.99 mmol) and silver trifluoromethanesulfonate (0.800 g, 3.17 mmol) in DCM (50 mL) was stirred for 6 h at 25° C. The solids were filtered out. The filtrate was concentrated under vacuum to afford RuCl-(S,S)-Ts-DPEN-OTf(hexamethylbenzene) as a brown solid.

Step 3. Ethyl 6-chloro-4-methylpyridine-3-carboxylate

Sulfuric acid (15.6 mL, 306 mmol) was added into a solution of 6-chloro-4-methylpyridine-3-carboxylic acid (10.0 g, 58.3 mmol) in EtOH (250 mL). The resulting solution was stirred for 48 h at 25° C. A saturated solution of NaHCO$_3$ in water (500 mL) was added to the reaction. Then EtOH was evaporated out. The residue was extracted with DCM (2×500 mL). The organic layers were combined, dried over anhydrous sodium sulfate, filtered and concentrated under vacuum. The residue was purified by silica gel chromatography (eluting with 1:15 ethyl acetate/pet. ether) to give ethyl 6-chloro-4-methylpyridine-3-carboxylate as a white solid. MS (ESI, m/z): 200, 202 [M+H]$^-$.

Step 4. Methyl 3-chloro-8-hydroxy-5,6-dihydroisoquinoline-7-carboxylate

A solution of LDA (12.5 mL, 2M in THF) was added to a solution of ethyl 6-chloro-4-methylpyridine-3-carboxylate (2.00 g, 10.0 mmol) in THF (100 mL) at −78° C. The resulting solution was stirred for 1 h at −78° C. Then methyl prop-2-enoate (2.25 mL, 24.9 mmol) was added and the reaction was stirred for 1 h at −78° C. The reaction was then quenched with water (50 mL). THF was removed in vacuo. The aqueous layer was extracted with DCM (3×50 mL). The organic layers were combined, dried over anhydrous sodium sulfate, filtered and concentrated under vacuum. The residue was purified by silica gel chromatography (eluting with 1:10 ethyl acetate/pet. ether) to give methyl 3-chloro-8-hydroxy-5,6-dihydroisoquinoline-7-carboxylate as a white solid. MS (ESI, m/z): 240, 242 [M+H]$^+$.

Step 5. Methyl 3-chloro-8-hydroxy-5,6,7,8-tetrahydroisoquinoline-7-carboxylate Et$_3$N (7.62 mL, 54.8 mmol) was added to a solution of formic acid (1.89 mL, 50.1 mmol) in MeOH (90 mL) at 0° C. Then methyl 3-chloro-8-hydroxy-5,6-dihydroisoquinoline-7-carboxylate (3.00 g, 12.5 mmol) and RuCl-(S,S)-Ts-DPEN-OTf(hexamethylbenzene) (82 mg, 0.099 mmol) was added. The resulting solution was stirred for 16 h at 25° C. The reaction was then poured into water (200 mL). The solvent was removed in vacuo. The aqueous layer was extracted with DCM (3×150 mL). The organic layers were combined, dried over anhydrous sodium sulfate, filtered and concentrated under vacuum. The residue was purified by silica gel chromatography (eluting with 1:5 ethyl acetate/pet. ether) to give methyl 3-chloro-8-hydroxy-5,6,7,8-tetrahydroisoquinoline-7-carboxylate as a white solid. MS (ESI, m/z): 242, 244 [M+H]$^-$.

Step 6. Methyl 3-[4-[(tert-butoxy)carbonyl]piperazin-1-yl]-5,6-dihydroisoquinoline-7-carboxylate A mixture of methyl 3-chloro-8-hydroxy-5,6,7,8-tetrahydroisoquinoline-7-carboxylate (0.500 g, 2.07 mmol), tert-butyl piperazine-1-carboxylate (0.750 g, 4.03 mmol), RuPhos Pd G3 (100 mg, 0.120 mmol), RuPhos (62.0 mg, 0.140 mmol) and Cs$_2$CO$_3$ (2.00 g, 6.16 mmol) in toluene (10 mL) was stirred for 16 h at 95° C. Four batches of this reaction was set up in parallel. After cooling to room temperature, the four batches of reaction mixture were poured into water (100 mL). The resulting mixture was extracted with acyl acetate (3×100 mL). The organic layers were combined, dried over anhydrous sodium sulfate, filtered and concentrated under vacuum. The residue was purified by silica gel chromatography (eluting with 1:4 ethyl acetate/pet. ether) to give methyl 3-[4-[(tert-butoxy)carbonyl]piperazin-1-yl]-5,6-dihydroisoquinoline-7-carboxylate as a white solid). MS (ESI, m/z): 374 [M+H]$^+$.

Step 7. Methyl 3-[4-[(tert-butoxy)carbonyl]piperazin-1-yl]-5,6-dihydroisoquinoline-7-carboxylate A mixture of methyl 3-[4-[(tert-butoxy)carbonyl]piperazin-1-yl]-5,6-dihydroisoquinoline-7-carboxylate (550 mg, 1.47 mmol) and Palladium on carbon (500 mg, 10%) in ethyl acetate (20 mL) was stirred for 3 h at 25° C. under hydrogen atmosphere (balloon). The solids were filtered out. The filtrate was concentrated under vacuum to give methyl 3-[4-[(tert-butoxy)carbonyl]piperazin-1-yl]-5,6,7,8-tetrahydroisoquinoline-7-carboxylate as a white solid. MS (ESI, m/z): 376 [M+H]$^+$.

Step 8. 3-[4-[(tert-Butoxy)carbonyl]piperazin-1-yl]-5,6,7,8-tetrahydroisoquinoline-7-carboxylic acid A solution of LiOH (200 mg, 8.35 mmol) in water (20 mL) was added to a solution of methyl 3-[$^4$-[(tert-butoxy)carbonyl]piperazin-1-yl]-5,6,7,8-tetrahydroisoquinoline-7-carboxylate (500 mg, 1.33 mmol) in THF (20 mL). The resulting solution was stirred for 2 h at 25° C. The resulting solution was concentrated under vacuum. The residue was purified via reverse phase chromatography (Column: X Bridge C18, 19×150 mm, 5 um; Mobile phase, A: water (containing 0.05% TFA) and B: ACN (0% to 30% in 25 mm)). The collected fraction was concentrated under vacuum to give 3-[4-[(tert-butoxy)carbonyl]piperazin-1-yl]-5,6,7,8-tetrahydroisoquinoline-7-carboxylic acid as a white solid. MS (ESI, m/z): 362 [M+H]$^+$.

Step 9. tert-Butyl 4-(7-[[(benzyloxy)carbonyl]amino]-5,6,7,8-tetrahydroisoquinolin-3-yl)piperazine-1-carboxylate A solution of 3-[4-[(tert-butoxy)carbonyl]piperazin-1-yl]-5,6,7,8-tetrahydroisoquinoline-7-carboxylic acid (400 mg, 1.11 mmol), DPPA (476 mL, 2.20 mmol) and Et$_3$N (0.460 mL, 3.72 mmol) in toluene (6 mL) was stirred for 2 h at 25° C. and then 2 h at 70° C. Then benzyl alcohol (1.14 mL, 11.0 mmol) was added. The resulting solution was stirred for 2 h at 70° C. After cooling to room temperature, the reaction was then poured into water (30 mL). The resulting mixture was extracted with acyl acetate (3×20 mL). The organic layers were combined, dried over anhydrous sodium sulfate, filtered and concentrated under vacuum. The residue was purified by silica gel chromatography (eluting with 1:1 ethyl acetate/pet. ether) to give tert-butyl 4-(7-[[(benzyloxy)carbonyl]amino]-5,6,7,8-tetrahydroisoquinolin-3-yl)piperazine-1-carboxylate as colorless oil. MS (ESI, m/z): 467 [M+H]+.

Step 10. tert-Butyl 4-(7-amino-5,6,7,8-tetrahydroisoquinolin-3-yl)piperazine-1-carboxylate A mixture of tert-butyl 4-(7-[[(benzyloxy)carbonyl]amino]-5,6,7,8-tetrahydroisoquinolin-3-yl)piperazine-1-carboxylate (200 mg, 0.430 mmol) and K₃PO₄ (228 mg, 1.07 mmol) in DMA (5 mL) was stirred for 1 h at 90° C. After cooling to room temperature, the residue was purified via reverse phase chromatography (Column: X Bridge C18, 19×150 mm, 5 um; Mobile Phase, A: water (containing 10 mmol/L NH₄HCO₃) and B: ACN (10% to 50% in 30 min)). The collected fraction was concentrated under vacuum to give tert-butyl 4-(7-amino-5,6,7,8-tetrahydroisoquinolin-3-1)piperazine-1-carboxylate as a white solid. MS (ESI, m/z): 333 [M+H]+.

Intermediate 59. tert-Butyl N-[1,4-dioxa-7-azaspiro[4.4]nonan-9-yl]carbamate

Step 1. 7-Benzyl 9-(2-hydroxyethyl) 1,4-dioxa-7-azaspiro[4.4]nonane-7,9-dicarboxylate A mixture of 1-benzyl 3-ethyl 4-oxopyrrolidine-1,3-dicarboxylate (5.00 g, 17.2 mmol), ethane-1,2-diol (3.20 g, 51.5 mmol), and PTSA (296 mg, 1.72 mmol) in toluene (100 mL) was stirred for 3 h at 110° C. with a Dean-Stark tube. The mixture was cooled to 27° C. and concentrated under vacuum. The residue was purified by reverse phase chromatography (Column: C18 silica gel; Mobile phase, A: water (containing 0.05% TFA) and B: ACN (5% to 55% in 20 min)) to afford 7-benzyl 9-(2-hydroxyethyl) 1,4-dioxa-7-azaspiro[4.4]nonane-7,9-dicarboxylate as yellow oil. MS (ESI, m/z): 352 [M+H]+.

Step 2. 7-[(Benzyloxy)carbonyl]-1,4-dioxa-7-azaspiro[4.4]nonane-9-carboxylic acid A mixture of 7-benzyl 9-(2-hydroxyethyl) 1,4-dioxa-7-azaspiro[4.4]nonane-7,9-dicarboxylate (2.80 g, 7.96 mmol) and sodium hydroxide (199 mg, 4.98 mmol) in MeOH (40 mL), THF (40 mL) and H₂O (40 mL) was stirred for 2 h at 28° C. THF and MeOH were removed under vacuum. The resulting mixture was acidified to pH 7-8 with HCl (1M), and then concentrated under vacuum. The residue was purified by reverse phase chromatography (Column: C18 silica gel; Mobile phase, A: water (containing 0.05% TFA) and B: ACN (5% to 30% in 20 min)) to afford 7-[(benzyloxy)carbonyl]-1,4-dioxa-7-azaspiro[4.4]nonane-9-carboxylic acid as yellow oil. MS (ESI, m/z): 308 [M+H]+.

Step 3. Benzyl 9-[[(tert-butoxy)carbonyl]amino]-1,4-dioxa-7-azaspiro[4.4]nonane-7-carboxylate DPPA (632 mg, 2.30 mmol) was added to a stirring solution of 7-[(benzyloxy)carbonyl]-1,4-dioxa-7-azaspiro[4.4]nonane-9-carboxylic acid (600 mg, 1.91 mmol) and Et₃N (0.398 mL, 2.87 mmol) in t-BuOH (10 mL) at 0° C. The resulting mixture was stirred for 2 h at 90° C. The mixture was allowed to cool. The resulting mixture was concentrated under vacuum. The mixture was purified by reverse phase chromatography (Column: C18 silica gel; Mobile phase, A: H₂O (containing 10 mmol/L NH₄HCO₃) and B: ACN (0% to 60% over 30 min)) to afford benzyl 9-[[(tert-butoxy)carbonyl]amino]-1,4-dioxa-7-azaspiro[4.4]nonane-7-carboxylate as a yellow oil. MS (ESI, mi): 379 [M+H]+.

Step 4. tert-Butyl N-[1,4-dioxa-7-azaspiro[4.4]nonan-9-yl]carbamate

A mixture of benzyl 9-[[(tert-butoxy)carbonyl]amino]-1,4-dioxa-7-azaspiro[4.4]nonane-7-carboxylate (200 mg, 0.518 mmol) and Pd/C (200 mg, 10%) in EtOAc (5 mL) was stirred for 2 h at 25° C. under hydrogen atmosphere. The resulting mixture was filtered, and the filter cake was washed with ethyl acetate (3×5 mL). The filtrate was concentrated under reduced pressure to afford tert-butyl N-[1,4-dioxa-7-azaspiro[4.4]nonan-9-yl]carbamate as a brown. MS (ESI, m/z): 245 [M+H]+.

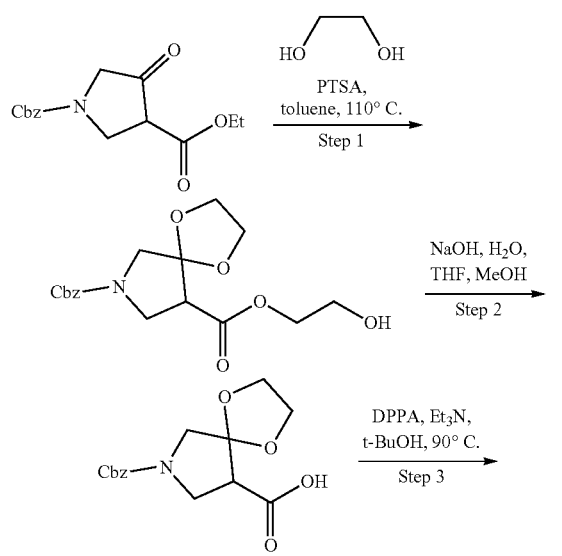

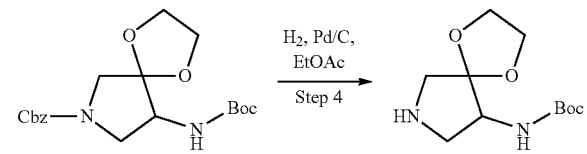

SYNTHETIC EXAMPLES OF COMPOUNDS OF FORMULA (I)

Example 1-1. (R)-3-Amino-6-methyl-N-(7-(piperazin-1-yl)chroman-3-yl)thieno[2,3-b]pyridine-2-carboxamide and Example 1-2. (S)-3-Amino-6-methyl-N-(7-(piperazin-1-yl)chroman-3-yl)thieno[2,3-b]pyridine-2-carboxamide

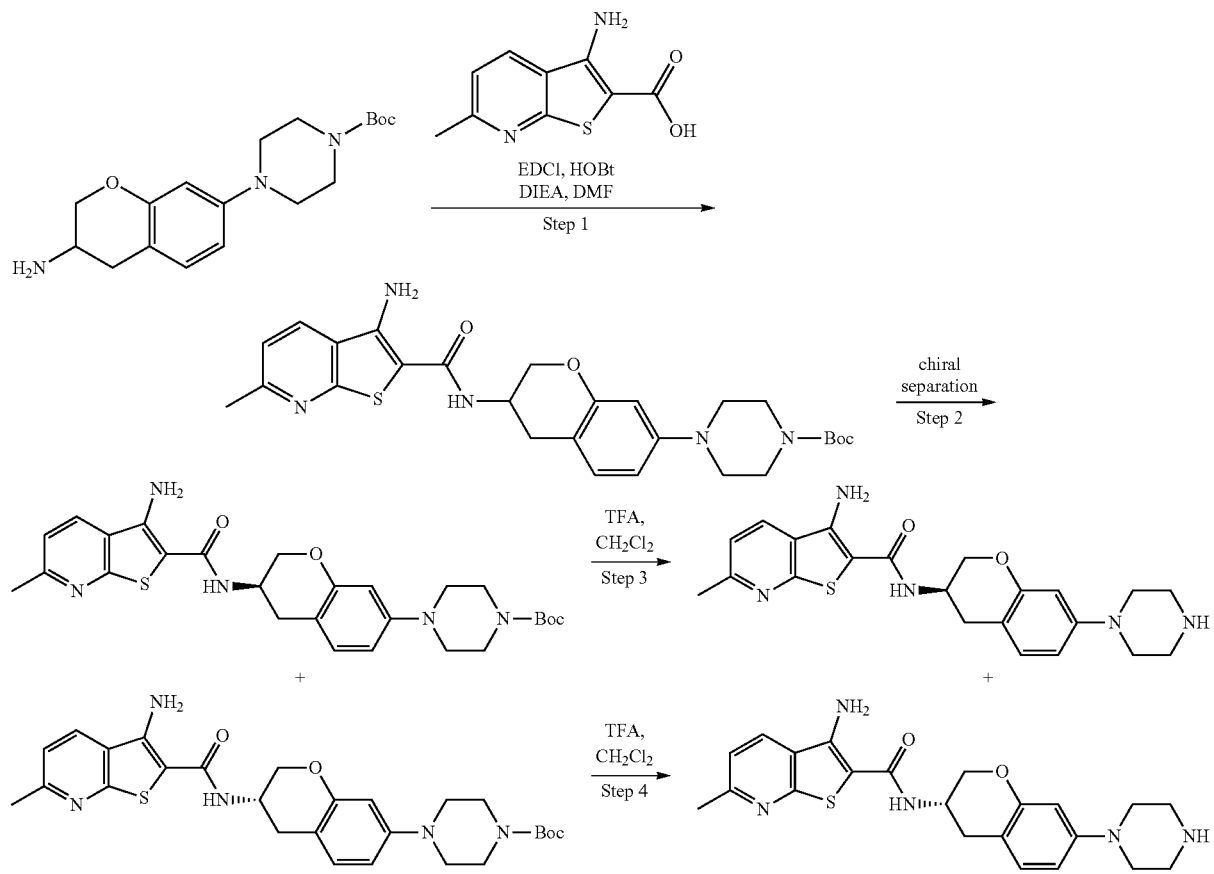

Step 1. tert-Butyl 4-(3-(3-amino-6-methylthieno[2,3-b]pyridine-2-carboxamido)chroman-7-yl)piperazine-1-carboxylate A solution of tert-butyl 4-(3-aminochroman-7-yl)piperazine-1-carboxylate, Intermediate 12, (130 mg, 0.27 mmol), EDCI (81 mg, 0.42 mmol), HOBt (57 mg, 0.42 mmol), DIEA (108 mg, 0.84 mmol), 3-amino-6-methylthieno[2,3-b]pyridine-2-carboxylic acid (58 mg, 0.28 mmol) in DMF (5 mL) was stirred for 18 h at room temperature. The reaction was quenched with 20 mL of water and was extracted with EtOAc (50 mL×3). The combined organic layers were washed with brine (30 mL×2), dried over anhydrous Na2SO4, filtered, and concentrated under vacuum. Purification by prep-HPLC (Column: XBridge Prep C18 OBD, 19×50 mm, 5 μm; Mobile phase A: water (10 mM NH$_4$HCO$_3$), B: ACN; Gradient: 40% B to 60% B in 13 min) afforded tert-butyl 4-(3-(3-amino-6-methylthieno[2,3-b]pyridine-2-carboxamido)chroman-7-yl)piperazine-1-carboxylate.

Step 2. tert-Butyl (R)-4-(3-(3-amino-6-methylthieno[2,3-b]pyridine-2-carboxamido)chroman-7-yl)piperazine-1-carboxylate and tert-Butyl (S)-4-(3-(3-amino-6-methylthieno[2,3-b]pyridine-2-carboxamido)chroman-7-yl)piperazine-1-carboxylate The racemic mixture of tert-butyl 4-(3-(3-amino-6-methylthieno[2,3-b]pyridine-2-carboxamido)chroman-7-yl)piperazine-1-carboxylate was separated by chiral HPLC (Column: Lux cellulose-4, 0.46×5 cm, 3 μm; Mobile phase: hexanes (0.1% Et$_2$NH):EtOH=60:40 in 6 min) to afford the title compounds as follows: tert-butyl (R)-4-(3-(3-amino-6-methylthieno[2,3-b]pyridine-2-carboxamido)chroman-7-yl)piperazine-1-carboxylate as a yellow solid (first eluting isomer, RT=3.87 min, stereochemistry assumed) and tert-butyl (S)-4-(3-(3-amino-6-methylthieno[2,3-b]pyridine-2-carboxamido)chroman-7-yl)piperazine-1-carboxylate as a yellow solid (second eluting isomer, RT=4.74 min, stereochemistry assumed).

Step 3. (R)-3-Amino-6-methyl-N-(7-(piperazin-1-yl)chroman-3-yl)thieno[2,3-b]pyridine-2-carboxamide A solution of (R)-4-(3-(3-amino-6-methylthieno[2,3-b]pyridine-2-carboxamido)chroman-7-yl)piperazine-1-carboxylate (6 mg, 0.01 mmol) and TFA (0.5 mL) in CH$_2$Cl$_2$ (2 mL) was stirred for 1 h at room temperature. The resulting mixture was concentrated under vacuum. The residue was purified by prep-HPLC (Column: XBridge Prep C$_{18}$ OBD, 19×50 mm, 5 μm; Mobile phase A: water (10 mM $NH_4HCO_3$), B: ACN; Gradient: 5% B to 30% B in 13 min) to give (R)-3-amino-6-methyl-N-(7-(piperazin-1-yl)chroman-3-yl)thieno[2,3-b]pyridine-2-carboxamide as a yellow solid. $^1$H NMR (CD$_3$OD, 400 MHz) δ(ppm): 8.18 (d, J=8.0 Hz, 1H), 7.28 (d, J=8.4 Hz, 1H), 6.95 (d, J=8.4 Hz, 1H), 6.54-6.56 (m, 1H), 6.41 (d, J=2.4 Hz, 1H), 4.40-4.47 (m, 1H), 4.21-4.24 (m, 1H), 3.88-3.93 (m, 1H), 3.07-3.12 (m, 4H), 2.95-3.02 (m, 5H), 2.82-2.88 (m, 1H), 2.62 (s, 3H). MS: (ESI, m/z): 424 [M+H]$^-$.

Step 4. (S)-3-Amino-6-methyl-N-(7-(piperazin-1-yl) chroman-3-yl)thieno[2,3-b]pyridine-2-carboxamide A procedure similar to Step 3 was applied to (S)-4-(3-(3-amino-6-methylthieno[2,3-b]pyridine-2-carboxamido)chroman-7-yl)piperazine-1-carboxylate (8 mg, 0.02 mmol) to afford (S)-3-amino-6-methyl-N-(7-(piperazin-1-yl)chroman-3-yl)thieno[2,3-b]pyridine-2-carboxamide as a white solid. H NMR (CD$_3$OD, 300 MHz) δ(ppm): 8.18 (d, J=8.4 Hz, 1H), 7.28 (d, J=8.7 Hz, 1H), 6.96 (d, J=8.7 Hz, 1H), 6.54-6.58 (m, 1H), 6.41 (d, J=2.1 Hz, 1H), 4.39-4.86 (m, 1H), 4.22-4.25 (m, 1H), 3.88-3.96 (m, 1H), 3.04-3.10 (m, 5H), 2.89-3.02 (m, 4H), 2.81-2.87 (m, 1H), 2.63 (s, 3H). MS: (ESI, m/z): 424 [M+H]$^+$.

The following examples in Table 9 were prepared using standard chemical manipulations and procedures similar to those used for the preparation of Examples 1-1 and 1-2.

TABLE 9

| Example Number | Structure and Compound Name | LRMS m/z [M + H]$^+$ | $^1$H NMR |
|---|---|---|---|
| 1-37[15] | 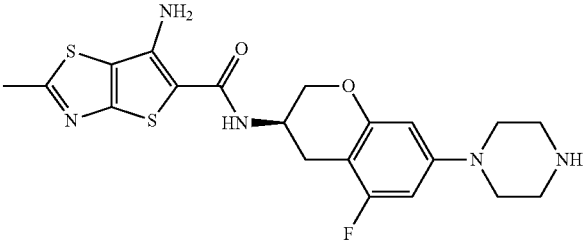 [SMILES: Cc1nc2sc(C(=O)N[C@H]3COc4cc(N5CCNCC5)cc(F)c4C3)c(N)c2s1]<br>(R)-6-amino-N-(5-fluoro-7-(piperazin-1-yl)chroman-3-yl)-2-methylthieno[2,3-d]thiazole-5-carboxamide | 448 | (CD$_3$OD, 300 MHz) δ (ppm): 6.33 (dd, J = 2.4, 12.6 Hz, 1H), 6.24 (s, 1H), 4.40-4.20 (m, 1H), 4.43-4.36 (m, 1H), 4.25-4.21 (m, 1H), 3.93-3.86 (m, 1H), 3.12-3.10 (m, 4H), 3.03-2.96 (m, 5H), 2.81 (s, 3H), 2.75-2.66 (m, 1H). |
| 1-38[15] | 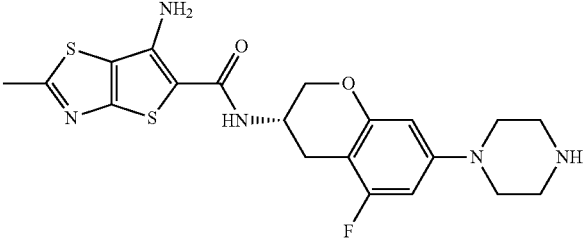 [SMILES: Cc1nc2sc(C(=O)N[C@@H]3COc4cc(N5CCNCC5)cc(F)c4C3)c(N)c2s1]<br>(S)-6-amino-N-(5-fluoro-7-(piperazin-1-yl)chroman-3-yl)-2-methylthieno[2,3-d]thiazole-5-carboxamide | 448 | (CD$_3$OD, 300 MHz) δ (ppm): 6.34 (dd, J = 2.4, 12.6 Hz, 1H), 6.24 (s, 1H), 4.40-4.20 (m, 1H), 4.43-4.36 (m, 1H), 4.25-4.21 (m, 1H), 3.93-3.86 (m, 1H), 3.12-3.10 (m, 4H), 3.03-2.96 (m, 5H), 2.81 (s, 3H), 2.75-2.66 (m, 1H). |
| 1-39[16] | 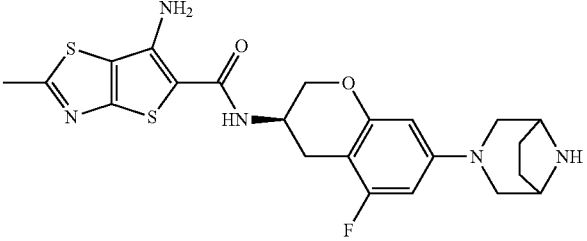 [SMILES: Cc1nc2sc(C(=O)N[C@H]3COc4cc(N5CC6CCC(C5)N6)cc(F)c4C3)c(N)c2s1]<br>N-((3R)-7-(3,8-diazabicyclo[3.2.1]octan-3-yl)-5-fluorochroman-3-yl)-6-amino-2-methylthieno[2,3-d]thiazole-5-carboxamide | 474 | (CD$_3$OD, 300 MHz) δ (ppm): 6.22 (dd, J = 2.4, 12.9 Hz, 1H), 6.12 (s, 1H), 4.40-4.37 (m, 1H), 4.23-4.18 (m, 1H), 3.91-3.85 (m, 1H), 3.64-3.62 (m, 2H), 3.42-3.31 (m, 2H), 3.11-2.65 (m, 7H), 1.87-1.85 (m, 4H). |

TABLE 9-continued

| Example Number | Structure and Compound Name | LRMS m/z [M + H]+ | 1H NMR |
|---|---|---|---|
| 1-40[16] | N-((3S)-7-(3,8-diazabicyclo[3.2.1]octan-3-yl)-5-fluorochroman-3-yl)-6-amino-2-methylthieno[2,3-d]thiazole-5-carboxamide | 474 | (CD$_3$OD, 300 MHz) δ (ppm): 6.21 (dd, J = 2.4, 12.9 Hz, 1H), 6.11 (s, 1H), 4.40-4.37 (m, 1H), 4.23-4.18 (m, 1H), 3.91-3.85 (m, 1H), 3.64-3.62 (m, 2H), 3.32-3.31 (m, 2H), 3.11-2.65 (m, 7H), 1.87-1.85 (m, 4H). |
| 1-41[17] | N-((3S)-7-(3,6-diazabicyclo[3.1.1]heptan-3-yl)-5-fluorochroman-3-yl)-3-amino-6-methylthieno[2,3-b]pyridine-2-carboxamide | 454 | (DMSO-d$_6$, 300 MHz) δ (ppm): 8.33 (d, J = 8.7 Hz, 1H). 7.56 (br s, 1H), 7.31 (d, J = 8.1 Hz, 1H), 7.23 (br s, 2H), 6.13 (dd, J = 2.1, 12.9 Hz, 1H), 5.96 (s, 1H), 4.34-4.25 (m, 1H), 4.19-4.15 (m, 1H), 3.87-3.81 (m, 1H), 3.67-3.64 (m, 2H), 3.41-3.32 (m, 4H), 2.90-2.73 (m, 2H), 2.70 (s, 3H), 1.69 (br s, 1H), 1.50-1.45 (m, 1H). |
| 1-42[17] | N-((3R)-7-(3,6-diazabicyclo[3.1.1]heptan-3-yl)-5-fluorochroman-3-yl)-3-amino-6-methylthieno[2,3-b]pyridine-2-carboxamide | 454 | (CD$_3$OD, 400 MHz) δ (ppm): 8.20 (d, J = 8.0 Hz, 1H). 7.30 (d, J = 8.4 Hz, 1H), 6.13 (dd, J = 2.4, 12.8 Hz, 1H), 6.06 (s, 1H), 4.45-4.40 (m, 1H), 4.25-4.21 (m, 1H), 3.95-3.87 (m, 3H), 3.55-3.49 (m, 4H), 3.01-2.96 (m, 1H), 2.77-2.70 (m, 2H), 2.65 (s, 3H), 1.68-1.67 (m, 1H). |

[15]Notes on procedures:

In step 1 the amine Intermediate 15-3 and the carboxylic acid Intermedate 24 were used. The enantiomers were separated by chiral HPLC using chiral column Chiral Art Cellulose-SB and mobile phase 10% IPA/MTBE to provide the precursor to Example 1-37 as the first eluting isomer and the precursor to Example 1-38 as the second eluting isomer.

[16]Notes on procedures:

In step 1, the carboxylic acid Intermediate 24 was used. The enantiomers were separated by chiral HPLC using chiral column Chiralpak ID-2 and mobile phase 40% EtOH/hexanes to provide the precursor to Example 1-39 as the first eluting isomer and the precursor to Example 1-40 as the second eluting isomer.

[17]Notes on procedures:

In step 1, the amine Intermediate 15-3 was used. The enantiomers were separated by chiral HPLC using chiral column Chiralpak IG and mobile phase 50% EtOH/hexanes to provide the precursor to Example 1-41 as the first eluting isomer and the precursor to Example 1-42 as the second eluting isomer.

Example 2-1. 3-Amino-N-((3R)-7-(9,9-difluoro-3,7-diazabicyclo[3.3.1]nonan-3-yl)chroman-3-yl)-6-methylthieno[2,3-b]pyridine-2-carboxamide

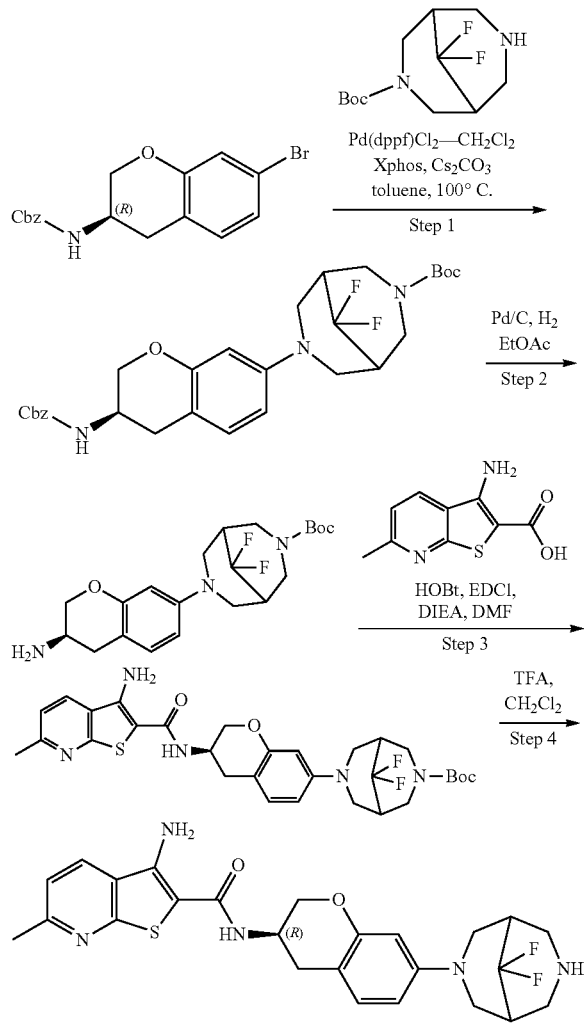

Step 1. tert-Butyl 7-((R)-3-(((benzyloxy)carbonyl)amino)chroman-7-yl)-9,9-difluoro-3,7-diazabicyclo[3.3.1]nonane-3-carboxylate A mixture of benzyl (R)-(7-bromochroman-3-yl)carbamate, Intermediate 2, (400 mg, 1.08 mmol), tert-butyl 9,9-difluoro-3,7-diazabicyclo[3.3.1]nonane-3-carboxylate, Intermediate 32, (288 mg, 1.06 mmol), Pd(dppf)Cl$_2$—CH$_2$Cl$_2$ (90 mg, 0.11 mmol), Xphos (105 mg, 0.22 mmol), and Cs$_2$CO$_3$ (1.076 g, 3.30 mmol) in toluene (40 mL) was stirred for 16 h at 100° C. After cooling to room temperature, the reaction was quenched with water (40 mL) and extracted with EtOAc (40 mL×3). The combined organic layers were dried over anhydrous sodium sulfate, filtered, and concentrated under vacuum. The residue was purified by silica gel chromatography (eluting with 1:4 EtOAc/pet. ether) to give tert-butyl 7-((R)-3-(((benzyloxy)carbonyl)amino)chroman-7-yl)-9,9-difluoro-3,7-diazabicyclo[3.3.1]nonane-3-carboxylate as a yellow oil. MS: (ESI, m/z): 544 [M+H]$^+$.

Step 2. tert-Butyl 7-((R)-3-aminochroman-7-yl)-9,9-difluoro-3,7-diazabicyclo[3.3.1]nonane-3-carboxylate A mixture of tert-butyl 7-((R)-3-(((benzyloxy)carbonyl)amino)chroman-7-yl)-9,9-difluoro-3,7-diazabicyclo[3.3.1]nonane-3-carboxylate (110 mg, 0.19 mmol) and Pd/C (20 mg, 10%) in EtOAc (10 mL) was stirred for 2 h at 30° C. under an atmosphere of hydrogen. The solids were filtered away and the filtrate was concentrated under vacuum to afford tert-butyl 7-((R)-3-aminochroman-7-yl)-9,9-difluoro-3,7-diazabicyclo[3.3.1]nonane-3-carboxylate as a yellow solid. MS: (ESI, m/z): 410 [M+H]$^-$.

Step 3. tert-Butyl 7-((R)-3-(3-amino-6-methylthieno[2,3-b]pyridine-2-carboxamido)chroman-7-yl)-9,9-difluoro-3,7-diazabicyclo[3.3.1]nonane-3-carboxylate A solution of tert-butyl 7-((R)-3-aminochroman-7-yl)-9,9-difluoro-3,7-diazabicyclol[3.3.1]nonane-3-carboxylate (70 mg, 0.16 mmol), 3-amino-6-methylthieno[2,3-b]pyridine-2-carboxylic acid (43 mg, 0.20 mmol), HOBt (45 mg, 0.33 mmol), EDCI (65 mg, 0.34 mmol), and DIEA (66 mg, 0.51 mmol) in DMF (15 mL) was stirred for 16 h at room temperature. The reaction was quenched by the addition of 25 mL of water. The resulting mixture was extracted with EtOAc (30 mL×3). The organic layers were combined, dried over anhydrous sodium sulfate, filtered, and concentrated under vacuum. Purification by silica gel chromatography (eluting with 1:1 EtOAc/pet. ether) afforded tert-butyl 7-((R)-3-(3-amino-6-methylthieno[2,3-b]pyridine-2-carboxamido)chroman-7-yl)-9,9-difluoro-3,7-diazabicyclo[3.3.1]nonane-3-carboxylate as a yellow solid. MS: (ESI, m/z): 600 [M+H]$^-$.

Step 4. 3-Amino-N-((3R)-7-(9,9-difluoro-3,7-diazabicyclo[3.3.1]nonan-3-yl)chroman-3-yl)-6-methylthieno[2,3-b]pyridine-2-carboxamide A solution of tert-butyl 7-((R)-3-(3-amino-6-methylthieno[2,3-b]pyridine-2-carboxamido)chroman-7-yl)-9,9-difluoro-3,7-diazabicyclo[3.3.1]nonane-3-carboxylate (50 mg, 0.08 mmol) and TFA (1 mL) in CH$_2$Cl$_2$ (3 mL) was stirred for 1 h at room temperature. The resulting mixture was concentrated under vacuum. The residue was dissolved in NH$_3$ (7M in MeOH) (5 mL) and stirred for 1 h. The mixture was concentrated and the crude product was purified by prep-HPLC (Column: XBridge Prep C18 OBD, 19×250 mm, 5 μm; Mobile phase A: water (10 mM NH$_4$HCO$_3$), B: ACN; Gradient: 30% B to 50% B in 7 min) to afford 3-amino-N-((3R)-7-(9,9-difluoro-3,7-diazabicyclo[3.3.1]nonan-3-yl)chroman-3-yl)-6-methylthieno[2,3-b]pyridine-2-carboxamide as a yellow solid. $^1$H NMR (CD$_3$OD, 300 MHz) δ(ppm): 8.19 (d, J=8.1 Hz, 1H) 7.29 (d, J=8.4 Hz, 1H), 6.99 (d, J=8.4 Hz, H), 6.64 (dd, J=2.4, 8.4 (z, 1H), 6.48 (s, 1H), 4.41-4.48 (0, 1H), 4.21-4.25 (n, 1H), 3.82-3.96 (m, 3H), 3.35-3.37 (m, 2H), 3.13-3.19 (m, 4H), 2.80-2.98 (m, 2H), 2.63 (s, 3H), 2.15-2.18 (1 m, 2H). MS: (ESI, m/z): 500 [M+H]$^+$.

The following examples in Table 10 were prepared using standard chemical manipulations and procedures similar to those used for the preparation of Example 2-1.

TABLE 10

| Example Number | Structure and Compound Name | LRMS m/z [M + H]+ | 1H NMR |
|---|---|---|---|
| 2-34[27] | (S)-7-amino-3-methyl-N-(7-methyl-6-(piperazin-1-yl)-1,2,3,4-tetrahydronaphthalen-2-yl)thieno[2,3-b]pyrazine-6-carboxamide | 437 | (CDCl$_3$, 300 MHz) δ (ppm): 8.46 (s, 1H), 6.93 (s, 1H), 6.80 (s, 1H), 4.43-4.40 (m, 1H), 3.41-3.32 (m, 4H), 3.18-3.10 (m, 5H), 2.97-2.84 (m, 3H), 2.73-2.63 (m, 5H), 2.31-2.10 (m, 5H), 1.95-1.85 (m, 1H). |
| 2-35[27] | (R)-7-amino-3-methyl-N-(7-methyl-6-(piperazin-1-yl)-1,2,3,4-tetrahydronaphthalen-2-yl)thieno[2,3-b]pyrazine-6-carboxamide | 437 | (CDCl$_3$, 300 MHz) δ (ppm): 8.47 (s, 1H), 6.94 (s, 1H), 6.81 (s, 1H), 4.42-4.40 (m, 1H), 3.40-3.32 (m, 4H), 3.18-3.10 (m, 5H), 2.98-2.84 (m, 3H), 2.74-2.63 (m, 5H), 2.29-2.10 (m, 5H), 1.94-1.85 (m, 1H) |
| 2-36[27] | (S)-7-amino-3-methyl-N-(5-methyl-6-(piperazin-1-yl)-1,2,3,4-tetrahydronaphthalen-2-yl)thieno[2,3-b]pyrazine-6-carboxamide | 437 | (CD$_3$OD, 300 MHz) δ (ppm): 8.58 (s, 1H), 6.92 (s, 2H), 4.28-4.18 (m, 1H), 3.09-3.00 (m, 5H), 2.95-2.75 (m, 7H), 2.69 (s, 3H), 2.25-2.19 (m, 4H), 1.92-1.79 (m, 1H). |
| 2-37[27] | (R)-7-amino-3-methyl-N-(5-methyl-6-(piperazin-1-yl)-1,2,3,4-tetrahydronaphthalen-2-yl)thieno[2,3-b]pyrazine-6-carboxamide | 437 | (CD$_3$OD, 300 MHz) δ (ppm): 8.59 (s, 1H), 6.93 (s, 2H), 4.28-4.18 (m, 1H), 3.12-3.00 (m, 5H), 2.99-2.79 (m, 7H), 2.76 (s, 3H), 2.27-2.19 (m, 4H), 1.92-1.79 (m, 1H). |
| 2-38[28] | 3-amino-N-((R)-7-((3S,4S)-3-amino-4-(methoxy-d3)pyrrolidin-1-yl)chroman-3-yl)-6-methylthieno[2,3-b]pyridine-2-carboxamide | 457 | not determined |

[27]Notes on procedures:
In Step 1, the bromides Intermediates 11-2 thru 11-5 were used. Pd$_2$(dba)$_3$/Xphos was used as the catalyst/ligand system.

[28]Notes on procedures:
In Step 1, the amine Intermediates 49 was used. In the coupling reaction, Xphos Pd G3 was used as the catalyst system, Cs$_2$CO$_3$ as the base, and 1,4-dioxane as the solvent. In Step 3, the amide coupling was accomplished with HATU and Et$_3$N in DMA at 50° C. In Step 4, the boc-deprotection was accomplished with HCl in dioxane/EtOAc.

Example 3-1. 3-Amino-N-((R)-7-((3S,4S)-3-amino-4-methoxypyrrolidin-1-yl)chroman-3-yl)-6-methyl-thieno[2,3-b]pyridine-2-carboxamide and

Example 3-2. 3-Amino-N-((R)-7-((3R,4R)-3-amino-4-methoxypyrrolidin-1-yl)chroman-3-yl)-6-methyl-thieno[2,3-b]pyridine-2-carboxamide

Method 1

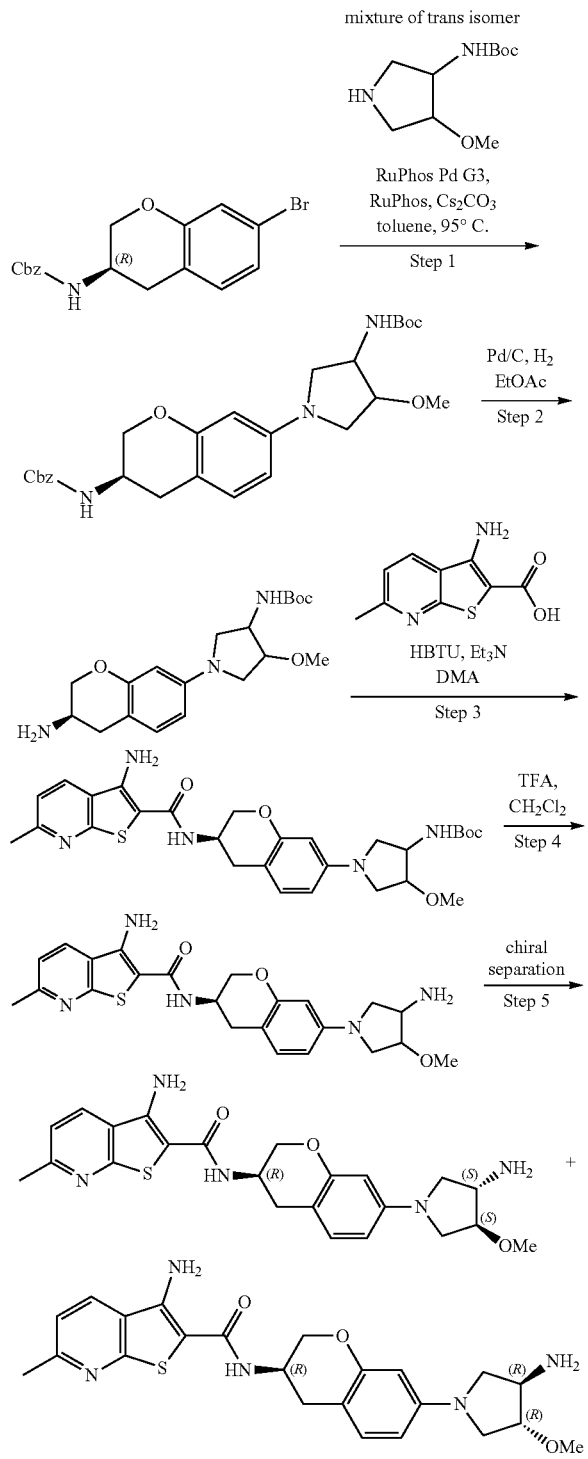

Step 1. Benzyl ((3R)-7-(3-((tert-butoxycarbonyl)amino)-4-methoxypyrrolidin-1-yl)chroman-3-yl)carbamate A mixture of benzyl (R)-(7-bromochroman-3-yl)carbamate, Intermediate 2, (170 mg, 0.47 mmol), tert-butyl N-(4-methoxypyrrolidin-3-yl)carbamate, Intermediate 35, (100 mg, 0.46 mmol), RuPhos Pd G3 (38 mg, 0.05 mmol), RuPhos (23 mg, 0.05 mmol), and Cs$_2$CO$_3$ (300 mg, 0.92 mmol) in toluene (10 mL) was stirred for 2 h at 95° C. After cooling to room temperature, the reaction was poured into water (20 mL). The resulting mixture was extracted with DCM (2×50 mL). The combined organic layers were dried over anhydrous sodium sulfate, filtered, and concentrated under vacuum. Purification by silica gel column (eluting with 1:1 EtOAc/pet. ether) afforded benzyl ((3R)-7-(3-((tert-butoxycarbonyl)amino)-4-methoxypyrrolidin-1-yl)chroman-3-yl)carbamate as a white solid. MS: (ESI, m/z): 498 [M+H]$^+$.

Step 2. tert-Butyl (1-((R)-3-aminochroman-7-yl)-4-methoxypyrrolidin-3-yl)carbamate A mixture of benzyl ((3R)-7-(3-((tert-butoxycarbonyl)amino)-4-methoxypyrrolidin-1-yl)chroman-3-yl)carbamate (80 mg, 0.16 mmol) and Pd/C (80 mg, 10%) in EtOAc (5 mL) was stirred for 3 h at room temperature under an atmosphere of hydrogen. The solids were filtered away and washed with EtOAc (10 mL×3). The filtrate was concentrated under vacuum to afford tert-butyl (1-((R)-3-aminochroman-7-yl)-4-methoxypyrrolidin-3-yl)carbamate as a colorless oil. MS: (ESI, m/z): 364 [M+H]$^+$.

Step 3. tert-Butyl (1-((R)-3-(3-amino-6-methylthieno[2,3-b]pyridine-2-carboxamido)chroman-7-yl)-4-methoxypyrrolidin-3-yl)carbamate A solution of tert-butyl (1-((R)-3-aminochroman-7-yl)-4-methoxypyrrolidin-3-yl)carbamate (40 mg, 0.11 mmol), 3-amino-6-methylthieno[2,3-b]pyridine-2-carboxylic acid (23 mg, 0.11 mmol), Et$_3$N (39 mg, 0.39 mmol), and HBTU (50 mg, 0.13 mmol) in DMA (2 mL) was stirred for 30 min at room temperature. Purification by reverse phase chromatography (Column: C18 silica gel; Mobile phase A: water (10 mM NH$_4$HCO$_3$), B: ACN; Gradient: 10% to 80% B over 10 min) afforded tert-butyl (1-((R)-3-(3-amino-6-methylthieno[2,3-b]pyridine-2-carboxamido)chroman-7-yl)-4-methoxypyrrolidin-3-yl)carbamate as a white solid. MS: (ESI, m/z): 554 [M+H]$^+$.

Step 4. 3-Amino-N-((3R)-7-(3-amino-4-methoxypyrrolidin-1-yl)chroman-3-yl)-6-methylthieno[2,3-b]pyridine-2-carboxamide A solution of tert-butyl (1-((R)-3-(3-amino-6-methylthieno[2,3-b]pyridine-2-carboxamido)chroman-7-yl)-4-methoxypyrrolidin-3-yl)carbamate (45 mg, 0.08 mmol) and TFA (1 mL) in CH$_2$Cl$_2$ (3 mL) was stirred for 30 min at room temperature. The resulting mixture was concentrated under vacuum. The crude product was purified by reverse phase chromatography (Column: C18 silica gel; Mobile phase A: water (10 mM NH$_4$HCO$_3$), B: ACN; Gradient: 10% to 80% B over 10 min) to afford 3-amino-N-((3R)-7-(3-amino-4-methoxypyrrolidin-1-yl)chroman-3-yl)-6-methylthieno[2,3-b]pyridine-2-carboxamide as a colorless oil. MS: (ESI, m/z): 454 [M+H]$^-$.

Step 5. Amino-N-((R)-7-((3S,4S)-3-amino-4-methoxypyrrolidin-1-yl)chroman-3-yl)-6-methylthieno[2,3-b]pyridine-2-carboxamide and 3-Amino-N-((R)-7-((3R,4R)-3-amino-4-methoxypyrrolidin-1-yl)chroman-3-yl)-6-methylthieno[2,3-b]pyridine-2-carboxamide The racemic mixture of 3-amino-N-((3R)-7-(3-amino-4-methoxypyrrolidin-1-yl)chroman-3-yl)-6-methylthieno[2,3- b]pyridine-2-carboxamide (35 mg, 0.077 mmol) was separated by chiral HPLC (Column: Chiralpak IE, 2×25 cm, 5 μm; Mobile phase: 50% EtOH/MTBE (0.1% Et$_2$NH) for 28 min; Flow rate: 16 mL/min) to afford the title compounds as follows: Amino-N-((R)-7-((3S,4S)-3-amino-4-methoxypyrrolidin-1-yl)chroman-3-yl)-6-methylthieno[2,3-b]pyridine-2-carboxamide as a yellow solid (first eluting isomer, RT=13.5 min). $^1$H NMR (DMSO-d$_6$, 300 MHz) δ(ppm): 8.32 (d, J=8.4 Hz, 1H). 7.49 (br s, 1H), 7.31 (d, J=8.1 Hz, JH), 7.21 (br s, 2H), 6.87 (d, J=8.4 Hz, 1H), 6.12-6.08 (br s, 1H), 5.91 (s, 1H), 4.31-4.21 (m, 1H), 4.16-4.11 (m, 1H), 3.79 (t, J=9.9 Hz, 1H), 3.63-3.62 (m, 1H), 3.51-3.46 (m, 1H), 3.42-3.32 (m, 2H), 2.93 (s, 3H), 3.13-3.09 (m, 1H), 2.91-2.82 (m, 3H), 2.58 (s, 3H), 2.12-1.96 (m, 2H). MS: (ESI, m/z): 454 [M+H]$^+$; and amino-N-((R)-7-((3R,4R)-3-amino-4-methoxypyrrolidin-1-yl)chroman-3-yl)-6-methylthieno[2,3-b]pyridine-2-carboxamide as a yellow solid (second eluting isomer, RT=20.2 min). $^1$H NMR (DMSO-d$_6$, 300 MHz) δ(ppm): 8.32 (d, J=8.1 Hz, 1H). 7.49 (br s, 1H), 7.31 (d, J=8.1 Hz, 1H), 7.21 (br s, 2H), 6.86 (d, J=8.4 Hz, 1H), 6.11-6.08 (br s, 1H), 5.91 (s, 1H), 4.31-4.21 (m, 1H), 4.16-4.11 (m, 1H), 3.79 (t, J=9.9 Hz, 1H), 3.63-3.62 (m, 1H), 3.51-3.46 (m, 1H), 3.42-3.32 (m, 2H), 2.93 (s, 3H), 3.13-3.09 (m, 1H), 2.91-2.81 (m, 3H), 2.58 (s, 3H), 2.12-1.96 (m, 2H).MS: (ESI, m/z): 454 [M+H]$^+$.

Example 3-1. 3-Amino-N-((R)-7-((3S,4S)-3-amino-4-methoxypyrrolidin-1-yl)chroman-3-yl)-6-methylthieno[2,3-b]pyridine-2-carboxamide Method 2.

Amino-N-((R)-7-((3S,4S)-3-amino-4-methoxypyrrolidin-1-yl)chroman-3-yl)-6-methylthieno[2,3-b]pyridine-2-carboxamide can also be prepared from tert-butyl ((3S,4S)-4-methoxypyrrolidin-3-yl)carbamate, Intermediate 36, using procedures similar to Method 1, without need for the Step 5 chiral separation.

The following examples in Table 11 were prepared using standard chemical manipulations and procedures similar to Method I for the preparation of Examples 3-1 and 3-2.

TABLE 11

| Example Number | Structure and Compound Name | LRMS m/z [M + H]$^+$ | $^1$H NMR |
|---|---|---|---|
| 3-17[8] | 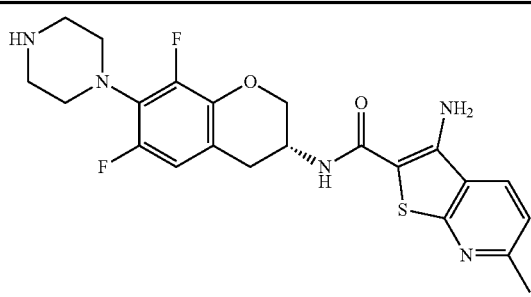<br>3-amino-N-[(3R)-6,8-difluoro-7-(piperazin-1-yl)-3,4-dihydro-2H-1-benzopyran-3-yl]-6-methylthieno[2,3-b]pyridine-2-carboxamide | 460 | (DMSO-d$_6$, 400 MHz) δ (ppm): 8.33 (d, J = 8.4 Hz, 1H), 7.63 (d, J = 7.6 Hz, 1H), 7.31 (d, J = 8.0 Hz, 1H), 7.24 (br s, 2H), 6.80 (d, J = 11.2 Hz, 1H), 4.43-4.29 (m, 1H), 4.25-4.22 (m, 1H), 3.90-3.85 (m, 1H), 2.99-2.92 (m, 6H), 2.78-2.76 (m, 4H), 2.58 (s, 3H). |
| 3-18[8] | 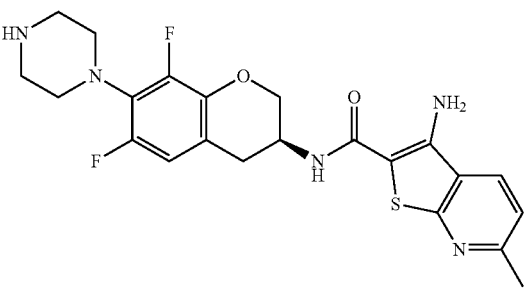 [SMILES: Cc1ccc2c(N)c(C(=O)N[C@@H]3COc4c(cc(F)c(N5CCNCC5)c4F)C3)sc2n1]<br>3-amino-N-[(3S)-6,8-difluoro-7-(piperazin-1-yl)-3,4-dihydro-2H-1-benzopyran-3-yl]-6-methylthieno[2,3-b]pyridine-2-carboxamide | 460 | (DMSO-d$_6$, 400 MHz) δ (ppm): 8.33 (d, J = 8.0 Hz, 1H), 7.62 (d, J = 7.6 Hz, 1H), 7.31 (d, J = 8.4 Hz, 1H), 7.23 (br s, 2H), 6.81 (d, J = 10.8 Hz, 1H), 4.36-4.28 (m, 1H), 4.26-4.22 (m, 1H), 3.91-3.86 (m, 1H), 3.09-3.03 (m, 4H), 2.95-2.88 (m, 2H), 2.84-2.82 (m, 4H), 2.58 (s, 3H). |

[8]Notes on procedures:
In Step 1, the bromide Intermediate 50 was used. The coupling reaction was accomplished using the precatalyst tBuXphos Pd G3 and the phosphazene base P$_2$-Et in DMSO at 25° C. In Step 5, chiral separation was performed with the chiral column Chiralpak IC and mobile phase 50% EtOH/hexanes (0.1% Et$_2$NH).

Example 6-1. (R)-1-(3-(3-Amino-6-methylthieno[2,3-b]pyridine-2-carboxamido)chroman-7-yl)piperidine-4-carboxylic acid

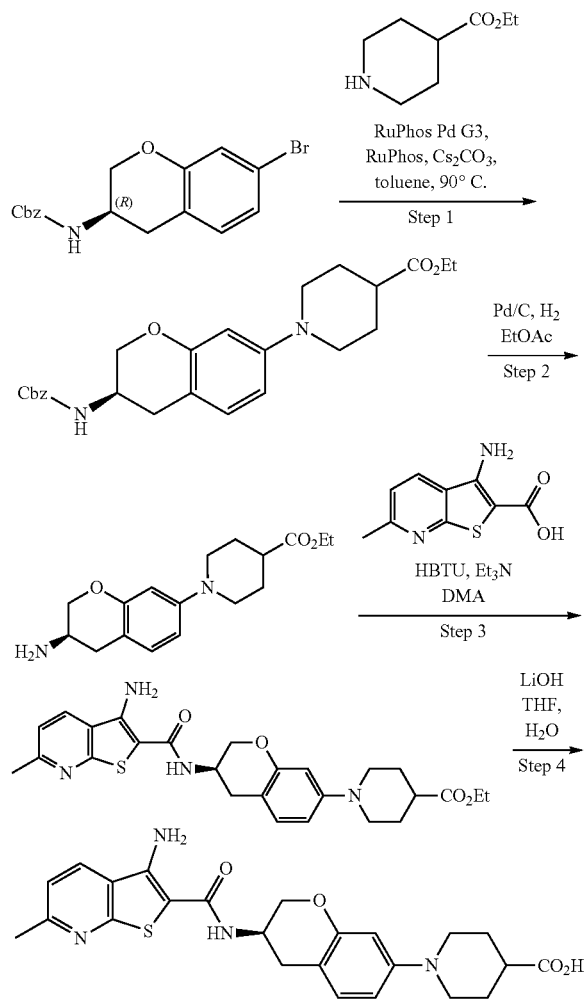

Step 1. Ethyl (R)-1-(3-(((benzyloxy)carbonyl)amino)chroman-7-yl)piperidine-4-carboxylate A mixture of benzyl (R)-(7-bromochroman-3-yl)carbamate, Intermediate 2, (200 mg, 0.52 mmol), ethyl piperidine-4-carboxylate (130 mg, 0.79 mmol), RuPhos Pd G3 (44 mg, 0.05 mmol), RuPhos (24 mg, 0.05 mmol), and Cs$_2$CO$_3$ (513 mg, 1.57 mmol) in toluene (30 mL) was stirred for 2 h at 90° C. After cooling to room temperature, the solids were filtered out and the filtrate was concentrated under vacuum. Purification by silica gel column (eluting with 1:1 EtOAc/pet. ether) afforded ethyl (R)-1-(3-(((benzyloxy)carbonyl)amino)chroman-7-yl)piperidine-4-carboxylate as a yellow solid. MS: (ESI, m/z): 439 [M+H]$^+$.

Step 2. Ethyl (R)-1-(3-aminochroman-7-yl)piperidine-4-carboxylate

A mixture of ethyl (R)-1-(3-(((benzyloxy)carbonyl)amino)chroman-7-yl)piperidine-4-carboxylate (180 mg, 0.32 mmol) and Pd/C (50 mg, 10%) in EtOAc (5 mL) was stirred for 2 h at room temperature under an atmosphere of hydrogen. The solids were filtered away and the filtrate was concentrated under vacuum to afford ethyl (R)-1-(3-aminochroman-7-yl)piperidine-4-carboxylate as a yellow oil. MS: (ESI, m/z): 305 [M+H]$^+$.

Step 3. Ethyl (R)-1-(3-(3-amino-6-methylthieno[2,3-b]pyridine-2-carboxamido)chroman-7-yl)piperidine-4-carboxylate A solution of ethyl (R)-1-(3-aminochroman-7-yl)piperidine-4-carboxylate (110 mg, 0.33 mmol), 3-amino-6-methylthieno[2,3-b]pyridine-2-carboxylic acid (107 mg, 0.49 mmol), Et$_3$N (99 mg, 0.98 mmol), and HBTU (185 mg, 0.49 mmol) in DMA (5 mL) was stirred for 2 h at room temperature. The reaction was then quenched by the addition of 5 mL of water. The resulting mixture was extracted EtOAc (3×10 mL). The combined organic layers were washed with brine (2×30 mL), dried over anhydrous sodium sulfate, filtered, and concentrated under vacuum. Purification by silica gel column (eluting with 1:1 EtOAc/pet. ether) afforded ethyl (R)-1-(3-(3-amino-6-methylthieno[2,3-b]pyridine-2-carboxamido)chroman-7-yl)piperidine-4-carboxylate as a yellow solid. MS: (ESI, m/z): 495 [M+H]$^+$.

Step 4. (R)-1-(3-(3-Amino-6-methylthieno[2,3-b]pyridine-2-carboxamido)chroman-7-yl)piperidine-4-carboxylic acid A mixture of ethyl (R)-1-(3-(3-amino-6-methylthieno[2,3-b]pyridine-2-carboxamido)chroman-7-yl)piperidine-4-carboxylate (40 mg, 0.07 mmol) and LiOH (1.6 mg, 0.07 mmol) in THF (2 mL) and water (0.5 mL) was stirred for 16 h at room temperature. The resulting mixture was concentrated under vacuum. The residue was diluted with water (5 mL) and the pH was adjusted to 4 with aq. 3N HCl. The resulting mixture was washed with DCM (3×10 mL). Purification by prep-HPLC (Column: XBridge Shield RP18 OBD, 19×150 mm, 5 μm; Mobile phase A: Water (10 mM NH$_4$HCO$_3$), B: ACN; Gradient: 5% B to 65% B in 7 min) afforded (R)-1-(3-(3-amino-6-methylthieno[2,3-b]pyridine-2-carboxamido)chroman-7-yl)piperidine-4-carboxylic acid as a yellow solid. H NMR (DMSO-d$_6$, 300 MHz) δ(ppm): 8.33 (d, J=8.4 Hz, 1H). 7.53 (br s, 1H), 7.31 (d, J=8.4 Hz, 1H), 7.22 (br s, 2H), 6.91 (d, J=8.7 Hz, 1H), 6.52 (dd, J=2.4, 8.4 Hz, 1H), 6.32 (s, 1H), 4.32-4.24 (m, 1H), 4.16-4.12 (m, 1H), 3.80 (t, J=9.9 Hz, 1H), 3.57-3.52 (m, 2H), 2.86-2.82 (m, 2H), 2.73-2.65 (m, 2H), 2.58 (s, 3H), 2.50-2.28 (m, 1H), 1.91-1.84 (m, 2H), 1.69-1.57 (m, 2H). MS: (ESI, m/z): 467 [M+H]$^+$.

The following examples in Table 13 were prepared using standard chemical manipulations and procedures similar to those used for the preparation of Example 6-1.

TABLE 13

| Example Number | Structure and Compound Name | LRMS m/z [M + H]+ | 1H NMR |
|---|---|---|---|
| 6-4[2] | 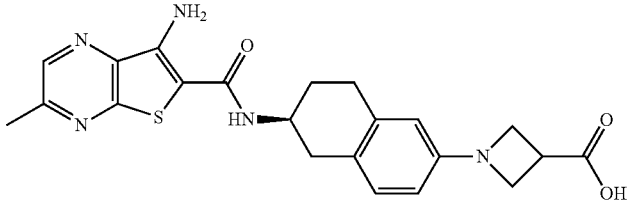 [SMILES: Cc1cnc2c(N)c(C(=O)N[C@H]3CCc4cc(N5CC(C(=O)O)C5)ccc4C3)sc2n1]<br>(S)-1-(6-(7-amino-3-methylthieno+8 2,3-b+9 pyrazine-6-carboxamido)-5,6,7,8-tetrahydronaphthalen-2-yl)azetidine-3-carboxylic acid | 438 | (DMSO-$d_6$, 300 MHz) δ (ppm): 8.64 (s, 1H), 7.81 (d, J = 7.5 Hz, 1H), 6.91-6.85 (m, 3H), 6.21 (d, J = 7.8 Hz, 1H), 6.14 (s, 1H), 4.27-4.18 (m, 1H), 3.89-3.81 (m, 2H), 3.76-3.72 (m, 2H), 3.29-3.24 (m, 1H), 2.89-2.68 (m, 4H), 2.65 (s, 3H), 2.04-1.95 (m, 1H), 1.81-1.70 (m, 3H). |

[2]Notes on procedures:
In Step 1, the bromide Intermediate 9 was used.

Example 7-1. (R)-3-amino-N-(7-(4-hydroxypiperidin-1-yl)chroman-3-yl)-6-methylthieno[2,3-b]pyridine-2-carboxamide

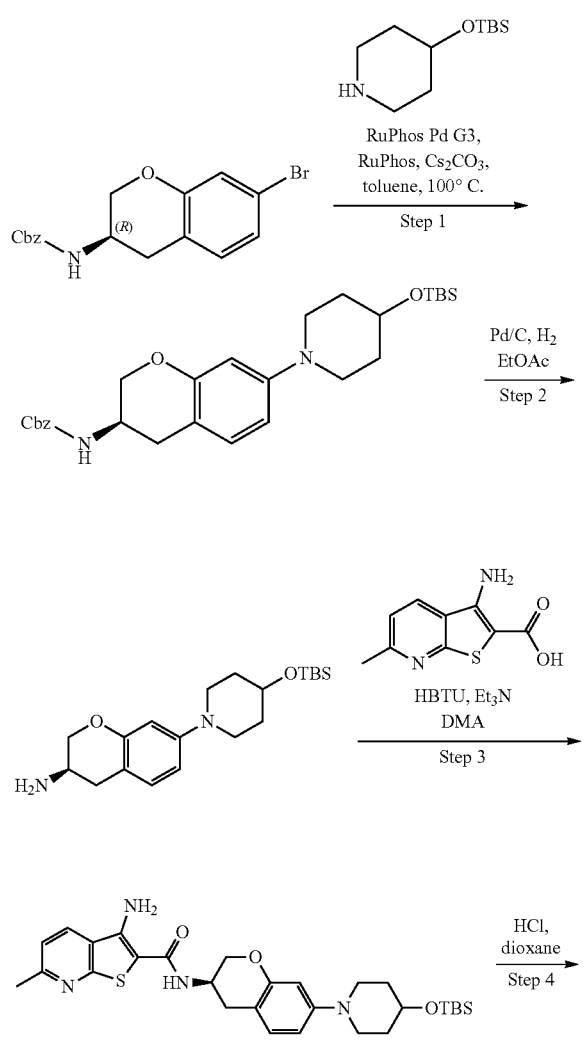

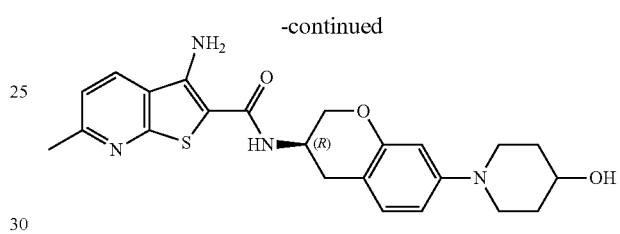

Step 1. Benzyl (R)-(7-(4-(tert-butyldimethylsilyloxy)piperidin-1-yl)chroman-3-yl)carbamate A mixture of benzyl (R)-(7-bromochroman-3-yl)carbamate, Intermediate 2, (200 mg, 0.55 mmol), 4-(tert-butyldimethylsilyloxy)piperidine, Intermediate 39, (142 mg, 0.66 mmol), RuPhos Pd G3 (46 mg, 0.05 mmol), RuPhos (26 mg, 0.06 mmol), and Cs$_2$CO$_3$ (539 mg, 1.65 mmol) in toluene (10 mL) was stirred for 3 h at 100° C. After cooling to room temperature, the solids were filtered out and the filtrate was concentrated under vacuum. Purification by silica gel column (eluting with 1:3 EtOAc/pet. ether) afforded benzyl (R)-(7-(4-(tert-butyldimethylsilyloxy)piperidin-1-yl)chroman-3-yl)carbamate as a yellow solid. MS: (ESI, m/z): 497 [M+H]$^+$.

Step 2. (R)-7-(4-(tert-butyldimethylsilyloxy)piperidin-1-yl)chroman-3-amine

A mixture of benzyl (R)-(7-(4-(tert-butyldimethylsilyloxy)piperidin-1-yl)chroman-3-yl)carbamate (170 mg, 0.34 mmol) and Pd/C (170 mg, 10%) in EtOAc (6 mL) was stirred for 2 h at room temperature under an atmosphere of hydrogen. The solids were filtered away and the filtrate was concentrated under vacuum to afford (R)-7-(4-(tert-butyldimethylsilyloxy)piperidin-1-yl)chroman-3-amine as a yellow solid. MS: (ESI, m/z): 363 [M+H]$^+$.

Step 3. (R)-3-amino-N-(7-(4-(tert-butyldimethylsilyloxy)piperidin-1-yl)chroman-3-yl)-6-methylthieno[2,3-b]pyridine-2-carboxamide A solution of (R)-7-(4-(tert-butyldimethylsilyloxy)piperidin-1-yl)chroman-3-amine (100 mg, 0.28 mmol), 3-amino- 6-methylthieno[2,3-b]pyridine-2-carboxylic acid (63 mg, 0.30 mmol), Et$_3$N (84 mg, 0.83 mmol), and HBTU (157 mg, 0.41 mmol) in DMA (5 mL) was stirred for 30 min at room temperature. The reaction was then quenched by the addition of 10 mL of water. The resulting mixture was extracted CH$_2$Cl$_2$ (3×15 mL). The combined organic layers were washed with brine (3×15 mL), dried over anhydrous sodium sulfate, filtered, and concentrated under vacuum. Purification by silica gel column (eluting with 1:1 EtOAc/pet. ether) afforded (R)-3-amino-N-(7-(4-(tert-butyldimethylsilyloxy)piperidin-1-yl)chroman-3-yl)-6-methylthieno[2,3-b]pyridine-2-carboxamide as a yellow solid. MS: (ESI, m/z): 553 [M+H]$^+$.

Step 4. (R)-3-amino-N-(7-(4-hydroxypiperidin-1-yl)chroman-3-yl)-6-methylthieno[2,3-b]pyridine-2-carboxamide A solution of (R)-3-amino-N-(7-(4-(tert-butyldimethylsilyloxy)piperidin-1-yl)chroman-3-yl)-6-methylthieno[2,3-b]pyridine-2-carboxamide (30 mg, 0.05 mmol) and HCl (4N in dioxane) (1 mL) in CH$_2$Cl$_2$ (3 mL) was stirred for 10 min at room temperature. The pH was adjusted to 8 with sat. aq. NaHCO$_3$. Purification by prep-HPLC (Column: XBridge Prep C18 OBD, 30×150 mm, 5 µm; Mobile phase A: Water (10 mM NH$_4$HCO$_3$), B: ACN; Flow rate: 60 mL/min; Gradient: 15% B to 50% B in 7 min) afforded (R)-3-amino-N-(7-(4-hydroxypiperidin-1-yl)chroman-3-yl)-6-methylthieno[2,3-b]pyridine-2-carboxamide as a white solid. $^1$H NMR (DMSO-d$_6$, 300 MHz) δ(ppm): 8.32 (d, J=8.1 Hz, 1H), 7.52 (br s, 1H), 7.32 (d, J=8.1 Hz, 1H), 7.22 (br s, 2H), 6.91 (d, J=8.4 Hz, 1H), 6.51 (dd, J=2.4, 8.4 Hz, 1H), 6.31 (s, 1H), 4.65 (br s, 1H), 4.29-4.26 (m, 1H), 4.17-4.13 (m, 1H), 3.80 (t, J=9.9 Hz, 1H), 3.64-3.58 (m, 1H), 3.48-3.44 (m, 2H), 2.87-2.73 (m, 4H), 2.59 (s, 3H), 1.80-1.76 (m, 2H), 1.48-1.43 (m, 2H). MS: (ESI, m/z): 439 [M+H]$^+$.

The following examples in Table 14 were prepared using standard chemical manipulations and procedures similar to those used for the preparation of Example 7-1.

TABLE 14

| Example Number | Structure and Compound Name | LRMS m/z [M + H]$^+$ | $^1$H NMR |
|---|---|---|---|
| 7-4[2] | 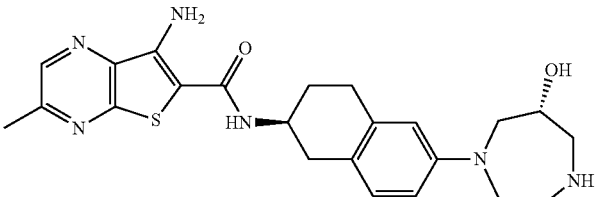<br>7-amino-N-((S)-6-((R)-6-hydroxy-1,4-diazepan-1-yl)-1,2,3,4-tetrahydronaphthalen-2-yl)-3-methylthieno+8 2,3-b+9 pyrazine-6-carboxamide | 453 | (DMSO-d$_6$, 300 MHz) δ (ppm): 8.63 (s, 1H), 7.77-7.74 (m, 1H), 6.94-6.84 (m, 3H), 6.71-6.49 (m, 2H), 5.14-5.07 (m, 1H), 4.14-3.95 (m, 2H), 3.66-3.58 (m, 2H), 3.42-3.16 (m, 3H), 3.00-2.70 (m, 8H), 2.63 (s, 3H), 1.98-1.89 (m, 1H), 1.80-1.67 (m, 1H). |
| 7-5[2] | 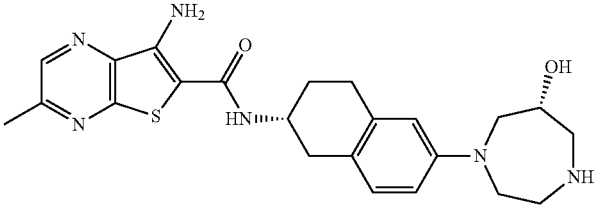 [SMILES: Cc1cnc2c(N)c(C(=O)N[C@@H]3CCc4cc(N5CCNC[C@@H](O)C5)ccc4C3)sc2n1]<br>7-amino-N-((R)-6-((R)-6-hydroxy-1,4-diazepan-1-yl)-1,2,3,4-tetrahydronaphthalen-2-yl)-3-methylthieno+8 2,3-b+9 pyrazine-6-carboxamide | 453 | (DMSO-d$_6$, 300 MHz) δ (ppm): 8.63 (s, 1H), 7.77-7.74 (m, 1H), 6.88-6.84 (m, 3H), 6.58-6.48 (m, 2H), 5.12-5.05 (m, 1H), 4.14-3.92 (m, 2H), 3.69-3.42 (m, 4H), 2.98-2.70 (m, 9H), 2.63 (s, 3H), 1.95-1.89 (m, 1H), 1.79-1.65 (m, 1H). |
| 7-6[2] | 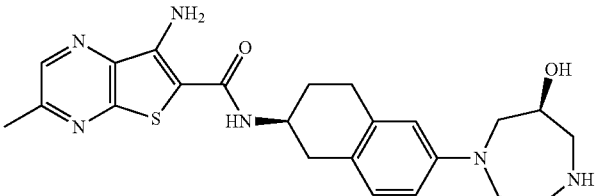<br>7-amino-N-((S)-6-((S)-6-hydroxy-1,4-diazepan-1-yl)-1,2,3,4-tetrahydronaphthalen-2-yl)-3-methylthieno+8 2,3-b+9 pyrazine-6-carboxamide | 453 | (DMSO-d$_6$, 300 MHz) δ (ppm): 8.65 (s, 1H), 7.78 (d, J = 7.8 Hz, 1H), 6.91-6.86 (m, 3H), 6.59-6.50 (m, 2H), 5.19-5.12 (m, 1H), 4.17-3.98 (m, 2H), 3.69-3.23 (m, 5H), 3.02-2.72 (m, 8H) 2.65 (s, 3H), 1.96-1.75 (m, 1H), 1.24-1.16 (m, 1H). |

TABLE 14-continued

| Example Number | Structure and Compound Name | LRMS m/z [M + H]+ | 1H NMR |
|---|---|---|---|
| 7-7[2] | 7-amino-N-((R)-6-((S)-6-hydroxy-1,4-diazepan-1-yl)-1,2,3,4-tetrahydronaphthalen-2-yl)-3-methylthieno+8 2,3-b+9 pyrazine-6-carboxamide | 453 | (DMSO-d$_6$, 300 MHz) δ (ppm): 8.65 (s, 1H), 7.78 (d, J = 7.5Hz, 1H), 6.91-6.87 (m, 3H), 6.61-6.52 (m, 2H), 5.33-5.28 (m, 1H), 4.12-4.03 (m, 2H), 3.70-3.29 (m, 5H), 3.09-2.72 (m, 8H), 2.65 (s, 3H), 1.96-1.74 (m, 1H), 1.23-1.16 (m, 1H). |
| 7-8[3] | 3-amino-N-((S)-6-((S)-3-(hydroxymethyl)piperazin-1-yl)-1,2,3,4-tetrahydronaphthalen-2-yl)-6-methylthieno+8 2,3-b+9 pyridine-2-carboxamide | 452 | (CD$_3$COD, 300 MHz) δ (ppm): 8.19 (d, J = 7.8 Hz, 1H), 7.29 (d, J = 7.8 Hz, 1H), 6.98 (d, J = 7.8 Hz, 1H), 6.80-6.73 (m, 2H), 4.28-4.20 (m, 1H), 3.59-3.46 (m, 5H), 3.14-2.91 (m, 5H), 2.80-2.63 (m, 5H), 2.48-2.40 (m, 1H), 2.18-2.10 (m, 1H), 1.89-1.78 (m, 1H). |
| 7-9[3] | 3-amino-N-((S)-6-((R)-3-(hydroxymethyl)piperazin-1-yl)-1,2,3,4-tetrahydronaphthalen-2-yl)-6-methylthieno+8 2,3-b+9 pyridine-2-carboxamide | 452 | (CD$_3$OD, 300 MHz) δ (ppm): 8.19 (d, J = 7.8 Hz, 1H), 7.29 (d, J = 7.8 Hz, 1H), 6.98 (d, J = 7.8 Hz, 1H), 6.80-6.73 (m, 2H), 4.28-4.17 (m, 1H), 3.62-3.47 (m, 4H), 3.18-3.12 (m, 1H), 3.08-2.86 (m, 5H), 2.82-2.69 (m, 2H), 2.64 (s, 3H), 2.49-2.39 (m, 1H), 2.17-2.08 (m, 1H), 1.91-1.73 (m, 1H). |
| 7-10[3] | 3-amino-N-((R)-6-((S)-3-(hydroxymethyl)piperazin-1-yl)-1,2,3,4-tetrahydronaphthalen-2-yl)-6-methylthieno+8 2,3-b+9 pyridine-2-carboxamide | 452 | (CD$_3$OD, 300 MHz) δ (ppm): 8.19 (d, J = 8.1 Hz, 1H), 7.29 (d, J = 8.1 Hz, 1H), 6.98 (d, J = 8.4 Hz, 1H), 6.80-6.73 (m, 2H), 4.27-4.21 (m, 1H), 3.60-3.47 (m, 4H), 3.10-2.91 (m, 6H), 2.80-2.64 (m, 5H), 2.47-2.41 (m, 1H), 2.18-2.09 (m, 1H), 1.91-1.73 (m, 1H). |

TABLE 14-continued

| Example Number | Structure and Compound Name | LRMS m/z [M + H]+ | 1H NMR |
|---|---|---|---|
| 7-11[3] | 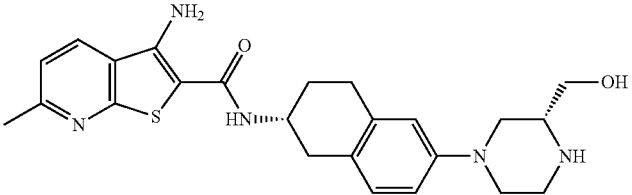 [SMILES: Cc1ccc2c(N)c(C(=O)N[C@@H]3CCc4cc(N5CCN[C@@H](CO)C5)ccc4C3)sc2n1]<br>3-amino-N-((R)-6-((R)-3-(hydroxymethyl)piperazin-1-yl)-1,2,3,4-tetrahydronaphthalen-2-yl)-6-methylthieno+8 2,3-b+9 pyridine-2-carboxamide | 452 | (CD$_3$OD, 300 MHz) δ (ppm): 8.20 (d, J = 7.5 Hz, 1H), 7.29 (d, J = 8.4 Hz, 1H), 6.98 (d, J = 6.6 Hz, 1H), 6.80-6.73 (m, 2H), 4.28-4.18 (m, 1H), 3.59-3.46 (m, 4H), 3.10-2.92 (m, 6H), 2.80-2.63 (m, 5H), 2.46-2.43 (m, 1H), 2.17-2.09 (m, 1H), 1.87-1.76 (m, 1H). |

[2]Notes on procedures:
In Step 1, racemic bromide Intermediate 8, the amine Intermediate 45, and Pd(dppf)Cl$_2$—CH$_2$Cl$_2$/Xphos as the catalyst/ligand system were used. Amidation was performed with EDCI, HOBt, and DIEA in DMF. Following Step 4, the racemate was separated by chiral HPLC using the chiral column Chiralpak IA and mobile phase 90% MeOH/DCM (0.1% Et$_2$NH) to provide a first eluted sample which was a mixture of 2 isomers; Example 7-5 as the second eluted sample (stereochemistry assumed), and Example 7-7 as the third eluted sample (stereochemistry assumed). The mixture of 2 isomers was further separated by chiral HPLC using the chiral column Chiralpak IC and mobile phase 30% EtOH/MTBE (0.1% Et$_2$NH) to provide Example 7-4 as the first eluted isomer and Example 7-6 as the second eluted isomer (stereochemistry assumed).
[3]Notes on procedures:
In Step 1, racemic bromide Intermediate 8, the amine Intermediate 46, and Pd(dppf)Cl$_2$—CH$_2$Cl$_2$/Xphos as the catalyst/ligand system were used. Amidation was performed with EDCI, HOBt, and DIEA in DMF. Following Step 4, the racemate was separated by chiral HPLC using the chiral column EnantioCel-C1 and mobile phase 25% EtOH/hexanes (0.1% Et$_2$NH) to provide a first eluted sample 1 which was a mixture of two isomers and a second eluted sample 2 which was a mixture of two isomers. Each of the two samples were further separated by SFC using the chiral column EnantioPak A1-5 and mobile phase 50% CO2/MeOH (0.1% iPrNH$_2$) to provide from sample 1, Example 7-8 as the first eluted isomer and Example 7-9 as the second eluted isomer; and from sample 2, Example 7-10 as the first eluted isomer and Example 7-11 as the second eluted isomer (stereochemistry assumed).

Example 10-1. (R)-3-amino-N-(5-fluoro-7-(piperazin-1-yl)chroman-3-yl)-6-methylthieno[2,3-b]pyridine-2-carboxamide

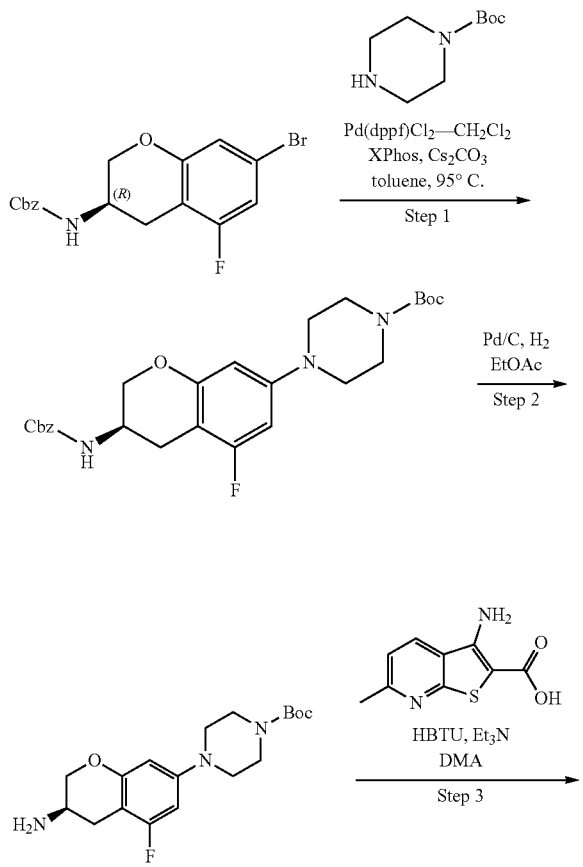

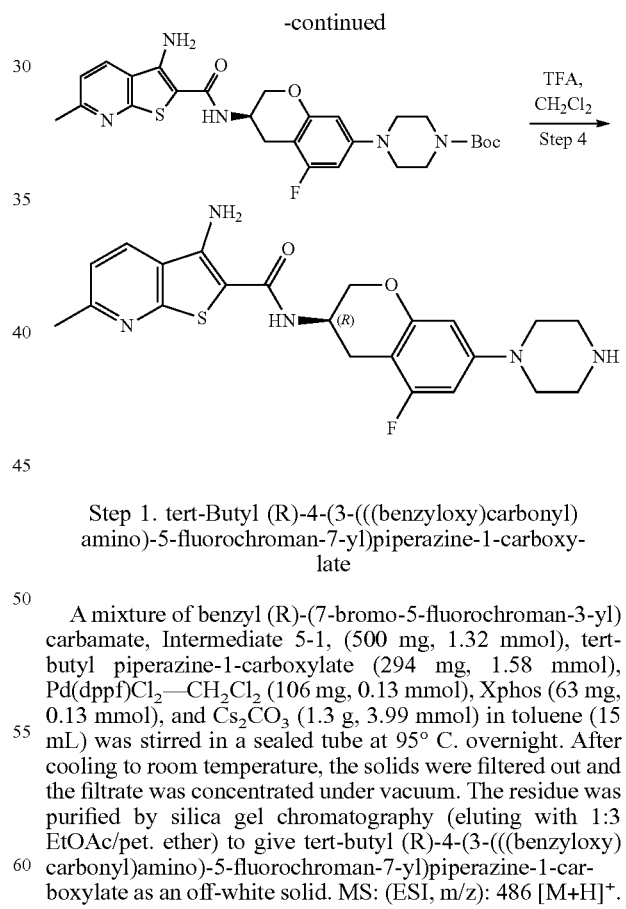

Step 1. tert-Butyl (R)-4-(3-(((benzyloxy)carbonyl)amino)-5-fluorochroman-7-yl)piperazine-1-carboxylate A mixture of benzyl (R)-(7-bromo-5-fluorochroman-3-yl) carbamate, Intermediate 5-1, (500 mg, 1.32 mmol), tert-butyl piperazine-1-carboxylate (294 mg, 1.58 mmol), Pd(dppf)Cl$_2$—CH$_2$Cl$_2$ (106 mg, 0.13 mmol), Xphos (63 mg, 0.13 mmol), and Cs$_2$CO$_3$ (1.3 g, 3.99 mmol) in toluene (15 mL) was stirred in a sealed tube at 95° C. overnight. After cooling to room temperature, the solids were filtered out and the filtrate was concentrated under vacuum. The residue was purified by silica gel chromatography (eluting with 1:3 EtOAc/pet. ether) to give tert-butyl (R)-4-(3-(((benzyloxy)carbonyl)amino)-5-fluorochroman-7-yl)piperazine-1-carboxylate as an off-white solid. MS: (ESI, m/z): 486 [M+H]+.

Step 2. tert-Butyl (R)-4-(3-amino-5-fluorochroman-7-yl)piperazine-1-carboxylate

A mixture of tert-butyl (R)-4-(3-(((benzyloxy)carbonyl)amino)-5-fluorochroman-7-yl)piperazine-1-carboxylate (4.9 g, 10.10 mmol) and Pd/C (0.5 g, 10%) in EtOAc (100 mL) was stirred for 1 h at room temperature under an atmosphere of hydrogen. The solids were filtered away and the filtrate was concentrated under vacuum to afford tert-butyl (R)-4-(3-amino-5-fluorochroman-7-yl)piperazine-1-carboxylate as yellow oil. MS: (ESI, m/z): 352 [M+H]$^+$.

Step 3. tert-Butyl (R)-4-(3-(3-amino-6-methylthieno[2,3-b]pyridine-2-carboxamido)-5-fluorochroman-7-yl)piperazine-1-carboxylate A solution of tert-butyl (R)-4-(3-amino-5-fluorochroman-7-yl)piperazine-1-carboxylate (3.5 g, 9.96 mmol), 3-amino-6-methylthieno[2,3-b]pyridine-2-carboxylic acid (2.5 g, 12.01 mmol), Et$_3$N (3.0 g, 29.65 mmol), and HBTU (4.5 g, 11.87 mmol) in DMA (30 mL) was stirred for 30 min at room temperature. The reaction was quenched by the addition of 60 mL of water. The resulting mixture was extracted with CH$_2$Cl$_2$ (50 mL×3). The organic layers were combined, dried over anhydrous sodium sulfate, filtered, and concentrated under vacuum. Purification by reverse phase chromatography (Column: C18 silica gel; Mobile phase A: water (10 mM NH$_4$HCO$_3$), B: ACN; Gradient: 0% to 100% B over 30 min; Flow rate: 90 mL/min) afforded tert-butyl (R)-4-(3-(3-amino-6-methylthieno[2,3-b]pyridine-2-carboxamido)-5-fluorochroman-7-yl)piperazine-1-carboxylate as an off-white solid. MS: (ESI, m/z): 542 [M+H]$^+$.

Step 4. (R)-3-Amino-N-(5-fluoro-7-(piperazin-1-yl)chroman-3-yl)-6-methylthieno[2,3-b]pyridine-2-carboxamide A solution of tert-butyl (R)-4-(3-(3-amino-6-methylthieno[2,3-b]pyridine-2-carboxamido)-5-fluorochroman-7-yl)piperazine-1-carboxylate (30 mg, 0.05 mmol) and TFA (1 mL) in CH$_2$Cl$_2$ (2 mL) was stirred for 30 min at room temperature. The resulting mixture was concentrated under vacuum. The crude product was purified by prep-HPLC (Column: XBridge Prep C18 OBD, 19×50 mm, 5 μm; Mobile phase A: water (10 mM NH$_4$HCO$_3$), B: ACN; Gradient: 25% B to 75% B in 7 min) to afford (R)-3-amino-N-(5-fluoro-7-(piperazin-1-yl)chroman-3-yl)-6-methylthieno[2,3-b]pyridine-2-carboxamide as a yellow solid. $^1$H NMR (DMSO-d$_6$, 400 MHz) δ(ppm): 8.33 (d, J=9 MHz, 1H), 7.58 (d, J=9 MHz, 1H), 7.31 (d, J=6 MHz, 1H), 7.22 (s, 2H), 6.43-6.40 (m, 1H), 6.17 (s, 1H), 4.40-4.20 (m, 1H), 4.19-4.12 (m, 1H), 3.89-3.82 (m, 1H), 3.32 (s, 1H), 3.01-2.97 (m, 4H), 2.80-2.74 (m, 6H), 2.58 (s, 3H). MS: (ESI, m/z): 442 [M+H]$^+$.

The following examples in Table 15 were prepared using standard chemical manipulations and procedures similar to those used for the preparation of Example 10-1.

TABLE 15

| Example Number | Structure and Compound Name | LRMS m/z [M + H]$^+$ | $^1$H NMR |
|---|---|---|---|
| 10-5[2,3] | (S)-3-amino-N-(5-fluoro-7-(piperazin-1-yl)chroman-3-yl)-6-methylthieno[2,3-b]pyridine-2-carboxamide | 442 | (DMSO-d$_6$, 400 MHz) δ (ppm): 8.33 (d, J = 9 MHz, 1H), 7.58 (d, J = 9 MHz, 1H), 7.31 (d, J = 6 MHz, 1H), 7.22 (s, 2H), 6.43-6.40 (m, 1H), 6.17 (s, 1H), 4.40-4.20 (m, 1h), 4.19-4.12 (m, 1H), 3.89-3.82 (m, 1H), 3.32 (s, 1H), 3.01-2.97 (m, 4H), 2.80-2.74 (m, 6H), 2.58 (s, 3H). |
| 10-6[2] | N-((3R)-7-(9-oxa-3,7-diazabicyclo[3.3.1]nonan-3-yl)-5-fluorochroman-3-yl)-3-amino-6-methylthieno[2,3-b]pyridine-2-carboxamide | 484 | (DMSO-d$_6$, 400 MHz) δ (ppm): 8.33 (d, J = 8.4 Hz, 1H), 7.58 (br s, 1H), 7.31 (d, J = 8.4 Hz, 1H), 7.23 (br s, 2H), 6.46 (dd, J = 2.0, 12.8 Hz, 1H), 6.24 (s, 1H), 4.32-4.27 (m, 1H), 4.20-4.15 (m, 1H), 3.86 (t, J = 10.0 Hz, 1H), 3.79-3.77 (m, 2H), 3.68-3.65 (m, 2H), 3.12-3.00 (m, 6H), 2.91-2.67 (m, 2 H), 2.58 (s, 3H), 2.01 (br s, 1H). |

TABLE 15-continued

| Example Number | Structure and Compound Name | LRMS m/z [M + H]+ | 1H NMR |
|---|---|---|---|
| 10-7[2,4,5] | N-((3R)-7-(3,6-diazabicyclo[3.1.1]heptan-3-yl)-5-fluorochroman-3-yl)-3-amino-4,6-dimethylthieno[2,3-b]pyridine-2-carboxamide | 468 | (CD3OD, 400 MHz) δ (ppm): 7.05 (s, 1H), 6.15 (d, J = 12.6 Hz, 1H), 6.06 (s, 1H), 4.48-4.37 (m, 1H), 4.28-4.23 (m, 1H), 3.96-3.93 (m, 1H), 3.85-3.83 (m, 2H), 3.52-3.48 (m, 4H), 3.12-2.93 (m, 1H), 2.79 (s, 3H), 2.77-2.55 (m, 2H), 1.67-1.64 (m, 1H). |
| 10-8[2,5] | N-((3R)-7-(3,6-diazabicyclo[3.1.1]heptan-3-yl)-5-fluorochroman-3-yl)-7-amino-3-methylthieno[2,3-b]pyrazine-6-carboxamide | 455 | (DMSO-d6, 400 MHz) δ (ppm): 8.65 (s, 1H), 7.80 (d, J = 7.2 Hz, 1H), 6.97 (br s, 2H), 6.14 (dd, J = 2.0, 12.8 Hz, 1H), 5.97 (s, 1H), 4.35-3.26 (m, 1H), 4.20-4.17 (m, 1H), 3.87 (t, J = 9.6 Hz, 1H), 3.67-3.66 (m, 2H), 3.41-3.31 (m, 4H), 2.92-2.86 (m, 1H), 2.79-2.68 (m, 1H), 2.66 (s, 3H), 2.50-2.49 (m, 1H), 1.46-1.45 (m, 1H). |
| 10-9[4,5] | (R)-3-amino-N-(5-fluoro-7-(piperazin-1-yl)chroman-3-yl)-4,6-dimethylthieno[2,3-b]pyridine-2-carboxamide | 456 | (CD3OD, 400 MHz) δ (ppm): 7.04 (s, 1H), 6.34 (dd, J = 2.4, 12.4 Hz, 1H), 6.25 (s, 1H), 4.45-4.4.40 (m, 1H), 4.32-4.10 (m, 1H), 3.94-3.90 (m, 1H), 3.14-3.11 (m, 4H), 3.01-2.95 (m, 5H), 2.78 (s, 3H), 2.76-2.74 (m, 1H), 2.50 (s, 3H). |
| 10-10[5] | (R)-7-amino-N-(5-fluoro-7-(piperazin-1-yl)chroman-3-yl)-3-methylthieno[2,3-b]pyrazine-6-carboxamide | 443 | (DMSO-d6, 400 MHz) δ (ppm): 8.66 (s, 1H), 7.85 (d, J = 7.2Hz, 1H), 6.70 (br s, 2H), 6.38 (dd, J = 2.4, 12.8 Hz, 1H), 6.17 (s, 1H), 4.34-4.25 (m, 2H), 4.19-4.16 (m, 1H), 3.89-3.84 (m, 1H), 3.00-2.98 (m, 4H), 2.91-2.85 (m, 6H), 2.79 (s, 3H). |

TABLE 15-continued

| Example Number | Structure and Compound Name | LRMS m/z [M + H]+ | 1H NMR |
|---|---|---|---|
| 10-11[6] | 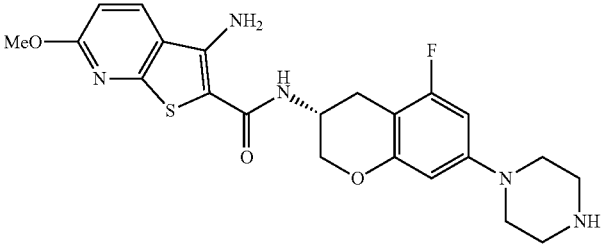 [SMILES: COc1ccc2c(N)c(C(=O)N[C@H]3COc4cc(N5CCNCC5)cc(F)c4C3)sc2n1]<br>(R)-3-amino-N-(5-fluoro-7-(piperazin-1-yl)chroman-3-yl)-6-methoxythieno[2,3-b]pyridine-2-carboxamide | 458 | (DMSO-d$_6$, 300 MHz) δ (ppm): 8.32 (d, J = 8.7 Hz, 1H). 7.46 (br s, 1H), 7.21 (br s, 2H), 6.68 (d, J = 9.0 Hz, 1H), 6.37 (dd, J = 2.1, 12.9 Hz, 1H), 6.17 (s, 1H), 4.30-4.21 (m, 1H), 4.19-4.16 (m, 1H), 3.93 (s, 3H), 3.83 (t, J = 9.9 Hz, 1H), 3.02-2.98 (m, 4H), 2.90-2.68 (m, 6H). |
| 10-12[2] | 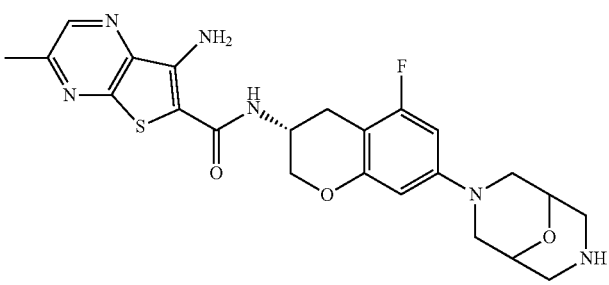 [SMILES: Cc1cnc2c(N)c(C(=O)N[C@H]3COc4cc(N5CC6CNCC(C5)O6)cc(F)c4C3)sc2n1]<br>N-((3R)-7-(9-oxa-3,7-diazabicyclo[3.3.1]nonan-3-yl)-5-fluorochroman-3-yl)-7-amino-3-methylthieno[2,3-b]pyrazine-6-carboxamide | 485 | (DMSO-d$_6$, 300 MHz) δ (ppm): 8.67 (s, 1H), 7.85 (br s, 1H), 7.00 (br s, 2H), 6.46 (dd, J = 2.1, 12.9 Hz, 1H), 6.23 (s, 1H), 4.34-4.28 (m, 1H), 4.28-4.15 (m, 1H), 3.91-3.85 (m, 1H), 3.74-3.65 (m, 4H), 3.10-2.70 (m, 9H), 2.70-2.55 (s, 3H). |
| 10-13[2,4] | 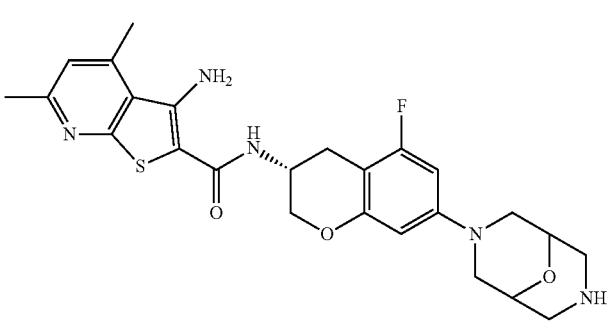 [SMILES: Cc1cc(C)c2c(N)c(C(=O)N[C@H]3COc4cc(N5CC6CNCC(C5)O6)cc(F)c4C3)sc2n1]<br>N-((3R)-7-(9-oxa-3,7-diazabicyclo[3.3.1]nonan-3-yl)-5-fluorochroman-3-yl)-3-amino-4,6-dimethylthieno[2,3-b]pyridine-2-carboxamide | 498 | (DMSO-d$_6$, 400 MHz) δ (ppm): 7.62 (br s, 1H). 7.04 (s, 1H), 6.87 (br s, 2H), 6.45 (dd, J = 2.0, 12.8 Hz, 1H), 6.23 (s, 1H), 4.30-4.25 (m, 1H), 4.19-4.16 (m, 1H), 3.86 (t, J = 10.0 Hz, 1H), 3.74-3.72 (m, 2H), 3.68-3.65 (m, 2H), 3.13-2.95 (m, 6H), 2.90-2.85 (m, 1H), 2.79-2.66 (m, 1H), 2.62 (s, 3H), 2.53 (s, 3H). |

TABLE 15-continued

| Example Number | Structure and Compound Name | LRMS m/z [M + H]+ | 1H NMR |
|---|---|---|---|
| 10-14[5,7] | (R)-3-amino-N-(5-fluoro-7-(piperazin-1-yl)chroman-3-yl)-6-methyl-4-(trifluoromethyl)thieno[2,3-b]pyridine-2-carboxamide | 510 | (DMSO-$d_6$, 300 MHz) δ (ppm): 7.97 (d, J = 6.9 Hz, 1H), 7.54 (br s, 1H), 6.68 (br s, 2H), 6.38 (d, J = 11.1 Hz, 1H), 6.21 (s, 1H), 4.32-4.16 (m, 2H), 3.90-3.84 (m, 1H), 3.09-2.70 (m, 10H), 2.50 (s, 3H), 2.30-2.27 (m, 1H). |
| 10-15[2,5,8] | 3-amino-N-[(3R)-5-fluoro-7-(piperazin-1-yl)-3,4-dihydro-2H-1-benzopyran-3-yl]-N,6-dimethylthieno[2,3-b]pyridine-2-carboxamide | 456 | (DMSO-$d_6$, 400 MHz) δ (ppm): 8.31 (d, J = 8.0 Hz, 1H), 7.31 (d, J = 8.4 Hz, 1H), 6.60 (br s, 2H), 6.40-6.37 (m, 1H), 6.17 (s, 1H), 4.57-4.53 (m, 1H), 4.29-4.27 (m, 1H), 4.18-4.13 (m, 1H), 3.05 (s, 3H), 3.00-2.98 (m, 4H), 2.95-2.88 (m, 2H), 2.85-2.84 (m, 4H), 2.57 (s, 3H). |
| 10-16[2,3,5,8] | 3-amino-N-[(3S)-5-fluoro-7-(piperazin-1-yl)-3,4-dihydro-2H-1-benzopyran-3-yl]-N,6-dimethylthieno[2,3-b]pyridine-2-carboxamide | 456 | (DMSO-$d_6$, 400 MHz) δ (ppm): 8.31 (d, J = 8.4 Hz, 1H), 7.31 (d, J = 8.0 Hz, 1H), 6.60 (br s, 2H), 6.41-6.37 (m, 1H), 6.17 (s, 1H), 4.57-4.55 (m, 1H), 4.30-4.27 (m, 1H), 4.18-4.13 (m, 1H), 3.05 (s, 3H), 3.00-2.84 (m, 7H), 2.79-2.77 (m, 4H), 2.57 (s, 3H). |

[2]Notes on procedures:
In Step 1, RuPhos Pd G3/RuPhos was used as the catalyst/ligand system.

[3]Notes on procedures:
In Step 1, benzyl (S)-(7-bromo-5-fluorochroman-3-yl)carbamate was used.

[4]Notes on procedures:
In Step 3, the carboxylic acid Intermediate 21 was used.

[5]Notes on procedures:
In Step 4, the crude product was treated with $NH_3$ in MeOH to afford the free base before purification by prep-HPLC.

[6]Notes on procedures:
In Step 3, the carboxylic acid Intermediate 19 was used.

[7]Notes on procedures:
In Step 3, the carboxylic acid Intermediate 22 was used.

[8]Notes on procedures:
Before the Cbz-deprotection (Step 2), the carbamate was methylated by treatment with NaH (2 eq.) and MeI (1.5 eq.) in DMF at 25° C. The reaction was quenched with water and an extractive workup with EtOAc was performed, followed by purification by silica gel chromatography, to afford the corresponding tert-butyl 4-(3-[[(benzyloxy)carbonyl](methyl)amino]-5-fluoro-3,4-dihydro-2H-1-benzopyran-7-yl)piperazine-1-carboxylate. MS (ESI, m/z): 500 [M + H]+.

Example 11-1. N-((2S)-6-(3,8-diazabicyclo[3.2.1]octan-3-yl)-1,2,3,4-tetrahydronaphthalen-2-yl)-3-amino-6-methylthieno[2,3-b]pyridine-2-carboxamide and

Example 11-2. N-((2R)-6-(3,8-diazabicyclo[3.2.1]octan-3-yl)-1,2,3,4-tetrahydronaphthalen-2-yl)-3-amino-6-methylthieno[2,3-b]pyridine-2-carboxamide Method 1

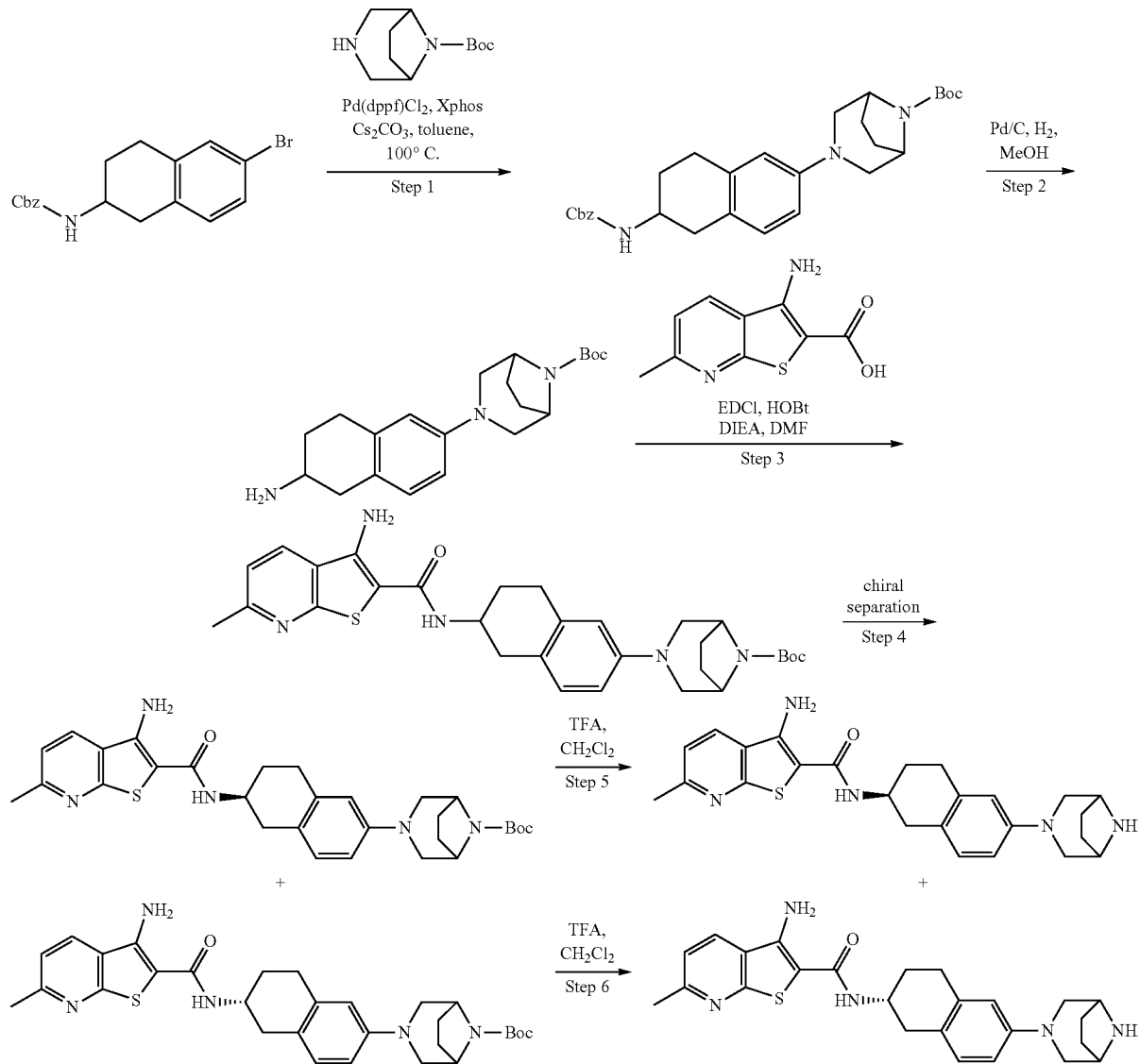

Step 1. tert-Butyl 3-(6-(((benzyloxy)carbonyl)amino)-5,6,7,8-tetrahydronaphthalen-2-yl)-3,8-diazabicyclo[3.2.1]octane-8-carboxylate A mixture of benzyl (6-bromo-1,2,3,4-tetrahydronaphthalen-2-yl)carbamate, Intermediate 8, (2 g, 5.55 mmol), tert-butyl 3,8-diazabicyclo[3.2.1]octane-8-carboxylate (1.171 g, 5.52 mmol), Pd(dppf)Cl₂ (404.96 mg, 0.55 mmol), Xphos (527 mg, 1.11 mmol), Cs₂CO₃ (5.3 g, 16.28 mmol) in toluene (40 mL) was stirred overnight at 100° C. After cooling to room temperature, the reaction mixture was concentrated under vacuum. Purification by silica gel chromatography (eluting with gradient 1:100 to 2:5 EtOAc/pet. ether) afforded tert-butyl 3-(6-(((benzyloxy)carbonyl)amino)-5,6,7,8-tetrahydronaphthalen-2-yl)-3,8-diazabicyclo[3.2.1]octane-8-carboxylate as a yellow solid. MS: (ESI, m/z): 492 [M+H]⁺.

Step 2. tert-Butyl 3-(6-amino-5,6,7,8-tetrahydronaphthalen-2-yl)-3,8-diazabicyclo[3.2.1]octane-8-carboxylate A mixture of tert-butyl 3-(6-(((benzyloxy)carbonyl)amino)-5,6,7,8-tetrahydronaphthalen-2-yl)-3,8-diazabicyclo[3.2.1]octane-8-carboxylate (1.4 g, 2.85 mmol) and Pd/C (1.4 g, 13.16 mmol) in ethanol (30 mL) was stirred for 1 h at room temperature under an atmosphere of hydrogen. The solids were filtered away and the filtrate was concentrated under vacuum. Purification by silica gel chromatography (eluting with 1:10 MeOH/CH$_2$Cl$_2$) afforded tert-butyl 3-(6-amino-5,6,7,8-tetrahydronaphthalen-2-yl)-3,8-diazabicyclo[3.2.1]octane-8-carboxylate as a yellow solid. MS: (ESI, m/z): 358 [M+H]$^+$.

Step 3. tert-Butyl 3-(6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate A mixture of 3-amino-6-methylthieno[2,3-b]pyridine-2-carboxylic acid (175 mg, 0.84 mmol), tert-butyl 3-(6-amino-5,6,7,8-tetrahydronaphthalen-2-yl)-3,8-diazabicyclo[3.2.1]octane-8-carboxylate (300 mg, 0.84 mmol), EDCI (193 mg, 1.01 mmol), HOBt (136 mg, 1.01 mmol), DIEA (325 mg, 2.52 mmol) in DMF (20 mL) was stirred for 18 h at 20° C. The reaction mixture was diluted with water (50 mL) and was extracted with ethyl acetate (3×50 mL). The combined organic layers were dried over anhydrous sodium sulfate, filtered and concentrated under vacuum. Purification by silica gel chromatography (eluting with 1:3 EtOAc/pet. ether) afforded tert-butyl 3-(6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate. MS: (ESI, m/z): 548 [M+H]$^+$.

Step 4. tert-Butyl 3-((S)-6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate and tert-Butyl 3-((R)-6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate The racemic mixture of tert-butyl 3-(6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate was separated by chiral HPLC (Column: (R,R)-WHELK-O1-Kromasil, 0.5×25 cm, 5 μm; Mobile phase: MeOH; Detector: UV 190 to 500 nm) to afford the title compounds as follows: tert-butyl 3-((S)-6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate as a white solid (first eluting isomer, RT=15.5 min) and tert-butyl 3-((R)-6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate as a white solid (second eluting isomer, RT=20.4 min).

Step 5. N-((2S)-6-(3,8-Diazabicyclo[3.2.1]octan-3-yl)-1,2,3,4-tetrahydronaphthalen-2-yl)-3-amino-6-methylthieno[2,3-b]pyridine-2-carboxamide A solution of tert-butyl 3-((S)-6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate (70 mg, 0.13 mmol) and TFA (7 mL) in DCM (28 mL) was stirred for 1 h at room temperature. The reaction mixture was concentrated under vacuum. The resulting solution was diluted with 5 mL of DCM. The pH value of the solution was adjusted to 8 with NH$_3$ (solution in MeOH). The resulting mixture was concentrated under vacuum. Purification by prep-HPLC (Column: XBridge BEH C18 OBD, 130 Å, 19×150 mm, 5 μm; Mobile phase A: water (10 mM NH$_4$HCO$_3$), B: ACN; Gradient: 5% B to 52% B over 8 min) afforded N-((2S)-6-(3,8-diazabicyclo[3.2.1]octan-3-yl)-1,2,3,4-tetrahydronaphthalen-2-yl)-3-amino-6-methylthieno[2,3-b]pyridine-2-carboxamide as an off-white solid. $^1$H NMR (CD$_3$OD, 400 MHz) δ(ppm): 8.19 (d, J=8.0 Hz, 1H), 7.30 (d, J=8.0 Hz, 1H), 6.93 (d, J=8.4 Hz, 1H), 6.65 (d, J=8.4 Hz, 1H), 6.58 (s, 1H), 4.24-4.23 (m, 1H), 3.63-3.60 (m, 2H), 3.45-3.41 (m, 2H), 3.02-2.68 (m, 6H), 2.64 (s, 3H), 2.14-2.08 (m, 1H), 1.92-1.75 (m, 5H). MS: (ESI, m/z): 449 [M+H]$^+$.

Step 6. N-((2R)-6-(3,8-Diazabicyclo[3.2.1]octan-3-yl)-1,2,3,4-tetrahydronaphthalen-2-yl)-3-amino-6-methylthieno[2,3-b]pyridine-2-carboxamide A solution of tert-butyl 3-((R)-6-(3-amino-6-methylthieno[2,3-b]pyridine-2-carboxamido)-5,6,7,8-tetrahydronaphthalen-2-yl)-3,8-diazabicyclo[3.2.1]octane-8-carboxylate (70 mg, 0.13 mmol) and TFA (7 mL) in DCM (28 mL) was stirred for 1 h at room temperature. The reaction mixture was concentrated under vacuum. The resulting solution was diluted with 5 mL of DCM. The pH value of the solution was adjusted to 8 with NH$_3$ (7M in MeOH). The resulting mixture was concentrated under vacuum. Purification by prep-HPLC (Column: XBridge BEH C18 OBD, 130 Å, 19×150 mm, 5 μm; Mobile phase A: water (10 mM NH$_4$HCO$_3$), B: ACN; Gradient: 5% B to 52% B over 8 min) afforded N-((2R)-6-(3,8-diazabicyclo[3.2.1]octan-3-yl)-1,2,3,4-tetrahydronaphthalen-2-yl)-3-amino-6-methylthieno[2,3-b]pyridine-2-carboxamide as an off-white solid. $^1$H NMR (CD$_3$OD, 400 MHz) δ(ppm): 8.20 (d, J=8.4 Hz, 1H), 7.30 (d, J=8.4 Hz, 1H), 6.93 (d, J=8.4 Hz, 1H), 6.66 (d, J=8.4 Hz, 1H), 6.59 (s, 1H), 4.26-4.17 (m, 1H), 3.65-3.61 (m, 2H), 3.45-3.39 (m, 3H), 3.00-2.71 (m, 6H), 2.64 (s, 3H), 2.12-2.09 (m, 1H), 1.91-1.75 (m, 5H). MS: (ESI, m/z): 449 [M+H]$^+$.

Example 11-1. N-((2S)-6-(3,8-diazabicyclo[3.2.1]octan-3-yl)-1,2,3,4-tetrahydronaphthalen-2-yl)-3-amino-6-methylthieno[2,3-b]pyridine-2-carboxamide Method 2

N-((2S)-6-(3,8-diazabicyclo[3.2.1]octan-3-yl)-1,2,3,4-tetrahydronaphthalen-2-yl)-3-amino-6-methylthieno[2,3-b]pyridine-2-carboxamide can also be prepared according to Method 1, starting from benzyl (S)-(6-bromo-1,2,3,4-tetrahydronaphthalen-2-yl)carbamate, Intermediate 9, and skipping the Step 4 chiral separation.

Example 11-2. N-((2R)-6-(3,8-diazabicyclo[3.2.1]octan-3-yl)-1,2,3,4-tetrahydronaphthalen-2-yl)-3-amino-6-methylthieno[2,3-b]pyridine-2-carboxamide Method 2

N-((2R)-6-(3,8-diazabicyclo[3.2.1]octan-3-yl)-1,2,3,4-tetrahydronaphthalen-2-yl)-3-amino-6-methylthieno[2,3-b]pyridine-2-carboxamide can also be prepared according to Method 1, starting from benzyl (R)-(6-bromo-1,2,3,4-tetrahydronaphthalen-2-yl)carbamate, Intermediate 10, and skipping the Step 4 chiral separation.

The following examples in Table 16 were prepared using standard chemical manipulations and procedures similar to Method 1 (or Method 2 where indicated) for the preparation of Examples 11-1 and 11-2.

TABLE 16

| Example Number | Structure and Compound Name | LRMS m/z [M + H]+ | 1H NMR |
|---|---|---|---|
| 11-15[7] | 3-amino-6-methyl-N-((3R,4R)-4-methyl-7-(piperazin-1-yl)chroman-3-yl)thieno[2,3-b]pyridine-2-carboxamide | 438 | (CD3OD, 300 MHz) δ (ppm): 8.22 (d, J = 12.0 Hz, 1H), 7.32 (d, J = 8.4 Hz, 1H), 7.09 (d, J =9 Hz, 1H), 6.63 (dd, J = 2.4, 8.4 Hz, 1H), 6.44 (s, 1H), 4.58-4.53 (m, 1H), 4.26-4.13 (m, 2H), 3.31-3.23 (m, 1H), 3.16-3.08 (m, 4H), 3.02-2.65 (m, 4H), 2.65 (s, 3H), 1.37 (d, J = 6.9 Hz, 3H). |
| 11-16[7] | 3-amino-6-methyl-N-((3R,4S)-4-methyl-7-(piperazin-1-yl)chroman-3-yl)thieno[2,3-b]pyridine-2-carboxamide | 438 | (CD3OD, 300 MHz) δ (ppm): 8.22 (d, J = 8.4 Hz, 1H), 7.32 (d, J = 8.4 Hz, 1H), 7.13 (d, J = 8.7 Hz, 1H), 6.62 (dd, J = 2.4, 8.4 Hz, 1H), 6.42 (s, 1H), 4.24-4.20 (m, 1H), 4.16-4.10 (m, 1H), 4.00-3.94 (m, 1H), 3.13-3.08 (m, 4H), 3.02-2.94 (m, 5H), 2.65 (s, 3H), 1.37 (d, J = 6.9 Hz, 3H) |
| 11-17[7] | 3-amino-6-methyl-N-((3S,4R)-4-methyl-7-(piperazin-1-yl)chroman-3-yl)thieno[2,3-b]pyridine-2-carboxamide | 438 | (CD3OD, 300 MHz) δ (ppm): 8.22 (d, J = 8.4 Hz, 1H), 7.32 (d, J = 8.4 Hz, 1H), 7.13 (d, J = 9.0 Hz, 1H), 6.63 (dd, J = 2.4, 8.4 Hz, 1H), 6.42 (s, 1H), 4.24-4.20 (m, 1H), 4.16-4.10 (m, 1H), 4.00-3.94 (m, 1H), 3.13-3.08 (m, 4H), 3.02-2.94 (m, 4H), 2.65 (s, 3H), 1.37 (d, J = 6.9 Hz, 3H). |
| 11-18[7] | 3-amino-6-methyl-N-((3S,4S)-4-methyl-7-(piperazin-1-yl)chroman-3-yl)thieno[2,3-b]pyridine-2-carboxamide | 438 | (CD3OD, 300 MHz) δ (ppm): 8.22 (d, J = 12.0 Hz, 1H), 7.32 (d, J = 8.4 Hz, 1H), 7.09 (d, J = 9 Hz, 1H), 6.63 (dd, J = 2.4, 8.4 Hz, 1H), 6.44 (s, 1H), 4.58-4.53 (m, 1H), 4.26-4.13 (m, 2H), 3.31-3.23 (m, 1H), 3.16-3.08 (m, 4H), 3.02-2.65 (m, 4H), 2.65 (s, 3H), 1.37 (d, J = 6.9 Hz, 3H). |
| 11-19[8] | (S)-7-amino-3-methyl-N-(6-(piperazin-1-yl)-1,2,3,4-tetrahydronaphthalen-2-yl)thieno[2,3-b]pyrazine-6-carboxamide | 423 | (CD3OD, 400 MHz) δ (ppm): 8.56 (s, 1H), 6.98 (d, J = 8.4 Hz, 1H), 6.79-6.72 (m, 2H), 4.27-4.23 (m, 1H), 3.13-2.74 (m, 12H), 2.67 (s, 3H), 2.14-2.10 (m, 1H), 1.86-1.76 (m, 1H). |

TABLE 16-continued

| Example Number | Structure and Compound Name | LRMS m/z [M + H]+ | 1H NMR |
|---|---|---|---|
| 11-20[8] | (R)-7-amino-3-methyl-N-(6-(piperazin-1-yl)-1,2,3,4-tetrahydronaphthalen-2-yl)thieno[2,3-b]pyrazine-6-carboxamide | 423 | (CD$_3$OD, 400 MHz) δ (ppm): 8.57 (s, 1H), 6.98 (d, J = 8.4 Hz, 1H), 6.80-6.73 (m, 2H), 4.28-4.23 (m, 1H), 3.13-2.74 (m, 12H), 2.68 (s, 3H), 2.14-2.11 (m, 1H), 1.87-1.75 (m, 1H). |
| 11-21[9] | (S)-3-amino-6-methyl-N-(6-(piperazin-1-yl)-1,2,3,4-tetrahydronaphthalen-2-yl)thieno[2,3-b]pyridine-2-carboxamide | 422 | (DMSO-d$_6$, 400 MHz) δ (ppm): 8.29 (s, 1H), 7.54 (d, J = 8.0 Hz, 1H), 7.30 (d, J = 8.4 Hz, 1H), 7.15 (s, 2H), 6.91 (d, J = 8.4 Hz, 1H), 6.72-6.70 (m, 1H), 6.62 (s, 1H), 4.13-4.09 (m, 1H), 2.98-2.96 (m, 4H), 2.87-2.67 (m, 8H), 2.58 (s, 3H), 1.98-1.95 (m, 1H), 1.79-1.71 (m, 1H). |
| 11-22[9] | (R)-3-amino-6-methyl-N-(6-(piperazin-1-yl)-1,2,3,4-tetrahydronaphthalen-2-yl)thieno[2,3-b]pyridine-2-carboxamide | 422 | (DMSO-d$_6$, 400 MHz) δ (ppm): 8.30 (d, J = 8.4 Hz, 1H), 7.54 (d, J = 8.0 Hz, 1H), 7.31 (d, J = 8.4 Hz, 1H), 7.15 (s, 2H), 6.91 (d, J = 8.4 Hz, 1H), 6.72-6.69 (m, 1H), 6.62 (s, 1H), 4.13-4.07 (m, 1H), 2.98-2.96 (m, 4H), 2.83-2.74 (m, 8H), 2.58 (s, 3H), 1.98-1.95 (m, 1H), 1.79-1.71 (m, 1H). |
| 11-23[10] | N-((2R)-6-(3,8-diazabicyclo[3.2.1]octan-3-yl)-1,2,3,4-tetrahydronaphthalen-2-yl)-7-ethyl-7H-pyrrolo[2,3-c]pyridazine-3-carboxamide | 431 | (CD$_3$OD, 400 MHz) δ (ppm): 8.51 (s, 1H), 8.51 (s, 1H), 7.90 (d, J = 3.6 Hz, 1H), 6.96 (d, J = 8.8 Hz, 1H), 6.75-6.67 (m, 2H), 6.61 (s, 1H), 4.59-4.54 (m, 2H), 4.41-4.36 (m, 1H), 3.62 (s, 2H), 3.46-3.43 (m, 2H), 3.13-3.07 (m, 1H), 2.95-2.80 (m, 5H), 2.19-2.16 (m, 1H), 2.00-1.84 (m, 5H), 1.56-1.53 (m, 3H). |
| 11-24[10] | N-((2S)-6-(3,8-diazabicyclo[3.2.1]octan-3-yl)-1,2,3,4-tetrahydronaphthalen-2-yl)-7-ethyl-7H-pyrrolo[2,3-c]pyridazine-3-carboxamide | 431 | (CD$_3$OD, 400 MHz) δ (ppm): 8.51 (s, 1H), 7.90 (d, J = 3.2 Hz, 1H), 6.96 (d, J = 8.4 Hz, 1H), 6.75-6.61 (m, 3H), 4.59-4.54 (m, 2H), 4.41-4.39 (m, 1H), 3.62 (s, 2H), 3.46-3.43 (m, 2H), 3.12-3.07 (m, 1H), 2.96-2.80 (m, 5H), 2.19-2.17 (m, 1H), 1.99-1.84 (m, 5H), 1.56-1.53 (m, 3H). |

TABLE 16-continued

| Example Number | Structure and Compound Name | LRMS m/z [M + H]+ | 1H NMR |
|---|---|---|---|
| 11-25[11] | 7-amino-3-methyl-N-((S)-6-((S)-3-(methylamino)pyrrolidin-1-yl)-1,2,3,4-tetrahydronaphthalen-2-yl)thieno[2,3-b]pyrazine-6-carboxamide | 437 | (CD$_3$OD, 300 MHz) δ (ppm): 8.57 (s, 1H), 6.95 (d, J = 8.4 Hz, 1H), 6.48 (d, J = 8.4 Hz, 1H), 6.34 (s, 1H), 4.26-4.21 (m, 1H), 3.56-3.41 (m, 3H), 3.13-3.08 (m, 2H), 3.08-2.68 (m, 4H), 2.69 (s, 3H), 2.53 (s, 3H), 2.36-2.30 (m, 1H), 2.18-1.48 (m, 3H). |
| 11-26[11] | 7-amino-3-methyl-N-((R)-6-((S)-3-(methylamino)pyrrolidin-1-yl)-1,2,3,4-tetrahydronaphthalen-2-yl)thieno[2,3-b]pyrazine-6-carboxamide | 437 | (CD$_3$OD, 300 MHz) δ (ppm): 8.57 (s, 1H), 6.95 (d, J = 8.4 Hz, 1H), 6.48 (d, J = 8.4 Hz, 1H), 6.41 (s, 1H), 4.26-4.21 (m, 1H), 3.76-3.74 (m, 1H), 3.54-3.41 (m, 2H), 3.37-3.34 (m, 1H), 3.29-3.27 (m, 1H), 3.03-2.90 (m, 3H), 2.81-2.67 (m, 7H), 2.44-2.41 (m, 1H), 2.15-2.11 (m, 2H), 1.87-1.83 (m, 1H). |
| 11-27[12] | 7-amino-3-methyl-N-((S)-6-((R)-3-(methylamino)pyrrolidin-1-yl)-1,2,3,4-tetrahydronaphthalen-2-yl)thieno[2,3-b]pyrazine-6-carboxamide | 437 | (CD$_3$OD, 400 MHz) δ (ppm): 8.58 (s, 1H), 6.92 (d, J = 8.0 Hz, 1H), 6.42 (d, J = 8.0 Hz, 1H), 6.34 (s, 1H), 4.28-4.23 (m, 1H), 3.51-3.43 (m, 1H), 3.41-3.33 (m, 2H), 3.28-3.24 (m, 1H), 3.15-3.08 (m, 1H), 3.01-2.86 (m, 3H), 2.79-2.70 (m, 1H), 2.69 (s, 3H), 2.44 (s, 3H), 2.31-2.25 (m, 1H), 2.17-2.11 (m, 1H), 1.95-1.81 (m, 2H). |
| 11-28[12] | 7-amino-3-methyl-N-((R)-6-((R)-3-(methylamino)pyrrolidin-1-yl)-1,2,3,4-tetrahydronaphthalen-2-yl)thieno[2,3-b]pyrazine-6-carboxamide | 437 | (CD$_3$OD, 400 MHz) δ (ppm): 8.58 (s, 1H), 6.92 (d, J = 8.0 Hz, 1H), 6.42 (d, J = 8.0 Hz, 1H), 6.34 (s, 1H), 4.32-4.26 (m, 1H), 3.51-3.45 (m, 1H), 3.41-3.33 (m, 2H), 3.28-3.24 (m, 1H), 3.11-3.08 (m, 1H), 3.01-2.86 (m, 3H), 2.79-2.73 (m, 1H), 2.69 (s, 3H), 2.45 (s, 3H), 2.29-2.25 (m, 1H), 2.14-2.11 (m, 1H), 1.95-1.81 (m, 2H). |
| 11-29[13] | N-((S)-6-((1S,4S)-2,5-diaza-bicyclo[2.2.1]heptan-2-yl)-1,2,3,4-tetrahydronaphthalen-2-yl)-7-amino-3-methylthieno[3,2-b]pyrazine-6-carboxamide | 435 | (DMSO-d$_6$, 400 MHz) δ (ppm): 8.65 (s, 1H), 7.80 (d, J = 8.0 Hz, 1H), 6.92 (br s, 2H), 6.85 (d, J = 8.40 Hz, 1H), 6.37-6.34 (br s, 1H), 6.26 (s, 1H), 4.25-4.23 (m, 1H), 4.19-4.06 (m, 1H), 3.56-3.54 (m, 1H), 3.46-3.44 (m, 1H), 2.97-2.71 (m, 7H), 2.68 (s, 3H), 2.20 (br s, 1H), 2.02-1.92 (m, 1H), 1.82-1.71 (m, 2H), 1.65-1.52 (m, 1H). |

TABLE 16-continued

| Example Number | Structure and Compound Name | LRMS m/z [M + H]+ | 1H NMR |
|---|---|---|---|
| 11-30[13] | N-((R)-6-((1S,4S)-2,5-diazabicyclo[2.2.1]heptan-2-yl)-1,2,3,4-tetrahydronaphthalen-2-yl)-7-amino-3-methylthieno[2,3-b]pyrazine-6-carboxamide | 435 | (DMSO-d6, 400 MHz) δ (ppm): 8.65 (s, 1H), 7.80 (d, J = 8.0 Hz, 1H), 6.92 (br s, 2H), 6.85 (d, J = 8.4 Hz, 1H), 6.37-6.34 (br s, 1H), 6.26 (s, 1H), 4.25-4.23 (m, 1H), 4.19-4.05 (m, 1H), 3.56-3.54 (m, 1H), 3.49-3.42 (m, 1H), 2.99-2.71 (m, 7H), 2.65 (s, 3H), 2.20 (br s, 1H), 2.01-1.92 (m, 1H), 1.81-1.69 (m, 2H), 1.64-1.57 (m, 1H). |
| 11-31[14] | N-((S)-6-((1R,4R)-2,5-diazabicyclo[2.2.1]heptan-2-yl)-1,2,3,4-tetrahydronaphthalen-2-yl)-7-amino-3-methylthieno[3,2-b]pyrazine-6-carboxamide | 435 | (DMSO-d6, 400 MHz) δ (ppm): 8.65 (s, 1H). 7.81 (d, J = 7.6 Hz, 1H), 6.93 (s, 2H), 6.85 (d, J = 8.40 Hz, 1H), 6.37-6.34 (m, 1H), 6.26 (d, J = 2.0 Hz, 1H), 4.24 (s, 1H), 4.13-4.10 (m, 1H), 3.56 (s, 1H), 3.47-3.45 (m, 1H), 2.86-2.71 (m, 7H), 2.68-2.65 (m, 4H), 1.98-1.95 (m, 1H), 1.75-1.73 (m, 2H), 1.62-1.58 (m, 1H). |
| 11-32[14] | N-((R)-6-((1R,4R)-2,5-diazabicyclo[2.2.1]heptan-2-yl)-1,2,3,4-tetrahydronaphthalen-2-yl)-7-amino-3-methylthieno[2,3-b]pyrazine-6-carboxamide | 435 | (DMSO-d6, 400 MHz) δ (ppm): 8.65 (s, 1H). 7.81 (d, J = 7.6 Hz, 1H), 6.93 (s, 2H), 6.85 (d, J = 8.40 Hz, 1H), 6.37-6.35 (m, 1H), 6.26 (d, J = 1.6 Hz, 1H), 4.24 (s, 1H), 4.13-4.10 (m, 1H), 3.57 (s, 1H), 3.47-3.45 (m, 1H), 2.86-2.71 (m, 7H), 2.68-2.65 (m, 4H), 1.98-1.95 (m, 1H), 1.76-1.72 (m, 2H), 1.62-1.60 (m, 1H). |
| 11-33[15] | (S)-6-amino-2-methyl-N-(6-(piperazin-1-yl)-1,2,3,4-tetrahydronaphthalen-2-yl)thieno[2,3-d]thiazole-5-carboxamide | 428 | (DMSO-d6, 300 MHz) δ (ppm): 7.45 (d, J = 7.8 Hz, 1H), 7.06 (s, 2H), 6.88 (d, J = 8.7 Hz, 1H), 6.68 (d, J = 8.1 Hz, 1H), 6.60 (s, 1H), 4.10-4.00 (m, 1H), 2.95-2.93 (m, 4H), 2.80-2.63 (m, 12H), 1.94-1.91 (m, 1H), 1.74-1.69 (m, 1H). |
| 11-34[15] | (R)-6-amino-2-methyl-N-(6-(piperazin-1-yl)-1,2,3,4-tetrahydronaphthalen-2-yl)thieno[2,3-d]thiazole-5-carboxamide | 428 | (DMSO-d6, 300 MHz) δ (ppm): 7.45 (d, J = 7.8 Hz, 1H), 7.06 (s, 2H), 6.88 (d, J = 8.7 Hz, 1H), 6.68 (d, J = 8.7 Hz, 1H), 6.60 (s, 1H), 4.10-4.00 (m, 1H), 2.95-2.94 (m, 4H), 2.85-2.63 (m, 12H), 1.95-1.91 (m, 1H), 1.76-1.67 (m, 1H). |

TABLE 16-continued

| Example Number | Structure and Compound Name | LRMS m/z [M + H]+ | 1H NMR |
|---|---|---|---|
| 11-35[16] | N-((2S)-6-(3,6-diazabicyclo[3.1.1]heptan-6-yl)-1,2,3,4-tetrahydronaphthalen-2-yl)-3-amino-6-methylthieno[2,3-b]pyridine-2-carboxamide | 434 | (CD$_3$OD, 300 MHz) (ppm): 8.65-8.43 (m, 1H), 8.19 (d, J = 8.4 Hz, 1H), 7.31 (d, J = 8.1 Hz, 1H), 7.04 (d, J = 8.1 Hz, 1H), 6.42-6.40 (m, 2H), 4.34 (d, J = 6.3 Hz, 1H), 4.35-4.15 (m, 1H), 3.75 (d, J = 13.2 Hz, 2H), 3.19 (d, J = 12.9 Hz, 2H), 3.10-2.86 (m, 4H), 2.85-2.68 (m, 1H), 2.64 (s, 3H), 2.19-2.05 (m, 1H), 1.94-1.75 (m, 2H). |
| 11-36[16] | N-((2R)-6-(3,6-diazabicyclo[3.1.1]heptan-6-yl)-1,2,3,4-tetrahydronaphthalen-2-yl)-3-amino-6-methylthieno[2,3-b]pyridine-2-carboxamide | 434 | (CD$_3$OD, 300 MHz) δ (ppm): 8.51 (s, 1H), 8.20 (d, J = 8.4 Hz, 1H), 7.31 (d, J = 8.4 Hz, 1H), 7.04 (d, J = 8.1 Hz, 1H), 6.48-6.40 (m, 2H), 4.34 (d, J = 6.0 Hz, 2H), 4.28-4.22 (m, 1H), 3.75 (d, J = 13.2 Hz, 2H), 3.19 (d, J = 12.9 Hz, 2H), 3.17-2.76 (m, 5H), 2.64 (s, 3H), 2.19-2.08 (m, 1H), 1.94-1.79 (m, 2H). |
| 11-37[17] | (R)-7-amino-N-(8-fluoro-6-(piperazin-1-yl)-1,2,3,4-tetrahydronaphthalen-2-yl)-3-methylthieno[2,3-b]pyrazine-6-carboxamide | 441 | (DMSO-d$_6$, 300 MHz) δ (ppm): 8.65 (s, 1H), 7.86 (d, J = 7.5 Hz, 1H), 6.93 (s, 2H), 6.58-6.50 (m, 2H), 4.19-4.03 (m, 1H), 3.03-2.73 (m, 11H), 2.65 (s, 3H), 2.61-2.55 (m, 1H), 2.04-1.96 (m, 1H), 1.81-1.69 (m, 1H). |
| 11-38[17] | (S)-7-amino-N-(8-fluoro-6-(piperazin-1-yl)-1,2,3,4-tetrahydronaphthalen-2-yl)-3-methylthieno[2,3-b]pyrazine-6-carboxamide | 441 | (DMSO-d$_6$, 300 MHz) δ (ppm): 8.95 (s, 1H), 7.86 (d, J = 7.5 Hz, 1H), 6.93 (s, 2H), 6.58-6.50 (m, 2H), 4.12-4.11 (m, 1H) 3.02-2.72 (m, 11H), 2.65 (s, 3H), 2.57-2.56 (m, 1H), 2.00-1.96 (m, 1H), 1.81-1.69 (m, 1H). |
| 11-39[18] | N-((2S)-6-(9-oxa-3,7-diazabicyclo[3.3.1]nonan-3-yl)-8-fluoro-1,2,3,4-tetrahydronaphthalen-2-yl)-3-amino-6-methylthieno[2,3-b]pyridine-2-carboxamide | 482 | (CD$_3$OD, 300 MHz) δ (ppm): 8.23 (d, J = 8.4 Hz, 1H), 7.33 (d, J = 8.4 Hz, 1H), 6.70-6.64 (m, 2H), 4.30-4.28 (m, 1H), 3.91 (s, 2H), 3.75 (d, J = 11.7 Hz, 2H), 3.21-2.97 (m, 9H), 2.67-2.56 (m, 4H), 2.15-2.06 (m, 1H), 1.93-1.83 (m, 1H). |

TABLE 16-continued

| Example Number | Structure and Compound Name | LRMS m/z [M + H]+ | 1H NMR |
|---|---|---|---|
| 11-40[18] | N-((2R)-6-(9-oxa-3,7-diazabicyclo[3.3.1]nonan-3-yl)-8-fluoro-1,2,3,4-tetrahydronaphthalen-2-yl)-3-amino-6-methylthieno[2,3-b]pyridine-2-carboxamide | 482 | (CD$_3$OD, 300 MHz) δ (ppm): 8.20 (d, J = 8.1Hz, 1H), 7.31 (d, J = 8.4 Hz, 1H), 6.66-6.62 (m, 2H), 4.30-4.28 (m, 1H), 3.88 (s, 2H), 3.72 (d, J = 12.3 Hz, 2H), 3.30-2.95 (m, 9H), 2.64-2.56 (m, 4H), 2.15-2.06 (m, 1H), 1.93-1.83 (m, 1H). |

[7]Notes on procedures:
In Step 1, the bromide Intermediate 44 and Ruphos Pd G3 as the catalyst were used. In Step 4, the 4 enantiomers were separated by chiral HPLC using the chiral column Cellulose SB and an eluent gradient of 0% to 5% EtOH/MTBE (0.1% Et$_2$NH). Stereochemistry of the separated enantiomers were arbitrarily assigned.
[8]Notes on procedures:
In Step 4, the enantiomers were separated by chiral HPLC using the chiral column Chiralpak ID and mobile phase MeOH. Stereochemistry of the separated enantiomers were arbitrarily assigned.
[9]Notes on procedures:
The enantiomers were separated after the Boc deprotection rather than in Step 4, by chiral HPLC using the chiral column Phenomenex Lux 5 μm Cellulose-4 and mobile phase 50% EtOH/hexanes. Stereochemistry of the separated enantiomers were arbitrarily assigned.
[10]Notes on procedures:
In Step 3, the carboxylic acid Intermediate 26 was used. In Step 4, the enantiomers were separated by chiral HPLC using the chiral column Phenomenex Lux 5 μm Cellulose-4 and mobile phase 50% EtOH/hexanes. Stereochemistry of the separated enantiomers were arbitrarily assigned.
[11]Notes on procedures:
In Step 1, tert-butyl N-methyl-N-[(3S)-pyrrolidin-3-yl]carbamate was used. In Step 4, the enantiomers were separated by chiral HPLC using the chiral column Chiralpak IA and mobile phase 35% EtOH/hexanes. Stereochemistry at the tetrahydronaphthalene amide was arbitrarily assigned.
[12]Notes on procedures:
In Step 1, tert-butyl N-methyl-N-[(3R)-pyrrolidin-3-yl]carbamate was used. In Step 4, the enantiomers were separated by chiral HPLC using the chiral column (R,R)-Whelk-O1-Kromasil and mobile phase 30% DCM/EtOH. Stereochemistry at the tetrahydronaphthalene amide was arbitrarily assigned.
[13]Notes on procedures:
In Step 1, tert-butyl (1S,4S)-2,5-diazabicyclo[2.2.1]heptane-2-carboxylate and Ruphos Pd G3 as the catalyst were used. In Step 4, the enantiomers were separated by chiral HPLC using the chiral column Chiralpak ID and an eluent gradient of 60% to 65% MeOH/DCM. Stereochemistry at the tetrahydronaphthalene amide was arbitrarily assigned.
[14]Notes on procedures:
In Step 1, tert-butyl (1R,4R)-2,5-diazabicyclo[2.2.1]heptane-2-carboxylate and Ruphos Pd G3 as the catalyst were used. In Step 4, the enantiomers were separated by chiral HPLC using the chiral column Chiralpak AD-H-SL001 and mobile phase 40% IPA/hexanes (0.1% Et$_2$NH). Stereochemistry at the tetrahydronaphthalene amide was arbitrarily assigned.
[15]Notes on procedures:
In Step 3, the carboxylic acid Intermediate 24 was used. In Step 4, the enantiomers were separated by SFC using the chiral column Phenomenex Lux 5 μm Cellulose-4 and mobile phase 60% EtOH/hexanes. Stereochemistry of the separated enantiomers were arbitrarily assigned.
[16]Notes on procedures:
Example 11 Method 2 was used. In Step 1, Ruphos Pd G3 was used as the catalyst.
[17]Notes on procedures:
In Step 1, the bromide Intermediate 11-1 was used. In Step 4, the enantiomers were separated by SFC using the chiral column Phenomenex Lux 5 μm Cellulose-4 and mobile phase 50% CO$_2$/EtOH:ACN (1:1). Stereochemistry of the separated enantiomers were arbitrarily assigned.
[18]Notes on procedures:
In Step 1, the bromide Intermediate 11-1 and Ruphos Pd G3 as the catalyst were used. In Step 4, the enantiomers were separated by chiral HPLC using the chiral column Phenomenex Lux 5 μm Cellulose-4 and mobile phase 50% EtOH/hexanes. Stereochemistry of the separated enantiomers were arbitrarily assigned.

Example 14-1. N-((2R)-6-(3,8-diazabicyclo[3.2.1]octan-3-yl)-5-cyano-1,2,3,4-tetrahydronaphthalen-2-yl)-3-amino-6-methylthieno[2,3-b]pyridine-2-carboxamide Example 14-2. N-((2S)-6-(3,8-diazabicyclo[3.2.1]octan-3-yl)-5-cyano-1,2,3,4-tetrahydronaphthalen-2-yl)-3-amino-6-methylthieno[2,3-b]pyridine-2-carboxamide Example 14-3. N-((2R)-6-(3,8-diazabicyclo[3.2.1]octan-3-yl)-7-cyano-1,2,3,4-tetrahydronaphthalen-2-yl)-3-amino-6-methylthieno[2,3-b]pyridine-2-carboxamide and Example 14-4. N-((2S)-6-(3,8-diazabicyclo[3.2.1]octan-3-yl)-7-cyano-1,2,3,4-tetrahydronaphthalen-2-yl)-3-amino-6-methylthieno[2,3-b]pyridine-2-carboxamide

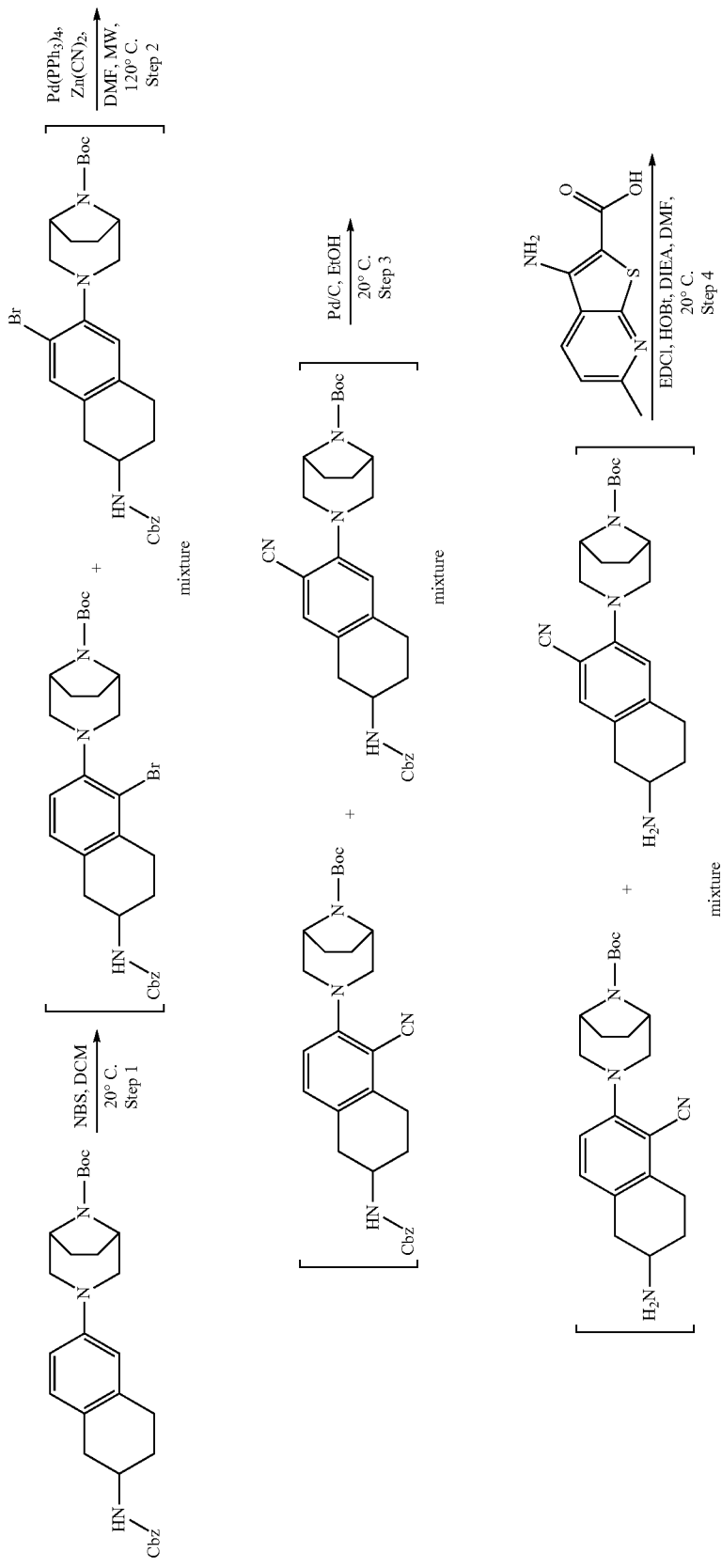

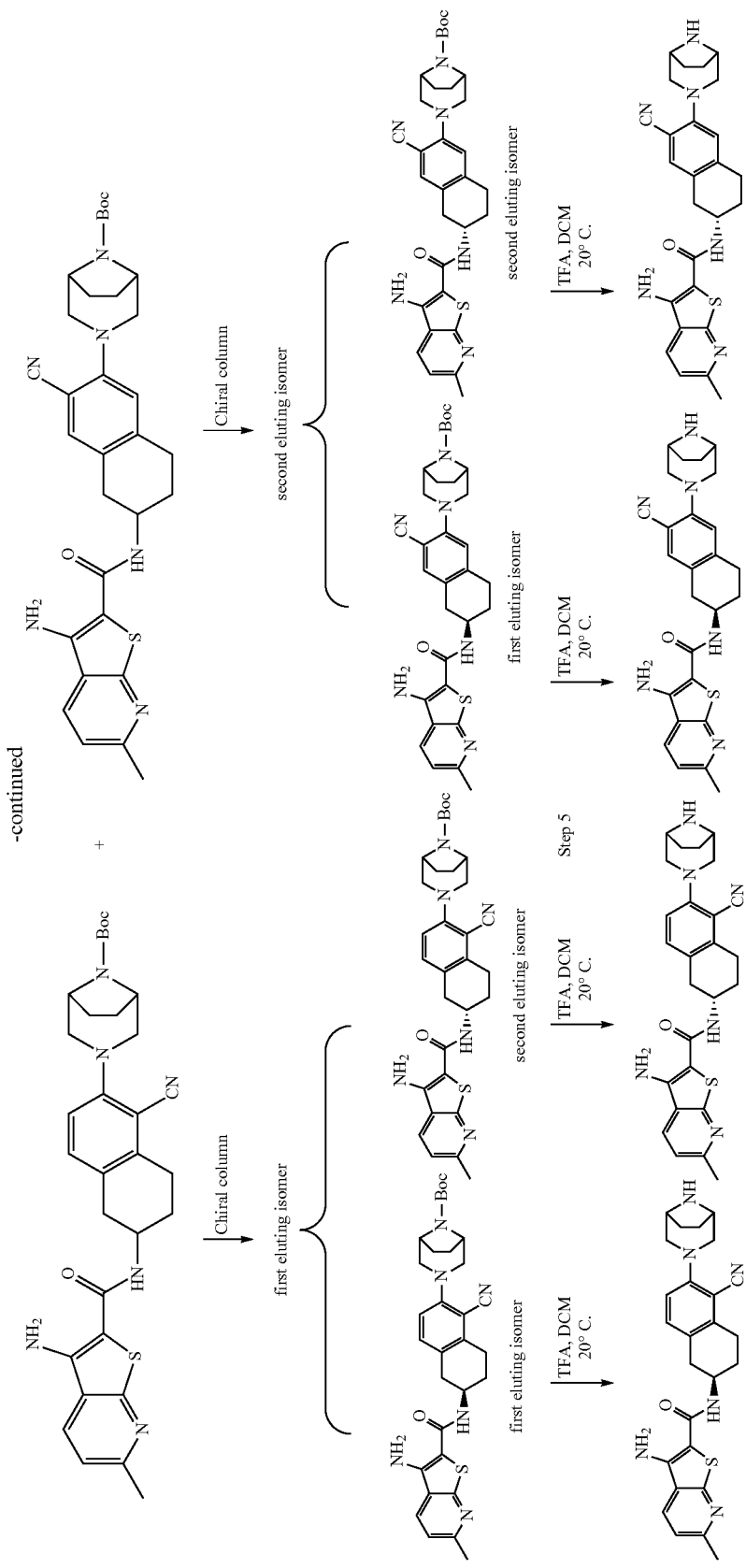

Step 1. Mixture of racemic tert-butyl 3-(6-(((benzyloxy)carbonyl)amino)-1-bromo-5,6,7,8-tetrahydronaphthalen-2-yl)-3,8-diazabicyclo[3.2.1]octane-8-carboxylate and racemic tert-butyl 3-(6-(((benzyloxy)carbonyl)amino)-3-bromo-5,6,7,8-tetrahydronaphthalen-2-yl)-3,8-diazabicyclo[3.2.1]octane-8-carboxylate Into a 250-mL round-bottom flask was added tert-butyl 3-(6-[[(benzyloxy)carbonyl]amino]-5,6,7,8-tetrahydronaphthalen-2-yl)-3,8-diazabicyclo[3.2.1]octane-8-carboxylate (1.2 g, 2.44 mmol) and DCM (96 mL). This was followed by the addition of a solution of NBS (478 mg, 2.69 mmol) in DCM (24 mL) dropwise with stirring at 0° C. The resulting solution was stirred for 2 h at 20° C., then was quenched by the addition of water (20 mL). The resulting solution was extracted with DCM (3×30 mL). The organic layers were combined, dried over anhydrous sodium sulfate, filtered and concentrated under vacuum to afford a residue that was purified by silica gel chromatography eluting with ethyl acetate/pet. ether (PE/EA=100:1 to 5:1) to afford a mixture of tert-butyl 3-(6-[[(benzyloxy)carbonyl]amino]-3-bromo-5,6,7,8-tetrahydronaphthalen-2-yl)-3,8-diazabicyclo[3.2.1]octane-8-carboxylate and tert-butyl 3-(6-[[(benzyloxy)carbonyl]amino]-1-bromo-5,6,7,8-tetrahydronaphthalen-2-yl)-3,8-diazabicyclo[3.2.1]octane-8-carboxylate as a yellow solid. MS: (ESI, m/z): 572 [M+H]$^+$.

Step 2. Mixture of racemic tert-butyl 3-(6-[[(benzyloxy)carbonyl]amino]-3-cyano-5,6,7,8-tetrahydronaphthalen-2-yl)-3,8-diazabicyclo[3.2.1]octane-8-carboxylate and tert-butyl 3-(6-[[(benzyloxy)carbonyl]amino]-1-cyano-5,6,7,8-tetrahydronaphthalen-2-yl)-3,8-diazabicyclo[3.2.1]octane-8-carboxylate Into a 20-mL sealed tube purged and maintained with an inert atmosphere of nitrogen, was added a mixture of tert-butyl 3-(6-[[(benzyloxy)carbonyl]amino]-3-bromo-5,6,7,8-tetrahydronaphthalen-2-yl)-3,8-diazabicyclo[3.2.1]octane-8-carboxylate and tert-butyl 3-(6-[[(benzyloxy)carbonyl]amino]-1-bromo-5,6,7,8-tetrahydronaphthalen-2-yl)-3,8-diazabicyclo[3.2.1]octane-8-carboxylate (460 mg, 0.81 mmol), Zn(CN)$_2$ (93 mg, 0.80 mmol,), Pd(PPh$_3$)$_4$ (93 mg, 0.08 mmol), and N,N-dimethylformamide (9 mL). The resulting mixture was irradiated with microwave for 1 h at 120° C. The reaction was cooled to room temperature and quenched by the addition of 20 mL of water. The resulting solution was extracted with ethyl acetate (3×15 mL). The organic layers were combined, dried over anhydrous sodium sulfate, filtered and concentrated under vacuum to afford a residue that was purified by silica gel chromatography and eluted with 100:1 to 2:1 ethyl acetate/pet. ether to afford a mixture of tert-butyl 3-(6-[[(benzyloxy)carbonyl]amino]-3-cyano-5,6,7,8-tetrahydronaphthalen-2-yl)-3,8-diazabicyclo[3.2.1]octane-8-carboxylate and tert-butyl 3-(6-[[(benzyloxy)carbonyl]amino]-1-cyano-5,6,7,8-tetrahydronaphthalen-2-yl)-3,8-diazabicyclo[3.2.1]octane-8-carboxylate as yellow oil. MS: (ESI, m/z): 517 [M+H]$^+$.

Step 3. Mixture of racemic tert-butyl 3-(6-amino-3-cyano-5,6,7,8-tetrahydronaphthalen-2-yl)-3,8-diazabicyclo[3.2.1]octane-8-carboxylate and racemic tert-butyl 3-(6-amino-1-cyano-5,6,7,8-tetrahydronaphthalen-2-yl)-3,8-diazabicyclo[3.2.1]octane-8-carboxylate Into a 50-mL round-bottom flask purged and maintained with nitrogen, was added a mixture of tert-butyl 3-(6-[[(benzyloxy)carbonyl]amino]-3-cyano-5,6,7,8-tetrahydronaphthalen-2-yl)-3,8-diazabicyclo[3.2.1]octane-8-carboxylate and tert-butyl 3-(6-[[(benzyloxy)carbonyl]amino]-1-cyano-5,6,7,8-tetrahydronaphthalen-2-yl)-3,8-diazabicyclo[3.2.1]octane-8-carboxylate (300 mg, 0.58 mmol), ethanol (20 mL), and Palladium carbon (300 mg). The resulting suspenstion was stirred for 1 h at 20° C. under hydrogen atmosphere. The solids were removed by filtration over celite and the filtrate was concentrated under vacuum to afford a crude residue that was purified by silica gel chromatography and eluted with DCM/methanol (DCM/MeOH=10:1) to afford a mixture of tert-butyl 3-(6-amino-3-cyano-5,6,7,8-tetrahydronaphthalen-2-yl)-3,8-diazabicyclo[3.2.1]octane-8-carboxylate and tert-butyl 3-(6-amino-1-cyano-5,6,7,8-tetrahydronaphthalen-2-yl)-3,8-diazabicyclo[30.2.1]octane-8-carboxylate as yellow oil. MS: (ESI, m/z): 383 [M+H]$^+$.

Step 4. tert-Butyl 3-((R)-6-(3-amino-6-methylthieno[2,3-b]pyridine-2-carboxamido)-1-cyano-5,6,7,8-tetrahydronaphthalen-2-yl)-3,8-diazabicyclo[3.2.1]octane-8-carboxylate (Peak A, enantiomer 1)

tert-butyl 3-((S)-6-(3-amino-6-methylthieno[2,3-b]pyridine-2-carboxamido)-1-cyano-5,6,7,8-tetrahydronaphthalen-2-yl)-3,8-diazabicyclo[3.2.1]octane-8-carboxylate (Peak A, enantiomer 2)

tert-butyl 3-((R)-6-(3-amino-6-methylthieno[2,3-b]pyridine-2-carboxamido)-3-cyano-5,6,7,8-tetrahydronaphthalen-2-yl)-3,8-diazabicyclo[3.2.1]octane-8-carboxylate (Peak B, enantiomer 1)

tert-butyl 3-((S)-6-(3-amino-6-methylthieno[2,3-b]pyridine-2-carboxamido)-3-cyano-5,6,7,8-tetrahydronaphthalen-2-yl)-3,8-diazabicyclo[3.2.1]octane-8-carboxylate (Peak B, enantiomer 2)

Into a 100-mL round-bottom flask was placed the mixture of tert-butyl 3-(6-amino-1-cyano-5,6,7,8-tetrahydronaphthalen-2-yl)-3,8-diazabicyclo[3.2.1]octane-8-carboxylate and tert-butyl 3-(6-amino-3-cyano-5,6,7,8-tetrahydronaphthalen-2-yl)-3,8-diazabicyclo[3.2.1]octane-8-carboxylate (150 μmg, 0.39 mmol), EDCI (90 mg, 0.47 mmol), HOBt (63 mg, 0.47 mmol,), DIEA (152 mg, 1.18 mmol), N,N-dimethylformamide (10 mL), and 3-amino-6-methylthieno[2,3-b]pyridine-2-carboxylic acid (98 mg, 0.47 mmol). The resulting solution was stirred for 2 h at 20° C., then was quenched by the addition of 20 mL of water. The solids were collected by filtration, and the solids were purified by prep-HPLC (Column: XBridge BEH C18 OBD, 5 m, 19×150 mm; Mobile phase: water (10 mM NH$_4$HCO$_3$), ACN (55% ACN up to 70% over 7 min)).

This mixture was then further purified by chiral HPLC (Column: Chiralpak OD-H, 5 μm, 20×250 mm; Mobile phase A: hexanes, B: EtOH, 50% B). This resulted in a single regioisomer peak A: (RT=8.45 min) and single regioisomer peak B: (RT=12.91 min).

The peak A was further purified by chiral HPLC (Column: Chiralpak IC, 5 μm, 20×250 mm; Mobile phase A: hexanes, B: EtOH, 50% B). This resulted in peak A, enantiomer 1: (RT=15.55 min) as a yellow solid and peak A, enantiomer 2: (RT=21.10 min) as a yellow solid. Stereochemistry of the separated peak A enantiomers were arbitrarily assigned. MS (for both enantiomers): (ESI, m/z): 573 [M+H]$^+$.

The peak B was further purified by chiral HPLC (Column: Chiralpak IB, 5 μm, 20×250 mm; Mobile phase A: hexanes, B: EtOH, 50% B). This resulted in peak B, enantiomer 1: (RT=7.65 min) as a yellow solid and peak B,enantiomer 2:

(RT=9.22 min) as a yellow solid. Stereochemistry of the separated peak B enantiomers were arbitrarily assigned. MS (for both enantiomers): (ESI, m/z): 573 [M+H]+.

Step 5. N-((2R)-6-(3,8-diazabicyclo[3.2.1]octan-3-yl)-5-cyano-1,2,3,4-tetrahydronaphthalen-2-yl)-3-amino-6-methylthieno[2,3-b]pyridine-2-carboxamide N-((2S)-6-(3,8-diazabicyclo[3.2.1]octan-3-yl)-5-cyano-1,2,3,4-tetrahydronaphthalen-2-yl)-3-amino-6-methylthieno[2,3-b]pyridine-2-carboxamide N-((2R)-6-(3,8-diazabicyclo[3.2.1]octan-3-yl)-7-cyano-1,2,3,4-tetrahydronaphthalen-2-yl)-3-amino-6-methylthieno[2,3-b]pyridine-2-carboxamide N-((2S)-6-(3,8-diazabicyclo[3.2.1]octan-3-yl)-7-cyano-1,2,3,4-tetrahydronaphthalen-2-yl)-3-amino-6-methylthieno[2,3-b]pyridine-2-carboxamide Representative Procedure and Spectra for the First Isomer:
Into a 50-mL round-bottom flask, was added tert-butyl 3-[(6R)-6-[3-amino-6-methylthieno[2,3-b]pyridine-2-amido]-1-cyano-5,6,7,8-tetrahydronaphthalen-2-yl]-3,8-diazabicyclo[3.2.1]octane-8-carboxylate (30 mg, 0.05 mmol), DCM (5 mL), and TFA (1 mL). The resulting solution was stirred for 1 h at 20° C., then was concentrated under vacuum to afford a crude residue that was diluted with 5 mL of DCM. The pH of the solution was adjusted to 8 with $NH_3$ in MeOH (7 M), then the resulting mixture was concentrated under vacuum to a residue that was purified by prep-HPLC (Column: XBridge BEH C18 OBD Prep Column, 130 Å, 5 μm, 19×150 mm; Mobile phase: water (10 mmol $NH_4HCO_3$), ACN (35% ACN up to 56% over 7 μmin)) to afford N-((2R)-6-(3,8-diazabicyclo[3.2.1]octan-3-yl)-5-cyano-1,2,3,4-tetrahydronaphthalen-2-yl)-3-amino-6-methylthieno[2,3-b]pyridine-2-carboxamide as a light yellow solid. $^1$H NMR (400 MHz, MeOH-$d_4$) δ(ppm): 8.20 (d, J=8.3 Hz, 1H), 7.29-7.30 (m, 2H), 6.94 (d, J=8.5 Hz, 1H), 4.21-4.24 (m, 1H), 3.55 (s, 2H), 3.20-3.27 (m, 2H), 2.91-3.19 (m, 5H), 2.79-2.80 (m, 1H), 2.64 (s, 3H), 2.18-2.20 (m, 3H), 1.79-1.94 (m, 3H). MS: (ESI, m/z): 473 [M+H]+.

The following examples in Table 18 were prepared using standard chemical manipulations and procedures similar to those used for the preparation of Example 14-1.

TABLE 18

| Example Number | Structure and Compound Name | LRMS m/z [M + H]+ | $^1$H NMR |
|---|---|---|---|
| 14-5 | N-((2R)-6-(3,8-diazabicyclo[3.2.1]octan-3-yl)-5-cyano-1,2,3,4-tetrahydronaphthalen-2-yl)-7-amino-3-methylthieno[2,3-b]pyrazine-6-carboxamide | 474 | (CD$_3$OD, 300 MHz) δ (ppm): 8.54 (s, 1H), 7.33 (s, 1H), 6.85 (s, 1H), 4.28-4.18 (m, 1H), 3.61-3.51 (m, 2H), 3.35-3.31 (m, 2H), 3.05-2.92 (m, 5H), 2.83-2.69 (m, 1H), 2.65 (s, 3H), 2.17-2.09 (m, 3H), 1.98-1.70 (m, 3H). |
| 14-6 | N-((2S)-6-(3,8-diazabicyclo[3.2.1]octan-3-yl)-5-cyano-1,2,3,4-tetrahydronaphthalen-2-yl)-7-amino-3-methylthieno[2,3-b]pyrazine-6-carboxamide | 474 | (CD$_3$OD, 300 MHz) δ (ppm): 8.55 (s, 1H), 7.28 (d, J = 8.4 Hz, 1H), 6.94 (d, J = 8.4 Hz, 1H), 4.27-4.19 (m, 1H), 3.61-3.59 (m, 2H), 3.33-3.31 (m, 2H), 3.18-2.88 (m, 5H), 2.83-2.74 (m, 1H), 2.65 (s, 3H), 2.25-2.12 (m, 3H), 1.92-1.75 (m, 3H). |
| 14-7 | N-((2R)-6-(3,8-diazabicyclo[3.2.1]octan-3-yl)-7-cyano-1,2,3,4-tetrahydronaphthalen-2-yl)-7-amino-3-methylthieno[2,3-b]pyrazine-6-carboxamide | 474 | (CD$_3$OD, 400 MHz) δ (ppm): 8.58 (s, 1H), 7.31 (d, J = 8.4 Hz, 1H), 6.97 (d, J = 8.4 Hz, 1H), 4.35-4.18 (m, 1H), 3.62-3.59 (m, 2H), 3.35-3.32 (m, 2H), 3.15-2.96 (m, 5H), 2.86-2.77 (m, 1H), 2.68 (s, 3H), 2.28-2.18 (m, 3H), 1.96-1.82 (m, 3H). |

TABLE 18-continued

| Example Number | Structure and Compound Name | LRMS m/z [M + H]+ | 1H NMR |
|---|---|---|---|
| 14-8 | 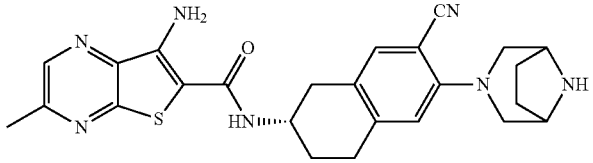 [SMILES: Cc1cnc2c(N)c(C(=O)N[C@H]3CCc4cc(N5CC6CCC(C5)N6)c(C#N)cc4C3)sc2n1]<br>N-((2S)-6-(3,8-diazabicyclo[3.2.1]octan-3-yl)-7-cyano-1,2,3,4-tetrahydronaphthalen-2-yl)-7-amino-3-methylthieno[2,3-b]pyrazine-6-carboxamide | 474 | (CD$_3$OD, 400 MHz) δ (ppm): 8.54 (s, 1H), 7.32 (s, 1H), 6.84 (s, 1H), 4.28-4.17 (m, 1H), 3.53-3.49 (m, 2H), 3.28-3.23 (m, 2H), 3.06-2.92 (m, 5H), 2.81-2.70 (m, 1H), 2.64 (s, 3H), 2.18-2.08 (m, 3H), 1.89-1.75 (m, 3H). |
| 14-9[1,2] | 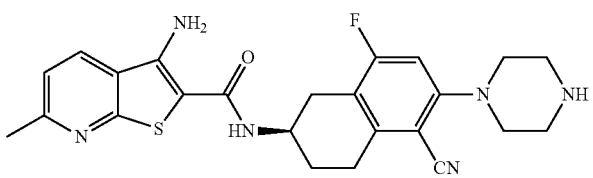 [SMILES: Cc1ccc2c(N)c(C(=O)N[C@@H]3CCc4c(C#N)c(N5CCNCC5)cc(F)c4C3)sc2n1]<br>(R)-3-amino-N-(5-cyano-8-fluoro-6-(piperazin-1-yl)-1,2,3,4-tetrahydronaphthalen-2-yl)-6-methylthieno[2,3-b]pyridine-2-carboxamide | 465 | (DMSO-d$_6$, 400 MHz) δ (ppm): 8.31 (d, J = 8.4 Hz, 1H), 7.67 (d, J = 7.6 Hz, 1H), 7.31 (d, J = 8.4 Hz, 1H), 7.18 (s, 2H), 6.86 (d, J = 11.6 Hz, 1H), 4.15 (s, 1H), 3.06-2.87 (m, 11H), 2.67-2.58 (m, 4H), 2.08-1.81 (m, 2H), 1.23 (s, 1H), 1.16-1.12 (m, 1H), 0.86 (s, 1H). |
| 14-10[1,2] | 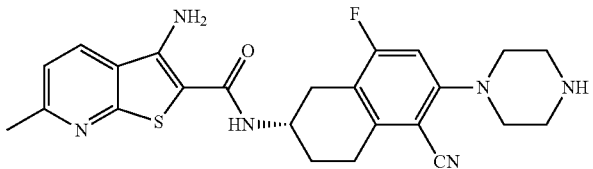 [SMILES: Cc1ccc2c(N)c(C(=O)N[C@H]3CCc4c(C#N)c(N5CCNCC5)cc(F)c4C3)sc2n1]<br>(S)-3-amino-N-(5-cyano-8-fluoro-6-(piperazin-1-yl)-1,2,3,4-tetrahydronaphthalen-2-yl)-6-methylthieno[2,3-b]pyridine-2-carboxamide | 465 | (DMSO-d$_6$, 400 MHz) δ (ppm): 8.31 (d, J = 8.4 Hz, 1H), 7.67 (d, J = 7.6 Hz, 1H), 7.31 (d, J = 8.4 Hz, 1H), 7.23 (s, 2H), 6.87 (d, J = 11.2 Hz, 1H), 4.15 (s, 1H), 3.07-2.82 (m, 11H), 2.78-2.58 (m, 4H), 2.11-1.80 (m, 2H), 1.23 (s, 1H), 1.17-1.13 (m, 1H), 0.86 (s, 1H). |
| 14-11[1,3] | 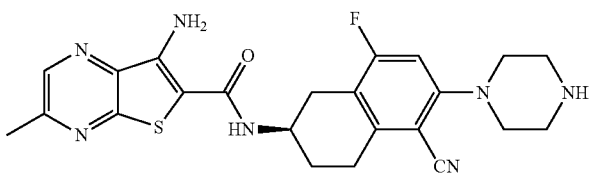 [SMILES: Cc1cnc2c(N)c(C(=O)N[C@@H]3CCc4c(C#N)c(N5CCNCC5)cc(F)c4C3)sc2n1]<br>(R)-7-amino-N-(5-cyano-8-fluoro-6-(piperazin-1-yl)-1,2,3,4-tetrahydronaphthalen-2-yl)-3-methylthieno[2,3-b]pyrazine-6-carboxamide | 466 | (DMSO-d$_6$, 400 MHz) δ (ppm): 8.65 (s, 1H), 7.92 (br s, 1H), 6.95 (br s, 2H), 6.88 (d, J = 11.6 Hz, 1H), 4.30-4.10 (m, 1H), 3.10-2.80 (m, 11H), 2.62-2.55 (m, 4H), 2.15-2.00 (m, 1H), 1.90-1.75 (m, 1H). |
| 14-12[1,3] | 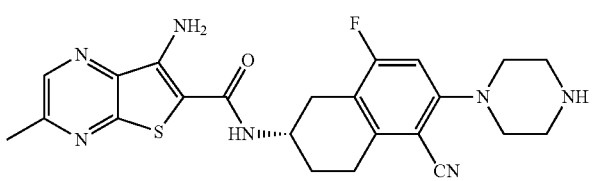<br>(S)-7-amino-N-(5-cyano-8-fluoro-6-(piperazin-1-yl)-1,2,3,4-tetrahydronaphthalen-2-yl)-3-methylthieno[2,3-b]pyrazine-6-carboxamide | 466 | (DMSO-d$_6$, 400 MHz) δ (ppm): 8.65 (s, 1H), 7.91 (br s, 1H), 6.94 (br s, 2H), 6.88 (d, J = 11.6 Hz, 1H), 4.30-4.10 (m, 1H), 3.10-2.80 (m, 11H), 2.62-2.55 (m, 4H), 2.15-2.00 (m, 1H), 1.90-1.75 (m, 1H). |

TABLE 18-continued

| Example Number | Structure and Compound Name | LRMS m/z [M + H]+ | 1H NMR |
|---|---|---|---|
| 14-13[1,4] | 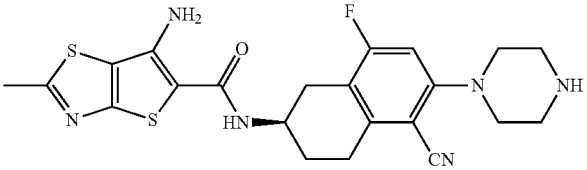 [SMILES: Cc1nc2sc(C(=O)N[C@@H]3CCc4c(C#N)c(N5CCNCC5)cc(F)c4C3)c(N)c2s1]<br>(R)-6-amino-N-(5-cyano-8-fluoro-6-(piperazin-1-yl)-1,2,3,4-tetrahydronaphthalen-2-yl)-2-methylthieno[2,3-d]thiazole-5-carboxamide | 471 | (DMSO-$d_6$, 400 MHz) δ (ppm): 7.58 (br s, 1H), 7.10 (br s, 2H), 6.85 (d, J = 11.6 Hz, 1H), 4.20-4.05 (m, 1H), 3.04-3.01 (m, 11H), 2.84 (s, 3H), 2.67-2.55 (m, 1H), 2.04-2.03 (m, 1H), 1.81-1.77 (m, 1H). |
| 14-14[1,4] | 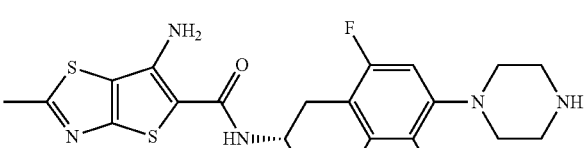<br>(S)-6-amino-N-(5-cyano-8-fluoro-6-(piperazin-1-yl)-1,2,3,4-tetrahydronaphthalen-2-yl)-2-methylthieno[2,3-d]thiazole-5-carboxamide | 471 | (DMSO-$d_6$, 400 MHz) δ (ppm): 7.58 (br s, 1H), 7.10 (br s, 2H), 6.84 (d, J = 11.6 Hz, 1H), 4.20-4.05 (m, 1H), 3.04-3.01 (m, 11H), 2.84 (s, 3H), 2.67-2.55 (m, 1H), 2.04-2.03 (m, 1H), 1.81-1.77 (m, 1H). |
| 14-15[1,5] | 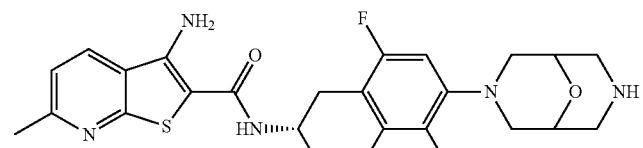<br>3-amino-N-[(2S)-5-cyano-8-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 507 | (DMSO-$d_6$, 400 MHz) δ (ppm): 8.31 (d, J = 8.0 Hz, 1H), 7.69 (d, J = 7.2 Hz, 1H), 7.31 (d, J = 8.4 Hz, 1H), 7.19 (br s, 2H), 6.95 (d, J = 11.6 Hz, 1H), 4.16-4.14 (m, 1H), 3.71-3.69 (m, 2H), 3.56-3.53 (m, 2H), 3.33-3.30 (m, 2H), 3.15-2.95 (m, 7H), 2.67-2.60 (m, 1H), 2.58 (s, 3H), 2.09-2.05 (m, 1H), 1.88-1.82 (m, 1H). |
| 14-16[1,5] | 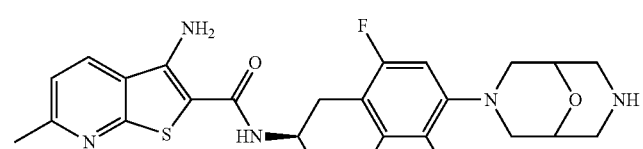<br>3-amino-N-[(2R)-5-cyano-8-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 507 | (DMSO-$d_6$, 400 MHz) δ (ppm): 8.31 (d, J = 8.0 Hz, 1H), 7.69 (d, J = 7.8 Hz, 1H), 7.31 (d, J = 8.4 Hz, 1H), 7.19 (br s, 2H), 6.95 (d, J = 11.6 Hz, 1H), 4.16-4.14 (m, 1H), 3.71-3.69 (m, 2H), 3.53-3.50 (m, 2H), 3.31-3.27 (m, 2H), 3.16-2.95 (m, 7H), 2.67-2.60 (m, 1H), 2.58 (s, 3H), 2.08-2.05 (m, 1H), 1.88-1.82 (m, 1H). |
| 14-17[1,6] | 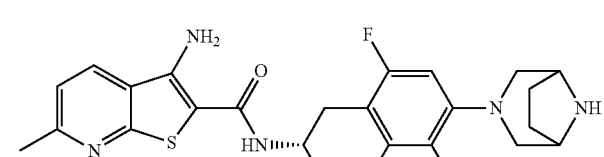<br>3-amino-N-[(2S)-5-cyano-6-{3,8-diazabicyclo[3.2.1]octan-3-yl}-8-fluoro-1,2,3,4-tetrahydronaphthalen-2-yl]-6-methylthieno[2,3-b]pyridine-2-carboxamide | 491 | (DMSO-$d_6$, 300 MHz) δ (ppm): 8.30 (d, J = 8.1 Hz, 1H), 7.66 (d, J = 7.5 Hz, 1H), 7.31 (d, J = 8.1 Hz, 1H), 7.18 (br s, 2H), 6.78 (d, J = 12.0 Hz, 1H), 4.15-4.14 (m, 1H), 3.44-3.42 (m, 2H), 3.33-3.25 (m, 2H), 3.05-2.82 (m, 5H), 2.61-2.55 (m, 4H), 2.07-2.03 (m, 1H), 1.94-1.75 (m, 3H), 1.66-1.63 (m, 2H). |

TABLE 18-continued

| Example Number | Structure and Compound Name | LRMS m/z [M + H]+ | 1H NMR |
|---|---|---|---|
| 14-18[1,6] | 3-amino-N-[(2R)-5-cyano-6-{3,8-diazabicyclo[3.2.1]octan-3-yl}-8-fluoro-1,2,3,4-tetrahydronaphthalen-2-yl]-6-methylthieno[2,3-b]pyridine-2-carboxamide | 491 | (DMSO-$d_6$, 300 MHz) δ (ppm): 8.30 (d, J = 8.1 Hz, 1H), 7.66 (d, J = 7.5 Hz, 1H), 7.31 (d, J = 8.1 Hz, 1H), 7.18 (br s, 2H), 6.78 (d, J = 11.7 Hz, 1H), 4.15-4.14 (m, 1H), 3.45-3.43 (m, 2H), 3.33-3.25 (m, 2H), 3.05-2.82 (m, 5H), 2.61-2.55 (m, 4H), 2.37 (br s, 1H), 2.07-2.03 (m, 1H), 1.94-1.75 (m, 3H), 1.66-1.63 (m, 2H). |
| 14-19[1,7] | 7-amino-N-[(2S)-5-cyano-6-{3,8-diazabicyclo[3.2.1]octan-3-yl}-8-fluoro-1,2,3,4-tetrahydronaphthalen-2-yl]-3-methylthieno[2,3-b]pyrazine-6-carboxamide | 492 | (DMSO-$d_6$, 300 MHz) δ (ppm): 8.65 (s, 1H), 7.90 (br s, 1H), 6.94 (br s, 2H), 6.79 (d, J = 11.7 Hz, 1H), 4.18-4.14 (m, 1H), 3.46-3.44 (m, 2H), 3.32-3.23 (m, 2H), 3.05-2.82 (m, 6H), 2.65 (s, 3H), 2.64-2.56 (m, 1H), 2.08-1.82 (m, 4H), 1.66-1.64 (m, 2H). |
| 14-20[1,7] | 7-amino-N-[(2R)-5-cyano-6-{3,8-diazabicyclo[3.2.1]octan-3-yl}-8-fluoro-1,2,3,4-tetrahydronaphthalen-2-yl]-3-methylthieno[2,3-b]pyrazine-6-carboxamide | 492 | (DMSO-$d_6$, 300 MHz) δ (ppm): 8.65 (s, 1H), 7.90 (br s, 1H), 6.94 (br s, 2H), 6.79 (d, J = 12.0 Hz, 1H), 4.18-4.15 (m, 1H), 3.44-3.42 (m, 2H), 3.32-3.22 (m, 2H), 3.05-2.82 (m, 6H), 2.65 (s, 3H), 2.64-2.56 (m, 1H), 2.08-1.82 (m, 4H), 1.68-1.64 (m, 2H). |
| 14-21[1,8] | 6-amino-N-[(2S)-5-cyano-6-{3,8-diazabicyclo[3.2.1]octan-3-yl}-8-fluoro-1,2,3,4-tetrahydronaphthalen-2-yl]-2-methylthieno[2,3-d][1,3]thiazole-5-carboxamide | 497 | (DMSO-$d_6$, 400 MHz) δ (ppm): 7.57 (br s, 1H), 7.11 (br s, 2H), 6.79 (d, J = 12.0 Hz, 1H), 4.11 (br s, 1H), 3.45-3.43 (m, 2H), 3.27-3.22 (m, 2H), 3.04-2.82 (m, 5H), 2.79 (s, 3H), 2.61-2.52 (m, 1H), 2.05-1.96 (m, 1H), 1.94-1.86 (m, 2H), 1.84-1.76 (m, 1H), 1.66-1.63 (m, 2H). |
| 14-22[1,8] | 6-amino-N-[(2R)-5-cyano-6-{3,8-diazabicyclo[3.2.1]octan-3-yl}-8-fluoro-1,2,3,4-tetrahydronaphthalen-2-yl]-2-methylthieno[2,3-d][1,3]thiazole-5-carboxamide | 497 | (DMSO-$d_6$, 400 MHz) δ (ppm): 7.59 (br s, 1H), 7.11 (br s, 2H), 6.79 (d, J = 12.0 Hz, 1H), 4.13-4.09 (m, 1H), 3.45-3.44 (m, 2H), 3.27-3.22 (m, 2H), 3.03-2.84 (m, 5H), 2.79 (s, 3H), 2.60-2.51 (m, 1H), 2.04-1.95 (m, 1H), 1.93-1.90 (m, 2H), 1.81-1.70 (m, 1H), 1.65-1.60 (m, 2H). |

TABLE 18-continued

| Example Number | Structure and Compound Name | LRMS m/z [M + H]+ | 1H NMR |
|---|---|---|---|
| 14-23[1,9,10] | 3-amino-N-[(2S)-6-[(3S,4S)-3-amino-4-methoxypyrrolidin-1-yl]-5-cyano-8-fluoro-1,2,3,4-tetrahydronaphthalen-2-yl]-6-methylthieno[2,3-b]pyridine-2-carboxamide | 495 | (DMSO-$d_6$, 400 MHz) δ (ppm): 8.31 (d, J = 8.4 Hz, 1H), 7.63 (d, J = 7.6 Hz, 1H), 7.31 (d, J = 8.4 Hz, 1H), 7.17 (br s, 2H), 6.48 (d, J = 12.4 Hz, 1H), 4.14-4.08 (m, 1H), 3.84-3.81 (m, 1H), 3.73-3.65 (m, 2H), 3.47-3.41 (m, 1H), 3.38-3.32 (m, 1H), 3.30 (s, 3H), 3.27-3.23 (m, 1H), 3.05-3.00 (m, 1H), 2.92-2.82 (m, 2H), 2.58 (s, 3H), 2.55-2.51 (m, 1H), 2.07-2.02 (m, 1H), 1.85-1.73 (m, 2H). |
| 14-24[1,9,10] | 3-amino-N-[(2R)-6-[(3S,4S)-3-amino-4-methoxypyrrolidin-1-yl]-5-cyano-8-fluoro-1,2,3,4-tetrahydronaphthalen-2-yl]-6-methylthieno[2,3-b]pyridine-2-carboxamide | 495 | (DMSO-$d_6$, 400 MHz) δ (ppm): 8.31 (d, J = 8.4 Hz, 1H), 7.64 (d, J = 7.6 Hz, 1H), 7.31 (d, J = 8.4 Hz, 1H), 7.17 (br s, 2H), 6.48 (d, J = 12.8 Hz, 1H), 4.14-4.08 (m, 1H), 3.86-3.83 (m, 1H), 3.73-3.66 (m, 2H), 3.45-3.42 (m, 1H), 3.38-3.35 (m, 1H), 3.30 (s, 3H), 3.27-3.23 (m, 1H), 3.05-2.75 (m, 3H), 2.58 (s, 3H), 2.07-2.01 (m, 1H), 1.85-1.73 (m, 2H). |

[1]Notes on procedures:

In Step 1, only one bromination regioisomer was observed, tert-butyl 4-(6-(((benzyloxy)carbonyl)amino)-1-bromo-4-fluoro-5,6,7,8-tetrahydronaphthalen-2-yl)piperazine-1-carboxylate.

[2]Notes on procedures:

Chiral separation of the enantiomers was performed after Step 5 rather than in Step 4, using the chiral column Chiralpak IA and Mobile Phase 50% EtOH/hexanes (0.1% Et$_2$NH). Stereochemistry of the separated enantiomers were arbitrarily assigned.

[3]Notes on procedures:

In Step 4, the amide coupling reaction was performed with HBTU and Et$_3$N in DMA. Chiral separation of the enantiomers was performed after Step 5 rather than in Step 4, using the chiral column Chiralpak IE and Mobile Phase 20% IPA/MTBE (0.1% Et$_2$NH). Stereochemistry of the separated enantiomers were arbitrarily assigned.

[4]Notes on procedures:

In Step 4, the carboxylic acid Intermediate 24 was used. The amide coupling reaction was performed with HBTU and Et$_3$N in DMA. Chiral separation of the enantiomers was performed after Step 5 rather than in Step 4, using the chiral column Chiralpak IA and Mobile Phase 40% EtOH/hexanes-DCM (5:1) (0.1% Et$_2$NH). Stereochemistry of the separated enantiomers were arbitrarily assigned.

[5]Notes on procedures:

In Step 4, the amide coupling reaction was performed with HBTU and Et$_3$N in DMA. Chiral separation of the enantiomers was performed after Step 5 rather than in Step 4, using the chiral column Chiralpak IG and Mobile Phase 30% EtOH/MTBE (containing 8 mM NH$_3$ in MeOH). Stereochemistry of the separated enantiomers were arbitrarily assigned.

[6]Notes on procedures:

In Step 4, the amide coupling reaction was performed with HBTU and Et$_3$N in DMA. The enantiomers were separated by chiral HPLC using the chiral column Chiralpak IC and Mobile Phase 15% EtOH/MTBE. Stereochemistry of the separated enantiomers were arbitrarily assigned.

[7]Notes on procedures:

In Step 4, the amide coupling reaction was performed with HBTU and Et$_3$N in DMA. The enantiomers were separated by chiral HPLC using the chiral column Chiralpak IG and Mobile Phase 30% EtOH/MTBE. Stereochemistry of the separated enantiomers were arbitrarily assigned.

[8]Notes on procedures:

In Step 4, the carboxylic acid Intermediate 24 was used. The amide coupling reaction was performed with HBTU and Et$_3$N in DMA. The enantiomers were separated by chiral HPLC using the chiral column Chiralpak IG and Mobile Phase 30% EtOH/MTBE. Stereochemistry of the separated enantiomers were arbitrarily assigned.

[9]Notes on procedures:

In Step 2, cyanation was achieved in the presence of Zn (2 eq), Zn(CN)2 (10 eq), Pd(P(t-Bu)$_3$)$_2$ (0.5 eq), and 4,4'-di-tert-butyl-2,2'-bipyridine (1 eq) in DMA, with heating at 97° C. for 2 h.

[10]Notes on procedures:

In Step 4, the amide coupling reaction was performed with HBTU and Et$_3$N in DMA. The enantiomers were separated by chiral HPLC using the chiral column Chiralpak ID-2 and Mobile Phase 15% EtOH/MTBE (0.1% Et$_2$NH). Stereochemistry of the separated enantiomers were arbitrarily assigned.

Example 21-1. N-((2R)-6-(3,8-Diazabicyclo[3.2.1]octan-3-yl)-5-fluoro-1,2,3,4-tetrahydronaphthalen-2-yl)-3-amino-6-methylthieno[2,3-b]pyridine-2-carboxamide tane-8-carboxylate and tert-butyl 3-(6-(((benzyloxy)carbonyl)amino)-1-fluoro-5,6,7,8-tetrahydronaphthalen-2-yl)-3,8-diazabicyclo[3.2.1]octane-8-carboxylate as a yellow oil. MS: (ESI, m/z): 510 [M+H]⁺.

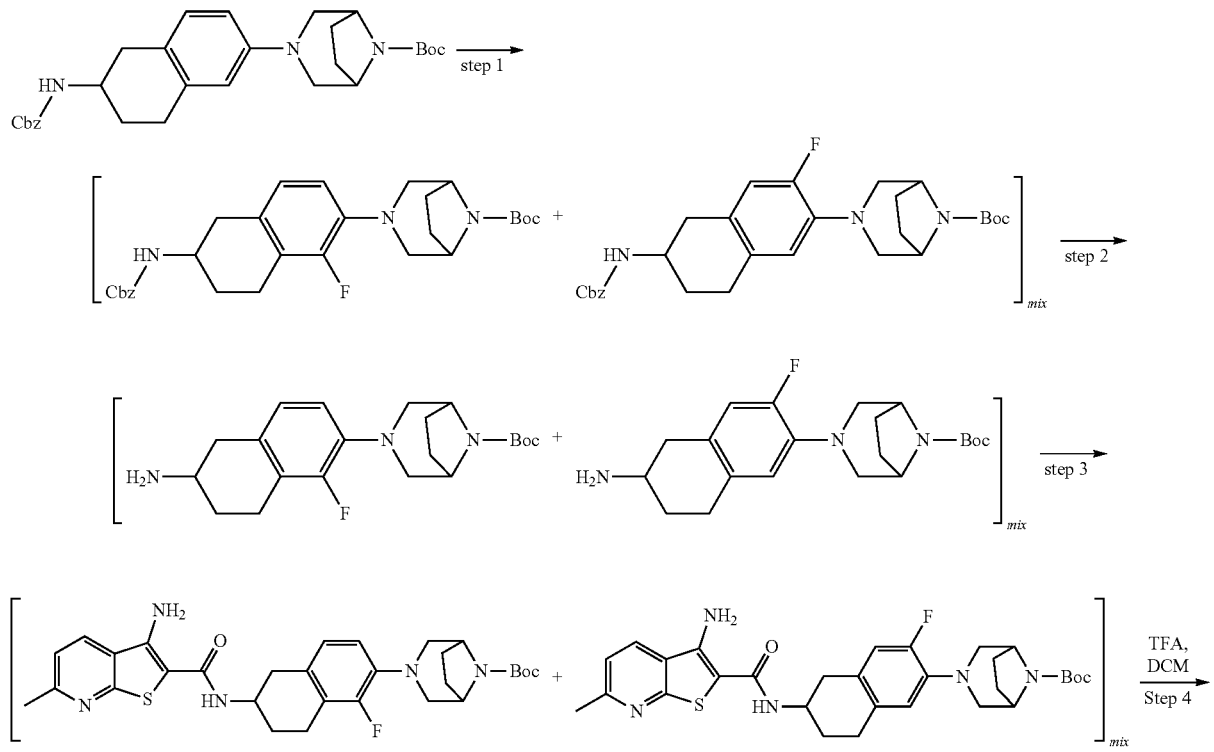

These regioisomers and enantiomers were separated by chromatography and carried on independently to the final compounds (only one representative shown here)

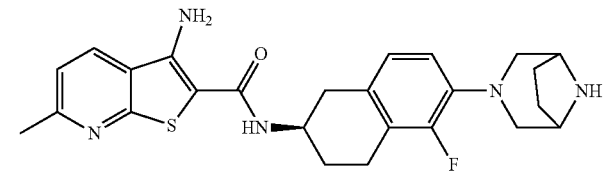 [SMILES: Cc1ccc2c(N)c(C(=O)N[C@@H]3CCc4c(C#N)c(N5CC6CCC(C5)N6)cc(F)c4C3)sc2n1]

Step 1. Mixture of tert-butyl 3-(6-(((benzyloxy)carbonyl)amino)-3-fluoro-5,6,7,8-tetrahydronaphthalen-2-yl)-3,8-diazabicyclo[3.2.1]octane-8-carboxylate and tert-butyl 3-(6-(((benzyloxy)carbonyl)amino)-1-fluoro-5,6,7,8-tetrahydronaphthalen-2-yl)-3,8-diazabicyclo[3.2.1]octane-8-carboxylate A solution of tert-butyl 3-(6-(((benzyloxy)carbonyl)amino)-5,6,7,8-tetrahydronaphthalen-2-yl)-3,8-diazabicyclo[3.2.1]octane-8-carboxylate (800 mg, 1.63 mmol) and Selectfluor (634 mg, 1.79 mmol) in ACN (16 mL) was stirred for 18 h at 20° C. The reaction was quenched by the addition of 30 mL of water. The resulting mixture was extracted with 3×10 mL of ethyl acetate. The organic layers were combined, dried over anhydrous sodium sulfate, filtered and concentrated under vacuum. The residue was purified by silica gel chromatography (eluting with 1%-50% EtOAC/pet. ether) to afford a mixture of the regioisomers tert-butyl 3-(6-(((benzyloxy)carbonyl)amino)-3-fluoro-5,6,7,8-tetrahydronaphthalen-2-yl)-3,8-diazabicyclo[3.2.1]oc- Step 2. Mixture of tert-butyl 3-(6-amino-3-fluoro-5,6,7,8-tetrahydronaphthalen-2-yl)-3,8-diazabicyclo[3.2.1]octane-8-carboxylate and tert-butyl 3-(6-amino-1-fluoro-5,6,7,8-tetrahydronaphthalen-2-yl)-3,8-diazabicyclo[3.2.1]octane-8-carboxylate A slurry of the mixture of tert-butyl 3-(6-[[(benzyloxy)carbonyl]amino]-3-fluoro-5,6,7,8-tetrahydronaphthalen-2-yl)-3,8-diazabicyclo[3.2.1]octane-8-carboxylate and tert-butyl 3-(6-[[(benzyloxy)carbonyl]amino]-1-fluoro-5,6,7,8-tetrahydronaphthalen-2-yl)-3,8-diazabicyclo[3.2.1]octane-8-carboxylate (508 mg, 1.00 mmol), and palladium on carbon (100 mg, 10%) in ethyl acetate (100 mL) was stirred for 1 h at 20° C. under a hydrogen atmosphere. The solids were filtered out. The resulting mixture was concentrated under vacuum. The residue was purified by silica gel chromatography (eluting with 1%-50% MeOH/DCM) to afford a mixture of the regioisomers tert-butyl 3-(6-amino-3-fluoro-5,6,7,8-tetrahydronaphthalen-2-yl)-3,8-diazabicyclo[3.2.1]octane-8-carboxylate and tert-butyl 3-(6-amino-1-fluoro-5, 6,7,8-tetrahydronaphthalen-2-yl)-3,8-diazabicyclo[3.2.1]octane-8-carboxylate as a white solid. MS: (ESI, m/z): 376 [M+H]⁺.

Step 3. Mixture of tert-butyl 3-(6-(3-amino-6-methylthieno[2,3-b]pyridine-2-carboxamido)-1-fluoro-5,6,7,8-tetrahydronaphthalen-2-yl)-3,8-diazabicyclo[3.2.1]octane-8-carboxylate and tert-butyl 3-(6-(3-amino-6-methylthieno[2,3-b]pyridine-2-carboxamido)-3-fluoro-5,6,7,8-tetrahydronaphthalen-2-yl)-3,8-diazabicyclo[3.2.1]octane-8-carboxylate A solution of the mixture of tert-butyl 3-(6-amino-1-fluoro-5,6,7,8-tetrahydronaphthalen-2-yl)-3,8-diazabicyclo[3.2.1]octane-8-carboxylate and tert-butyl 3-(6-amino-3-fluoro-5,6,7,8-tetrahydronaphthalen-2-yl)-3,8-diazabicyclo[3.2.1]octane-8-carboxylate (150 mg, 0.40 mmol), 3-amino-6-methylthieno[2,3-b]pyridine-2-carboxylic acid (99 mg, 479.45 mmol), EDCI (92 mg, 0.48 mmol), HOBt (65 mg, 0.48 mmol), and DIEA (155 mg, 1.20 mmol) in DMF (5 mL) was stirred for 2 h at 20° C. The reaction was quenched by the addition of 20 mL of water. The solids were collected by filtration and the crude product was purified by prep-HPLC (Column: XBridge BEH C18 OBD, 130 Å, 5 m, 19×150 mm; Mobile phase A: water (10 mM $NH_4HCO_3$), B: ACN (60% ACN to 80% over 7 min)) to afford a mixture of the titled compounds.

Chiral separation. The mixture of regioisomers and enantiomers were partially separated by chiral HPLC (Column: Chiralpak IA, 250×20 mm, 5 um; Flow: 15 mL/min; Mobile Phase 10% MeOH/MTBE; Wavelength: from 190 nm to 500 nm) to afford a mixture of tert-butyl 3-((R)-6-(3-amino-6-methylthieno[2,3-b]pyridine-2-carboxamido)-1-fluoro-5,6,7,8-tetrahydronaphthalen-2-yl)-3,8-diazabicyclo[3.2.1]octane-8-carboxylate and tert-butyl 3-((R)-6-(3-amino-6-methylthieno[2,3-b]pyridine-2-carboxamido)-3-fluoro-5,6,7,8-tetrahydronaphthalen-2-yl)-3,8-diazabicyclo[3.2.1]octane-8-carboxylate (Peak 1: RT=7.37 min; stereochemistry arbitrarily assigned); tert-butyl 3-((S)-6-(3-amino-6-methylthieno[2,3-b]pyridine-2-carboxamido)-1-fluoro-5,6,7,8-tetrahydronaphthalen-2-yl)-3,8-diazabicyclo[3.2.1]octane-8-carboxylate as a white solid (Peak 2: RT=7.69 min; stereochemistry arbitrarily assigned); and tert-butyl 3-((S)-6-(3-amino-6-methylthieno[2,3-b]pyridine-2-carboxamido)-3-fluoro-5,6,7,8-tetrahydronaphthalen-2-yl)-3,8-diazabicyclo[3.2.1]octane-8-carboxylate as a white solid (Peak 3: RT=13.70 min; stereochemistry arbitrarily assigned).

Peak 1 was further purified by chiral HPLC (Column: Phenomenex Lux 5u Cellulose-4, AXIA Packed, 250×21.5 mm, 5 um; Flow: 18 mL/min, Mobile Phase: MeOH; Wavelength: from 190 nm to 500 nm) to afford tert-butyl 3-((R)-6-(3-amino-6-methylthieno[2,3-b]pyridine-2-carboxamido)-1-fluoro-5,6,7,8-tetrahydronaphthalen-2-yl)-3,8-diazabicyclo[3.2.1]octane-8-carboxylate as a white solid (RT=13.56 min; stereochemistry arbitrarily assigned), and tert-butyl 3-((R)-6-(3-amino-6-methylthieno[2,3-b]pyridine-2-carboxamido)-3-fluoro-5,6,7,8-tetrahydronaphthalen-2-yl)-3,8-diazabicyclo[3.2.1]octane-8-carboxylate as a white solid (RT=17.31 min; stereochemistry arbitrarily assigned). MS for all 4 isomers: (ESI, m/z): 566 [M+H]⁺.

Step 4. N-((2R)-6-(3,8-Diazabicyclo[3.2.1]octan-3-yl)-5-fluoro-1,2,3,4-tetrahydronaphthalen-2-yl)-3-amino-6-methylthieno[2,3-b]pyridine-2-carboxamide A solution of tert-butyl 3-((R)-6-(3-amino-6-methylthieno[2,3-b]pyridine-2-carboxamido)-3-fluoro-5,6,7,8-tetrahydronaphthalen-2-yl)-3,8-diazabicyclo[3.2.1]octane-8-carboxylate (25 mg, 0.04 mmol) and TFA (1 mL) in DCM (5 mL) was stirred for 1 h at 20° C. The resulting mixture was concentrated under vacuum. The residue was diluted with 5 mL of DCM. The pH of the solution was adjusted to 8 with $NH_3$. in MeOH (7 M). The resulting mixture was concentrated under vacuum. The residue was purified by prep-HPLC (Column: XBridge Prep C18 OBD, 130 Å, 5 μm, 19×150 mm; Mobile phase: water (10 mM $NH_4HCO_3$), ACN (25% ACN up to 55% over 7 min)) to afford N-((2R)-6-(3,8-diazabicyclo[3.2.1]octan-3-yl)-5-fluoro-1,2,3,4-tetrahydronaphthalen-2-yl)-3-amino-6-methylthieno[2,3-b]pyridine-2-carboxamide as an off-white solid. ¹H NMR (Methanol-d₄, 400 MHz) δ(ppm): 8.20 (d, J=8.0 Hz, 1H), 7.30 (d, J=8.0 Hz, 1H), 6.80-6.76 (m, 2H), 4.25-4.17 (m, 1H), 3.53-3.51 (m, 2H), 3.16-3.14 (m, 2H), 3.10-2.99 (m, 2H), 2.92-2.90 (m, 2H), 2.82-2.74 (m, 2H), 2.64 (s, 3H), 2.18-2.12 (m, 1H), 2.04-2.02 (m, 2H), 1.87-1.82 (m, 3H). MS: (ESI, m/z): 466 [M+H]⁺.

The first three examples in Table 19 were prepared from the remaining three isomers isolated in Step 3 using standard chemical manipulations and procedures similar to those used for the preparation of Example 21-1. The rest of the examples in Table 19 were prepared using standard chemical manipulations and procedures similar to those used for the preparation of Examples 21-1 thru 21-4.

TABLE 19

| Example Number | Structure and Compound Name | LRMS m/z [M + H]⁺ | ¹H NMR |
| --- | --- | --- | --- |
| 21-2 | N-((2S)-6-(3,8-diazabicyclo[3.2.1]octan-3-yl)-5-fluoro-1,2,3,4-tetrahydronaphthalen-2-yl)-3-amino-6-methylthieno[2,3-b]pyridine-2-carboxamide | 466 | (CD₃OD, 400 MHz) δ (ppm): 8.20 (d, J = 8.4 Hz, 1H), 7.30 (d, J = 8.4 Hz, 1H), 6.84-6.75 (m, 2H), 4.25-4.16 (m, 1H), 3.66-3.62 (s, 2H), 3.21-3.18 (m, 2H), 3.05-2.95 (m, 4H), 2.82-2.75 (m, 2H), 2.64 (s, 3H), 2.18-2.07 (m, 3H), 1.91-1.81 (m, 2H), 1.81-1.76 (m, 1H). |

TABLE 19-continued

| Example Number | Structure and Compound Name | LRMS m/z [M + H]+ | 1H NMR |
|---|---|---|---|
| 21-3 | N-((2R)-6-(3,8-diazabicyclo[3.2.1]octan-3-yl)-7-fluoro-1,2,3,4-tetrahydronaphthalen-2-yl)-3-amino-6-methylthieno[2,3-b]pyridine-2-carboxamide | 466 | (CD$_3$OD, 400 MHz) δ (ppm): 8.19 (d, J = 8.4 Hz, 1H), 7.30 (d, J = 8.4 Hz, 1H), 6.75-6.65 (m, 2H), 4.22-4.20 (m, 1H), 3.52-3.49 (m, 2H), 3.16-3.13 (m, 2H), 3.03-2.70 (m, 6H), 2.64 (s, 3H), 2.14-1.96 (m, 3H), 1.88-1.73 (m, 3H). |
| 21-4 | N-((2S)-6-(3,8-diazabicyclo[3.2.1]octan-3-yl)-7-fluoro-1,2,3,4-tetrahydronaphthalen-2-yl)-3-amino-6-methylthieno[2,3-b]pyridine-2-carboxamide | 466 | (CD$_3$OD, 400 MHz) δ (ppm): 8.19 (d, J = 8.4 Hz, 1H), 7.30 (d, J = 8.0 Hz, 1H), 6.78-6.67 (m, 2H), 4.25-4.17 (m, 1H), 3.67-3.63 (m, 2H), 3.21-3.18 (m, 2H), 3.03-2.72 (m, 6H), 2.64 (s, 3H), 2.11-2.05 (m, 3H), 1.90-1.79 (m, 3H). |
| 21-5[1] | (R)-3-amino-N-(5-fluoro-6-(piperazin-1-yl)-1,2,3,4-tetrahydronaphthalen-2-yl)-6-methylthieno[2,3-b]pyridine-2-carboxamide | 440 | (CD$_3$OD, 400 MHz) δ (ppm): 8.19 (d, J = 8.3 Hz, 1H), 7.38-7.29 (m, 1H), 6.94-6.78 (m, 2H), 4.32-4.19 (m, 1H), 3.09-2.94 (m, 10H), 2.85-2.70 (m, 2H), 2.64 (s, 3H), 2.25-2.13 (m, 1H), 1.82-1.75 (m, 1H). |
| 21-6[1] | (S)-3-amino-N-(5-fluoro-6-(piperazin-1-yl)-1,2,3,4-tetrahydronaphthalen-2-yl)-6-methylthieno[2,3-b]pyridine-2-carboxamide | 440 | (CD$_3$OD, 400 MHz) δ (ppm): 8.19 (d, J = 8.3 Hz, 1H), 7.35-7.28 (m, 1H), 6.90-6.80 (m, 2H), 4.33-4.19 (m, 1H), 3.00 (s, 10H), 2.85-2.70 (m, 2H), 2.64 (s, 3H), 2.19-2.08 (m, 1H), 1.83-1.75 (m, 1H). |
| 21-7[1] | (R)-3-amino-N-(7-fluoro-6-(piperazin-1-yl)-1,2,3,4-tetrahydronaphthalen-2-yl)-6-methylthieno[2,3-b]pyridine-2-carboxamide | 440 | (CD$_3$OD, 400 MHz) δ (ppm): 8.19 (d, J = 8.3 Hz, 1H), 7.35-7.28 (m, 1H), 6.82-6.73 (m, 2H), 4.29-4.18 (m, 1H), 3.04-2.93 (m, 9H), 2.94-2.85 (m, 2H), 2.85-2.67 (m, 1H), 2.64 (s, 3H), 2.18-2.09 (m, 1H), 1.88-1.74 (m, 1H). |

TABLE 19-continued

| Example Number | Structure and Compound Name | LRMS m/z [M + H]+ | 1H NMR |
|---|---|---|---|
| 21-8[1] | 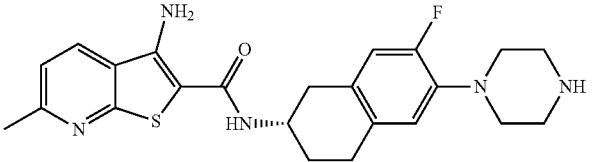<br>(S)-3-amino-N-(7-fluoro-6-(piperazin-1-yl)-1,2,3,4-tetrahydronaphthalen-2-yl)-6-methylthieno[2,3-b]pyridine-2-carboxamide | 440 | (CD₃OD, 400 MHz) δ (ppm): 8.19 (d, J = 8.3 Hz, 1H), 7.35-7.28 (m, 1H), 6.90-6.80 (m, 2H), 4.33-4.19 (m, 1H), 3.00 (s, 10H), 2.85-2.70 (m, 2H), 2.64 (s, 3H), 2.19-2.08 (m, 1H), 1.83-1.75 (m, 1H). |
| 21-9[2] | 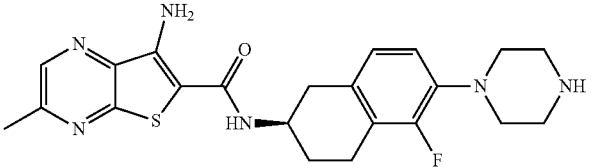 [SMILES: Cc1cnc2c(N)c(C(=O)N[C@@H]3CCc4c(ccc(N5CCNCC5)c4F)C3)sc2n1]<br>(R)-7-amino-N-(5-fluoro-6-(piperazin-1-yl)-1,2,3,4-tetrahydronaphthalen-2-yl)-3-methylthieno[2,3-b]pyrazine-6-carboxamide | 441 | (DMSO-d₆, 400 MHz) δ (ppm): 8.64 (s, 1H), 7.81 (d, J = 7.7 Hz, 1H), 6.78-6.94 (m, 3H), 6.71 (d, J = 9.0 Hz, 1H), 4.12 (s, 1H), 2.6-2.96 (m, 16H), 1.98 (d, J = 12.1 Hz, 1H), 1.67-1.82 (m, 1H). |
| 21-10[2] | 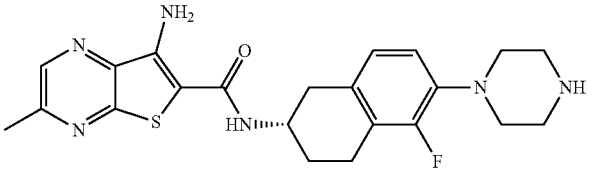 [SMILES: Cc1cnc2c(N)c(C(=O)N[C@H]3CCc4c(ccc(N5CCNCC5)c4F)C3)sc2n1]<br>(S)-7-amino-N-(5-fluoro-6-(piperazin-1-yl)-1,2,3,4-tetrahydronaphthalen-2-yl)-3-methylthieno[2,3-b]pyrazine-6-carboxamide | 441 | (DMSO-d₆, 400 MHz) δ (ppm): 8.63 (s, 1H), 7.82 (d, 1H), 6.90 (s, 2H), 6.83 (d, 1H), 6.71 (d, 1H), 4.11 (s, 1H), 2.75-2.88 (m, 13H), 2.63 (s, 3H), 1.69-2.01 (m, 2H). |
| 21-11[2] | 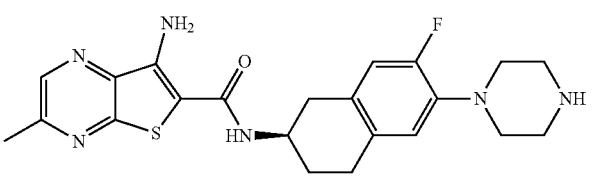 [SMILES: Cc1cnc2c(N)c(C(=O)N[C@@H]3CCc4cc(N5CCNCC5)c(F)cc4C3)sc2n1]<br>(R)-7-amino-N-(7-fluoro-6-(piperazin-1-yl)-1,2,3,4-tetrahydronaphthalen-2-yl)-3-methylthieno[2,3-b]pyrazine-6-carboxamide | 441 | (DMSO-d₆, 400 MHz) δ (ppm): 8.63 (s, 1H), 7.82 (d, J = 7.7 Hz, 1H), 6.91 (s, 2H), 6.82 (d, J = 8.2 Hz, 2H), 4.11 (s, 1H), 2.88 (s, 10H), 2.66-2.83 (m, 1H), 2.63 (s, 5H), 2.01 (s, 1H), 1.70-1.72 (m, 1H). |

TABLE 19-continued

| Example Number | Structure and Compound Name | LRMS m/z [M + H]+ | 1H NMR |
|---|---|---|---|
| 21-12[2] | (S)-7-amino-N-(7-fluoro-6-(piperazin-1-yl)-1,2,3,4-tetrahydronaphthalen-2-yl)-3-methylthieno[2,3-b]pyrazine-6-carboxamide | 441 | (DMSO-$d_6$, 400 MHz) δ (ppm): 8.64 (s, 1H), 7.82 (d, J = 7.7 Hz, 1H), 6.77-6.91 (m, 4H), 4.10 (br s, 1H), 2.64-2.95 (m, 16H), 2.63 (s, 5H), 2.01 (br s, 1H), 1.65-1.81 (m, 1H). |

[1]Notes on procedures:
The mixture of regioisomers and enantiomers were partially separated by chiral HPLC using the chiral column Chiralpak-AD-H-SL002 and mobile phase 50% EtOH/hexanes to provide the precursor to Example 21-7 as the first eluted sample, the precursor to Example 21-8 as the second eluted sample, and a mixture of two peaks as the third eluted sample. The mixture was further separated by chiral HPLC using the chiral column Chiralpak-IC and mobile phase 30% IPA/MTBE to provide the precursor to Example 21-5 as the first eluted sample and the precursor to Example 21-6 as the second eluted sample. Stereochemistry of the separated enantiomers were arbitrarily assigned.

[2]Notes on procedures:
The mixture of regioisomers and enantiomers were partially separated by chiral HPLC using the chiral column Chiralpak-IA and mobile phase EtOH to provide the precursor to Example 21-9 as the first eluted sample, a mixture of two peaks as the second eluted sample, and the precursor to Example 21-12 as the third eluted sample. The mixture was further separated by chiral HPLC using the chiral column (R,R)-Whelk-O1-Kromasil and mobile phase 10% EtOH/MTBE to provide the precursor to Example 21-10 as the first eluted sample and the precursor to Example 21-11 as the second eluted sample. Stereochemistry of the separated enantiomers were arbitrarily assigned.

Example 22-1. (S)-3-Amino-N-(5,8-difluoro-6-(piperazin-1-yl)-1,2,3,4-tetrahydronaphthalen-2-yl)-6-methylthieno[2,3-b]pyridine-2-carboxamide and Example 22-2. (R)-3-Amino-N-(5,8-difluoro-6-(piperazin-1-yl)-1,2,3,4-tetrahydronaphthalen-2-yl)-6-methylthieno[2,3-b]pyridine-2-carboxamide

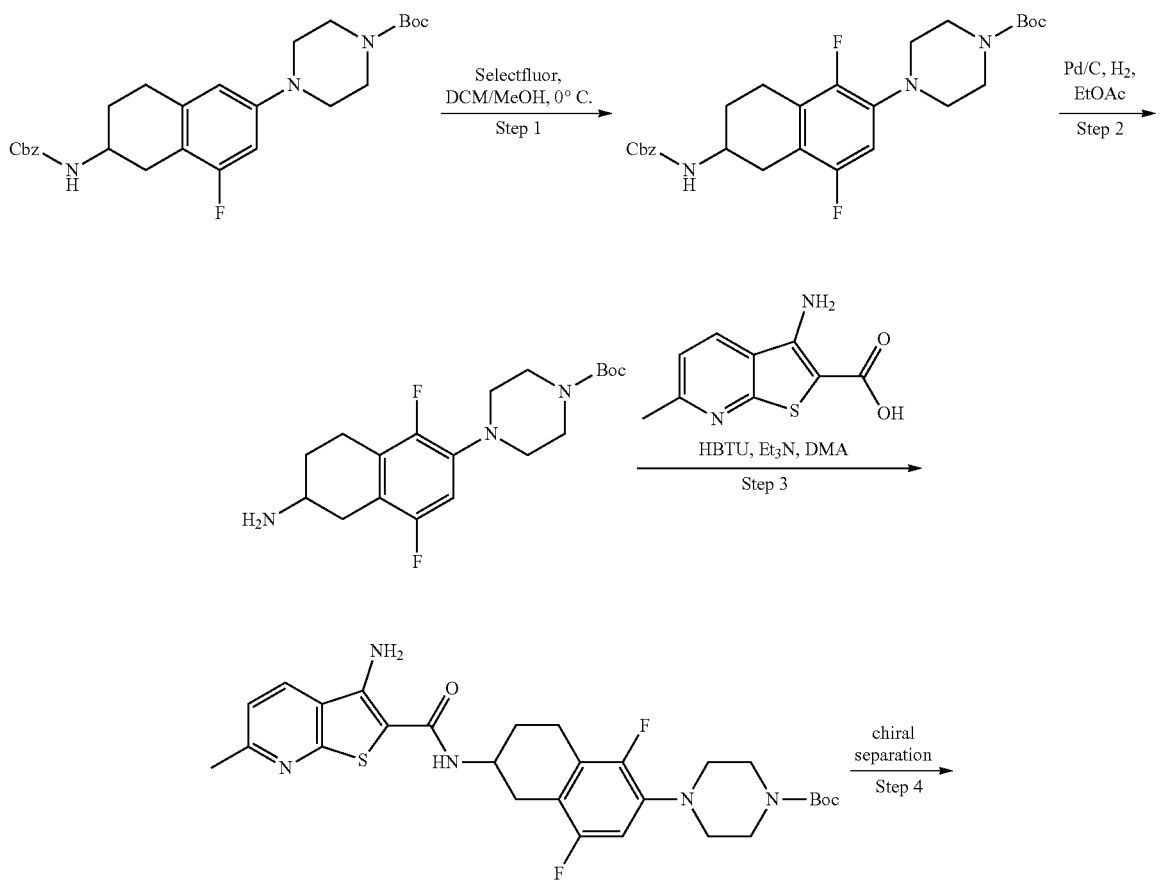

-continued

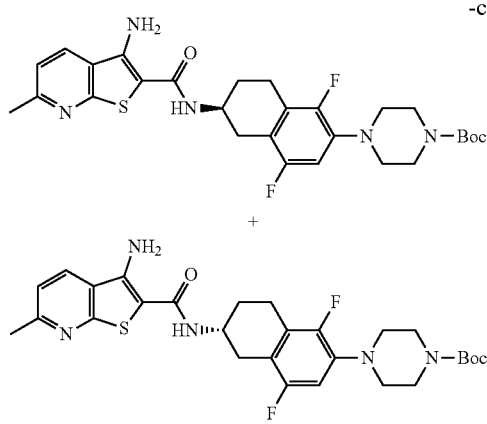

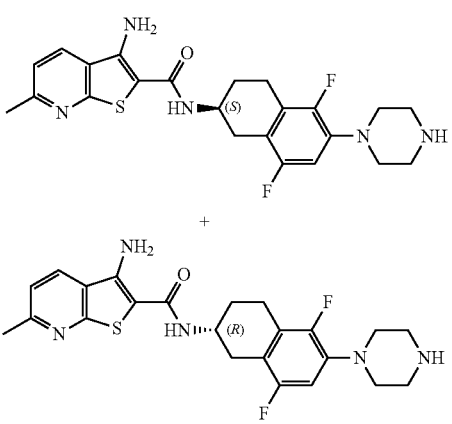

Step 1. tert-Butyl 4-(6-(benzyloxycarbonylamino)-1,4-difluoro-5,6,7,8-tetrahydronaphthalen-2-yl)piperazine-1-carboxylate To a solution of tert-butyl 4-(6-(benzyloxycarbonylamino)-4-fluoro-5,6,7,8-tetrahydronaphthalen-2-yl)piperazine-1-carboxylate (3.00 g, 6.20 mmol) in 1:1 DCM/MeOH (100 mL) was added Selectfluor (2.20 g, 6.20 mmol) at 0° C. The resulting solution was stirred overnight at 20° C. Two additional portions of Selectfluor (1.1 g, 3.1 mmol) were added at 0° C. and stirred for 4 h at 20° C. The reaction mixture was then poured into 80 mL of water. The resulting mixture was extracted with 3×100 mL of DCM. The organic layers were combined, dried over anhydrous sodium sulfate, filtered and concentrated under vacuum. The residue was purified by silica gel chromatography (eluting with 3:1 pet. ether/ethyl acetate) to afford tert-butyl 4-(6-(benzyloxycarbonylamino)-1,4-difluoro-5,6,7,8-tetrahydronaphthalen-2-yl)piperazine-1-carboxylate as a light yellow solid. MS: (ESI, m/z): 502 [M+H]⁻.

Step 2. tert-Butyl 4-(6-amino-1,4-difluoro-5,6,7,8-tetrahydronaphtha-len-2-yl)piperazine-1-carboxylate A solution of tert-butyl 4-(6-(benzyloxycarbonylamino)-1,4-difluoro-5,6,7,8-tetrahydronaphthalen-2-yl)piperazine-1-carboxylate (530 mg, 1.06 mmol) and palladium on carbon (100 mg, 10%) in ethyl acetate (10 mL) was stirred for 2 h at 20° C. under a hydrogen atmosphere. The solids were filtered out. The filtrate was concentrated under vacuum to afford tert-butyl 4-(6-amino-1,4-difluoro-5,6,7,8-tetrahydronaphthalen-2-yl)piperazine-1-carboxylate as a yellow solid. MS: (ESI, m/z): 368 [M+H]⁺.

Step 3. tert-Butyl 4-(6-(3-amino-6-methylthieno[2,3-b]pyridine-2-carboxamido)-1,4-difluoro-5,6,7,8-tetrahydronaphthalen-2-yl)piperazine-1-carboxylate A solution of tert-butyl 4-(6-amino-1,4-difluoro-5,6,7,8-tetrahydronaphthalen-2-yl)piperazine-1-carboxylate (360 mg, 0.74 mmol, 75% purity), 3-amino-6-methylthieno[2,3-b]pyridine-2-carboxylic acid (188 mg, 0.90 mmol), HBTU (343 mg, 0.90 mmol), and Et₃N (0.31 mL, 2.26 mmol) in DMA (5 mL) was stirred for 30 min at 20° C. The crude product was purified by reverse phase chromatography (Column: C18 silica gel; Mobile phase A: water (0.05% formic acid), B: ACN (0% ACN up to 80% in 30 min)). The collected fraction was concentrated under vacuum to afford tert-butyl 4-(6-(3-amino-6-methylthieno[2,3-b]pyridine-2-carboxamido)-1,4-difluoro-5,6,7,8-tetrahydronaphthalen-2-yl)piperazine-1-carboxylate as a yellow solid. MS: (ESI, m/z): 558 [M+H]⁺.

Step 4. Chiral Separation

The racemate tert-butyl 4-(6-(3-amino-6-methylthieno[2,3-b]pyridine-2-carboxamido)-1,4-difluoro-5,6,7,8-tetrahydronaphthalen-2-yl)piperazine-1-carboxylate (250 mg) was separated by chiral HPLC (Column: ChiralArt Cellulose-SB, 2×25 cm, 5 μm; Mobile Phase: 30% EtOH/hexanes for 13 min). The first eluting isomer (RT=9.05 min) was concentrated under vacuum to afford (S)-tert-butyl 4-(6-(3-amino-6-methylthieno[2,3-b]pyridine-2-carboxamido)-1,4-difluoro-5,6,7,8-tetrahydronaphthalen-2-yl)piperazine-1-carboxylate as a yellow solid (stereochemistry arbitrarily assigned). The second eluting isomer (RT=10.15 min) was concentrated under vacuum to afford (R)-tert-butyl 4-(6-(3-amino-6-methylthieno[2,3-b]pyridine-2-carboxamido)-1,4-difluoro-5,6,7,8-tetrahydr-onaphthalen-2-yl)piperazine-1-carboxylate as a yellow solid (stereochemistry arbitrarily assigned). MS for both isomers: (ESI, m/z): 558 [M+H]⁺.

Step 5. (S)-3-Amino-N-(5,8-difluoro-6-(piperazin-1-yl)-1,2,3,4-tetrahydronaphthalen-2-yl)-6-methylthieno[2,3-b]pyridine-2-carboxamide A solution of (S)-tert-butyl 4-(6-(3-amino-6-methylthieno[2,3-b]pyridine-2-carboxamido)-1,4-difluoro-5,6,7,8-tetrahydronaphthalen-2-yl)piperazine-1-carboxylate (60 mg, 0.11 mmol) and trifluoroacetic acid (1 mL) in DCM (3 mL) was stirred for 1 h at 20° C. The resulting mixture was concentrated under vacuum. The residue was purified by prep-HPLC (Column: XBridge Prep OBD C18, 30×150 mm, 5 μm; Mobile phase A: water (0.05% NH₄OH), B: ACN (15% ACN up to 50% in 7 min)). The collected fraction was lyophilized to afford (S)-3-amino-N-(5,8-difluoro-6-(piperazin-1-yl)-1,2,3,4-tetrahydronaphthalen-2-yl)-6-methylthieno[2,3-b]pyridine-2-carboxamide as an off-white solid. H NMR (CD₃OD, 300 MHz) δ (ppm): 8.17 (d, J=8.1 Hz, 1H), 7.30 (d, J=8.4 Hz, 1H), 6.67-6.65 (m, 1H), 4.25-4.17 (m, 1H), 3.14-2.97 (m, 10H), 2.82-2.70 (m, 1H), 2.64-2.54 (m, 4H), 1.89-1.74 (m, 1H). MS: (ESI, m/z): 458 [M+H]⁺.

Step 6. (R)-3-amino-N-(5,8-difluoro-6-(piperazin-1-yl)-1,2,3,4-tetrahydronaphthalen-2-yl)-6-methylthieno[2,3-b]pyridine-2-carboxamide A solution of (R)-tert-butyl 4-(6-(3-amino-6-methylthieno[2,3-b]pyridine-2-carboxamido)-1,4-difluoro-5,6,7,8- tetrahydronaphthalen-2-yl)piperazine-1-carboxylate (90 mg, 0.16 mmol) and trifluoroacetic acid (1.5 mL) in DCM (4 mL) was stirred for 1 h at 20° C. The resulting mixture was concentrated under vacuum. The residue was purified by prep-HPLC (Column, XBridge Prep OBD C18, 30×150 mm, 5 μm; mobile phase A: water (0.05% NH₄OH), B: ACN (15% ACN up to 50% in 7 min)). The collected fraction was lyophilized to afford (R)-3-amino-N-(5,8-difluoro-6-(piperazin-1-yl)-1,2,3,4-tetrahydronaphthalen-2-yl)-6-methylthieno[2,3-b]pyridine-2-carboxamide as an off-white solid. ¹H NMR (DMSO-d₆, 300 MHz) δ (ppm): 8.31 (d, J=8.4 Hz, 1H), 7.64 (d, J=7.5 Hz, 1H), 7.31 (d, J=8.1 Hz, 1H), 7.17 (s, 2H), 6.70-6.68 (m, 1H), 4.13-4.04 (m, 1H), 2.92-2.81 (m, 10H), 2.73-2.55 (m, 5H), 2.06-1.97 (m, 1H), 1.78-1.68 (m, 1H). MS: (ESI, m/z): 458 [M+H]⁺.

The following examples in Table 20 were prepared using standard chemical manipulations and procedures similar to those used for the preparation of Examples 22-1 and 22-2.

TABLE 20

| Example Number | Structure and Compound Name | LRMS m/z [M + H]⁺ | ¹H NMR |
|---|---|---|---|
| 22-3¹ | N-((2S)-6-(9-oxa-3,7-diazabicyclo[3.3.1]nonan-3-yl)-5,8-difluoro-1,2,3,4-tetrahydronaphthalen-2-yl)-3-amino-6-methylthieno[2,3-b]pyridine-2-carboxamide | 500 | (DMSO-d₆, 300 MHz) δ (ppm): 8.31 (d, J = 8.4 Hz, 1H), 7.66 (br s, 1H), 7.31 (d, J = 8.4 Hz, 1H), 7.18 (br s, 2H), 6.78-6.75 (m, 1H), 4.20-4.00 (m, 1H), 3.75-3.65 (m, 2H), 3.48-3.38 (m, 2H), 3.27-3.08 (m, 4H), 3.01-2.82 (m, 4H), 2.80-2.60 (m, 2H), 2.58 (s, 3H), 2.10-1.97 (m, 1H), 1.88-1.62 (m, 1H). |
| 22-4¹ | N-((2R)-6-(9-oxa-3,7-diazabicyclo[3.3.1]nonan-3-yl)-5,8-difluoro-1,2,3,4-tetrahydronaphthalen-2-yl)-3-amino-6-methylthieno[2,3-b]pyridine-2-carboxamide | 500 | (DMSO-d₆, 300 MHz) δ (ppm): 8.31 (d, J = 8.1 Hz, 1H), 7.66 (br s, 1H), 7.31 (d, J = 8.4 Hz, 1H), 7.18 (br s, 2H), 6.78-6.75 (m, 1H), 4.20-4.00 (m, 1H), 3.75-3.65 (m, 2H), 3.48-3.38 (m, 2H), 3.27-3.08 (m, 4H), 3.01-2.82 (m, 4H), 2.80-2.60 (m, 2H), 2.58 (s, 3H), 2.10-1.98 (m, 1H), 1.88-1.62 (m, 1H). |
| 22-5² | 3-amino-N-[(2S)-6-{3,8-diazabicyclo[3.2.1]octan-3-yl}-5,8-difluoro-1,2,3,4-tetrahydronaphthalen-2-yl]-6-methylthieno[2,3-b]pyridine-2-carboxamide | 484 | (DMSO-d₆, 300 MHz) δ (ppm): 8.30 (d, J = 8.4 Hz, 1H), 7.63 (d, J = 7.6 Hz, 1H), 7.31 (d, J = 8.0 Hz, 1H), 7.17 (br s, 2H), 6.61-6.57 (m, 1H), 4.09-4.07 (m, 1H), 3.40-3.98 (m, 2H), 3.08-3.03 (m, 2H), 2.95-2.62 (m, 5H), 2.59-2.57 (m, 4H), 2.37-2.30 (m, 1H), 2.02-1.99 (m, 1H), 1.80-1.61 (m, 5H). |

TABLE 20-continued

| Example Number | Structure and Compound Name | LRMS m/z [M + H]+ | 1H NMR |
|---|---|---|---|
| 22-6[2] | 3-amino-N-(2R)-6-{3,8-diazabicyclo[3.2.1]octan-3-yl}-5,8-difluoro-1,2,3,4-tetrahydronaphthalen-2-yl]-6-methylthieno[2,3-b]pyridine-2-carboxamide | 484 | (DMSO-d6, 300 MHz) δ (ppm): 8.31 (d, J = 8.4 Hz, 1H), 7.64 (d, J = 8.0 Hz, 1H), 7.31 (d, J = 8.0 Hz, 1H), 7.17 (br s, 2H), 6.61-6.57 (m, 1H), 4.14-4.05 (m, 1H), 3.40-3.98 (m, 2H), 3.09-3.02 (m, 2H), 2.96-2.87 (m, 2H), 2.81-2.75 (m, 2H), 2.70-2.61 (m, 1H), 2.59-2.57 (m, 4H), 2.34-2.32 (m, 1H), 2.04-1.97 (m, 1H), 1.81-1.77 (m, 2H), 1.76-1.68 (m, 1H), 1.67-1.61 (m, 2H). |

[1]Notes on procedures:
In Step 4, the stereoisomers were separated by chiral HPLC using the chiral column Chiralpak IG and mobile phase 15% EtOH/MTBE. Stereochemistry of the separated enantiomers were arbitrarily assigned.
[2]Notes on procedures:
In Step 4, the stereoisomers were separated by chiral HPLC using the chiral column Chiral Art Cellulose-SB and mobile phase 10% EtOH/MTBE. Stereochemistry of the separated enantiomers were arbitrarily assigned.

Example 23-1. 7-Amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide Method 1

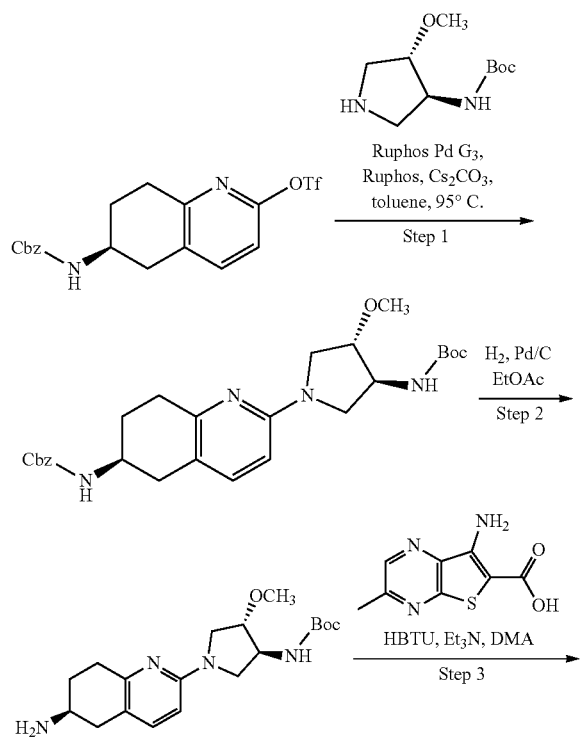

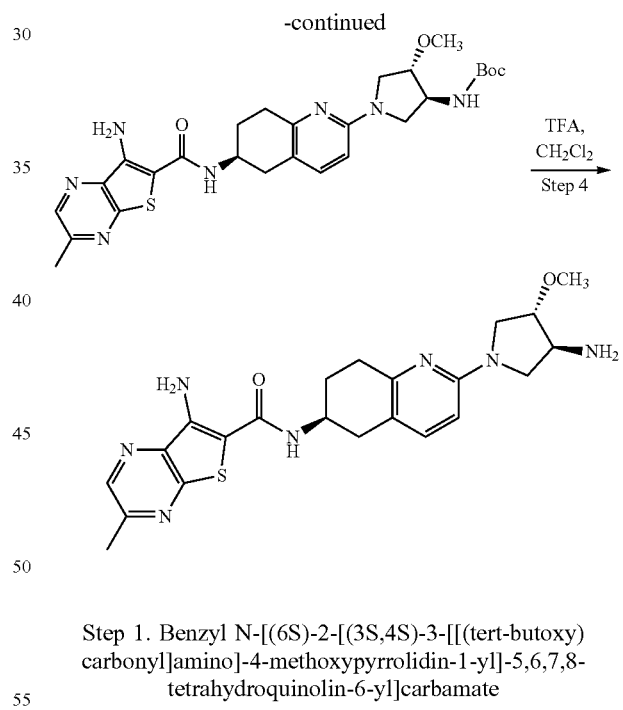

Step 1. Benzyl N-[(6S)-2-[(3S,4S)-3-[[(tert-butoxy)carbonyl]amino]-4-methoxypyrrolidin-1-yl]-5,6,7,8-tetrahydroquinolin-6-yl]carbamate A mixture of benzyl N-[(6S)-2-(trifluoromethanesulfonyloxy)-5,6,7,8-tetrahydroquinolin-6-yl]carbamate (Intermediate 47-2) (500 mg, 1.16 mmol), tert-butyl N-[(3S,4S)-4-methoxypyrrolidin-3-yl]carbamate (300 mg, 1.39 mmol), RuPhos Pd G3 (195 mg, 0.230 mmol), RuPhos (108 mg, 0.230 mmol), and Cs2CO3 (1.14 g, 3.49 mmol) in toluene (10 mL) was stirred for 3 h at 95° C. After cooling to 20° C., the solids were filtered out and the filtrate was concentrated under vacuum. The residue was purified by silica gel chromatography (eluting with 5:2 pet. ether/ethyl acetate) to give benzyl N-[(6S)-2-[(3S,4S)-3-[[(tert-butoxy)carbonyl]

amino]-4-methoxypyrrolidin-1-yl]-5,6,7,8-tetrahydroquinolin-6-yl]carbamate as a brown solid. MS (ESI, m/z): 497 [M+H]+.

Step 2. tert-butyl N-[(3S,4S)-1-[(6S)-6-Amino-5,6,7,8-tetrahydroquinolin-2-yl]-4-methoxypyrrolidin-3-yl]carbamate A mixture of benzyl N-[(6S)-2-[(3S,4S)-3-[[(tert-butoxy)carbonyl]amino]-4-methoxypyrrolidin-1-yl]-5,6,7,8-tetrahydroquinolin-6-yl]carbamate (450 mg, 0.910 mmol) and Palladium on carbon (450 mg, 10%) in ethyl acetate (10 mL) was stirred for 3 h at 20° C. under a hydrogen atmosphere (balloon). The solids were filtered out. The filtrate was concentrated under vacuum to give tert-butyl N-[(3S,4S)-1-[(6S)-6-amino-5,6,7,8-tetrahydroquinolin-2-yl]-4-methoxypyrrolidin-3-yl]carbamate as a white solid. MS (ESI, m/z): 362 [M+H]+.

Step 3. tert-butyl N-[(3S,4S)-1-(6-[7-Amino-3-methylthieno[2,3-b]pyrazine-6-amido]-5,6,7,8-tetrahydroquinolin-2-yl)-4-methoxypyrrolidin-3-yl]carbamate Triethylamine (0.400 mL, 2.92 mmol) and HBTU (377 mg, 0.990 mmol) were added to a stirring solution of tert-butyl N-[(3S,4S)-1-(6-amino-5,6,7,8-tetrahydroquinolin-2-yl)-4-methoxypyrrolidin-3-yl]carbamate (300 mg, 0.830 mmol) and 7-amino-3-methylthieno[2,3-b]pyrazine-6-carboxylic acid (174 mg, 0.830 mmol) in DMA (5 mL). The resulting solution was stirred for 2 h at 20° C. The mixture was purified by reversed phase chromatography (Column: C18 silica gel; Mobile phase, A: water (10 mM NH4HCO3) and B: ACN (0% to 70% B over 30 min)). The collected fraction was concentrated under vacuum to give tert-butyl N-[(3S,4S)-1-(6-[7-amino-3-methylthieno[2,3-b]pyrazine-6-amido]-5,6,7,8-tetrahydroquinolin-2-yl)-4-methoxypyrrolidin-3-yl]carbamate as a green solid. MS (ESI, m/z): 554 [M+H]−.

Step 4. 7-Amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide A solution of tert-butyl N-[(3S,4S)-1-[(6S)-6-[7-amino-3-methylthieno[2,3-b]pyrazine-6-amido]-5,6,7,8-tetrahydroquinolin-2-yl]-4-methoxypyrrolidin-3-yl]carbamate (300 mg, 0.470 mmol) and TFA (3 mL) in DCM (10 mL) was stirred for 30 min at 20° C. and then concentrated under vacuum. The residue was treated with a solution of NH3 in MeOH (15 mL, 7M) for 1 h at 20° C. The resulting solution was concentrated under vacuum. The residue was purified by prep-HPLC (Column: XBridge Prep C18 OBD, 19×150 mm 5 μm; Mobile Phase, A: water (containing 10 mM NH4HCO3) and B: ACN (20% to 42% B over 7 min)) to afford 7-amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide as a yellow solid. MS (ESI, m/z): 454 [M+H]−. 1H NMR (DMSO-d6, 400 MHz) δ(ppm): 8.65 (s, 1H), 7.81 (d, J=7.6 Hz, 1H), 7.20 (d, J=8.8 Hz, 1H), 6.92 (br s, 2H), 6.23 (d, J=8.4 Hz, 1H), 4.28-4.12 (m, 1H), 3.62-3.59 (m, 2H), 3.48-3.41 (m, 2H), 3.36-3.33 (m, 4H), 3.14-3.12 (m, 1H), 2.84-2.73 (m, 4H), 2.66 (s, 3H), 2.05-2.00 (m, 1H), 1.90-1.83 (m, 1H), 1.79 (br s, 2H).

Example 23-1. 7-Amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide and Example 23-2. 7-Amino-N-[(6R)-2-[(3S,4S)-3-amino-4-methoxypyrrolidin-1-yl]-5,6,7,8-tetrahydroquinolin-6-yl]-3-methylthieno[2,3-b]pyrazine-6-carboxamide Method 2

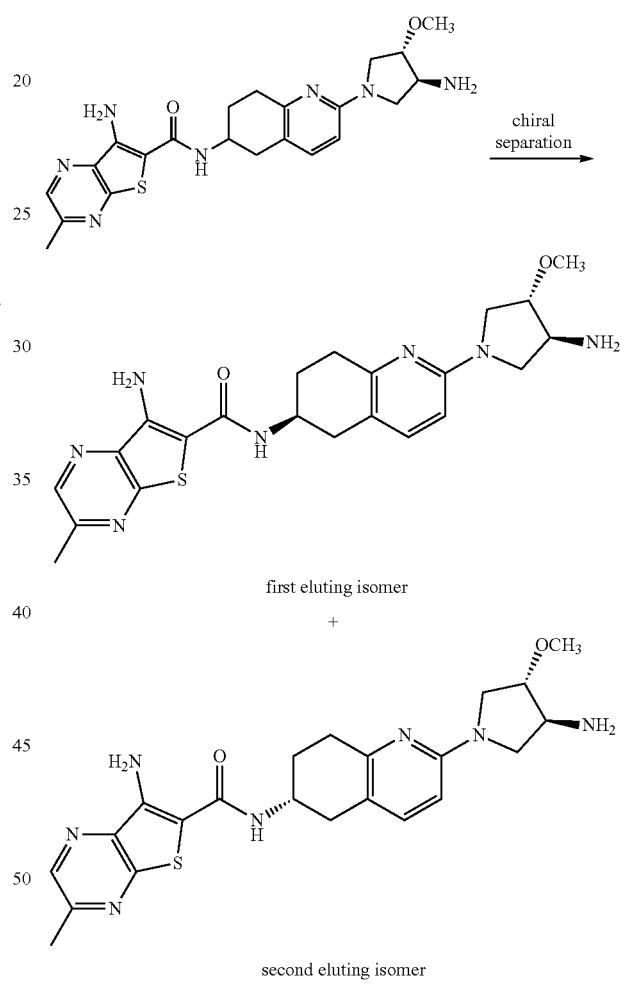

7-Amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide was also obtained starting from the racemate benzyl N-[2-(trifluoromethanesulfonyloxy)-5,6,7,8-tetrahydroquinolin-6-yl]carbamate (Intermediate 47-1) and following procedures similar to Method 1. The enantiomers of the racemate 7-amino-N-[2-[(3S,4S)-3-amino-4-methoxypyrrolidin-1-yl]-5,6,7,8-tetrahydroquinolin-6-yl]-3-methylthieno[2,3-b]pyrazine-6-carboxamide were separated by chiral HPLC using the chiral column Chiralpak IE and the eluent system 50% EtOH/MTBE (containing 2 mM NH3 in MeOH) to provide 7-amino-N-

[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide as a yellow solid as the first eluted isomer and 7-amino-N-[(6R)-2-[(3S,4S)-3-amino-4-methoxypyrrolidin-1-yl]-5,6,7,8-tetrahydroquinolin-6-yl]-3-methylthieno[2,3-b]pyrazine-6-carboxamide as a yellow solid as the second eluted isomer. $^1$H NMR (DMSO-$d_6$, 400 MHz) δ(ppm): 8.65 (s, 1H), 7.83 (d, J=7.6 Hz, 1H), 7.20 (d, J=8.4 Hz, 1H), 6.93 (br, 2H), 6.24 (d, J=8.8 Hz, 1H), 4.20-4.11 (m, 1H), 3.63-3.56 (m, 2H), 3.47-3.44 (m, 2H), 3.33 (s, 3H), 3.15-3.13 (m, 1H), 2.84-2.73 (m, 4H), 2.65 (s, 3H), 2.05-1.98 (m, 1H), 1.91-1.83 (in, 2H). MS (ESI, m/z): 454 [M+H]$^+$.

The following examples in Table 21 were prepared using standard chemical manipulations and procedures similar to Method 1 (or Method 2 where indicated) for the preparation of Example 23-1.

TABLE 21

| Example Number | Structure and Compound Name | LRMS m/z [M + H]$^+$ | $^1$H NMR |
|---|---|---|---|
| 23-3[1] | 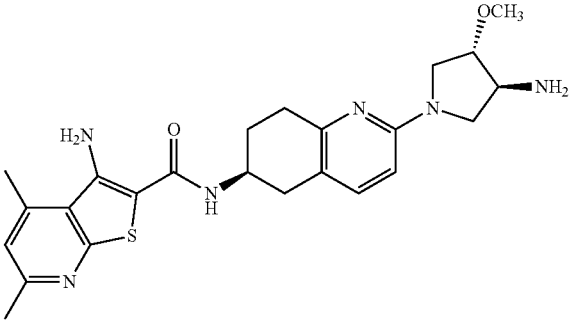 [SMILES: CO[C@H]1CN(c2ccc3c(n2)CC[C@H](NC(=O)c2sc4nc(C)cc(C)c4c2N)C3)C[C@@H]1N]<br>3-amino-N-[(6S)-2-[(3S,4S)-3-amino-4-methoxypyrrolidin-1-yl]-5,6,7,8-tetrahydroquinolin-6-yl]-4,6-dimethylthieno[2,3-b]pyridine-2-carboxamide | 467 | (DMSO-$d_6$, 400 MHz) δ (ppm): 7.59 (d, J = 7.6 Hz, 1H), 7.19 (d, J = 8.4 Hz, 1H), 7.04 (s, 1H), 6.81 (br s, 2H), 6.23 (d, J = 8.4 Hz, 1H), 4.08-4.15 (m, 1H), 3.61-3.63 (m, 2H), 3.43-3.33 (m, 3H), 3.30 (s, 3H), 3.13-3.11 (m, 1H), 2.81-2.69 (m, 7H), 2.58 (s, 3H), 1.99-1.72 (m, 3H). |
| 23-4[2] | 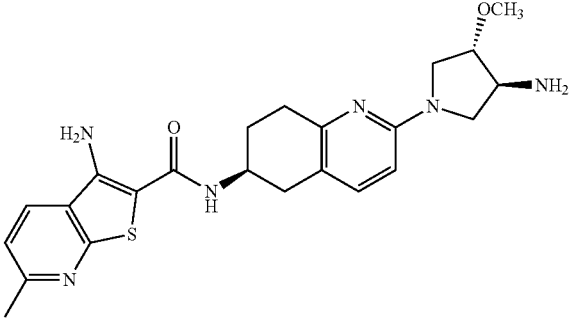 [SMILES: CO[C@H]1CN(c2ccc3c(n2)CC[C@H](NC(=O)c2sc4nc(C)ccc4c2N)C3)C[C@@H]1N]<br>3-amino-N-[(6S)-2-[(3S,4S)-3-amino-4-methoxypyrrolidin-1-yl]-5,6,7,8-tetrahydroquinolin-6-yl]-6-methylthieno[2,3-b]pyridine-2-carboxamide | 453 | (DMSO-$d_6$, 400 MHz) δ (ppm): 8.31 (d, J = 8.4 Hz, 1H), 7.58 (d, J = 7.6 Hz, 1H), 7.31 (d, J = 8.4 Hz, 1H), 7.20-7.17 (m, 3H), 6.23 (d, J = 8.4 Hz, 1H), 4.16-4.07 (m, 1H), 3.62-3.58 (m, 2H), 3.47-3.41 (m, 2H), 3.29 (s, 3H), 3.12 (d, J = 8.4 Hz, 1H), 2.82-2.68 (m, 4H), 2.59 (s, 3H), 2.01-1.98 (m, 1H), 1.82-1.74 (m, 2H). |

TABLE 21-continued

| Example Number | Structure and Compound Name | LRMS m/z [M + H]⁺ | ¹H NMR |
|---|---|---|---|
| 23-5² | 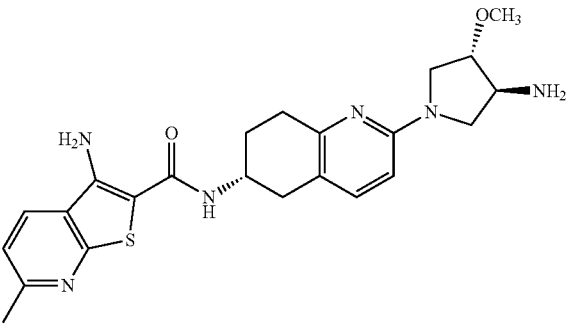 [SMILES: CO[C@H]1CN(c2ccc3c(n2)CC[C@@H](NC(=O)c2sc4nc(C)ccc4c2N)C3)C[C@@H]1N]<br>3-amino-N-[(6R)-2-[(3S,4S)-3-amino-4-methoxypyrrolidin-1-yl]-5,6,7,8-tetrahydroquinolin-6-yl]-6-methylthieno[2,3-b]pyridine-2-carboxamide | 453 | (DMSO-d$_6$, 400 MHz) δ ppm: 8.30 (d, J = 8.0 Hz, 1H), 7.60 (d, J = 8.0 Hz, 1H), 7.31 (d, J = 8.0 Hz, 1H), 7.20-7.18 (m, 3H), 6.22 (d, J = 8.4 Hz, 1H), 4.14-4.07 (m, 1H), 3.61-3.57 (m, 2H), 3.44-3.42 (m, 2H), 3.29 (s, 3H), 3.13 (d, J = 8.0 Hz, 1H), 2.81-2.68 (m, 4H), 2.58 (s, 3H), 2.01-1.98 (m, 1H), 1.82-1.74 (m, 2H). |
| 23-6 | 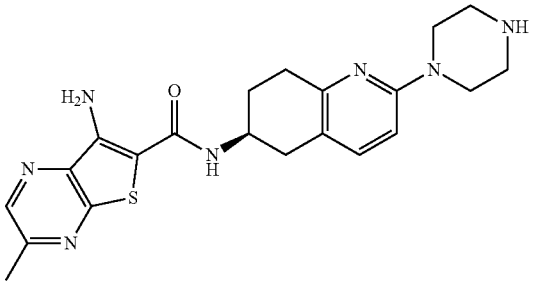 [SMILES: Cc1cnc2c(N)c(C(=O)N[C@H]3CCc4nc(N5CCNCC5)ccc4C3)sc2n1]<br>7-amino-3-methyl-N-[(6S)-2-(piperazin-1-yl)-5,6,7,8-tetrahydroquinolin-6-yl]thieno[2,3-b]pyrazine-6-carboxamide | 424 | (DMSO-d$_6$, 400 MHz) δ (ppm): 8.65 (s, 1H), 7.83 (d, J = 8.0 Hz, 1H), 7.24 (d, J = 8.4 Hz, 1H), 6.92 (br s, 2H), 6.63-6.57 (m, 1H), 4.18-4.14 (m, 1H), 3.41-3.33 (m, 3H), 2.86-2.70 (m, 9H), 2.56 (s, 3H), 2.04-2.01 (m, 1H), 1.92-1.82 (m, 1H). |
| 23-7³ | 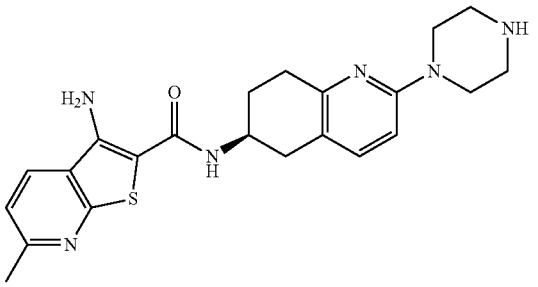 [SMILES: Cc1ccc2c(N)c(C(=O)N[C@H]3CCc4nc(N5CCNCC5)ccc4C3)sc2n1]<br>3-amino-6-methyl-N-[(6S)-2-(piperazin-1-yl)-5,6,7,8-tetrahydroquinolin-6-yl]thieno[2,3-b]pyridine-2-carboxamide | 423 | (DMSO-d$_6$, 300 MHz) δ (ppm): 8.31 (d, J = 8.0 Hz, 1H) 7.59 (d, J = 8.0 Hz, 1H), 7.31 (d, J = 8.4 Hz, 1H), 7.23 (d, J = 8.4 Hz, 1H), 7.17 (br s, 2H), 6.58 (d, J = 8.4 Hz, 1H), 4.18-4.16 (m, 1H), 3.34-3.32 (m, 4H), 2.94-2.68 (m, 8H), 2.58 (s, 3H), 2.08-1.90 (m, 1H), 1.88-1.80 (m, 1H). |

TABLE 21-continued

| Example Number | Structure and Compound Name | LRMS m/z [M + H]+ | 1H NMR |
|---|---|---|---|
| 23-8[3] | 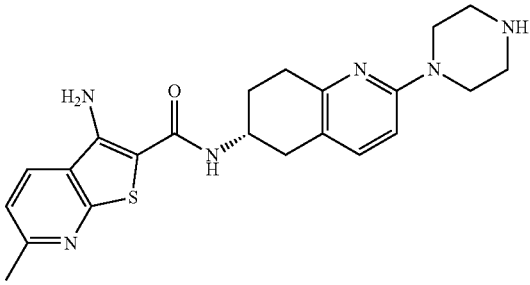 [SMILES: Cc1ccc2c(N)c(C(=O)N[C@@H]3CCc4nc(N5CCNCC5)ccc4C3)sc2n1]<br>3-amino-6-methyl-N-[(6R)-2-(piperazin-1-yl)-5,6,7,8-tetrahydroquinolin-6-yl]thieno[2,3-b]pyridine-2-carboxamide | 423 | (DMSO-$d_6$, 300 MHz) δ (ppm): 8.31 (d, J = 8.0 Hz, 1H) 7.59 (d, J = 8.0 Hz, 1H), 7.31 (d, J = 8.4 Hz, 1H), 7.23 (d, J = 8.4 Hz, 1H), 7.17 (br s, 2H), 6.58 (d, J = 8.4 Hz, 1H), 4.18-4.16 (m, 1H), 3.34-3.32 (m, 4H), 2.94-2.68 (m, 8H), 2.58 (s, 3H), 2.08-1.90 (m, 1H), 1.88-1.80 (m, 1H). |
| 23-9[4] | 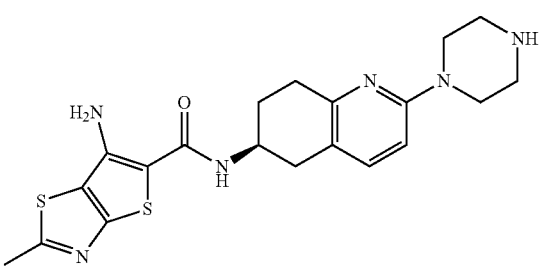 [SMILES: Cc1nc2sc(C(=O)N[C@H]3CCc4nc(N5CCNCC5)ccc4C3)c(N)c2s1]<br>3-amino-6-methyl-N-[(6R)-2-(piperazin-1-yl)-5,6,7,8-tetrahydroquinolin-6-yl]thieno[2,3-b]pyridine-2-carboxamide | 429 | (DMSO-$d_6$, 400 MHz) δ (ppm): 7.59 (d, J = 7.6 Hz, 1H), 7.23 (d, J = 8.4 Hz, 1H), 7.08 (br s, 2H), 6.58 (d, J = 8.4 Hz, 1H), 4.13-4.07 (m, 1H), 3.41-3.32 (m, 4H), 2.79-2.68 (m, 11H), 2.00-1.97 (m, 1H), 1.86-1.80 (m, 1H). |
| 23-10 | 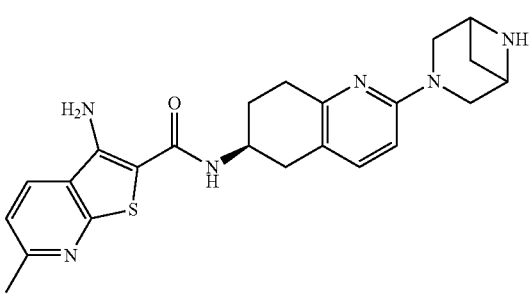 [SMILES: Cc1ccc2c(N)c(C(=O)N[C@H]3CCc4nc(N5CC6CC(C5)N6)ccc4C3)sc2n1]<br>3-amino-N-[(6S)-2-{3,6-diazabicyclo[3.1.1]heptan-3-yl}-5,6,7,8-tetrahydroquinolin-6-yl]-6-methylthieno[2,3-b]pyridine-2-carboxamide | 435 | (DMSO-$d_6$, 400 MHz) δ (ppm): 8.31 (d, J = 8.4 Hz, 1H), 7.58 (d, J = 7.6 Hz, 1H), 7.31 (d, J = 8.4 Hz, 1H), 7.25 (d, J = 8.4 Hz, 1H), 7.16 (br s, 2H), 6.40 (d, J = 8.4 Hz, 1H), 4.18-4.12 (m, 1H), 3.67-3.66 (m, 2H), 3.57-3.50 (m, 4H), 3.40-3.33 (m, 2H), 2.83-2.75 (m, 4H), 2.59 (s, 3H), 2.03-2.00 (m, 1H), 1.89-1.84 (m, 1H), 1.44 (d, J = 8.0 Hz, 1H). |

TABLE 21-continued

| Example Number | Structure and Compound Name | LRMS m/z [M + H]+ | 1H NMR |
|---|---|---|---|
| 23-11 | 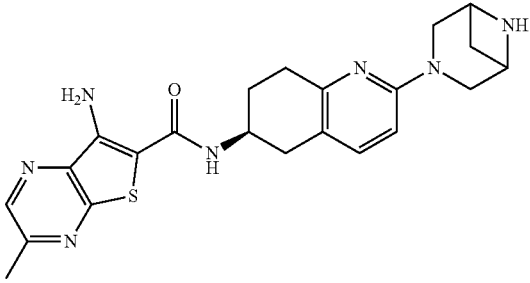 [SMILES: Cc1cnc2c(N)c(C(=O)N[C@H]3CCc4nc(N5CC6CC(C5)N6)ccc4C3)sc2n1]　7-amino-N-[(6S)-2-{3,6-diazabicyclo[3.1.1]heptan-3-yl}-5,6,7,8-tetrahydroquinolin-6-yl]-3-methylthieno[2,3-b]pyrazine-6-carboxamide | 436 | (DMSO-$d_6$, 400 MHz) δ (ppm): 8.65 (s, 1H), 7.83 (d, J = 8.0 Hz, 1H), 7.26 (d, J = 8.4 Hz, 1H), 6.92 (br s, 2H), 6.40 (d, J = 9.2 Hz, 1H), 4.19-4.16 (m, 1H), 3.68-3.66 (m, 2H), 3.60-3.51 (m, 4H), 3.33-3.20 (m, 2H), 2.83-2.76 (m, 4H), 2.66 (s, 3H), 2.05-2.02 (m, 1H), 1.90-1.87 (m, 1H), 1.44 (d, J = 8.8 Hz, 1H). |
| 23-12 | 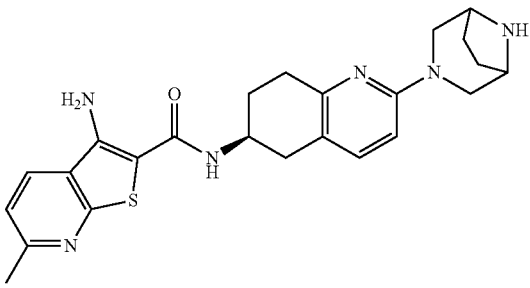 [SMILES: Cc1ccc2c(N)c(C(=O)N[C@H]3CCc4nc(N5CC6CCC(C5)N6)ccc4C3)sc2n1]　3-amino-N-[(6S)-2-{3,8-diazabicyclo[3.2.1]octan-3-yl}-5,6,7,8-tetrahydroquinolin-6-yl]-6-methylthieno[2,3-b]pyridine-2-carboxamide | 449 | (DMSO-$d_6$, 400 MHz) δ (ppm): 8.31 (d, J = 8.8 Hz, 1H), 7.56 (d, J = 7.2 Hz, 1H), 7.31 (d, J = 8.4 Hz, 1H), 7.22-7.15 (m, 3H), 6.45 (d, J = 8.8 Hz, 1H), 4.14 (br s, 1H), 3.77-3.75 (m, 2H), 3.47 (s, 2H), 2.82-2.68 (m, 6H), 2.59 (s, 3H), 2.02-1.83 (m, 2H), 1.63-1.54 (m, 4H). |
| 23-13 | 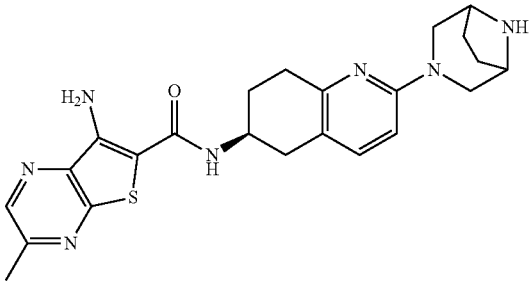 [SMILES: Cc1cnc2c(N)c(C(=O)N[C@H]3CCc4nc(N5CC6CCC(C5)N6)ccc4C3)sc2n1]　7-amino-N-[(6S)-2-{3,8-diazabicyclo[3.2.1]octan-3-yl}-5,6,7,8-tetrahydroquinolin-6-yl]-3-methylthieno[2,3-b]pyrazine-6-carboxamide | 450 | (DMSO-$d_6$, 300 MHz) δ (ppm): 8.65 (s, 1H), 7.82 (d, J = 7.6 Hz, 1H), 7.42 (d, J = 8.4 Hz, 1H), 6.93 (br s, 2H), 6.47-6.42 (m, 1H), 4.16 (br s, 1H), 3.77-3.73 (m, 2H), 2.85-2.66 (m, 6H), 2.58 (s, 3H), 2.41 (s, 1H), 2.03-1.81 (m, 2H), 1.67-1.54 (m, 4H). |

TABLE 21-continued

| Example Number | Structure and Compound Name | LRMS m/z [M + H]+ | 1H NMR |
|---|---|---|---|
| 23-14[1] | 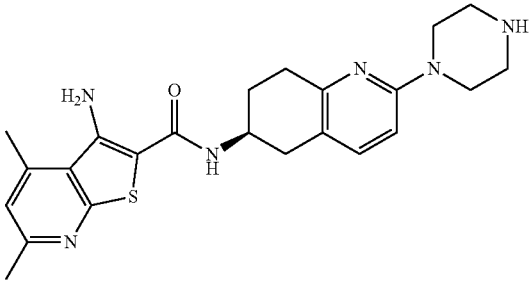 [SMILES: Cc1cc(C)c2c(N)c(C(=O)N[C@H]3CCc4nc(N5CCNCC5)ccc4C3)sc2n1]<br>3-amino-4,6-dimethyl-N-[(6S)-2-(piperazin-1-yl)-5,6,7,8-tetrahydroquinolin-6-yl]thieno[2,3-b]pyridine-2-carboxamide | 437 | (DMSO-$d_6$, 400 MHz) δ (ppm): 7.61 (d, J = 8.0 Hz, 1H), 7.24 (d, J = 8.8 Hz, 1H), 7.14 (s, 1H), 6.82 (br, 2H), 6.58 (d, J = 8.8 Hz, 1H), 4.16-4.14 (m, 1H), 3.41-3.33 (m, 6H), 2.82-2.73 (m, 12H), 2.00-1.99 (m,1H), 1.88-1.83 (m, 1H). |
| 23-15[5] | 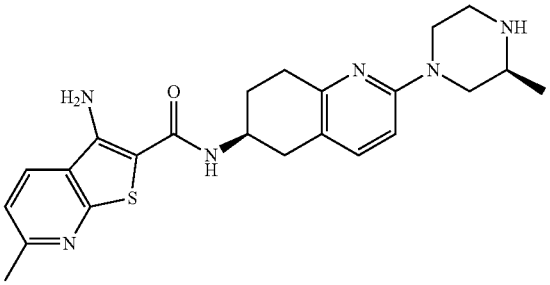 [SMILES: Cc1ccc2c(N)c(C(=O)N[C@H]3CCc4nc(N5CCN[C@@H](C)C5)ccc4C3)sc2n1]<br>3-amino-6-methyl-N-[(6S)-2-[(3S)-3-methylpiperazin-1-yl]-5,6,7,8-tetrahydroquinolin-6-yl]thieno[2,3-b]pyridine-2-carboxamide | 437 | (DMSO-$d_6$, 400 MHz) δ (ppm): 8.31 (d, J = 8.0 Hz, 1H), 7.58 (d, J = 7.6 Hz, 1H), 7.32 (d, J = 8.4 Hz, 1H), 7.23 (d, J = 8.8 Hz, 1H), 7.16 (br s, 2H), 6.59 (d, J = 8.4 Hz, 1H), 4.14-4.00 (m, 3H), 2.94-2.91 (m, 1H), 2.84-2.65 (m, 6H), 2.63-2.60 (m, 4H), 2.26-2.20 (m, 1H), 1.99-2.03 (m, 2H), 1.91-1.83 (m, 1H), 1.03-1.01 (d, J = 8.0 Hz, 1H). |
| 23-16[6] | 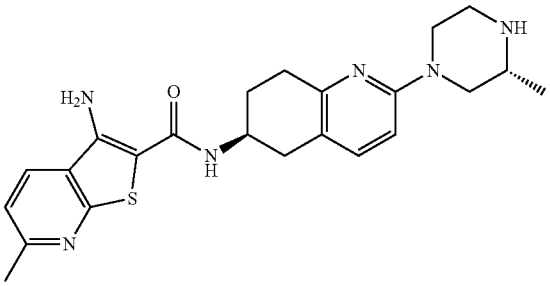 [SMILES: Cc1ccc2c(N)c(C(=O)N[C@H]3CCc4nc(N5CCN[C@H](C)C5)ccc4C3)sc2n1]<br>3-amino-6-methyl-N-[(6S)-2-[(3R)-3-methylpiperazin-1-yl]-5,6,7,8-tetrahydroquinolin-6-yl]thieno[2,3-b]pyridine-2-carboxamide | 437 | (DMSO-$d_6$, 400 MHz) δ (ppm): 8.31 (d, J = 8.4 Hz, 1H), 7.57 (d, J = 8.0 Hz, 1H), 7.31 (d, J = 8.4 Hz, 1H), 7.23 (d, J = 8.4 Hz, 1H), 7.16 (br s, 2H), 6.59 (d, J = 8.0 Hz, 1H), 4.13-4.00 (m, 3H), 2.94-2.61 (m, 7H), 2.59 (s, 3H), 2.26-2.20 (m, 2H), 1.99-1.83 (m, 2H), 1.02 (d, J = 6.4 Hz, 3H). |

TABLE 21-continued

| Example Number | Structure and Compound Name | LRMS m/z [M + H]+ | 1H NMR |
|---|---|---|---|
| 23-17[7] | 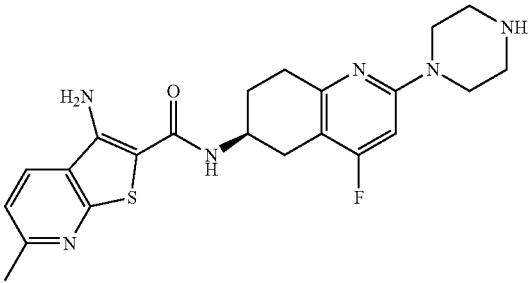 [SMILES: Cc1ccc2c(N)c(C(=O)N[C@H]3CCc4nc(N5CCNCC5)cc(F)c4C3)sc2n1]<br>3-amino-N-[(6S)-4-fluoro-2-(piperazin-1-yl)-5,6,7,8-tetrahydroquinolin-6-yl]-6-methylthieno[2,3-b]pyridine-2-carboxamide | 441 | (DMSO-$d_6$, 400 MHz) δ (ppm): 8.31 (d, J = 8.0 Hz, 1H), 7.63 (d, J = 7.2 Hz, 1H), 7.31 (d, J = 8.4 Hz, 1H), 7.17 (br s, 2H), 6.48 (d, J = 12.8 Hz, 1H), 4.22-4.12 (m, 1H), 3.36-3.20 (m, 4H), 2.90-2.84 (m, 1H), 2.82-2.75 (m, 6H), 2.59-2.54 (m, 4H), 2.04-1.98 (m, 1H), 1.92-1.83 (m, 1H). |
| 23-18[8] | 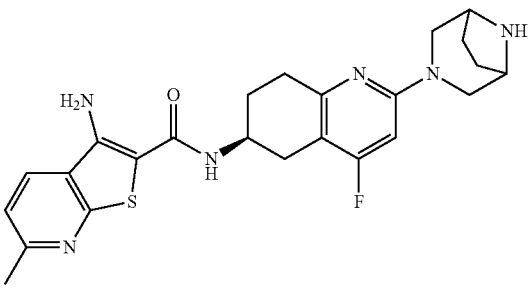 [SMILES: Cc1ccc2c(N)c(C(=O)N[C@H]3CCc4nc(N5CC6CCC(C5)N6)cc(F)c4C3)sc2n1]<br>N-((6S)-2-(3,8-diazabicyclo[3.2.1]octan-3-yl)-4-fluoro-5,6,7,8-tetrahydroquinolin-6-yl)-3-amino-6-methylthieno[2,3-b]pyridine-2-carboxamide | 467 | (DMSO-$d_6$, 400 MHz) δ (ppm): 8.31 (d, J = 8.4 Hz, 1H), 7.63 (d, J = 7.9 Hz, 1H), 7.31 (d, J = 8.4 Hz, 1H), 7.17 (br s, 2H), 6.33 (d, J = 12.6 Hz, 1H), 4.16-4.14 (m, 1H), 3.76-3.73 (m, 2H), 3.48-3.46 (m, 2H), 2.89-2.74 (m, 5H), 2.59-2.53 (m, 4H), 1.98-1.83 (m, 2H), 1.75-1.63 (m, 4 H). |

[1]Notes on procedures:

In Step 3, the carboxylic acid Intermediate 21 was used.

[2]Notes on procedures:

Following Method 2, the stereoisomers were separated by chiral HPLC using the chiral column Chiralpak IE and the eluent gradient 30% to 35% EtOH/MTBE (containing 2 mM $NH_3$ in MeOH).

[3]Notes on procedures:

Following Method 2, the stereoisomers were separated by chiral HPLC using the chiral column Chiralpak ID-3 and mobile phase 30% EtOH/(hexanes:DCM = 3:1, containing 0.1% DIEA).

[4]Notes on procedures:

In Step 3, the carboxylic acid Intermediate 24 was used.

[5]Notes on procedures:

In Step 1, tert-butyl (2S)-2-methylpiperazine-1-carboxylate was used.

[6]Notes on procedures:

In Step 1, tert-butyl (2R)-2-methylpiperazine-1-carboxylate was used.

7Notes on procedures:

Skipping Step 1 and Step 2, the amine Intermediate 52-1 was used in Step 3.

[8]Notes on procedures:

Skipping Step 1 and Step 2, the amine Intermediate 52-2 was used in Step 3.

Example 24-1. 3-Amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide Method 1

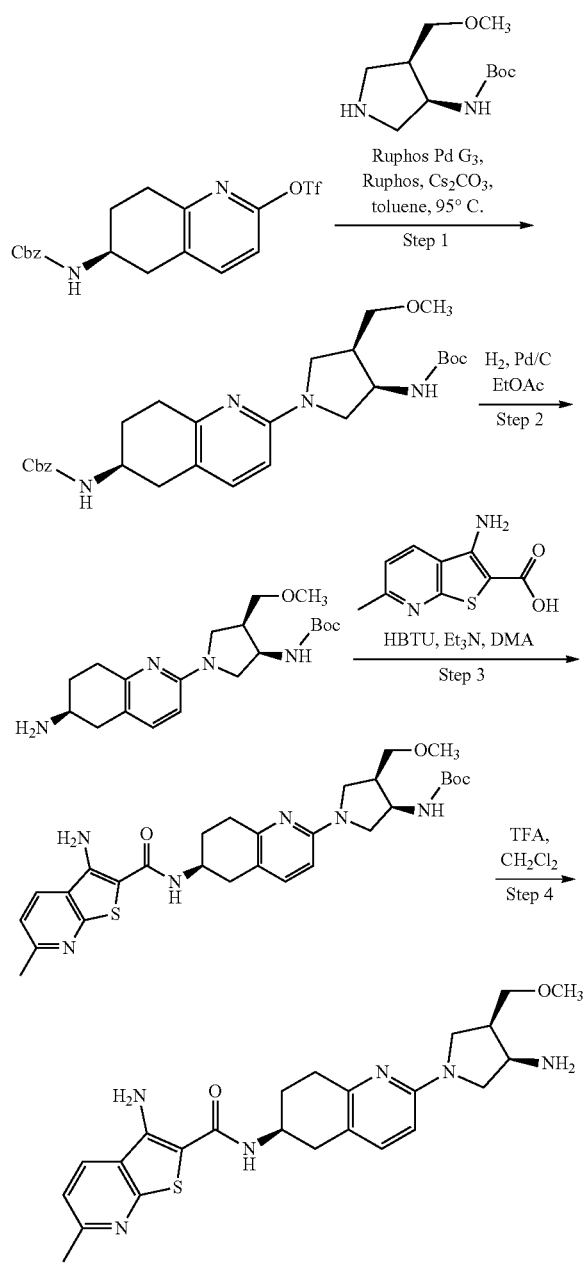

Step 1. Benzyl N-[(6S)-2-[(3R,4R)-3-[[(tert-butoxy)carbonyl]amino]-4-(methoxymethyl)pyrrolidin-1-yl]-5,6,7,8-tetrahydroquinolin-6-yl]carbamate A mixture of benzyl N-[(6S)-2-(trifluoromethanesulfonyloxy)-5,6,7,8-tetrahydroquinolin-6-yl]carbamate (Intermediate 47-2) (800 μmg, 1.85 μmmol), tert-butyl N-[(3R,4R)-4-(methoxymethyl)pyrrolidin-3-yl]carbamate (Intermediate 48-2) (513 mg, 2.23 mmol), RuPhos Pd G3 (155 mg, 0.186 mmol), RuPhos (86.7 mg, 0.186 mmol) and Cs$_2$CO$_3$ (1.21 g, 3.71 mmol) in toluene (10 mL) was stirred for 3 h at 90° C. After cooling to 25° C., the solids were filtered out. The filtrate was concentrated under vacuum. The residue was purified by silica gel chromatography (eluting with 1:2 ethyl acetate/pet. ether) to afford benzyl N-[(6S)-2-[(3R,4R)-3-[[(tert-butoxy)carbonyl]amino]-4-(methoxymethyl)pyrrolidin-1-yl]-5,6,7,8-tetrahydroquinolin-6-yl]carbamate as a white solid. MS (ESI, m/z): 511 [M+H]$^+$.

Step 2. tert-Butyl N-[1-[(6S)-6-amino-5,6,7,8-tetrahydroquinolin-2-yl]-4-(methoxymethyl)pyrrolidin-3-yl]carbamate A mixture of benzyl N-[(6S)-2-[(3R,4R)-3-[[(tert-butoxy)carbonyl]amino]-4-(methoxymethyl)pyrrolidin-1-yl]-5,6,7,8-tetrahydroquinolin-6-yl]carbamate (550 mg, 1.07 mmol) and palladium on carbon (80 mg, 10%) in ethyl acetate (5 mL) was stirred for 1 h at 25° C. under a hydrogen atmosphere (balloon). The solids were filtered out. The filtrate was concentrated under vacuum to give tert-butyl N-[1-[(6S)-6-amino-5,6,7,8-tetrahydroquinolin-2-yl]-4-(methoxymethyl)pyrrolidin-3-yl]carbamate as a white solid (crude). MS (ESI, m/z): 377 [M+H]$^-$.

Step 3. tert-Butyl N-[(3R,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]carbamate Et$_3$N (0.50 mL, 3.58 mmol) and HBTU (453 mg, 1.19 mmol) were added to a stirring solution of tert-butyl N-[(3R,4R)-1-[(6S)-6-amino-5,6,7,8-tetrahydroquinolin-2-yl]-4-(methoxymethyl)pyrrolidin-3-yl]carbamate (450 mg, 1.19 mmol) and 3-amino-6-methylthieno[2,3-b]pyridine-2-carboxylic acid (248 mg, 1.19 mmol) in DMA (4 mL). The resulting solution was stirred for 2 h at 25° C. The mixture was purified by reverse phase chromatography (Column: C18 silica gel; Mobile phase, A: water (containing 0.05% TFA) and B: ACN (15% to 90% over 25 min)). The collected fraction was concentrated under vacuum to give tert-butyl N-[(3R,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]carbamate as a yellow solid. MS (ESI, m/z): 567 [M+H]$^+$.

Step 4. 3-Amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide A solution of tert-butyl N-[(3R,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]carbamate (450 μmg, 0.794 mmol) and TFA (3 mL) in DCM (12 mL) was stirred for 1 h at 25° C. The mixture was concentrated under vacuum. The residue was treated with a solution of NH$_3$ in MeOH (2 mL, 7M). The resulting mixture was stirred for 10 min and concentrated under vacuum. The residue was purified by prep-HPLC (Column: XBridge Shield RP18 OBD, 30×150 mm, 5 μm; Mobile Phase A: water (10 mM NH$_4$HCO$_3$) and B: ACN (27% to 37% over 7 min); Flow rate: 60 mL/min). The collected fraction was lyophilized to give 3-amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide as a white solid. MS (ESI, m/z): 467 [M+H]⁻. ¹H NMR (DMSO-d6, 400 MHz) δ(ppm): 8.31 (d, J=8.0 Hz, 1H), 7.59 (d, J=8.0 Hz, 1H), 7.31 (d, J=8.4 Hz, 1H), 7.19-7.17 (m, 3H), 6.20 (d, J=8.4 Hz, 1H), 4.15-4.08 (m, 1H), 3.61-3.51 (m, 2H), 3.52-3.35 (m, 3H), 3.29 (s, 3H), 3.25-3.15 (m, 2H), 2.81-2.64 (m, 4H), 2.60 (s, 3H), 2.49-2.38 (m, 1H), 2.09-1.98 (m, 1H), 1.91-1.80 (m, 1H), 1.61 (br s, 2H).

Example 24-1. 3-Amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide and Example 24-2. 3-Amino-N-[(6S)-2-[(3S,4S)-3-amino-4-(methoxymethyl)pyrrolidin-1-yl]-5,6,7,8-tetrahydroquinolin-6-yl]-6-methylthieno[2,3-b]pyridine-2-carboxamide rahydroquinolin-2-yl]-4-(methoxymethyl)pyrrolidin-3-yl]carbamate (Step 3 product) were separated by chiral HPLC using the chiral column Chiralpak IA and Mobile Phase, 50% A: hexanes:DCM=3:1 and 50% B: EtOH (containing 0.1% Et₂NH) to provide tert-butyl N-[(3R,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]carbamate as a white solid as the first eluted isomer (RT=9.3 min) and tert-butyl N-[(3S,4S)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]carbamate as a white solid as the second eluted isomer (RT=11.3 min).

3-Amino-N-[(6S)-2-[(3S,4S)-3-amino-4-(methoxymethyl)pyrrolidin-1-yl]-5,6,7,8-tetrahydroquinolin-6-yl]-6-methylthieno[2,3-b]pyridine-2-carboxamide was obtained

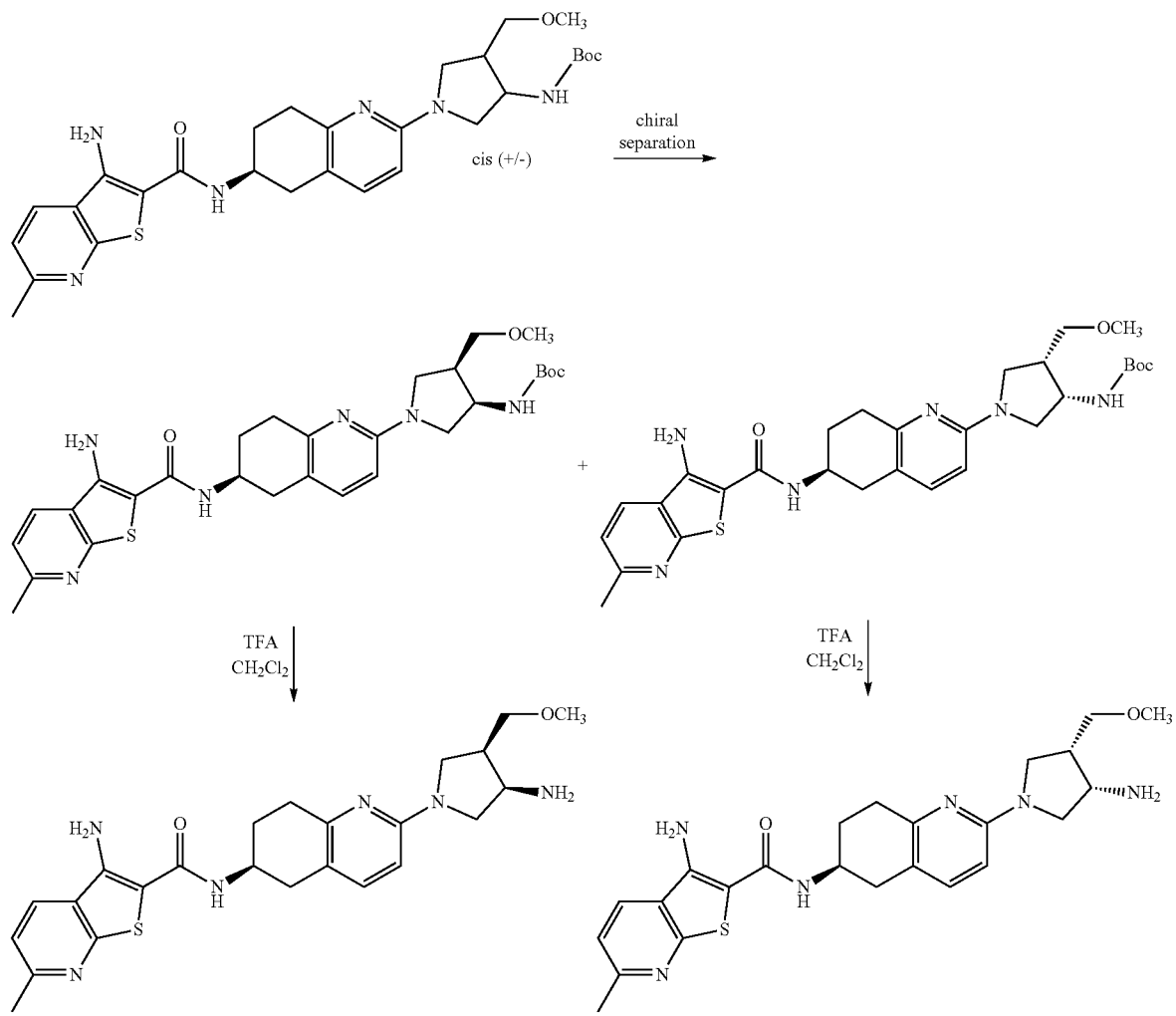

3-Amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide was also obtained starting from the cis racemate tert-butyl N-[4-(methoxymethyl)pyrrolidin-3-yl]carbamate (Intermediate 48-1) and following procedures similar to Method 1. The enantiomers of the cis racemate tert-butyl N-[1-[(6S)-6-[3-amino-6-methylthieno[2,3-b]pyridine-2-amido]-5,6,7,8-tetfrom conversion of tert-butyl N-[(3S,4S)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]carbamate following procedures similar to Method 1, Step 4. ¹H NMR (DMSO-d₆, 400 MHz) δ(ppm): 8.30 (d, J=8.0 Hz, 1H), 7.56 (br s, 1H), 7.31 (d, J=8.4 Hz, 1H), 7.18-7.16 (m, 3H), 6.20 (d, J=8.4 Hz, 1H), 4.18-4.09 (m, 1H), 3.61-3.51 (m, 2H), 3.50-3.39 (m, 3H), 3.28 (s, 3H), 3.21-3.17 (m, 2H), 2.81-2.64 (m, 4H), 2.67 (s, 3H), 2.46-2.40 (m, 1H), 2.09-1.91 (m, 1H), 1.91-1.80 (m, 1H), 1.55 (br s, 2H). MS (ESI, m/z): 467 [M+H]⁺.

Example 25. 3-Amino-N-[(6S)-2-[(3S,4R)-3-amino-4-(difluoromethyl)pyrrolidin-1-yl]-5,6,7,8-tetrahydroquinolin-6-yl]-6-methylthieno[2,3-b]pyridine-2-carboxamide

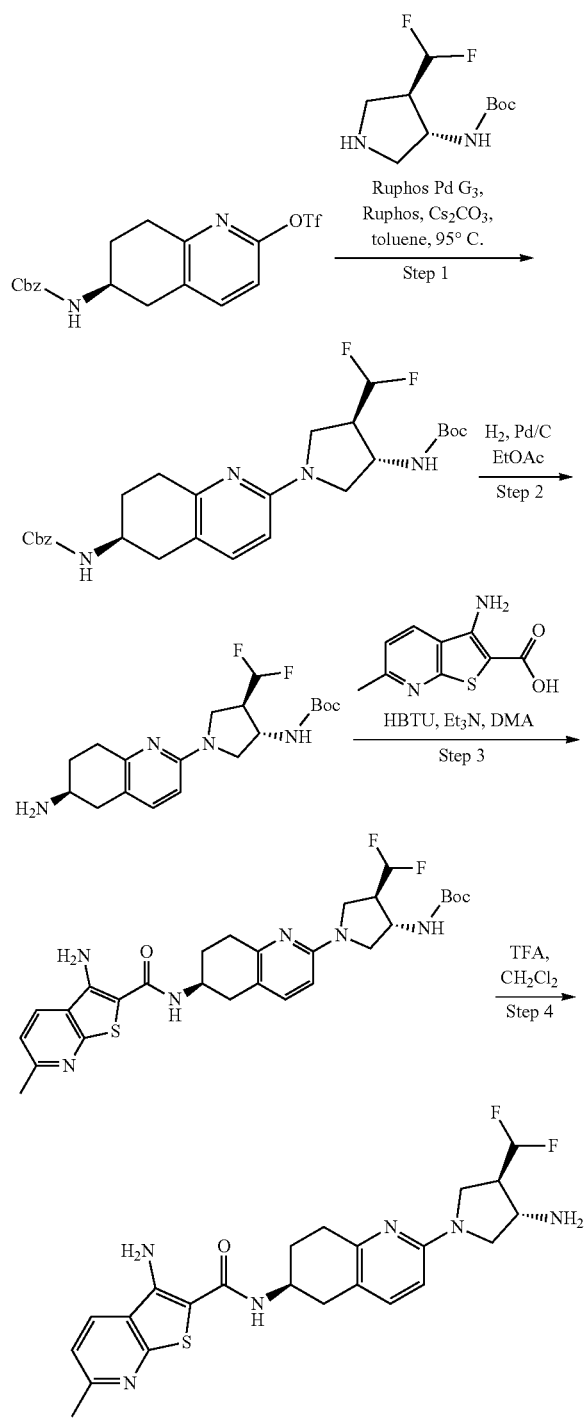

Step 1. Benzyl N-[(6S)-2-[(3S,4R)-3-[[(tert-butoxy)carbonyl]amino]-4-(difluoromethyl)pyrrolidin-1-yl]-5,6,7,8-tetrahydroquinolin-6-yl]carbamate A mixture of benzyl N-[(6S)-2-(trifluoromethanesulfonyloxy)-5,6,7,8-tetrahydroquinolin-6-yl]carbamate (Intermediate 47-2) (480 mg, 1.09 mmol), tert-butyl N-[(3S,4R)-4-(difluoromethyl)pyrrolidin-3-yl]carbamate (Intermediate 51-2) (284 mg, 1.20 mmol), RuPhos (51.0 mg, 0.109 mmol), RuPhos Pd G3 (91.0 mg, 0.109 mmol) and Cs₂CO₃ (890 mg, 2.73 mmol) in toluene (10 mL) was stirred for 4 h at 95° C. After cooled to 25° C., the solids were filtered out. The filtrate was concentrated under reduced pressure. The residue was purified by silica gel chromatography (eluting with 1:1 ethyl acetate/pet. ether) to afford benzyl N-[(6S)-2-[(3S,4R)-3-[[(tert-butoxy)carbonyl]amino]-4-(difluoromethyl)pyrrolidin-1-yl]-5,6,7,8-tetrahydroquinolin-6-yl]carbamate as a white solid. MS (ESI, m/z): 517 [M+H]⁺.

Step 2. tert-butyl N-[(3S,4R)-1-[(6S)-6-amino-5,6,7,8-tetrahydroquinolin-2-yl]-4-(difluoromethyl)pyrrolidin-3-yl]carbamate A mixture of benzyl N-[(6S)-2-[(3S,4R)-3-[[(tert-butoxy)carbonyl]amino]-4-(difluoromethyl)pyrrolidin-1-yl]-5,6,7,8-tetrahydroquinolin-6-yl]carbamate (350 mg, 0.664 mmol) and Pd/C (350 mg, 10%) in ethyl acetate (10 mL) was stirred 2 h at 25° C. under hydrogen atmosphere. The solids were filtered out and the filter cake was washed with ethyl acetate (3×10 mL). The filtrate was concentrated under reduced pressure to afford tert-butyl N-[(3S,4R)-1-[(6S)-6-amino-5,6,7,8-tetrahydroquinolin-2-yl]-4-(difluoromethyl)pyrrolidin-3-yl]carbamate as a brown solid. MS (ESI, m/z): 383 [M+H]⁺.

Step 3. tert-Butyl N-[(3S,4R)-1-[(6S)-6-[3-amino-6-methylthieno[2,3-b]pyridine-2-amido]-5,6,7,8-tetrahydroquinolin-2-yl]-4-(difluoromethyl)pyrrolidin-3-yl]carbamate A solution of tert-butyl N-[(3S,4R)-1-[(6S)-6-amino-5,6,7,8-tetrahydroquinolin-2-yl]-4-(difluoromethyl)pyrrolidin-3-yl]carbanate (240 mg, 0.615 mmol), 3-amino-6-methylthieno[2,3-b]pyridine-2-carboxylic acid (141 mg, 0.677 mmol), Et₃N (0.260 mL, 1.85 mmol) and HBTU (280 mg, 0.738 mmol) in DMA (5 mL) was stirred for 6 h at 25° C. The mixture was purified by reverse phase chromatography (Column: C18 silica gel; Mobile phase, A: water (containing 0.1% TFA) and B: ACN (0% to 60% in 30 min)) to afford tert-butyl N-[(3S,4R)-1-[(6S)-6-[3-amino-6-methylthieno[2,3-b]pyridine-2-amido]-5,6,7,8-tetrahydroquinolin-2-yl]-4-(difluoromethyl)pyrrolidin-3-yl]carbamate as a yellow solid. MS (ESI, m/z): 573 [M+H]⁺.

Step 4. 3-Amino-N-[(6S)-2-[(3S,4R)-3-amino-4-(difluoromethyl)pyrrolidin-1-yl]-5,6,7,8-tetrahydroquinolin-6-yl]-6-methylthieno[2,3-b]pyridine-2-carboxamide To a stirring solution of tert-butyl N-[(3S,4R)-1-[(6S)-6-[3-amino-6-methylthieno[2,3-b]pyridine-2-amido]-5,6,7,8-tetrahydroquinolin-2-yl]-4-(difluoromethyl)pyrrolidin-3-yl]carbamate (300 mg, 0.513 mmol) in DCM (15 mL) was added TFA (5 mL) dropwise at 0° C. The resulting mixture was stirred for 40 min at 25° C. The resulting mixture was concentrated under vacuum. The resulting mixture was concentrated under vacuum. The residue was treated with NH₃ (15 mL, 7 M in MeOH). The solution was stirred for 30 min at 25° C. and concentrated under vacuum. The residue was purified by prep-HPLC (Column: XBridge Prep Phenyl OBD, 19×150 mm, 5 μm; Mobile Phase, A: water (10 mM NH₄HCO₃) and B: ACN (20% to 37% in 8 min); Flow rate: 60 mL/min). The product fraction was lyophilized to afford 3-amino-N-[(6S)-2-[(3S,4R)-3-amino-4-(difluoromethyl)pyrrolidin-1-yl]-5,6,7,8-tetrahydroquinolin-6-yl]-6-methyl-thieno[2,3-b]pyridine-2-carboxamide as a white solid. MS (ESI, m/z): 473 [M+H]⁺. ¹H NMR (DMSO-d₆, 400 MHz) δ(ppm): 8.31 (d, J=8.0 Hz, 1H), 7.59 (d, J=7.6 Hz, 1H), 7.31 (d, J=8.4 Hz, 1H), 7.21 (d, J=8.4 Hz, 1H), 7.17 (br s, 2H), 6.34-6.05 (m, 2H), 3.68-3.57 (m, 2H), 3.51-3.48 (m, 1H), 3.39-3.77 (m, 1H), 3.04-3.00 (m, 1H), 2.81-2.75 (m, 4H), 2.72 (s, 3H), 2.48-2.42 (m, 1H), 2.08-1.91 (m, 1H), 1.90-1.78 (m, 3H).

Example 26-1. 3-Amino-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide and Example 26-2. 3-Amino-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide

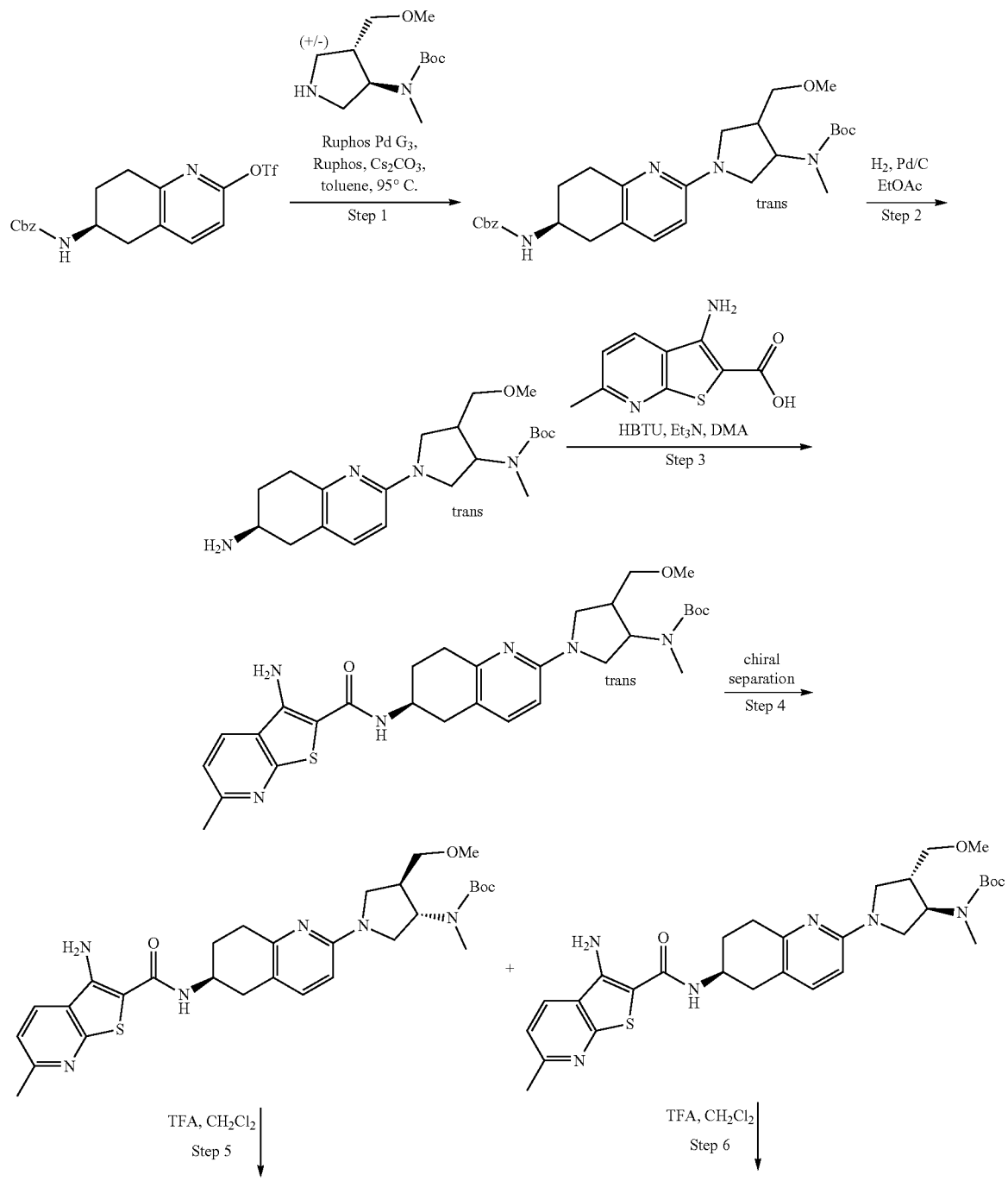

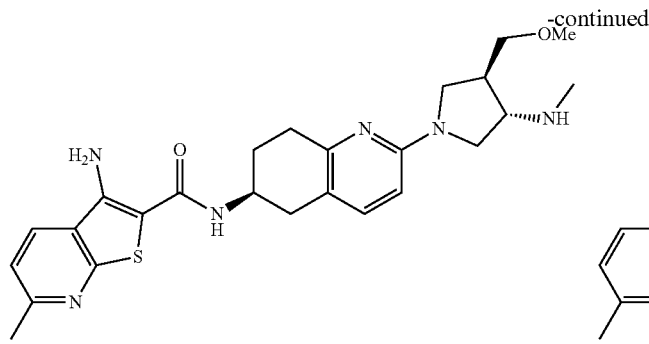
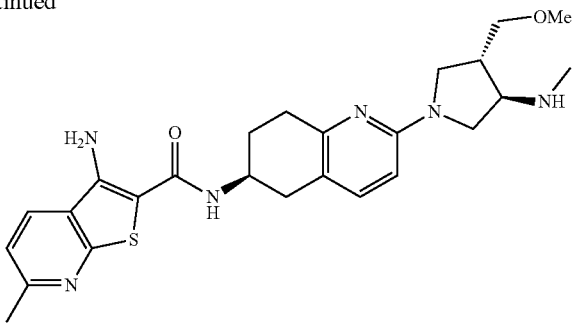

Step 1. trans-Benzyl N-[(6S)-2-(3-[[(tert-butoxy)carbonyl](methyl)amino]-4-(methoxymethyl)pyrrolidin-1-yl)-5,6,7,8-tetrahydroquinolin-6-yl]carbamate A mixture of benzyl N-[(6S)-2-(trifluoromethanesulfonyloxy)-5,6,7,8-tetrahydroquinolin-6-yl]carbamate (Intermediate 47-2) (200 mg, 0.446 mmol), trans-tert-butyl N-[4-(methoxymethyl)pyrrolidin-3-yl]-N-methylcarbamate (Intermediate 53) (121 mg, 0.446 mmol), RuPhos (42.0 mg, 0.090 mmol), RuPhos Pd G3 (38.0 mg, 0.045 mmol) and Cs$_2$CO$_3$ (291 mg. 0.893 mmol) in toluene (4 mL) was stirred for 3 h at 90° C. The solids were filtered out. The filtrate was concentrated under reduced pressure. The residue was purified by silica gel chromatography (eluting with 1:1 ethyl acetate/pet. ether) to afford trans-benzyl N-[(6S)-2-(3-[[(tert-butoxy)carbonyl](methyl)amino]-4-(methoxymethyl)pyrrolidin-1-yl)-5,6,7,8-tetrahydroquinolin-6-yl]carbamate as a yellow solid. MS (ESI, m/z): 525 [M+H]$^+$.

Step 2. trans-tert-Butyl N-[1-[(6S)-6-amino-5,6,7,8-tetrahydroquinolin-2-yl]-4-(methoxymethyl)pyrrolidin-3-yl]-N-methylcarbamate A mixture of trans-benzyl N-[(6S)-2-(3-[[(tert-butoxy)carbonyl](methyl)amino]-4-(methoxymethyl)pyrrolidin-1-yl)-5,6,7,8-tetrahydroquinolin-6-yl]carbamate (180 mg, 0.326 mmol) and palladium on carbon(180 mg, 10%) in ethyl acetate (10 mL) was stirred for 3 h at 25° C. under hydrogen atmosphere (balloon). The solids were filtered out. The filtrate was concentrated under reduced pressure to afford trans-tert-butyl N-[1-[(6S)-6-amino-5,6,7,8-tetrahydroquinolin-2-yl]-4-(methoxymethyl)pyrrolidin-3-yl]-N-methylcarbamate as a white solid. MS (ESI, m/z): 391 [M+H]$^+$.

Step 3. trans-tert-Butyl N-[1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate HBTU (122 mg, 0.322 mmol) was added to a stirring solution of trans-tert-butyl N-[1-[(6S)-6-amino-5,6,7,8-tetrahydroquinolin-2-yl]-4-(methoxymethyl)pyrrolidin-3-yl]-N-methylcarbamate (70.0 mg, 0.179 mmol), 3-amino-6-methylthieno[2,3-b]pyridine-2-carboxylic acid (39.0 mg, 0.189 mmol) and Et$_3$N (0.075 mL, 0.537 mmol) in DMA (2 mL). The resulting solution was stirred for 1 h at 25° C. The resulting mixture was purified by reverse phase chromatography (Column: C18 silica gel; Mobile phase, A: water (containing 10 mmol/L NH$_4$HCO$_3$) and B: ACN (5% to 80% in 30 min)). The collected fraction was concentrated under vacuum to give trans-tert-butyl N-[1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate as a yellow solid. MS (ESI, m/z): 581 [M+H]$^-$.

Step 4. tert-Butyl N-[(3R,4S)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate and tert-butyl N-[(3S,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate trans-tert-Butyl N-[1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate (40.0 mg, 0.0690 mmol) was separated by chiral HPLC (Column: Chiralpak IA, 2×25 cm, 5 μm; Mobile phase, A: hexanes:DCM=3:1 (containing 0.1% Et$_2$NH) and B: EtOH (hold 30% in 30 min); Flow rate: 12 mL/min). The first eluting isomer (RT=11.8 min) was collected and concentrated under vacuum to give a yellow solid, stereochemistry on the pyrrolidine arbitrarily assigned as tert-butyl N-[(3S,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate. The second eluting isomer (RT=21.4 min) was collected and concentrated under vacuum to give a yellow solid, stereochemistry on the pyrrolidine arbitrarily assigned as tert-butyl N-[(3R,4S)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate. MS (ESI, m/z): 581 [M+H]$^-$.

Step 5. 3-Amino-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide A solution of tert-butyl N-[(3S,4R)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate (11.0 mg, 0.0190 mmol) and TFA (0.500 mL) in DCM (1.50 mL) was stirred for 30 min at 25° C. The resulting mixture was concentrated under vacuum. The residue was treated with a solution of NH$_3$ (2.00 mL, 7M in MeOH). The resulting solution was stirred for 30 min at 25° C. and concentrated under vacuum. The residue was purified by prep-HPLC (Column: XBridge Shield RP18 OBD, 5 μm, 19×150 mm; Mobile Phase A: water (10 mM NH$_4$HCO$_3$) and B: ACN (0% to 55% in 7 min); Flow rate: 25 mL/min).

The collected fraction was lyophilized to give 3-amino-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide as a white solid. MS (ESI, m/z): 481 [M+H]⁻. ¹H-NMR (DMSO-d₆, 400 MHz) δ(ppm): 8.31 (d, J=8.4 Hz, 1H), 7.59 (br s, 1H), 7.31 (d, J=8.0 Hz, 1H), 7.20-7.17 (m, 3H), 6.24 (d, J=8.0 Hz, 1H), 4.14-4.10 (m, 1H), 3.64-3.59 (m, 1H), 3.54-3.50 (m, 1H), 3.46-3.27 (m, 8H), 3.17-3.10 (m, 5H), 2.55 (s, 3H), 2.35-2.30 (m, 4H), 2.02-1.97 (m, 1H), 1.88-1.82 (m, 1H).

Step 6. 3-Amino-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide A solution of tert-butyl N-[(3R,4S)-1-[(6S)-6-[3-amino-6-methylthieno[2,3-b]pyridine-2-amido]-5,6,7,8-tetrahydroquinolin-2-yl]-4-(methoxymethyl)pyrrolidin-3-yl]-N-methylcarbamate (13.0 mg, 0.022 mmol) and TFA (0.500 mL) in DCM (1.50 mL) was stirred for 30 min at 25° C. The resulting mixture was concentrated under vacuum. The residue was treated with a solution of NH₃ (2.00 mL, 7M in MeOH). The resulting solution was stirred for 30 min at 25° C. and concentrated under vacuum. The residue was purified by prep-HPLC (Column: XBridge Shield RP18 OBD, 5 m, 19×150 mm; Mobile phase, A: water (10 mM NH₄HCO₃) and B: ACN (20% to 45% in 7 min); Flow rate: 25 mL/min). The collected fraction was lyophilized to give 3-amino-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide as a white solid. MS (ESI, m/z): 481 [M+H]⁻. ¹H-NMR (DMSO-de, 400 MHz) δ(ppm): 8.31 (d, J=8.0 Hz, 1H), 7.59 (br s, 1H), 7.31 (d, J=8.4 Hz, 1H), 7.20-7.17 (m, 3H), 6.24 (d, J=8.4 Hz, 1H), 4.14-4.10 (m, 1H), 3.65-3.60 (m, 1H), 3.55-3.51 (m, 1H), 3.46-3.27 (m, 5H), 3.16-3.10 (m, 2H), 3.02-3.00 (m, 1H), 2.76-2.72 (m, 4H), 2.59 (s, 3H), 2.34-2.32 (m, 4H), 2.02-1.97 (m, 1H), 1.88-1.82 (m, 1H).

Example 27-1. 3-Amino-N-[(6S)-2-[(3R,4R)-3-amino-4-(fluoromethyl)pyrrolidin-1-yl]-5,6,7,8-tetrahydroquinolin-6-yl]-6-methylthieno[2,3-b]pyridine-2-carboxamide and Example 27-2. 3-Amino-N-[(6S)-2-[(3S,4S)-3-amino-4-(fluoromethyl)pyrrolidin-1-yl]-5,6,7,8-tetrahydroquinolin-6-yl]-6-methylthieno[2,3-b]pyridine-2-carboxamide

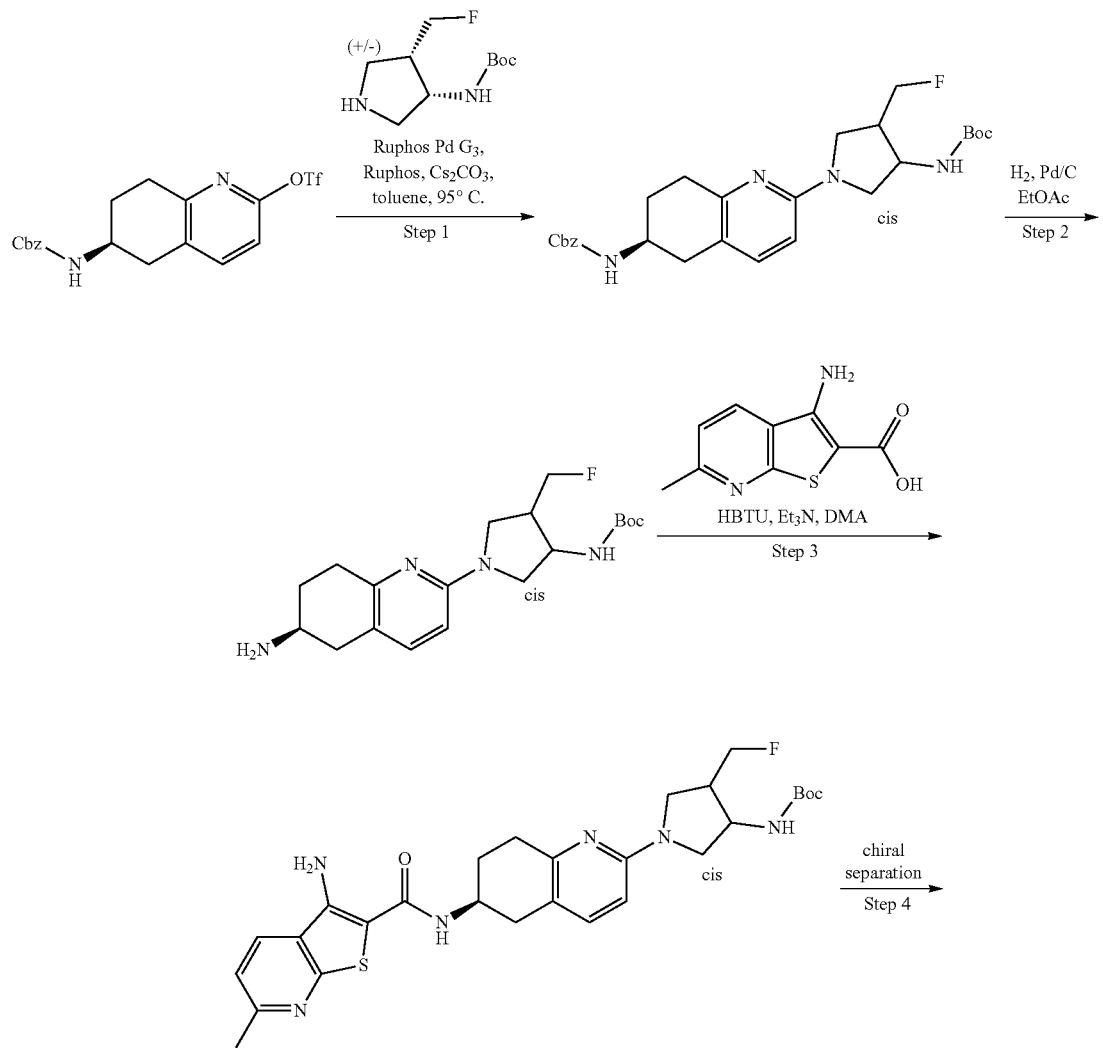

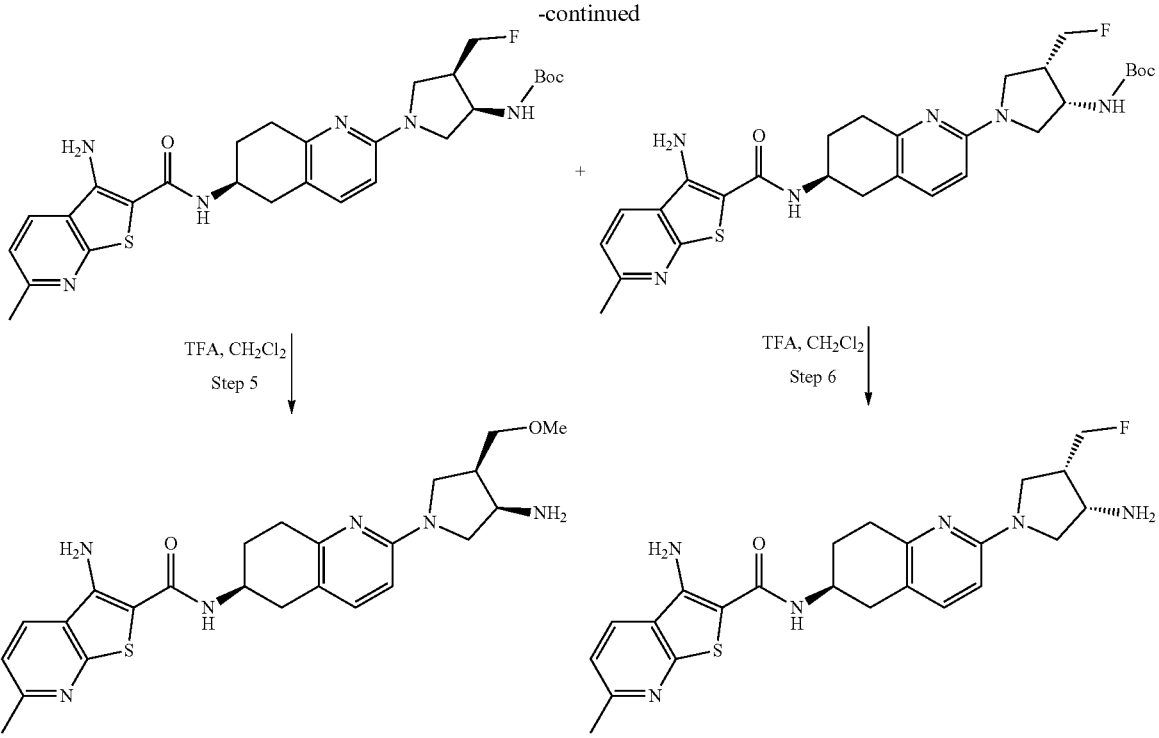

Step 1. cis-Benzyl N-[(6S)-2-(3-[[(tert-butoxy)carbonyl]amino]-4-(fluoromethyl)pyrrolidin-1-yl)-5,6,7,8-tetrahydroquinolin-6-yl]carbamate A mixture of cis-tert-butyl N-[4-(fluoromethyl)pyrrolidin-3-yl]carbamate (Intermediate 54) (150 mg, 0.687 mmol), benzyl N-[(6S)-2-(trifluoromethanesulfonyloxy)-5,6,7,8-tetrahydroquinolin-6-yl]carbamate (Intermediate 47-2) (150 mg, 0.342 mmol), RuPhos (16.0 mg, 0.034 mmol), RuPhos Pd G3 (29.0 mg, 0.035 mmol) and $Cs_2CO_3$ (278 mg, 0.853 mmol) in toluene (5 mL) was stirred for 2 h at 95° C. After cooled to 25° C., the solids were filtered out. The filtrate was concentrated under vacuum. The residue was purified by silica gel chromatography (eluting with 1:1 ethyl acetate/pet. ether) to afford cis-benzyl N-[(6S)-2-(3-[[(tert-butoxy)carbonyl]amino]-4-(fluoromethyl)pyrrolidin-1-yl)-5,6,7,8-tetrahydroquinolin-6-yl]carbamate as a white solid. MS (ESI, m/z): 499 $[M+H]^+$.

Step 2. cis-tert-Butyl N-[1-[(6S)-6-amino-5,6,7,8-tetrahydroquinolin-2-yl]-4-(fluoromethyl)pyrrolidin-3-yl]carbamate A mixture of cis-benzyl N-[(6S)-2-(3-[[(tert-butoxy)carbonyl]amino]-4-(fluoromethyl)pyrrolidin-1-yl)-5,6,7,8-tetrahydroquinolin-6-yl]carbamate (130 mg, 0.256 mmol) and Palladium on carbon (130 mg, 10%) in ethyl acetate (5 mL) was stirred for 2 h at 25° C. under hydrogen atmosphere (balloon). The resulting mixture was filtered. The filtrate was concentrated under reduced pressure to afford cis-tert-butyl N-[1-[(6S)-6-amino-5,6,7,8-tetrahydroquinolin-2-yl]-4-(fluoromethyl)pyrrolidin-3-yl]carbamate as a brown solid. MS (ESI, m/z): 365 $[M+H]^+$.

Step 3. cis-tert-Butyl N-[1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate HBTU (92.0 mg, 0.243 mmol) was added to a solution of cis-tert-butyl N-[(3R,4R)-1-[(6S)-6-amino-5,6,7,8-tetrahydroquinolin-2-yl]-4-(fluoromethyl)pyrrolidin-3-yl]carbamate (75.0 mg, 0.202 mmol), 3-amino-6-methylthieno[2,3-b]pyridine-2-carboxylic acid (45.0 mg, 0.216 mmol) and $Et_3N$ (0.084 mL, 0.603 mmol) in DMA (3 mL). The resulting solution was stirred for 1 h at 25° C. The mixture was purified by reverse phase chromatography (Column: C18 silica gel; Mobile phase, A: water (containing 10 mmol/L $NH_4HCO_3$) and B: ACN (0% to 100% in 30 min)) to afford cis-tert-butyl N-[1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate as a yellow solid. MS (ESI, m/z): 555 $[M+H]^+$.

Step 4. tert-Butyl N-[(3R,4R)-1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate and tert-Butyl N-[(3S,4S)-1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate cis-tert-Butyl N-[1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate (70.0 mg, 0.124 mmol) was separated by chiral HPLC (Column: Chiralpak IG, 20×250 mm, 5 μm; Mobile phase, A: hexanes:DCM=3:1(containing 0.1% $Et_2NH$) and B: IPA (hold 30% in 16 min)). The first eluting isomer (RT=10.09 min) was collected and concentrated under vacuum to afford a white solid, stereochemistry on the pyrrolidine arbitrarily assigned as tert-butyl N-[(3R,4R)-1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate. The second eluting isomer (RT=13.22 min) was collected and concentrated under vacuum to afford a white solid, stereochemistry on the pyrrolidine arbitrarily assigned as tert-butyl N-[(3S,4S)-1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbanate. MS (ESI, m/z): 555 [M+H]+

Step 5. 3-Amino-N-[(6S)-2-[(3R,4R)-3-amino-4-(fluoromethyl)pyrrolidin-1-yl]-5,6,7,8-tetrahydroquinolin-6-yl]-6-methylthieno[2,3-b]pyridine-2-carboxamide A solution of tert-butyl N-[(3R,4R)-1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate (15.0 mg, 0.027 mmol) and TFA (0.5 mL) in DCM (1.5 mL) was stirred for 25 min at 25° C. The resulting mixture was concentrated under vacuum. The residue was treated with a solution of NH$_3$ (1.0 mL, 7M in MeOH). The resulting solution was stirred for 30 min and then concentrated under vacuum. The residue was purified by prep-HPLC (Column: XBridge Prep OBD C18 Column, 30×150 mm 5 μm; Mobile phase, A: water (containing 10 mmol/L NH$_4$HCO$_3$) and B: ACN (20% to 45% in 7 min)). The collected fraction was lyophilized to afford 3-amino-N-[(6S)-2-[(3R,4R)-3-amino-4-(fluoromethyl)pyrrolidin-1-yl]-5,6,7,8-tetrahydroquinolin-6-yl]-6-methylthieno[2,3-b]pyridine-2-carboxamide as a white solid. MS (ESI, m/z): 455 [M+H]+. $^1$H NMR (DMSO-d$_6$, 400 MHz) δ (ppm): 8.31 (d, J=8.0 Hz, 1H), 7.58 (d, J=8.4 Hz, 1H), 7.31 (d, J=8.0 Hz, 1H), 7.20 (d, J=8.4 Hz, 1H), 7.16 (br s, 2H), 6.23 (d, J=8.4 Hz, 1H), 4.81-4.47 (m, 2H), 4.11-4.09 (m, 1H), 3.61-3.60 (m, 1H), 3.54-3.46 (m, 2H), 3.33-3.28 (m, 11H), 3.20-3.18 (m, 1H), 2.81-2.68 (m, 4H), 2.59 (s, 3H), 2.02-1.96 (m, 1H), 1.90-1.66 (m, 2H).

Step 6. 3-Amino-N-[(6S)-2-[(3S,4S)-3-amino-4-(fluoromethyl)pyrrolidin-1-yl]-5,6,7,8-tetrahydroquinolin-6-yl]-6-methylthieno[2,3-b]pyridine-2-carboxamide A solution of tert-butyl N-[(3S,4S)-1-[(6S)-6-[3-amino-6-methylthieno[2,3-b]pyridine-2-amido]-5,6,7,8-tetrahydroquinolin-2-yl]-4-(fluoromethyl)pyrrolidin-3-yl]carbamate (15.0 mg, 0.027 mmol) and TFA (0.5 mL) in DCM (1.5 mL) was stirred for 25 min at 25° C. The resulting mixture was concentrated under vacuum. NH$_3$ (1.0 mL, 7M in MeOH) was added to the residue. The resulting solution was stirred for 30 min and concentrated under vacuum. The residue was purified by prep-HPLC (Column: XBridge Prep OBD C18 Column, 30×150 mm Sum; Mobile phase, A: water (containing 10 mmol/L NH$_4$HCO$_3$) and B: ACN (20% to 45% in 7 min)). The collected fraction was lyophilized to afford 3-amino-N-[(6S)-2-[(3S,4S)-3-amino-4-(fluoromethyl)pyrrolidin-1-yl]-5,6,7,8-tetrahydroquinolin-6-yl]-6-methylthieno[2,3-b]pyridine-2-carboxamide as a white solid. MS (ESI, m/z): 455 [M+H]+. $^1$H NMR (DMSO-dr, 400 MHz) δ (ppm): 8.31 (d, J=8.0 Hz, 1H), 7.58 (d, J=7.6 Hz, 1H), 7.31 (d, J=8.4 Hz, 1H), 7.20 (d, J=8.8 Hz, 1H), 7.16 (br s, 2H), 6.23 (d, J=8.4 Hz, 1H), 4.81-4.47 (m, 2H), 4.12-4.09 (m, 1H), 3.61-3.60 (m, 1H), 3.53-3.47 (m, 2H), 3.33-3.27 (m, 1H), 3.21-3.18 (m, 1H), 2.81-2.68 (m, 4H), 2.59 (s, 3H), 2.02-1.96 (m, 1H), 1.90-1.66 (m, 2H).

Example 28-1. 3-amino-N-[(6S)-2-[(3S,4S)-3-amino-4-(2-methoxyethoxy)pyrrolidin-1-yl]-5,6,7,8-tetrahydroquinolin-6-yl]-6-methylthieno[2,3-b]pyridine-2-carboxamide and Example 28-2. 3-amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide

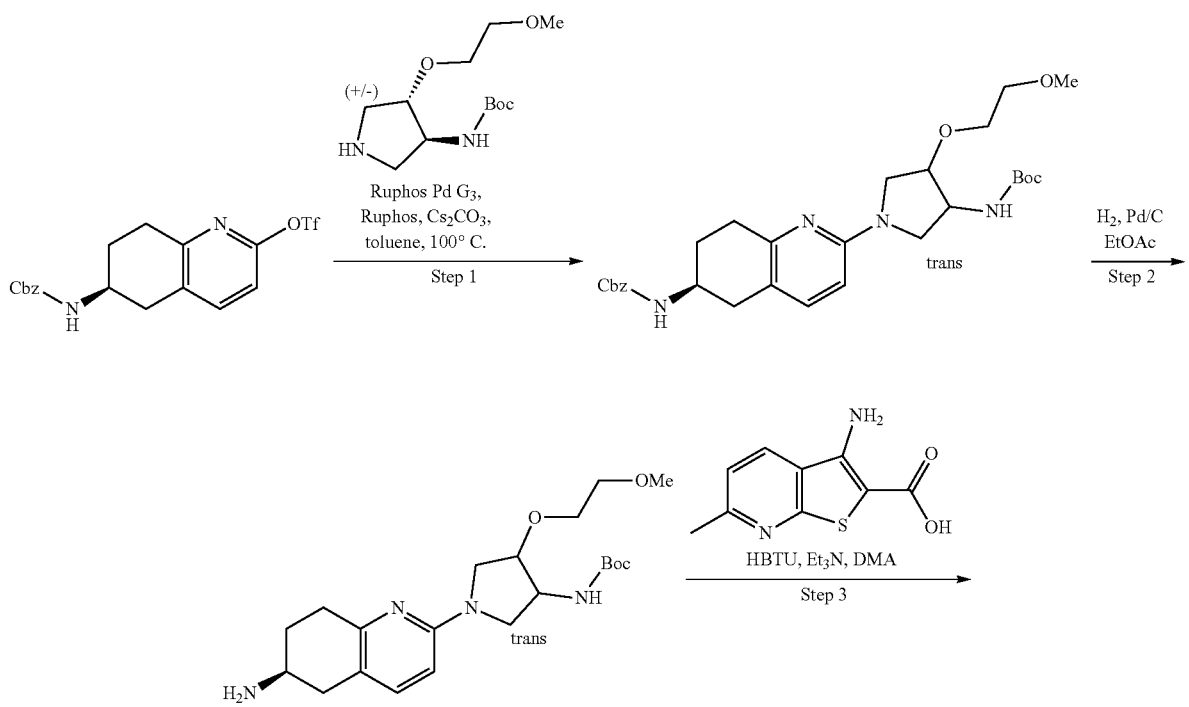

-continued

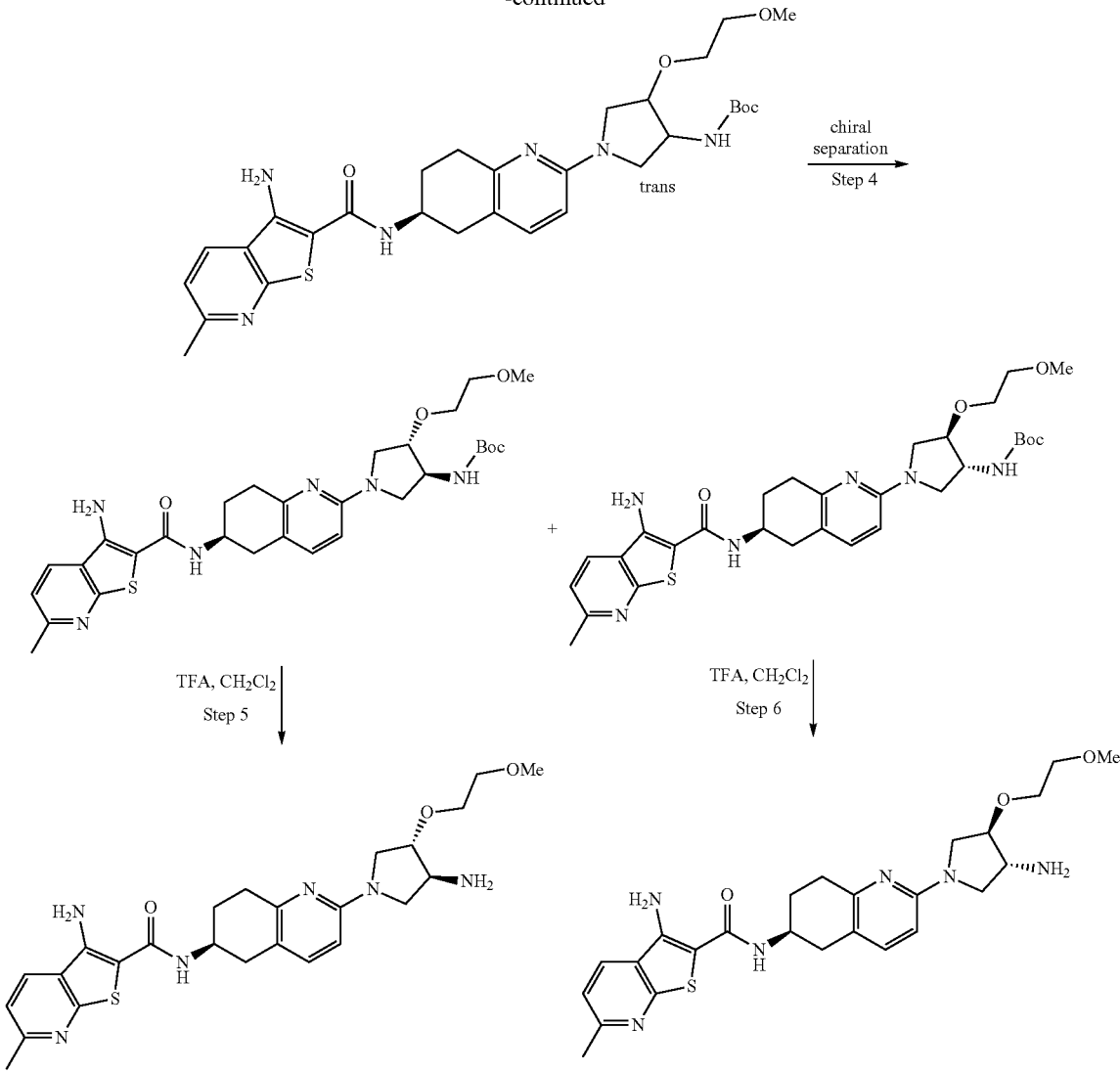

Step 1. trans-Benzyl N-[(6S)-2-(3-[[(tert-butoxy)carbonyl]amino]-4-(2-methoxyethoxy)pyrrolidin-1-yl)-5,6,7,8-tetrahydroquinolin-6-yl]carbamate A mixture of benzyl N-[(6S)-2-(trifluoromethanesulfonyloxy)-5,6,7,8-tetrahydroquinolin-6-yl]carbamate (Intermediate 47-2) (200 μmg, 0.465 μmmol), trans-tert-butyl N-[4-(2-methoxyethoxy)pyrrolidin-3-yl]carbamate (Intermediate 55) (157 mg, 0.603 mmol), RuPhos Pd G3 (38.9 mg, 0.046 mmol), RuPhos (22.0 mg, 0.047 mmol) and Cs$_2$CO$_3$ (454 mg, 1.39 mmol) in toluene (4 mL) was stirred for 3 h at 100° C. After cooling to 26° C., the solids were filtered out. The filtrate was concentrated under vacuum. The residue was purified by silica gel chromatography (eluting with 1:1 ethyl acetate/pet. ether) to give trans-benzyl N-[(6S)-2-(3-[[(tert-butoxy)carbonyl]amino]-4-(2-methoxyethoxy)pyrrolidin-1-yl)-5,6,7,8-tetrahydroquinolin-6-yl]carbamate as a yellow solid. MS (ESI, m/z): 541 [M+H]$^+$.

Step 2. trans-tert-Butyl N-[1-[(6S)-6-amino-5,6,7,8-tetrahydroquinolin-2-yl]-4-(2-methoxyethoxy)pyrrolidin-3-yl]carbamate A mixture of trans-benzyl N-[(6S)-2-(3-[[(tert-butoxy)carbonyl]amino]-4-(2-methoxyethoxy)pyrrolidin-1-yl)-5,6,7,8-tetrahydroquinolin-6-yl]carbamate (140 mg, 0.259 mmol) and Palladium on carbon (70.0 mg, 10%) in ethyl acetate (10 mL) was stirred for 3 h at 26° C. under an atmosphere of hydrogen (balloon). The solids were filtered out. The filtrate was concentrated under vacuum to give trans-tert-butyl N-[1-[(6S)-6-amino-5,6,7,8-tetrahydroquinolin-2-yl]-4-(2-methoxyethoxy)pyrrolidin-3-yl]carbamate as a black solid. MS (ESI, m/z): 407 [M+H]$^-$.

Step 3. trans-tert-Butyl N-[1-[(6S)-6-[3-amino-6-methylthieno[2,3-b]pyridine-2-amido]-5,6,7,8-tetrahydroquinolin-2-yl]-4-(2-methoxyethoxy)pyrrolidin-3-yl]carbamate HBTU (112 mg, 0.295 mmol) was added to a solution of trans-tert-butyl N-[1-[(6S)-6-amino-5,6,7,8-tetrahydroquinolin-2-yl]-4-(2-methoxyethoxy)pyrrolidin-3-yl]carbamate (100 mg, 0.246 mmol), Et$_3$N (0.103 mL, 0.741 mmol) and 3-amino-6-methylthieno[2,3-b]pyridine-2-carboxylic acid (61.0 mg, 0.293 mmol) in DMA (2 mL). The resulting solution was stirred for 1 h at 26° C. The mixture was purified reverse phase chromatography (Column: C18 silica gel; Mobile phase, A: water (containing 0.05% TFA) and B: ACN (20% to 85% in 25 min)). The collected fraction was concentrated under vacuum to give trans-tert-butyl N-[1-[(6S)-6-[3-amino-6-methylthieno[2,3-b]pyridine-2-amido]-5,6,7,8-tetrahydroquinolin-2-yl]-4-(2-methoxyethoxy)pyrrolidin-3-yl]carbamate as a yellow solid. MS (ESI, m/z): 597 [M+H]$^+$.

Step 4. 3-Amino-N-[(6S)-2-[(3S,S-3-amino-4-(2-methoxyethoxy)pyrrolidin-1-yl]-5,6,7,8-tetrahydroquinolin-6-yl]-6-methylthieno[2,3-b]pyridine-2-carboxamide and 3-Amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide trans-tert-Butyl N-[1-[(6S)-6-[3-amino-6-methylthieno[2,3-b]pyridine-2-amido]-5,6,7,8-tetrahydroquinolin-2-yl]-4-(2-methoxyethoxy)pyrrolidin-3-yl]carbamate (120 mg, 0.201 mmol) was separated by chiral HPLC (Column: Chiralpak IG, 2×25 cm, 5 μm; Mobile phase, A: hexanes:DCM=3:1 (0.1% Et$_2$NH) and B: EtOH (hold 40% in 20 min)). The first eluting isomer (RT=12.26 min) was collected and concentrated under vacuum to give a yellow solid, stereochemistry on the pyrrolidine arbitrarily assigned as 3-amino-N-[(6S)-2-[(3S,4S)-3-amino-4-(2-methoxyethoxy)pyrrolidin-1-yl]-5,6,7,8-tetrahydroquinolin-6-yl]-6-methylthieno[2,3-b]pyridine-2-carboxamide. The second eluting isomer (RT=17.55 min) was collected and concentrated under vacuum to give a yellow solid, stereochemistry on the pyrrolidine arbitrarily assigned as 3-amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide. MS (ESI, m/z): 597 [M+H]$^-$.

Step 5. 3-Amino-N-[(6S)-2-[(3S,4S)-3-amino-4-(2-methoxyethoxy)pyrrolidin-1-yl]-5,6,7,8-tetrahydroquinolin-6-yl]-6-methylthieno[2,3-b]pyridine-2-carboxamide A solution of tert-butyl N-[(3S,4S)-1-[(6S)-6-[3-amino-6-methylthieno[2,3-b]pyridine-2-amido]-5,6,7,8-tetrahydroquinolin-2-yl]-4-(2-methoxyethoxy)pyrrolidin-3-yl]carbamate (27.0 mg, 0.047 mmol) and TFA (1.00 mL) in DCM (3 mL) was stirred for 30 min at 26° C. The resulting mixture was concentrated under vacuum. The residue was treated with a solution of NH$_3$ (2.00 mL, 7M in MeOH). The resulting solution was stirred for 30 min, and then concentrated under vacuum. The residue was purified by prep-HPLC (Column: XBridge Prep OBD C18, 19×150 mm, 5 m, 13 nm; Mobile phase, A: water (10 mM NH$_4$HCO$_3$) and B: ACN (18% to 40% in 8 min), Flow rate: 60 mL/min). The collected fraction was lyophilized to give 3-amino-N-[(6S)-2-[(3S,4S)-3-amino-4-(2-methoxyethoxy)pyrrolidin-1-yl]-5,6,7,8-tetrahydroquinolin-6-yl]-6-methylthieno[2,3-b]pyridine-2-carboxamide as a white solid. MS (ESI, m/z): 497 [M+H]$^+$. $^1$H NMR (DMSO-d$_6$, 400 MHz) δ(ppm): 8.31 (d, J=8.4 Hz, 1H), 7.59 (d, J=8.0 Hz, 1H), 7.31 (d, J=8.4 Hz, 1H), 7.19 (d, J=8.8 Hz, 1H), 7.17 (br s, 2H), 6.22 (d, J=8.4 Hz, 1H), 4.14-4.10 (m, 1H), 3.75-3.74 (m 1H), 3.64-3.55 (m, 3H), 3.49-3.31 (m, 5H), 3.24 (s, 3H), 3.14-3.12 (m, 1H), 2.82-2.72 (m, 4H), 2.59 (s, 3H), 2.03-1.82 (m, 4H).

Step 6. 3-amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide A solution of tert-butyl N-[(3R,4R)-1-[(6S)-6-[3-amino-6-methylthieno[2,3-b]pyridine-2-amido]-5,6,7,8-tetrahydroquinolin-2-yl]-4-(2-methoxyethoxy)pyrrolidin-3-yl]carbamate (26.0 mg, 0.045 mmol) and TFA (1.00 mL) in DCM (3 mL) was stirred for 30 min at 25° C. The resulting mixture was concentrated under vacuum. NH$_3$ (2.00 mL, 7M in MeOH) was added to the residue. The resulting solution was stirred for 30 min, and then concentrated under vacuum. The residue was purified by prep-HPLC (Column: X Bridge Prep OBD C18, 30×150 mm, 5 μm; Mobile phase, A: water (10 mM NH$_4$HCO$_3$) and B: ACN (18% to 40% in 8 min), Flow rate: 60 mL/min). The collected fraction was lyophilized to give 3-amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide as a white solid. MS (ESI, m/z): 497 [M+H]$^+$. $^1$H NMR (DMSO-dc, 400 MHz) δ(ppm): 8.31 (d, J=8.4 Hz, 1H), 7.59 (d, J=8.0 Hz, 1H), 7.31 (d, J=8.4 Hz, 1H), 7.19 (d, J=8.8 Hz, 1H), 7.17 (br s, 2H), 6.22 (d, J=8.4 Hz, 1H), 4.15-4.11 (m, 1H), 3.75-3.74 (m 1H), 3.63-3.59 (m, 3H), 3.48-3.33 (m, 5H), 3.24 (s, 3H), 3.14-3.11 (m, 1H), 2.80-2.72 (m, 4H), 2.59 (s, 3H), 2.01-1.82 (m, 4H).

Example 29-1. 3-Amino-N-[(6S)-2-[(9S)-9-amino-1,4-dioxa-7-azaspiro[4.4]nonan-7-yl]-5,6,7,8-tetrahydroquinolin-6-yl]-6-methylthieno[2,3-b]pyridine-2-carboxamide and Example 29-2. 3-Amino-N-[(6S)-2-[(9R)-9-amino-1,4-dioxa-7-azaspiro[4.4]nonan-7-yl]-5,6,7,8-tetrahydroquinolin-6-yl]-6-methylthieno[2,3-b]pyridine-2-carboxamide

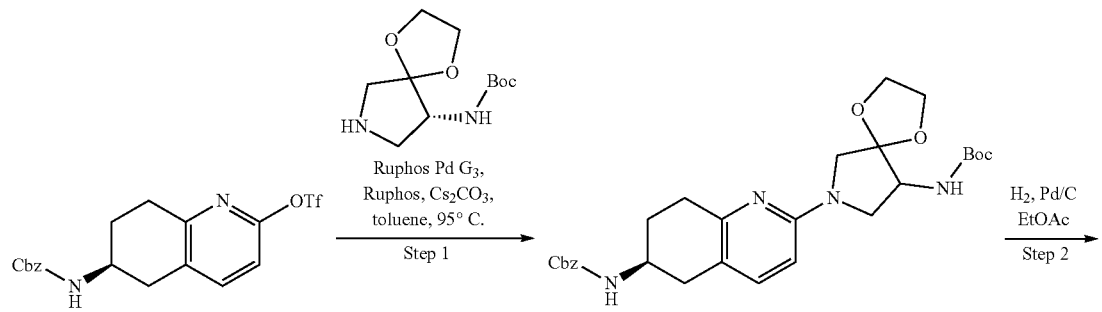

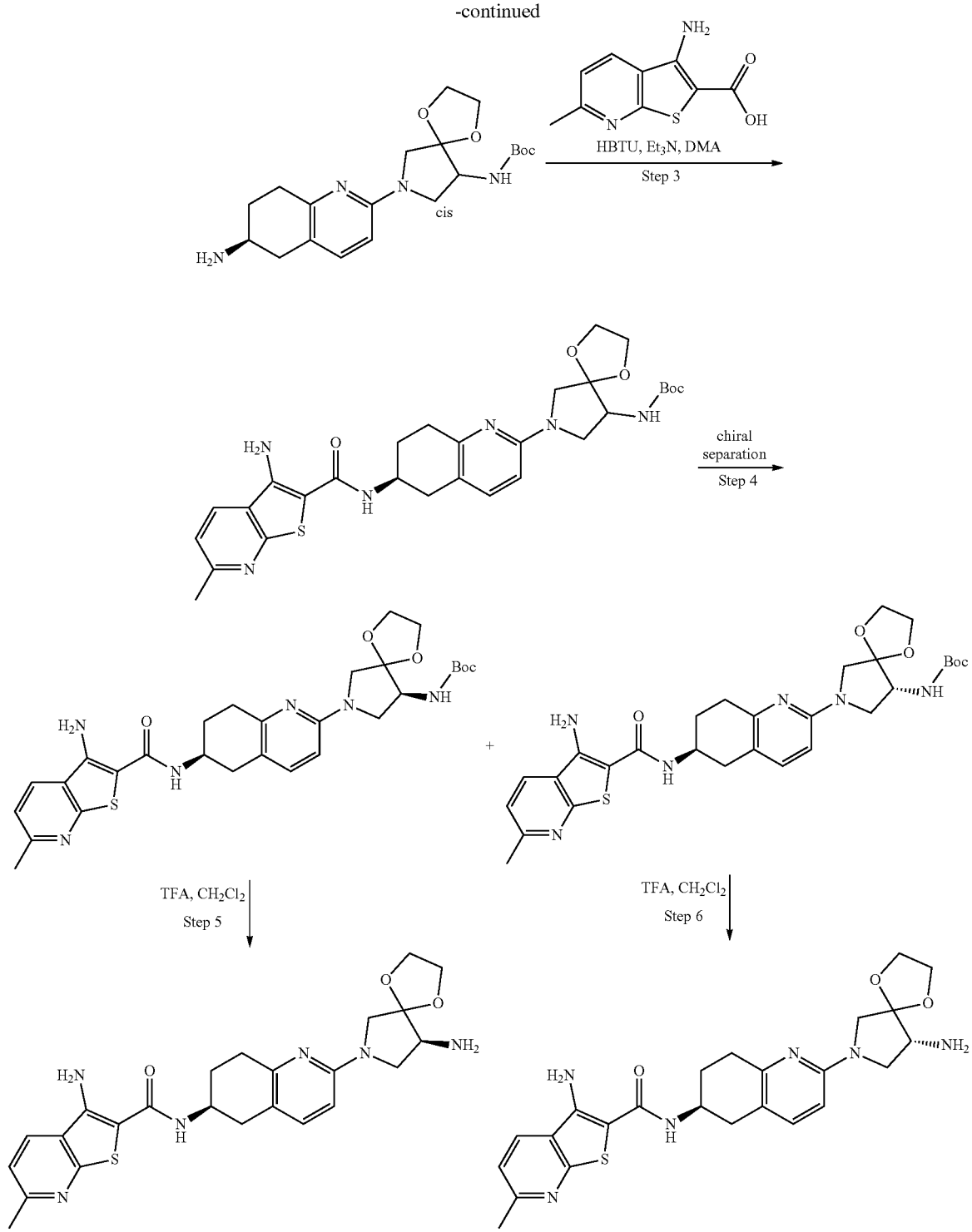

Step 1. Benzyl N-[(6S)-2-(9-[[(tert-butoxy)carbonyl]amino]-1,4-dioxa-7-azaspiro[4.4]nonan-7-yl)-5,6,7,8-tetrahydroquinolin-6-yl]carbamate A mixture of benzyl N-[(6S)-2-(trifluoromethanesulfonyloxy)-5,6,7,8-tetrahydroquinolin-6-yl]carbamate (Intermediate 47-2) (180 mg, 0.410 mmol), tert-butyl N-[1,4-dioxa-7-azaspiro[4.4]nonan-9-yl]carbamate (Intermediate 59) (150 mg, 0.614 mmol), RuPhos (19.0 mg, 0.041 mmol), RuPhos Pd G3 (34.0 mg, 0.041 mmol) and Cs$_2$CO$_3$ (334 mg, 1.025 mmol) in toluene (10 mL) was stirred for 3 h at 95° C. The mixture was allowed to cool down to 25° C., filtered, and the filtrate was concentrated under vacuum. The residue was purified by silica gel chromatography (eluting with 1:1 ethyl acetate/pet. ether) to afford benzyl N-[(6S)-2-(9-[[(tert-butoxy)carbonyl]amino]-1,4-dioxa-7-azaspiro[4.4]nonan-7-yl)-5,6,7,8-tetrahydroquinolin-6-yl]carbamate as a white solid. MS (ESI, m/z): 525 [M+H]$^+$.

Step 2. tert-Butyl N-[7-[(6S)-6-amino-5,6,7,8-tetrahydroquinolin-2-yl]-1,4-dioxa-7-azaspiro[4.4]nonan-9-yl]carbamate A mixture of benzyl N-[(6S)-2-(9-[[(tert-butoxy)carbonyl]amino]-1,4-dioxa-7-azaspiro[4.4]nonan-7-yl)-5,6,7,8-tetrahydroquinolin-6-yl]carbamate (180 mg, 0.336 mmol) and Pd/C (180 mg, 10%) in ethyl acetate (5 mL) was stirred for 2 h at 25° C. The resulting mixture was filtered, and the filter cake was washed with ethyl acetate (3×5 mL). The filtrate was concentrated under reduced pressure to afford tert-butyl N-[7-[(6S)-6-amino-5,6,7,8-tetrahydroquinolin-2-yl]-1,4-dioxa-7-azaspiro[4.4]nonan-9-yl]carbamate as a brown solid. MS (ESI, m/z): 391 [M+H]+.

Step 3. tert-Butyl N-[7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate HBTU (114 mg, 0.301 mmol) was added to a solution of tert-butyl N-[7-[(6S)-6-amino-5,6,7,8-tetrahydroquinolin-2-yl]-1,4-dioxa-7-azaspiro[4.4]nonan-9-yl]carbamate (100 mg, 0.251 mmol), 3-amino-6-methylthieno[2,3-b]pyridine-2-carboxylic acid (57.0 mg, 0.274 mmol) and Et3N (0.104 mL, 0.751 mmol) in DMA (3 mL). The reaction was stirred for 3 h at 25° C. The residue was purified by reverse phase chromatography (Column: C18 silica gel; Mobile phase, A: water (containing 0.1% TFA) and B: ACN (0% to 60% in 30 min)) to afford tert-butyl N-[7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate as a yellow solid. MS (ESI, m/z): 581 [M+H]+.

Step 4. tert-Butyl N-[(9S)-7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate and tert-Butyl N-[(9R)-7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate tert-Butyl N-[7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate (100 mg, 0.169 mmol) was separated by chiral HPLC (Column: Chiralpak IF, 2×25 cm, 5 μm; Mobile phase, A: MTBE (0.1% Et2NH) and B: EtOH (hold 30% in 24 min); Flow rate: 12 mL/min). The first eluting isomer (RT=15.97 min) was collected and concentrated under vacuum to afford a yellow solid, stereochemistry on the pyrrolidine arbitrarily assigned as tert-butyl N-[(9S)-7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate. MS (ESI, m/z): 581 [M+H]+.

The second eluting isomer (RT=20.62 min) was collected and concentrated under vacuum to afford a yellow solid, stereochemistry on the pyrrolidine arbitrarily assigned as tert-butyl N-[(9R)-7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate. MS (ESI, m/z): 581 [M+H]+.

Step 5. 3-Amino-N-[(6S)-2-[(9S)-9-amino-1,4-dioxa-7-azaspiro[4.4]nonan-7-yl]-5,6,7,8-tetrahydroquinolin-6-yl]-6-methylthieno[2,3-b]pyridine-2-carboxamide A solution of tert-butyl N-[(9S)-7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate (40 mg, 0.068 mmol) and TFA (0.50 mL) in DCM (1.5 mL) was stirred for 30 min at 25° C. The resulting solution was concentrated under vacuum. NH3 (2.0 mL, 7M in MeOH) was added to the residue. The resulting solution was stirred for 30 min at 25° C., and then was concentrated under vacuum. The residue was purified by prep-HPLC (Column: X Bridge Prep C18 OBD, 19×150 mm, 5 μm; Mobile phase, A: water (0.05% NH4HCO3) and B: ACN (20% to 35% in 7 min)). The collected fraction was lyophilized to afford 3-amino-N-[(6S)-2-[(9S)-9-amino-1,4-dioxa-7-azaspiro[4.4]nonan-7-yl]-5,6,7,8-tetrahydroquinolin-6-yl]-6-methylthieno[2,3-b]pyridine-2-carboxamide as a white solid. MS (ESI, m/z): 481 [M+H]+. 1H-NMR (CDCl3, 400 MHz) δ(ppm): 7.82 (d, J=8.0 Hz, 1H), 7.22-7.20 (m, 1H), 6.20 (d, J=8.0 Hz, 1H), 6.06-6.02 (m, 2H), 5.52 (d, J=7.2 Hz, 1H), 4.48-4.42 (m, 1H), 4.14-4.09 (m, 4H), 3.82-3.69 (m, 2H), 3.53-3.50 (m, 2H), 3.24-3.20 (m, 1H), 3.09-3.08 (m, 1H), 2.94-2.86 (m, 2H), 2.70-2.64 (m, 4H), 2.26-2.23 (m, 1H), 1.98-1.91 (m, 1H).

Step 6. 3-Amino-N-[(6S)-2-[(9R)-9-amino-1,4-dioxa-7-azaspiro[4.4]nonan-7-yl]-5,6,7,8-tetrahydroquinolin-6-yl]-6-methylthieno[2,3-b]pyridine-2-carboxamide A solution of tert-butyl N-[(9R)-7-[(6S)-6-[3-amino-6-methylthieno[2,3-b]pyridine-2-amido]-5,6,7,8-tetrahydroquinolin-2-yl]-1,4-dioxa-7-azaspiro[4.4]nonan-9-yl]carbamate (40.0 mg, 0.068 mmol) and TFA (0.50 mL) in DCM (1.5 mL) was stirred for 30 min at 25° C. The resulting solution was concentrated under vacuum. NH3 (2.0 mL, 7M in MeOH) was added to the residue. The resulting solution was stirred for 30 min at 25° C., and then was concentrated under vacuum. The residue was purified by prep-HPLC (Column: XBridge Prep C18 OBD, 19×150 mm, 5 μm; Mobile phase, A: water (0.05% NH4HCO3) and B: ACN (20% to 35% in 7 min)). The collected fraction was lyophilized to afford 3-amino-N-[(6S)-2-[(9R)-9-amino-1,4-dioxa-7-azaspiro[4.4]nonan-7-yl]-5,6,7,8-tetrahydroquinolin-6-yl]-6-methylthieno[2,3-b]pyridine-2-carboxamide as a white solid. MS (ESI, m/z): 481 [M+H]+. 1H-NMR (CDCl3, 400 MHz) δ (ppm): 7.82 (d, J=8.4 Hz, 1H), 7.22-7.20 (m, 1H), 6.20 (d, J=8.4 Hz, 1H), 6.06-6.00 (m, 2H), 5.53 (d, J=6.8 Hz, 1H), 4.48-4.42 (m, 1H), 4.14-4.09 (m, 4H), 3.82-3.67 (m, 2H), 3.53-3.501 (m, 2H), 3.27-3.22 (m, 1H), 3.10-3.08 (m, 1H), 2.95-2.90 (m, 2H), 2.70-2.65 (m, 4H), 2.24-2.20 (m, 1H), 1.93-1.87 (m, 1H).

Example 30-1. 3-Amino-N-[(6S)-3-fluoro-2-(piperazin-1-yl)-5,6,7,8-tetrahydroquinolin-6-yl]-6-methylthieno[2,3-b]pyridine-2-carboxamide and

Example 30-2. 3-Amino-N-[(6R)-3-fluoro-2-(piperazin-1-yl)-5,6,7,8-tetrahydroquinolin-6-yl]-6-methylthieno[2,3-b]pyridine-2-carboxamide

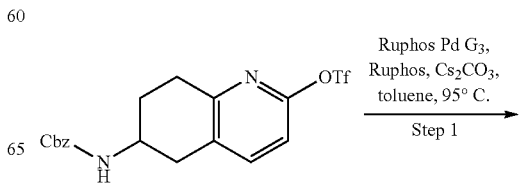

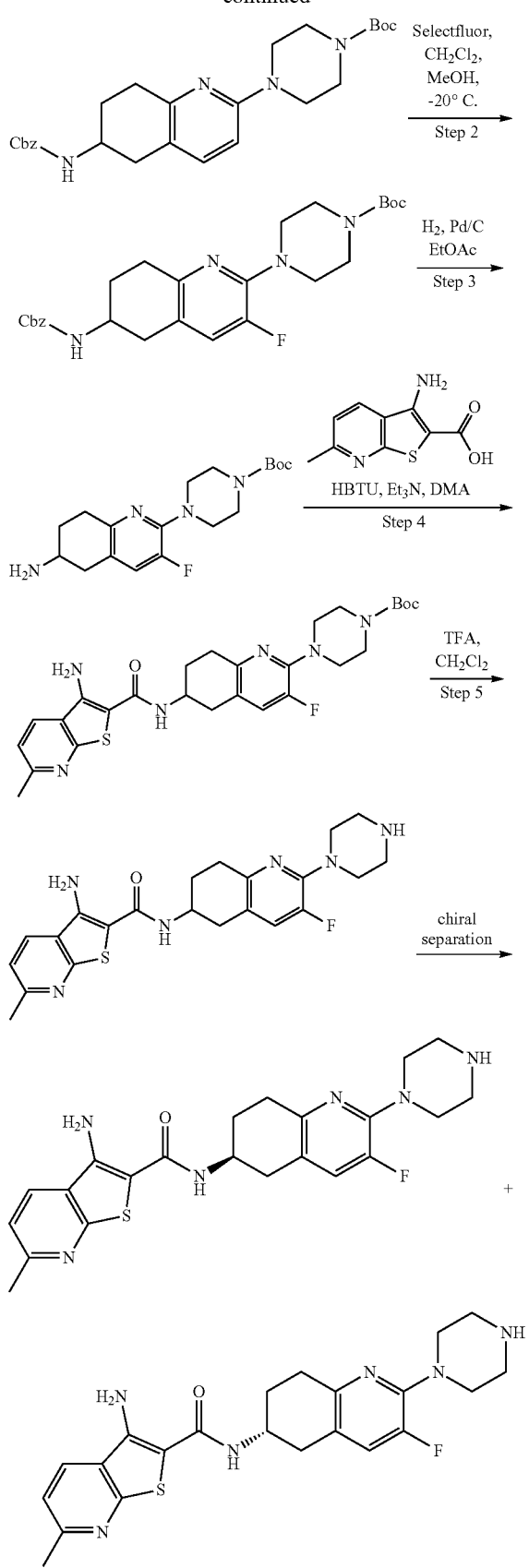

Step 1. tert-Butyl 4-(6-[[(benzyloxy)carbonyl]amino]-5,6,7,8-tetrahydroquinolin-2-yl)piperazine-1-carboxylate A mixture of benzyl N-[2-[(trifluoromethane)sulfonyloxy]-5,6,7,8-tetrahydroquinolin-6-yl]carbamate (Intermediate 47-1) (400 mg, 0.930 mmol), tert-butyl piperazine-1-carboxylate (208 mg, 1.12 mol), RuPhos (87.0 mg, 0.190 mmol), RuPhos Pd G3 (76.0 mg, 0.090 mmol), and $Cs_2CO_3$ (758 mg, 2.33 mmol) in toluene (15 mL) was stirred for 3 h at 95° C. After cooling to 25° C., the solid was filtered out. The filtrate was concentrated under vacuum. The residue was purified by silica gel chromatography (eluting with 1:3 ethyl acetate/pet. ether) to afford tert-butyl 4-(6-[[(benzyloxy)carbonyl]amino]-5,6,7,8-tetrahydroquinolin-2-yl)piperazine-1-carboxylate as a white solid. MS (ESI, m/z): 467 $[M+H]^+$.

Step 2. tert-Butyl 4-(6-[[(benzyloxy)carbonyl]amino]-3-fluoro-5,6,7,8-tetrahydroquinolin-2-yl)piperazine-1-carboxylate A solution of SelectFluor (683 mg, 1.93 mmol) in ACN (10 mL) was added to a stirring solution of tert-butyl 4-(6-[[(benzyloxy)carbonyl]amino]-5,6,7,8-tetrahydroquinolin-2-yl)piperazine-1-carboxylate (600 mg, 1.29 mmol) in DCM (30 mL) and MeOH (30 mL). The resulting solution was stirred for 1 h at −20° C. The resulting mixture was concentrated under vacuum. The residue was purified by prep-HPLC (Column: XBridge Prep C18 OBD, 5 μm, 19×150 mm; Mobile Phase, A: water (0.05% TFA) and B: ACN (55% to 85% in 7 min)). The collected fraction was concentrated under vacuum to give tert-butyl 4-(6-[[(benzyloxy)carbonyl]amino]-3-fluoro-5,6,7,8-tetrahydroquinolin-2-yl)piperazine-1-carboxylate as an off-white solid. MS (ESI, m/z):485 $[M+H]^+$.

Step 3. tert-Butyl 4-(6-amino-3-fluoro-5,6,7,8-tetrahydroquinolin-2-yl)piperazine-1-carboxylate A mixture of tert-butyl 4-(6-[[(benzyloxy)carbonyl]amino]-3-fluoro-5,6,7,8-tetrahydroquinolin-2-yl)piperazine-1-carboxylate (70.0 mg, 0.140 mmol) and palladium on carbon (70.0 mg, 10%) in ethyl acetate (5 mL) was stirred for 1 h at 25° C. under hydrogen atmosphere (balloon). The solids were filtered out. The filtrate was concentrated under vacuum to give tert-butyl 4-(6-amino-3-fluoro-5,6,7,8-tetrahydroquinolin-2-yl)piperazine-1-carboxylate as an off-white solid. MS (ESI, m/z): 351 $[M+H]^+$.

Step 4. tert-Butyl 4-(6-[3-amino-6-methylthieno[2,3-b]pyridine-2-amido]-3-fluoro-5,6,7,8-tetrahydroquinolin-2-yl)piperazine-1-carboxylate HBTU (58.0 mg, 0.150 mmol) was added to a solution of 4-(6-amino-3-fluoro-5,6,7,8-tetrahydroquinolin-2-yl)piperazine-1-carboxylate (45.0 mg, 0.130 mmol), 3-amino-6-methylthieno[2,3-b]pyridine-2-carboxylic acid (32.0 mg, 0.150 mmol) and $Et_3N$ (54.0 KL, 0.390 mmol) in DMA (2 mL). The resulting solution was stirred for 30 min at 25° C. The mixture was purified via reverse phase chromatography (Column: C18 silica gel; Mobile phase, A: water (containing 10 mmoL/L $NH_4HCO_3$) and B: ACN (0% to 85% within 25 min)). The collected fraction was concentrated under vacuum to give tert-butyl 4-(6-[3-amino-6-methylthieno[2, 3-b]pyridine-2-amido]-3-fluoro-5,6,7,8-tetrahydroquinolin-2-yl)piperazine-1-carboxylate as an off-white solid. MS (ESI, m/z): 541 [M+H]+.

Step 5. 3-Amino-N-[(6S)-3-fluoro-2-(piperazin-1-yl)-5,6,7,8-tetrahydroquinolin-6-yl]-6-methylthieno[2,3-b]pyridine-2-carboxamide and 3-Amino-N-[(6R)-3-fluoro-2-(piperazin-1-yl)-5,6,7,8-tetrahydroquinolin-6-yl]-6-methylthieno[2,3-b]pyridine-2-carboxamide A solution of tert-butyl 4-[3-amino-6-(3-amino-6-methyl-1-benzothiophene-2-amido)-5,6,7,8-tetrahydroquinolin-2-yl]piperazine-1-carboxylate (40.0 mg, 0.070 mmol) and TFA (1.00 mL) in DCM (3 mL) was stirred for 1 h at 25° C. The resulting mixture was concentrated under vacuum to give TFA salt of 3-amino-N-[3-fluoro-2-(piperazin-1-yl)-5,6,7,8-tetrahydroquinolin-6-yl]-6-methylthieno[2,3-b]pyridine-2-carboxamide as a yellow solid. The enantiomers were separated by chiral HPLC (Column: Chiralpak IC, 2×25 cm, 5 μm; Mobile Phase, A: Hex (0.2% Et$_2$NH) and B: EtOH (hold 50% in 20 min); Flow rate: 15 mL/min). The first eluting isomer (RT=11.3 min) was concentrated under vacuum and then lyophilized to afford an off-white solid, stereochemistry arbitrarily assigned as 3-amino-N-[(6S)-3-fluoro-2-(piperazin-1-yl)-5,6,7,8-tetrahydroquinolin-6-yl]-6-methylthieno[2,3-b]pyridine-2-carboxamide. MS (ESI, m/z): 441 [M+H]+. $^1$H-NMR (DMSO-d$_6$, 300 MHz) δ(ppm): 8.30 (d, J=8.4 Hz, 1H), 7.60 (d, J=7.5 Hz, 1H), 7.32-7.22 (m, 2H), 7.16 (br s, 2H), 4.14 (br s, 1H), 3.25-3.21 (m, 4H), 2.83-2.72 (m, 8H), 2.58 (s, 3H), 1.98-1.86 (m, 2H).

The second eluting isomer (RT=16.9 min) was concentrated under vacuum and then lyophilized with ACN and water to afford an off-white solid, stereochemistry arbitrarily assigned as 3-amino-N-[(6R)-3-fluoro-2-(piperazin-1-yl)-5,6,7,8-tetrahydroquinolin-6-yl]-6-methylthieno[2,3-b]pyridine-2-carboxamide. MS (ESI, m/z): 441 [M+H]+. $^1$H-NMR (DMSO-d$_6$, 300 MHz) δ(ppm): 8.30 (d, J=8.1 Hz, 1H), 7.60 (d, J=7.8 Hz, 1H), 7.32-7.21 (m, 2H), 7.16 (br s, 2H), 4.15 (br s, 1H), 3.22-3.20 (m, 4H), 2.83-2.72 (m, 8H), 2.58 (s, 3H), 2.07-1.83 (m, 2H).

Example 31-1. 3-Amino-N-[(6S)-2-[(3S,4S)-3-amino-4-(propan-2-yloxy)pyrrolidin-6-yl]-5,6,7,8-tetrahydroquinazolin-6-yl]-4,6-dimethylthieno[2,3-b]pyridine-2-carboxamide and Example 31-2. 3-Amino-N-[(6R)-2-[(3S,4S)-3-amino-4-(propan-2-yloxy)pyrrolidin-1-yl]-5,6,7,8-tetrahydroquinazolin-6-yl]-4,6-dimethylthieno[2,3-b]pyridine-2-carboxamide

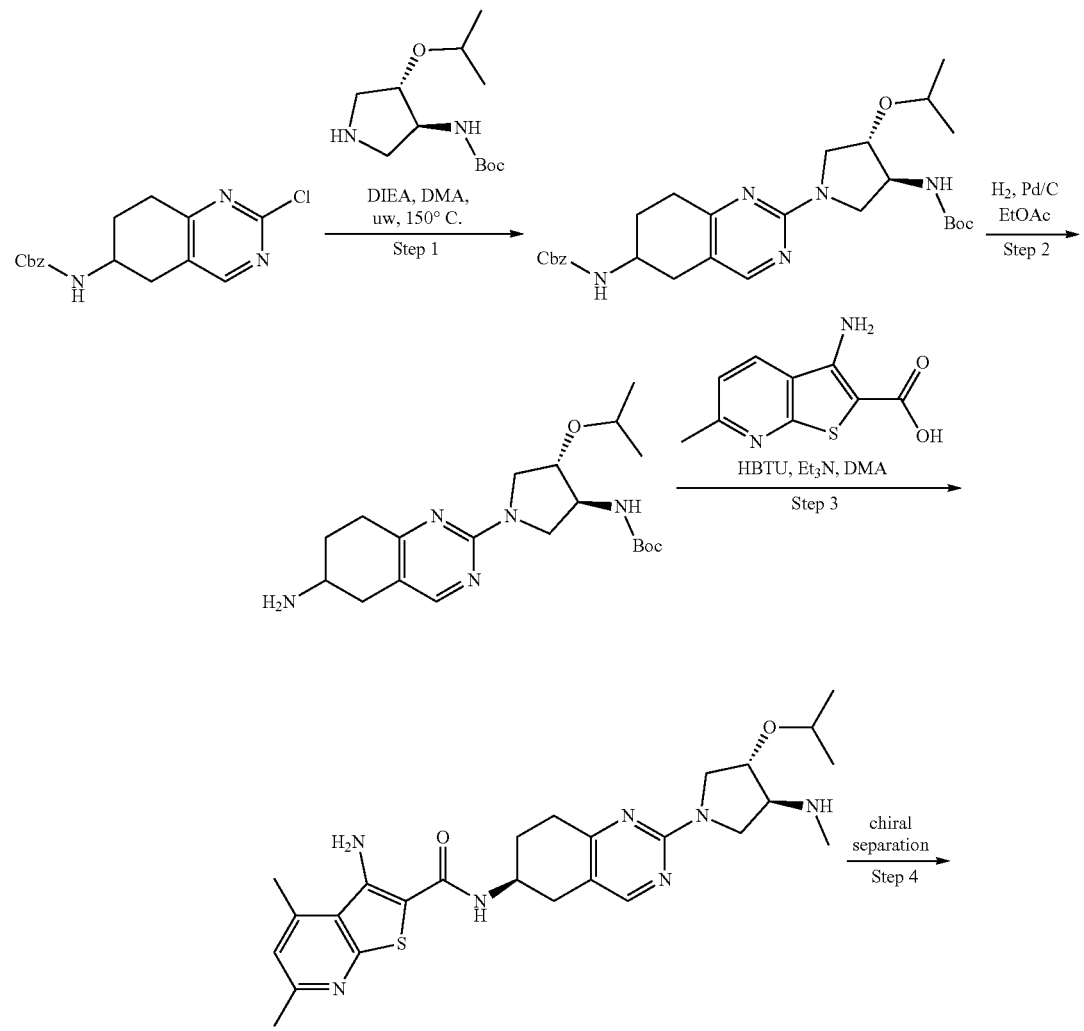

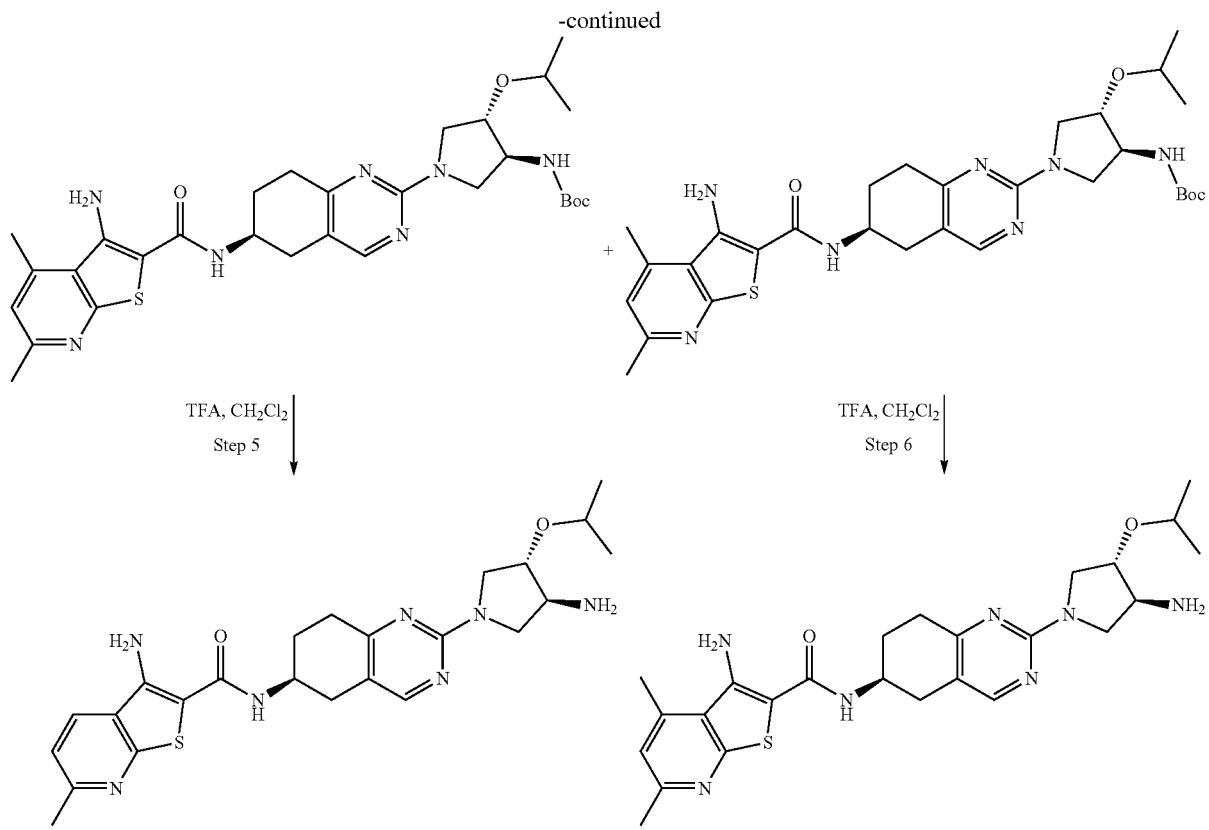

Step 1. Benzyl N-[2-[(3S,4S)-3-[[(tert-butoxy)carbonyl]amino]-4-(propan-2-yloxy)pyrrolidin-1-yl]-5,6,7,8-tetrahydroquinazolin-6-yl]carbamate A solution of benzyl N-(2-chloro-5,6,7,8-tetrahydroquinazolin-6-yl)carbamate (Intermediate 57) (300 μmg, 0.944 μmmol), tert-butyl N-[(3S,4S)-4-(propan-2-yloxy)pyrrolidin-3-yl]carbamate (Intermediate 56) (276 mg, 1.133 mmol) and DIEA (0.312 mL, 1.89 mmol) in DMA (10 mL) was microwaved for 1 h at 150° C. After cooling to 25° C., the residue was purified by reverse phase chromatography (Column: C18 silica gel; Mobile phase, A: water (containing 10 mmol/L NH$_4$HCO$_3$) and B: ACN (0% to 70% in 20 min)). The collected fraction was concentrated under vacuum to afford benzyl N-[2-[(3S,4S)-3-[[(tert-butoxy)carbonyl]amino]-4-(propan-2-yloxy)pyrrolidin-1-yl]-5,6,7,8-tetrahydroquinazolin-6-yl]carbamate as a brown solid. MS (ESI, m/z): 526 [M+H]$^+$.

Step 2. tert-Butyl N-[(3S,4S)-1-(6-amino-5,6,7,8-tetrahydroquinazolin-2-yl)-4-(propan-2-yloxy)pyrrolidin-3-yl]carbamate A mixture of benzyl N-[2-[(3S,4S)-3-[[(tert-butoxy)carbonyl]amino]-4-(propan-2-yloxy)pyrrolidin-1-yl]-5,6,7,8-tetrahydroquinazolin-6-yl]carbamate (300 mg, 0.542 mmol) and Palladium on carbon (300 mg, 10%) in ethyl acetate (20 mL) was stirred for 2 h at 20° C. under hydrogen atmosphere (balloon). The resulting mixture was filtered and the filter cake was washed with ethyl acetate (3×10 mL). The filtrate was concentrated under vacuum to afford tert-butyl N-[(3S,4S)-1-(6-amino-5,6,7,8-tetrahydroquinazolin-2-yl)-4-(propan-2-yloxy)pyrrolidin-3-yl]carbamate as a brown solid. MS (ESI, m/z): 392 [M+H]$^+$.

Step 3. tert-Butyl N-[(3S,4S)-1-[6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate HBTU (140 mg, 0.370 mmol) was added to a solution of tert-butyl N-[(3S,4S)-1-(6-amino-5,6,7,8-tetrahydroquinazolin-2-yl)-4-(propan-2-yloxy)pyrrolidin-3-yl]carbamate (100 mg, 0.230 mmol), Et$_3$N (0.096 mL, 0.690 mmol) and 3-amino-4,6-dimethylthieno[2,3-b]pyridine-2-carboxylic acid (Intermediate 21) (70.0 mg, 0.300 mmol) in DMA (3 mL). The resulting solution was stirred for 3 h at 25° C. The residue was purified by reverse phase chromatography (Column: C18 silica gel; Mobile phase, A: water (containing 10 mmol/L NH$_4$HCO$_3$) and B: ACN (10% to 60% in 30 min)). The collected fraction was concentrated to give tert-butyl N-[(3S,4S)-1-[6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate as a white solid. MS (ESI, m/z): 596 [M+H]$^+$.

Step 4. tert-Butyl N-[(3S,4S)-1-[(6S)-6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate and tert-Butyl N-[(3S,4S)-1-[(6R)-6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate tert-Butyl N-[(3S,4S)-1-[6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate (65.0 mg, 0.109 mmol) was separated by chiral HPLC (Column:

Chiralpak IA, 2×25 cm, 5 μm; Mobile phase, A: hexanes: DCM=3:1 and B: EtOH (hold 50% in 19 min); Flow rate: 16 mL/min). The first eluting isomer (RT=11.42 min) was collected and concentrated to give a white solid, stereochemistry of the amide arbitrarily assigned as tert-butyl N-[(3S, 4S)-1-[(6S)-6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate. The second eluting isomer (RT=15.96 min) was collected and concentrated under vacuum to give a white solid, stereochemistry of the amide arbitrarily assigned as tert-butyl N-[(3S,4S)-1-[(6R)-6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate. MS (ESI, m/z): 596 [M+H]$^+$.

Step 5. 3-Amino-N-[(6S)-2-[(3S,4S)-3-amino-4-(propan-2-yloxy)pyrrolidin-1-yl]-5,6,7,8-tetrahydroquinazolin-6-yl]-4,6-dimethylthieno[2,3-b]pyridine-2-carboxamide A solution of tert-butyl N-[(3S,4S)-1-[(6S)-6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate(28.0 μmg, 0.05 mmol) and TFA (0.5 mL) in DCM (1.5 mL) was stirred for 30 min at 25° C. The resulting mixture was concentrated under vacuum. The residue was treated with a solution of NH$_3$ (1.0 mL, 7M in MeOH). The resulting solution was stirred for 30 min and concentrated under vacuum. The residue was purified by prep-HPLC (Column: XBridge Shield RP18 OBD, 30×150 mm, 5 μm; Mobile phase, A: water (10 mM NH$_4$HCO$_3$) and B: ACN (25% to 45% in 7 min); Flow rate: 60 mL/min). The collected fraction was lyophilized to give 3-amino-N-[(6S)-2-[(3S,4S)-3-amino-4-(propan-2-yloxy)pyrrolidin-1-yl]-5,6,7,8-tetrahydroquinazolin-6-yl]-4,6-dimethylthieno[2,3-b]pyridine-2-carboxamide as a white solid. MS (ESI, m/z): 496 [M+H]$^+$. $^1$H NMR (DMSO-d$_6$, 400 MHz) S (ppm): 8.06 (s, 1H), 7.64 (br s, 1H), 7.04 (s, 1H), 6.82 (br s, 2H), 4.14-4.11 (m, 1H), 3.78-3.73 (m, 1H), 3.71-3.70 (m, 2H), 3.57-3.53 (m, 1H), 3.37-3.32 (m, 5H), 3.25-3.22 (m, 1H), 2.82-2.62 (m, 7H), 2.01-1.98 (m, 1H), 1.91-1.83 (m, 1H), 1.74 (br s, 2H), 1.12-1.08 (m, 6H).

Step 6. 3-Amino-N-[(6R)-2-[(3S,4S)-3-amino-4-(propan-2-yloxy)pyrrolidin-1-yl]-5,6,7,8-tetrahydroquinazolin-6-yl]-4,6-dimethylthieno[2,3-b]pyridine-2-carboxamide A solution of tert-butyl N-[(3S,4S)-1-[(6R)-6-[3-amino-4,6-dimethylthieno[2,3-b]pyridine-2-amido]-5,6,7,8-tetrahydroquinazolin-2-yl]-4-(propan-2-yloxy)pyrrolidin-3-yl]carbamate(27.0 μmg, 0.05 mmol) and TFA (0.5 mL) in DCM (1.5 mL) was stirred for 30 min at 25° C. The resulting mixture was concentrated under vacuum. NH$_3$ (1.0 mL, 7M in MeOH) was added to the residue. The resulting solution was stirred for 30 min and concentrated under vacuum. The residue was purified by prep-HPLC (Column: XBridge Shield RP18 OBD, 30×150 mm, 5 μm; Mobile phase, A: water (10 mM NH$_4$HCO$_3$) and B: ACN (25% to 50% in 7 min); Flow rate: 60 mL/min). The collected fraction was lyophilized to give 3-amino-N-[(6R)-2-[(3S,4S)-3-amino-4-(propan-2-yloxy)pyrrolidin-1-yl]-5,6,7,8-tetrahydroquinazolin-6-yl]-4,6-dimethylthieno[2,3-b]pyridine-2-carboxamide as a white solid. MS (ESI, m/z): 496 [M+H]$^-$. $^1$H NMR (DMSO-d$_6$, 400 MHz) δ (ppm): 8.07 (s, 1H), 7.65 (br s, 1H), 7.05 (s, 1H), 6.83 (br s, 2H), 4.16-4.13 (m, 1H), 3.79-3.74 (m, 1H), 3.72-3.71 (m, 2H), 3.57-3.53 (m, 1H), 3.38-3.33 (m, 5H), 3.26-3.23 (m, 1H), 2.83-2.62 (m, 7H), 2.01-1.99 (m, 1H), 1.92-1.83 (m, 1H), 1.74 (br s, 2H), 1.12-1.08 (m, 6H).

The following examples in Table 22 were prepared using standard chemical manipulations and procedures similar to those used for the preparation of Examples 31-1 and 31-2.

TABLE 22

| Example Number | Structure and Compound Name | LRMS m/z [M + H]$^+$ | $^1$H NMR |
|---|---|---|---|
| 31-3[1] | 3-amino-6-methyl-N-[(6'S)-2'-(piperazin-1-yl)-6',7'-dihydro-5'H-spiro[cyclopropane-1,8'-quinoline]-6'-yl]thieno[2,3-b]pyridine-2-carboxamide | 449 | (DMSO-d6, 400 MHz) δ (ppm): 8.31 (d, J = 8.4 Hz, 1H), 7.52 (d, J = 7.6 Hz, 1H), 7.31 (d, J = 8.4 Hz, 1H), 7.20 (d, J = 8.4 Hz, 1H), 7.16 (br s, 2H), 6.58-6.51 (m, 1H), 4.33-4.27 (m, 1H), 3.44-3.27 (m, 4H), 2.88-2.82 (m, 2H), 2.75-2.68 (m, 4H), 2.59 (s, 3H), 2.39 (br s, 1H), 2.29-2.22 (m, 1H), 1.53-1.45 (m, 2H), 0.92-0.86 (m, 1H), 0.71-0.69 (m, 2H). |

TABLE 22-continued

| Example Number | Structure and Compound Name | LRMS m/z [M + H]+ | 1H NMR |
|---|---|---|---|
| 31-4[1] | 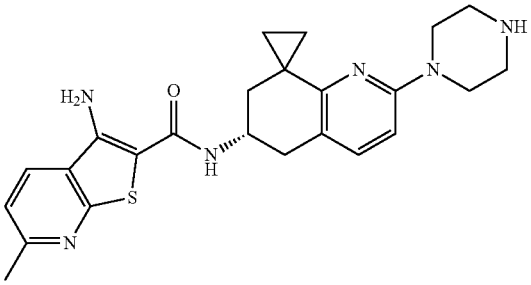 [SMILES: Cc1ccc2c(N)c(C(=O)N[C@H]3Cc4ccc(N5CCNCC5)nc4C4(CC4)C3)sc2n1]

3-amino-6-methyl-N-[(6'R)-2'-(piperazin-1-yl)-6',7'-dihydro-5'H-spiro[cyclopropane-1,8'-quinoline]-6'-yl]thieno[2,3-b]pyridine-2-carboxamide | 449 | (DMSO-d6, 400 MHz) δ (ppm): 8.31 (d, J = 8.0 Hz, 1H), 7.52 (d, J = 7.6 Hz, 1H), 7.31 (d, J = 8.4 Hz, 1H), 7.20 (d, J = 8.4 Hz, 1H), 7.16 (br s, 2H), 6.52 (d, J = 8.4 Hz, 1H), 4.32-4.28 (m, 1H), 3.43-3.28 (m, 4H), 2.88-2.82 (m, 2H), 2.75-2.64 (m, 4H), 2.59 (s, 3H), 2.39-2.34 (m, 1H), 2.29-2.22 (m, 1H), 1.53-1.40 (m, 2H), 0.92-0.86 (m, 1H), 0.71-0.69 (m, 2H). |

[1]Notes on procedures: In Step 1, the triflate Intermediate 47-4 was used. In Step 4, the enantiomers were separated by chiral HPLC using the column Chiralpak IC and Mobile Phase 10% EtOH/MTBE (containing 10 mmol/L NH3 in MeOH) to afford the precursor to Example 31-3 as the first eluted isomer (stereochemistry arbitrarily assigned); and the precursor to Example 31-4 as the second eluted isomer (stereochemistry arbitrarily assigned).

Example 32-1. 3-Amino-6-methyl-N-[(7S)-3-(piperazin-1-yl)-5,6,7,8-tetrahydroisoquinolin-7-yl]thieno[2,3-b]pyridine-2-carboxamide and

Example 32-2. 3-Amino-6-methyl-N-[(7R)-3-(piperazin-1-yl)-5,6,7,8-tetrahydroisoquinolin-7-yl]thieno[2,3-b]pyridine-2-carboxamide

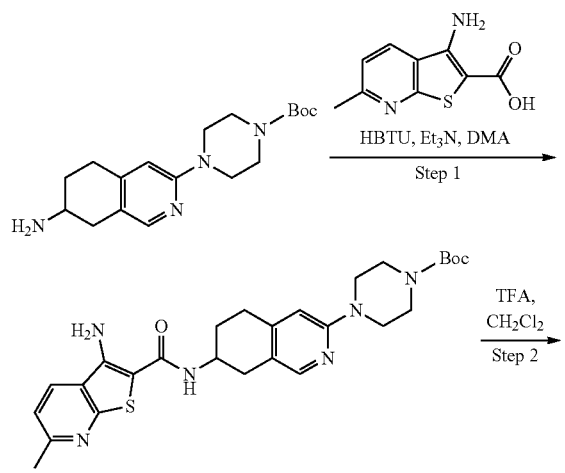

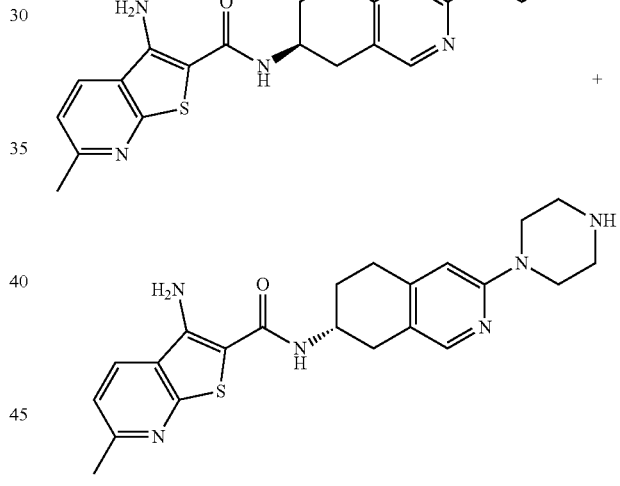

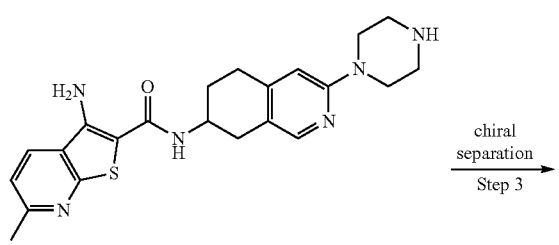

Step 1. tert-Butyl 4-(7-[3-amino-6-methylthieno[2,3-b]pyridine-2-amido]-5,6,7,8-tetrahydroisoquinolin-3-yl)piperazine-1-carboxylate HBTU (70.0 mg, 0.180 mmol) was added to a solution of tert-butyl 4-(7-amino-5,6,7,8-tetrahydroisoquinolin-3-yl)piperazine-1-carboxylate (Intermediate 58) (30 mg, 0.090 mmol), 3-amino-6-methylthieno[2,3-b]pyridine-2-carboxylic acid (20.0 mg, 0.100 mmol) and Et3N (0.038 mL, 0.270 mmol) in DMA (2 mL). The resulting solution was stirred for 30 min at 25° C. The mixture was purified via reverse phase chromatography (Column: X Bridge C18, 19×150 mm, 5 um; Mobile Phase, A: water (containing 10 mmol/L NH4HCO3) and B: ACN (10% to 80% in 30 min)). The collected fraction was concentrated under vacuum to give tert-butyl 4-(7-[3-amino-6-methylthieno[2,3-b]pyridine-2-amido]-5,6,7,8-tetrahydroisoquinolin-3-yl)piperazine-1-carboxylate as a white solid. MS (ESI, m/z): 523 [M+H]+.

Step 2. 3-Amino-6-methyl-N-[3-(piperazin-1-yl)-5,6,7,8-tetrahydroisoquinolin-7-yl]thieno[2,3-b]pyridine-2-carboxamide A solution of tert-butyl 4-(7-[3-amino-6-methylthieno[2,3-b]pyridine-2-amido]-5,6,7,8-tetrahydroisoquinolin-3-yl)piperazine-1-carboxylate (35.0 mg, 0.070 mmol) and TFA (0.50 mL) in DCM (1.50 mL) was stirred for 30 min at 25° C. The reaction mixture was concentrated under vacuum. Then a solution of NH$_3$ (2 mL, 7M in methanol) was added. The resulting solution was stirred for 30 min at 25° C. The resulting solution was concentrated under vacuum to give 3-amino-6-methyl-N-[3-(piperazin-1-yl)-5,6,7,8-tetrahydroisoquinolin-7-yl]thieno[2,3-b]pyridine-2-carboxamide as a white solid. MS (ESI, m/z): 423 [M+H]$^+$.

Step 3. 3-Amino-6-methyl-N-[(7S)-3-(piperazin-1-yl)-5,6,7,8-tetrahydroisoquinolin-7-yl]thieno[2,3-b]pyridine-2-carboxamide and 3-Amino-6-methyl-N-[(7R)-3-(piperazin-1-yl)-5,6,7,8-tetrahydroisoquinolin-7-yl]thieno[2,3-b]pyridine-2-carboxamide The racemate 3-amino-6-methyl-N-[3-(piperazin-1-yl)-5,6,7,8-tetrahydroisoquinolin-7-yl]thieno[2,3-b]pyridine-2-carboxamide (25.0 mg, 0.059 mmol) was separated into its enantiomers by chiral HPLC (Column: Chiralpak IG, 2×25 cm, 5 um; Mobile phase, A: MTBE (containing 0.1% Et$_2$NH) and B: ethanol (hold 50% in 20 min)). The first eluting isomer (RT=12.37 min) was concentrated under vacuum and then lyophilized to give a white solid, stereochemistry arbitrarily assigned as 3-amino-6-methyl-N-[(7S)-3-(piperazin-1-yl)-5,6,7,8-tetrahydroisoquinolin-7-yl]thieno[2,3-b]pyridine-2-carboxamide. MS (ESI, m/z): 423 [M+H]$^+$. H NMR (CD$_3$OD, 400 MHz) δ(ppm): 8.22 (d, J=8.0 Hz, 1H), 7.89 (s, 1H), 7.33 (d, J=8.0 Hz, 1H), 6.63 (s, 1H), 4.25-4.23 (m, 1H), 3.49-3.43 (m, 4H), 3.06-2.98 (m, 1H), 2.97-2.92 (m, 6H), 2.82-2.69 (m, 1H), 2.66 (s, 3H), 2.15-2.13 (m, 1H), 1.89-1.81 (m, 1H). The second eluting isomer (RT=17.03 min) was concentrated under vacuum and then lyophilized to give a white solid, stereochemistry arbitrarily assigned as 3-amino-6-methyl-N-[(7R)-3-(piperazin-1-yl)-5,6,7,8-tetrahydroisoquinolin-7-yl]thieno[2,3-b]pyridine-2-carboxamide. MS (ESI, m/z): 423 [M+H]$^+$. $^1$H NMR (CD$_3$OD, 400 MHz) δ(ppm): 8.22 (d, J=8.0 Hz, 1H), 7.89 (s, 1H), 7.33 (d, J=8.0 Hz, 1H), 6.63 (s, 1H), 4.25-4.23 (m, 1H), 3.49-3.43 (m, 4H), 3.15-2.98 (m, 1H), 2.97-2.93 (m, 6H), 2.82-2.72 (m, 1H), 2.76 (s, 3H), 2.15-2.13 (m, 1H), 1.89-1.81 (m, 1H).

Example 33-1. (R)-3-amino-N-(5-fluoro-7-(piperazin-1-yl)chroman-3-yl-4,4-d2)-6-methylthieno[2,3-b]pyridine-2-carboxamide

Example 33-2. (S)-3-amino-N-(5-fluoro-7-(piperazin-1-yl)chroman-3-yl-4,4-d2)-6-methylthieno[2,3-b]pyridine-2-carboxamide

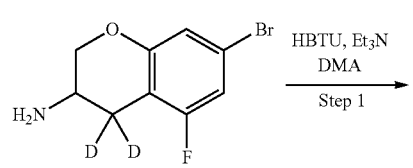

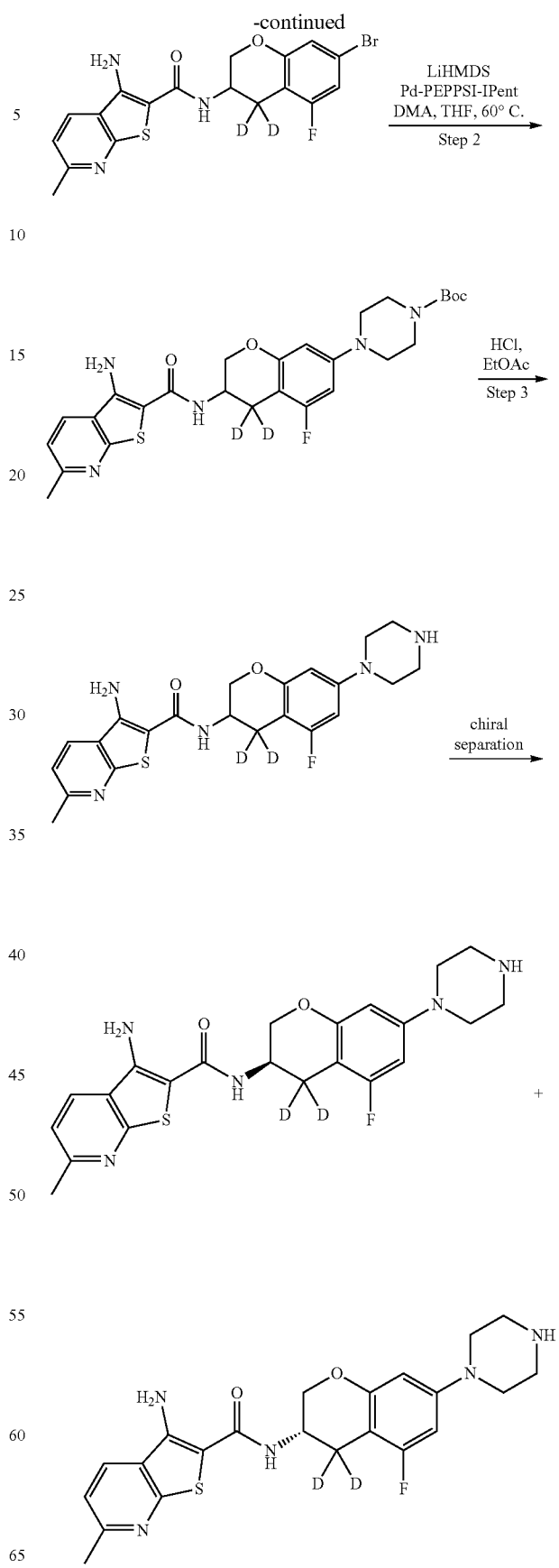

Step 1. 3-Amino-N-(7-bromo-5-fluorochroman-3-yl-4,4-d2)-6-methylthieno[2,3-b]pyridine-2-carboxamide A solution of 7-bromo-5-fluorochroman-4,4-d2-3-amine (Intermediate 5-2) (340 mg, 1.370 mmol), 3-amino-6-methylthieno[2,3-b]pyridine-2-carboxylic acid (342 mg, 1.645 mmol), Et₃N (0.287 ml, 2.056 mmol), and HBTU (624 mg, 1.645 mmol) in DMA (5 mL) was stirred at room temperature for 4 h. The reaction was reduced in volume by half under reduced pressure. EtOAc (5 mL) and H₂O (3 mL) were added. The organic layer was separated, dried over Na₂SO₄, filtered, and concentrated. The residue was purified by silica gel chromatography (eluting with 2% to 100% EtOAc/hexanes). Desired fractions were combined and concentrated to afford 3-amino-N-(7-bromo-5-fluorochroman-3-yl-4,4-d2)-6-methylthieno[2,3-b]pyridine-2-carboxamide as a yellow solid. MS: (ESI, m/z): 438 [M+H]⁻. ¹H NMR (CDCl₃, 300 MHz) δ(ppm): 7.61-7.83 (m, 1H), 7.03-7.13 (m, 1H), 6.69-6.90 (m, 2H), 6.00 (br s, 2H), 5.59 (br d, J=6.7 Hz, 1H), 4.47-4.82 (m, 1H), 3.95-4.29 (m, 3H), 2.85-2.86 (m, 1H), 2.67-2.79 (m, 3H), 2.59 (d, J=3.2 Hz, 3H).

Step 2. tert-Butyl 4-(3-(3-amino-6-methylthieno[2,3-b]pyridine-2-carboxamido)-5-fluorochroman-7-yl-4,4-d2)piperazine-1-carboxylate A solution of 3-amino-N-(7-bromo-5-fluorochroman-3-yl-4,4-d2)-6-methylthieno[2,3-b]pyridine-2-carboxamide (150 mg, 0.342 mmol) was combined with tert-butyl piperazine-1-carboxylate (127 mg, 0.684 mmol) in anhydrous DMA (3.42 mL). A 1M in THF solution of LiHMDS (3.42 mL, 3.42 mmol) was added and the reaction was flushed with N₂ for 20 min. Pd-PEPPSI-IPent (34.2 mg, 0.034 mmol) was added and the reaction was stirred at 60° C. for 16 h. The reaction was diluted with 10 mL of EtOAc and washed with 3 mL of H₂O. The organic layer was separated, dried over anhydrous Na₂SO₄, filtered, and concentrated. The residue was purified by silica gel chromatography (eluting with 5% to 80% EtOAc/hexanes). Desired fractions were combined and concentrated to afford tert-butyl 4-(3-(3-amino-6-methylthieno[2,3-b]pyridine-2-carboxamido)-5-fluorochroman-7-yl-4,4-d2)piperazine-1-carboxylate as an off-white solid. MS: (ESI, m/z): 544 [M+H]⁺.

Step 3. 3-Amino-N-(5-fluoro-7-(piperazin-1-yl)chroman-3-yl-4,4-d2)-6-methylthieno[2,3-b]pyridine-2-carboxamide HCl (4M in 1,4-dioxane, 0.276 mL, 1.104 mmol) was added to a suspension of tert-butyl 4-(3-(3-amino-6-methylthieno[2,3-b]pyridine-2-carboxamido)-5-fluorochroman-7-yl-4,4-d2)piperazine-1-carboxylate in EtOAc (1 mL). The reaction was stirred at 22° C. for 16 h. The reaction was concentrated to dryness under vacuum. The residue was purified by chiral HPLC using chiral column Chiralpak IA (Mobile Phase A: hexanes (0.1% Et₂NH), and B: EtOH (0.1% Et₂NH); 50% B) to afford Peak 1 whose stereochemistry was arbitrarily assigned as (R)-3-amino-N-(5-fluoro-7-(piperazin-1-yl)chroman-3-yl-4,4-d2)-6-methylthieno[2,3-b]pyridine-2-carboxamide and Peak 2 whose stereochemistry was arbitrarily assigned as (S)-3-amino-N-(5-fluoro-7-(piperazin-1-yl)chroman-3-yl-4,4-d2)-6-methylthieno[2,3-b]pyridine-2-carboxamide. MS: (ESI, m/z): 444 [M+H]⁺.

The following examples in Table 23 were prepared using standard chemical manipulations and procedures similar to those used for the preparation of Examples 33-1 and 33-2.

TABLE 23

| Example Number | Structure and Compound Name | LRMS m/z [M + H]⁺ | ¹H NMR |
|---|---|---|---|
| 33-3[1] | 3-amino-N-[(3R)-7-[(1R,6S)-3,8-diazabicyclo[4.2.0]octan-8-yl]-3,4-dihydro-2H-1-benzopyran-3-yl]-6-methylthieno[2,3-b]pyridine-2-carboxamide | 450 | (DMSO-d6, 400 MHz) δ (ppm): 8.31 (d, J = 8.0 Hz, 1H), 7.50 (d, J = 7.6 Hz, 1H), 7.32 (d, J = 8.4 Hz, 1H), 7.21 (br s, 2H), 6.87 (d, J = 8.4 Hz, 1H), 6.09-6.06 (m, 1H), 5.90 (s, 1H), 4.29-4.26 (m, 1H), 4.16-4.12 (m, 1H), 3.82-3.75 (m, 2H), 3.65-3.45 (m, 2H), 3.32-3.18 (m, 1H), 3.08-3.05 (m, 1H), 2.89-2.82 (m, 4H), 2.59 (s, 3H), 2.44-2.38 (m, 1H), 1.92-1.88 (m, 1H), 1.80-1.63 (m, 1H). |

TABLE 23-continued

| Example Number | Structure and Compound Name | LRMS m/z [M + H]+ | 1H NMR |
|---|---|---|---|
| 33-4[1] | 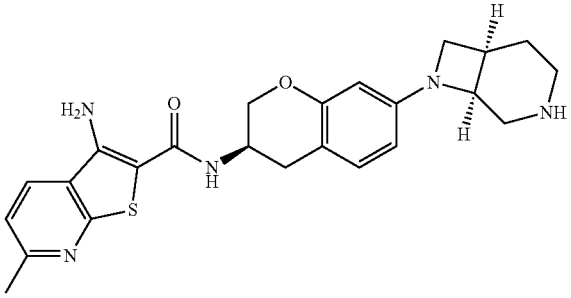 [SMILES: Cc1ccc2c(N)c(C(=O)N[C@H]3COc4cc(N5C[C@H]6CCNC[C@H]65)ccc4C3)sc2n1]<br><br>3-amino-N-[(3R)-7-[(1S,6R)-3,8-diazabicyclo[4.2.0]octan-8-yl]-3,4-dihydro-2H-1-benzopyran-3-yl]-6-methylthieno[2,3-b]pyridine-2-carboxamide | 450 | (DMSO-d6, 400 MHz) δ (ppm): 8.33 (d, J = 8.4 Hz, 1H), 7.50 (d, J = 7.6 Hz, 1H), 7.32 (d, J = 8.4 Hz, 1H), 7.21 (br s, 2H), 6.87 (d, J = 8.0 Hz, 1H), 6.10-6.07 (m, 1H), 5.91 (s, 1H), 4.27-4.25 (m, 1H), 4.16-4.13 (m, 1H), 3.82-3.77 (m, 2H), 3.65-3.47 (m, 2H), 3.32-3.30 (m, 1H), 3.09-3.06 (m, 1H), 2.91-2.84 (m, 4H), 2.59 (s, 3H), 2.45-2.40 (m, 1H), 1.93-1.89 (m, 1H), 1.70-1.61 (m, 1H). |

[1]Notes on procedures:
In Step 1, 7-bromochroman-3-amine was used as the amine coupling partner to afford the racemate 3-amino-N-(7-bromochroman-3-yl)-6-methylthieno[2,3-b]pyridine-2-carboxamide. The enantiomers were separated by SFC using the chiral column ChiralArt Amylose-SA and Mobile Phase, A: $CO_2$, 65% and B: EtOH:DCM = 1:1 to afford (R)-3-amino-N-(7-bromochroman-3-yl)-6-methylthieno[2,3-b]pyridine-2-carboxamide as the first eluted isomer and (S)-3-amino-N-(7-bromochroman-3-yl)-6-methylthieno[2,3-b]pyridine-2-carboxamide as the second eluted isomer. In Step 2, cis-tert-butyl 3,8-diazabicyclo[4.2.0]octane-3-carboxylate was used as the amine coupling partner to afford cis-tert-butyl 8-[(3R)-3-[3-amino-6-methylthieno[2,3-b]pyridine-2-amido]-3,4-dihydro-2H-1-benzopyran-7-yl]-3,8-diazabicyclo[4.2.0]octane-3-carboxylate. The cis isomers were separated by chiral HPLC using the chiral column Chiralpak IE and mobile phase 10% EtOH/MTBE (0.1% Et2NH) to afford the precursor to Example 33-3 as the first eluted isomer (stereochemistry arbitrarily assigned) and the precursor to Example 33-4 as the second eluted isomer (stereochemistry arbitrarily assigned). In Step 3, boc-deprotection was accomplished by treatment with TFA in DCM.

Example 34. 3-Amino-N-[(3R)-7-(4-cyano-1,1-di-oxo-1M6-thian-4-yl)-3,4-dihydro-2H-1-benzopyran-3-yl]-6-methylthieno[2,3-b]pyridine-2-carboxamide

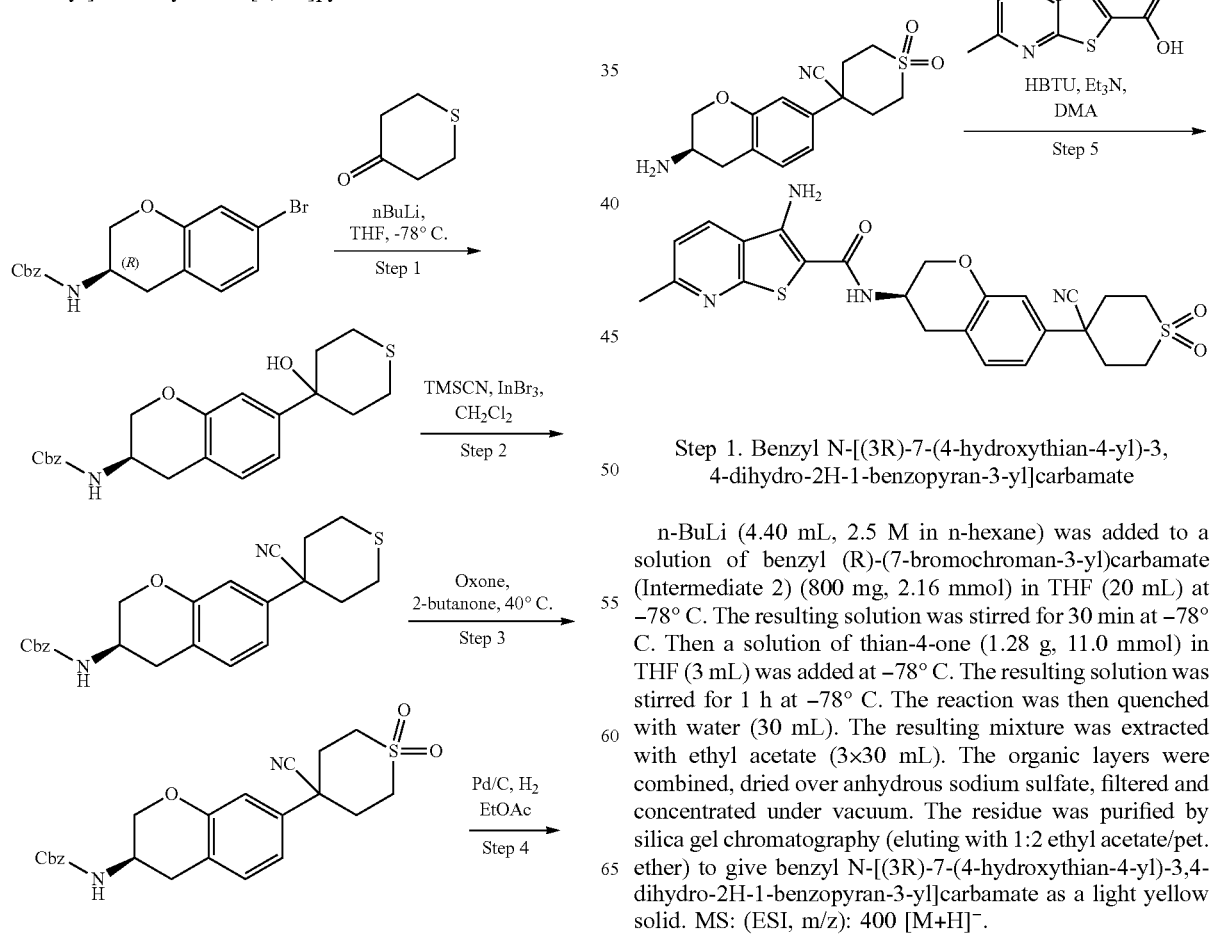

Step 1. Benzyl N-[(3R)-7-(4-hydroxythian-4-yl)-3,4-dihydro-2H-1-benzopyran-3-yl]carbamate n-BuLi (4.40 mL, 2.5 M in n-hexane) was added to a solution of benzyl (R)-(7-bromochroman-3-yl)carbamate (Intermediate 2) (800 mg, 2.16 mmol) in THF (20 mL) at −78° C. The resulting solution was stirred for 30 min at −78° C. Then a solution of thian-4-one (1.28 g, 11.0 mmol) in THF (3 mL) was added at −78° C. The resulting solution was stirred for 1 h at −78° C. The reaction was then quenched with water (30 mL). The resulting mixture was extracted with ethyl acetate (3×30 mL). The organic layers were combined, dried over anhydrous sodium sulfate, filtered and concentrated under vacuum. The residue was purified by silica gel chromatography (eluting with 1:2 ethyl acetate/pet. ether) to give benzyl N-[(3R)-7-(4-hydroxythian-4-yl)-3,4-dihydro-2H-1-benzopyran-3-yl]carbamate as a light yellow solid. MS: (ESI, m/z): 400 [M+H]−.

Step 2. Benzyl N-[(3R)-7-(4-cyanothian-4-yl)-3,4-dihydro-2H-1-benzopyran-3-yl]carbamate A solution of TMSCN (120 mg, 1.21 mmol) in DCM (1 mL) was added to a mixture of InBr₃ (11.0 mg, 0.030 mmol) and DCM (1 mL). Then a solution of benzyl N-[(3R)-7-(4-hydroxythian-4-yl)-3,4-dihydro-2H-1-benzopyran-3-yl]carbamate (120 mg, 0.300 mmol) in DCM (1 mL) was added over 30 min. The resulting mixture was stirred for 30 min at 29° C. Three batches were thus run in parallel and combined for quenching with water (10 mL). The resulting mixture was extracted with DCM (3×15 mL). The organic layers were combined, dried over anhydrous sodium sulfate, filtered and concentrated under vacuum. The residue was purified by a silica gel chromatography (eluting with 1:3 ethyl acetate/pet. ether) to give benzyl N-[(3R)-7-(4-cyanothian-4-yl)-3,4-dihydro-2H-1-benzopyran-3-yl]carbamate as an off-white solid. MS: (ESI, m/z): 409 [M+H]⁺.

Step 3. Benzyl N-[(3R)-7-(4-cyano-1,1-dioxo-1λ6-thian-4-yl)-3,4-dihydro-2H-1-benzopyran-3-yl]carbamate A mixture of benzyl N-[(3R)-7-(4-cyanothian-4-yl)-3,4-dihydro-2H-1-benzopyran-3-yl]carbamate (160 mg, 0.390 mmol) and oxone (650 mg, 3.87 mmol) in 2-butanone (10 mL) was stirred for 12 h at 40° C. The solids were filtered out. The filtrate was concentrated under vacuum. The residue was purified via a silica gel chromatography (eluting with 1:1 ethyl acetate/pet. ether) to give benzyl N-[(3R)-7-(4-cyano-1,1-dioxo-1λ6-thian-4-yl)-3,4-dihydro-2H-1-benzopyran-3-yl]carbamate as a white solid. MS: (ESI, m/z): 441 [M+H]⁺.

Step 4. 4-[(3R)-3-Amino-3,4-dihydro-2H-1-benzopyran-7-yl]-1,1-dioxo-1λ6-thiane-4-carbonitrile A mixture of benzyl N-[(3R)-7-(4-cyano-1,1-dioxo-1λ6-thian-4-yl)-3,4-dihydro-2H-1-benzopyran-3-yl]carbanmate (80.0 mg, 0.180 mmol) and palladium on carbon (80.0 mg, 10%) in ethyl acetate (10 mL) was stirred for 1 h at 29° C. under hydrogen atmosphere (balloon). The solids were filtered out. The filtrate was concentrated under vacuum to afford 4-[(3R)-3-amino-3,4-dihydro-2H-1-benzopyran-7-yl]-1,1-dioxo-1λ6-thiane-4-carbonitrile as an off-white solid. MS: (ESI, m/z): 307 [M+H]⁺.

Step 5. 3-Amino-N-[(3R)-7-(4-cyano-1,1-dioxo-1λ6-thian-4-yl)-3,4-dihydro-2H-1-benzopyran-3-yl]-6-methylthieno[2,3-b]pyridine-2-carboxamide HBTU (68.0 mg, 0.180 mmol) was added to a solution of 4-[(3R)-3-amino-3,4-dihydro-2H-1-benzopyran-7-yl]-1,1-dioxo-1λ6-thiane-4-carbonitrile (50.0 mg, 0.160 mmol), Et₃N (0.067 mL, 0.480 mmol) and 3-amino-6-methylthieno[2,3-b]pyridine-2-carboxylic acid (34.0 mg, 0.160 mmol) in DMA (2 mL). The resulting solution was stirred for 30 min at 29° C. The mixture was purified by prep-HPLC (Column: XBridge Prep C18 OBD, 19×150 mm 5 μm; Mobile phase, A: water (10 mM NH₄HCO₃) and B: ACN (30% to 60% in 7 min)). The collected fraction was lyophilized to give 3-amino-N-[(3R)-7-(4-cyano-1,1-dioxo-1λ6-thian-4-yl)-3,4-dihydro-2H-1-benzopyran-3-yl]-6-methylthieno[2,3-b]pyridine-2-carboxamide as a light yellow solid. MS (ESI, m/z): 497 [M+H]⁺. ¹H NMR (DMSO-d₆, 400 MHz) δ(ppm): 8.33 (d, J=8.4 Hz, 1H), 7.63 (d, J=7.6 Hz, 1H), 7.32 (d, J=8.4 Hz, 2H), 7.24-7.22 (m, 3H), 7.10-7.08 (m, 1H), 6.99 (d, J=2.0 Hz, 1H), 4.37-4.32 (m, 1H), 4.26-4.22 (m, 1H), 3.93-3.88 (m, 1H), 3.42-3.27 (m, 4H), 3.01-2.99 (m, 2H), 2.59-2.50 (m, 7H).

Example 35. 3-Amino-6-methyl-N-[(3R)-5,6,8-trifluoro-7-(piperazin-1-yl)-3,4-dihydro-2H-1-benzopyran-3-yl]thieno[2,3-b]pyridine-2-carboxamide

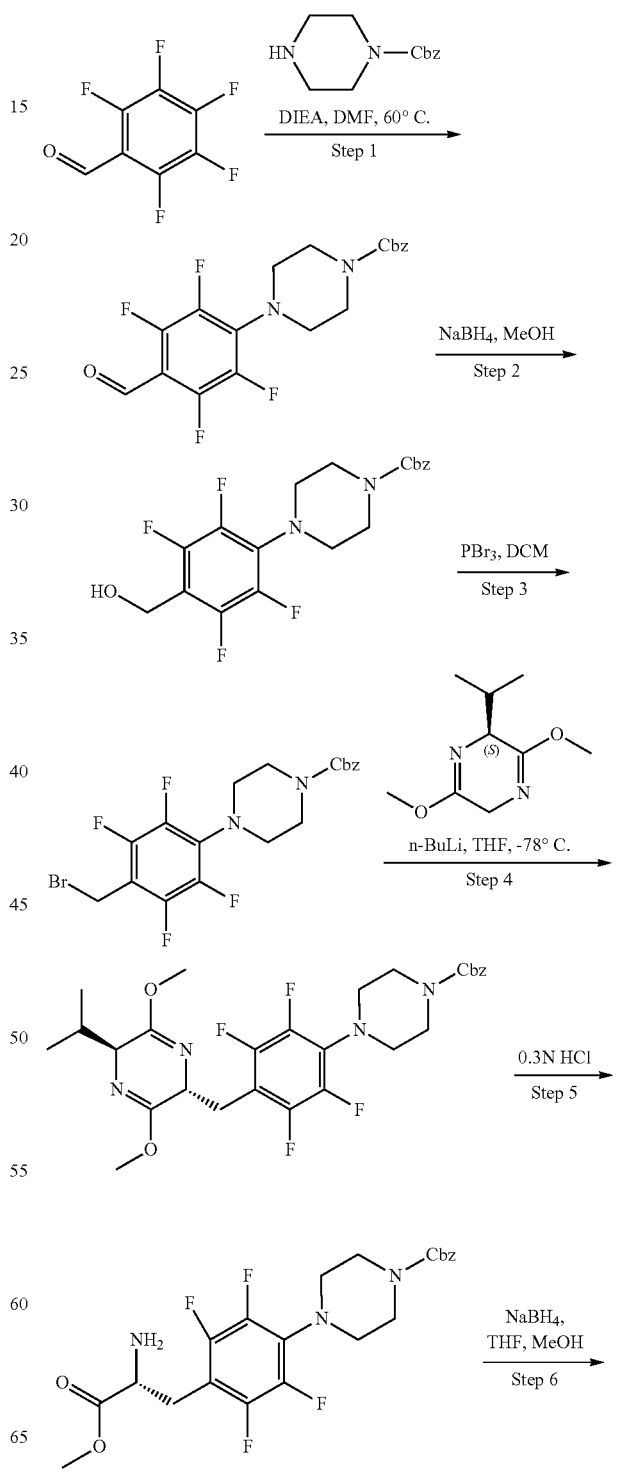

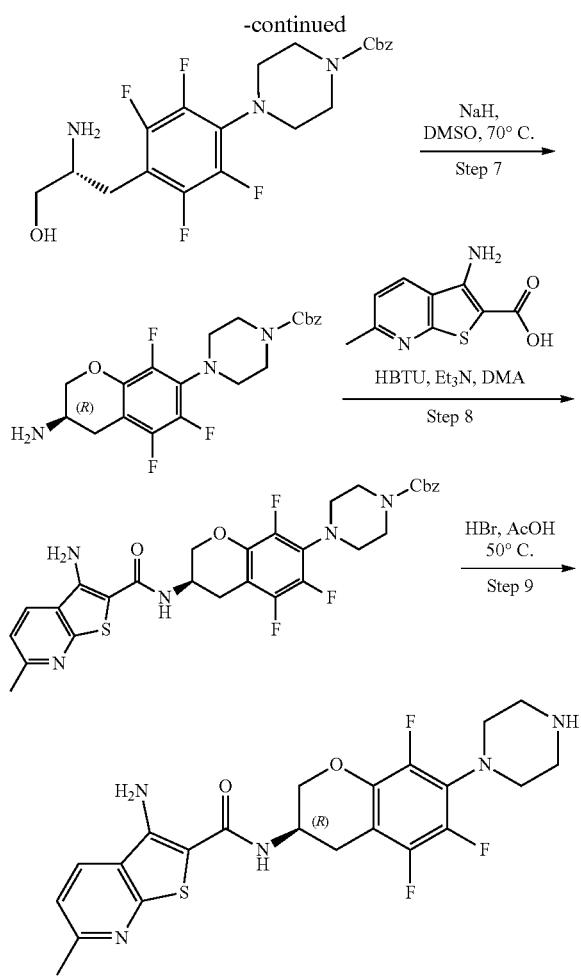

Step 1. Benzyl 4-(2,3,5,6-tetrafluoro-4-formylphenyl)piperazine-1-carboxylate

A solution of 2,3,4,5,6-pentafluorobenzaldehyde (10.0 g, 51.0 mmol), benzyl piperazine-1-carboxylate (11.2 g, 50.8 mmol) and DIEA (15.9 mL, 95.9 mmol) in DMF (50 mL) was stirred for 12 h at 60° C. The reaction was quenched by the addition of water (50 mL), and extracted with ethyl acetate (3×50 mL). The organic layers were combined, washed with water (6×100 mL), dried over anhydrous sodium sulfate, filtered and concentrated under vacuum. The residue was purified by silica gel chromatography (eluting with 1:5 ethyl acetate/pet. ether) to give benzyl 4-(2,3,5,6-tetrafluoro-4-formylphenyl)piperazine-1-carboxylate as a white solid. MS (ESI, m/z): 397 [M+H]+.

Step 2. Benzyl 4-[2,3,5,6-tetrafluoro-4-(hydroxymethyl)phenyl]piperazine-1-carboxylate To a solution of benzyl 4-(2,3,5,6-tetrafluoro-4-formylphenyl)piperazine-1-carboxylate (4.00 g, 10.1 mmol) in methanol (40 mL) was added NaBH4 (950 mg, 25.1 mmol) at <10° C. The resulting solution was stirred for 2 h at 25° C. The solvent was removed under vacuum. The residue was diluted with water (100 mL). The resulting mixture was extracted with ethyl acetate (3×50 mL). The organic layers were combined, dried over anhydrous sodium sulfate, filtered and concentrated under vacuum to give benzyl 4-[2,3,5,6-tetrafluoro-4-(hydroxymethyl)phenyl]piperazine-1-carboxylate as a white solid. MS: (ESI, m/z): 399 [M+H]+.

Step 3. Benzyl 4-[4-(bromomethyl)-2,3,5,6-tetrafluorophenyl]piperazine-1-carboxylate A solution of benzyl 4-[2,3,5,6-tetrafluoro-4-(hydroxymethyl)phenyl]piperazine-1-carboxylate (5.70 g, 14.3 mmol) and PBr3 (3.85 g, 14.2 mmol) in DCM (40 mL) was stirred for 2 h at 25° C. The reaction was then quenched by the addition of water (40 mL). The resulting mixture was extracted with DCM (3×30 mL). The organic layers were combined, washed with brine (30 mL), dried over anhydrous sodium sulfate, filtered and concentrated under vacuum to give benzyl 4-[4-(bromomethyl)-2,3,5,6-tetrafluorophenyl]piperazine-1-carboxylate as a white solid. MS (ESI, m/z): 461, 463 [M+H]+.

Step 4. Benzyl 4-(4-[[(2R,5S)-3,6-dimethoxy-5-(propan-2-yl)-2,5-dihydropyrazin-2-yl]methyl]-2,3,5,6-tetrafluorophenyl)piperazine-1-carboxylate To a solution of (2S)-3,6-dimethoxy-2-(propan-2-yl)-2,5-dihydropyrazine (1.84 g, 9.99 mmol) in THF (50 mL) was added n-BuLi (6.0 mL, 2.5M in n-hexane) at −78° C. The resulting solution was stirred for 30 min at −78° C. To this was added benzyl 4-[4-(bromomethyl)-2,3,5,6-tetrafluorophenyl]piperazine-1-carboxylate (4.60 g, 9.97 mmol) at −78° C. The resulting solution was stirred for 2 h at −78° C. The reaction was then quenched by the addition of NH4Cl (sat., aq.) (40 mL). The resulting mixture was extracted with ethyl acetate (3×30 mL). The organic layers were combined, washed with brine (3×30 mL), dried over anhydrous sodium sulfate, filtered and concentrated under vacuum. The residue was purified by reversed phase chromatography (Column: C18 silica gel; Mobile phase, A: water (containing 0.05% TFA) and B: ACN (5% to 75% in 30 min) to give benzyl 4-(4-[[(2R,5S)-3,6-dimethoxy-5-(propan-2-yl)-2,5-dihydropyrazin-2-yl]methyl]-2,3,5,6-tetrafluorophenyl)piperazine-1-carboxylate as yellow oil. MS (ESI, m/z): 565 [M+H]+.

Step 5. Benzyl 4-[4-[(2R)-2-amino-3-methoxy-3-oxopropyl]-2,3,5,6-tetrafluorophenyl]piperazine-1-carboxylate Hydrochloric acid (100 mL, 0.3N) was added into a stirring solution of benzyl 4-(4-[[(2R,5S)-3,6-dimethoxy-5-(propan-2-yl)-2,5-dihydropyrazin-2-yl]methyl]-2,3,5,6-tetrafluorophenyl)piperazine-1-carboxylate (5.86 g, 10.3 mmol) in ACN (100 mL) at <10° C. The resulting solution was stirred for 1 h at 25° C. The solvent was removed under vacuum. The pH value of the residue was adjusted to 9-10 with NaHCO3 (sat. aq.). The resulting mixture was extracted with ethyl acetate (3×30 mL). The organic layers were combined, washed with brine (50 mL), dried over anhydrous sodium sulfate, filtered and concentrated under vacuum to give benzyl 4-[4-[(2R)-2-amino-3-methoxy-3-oxopropyl]-2,3,5,6-tetrafluorophenyl]piperazine-1-carboxylate as a yellow solid. MS (ESI, m/z): 470 [M+H]+.

Step 6. Benzyl 4-[4-[(2R)-2-amino-3-hydroxypropyl]-2,3,5,6-tetrafluorophenyl]piperazine-1-carboxylate Into a solution of benzyl 4-[4-[(2R)-2-amino-3-methoxy-3-oxopropyl]-2,3,5,6-tetrafluorophenyl]piperazine-1-carboxylate (3.83 g, 8.16 mmol) in methanol (10 mL) and THF (40 mL) was added NaBH₄ (900 mg, 23.7 mmol) at <10° C. The resulting solution was stirred for 3 h at 25° C. The solvent was concentrated under vacuum. The residue was diluted with water (50 mL). The resulting mixture was extracted with ethyl acetate (3×50 mL). The organic layers were combined, washed with brine (3×30 mL), dried over anhydrous sodium sulfate, filtered and concentrated under vacuum. The residue was purified by reversed phase chromatography (Column: C18 silica gel; Mobile phase, A: water (containing 0.05% TFA) and B: ACN (5% to 80% in 30 min)) to afford benzyl 4-[4-[(2R)-2-amino-3-hydroxypropyl]-2,3,5,6-tetrafluorophenyl]piperazine-1-carboxylate as a yellow oil. MS (ESI, m/z): 442 [M+H]⁻.

Step 7. Benzyl 4-[(3R)-3-amino-5,6,8-trifluoro-3,4-dihydro-2H-1-benzopyran-7-yl]piperazine-1-carboxylate Sodium hydride (34.0 mg, 1.42 mmol, 60%) was added into a stirring solution of benzyl 4-[4-[(2R)-2-amino-3-hydroxypropyl]-2,3,5,6-tetrafluorophenyl]piperazine-1-carboxylate (400 mg, 0.910 mmol) in DMSO (10 mL). The resulting solution was stirred for 30 min at 25° C. and then 2 h at 70° C. After cooling to 25° C., the reaction was quenched by the addition of water (40 mL). The resulting mixture was extracted with ethyl acetate (3×20 mL). The organic layers were combined, washed with brine (20 mL), dried over anhydrous sodium sulfate, filtered and concentrated under vacuum. The residue was purified by reversed phase chromatography (Column: C18 silica gel; Mobile phase, A: water (containing 0.05% TFA) and B: ACN (20% to 70% in 30 min)) to give benzyl 4-[(3R)-3-amino-5,6,8-trifluoro-3,4-dihydro-2H-1-benzopyran-7-yl]piperazine-1-carboxylate as a yellow oil. MS (ESI, m/z): 422 [M+H]⁺.

Step 8. Benzyl 4-[(3R)-3-[3-amino-6-methylthieno[2,3-b]pyridine-2-amido]-5,6,8-trifluoro-3,4-dihydro-2H-1-benzopyran-7-yl]piperazine-1-carboxylate To a solution of benzyl 4-[(3R)-3-amino-5,6,8-trifluoro-3,4-dihydro-2H-1-benzopyran-7-yl]piperazine-1-carboxylate (70.0 mg, 0.170 mmol) and 3-amino-6-methylthieno[2,3-b]pyridine-2-carboxylic acid (41.5 mg, 0.200 mmol) in DMA (2 mL) was added Et₃N (0.068 mL, 0.49 mmol) and HBTU (75.0 mg, 0.200 mmol). The resulting solution was stirred for 1 h at 25° C. The mixture was purified by reversed phase chromatography (Column: C18 silica gel; Mobile phase, A: water (containing 0.05% TFA) and B: ACN (5% to 80% in 30 min)) to afford benzyl 4-[(3R)-3-[3-amino-6-methylthieno[2,3-b]pyridine-2-amido]-5,6,8-trifluoro-3,4-dihydro-2H-1-benzopyran-7-yl]piperazine-1-carboxylate as a yellow oil. MS (ESI, m/z): 612 [M+H]⁻.

Step 9. 3-Amino-6-methyl-N-[(3R)-5,6,8-trifluoro-7-(piperazin-1-yl)-3,4-dihydro-2H-1-benzopyran-3-yl]thieno[2,3-b]pyridine-2-carboxamide To a solution of benzyl 4-[(3R)-3-[3-amino-6-methylthieno[2,3-b]pyridine-2-amido]-5,6,8-trifluoro-3,4-dihydro-2H-1-benzopyran-7-yl]piperazine-1-carboxylate (50.0 mg, 0.080 mmol) in CH₃COOH (1.5 mL) was added hydrobromic acid (1.5 mL, 48%). The resulting solution was stirred for 1 h at 50° C. The resulting mixture was concentrated under vacuum. The residue was purified by prep-HPLC (Column: XBridge Shield RP18 OBD Column; Mobile phase, A: water (containing 10 mmol/L NH₄HCO₃) and B: ACN (25% to 65% B in 8 min)). The collected fraction was lyophilized to give 3-amino-6-methyl-N-[(3R)-5,6,8-trifluoro-7-(piperazin-1-yl)-3,4-dihydro-2H-1-benzopyran-3-yl]thieno[2,3-b]pyridine-2-carboxamide as a white solid. MS (ESI, m/z): 478 [M+H]⁺. ¹H NMR (DMSO-d₆, 400 MHz) δ(ppm): 8.33 (d, J=8.4 Hz, 1H), 7.70 (d, J=6.8 Hz, 1H), 7.31 (d, J=8.4 Hz, 1H), 7.25 (br s, 2H), 4.36-4.30 (m, 1H), 4.26-4.23 (m, 1H), 3.99-3.95 (m, 1H), 3.04-2.94 (m, 5H), 2.90-2.84 (m, 1H), 2.79-2.77 (m, 4H), 2.58 (s, 3H).

Example 288. 3-amino-N-[(3R)-7-[(3R)-3-aminopyrrolidin-1-yl]-3,4-dihydro-2H-1-benzopyran-3-yl]-6-methylthieno[2,3-b]pyridine-2-carboxamide

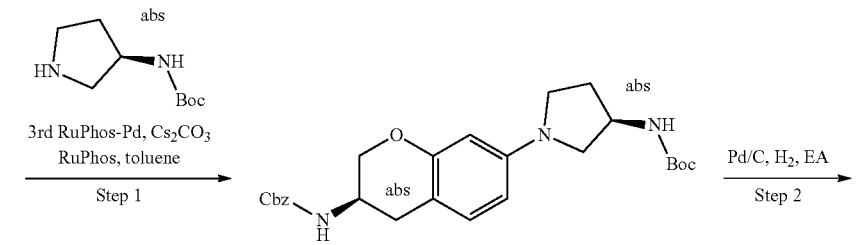

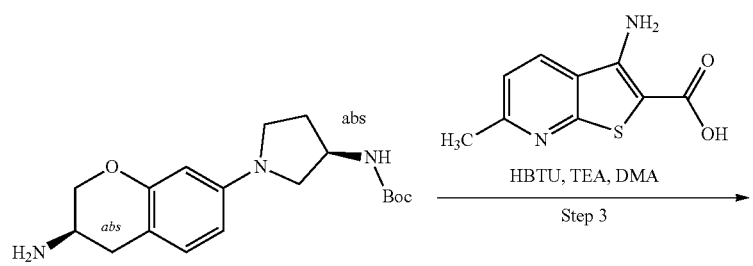

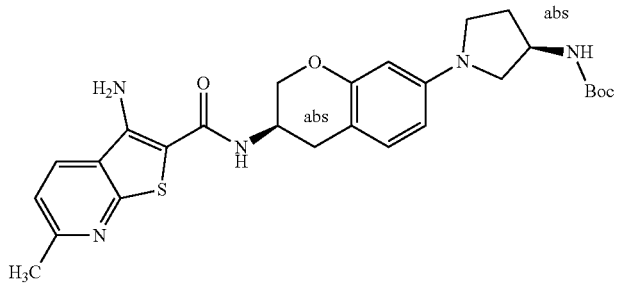

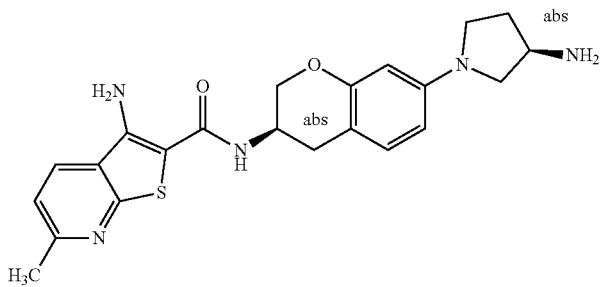

Step 1. Benzyl N-[(3R)-7-[(3R)-3-[[(tert-butoxy)carbonyl]amino]pyrrolidin-1-yl]-3,4-dihydro-2H-1-benzopyran-3-yl]carbamate A mixture of benzyl N-[(3R)-7-bromo-3,4-dihydro-2H-1-benzopyran-3-yl]carbamate (150 mg, 0.400 mmol), tert-butyl N-[(3R)-pyrrolidin-3-yl]carbamate (94.0 mg, 0.500 mmol), Cs$_2$CO$_3$ (274 mg, 0.840 mmol), RuPhos (40.0 mg, 0.090 mmol) and 3 generation RuPhos precatalyst (35.0 mg, 0.040 mmol) in toluene (4 mL) was stirred for 3 h at 90° C. After cooling to 25° C., the solids were filtered out. The filtrate was concentrated under reduced pressure. The residue was purified by silica gel chromatography (eluting with 1:3 ethyl acetate/petroleum ether) to afford benzyl N-[(3R)-7-[(3R)-3-[[(tert-butoxy)carbonyl]amino]pyrrolidin-1-yl]-3,4-dihydro-2H-1-benzopyran-3-yl]carbamate as a yellow solid (145 mg, 75%). LCMS (ES, m/z): 468 [M+H]$^-$.

Step 2. Tert-butyl N-[(3R)-1-[(3R)-3-amino-3,4-dihydro-2H-1-benzopyran-7-yl]pyrrolidin-3-yl]carbamate A mixture of benzyl N-[(3R)-7-[(3R)-3-[[(tert-butoxy)carbonyl]amino]pyrrolidin-1-yl]-3,4-dihydro-2H-1-benzopyran-3-yl]carbamate (145 mg, 0.300 mmol) and Pd/C (100 mg, 10%) in EA (6 mL) was stirred for 3 h at 25° C. under hydrogen atmosphere (balloon). The solids were filtered out. The filtrate was concentrated under reduced pressure to afford tert-butyl N-[(3R)-1-[(3R)-3-amino-3,4-dihydro-2H-1-benzopyran-7-yl]pyrrolidin-3-yl]carbamate as a light brown solid (95.0 mg, crude). LCMS (ES, m/z): 334 [M+H]$^+$.

Step 3. Tert-butyl N-[(3R)-1-[(3R)-3-[3-amino-6-methylthieno[2,3-b]pyridine-2-amido]-3,4-dihydro-2H-1-benzopyran-7-yl]pyrrolidin-3-yl]carbamate HBTU (154 mg, 0.400 mmol) was added to a solution of tert-butyl N-[(3R)-1-[(3R)-3-amino-3,4-dihydro-2H-1-benzopyran-7-yl]pyrrolidin-3-yl]carbamate (90.0 μmg, 0.260 μmmol), 3-amino-6-methylthieno[2,3-b]pyridine-2-carboxylic acid (84.0 mg, 0.400 mmol) and TEA (0.150 mL, 1.07 mmol) in DMA (3 mL). The resulting solution was stirred for 3 h at 25° C. The mixture was purified by reverse phase chromatography (Column: C18 silica gel; Mobile phase, A: water (containing 10 mmol/L NH$_4$HCO$_3$) and B: ACN (5% to 80% in 30 min); Detector: UV 254/220 nm). The collected fraction was concentrated to give tert-butyl N-[(3R)-1-[(3R)-3-[3-amino-6-methylthieno[2,3-b]pyridine-2-amido]-3,4-dihydro-2H-1-benzopyran-7-yl]pyrrolidin-3-yl]carbamate as a yellow solid (85.0 mg, 61%). LCMS (ES, m/z): 524 [M+H]$^+$.

Step 4. 3-Amino-N-[(3R)-7-[(3R)-3-aminopyrrolidin-1-yl]-3,4-dihydro-2H-1-benzopyran-3-yl]-6-methylthieno[2,3-b]pyridine-2-carboxamide A solution of tert-butyl N-[(3R)-1-[(3R)-3-[3-amino-6-methylthieno[2,3-b]pyridine-2-amido]-3,4-dihydro-2H-1-benzopyran-7-yl]pyrrolidin-3-yl]carbamate (42.0 mg, 0.080 mmol) and TFA (0.500 mL) in DCM (1.50 mL) was stirred for 25 min at 25° C. The resulting mixture was concentrated under vacuum. A solution of NH$_3$ (1.00 mL, 7M in MeOH) was added to the residue. The resulting solution was stirred for 0.5 h and concentrated under vacuum. The residue was purified by Prep-HPLC (Column: XBridge Shield RP18 OBD, 30×150 mm, 5 um; Mobile Phase, A: water (containing 10 mmol/L NH$_4$HCO$_3$) and B: ACN (25% to 55% in 7 min); Detector: UV 254 nm). The collected fraction was lyophilized to give 3-amino-N-[(3R)-7-[(3R)-3-aminopyrrolidin-1-yl]-3,4-dihydro-2H-1-benzopyran-3-yl]-6-methylthieno[2,3-b]pyridine-2-carboxamide as a yellow solid (20.0 mg, 60%). $^1$H-NMR (DMSO-d$_6$, 400 MHz) δ (ppm): 8.33 (d, J=8.4 Hz, 1H), 7.48 (br s, 1H), 7.32 (d, J=8.4 Hz, 1H), 7.21 (br s, 2H), 6.86 (d, J=8.4 Hz, 1H), 6.10 (d, J=8.0 Hz, 1H), 5.90 (s, 1H), 4.30-4.26 (m, 1H), 4.16-4.12 (m, 1H), 3.82-3.77 (m, 1H), 3.55-3.53 (m, 1H), 3.30-3.25 (m, 2H), 3.19-3.13 (m, 1H), 2.89-2.80 (m, 3H), 2.59 (s, 3H), 2.10-1.90 (m, 2H), 1.72-1.64 (m, 2H). LCMS (ES, m/z): 424 [M+H]$^+$.

Example 400. N-[(6S)-2-[(3R,4R)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide and
Example 401. N-[(6S)-2-[(3S,4S)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide
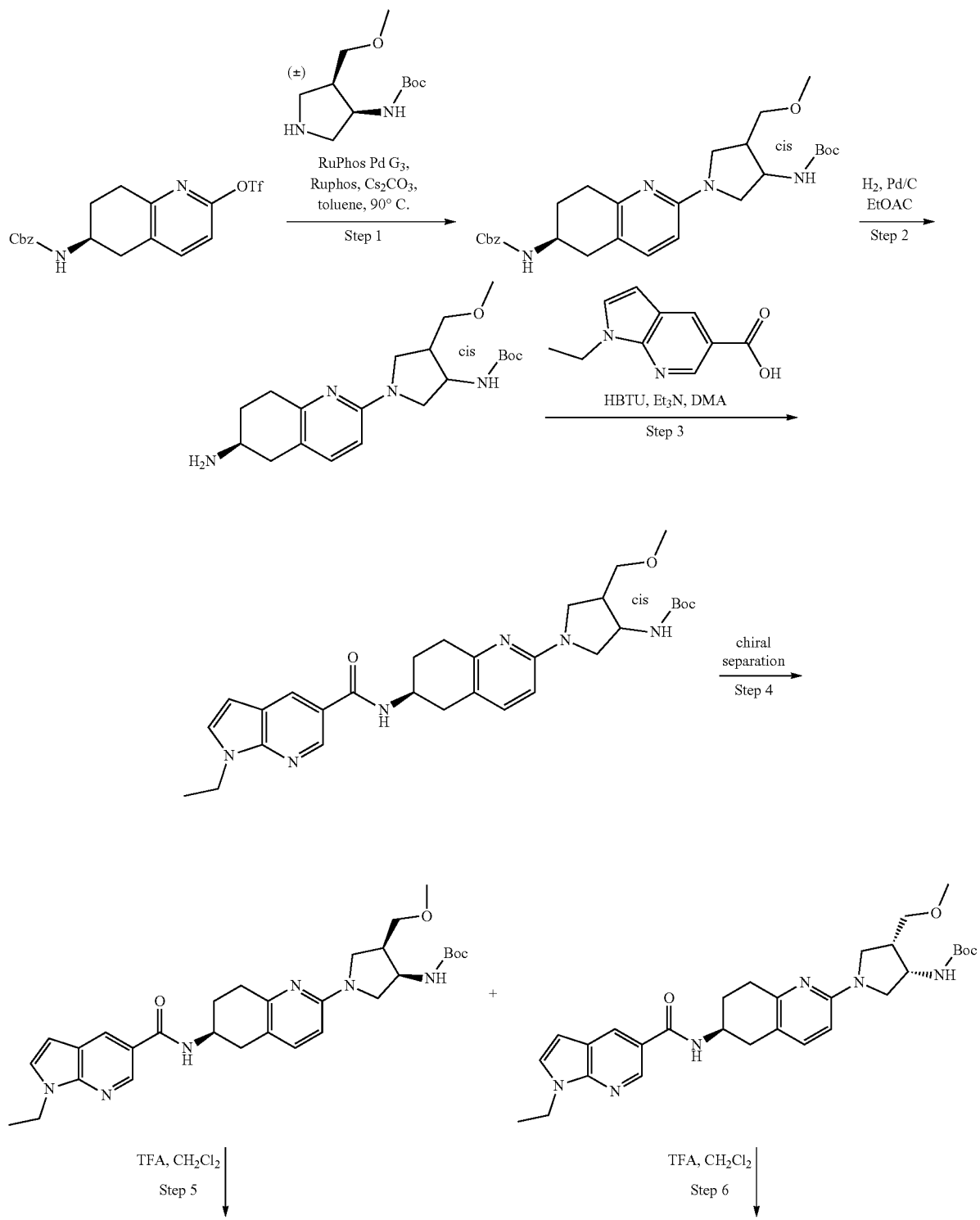

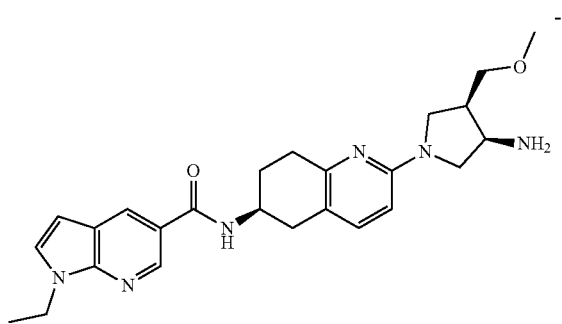
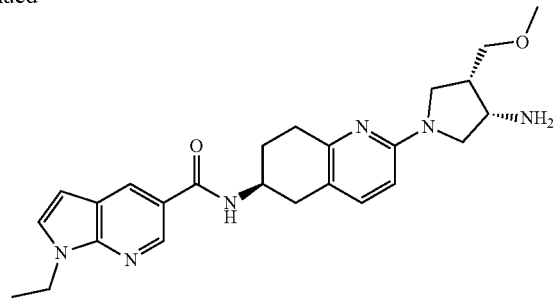

Step 1. cis-Benzyl N-[(6S)-2-(3-[[(tert-butoxy)carbonyl]amino]-4-(methoxymethyl)pyrrolidin-1-yl)-5,6,7,8-tetrahydroquinolin-6-yl]carbamate A solution of benzyl N-[(6S)-2-(trifluoromethanesulfonyloxy)-5,6,7,8-tetrahydroquinolin-6-yl]carbamate (Intermediate 47-2) (300 mg, 0.690 mmol), cis-tert-butyl N-[4-(methoxymethyl)pyrrolidin-3-yl]carbamate (192 mg, 0.825 mmol) (Intermediate 48-1), Cs$_2$CO$_3$ (454 mg, 1.38 mmol), RuPhos (65.0 mg, 0.138 mmol) and RuPhos Pd G3 (58.0 mg, 0.069 mmol) in toluene (10 mL) was stirred for 3 h at 90° C. After cooling to ambient temperature (~23° C.), the solids were filtered out and the filtrate was concentrated under vacuum. The residue was purified by reverse phase chromatography (Column: XBridge Prep C18 OBD, 19×150 mm 5 μm; Mobile Phase, A: water (containing 10 mM NH$_4$HCO3) and B: ACN (50% to 70% B over 30 min)) to afford cis-benzyl N-[(6S)-2-(3-[[(tert-butoxy)carbonyl]amino]-4-(methoxymethyl)pyrrolidin-1-yl)-5,6,7,8-tetrahydroquinolin-6-yl]carbamate as a colorless oil. MS (ESI, m/z): 511 [M+H]$^+$.

Step 2. cis-tert-Butyl N-[1-[(6S)-6-amino-5,6,7,8-tetrahydroquinolin-2-yl]-4-(methoxymethyl)pyrrolidin-3-yl]carbamate A mixture of cis-benzyl N-[(6S)-2-(3-[[(tert-butoxy)carbonyl]amino]-4-(methoxymethyl)pyrrolidin-1-yl)-5,6,7,8-tetrahydroquinolin-6-yl]carbamate (240 mg, 0.465 mmol) and Palladium on carbon (240 mg, 10%) in ethyl acetate (15 mL) was stirred for 16 h at 25° C. under a hydrogen atmosphere (balloon). The solids were filtered out and the filter cake was washed with MeOH (3×10 mL). The filtrate was concentrated under vacuum to give cis-tert-butyl N-[1-[(6S)-6-amino-5,6,7,8-tetrahydroquinolin-2-yl]-4-(methoxymethyl)pyrrolidin-3-yl]carbamate as a red solid. MS (ESI, m/z): 377 [M+H]$^+$.

Step 3. cis-tert-Butyl N-[1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate HBTU (176 mg, 0.459 mmol) was added to a stirring solution of cis-tert-butyl N-[1-[(6S)-6-amino-5,6,7,8-tetrahydroquinolin-2-yl]-4-(methoxymethyl)pyrrolidin-3-yl]carbamate (160 μmg, 0.421 mmol), 1-ethyl-1H-pyrrolo[2,3-b]pyridine-5-carboxylic acid (Intermediate 25) (80.0 mg, 0.417 mmol), and Et$_3$N (0.180 mL, 1.76 mmol) in DMA (4 mL). The resulting solution was stirred for 0.5 h at 25° C. The resulting mixture was purified by reverse phase chromatography (Column: XBridge Prep C18 OBD, 19×150 mm 5 μm; Mobile Phase, A: water (containing 10 mM NH$_4$HCO3) and B: ACN (50% to 70% B over 20 min)). The collected fraction was concentrated under vacuum to cis-tert-butyl N-[1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate.

Step 4. tert-Butyl N-[(3R,4R)-1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate and tert-Butyl N-[(3S,4S)-1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate The racemate cis-tert-butyl N-[1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate was separated by chiral HPLC (Column: Chiralpak IF, 2×25 cm, 5 μm; Mobile phase, A: hexanes:DCM=3:1 (containing 0.1% Et$_2$NH) and B: EtOH (hold 30% in 13 min); Flow rate: 30 mL/min). The first eluting isomer (RT=8.4 min) was collected and concentrated under vacuum to give a white solid, stereochemistry on the pyrrolidine arbitrarily assigned as tert-butyl N-[(3R,4R)-1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate. The second eluting isomer (RT=10.2 min) was collected and concentrated under vacuum to give a white solid, stereochemistry on the pyrrolidine arbitrarily assigned as tert-butyl N-[(3S,4S)-1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate. MS (ESI, m/z): 549 [M+H]$^+$.

Step 5. N-[(6S)-2-[(3R,4R)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide A solution of tert-butyl N-[(3R,4R)-1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate (60.0 mg, 0.108 mmol) and TFA (1.00 mL) in DCM (3 mL) was stirred for 30 min at 25° C. The resulting mixture was concentrated under vacuum. The residue was treated with a solution of NH$_3$ (3.00 mL, 7M in MeOH) dropwise at 25° C. The resulting mixture was stirred for additional 10 min at 25° C. and concentrated under vacuum. The residue was purified by prep-HPLC (Column: XBridge Prep C18 OBD, 5 μm, 19×150 mm; Mobile Phase A: water (10 mM NH$_4$HCO$_3$) and B: ACN (30% to 50% in 10 min)). The collected fraction was lyophilized to give N-[(6S)-2-[(3R,4R)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide as a white solid. MS (ESI, m/z): 449 [M+H]+. 1H-NMR (DMSO-$d_6$, 400 MHz) δ(ppm): 8.77 (s, 1H), 8.47-8.45 (m, 2H), 7.69 (d, J=3.6 Hz, 1H), 7.20 (d, J=8.4 Hz, 1H), 6.59 (d, J=3.6 Hz, 1H), 6.21 (d, J=8.4 Hz, 1H), 4.36-4.30 (m, 2H), 4.22-4.17 (m, 1H), 3.60-3.33 (m, 5H), 3.28 (s, 3H), 3.23-3.18 (m, 2H), 2.88-2.81 (m, 1H), 2.80-2.77 (m, 2H), 2.71-2.67 (m, 1H), 2.41-2.38 (m, 1H), 2.10-2.05 (m, 1H), 1.88-1.82 (m, 1H), 1.59 (br s, 2H), 1.41-1.38 (m, 4H).

Step 6. N-[(6S)-2-[(3S,4S)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide A solution of tert-butyl N-[(3S,4S)-1-[(6S)-6-[1-ethyl-1H-pyrrolo[2,3-b]pyridine-5-amido]-5,6,7,8-tetrahydroquinolin-2-yl]-4-(methoxymethyl)pyrrolidin-3-yl]carbamate (60.0 mg, 0.108 mmol) and TFA (1.00 mL) in DCM (10 mL) was stirred for 30 min at 25° C. The resulting mixture was concentrated under vacuum. The residue was treated with a solution of NH3 (3.00 mL, 7M in MeOH) dropwise at 25° C. The resulting mixture was stirred for additional 10 min at 25° C. and concentrated under vacuum. The residue was purified by prep-HPLC (Column: XBridge Prep C18 OBD, 5 μm, 19×150 mm; Mobile Phase A: water (10 mM NH4HCO3) and B: ACN (30% to 50% in 10 min)). The collected fraction was lyophilized to give N-[(6S)-2-[(3S,4S)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide as a white solid. MS (ESI, m/z): 449 [M+H]+. 1H-NMR (DMSO-$d_6$, 400 MHz) δ(ppm): 8.77 (d, J=2.0 Hz, 1H), 8.47-8.45 (m, 2H), 7.68 (d, J=3.6 Hz, 1H), 7.19 (d, J=8.4 Hz, 1H), 6.59 (d, J=3.2 Hz, 1H), 6.21 (d, J=8.4 Hz, 1H), 4.36-4.30 (m, 2H), 4.18-4.13 (m, 1H), 3.60-3.35 (m, 5H), 3.28 (s, 3H), 3.22-3.17 (m, 2H), 2.88-2.86 (m, 1H), 2.78-2.77 (m, 2H), 2.71-2.67 (m, 1H), 2.41-2.37 (m, 1H), 2.11-2.04 (m, 1H), 1.90-1.80 (m, 1H), 1.55 (br s, 2H), 1.41-1.38 (m, 3H).

Example 424. 3-amino-N-[(3R)-7-[(3S,4S)-3-amino-4-(fluoromethyl)pyrrolidin-1-yl]-3,4-dihydro-2H-1-benzopyran-3-yl]-6-methylthieno[2,3-b]pyridine-2-carboxamide

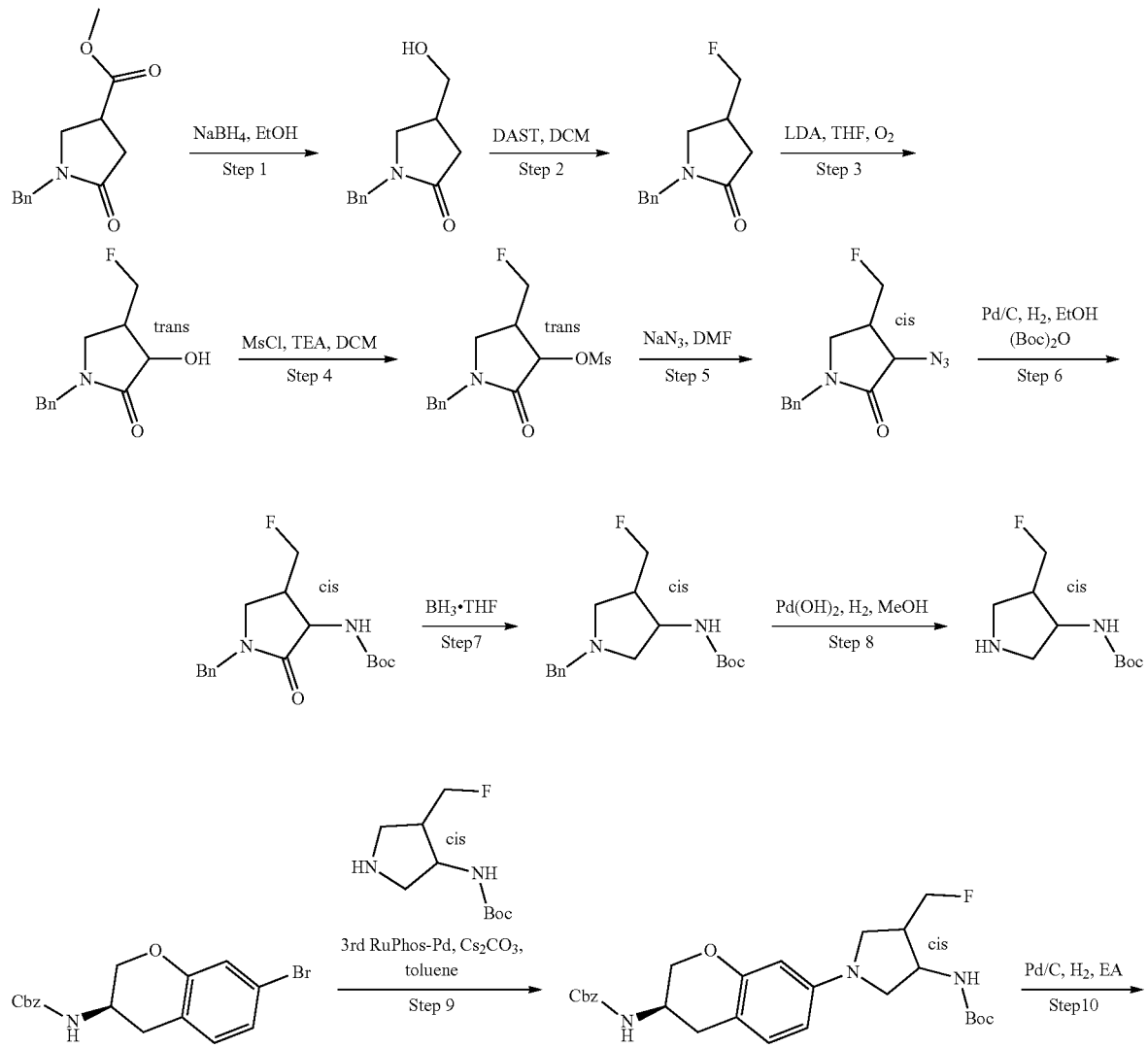

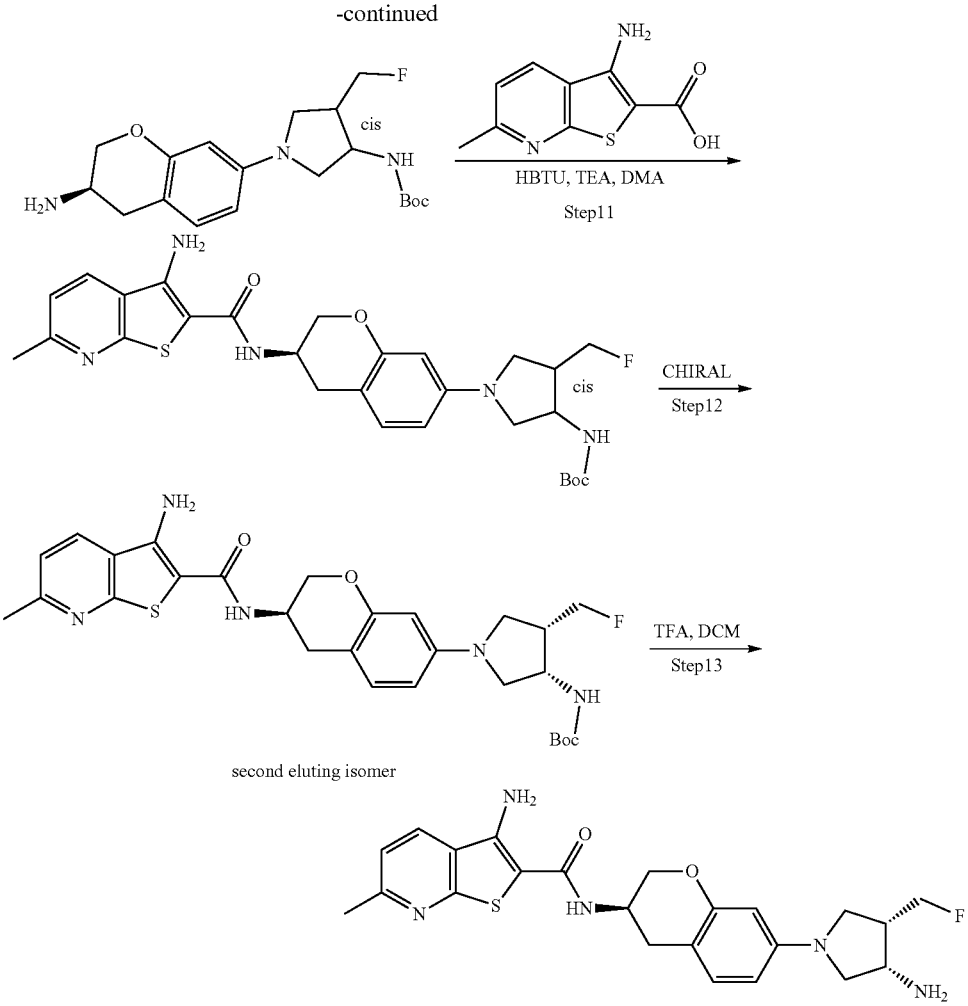

Step 1.
1-Benzyl-4-(hydroxymethyl)pyrrolidin-2-one

NaBH$_4$ (24.0 g, 634 mmol) was added to a solution of methyl 1-benzyl-5-oxopyrrolidine-3-carboxylate (50.0 g, 214 mmol) in ethanol (800 mL) at 0° C. The resulting solution was stirred for 4 h at 25° C. The reaction was quenched with water (50 mL). The mixture was concentrated under vacuum. The residue was diluted with water (200 mL). The resulting mixture was extracted with dichloromethane (3×500 mL). The organic layers were combined, dried over anhydrous sodium sulfate, filtered and concentrated under vacuum. The residue was purified by silica gel chromatography (eluting with 10/1 dicholoromethane/methanol) to give 1-benzyl-4-(hydroxymethyl)pyrrolidin-2-one as white oil (35.0 g, 76%). LCMS (ES, m/z): 206[M+H]$^+$.

Step 2. 1-Benzyl-4-(fluoromethyl)pyrrolidin-2-one

DAST (32.2 mL, 244 mmol) was added to a solution of 1-benzyl-4-(hydroxymethyl)pyrrolidin-2-one (20.0 g, 97.5 mmol) in DCM (300 mL) at −78 DC. The resulting solution was stirred for 16 h at 25° C. The reaction was poured into ice-water (200 mL). The resulting mixture was extracted with DCM (3×200 mL). The organic layers were combined, dried over anhydrous sodium sulfate, filtered and concentrated under vacuum. The residue was purified via reverse phase chromatography (Column: C18 column; Mobile phase, A: water (containing 10 mmol/L NH$_4$HCO$_3$) and B: CH$_3$CN (0% to 50% in 45 min); Detector: 254/220 nm) to give 1-benzyl-4-(fluoromethyl)pyrrolidin-2-one as yellow oil (12.0 g, 53%). LCMS (ES, m/z): 208 [M+H]$^+$.

Step 3. Trans-1-benzyl-4-(fluoromethyl)-3-hydroxy-pyrrolidin-2-one

A solution of LDA (24.0 mL, 2M in THF) was added to a solution of 1-benzyl-4-(fluoromethyl)pyrrolidin-2-one (5.00 g, 23.6 mmol) in tetrahydrofuran (100 mL) at −78° C. The resulting solution was stirred for 1 h at −78° C. Then O$_2$ was introduced in. The resulting solution was stirred for 3 h at −78° C. The reaction was quenched by the addition of water (50 mL). The solvent was removed under vacuum. The residue was extracted with CH$_2$Cl$_2$ (3×100 mL). The organic layers were combined, dried over anhydrous Na$_2$SO$_4$, filtered and concentrated under reduced pressure. The residue was purified by reverse phase chromatography (Column: C18 silica gel; Mobile phase, A: water (containing 0.1% TFA) and B: ACN (0% to 60% in 30 min); Detector: UV 220 nm & 254 nm) to afford trans-1-benzyl-4-(fluoromethyl)-3-hydroxypyrrolidin-2-one as a brown oil (3.00 g, 56%). LCMS (ES, m/z): 224 [M+H]$^+$.

Step 4. Trans-1-benzyl-4-(fluoromethyl)-2-oxopyrrolidin-3-yl methanesulfonate MsCl (2.75 mL, 35.5 mmol) was added to a stirring solution of trans-1-benzyl-4-(fluoromethyl)-3-hydroxypyrrolidin-2-one (5.40 g, 23.7 mmol) and TEA (6.59 mL, 47.4 mmol) in DCM (70 mL) at 0° C. The resulting mixture was stirred for 2 h at 25° C. The reaction was quenched by the addition of water (50 mL) at 0° C. The resulting mixture was extracted with $CH_2C12(3 \times 50$ mL). The organic layers were combined, dried over anhydrous $Na_2SO_4$, filtered and concentrated under reduced pressure to afford trans-1-benzyl-4-(fluoromethyl)-2-oxopyrrolidin-3-yl methanesulfonate as a brown oil (6.00 g, crude). LCMS (ES, m/z): 302 [M+H]$^+$.

Step 5. Cis-3-azido-1-benzyl-4-(fluoromethyl)pyrrolidin-2-one

A mixture of trans-1-benzyl-4-(fluoromethyl)-2-oxopyrrolidin-3-yl methanesulfonate (6.00 g, 19.5 mmol) and $NaN_3$ (3.81 g, 58.6 mmol) in DMF (150 mL) was stirred for 1 h at 100° C. The mixture was allowed to cool down to 25° C. The reaction was quenched by the addition of water (500 mL) at 25° C. The resulting mixture was extracted with ethyl acetate (3×200 mL). The combined organic layers were washed with brine (300 mL), dried over anhydrous $Na_2SO_4$, filtered and concentrated under reduced pressure. The residue was purified by silica gel chromatography (eluting with 1:1 ethyl acetate/petroleum ether) to afford cis-3-azido-1-benzyl-4-(fluoromethyl)pyrrolidin-2-one as a yellow oil (4.20 g, 85%). LCMS (ES, m/z): 249 [M+H]$^+$.

Step 6. Cis-tert-butyl N-[1-benzyl-4-(fluoromethyl)-2-oxopyrrolidin-3-yl]carbamate A mixture of 3-azido-1-benzyl-4-(fluoromethyl)pyrrolidin-2-one (4.00 g, 15.8 mmol), Palladium on carbon (4.00 g, 10%) and di-tert-butyl dicarbonate (6.89 g, 31.6 mmol) in EtOH (100 mL) was stirred for 3 h at 25° C. under hydrogen atmosphere (balloon). The solids were filtered out. The filtrate was concentrated under vacuum. The residue was purified by silica gel chromatography (eluting with 1:1 ethyl acetate/petroleum ether) to afford cis-tert-butyl N-[1-benzyl-4-(fluoromethyl)-2-oxopyrrolidin-3-yl]carbamate as a white solid (2.40 g, 46%). LCMS (ES, m/z): 323 [M+H]$^-$.

Step 7. Cis-tert-butyl N-[1-benzyl-4-(fluoromethyl)pyrrolidin-3-yl]carbamate A solution of $BH_3$ (30 mL, 1M in THF) was added to a stirring solution of cis-tert-butyl N-[1-benzyl-4-(fluoromethyl)-2-oxopyrrolidin-3-yl]carbamate (2.40 g, 7.30 mmol) in THF (60 mL) at 0° C. The resulting mixture was stirred for 16 h at 25° C. The resulting mixture was concentrated under vacuum. Then EtOH (60 mL), $H_2O$ (15 mL) and TEA (15 mL) were added. The resulting mixture was stirred for 2 h at 80° C. The resulting mixture was cooled to 25° C. and concentrated under vacuum. The residue was purified by reverse phase chromatography (Column: C18 Column; Mobile phase, A: water (containing 10 mmol/L $NH_4HCO_3$) and B: ACN (0% to 100% in 30 min); Detector: UV220 nm &200 nm) to afford cis-tert-butyl N-[1-benzyl-4-(fluoromethyl)pyrrolidin-3-yl]carbamate as a white solid (1.00 g, 44%). LCMS (ES, m/z): 309 [M+H]$^+$.

Step 8. Cis-tert-butyl N-[4-(fluoromethyl)pyrrolidin-3-yl]carbamate

A mixture of tert-butyl N-[1-benzyl-4-(fluoromethyl)pyrrolidin-3-yl]carbanmate (450 mg, 1.43 mmol) and Pd(OH)$_2$ on carbon (450 mg, 20%) in ethyl acetate (10 mL) was stirred for 2 h at 25° C. under hydrogen atmosphere (balloon). The solids were filtered out. The filtrate was concentrated under reduced pressure to afford cis-tert-butyl N-[4-(fluoromethyl)pyrrolidin-3-yl]carbamate as a brown oil (300 mg, crude). LCMS (ES, m/z): 219 [M+H]$^+$.

Step 9. Cis-benzyl N-[(3R)-7-(3-[[(tert-butoxy)carbonyl]amino]-4-(fluoromethyl)pyrrolidin-1-yl)-3,4-dihydro-2H-1-benzopyran-3-yl]carbamate A mixture of tert-butyl N-[4-(fluoromethyl)pyrrolidin-3-yl]carbamate (133 mg, 0.349 mmol), cis-benzyl N-[(3R)-7-bromo-3,4-dihydro-2H-1-benzopyran-3-yl]carbamate (76.1 mg, 0.331 mmol), $Cs_2CO_3$ (227 mg, 0.698 mmol), RuPhos (32.6 mg, 0.070 mmol) and 3rd Generation RuPhos precatalyst (29.2 mg, 0.035 mmol) in toluene (3 mL) was stirred for 6 h at 100° C. After cooled to 25° C., the solids were filtered out and the filtrate was concentrated under reduced pressure. The residue was purified by silica gel chromatography (eluting with 1:2 ethyl acetate/petroleum ether) to afford the cis-benzyl N-[(3R)-7-(3-[[(tert-butoxy)carbonyl]amino]-4-(fluoromethyl)pyrrolidin-1-yl)-3,4-dihydro-2H-1-benzopyran-3-yl]carbamate as an off-white solid (120 mg, 65%). LCMS (ES, m/z): 500[M+H]$^+$.

Step 10. Cis-tert-butyl N-[1-[(3R)-3-amino-3,4-dihydro-2H-1-benzopyran-7-yl]-4-(fluoromethyl) pyrrolidin-3-yl]carbamate A mixture of cis-benzyl N-[(3R)-7-(3-[[(tert-butoxy)carbonyl]amino]-4-(fluoromethyl)pyrrolidin-1-yl)-3,4-dihydro-2H-1-benzopyran-3-yl]carbamate (155 mg, 0.295 mmol) and palladium on carbon (160 mg, 10%) in ethyl acetate (15 mL) was stirred for 2 h at 25° C. under hydrogen atmosphere (balloon). The solids were filtered out. The filtrate was concentrated under vacuum to give cis-tert-butyl N-[1-[(3R)-3-amino-3,4-dihydro-2H-1-benzopyran-7-yl]-4-(fluoromethyl)pyrrolidin-3-yl]carbamate as an off-white solid (100 mg, crude). LCMS (ES, m/z): 366 [M+H]$^+$.

Step 11. Cis-tert-butyl N-[1-[(3R)-3-[3-amino-6-methylthieno[2,3-b]pyridine-2-amido]-3,4-dihydro-2H-1-benzopyran-7-yl]-4-(fluoromethyl)pyrrolidin-3-yl]carbamate HBTU (156 mg, 0.410 mmol) was added to a solution of cis-tert-butyl N-[1-[(3R)-3-amino-3,4-dihydro-2H-1-benzopyran-7-yl]-4-(fluoromethyl)pyrrolidin-3-yl]carbamate (100 mg, 0.274 mmol), 3-amino-6-methylthieno[2,3-b]pyridine-2-carboxylic acid (51.3 mg, 0.246 mmol) and TEA (0.114 ml, 0.821 mmol) in DMA (3 mL). The resulting solution was stirred for 1 h at 25° C. The mixture was purified by reverse phase chromatography (Column: C18 silica gel; Mobile Phase, A: water (containing 10 mmol/L $NH_4HCO_3$) and B: ACN (0% to 60% in 30 min); Detector: UV 220 nm). The collected fractions were concentrated under vacuum to give cis-tert-butyl N-[1-[(3R)-3-[3-amino-6-methylthieno[2,3-b]pyridine-2-amido]-3,4-dihydro-2H-1-benzopyran-7-yl]-4-(fluoromethyl)pyrrolidin-3-yl]carbamate as a yellow solid (95.0 mg, 59%). LCMS (ES, m/z): 556 [M+H]$^+$.

Step 12. tert-butyl N-[(3S,4S)-1-[(3R)-3-[3-amino-6-methylthieno[2,3-b]pyridine-2-amido]-3,4-dihydro-2H-1-benzopyran-7-yl]-4-(fluoromethyl)pyrrolidin-3-yl]carbamate Cis-tert-butyl N-[1-[(3R)-3-[3-amino-6-methylthieno[2,3-b]pyridine-2-amido]-3,4-dihydro-2H-1-benzopyran-7- yl]-4-(fluoromethyl)pyrrolidin-3-yl]carbamate (95.0 mg, 0.171 mmol) was separated by Chiral-Prep-HPLC (Column: CHIRALPAK IG, 2×250 mm, 5 um; Mobile phase, A: MTBE (containing 0.1% IPA) and B: IPA (hold 30% in 16 min); Flow rate: 20 mL/min; Detector: UV 220/254 nm). The first eluting isomer ($RT_1$=11.150 min) was collected and concentrated under vacuum to give a yellow solid whose stereochemistry was arbitrarily assigned as tert-butyl N-[(3R,4R)-1-[(3R)-3-[3-amino-6-methylthieno[2,3-b]pyridine-2-amido]-3,4-dihydro-2H-1-benzopyran-7-yl]-4-(fluoromethyl)pyrrolidin-3-yl]carbamate. The second eluting isomer ($RT_2$=14.269 min) was collected and concentrated under vacuum to give a yellow solid whose stereochemistry was arbitrarily assigned as tert-butyl N-[(3S,4S)-1-[(3R)-3-[3-amino-6-methylthieno[2,3-b]pyridine-2-amido]-3,4-dihydro-2H-1-benzopyran-7-yl]-4-(fluoromethyl)pyrrolidin-3-yl]carbamate. LCMS (ES, m/z): 556 [M+H]$^+$.

Step 13. 3-Amino-N-[(3R)-7-[(3S,4S)-3-amino-4-(fluoromethyl)pyrrolidin-1-yl]-3,4-dihydro-2H-1-benzopyran-3-yl]-6-methylthieno[2,3-b]pyridine-2-carboxamide A solution of tert-butyl N-[(3S,4S)-1-[(3R)-3-[3-amino-6-methylthieno[2,3-b]pyridine-2-amido]-3,4-dihydro-2H-1-benzopyran-7-yl]-4-(fluoromethyl)pyrrolidin-3-yl]carbamate (30.0 mg, 0.051 mmol) and TFA (1.00 mL) in DCM (3.00 mL) was stirred for 30 min at 25° C. The resulting mixture was concentrated under vacuum. A solution of $NH_3$ (2.00 mL, 7M in MeOH) was added into the residue. The resulting solution was stirred for 0.5 h at 25° C. and concentrated under vacuum. The residue was purified by Prep-HPLC (Column: XBridge Shield RP18 OBD Column 19×150 mm, 5 um; Mobile Phase A: water (containing 10 mmol/L $NH_4HCO_3$) and B: ACN (30% to 50% in 7 min); Flow rate: 60 mL/min; Detector: 254 nm). The collected fractions were lyophilized to afford 3-amino-N-[(3R)-7-[(3S,4S)-3-amino-4-(fluoromethyl)pyrrolidin-1-yl]-3,4-dihydro-2H-1-benzopyran-3-yl]-6-methylthieno[2,3-b]pyridine-2-carboxamide as off-white solid (12.5 mg, 51%). $^1$H-NMR (DMSO-$d_6$, 400 MHz) δ (ppm): 8.32 (d, J=8.0 Hz, 1H), 7.50 (br s, 1H), 7.31 (d, J=8.0 Hz, 1H), 7.22 (br s, 2H), 6.87 (d, J=8.4 Hz, 1H), 6.09 (d, J=6.8 Hz, 1H), 5.90 (s, 1H), 4.81-4.46 (m, 2H), 4.29-4.23 (m, 1H), 4.15-4.12 (m, 1H), 3.81-3.76 (m, 1H), 3.61-3.60 (m, 1H), 3.42-3.34 (m, 1H), 3.28-3.26 (m, 1H), 3.16-3.12 (m, 1H), 2.97-2.95 (m, 1H), 2.89-2.83 (m, 2H), 2.59-2.57 (m, 4H), 1.86 (br s, 2H). LCMS (ES, m/z): 456 [M+H]$^+$.

Example 439. 3-amino-N-[(3R)-7-[(5R,9R)-9-amino-2-oxa-7-azaspiro[4.4]nonan-7-yl]-3,4-dihydro-2H-1-benzopyran-3-yl]-6-methylthieno[2,3-b]pyridine-2-carboxamide

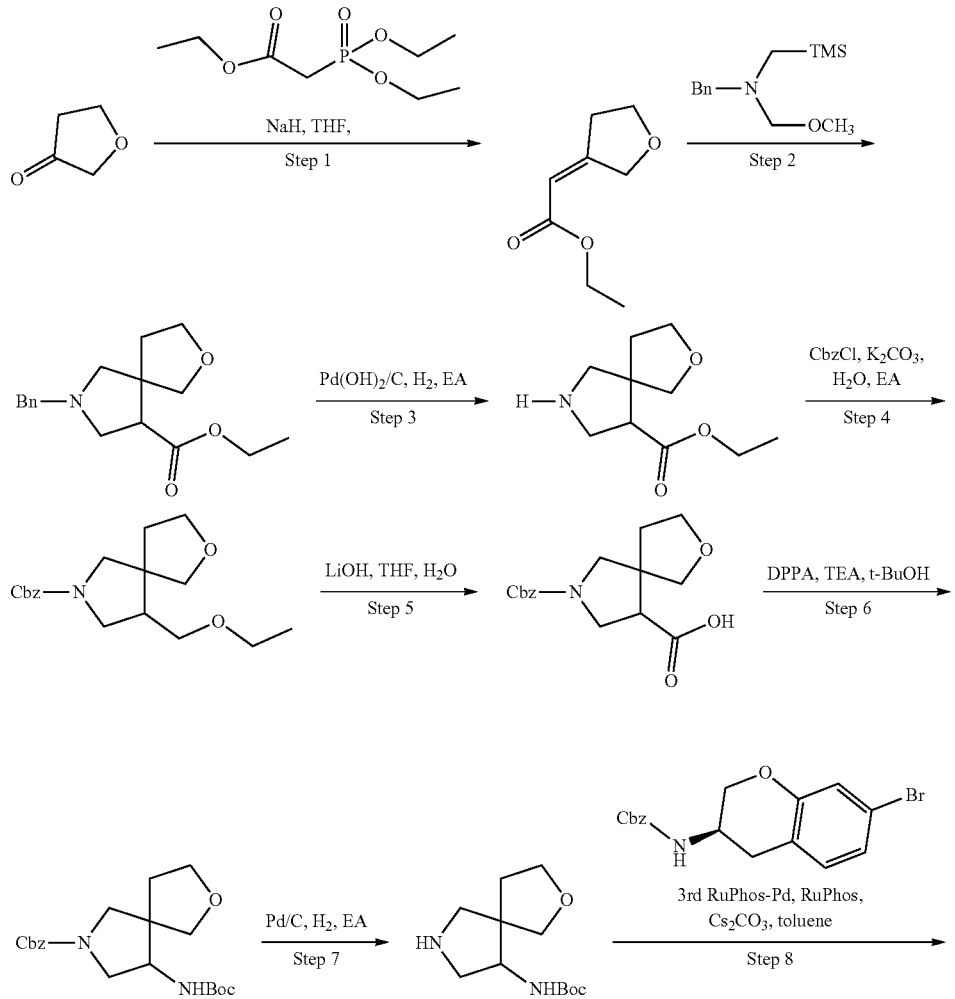

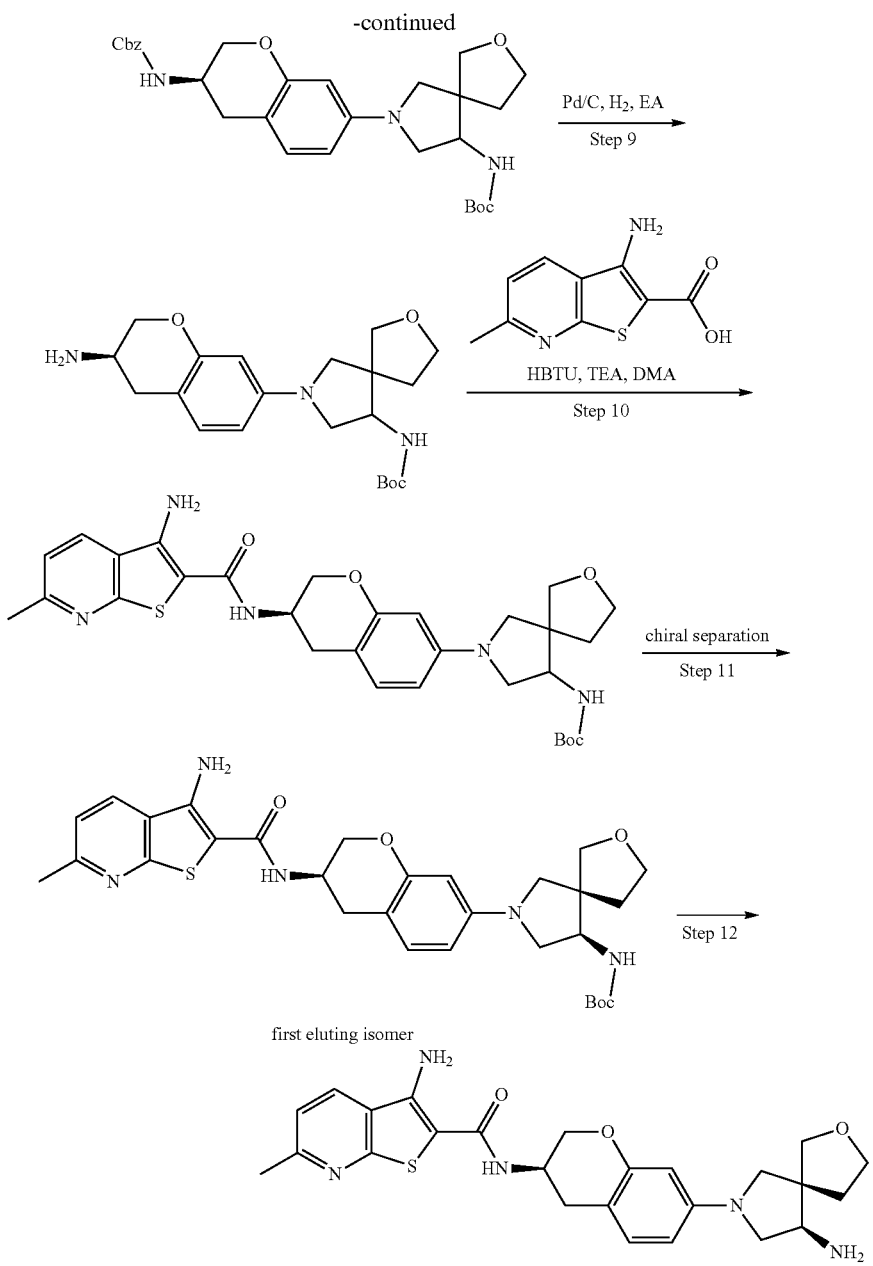

Step 1. Ethyl 2-[(3Z)-oxolan-3-ylidene]acetate

To a stirred solution of ethyl 2-(diethoxyphosphoryl)acetate (26.0 g, 110 mmol) in THF (300 mL) was added NaH (2.60 g, 60%) in portions at 0° C. The reaction was stirred for 1.5 h at 0° C. Then a solution of oxolan-3-one (5.00 g, 55.2 mmol) in THF was added. The reaction was stirred for 12 h at 25° C. The reaction was quenched with water (300 mL). The resulting mixture was extracted with EtOAc (3×300 mL). The combined organic layers were washed with brine (1×200 mL), dried over anhydrous $Na_2SO_4$. After filtration, the filtrate was concentrated under reduced pressure. The residue was purified by silica gel chromatography (eluting with 1:3 ethyl acetate/petroleum ether) to give ethyl 2-[(3Z)-oxolan-3-ylidene]acetate as an off-white oil (6.00 g, 66%). LCMS (ES, m/z): 157 [M+H]⁻.

Step 2. Ethyl 7-benzyl-2-oxa-7-azaspiro[4.4]nonane-9-carboxylate

TFA (104 mg, 0.912 mmol) was added to a solution of ethyl 2-[(3Z)-oxolan-3-ylidene]acetate (5.00 g, 30.4 mmol) and benzyl(methoxymethyl)[(trimethylsilyl)methyl]amine (11.1 g, 45.6 mmol) in toluene (10 mL). The reaction was stirred for 1.5 h at 60° C. The resulting mixture was cooled to 25° C. then was poured into $NaHCO_3$ (1×20 mL). The resulting mixture was extracted with EtOAc (3×50 mL). The combined organic layers were washed with brine (1×50 mL), dried over anhydrous $Na_2SO_4$. After filtration, the filtrate was concentrated under reduced pressure. The residue was purified by silica gel chromatography Column (eluting with 1:3 THF/petroleum ether) to afford ethyl 7-benzyl-2-oxa-7-azaspiro[4.4]nonane-9-carboxylate as a off-white oil (3.00 g, 30%). LCMS (ES, m/z): 290 [M+H].

Step 3. Ethyl 2-oxa-7-azaspiro[4.4]nonane-9-carboxylate

A mixture of ethyl 7-benzyl-2-oxa-7-azaspiro[4.4]nonane-9-carboxylate (3.00 g, 9.85 mmol) and Pd(OH)₂/C (2.38 g, 20%) in MeOH (30 mL) was stirred for 3.5 h at 25° C. under hydrogen atmosphere (balloon). The resulting mixture was filtered, the filter cake was washed with MeOH (1×30 mL). The filtrate was concentrated under reduced pressure to give ethyl 2-oxa-7-azaspiro[4.4]nonane-9-carboxylate as a yellow oil (1.90 g, 92%). LCMS (ES, m/z): 200 [M+H]⁺.

Step 4. 7-benzyl 9-ethyl 2-oxa-7-azaspiro[4.4]nonane-7,9-dicarboxylate

CbzCl (4.00 ml, 28.0 mmol) was added to a stirred solution of ethyl 2-oxa-7-azaspiro[4.4]nonane-9-carboxylate (3.91 g, 18.6 mmol) and K₂CO₃ (5.21 g, 37.3 mmol) in EA (20.0 mL) and H₂O (15.0 mL) at 0° C. The reaction was stirred for 3 h at 25° C. The resulting mixture was extracted with EtOAc (3×40 mL). The combined organic layers were washed with brine (1×40 mL), dried over anhydrous Na₂SO₄. After filtration, the filtrate was concentrated under reduced pressure. The residue was purified by reverse phase chromatography (Column: C18 silica gel; Mobile phase, A: water (containing 10 mmol/L NH₄HCO₃) and B: ACN (0% to 60% in 30 min); Detector: UV 220 nm & 254 nm). The collected fraction was concentrated to give 7-benzyl 9-ethyl 2-oxa-7-azaspiro[4.4]nonane-7,9-dicarboxylate as a brown yellow oil (3.60 g, 55%). LCMS (ES, m/z):334 [M+H]⁺.

Step 5. 7-[(benzyloxy)carbonyl]-2-oxa-7-azaspiro[4.4]nonane-9-carboxylic acid LiOH (1.28 g, 0.053 mmol) was added to a solution of 7-benzyl 9-ethyl 2-oxa-7-azaspiro[4.4]nonane-7,9-dicarboxylate (3.70 g, 10.5 mmol) in THF (10 mL) and H₂O (10 mL). The reaction was stirred for 2 h at 25° C. The THF was evaporated out under vacuum. The resulting mixture was acidified to pH 4 with HCl (1 mol/L). The resulting mixture was extracted with DCM (3×50 mL). The combined organic layers were washed with brine (1×40 mL), dried over anhydrous Na₂SO₄. After filtration, the filtrate was concentrated under reduced pressure to give 7-[(benzyloxy)carbonyl]-2-oxa-7-azaspiro[4.4]nonane-9-carboxylic acid as a yellow oil (2.80 g, 83%). LCMS (ES, m/z): 306 [M+H]⁺.

Step 6. Benzyl 9-[[(tert-butoxy)carbonyl]amino]-2-oxa-7-azaspiro[4.4]nonane-7-carboxylate To a stirred solution of 7-[(benzyloxy)carbonyl]-2-oxa-7-azaspiro[4.4]nonane-9-carboxylic acid (3.00 g, 9.33 mmol) in t-BuOH (10 mL) was added TEA (2.60 ml, 18.7 mmol) and DPPA (3.08 g, 11.2 mmol). The reaction was stirred for 2 h at 90° C. The mixture was cooled, and concentrated under vacuum. The residue was purified by reverse phase chromatography (Column: C18 silica gel; Mobile Phase, A: water (containing 10 mmol/L NH₄HCO₃) and B: ACN (0% to 60% in 30 min); Detector: UV 220 nm). The collected fractions were concentrated to give benzyl 9-[[(tert-butoxy)carbonyl]amino]-2-oxa-7-azaspiro[4.4]nonane-7-carboxylate as a off-white solid (1.40 g, 38%). LCMS (ES, m/z): 377 [M+H]⁺.

Step 7. Tert-butyl N-[2-oxa-7-azaspiro[4.4]nonan-9-yl]carbamate

A mixture of benzyl 9-[[(tert-butoxy)carbonyl]amino]-2-oxa-7-azaspiro[4.4]nonane-7-carboxylate (1.40 g, 3.53 mmol) and palladium on carbon (1.40 g, 10%) in ethyl acetate (50 mL) was stirred for 2 h at 25° C. under hydrogen atmosphere (balloon). The solids were filtered out. The filtrate was concentrated under vacuum to give tert-butyl N-[2-oxa-7-azaspiro[4.4]nonan-9-yl]carbamate as an off-white oil (755 mg, crude). LCMS (ES, m/z): 243 [M+H]⁺.

Step 8. Benzyl N-[(3R)-7-(9-[[(tert-butoxy)carbonyl]amino]-2-oxa-7-azaspiro[4.4]nonan-7-yl)-3,4-dihydro-2H-1-benzopyran-3-yl]carbamate A mixture of benzyl N-[(3R)-7-bromo-3,4-dihydro-2H-1-benzopyran-3-yl]carbamate (400 mg, 1.10 mmol), tert-butyl N-[2-oxa-7-azaspiro[4.4]nonan-9-yl]carbamate (300 mg. 1.24 mmol), 3rd Generation RuPhos precatalyst (92.4 mg, 0.110 mmol), RuPhos (51.5 mg, 0.110 mmol) and Cs₂CO₃ (1.08 g, 3.31 mmol) in toluene (8 mL) was stirred for 3 h at 95° C. The mixture was cooled. The solids were filtered out, and the filtrate was concentrated under vacuum. The residue was purified by silica gel chromatography (eluting with 1:3 ethyl acetate/petroleum ether) to give benzyl N-[(3R)-7-(9-[[(tert-butoxy)carbonyl]amino]-2-oxa-7-azaspiro[4.4]nonan-7-yl)-3,4-dihydro-2H-1-benzopyran-3-yl]carbamate as an off-white solid (350 mg, 61%). LCMS (ES, m/z): 524 [M+H]⁺.

Step 9. Tert-butyl N-[1-[(6S)-6-amino-5,6,7,8-tetrahydroquinolin-2-yl]-4-(fluoromethyl)-4-methylpyrrolidin-3-yl]carbamate A mixture of benzyl N-[(6S)-2-(4-[[(tert-butoxy)carbonyl]amino]-3-(fluoromethyl)-3-methylpyrrolidin-1-yl)-5,6,7,8-tetrahydroquinolin-6-yl]carbamate (350 mg, 0.683 mmol) and Palladium on carbon (190 mg, 10%) in EA (8 mL) was stirred for 16 h at 28° C. under an atmosphere of hydrogen (balloon). The solids were filtered out. The filtrate was concentrated under vacuum to give tert-butyl N-[1-[(6S)-6-amino-5,6,7,8-tetrahydroquinolin-2-yl]-4-(fluoromethyl)-4-methylpyrrolidin-3-yl]carbamate as yellow oil (250 mg, 93%). LCMS (ES, m/z): 390 [M+H]⁺.

Step 10. Tert-butyl N-[1-[(6S)-6-[3-amino-6-methylthieno[2,3-b]pyridine-2-amido]-5,6,7,8-tetrahydroquinolin-2-yl]-4-(fluoromethyl)-4-methylpyrrolidin-3-yl]carbamate HBTU (300 mg, 0.791 mmol) was added to a solution of tert-butyl N-[1-[(6S)-6-amino-5,6,7,8-tetrahydroquinolin-2-yl]-4-(fluoromethyl)-4-methylpyrrolidin-3-yl]carbamate (250 mg, 0.661 mmol), 3-amino-6-methylthieno[2,3-b]pyridine-2-carboxylic acid (151 mg, 0.725 mmol) and TEA (0.280 mL, 2.72 mmol) in DMA (5 mL). The resulting solution was stirred for 1 h at 28° C. The mixture was purified by reverse phase chromatography (Column: C18 silica gel; Mobile phase, A: water (containing 0.05% TFA) and B: ACN (10% to 70% in 25 min); Detector: UV 220/254 nm) to afford tert-butyl N-[1-[(6S)-6-[3-amino-6-methylthieno[2,3-b]pyridine-2-amido]-5,6,7,8-tetrahydroquinolin-2-yl]-4-(fluoromethyl)-4-methylpyrrolidin-3-yl]carbamate as a yellow solid (260 mg, 69%). LCMS (ES, m/z): 580 [M+H]⁺.

Step 11. Tert-butyl N-[(5R,9R)-7-[(3R)-3-[3-amino-6-methylthieno[2,3-b]pyridine-2-amido]-3,4-dihydro-2H-1-benzopyran-7-yl]-2-oxa-7-azaspiro[4.4]nonan-9-yl]carbamate The tert-butyl N-[7-[(3R)-3-[3-amino-6-methylthieno[2,3-b]pyridine-2-amido]-3,4-dihydro-2H-1-benzopyran-7- yl]-2-oxa-7-azaspiro[4.4]nonan-9-yl]carbamate (260 mg, 0.431 mmol) was separated by Chiral-Prep-HPLC (Column: CHIRALPAK IF, 2×25 μcm, 5 um; Mobile Phase, A: Hex: DCM(3:1)(containing 10 mM NH₃-MEOH)—HPLC and B: EtOH—HPLC (hold 50% in 20 min); Flow rate: 15 mL/min; Detector: UV 254/220 nm). The third eluting isomer (RT3=11.68 min) was collected and concentrated under vacuum to afford a yellow solid whose stereochemistry was arbitrarily assigned as tert-butyl N-[(5S,9S)-7-[(3R)-3-[3-amino-6-methylthieno[2,3-b]pyridine-2-amido]-3,4-dihydro-2H-1-benzopyran-7-yl]-2-oxa-7-azaspiro[4.4]nonan-9-yl]carbamate. The fourth eluting isomer (RT4=13.805 min) was collected and concentrated under vacuum to afford a yellow solid whose stereochemistry was arbitrarily assigned as tert-butyl N-[(5R,9S)-7-[(3R)-3-[3-amino-6-methylthieno[2,3-b]pyridine-2-amido]-3,4-dihydro-2H-1-benzopyran-7-yl]-2-oxa-7-azaspiro[4.4]nonan-9-yl]carbamate. And mixture A (mixture of the first isomer and second eluting isomers) was separated by Chiral-Prep-HPLC (Column: CHIRALPAK IC, 2×25 cm, 5 um; Mobile Phase, A: Hex:DCM(3:1)(containing 0.2% IPA)—HPLC and B: MeOH:DCM(1:1)—HPLC (hold 60% in 20 min); Flow rate: 20 mL/min; Detector: UV 254/220 nm). The first eluting isomer (RT1=8.3 min) was collected and concentrated under vacuum to afford a yellow solid whose stereochemistry was arbitrarily assigned as tert-butyl N-[(5R,9R)-7-[(3R)-3-[3-amino-6-methylthieno[2,3-b]pyridine-2-amido]-3,4-dihydro-2H-1-benzopyran-7-yl]-2-oxa-7-azaspiro[4.4]nonan-9-yl]carbamate. The second eluting isomer (RT2=15 min) was collected and concentrated under vacuum to afford a yellow solid whose stereochemistry was arbitrarily assigned as tert-butyl N-[(5S,9R)-7-[(3R)-3-[3-amino-6-methylthieno[2,3-b]pyridine-2-amido]-3,4-dihydro-2H-1-benzopyran-7-yl]-2-oxa-7-azaspiro[4.4]nonan-9-yl]carbamate. LCMS (ES, m/z): 580 [M+H]⁻.

Step 12. 3-amino-N-[(3R)-7-[(5R,9R)-9-amino-2-oxa-7-azaspiro[4.4]nonan-7-yl]-3,4-dihydro-2H-1-benzopyran-3-yl]-6-methylthieno[2,3-b]pyridine-2-carboxamide A solution of tert-butyl N-[(5R,9R)-7-[(3R)-3-[3-amino-6-methylthieno[2,3-b]pyridine-2-amido]-3,4-dihydro-2H-1-benzopyran-7-yl]-2-oxa-7-azaspiro[4.4]nonan-9-yl]carbamate (34.0 mg, 0.059 mmol) and TFA (1 mL) in DCM (3 mL) was stirred for 0.5 h at 25° C. The resulting mixture was concentrated under vacuum. NH₃ (7M in MeOH, 2 mL) was added to the residue. The resulting solution was stirred for 0.5 h, and then concentrated under vacuum. The residue was purified by Prep-HPLC (Column: X Select CSH Prep C18 OBD Column 19×150 mm 5 um; Mobile Phase A: water (containing 10 mmol/L NH₄HCO₃) and B: ACN (20% to 45% in 8 min), Flow rate: 25 mL/min; Detector UV 254 nm). The collected fraction was lyophilized to give 3-amino-N-[(3R)-7-[(5R,9R)-9-amino-2-oxa-7-azaspiro[4.4]nonan-7-yl]-3,4-dihydro-2H-1-benzopyran-3-yl]-6-methylthieno[2,3-b]pyridine-2-carboxamide as a white solid (14.0 mg, 50%). ¹H-NMR (DMSO-d₆, 400 MHz) S (ppm): 8.32 (d, 0.1=8.4 Hz, 1H), 7.48 (br s, 1H), 7.31 (d, J=8.4 Hz, 1H), 7.21 (br s, 2H), 6.86 (d, J=8.4 Hz, 1H), 6.08 (d, J=6.8 Hz, 1H), 5.88 (s, 1H), 4.27-4.24 (m, 1H), 4.15-4.12 (m, 1H), 3.81-3.77 (m, 3H), 3.55 (d, J=8.4 Hz, 1H), 3.48 (d, J=8.4 Hz, 1H), 3.39-3.36 (m, 1H), 3.32-3.23 (m, 2H), 3.14-3.11 (m, 1H), 2.92-2.90 (m, 1H), 2.89-2.81 (m, 2H), 2.58 (s, 3H), 2.10-2.06 (m, 1H), 1.72 (br s, 2H), 1.61-1.57 (m, 1H). LCMS (ES, m/z): 480 [M+H]⁺.

Example 525. (R)-3-Amino-6-methyl-N-(7-(piperazin-1-yl)-3,4-dihydro-2H-pyrano[2,3-b]pyridin-3-yl)thieno[2,3-b]pyridine-2-carboxamide

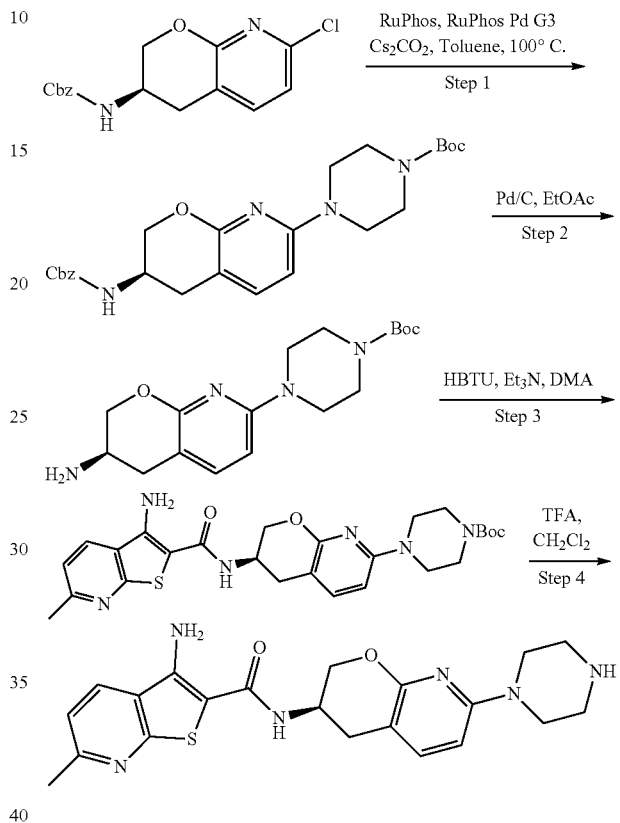

Step 1. tert-Butyl (R)-4-(3-(((benzyloxy)carbonyl)amino)-3,4-dihydro-2H-pyrano[2,3-b]pyridin-7-yl)piperazine-1-carboxylate A solution of benzyl (R)-(7-chloro-3,4-dihydro-2H-pyrano[2,3-b]pyridin-3-yl)carbamate (Intermediate 43) (200 mg, 0.56 mmol), tert-butyl piperazine-1-carboxylate (140 mg, 0.75 mmol), RuPhos Pd G3 (52 mg, 0.06 mmol), RuPhos (59 mg, 0.13 mmol) and Cs₂CO₃ (618 mg, 1.90 mmol) in toluene (5 mL) was stirred for 3 h at 100° C. After cooling to 25° C., the reaction was then quenched by the addition of 10 mL of water. The resulting mixture was extracted with 3×10 mL of ethyl acetate and the organic layers combined, dried over anhydrous sodium sulfate, filtered and concentrated under vacuum. The residue was purified by silica gel chromatography (eluting with 1:3 ethyl acetate/pet. ether) to give tert-butyl (R)-4-(3-(((benzyloxy)carbonyl)amino)-3,4-dihydro-2H-pyrano[2,3-b]pyridin-7-yl)piperazine-1-carboxylate as an off-white solid. MS: (ESI, m/z): 469 [M+H]⁺.

Step 2. tert-Butyl (R)-4-(3-amino-3,4-dihydro-2H-pyrano[2,3-b]pyridin-7-yl)piperazine-1-carboxylate C A suspension of tert-butyl (R)-4-(3-(((benzyloxy)carbonyl)amino)-3,4-dihydro-2H-pyrano[2,3-b]pyridin-7-yl)

piperazine-1-carboxylate (270 mg, 0.52 mmol) and Palladium on carbon (30 mg, 10%) in ethyl acetate (20 mL) was stirred for 4 h at 25° C. The solids were filtered out. The filtrate was concentrated under vacuum to tert-butyl (R)-4-(3-amino-3,4-dihydro-2H-pyrano[2,3-b]pyridin-7-yl)piperazine-1-carboxylate as a brown oil. MS: (ESI, m/z): 335 [M+H]⁺.

Step 3. tert-Butyl (R)-4-(3-(3-amino-6-methylthieno[2,3-b]pyridine-2-carboxamido)-3,4-dihydro-2H-pyrano[2,3-b]pyridin-7-yl)piperazine-1-carboxylate A solution of tert-butyl (R)-4-(3-amino-3,4-dihydro-2H-pyrano[2,3-b]pyridin-7-yl)piperazine-1-carboxylate (50 mg, 0.13 mmol), 3-amino-6-methylthieno[2,3-b]pyridine-2-carboxylic acid (34 mg, 0.16 mmol), HBTU (62 mg, 0.16 mmol) and Et₃N (45 mg, 0.44 mmol) in DMA (3 mL) was stirred for 30 min at 25° C. The reaction was then quenched by the addition of 10 mL of water. The resulting mixture was extracted with 3×10 mL of ethyl acetate. The organic layers combined, dried over anhydrous sodium sulfate, filtered and concentrated under vacuum. The residue was purified by reverse phase chromatography (Column: C18 silica gel; Mobile phase A: water (0.1% formic acid), B: ACN; Flow rate: 50 mL/min; Gradient: 0% increasing to 100% B within 40 min). The collected fraction was concentrated under vacuum. The collected fraction was concentrated under vacuum to give tert-butyl (R)-4-(3-(3-amino-6-methylthieno[2,3-b]pyridine-2-carboxamido)-3,4-dihydro-2H-pyrano[2,3-b]pyridin-7-yl)piperazine-1-carboxylate as a yellow solid. MS: (ESI, m/z): 525 [M+H]⁺.

Step 4. (R)-3-Amino-6-methyl-N-(7-(piperazin-1-yl)-3,4-dihydro-2H-pyrano[2,3-b]pyridin-3-yl)thieno[2,3-b]pyridine-2-carboxamide A solution of tert-butyl (R)-4-(3-(3-amino-6-methylthieno[2,3-b]pyridine-2-carboxamido)-3,4-dihydro-2H-pyrano[2,3-b]pyridin-7-yl)piperazine-1-carboxylate (30 mg, 0.05 mmol) and TFA (1 mL) in DCM (3 mL) was stirred for 30 min at 25° C. The resulting mixture was concentrated under vacuum. The residue was purified by prep-HPLC (Column: XBridge Shield RP18 OBD, 19×250 mm, 10 μm; Mobile phase A: Water (10 mM NH₄HCO₃), B: ACN; Gradient: 20% B to 38% B in 8 min). The collected fraction was lyophilized to give (R)-3-amino-6-methyl-N-(7-(piperazin-1-yl)-3,4-dihydro-2H-pyrano[2,3-b]pyridin-3-yl)thieno[2,3-b]pyridine-2-carboxamide as an off-white solid. ¹H NMR (DMSO-d₆, 400 MHz) δ(ppm): 8.33 (d, J=8.4 Hz, 1H), 7.55 (br s, 1H), 7.32-7.27 (m, 2H), 7.22 (br s, 2H), 6.37 (d, J=8.4 Hz, 1H), 4.33-4.20 (m, 2H), 3.99-3.94 (m, 1H), 3.49-3.31 (m, 5H), 2.89-2.74 (m, 6H), 2.59 (s, 3H). MS: (ESI, m/z): 425 [M+H]⁺.

Example 526. (R)-3-Amino-N-(6-fluoro-7-(piperazin-1-yl)-3,4-dihydro-2H-pyrano[2,3-b]pyridin-3-yl)-6-methylthieno[2,3-b]pyridine-2-carboxamide

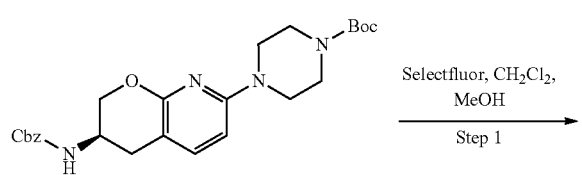

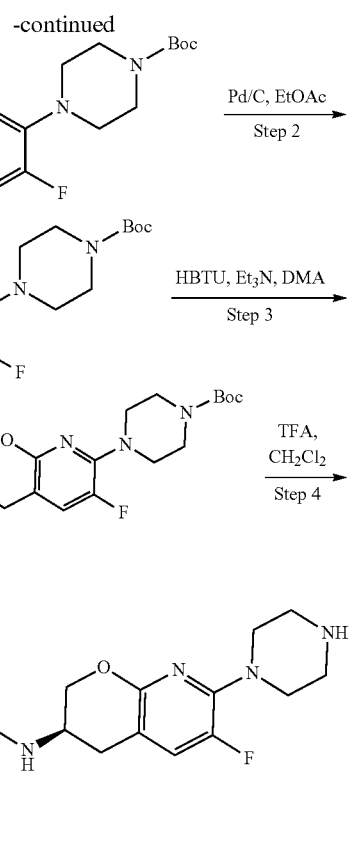

Step 1. tert-Butyl (R)-4-(3-(((benzyloxy)carbonyl)amino)-6-fluoro-3,4-dihydro-2H-pyrano[2,3-b]pyridin-7-yl)piperazine-1-carboxylate To a solution of tert-butyl (R)-4-(3-(((benzyloxy)carbonyl)amino)-3,4-dihydro-2H-pyrano[2,3-b]pyridin-7-yl)piperazine-1-carboxylate (580 mg, 1.24 mmol) in DCM (25 mL) and MeOH (25 mL) was added Selectfluor (441 mg, 1.24 mmol) at −20° C. The resulting mixture was stirred for 2 h at 25° C. The solvent was removed under vacuum. The residue was diluted with water (30 mL). The resulting mixture was extracted with DCM (3×30 mL). The combined organic layers were dried over anhydrous Na₂SO₄, filtered and concentrated under vacuum. The residue was purified by silica gel chromatography (eluting with 1:10-1:3 ethyl acetate/pet. ether) to afford tert-butyl (R)-4-(3-(((benzyloxy)carbonyl)amino)-6-fluoro-3,4-dihydro-2H-pyrano[2,3-b]pyridin-7-yl)piperazine-1-carboxylate as an off-white solid. MS: (ESI, m/z): 487 [M+H]⁺.

Step 2. tert-Butyl (R)-4-(3-amino-6-fluoro-3,4-dihydro-2H-pyrano[2,3-b]pyridin-7-yl)piperazine-1-carboxylate A suspension of tert-butyl (R)-4-(3-(((benzyloxy)carbonyl)amino)-6-fluoro-3,4-dihydro-2H-pyrano[2,3-b]pyridin-7-yl)piperazine-1-carboxylate (150 mg, 0.31 mmol) and Palladium on carbon (20 mg, 10%) in ethyl acetate (5 mL) was stirred for 2 h at 25° C. under hydrogen atmosphere. The solids were filtered out. The filtrate was concentrated under vacuum to give tert-butyl (R)-4-(3-amino-6-fluoro-3,4-dihydro-2H-pyrano[2,3-b]pyridin-7-yl)piperazine-1-carboxylate as a yellow oil. MS: (ESI, m/z): 353 [M+H]+.

Step 3. tert-Butyl (R)-4-(3-(3-amino-6-methylthieno[2,3-b]pyridine-2-carboxamido)-6-fluoro-3,4-dihydro-2H-pyrano[2,3-b]pyridin-7-yl)piperazine-1-carboxylate A solution of tert-butyl (R)-4-(3-amino-6-fluoro-3,4-dihydro-2H-pyrano[2,3-b]pyridin-7-yl)piperazine-1-carboxylate (90 mg, 190 mmol), 3-amino-6-methylthieno[2,3-b]pyridine-2-carboxylic acid (56.0 mg. 270 mmol), HBTU (107 mg, 0.28 mmol) and Et$_3$N (77 mg, 0.76 mmol) in DMA (4 mL) was stirred for 1 h at 25° C. The reaction was quenched with water (10 mL). The resulting mixture was extracted with ethyl acetate (3×10 mL). The organic layers were combined, dried over anhydrous sodium sulfate, filtered and concentrated under vacuum. The residue was purified by reverse phase chromatography (Column: C18 silica gel; Mobile phase A: water (0.1% TFA), B: ACN; Flow rate: 50 mL/min; Gradient: 0% B to 70% B within 40 min). The collected fractions were concentrated under vacuum to afford tert-butyl (R)-4-(3-(3-amino-6-methylthieno[2,3-b]pyridine-2-carboxamido)-6-fluoro-3,4-dihydro-2H-pyrano[2,3-b]pyridin-7-yl)piperazine-1-carboxylate as a yellow solid. MS: (ESI, m/z): 543 [M+H]+.

Step 4. (R)-3-Amino-N-(6-fluoro-7-(piperazin-1-yl)-3,4-dihydro-2H-pyrano[2,3-b]pyridin-3-yl)-6-methylthieno[2,3-b]pyridine-2-carboxamide A solution of tert-butyl (R)-4-(3-(3-amino-6-methylthieno[2,3-b]pyridine-2-carboxamido)-6-fluoro-3,4-dihydro-2H-pyrano[2,3-b]pyridin-7-yl)piperazine-1-carboxylate (100 mg, 0.18 mmol) and TFA (1 mL) in DCM (3 mL) was stirred for 30 min at 25° C. The resulting mixture was concentrated under vacuum. A solution of NH$_3$ in methanol (7M) (5 mL) was added. The resulting mixture was stirred for 30 min at 25° C. The resulting mixture was concentrated under vacuum. The residue was purified by prep-HPLC (Column: XBridge Prep OBD C18, 30×150 mm 5 μm; Mobile Phase A: Water (10 mM NH$_4$HCO$_3$), B: ACN; Flow rate: 60 mL/min; Gradient: 20% B to 45% B in 7 min) to afford (R)-3-amino-N-(6-fluoro-7-(piperazin-1-yl)-3,4-dihydro-2H-pyrano[2,3-b]pyridin-3-yl)-6-methylthieno[2,3-b]pyridine-2-carboxamide as an off-white solid. $^1$H NMR (DMSO-d$_6$, 300 MHz) δ(ppm): 8.32 (d, J=8.1 Hz, 1H), 7.59 (br s, 1H), 7.36-7.30 (m, 2H), 7.21 (br s, 2H), 4.33-4.19 (m, 2H), 4.01-3.95 (m, 1H), 3.23-3.20 (m, 4H), 2.89-2.73 (m, 6H), 2.58 (s, 3H). MS: (ESI, m/z): 443 [M+H]+.

Example 601. 6-amino-N-[(3R)-7-[3,8-diazabicyclo[3.2.1]octan-3-yl]-5,8-difluoro-3,4-dihydro-2H-1-benzopyran-3-yl]-2-methylthieno[2,3-d][1,3]thiazole-5-carboxamide

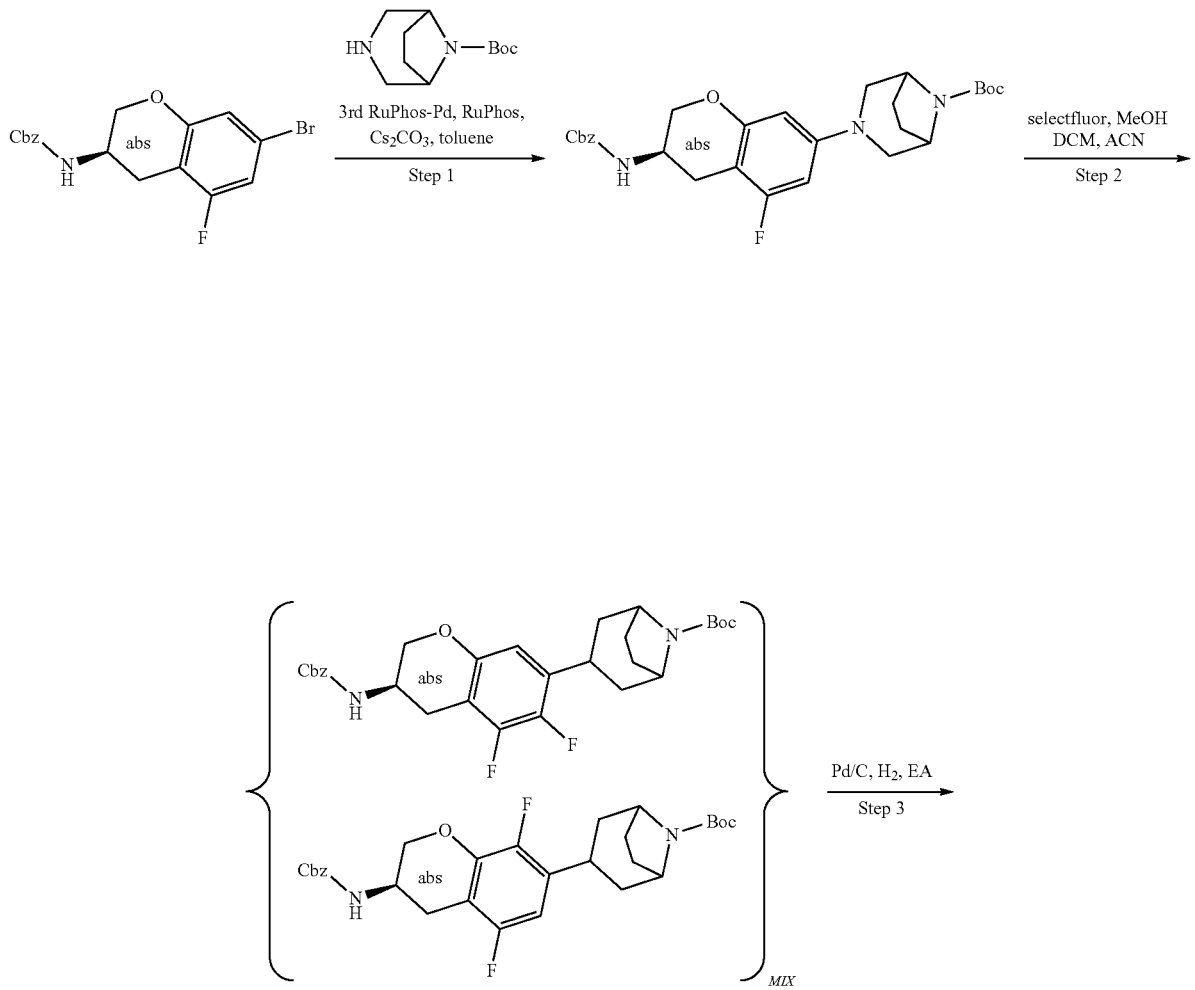

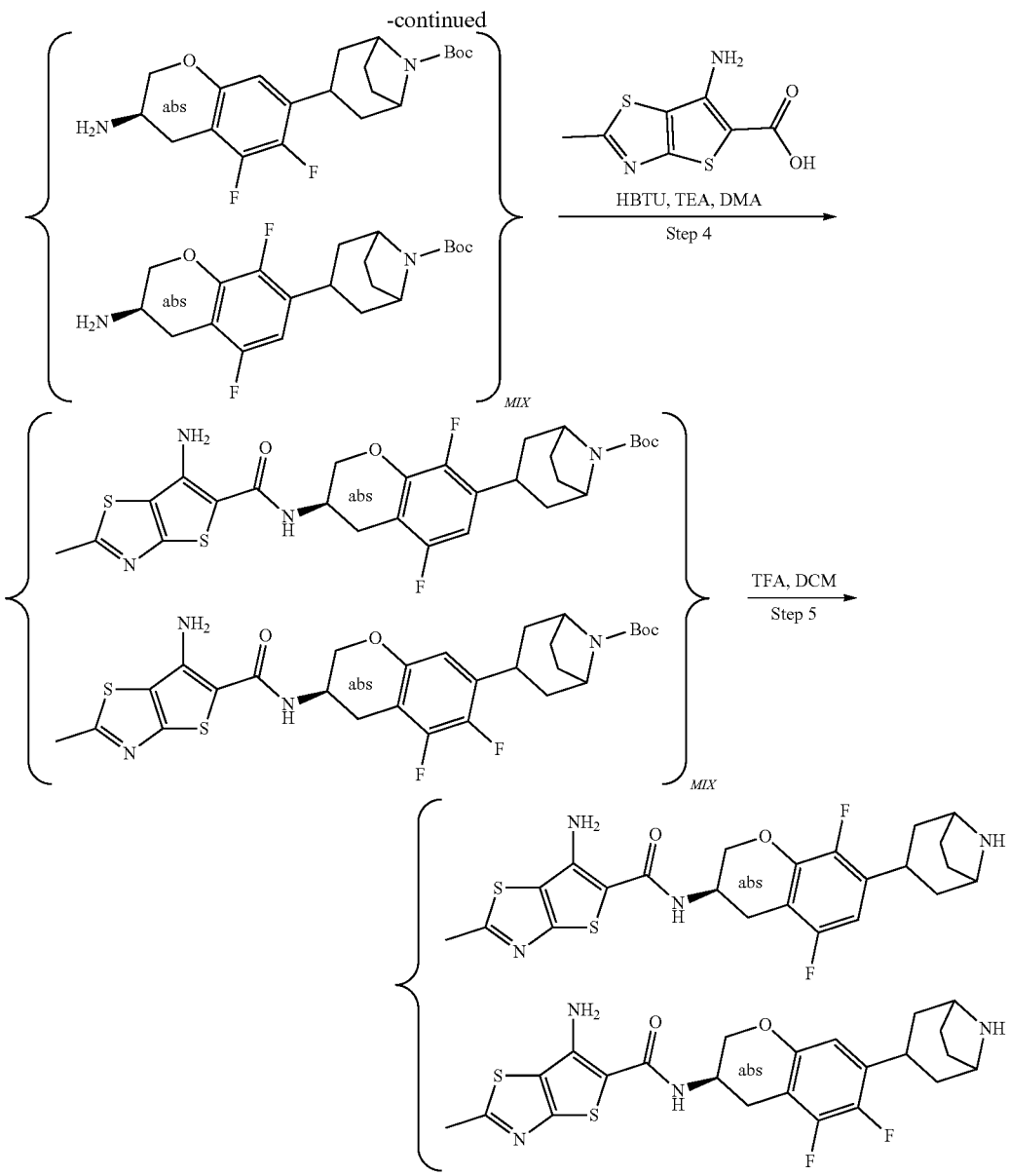

Step 1: Tert-butyl 3-[(3R)-3-[[(benzyloxy)carbonyl]amino]-5-fluoro-3,4-dihydro-2H-1-benzopyran-7-yl]-3,8-diazabicyclo[3.2.1]octane-8-carboxylate A mixture of benzyl N-[(3R)-7-bromo-5-fluoro-3,4-dihydro-2H-1-benzopyran-3-yl]carbamate (500 mg, 1.32 mmol), tert-butyl 3,8-diazabicyclo[3.2.1]octane-8-carboxylate (364 mg, 1.71 mmol), Cs₂CO₃ (1.30 g, 3.99 mmol), RuPhos (123 mg, 0.260 mmol), 3rd Generation RuPhos precatalyst (110 mg, 0.130 mmol) in toluene (10 mL) was stirred for 3 h at 100° C. (The reaction was set up 3 batches in parallel). The reaction mixture was cooled. All the mixtures were combined. The solids were filtered out. The filtrate was concentrated under vacuum. The residue was purified via a silica gel chromatography (eluting with 1:3 ethyl acetate/petroleum ether) to afforded tert-butyl 3-[(3R)-3-[[(benzyloxy)carbonyl]amino]-5-fluoro-3,4-dihydro-2H-1-benzopyran-7-yl]-3,8-diazabicyclo[3.2.1]octane-8-carboxylate as a light yellow solid (1.20 g, 60%). LCMS (ES, m/z): 512 [M+H]⁺.

Step 2. The mixture of tert-butyl 3-[(3R)-3-[[(benzyloxy)carbonyl]amino]-5,6-difluoro-3,4-dihydro-2H-1-benzopyran-7-yl]-3,8-diazabicyclo[3.2.1]octane-8-carboxylate and tert-butyl 3-[(3R)-3-[[(benzyloxy)carbonyl]amino]-5,8-difluoro-3,4-dihydro-2H-1-benzopyran-7-yl]-3,8-diazabicyclo[3.2.1]octane-8-carboxylate Selectfluor (727 mg, 2.05 mmol) was added to a solution of tert-butyl 3-[(3R)-3-[[(benzyloxy)carbonyl]amino]-5-fluoro-3,4-dihydro-2H-1-benzopyran-7-yl]-3,8-diazabicyclo[3.2.1]octane-8-carboxylate (700 mg, 1.37 mmol) in a mix-solution of ACN (35 mL), methanol (35 mL) and dichloromethane (35 mL) at −20° C. The resulting solution was stirred for 1 h at −20° C., then warmed to 28° C. slowly and stirred for 10 h at 28° C. The reaction was then quenched with water (20 mL). The organic layer was evaporated out. The aqueous layer was extracted with dichloromethane (3×30 mL), dried over anhydrous sodium sulfate, filtered and concentrated under vacuum. The residue was purified by silica gel chromatography (eluting with 1:3 ethyl acetate/petroleum ether) to afford the mixture of tert-butyl 3-[(3R)-3-[[(benzyloxy)carbonyl]amino]-5,6-difluoro-3,4-dihydro-2H-1-benzopyran-7-yl]-3,8-diazabicyclo[3.2.1]octane-8-carboxylate and tert-butyl 3-[(3R)-3-[[(benzyloxy)carbonyl]amino]-5,8-difluoro-3,4-dihydro-2H-1-benzopyran-7-yl]-3,8-diazabicyclo[3.2.1]octane-8-carboxylate as a light yellow solid (270 mg, 37%). LCMS (ES, m/z): 530 [M+H]$^+$.

Step 3. The mixture of tert-butyl 3-[(3R)-3-amino-5,6-difluoro-3,4-dihydro-2H-1-benzopyran-7-yl]-3,8-diazabicyclo[3.2.1]octane-8-carboxylate and tert-butyl 3-[(3R)-3-amino-5,8-difluoro-3,4-dihydro-2H-1-benzopyran-7-yl]-3,8-diazabicyclo[3.2.1]octane-8-carboxylate A mixture of Palladium on carbon (220 μmg, 10%), tert-butyl 3-[(3R)-3-[[(benzyloxy)carbonyl]amino]-5,6-difluoro-3,4-dihydro-2H-1-benzopyran-7-yl]-3,8-diazabicyclo[3.2.1]octane-8-carboxylate and tert-butyl 3-[(3R)-3-[[(benzyloxy)carbonyl]amino]-5,8-difluoro-3,4-dihydro-2H-1-benzopyran-7-yl]-3,8-diazabicyclo[3.2.1]octane-8-carboxylate (260 mg, 0.490 mmol) in ethyl acetate (20 mL) was stirred for 1.5 h at 28° C. The solids were filtered out. The filtrate was concentrated under vacuum to afford the mixture of tert-butyl 3-[(3R)-3-amino-5,6-difluoro-3,4-dihydro-2H-1-benzopyran-7-yl]-3,8-diazabicyclo[3.2.1]octane-8-carboxylate and tert-butyl 3-[(3R)-3-amino-5,8-difluoro-3,4-dihydro-2H-1-benzopyran-7-yl]-3,8-diazabicyclo[3.2.1]octane-8-carboxylate as a yellow solid (160 mg, 82%). LCMS (ES, m/z): 396 [M+H]$^+$.

Step 4. The mixture of tert-butyl 3-[(3R)-3-[6-amino-2-methylthieno[2,3-d][1,3]thiazole-5-amido]-5,8-difluoro-3,4-dihydro-2H-1-benzopyran-7-yl]-3,8-diazabicyclo[3.2.1]octane-8-carboxylate and tert-butyl 3-[(3R)-3-[6-amino-2-methylthieno[2,3-d][1,3]thiazole-5-amido]-5,6-difluoro-3,4-dihydro-2H-1-benzopyran-7-yl]-3,8-diazabicyclo[3.2.1]octane-8-carboxylate HBTU(84 mg, 0.222 mmol) was added to a solution of 6-amino-2-methylthieno[2,3-d][1,3]thiazole-5-carboxylic acid(43.0 mg, 0.202 mmol), TEA(0.084 mL, 0.606 mmol) and the mixture of tert-butyl 3-[(3R)-3-amino-5,8-difluoro-3,4-dihydro-2H-1-benzopyran-7-yl]-3,8-diazabicyclo[3.2.1] octane-8-carboxylate and tert-butyl 3-[(3R)-3-amino-5,6-difluoro-3,4-dihydro-2H-1-benzopyran-7-yl]-3,8-diazabicyclo[3.2.1]octane-8-carboxylate (80.0 mg, 0.202 mmol) in DMA(2.50 mL). The resulting mixture was stirred for 1 h 29° C. The residue was purified by reverse phase chromatography (Column, C18 silica gel; Mobile phase, A: water (containing 0.5% TFA) and B: ACN (0 to 100% within 40 min); Detector, UV 220 nm). The collection fraction was concentrated under vacuum to afford the mixture of tert-butyl 3-[(3R)-3-[6-amino-2-methylthieno[2,3-d][1,3]thiazole-5-amido]-5,8-difluoro-3,4-dihydro-2H-1-benzopyran-7-yl]-3,8-diazabicyclo[3.2.1]octane-8-carboxylate and tert-butyl 3-[(3R)-3-[6-amino-2-methylthieno[2,3-d][1,3]thiazole-5-amido]-5,6-difluoro-3,4-dihydro-2H-1-benzopyran-7-yl]-3,8-diazabicyclo[3.2.1]octane-8-carboxylateas a yellow solid(70.0 mg, 55%). LCMS (ES, m/z): 592 [M+H]$^+$.

Step 5. 6-amino-N-[(3R)-7-[3,8-diazabicyclo[3.2.1]octan-3-yl]-5,8-difluoro-3,4-dihydro-2H-1-benzopyran-3-yl]-2-methylthieno[2,3-d][1,3]thiazole-5-carboxamide A solution of TFA (1.00 mL) and the mixture of tert-butyl 3-[(3R)-3-[6-amino-2-methylthieno[2,3-d][1,3]thiazole-5-amido]-5,8-difluoro-3,4-dihydro-2H-1-benzopyran-7-yl]-3,8-diazabicyclo[3.2.1]octane-8-carboxylate and tert-butyl 3-[(3R)-3-[6-amino-2-methylthieno[2,3-d][1,3]thiazole-5-amido]-5,6-difluoro-3,4-dihydro-2H-1-benzopyran-7-yl]-3,8-diazabicyclo[3.2.1]octane-8-carboxylate (60.0 mg, 0.101 mmol) in DCM (3 mL) was stirred for 0.5 h at 27° C. The resulting mixture was concentrated under vacuum. The residue was purified by Prep-HPLC (Column: XBridge Shield RP18 OBD Column, 5 μm, 19×150 mm; Mobile phase, A: water (containing 0.05% NH$_4$HCO$_3$) and B: ACN (20% to 55% in 12 min); Flow rate: 20 mL/min; Detector: 220 nm; Detector, UV 220 nm). The first eluting isomer (Rt$_1$=9.92 min) was collected and lyophilized to afford 6-amino-N-[(3R)-7-[3,8-diazabicyclo[3.2.1]octan-3-yl]-5,8-difluoro-3,4-dihydro-2H-1-benzopyran-3-yl]-2-methylthieno[2,3-d][1,3]thiazole-5-carboxamide as a white solid (6.20 mg, 13%). $^1$H-NMR (DMSO-d$_6$, 300 MHz) δ (ppm): 7.57 (d, J=6.9 Hz, 1H), 7.17 (br s, 2H), 6.36-6.30 (m, 1H), 40.29-4.22 (m, 2H), 3.95-3.88 (m, 1H), 3.38-3.34 (m, 2H), 3.07-3.04 (m, 2H), 2.95-2.87 (m, 1H), 2.80-2.72 (m, 6H), 1.79-1.64 (m, 4H). LCMS (ES, m/z): 492 [M+H]$^+$.

Example 602. N-((2S)-6-(3,8-diazabicyclo[3.2.1] octan-3-yl)-5-cyano-8-fluoro-1,2,3,4-tetrahydronaphthalen-2-yl)-3-amino-6-methylthieno[2,3-b] pyridine-2-carboxamide

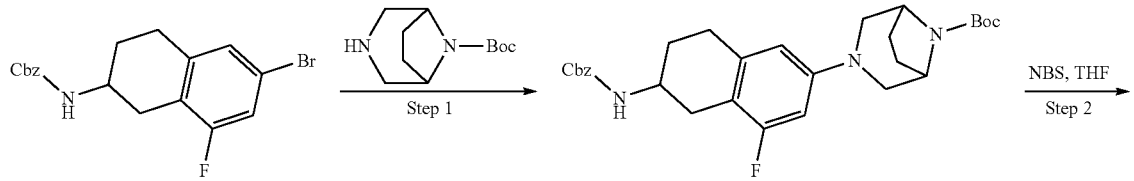

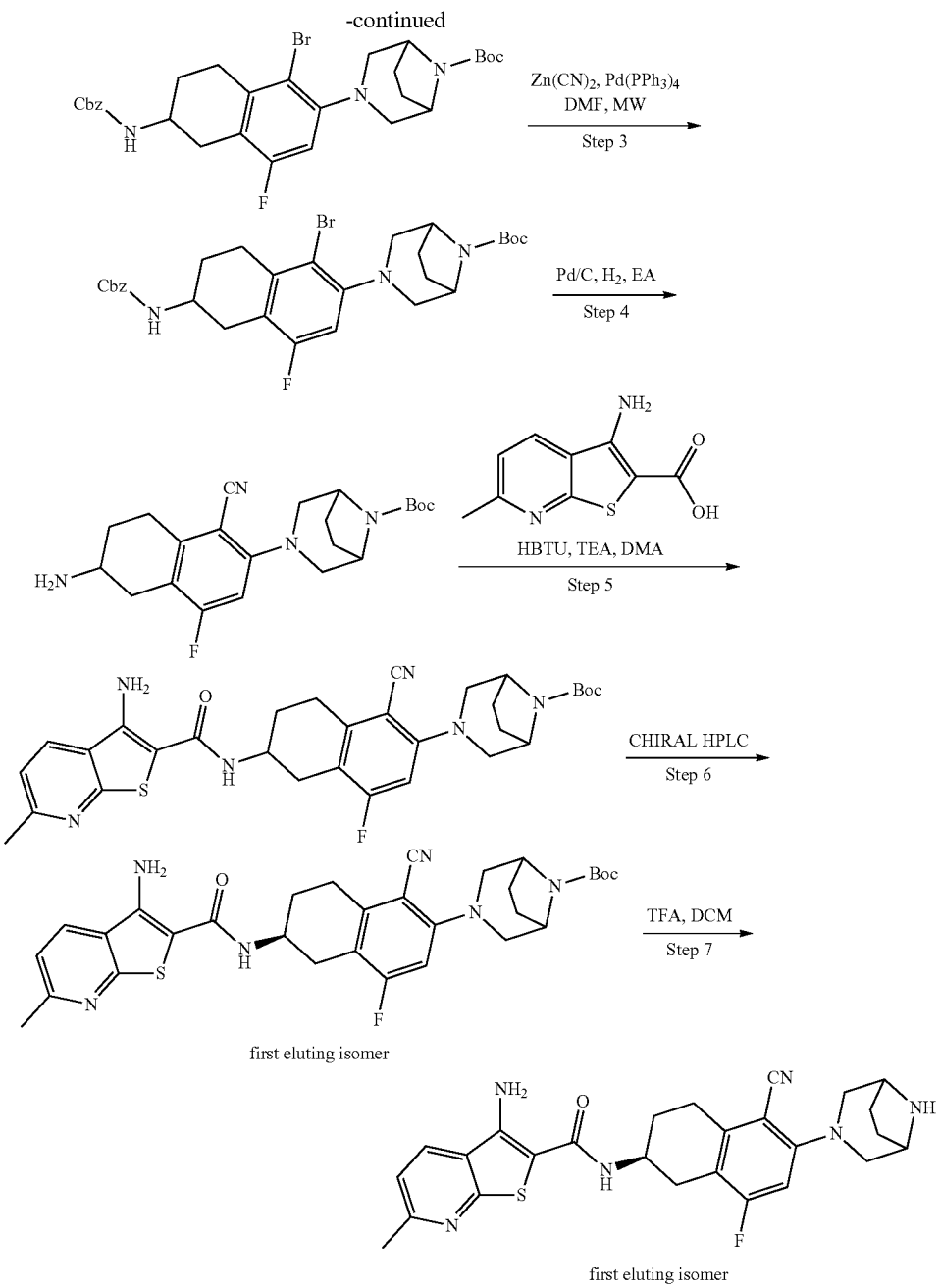

Step 1. Tert-butyl 3-(6-[[(benzyloxy)carbonyl]amino]-4-fluoro-5,6,7,8-tetrahydronaphthalen-2-yl)-3,8-diazabicyclo[3.2.1]octane-8-carboxylate A mixture of benzyl N-(6-bromo-8-fluoro-1,2,3,4-tetrahydronaphthalen-2-yl)carbamate (500 mg, 1.32 mmol), tert-butyl 3,8-diazabicyclo[3.2.1]octane-8-carboxylate (337 mg, 1.59 mmol), RuPhos (124 mg, 0.270 mmol), 3rd Generation RuPhos precatalyst (110 mg, 0.130 mmol) and $Cs_2CO_3$ (1.30 g, 3.99 mmol) in toluene (10 mL) was stirred for 3 h at 100° C. (3 batches in parallel). After cooled to room temperature (20° C.), the mixture solution of 3 batches was combined. The solids were filtered out. The filtrate was concentrated under vacuum. The residue was purified by silica gel column chromatography (eluting with 1:3 ethyl acetate/petroleum ether) to give tert-butyl 3-(6-[[(benzyloxy)carbonyl]amino]-4-fluoro-5,6,7,8-tetrahydronaphthalen-2-yl)-3,8-diazabicyclo[3.2.1]octane-8-carboxylate as a light yellow solid (1.35 g, 67%). LCMS (ES, m/z): 510[M+H]$^+$.

Step 2. Tert-butyl 3-(6-[[(benzyloxy)carbonyl]amino]-1-bromo-4-fluoro-5,6,7,8-tetrahydronaphthalen-2-yl)-3,8-diazabicyclo[3.2.1]octane-8-carboxylate Into a solution of tert-butyl 3-(6-[[(benzyloxy)carbonyl]amino]-4-fluoro-5,6,7,8-tetrahydronaphthalen-2-yl)-3,8-diazabicyclo[3.2.1]octane-8-carboxylate (1.10 μg, 2.16 μmmol) in tetrahydrofuran (50 mL) was added NBS (460 mg, 2.58 mmol) at −10° C. The resulting solution was stirred for 2 h at –10° C. under no light conditions. The reaction was then poured into water (50 mL). The solvent was removed under vacuum. The aqueous layer was extracted with dichloromethane (3×50 mL). The organic layers were combined, dried over anhydrous sodium sulfate, filtered and concentrated under vacuum. The residue was purified by silica gel column chromatography (eluting with 1/2 ethyl acetate/petroleum ether) to give tert-butyl 3-(6-[[(benzyloxy)carbonyl]amino]-1-bromo-4-fluoro-5,6,7,8-tetrahydronaphthalen-2-yl)-3,8-diazabicyclo[3.2.1]octane-8-carboxylate as a white solid (1.10 g, 82%). LCMS (ES, m/z): 588, 590[M+H]$^+$.

Step 3. Tert-butyl 3-(6-[[(benzyloxy)carbonyl]amino]-1-cyano-4-fluoro-5,6,7,8-tetrahydronaphthalen-2-yl)-3,8-diazabicyclo[3.2.1]octane-8-carboxylate A mixture of tert-butyl 3-(6-[[(benzyloxy)carbonyl]amino]-1-bromo-4-fluoro-5,6,7,8-tetrahydronaphthalen-2-yl)-3,8-diazabicyclo[3.2.1]octane-8-carboxylate (1.00 g, 1.70 mmol), Zn(CN)$_2$ (1.00 g, 8.51 mmol) and Pd(PPh$_3$)$_4$ (393 mg, 0.340 mmol) in NMP (20 mL) was irradiated with microwave for 2.5 h at 120° C. After cooled to room temperature (20° C.), the reaction was then poured into water (60 mL). The resulting mixture was extracted with dichloromethane (3×50 mL). The organic layers were combined, washed with water (50 mL), dried over anhydrous sodium sulfate, filtered and concentrated under vacuum. The residue was purified by silica gel column chromatography (eluting with 1/4 ethyl acetate/petroleum ether) to give tert-butyl 3-(6-[[(benzyloxy)carbonyl]amino]-1-cyano-4-fluoro-5,6,7,8-tetrahydronaphthalen-2-yl)-3,8-diazabicyclo[3.2.1]octane-8-carboxylate as a white solid (600 mg, 63%). LCMS (ES, m/z): 535[M+H]$^+$.

Step 4. Tert-butyl 3-(6-amino-1-cyano-4-fluoro-5,6,7,8-tetrahydronaphthalen-2-yl)-3,8-diazabicyclo[3.2.1]octane-8-carboxylate A mixture of tert-butyl 3-(6-[[(benzyloxy)carbonyl]amino]-1-cyano-4-fluoro-5,6,7,8-tetrahydronaphthalen-2-yl)-3,8-diazabicyclo[3.2.1]octane-8-carboxylate (400 mg, 0.750 mmol) and Palladium on carbon (400 mg, 10%) in ethyl acetate (20 mL) was stirred for 1 h at 20° C. under hydrogen atmosphere (balloon). The solid was filtered out. The filtrate was concentrated under vacuum to give tert-butyl 3-(6-amino-1-cyano-4-fluoro-5,6,7,8-tetrahydronaphthalen-2-yl)-3,8-diazabicyclo[3.2.1]octane-8-carboxylate as light yellow oil (200 mg, crude). LCMS (ES, m/z): 401[M+H]$^+$.

Step 5. Tert-butyl 3-(6-[3-amino-6-methylthieno[2,3-b]pyridine-2-amido]-1-cyano-4-fluoro-5,6,7,8-tetrahydronaphthalen-2-yl)-3,8-diazabicyclo[3.2.1]octane-8-carboxylate Into a solution of tert-butyl 3-(6-amino-1-cyano-4-fluoro-5,6,7,8-tetrahydronaphthalen-2-yl)-3,8-diazabicyclo[3.2.1]octane-8-carboxylate (75.0 mg, 0.190 mmol) and 3-amino-6-methylthieno[2,3-b]pyridine-2-carboxylic acid (47.0 mg, 0.220 mmol) in DMA (2.5 mL) was added TEA (0.092 mL, 0.660 mmol) and HBTU (107 mg, 0.280 mmol). The resulting solution was stirred for 3 h at 20° C. The residue was purified by reverse phase chromatography (Column: C18 silica gel; Mobile phase, A: water (containing 10 mmol/L NH$_4$HCO$_3$) and B: ACN (0% to 70% in 30 min); Flow rate: 60 mL/min; Detector: UV 254/220 nm) to give tert-butyl 3-(6-[3-amino-6-methylthieno[2,3-b]pyridine-2-amido]-1-cyano-4-fluoro-5,6,7,8-tetrahydronaphthalen-2-yl)-3,8-diazabicyclo[3.2.1]octane-8-carboxylate as a yellow solid (80.0 mg, 72%). LCMS (ES, m/z): 591[M+H]$^+$.

Step 6. Tert-butyl 3-((S)-6-(3-amino-6-methylthieno[2,3-b]pyridine-2-carboxamido)-1-cyano-4-fluoro-5,6,7,8-tetrahydronaphthalen-2-yl)-3,8-diazabicyclo[3.2.1]octane-8-carboxylate Tert-butyl 3-(6-[3-amino-6-methylthieno[2,3-b]pyridine-2-amido]-1-cyano-4-fluoro-5,6,7,8-tetrahydronaphthalen-2-yl)-3,8-diazabicyclo[3.2.1]octane-8-carboxylate (80.0 mg, 0.135 mmol) was separated via Chiral-HPLC(Column: CHIRALPAK IC, 2×25 cm, 5 um; Mobile Phase, A: MTBE and B: EtOH (hold 15% in 13 min); Flow rate: 20 mL/min; Detector: 220 nm). The first eluting isomer (RT$_1$=6.944 min) was collected and concentrated under vacuum to give a white solid whose stereochemistry was arbitrarily assigned as tert-butyl 3-((S)-6-(3-amino-6-methylthieno[2,3-b]pyridine-2-carboxamido)-1-cyano-4-fluoro-5,6,7,8-tetrahydronaphthalen-2-yl)-3,8-diazabicyclo[3.2.1]octane-8-carboxylate. The second eluting isomer (RT$_2$=8.717 min) was collected and concentrated under vacuum to give a white solid whose stereochemistry was arbitrarily assigned as tert-butyl 3-((R)-6-(3-amino-6-methylthieno[2,3-b]pyridine-2-carboxamido)-1-cyano-4-fluoro-5,6,7,8-tetrahydronaphthalen-2-yl)-3,8-diazabicyclo[3.2.1]octane-8-carboxylate. LCMS (ES, m/z): 591[M+H]$^+$.

Step 7. 3-Amino-N-[(2S)-5-cyano-6-[3,8-diazabicyclo[3.2.1]octan-3-yl]-8-fluoro-1,2,3,4-tetrahydronaphthalen-2-yl]-6-methylthieno[2,3-b]pyridine-2-carboxamide A solution of tert-butyl 3-[(6S)-6-[3-amino-6-methylthieno[2,3-b]pyridine-2-amido]-1-cyano-4-fluoro-5,6,7,8-tetahydronaphthalen-2-yl]-3,8-diazabicyclo[3.2.1]octane-8-carboxylate (35.0 mg, 0.060 mmol) and TFA (1 mL) in dichloromethane (3 mL) was stirred for 20 min at 20° C. The resulting solution was concentrated under vacuum. The residue was treated with 2 mL of a solution of NH$_3$ (7 M) in MeOH. The resulting solution was stirred for 30 min at 26° C., and then concentrated under vacuum. The residue was purified via Prep-HPLC (Column: XBridge Shield RP18 OBD Column, 5 µm, 19×150 mm; Mobile Phase, A: water (10 mmol/L NH$_4$HCO$_3$) and B: ACN (30% to 60% in 7 min); Flow rate: 20 mL/min; Detector: 220 nm). The collected fraction was lyophilized to give 3-amino-N-[(2S)-5-cyano-6-[3,8-diazabicyclo[3.2.1]octan-3-yl]-8-fluoro-1,2,3,4-tetrahydronaphthalen-2-yl]-6-methylthieno[2,3-b]pyridine-2-carboxamide as a white solid (10.0 mg, 34%). $^1$H-NMR (DMSO-d$_6$, 300 MHz) δ (ppm): 8.30 (d, J=8.1 Hz, 1H), 7.66 (d, J=7.5 Hz, 1H), 7.31 (d, J=8.1 Hz, 1H), 7.18 (br s, 2H), 6.78 (d, J=12.0 Hz, 1H), 4.15-4.14 (m, 1H), 3.44-3.42 (m, 2H), 3.33-3.25 (m, 2H), 3.05-2.82 (m, 5H), 2.61-2.55 (m, 4H), 2.07-2.03 (m, 1H), 1.94-1.75 (m, 3H), 1.66-1.63 (m, 2H). LCMS (ES, m/z): 491[M+H]$^+$.

Example 603. 3-Amino-N-[(2S)-6-[3,8-diazabicyclo [3.2.1] octan-3-yl]-5,8-difluoro-1,2,3,4-tetrahydronaphthalen-2-yl]-6-methylthieno[2,3-b]pyridine-2-carboxamide mL) and the organic layers were combined, dried over anhydrous sodium sulfate, filtered and concentrated under vacuum. The residue was purified by silica gel chromatography (eluting with 1:3 ethyl acetate/petroleum ether) to give

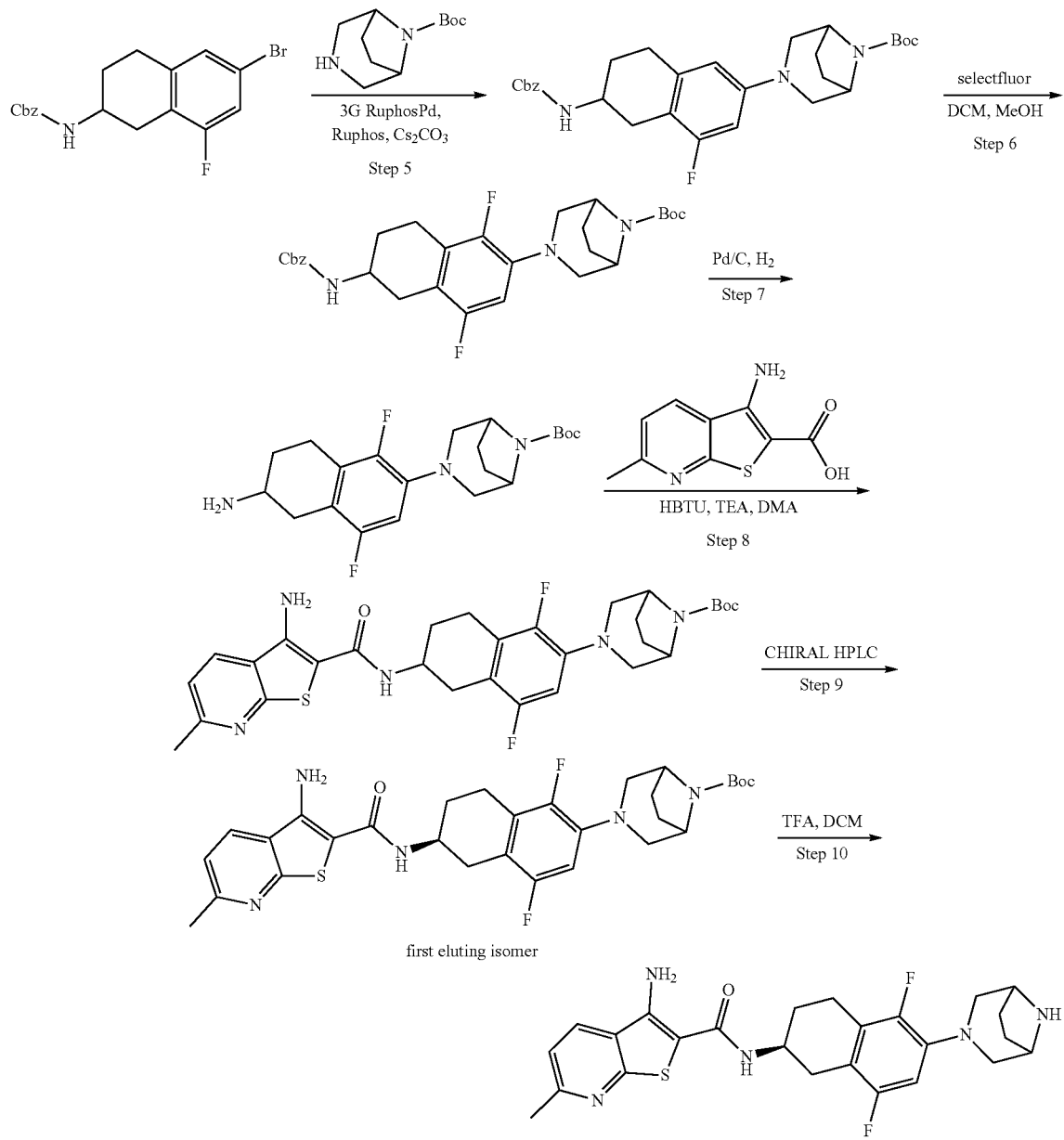

first eluting isomer

Step 5. Tert-butyl 3-(6-(((benzyloxy)carbonyl)amino)-4-fluoro-5,6,7,8-tetrahydronaphthalen-2-yl)-3,8-diazabicyclo[3.2.1]octane-8-carboxylate A mixture of benzyl N-(6-bromo-8-fluoro-1,2,3,4-tetrahydronaphthalen-2-yl)carbamate (1.50 g, 3.97 mmol), tert-butyl 3,8-diazabicyclo[3.2.1]octane-8-carboxylate (1.01 g, 4.78 mmol), toluene (30 mL), Cs2CO3 (3.90 g, 12.0 mmol), RuPhos (342 mg, 0.81 mmol), 3rd Generation RuPhos precatalyst (330 mg, 0.39 mmol) was stirred for 3 h at 100° C. in an oil bath. After cooling to 25° C., the reaction was then quenched by the addition of water (50 mL). The resulting mixture was extracted with dichloromethane (2×50 mL) tert-butyl 3-(6-[[(benzyloxy)carbonyl]amino]-4-fluoro-5,6,7,8-tetrahydronaphthalen-2-yl)-3,8-diazabicyclo[3.2.1]octane-8-carboxylate as a light yellow solid (1.35 g, 67%). LCMS: (ES, m/z): 510 [M+H]$^+$.

Step 6. Tert-butyl 3-(6-[[(benzyloxy)carbonyl]amino]-1,4-difluoro-5,6,7,8-tetrahydronaphthalen-2-yl)-3,8-diazabicyclo[3.2.1]octane-8-carboxylate Selectfluor (521 mg, 1.47 mmol) was added dropwise to a stirring solution of tert-butyl 3-(6-[[(benzyloxy)carbonyl]amino]-4-fluoro-5,6,7,8-tetrahydronaphthalen-2-yl)-3,8-diazabicyclo[3.2.1]octane-8-carboxylate (500 mg, 0.980 mmol) in a mixture of methanol (25 mL) and dichloromethane (25 mL) at −20° C. The resulting solution was then stirred for 10 h at 25° C. The resulting mixture was concentrated under vacuum. The residue was purified by silica gel chromatography (eluting with 3:17 ethyl acetate/petroleum ether) to give tert-butyl 3-(6-[[(benzyloxy)carbonyl]amino]-1,4-difluoro-5,6,7,8-tetrahydronaphthalen-2-yl)-3,8-diazabicyclo[3.2.1]octane-8-carboxylate as a white solid (180 mg, 35%). LCMS (ES, m/z): 528 [M+H]$^+$.

Step 7. Tert-butyl 3-(6-amino-1,4-difluoro-5,6,7,8-tetrahydronaphthalen-2-yl)-3,8-diazabicyclo[3.2.1]octane-8-carboxylate A mixture of tert-butyl 3-(6-[[(benzyloxy)carbonyl]amino]-1,4-difluoro-5,6,7,8-tetrahydronaphthalen-2-yl)-3,8-diazabicyclo[3.2.1]octane-8-carboxylate (150 mg, 0.28 mmol), Palladium on carbon (110 mg, 10%) and ethyl acetate (8 mL) was stirred for 1 h at 25° C. perature under hydrogen atmosphere. The solids were filtered out. The filtrate was concentrated under vacuum to give tert-butyl 3-(6-amino-1,4-difluoro-5,6,7,8-tetrahydronaphthalen-2-yl)-3,8-diazabicyclo[3.2.1]octane-8-carboxylate as yellow oil (100 mg, 89%). LCMS (ES, mi): 394 [M+H]$^+$.

Step 8. Tert-butyl 3-(6-[3-amino-6-methylthieno[2,3-b]pyridine-2-amido]-1,4-difluoro-5,6,7,8-tetrahydronaphthalen-2-yl)-3,8-diazabicyclo[3.2.1]octane-8-carboxylate A solution of tert-butyl 3-(6-amino-1,4-difluoro-5,6,7,8-tetrahydronaphthalen-2-yl)-3,8-diazabicyclo[3.2.1]octane-8-carboxylate (100 mg, 0.250 mmol), 3-amino-6-methylthieno[2,3-b] pyridine-2-carboxylic acid (56.0 mg, 0.270 mmol), TEA (0.1 mL, 0.76 mmol), HBTU (106 mg, 0.28 mmol) in DMA (3 mL) was stirred for 2 h at 25° C. The mixture was purified by reversed phase chromatography (Column, C18 silica gel; Mobile phase, A: H$_2$O (containing 0.5% TFA) and B: ACN (0 to 100% within 40 min); Detector, UV 220 nm). The collected fraction was concentrated under vacuum to give tert-butyl 3-(6-[3-amino-6-methylthieno[2,3-b]pyridine-2-amido]-1,4-difluoro-5,6,7,8-tetrahydronaphthalen-2-yl)-3,8-diazabicyclo[3.2.1]octane-8-carboxylate as a yellow solid (100 mg, 67%). LCMS (ES, m/z): 584 [M+H]$^+$.

Step 9. Tert-butyl 3-[(6S)-6-[3-amino-6-methylthieno[2,3-b]pyridine-2-amido]-1,4-difluoro-5,6,7,8-tetrahydronaphthalen-2-yl]-3,8-diazabicyclo[3.2.1]octane-8-carboxylate and tert-butyl 3-[(6R)-6-[3-amino-6-methylthieno[2,3-b]pyridine-2-amido]-1,4-difluoro-5,6,7,8-tetrahydronaphthalen-2-yl]-3,8-diazabicyclo[3.2.1]octane-8-carboxylate Tert-butyl 3-(6-[3-amino-6-methylthieno[2,3-b]pyridine-2-amido]-1,4-difluoro-5,6,7,8-tetrahydronaphthalen-2-yl)-3,8-diazabicyclo[3.2.1]octane-8-carboxylate (80.0 mg, 0.137 mmol) was separated by Chiral-Prep-HPLC (Column: CHIRAL ART Cellulose-SB, 2×25 cm, 5 um; Mobile Phase A: MTBE, Mobile Phase B: EtOH (hold 10% B in 10 min); Flow rate: 20 mL/min; Detector: 254/220 nm; RT$_1$: 7.015 min; RT$_2$: 8.508 min). The first eluting isomer (RT$_1$=7.015 min) was concentrated under vacuum to give a yellow oil whose stereochemistry was arbitrarily assigned as tert-butyl 3-[(6S)-6-[3-amino-6-methylthieno[2,3-b]pyridine-2-amido]-1,4-difluoro-5,6,7,8-tetrahydronaphthalen-2-yl]-3,8-diazabicyclo[3.2.1]octane-8-carboxylate. And the second eluting isomer (RT$_2$=8.508 min) was concentrated under vacuum to give a yellow oil whose stereochemistry was arbitrarily assigned as tert-butyl 3-[(6R)-6-[3-amino-6-methylthieno[2,3-b] pyridine-2-amido]-1,4-difluoro-5,6,7,8-tetrahydronaphthalen-2-yl]-3,8-diazabicyclo[3.2.1]octane-8-carboxylate. LCMS (ES, m/z): 584 [M+H]$^-$.

Step 10. 3-Amino-N-[(2S)-6-[3,8-diazabicyclo[3.2.1]octan-3-yl]-5,8-difluoro-1,2,3,4-tetrahydronaphthalen-2-yl]-6-methylthieno[2,3-b]pyridine-2-carboxamide A solution of tert-butyl 3-[(6S)-6-[3-amino-6-methylthieno[2,3-b]pyridine-2-amido]-1,4-difluoro-5,6,7,8-tetrahydronaphthalen-2-yl]-3,8-diazabicyclo[3.2.1]octane-8-carboxylate (35.0 mg, 0.060 mmol), trifluoroacetic acid (1 mL) in dichloromethane (3 mL). The resulting solution was stirred for 1 h at 25° C. The resulting mixture was concentrated under vacuum. The residue was purified by Prep-HPLC (Column, XBridge Prep C18 OBD Column, 19×150 mm 5 um; Mobile phase, A: water (containing 0.05% NH$_4$HCO$_3$) and B: ACN (25% to 50% in 12 min); Detector, UV 220 nm). The product fraction was concentrated and lyophilized to give 3-amino-N-[(2S)-6-[3,8-diazabicyclo[3.2.1]octan-3-yl]-5,8-difluoro-1,2,3,4-tetrahydronaphthalen-2-yl]-6-methylthieno[2,3-b]pyridine-2-carboxamide as an off-white solid (19.1 mg, 66%). LCMS (ES, m/z): 484 [M+H]$^+$. $^1$H-NMR (DMSO-d$_6$, 400 MHz) S (ppm): 8.30 (d, J=8.4 Hz, 1H), 7.63 (d, J=7.6 Hz, 1H), 7.31 (d, J=8.0 Hz, 1H), 7.17 (br s, 2H), 6.61-6.57 (m, 1H), 4.09-4.07 (m, 1H), 3.40-3.98 (m, 2H), 3.08-3.03 (m, 2H), 2.95-2.62 (m, 5H), 2.59-2.57 (m, 4H), 2.37-2.30 (m, 1H), 2.02-1.99 (m, 1H), 1.80-1.61 (m, 5H).

Step 1. Cis-tert-butyl 1-[(3R)-3-[[(benzyloxy)carbonyl]amino]-5-fluoro-3,4-dihydro-2H-1-benzopyran-7-yl]-octahydropyrrolo[2,3-c]pyrrole-5-carboxylate A solution of benzyl N-[(3R)-7-bromo-5-fluoro-3,4-dihydro-2H-1-benzopyran-3-yl]carbamate (1.00 g, 2.53 mmol), tert-butyl octahydropyrrolo[2,3-c]pyrrole-5-carboxylate (614 mg, 2.78 mmol), BTMG (1.73 g, 10.100 mmol), 3rd Generation t-BuXPhos precatalyst (602 mg, 0.757 mmol) and cis-tert-butyl hexahydropyrrolo[3,4-b]pyrrole-5(1H)-carboxylate (644 mg, 3.04 mmol) in DMSO (30 mL) was stirred for 1 h at 25° C. The reaction was then quenched by the addition of water (30 mL). The resulting mixture was extracted with ethyl acetate (3×30 mL). The organic layers were combined, washed with brine (2×100 mL), dried over anhydrous sodium sulfate, filtered and concentrated under vacuum. The residue was purified by a silica gel chromatography (eluting with 1:2 ethyl acetate/petroleum ether) to afford cis-tert-butyl 1-[(3R)-3-[[(benzyloxy)carbonyl]amino]-5-fluoro-3,4-dihydro-2H-1-benzopyran-7-yl]-octahydropyrrolo[2,3-c]pyrrole-5-carboxylate as a yellow solid (1.00 g, 74%). LCMS (ES, m/z): 512 [M+H]$^+$.

Step 2. Cis-tert-butyl 1-[(3R)-3-amino-5-fluoro-3,4-dihydro-2H-1-benzopyran-7-yl]-octahydropyrrolo[2,3-c]pyrrole-5-carboxylate A mixture of cis-tert-butyl 1-[(3R)-3-[[(benzyloxy)carbonyl]amino]-5-fluoro-3,4-dihydro-2H-1-benzopyran-7-yl]-octahydropyrrolo[2,3-c]pyrrole-5-carboxylate (1.00 g, 1.88 mmol) and Palladium on carbon (1.10 g, 10%) in ethyl acetate (30 mL) was stirred for 2 h at 25° C. under hydrogen atmosphere. The solids were filtered out and the filtrate was concentrated under vacuum afford cis-tert-butyl 1-[(3R)-3-amino-5-fluoro-3,4-dihydro-2H-1-benzopyran-7-yl]-octahydropyrrolo[2,3-c]pyrrole-5-carboxylate as a light yellow solid (750 mg, crude). LCMS (ES, m/z): 378 [M+H]+.

Step 3. Cis-tert-butyl 1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate A solution of cis-tert-butyl 1-[(3R)-3-amino-5-fluoro-3,4-dihydro-2H-1-benzopyran-7-yl]-octahydropyrrolo[2,3-c]pyrrole-5-carboxylate (720 mg, 1.72 mmol), 3-amino-6-methylthieno[2,3-b]pyridine-2-carboxylic acid (357 mg, 1.72 mmol), HBTU (1.02 g, 2.58 mmol) and TEA (0.953 mL, 6.87 mmol) in DMA (5 μmL) was stirred for 1 h at 25° C. The mixture was purified by reverse phase chromatography (Column: C18 silica gel; Mobile phase, A: water (containing 10 mmol/L NH4HCO3) and B: ACN (5% to 80% in 30 min); Detector: UV 254/220 nm). The collected fraction was concentrated to give cis-tert-butyl 1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate as a light yellow solid(700 mg, 69%). LCMS (ES, m/z): 568 [M+H]+.

Step 4. Tert-butyl (3aR,6aR)-1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate and tert-butyl (3aS,6aS)-1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate Cis-tert-butyl 1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate (700 mg, 1.18 mmol) was separated via Chiral-Prep-HPLC (Column: Chiralpak IC, 2×25 cm, 5 um; Mobile Phase, A: MTBE (containing 10 mM NH3-MeOH) and B: EtOH (hold 30% in 12 min); Flow rate: 20 mL/min; Detector: 254/220 nm; RT1: 6.456 min; RT2: 9.216 min. The first eluting isomer (RT1: 6.456 min) was collected and concentrated to afford a light yellow solid whose stereochemistry was arbitrarily assigned as tert-butyl (3aS,6aS)-1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate and the second eluting isomer (RT2: 9.216 min) was collected and concentrated to afford a light yellow solid whose stereochemistry was arbitrarily assigned as tert-butyl (3aR,6aR)-1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate. LCMS (ES, m/z): 568 [M+H]+.

Step 5. 3-Amino-N-((R)-5-fluoro-7-((3aS,6aS)-hexahydropyrrolo[3,4-b]pyrrol-1(2H)-yl)chroman-3-yl)-6-methylthieno[2,3-b]pyridine-2-carboxamide A solution of tert-butyl (3aS,6aS)-1-[(3R)-3-[3-amino-6-methylthieno[2,3-b]pyridine-2-amido]-5-fluoro-3,4-dihydro-2H-1-benzopyran-7-yl]-octahydropyrrolo[2,3-c]pyrrole-5-carboxylate (250 mg, 0.418 mmol) and trifluoroacetic acid (5 mL) in dichloromethane (6 mL) was stirred for 30 min at 25° C. The resulting solution was concentrated under vacuum. The residue was dissolved in a solution of NH3 (10 mL, 7M in methanol). The resulting solution was stirred for 30 min at 25° C. and concentrated under vacuum. The residue was purified by Prep-HPLC (Column, XBridge Prep C18 OBD Column, 19×150 mm 5 μm; Mobile phase, A: water (containing 10 mmol/L NH4HCO3) and B: ACN (20% up to 50% in 7 min); Detector, UV 254/220 nm). The collected fraction was lyophilized to give N-[(3R)-7-[(3aS,6aS)-octahydropyrrolo[2,3-c]pyrrol-1-yl]-5-fluoro-3,4-dihydro-2H-1-benzopyran-3-yl]-3-amino-6-methylthieno[2,3-b]pyridine-2-carboxamide as a light yellow solid (95.0 mg, 48%). 1H-NMR (DMSO-d6, 400 MHz) δ (ppm): 8.33 (d, J=8.4 Hz, 1H), 7.57 (br s, 1H), 7.32 (d, J=8.4 Hz, 1H), 7.23 (br s, 2H), 5.99 (d, J=11.2 Hz, 1H), 5.81 (s, 1H), 4.31-4.24 (m, 1H), 4.18-4.15 (m, 1H), 3.89-3.81 (m, 2H), 3.43-3.41 (m, 1H), 3.11-3.05 (m, 1H), 2.88-2.63 (m, 7H), 2.59 (s, 3H), 2.05-2.01 (m, 1H), 1.76-1.71 (m, 1H). LCMS (ES, m/z): 468 [M+H]+.

Example 606. 5-chloro-N-[(3R)-8-cyano-7-[3,8-diazabicyclo[3.2.1]octan-3-yl]-5-fluoro-3,4-dihydro-2H-1-benzopyran-3-yl]-7-ethyl-7H-pyrrolo[2,3-c]pyridazine-3-carboxamide

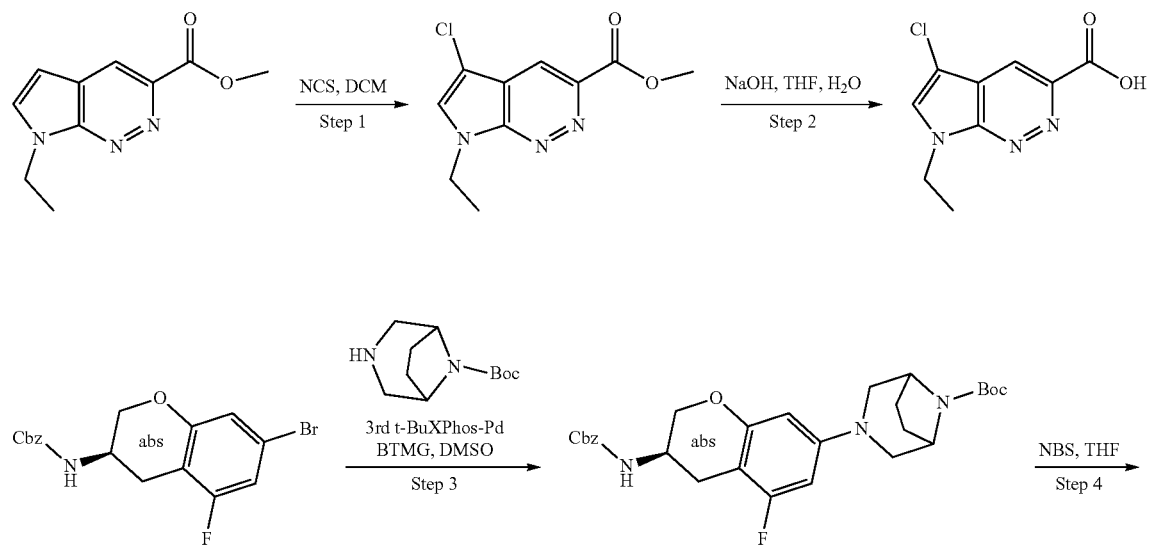

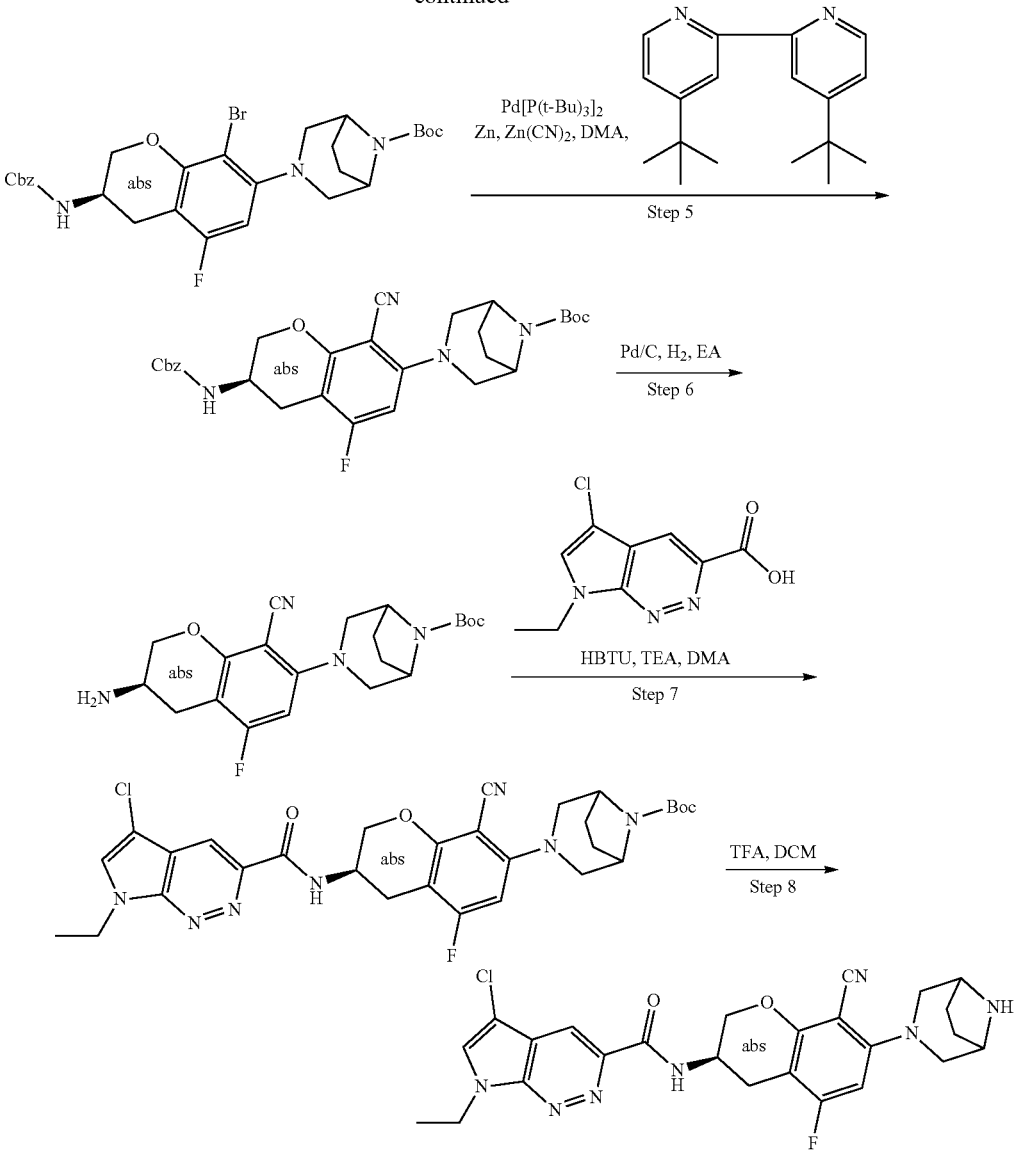

Step 1. 5-chloro-7-ethyl-7H-pyrrolo[2,3-c]pyridazine-3-carboxylate

A solution of methyl 7-ethyl-7H-pyrrolo[2,3-c]pyridazine-3-carboxylate(1.20 g, 5.84 mmol) and NCS (3.12 g, 23.3 mmol) in DCM (30 mL) was stirred for 18 h at 25° C. The resulting solution was diluted with water (50 ml), extracted with DCM (3×30 mL), dried over anhydrous sodium sulfate, filtered and concentrated under vacuum. The residue was purified by silica gel chromatography (eluting with 1:10 MeOH/DCM) to give methyl 5-chloro-7-ethyl-7H-pyrrolo[2,3-c]pyridazine-3-carboxylate as a yellow solid (1.30 g, 88%). LCMS (ES, m/z): 240, 242 [M+H]$^+$.

Step 2. 5-chloro-7-ethyl-7H-pyrrolo[2,3-c]pyridazine-3-carboxylic acid

NaOH (1.08 g, 27.1 mmol) was added to a solution of methyl 5-chloro-7-ethyl-7H-pyrrolo[2,3-c]pyridazine-3-carboxylate (1.30 g, 5.42 mmol) in THF (20 mL) and H$_2$O (20 mL) at <10° C. The resulting solution was stirred for 16 h at 25° C. The THF was concentrated under vacuum. The residue was diluted with water (20 mL). The pH value of the solution was adjusted to 6 with HCl (1 M) and the mixture was concentrated under vacuum. The residue was purified by reverse phase chromatography (Column: C18 silica gel; Mobile phase, A: water (containing 0.05% TFA) and B: ACN (5% B to 80% B in 30 min); Detector: UV 254/220 nm) to afford 5-chloro-7-ethyl-7H-pyrrolo[2,3-c]pyridazine-3-carboxylic acid as a yellow solid (440 mg, 34%).LCMS (ES, m/%): 256, 258 [M+H]$^+$.

Step 3. Tert-butyl 3-[(3R)-3-[[(benzyloxy)carbonyl]amino]-5-fluoro-3,4-dihydro-2H-1-benzopyran-7-yl]-3,8-diazabicyclo[3.2.1]octane-8-carboxylate A solution of BTMG (362 mg, 2.10 mmol) in DMSO (2 mL) was added into a solution of benzyl N-[(3R)-7-bromo-5-fluoro-3,4-dihydro-2H-1-benzopyran-3-yl]carbamate (500 mg, 1.05 mmol), tert-butyl 3,8-diazabicyclo[3.2.1]octane-8-carboxylate (336 mg, 1.57 mmol) and 3rd Generation t-BuXPhos precatalyst (84.0 mg, 0.105 mmol) in DMSO (8 mL). The resulting solution was stirred for 2 h at 20° C. The reaction was quenched with water (20 mL). The resulting mixture was extracted with ethyl acetate (3×30 mL). The organic layers were combined, washed with water (3×45 mL), dried over anhydrous sodium sulfate, filtered and concentrated under vacuum. The residue was purified by silica gel chromatography (eluting with 1:3 ethyl acetate/petroleum ether) to afford tert-butyl 3-[(3R)-3-[[(benzyloxy)carbonyl]amino]-5-fluoro-3,4-dihydro-2H-1-benzopyran-7-yl]-3,8-diazabicyclo[3.2.1]octane-8-carboxylate as a yellow solid (460 mg, 81%). LCMS (ES, m/z): 512 [M+H]$^+$.

Step 4. Tert-butyl 3-[(3R)-3-[[(benzyloxy)carbonyl]amino]-8-bromo-5-fluoro-3,4-dihydro-2H-1-benzopyran-7-yl]-3,8-diazabicyclo[30.2.1]octane-8-carboxylate NBS (160 mg, 0.899 mmol) was added to a solution of tert-butyl 3-[(3R)-3-[[(benzyloxy)carbonyl]amino]-5-fluoro-3,4-dihydro-2H-1-benzopyran-7-yl]-3,8-diazabicyclo[3.2.1]octane-8-carboxylate (460 mg, 0.899 mmol) in THF (20 mL) at 0° C. in darkness. The resulting solution was stirred for 2 h at 0° C. The reaction was then quenched by the addition of water (20 mL). The resulting mixture was extracted with EA (3×30 mL). The organic layers were combined, dried over anhydrous sodium sulfate, filtered and concentrated under vacuum. The residue was purified via a silica gel chromatography (eluting with 1:3 ethyl acetate/petroleum ether) to give tert-butyl 3-[(3R)-3-[[(benzyloxy)carbonyl]amino]-8-bromo-5-fluoro-3,4-dihydro-2H-1-benzopyran-7-yl]-3,8-diazabicyclo[3.2.1]octane-8-carboxylate as an off-white solid (230 mg, 41%). LCMS (ES, m/z): 590, 592 [M+H]$^+$.

Step 5. Tert-butyl 3-[(3R)-3-[[(benzyloxy)carbonyl]amino]-8-cyano-5-fluoro-3,4-dihydro-2H-1-benzopyran-7-yl]-3,8-diazabicyclo[3.2.1]octane-8-carboxylate A mixture of tert-butyl 3-[(3R)-3-[[(benzyloxy)carbonyl]amino]-8-bromo-5-fluoro-3,4-dihydro-2H-1-benzopyran-7-yl] (230 mg, 0.390 mmol), 4-tert-butyl-2-(4-tert-butylpyridin-2-yl)pyridine (104 mg, 0.390 mmol), Pd(t-Bu$_3$P)$_2$ (99.5 mg, 0.195 mmol), Zn (50.9 mg, 0.779 mmol) and Zn(CN)$_2$ (457 mg, 3.89 mmol) in DMA (6 mL) was stirred for 1 h at 100° C. The mixture was allowed to cool down to 25° C. The solids were filtered out and the filtrate was concentrated under vacuum. The residue was purified by reverse phase chromatography (Column: C18 silica gel; Mobile phase, A: water (containing 0.05% TFA) and B: ACN (5% to 80% in 30 min); Detector: UV 254/220 nm) to afford tert-butyl 3-[(3R)-3-[[(benzyloxy)carbonyl]amino]-8-cyano-5-fluoro-3,4-dihydro-2H-1-benzopyran-7-yl]-3,8-diazabicyclo[3.2.1]octane-8-carboxylate as a white solid (155 mg, 70%). LCMS (ES, m/z): 537 [M+H]$^-$.

Step 6. Tert-butyl 3-[(3R)-3-amino-8-cyano-5-fluoro-3,4-dihydro-2H-1-benzopyran-7-yl]-3,8-diazabicyclo[3.2.1]octane-8-carboxylate A mixture of tert-butyl 3-[(3R)-3-[[(benzyloxy)carbonyl]amino]-8-bromo-5-fluoro-3,4-dihydro-2H-1-benzopyran-7-yl]-3,8-diazabicyclo[3.2.1]octane-8-carboxylate (155 mg, 0.289 mmol) and Pd/C (150 mg, 10%) in EA (15 mL) was stirred for 16 h at 24° C. under an atmosphere of hydrogen (balloon). The solids were filtered out. The filtrate concentrated under vacuum to give tert-butyl 3-[(3R)-3-amino-8-cyano-5-fluoro-3,4-dihydro-2H-1-benzopyran-7-yl]-3,8-diazabicyclo[3.2.1]octane-8-carboxylate as a colorless solid (110 mg, crude). LCMS (ES, m/z): 403 [M+H]$^+$.

Step 7. Tert-butyl 3-[(3R)-3-[5-chloro-7-ethyl-7H-pyrrolo[2,3-c]pyridazine-3-amido]-8-cyano-5-fluoro-3,4-dihydro-2H-1-benzopyran-7-yl]-3,8-diazabicyclo[3.2.1]octane-8-carboxylate HBTU (118 mg, 0.313 mmol) was added to a solution of tert-butyl 3-[(3R)-3-amino-8-cyano-5-fluoro-3,4-dihydro-2H-1-benzopyran-7-yl]-3,8-diazabicyclo[3.2.1]octane-8-carboxylate (105 mg, 0.261 mmol), 5-chloro-7-ethyl-7H-pyrrolo[2,3-c]pyridazine-3-carboxylic acid (70.6 mg, 0.313 mmol) and TEA (0.110 mL, 0.780 mmol) in DMA (4 mL). The resulting solution was stirred for 1 h at 25° C. The mixture was purified by reverse phase chromatography (Column: C18 silicagel; Mobile phase, A: water (containing 0.05% TFA) and B: ACN (5% to 80% in 30 min); Detector: UV 254/220 nm) to afford tert-butyl 3-[(3R)-3-[5-chloro-7-ethyl-7H-pyrrolo[2,3-c]pyridazine-3-amido]-8-cyano-5-fluoro-3,4-dihydro-2H-1-benzopyran-7-yl]-3,8-diazabicyclo[3.2.1]octane-8-carboxylate as a yellow solid (120 mg, 72%). LCMS (ES, m/z): 610,612 [M+H]$^+$.

Step 8. 5-Chloro-N-[(3R)-8-cyano-7-[3,8-diazabicyclo[3.2.1]octan-3-yl]-5-fluoro-3,4-dihydro-2H-1-benzopyran-3-yl]-7-ethyl-7H-pyrrolo[2,3-c]pyridazine-3-carboxamide A solution of tert-butyl 3-[(3R)-3-[5-chloro-7-ethyl-7H-pyrrolo[2,3-c]pyridazine-3-amido]-8-cyano-5-fluoro-3,4-dihydro-2H-1-benzopyran-7-yl]-3,8-diazabicyclo[3.2.1]octane-8-carboxylate (60.0 mg. 0.098 mmol) and TFA (1.00 mL) in DCM (3 mL) was stirred for 30 min at 25° C. The resulting mixture was concentrated under vacuum. A solution of NH$_3$ (2.00 mL, 7M in MeOH) was added to the residue. The resulting solution was stirred for 0.5 h and then concentrated under vacuum. The residue was purified by Prep-HPLC (Column: XBridge Prep C18 OBD Column, 19×150 mm 5 μm; Mobile phase, A: water (containing 10 mmol/L NH$_4$HCO$_3$) and B: ACN (23% to 38% in 8 min): Detector, UV 220/254 nm). The collected fraction was lyophilized to give 5-chloro-N-[(3R)-8-cyano-7-[3,8-diazabicyclo[3.2.1]octan-3-yl]-5-fluoro-3,4-dihydro-2H-1-benzopyran-3-yl]-7-ethyl-7H-pyrrolo[2,3-c]pyridazine-3-carboxamide as a white solid (19.8 mg, 39%). $^1$H-NMR (DMSO-d$_6$, 400 MHz) S (ppm): 9.19 (br s, 1H), 8.40 (s, 1H), 8.36 (s, 1H), 6.50 (d, J=9.6 Hz, 1H), 4.55-4.50 (m, 3H), 4.41-4.38 (m, 1H), 4.31-4.27 (m, 1H), 3.46-3.44 (m, 2H), 3.32-3.28 (m, 2H), 2.98-2.89 (m, 4H), 1.90-1.89 (m, 2H), 1.65-1.63 (m, 2H), 1.51-1.47 (m, 3H). LCMS (ES, m/z): 510,512 [M+H]$^+$.

Example 611-1. 3-amino-N-[(3R)-7-[(4S,5R)-4-amino-6-oxa-2-azaspiro[4.5]decan-2-yl]-3,4-dihydro-2H-1-benzopyran-3-yl]-6-methylthieno[2,3-b]pyridine-2-carboxamide
Example 611-2. 3-amino-N-[(3R)-7-[(4R,5S)-4-amino-6-oxa-2-azaspiro[4.5]decan-2-yl]-3,4-dihydro-2H-1-benzopyran-3-yl]-6-methylthieno[2,3-b]pyridine-2-carboxamide
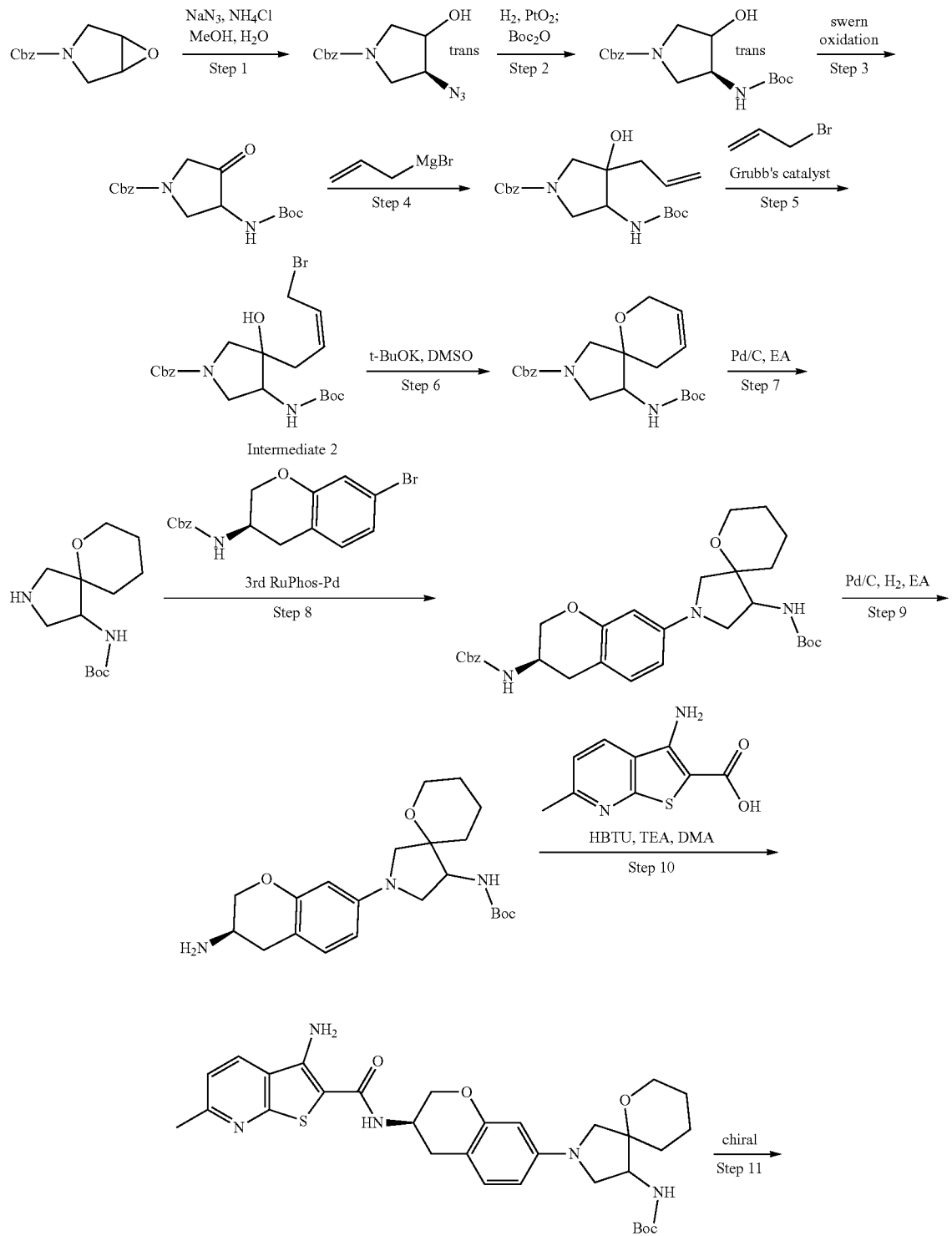

-continued

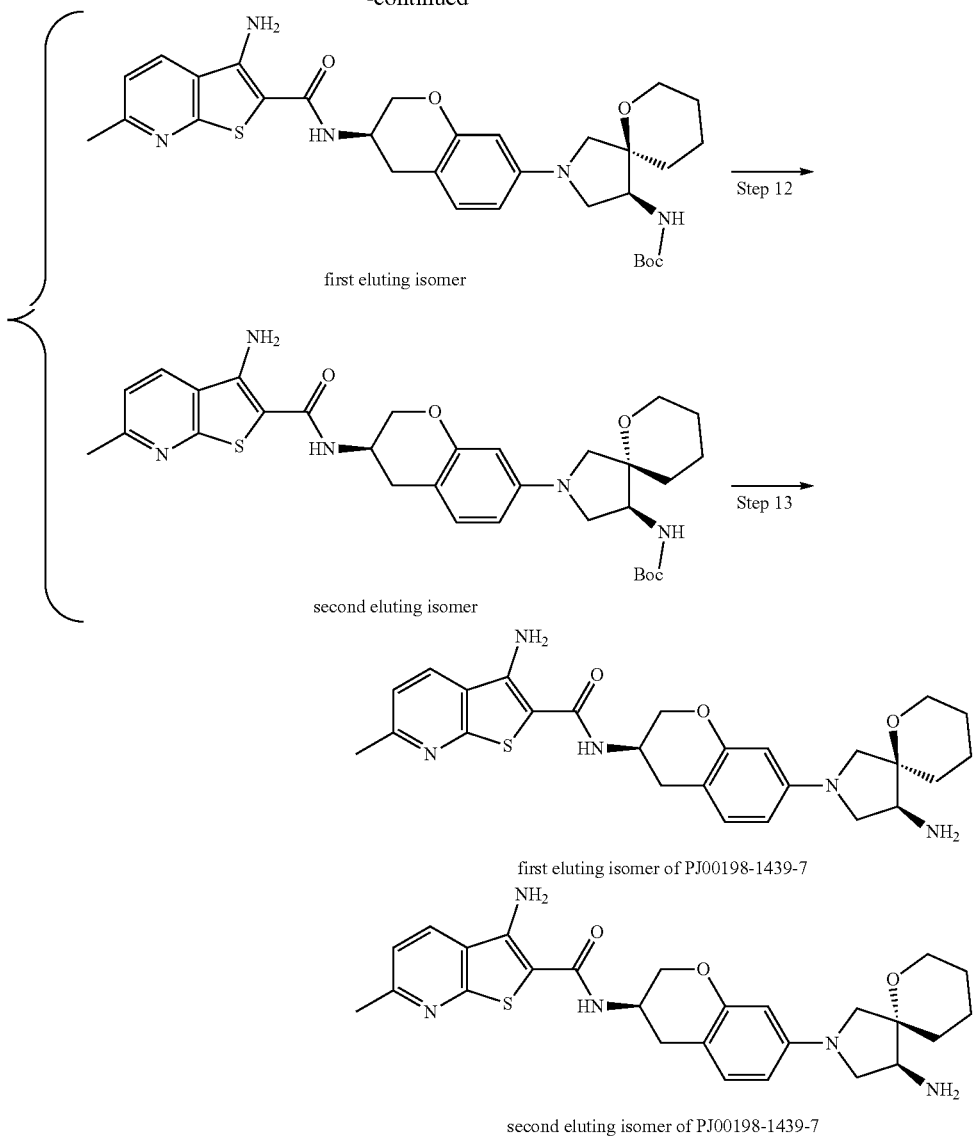

first eluting isomer second eluting isomer first eluting isomer of PJ00198-1439-7 second eluting isomer of PJ00198-1439-7

Step 11. Trans-benzyl 3-azido-4-hydroxypyrrolidine-1-carboxylate

A solution of NaN$_3$ (17.4 g, 267 mmol) in water (58 mL) was added to a solution of benzyl 6-oxa-3-azabicyclo[3.1.0]hexane-3-carboxylate (29.0 g, 133 mmol) and NH$_4$Cl (7.15 g, 134 mmol) in methanol (348 mL). The resulting solution was stirred for 16 h at 60° C. After cooling to 25° C., the pH value was adjusted to 7-8 with NaOH (1M). The resulting solution was then quenched by the addition of water (100 mL). The solvent was removed under vacuum and the residue was extracted with dichloromethane (2×150 mL). The organic layer was combined, dried over anhydrous sodium sulfate, filtered and concentrated under vacuum to give trans-benzyl 3-azido-4-hydroxypyrrolidine-1-carboxylate as light-yellow oil (35.0 g, crude). LCMS (ES, m/z): 263 [M+H]$^+$.

Step 2. Trans-benzyl 3-[[(tert-butoxy)carbonyl]amino]-4-hydroxypyrrolidine-1-carboxylate A mixture of trans-benzyl 3-azido-4-hydroxypyrrolidine-1-carboxylate (35.0 g, 133 mmol) and PtO$_2$ (10.0 g, 44.1 mmol) in ethyl acetate (2.00 L) was stirred for 16 h at 25° C. under hydrogen atmosphere (balloon). The solids were filtered out, and the filtrate was concentrated under vacuum to give trans-benzyl 3-amino-4-hydroxypyrrolidine-1-carboxylate as light yellow oil (30.0 g, crude). Trans-benzyl 3-amino-4-hydroxypyrrolidine-1-carboxylate (30.0 g, 127 mmol) was dissolved in THF (500 mL) and H$_2$O (500 mL). Then TEA (53.0 mL, 381 mmol) and (Boc)$_2$O (33.3 g, 152 mmol) was added under 5° C. The resulting solution was stirred for 16 h at 25° C. The solvent was removed under vacuum. The residue was extracted with ethyl acetate (3×300 mL). The organic layers were combined, dried over anhydrous sodium sulfate, filtered and concentrated under vacuum. The residue was washed with ethyl acetate/petroleum ether (1:10) to give trans-benzyl 3-[[(tert-butoxy)

carbonyl]amino]-4-hydroxypyrrolidine-1-carboxylate as while solid (35.0 g, 82%). LCMS (ES, m/z): 337 [M+H]⁻.

Step 3. Benzyl 3-[[(tert-butoxy)carbonyl]amino]-4-oxopyrrolidine-1-carboxylate

DMSO (15.0 mL, 339 mmol) was added to a solution of oxalic dichloride (7.55 mL, 89.2 mmol) in anhydrous THF (120 mL) at −78° C. After stirring for 15 minutes at −78° C., a solution of trans-benzyl 3-[[(tert-butoxy)carbonyl]amino]-4-hydroxypyrrolidine-1-carboxylate (30.0 g, 89.2 mmol) in anhydrous THF (600 mL) was added at −78° C., which was followed by the addition of TEA (37.2 mL, 268 mmol) at −78° C. The reaction was stirred for 30 minutes under −60° C. The reaction mixture was quenched with H₂O (50 mL). The organic layer was collected, and the aqueous phase was extracted with ethyl acetate (2×30 mL). The organics were combined, dried over anhydrous sodium sulfate, filtered, and concentrated. The residue was purified by silica gel chromatography (eluting with 1/10 ethyl acetate/petroleum ether) to give benzyl 3-[[(tert-butoxy)carbonyl]amino]-4-oxopyrrolidine-1-carboxylate as light yellow solid (21.0 g, 67%). LCMS (ES, m/z): 335[M+H]⁺.

Step 4. Benzyl 4-[[(tert-butoxy)carbonyl]amino]-3-hydroxy-3-(prop-2-en-1-yl)pyrrolidine-1-carboxylate Bromo(prop-2-en-1-yl)magnesium (59.8 mL, 1M in THF) was added to a solution of benzyl 3-[[(tert-butoxy)carbonyl]amino]-4-oxopyrrolidine-1-carboxylate (10.0 g, 29.9 mmol) in THF (100 mL) at −78° C. The resulting solution was stirred for 2 h at from −78° C. to 10° C. The resulting solution was quenched with water (100 mL), extracted with EA (3×100 mL). The combined organic layers were washed with brine (2×200 mL), dried over anhydrous sodium sulfate, filtered and concentrated under vacuum to give benzyl 4-[[(tert-butoxy)carbonyl]amino]-3-hydroxy-3-(prop-2-en-1-yl)pyrrolidine-1-carboxylate as light yellow oil (11.0 g, 87%). LCMS (ES, m/z): 377[M+H]⁺.

Step 5. Benzyl 3-[(2E)-4-bromobut-2-en-1-yl]-4-[[(tert-butoxy)carbonyl]amino]-3-hydroxypyrrolidine-1-carboxylate Grubbs 2nd (1.24 g, 1.46 mmol) was added to a solution of benzyl 4-[[(tert-butoxy)carbonyl]amino]-3-hydroxy-3-(prop-2-en-1-yl)pyrrolidine-1-carboxylate (11.0 g, 29.2 mmol) and 3-bromoprop-1-ene (14.1 g, 116 mmol) in DCM (200 mL). The resulting solution was stirred for 1 h at 25° C., and then was concentrated under vacuum. The residue was purified via reverse phase chromatography (Column: C18 silica gel; Mobile phase, A: water (containing 0.05% TFA) and B: CH₃CN(0% to 70% in 30 min); Detector: 220/254 μnm) to give benzyl 3-[(2E)-4-bromobut-2-en-1-yl]-4-[[(tert-butoxy)carbonyl]amino]-3-hydroxypyrrolidine-1-carboxylate as off-white solid (6.80 g, 47%). LCMS (ES, m/z): 469,471[M+H]⁺.

Step 6. Cis-benzyl 4-[[(tert-butoxy)carbonyl]amino]-6-oxa-2-azaspiro[4.5]dec-8-ene-2-carboxylate t-BuOK (20.8 mL, 1 M in THF) was added to a solution of benzyl 3-[(2Z)-4-bromobut-2-en-1-yl]-4-[[(tert-butoxy)carbonyl]amino]-3-hydroxypyrrolidine-1-carboxylate (4.90 g, 10.4 mmol) in DMSO (40.0 mL) at 25° C. The resulting solution was stirred for 1 h at 25° C. The reaction was quenched with ice/water (10 mL). The resulting solution was extracted with EA (3×50 mL). The organic layer was concentrated and then was purified via reverse phase chromatography (Column: C18 silica gel; Mobile phase, A: water (containing 0.5% TFA) and B: CH₃CN (0% to 70% in 45 min); Detector: 200/210 nm) to give cis-benzyl 4-[[(tert-butoxy)carbonyl]amino]-6-oxa-2-azaspiro[4.5]dec-8-ene-2-carboxylate as yellow oil (550 mg, 12%).(The configuration was assumed to be cis). LCMS (ES, m/z): 389[M+H]1.

Step 7. Cis-tert-butyl N-[6-oxa-2-azaspiro[4.5]decan-4-yl]carbamate

A mixture of cis-benzyl 4-[[(tert-butoxy)carbonyl] amino]-6-oxa-2-azaspiro[4.5]dec-8-ene-2-carboxylate (550 mg. 1.41 mmol) and Pd(OH)₂/C (300 mg, 20%) in MeOH (20 mL) was stirred for 2 h at 35° C. under hydrogen atmosphere (balloon). The solids were filtered out, and the filtrate was concentrated under vacuum to give cis-tert-butyl N-[6-oxa-2-azaspiro[4.5]decan-4-yl]carbamate as off-white oil (350 mg. 88%). LCMS (ES, m/z): 389[M+H]⁺.

Step 8. Cis-benzyl N-[(3R)-7-[4-[(tert-butoxycarbonyl)amino]-6-oxa-2-azaspiro[4.5]decan-2-yl]-3,4-dihydro-2H-1-benzopyran-3-yl]carbamate A mixture of benzyl N-[(3R)-7-bromo-3,4-dihydro-2H-1-benzopyran-3-yl]carbamate (200 mg, 0.552 mmol), cis-tert-butyl N-[6-oxa-2-azaspiro[4.5]decan-4-yl]carbamate (155 mg, 0.607 mmol), 3rd Generation RuPhos precatalyst (46.2 mg, 0.055 mmol), RuPhos (51.5 mg, 0.110 mmol) and Cs₂CO₃ (539 mg, 1.65 mmol) in toluene (10.0 mL) was stirred for 3 h at 95° C. The mixture was cooled. The solids were filtered out. The filtrate was concentrated under vacuum. The residue was purified by silica gel chromatography (eluting with 1:2 ethyl acetate/petroleum ether) to afford cis-benzyl N-[(3R)-7-[4-[(tert-butoxycarbonyl) amino]-6-oxa-2-azaspiro[4.5]decan-2-yl]-3,4-dihydro-2H-1-benzopyran-3-yl]carbamate as yellow solid (110 mg. 35%). LCMS (ES, m/z): 538[M+H]⁺.

Step 9. Cis-tert-butyl N-[2-[(3R)-3-amino-3,4-dihydro-2H-1-benzopyran-7-yl]-6-oxa-2-azaspiro[4.5]decan-4-yl]carbamate A mixture of cis-benzyl N-[(3R)-7-[4-[(tert-butoxycarbonyl)amino]-6-oxa-2-azaspiro[4.5]decan-2-yl]-3,4-dihydro-2H-1-benzopyran-3-yl]carbamate (110 mg, 0.205 mmol) and Pd/C (100 mg, 10%) in EA (10.0 mL) was stirred for 16 h at 25° C. under hydrogen atmosphere (balloon). The solids were filtered out. The filtrate was concentrated under vacuum to give cis-tert-butyl N-[2-[(3R)-3-amino-3,4-dihydro-2H-1-benzopyran-7-yl]-6-oxa-2-azaspiro[40.5]decan-4-yl]carbamate as a white solid (70.0 mg, 80%). LCMS (ES, m/z): 404[M+H]⁺.

Step 10. Cis-tert-butyl N-[2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate HBTU (78.9 mg, 0.208 mmol) was added to a solution of cis-tert-butyl N-[2-[(3R)-3-amino-3,4-dihydro-2H-1-benzopyran-7-yl]-6-oxa-2-azaspiro[4.5]decan-4-yl]carbamate (70.0 mg, 0.173 mmol), 3-amino-6-methylthieno[2,3-b] pyridine-2-carboxylic acid (43.3 mg, 0.208 mmol) and TEA (0.070 mL, 0.504 mmol) in DMA (3 mL). The resulting solution was stirred for 1 h at 25° C. The mixture was purified by reverse phase chromatography (Column: C18 silica gel; Mobile phase, A: water (containing 0.05% TFA) and B: ACN (5% to 80% in 30 min); Detector: UV 254/220 nm) to afford cis-tert-butyl N-[2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate as a yellow solid (70.0 mg, 64%). LCMS (ES, m/z): 594[M+H]$^+$.

Step 11. Tert-butyl N-[(4S,5R)-2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate and tert-butyl N-[(4R,5S)-2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate A Tert-butyl N-[2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate (70.0 mg, 0.118 mmol) was separated via Chiral-Prep-HPLC with the following conditions (Column: CHIRALPAK IA, 2×25 cm, 5 um; Mobile phase, A: HEX:DCM=3:1(containing 0.2% IPA) and B: EtOH (hold 50% in 16 min); Flow rate: 16 mL/min; Detector, UV 254/220 nm). The first eluting isomer (RT1=8.989 nm) was collected and concentrated under vacuum to afford tert-butyl N-[(4S,5R)-2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate as a yellow solid (25.0 mg, 33%); The second eluting isomer (RT2=14.735 min) was collected and concentrated under vacuum to afford tert-butyl N-[(4R,5S)-2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate as a yellow solid (20.0 mg, 27%). LCMS (ES, m/z): 594[M+H]$^+$.

Step 12. 3-amino-N-[(3R)-7-[(4S,5R)-4-amino-6-oxa-2-azaspiro[4.5]decan-2-yl]-3,4-dihydro-2H-1-benzopyran-3-yl]-6-methylthieno[2,3-b]pyridine-2-carboxamide A solution of tert-butyl N-[(4S,5R)-2-[(3R)-3-[3-amino-6-methylthieno[2,3-b]pyridine-2-amido]-3,4-dihydro-2H-1-benzopyran-7-yl]-6-oxa-2-azaspiro[40.5]decan-4-yl]carbamate (25.0 mg, 0.042 mmol) and TFA (0.500 mL) in DCM (1.50 mL) was stirred for 30 min at 25° C. The resulting solution was concentrated under vacuum. NH$_3$ (2.00 mL, 7M in MeOH) was added into the residue. The resulting solution was stirred for 0.5 h at 25° C., and then was concentrated under vacuum. The residue was purified via Prep-HPLC (Column, XBridge Shield RP18 OBD Column, 30×150 mm 5 um; Mobile phase, A: water (containing 0.05% NH$_4$HCO$_3$) and B: ACN (30% to 55% in 7 min); Detector, UV 220/254 nm). The collected fraction was lyophilized to afford 3-amino-N-[(3R)-7-[(4S,5R)-4-amino-6-oxa-2-azaspiro[4.5]decan-2-yl]-3,4-dihydro-2H-1-benzopyran-3-yl]-6-methylthieno[2,3-b]pyridine-2-carboxamide as a white solid (9.3 mg, 43%). $^1$H-NMR (DMSO-d$_6$, 400 MHz) S (ppm): LCMS (ES, m/z): 494[M+H]$^+$ Step 13. 3-amino-N-[(3R)-7-[(4R,5S)-4-amino-6-oxa-2-azaspiro[4.5]decan-2-yl]-3,4-dihydro-2H-1-benzopyran-3-yl]-6-methylthieno[2,3-b]pyridine-2-carboxamide A solution of tert-butyl N-[(4R,5S)-2-[(3R)-3-[3-amino-6-methylthieno[2,3-b]pyridine-2-amido]-3,4-dihydro-2H-1-benzopyran-7-yl]-6-oxa-2-azaspiro[4.5]decan-4-yl]carbamate (20.0 mg, 0.034 mmol) and TFA (0.500 mL) in DCM (1.50 mL) was stirred for 30 min at 25° C. The resulting solution was concentrated under vacuum. NH$_3$ (2.00 mL, 7M in MeOH) was added into the residue. The resulting solution was stirred for 0.5 h at 25° C., and then was concentrated under vacuum. The residue was purified via Prep-HPLC (Column, XBridge Shield RP18 OBD Column, 30×150 mm 5 um; Mobile phase, A: water (containing 0.05% NH$_4$HCO$_3$) and B: ACN (30% to 55% in 7 min); Detector, UV 220/254 nm). The collected fraction was lyophilized to afford 3-amino-N-[(3R)-7-[(4R,5S)-4-amino-6-oxa-2-azaspiro[4.5]decan-2-yl]-3,4-dihydro-2H-1-benzopyran-3-yl]-6-methylthieno[2,3-b]pyridine-2-carboxamide as a white solid (10.2 mg, 60%). $^1$H-NMR (DMSO-d$_6$, 400 MHz) S (ppm): 8.31 (d, J=8.0 Hz, 1H), 7.47 (d, J=7.6 Hz, 1H), 7.32 (d, J=8.4 Hz, 1H), 7.21 (s, 2H), 6.87 (d, J=8.4 Hz, 1H), 6.11 (d, J=8.4 Hz, 1H), 5.91 (s, 1H), 4.29-4.26 (m, 1H), 4.16-4.12 (m, 1H), 3.82-3.80 (m, 1H), 3.77-3.64 (m, 2H), 3.60-3.58 (m, 1H), 3.37-3.35 (m, 1H), 3.11-3.03 (m, 2H), 2.85-2.81 (m, 3H), 2.59 (s, 3H), 1.76-1.70 (m, 2H), 1.58-1.43 (m, 6H). LCMS (ES, m/z): 494[M+H]$^+$.

Example 612-1. 3-amino-N-[(3R)-7-[(4S,5R,9S)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide Example 612-2. 3-amino-N-[(3R)-7-[(4R,5R,9S)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide Example 612-3. 3-amino-N-[(3R)-7-[(4S,5R,9R)-9-amino-4-methyl-1-oxa-7-azaspiro-[4.4]nonan-7-yl-]3,4-dihydro-2H-1-benzopyran-3-yl]-6-methylthieno[2,3-b]pyridine-2-carboxamide Example 612-4. 3-amino-N-[(3R)-7-[(4R,5S,9R)-9-amino-4-methyl-1-oxa-7-azspiro[4.4]nonan-7-yl]-3,4-dihydro-2H-1-benzopyran-3-yl]-6-methylthieno[2,3-b]pyridine-2-carboxamide

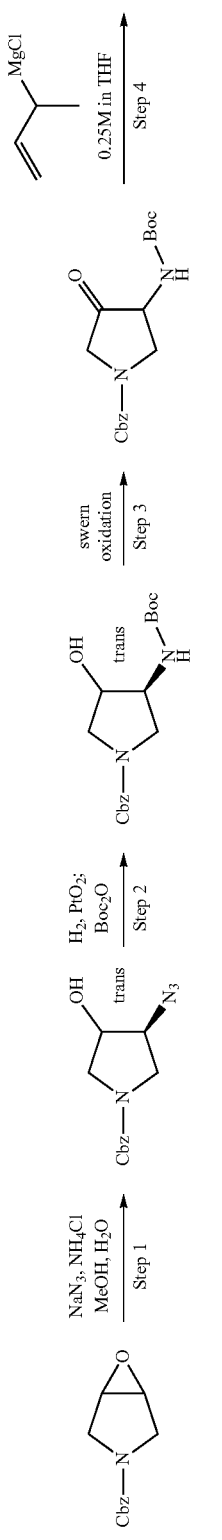
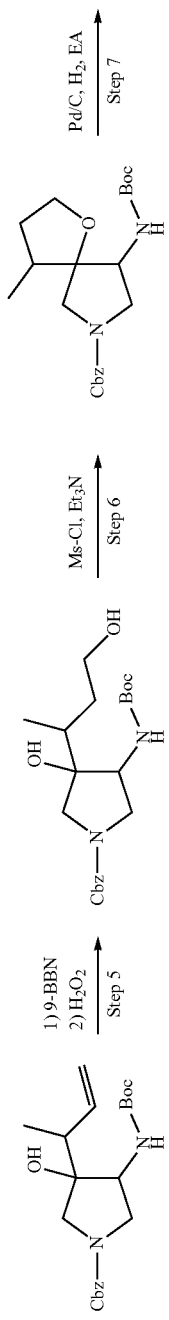
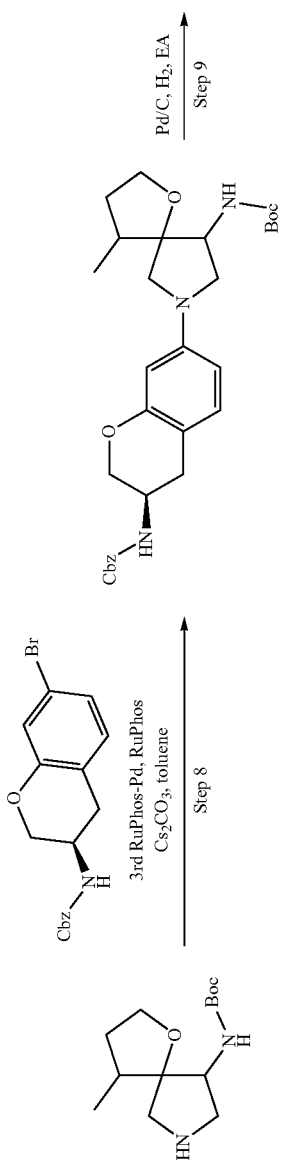

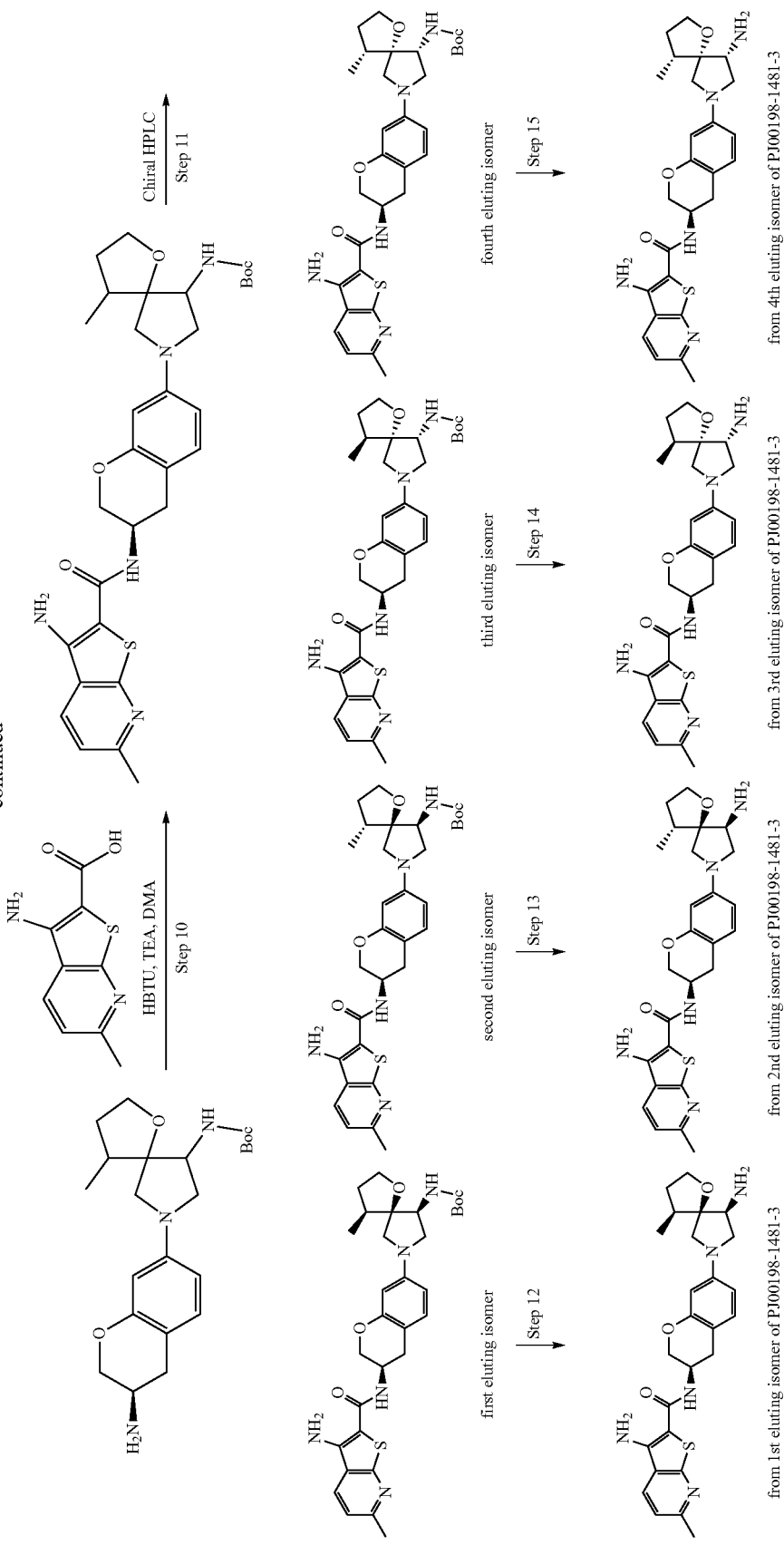

Step 1. Trans-benzyl 3-azido-4-hydroxypyrrolidine-1-carboxylate

A solution of NaN$_3$ (17.4 g, 267 mmol) in water (58 mL) was added to a solution of benzyl 6-oxa-3-azabicyclo[3.1.0]hexane-3-carboxylate (29.0 g, 133 mmol) and NH$_4$Cl (7.15 g, 134 mmol) in methanol (348 mL). The resulting solution was stirred for 16 h at 60° C. After cooling to 25° C., the pH value was adjusted to 7-8 with NaOH (1M). The resulting solution was then diluted with water (100 mL). The solvent was removed under vacuum and the residue was extracted with dichloromethane (2×150 mL). The organic layer was combined, dried over anhydrous sodium sulfate, filtered and concentrated under vacuum to give trans-benzyl 3-azido-4-hydroxypyrrolidine-1-carboxylate as light-yellow oil (35.0 g, crude). LCMS (ES, m/z): 263 [M+H]$^+$.

Step 2. Trans-benzyl 3-[[(tert-butoxy)carbonyl]amino]-4-hydroxypyrrolidine-1-carboxylate A mixture of trans-benzyl 3-azido-4-hydroxypyrrolidine-1-carboxylate (35.0 g, 133 mmol) and PtO$_2$ (10.0 g, 44.1 mmol) in ethyl acetate (2.00 L) was stirred for 16 h at 25° C. under hydrogen atmosphere (balloon). The solids were filtered out, and the filtrate was concentrated under vacuum to give trans-benzyl 3-amino-4-hydroxypyrrolidine-1-carboxylate as light yellow oil (30.0 g, crude). Trans-benzyl 3-amino-4-hydroxypyrrolidine-1-carboxylate (30.0 g, 127 mmol) was dissolved in THF (500 mL) and H$_2$O (500 mL). Then TEA (53.0 mL, 381 mmol) and (Boc)$_2$O (33.3 g, 152 mmol) was added under 5° C. The resulting solution was stirred for 16 h at 25° C. The solvent was removed under vacuum. The residue was extracted with ethyl acetate (3×300 mL). The organic layers were combined, dried over anhydrous sodium sulfate, filtered and concentrated under vacuum. The residue was washed with ethyl acetate/petroleum ether (1:10) to give trans-benzyl 3-[[(tert-butoxy)carbonyl]amino]-4-hydroxypyrrolidine-1-carboxylate as while solid (35.0 g, 82%). LCMS (ES, m/z): 337 [M+H]$^-$.

Step 3. Benzyl 3-[[(tert-butoxy)carbonyl]amino]-4-oxopyrrolidine-1-carboxylate DMSO (15.0 mL, 339 mmol) was added to a solution of oxalic dichloride (7.55 mL, 89.2 mmol) in anhydrous THF (120 mL) at −78° C. After stirring for 15 minutes at −78° C., a solution of trans-benzyl 3-[[(tert-butoxy)carbonyl]amino]-4-hydroxypyrrolidine-1-carboxylate (30.0 g, 89.2 mmol) in anhydrous THF (600 mL) was added at −78° C., which was followed by the addition of TEA (37.2 mL, 268 mmol) at −78° C. The reaction was stirred for 30 minutes under −60° C. The reaction was quenched with H$_2$O (50 mL). The organic layer was collected, and the aqueous phase was extracted with ethyl acetate (2×30 mL). The organics were combined, dried over anhydrous sodium sulfate, filtered, and concentrated. The residue was purified by silica gel chromatography (eluting with 1/10 ethyl acetate/petroleum ether) to give benzyl 3-[[(tert-butoxy)carbonyl]amino]-4-oxopyrrolidine-1-carboxylate as light yellow solid (21.0 g, 67%). LCMS (ES, m/z): 335[M+H]$^+$.

Step 4. Benzyl 3-(but-3-en-2-yl)-4-[[(tert-butoxy)carbonyl]amino]-3-hydroxypyrrolidine-1-carboxylate A solution of (but-3-en-2-yl)(chloro)magnesium (46.6 mL, 0.25 M in THF) was added into a stirring solution of benzyl 3-[[(tert-butoxy)carbonyl]amino]-4-oxopyrrolidine-1-carboxylate (1.50 g, 4.48 mmol) in THF (40 mL) at −78° C. The temperature was increased to −10° C. naturally. The reaction was then quenched by NH$_4$Cl (40 mL, sat.). The resulting mixture was extracted with ethyl acetate (3×20 mL), dried over anhydrous sodium sulfate, filtered and the filtrate was concentrated under vacuum. The residue was purified via reverse phase chromatography (Column: C18 silica gel; Mobile phase, A: water (containing 0.05% TFA) and B: ACN (5% to 30% in 20 min); Detector: UV 254/220 nm) to afford benzyl 3-(but-3-en-2-yl)-4-[[(tert-butoxy)carbonyl]amino]-3-hydroxypyrrolidine-1-carboxylate (1.10 g, 60%). LCMS (ES, m/z): 391 [M+H]$^+$.

Step 5. Benzyl 4-[(tert-butoxycarbonyl)amino]-3-hydroxy-3-(4-hydroxybutan-2-yl)pyrrolidine-1-carboxylate A solution of 9-borabicyclo[3.3.1]nonane (30.7 mL, 0.5M in THF) was added to a solution of benzyl 3-(but-3-en-2-yl)-4-[(tert-butoxycarbonyl)amino]-3-hydroxypyrrolidine-1-carboxylate (600 mg, 1.53 mmol) in THF (40 mL) at 0° C. After the mixture was stirred for 15 hours at 21° C., H$_2$O$_2$ (20 mL, 30%) and NaOAc (20 mL, sat.) were added to the solution at 0° C. The resulting mixture was stirred for 1 h at 20° C. The reaction was quenched with MeOH at 0° C. and the solution was stirred for 2 hours at 21° C. The resulting mixture was concentrated under reduced pressure. The residue was dissolved in ethyl acetate (10 mL), washed with water (2×5 mL). The organic layers were combined, dried over anhydrous sodium sulfate, filtered and concentrated under vacuum. The residue was purified by reverse phase chromatography (Column: C18 silica gel; Mobile phase, A: water (containing 0.05% TFA) and B: ACN (20% to 85% in 20 min); Detector: 220/254 nm) to afford benzyl 4-[(tert-butoxycarbonyl)amino]-3-hydroxy-3-(4-hydroxybutan-2-yl)pyrrolidine-1-carboxylate as yellow oil (500 mg, 76%). LCMS (ES, m/z): 409[M+H]$^-$.

Step 6. Benzyl 9-[(tert-butoxycarbonyl)amino]-4-methyl-1-oxa-7-azaspiro[4.4]nonane-7-carboxylate A solution of benzyl 4-[(tert-butoxycarbonyl)amino]-3-hydroxy-3-(4-hydroxybutan-2-yl)pyrrolidine-1-carboxylate (440 mg, 1.08 mmol), Et$_3$N (0.450 mL, 3.23 mmol) and MsCl (172 mg, 1.51 mmol) in DCM (4 mL) was stirred for 1 h at 20° C. and stirred for 1 h at 60° C. The mixture was concentrated under vacuum. The residue was purified by reverse phase chromatography (Column: C18 silica gel; Mobile phase, A: water (containing 0.05% NH$_4$HCO$_3$) and B: ACN (15% to 80% ACN in 20 min); Detector: UV 254/220 nm). The collected fraction was concentrated under vacuum to give benzyl 9-[(tert-butoxycarbonyl)amino]-4-methyl-1-oxa-7-azaspiro[4.4]nonane-7-carboxylate as a yellow solid (400 mg,54%). LCMS (ES, m/z): 391[M+H]$^+$.

Step 7. Tert-butyl N-[4-methyl-1-oxa-7-azaspiro[4.4]nonan-9-yl]carbamate

A mixture of benzyl 9-[[(tert-butoxy)carbonyl]amino]-4-methyl-1-oxa-7-azaspiro[4.4]nonane-7-carboxylate (550 mg, 1.41 mmol), Pd/C (400 mg, 10%) and EA (15 mL) was stirred for 3 h at 28° C. under hydrogen atmosphere (balloon). The solids were filtered out. The filtrate was concentrated under vacuum to give tert-butyl N-[4-methyl-1-oxa- 7-azaspiro[4.4]nonan-9-yl]carbamate as yellow solid (200 mg, crude). LCMS (ES, m/z): 257[M+H]+.

Step 8. Benzyl N-[(3R)-7-(9-[[(tert-butoxy)carbonyl]amino]-4-methyl-1-oxa-7-azaspiro[4.4]nonan-7-yl)-3,4-dihydro-2H-1-benzopyran-3-yl]carbamate A mixture of benzyl N-[(3R)-7-bromo-3,4-dihydro-2H-1-benzopyran-3-yl]carbamate (200 mg, 0.621 mmol), tert-butyl N-[4-methyl-1-oxa-7-azaspiro[4.4]nonan-9-yl]carbamate (142 mg, 0.621 mmol), 3rd Generation RuPhos precatalyst(46.2 mg, 0.062 mmol), RuPhos(51.2 mg, 0.110 mmol), $Cs_2CO_3$ (539 mg, 1.66 mmol) and toluene (7 mL) was stirred for 3 h at 95° C. After cooled to 28° C., the solids were filtered out. The filtrate was concentrated under vacuum. The residue was purified by silica gel chromatography (eluting with 1:3 ethyl acetate/petroleum ether) to afford benzyl N-[(3R)-7-(9-[[(tert-butoxy)carbonyl]amino]-4-methyl-1-oxa-7-azaspiro[4.4]nonan-7-yl)-3,4-dihydro-2H-1-benzopyran-3-yl]carbamate as a yellow solid (110 mg, 33%). LCMS (ES, m/z): 538[M+H]+.

Step 9. Tert-butyl N-[7-[(3R)-3-amino-3,4-dihydro-2H-1-benzopyran-7-yl]-4-methyl-1-oxa-7-azaspiro[4.4]nonan-9-yl]carbamate A mixture of benzyl N-[(3R)-7-(9-[[(tert-butoxy)carbonyl]amino]-4-methyl-1-oxa-7-azaspiro[4.4]nonan-7-yl)-3,4-dihydro-2H-1-benzopyran-3-yl]carbamate (110 mg, 0.205 mmol) and Pd/C (110 mg, 10%) in EA (5 mL) was stirred for 1 h at 28° C. under hydrogen atmosphere (balloon). The solids were filtered out. The filtrate was concentrated under vacuum to give tert-butyl N-[7-[(3R)-3-amino-3,4-dihydro-2H-1-benzopyran-7-yl]-4-methyl-1-oxa-7-azaspiro[4.4]nonan-9-yl]carbamate as yellow oil (100 mg, crude). LCMS (ES, m/z): 404[M+H]+.

Step 10. Tert-butyl N-[7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate HBTU (112 mg, 0.297 mmol) was added to a solution of tert-butyl N-[7-[(3R)-3-amino-3,4-dihydro-2H-1-benzopyran-7-yl]-4-methyl-1-oxa-7-azaspiro[4.4]nonan-9-yl]carbamate (100 μmg, 0.248 mmol), 3-amino-6-methylthieno[2,3-b]pyridine-2-carboxylic acid (51.6 mg, 0.248 mmol) and TEA (0.100 mL, 0.987 mmol) in DMA (2 mL). The resulting solution was stirred for 2 h at 25° C. The resulting mixture was purified by reverse phase chromatography (Column: C18 silica gel; Mobile phase, A: water (containing 10 mmol/L $NH_4HCO_3$) and B: ACN (5% to 80% in 30 min); Detector: UV 254/220 nm). The collected fraction was concentrated to afford tert-butyl N-[7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate as a yellow solid (100 mg, 65%). LCMS (ES, m/z): 594[M+H]+.

Step 11. Tert-butyl N-[(4S,5R,9S)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate, tert-butyl N-[(4S,5S,9R)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate, tert-butyl N-[(4R,5R,9S)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate and tert-butyl N-[(4R,5S,9R)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate Tert-butyl N-[7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate (100 mg. 0.168 mmol) was separated by Chiral-Prep-HPLC (Column: Chiralpak IA, 2×25 cm, 5 um; Mobile Phase, A: HEX:DCM=3:1(containing 0.2% IPA) and B: IPA:DCM=1:1(hold 60% in 16 min); Flow rate: 20 mL/min; 220/254 nm). The first eluting isomer (RT1:5.379 min) was collected and concentrated under vacuum to afford tert-butyl N-[(4S,5R,9S)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate as a yellow solid (15.0 mg, 14%). The second eluting isomer (RT2:7.043 min) was collected and concentrated under vacuum to afford tert-butyl N-[(4S,5S,9R)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate as a yellow solid (15.0 mg, 14%). The third eluting isomer (RT3:9.337 min) was collected and concentrated under vacuum to afford tert-butyl N-[(4R,5R,9S)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate as a yellow solid (15.0 mg, 14%). The forth eluting isomer (RT4: 14.107 min) was collected and concentrated under vacuum to afford tert-butyl N-[(4R,5S,9R)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate as a yellow solid (15.0 mg, 14%). LCMS (ES, m/z): 594[M+H]+.

Step 12. 3-Amino-N-[(3R)-7-[(4S,5R,9S)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide A solution of tert-butyl N-[(4S,5R,9S)-7-[(3R)-3-[3-amino-6-methylthieno[2,3-b]pyridine-2-amido]-3,4-dihydro-2H-1-benzopyran-7-yl]-4-methyl-1-oxa-7-azaspiro[4.4]nonan-9-yl]carbamate (11.0 mg, 0.019 mmol) and TFA (1 mL) in DCM (2 mL) was stirred for 30 min at 25° C. The resulting mixture was concentrated under vacuum. A solution of $NH_3$ (2.00 mL, 7M in MeOH) was added to the residue. The resulting solution was stirred for 0.5 h at 25° C. and then concentrated under vacuum. The residue was purified by Prep-HPLC (Column: XBridge Shield RP18 OBD Column, 5 μm, 19×150 mm; Mobile Phase, A: water (containing 10 mmol/L $NH_4HCO_3$) and B: ACN (30% to 50% in 8 min); Flow rate: 25 mL/min; Detector: 220 nm). The collected fraction was lyophilized to give 3-amino-N-[(3R)-7-[(4S,5R,9S)-9-amino-4-methyl-1-oxa-7-azaspiro[4.4]nonan-7-yl]-3,4-dihydro-2H-1-benzopyran-3-yl]-6- methylthieno[2,3-b]pyridine-2-carboxamide as a white solid (7.20 mg, 76%). H-NMR (DMSO-dr, 400 MHz) S (ppm): 8.33 (d, J=8.0 Hz, 1H), 7.47 (br s, 1H), 7.32 (d, J=8.4 Hz, 1H), 7.21 (br s, 2H), 6.87 (d, J=8.0 Hz, 1H), 6.08 (d, J=6.8 Hz, 1H), 5.89 (s, 1H), 4.30-4.20 (m, 1H), 4.16-4.13 (m, 1H), 3.86-3.72 (m, 3H), 3.41-3.32 (m, 1H), 3.26-3.21 (m, 2H), 3.07-3.04 (m, 1H), 2.86-2.82 (m, 3H), 2.59 (s, 3H), 2.30-2.24 (m, 1H), 2.17-2.13 (m, 1H), 1.93 (br s, 2H), 1.64-1.59 (m, 1H), 1.03 (d, J=6.8 Hz, 3H). LCMS (ES, m/z): 494[M+H]$^-$.

Step 13. 3-Amino-N-[(3R)-7-[(4R,5R,9S)-9-amino-4-methyl-1-oxa-7-azaspiro[4.4]nonan-7-yl]-3,4-di-hydro-2H-1-benzopyran-3-yl]-6-methylthieno[2,3-b]pyridine-2-carboxamide A solution of tert-butyl N-[(4R,5R,9S)-7-[(3R)-3-[3-amino-6-methylthieno[2,3-b]pyridine-2-amido]-3,4-di-hydro-2H-1-benzopyran-7-yl]-4-methyl-1-oxa-7-azaspiro[4.4]nonan-9-yl]carbamate (12.0 mg, 0.020 mmol) and TFA (1.00 mL) in DCM (3 mL) was stirred for 30 min at 25° C. The resulting mixture was concentrated under vacuum. A solution of NH$_3$ (2 mL, 7M in MeOH) was added to the residue. The resulting solution was stirred for 0.5 h at 25° C. and then concentrated under vacuum. The residue was purified by Prep-HPLC (Column: XBridge Prep C18 OBD Column, 19×150 mm 5 um; Mobile phase, A: water (containing 10 mmol/L NH$_4$HCO$_3$) and B: ACN (30% to 50% in 8 min); Flow rate: 25 mL/min; Detector: 220 nm). The collected fraction was lyophilized to give 3-amino-N-[(3R)-7-[(4R,5R,9S)-9-amino-4-methyl-1-oxa-7-azaspiro[4.4]nonan-7-yl]-3,4-dihydro-2H-1-benzopyran-3-yl]-6-methyl-thieno[2,3-b]pyridine-2-carboxamide as a white solid (8.10 mg, 78%). $^1$H-NMR (DMSO-d$_6$, 400 MHz) S (ppm): 8.33 (d, J=8.0 Hz, 1H), 7.47 (br s, 1H), 7.32 (d, J=8.0 Hz, 1H), 7.21 (br s, 2H), 6.87 (d, J=8.4 Hz, 1H), 6.05-6.03 (m, 1H), 5.84 (s, 1H), 4.31-4.21 (m, 1H), 4.15-4.12 (m, 1H), 3.98-3.95 (m, 1H), 3.81-3.76 (m, 1H), 3.70-3.67 (m, 1H), 3.39-3.32 (m, 1H), 3.29-3.25 (m, 2H), 3.10-3.07 (m, 1H), 2.85-2.80 (m, 3H), 2.59 (s, 3H), 2.20-2.12 (m, 1H), 2.07-1.99 (m, 1H), 1.88-1.79 (m, 1H), 1.50 (br s, 2H), 1.14 (d, J=6.8 Hz, 3H). LCMS (ES, m/z): 494[M+H]$^+$.

Step 14. 3-Amino-N-[(3R)-7-[(4S,5S,9R)-9-amino-4-methyl-1-oxa-7-azaspiro[4.4]nonan-7-yl]-3,4-di-hydro-2H-1-benzopyran-3-yl]-6-methylthieno[2,3-b]pyridine-2-carboxamide A solution of tert-butyl N-[(4S,5S,9R)-7-[(3R)-3-[3-amino-6-methylthieno[2,3-b]pyridine-2-amido]-3,4-di-hydro-2H-1-benzopyran-7-yl]-4-methyl-1-oxa-7-azaspiro[4.4]nonan-9-yl]carbamate (10.0 mg, 0.017 mmol) and TFA (1 mL) in DCM (2 mL) was stirred for 30 min at 25° C. The resulting mixture was concentrated under vacuum. A solution of NH$_3$ (1.00 mL, 7M in MeOH) was added to the residue. The resulting solution was stirred for 0.5 h at 25° C. and then concentrated under vacuum. The residue was purified by Prep-HPLC (Column: XBridge Prep C18 OBD Column, 19×150 mm, 5 um; Mobile phase, A: water (containing 10 mmol/L NH$_4$HCO$_3$) and B: ACN (30% to 50% in 8 min); Flow rate: 60 mL/min; Detector: 220 nm). The collected fraction was lyophilized to give 3-amino-N-[(3R)-7-[(4S,5S,9R)-9-amino-4-methyl-1-oxa-7-azaspiro[4.4] nonan-7-yl]-3,4-dihydro-2H-1-benzopyran-3-yl]-6-methyl-thieno[2,3-b]pyridine-2-carboxamide as a white solid (7.30 mg, 84%). $^1$H-NMR (DMSO-d$_6$, 400 MHz) S (ppm): 8.33 (d, J=8.0 Hz, 1H), 7.47 (br s, 1H), 7.32 (d, 0.1=8.4 Hz, 1H), 7.21 (br s, 2H), 6.86 (d, J=8.4 Hz, 1H), 6.08-6.06 (m, 1H), 5.88 (s, 1H), 4.31-4.20 (m, 1H), 4.15-4.12 (m, 1H), 3.83-3.72 (m, 3H), 3.40-3.32 (m, 1H), 3.25-3.18 (m, 2H), 3.06-3.04 (m, 1H), 2.85-2.82 (m, 3H), 2.59 (s, 3H), 2.28-2.22 (m, 1H), 2.20-2.11 (m, 1H), 1.63-1.58 (m, 3H), 1.03 (d, J=6.8 Hz, 3H). LCMS (ES, m/z): 494[M+H]$^+$.

Step 15. 3-Amino-N-[(3R)-7-[(4R,5S,9R)-9-amino-4-methyl-1-oxa-7-azaspiro[4.4]nonan-7-yl]-3,4-di-hydro-2H-1-benzopyran-3-yl]-6-methylthieno[2,3-b]pyridine-2-carboxamide A solution of tert-butyl N-[(4R,5S,9R)-7-[(3R)-3-[3-amino-6-methylthieno[2,3-b]pyridine-2-amido]-3,4-di-hydro-2H-1-benzopyran-7-yl]-4-methyl-1-oxa-7-azaspiro[4.4]nonan-9-yl]carbamate (12.0 mg 0.020 mmol) and TFA (1.00 mL) in DCM (2 mL) was stirred for 30 min at 25° C. The resulting mixture was concentrated under vacuum. A solution of NH$_3$ (1.00 mL, 7M in MeOH) was added to the residue. The resulting solution was stirred for 0.5 h at 25° C. and then concentrated under vacuum. The residue was purified by Prep-HPLC (Column: XBridge Prep C18 OBD Column, 19×150 mm 5 um; Mobile phase, A: water (containing 10 mmol/L NH$_4$HCO$_3$) and B: ACN (30% to 50% in 8 min); Flow rate: 25 mL/min; Detector: 220 nm). The collected fraction was lyophilized to give 3-amino-N-[(3R)-7-[(4R,5S,9R)-9-amino-4-methyl-1-oxa-7-azaspiro[4.4] nonan-7-yl]-3,4-dihydro-2H-1-benzopyran-3-yl]-6-methyl-thieno[2,3-b]pyridine-2-carboxamide as a white solid (7.60 mg, 73%). $^1$H-NMR (DMSO-dc, 400 MHz) S (ppm): 8.33 (d, J=8.0 Hz, 1H), 7.47 (br s 7.6 Hz, 1H), 7.32 (d, J=8.4 Hz, 1H), 7.21 (br s, 2H), 6.87 (d, J=8.4 Hz, 1H), 6.05-6.03 (m, 1H), 5.84 (s, 1H), 4.31-4.21 (m, 1H), 4.15-4.12 (m, 1H), 3.98-3.95 (m, 1H), 3.82-3.77 (m, 1H), 3.70-3.67 (m, 1H), 3.40-3.32 (m, 1H), 3.29-3.25 (m, 2H), 3.10-3.08 (m, 1H), 2.85-2.80 (m, 3H), 2.59 (s, 3H), 2.19-2.12 (m, 1H), 2.07-1.99 (m, 1H), 1.88-1.79 (m, 1H), 1.51 (br s, 2H), 1.14 (d, J=6.8 Hz, 3H). LCMS (ES, m/z): 494[M+H]$^+$.

Example A-1(a): Biochemical Assay: Ubiquitin-Rhodamine 110 Assay for USP28 Activity The assay was performed in a final volume of 9 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of 10-point, 3-fold serial dilution in DMSO was pre-dispensed into 1536 assay plates (Corning, #3724BC) for a final test concentration of 25 μM to 1.3 nM, top to lowest dose, respectively. Enzyme USP28, construct His-tagged USP28-FL-mammalian, (protein expression and purification procedure described below). Concentration and incubation times were optimized for the maximal signal-to-background while maintaining initial velocity conditions at a fixed substrate concentration. The final concentration of the enzyme in the assay was 75 μM. Final substrate (Ub-Rh110; Ubiquitin-Rhodamine 110, UbiQ-126) concentration was 25 nM with [Ub-Rh110]<<Km. 3 μL of 2× enzyme was added to assay plates (pre-stamped with compound) preincubated with USP25 for 30 minutes and then 3 μL of 2× Ub-Rh110 was added to assay plates. Plates were incubated for 45 minutes at room temperature before addition of 3 μL of stop solution (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Procedure for the Protein expression and purification for construct His-tagged USP28-FL-mammalian Expression of USP28 (1-1077)-TEV-6*His (pTT5 vector) was carried out in Expi293f cells (sequence derived from uniprot ID: Q96RU2-1). Cells were re-suspended in lysis buffer B 50 mM Bicine, pH 8.0, 20 mM NaCl, 5% glycerol, 0.1% CHAPS, 5 mM β-ME, 1 mM PMSF, 1 ug/ml Leupeptin, 1 ug/ml Pepstatin) and lysed by sonication. Insoluble material was removed by centrifugation and the supernatant was loaded onto a Ni-NTA column (GE Healthcare) equilibrated with Ni Buffer A (50 mM Bicine, pH 8.0, 20 mM NaCl, 5% glycerol, 0.1% CHAPS, 5 mM R-ME.) and washed with Ni Buffer A+20 mM imidazole until $A_{280}$ reached baseline. The protein was eluted with Ni Buffer B (50 mM Bicine, pH 8.0, 20 mM NaCl, 5% glycerol, 0.1% CHAPS, 5 mM β-ME, 300 mM imidazole.). The protein was further purified using a Superdex™ 200 10/300 GL column (GE Healthcare) equilibrated with 50 mM Bicine, pH 8.0, 20 mM NaCl, 5% glycerol, 0.1% CHAPS, 5 mM β-ME. The protein was concentrated to 2.5 mg ml-1, flash-frozen in liquid $N_2$ and stored at −80° C.

Example A-1(b): Biochemical Assay:
Ubiquitin-Rhodamine 110 Assay for USP28
Activity Each assay was performed in a final volume of 20 μL in assay buffer containing 20 mM Tris-HCl (pH 8.0, (1M Tris-HCl, pH 8.0 solution; Corning 46-031-CM)), 2 mM $CaCl_2$ (1M Calcium Chloride solution; Sigma #21114) 2 mM BME (2-Mercaptoethanol; Sigma 63689-25ML-F), 0.01% Prionex (0.22 μM filtered, Sigma #G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 μM ($DMSO_{(fc)}$=0.5%). Enzyme (USP28, construct USP28 (USP28-5(1-1077)-TEV-6*His; LifeSensors) concentration and incubation times were optimized for the maximal signal-to-background while maintaining initial velocity conditions at a fixed substrate concentration. The final concentration of the enzyme in the assay was 400 μM. Final substrate (Ub-Rh110; Ubiquitin-Rhodamine 110, R&D Systems #U-555) concentration was 25 nM with [Ub-Rh110]<<Km. 10 μL of 2× enzyme was added to assay plates (pre-stamped with compound) either simultaneously with 2× Ub-Rh110 or preincubated with USP28 40 minutes prior to the addition of 10 μL of 2× Ub-Rh110 to compound plates. Plates were incubated stacked for 90 minutes at room temperature before fluorescence was read on the Envision (Excitation at 485 nm and Emission at 535 nm; Perkin Elmer) or on the PheraSTAR (Excitation at 485 nm and Emission at 535 nm; BMG Labtech).

For follow-up studies, each assay was performed in a final volume of 15 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of either an 8-point or 10-point, 3-fold serial dilution in DMSO was pre-dispensed into assay plates (Perkin Elmer, ProxiPlate-384 F Plus, #) for a final test concentration of either 25 μM to 11 nM or 25 μM to 1.3 nM, respectively. Enzyme USP28, construct USP28 (USP28-5 (1-1077)-TEV-6*His; LifeSensors) concentration and incubation times were optimized for the maximal signal-to-background while maintaining initial velocity conditions at a fixed substrate concentration. The final concentration of the enzyme in the assay was 75 μM. Final substrate (Ub-Rh110; Ubiquitin-Rhodamine 110, R&D Systems #U-555) concentration was 25 nM with [Ub-Rh110]<<Km. 5 μL of 2× enzyme was added to assay plates (pre-stamped with compound) preincubated with USP28 for 30 minutes and then 5 μL of 2× Ub-Rh110 was added to assay plates. Plates were incubated stacked for 20 minutes at room temperature before 5 μL of stop solution was added (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Example A-2: In Vivo Xenograft Studies

Figure 2:
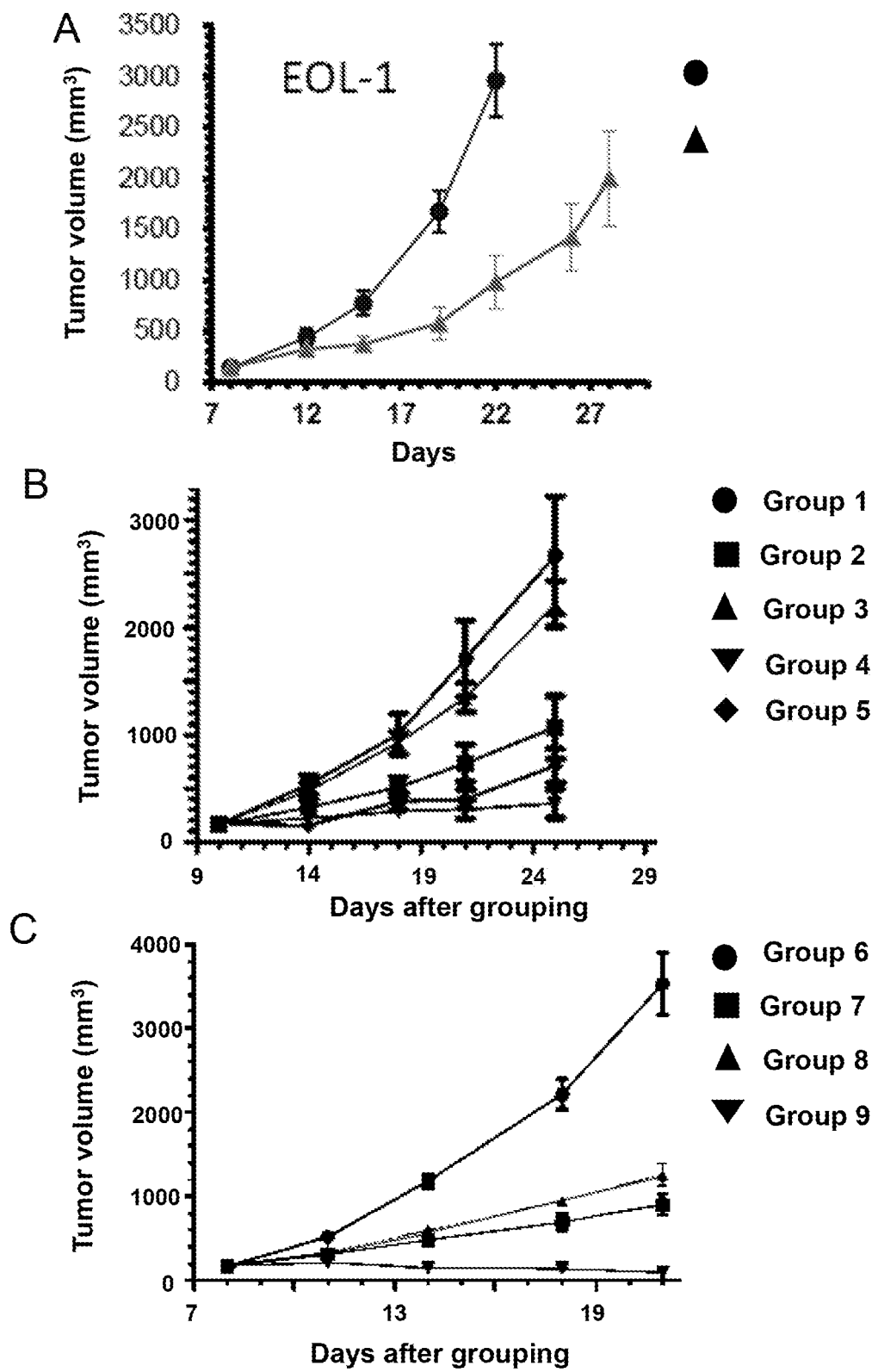
FIG. 2 is a graphical representation of a xenograft study illustrating the effect of compounds of the present disclosure on tumor size.

Mice were injected subcutaneously in the flank with human eosinophil EOL-1 (DSMZ no. ACC 386) cells (NCI). Injections with cells (circles, FIG. 2A) and with vehicle alone (triangles, FIG. 2B) were monitored, and when tumors reached a critical size (for example, about 1000 $mm^3$), mice were randomized into treatment groups, including vehicle control and reference standard groups. The groups, as shown in FIG. 2B are as follows: Group 1, vehicle administered orally every other day; Group 2, first test compound ((S)-amino-N-(5-fluoro-7-(piperazin-1-yl)chroman-3-yl)-6-methylthieno[2,3-b]pyridine-2-carboxamide) at 120 mg/kg, administered orally every other day; Group 3, first test compound at 80 mg/kg, administered orally every other day; Group 4, first test compound at 80 mg/kg, administered subcutaneously twice per day, every other day thereafter; Group 5, first test compound at 60 mg/kg, administered subcutaneously twice per day for four consecutive days, with no administration for three days. In FIG. 2C, Group 6 represents oral administration of vehicle every other day; Group 7, first test compound at 50 mg/kg, administered subcutaneously twice per day for five consecutive days, and then not administered for two days; Group 8, second test compound (7-amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide) at 40 mg/kg, administered orally twice per day; and Group 9, second test compound at 60 mg/kg, administered orally twice per day. The mice were weighed and tumors measured using vernier calipers on indicated days. Tumor volume was calculated according to the formula (length×$width^2$)/2. The administration of the test compounds showed slowing of tumor growth over time.

Example A-3: Biochemical Assay:
Ubiquitin-Rhodamine 110 Assay for USP25
Activity The assay was performed in a final volume of 9 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of 10-point, 3-fold serial dilution in DMSO was pre-dispensed into 1536 assay plates (Corning, #3724BC) for a final test concentration of 25 μM to 1.3 nM, top to lowest dose, respectively. Enzyme USP25, construct USP25-His6, (Boston Biochem E-546). Concentration and incubation times were optimized for the maximal signal-to-background while maintaining initial velocity conditions at a fixed substrate concentration. The final concentration of the enzyme in the assay was 75 μM. Final substrate (Ub-Rh110; Ubiquitin-Rhodamine 110, R&D Systems #U-555) concentration was 25 nM with [Ub-Rh110]<<Km. 3 μL of 2× enzyme was added to assay plates (pre-stamped with compound) preincubated with USP25 for 30 minutes and then 3 μL of 2× Ub-Rh110 was added to assay plates. Plates were incubated for 45 minutes at room temperature before addition of 3 μL of stop solution (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

For assay formats Example A-1(a), A-1(b), and A-2, data were reported as percent inhibition compared with control wells based on the following equation: % inh=1−((FLU−$Ave_{Low}$)/($Ave_{High}$−$Ave_{Low}$)) where FLU=measured Fluorescence, $Ave_{Low}$=average Fluorescence of no enzyme control (n=16), and $Ave_{High}$h=average Fluorescence of DMSO control (n=16). $IC_{50}$ values were determined by curve fitting of the standard 4 parameter logistic fitting algorithm included in the Activity Base software package: IDBS XE Designer Model 205. Data is fitted using the Levenburg Marquardt algorithm.

The activity of compounds in the biochemical $IC_{50}$ assays ($IC_{50}$ ranges) according to the present disclosure are reported in Table 24 below according to the following:

"+"L>2 μM; "++": 0.2-2 μM; "+++": 0.05-0.2 μM; "++++": 0.001-0.05 μM.

TABLE 24

| Ex. # | Chemical Name | MS m/z [M + H]+ | 1H NMR | USP28 A-1(a) | USP28 A-1(b) | USP25 A-3 |
|---|---|---|---|---|---|---|
| 1-37 | (R)-6-amino-N-(5-fluoro-7-(piperazin-1-yl)chroman-3-yl)-2-methylthieno[2,3-d]thiazole-5-carboxamide | see above | see above | + | + | + |
| 1-38 | (S)-6-amino-N-(5-fluoro-7-(piperazin-1-yl)chroman-3-yl)-2-methylthieno[2,3-d]thiazole-5-carboxamide | see above | see above | ++++ | ++ | ++ |
| 1-39 | N-((3R)-7-(3,8-diazabicyclo[3.2.1]octan-3-yl)-5-fluorochroman-3-yl)-6-amino-2-methylthieno[2,3-d]thiazole-5-carboxamide | see above | see above | ++++ | ++ | ++ |
| 1-40 | N-((3S)-7-(3,8-diazabicyclo[3.2.1]octan-3-yl)-5-fluorochroman-3-yl)-6-amino-2-methylthieno[2,3-d]thiazole-5-carboxamide | see above | see above | ++ | + | + |
| 1-41 | N-((3S)-7-(3,6-diazabicyclo[3.1.1]heptan-3-yl)-5-fluorochroman-3-yl)-3-amino-6-methylthieno[2,3-b]pyridine-2-carboxamide | see above | see above | ++++ | +++ | +++ |
| 1-42 | N-((3R)-7-(3,6-diazabicyclo[3.1.1]heptan-3-yl)-5-fluorochroman-3-yl)-3-amino-6-methylthieno[2,3-b]pyridine-2-carboxamide | see above | see above | ++ | + | + |
| 2-34 | (S)-7-amino-3-methyl-N-(7-methyl-6-(piperazin-1-yl)-1,2,3,4-tetrahydronaphthalen-2-yl)thieno[2,3-b]pyrazine-6-carboxamide | see above | see above | +++ | ++ | + |
| 2-35 | (R)-7-amino-3-methyl-N-(7-methyl-6-(piperazin-1-yl)-1,2,3,4-tetrahydronaphthalen-2-yl)thieno[2,3-b]pyrazine-6-carboxamide | see above | see above | + | + | + |
| 2-36 | (S)-7-amino-3-methyl-N-(5-methyl-6-(piperazin-1-yl)-1,2,3,4-tetrahydronaphthalen-2-yl)thieno[2,3-b]pyrazine-6-carboxamide | see above | see above | ++ | + | + |
| 2-37 | (R)-7-amino-3-methyl-N-(5-methyl-6-(piperazin-1-yl)-1,2,3,4-tetrahydronaphthalen-2-yl)thieno[2,3-b]pyrazine-6-carboxamide | see above | see above | ++++ | +++ | ++ |
| 2-38 | 3-amino-N-[(3R)-7-[(3S,4S)-3-amino-4-(Å²Hâ,f)methoxypyrrolidin-1-yl]-3,4-dihydro-2H-1-benzopyran-3-yl]-6-methylthieno[2,3-b]pyridine-2-carboxamide | see above | see above | +++ | | ++ |
| 3-17 | 3-amino-N-[(3R)-6,8-difluoro-7-(piperazin-1-yl)-3,4-dihydro-2H-1-benzopyran-3-yl]-6-methylthieno[2,3-b]pyridine-2-carboxamide | see above | see above | ++++ | | +++ |
| 3-18 | 3-amino-N-[(3S)-6,8-difluoro-7-(piperazin-1-yl)-3,4-dihydro-2H-1-benzopyran-3-yl]-6-methylthieno[2,3-b]pyridine-2-carboxamide | see above | see above | ++ | | + |

TABLE 24-continued

| | | | | | | |
|---|---|---|---|---|---|---|
| 6-4 | (S)-1-(6-(7-amino-3-methylthieno[2,3-b]pyrazine-6-carboxamido)-5,6,7,8-tetrahydronaphthalen-2-yl)azetidine-3-carboxylic acid | see above | see above | ++ | + | ++ |
| 7-4 | 7-amino-N-((S)-6-((R)-6-hydroxy-1,4-diazepan-1-yl)-1,2,3,4-tetrahydronaphthalen-2-yl)-3-methylthieno[2,3-b]pyrazine-6-carboxamide | see above | see above | +++ | ++ | ++ |
| 7-5 | 7-amino-N-((R)-6-((R)-6-hydroxy-1,4-diazepan-1-yl)-1,2,3,4-tetrahydronaphthalen-2-yl)-3-methylthieno[2,3-b]pyrazine-6-carboxamide | see above | see above | +++ | ++ | ++ |
| 7-6 | 7-amino-N-((S)-6-((S)-6-hydroxy-1,4-diazepan-1-yl)-1,2,3,4-tetrahydronaphthalen-2-yl)-3-methylthieno[2,3-b]pyrazine-6-carboxamide | see above | see above | ++ | ++ | + |
| 7-7 | 7-amino-N-((R)-6-((S)-6-hydroxy-1,4-diazepan-1-yl)-1,2,3,4-tetrahydronaphthalen-2-yl)-3-methylthieno[2,3-b]pyrazine-6-carboxamide | see above | see above | ++ | + | + |
| 7-8 | 3-amino-N-((S)-6-((S)-3-(hydroxymethyl)piperazin-1-yl)-1,2,3,4-tetrahydronaphthalen-2-yl)-6-methylthieno[2,3-b]pyridine-2-carboxamide | see above | see above | ++ | + | + |
| 7-9 | 3-amino-N-((S)-6-((R)-3-(hydroxymethyl)piperazin-1-yl)-1,2,3,4-tetrahydronaphthalen-2-yl)-6-methylthieno[2,3-b]pyridine-2-carboxamide | see above | see above | ++ | + | + |
| 7-10 | 3-amino-N-((R)-6-((S)-3-(hydroxymethyl)piperazin-1-yl)-1,2,3,4-tetrahydronaphthalen-2-yl)-6-methylthieno[2,3-b]pyridine-2-carboxamide | see above | see above | +++ | ++ | ++ |
| 7-11 | 3-amino-N-((R)-6-((R)-3-(hydroxymethyl)piperazin-1-yl)-1,2,3,4-tetrahydronaphthalen-2-yl)-6-methylthieno[2,3-b]pyridine-2-carboxamide | see above | see above | +++ | ++ | ++ |
| 10-5 | (S)-3-amino-N-(5-fluoro-7-(piperazin-1-yl)chroman-3-yl)-6-methylthieno[2,3-b]pyridine-2-carboxamide | see above | see above | ++ | + | + |
| 10-6 | N-((3R)-7-(9-oxa-3,7-diazabicyclo[3.3.1]nonan-3-yl)-5-fluorochroman-3-yl)-3-amino-6-methylthieno[2,3-b]pyridine-2-carboxamide | see above | see above | ++++ | ++++ | +++ |
| 10-7 | N-((3R)-7-(3,6-diazabicyclo[3.1.1]heptan-3-yl)-5-fluorochroman-3-yl)-3-amino-4,6-dimethylthieno[2,3-b]pyridine-2-carboxamide | see above | see above | ++++ | +++ | +++ |
| 10-8 | N-((3R)-7-(3,6-diazabicyclo[3.1.1]heptan-3-yl)-5-fluorochroman-3-yl)-7-amino-3-methylthieno[2,3-b]pyrazine-6-carboxamide | see above | see above | ++++ | +++ | +++ |
| 10-9 | (R)-3-amino-N-(5-fluoro-7-(piperazin-1-yl)chroman-3-yl)-4,6-dimethylthieno[2,3-b]pyridine-2-carboxamide | see above | see above | ++++ | +++ | +++ |
| 10-10 | (R)-7-amino-N-(5-fluoro-7-(piperazin-1-yl)chroman-3-yl)-3-methylthieno[2,3-b]pyrazine-6-carboxamide | see above | see above | ++++ | +++ | +++ |
| 10-11 | (R)-3-amino-N-(5-fluoro-7-(piperazin-1-yl)chroman-3-yl)-6-methoxythieno[2,3-b]pyridine-2-carboxamide | see above | see above | ++++ | ++ | +++ |
| 10-12 | N-((3R)-7-(9-oxa-3,7-diazabicyclo[3.3.1]nonan-3-yl)-5-fluorochroman-3-yl)-7-amino-3-methylthieno[2,3-b]pyrazine-6-carboxamide | see above | see above | ++++ | ++++ | ++++ |
| 10-13 | N-((3R)-7-(9-oxa-3,7-diazabicyclo[3.3.1]nonan-3-yl)-5-fluorochroman-3-yl)-3-amino-4,6-dimethylthieno[2,3-b]pyridine-2-carboxamide | see above | see above | ++++ | ++++ | ++++ |

TABLE 24-continued

| | | | | | | |
|---|---|---|---|---|---|---|
| 10-14 | (R)-3-amino-N-(5-fluoro-7-(piperazin-1-yl)chroman-3-yl)-6-methyl-4-(trifluoromethyl)thieno[2,3-b]pyridine-2-carboxamide | see above | see above | ++++ | ++ | +++ |
| 10-15 | 3-amino-N-[(3R)-5-fluoro-7-(piperazin-1-yl)-3,4-dihydro-2H-1-benzopyran-3-yl]-N,6-dimethylthieno[2,3-b]pyridine-2-carboxamide | see above | see above | + | | + |
| 10-16 | 3-amino-N-[(3S)-5-fluoro-7-(piperazin-1-yl)-3,4-dihydro-2H-1-benzopyran-3-yl]-N,6-dimethylthieno[2,3-b]pyridine-2-carboxamide | see above | see above | + | | |
| 11-15 | 3-amino-6-methyl-N-((3R,4R)-4-methyl-7-(piperazin-1-yl)chroman-3-yl)thieno[2,3-b]pyridine-2-carboxamide | see above | see above | + | + | + |
| 11-16 | 3-amino-6-methyl-N-((3R,4S)-4-methyl-7-(piperazin-1-yl)chroman-3-yl)thieno[2,3-b]pyridine-2-carboxamide | see above | see above | + | + | + |
| 11-17 | 3-amino-6-methyl-N-((3S,4S)-4-methyl-7-(piperazin-1-yl)chroman-3-yl)thieno[2,3-b]pyridine-2-carboxamide | see above | see above | + | + | + |
| 11-18 | 3-amino-6-methyl-N-((3S,4R)-4-methyl-7-(piperazin-1-yl)chroman-3-yl)thieno[2,3-b]pyridine-2-carboxamide | see above | see above | ++ | + | ++ |
| 11-19 | (S)-7-amino-3-methyl-N-(6-(piperazin-1-yl)-1,2,3,4-tetrahydronaphthalen-2-yl)thieno[2,3-b]pyrazine-6-carboxamide | see above | see above | | ++ | ++ |
| 11-20 | (R)-7-amino-3-methyl-N-(6-(piperazin-1-yl)-1,2,3,4-tetrahydronaphthalen-2-yl)thieno[2,3-b]pyrazine-6-carboxamide | see above | see above | ++ | + | + |
| 11-21 | (S)-3-amino-6-methyl-N-(6-(piperazin-1-yl)-1,2,3,4-tetrahydronaphthalen-2-yl)thieno[2,3-b]pyridine-2-carboxamide | see above | see above | ++ | ++ | + |
| 11-22 | (R)-3-amino-6-methyl-N-(6-(piperazin-1-yl)-1,2,3,4-tetrahydronaphthalen-2-yl)thieno[2,3-b]pyridine-2-carboxamide | see above | see above | +++ | ++ | ++ |
| 11-23 | N-((2R)-6-(3,8-diazabicyclo[3.2.1]octan-3-yl)-1,2,3,4-tetrahydronaphthalen-2-yl)-7-ethyl-7H-pyrrolo[2,3-c]pyridazine-3-carboxamide | see above | see above | ++ | + | + |
| 11-24 | N-((2S)-6-(3,8-diazabicyclo[3.2.1]octan-3-yl)-1,2,3,4-tetrahydronaphthalen-2-yl)-7-ethyl-7H-pyrrolo[2,3-c]pyridazine-3-carboxamide | see above | see above | ++ | + | + |
| 11-25 | 7-amino-3-methyl-N-((S)-6-((S)-3-(methylamino)pyrrolidin-1-yl)-1,2,3,4-tetrahydronaphthalen-2-yl)thieno[2,3-b]pyrazine-6-carboxamide | see above | see above | +++ | ++ | ++ |
| 11-26 | 7-amino-3-methyl-N-((R)-6-((S)-3-(methylamino)pyrrolidin-1-yl)-1,2,3,4-tetrahydronaphthalen-2-yl)thieno[2,3-b]pyrazine-6-carboxamide | see above | see above | + | + | + |
| 11-27 | 7-amino-3-methyl-N-((S)-6-((R)-3-(methylamino)pyrrolidin-1-yl)-1,2,3,4-tetrahydronaphthalen-2-yl)thieno[2,3-b]pyrazine-6-carboxamide | see above | see above | +++ | ++ | ++ |
| 11-28 | 7-amino-3-methyl-N-((R)-6-((R)-3-(methylamino)pyrrolidin-1-yl)-1,2,3,4-tetrahydronaphthalen-2-yl)thieno[2,3-b]pyrazine-6-carboxamide | see above | see above | ++ | + | + |
| 11-29 | N-((S)-6-((1S,4S)-2,5-diazabicyclo[2.2.1]heptan-2-yl)-1,2,3,4-tetrahydronaphthalen-2-yl)-7-amino-3-methylthieno[2,3-b]pyrazine-6-carboxamide | see above | see above | +++ | ++ | ++ |
| 11-30 | N-((R)-6-((1S,4S)-2,5-diazabicyclo[2.2.1]heptan-2-yl)-1,2,3,4-tetrahydronaphthalen-2-yl)-7-amino-3-methylthieno[2,3-b]pyrazine-6-carboxamide | see above | see above | ++ | ++ | ++ |
| 11-31 | N-((S)-6-((1R,4R)-2,5-diazabicyclo[2.2.1]heptan-2-yl)-1,2,3,4-tetrahydronaphthalen-2-yl)-7-amino-3-methylthieno[2,3-b]pyrazine-6-carboxamide | see above | see above | +++ | ++ | ++ |
| 11-32 | N-((R)-6-((1R,4R)-2,5-diazabicyclo[2.2.1]heptan-2-yl)-1,2,3,4-tetrahydronaphthalen-2-yl)-7-amino-3-methylthieno[2,3-b]pyrazine-6-carboxamide | see above | see above | ++ | ++ | ++ |

TABLE 24-continued

| | | | | | | |
|---|---|---|---|---|---|---|
| 11-33 | (S)-6-amino-2-methyl-N-(6-(piperazin-1-yl)-1,2,3,4-tetrahydronaphthalen-2-yl) thieno[2,3-d]thiazole-5-carboxamide | see above | see above | ++ | + | ++ |
| 11-34 | (R)-6-amino-2-methyl-N-(6-(piperazin-1-yl)-1,2,3,4-tetrahydronaphthalen-2-yl)thieno[2,3-d]thiazole-5-carboxamide | see above | see above | +++ | ++ | + |
| 11-35 | N-((2S)-6-(3,6-diazabicyclo[3.1.1]heptan-6-yl)-1,2,3,4-tetrahydronaphthalen-2-yl)-3-amino-6-methylthieno[2,3-b]pyridine-2-carboxamide | see above | see above | ++++ | ++ | ++ |
| 11-36 | N-((2R)-6-(3,6-diazabicyclo[3.1.1]heptan-6-yl)-1,2,3,4-tetrahydronaphthalen-2-yl)-3-amino-6-methylthieno[2,3-b]pyridine-2-carboxamide | see above | see above | ++ | ++ | ++ |
| 11-37 | (R)-7-amino-N-(8-fluoro-6-(piperazin-1-yl)-1,2,3,4-tetrahydronaphthalen-2-yl)-3-methylthieno[2,3-b]pyrazine-6-carboxamide | see above | see above | ++ | + | + |
| 11-38 | (S)-7-amino-N-(8-fluoro-6-(piperazin-1-yl)-1,2,3,4-tetrahydronaphthalen-2-yl)-3-methylthieno[2,3-b]pyrazine-6-carboxamide | see above | see above | +++ | +++ | ++ |
| 11-39 | N-((2S)-6-(9-oxa-3,7-diazabicyclo[3.3.1]nonan-3-yl)-8-fluoro-1,2,3,4-tetrahydronaphthalen-2-yl)-3-amino-6-methylthieno[2,3-b]pyridine-2-carboxamide | see above | see above | ++ | ++ | + |
| 11-40 | N-((2R)-6-(9-oxa-3,7-diazabicyclo[3.3.1]nonan-3-yl)-8-fluoro-1,2,3,4-tetrahydronaphthalen-2-yl)-3-amino-6-methylthieno[2,3-b]pyridine-2-carboxamide | see above | see above | | ++++ | +++ |
| 14-5 | N-((2R)-6-(3,8-diazabicyclo[3.2.1]octan-3-yl)-5-cyano-1,2,3,4-tetrahydronaphthalen-2-yl)-7-amino-3-methylthieno[2,3-b]pyrazine-6-carboxamide | see above | see above | ++++ | +++ | +++ |
| 14-6 | N-((2S)-6-(3,8-diazabicyclo[3.2.1]octan-3-yl)-5-cyano-1,2,3,4-tetrahydronaphthalen-2-yl)-7-amino-3-methylthieno[2,3-b]pyrazine-6-carboxamide | see above | see above | ++ | + | + |
| 14-7 | N-((2R)-6-(3,8-diazabicyclo[3.2.1]octan-3-yl)-7-cyano-1,2,3,4-tetrahydronaphthalen-2-yl)-7-amino-3-methylthieno[2,3-b]pyrazine-6-carboxamide | see above | see above | ++ | ++ | + |
| 14-8 | N-((2S)-6-(3,8-diazabicyclo[3.2.1]octan-3-yl)-7-cyano-1,2,3,4-tetrahydronaphthalen-2-yl)-7-amino-3-methylthieno[2,3-b]pyrazine-6-carboxamide | see above | see above | ++++ | ++++ | +++ |
| 14-9 | (R)-3-amino-N-(5-cyano-8-fluoro-6-(piperazin-1-yl)-1,2,3,4-tetrahydronaphthalen-2-yl)-6-methylthieno[2,3-b]pyridine-2-carboxamide | see above | see above | ++ | + | + |
| 14-10 | (S)-3-amino-N-(5-cyano-8-fluoro-6-(piperazin-1-yl)-1,2,3,4-tetrahydronaphthalen-2-yl)-6-methylthieno[2,3-b]pyridine-2-carboxamide | see above | see above | ++++ | +++ | ++ |
| 14-11 | (R)-7-amino-N-(5-cyano-8-fluoro-6-(piperazin-1-yl)-1,2,3,4-tetrahydronaphthalen-2-yl)-3-methylthieno[2,3-b]pyrazine-6-carboxamide | see above | see above | ++++ | | ++ |
| 14-12 | (S)-7-amino-N-(5-cyano-8-fluoro-6-(piperazin-1-yl)-1,2,3,4-tetrahydronaphthalen-2-yl)-3-methylthieno[2,3-b]pyrazine-6-carboxamide | see above | see above | ++ | | + |
| 14-13 | (R)-6-amino-N-(5-cyano-8-fluoro-6-(piperazin-1-yl)-1,2,3,4-tetrahydronaphthalen-2-yl)-2-methylthieno[2,3-d]thiazole-5-carboxamide | see above | see above | ++ | | + |
| 14-14 | (S)-6-amino-N-(5-cyano-8-fluoro-6-(piperazin-1-yl)-1,2,3,4-tetrahydronaphthalen-2-yl)-2-methylthieno[2,3-d]thiazole-5-carboxamide | see above | see above | ++++ | | ++ |

TABLE 24-continued

| | | | | | |
|---|---|---|---|---|---|
| 14-15 | 3-amino-N-[(2S)-5-cyano-8-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | see above | see above | ++++ | ++++ |
| 14-16 | 3-amino-N-[(2R)-5-cyano-8-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | see above | see above | +++ | ++ |
| 14-17 | 3-amino-N-[(2S)-5-cyano-6-(3,8-diazabicyclo[3.2.1]octan-3-yl}-8-fluoro-1,2,3,4-tetrahydronaphthalen-2-yl]-6-methylthieno[2,3-b]pyridine-2-carboxamide | see above | see above | ++++ | ++++ |
| 14-18 | 3-amino-N-[(2R)-5-cyano-6-{3,8-diazabicyclo[3.2.1]octan-3-yl}-8-fluoro-1,2,3,4-tetrahydronaphthalen-2-yl]-6-methylthieno[2,3-b]pyridine-2-carboxamide | see above | see above | +++ | + |
| 14-19 | 7-amino-N-[(2S)-5-cyano-6-{3,8-diazabicyclo[3.2.1]octan-3-yl}-8-fluoro-1,2,3,4-tetrahydronaphthalen-2-yl]-3-methylthieno[2,3-b]pyrazine-6-carboxamide | see above | see above | ++++ | +++ |
| 14-20 | 7-amino-N-[(2R)-5-cyano-6-{3,8-diazabicyclo[3.2.1]octan-3-yl}-8-fluoro-1,2,3,4-tetrahydronaphthalen-2-yl]-3-methylthieno[2,3-b]pyrazine-6-carboxamide | see above | see above | ++ | + |
| 14-21 | 6-amino-N-[(2S)-5-cyano-6-{3,8-diazabicyclo[3.2.1]octan-3-yl}-8-fluoro-1,2,3,4-tetrahydronaphthalen-2-yl]-2-methylthieno[2,3-d][1,3]thiazole-5-carboxamide | see above | see above | ++++ | +++ |
| 14-22 | 6-amino-N-[(2R)-5-cyano-6-{3,8-diazabicyclo[3.2.1]octan-3-yl}-8-fluoro-1,2,3,4-tetrahydronaphthalen-2-yl]-2-methylthieno[2,3-d][1,3]thiazole-5-carboxamide | see above | see above | ++ | + |
| 14-23 | 3-amino-N-[(2S)-6-[(3S,4S)-3-amino-4-methoxypyrrolidin-1-yl]-5-cyano-8-fluoro-1,2,3,4-tetrahydronaphthalen-2-yl]-6-methylthieno[2,3-b]pyridine-2-carboxamide | see above | see above | ++++ | ++ |
| 14-24 | 3-amino-N-[(2R)-6-[(3S,4S)-3-amino-4-methoxypyrrolidin-1-yl]-5-cyano-8-fluoro-1,2,3,4-tetrahydronaphthalen-2-yl]-6-methylthieno[2,3-b]pyridine-2-carboxamide | see above | see above | ++ | + |
| 21-1 | N-((2R)-6-(3,8-diazabicyclo[3.2.1]octan-3-yl)-5-fluoro-1,2,3,4-tetrahydronaphthalen-2-yl)-3-amino-6-methylthieno[2,3-b]pyridine-2-carboxamide | see above | see above | +++ | ++ | + |
| 21-2 | N-((2S)-6-(3,8-diazabicyclo[3.2.1]octan-3-yl)-5-fluoro-1,2,3,4-tetrahydronaphthalen-2-yl)-3-amino-6-methylthieno[2,3-b]pyridine-2-carboxamide | see above | see above | ++++ | ++ | ++ |
| 21-3 | N-((2R)-6-(3,8-diazabicyclo[3.2.1]octan-3-yl)-7-fluoro-1,2,3,4-tetrahydronaphthalen-2-yl)-3-amino-6-methylthieno[2,3-b]pyridine-2-carboxamide | see above | see above | ++++ | ++++ | +++ |
| 21-4 | N-((2S)-6-(3,8-diazabicyclo[3.2.1]octan-3-yl)-7-fluoro-1,2,3,4-tetrahydronaphthalen-2-yl)-3-amino-6-methylthieno[2,3-b]pyridine-2-carboxamide | see above | see above | ++ | ++ | + |
| 21-5 | (R)-3-amino-N-(5-fluoro-6-(piperazin-1-yl)-1,2,3,4-tetrahydronaphthalen-2-yl)-6-methylthieno[2,3-b]pyridine-2-carboxamide | see above | see above | ++++ | ++++ | +++ |
| 21-6 | (S)-3-amino-N-(5-fluoro-6-(piperazin-1-yl)-1,2,3,4-tetrahydronaphthalen-2-yl)-6-methylthieno[2,3-b]pyridine-2-carboxamide | see above | see above | ++ | ++ | + |
| 21-7 | (R)-3-amino-N-(7-fluoro-6-(piperazin-1-yl)-1,2,3,4-tetrahydronaphthalen-2-yl)-6-methylthieno[2,3-b]pyridine-2-carboxamide | see above | see above | +++ | +++ | ++ |

TABLE 24-continued

| | | | | | | |
|---|---|---|---|---|---|---|
| 21-8 | (S)-3-amino-N-(7-fluoro-6-(piperazin-1-yl)-1,2,3,4-tetrahydronaphthalen-2-yl)-6-methylthieno[2,3-b]pyridine-2-carboxamide | see above | see above | ++ | + | + |
| 21-9 | (S)-7-amino-N-(5-fluoro-6-(piperazin-1-yl)-1,2,3,4-tetrahydronaphthalen-2-yl)-3-methylthieno[2,3-b]pyrazine-6-carboxamide | see above | see above | +++ | ++ | ++ |
| 21-10 | (R)-7-amino-N-(5-fluoro-6-(piperazin-1-yl)-1,2,3,4-tetrahydronaphthalen-2-yl)-3-methylthieno[2,3-b]pyrazine-6-carboxamide | see above | see above | + | + | + |
| 21-11 | (S)-7-amino-N-(7-fluoro-6-(piperazin-1-yl)-1,2,3,4-tetrahydronaphthalen-2-yl)-3-methylthieno[2,3-b]pyrazine-6-carboxamide | see above | see above | ++ | ++ | + |
| 21-12 | (R)-7-amino-N-(7-fluoro-6-(piperazin-1-yl)-1,2,3,4-tetrahydronaphthalen-2-yl)-3-methylthieno[2,3-b]pyrazine-6-carboxamide | see above | see above | ++++ | ++++ | ++ |
| 22-1 | (S)-3-amino-N-(5,8-difluoro-6-(piperazin-1-yl)-1,2,3,4-tetrahydronaphthalen-2-yl)-6-methylthieno[2,3-b]pyridine-2-carboxamide | see above | see above | ++ | ++ | + |
| 22-2 | (R)-3-amino-N-(5,8-difluoro-6-(piperazin-1-yl)-1,2,3,4-tetrahydronaphthalen-2-yl)-6-methylthieno[2,3-b]pyridine-2-carboxamide | see above | see above | ++++ | +++ | +++ |
| 22-3 | N-((2S)-6-(9-oxa-3,7-diazabicyclo[3.3.1]nonan-3-yl)-5,8-difluoro-1,2,3,4-tetrahydronaphthalen-2-yl)-3-amino-6-methylthieno[2,3-b]pyridine-2-carboxamide | see above | see above | ++ | | + |
| 22-4 | N-((2R)-6-(9-oxa-3,7-diazabicyclo[3.3.1]nonan-3-yl)-5,8-difluoro-1,2,3,4-tetrahydronaphthalen-2-yl)-3-amino-6-methylthieno[2,3-b]pyridine-2-carboxamide | see above | see above | ++++ | | ++++ |
| 22-5 | 3-amino-N-[(2S)-6-{3,8-diazabicyclo[3.2.1]octan-3-yl}-5,8-difluoro-1,2,3,4-tetrahydronaphthalen-2-yl]-6-methylthieno[2,3-b]pyridine-2-carboxamide | see above | see above | ++++ | | ++++ |
| 22-6 | 3-amino-N-[(2R)-6-{3,8-diazabicyclo[3.2.1]octan-3-yl}-5,8-difluoro-1,2,3,4-tetrahydronaphthalen-2-yl]-6-methylthieno[2,3-b]pyridine-2-carboxamide | see above | see above | ++ | | + |
| 23-1 | 7-amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide | see above | see above | ++ | | + |
| 23-2 | 7-amino-N-[(6R)-2-[(3S,4S)-3-amino-4-methoxypyrrolidin-1-yl]-5,6,7,8-tetrahydroquinolin-6-yl]-3-methylthieno[2,3-b]pyrazine-6-carboxamide | see above | see above | + | | + |
| 23-3 | 3-amino-N-[(6S)-2-[(3S,4S)-3-amino-4-methoxypyrrolidin-1-yl]-5,6,7,8-tetrahydroquinolin-6-yl]-4,6-dimethylthieno[2,3-b]pyridine-2-carboxamide | see above | see above | +++ | | + |
| 23-4 | 3-amino-N-[(6S)-2-[(3S,4S)-3-amino-4-methoxypyrrolidin-1-yl]-5,6,7,8-tetrahydroquinolin-6-yl]-6-methylthieno[2,3-b]pyridine-2-carboxamide | see above | see above | +++ | | + |
| 23-5 | 3-amino-N-[(6R)-2-[(3S,4S)-3-amino-4-methoxypyrrolidin-1-yl]-5,6,7,8-tetrahydroquinolin-6-yl]-6-methylthieno[2,3-b]pyridine-2-carboxamide | see above | see above | ++ | | + |
| 23-6 | 7-amino-3-methyl-N-[(6S)-2-(piperazin-1-yl)-5,6,7,8-tetrahydroquinolin-6-yl]thieno[2,3-b]pyrazine-6-carboxamide | see above | see above | +++ | | ++ |
| 23-7 | 3-amino-6-methyl-N-[(6S)-2-(piperazin-1-yl)-5,6,7,8-tetrahydroquinolin-6-yl]thieno[2,3-b]pyridine-2-carboxamide | see above | see above | ++++ | | ++ |

TABLE 24-continued

| | | | | | |
|---|---|---|---|---|---|
| 23-8 | 3-amino-6-methyl-N-[(6R)-2-(piperazin-1-yl)-5,6,7,8-tetrahydroquinolin-6-yl]thieno[2,3-b]pyridine-2-carboxamide | see above | see above | +++ | + |
| 23-9 | 6-amino-2-methyl-N-[(6S)-2-(piperazin-1-yl)-5,6,7,8-tetrahydroquinolin-6-yl]thieno[2,3-d][1,3]thiazole-5-carboxamide | see above | see above | +++ | + |
| 23-10 | 3-amino-N-[(6S)-2-{3,6-diazabicyclo[3.1.1]heptan-3-yl}-5,6,7,8-tetrahydroquinolin-6-yl]-6-methylthieno[2,3-b]pyridine-2-carboxamide | see above | see above | +++ | ++ |
| 23-11 | 7-amino-N-[(6S)-2-{3,6-diazabicyclo[3.1.1]heptan-3-yl}-5,6,7,8-tetrahydroquinolin-6-yl]-3-methylthieno[2,3-b]pyrazine-6-carboxamide | see above | see above | ++ | ++ |
| 23-12 | 3-amino-N-[(6S)-2-{3,8-diazabicyclo[3.2.1]octan-3-yl}-5,6,7,8-tetrahydroquinolin-6-yl]-6-methylthieno[2,3-b]pyridine-2-carboxamide | see above | see above | ++++ | ++ |
| 23-13 | 7-amino-N-[(6S)-2-{3,8-diazabicyclo[3.2.1]octan-3-yl}-5,6,7,8-tetrahydroquinolin-6-yl]-3-methylthieno[2,3-b]pyrazine-6-carboxamide | see above | see above | ++++ | ++ |
| 23-14 | 3-amino-4,6-dimethyl-N-[(6S)-2-(piperazin-1-yl)-5,6,7,8-tetrahydroquinolin-6-yl]thieno[2,3-b]pyridine-2-carboxamide | see above | see above | ++++ | ++ |
| 23-15 | 3-amino-6-methyl-N-[(6S)-2-[(3S)-3-methylpiperazin-1-yl]-5,6,7,8-tetrahydroquinolin-6-yl]thieno[2,3-b]pyridine-2-carboxamide | see above | see above | ++++ | ++ |
| 23-16 | 3-amino-6-methyl-N-[(6S)-2-[(3R)-3-methylpiperazin-1-yl]-5,6,7,8-tetrahydroquinolin-6-yl]thieno[2,3-b]pyridine-2-carboxamide | see above | see above | ++++ | ++ |
| 23-17 | 3-amino-N-[(6S)-4-fluoro-2-(piperazin-1-yl)-5,6,7,8-tetrahydroquinolin-6-yl]-6-methylthieno[2,3-b]pyridine-2-carboxamide | see above | see above | ++++ | ++ |
| 23-18 | 3-amino-N-[(6S)-2-{3,8-diazabicyclo[3.2.1]octan-3-yl}-4-fluoro-5,6,7,8-tetrahydroquinolin-6-yl]-6-methylthieno[2,3-b]pyridine-2-carboxamide | see above | see above | ++++ | ++ |
| 24-1 | 3-amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide | see above | see above | +++ | + |
| 24-2 | 3-amino-N-[(6S)-2-[(3S,4S)-3-amino-4-(methoxymethyl)pyrrolidin-1-yl]-5,6,7,8-tetrahydroquinolin-6-yl]-6-methylthieno[2,3-b]pyridine-2-carboxamide | see above | see above | +++ | ++ |
| 25 | 3-amino-N-[(6S)-2-[(3S,4R)-3-amino-4-(difluoromethyl)pyrrolidin-1-yl]-5,6,7,8-tetrahydroquinolin-6-yl]-6-methylthieno[2,3-b]pyridine-2-carboxamide | see above | see above | +++ | ++ |
| 26-1 | 3-amino-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide | see above | see above | +++ | |
| 26-2 | 3-amino-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide | see above | see above | +++ | |
| 27-1 | 3-amino-N-[(6S)-2-[(3R,4R)-3-amino-4-(fluoromethyl)pyrrolidin-1-yl]-5,6,7,8-tetrahydroquinolin-6-yl]-6-methylthieno[2,3-b]pyridine-2-carboxamide | see above | see above | +++ | |

TABLE 24-continued

| | | | | | |
|---|---|---|---|---|---|
| 27-2 | 3-amino-N-[(6S)-2-[(3S,4S)-3-amino-4-(fluoromethyl)pyrrolidin-1-yl]-5,6,7,8-tetrahydroquinolin-6-yl]-6-methylthieno[2,3-b]pyridine-2-carboxamide | see above | see above | +++ | |
| 28-1 | 3-amino-N-[(6S)-2-[(3S,4S)-3-amino-4-(2-methoxyethoxy)pyrrolidin-1-yl]-5,6,7,8-tetrahydroquinolin-6-yl]-6-methylthieno[2,3-b]pyridine-2-carboxamide | see above | see above | ++ | |
| 28-2 | 3-amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide | see above | see above | ++ | |
| 29-1 | 3-amino-N-[(6S)-2-[(9S)-9-amino-1,4-dioxa-7-azaspiro[4.4]nonan-7-yl]-5,6,7,8-tetrahydroquinolin-6-yl]-6-methylthieno[2,3-b]pyridine-2-carboxamide | see above | see above | ++ | |
| 29-2 | 3-amino-N-[(6S)-2-[(9R)-9-amino-1,4-dioxa-7-azaspiro[4.4]nonan-7-yl]-5,6,7,8-tetrahydroquinolin-6-yl]-6-methylthieno[2,3-b]pyridine-2-carboxamide | see above | see above | ++ | |
| 30-1 | 3-amino-N-[(6S)-3-fluoro-2-(piperazin-1-yl)-5,6,7,8-tetrahydroquinolin-6-yl]-6-methylthieno[2,3-b]pyridine-2-carboxamide | see above | see above | ++++ | ++ |
| 30-2 | 3-amino-N-[(6R)-3-fluoro-2-(piperazin-1-yl)-5,6,7,8-tetrahydroquinolin-6-yl]-6-methylthieno[2,3-b]pyridine-2-carboxamide | see above | see above | ++ | + |
| 31-1 | 3-amino-N-[(6S)-2-[(3S,4S)-3-amino-4-(propan-2-yloxy)pyrrolidin-1-y[]-5,6,7,8-tetrahydroquinazolin-6-yl]-4,6-dimethylthieno[2,3-b]pyridine-2-carboxamide | see above | see above | +++ | |
| 31-2 | 3-amino-N-[(6R)-2-[(3S,4S)-3-amino-4-(propan-2-yloxy)pyrrolidin-1-yl]-5,6,7,8-tetrahydroquinazolin-6-yl]-4,6-dimethylthieno[2,3-b]pyridine-2-carboxamide | see above | see above | + | |
| 31-3 | 3-amino-6-methyl-N-[(6'S)-2'-(piperazin-1-yl)-6',7'-dihydro-5'H-spiro[cyclopropane-1,8'-quinoline]-6'-yl]thieno[2,3-b]pyridine-2-carboxamide | see above | see above | +++ | + |
| 31-4 | 3-amino-6-methyl-N-[(6'R)-2'-(piperazin-1-yl)-6',7'-dihydro-5'H-spiro[cyclopropane-1,8'-quinoline]-6'-yl]thieno[2,3-b]pyridine-2-carboxamide | see above | see above | ++++ | ++ |
| 32-1 | 3-amino-6-methyl-N-[(7S)-3-(piperazin-1-yl)-5,6,7,8-tetrahydroisoquinolin-7-yl]thieno[2,3-b]pyridine-2-carboxamide | see above | see above | +++ | |
| 32-2 | 3-amino-6-methyl-N-[(7R)-3-(piperazin-1-yl)-5,6,7,8-tetrahydroisoquinolin-7-yl]thieno[2,3-b]pyridine-2-carboxamide | see above | see above | ++ | |
| 33-1 | 3-amino-N-[(3R)-5-fluoro-7-(piperazin-1-yl)-3,4-dihydro(4,4-Â²Hâ‚‚)-2H-1-benzopyran-3-yl]-6-methylthieno[2,3-b]pyridine-2-carboxamide | see above | see above | ++++ | ++ |
| 33-2 | 3-amino-N-[(3S)-5-fluoro-7-(piperazin-1-yl)-3,4-dihydro(4,4-Â²Hâ‚‚)-2H-1-benzopyran-3-yl]-6-methylthieno[2,3-b]pyridine-2-carboxamide | see above | see above | ++ | + |
| 33-3 | 3-amino-N-[(3R)-7-[(1R,6S)-3,8-diazabicyclo[4.2.0]octan-8-yl]-3,4-dihydro-2H-1-benzopyran-3-yl]-6-methylthieno[2,3-b]pyridine-2-carboxamide | see above | see above | ++++ | +++ |
| 33-4 | 3-amino-N-[(3R)-7-[(1S,6R)-3,8-diazabicyclo[4.2.0]octan-8-yl]-3,4-dihydro-2H-1-benzopyran-3-yl]-6-methylthieno[2,3-b]pyridine-2-carboxamide | see above | see above | ++++ | ++ |
| 34 | 3-amino-N-[(3R)-7-(4-cyano-1,1-dioxo-1A6-thian-4-yl)-3,4-dihydro-2H-1-benzopyran-3-yl]-6-methylthieno[2,3-b]pyridine-2-carboxamide | see above | see above | ++++ | ++++ |

TABLE 24-continued

| | | | | | | |
|---|---|---|---|---|---|---|
| 35 | 3-amino-6-methyl-N-[(3R)-5,6,8-trifluoro-7-(piperazin-1-yl)-3,4-dihydro-2H-1-benzopyran-3-yl]thieno[2,3-b]pyridine-2-carboxamide | see above | see above | ++++ | | +++ |
| 36 | (R)-7-amino-2-ethyl-N-(7-(piperazin-1-yl)chroman-3-yl)thieno[2,3-b]pyrazine-6-carboxamide | 439 | (DMSO-d6, 400 MHz) δ (ppm): 8.68 (s, 1H), 7.83-7.81 (br s, 1H), 6.95-6.91 (m, 3H), 6.52 (dd, J = 2.4, 8.4 Hz, 1H), 6.32 (s, 1H), 4.35-4.26 (m, 1H), 4.19-4.16 (m, 1H), 3.85-3.80 (m, 1H), 3.46-3.33 (m, 1H), 3.03-3.01 (m, 4H), 2.98-2.94 (m, 2H), 2.93-2.87 (m, 6H), 1.37-1.35 (m, 3H). | ++ | ++ | ++ |
| 37 | (S)-7-amino-2-ethyl-N-(7-(piperazin-1-yl)chroman-3-yl)thieno[2,3-b]pyrazine-6-carboxamide | 439 | (DMSO-d6, 400 MHz) δ (ppm): 8.68 (s, 1H), 7.83-7.81 (br s, 1H), 6.94-6.91 (m, 3H), 6.51 (dd, J = 2.4, 8.4 Hz, 1H), 6.30 (s, 1H), 4.35-4.26 (m, 1H), 4.19-4.15 (m, 1H), 3.85-3.80 (m, 1H), 3.44-3.33 (m, 1H), 3.03-2.93 (m, 6H), 2.88-2.81 (m, 6H), 1.37-1.35 (m, 3H). | + | + | + |
| 38 | (R)-1-(difluoromethyl)-N-(7-(piperazin-1-yl)chroman-3-yl)-1H-pyrrolo[2,3-b]pyridine-5-carboxamide | 428 | (CD2Cl2, 300 MHz) δ (ppm): 8.66-8.71 (m, 1 H), 8.29-8.33 (m, 1 H), 7.86 (t, J = 60 Hz, 1 H), 7.58 (d, J = 3.81 Hz, 1 H), 6.95 (d, J = 8.50 Hz, 1 H), 6.72 (dd, J = 3.81, 0.59 Hz, 1 H), 6.52 (dd, J = 8.50, 2.64 Hz, 1 H), 6.46 (br d, J = 7.62 Hz, 1 H), 6.39 (d, J = 2.64 Hz, 1 H), 4.60-4.68 (m, 1 H), 4.16-4.28 (m, 2 H), 3.10-3.20 (m, 2 H), 3.02-3.08 (m, 3 H), 2.92-2.99 (m, 3 H), 2.77-2.86 (m, 2 H). | ++ | + | + |
| 39 | (S)-1-(difluoromethyl)-N-(7-(piperazin-1-yl)chroman-3-yl)-1H-pyrrolo[2,3-b]pyridine-5-carboxamide | 428 | (CD2Cl2, 300 MHz) δ (ppm): 8.69 (d, J = 1.76 Hz, 1 H), 8.31 (d, J = 2.05 Hz, 1 H), 7.86 (t, J = 60 Hz, 1 H), 7.58 (d, J = 3.81 Hz, 1 H), 6.95 (d, J = 8.50 Hz, 1 H), 6.72 (dd, J = 4.10, 0.59 Hz, 1 H), 6.52 (dd, J = 8.35, 2.49 Hz, 1 H), 6.46 (br d, J = 7.92 Hz, 1 H), 6.39 (d, J = 2.64 Hz, 1 H), 4.59-4.69 (m, 1 H), 4.15-4.29 (m, 2 H), 3.10-3.21 (m, 2 H), 3.02-3.09 (m, 3 H), 2.92-3.00 (m, 3 H), 2.76-2.87 (m, 2 H). | + | + | + |
| 40 | N-((3R)-7-(3,8-diazabicyclo[3.2.1]octan-3-yl)-6-fluorochroman-3-yl)-7-amino-3-methylthieno[2,3-b]pyrazine-6-carboxamide | 469 | (MeOH-d4, 300 MHz) δ (ppm): 8.57 (s, 1H), 6.80 (d, J = 12.9 Hz, 1H), 6.42 (d, J = 7.8 Hz, 1H), 4.57-4.43 (m, 2H), 4.25-4.21 (m, 1H), 3.96-3.89 (m, 1H), 3.82-3.78 (m, 2H), 3.26-3.25 (m, 1H), 3.07-2.83 (m, 4H), 2.67 (s, 3H), 2.13-2.09 (m, 1H), 1.97-1.94 (m, 2H). | ++++ | +++ | +++ |
| 41 | N-((3S)-7-(3,8-diazabicyclo[3.2.1]octan-3-yl)-6-fluorochroman-3-yl)-7-amino-3-methylthieno[2,3-b]pyrazine-6-carboxamide | 469 | (MeOH-d4, 300 MHz) δ (ppm): 8.57 (s, 1H), 6.80 (d, J = 12.9 Hz, 1H), 6.42 (d, J = 7.8 Hz, 1H), 4.57-4.43 (m, 2H), 4.25-4.20 (m, 1H), 3.96-3.89 (m, 1H), 3.82-3.78 (m, 2H), 3.26-3.25 (m, 1H), 3.03-2.83 (m, 4H), 2.67 (s, 3H), 2.13-2.09 (m, 2H), 1.96-1.93 (m, 2H). | ++ | + | + |
| 42 | 3-amino-N-((S)-7-((3aS,6aS)-hexahydropyrrolo[3,4-c]pyrrol-2(1H)-yl)chroman-3-yl)-6-methylthieno[2,3-b]pyridine-2-carboxamide | 450 | (MeOH-d4, 300 MHz) δ (ppm): 8.20 (d, J = 8.4 Hz, 1H), 7.30 (d, J = 8.4 Hz, 1H), 6.88 (d, J = 8.4 Hz, 1H), 6.16 (dd, J = 2.4, 8.4 Hz, 1H), 6.00 (s, 1H), 4.48-4.37 (m, 1H), 4.24-4.21 (m, 1H), 3.92-3.87 (m, 1H), 3.63-3.45 (m, 2H), 3.41-3.35 (m, 2H), 3.14-3.08 (m, 2H), 3.02- | | ++ | ++ |

TABLE 24-continued

| | | | | | | |
|---|---|---|---|---|---|---|
| 43 | 3-amino-N-((R)-7-((3aR,6aR)-hexahydropyrrolo[3,4-c]pyrrol-2(1H)-yl)chroman-3-yl)-6-methylthieno[2,3-b]pyridine-2-carboxamide | 450 | (MeOH-d4, 300 MHz) δ (ppm): 8.10 (d, J = 8.4 Hz, 1H), 7.20 (d, J = 8.4 Hz, 1H), 6.79 (d, J = 8.4 Hz, 1H), 6.06 (dd, J = 2.4, 8.4 Hz, 1H), 5.9 (s, 1H), 4.38-4.27 (m, 1H), 4.16-4.08 (m, 1H), 3.81-3.78 (m, 1H), 3.38-3.33 (m, 2H), 3.28-3.24 (m, 2H), 3.02-2.97 (m, 2H), 2.92-2.68 (m, 4H), 2.56 (s, 3H), 2.38-2.27 (m, 2H). 2.78 (m, 4H), 2.63 (s, 3H), 2.46-2.38 (m, 2H). | ++ | + | + |
| 44 | 3-amino-N-((S)-7-((3aR,6aR)-hexahydropyrrolo[3,4-c]pyrrol-2(1H)-yl)chroman-3-yl)-6-methylthieno[2,3-b]pyridine-2-carboxamide | 450 | (MeOH-d4, 300 MHz) δ (ppm): 820 (d, J = 8.4 Hz, 1H), 7.30 (d, J = 8.4 Hz, 1H), 6.89 (d, J = 8.4 Hz, 1H), 6,16 (dd, J = 2.4, 8.4 Hz, 1H), 6.00 (s, 1H), 4.48-4.37 (m, 1H), 4.24-4.21 (m, 1H), 3.92-3.87 (m, 1H), 3.63-3.45 (m, 2H), 3.41-3.35 (m, 2H), 3.14-3.08 (m, 2H), 3.02-2.78 (m, 4H), 2.63 (s, 3H), 2.48-2.38 (m, 2H). | + | + | + |
| 45 | (R)-6-amino-2-cyclopropyl-N-(7-(piperazin-1-yl)chroman-3-yl)thieno[2,3-d]thiazole-5-carboxamide | 456 | (DMSO-d6, 300 MHz) δ (ppm): 7.40 (br s, 1H), 7.11 (br s, 2H), 6.91 (d, J = 8.4 Hz, 1H), 6.49 (dd, J = 2.4, 8.4 Hz, 1H), 6.29 (s, 1H), 4.24-4.11(m, 2H), 3.77 (t, J = 9.9 Hz, 1H), 3.00-2.97 (m, 4H), 2.84-2.82 (m, 6H), 2.54-2.51 (m, 1H), 1.23-1.18 (m, 1H), 1.11-1.09 (m, 2H). | +++ | ++ | ++ |
| 46 | N-((3S)-7-(3,8-diazabicyclo[3.2.1]octan-3-yl)-6-fluorochroman-3-yl)-6-amino-2-methylthieno[2,3-d]thiazole-5-carboxamide | 474 | (MeOH-d4, 300 MHz) δ (ppm): 6.80 (d, J = 12.9 Hz, 1H), 6.43 (d, J = 7.5 Hz, 1H), 4.62-4.59 (m, 1H), 4.44-4.35 (m, 1H), 4.23-4.19 (m, 1H), 3.92-3.85 (m, 2H), 3.31-3.29 (m, 2H), 3.08-2.78 (m, 7H), 2.17-2.15 (m, 2H), 2.09-1.91 (m, 2H). | ++++ | ++ | ++ |
| 47 | N-((3R)-7-(3,8-diazabicyclo[3.2.1]octan-3-yl)-6-fluorochroman-3-yl)-6-amino-2-methylthieno[2,3-d]thiazole-5-carboxamide | 474 | (MeOH-d4, 300 MHz) δ (ppm): 6.75 (d, J = 13.2 Hz, 1H), 6.36 (d, J = 7.5 Hz, 1H), 4.41-4.34 (m, 1H), 4.21-4.17 (m, 1H), 3.90-3.84 (m, 2H), 3.54-3.51 (m, 2H), 3.20-3.15 (m, 2H), 2.99-2.84 (m, 7H), 2.01-1.97 (m, 2H), 1.91-1.84 (m, 2H). | ++ | + | + |
| 48 | (R)-3-amino-N-(5-chloro-7-(piperazin-1-yl)chroman-3-yl)-6-methylthieno[2,3-b]pyridine-2-carboxamide | 458, 460 | (DMSO-d6, 300 MHz) δ (ppm): 8.33 (d, J = 8.4 Hz, 1H), 7.60 (br s, 1H), 7.31 (d, J = 8.4 Hz, 1H), 7.22 (br s, 2H), 6.64 (s, 1H), 6.33 (s, 1H), 4.36-4.27 (m, 1H), 4.17-4.14 (m, 1H), 3.85-3.79 (m, 1H), 3.08-3.01 (m, 5H), 2.97-2.74 (m, 6H), 2.58 (s, 3H). | ++++ | +++ | +++ |
| 49 | (S)-3-amino-N-(5-chloro-7-(piperazin-1-yl)chroman-3-yl)-6-methylthieno[2,3-b]pyridine-2-carboxamide | 458, 460 | (DMSO-d6, 300 MHz) δ (ppm): 8.33 (d, J = 8.7 Hz, 1H), 7.60 (br s, 1H), 7.31 (d, J = 8.7 Hz, 1H), 7.23 (br s, 2H), 6.64 (s, 1H), 6.34 (s, 1H), 4.36-4.27 (m, 1H), 4.17-4.14 (m, 1H), 3.85-3.79 (m, 1H), 3.08-3.01 (m, 5H), 2.97-2.74 (m, 6H), 2.58 (s, 3H). | ++ | + | + |
| 50 | N-((3R)-7-(3,8-diazabicyclo[3.2.1]octan-3-yl)chroman-3-yl)-5,6,7,8-tetrahydro-1,8-naphthyridine-3-carboxamide | 420 | (DMSO-d6, 400 MHz) δ (ppm): 8.31 (s, 1H), 7.96 (br s, 1H), 7.62 (s, 1H), 7.06 (s, 1H), 6.87 (d, J = 8.4 Hz, 1H), 6.37 (d, J = 8.0 Hz, 1H), 6.16 (s, 1H), 4.23-4.21 (m, 1H), 4.14-4.11 (m, 1H), 3.74 (t, J = 9.6 Hz, 1H), 3.45-3.32 (m, 2H), 3.33-3.31 (m, 4H), 2.87-2.73 (m, 2H), 2.67-2.65 (m, 4H), 2.42-2.28 (br s, 1H), 1.78-1.77 (m, 2H), 1.65-1.63 (m, 4H). | +++ | ++ | ++ |

TABLE 24-continued

| 51 | N-((3R)-7-(3,8-diazabicyclo[3.2.1]octan-3-yl)chroman-3-yl)-3,4-dihydro-2H-pyrano[2,3-b]pyridine-6-carboxamide | 421 | (DMSO-d6, 300 MHz) δ (ppm): 8.48 (s, 1H), 8.33 (br s, 1H), 7.98 (s, 1H), 6.89 (d, J = 8.4 Hz, 1H), 6.39 (dd, J = 2.1, 8.4 Hz, 1H), 6.18 (s, 1H), 4.34-4.13 (m, 4H), 3.83-3.78 (m, 1H), 3.48-3.46 (m, 2H), 3.32-3.29 (m, 2H), 2.94-2.74 (m, 5H), 2.69-2.66 (m, 2H), 1.97-1.90 (m, 2H), 1.67-1.65 (m, 4H). | ++ | + | + |
| --- | --- | --- | --- | --- | --- | --- |
| 52 | (R)-6-(benzylamino)-N-(7-(piperazin-1-yl)chroman-3-yl)nicotinamide | 444 | (DMSO-d6, 300 MHz) δ (ppm): 8.50 (s, 1H), 8.04 (d, J = 6.9 Hz, 1H), 7.82 (dd, J = 2.4, 9.0 Hz, 1H), 7.61 (br s, 1H), 7.32-7.20 (m, 5H), 6.91(d, J = 8.4 Hz, 1H), 6.53-6.47(m, 2H), 6.28 (s, 1H), 4.52 (m, 2H), 4.23-4.12 (m, 2H), 3.79-3.72 (m, 1H), 2.97-2.73 (m, 10H). | ++ | + | ++ |
| 53 | 6-(((S)-1-phenylethyl)amino)-N-((R)-7-(piperazin-1-yl)chroman-3-yl)nicotinamide | 458 | (DMSO-d6, 300 MHz) δ (ppm): 8.45 (s, 1H), 8.00 (br s, 1H), 7.79-7.76 (m, 1H), 7.55 (d, J = 8.4 Hz, 1H), 7.37-7.18 (m, 5H), 6.90 (d, J = 8.4 Hz, 1H), 6.47 (d, J = 8.7 Hz, 2H), 6.27 (s, 1H), 5.17-5.03 (m, 1H), 4.28-4.11 (m, 2H), 3.77-3.74 (m, 1H), 2.97-2.73 (m, 10H), 1.43 (d, J = 7.2 Hz, 3H). | + | + | + |
| 54 | 6-(((R)-1-phenylethyl)amino)-N-((R)-7-(piperazin-1-yl)chroman-3-yl)nicotinamide | 458 | (DMSO-d6, 300 MHz) δ (ppm): 8. 44 (s, 1H), 8.00 (br s, 1H), 7.80-7.76 (m, 1H), 7.56 (d, J = 7.8 Hz, 1H), 7.37-7.18 (m, 5H), 6.90 (d, J = 8.7 Hz, 1H), 6.49-6.46 (m, 2H), 6.27 (s, 1H), 5.15-5.01 (m, 1H), 4.14-4.10 (m, 2H), 3.76-3.69 (m, 1H), 2.84-2.74 (m, 10H), 1.44 (d, J = 6.9 Hz, 3H). | + | + | + |
| 55 | (R)-3-amino-N-(5,8-difluoro-7-(piperazin-1-yl)chroman-3-yl)-6-methylthieno[2,3-b]pyridine-2-carboxamide | 460 | (DMSO-d6, 400 MHz) δ (ppm): 8.33 (d, J = 8.0 Hz, 1H), 7.66 (br s, 1H), 7.31 (d, J = 8.4 Hz, 1H), 7.24 (br s, 2H), 6.49-6.38 (m, 1H), 4.43-4.09 (m, 2H), 3.97-3.95 (m, 1H), 3.01-2.69 (m, 10H), 2.58 (s, 3H). | ++++ | ++++ | +++ |
| 56 | (R)-6-amino-N-(5,8-difluoro-7-(piperazin-1-yl)chroman-3-yl)-2-methylthieno[2,3-d]thiazole-5-carboxamide | 466 | (DMSO-d6, 300 MHz) δ (ppm): 7.58 (d, J = 6.8 Hz, 1H), 7.16 (s, 2H), 6.46-6.42 (m, 1H), 4.30-4.24 (m, 2H), 3.92 (m, 1H), 3.32-2.33 (m, 10H), 2.08 (s, 3H). | ++++ | +++ | ++ |
| 57 | (R)-7-hydroxy-N-((R)-7-(piperazin-1-yl)chroman-3-yl)-6,7-dihydro-5H-cyclopenta[b]pyridine-3-carboxamide | 395 | (DMSO-d6, 300 MHz) δ (ppm): 8.84 (s, 1H), 8.56 (br s, 1H), 8.05 (s, 1H), 6.94 (d, J = 8.4 Hz, 1H), 6.52 (dd, J = 2.4, 8.4 Hz, 1H), 6.32 (s, 1H), 5.50 (d, J = 5.6 Hz, 1H), 4.98-4.96 (m, 1H), 4.29-4.27 (m, 1H), 4.20-4.17 (m, 1H), 3.86-3.83 (m, 1H), 3.03-2.75 (m, 12H), 2.49-2.33 (m, 2H), 1.86-1.84 (m, 1H). | + | + | + |
| 58 | (S)-7-hydroxy-N-((R)-7-(piperazin-1-yl)chroman-3-yl)-6,7-dihydro-5H-cyclopenta[b]pyridine-3-carboxamide | 395 | (DMSO-d6, 300 MHz) δ (ppm): 8.84 (s, 1H), 8.55 (br s, 1H), 8.05 (s, 1H), 6.94 (d, J = 8.4 Hz, 1H), 6.52 (dd, J = 2.4, 8.4 Hz, 1H), 6.32 (s, 1H), 5.50 (d, J = 5.6 Hz, 1H), 4.98-4.96 (m, 1H), 4.29-4.27 (m, 1H), 4.20-4.17 (m, 1H), 3.86-3.83 (m, 1H), 3.03-2.75 (m, 12H), 2.49-2.33 (m, 2H), 1.86-1.84 (m, 1H). | ++ | + | + |
| 59 | (R)-1-benzyl-N-(7-(piperazin-1-yl)chroman-3-yl)-1H-pyrrolo[2,3-b]pyridine-5-carboxamide | 468 | (DMSO-d6, 300 MHz) δ (ppm): 8.76 (s, 1H), 8.52-8.40 (m, 2H), 7.72 (d, J = 3.6 Hz, 1H), 7.33-7.22 (m, 5H), 6.93 (d, J = 8.4 Hz, 1H), 6.64 (d, J = 3.6 | ++++ | +++ | ++++ |

TABLE 24-continued

| # | Name | MW | NMR | | | |
|---|---|---|---|---|---|---|
| | | | Hz, 1H), 6.51 (dd, J = 2.4, 8.4 Hz, 1H), 6.30 (s, 1H), 5.52 (s, 2H), 4.40-4.25 (m, 1H), 4.24-4.15 (m, 1H), 3.84 (t, J = 9.6 Hz, 1H), 2.98-2.87 (m, 5H), 2.84-2.73 (m, 5H). | | | |
| 60 | (R)-7-amino-N-(8-cyano-5-fluoro-7-(piperazin-1-yl)chroman-3-yl)-3-methylthieno[2,3-b]pyrazine-6-carboxamide | 468 | (DMSO-d6, 300 MHz) δ (ppm): 8.66 (s, 1H), 7.96 (br s, 1H), 7.01 (br s, 2H), 6.56 (d, J = 9.3 Hz, 1H), 4.39-4.35 (m, 2H), 4.17-4.09 (m, 1H), 3.06-2.92 (m, 5H), 2.83-2.74 (m, 5H), 2.65 (s, 3H), 2.27 (br s, 1H). | +++ | ++ | ++ |
| 61 | (R)-3-amino-N-(5,6-difluoro-7-(piperazin-1-yl)chroman-3-yl)-6-methylthieno[2,3-b]pyridine-2-carboxamide | 460 | (DMSO-d6, 400 MHz) δ (ppm): 8.33 (d, J = 8.4 Hz, 1H), 7.62 (br s, 1H), 7.31 (d, J = 8.4 Hz, 1H), 7.23 (br s, 2H), 6.27 (d, J = 5.6 Hz, 1H), 4.34-4.27 (m, 1H), 4.18-4.14 (m, 1H), 3.88 (t, J = 10.0 Hz, 1H), 2.93-2.81 (m, 10H), 2.58 (s, 3H), 2.41 (br s, 1H). | ++++ | +++ | +++ |
| 62 | 3-amino-N-((R)-7-((3S,4R)-3-hydroxypiperidin-4-yl)chroman-3-yl)-6-methylthieno[2,3-b]pyridine-2-carboxamide | 439 | (DMSO-d6, 400 MHz) δ (ppm): 8.32 (d, J = 8.4 Hz, 1H), 7.56 (br s, 1H), 7.31 (d, J = 8.0 Hz, 1H), 7.22 (br s, 2H), 6.98 (d, J = 7.6 Hz, 1H), 6.77 (d, J = 8.0 Hz, 1H), 6.70 (s, 1H), 4.36-4.30 (m, 1H), 4.29-4.24 (m, 1H), 4.22-4.16 (m, 1H), 3.82 (t, J = 10.0 Hz, 1H), 3.62-3.58 (m, 1H), 3.02-2.85 (m, 4H), 2.74-2.55 (m, 7H), 2.01-1.89 (m, 1H), 1.38-1.34 (m, 1H). | ++++ | ++++ | ++++ |
| 63 | 3-amino-N-((R)-7-((3R,4S)-3-hydroxypiperidin-4-yl)chroman-3-yl)-6-methylthieno[2,3-b]pyridine-2-carboxamide | 439 | (DMSO-d6, 400 MHz) δ (ppm): 8.32 (d, J = 8.0 Hz, 1H), 7.55 (br s, 1H), 7.31 (d, J = 8.0 Hz, 1H), 7.22 (br s, 2H), 6.98 (d, J = 7.6 Hz, 1H), 6.77 (d, J = 7.6 Hz, 1H), 6.70 (s, 1H), 4.36-4.30 (m, 1H), 4.29-4.24 (m, 1H), 4.22-4.16 (m, 1H), 3.82 (t, J = 10.0 Hz, 1H), 3.62-3.58 (m, 1H), 3.02-2.85 (m, 4H), 2.74-2.55 (m, 7H), 2.02-1.88 (m, 1H), 1.38-1.35 (m, 1H). | ++++ | +++ | +++ |
| 64 | 3-amino-N-((R)-7-((3R,4R)-3-hydroxypiperidin-4-yl)chroman-3-yl)-6-methylthieno[2,3-b]pyridine-2-carboxamide | 439 | (DMSO-d6, 400 MHz) δ (ppm), 8.32 (d, J = 8.4 Hz, 1H), 7.57 (br s, 1H), 7.31 (d, J = 8.0 Hz, 1H), 7.22 (br s, 2H), 6.99 (d, J = 8.0 Hz, 1H), 6.74 (d, J = 7.6 Hz, 1H), 6.64 (s, 1H), 4.37-4.28 (m, 1H), 4.19-4.17 (m, 1H), 3.82 (t, J = 10.0 Hz, 1H), 3.43-3.37 (m, 1H), 3.05-2.84 (m, 4H), 2.58 (s, 3H), 2.50-2.21 (m, 4H), 1.65-1.60 (m, 1H), 1.53-1.42 (m, 1H). | ++++ | | +++ |
| 65 | 3-amino-N-((R)-7-((3S,4S)-3-hydroxypiperidin-4-yl)chroman-3-yl)-6-methylthieno[2,3-b]pyridine-2-carboxamide | 439 | (DMSO-d6, 400 MHz) δ (ppm): 8.32 (d, J = 8.4 Hz, 1H), 7.56 (br s, 1H), 7.31 (d, J = 8.4 Hz, 1H), 7.22 (br s, 2H), 6.99 (d, J = 7.6 Hz, 1H), 6.74 (d, J = 7.6 Hz, 1H), 6.64 (s, 1H), 4.35-4.29 (m, 1H), 4.19-4.17 (m, 1H), 3.82 (t, J = 10.0 Hz, 1H), 3.43-3.37 (m, 1H), 3.05-2.84 (m, 4H), 2.58 (s, 3H), 2.50-2.21 (m, 4H), 1.65-1.60 (m, 1H), 1.53-1.42 (m, 1H). | ++++ | | +++ |
| 66 | (R)-6-amino-N-(5,6-difluoro-7-(piperazin-1-yl)chroman-3-yl)-2-methylthieno[2,3-d]thiazole-5-carboxamide | 466 | (DMSO-d6, 300 MHz) δ (ppm): 7.53 (d, J = 6.9 Hz, 1H), 7.15 (s, 2H), 6.27-6.24 (m, 1H), 4.27-4.15 (m, 1H), 4.13-4.12 (m, 1H), 3.89-3.82 (m, 1H), 2.96-2.87 (m, 5H), 2.82-2.73 (m, 8H). | ++++ | | ++ |

TABLE 24-continued

| | | | | | |
|---|---|---|---|---|---|
| 67 | (R)-7-amino-N-(6-cyano-5-fluoro-7-(piperazin-1-yl)chroman-3-yl)-3-methylthieno[2,3-b]pyrazine-6-carboxamide | 468 | (DMSO-d6, 300 MHz) δ (ppm): 8.66 (s, 1H), 7.91 (br s, 1H), 7.01 (br s, 2H), 6.37 (s, 1H), 4.31-4.27 (m, 2H), 4.10-4.07 (m, 1H), 3.05-3.02 (m, 5H), 2.85-2.83 (m, 5H), 2.65 (s, 3H). | ++++ | +++ |
| 68 | (R)-3-amino-N-(5,8-difluoro-7-(piperazin-1-yl)chroman-3-yl)-6-methylfuro[2,3-b]pyridine-2-carboxamide | 444 | (MeOH-d4, 300 MHz) δ (ppm): 8.12 (d, J = 8.7 Hz, 1H), 7.21 (d, J = 8.7 Hz, 1H), 6.45-6.32 (m, 1H), 4.63-4.40 (m, 1H), 3.38-3.29 (m, 1H), 4.12-3.96 (m, 1H), 3.15-2.94 (m, 9H), 2.90-2.78 (m, 1H), 2.61 (s, 3H). | ++ | + |
| 69 | 3-amino-N-((R)-7-((R)-3,3-difluoropiperidin-4-yl)chroman-3-yl)-6-methylthieno[2,3-b]pyridine-2-carboxamide | 459 | (DMSO-d6, 300 MHz) δ (ppm): 8.32 (d, J = 8.1 Hz, 1H), 7.60 (br s, 1H), 7.31 (d, J = 8.4 Hz, 1H), 7.23 (br s, 2H), 7.03 (d, J = 6.8 Hz, 1H) 6.80 (d, J = 8.1 Hz, 1H), 6.72 (s, 1H), 4.33-4.25 (m, 1H), 4.21-4.14 (m, 1H), 3.85 (t, J = 9.9 Hz, 1H), 3.13-3.02 (m, 2H), 3.02-2.92 (m, 4H), 2.91-2.74 (m, 1H), 2.62-2.60 (m, 1H), 2.58 (s, 3H), 2.49 (br s, 1H), 1.93-1.74 (m, 1H), 1.75-1.69 (m, 1H). | ++++ | +++ |
| 70 | 3-amino-N-((R)-7-((S)-3,3-difluoropiperidin-4-yl)chroman-3-yl)-6-methylthieno[2,3-b]pyridine-2-carboxamide | 459 | (DMSO-d6, 300 MHz) δ (ppm): 8.33 (d, J = 8.1 Hz, 1H), 7.60 (br s, 1H), 7.32 (d, J = 8.4 Hz, 1H), 7.23 (br s, 2H), 7.03 (d, J = 6.8 Hz, 1H) 6.80 (d, J = 7.5 Hz, 1H), 6.72 (s, 1H), 4.32-4.25 (m, 1H), 4.21-4.17 (m, 1H), 3.85 (t, J = 9.9 Hz, 1H), 3.13-3.02 (m, 2H), 3.02-2.92 (m, 4H), 2.91-2.73 (m, 1H), 2.62-2.60 (m, 1H), 2.58 (s, 3H), 2.49 (br s, 1H), 1.94-1.74 (m, 1H), 1.74-1.69 (m, 1H). | ++++ | ++++ |
| 71 | (R)-7-amino-3-methyl-N-(7-(piperazin-1-yl)-3,4-dihydro-2H-pyrano[3,2-c]pyridin-3-yl)thieno[2,3-b]pyrazine-6-carboxamide | 426 | (DMSO-d6, 300 MHz) δ (ppm): 8.65 (s, 1H), 7.84-7.82 (m, 2H), 6.99 (br s, 2H), 6.14 (s, 1H), 4.29-4.21 (m, 2H), 3.94-3.88 (m, 1H), 3.32-3.27 (m, 4H), 2.85-2.82 (m, 2H), 2.76-2.70 (m, 4H), 2.65 (s, 3H). | +++ | ++ |
| 72 | (R)-3-amino-5-fluoro-6-methyl-N-(7-(piperazin-1-yl)-3,4-dihydro-2H-pyrano[3,2-c]pyridin-3-yl)thieno[2,3-b]pyridine-2-carboxamide | 443 | (DMSO-d6, 300 MHz) δ (ppm): 8.31 (d, J = 10.2 Hz, 1H), 7.83 (s, 1H), 7.67 (br s, 1H), 7.19 (br s, 2H), 6.14 (s, 1H), 4.30-4.19 (m, 2H), 3.93-3.86 (m, 1H), 3.31-3.27 (m, 4H), 2.84-2.81 (m, 2H), 2.79-2.73 (m, 4H), 2.56-2.51 (s, 3H). | ++++ | ++ |
| 73 | (7S)-N-((3R)-7-(3,8-diazabicyclo[3.2.1]octan-3-yl)chroman-3-yl)-7-methyl-5,6,7,8-tetrahydro-1,8-naphthyridine-3-carboxamide | 434 | (DMSO-d6, 400 MHz) δ (ppm): 8.33 (s, 1H), 7.98 (br s, 1H), 7.63 (s, 1H), 7.08 (s, 1H), 6.87 (d, J = 8.4 Hz, 1H), 6.38-6.35 (m, 1H), 6.16 (s, 1H), 4.25-4.18 (m, 1H), 4.13-4.10 (m, 1H), 3.76-3.71 (m, 1H), 3.47 (s, 3H), 3.34-3.28 (m, 2H), 2.87-2.73 (m, 2H), 2.69-2.65 (m, 4H), 1.88-1.84 (m, 1H), 1.66-1.64 (m, 4H), 1.45-1.36 (m, 1H), 1.17 (d, J = 6.4 Hz, 3H). | + | + |
| 74 | (7R)-N-((3R)-7-(3,8-diazabicyclo[3.2.1]octan-3-yl)chroman-3-yl)-7-methyl-5,6,7,8-tetrahydro-1,8-naphthyridine-3-carboxamide | 434 | (DMSO-d6, 400 MHz) δ (ppm): 8.33 (s, 1H), 7.98 (br s, 1H), 7.63 (s, 1H), 7.08 (s, 1H), 6.87 (d, J = 8.4 Hz, 1H), 6.38-6.35 (m, 1H), 6.16 (s, 1H), 4.27-4.18 (m, 1H), 4.13-4.10 (m, 1H), 3.76-3.71 (m, 1H), 3.47 (s, 3H), 3.34-3.22 (m, 2H), 2.87-2.73 (m, 2H), 2.68-2.65 (m, 4H), 1.89-1.84 (m, 1H), 1.66-1.64 (m, 4H), 1.45-1.36 | +++ | ++ |

TABLE 24-continued

| | | | | | |
|---|---|---|---|---|---|
| | | | (m, 1H), 1.17 (d, J = 6.4 Hz, 3H). | | |
| 75 | N-((R)-7-((1S,4S)-2,5-diazabicyclo[2.2.2]octan-2-yl)-3,4-dihydro-2H-pyrano[3,2-c]pyridin-3-yl)-3-amino-6-methylthieno[2,3-b]pyridine-2-carboxamide | 451 | (DMSO-d6, 300 MHz) δ (ppm): 8.33 (d, J = 8.1 Hz, 1H), 7.76 (s, 1H), 7.58 (br s, 1H), 7.32 (d, J = 8.4 Hz, 1H), 7.23 (s, 1H), 5.81 (s, 1H), 4.50-4.49 (m, 1H), 4.27-4.19 (m, 2H), 3.88 (t, J = 9.9 Hz, 1H), 3.46-3.35 (m, 1H), 3.33-3.28 (m, 1H), 3.19-2.91 (m, 3H), 2.88-2.74 (m, 2H), 2.58 (s, 3H), 1.94-1.72 (m, 3H), 1.72-1.59 (m, 1H). | ++++ | ++++ |
| 76 | N-((R)-7-((1R,4R)-2,5-diazabicyclo[2.2.2]octan-2-yl)-3,4-dihydro-2H-pyrano[3,2-c]pyridin-3-yl)-3-amino-6-methylthieno[2,3-b]pyridine-2-carboxamide | 451 | (DMSO-d6, 300 MHz) δ (ppm): 8.32 (d, J = 8.1 Hz, 1H), 7.76 (s, 1H), 7.58 (br s, 1H), 7.31 (d, J = 8.4 Hz, 1H), 7.23 (s, 1H), 5.81 (s, 1H), 4.50-4.49 (m, 1H), 4.27-4.18 (m, 2H), 3.88 (t, J = 9.9 Hz, 1H), 3.46-3.34 (m, 1H), 3.33-3.27 (m, 1H), 3.19-2.91 (m, 3H), 2.88-2.74 (m, 2H), 2.58 (s, 3H), 1.94-1.72 (m, 3H), 1.72-1.58 (m, 1H). | ++++ | +++ |
| 77 | N-((3R)-7-(3,6-diazabicyclo[3.1.1]heptan-3-yl)-8-cyano-5-fluorochroman-3-yl)-7-amino-3-methylthieno[2,3-b]pyrazine-6-carboxamide | 480 | (MeOH-d4, 300 MHz) δ (ppm): 8.57 (s, 1H), 6.29 (s, 1H), 4.52-4.45 (m, 1H), 4.40-4.37 (m, 1H), 4.18-4.16 (m, 1H), 3.95-3.92 (m, 2H), 3.84-3.79 (m, 4H), 3.13-2.96 (m, 1H), 2.78-2.70(m, 2H), 2.68 (s, 3H), 1.70 (d, J = 9.2 Hz, 1H). | +++ | ++ |
| 78 | N-((3R)-7-(9-oxa-3,7-diazabicyclo[3.3.1]nonan-3-yl)-5,8-difluorochroman-3-yl)-3-amino-6-methylthieno[2,3-b]pyridine-2-carboxamide | 502 | (DMSO-d6, 300 MHz) δ (ppm): 8.33 (d, J = 8.4 Hz, 1H), 7.67 (br s, 1H), 7.31 (d, J = 8.1 Hz, 1H), 7.24 (br s, 2H), 6.52-6.46 (m, 1H), 4.33-4.27 (m, 2H), 4.00-3.94 (m, 1H), 3.67-3.65 (m, 2H), 3.42-3.36 (m, 3H), 3.23-3.10 (m, 4H), 2.99-2.79 (m, 4H), 2.58 (s, 3H). | ++++ | ++++ |
| 79 | N-((3R)-7-(9-oxa-3,7-diazabicyclo[3.3.1]nonan-3-yl)-5,6-difluorochroman-3-yl)-3-amino-6-methylthieno[2,3-b]pyridine-2-carboxamide | 502 | (DMSO-d6, 300 MHz) δ (ppm): 8.33 (d, J = 8.4 Hz, 1H), 7.62 (br s, 1H), 7.31 (d, J = 8.4 Hz, 1H), 7.24 (br s, 2H), 6.31-6.28 (m, 1H), 4.33-4.28 (m, 1H), 4.20-4.15 (m, 1H), 3.93-3.87 (m, 1H), 3.66-3.65 (m, 2H), 3.42-3.36 (m, 3H), 3.20-3.09 (m, 4H), 2.98-2.73 (m, 4H), 2.58 (s, 3H). | ++++ | ++++ |
| 80 | 3-amino-N-((R)-7-((3R,4R)-3-fluoropiperidin-4-yl)chroman-3-yl)-6-methylthieno[2,3-b]pyridine-2-carboxamide | 441 | (DMSO-d6, 400 MHz) δ (ppm): 8.33 (d, J = 8.4 Hz, 1H), 7.58 (br s, 1H), 7.31 (d, J = 8.4 Hz, 1H), 7.23 (br s, 2H), 7.05 (d, J = 12.0 Hz, 1H), 6.80 (d, J = 8.0 Hz, 1H), 6.70 (s, 1H), 4.70-4.57 (m, 1H), 4.33-4.29 (m, 1H), 4.20-4.17 (m, 1H), 3.84 (t, J = 10.0 Hz, 1H), 3.32-2.62 (m, 7H), 2.58 (s, 3H), 1.93-1.88 (m, 1H), 1.56-1.52 (m, 1H). | ++++ | +++ |
| 81 | 3-amino-N-((R)-7-((3S,4S)-3-fluoropiperidin-4-yl)chroman-3-yl)-6-methylthieno[2,3-b]pyridine-2-carboxamide | 441 | (DMSO-d6, 400 MHz) δ (ppm): 8.33 (d, J = 8.4 Hz, 1H), 7.58 (br s, 1H), 7.31 (d, J = 8.4 Hz, 1H), 7.22 (br s, 2H), 7.04 (d, J = 8.0 Hz, 1H), 6.80 (d, J = 8.0 Hz, 1H), 6.71 (s, 1H), 4.70-4.57 (m, 1H), 4.33-4.29 (m, 1H), 4.20-4.17 (m, 1H), 3.84 (t, J = 10.0 Hz, 1H), 3.32-2.61 (m, 7H), 2.58 (s, 3H), 1.93-1.88 (m, 1H), 1.56-1.52 (m, 1H). | ++++ | +++ |

TABLE 24-continued

| | | | | | |
|---|---|---|---|---|---|
| 82 | 3-amino-N-((R)-7-((3S,4R)-3-fluoropiperidin-4-yl)chroman-3-yl)-6-methylthieno[2,3-b]pyridine-2-carboxamide | 441 | (DMSO-d6, 400 MHz) δ (ppm): 8.33 (d, J = 8.0 Hz, 1H), 7.59 (br s, 1H), 7.31 (d, J = 8.0 Hz, 1H), 7.23 (br s, 2H), 7.05 (d, J = 7.6 Hz, 1H), 6.81-6.79 (m, 1H), 6.71 (s, 1H), 4.60-4.57 (m, 1H), 4.34-4.30 (m, 1H), 4.20-4.17 (m, 1H), 3.84 (t, J = 10.0 Hz, 1H), 3.27-3.24 (m, H), 2.98-2.86 (m, 3H), 2.69-2.61 (m, 1H), 2.58 (s, 3H), 2.50-2.43 (m, 2H), 1.74-1.71 (m, 1H), 1.61-1.54 (m, 1H). | ++++ | ++++ |
| 83 | 3-amino-N-((R)-7-((3R,4S)-3-fluoropiperidin-4-yl)chroman-3-yl)-6-methylthieno[2,3-b]pyridine-2-carboxamide | 441 | (DMSO-d6, 400 MHz) δ (ppm): 8.33 (d, J = 8.4 Hz, 1H), 7.59 (br s, 1H), 7.32 (d, J = 8.4 Hz, 1H), 7.23 (br s, 2H), 7.05 (d, J = 7.6 Hz, 1H), 6.81-6.79 (m, 1H), 6.72 (s, 1H), 4.60-4.57 (m, 1H), 4.34-4.30 (m, 1H), 4.20-4.17 (m, 1H), 3.84 (t, J = 10.0 Hz, 1H), 3.27-3.24 (m, H), 2.98-2.86 (m, 3H), 2.69-2.61 (m, 1H), 2.58 (s, 3H), 2.50-2.43 (m, 2H), 1.74-1.71 (m, 1H), 1.61-1.54 (m, 1H). | ++++ | +++ |
| 84 | N-((R)-5,8-difluoro-7-((3R,4S)-3-hydroxypiperidin-4-yl)chroman-3-yl)-7-ethyl-7H-pyrrolo[2,3-c]pyridazine-3-carboxamide | 458 | (DMSO-d6, 300 MHz) δ (ppm): 9.06 (d, J = 7.8 Hz, 1H), 8.47 (s, 1H), 8.10 (br s, 1H), 6.76-6.71 (m, 2H), 4.66 (br s, 1H), 4.58-4.42 (m, 3H), 4.47-4.30 (m, 1H), 4.22-4.16 (m, 1H), 3.68-3.67 (m, 1H), 3.20-3.00 (m, 4H), 3.00-2.80 (m, 2H), 2.78-2.58 (m, 1H), 2.06-1.97 (m, 1H), 1.47 (t, J = 7.2 Hz, 3H), 1.40-1.30 (m, 1H), 1.38-1.35 (m, 1H). | ++ | + |
| 85 | N-((R)-5,8-difluoro-7-((3S,4R)-3-hydroxypiperidin-4-yl)chroman-3-yl)-7-ethyl-7H-pyrrolo[2,3-c]pyridazine-3-carboxamide | 458 | (DMSO-d6, 300 MHz) δ (ppm): 9.08 (d, J = 7.5 Hz, 1H), 8.47 (s, 1H), 8.10 (br s, 1H), 6.76-6.70 (m, 2H), 5.31 (br s, 1H), 4.55-4.47 (m, 3H), 4.35-4.33 (m, 1H), 4.23-4.17 (m, 1H), 3.90-3.89 (m, 1H), 3.22-3.17 (m, 2H), 3.15-2.91 (m, 5H), 2.26-2.18 (m, 1H), 1.56-1.55 (m, 1H), 1.47 (t, J = 7.2 Hz, 3H), 1.28-1.24 (m, 1H). | ++ | + |
| 86 | 3-amino-N-((R)-7-((3R,4R)-3-amino-4-methoxypyrrolidin-1-yl)-5,8-difluorochroman-3-yl)-6-methylthieno[2,3-b]pyridine-2-carboxamide | 490 | (DMSO-d6, 400 MHz) δ (ppm): 8.32 (d, J = 8.4 Hz, 1H), 7.63 (br s, 1H), 7.32 (d, J = 8.4 Hz, 1H), 7.23 (br s, 2H), 6.15 (dd, J = 2.4, 12.4 Hz, 1H), 4.30-4.24 (m, 2H), 3.95-3.90 (m, 1H), 3.67-3.61 (m, 2H), 3.52-3.50 (m, 1H), 3.41-3.40 (m, 1H), 3.29 (s, 3H), 3.25-3.22 (m, 1H), 3.05-3.02 (m, 1H), 2.89-2.80 (m, 1H), 2.78-2.74 (m, 1H), 2.59 (s, 3H), 2.48-2.18 (br s, 2H). | ++++ | ++ |
| 87 | 3-amino-N-((R)-7-((3S,4S)-3-amino-4-methoxypyrrolidin-1-yl)-5,8-difluorochroman-3-yl)-6-methylthieno[2,3-b]pyridine-2-carboxamide | 490 | (DMSO-d6, 400 MHz) δ (ppm): 8.32 (d, J = 8.4 Hz, 1H), 7.62 (br s, 1H), 7.32 (d, J = 8.4 Hz, 1H), 7.24 (br s, 2H), 6.15 (dd, J = 2.4, 12.4 Hz, 1H), 4.30-4.24 (m, 2H), 3.95-3.90 (m, 1H), 3.67-3.61 (m, 2H), 3.52-3.50 (m, 1H), 3.41-3.40 (m, 1H), 3.29 (s, 3H), 3.25-3.22 (m, 1H), 3.05-3.02 (m, 1H), 2.89-2.80 (m, 1H), 2.78-2.74 (m, 1H), 2.59 (s, 3H), 2.48-2.18 (br s, 2H). | ++++ | ++ |

TABLE 24-continued

| | | | | | |
|---|---|---|---|---|---|
| 88 | N-((3R)-7-(9-oxa-3,7-diazabicyclo[3.3.1]nonan-3-yl)chroman-3-yl)-3-amino-4-(difluoromethyl)-6-methylthieno[2,3-b]pyridine-2-carboxamide | 516 | (DMSO-d6, 400 MHz) δ (ppm): 7.83 (br s, 1H), 7.80-7.56 (m, 1H), 7.55 (s, 1H), 6.97 (d, J = 8.4 Hz, 1H), 6.76 (br s, 2H), 6.58 (d, J = 8.8 Hz, 1H), 6.37 (s, 1H), 4.38-4.25 (m, 1H), 4.20-4.12 (m, 1H), 3.85-3.80 (m, 1H), 3.74-3.60 (m, 4H), 3.12-3.03 (m, 2H), 3.01-2.91(m, 4H), 2.90-2.85 (m, 2H), 2.65 (s, 1H). | ++++ | ++++ |
| 89 | (1aS,7bR)-N-((3R)-7-(3,8-diazabicyclo[3.2.1]octan-3-yl)-5,8-difluorochroman-3-yl)-1a,2,3,7b-tetrahydro-1H-cyclopropa[c][1,8]naphthyridine-6-carboxamide | 468 | (DMSO-d6, 400 MHz) δ (ppm): 8.29 (s, 1H), 8.17 (br s, 1H), 7.86 (s, 1H), 6.63 (s, 1H), 6.36-6.30 (m, 1H), 4.40-4.22 (m, 2H), 3.98-3.90 (m, 1H), 3.60-3.49 (m, 4H), 3.11-3.07 (m, 2H), 3.00-2.72 (m, 4H), 2.00-1.60 (m, 6H), 0.96-0.94 (m, 2H). | ++++ | +++ |
| 90 | (1aR,7bS)-N-((3R)-7-(3,8-diazabicyclo[3.2.1]octan-3-yl)-5,8-difluorochroman-3-yl)-1a,2,3,7b-tetrahydro-1H-cyclopropa[c][1,8]naphthyridine-6-carboxamide | 468 | (DMSO-d6, 400 MHz) δ (ppm): 8.26 (s, 1H), 8.18-8.16 (m, 1H), 7.86 (s, 1H), 6.63 (s, 1H), 6.40-6.30 (m, 1H), 4.40-4.22 (m, 2H), 3.98-3.90 (m, 1H), 3.60-3.49 (m, 4H), 3.11-3.07 (m, 2H), 3.00-2.72 (m, 4H), 2.00-1.60 (m, 6H), 0.96-0.94 (m, 2H). | ++ | ++ |
| 91 | 3-amino-N-[(3R)-7-[(3R,4R)-3-amino-4-methoxypyrrolidin-1-yl]-8-fluoro-3,4-dihydro-2H-1-benzopyran-3-yl]-6-methylthieno[2,3-b]pyridine-2-carboxamide | 472 | (DMSO-d6, 400 MHz) δ (ppm): 8.33 (d, J = 8.3 Hz, 1H), 7.56 (br s, 1H), 7.31 (d, J = 8.3 Hz, 1H), 7.23 (br s, 2H), 6.71 (d, J = 8.4 Hz, 1H), 6.28-6.21 (m, 1H), 4.36-4.20 (m, 2H), 3.91-3.82 (m, 1H), 3.65-3.58 (m, 2H), 3.54-3.45 (m, 1H), 3.41-3.34 (m, 1H), 3.28 (s, 3H), 3.20-3.18 (m, 1H), 3.02-2.95 (m, 1H), 2.89 (m, 2H), 2.58 (s, 3H), 2.05-1.95 (m, 2H). | ++ | ++ |
| 92 | 3-amino-N-[(3R)-7-[(3S,4S)-3-amino-4-methoxypyrrolidin-1-yl]-8-fluoro-3,4-dihydro-2H-1-benzopyran-3-yl]-6-methylthieno[2,3-b]pyridine-2-carboxamide | 472 | (DMSO-d6, 400 MHz) δ (ppm): 8.33 (d, J = 8.3 Hz, 1H), 7.58 (br s, 1H), 7.32 (d, J = 8.3 Hz, 1H), 7.24 (br s, 2H), 6.71 (d, J = 8.5 Hz, 1H), 6.25-6.21 (m, 1H), 4.37-4.20 (m, 2H), 3.86-3.81 (m, 1H), 3.67-3.56 (m, 2H), 3.58-3.41 (m, 3H), 3.42-3.35 (m, 2H), 3.28-3.24 (m, 3H), 3.21-3.18 (m, 1H), 3.05-2.95 (m,1H), 2.90-2.85(m, 2H), 2.60-2.55 (s, 3H), 1.85-1.60 (s, 2H). | ++++ | ++ |
| 93 | 3-amino-N-[(3R)-7-[(3R,4R)-3-amino-4-methoxypyrrolidin-1-yl]-6-fluoro-3,4-dihydro-2H-1-benzopyran-3-yl]-6-methylthieno[2,3-b]pyridine-2-carboxamide | 472 | (DMSO-d6, 400 MHz) δ (ppm): 8.33 (d, J = 8.0 Hz, 1H), 7.53 (br s, 1H), 7.31 (d, J = 8.4 Hz, 1H), 7.22 (br s, 2H), 6.82 (d, J = 14.0 Hz, 1H), 6.09 (d, J = 8.0 Hz, 1H), 4.29-4.25 (m, 1H), 4.14-4.11 (m, 1H), 3.82-3.77 (m, 1H), 3.64-3.60 (m, 2H), 3.50-3.43 (m, 2H), 3.29 (s, 3H), 3.20-3.17 (m, 1H), 3.04-3.02 (m, 1H), 2.90-2.80 (m, 2H), 2.58 (s, 3H). | +++ | ++ |
| 94 | 3-amino-N-[(3R)-7-[(3S,4S)-3-amino-4-methoxypyrrolidin-1-yl]-6-fluoro-3,4-dihydro-2H-1-benzopyran-3-yl]-6-methylthieno[2,3-b]pyridine-2-carboxamide | 472 | (DMSO-d6, 400 MHz) δ (ppm): 8.32 (d, J = 8.4 Hz, 1H), 7.53 (br s, 1H), 7.31 (d, J = 8.0 Hz, 1H), 7.22 (br s, 2H), 6.82 (d, J = 14.0 Hz, 1H), 6.08 (d, J = 8.0 Hz, 1H), 4.29-4.25 (m, 1H), 4.14-4.11 (m, 1H), 3.80-3.75 (m, 1H), 3.62-3.61 (m, 2H), 3.48-3.45 (m, 2H), 3.28 (s, 3H), 3.20-3.17 (m, 1H), 2.97-2.95 (m, 1H), 2.84-2.82 (m, 2H), 2.58 (s, 3H). | ++++ | ++ |

TABLE 24-continued

| | | | | | |
|---|---|---|---|---|---|
| 95 | 3-amino-N-[(3R)-8-cyano-7-(3,8-diazabicyclo[3.2.1]octan-3-yl)-5-fluoro-3,4-dihydro-2H-1-benzopyran-3-yl]-6-methylthieno[2,3-b]pyridine-2-carboxamide | 493 | (DMSO-d6, 400 MHz) δ (ppm): 8.32 (d, J = 8.4 Hz, 1H), 7.70 (d, J = 6.8 Hz, 1H), 7.31 (d, J = 8.4 Hz, 1H), 7.24 (br s, 2H), 6.47 (d, J = 12.0 Hz, 1H), 4.34-4.32 (m, 2H), 4.09-4.08 (m, 1H), 3.43 (s, 2H), 3.29-3.26 (m, 2H), 2.89-2.87 (m, 3H), 2.80-2.73 (m, 1H), 2.58 (s, 3H), 1.89-1.86 (m, 2H), 1.65-1.63 (m, 2H). | ++++ | ++ |
| 96 | 3-amino-N-[(3R)-8-cyano-5-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide | 509 | (DMSO-d6, 400 MHz) δ (ppm): 8.34 (d, J = 8.4 Hz, 1H), 7.74 (d, J = 6.8 Hz, 1H), 7.33 (d, J = 8.0 Hz, 1H), 7.27 (br s, 2H), 6.65 (d, J = 11.6 Hz, 1H), 4.39-4.37 (m, 2H), 4.16-4.11 (m, 1H), 3.70 (s, 2H), 3.57-3.53 (m, 2H), 3.30-3.28 (m, 2H), 3.18-2.94 (m, 5H), 2.85-2.79 (m, 1H), 2.60 (s, 3H). | ++++ | +++ |
| 97 | 7-amino-N-[(3R)-7-{3,8-diazabicyclo[3.2.1]octan-3-yl}-5,6-difluoro-3,4-dihydro-2H-1-benzopyran-3-yl]-3-methylthieno[2,3-b]pyrazine-6-carboxamide | 487 | (DMSO-d6, 400 MHz) δ (ppm): 8.65 (s, 1H), 7.85 (d, J = 6.8 Hz, 1H), 6.99 (br s, 2H), 6.16 (d, J = 6.4 Hz, 1H), 4.33-4.29 (m, 1H), 4.17-4.14 (m, 1H), 3.92-3.87 (m, 1H), 3.42-3.35 (m, 2H), 3.09-3.06 (m, 2H), 2.97-2.92 (m, 1H), 2.84-2.79 (m, 3H), 2.65 (s, 3H), 1.79-1.78 (m, 2H), 1.67-1.66 (m, 1H). | ++++ | ++++ |
| 98 | 6-amino-N-[(3R)-7-{3,8-diazabicyclo[3.2.1]octan-3-yl}-5,8-difluoro-3,4-dihydro-2H-1-benzopyran-3-yl]-2-methylthieno[2,3-d][1,3]thiazole-5-carboxamide | 492 | (DMSO-d6, 300 MHz) δ (ppm): 7.57 (d, J = 6.9 Hz, 1H), 7.17 (br s, 2H), 6.36-6.30 (m, 1H), 4.29-4.22 (m, 2H), 3.95-3.88 (m, 1H), 3.38-3.34 (m, 2H), 3.07-3.04 (m, 2H), 2.95-2.87 (m, 1H), 2.80-2.72 (m, 6H), 1.79-1.64 (m, 4H). | ++++ | +++ |
| 99 | 3-amino-N-[(2S)-5-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 482 | (DMSO-d6, 400 MHz) δ (ppm): 9.18 (s, 1H), 8.32-8.30 (m, 2H), 7.61 (d, J = 8.0 Hz, 1H), 7.32 (d, J = 8.0 Hz, 1H), 7.19-7.12 (m, 1H), 6.95-6.89 (m, 2H), 4.15-4.11 (m, 1H), 3.50-3.36 (m, 6H), 3.26-3.18 (m, 2H), 2.99-2.94 (m, 2H), 2.86-2.82 (m, 1H), 2.79-2.67 (m, 1H), 2.59 (s, 3H), 2.08-2.04 (m, 1H), 1.82-1.71 (m, 1H). | ++++ | ++++ |
| 100 | 3-amino-N-[(2R)-5-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 482 | (DMSO-d6, 400 MHz) δ (ppm): 9.16 (s, 1H), 8.32-8.30 (m, 2H), 7.60 (d, J = 8.0 Hz, 1H), 7.31 (d, J = 8.4 Hz, 1H), 7.23-7.10 (m, 1H), 6.97-6.89 (m, 2H), 4.16-4.10 (m, 1H), 3.48-3.35 (m, 6H), 3.26-3.18 (m, 2H), 2.99-2.95 (m, 2H), 2.86-2.82 (m, 1H), 2.79-2.66 (m, 1H), 2.59 (s, 3H), 2.08-2.04 (m, 1H), 1.82-1.72 (m, 1H). | +++ | + |
| 101 | 3-amino-N-[(2S)-7-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 482 | (DMSO-d6, 400 MHz) δ (ppm): 8.31 (d, J = 8.0 Hz, 1H), 7.60 (d, J = 8.00 Hz, 1H), 7.31 (s, J = 8.00 Hz, 1H), 7.17 (br, 1H), 6.93 (d, J = 16.6 Hz, 1H), 6.70 (d, J = 16.6 Hz, 1H), 4.13-4.09 (m, 1H), 3.70-3.62 (m, 2H), 3.58-3.51 (m, 1H), 3.23-3.09 (m, 5H), 3.08-2.78 (m, 7H), 2.57 (s, 3H), 2.01-1.90 (m, 1H), 1.89-1.68 (m, 1H). | ++++ | ++ |

| | | | | | |
|---|---|---|---|---|---|
| | | | TABLE 24-continued | | |
| 102 | 3-amino-N-[(2S)-5-cyano-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 489 | (DMSO-d6, 400 MHz) δ (ppm): 8.31 (d, J = 8.0 Hz, 1H), 7.65 (d, J = 8.00 Hz, 1H), 7.39 (d, J = 8.8 Hz ) 7.31 (d, J = 8.00 Hz, 1H), 7.18 (br s, 2H), 7.04 (d, J = 8.40 Hz, 1H), 4.19-4.09 (m, 1H), 3.70-3.65 (m, 2H), 3.54-3.43 (m, 2H), 3.29-3.20 (m, 2H), 3.08-2.70 (m, 9H), 2.58 (s, 3H), 2.09-1.99 (m, 1H), 1.89-1.70 (m, 1H). | ++++ | +++ |
| 103 | 3-amino-N-[(3R)-7-{3,8-diazabicyclo[3.2.1]octan-3-yl}-8-fluoro-3,4-dihydro-2H-1-benzopyran-3-yl]-6-methylthieno[2,3-b]pyridine-2-carboxamide | 468 | (DMSO-d6, 400 MHz) δ (ppm): 8.31 (d, J = 8.4 Hz, 1H), 7.62 (br s, 1H), 7.31 (d, J = 8.4 Hz, 1H), 7.21 (br s, 2H), 6.78 (d, J = 8.0 Hz, 1H), 6.47-6.43 (m, 1H), 4.37-4.23 (m, 2H), 3.91-3.85 (m, 1H), 3.33-3.20 (m, 2H), 3.02-3.01 (m, 2H), 2.93-2.91 (m, 2H), 2.81-2.79 (m, 2H), 2.58 (s, 3H), 1.81-1.79 (m, 2H), 1.69-1.63 (m, 2H). | ++++ | +++ |
| 104 | 3-amino-N-[(3R)-7-{3,8-diazabicyclo[3.2.1]octan-3-yl}-6-fluoro-3,4-dihydro-2H-1-benzopyran-3-yl]-6-methylthieno[2,3-b]pyridine-2-carboxamide | 468 | (DMSO-d6, 300 MHz) δ (ppm): 8.30 (d, J = 6.0 Hz, 1H), 7.54 (br s, 1H), 7.31 (d, J = 8.4 Hz, 1H), 7.22 (br s, 2H), 6.85 (d, J = 13.5 Hz, 1H), 6.29 (d, J = 7.8 Hz, 1H), 4.27-4.23 (m, 1H), 4.15-4.11 (m, 1H), 3.83-3.76 (m, 1H), 3.38-3.33 (m, 3H), 3.07-2.93 (m, 2H), 2.86-2.64 (m, 2H), 2.81-2.71 (m, 2H), 2.58 (s, 3H), 1.87-1.71 (m, 2H), 1.65-1.60 (m, 2H). | ++++ | +++ |
| 105 | 3-amino-N-[(3R)-8-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide | 484 | (DMSO-d6, 400 MHz) δ (ppm): 8.33 (d, J = 8.4 Hz, 1H), 7.61 (br s, 1H), 7.31 (d, J = 8.4 Hz, 1H), 7.23 (br s, 2H), 6.87 (d, J = 8.4 Hz, 1H), 6.60-6.55 (m, 1H), 4.37-4.26 (m, 2H), 3.90-3.88 (m, 1H), 3.53-3.51 (m, 2H), 3.32-3.10 (m, 6H), 2.99-2.95 (m, 4H), 2.55 (s, 3H). | ++++ | ++++ |
| 106 | 3-amino-N-[(3R)-6-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide | 484 | (DMSO-d6, 400 MHz) δ (ppm): 8.33 (d, J = 8.4 Hz, 1H), 7.58 (br s, 1H), 7.32 (d, J = 8.4 Hz, 1H), 7.23 (br s, 2H), 6.96 (d, J = 12.8 Hz, 1H), 6.43 (d, J = 7.6 Hz, 1H), 4.30-4.22 (m, 1H), 4.19-4.11 (m, 1H), 3.85-3.82 (m, 1H), 3.66-3.64 (m, 2H), 3.40-3.37 (m, 2H), 3.17-3.09 (m, 4H), 2.98-2.89 (m, 4H), 2.58 (s, 3H). | ++++ | +++ |
| 107 | 7-amino-N-[(3R)-7-(3,8-diazabicyclo[3.2.1]octan-3-yl)-5,8-difluoro-3,4-dihydro-2H-1-benzopyran-3-yl]-3-methylthieno[2,3-b]pyrazine-6-carboxamide | 487 | (DMSO-d6, 300 MHz) δ (ppm): 8.67 (s, 1H), 7.90 (d, J = 6.9 Hz, 1H), 7.00 (br s, 2H), 6.37-6.31 (m, 1H), 4.40-4.24 (m, 2H), 4.00-3.94 (m, 1H), 3.40-3.33 (m, 2H), 3.08-3.05 (m, 2H), 2.99-2.91 (m, 1H), 2.84-2.73 (m, 3H), 2.65 (s, 3H), 1.80-1.73 (m, 2H), 1.66-1.65 (m, 2H). | ++++ | ++++ |
| 108 | 6-amino-N-[(3R)-7-{3,8-diazabicyclo[3.2.1]octan-3-yl}-5,6-difluoro-3,4-dihydro-2H-1-benzopyran-3-yl]-2-methylthieno[2,3-d][1,3]thiazole-5-carboxamide | 492 | (DMSO-d6, 300 MHz) δ (ppm): 7.52 (d, J = 7.2 Hz, 1H), 7.15 (br s, 2H), 6.15 (d, J = 5.4 Hz, 1H), 4.27-4.24 (m, 1H), 4.15-4.12 (m, 1H), 3.87-3.81 (m, 1H), 3.39-3.33 (m, 2H), 3.08-3.05 (m, 1H), 2.94-2.87 (m, 1H), 2.79-2.72 (m, 6H), 1.79-1.65 (m, 4H). | ++++ | +++ |

TABLE 24-continued

| | | | | | |
|---|---|---|---|---|---|
| 109 | 3-amino-N-[(2S)-7-cyano-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide | 489 | (DMSO-d6, 400 MHz) δ (ppm): 8.30 (d, J = 8.4 Hz, 1H), 7.63 (d, J = 7.6 Hz, 1H), 7.53 (s, 1H), 7.31 (d, J = 8.0 Hz) 7.17 (br s, 2H), 6.96 (s, 1H), 4.19-4.09 (m, 1H), 3.70-3.65 (m, 2H), 3.51-3.48 (m, 2H), 3.29-3.19 (m, 2H), 3.18-2.65 (m, 9H), 2.58 (s, 3H), 1.99-1.90 (m, 1H), 1.89-1.70 (m, 1H). | ++++ | ++ |
| 110 | 3-amino-N-[(3R)-7-[(1S,4S)-2,5-diazabicyclo[2.2.1]heptan-2-yl]-5,8-difluoro-3,4-dihydro-2H-1-benzopyran-3-yl]-6-methylthieno[2,3-b]pyridine-2-carboxamide | 472 | (DMSO-d6, 400 MHz) δ (ppm): 8.33 (d, J = 8.4 Hz, 1H), 7.64 (d, J = 7.2 Hz, 1H), 7.31 (d, J = 8.4 Hz, 1H), 7.24 (br s, 2H), 6.21-6.15 (m, 1H), 4.26-4.23 (m, 3H), 3.95-3.88 (m, 1H), 3.61-3.54 (m, 2H), 3.01-2.72 (m, 5H), 2.58 (s, 3H), 1.73 (d, J = 9.6 Hz, 1H), 1.60 (d, J = 9.3 Hz, 1H). | ++++ | +++ |
| 111 | 3-amino-N-[(3R)-7-[(1R,4R)-2,5-diazabicyclo[2.2.1]heptan-2-yl]-5,8-difluoro-3,4-dihydro-2H-1-benzopyran-3-yl]-6-methylthieno[2,3-b]pyridine-2-carboxamide | 472 | (DMSO-d6, 400 MHz) δ (ppm): 8.34 (d, J = 8.4 Hz, 1H), 7.64 (br s, 1H), 7.32 (d, J = 8.0 Hz, 1H), 7.24 (br s, 2H), 6.20-6.15 (m, 1H), 4.31-4.23 (m, 3H), 3.92-3.87 (m, 1H), 3.59-3.57 (m, 1H), 3.57-3.53 (m, 1H), 3.00-2.97 (m, 1H), 2.91-2.77 (m, 4H), 2.58-2.55 (s, 3H), 1.76-1.72 (m, 1H), 1.62-1.55 (m, 1H). | ++++ | +++ |
| 112 | 3-amino-N-[(3R)-7-[(1S,4S)-2,5-diazabicyclo[2.2.1]heptan-2-yl]-5,6-difluoro-3,4-dihydro-2H-1-benzopyran-3-yl]-6-methylthieno[2,3-b]pyridine-2-carboxamide | 472 | (DMSO-d6, 400 MHz) δ (ppm): 8.34 (d, J = 8.4 Hz, 1H), 7.61 (d, J = 7.2 Hz, 1H), 7.31 (d, J = 8.0 Hz, 1H), 7.24 (br s, 2H), 6.13 (d, J = 6.4 Hz, 1H), 4.49 (s, 1H), 4.28-4.15 (m, 3H), 3.89-3.84 (m, 1H), 3.67-3.65 (m, 2H), 3.23-3.14 (m, 1H), 2.99-2.74 (m, 2H), 2.58 (s, 3H), 2.14 (d, J = 10.8 Hz, 1H), 1.92 (d, J = 10.0 Hz, 1H). | ++++ | ++ |
| 113 | 3-amino-N-[(3R)-7-{9,9-difluoro-3,7-diazabicyclo[3.3.1]nonan-3-yl}-2H,3H,4H-pyrano[2,3-b]pyridin-3-yl]-6-methylthieno[2,3-b]pyridine-2-carboxamide | 501 | (DMSO-d6, 400 MHz) δ (ppm): 8.33 (d, J = 8.4 Hz, 1H), 7.58 (d, J = 7.2 Hz, 1H), 7.38-7.31 (m, 2H), 7.23 (br s, 2H), 6.44 (d, J = 8.4 Hz, 1H), 4.29-4.23 (m, 4H), 4.02-3.98 (m, 1H), 3.19-3.14 (m, 4H), 2.98-2.85 (m, 4H), 2.59 (s, 3H), 2.16-2.14 (m, 2H), 1.85 (br s, 1H). | ++++ | ++ |
| 114 | 3-amino-N-[(3R)-7-{9,9-difluoro-3,7-diazabicyclo[3.3.1]nonan-3-yl}-2H,3H,4H-pyrano[3,2-c]pyridin-3-yl]-6-methylthieno[2,3-b]pyridine-2-carboxamide | 501 | (DMSO-d6, 400 MHz) δ (ppm): 8.33 (d, J = 8.4 Hz, 1H), 7.88 (s, 1H), 7.60 (br s, 1H), 7.31 (d, J = 8.0 Hz, 1H), 7.24 (br s, 2H), 6.22 (s, 1H), 4.31-4.21 (m, 4H), 3.94-3.89 (m, 1H), 3.19-3.13 (m, 4H), 2.97-2.80 (m, 4H), 2.58 (s, 3H), 2.14-2.10 (m, 2H). | ++++ | |
| 115 | 3-amino-N-[(3R)-7-[(3S,4S)-3-amino-4-ethoxypyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.50 (br s, 1H), 7.32 (d, J = 8.0 Hz, 1H), 7.21 (br s, 2H), 6.87 (d, J = 8.4 Hz, 1H), 6.10 (d, J = 8.4 Hz, 1H), 5.90 (s, 1H), 4.33-4.31 (m, 1H), 4.15-4.12 (m, 1H), 3.80-3.77 (m, 1H), 3.76-3.74 (m, 1H), 3.54-3.45 (m, 3H), 3.38-3.3.37 (m, 2H), 3.30 (s, 3H), 3.13-3.11 (m, 1H), 3.09-3.06 (m, 1H), 2.88-2.81 (m, 2H), 2.58 (s, 3H), 1.81 (br s, 2H), 1.12 (d, J = 8.4 Hz, 3H). | | ++ |

TABLE 24-continued

| | | | | | |
|---|---|---|---|---|---|
| 116 | 3-amino-N-[(2S)-6-[(3S,4S)-3-amino-4-methoxypyrrolidin-1-yl]-1,2,3,4-tetrahydronaphthalen-2-yl]-6-methylthieno[2,3-b]pyridine-2-carboxamide | 452 | (DMSO-d6, 400 MHz) δ (ppm): 8.30 (d, J = 8.4 Hz, 1H), 7.53 (br s, 1H), 7.30 (d, J = 8.0 Hz, 1H), 7.15 (br s, 2H), 6.86 (d, J = 8.4 Hz, 1H), 6.32-6.29 (m, 1H), 6.22 (d, J = 2.0 Hz, 1H), 4.14-4.08 (m, 1H), 3.64-3.62 (m, 1H), 3.52-3.48 (m, 1H), 3.43-3.34 (m, 2 H), 3.30 (s, 3H), 3.13-3.10 (m, 1H), 2.91-2.71 (m, 5H), 2.58 (s, 3H), 1.98-1.95 (m, 1H), 1.77-1.72 (m, 1H). | +++ | ++ |
| 117 | 7-amino-N-[(3R)-7-[(3S,4S)-3-amino-4-methoxypyrrolidin-1-yl]-3,4-dihydro-2H-1-benzopyran-3-yl]-3-methylthieno[2,3-b]pyrazine-6-carboxamide | 455 | (DMSO-d6, 300 MHz) δ (ppm): 8.66 (s, 1H), 7.75 (br s, 1H), 6.97 (br s, 2H), 6.88 (d, J = 8.4 Hz, 1H), 6.13-6.09 (m, 1H), 5.92 (d, J = 2.1 Hz, 1H), 4.32-4.25 (m, 1H), 4.19-4.13 (m, 1H), 3.84-3.81 (m, 1H), 3.64-3.62 (m, 1H), 3.49-3.37 (m, 3H), 3.30 (s, 3H), 3.14-3.10 (m, 1H), 2.91-2.84 (m, 3H), 2.66 (s, 3H), 1.72 (br s, 1H). | ++++ | ++ |
| 118 | 6-amino-N-[(3R)-7-[(3,4S)-3-amino-4-methoxypyrrolidin-1-yl]-3,4-dihydro-2H-1-benzopyran-3-yl]-2-methylthieno[2,3-d][1,3]thiazole-5-carboxamide | 460 | (DMSO-d6, 400 MHz) δ (ppm): 7.40 (br s, 1H), 7.13 (s, 2H), 6.87-6.85 (m, 1H), 6.10-6.08 (m, 1H), 5.90 (s, 1H), 4.25-4.22 (m, 1H), 4.12-4.10 (m 1H), 3.77-3.73 (m, 1H), 3.63-3.61(m, 1H), 3.49-3.40 (m, 3H), 3.29 (s, 3H), 3.11-3.09 (m, 1H), 2.89-2.87 (m, 1H), 2.80-2.78 (m, 5H), 1.77 (br s, 2H). | +++ | ++ |
| 119 | 3-amino-N-[(3R)-7-[(3S,4S)-3-amino-4-methoxypiperidin-1-yl]-3,4-dihydro-2H-1-benzopyran-3-yl]-6-methylthieno[2,3-b]pyridine-2-carboxamide | 468 | (DMSO-d6, 300 MHz) δ (ppm): 8.33 (d, J = 8.4 Hz, 1H), 7.53 (d, J = 7.5 Hz, 1H), 7.32 (d, J = 8.4 Hz, 1H), 7.22 (br s, 2H), 6.93 (d, J = 8.4 Hz, 1H), 6.54-6.50 (m, 1H), 6.33 (d, J = 2.1 Hz, 1H), 4.32-4.28 (m, 1H), 4.18-4.15 (m, 1H), 3.86-3.79 (m, 1H), 3.70-3.55 (m, 2H), 3.38 (s, 3H), 3.23-3.21 (m, 1H), 3.02-2.98 (m, 1H), 2.88-2.75 (m, 4H), 2.59 (s, 3H), 2.12-2.08 (m, 1H), 2.08-2.02 (m, 1H), 1.42-1.32 (m, 1H). | +++ | ++ |
| 120 | 3-amino-N-[(3R)-7-[(3R,4R)-3-amino-4-methoxypiperidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.0 Hz, 1H), 7.53 (d, J = 7.2 Hz, 1H), 7.32 (d, J = 8.4 Hz, 1H), 7.21 (br s, 2H), 6.91 (d, J = 8.4 Hz, 1H), 6.51-6.48 (m, 1H), 6.31 (d, J = 2.4 Hz, 1H), 4.28-4.26 (m, 1H), 4.16-4.13 (m, 1H), 3.82-3.77 (m, 1H), 3.55-3.51 (m, 2H), 3.35 (s, 3H), 2.95-2.83 (m, 3H), 2.72-2.65 (m, 2H), 2.58 (s, 3H), 2.50-2.41 (m, 1H), 2.08-2.02 (m, 1H), 1.75-1.55 (br s, 2H), 1.33-1.30 (m, 1H). | ++++ | ++ |
| 121 | 3-amino-N-[(3R)-7-[(3S,4R)-3-amino-4-methoxypyrrolidin-1-yl]-3,4-dihydro-2H-1-benzopyran-3-yl]-6-methylthieno[2,3-b]pyridine-2-carboxamide | 454 | (DMSO-d6, 400 MHz) δ (ppm): 8.33 (d, J = 8.0 Hz, 1H), 7.51 (br s, 1H), 7.32 (d, J = 8.0 Hz, 1H), 7.22 (br s, 2H), 6.87 (d, J = 8.8 Hz, 1H), 6.12-6.07 (m, 1H), 5.89 (s, 1H), 4.30-4.23 (m, 1H), 4.15-4.12 (m, 1H), 3.81-3.73 (m, 2H), 3.49-3.48 (m, 1H), 3.30-3.28 (m, 6H), 2.85-2.81 (m, 3H), 2.59 (s, 3H), 1.26 (br s, 2H). | ++++ | ++ |

TABLE 24-continued

| | | | | | |
|---|---|---|---|---|---|
| 122 | 3-amino-N-[(3R)-7-[(3R,4S)-3-amino-4-methoxypyrrolidin-1-yl]-3,4-dihydro-2H-1-benzopyran-3-yl]-6-methylthieno[2,3-b]pyridine-2-carboxamide | 454 | (DMSO-d6, 400 MHz) δ (ppm): 8.33 (d, J = 8.0 Hz, 1H), 7.50 (br s, 1H), 7.32 (d, J = 8.4 Hz, 1H), 7.22 (s, 2H), 6.87 (d, J = 8.4 Hz, 1H), 6.09-6.07 (m, 1H), 5.89 (s, 1H), 4.29-4.28 (m, 1H), 4.15-4.13 (m, 1H), 3.81-3.74 (m, 2H), 3.51-3.48 (m, 1H), 3.30-3.27 (m, 6H), 2.85-2.81 (m, 3H), 2.59 (s, 3H), 1.24 (br s, 2H). | ++++ | ++ |
| 123 | 3-amino-6-methyl-N-[(3R)-7-[(1s,3S)-3-aminocyclobutyl]-3,4-dihydro-2H-1-benzopyran-3-yl]thieno[2,3-b]pyridine-2-carboxamide | 409 | (DMSO-d6, 400 MHz) δ (ppm): 8.34 (d, J = 8.4 Hz, 1H), 7.58 (d, J = 7.2 Hz, 1H), 7.32 (d, J = 8.4 Hz, 1H), 7.28-7.20 (m, 2H), 7.03 (d, J = 8.0 Hz, 1H), 6.79 (d, J = 8.4 Hz, 1H), 6.67-6.65 (m, 1H), 4.33-4.25 (m, 1H), 4.20-4.17 (d, J = 10.4 Hz, 1H), 3.86-3.81 (m, 1H), 3.55-3.52 (m, 1H), 3.49-3.44 (m, 1H), 2.98-2.89 (m, 2H), 2.58-2.53 (s, 3H), 2.30-2.20 (m, 2H), 2.18-2.07 (m, 2H). | ++++ | ++ |
| 124 | 3-amino-6-methyl-N-[(3R)-7-[(1r,3r)-3-aminocyclobutyl]-3,4-dihydro-2H-1-benzopyran-3-yl]thieno[2,3-b]pyridine-2-carboxamide | 409 | (DMSO-d6, 400 MHz) δ (ppm): 8.31 (d, J = 8.4 Hz, 1H), 7.32 (d, J = 8 Hz, 1H), 7.02 (d, J = 7.6 Hz, 1H), 6.79-6.76 (m, 1H), 6.69-6.68 (s, 1H), 4.33-4.25 (m, 1H), 4.18-4.16 (d, J = 10 Hz, 1H), 3.86-3.81 (m, 1H), 3.29-3.21 (m, 1H), 2.95-2.88 (m, 3H), 2.57-2.55 (s, 3H), 2.54-2.52 (m, 2H), 1.78-1.76 (m, 2H). | ++++ | ++ |
| 125 | 3-amino-6-methyl-N-[(3R)-7-{3-oxa-9-azabicyclo[3.3.1]nonan-7-yl}-3,4-dihydro-2H-1-benzopyran-3-yl]thieno[2,3-b]pyridine-2-carboxamide | 465 | (DMSO-d6, 400 MHz) δ (ppm): 8.33 (d, J = 8.4 Hz, 1H), 7.58 (d, J = 7.6 H, 1H), 7.32 (d, J = 8.0 Hz, 1H), 7.24 (br s, 2H), 7.02 (d, J = 8.0 Hz, 1H), 6.78 (d, J = 8.0 Hz, 1H), 6.68 (s, 1H), 4.33-4.17 (m, 2H), 3.86-3.75 (m, 6H), 2.99-2.83 (m, 4H), 2.59 (s, 3H), 2.43 (br s, 1H), 1.87-1.81 (m, 4H). | ++++ | +++ |
| 126 | 3-amino-N-[(3R)-6-cyano-7-(3,8-diazabicyclo[3.2.1]octan-3-yl}-5-fluoro-3,4-dihydro-2H-1-benzopyran-3-yl]-6-methylthieno[2,3-b]pyridine-2-carboxamide | 493 | (DMSO-d6, 400 MHz) δ (ppm): 8.32 (d, J = 8.0 Hz, 1H), 7.70 (d, J = 6.4 Hz, 1H), 7.31 (d, J = 8.4 Hz, 1H), 7.24 (br s, 2H), 6.29 (s, 1H), 4.30-4.25 (m, 2H), 4.06-4.01 (m, 1H), 3.48 (s, 2H), 3.33-3.28 (m, 2H), 2.96-2.67 (m, 4H), 2.58 (s, 3H), 1.88-1.87 (m, 2H), 1.67-1.65 (m, 2H). | ++++ | ++++ |
| 127 | 3-amino-N-[(3R)-6-cyano-5-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide | 509 | (DMSO-d6, 400 MHz) δ (ppm): 8.33 (d, J = 8.4 Hz, 1H), 7.66 (d, J = 6.8 Hz, 1H), 7.31 (d, J = 8.4 Hz, 1H), 7.28 (br s, 2H), 6.43 (s, 1H), 4.34-4.28 (m, 2H), 4.10-4.05 (m, 1H), 3.71 (s, 2H), 3.57-3.51 (m, 2H), 3.29-3.26 (m, 2H), 3.16-3.12 (m, 2H), 3.04-2.94 (m, 3H), 2.86-2.82 (m, 1H), 2.58 (s, 3H). | ++++ | +++ |
| 128 | 3-amino-N-[(3R)-7-[(3S,4S)-4-amino-3-methoxypiperidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.0 Hz, 1H), 7.53 (d, J = 7.2 Hz, 1H), 7.31 (d, J = 8.4 Hz, 1H), 7.22 (s, 2H), 6.92 (d, J = 8.8 Hz, 1H), 6.55-6.53 (m, 1H), 6.35 (d, J = 2.0 Hz, 1H), 4.28 (br s, 1H), 4.17-4.13 (m, 1H), 3.86-3.77 (m, 2H), 3.53-3.50 (m, 1H), 3.39 (s, 3H), 2.89-2.83 (m, 3H), 2.67-2.55 (m, 6H), 2.38-2.35 (m, 1H), 1.88-1.70 (m, 2H), 1.38-1.29 (m, 1H). | ++++ | ++ |

TABLE 24-continued

| 129 | 3-amino-N-[(3R)-7-[(3R,4R)-4-amino-3-methoxypiperidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.0 Hz, 1H), 7.53 (br s, 1H), 7.31 (d, J = 8.4 Hz, 1H), 7.22 (br s, 2H), 6.91 (d, J = 8.4 Hz, 1H), 6.55-6.53 (m, 1H), 6.35 (d, J = 2.4 Hz, 1H), 4.30-4.26 (m, 1H), 4.17-4.13 (m, 1H), 3.85-3.77 (m, 2H), 3.54-3.51 (m, 1H), 3.39 (s, 3H), 2.90-2.84 (m, 3H), 2.66-2.53 (m, 6H), 2.37-2.32 (m, 1H), 1.79-1.68 (m, 2H), 1.36-1.32 (m, 1H). | ++++ | ++ |
| 130 | 7-amino-N-[(2S)-6-[(3S,4S)-3-amino-4-methoxypyrrolidin-1-yl]-1,2,3,4-tetrahydronaphthalen-2-yl]-3-methylthieno[2,3-b]pyrazine-6-carboxamide | 453 | (DMSO-d6, 400 MHz) δ (ppm): 8.65 (s, 1H), 7.79 (d, J = 8.0 Hz, 1H), 6.91 (br s, 2H), 6.87 (d, J = 8.4 Hz, 1H), 6.32 (dd, J = 8.0, 2.0 Hz, 1H), 6.24 (s, 1H), 4.16-4.11 (m, 1H), 3.65-3.63 (m, 1H), 3.53-3.49 (m, 1H), 3.42-3.35 (m, 2H), 3.32 (s, 3H), 3.14-3.11 (m, 1H), 2.92-2.79 (m, 5H), 2.65 (s, 3H), 2.10-1.90 (m, 3H), 1.79-1.73 (m, 1H). | +++ | ++ |
| 131 | N-[(2S)-6-[(3S,4S)-3-amino-4-methoxypyrrolidin-1-yl]-1,2,3,4-tetrahydronaphthalen-2-yl]-7-ethyl-7H-pyrrolo[2,3-c]pyridazine-3-carboxamide | 435 | (DMSO-d6, 400 MHz) δ (ppm): 8.87 (d, J = 8.4 Hz, 1H), 8.45 (s, 1H), 8.09 (d, J = 3.2 Hz, 1H), 6.90 (d, J = 8.4 Hz, 1H), 6.75 (d, J = 3.6 Hz, 1H), 6.37-6.29 (m, 1H), 6.29 (s, 1H), 4.52 (dd, J = 14.4, 7.2 Hz, 2H), 4.33-4.27 (m, 1H), 3.64-3.63 (m, 1H), 3.54-3.50 (m, 1H), 3.37-3.33 (m, 2H), 3.31 (s, 3H), 3.15-3.13 (m, 1H), 2.95-2.79 (m, 5H), 2.01-1.86 (m, 2H), 1.48 (t, J = 7.2 Hz, 3H). | + | + |
| 132 | N-[(2S)-6-[(3S,4S)-3-amino-4-methoxypyrrolidin-1-yl]-1,2,3,4-tetrahydronaphthalen-2-yl]-1-ethyl-1H-pyrrolo[2,3-b]pyridine-5-carboxamide | 434 | (DMSO-d6, 400 MHz) δ (ppm): 8.77 (s, 1H), 8.47 (s, 1H), 8.41 (d, J = 7.6 Hz, 1H), 7.68 (d, J = 3.6 Hz, 1H), 6.89 (d, J = 8.4 Hz, 1H), 6.59 (d, J = 3.6 Hz, 1H), 6.34-6.32 (m, 1H), 6.24 (s, 1H), 4.33 (dd, J = 14.4, 7.2 Hz, 2H), 4.16-4.12 (m, 1H), 3.65-3.64 (m, 1H), 3.53-3.43 (m, 1H), 3.43-3.35 (m, 2H), 3.31 (s, 3H), 3.15-3.12 (m, 1H), 2.95-2.90 (m, 2H), 2.90-2.81 (m, 2H), 2.2.78-2.71 (m, 1H), 2.10-2.01 (m, 1H), 1.92 (br s, 2H), 1.83-1.67 (m, 1H), 1.40 (t, J = 7.2 Hz, 3H). | ++ | + |
| 133 | 6-amino-N-[(2S)-6-[(3S,4S)-3-amino-4-methoxypyrrolidin-1-yl]-1,2,3,4-tetrahydronaphthalen-2-yl]-2-methylthieno[2,3-d][1,3]thiazole-5-carboxamide | 458 | (DMSO-d6, 400 MHz) δ (ppm): 7.43 (d, J = 7.6 Hz, 1H), 7.07 (br s, 2H), 6.86 (d, J = 8.0 Hz, 1H), 6.31 (dd, J = 8.4, 2.4 Hz, 1H), 6.22 (s, 1H), 4.12-4.04 (m, 1H), 3.64-3.62 (m, 1H), 3.53-3.50 (m, 1H), 3.48-3.32 (m, 2H), 3.30 (s, 3H), 3.14-3.11 (m, 1H), 2.92-2.89 (m, 1H), 2.84-2.78 (m, 6H), 2.72-2.68 (m, 1H), 1.96-1.94 (m, 1H), 1.85-1.65 (m, 3H). | +++ | + |
| 134 | 3-amino-N-[(2S)-6-[(3S,4S)-3-amino-4-methoxypyrrolidin-1-yl]-1,2,3,4-tetrahydronaphthalen-2-yl]-6-methoxythieno[2,3-b]pyridine-2-carboxamide | 468 | (DMSO-d6, 400 MHz) δ (ppm): 8.30 (d, J = 7.2 Hz, 1H), 7.41 (d, J = 7.6 Hz, 1H), 7.13 (br s, 2H), 6.87 (dd, J = 8.4, 2.0 Hz, 2H), 6.32 (dd, J = 8.0, 2.0 Hz, 1H), 6.22 (s, 1H), 4.14-4.06 (m, 1H), 3.94 (s, 3H), 3.65-3.63 (m, 1H), 3.52-3.47 (m, 1H), 3.42-3.35 (m, 2H), 3.30 (s, 3H), 3.14-3.12 (m, 1H), 2.93-2.69 (m, 5H), | ++ | + |

TABLE 24-continued

| | | | | | |
|---|---|---|---|---|---|
| 135 | 3-amino-N-[(2S)-6-[(3S,4S)-3-amino-4-methoxypyrrolidin-1-yl]-1,2,3,4-tetrahydronaphthalen-2-yl]-5-fluoro-6-methoxythieno[2,3-b]pyridine-2-carboxamide | 486 | (DMSO-d6, 400 MHz) δ (ppm): 8.32 (d, J = 10.8 Hz, 1H), 7.49 (d, J = 7.6 Hz, 1H), 7.08 (br s, 2H), 6.87 (d, J = 8.4 Hz, 1H), 6.31 (dd, J = 8.0, 2.0 Hz, 1H), 6.23 (s, 1H), 4.09-4.03 (m, 4H), 3.65-3.63 (m, 1H), 3.53-3.52 (m, 1H), 3.48-3.42 (m, 2H), 3.41 (s, 3H), 3.14-3.11 (m, 1H), 2.92-2.71 (m, 5H), 2.01-1.95 (m, 1H), 1.85-1.68 (m, 3H). | ++ | + |
| 136 | 3-amino-N-[(2S)-6-[(3S,4S)-3-amino-4-methoxypyrrolidin-1-yl]-8-fluoro-1,2,3,4-tetrahydronaphthalen-2-yl]-6-methylthieno[2,3-b]pyridine-2-carboxamide | 470 | (DMSO-d6, 400 MHz) δ (ppm): 8.31 (d, J = 8.4 Hz, 1H), 7.60 (d, J = 7.6 Hz, 1H), 7.31 (d, J = 8.0 Hz, 1H), 7.17 (br s, 2H), 6.14 (d, J = 12.4 Hz, 1H), 6.09 (s, 1H), 4.14-4.08 (m, 1H), 3.63-3.61 (m, 1H), 3.54-3.41 (m, 3H), 3.37 (s, 3H), 3.17-3.12 (m, 1H), 3.95-3.79 (m, 4H), 2.59-2.52 (m, 4H), 2.00-1.95 (m, 1H), 1.81-1.69 (m, 3H). | + | + |
| 137 | 3-amino-N-[(2R)-6-[(3S,4S)-3-amino-4-methoxypyrrolidin-1-yl]-8-fluoro-1,2,3,4-tetrahydronaphthalen-2-yl]-6-methylthieno[2,3-b]pyridine-2-carboxamide | 470 | (DMSO-d6, 400 MHz) δ (ppm): 8.31 (d, J = 8.4 Hz, 1H), 7.60 (d, J = 7.6 Hz, 1H), 7.31 (d, J = 8.4 Hz, 1H), 7.17 (br s, 2H), 6.14 (d, J = 12.8 Hz, 1H), 6.09 (s, 1H), 4.14-4.08 (m, 1H), 3.63-3.61 (m, 1H), 3.54-3.41 (m, 3H), 3.37 (s, 3H), 3.17-3.12 (m, 1H), 3.95-3.79 (m, 4H), 2.59 (s, 3H), 2.57-2.51 (m, 1H), 1.97-1.94 (m, 1H), 1.81-1.69 (m, 3H). | +++ | + |
| 138 | N-[(2S)-6-[(3S,4S)-3-amino-4-methoxypyrrolidin-1-yl]-8-fluoro-1,2,3,4-tetrahydronaphthalen-2-yl]-7-ethyl-7H-pyrrolo[2,3-c]pyridazine-3-carboxamide | 453 | (DMSO-d6, 400 MHz) δ (ppm): 8.98 (d, J = 8.4 Hz, 1H), 8.46 (s, 1H), 8.10 (d, J = 3.2 Hz, 1H), 6.75 (d, J = 3.6 Hz, 1H), 6.16 (d, J = 12.4 Hz, 1H), 6.12 (s, 1H), 4.53 (dd, J = 14.4, 7.2 Hz, 2H), 4.33-4.25 (m, 1H), 3.65-3.63 (m, 1H), 3.55-3.45 (m, 1H), 3.42-3.40 (m, 1H), 3.35-3.32 (m, 1H), 3.30 (s, 3H), 3.17-3.14 (m, 1H), 2.98-2.80 (m, 4H), 2.70-2.61 (m, 1H), 2.13-1.85 (m, 2H), 1.72 (br s, 2H), 1.49 (t, J = 7.2 Hz, 3H). | + | + |
| 139 | N-[(2R)-6-[(3S,4S)-3-amino-4-methoxypyrrolidin-1-yl]-8-fluoro-1,2,3,4-tetrahydronaphthalen-2-yl]-7-ethyl-7H-pyrrolo[2,3-c]pyridazine-3-carboxamide | 453 | (DMSO-d6, 400 MHz) δ (ppm): 8.98 (d, J = 8.4 Hz, 1H), 8.46 (s, 1H), 8.10 (d, J = 3.6 Hz, 1H), 6.75 (d, J = 3.2 Hz, 1H), 6.16 (d, J = 12.4 Hz, 1H), 6.12 (s, 1H), 4.53 (dd, J = 14.4, 7.2 Hz, 2H), 4.33-4.25 (m, 1H), 3.65-3.63 (m, 1H), 3.55-3.45 (m, 1H), 3.42-3.40 (m, 1H), 3.35-3.32 (m, 1H), 3.30 (s, 3H), 3.16-3.14 (m, 1H), 2.98-2.80 (m, 4H), 2.70-2.61 (m, 1H), 2.13-1.85 (m, 2H), 1.71 (br s, 2H), 1.49 (t, J = 7.2 Hz, 3H). | + | + |
| 140 | 3-amino-N-[(3R)-7-[(3S,4S)-3-amino-4-cyclopropoxypyrrolidin-1-yl]-3,4-dihydro-2H-1-benzopyran-3-yl]-6-methylthieno[2,3-b]pyridine-2-carboxamide | 480 | (DMSO-d6, 400 MHz) δ (ppm): 8.32 (d, J = 8.0 Hz, 1H), 7.49 (br s, 1H), 7.32 (d, J = 8.4 Hz, 1H), 7.21 (br s, 2H), 6.87 (d, J = 8.4 Hz, 1H), 6.10 (d, J = 8.8 Hz, 1H), 5.91 (s, 1H), 4.30-4.26 (m, 1H), 4.16-4.12 (m, 1H), 3.84-3.76 (m, 2H), 3.54-3.50 (m, 1H), 3.45-3.37 (m, 3H), 3.15-3.13 (m, 1H), 2.89-2.82 (m, 3H), 2.59 | ++++ | ++ |

TABLE 24-continued

| | | | | | |
|---|---|---|---|---|---|
| 141 | 3-amino-N-[(3R)-7-[(3S,4S)-3-amino-4-cyclobutoxypyrrolidin-1-yl]-3,4-dihydro-2H-1-benzopyran-3-yl]-6-methylthieno[2,3-b]pyridine-2-carboxamide | 494 | (s, 3H), 1.80 (br s, 2H), 0.52-0.47 (m, 4 H). (DMSO-d6, 400 MHz) δ (ppm): 8.33 (d, J = 8.4 Hz, 1H), 7.48 (d, J = 7.2 Hz, 1H), 7.32 (d, J = 8.4 Hz, 1H), 7.21 (br s, 2H), 6.87 (d, J = 8.0 Hz, 1H), 6.09 (d, J = 8.0 Hz, 1H), 5.90 (s, 1H), 4.28 (br s, 1H), 4.15-4.13 (m, 1H), 4.07-4.03 (m, 1H), 3.81-3.76 (m, 1H), 3.69 (s, 1H), 3.49-3.46 (m, 1H), 3.37-3.35 (m, 2H), 3.04 (d, J = 8.0 Hz,, 1H), 2.89-2.82 (m, 3H), 2.59 (s, 3H), 2.18-2.08 (m, 2H), 1.87-1.40 (m, 6H). | ++++ | +++ |
| 142 | 3-amino-N-[(6S)-2-[(3S,4S)-3-amino-4-ethoxypyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.33 (d, J = 10.4 Hz, 1H), 7.56 (br s, 1H), 7.31 (d, J = 8.4 Hz, 1H), 7.20-7.16 (m, 3H), 6.22 (d, J = 8.8 Hz, 1H), 4.13-4.10 (m, 1H), 3.72-3.70 (m, 1H), 3.64-3.61 (m, 1H), 3.52-3.40 (m, 4H), 3.32-3.29 (m, 1H), 3.12-3.10 (m, 1H), 2.81-2.68 (m, 4H), 2.59 (s, 3H), 2.05-1.97 (m, 1H), 1.87-1.67 (m, 3H), 1.12 (t, J = 8.0 Hz, 3H). | ++ | + |
| 143 | 3-amino-N-[(2S)-6-[(3S,4R)-3-amino-4-methoxypyrrolidin-1-yl]-1,2,3,4-tetrahydronaphthalen-2-yl]-6-methylthieno[2,3-b]pyridine-2-carboxamide | 452 | (DMSO-d6, 400 MHz) δ (ppm): 8.30 (d, J = 8.0 Hz, 1H), 7.52 (d, J = 9.2 Hz, 1H), 7.31 (d, J = 8.0 Hz, 1H), 7.15 (br s, 2H), 6.86 (d, J = 8.0 Hz, 1H), 6.30-6.28 (m, 1H), 6.21 (s, 1H), 4.12-4.09 (m, 1H), 3.75-3.70 (m, 1H), 3.52-3.50 (m, 1H), 3.35 3.25 (m, 6H), 2.86-2.68 (m, 5H), 2.59 (s, 3H), 1.98-1.95 (m, 1H), 1.77-1.71 (m, 1H), 1.57 (br s, 2H). | ++++ | ++ |
| 144 | 3-amino-N-[(2S)-6-[(3R,4S)-3-amino-4-methoxypyrrolidin-1-yl]-1,2,3,4-tetrahydronaphthalen-2-yl]-6-methylthieno[2,3-b]pyridine-2-carboxamide | 452 | (DMSO-d6, 400 MHz) δ (ppm): 8.30 (d, J = 8.0 Hz, 1H), 7.52 (d, J = 9.2 Hz, 1H), 7.31 (d, J = 8.0 Hz, 1H), 7.15 (br s, 2H), 6.86 (d, J = 8.0 Hz, 1H), 6.30-6.28 (m, 1H), 6.21 (s, 1H), 4.12-4.09 (m, 1H), 3.75-3.70 (m, 1H), 3.52-3.50 (m, 1H), 3.35 3.25 (m, 6H), 2.86-2.68 (m, 5H), 2.59 (s, 3H), 1.98-1.95 (m, 1H), 1.77-1.57 (m, 3H). | +++ | ++ |
| 145 | 3-amino-N-[(3R)-7-[(3S,4R)-3-amino-4-methoxypyrrolidin-1-yl]-5-fluoro-3,4-dihydro-2H-1-benzopyran-3-yl]-6-methylthieno[2,3-b]pyridine-2-carboxamide | 472 | (DMSO-d6, 400 MHz) δ (ppm): 8.33 (d, J = 8.4 Hz, 1H), 7.55 (br s, 1H), 7.32 (d, J = 8.4 Hz, 1H), 7.23 (br s, 2H), 5.94 (d, J = 14.0 Hz, 1H), 5.77 (s, 1H), 4.28-4.24 (m, 1H), 4.18-4.16 (m, 1H), 3.86-3.81 (m, 1H), 3.74-3.73 (m, 1H), 3.50-3.47 (m, 1H), 3.33(s, 3H), 3.28-3.22 (m, 3H), 2.87-2.83(m, 2H), 2.75-2.71 (m, 1H), 2.59 (s, 3H), 1.66 (br s, 2H). | ++++ | ++ |
| 146 | 3-amino-N-[(3R)-7-[(3R,4S)-3-amino-4-methoxypyrrolidin-1-yl]-5-fluoro-3,4-dihydro-2H-1-benzopyran-3-yl]-6-methylthieno[2,3-b]pyridine-2-carboxamide | 472 | (DMSO-d6, 400 MHz) δ (ppm): 8.33 (d, J = 8.4 Hz, 1H), 7.55 (br s, 1H), 7.32 (d, J = 8.4 Hz, 1H), 7.22 (br s, 2H), 5.94 (d, J = 12.4 Hz, 1H), 5.77 (s, 1H), 4.29-4.26 (m, 1H), 4.17-4.15 (m, 1H), 3.86-3.81 (m, 1H), 3.74-3.73 (m, 1H), 3.49-3.46 (m, 1H), 3.34-3.22(m, 6H), 2.87-2.83 (m, 2H), 2.75-2.71 (m, 1H), 2.59 (s, 3H), 1.66 (br s, 2H). | ++++ | ++ |

| | | | | | |
|---|---|---|---|---|---|
| 147 | 7-amino-N-[(3R)-7-[(3S,4R)-3-amino-4-methoxypyrrolidin-1-yl]-3,4-dihydro-2H-1-benzopyran-3-yl]-3-methylthieno[2,3-b]pyrazine-6-carboxamide | 455 | (DMSO-d6, 400 MHz) δ (ppm): 8.65 (s, 1H), 7.73 (d, J = 7.6 Hz, 1H), 6.96 (br s, 2H), 6.87 (d, J = 8.0 Hz, 1H), 6.08 (d, J = 8.0 Hz, 1H), 5.89 (s, 1H), 4.29-4.21 (m, 1H), 4.17-4.14 (m, 1H), 3.83-3.78 (m, 1H), 3.75-3.73 (m, 1H), 3.51-3.46 (m, 1H), 3.38 (s, 3H), 3.27-3.26 (m, 3H), 2.86-2.82 (m, 3H), 2.65 (s, 3H), 1.75 (br s, 2H). | +++ | ++ |
| 148 | 7-amino-N-[(3R)-7-[(3R,4S)-3-amino-4-methoxypyrrolidin-1-yl]-3,4-dihydro-2H-1-benzopyran-3-yl]-3-methylthieno[2,3-b]pyrazine-6-carboxamide | 455 | (DMSO-d6, 400 MHz) δ (ppm): 8.65 (s, 1H), 7.74 (d, J = 7.2 Hz, 1H), 6.96 (s, 2H), 6.87 (d, J = 9.2 Hz, 1H), 6.08 (d, J = 6.4 Hz, 1H), 5.89 (s, 1H), 4.29-4.21 (m, 1H), 4.17-4.14 (m, 1H), 3.83-3.78 (m, 1H), 3.75-3.73 (m, 1H), 3.49-3.48 (m, 1H), 3.34 (s, 3H), 3.32-3.27 (m, 1H), 3.27-3.24 (m, 2H), 2.85-2.82 (m, 3H), 2.65 (s, 3H), 1.70 (br s, 2H). | ++++ | ++ |
| 149 | 6-amino-N-[(3R)-7-[(3S,4R)-3-amino-4-methoxypyrrolidin-1-yl]-3,4-dihydro-2H-1-benzopyran-3-yl]-2-methylthieno[2,3-d][1,3]thiazole-5-carboxamide | 460 | (DMSO-d6, 400 MHz) δ (ppm): 7.39 (br s, 1H), 7.12 (br s, 2H), 6.86 (d, J = 8.4 Hz, 1H), 6.07 (d, J = 10.8 Hz, 1H), 5.88 (s, 1H), 4.26-4.22 (m, 1H), 4.13-4.10 (m, 1H), 3.78-3.73 (m, 2H), 3.50-3.46 (m, 1H), 3.33-3.31 (m, 3H), 3.29-3.27 (m, 3H), 2.86-2.79 (m, 6H), 1.75 (br s, 2H). | ++++ | ++ |
| 150 | 6-amino-N-[(3R)-7-[(3R,4S)-3-amino-4-methoxypyrrolidin-1-yl]-3,4-dihydro-2H-1-benzopyran-3-yl]-2-methylthieno[2,3-d][1,3]thiazole-5-carboxamide | 460 | (DMSO-d6, 400 MHz) δ (ppm): 7.39 (br s, 1H), 7.12 (br s, 2H), 6.85 (d, J = 8.0 Hz, 1H), 6.07 (d, J = 10.4 Hz, 1H), 5.87 (s, 1H), 4.26-4.22 (m, 1H), 4.13-4.10 (m, 1H), 3.76-3.73 (m, 2H), 3.50-3.46 (m, 1H), 3.33-3.31 (m, 3H), 3.29-3.27 (m, 3H), 2.83-2.79 (m, 6H), 1.60 (br s, 2H). | +++ | ++ |
| 151 | 3-amino-N-[(3R)-7-[(3S,4R)-3-amino-4-ethoxypyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.27 (d, J = 7.6 Hz, 1H), 7.30 (d, J = 8.4 Hz, 1H), 6.86 (d, J = 8.0 Hz, 1H), 6.06 (d, J = 8.0 Hz, 1H), 5.87 (s, 1H), 4.27-4.25 (m, 2H), 4.13-4.11 (m, 1H), 3.85-3.77 (m, 2H), 3.49-3.42 (m, 3H), 3.38-3.28 (m, 2H), 3.21-3.18 (m, 1H), 2.85-2.81 (m, 3H), 2.57 (s, 3H), 1.14-1.12 (m, 3H). | ++++ | ++ |
| 152 | 3-amino-N-[(3R)-7-[(3R,4S)-3-amino-4-ethoxypyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.29 (d, J = 8.4 Hz, 1H), 7.31 (d, J = 8.4 Hz, 1H), 6.86 (d, J = 9.2 Hz, 1H), 6.07 (d, J = 7.2 Hz, 1H), 5.87 (s, 1H), 4.26 (br s, 2H), 4.14-4.11 (m, 1H), 3.84-3.77 (m, 2H), 3.46-3.44 (m, 2H), 3.35-3.28 (m, 2H), 3.21-3.19 (m, 1H), 2.85-2.81 (m, 3H), 2.58 (s, 3H), 1.15-1.12 (m, 3H). | ++++ | ++ |
| 153 | N-[(3R)-7-[(4aS,7aR)-octahydropyrrolo[3,4-b]morpholin-6-yl]-3,4-dihydro-2H-1-benzopyran-3-yl]-3-amino-6-methylthieno[2,3-b]pyridine-2-carboxamide | 466 | (DMSO-d6, 400 MHz) δ (ppm): 8.33 (d, J = 8.0 Hz, 1H), 7.47 (br s, 1H), 7.32 (d, J = 8.4 Hz, 1H), 7.21 (br s, 2H), 6.87 (d, J = 8.4 Hz, 1H), 6.09 (d, J = 10.4 Hz, 1H), 5.90 (s, 1H), 4.30-4.26 (m, 1H), 4.15-4.13 (m, 1H), 3.97-3.95 (m, 1H), 3.82-3.77 (m, 1H), 3.68-3.66 (m, 1H), 3.49-3.37 (m, 3H), 3.31-3.29 (m, 1H), 3.15-3.11 (m, 2H), 2.96-2.82 (m, 3H), 2.59 (s, 3H), 2.55-2.50 (m, 1H). | +++ | ++ |

TABLE 24-continued

| | | | | | |
|---|---|---|---|---|---|
| 154 | N-[(3R)-7-[(4aR,7aS)-octahydropyrrolo[3,4-b]morpholin-6-yl]-3,4-dihydro-2H-1-benzopyran-3-yl]-3-amino-6-methylthieno[2,3-b]pyridine-2-carboxamide | 466 | (DMSO-d6, 400 MHz) δ (ppm): 8.33 (d, J = 8.4 Hz, 1H), 7.47 (br s, 1H), 7.32 (d, J = 8.0 Hz, 1H), 7.21 (br s, 2H), 6.87 (d, J = 8.4 Hz, 1H), 6.09 (d, J = 8.4 Hz, 1H), 5.90 (s, 1H), 4.30-4.26 (m, 1H), 4.15-4.13 (m, 1H), 3.97-3.95 (m, 1H), 3.82-3.77 (m, 1H), 3.68-3.66 (m, 1H), 3.49-3.37 (m, 3H), 3.15-3.10 (m, 2H), 2.95-2.82 (m, 3H), 2.59 (s, 3H), 2.55-2.51 (m, 1H). | +++ | ++ |
| 155 | 3-amino-N-[(3R)-7-[(2S)-2-(methoxymethyl)piperazin-1-yl]-3,4-dihydro-2H-1-benzopyran-3-yl]-6-methylthieno[2,3-b]pyridine-2-carboxamide | 468 | (DMSO-d6, 300 MHz) δ (ppm): 8.22-8.41 (m, 2H), 7.52 (br d, J = 7.62 Hz, 1H), 7.31 (d, J = 8.21 Hz, 1H), 7.10-7.26 (m, 2H), 6,74-7.10 (m, 2H), 6.40-6.73 (m, 1H), 6.33 (s, 1H), 6.20-6.30 (m, 1H), 4.27 (br d, J = 7.92 Hz, 1H), 4.10-4.21 (m, 1H), 3.61-3.97 (m, 3H), 3.27-3.43 (m, 1H), 3.02-3.22 (m, 4H), 2.65-3.01 (m, 5H), 2.56-2.60 (m, 3H). | ++++ | +++ |
| 156 | 3-amino-N-[(3R)-7-[(2R)-2-(methoxymethyl)piperazin-1-yl]-3,4-dihydro-2H-1-benzopyran-3-yl]-6-methylthieno[2,3-b]pyridine-2-carboxamide | 468 | (DMSO-d6, 300 MHz) δ (ppm): 8.26-8.48 (m, 1H), 8.13-8.25 (m, 4H), 7.53 (br d, J = 7.62 Hz, 1H), 7.16-7.51 (m, 4H), 6.85-7.16 (m, 1H), 6.43-6.70 (m, 1H), 6.29-6.41 (m, 1H), 4.29 (br s, 1H), 4.04-4.24 (m, 2H), 3.76-4.01 (m, 3H), 3.51-3.75 (m, 2H), 3.28-3.50 (m, 3H), 2.94-3.21 (m, 6H), 2.79-2.94 (m, 3H), 2.57-2.74 (m, 5H), 2.43-2.48 (m, 1H), 1.31-1.46 (m, 1H). | +++ | ++ |
| 157 | 3-amino-N-[(3R)-7-[(3R)-3-(methoxymethyl)piperazin-1-yl]-3,4-dihydro-2H-1-benzopyran-3-yl]-6-methylthieno[2,3-b]pyridine-2-carboxamide | 468 | 1H NMR not taken. | ++++ | ++ |
| 158 | 3-amino-N-[(3R)-7-[(3S)-3-(methoxymethyl)piperazin-1-yl]-3,4-dihydro-2H-1-benzopyran-3-yl]-6-methylthieno[2,3-b]pyridine-2-carboxamide | 468 | 1H NMR not taken. | +++ | ++ |
| 159 | 3-amino-N-[(3R)-5,6-difluoro-7-(piperazin-1-yl)-3,4-dihydro-2H-1-benzopyran-3-yl]-4,6-dimethylthieno[2,3-b]pyridine-2-carboxamide | 474 | (DMSO-d6, 400 MHz) δ (ppm): 7.65 (br s, 1H), 7.04 (s, 1H), 6.88 (br s, 2H), 6.28 (s, 1H), 4.36-4.28 (m, 1H), 4.18-4.16 (m, 1H), 3.91-3.86 (m, 1H), 2.95-2.79 (m, 10H), 2.73 (s, 3H), 2.51 (s, 3H). | + | + |
| 160 | 3-amino-N-[(3S)-5,6-difluoro-7-(piperazin-1-yl)-3,4-dihydro-2H-1-benzopyran-3-yl]-4,6-dimethylthieno[2,3-b]pyridine-2-carboxamide | 474 | (DMSO-d6, 400 MHz) δ (ppm): 7.66 (br s, 1H), 7.05 (s, 1H), 6.88 (br s, 2H), 6.27 (d, J = 6.8 Hz, 1H), 4.35-4.25 (m, 1H), 4.18-4.16 (m, 1H), 3.90-3.86 (m, 1H), 2.95-2.85 (m, 5H), 2.85-2.78 (m, 5H), 2.73 (s, 3H), 2.51 (s, 3H). | ++++ | ++ |
| 161 | 3-amino-N-[(3R)-7-[(3R,4R)-3-amino-4-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.0 Hz, 1H), 7.49 (br s, 1H), 7.32 (d, J = 8.4 Hz, 1H), 7.22 (br s, 2H), 6.87 (d, J = 8.0 Hz, 1H), 6.10-6.07 (m, 1H), 5.88 (s, 1H), 4.31-4.26 (m, 1H), 4.16-4.13 (m, 1H), 3.81-3.77 (m, 1H), 3.60-3.55 (m, 2H), 3.41-3.33 (m, 2H), 3.28 (s, 3H), 3.25-3.21 (m, 1H), 3.09-3.05 (m, 1H), 2.96-2.93 (m, 1H), 2.85-2.82 (m, 2H), 2.59 (s, 3H), 2.52-2.41 (m, 1H), 1.53 (br s, 2H). | ++++ | ++ |

TABLE 24-continued

| | | | | | |
|---|---|---|---|---|---|
| 162 | 3-amino-N-[(3R)-7-[(3S,4S)-3-amino-4-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.0 Hz, 1H), 7.47 (br s, 1H), 7.31 (d, J = 8.4 Hz, 1H), 7.20 (br s, 2H), 6.86 (d, J = 8.4 Hz, 1H), 6.09-6.07 (m, 1H), 5.88 (s, 1H), 4.31-4.26 (m, 1H), 4.15-4.12 (m, 1H), 3.82-3.77 (m, 1H), 3.60-3.54 (m, 2H), 3.41-3.35 (m, 2H), 3.28 (s, 3H), 3.25-3.21 (m, 1H), 3.09-3.05 (m, 1H), 2.96-2.93 (m, 1H), 2.85-2.81 (m, 2H), 2.59 (s, 3H), 2.52-2.41 (m, 1H), 1.53 (br s, 2H) | ++++ | +++ |
| 163 | 3-amino-N-[(3R)-7-[(3S,4R)-3-amino-4-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.0 Hz, 1H), 7.49 (br s, 1H), 7.32 (d, J = 8.4 Hz, 1H), 7.22 (br s, 2H), 6.86 (d, J = 8.4 Hz, 1H), 6.10-6.07 (m, 1H), 5.88 (d, J = 2.0 Hz, 1H), 4.29-4.25 (m, 1H), 4.15-4.12 (m, 1H), 3.81-3.76 (m, 1H), 3.51-3.48 (m, 1H), 3.43-3.40 (m, 2H), 3.39-3.30 (m, 1H), 3.27 (s, 3H), 3.23-3.18 (m, 1H), 3.00-2.95 (m, 1H), 2.89-2.81 (m, 3H), 2.58 (s, 3H), 2.19-2.13 (m, 1H), 1.86 (br s, 2H) | ++++ | ++ |
| 164 | 3-amino-N-[(3R)-7-[(3R,4S)-3-amino-4-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8 Hz, 1H), 7.49 (br s, 1H), 7.32 (d, J = 8.4 Hz, 1H), 7.22 (br s, 2H), 6.86 (d, J = 8.4 Hz, 1H), 6.10-6.07 (m, 1H), 5.88 (d, J = 2.0 Hz, 1H), 4.30-4.25 (m, 1H), 4.15-4.12 (m, 1H), 3.81-3.76 (m, 1H), 3.51-3.48 (m, 1H), 3.43-3.39 (m, 2H), 3.35-3.30 (m, 1H), 3.27 (s, 3H), 3.23-3.17 (m, 1H), 3.00-2.96 (m, 1H), 2.89-2.81 (m, 3H), 2.58 (s, 3H), 2.18-2.13 (m, 1H), 1.84 (br s, 2H). | ++++ | ++ |
| 165 | N-[(3R)-7-[(3aR,6aR)-octahydropyrrolo[2,3-c]pyrrol-1-yl]-3,4-dihydro-2H-1-benzopyran-3-yl]-3-amino-6-methylthieno[2,3-b]pyridine-2-carboxamide | 450 | (DMSO-d6, 400 MHz) δ (ppm): 8.33 (d, J = 8.0 Hz, 1H), 7.50 (br s, 1H), 7.32 (d, J = 8.0 Hz, 1H), 7.22 (br s, 2H), 6.88 (d, J = 8.4 Hz, 1H), 6.15 (dd, J = 8.4, 2.0 Hz, 1H), 5.95 (s, 1H), 4.32-4.29 (m, 1H), 4.16-4.13 (m, 1H), 3.89-3.85 (m, 1H), 3.77-3.82 (m, 1H), 3.40-3.32 (m, 1H), 3.05-3.03 (m, 1H), 2.86-2.64 (m, 7H), 2.59 (s, 3H), 2.04-2.02 (m, 1H), 1.75-1.72 (m, 1H). | ++++ | +++ |
| 166 | N-[(3R)-7-[(3aS,6aS)-octahydropyrrolo[2,3-c]pyrrol-1-yl]-3,4-dihydro-2H-1-benzopyran-3-yl]-3-amino-6-methylthieno[2,3-b]pyridine-2-carboxamide | 450 | (DMSO-d6, 400 MHz) δ (ppm): 8.33 (d, J = 8.4 Hz, 1H), 7.50 (d, J = 7.6 Hz, 1H), 7.32 (d, J = 8.4 Hz, 1H), 7.21 (s, 2H), 6.88 (d, J = 8.4 Hz, 1H), 6.16-6.13 (m, 1H), 5.95 (d, J = 2.4 Hz, 1H), 4.29-4.27 (m, 1H), 4.16-4.13 (m, 1H), 3.88-3.86 (m, 1H), 3.85-3.77 (m, 1H), 3.38-3.36 (m, 1H), 3.05-3.03 (m, 1H), 2.86-2.64 (m, 7H), 2.59 (s, 3H), 2.08-2.03 (m, 1H), 1.75-1.72 (m, 1H). | ++++ | +++ |
| 167 | 3-amino-N-[(3R)-7-[(3R,4R)-3-amino-4-(difluoromethyl)pyrrolidin-1-yl]-3,4-dihydro-2H-1-benzopyran-3-yl]-6-methylthieno[2,3-b]pyridine-2-carboxamide | 474 | (DMSO-d6, 300 MHz) δ (ppm): 8.33 (d, J = 8.4 Hz, 1H), 7.50 (d, J = 8.0 Hz, 1H), 7.32 (d, J = 8.4 Hz, 1H), 7.22 (br s, 2H), 6.89 (d, J = 8.4 Hz, 1H), 6.38-6.12 (m, 2H), 5.94 (s, 1H), 4.28-4.26 (m, 1H), 4.16-4.14 (m, 1H), 3.82-3.79 | ++++ | ++ |

TABLE 24-continued

| | | | | | |
|---|---|---|---|---|---|
| 168 | 3-amino-N-[(3R)-7-[(3S,4S)-3-amino-4-(difluoromethyl)pyrrolidin-1-yl]-3,4-dihydro-2H-1-benzopyran-3-yl]-6-methylthieno[2,3-b]pyridine-2-carboxamide | 474 | (m, 1H), 3.77-3.67 (m, 1H), 3.44-3.25 (m, 3H), 3.03-3.00 (m, 1H), 2.90-2.86 (m, 2H), 2.72-2.68 (m, 1H), 2.59 (s, 3H), 2.20 (br s, 2H).<br>(DMSO-d6, 400 MHz) δ (ppm): 8.33 (d, J = 8.4 Hz, 1H), 7.50 (d, J = 7.6 Hz, 1H), 7.32 (d, J = 8.4 Hz, 1H), 7.22 (br s, 2H), 6.89 (d, J = 8.4 Hz, 1H), 6.38-6.12 (m, 2H), 5.93 (s, 1H), 4.28-4.26 (m, 1H), 4.16-4.14 (m, 1H), 3.82-3.80 (m, 1H), 3.77-3.67 (m, 1H), 3.44-3.27 (m, 3H), 3.03-3.00 (m, 1H), 2.86-2.82(m, 2H), 2.72-2.68 (m, 1H), 2.59(s, 3H), 1.80 (br s, 2H). | ++++ | ++ |
| 169 | 3-amino-N-[(3R)-5-fluoro-7-(piperazin-1-yl)-3,4-dihydro-2H-1-benzopyran-3-yl]-6-methylfuro[2,3-b]pyridine-2-carboxamide | 426 | (DMSO-d6, 400 MHz) δ (ppm): 8.20 (d, J = 8.0 Hz, 1H), 7.96 (d, J = 7.6 Hz, 1H), 7.23 (d, J = 8.0 Hz, 1H), 6.42 (d, J = 13.6 Hz, 1H), 6.27-6.13 (m, 3H), 4.35-4.25 (m, 1H), 4.19-4.17 (m, 1H), 3.93-3.88 (m, 1H), 3.07-2.91 (m, 4H), 2.89-2.78 (m, 6H), 2.54 (s, 3H). | ++ | + |
| 170 | 3-amino-N-[(3R)-7-{3,8-diazabicyclo[3.2.1]octan-3-yl}-5-fluoro-3,4-dihydro-2H-1-benzopyran-3-yl]-6-methylfuro[2,3-b]pyridine-2-carboxamide | 452 | (DMSO-d6, 400 MHz) δ (ppm): 8.19 (d, J = 7.6 Hz, 1H), 7.92 (d, J = 8.0 Hz, 1H), 7.22 (d, J = 8.0 Hz, 1H), 6.25-6.20 (m, 3H), 6.05 (s, 1H), 4.28 (br s, 1H), 4.18-4.12 (m, 1H), 3.92-3.90 (m, 1H), 3.48 (s, 2H), 3.32-3.29 (m, 2H), 2.85-2.79 (m, 2H), 2.70-2.68 (m, 2H), 2.54 (s, 3H), 1.65 (s, 4H) | ++ | + |
| 171 | 3-amino-N-[(2S)-6-{3,8-diazabicyclo[3.2.1]octan-3-yl}-1,2,3,4-tetrahydronaphthalen-2-yl]-6-methylfuro[2,3-b]pyridine-2-carboxamide | 432 | (DMSO-d6, 400 MHz) δ (ppm): 8.17 (d, J = 8.0 Hz, 1H), 7.91 (br s, 1H), 7.22 (d, J = 8.0 Hz, 1H), 6.88 (d, J = 8.0 Hz, 1H), 6.62 (d, J = 8.0 Hz, 1H), 6.51 (s, 1H), 6.11 (br s, 2H), 4.18-4.05 (m, 1H), 3.52-3.51 (m, 2H), 3.32-3.31 (m, 2H), 2.85-2.78 (m, 4H), 2.70-2.67 (m, 3H), 2.55 (s, 3H), 2.02-1.90 (m, 1H), 1.85-1.75 (m, 1H), 1.69-1.66 (m, 4H). | + | + |
| 172 | 3-amino-N-[(3R)-7-{3,8-diazabicyclo[3.2.1]octan-3-yl}-5,8-difluoro-3,4-dihydro-2H-1-benzopyran-3-yl]-6-methylfuro[2,3-b]pyridine-2-carboxamide | 470 | (DMSO-d6, 400 MHz) δ (ppm): 8.20 (d, J = 8.0 Hz, 1H), 8.05 (br s, 1H), 7.23 (d, J = 7.6 Hz, 1H), 6.36-6.34 (m, 1H), 6.20 (br s, 2H), 4.33-4.27 (m, 1H), 4.26 (d, J = 10.4 Hz, 1H), 4.02-3.97 (m, 1H), 3.39-3.32 (s, 2H), 3.09-3.06 (m, 2H), 2.93-2.86 (m, 2H), 2.84-2.78 (m, 2H), 2.54 (s, 3H), 2.34-2.33 (m, 1H), 1.81-1.78 (m, 2H), 1.65-1.64 (m, 2H). | ++ | + |
| 173 | 3-amino-N-[(3R)-7-(3,8-diazabicyclo[3.2.1]octan-3-yl)-2H,3H,4H-pyrano[2,3-b]pyridin-3-yl]-6-methylthieno[2,3-b]pyridine-2-carboxamide | 451 | (DMSO-d6, 400 MHz) δ (ppm): 8.33 (d, J = 8.4 Hz, 1H), 7.57 (d, J = 7.2 Hz, 1H), 7.33-7.23 (m, 4H), 6.24 (d, J = 8.4 Hz, 1H), 4.33-4.24 (m, 1H), 4.22-4.19 (m, 1H), 3.98-3.93 (m, 1H), 3.70-3.66 (m, 1H), 3.47-3.45 (m, 2H), 2.88-2.76 (m, 4H), 2.59 (s, 3H), 2.51-2.42 (m, 1H), 1.65-1.55 (m, 4H). | +++ | ++ |
| 174 | 7-amino-N-[(3R)-7-[(3S,4S)-3-amino-4-methoxypyrrolidin-1-yl]-8-cyano-5-fluoro-3,4-dihydro-2H-1-benzopyran-3-yl]-3-methylthieno[2,3-b]pyrazine-6-carboxamide | 498 | (DMSO-d6, 400 MHz) δ (ppm): 8.66 (s, 1H), 7.90 (d, J = 6.8 Hz, 1H), 7.00 (br s, 1H), 6.20 (d, J = 12.8 Hz, 1H), 4.35-4.33 (m, 2H), 4.08-4.03 (m, 1H), 3.83-3.79 (m, 1H), 3.71-3.64(m, 2H), 3.47- | ++ | + |

TABLE 24-continued

| | | | | | |
|---|---|---|---|---|---|
| | | | 3.46(m, 1H), 3.40-3.37 (m, 1H), 3.31 (s, 3H), 3.24-3.22 (m, 1H), 2.90-2.84 (m, 1H), 2.76-2.70 (m, 1H), 2.66 (S, 3H), 1.75 (br s, 2H). | | |
| 175 | 3-amino-N-[(3R)-7-[(3S,4S)-3-amino-4-methoxypyrrolidin-1-yl]-8-cyano-5-fluoro-3,4-dihydro-2H-1-benzopyran-3-yl]-6-methylthieno[2,3-b]pyridine-2-carboxamide | 497 | (DMSO-d6, 400 MHz) δ (ppm): 8.32 (d, J = 8.4 Hz, 1H), 7.65 (d, J = 6.8 Hz, 1H), 7.32 (d, J = 8.4 Hz, 1H), 7.24 (br s, 2H), 6.18 (d, J = 12.8 Hz, 1H), 4.34-4.31 (m, 2H), 4.06-4.01 (m, 1H), 3.82-3.80 (m, 1H) 3.70-3.64 (m, 2H), 3.47-3.37(m, 2H), 3.33 (s, 3H), 3.24-3.21(m, 1H), 2.87-2.83 (m, 1H), 2.75-2.71 (m, 1H), 2.59 (s, 3H), 1.78 (br s, 2H). | +++ | + |
| 176 | 7-amino-N-[(3R)-7-[(3S,4S)-3-amino-4-methoxypyrrolidin-1-yl]-6-cyano-3,4-dihydro-2H-1-benzopyran-3-yl]-3-methylthieno[2,3-b]pyrazine-6-carboxamide | 480 | (DMSO-d6, 400 MHz) δ (ppm): 8.66 (s, 1H), 7.83 (br s, 1H), 7.31 (s, 1H), 6.99 (br s, 2H), 6.11 (s, 1H), 4.32-4.24 (m, 2H), 3.95-3.90 (m, 1H), 3.80-3.76 (m, 1H), 3.66-3.63 (m, 2H), 3.46-3.45 (m, 1H), 3.37-3.34 (m, 1H), 3.32 (s, 3H), 3.19-3.16 (m, 1H), 2.94-2.81 (m, 2H), 2.68 (s, 3H), 1.78 (br s, 2H). | ++++ | +++ |
| 177 | 3-amino-N-[(3R)-7-[(3S,4S)-3-amino-4-methoxypyrrolidin-1-yl]-6-cyano-3,4-dihydro-2H-1-benzopyran-3-yl]-6-methylthieno[2,3-b]pyridine-2-carboxamide | 479 | (DMSO-d6, 400 MHz) δ (ppm): 8.33 (d, J = 8.0 Hz, 1H), 7.58 (br s 1H), 7.33-7.31 (m, 2H), 7.22 (br s, 2H), 6.10 (s, 2H), 4.32-4.22 (m, 2H), 3.92-3.88 (m, 1H), 3.79-3.76 (m, 1H), 3.67-3.63 (m, 2H), 3.45 (s, 1H), 3.37-3.33 (m, 1H), 3.32 (s, 3H), 3.18-3.16 (m, 1H), 2.91-2.80 (m, 2H), 2.59 (s, 3H), 1.77 (br s, 2H). | ++++ | +++ |
| 178 | 3-amino-N-[(2S)-6-[(3S,4S)-3-amino-4-methoxypyrrolidin-1-yl]-5-cyano-1,2,3,4-tetrahydronaphthalen-2-yl]-6-methylthieno[2,3-b]pyridine-2-carboxamide | 477 | (DMSO-d6, 400 MHz) δ (ppm): 8.31 (d, J = 8.4 Hz, 1H), 7.58 (d, J = 7.6 Hz, 1H), 7.31 (d, J = 8.4 Hz, 1H), 7.15-7.13 (m, 3H), 6.61 (d, J = 8.8 Hz, 1H), 4.14-4.08 (m, 1H), 3.86-3.82 (m, 1H), 3.73-3.71 (m, 1H), 3.65-3.64 (m, 1H), 3.46-3.45 (m, 1H), 3.40-3.38 (m, 1H), 3.31 (s, 3H), 3.22-3.20 (m, 1H), 3.05-2.97 (m, 1H), 2.88-2.84 (m, 2H), 2.78-2.68 (m, 1H), 2.59 (s, 3H), 2.09-2.01 (m, 1H), 1.85-1.74 (m, 3H). | ++++ | ++ |
| 179 | 3-amino-N-[(3R)-7-[(3S,4S)-3-amino-4-methoxypyrrolidin-1-yl]-2H,3H,4H-pyrano[3,2-c]pyridin-3-yl]-6-methylthieno[2,3-b]pyridine-2-carboxamide | 455 | (DMSO-d6, 400 MHz) δ (ppm): 8.33 (d, J = 8.4 Hz, 1H), 7.78 (s, 1H), 7.56 (d, J = 7.6 Hz, 1H), 7.32 (d, J = 8.4 Hz, 1H), 7.22 (br s, 2H), 5.78 (s, 1H), 4.32-4.27 (m, 1H), 4.25-4.19 (m, 1H), 3.91-3.86 (m, 1H), 3.61-3.55 (m, 2H), 3.44-3.40 (m, 2H), 3.33-3.30 (m, 1H), 3.29 (s, 3H), 3.11-3.08 (m, 1H), 2.85-2.81 (m, 2H), 2.59 (s, 3H), 1.74-1.71 (m, 2H). | ++++ | |
| 180 | 3-amino-N-[(3R)-7-[(3S,4S)-3-amino-4-ethoxypyrrolidin-1-yl]-2H,3H,4H-pyrano[3,2-c]pyridin-3-yl]-6-methylthieno[2,3-b]pyridine-2-carboxamide | 469 | (DMSO-d6, 400 MHz) δ (ppm): 8.33 (d, J = 8.4 Hz, 1H), 7.78 (s, 1H), 7.56 (d, J = 7.6 Hz, 1H), 7.32 (d, J = 8.4 Hz, 1H), 7.22 (br s, 2H), 5.77 (s, 1H), 4.32-4.23 (m, 1H), 4.22-4.20 (m, 1H), 3.91-3.89 (m, 1H), 3.71-3.69 (m, 1H), (s, 1H), 3.62-3.57 (m, 1H), 3.52 (t, J = 6.8 Hz, 2H), 3.49-3.32 (m, 1H), 3.31-3.27 (m, 1H), 3.09-3.07 (m, 1H), 2.85-2.81 (m, 2H), 2.58 (s, 3H), 1.74- | ++++ | |

TABLE 24-continued

| | | | | | |
|---|---|---|---|---|---|
| 181 | 7-amino-N-[(3R)-7-[(3S,4S)-3-amino-4-methoxypyrrolidin-1-yl]-2H,3H,4H-pyrano[2,3-b]pyridin-3-yl]-3-methylthieno[2,3-b]pyrazine-6-carboxamide | 456 | 1.69 (m, 2H), 1.11 (t, J = 7.2 Hz, 3H).<br>(DMSO-d6, 400 MHz) δ (ppm): 8.66 (s, 1H), 7.78 (d, J = 7.2 Hz, 1H), 7.26 (d, J = 8.0 Hz, 1H), 6.97 (br s, 2H), 6.02 (d, J = 8.4 Hz, 1H), 4.32-4.28 (m, 1H), 4.24-4.21 (m, 1H), 4.00-3.95 (m, 1H), 3.62-3.55 (m, 2H), 3.43-3.40 (m, 2H), 3.32-3.29 (m, 4H), 3.11-3.08 (m, 1H), 2.85-2.83 (m, 2H), 2.65 (s, 3H), 1.77 (brs, 2H). | ++ | + |
| 182 | 7-amino-N-[(3R)-7-[(3S,4S)-3-amino-4-ethoxypyrrolidin-1-yl]-2H,3H,4H-pyrano[2,3-b]pyridin-3-yl]-3-methylthieno[2,3-b]pyrazine-6-carboxamide | 470 | (DMSO-d6, 400 MHz) δ (ppm): 8.66 (s, 1H), 7.78 (d, J = 7.6 Hz, 1H), 7.26 (d, J = 8.4 Hz, 1H), 6.97 (br, 2H), 6.02 (d, J = 8.4 Hz, 1H), 4.32-4.26 (m, 1H), 4.24-4.21 (m, 1H), 4.00-3.95 (m, 1H), 3.72-3.70 (m, 1H), 3.61-3.57 (m, 1H), 3.54-3.52 (m, 2H), 3.51-3.41 (m, 2H), 3.29-3.26 (m, 1H), 3.10-3.08 (m, 1H), 2.85-2.83 (m, 2H), 2.66 (s, 3H), 1.79 (brs, 2H), 1.15-1.08 (m, 3H). | ++ | + |
| 183 | 3-amino-N-[(6S)-2-[(3S,4S)-3-amino-4-methoxypyrrolidin-1-yl]-3-fluoro-5,6,7,8-tetrahydroquinolin-6-yl]-6-methylthieno[2,3-b]pyridine-2-carboxamide | 471 | (DMSO-d6, 400 MHz) δ (ppm): 8.31 (d, J = 8.4 Hz, 1H), 7.58 (br s, 1H), 7.31 (d, J = 8.4 Hz, 1H), 7.16-7.12 (m, 3H), 4.15-4.12 (m, 1H), 3.80-3.77 (m, 1H), 3.66-3.58 (m, 2H), 3.48-3.45 (m, 1H), 3.40-3.39 (m, 1H), 3.32-3.26 (m, 4H), 2.84-2.66 (m, 4H), 2.59 (s, 3H), 2.01-1.90 (m, 1H), 1.89-1.82 (m, 1H), 1.74 (br s, 2H). | +++ | + |
| 184 | N-[(3R)-7-[(4aR,7aS)-octahydropyrrolo[3,4-b]morpholin-4-yl]-3,4-dihydro-2H-1-benzopyran-3-yl]-3-amino-6-methylthieno[2,3-b]pyridine-2-carboxamide | 466 | (DMSO-d6, 400 MHz) δ (ppm): 8.33 (d, J = 8.0 Hz, 1H), 7.53 (d, J = 7.6 Hz, 1H), 7.32 (d, J = 8.4 Hz, 1H), 7.22 (s, 2H), 6.92 (d, J = 8.8 Hz, 1H), 6.52-6.49 (m, 1H), 6.29 (s, 1H), 4.29 (br s, 1H), 4.17-4.14 (m, 1H), 3.97-3.90 (m, 3H), 3.83-3.78 (m, 1H), 3.56-3.53 (m, 1H), 3.22-3.11 (m, 2H), 2.90-2.73 (m, 5H), 2.59 (s, 3H). | ++++ | +++ |
| 185 | N-[(3R)-7-[(4aS,7aR)-octahydropyrrolo[3,4-b]morpholin-4-yl]-3,4-dihydro-2H-1-benzopyran-3-yl]-3-amino-6-methylthieno[2,3-b]pyridine-2-carboxamide | 466 | (DMSO-d6, 400 MHz) δ (ppm): 8.33 (d, J = 8.0 Hz, 1H), 7.52 (d, J = 7.6 Hz, 1H), 7.32 (d, J = 8.4 Hz, 1H), 7.22 (s, 2H), 6.92 (d, J = 8.8 Hz, 1H), 6.51-6.49 (m, 1H), 6.30 (s, 1H), 4.31-4.27 (br s, 1H), 4.17-4.15 (m, 1H), 3.97-3.91 (m, 2H), 3.83-3.78 (m, 1H), 3.59-3.54 (m, 1H), 3.26-3.12 (m, 2H), 2.91-2.78 (m, 5H), 2.59 (s, 3H). | ++++ | +++ |
| 186 | 3-amino-N-[(6S)-2-[(3S,4S)-3-amino-4-methoxypyrrolidin-1-yl]-5,6,7,8-tetrahydroquinazolin-6-yl]-6-methylthieno[2,3-b]pyridine-2-carboxamide | 454 | (DMSO-d6, 400 MHz) δ (ppm): 8.31 (d, J = 8.4 Hz, 1H), 8.06 (s, 1H), 7.62 (br s, 1H), 7.31 (d, J = 8.4 Hz, 1H), 7.17 (br s, 2H), 4.16-4.11 (m, 1H), 3.69-3.62 (m, 2H), 3.53-3.43 (m, 3H), 3.29-3.27 (m, 4H), 2.84-2.73 (m, 3H), 2.68-2.59 (m, 4H), 2.01-1.98 (m, 1H), 1.90-1.80 (m, 1H), 1.73 (br s, 2H). | + | |
| 187 | 3-amino-N-[(6R)-2-[(3S,4S)-3-amino-4-methoxypyrrolidin-1-yl]-5,6,7,8-tetrahydroquinazolin-6-yl]-6-methylthieno[2,3-b]pyridine-2-carboxamide | 454 | (DMSO-d6, 400 MHz) δ (ppm): 8.31 (d, J = 8.0 Hz, 1H), 8.06 (s, 1H), 7.62 (br s, 1H), 7.31 (d, J = 8.4 Hz, 1H), 7.17 (br s, 2H), 4.15-4.11 (m, 1H), 3.69-3.62 (m, 2H), 3.54-3.43 (m, 3H), 3.29-3.27 (m, | ++ | |

TABLE 24-continued

| | | | | | |
|---|---|---|---|---|---|
| 188 | N-[(2S)-6-[(3S,4S)-3-amino-4-methoxypyrrolidin-1-yl]-1,2,3,4-tetrahydronaphthalen-2-yl]-5H,6H,6aH,7H,7aH-cyclopropa[c]1,8-naphthyridine-2-carboxamide | 434 | 4H), 2.84-2.73 (m, 3H), 2.68-2.59 (m, 4H), 2.01-1.98 (m, 1H), 1.90-1.73 (m, 3H). (DMSO-d6, 400 MHz) δ (ppm): 8.29 (s, 1H), 8.04 (d, J = 7.2 Hz, 1H), 7.87 (s, 1H), 6.87 (d, J = 8.4 Hz, 1H), 6.52 (s, 1H), 6.31 (d, J = 8.4 Hz, 1H), 6.23 (s, 1H), 4.11-4.03 (m, 1H), 3.64-3.62 (m, 1H), 3.53-3.49 (m, 1H), 3.41-3.35 (m, 5H), 3.32 (s, 3H), 3.14-3.11 (m, 1H), 2.92-2.79 (m, 3H), 2.67-2.64 (m, 1H), 1.98-1.93 (m, 2H), 1.82-1.64 (m, 4H), 0.97-0.93 (m, 2H). | ++ | + |
| 189 | (6aS,7aR)-N-[(2S)-6-[(3S,4S)-3-amino-4-methoxypyrrolidin-1-yl]-1,2,3,4-tetrahydronaphthalen-2-yl]-5H,6H,6aH,7H,7aH-cyclopropa[c]1,8-naphthyridine-2-carboxamide | 434 | (DMSO-d6, 400 MHz) δ (ppm): 8.29 (s, 1H), 8.04 (d, J = 8.0 Hz, 1H), 7.86 (s, 1H), 6.86 (d, J = 8.0 Hz, 1H), 6.53 (s, 1H), 6.31 (d, J = 8.0 Hz, 1H), 6.23 (s, 1H), 4.11-4.03 (m, 1H), 3.65-3.63 (m, 1H), 3.52-3.49 (m, 1H), 3.42-3.34 (m, 4H), 3.32 (s, 3H), 3.14-3.11 (m, 1H), 2.92-2.78 (m, 4H), 2.67-2.63 (m, 1H), 2.06-1.93 (m, 4H), 1.74-1.64 (m, 4H), 0.96-0.91 (m, 2H). | ++ | + |
| 190 | (6aR,7aS)-N-[(2S)-6-[(3S,4S)-3-amino-4-methoxypyrrolidin-1-yl]-1,2,3,4-tetrahydronaphthalen-2-yl]-5H,6H,6aH,7H,7aH-cyclopropa[c]1,8-naphthyridine-2-carboxamide | 434 | (DMSO-d6, 400 MHz) δ (ppm): 8.29 (s, 1H), 8.05 (d, J = 7.6 Hz, 1H), 7.86 (s, 1H), 6.86 (d, J = 8.4 Hz, 1H), 6.53 (s, 1H), 6.31 (dd, J = 8.0, 2.0 Hz, 1H), 6.23 (s, 1H), 4.11-4.03 (m, 1H), 3.65-3.63 (m, 1H), 3.52-3.49 (m, 1H), 3.42-3.34 (m, 4H), 3.32 (s, 3H), 3.14-3.11 (m, 1H), 2.92-2.78 (m, 4H), 2.67-2.63 (m, 1H), 2.04-1.93 (m, 4H), 1.74-1.64 (m, 4H), 0.96-0.92 (m, 2H). | + | + |
| 191 | (6aS,7aR)-N-[(2S)-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 448 | (DMSO-d6, 400 MHz) δ (ppm): 8.29 (s, 1H), 8.10 (br s, 1H), 7.86 (s, 1H), 6.55 (s, 1 H), 6.42 (d, J = 12.4 Hz, 1H), 6.36 (br s, 1 H), 4.13-4.07 (m, 1H), 3.48-3.46 (m, 2H), 3.39-3.37 (m, 4H), 2.94-2.89 (m, 1H), 2.82-2.76 (m, 2H), 2.73-2.68 (m, 2H), 2.50-2.35 (m, 1H), 1.98-1.95 (m, 2H), 1.76-1.62 (m, 6H), 0.96-0.91 (m, 2H). | + | + |
| 192 | (6aR,7aS)-N-[(2S)-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 448 | (DMSO-d6, 400 MHz) δ (ppm): 8.29 (s, 1H), 8.09 (br s, 1H), 7.86 (s, 1H), 6.55 (s, 1 H), 6.42 (d, J = 13.6 Hz, 1H), 6.36 (br s, 1 H), 4.13-4.07 (m, 1H), 3.48-3.46 (m, 2H), 3.39-3.37 (m, 2H), 3.33-3.20 (m, 2H), 2.94-2.89 (m, 1H), 2.82-2.76 (m, 2H), 2.73-2.68 (m, 2H), 2.50-2.35 (m, 1H), 1.98-1.95 (m, 2H), 1.76-1.62 (m, 6H), 0.97-0.91 (m, 2H). | +++ | +++ |
| 193 | (6aS,7aR)-N-[(2R)-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 448 | (DMSO-d6, 400 MHz) δ (ppm): 8.29 (s, 1H), 8.09 (br s, 1H), 7.86 (s, 1H), 6.54 (s, 1 H), 6.42 (d, J = 13.6 Hz, 1H), 6.36 (br s, 1 H), 4.13-4.07 (m, 1H), 3.48-3.43 (m, 2H), 3.41-3.38 (m, 2H), 3.34-3.32 (m, 2H), 2.94-2.89 (m, 1H), 2.81-2.75 (m, 2H), 2.71-2.64 (m, 2H), 2.50-2.33 (m, 1H), 1.98-1.92 (m, 2H), 1.74-1.66 (m, 6H), 0.97-0.90 (m, 2H). | ++ | + |

| | | | | | |
|---|---|---|---|---|---|
| 194 | (6aR,7aS)-N-[(2R)-6-(3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 448 | (DMSO-d6, 400 MHz) δ (ppm): 8.29 (s, 1H), 8.09 (br s, 1H), 7.86 (s, 1H), 6.55 (s, 1 H), 6.42 (d, J = 12.8 Hz, 1H), 6.37 (br s, 1 H), 4.13-4.07 (m, 1H), 3.48-3.46 (m, 2H), 3.39-3.37 (m, 2H), 3.33-3.20 (m, 2H), 2.94-2.89 (m, 1H), 2.82-2.76 (m, 2H), 2.73-2.68 (m, 2H), 2.50-2.35 (m, 1H), 1.98-1.93 (m, 2H), 1.76-1.63 (m, 6H), 0.96-0.90 (m, 2H). | ++ | ++ |
| 195 | (6aS,7aR)-N-[(2S)-5-cyano-6-(3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 473 | (DMSO-d6, 400 MHz) δ (ppm): 8.28 (s, 1H), 8.13 (br s, 1H), 7.85 (s, 1H), 6.79 (d, J = 12.0 Hz, 1H), 6.56 (br s, 1H), 4.18-4.11 (m, 1H), 3.45-3.43 (m, 2H), 3.38-3.37 (m, 2H), 3.26-3.23 (m, 2H), 3.03-2.88 (m, 5H), 2.57-2.51 (m, 1H), 2.05-2.03 (m, 1H), 1.98-1.90 (m, 3H), 1.81-1.72 (m, 2H), 1.66-1.64 (m, 2H), 0.96-0.91 (m, 2H). | ++++ | +++ |
| 196 | (6aR,7aS)-N-[(2S)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 473 | (DMSO-d6, 400 MHz) δ (ppm): 8.28 (s, 1H), 8.13 (br s, 1H), 7.86 (s, 1H), 6.79 (d, J = 12.0 Hz, 1H), 6.56 (br s, 1H), 4.18-4.12 (m, 1H), 3.45-3.43 (m, 2H), 3.38-3.37 (m, 2H), 3.26-3.23 (m, 2H), 3.03-2.88 (m, 5H), 2.68 (br s, 1H), 2.57-2.51 (m, 1H), 2.07-2.03 (m, 1H), 1.98-1.90 (m, 3H), 1.81-1.72 (m, 2H), 1.66-1.64 (m, 2H), 0.95-0.91 (m, 2H). | + | + |
| 197 | (6aS,7aR)-N-[(2R)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 473 | (DMSO-d6, 400 MHz) δ (ppm): 8.29 (s, 1H), 8.13 (br s, 1H), 7.86 (s, 1H), 6.79 (d, J = 11.6 Hz, 1H), 6.57 (br s, 1H), 4.18-4.11 (m, 1H), 3.45-3.43 (m, 2H), 3.38-3.37 (m, 2H), 3.26-3.23 (m, 2H), 3.03-2.88 (m, 5H), 2.57-2.51 (m, 1H), 2.05-2.03 (m, 1H), 1.98-1.90 (m, 3H), 1.81-1.72 (m, 2H), 1.66-1.64 (m, 2H), 0.95-0.85 (m, 2H). | + | + |
| 198 | (6aR,7aS)-N-[(2R)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide | 473 | (DMSO-d6, 400 MHz) δ (ppm): 8.28 (s, 1H), 8.13 (br s, 1H), 7.86 (s, 1H), 6.79 (d, J = 12.0 Hz, 1H), 6.56 (br s, 1H), 4.18-4.11 (m, 1H), 3.46-3.43 (m, 2H), 3.39-3.37 (m, 2H), 3.27-3.24 (m, 2H), 3.05-2.89 (m, 5H), 2.57-2.51 (m, 1H), 2.05-2.03 (m, 1H), 1.98-1.92 (m, 3H), 1.87-1.81 (m, 2H), 1.79-1.76 (m, 2H), 0.96-0.91 (m, 2H). | ++ | ++ |
| 199 | 7-amino-N-[(3R)-7-[(3S,4S)-3-amino-4-methoxypyrrolidin-1-yl]-6-cyano-5-fluoro-3,4-dihydro-2H-1-benzopyran-3-yl]-3-methylthieno[2,3-b]pyrazine-6-carboxamide | 498 | (DMSO-d6, 400 MHz) δ (ppm): 8.66 (s, 1H), 7.86 (d, J = 6.4 Hz, 1H), 6.99 (br s, 2H), 5.97 (s, 1H), 4.32-4.24 (m, 2H), 4.04-3.99 (m, 1H), 3.81-3.78 (m, 1H), 3.65 (br s, 2H), 3.47 (s, 1H), 3.40-3.37(m, 1H), 3.33 (s, 3H), 3.23-3.20 (m, 1H), 2.95-2.91 (m, 1H), 2.79-2.73 (m, 1H), 2.65 (s, 3H), 1.90-1.79 (br s, 2H). | ++++ | +++ |
| 200 | 3-amino-N-[(3R)-7-[(3S,4S)-3-amino-4-methoxypyrrolidin-1-yl]-6-cyano-5-fluoro-3,4-dihydro-2H-1-benzopyran-3-yl]-6-methylthieno[2,3-b]pyridine-2-carboxamide | 497 | (DMSO-d6, 400 MHz) δ (ppm): 8.35 (d, J = 8.4 Hz, 1H), 7.63 (d, J = 6.8 Hz, 1H), 7.32 (d, J = 8.4 Hz, 1H), 7.23 (br s, 2H), 5.98 (s, 1H), 4.33-4.24 (m, 2H), 4.02-3.99 (m, 1H), 3.81-3.78 (m, 1H), 3.66-3.64 (m, 2H), 3.48-3.37(m, 2H), 3.33 (s, 3H), 3.23-3.21(m, | ++++ | +++ |

TABLE 24-continued

| | | | | | |
|---|---|---|---|---|---|
| 201 | 3-amino-N-[(2S)-6-[(3S,4S)-3-amino-4-methoxypyrrolidin-1-yl]-7-cyano-1,2,3,4-tetrahydronaphthalen-2-yl]-6-methylthieno[2,3-b]pyridine-2-carboxamide | 477 | 1H), 2.94-2.87 (m, 1H), 2.79-2.72 (m, 1H), 2.59 (s, 3H), 1.87-1.75 (br s, 2H). (DMSO-d6, 400 MHz) δ (ppm): 8.30 (d, J = 8.0 Hz, 1H), 7.58 (d, J = 7.6 Hz, 1H), 7.31 (d, J = 8.0 Hz, 1H), 7.26 (s, 1H), 7.16 (br s, 2H), 6.51 (s, 1H), 4.13-4.08 (m, 1H), 3.83-3.79 (m, 1H), 3.70-3.66 (m, 2H), 3.47-3.46 (m, 1H), 3.38-3.35 (m, 1H), 3.30 (s, 3H), 3.19-3.17 (m, 1H), 2.91-2.82 (m, 3H), 2.72-2.66 (m, 1H), 2.59 (s, 3H), 1.98-1.95 (m, 1H), 1.80-1.71 (m, 3H). | | ++ |
| 202 | 3-amino-N-[(3R)-7-[(3S,4S)-3-amino-4-(propan-2-yloxy)pyrrolidin-1-yl]-3,4-dihydro-2H-1-benzopyran-3-yl]-6-methylthieno[2,3-b]pyridine-2-carboxamide | 482 | (DMSO-d6, 400 MHz) δ (ppm): 8.32 (d, J = 8.4 Hz, 1H), 7.48 (d, J = 7.2 Hz, 1H), 7.32 (d, J = 8.4 Hz, 1H), 7.21 (br s, 2 H), 6.86 (d, J = 8.4 Hz, 1H), 6.09 (d, J = 8.4 Hz, 1H), 5.90 (s, 1H), 4.31-4.24 (m, 1H), 4.15-4.13 (m, 1H), 3.79-3.70 (m, 3H), 3.54-3.50 (m, 1H), 3.38-3.32 (m, 3H), 3.02-2.99 (m, 1H), 2.88-2.79 (m, 3H), 2.59 (s, 3H), 1.69 (br s, 2H), 1.13-1.08 (m, 3H). | ++++ | ++ |
| 203 | 3-amino-N-[(6S)-2-[(3S,4S)-3-amino-4-methoxypyrrolidin-1-yl]-5,6,7,8-tetrahydroquinolin-6-yl]-5-fluoro-6-methylthieno[2,3-b]pyridine-2-carboxamide | 471 | (DMSO-d6, 400 MHz) δ (ppm): 8.29 (d, J = 10.4 Hz, 1H), 7.65 (d, J = 7.6 Hz, 1H), 7.19 (d, J = 8.4 Hz, 1H), 7.12 (br s, 2H), 6.23 (d, J = 8.4 Hz, 1H), 4.19-4.08 (m, 1H), 3.62-3.59 (m, 2H), 3.48-3.43 (m, 2H), 3.36-3.35 (m, 1H), 3.32 (s, 3H), 3.13-3.11 (m, 1H), 2.82-2.68 (m, 4H), 2.57 (s, 3H), 2.01-1.99 (m, 1H), 1.90-1.80 (m, 1H), 1.70 (br s, 2H). | +++ | + |
| 204 | 3-amino-5-fluoro-6-methyl-N-[(6S)-2-(piperazin-1-yl)-5,6,7,8-tetrahydroquinolin-6-yl]thieno[2,3-b]pyridine-2-carboxamide | 441 | (DMSO-d6, 400 MHz) δ (ppm): 8.30 (d, J = 10.8 Hz, 1H), 7.67 (d, J = 8.0 Hz, 1H), 7.24 (d, J = 8.0 Hz, 1H), 7.12 (br s, 2H), 6.59 (d, J = 8.8 Hz, 1H), 4.15-4.11 (m, 1H), 3.34-3.31 (m, 4H), 2.84-2.68 (m, 8H), 2.56 (s, 3H), 2.07-1.98 (m, 1H), 1.90-1.85 (m, 1H). | ++++ | ++ |
| 205 | 3-amino-6-methyl-N-[(6S,8S)-8-methyl-2-(piperazin-1-yl)-5,6,7,8-tetrahydroquinolin-6-yl]thieno[2,3-b]pyridine-2-carboxamide | 437 | (DMSO-d6, 400 MHz) δ (ppm): 8.31 (d, J = 8.0 Hz, 1H), 7.59 (d, J = 7.6 Hz, 1H), 7.31 (d, J = 8.0 Hz, 1H), 7.23 (d, J = 8.4 Hz, 1H), 7.17 (s, 2H), 6.59 (d, J = 8.0 Hz, 1H), 4.16-4.11 (m, 1H), 3.36-3.33 (m, 4H), 2.84-2.73 (m, 7H), 2.60 (s, 3H), 2.17-2.11 (m, 1H), 1.64-1.55 (m, 1H), 1.32 (d, J = 6.4 Hz, 3H). | ++ | + |
| 206 | 3-amino-6-methyl-N-[(6R,8S)-8-methyl-2-(piperazin-1-yl)-5,6,7,8-tetrahydroquinolin-6-yl]thieno[2,3-b]pyridine-2-carboxamide | 437 | (DMSO-d6, 400 MHz) δ (ppm): 8.33 (d, J = 7.2 Hz, 1H), 7.54 (d, J = 8.0 Hz, 1H), 7.31 (d, J = 8.0 Hz, 1H), 7.23 (d, J = 8.0 Hz, 1H), 7.16 (s, 2H), 6.59 (d, J = 8.0 Hz, 1H), 4.34-4.30 (m, 1H), 3.34-3.32 (m, 4H), 2.93-2.65 (m, 7H), 2.59 (s, 3H), 2.09-2.02 (m, 1H), 1.79-1.76 (m, 1H), 1.34 (d, J = 4.4 Hz, 3H). | +++ | + |
| 207 | 3-amino-6-methyl-N-[(6S,8R)-8-methyl-2-(piperazin-1-yl)-5,6,7,8-tetrahydroquinolin-6-yl]thieno[2,3-b]pyridine-2-carboxamide | 437 | (DMSO-d6, 400 MHz) δ (ppm): 8.31 (d, J = 8.4 Hz, 1H), 7.54 (d, J = 7.2 Hz, 1H), 7.31 (d, J = 8.4 Hz, 1H), 7.23 (d, J = 8.4 Hz, 1H), 7.16 (s, 2H), 6.59 (d, J = 8.0 Hz, 1H), 4.32 (br s, 1H), 3.34-3.32 (m, 4H), 2.92-2.69 (m, 7H), 2.59 (s, | ++ | + |

TABLE 24-continued

| | | | | | |
|---|---|---|---|---|---|
| | | | 3H), 2.09-2.02(m, 1H), 1.79-1.76 (m, 1H), 1.29 (d, J = 6.8 Hz, 3H). | | |
| 208 | 3-amino-6-methyl-N-[(6R,8R)-8-methyl-2-(piperazin-1-yl)-5,6,7,8-tetrahydroquinolin-6-yl]thieno[2,3-b]pyridine-2-carboxamide | 437 | (DMSO-d6, 400 MHz) δ (ppm): 8.31 (d, J = 8.0 Hz, 1H), 7.59 (d, J = 7.2 Hz, 1H), 7.31 (d, J = 8.4 Hz, 1H), 7.23 (d, J = 8.4 Hz, 1H), 7.16 (s, 2H), 6.58 (d, J = 8.8 Hz, 1H), 4.17-4.14 (m, 1H), 3.35-3.33 (m, 4H), 2.86-2.72 (m, 7H), 2.59 (s, 3H), 2.13-2.11(m, 1H), 1.63-1.54 (m, 1H), 1.31 (d, J = 6.8 Hz, 3H). | ++++ | ++ |
| 209 | 3-amino-6-methyl-N-[(3R)-7-{3-oxa-7,9-diazabicyclo[3.3.1]nonan-9-yl}-3,4-dihydro-2H-1-benzopyran-3-yl]thieno[2,3-b]pyridine-2-carboxamide | 466 | (DMSO-d6, 400 MHz) δ (ppm): 8.33 (d, J = 8.4 Hz, 1H), 7.52 (br s, 1H), 7.32 (d, J = 8.0 Hz, 1H), 7.22 (br s, 2H), 6.93 (d, J = 8.4 Hz, 1H), 6.43 (d, J = 8.4 Hz, 1H), 6.27 (s, 1H), 4.33-4.29 (m, 1H), 4.17-4.13 (m, 1H), 4.02-3.98 (m, 2H), 3.90-3.80 (m, 3H), 3.62-3.59 (m, 2H), 3.02-2.98 (m, 4H), 2.87-2.85 (m, 2H), 2.59 (s, 3H). | ++++ | ++++ |
| 210 | 3-amino-N-[(6S)-2-[(3S,4S)-4-amino-3-methoxy-3-methylpyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.4 Hz, 1H), 7.57 (d, J = 7.6 Hz, 1H), 7.32 (d, J = 8.4 Hz, 1H), 7.19-7.16 (m, 3H), 6.20 (d, J = 8.4 Hz, 1H), 4.12-4.05 (m, 1H), 3.59-3.55 (m, 1H), 3.47-3.44 (m, 1H), 3.29-3.25 (m, 2H), 3.20-3.17 (s, 3H), 3.06-3.02 (m, 1H), 2.81-2.71 (m, 4H), 2.61-2.58 (s, 3H), 2.05-1.95 (m, 1H), 1.89-1.82 (m, 1H), 1.68-1.62 (m, 2H), 1.25 (s, 3H). | +++ | + |
| 211 | 3-amino-N-[(6S)-2-[(3R,4R)-4-amino-3-methoxy-3-methylpyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.57 (d, J = 7.6 Hz, 1H), 7.32 (d, J = 8.4 Hz, 1H), 7.18-7.16 (m, 3H), 6.20 (d, J = 8.4 Hz, 1H), 4.12-4.05 (m, 1H), 3.58-3.54 (m, 1H), 3.49-3.46 (m, 1H), 3.28-3.25 (m, 2H), 3.20-3.16 (s, 3H), 3.07-3.02 (m, 1H), 2.81-2.67 (m, 4H), 2.59-2.55 (s, 3H), 2.05-1.95 (m, 1H), 1.89-1.86 (m, 1H), 1.65-1.55 (m, 2H), 1.25 (m, 3H). | +++ | + |
| 212 | 3-amino-N-[(3R)-7-[(3S,4S)-3-methoxy-4-(methylamino)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.4 Hz, 1H), 7.49 (d, J = 7.6 Hz, 1H), 7.31 (d, J = 8.4 Hz, 1H), 7.21 (br s, 1H), 6.86 (d, J = 8.4 Hz, 1H), 6.12-6.10 (m, 1H), 5.93 (s, 1H), 4.30-4.26 (m, 1H), 4.15-4.12 (m, 1H), 3.81-3.76 (m, 2H), 3.40-3.33 (m, 2H), 3.29 (s, 3H), 3.16-3.11 (m, 2H), 2.99-2.96 (m, 1H), 2.89-2.81 (m, 2H), 2.58 (s, 3H), 2.31 (s, 3H), 1.86 (br s, 1H). | ++++ | ++ |
| 213 | 3-amino-N-[(3R)-7-[(3S,4S)-3-acetamido-4-methoxypyrrolidin-1-yl]-3,4-dihydro-2H-1-benzopyran-3-yl]-6-methylthieno[2,3-b]pyridine-2-carboxamide | 496 | (DMSO-d6, 400 MHz) δ (ppm): 8.32 (d, J = 8.4 Hz, 1H), 8.16 (d, J = 7.2 Hz, 1H), 7.49 (d, J = 7.6 Hz, 1H), 7.31 (d, J = 8.0 Hz, 1H), 7.21 (br s, 1H), 6.89 (d, J = 8.0 Hz, 1H), 6.16-6.13 (m, 1H), 5.96 (s, 1H), 4.27 (br s, 2H), 4.16-4.13 (m, 1H), 3.92-3.77 (m, 2H), 3.50-3.41 (m, 2H), 3.31 (s, 3H), 3.16-3.14 (m, 1H), 3.05-3.02 (m, 1H), 2.90-2.82 (m, 2H), 2.58 (s, 3H), 1.82 (s, 3H). | +++ | ++ |

TABLE 24-continued

| 214 | 3-amino-N-[(3R)-7-[(4R)-4-amino-3,3-dimethylpyrrolidin-1-yl]-3,4-dihydro-2H-1-benzopyran-3-yl]-6-methylthieno[2,3-b]pyridine-2-carboxamide | 452 | (DMSO-d6, 400 MHz) δ (ppm): 8.32 (d, J = 8.4 Hz, 1H), 7.48 (br s, 1H), 7.31 (d, J = 8.4 Hz, 1H), 7.21 (br s, 2H), 6.85 (d, J = 8.4 Hz, 1H), 6.04 (d, J = 8.0 Hz, 1H), 5.83 (s, 1H), 4.28-4.26 (m, 1H), 4.15-1.13 (m, 1H), 3.80-3.75 (m, 1H), 3.39-3.32 (m, 1H), 3.09-3.01 (m, 2H), 2.94-2.91 (m, 1H), 2.89-2.78 (m, 3H), 2.54 (s, 3H), 1.55 (br s, 2H), 1.05 (s, 3H), 0.90 (s, 3H). | ++++ | +++ |
| --- | --- | --- | --- | --- | --- |
| 215 | 3-amino-N-[(3R)-7-[(4S)-4-amino-3,3-dimethylpyrrolidin-1-yl]-3,4-dihydro-2H-1-benzopyran-3-yl]-6-methylthieno[2,3-b]pyridine-2-carboxamide | 452 | (DMSO-d6, 400 MHz) δ (ppm): 8.32 (d, J = 8.0 Hz, 1H), 7.47 (br s, 1H), 7.31 (d, J = 8.0 Hz, 1H), 7.21 (br s, 2H), 6.84 (d, J = 8.4 Hz, 1H), 6.04 (d, J = 8.8 Hz, 1H), 5.85 (s, 1H), 4.28-4.26 (m, 1H), 4.14-4.12 (m, 1H), 3.80-3.75 (m, 1H), 3.39-3.32 (m, 1H), 3.09-3.01 (m, 2H), 2.94-2.91 (m, 1H), 2.88-2.76 (m, 3H), 2.58 (s, 3H), 1.55 (br s, 2H), 1.05 (s, 3H), 0.90 (s, 3H). | ++++ | +++ |
| 216 | N-[(6S)-2-[(3aS,6aS)-octahydropyrrolo[2,3-c]pyrrol-1-yl]-5,6,7,8-tetrahydroquinolin-6-yl]-3-amino-6-methylthieno[2,3-b]pyridine-2-carboxamide | 449 | (DMSO-d6, 400 MHz) δ (ppm): 8.31 (d, J = 8.4 Hz, 1H), 7.57 (d, J = 7.6 Hz, 1H), 7.31 (d, J = 8.4 Hz, 1H), 7.23-7.16 (m, 3H), 6.27 (d, J = 8.4 Hz, 1H), 4.16-4.12 (m, 2H), 3.49-3.45 (m, 2H), 3.40-3.33 (m, 1H), 2.90-2.63 (m, 9H), 2.58 (s, 3H), 2.05-1.98 (m, 2H), 1.90-1.69 (m, 2H). | ++++ | ++ |
| 217 | N-[(6S)-2-[(3aR,6aR)-octahydropyrrolo[2,3-c]pyrrol-1-yl]-5,6,7,8-tetrahydroquinolin-6-yl]-3-amino-6-methylthieno[2,3-b]pyridine-2-carboxamide | 449 | (DMSO-d6, 400 MHz) δ (ppm): 8.31 (d, J = 8.4 Hz, 1H), 7.57 (d, J = 7.6 Hz, 1H), 7.31 (d, J = 8.0 Hz, 1H), 7.20-7.16 (m, 3H), 6.27 (d, J = 8.8 Hz, 1H), 4.16-4.12 (m, 2H), 3.50-3.36 (m, 3H), 2.90-2.63 (m, 9H), 2.59 (s, 3H), 2.05-1.99 (m, 2H), 1.88-1.71 (m, 2H) | ++++ | +++ |
| 218 | N-[(6S)-2-[(3aS,6aS)-octahydropyrrolo[2,3-c]pyrrol-1-yl]-5,6,7,8-tetrahydroquinolin-6-yl]-3-amino-4,6-dimethylthieno[2,3-b]pyridine-2-carboxamide | 463 | (DMSO-d6, 400 MHz) δ (ppm): 7.60 (d, J = 8.0 Hz, 1H), 7.19 (d, J = 8.4 Hz, 1H), 7.04 (s, 1H), 6.82 (br s, 2H), 6.27 (d, J = 8.4 Hz, 1H), 4.14-4.13 (m, 2H), 3.51-3.32 (m, 3H), 2.90-2.63 (m, 12H), 2.51 (s, 3H), 2.03-1.98 (m, 2H), 1.87-1.69 (m, 2H). | +++ | ++ |
| 219 | N-[(6S)-2-[(3aR,6aR)-octahydropyrrolo[2,3-c]pyrrol-1-yl]-5,6,7,8-tetrahydroquinolin-6-yl]-3-amino-4,6-dimethylthieno[2,3-b]pyridine-2-carboxamide | 463 | (DMSO-d6, 400 MHz) δ (ppm): 7.61 (d, J = 7.6 Hz, 1H), 7.19 (d, J = 8.4 Hz, 1H), 7.04 (s, 1H), 6.82 (br s, 2H), 6.26 (d, J = 8.4 Hz, 1H), 4.14-4.12 (m, 2H), 3.50-3.41 (m, 1H), 3.39-3.33 (m, 2H), 2.91-2.62 (m, 12H), 2.51 (s, 3H), 2.05-1.99 (m, 2H), 1.90-1.69 (m, 2H). | ++++ | +++ |
| 220 | N-[(3R)-7-[(3aS,6aS)-octahydropyrrolo[2,3-c]pyrrol-1-yl]-5-fluoro-3,4-dihydro-2H-1-benzopyran-3-yl]-3-amino-6-methylthieno[2,3-b]pyridine-2-carboxamide | 468 | (DMSO-d6, 400 MHz) δ (ppm): 8.33 (d, J = 8.4 Hz, 1H), 7.57 (br s, 1H), 7.32 (d, J = 8.4 Hz, 1H), 7.23 (br s, 2H), 5.99 (d, J = 11.2 Hz, 1H), 5.81 (s, 1H), 4.31-4.24 (m, 1H), 4.18-4.15 (m, 1H ), 3.89-3.81 (m, 2H), 3.43-3.41 (m, 1H), 3.11-3.05 (m, 1H), 2.88-2.63 (m, 7H), 2.59 (s, 3H), 2.05-2.01 (m, 1H), 1.76-1.71 (m, 1H). | ++++ | +++ |

TABLE 24-continued

| 221 | N-[(3R)-7-[(3aR,6aR)-octahydropyrrolo[2,3-c]pyrrol-1-yl]-5-fluoro-3,4-dihydro-2H-1-benzopyran-3-yl]-3-amino-6-methylthieno[2,3-b]pyridine-2-carboxamide | 468 | (DMSO-d6, 400 MHz) δ (ppm): 8.34 (d, J = 8.4 Hz, 1H), 7.58 (br s, 1H), 7.32 (d, J = 8.0 Hz, 1H), 7.23 (br s, 2H), 6.01-5.98 (m, 1H), 5.82 (s, 1H), 4.31-4.24 (m, 1H), 4.18-4.16 (m, 1H ), 3.91-3.82 (m, 2H), 3.39-3.35 (m, 1H), 3.11-3.05 (m, 1H), 2.88-2.64 (m, 7H), 2.60 (s, 3H), 2.06-2.00 (m, 1H), 1.77-1.70 (m, 1H). | ++++ | ++ |
|---|---|---|---|---|---|
| 222 | N-[(3R)-7-[(3aS,6aS)-octahydropyrrolo[2,3-c]pyrrol-1-yl]-5-fluoro-3,4-dihydro-2H-1-benzopyran-3-yl]-3-amino-4,6-dimethylthieno[2,3-b]pyridine-2-carboxamide | 482 | (DMSO-d6, 400 MHz) δ (ppm): 7.60 (br s, 1H), 7.05 (s, 1H), 6.87 (br s, 2H), 5.99 (d, J = 12.4 Hz, 1H), 5.81 (s, 1H), 4.30-4.26 (m, 1H), 4.17-4.15 (m, 1H), 3.91-3.81 (m, 2H), 3.38-3.34 (m, 1H), 3.11-3.05 (m, 1H), 2.88-2.63 (m, 10H), 2.57 (s, 3H), 2.08-1.99 (m, 1H), 1.78-1.70 (m, 1H). | ++++ | +++ |
| 223 | N-[(3R)-7-[(3aR,6aR)-octahydropyrrolo[2,3-c]pyrrol-1-yl]-5-fluoro-3,4-dihydro-2H-1-benzopyran-3-yl]-3-amino-4,6-dimethylthieno[2,3-b]pyridine-2-carboxamide | 482 | (DMSO-d6, 400 MHz) δ (ppm): 7.61 (br s, 1H), 7.05 (s, 1H), 6.87 (br s, 2H), 5.99 (d, J = 12.8 Hz, 1H), 5.81 (s, 1H), 4.29-4.25 (m, 1H), 4.17-4.15 (m, 1H), 3.90-3.81 (m, 2H), 3.39-3.35 (m, 1H), 3.11-3.05 (m, 1H), 2.88-2.64 (m, 10H), 2.55 (s, 3H), 2.06-2.01 (m, 1H), 1.78-1.70 (m, 1H). | ++++ | +++ |
| 224 | N-[(3R)-7-[(3aR,7aS)-octahydro-1H-pyrrolo[2,3-c]pyridin-1-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.32 (d, J = 8.0 Hz, 1H), 7.48 (br s, 1H), 7.31 (d, J = 8.4 Hz, 1H), 7.21 (br s, 2H), 6.84 (d, J = 8.4 Hz, 1H), 6.14 (d, J = 8.0 Hz, 1H), 5.91 (s, 1H), 4.28-4.26 (m, 1H), 4.14-4.12 (m, 1H), 3.80-3.75 (m, 1H), 3.60-3.55 (m, 1H), 3.28-3.23 (m, 1H), 3.14-3.06 (m, 2H), 2.83-2.80 (m, 2H), 2.71-2.66 (m, 1H), 2.58-2.54 (m, 4H), 2.34-2.28 (m, 1H), 2.25-2.19 (m, 1H), 2.17-2.07 (m, 1H), 1.85-1.75 (m, 2H), 1.61-1.58 (m, 1H). | ++++ | +++ |
| 225 | N-[(3R)-7-[(3aS,7aR)-octahydro-1H-pyrrolo[2,3-c]pyridin-1-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.32 (d, J = 8.0 Hz, 1H), 7.49 (br s, 1H), 7.31 (d, J = 8.0 Hz, 1H), 7.21 (br s, 2H), 6.84 (d, J = 8.0 Hz, 1H), 6.13 (d, J = 7.6 Hz, 1H), 5.91 (s, 1H), 4.28-4.25 (m, 1H), 4.14-4.12 (m, 1H), 3.80-3.75 (m, 1H), 3.60-3.57 (m, 1H), 3.28-3.23 (m, 1H), 3.14-3.08 (m, 2H), 2.87-2.77 (m, 2H), 2.69-2.67 (m, 1H), 2.58-2.54 (m, 4H), 2.32-2.28 (m, 1H), 2.25-2.07 (m, 2H), 1.87-1.76 (m, 2H), 1.61-1.58 (m, 1H). | ++++ | ++++ |
| 226 | N-[(3R)-7-[(3aS,6aS)-octahydropyrrolo[2,3-c]pyrrol-1-yl]-3,4-dihydro-2H-1-benzopyran-3-yl]-3-amino-4,6-dimethylthieno[2,3-b]pyridine-2-carboxamide | 464 | (DMSO-d6, 400 MHz) δ (ppm): 7.54 (br s, 1H), 7.05 (s, 1H), 6.89-6.86 (m, 3H), 6.15 (d, J = 8.8 Hz, 1H), 5.96 (s, 1H), 4.31-4.28 (m, 1H), 4.16-4.12 (m, 1H), 3.89-3.82 (m, 1H), 3.80-3.77 (m, 1H), 3.40-3.32 (m, 1H), 3.08-3.02 (m, 1H), 2.90-2.77 (m, 8H), 2.67-2.59 (m, 2H), 2.51 (m, 3H), 2.06-2.00 (m, 1H), 1.78-1.69 (m, 1H). | ++++ | +++ |

TABLE 24-continued

| | | | | | |
|---|---|---|---|---|---|
| 227 | N-[(3R)-7-[(3aR,6aR)-octahydropyrrolo[2,3-c]pyrrol-1-yl]-3,4-dihydro-2H-1-benzopyran-3-yl]-3-amino-4,6-dimethylthieno[2,3-b]pyridine-2-carboxamide | 464 | (DMSO-d6, 400 MHz) δ (ppm): 7.55 (br s, 1H), 7.04 (s, 1H), 6.89-6.86 (m, 3H), 6.18-6.15 (m, 1H), 5.99-5.98 (m, 1H), 4.31-4.27 (m, 1H), 4.16-4.13 (m, 1H), 4.02-3.97 (m, 1H), 3.83-3.80 (m, 1H), 3.46-3.41 (m, 1H), 3.12-3.01 (m, 2H), 2.99-2.81 (m, 6H), 2.73-2.70 (m, 3H), 2.51 (m, 3H), 2.09-2.02 (m, 1H), 1.86-1.79 (m, 1H). | ++++ | +++ |
| 228 | (6aS,7aR)-N-[(3R)-8-cyano-7-(3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide | 475 | (DMSO-d6, 400 MHz) δ (ppm): 8.29 (d, J = 2.0 Hz, 1H), 8.19 (d, J = 6.4 Hz, 1H), 7.86 (d, J = 2.0 Hz, 1H), 6.63 (br s, 1H), 6.49 (d, J = 11.6 Hz, 1H), 4.35-4.31 (m, 2H), 4.15-4.10 (m, 1H), 3.45-3.42 (m, 2H), 3.39-3.27 (m, 4H), 2.98-2.88 (m, 3H), 2.75-2.69 (m, 1H), 1.99-1.85 (m, 3H), 1.77-1.64 (m, 2H), 0.96-0.90 (m, 2H). | ++ | ++ |
| 229 | (6aR,7aS)-N-[(3R)-8-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide | 475 | (DMSO-d6, 400 MHz) δ (ppm): 8.28 (d, J = 2.0 Hz, 1H), 8.19 (d, J = 6.4 Hz, 1H), 7.85 (d, J = 2.0 Hz, 1H), 6.63 (br s, 1H), 6.49 (d, J = 12.0 Hz, 1H), 4.35-4.30 (m, 2H), 4.15-4.10 (m, 1H), 3.44-3.42 (m, 2H), 3.38-3.26 (m, 4H), 2.97-2.88 (m, 3H), 2.74-2.68 (m, 1H), 1.98-1.87 (m, 3H), 1.76-1.64 (m, 2H), 0.96-0.90 (m, 2H). | ++ | + |
| 230 | 3-amino-N-[(3R)-8-cyano-7-{3,8-diazabicyclo[3.2.1]octan-3-yl}-5-fluoro-3,4-dihydro-2H-1-benzopyran-3-yl]-4,6-dimethylthieno[2,3-b]pyridine-2-carboxamide | 507 | (DMSO-d6, 400 MHz) δ (ppm): 7.73 (d, J = 6.8 Hz, 1H), 7.04 (s, 1H), 6.88 (br s, 2H), 6.48 (d, J = 11.6 Hz, 1H), 4.39-4.32 (m, 2H), 4.11-4.06 (m, 1H), 3.46-3.44 (m, 2H), 3.31-3.27 (m, 5H), 2.94-2.88 (m, 3H), 2.80-2.76 (m, 1H), 2.72 (s, 3H), 1.92-1.85 (m, 2H), 1.68-1.65 (m, 2H). | ++++ | ++ |
| 231 | N-[(3R)-7-[(3aR,6R,7aR)-6-amino-octahydro-1H-indol-1-yl]-3,4-dihydro-2H-1-benzopyran-3-yl]-3-amino-6-methylthieno[2,3-b]pyridine-2-carboxamide | 478 | (DMSO-d6, 400 MHz) δ (ppm): 8.33 (d, J = 8.0 Hz, 1H), 7.50 (d, J = 7.2 Hz, 1H), 7.32 (d, J = 8.4 Hz, 1H), 7.22 (br s, 2H), 6.84 (d, J = 8.0 Hz, 1H), 6.15 (d, J = 8.4 Hz, 1H), 5.96 (s, 1H), 4.31-4.22 (m, 1H), 4.15-4.12 (m, 1H), 3.89-3.87 (m, 1H), 3.81-3.76 (m, 1H), 3.32-3.25 (m, 1H), 3.13-3.11 (m, 1H), 2.95-2.89 (m, 1H), 2.85-2.77 (m, 2H), 2.59 (s, 3H), 2.22-2.19 (m, 1H), 2.03-1.95 (m, 1H), 1.90-1.55 (m, 6H), 1.50-1.36 (m, 2H), 1.26-1.18 (m, 1H). | ++++ | ++++ |
| 232 | N-[(3R)-7-[(3aR,6S,7aR)-6-amino-octahydro-1H-indol-1-yl]-3,4-dihydro-2H-1-benzopyran-3-yl]-3-amino-6-methylthieno[2,3-b]pyridine-2-carboxamide | 478 | (DMSO-d6, 400 MHz) δ (ppm): 8.33 (d, J = 8.4 Hz, 1H), 7.48 (d, J = 7.6 Hz, 1H), 7.32 (d, J = 8.0 Hz, 1H), 7.21 (br s, 2H), 6.84 (d, J = 8.0 Hz, 1H), 6.13 (d, J = 7.6 Hz, 1H), 5.93 (s, 1H), 4.31-4.23 (m, 1H), 4.15-4.12 (m, 1H), 3.91-3.68 (m, 2H), 3.22-3.17 (m, 2H), 2.84-2.82 (m, 2H), 2.68-2.59 (m, 4H), 2.30-2.17 (m, 1H), 2.09-1.94 (m, 2H), 1.86-1.67 (m, 3H), 1.60-1.53 (m, 1H), 1.21-1.16 (m, 1H), 0.84-0.74 (m, 1H). | ++++ | +++ |

TABLE 24-continued

| | | | | | |
|---|---|---|---|---|---|
| 233 | N-[(3R)-7-[(3aS,6R,7aS)-6-amino-octahydro-1H-indol-1-yl]-3,4-dihydro-2H-1-benzopyran-3-yl]-3-amino-6-methylthieno[2,3-b]pyridine-2-carboxamide | 478 | (DMSO-d6, 400 MHz) δ (ppm): 8.33 (d, J = 8.0 Hz, 1H), 7.48 (d, J = 7.6 Hz, 1H), 7.32 (d, J = 8.4 Hz, 1H), 7.21 (br s, 2H), 6.84 (d, J = 8.4 Hz, 1H), 6.13 (d, J = 8.0 Hz, 1H), 5.93 (s, 1H), 4.31-4.23 (m, 1H), 4.15-4.12 (m, 1H), 3.91-3.68 (m, 2H), 3.22-3.17 (m, 2H), 2.84-2.82 (m, 2H), 2.68-2.59 (m, 4H), 2.30-2.17 (m, 1H), 2.12-2.08 (m, 1H), 2.04-1.96 (m, 1H), 1.89-1.67 (m, 4H), 1.60-1.56 (m, 1H), 1.24-1.19 (m, 1H), 0.87-0.77 (m, 1H). | ++++ | ++++ |
| 234 | N-[(3R)-7-[(3aS,6S,7aS)-6-amino-octahydro-1H-indol-1-yl]-3,4-dihydro-2H-1-benzopyran-3-yl]-3-amino-6-methylthieno[2,3-b]pyridine-2-carboxamide | 478 | (DMSO-d6, 400 MHz) δ (ppm): 8.33 (d, J = 8.0 Hz, 1H), 7.49 (d, J = 8.0 Hz, 1H), 7.32 (d, J = 7.6 Hz, 1H), 7.21 (br s, 2H), 6.84 (d, J = 7.6 Hz, 1H), 6.16 (d, J = 8.4 Hz, 1H), 5.96 (s, 1H), 4.31-4.22 (m, 1H), 4.16-4.12 (m, 1H), 3.89-3.87 (m, 1H), 3.81-3.76 (m, 1H), 3.32-3.25 (m, 1H), 3.13-3.11 (m, 1H), 2.93-2.88 (m, 1H), 2.84-2.78 (m, 2H), 2.59 (s, 3H), 2.22-2.19 (m, 1H), 2.03-1.96 (m, 1H), 1.90-1.55 (m, 5H), 1.51-1.37 (m, 2H), 1.24-1.18 (m, 1H). | ++++ | +++ |
| 235 | N-[(3R)-7-[(3aS,7aR)-octahydro-1H-pyrrolo[3,2-c]pyridin-1-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.32 (d, J = 8.0 Hz, 1H), 7.49 (d, J = 7.6 Hz, 1H), 7.31 (d, J = 8.0 Hz, 1H), 7.22 (s, 2H), 6.83 (d, J = 8.0 Hz, 1H), 6.13 (d, J = 8.0 Hz, 1H), 5.92 (s, 1H), 4.27 (br s, 1H), 4.14-4.12 (m, 1H), 3.80-3.75 (m, 1H), 3.72-3.68 (m, 1H), 3.25-3.16 (m, 2H), 2.94-2.75 (m, 5H), 2.59 (s, 3H), 2.43-2.33 (m, 1H), 2.25-2.16 (m, 2H), 1.90-1.82 (m, 2H), 1.19-1.10 (m, 1H). | ++++ | +++ |
| 236 | N-[(3R)-7-[(3aR,7aS)-octahydro-1H-pyrrolo[3,2-c]pyridin-1-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.32 (d, J = 8.0 Hz, 1H), 7.49 (d, J = 7.6 Hz, 1H), 7.32 (d, J = 8.8 Hz, 1H), 7.21 (s, 2H), 6.83 (d, J = 8.4 Hz, 1H), 6.14 (d, J = 8.4 Hz, 1H), 5.92 (s, 1H), 4.27 (br s, 1H), 4.14-4.12 (m, 1H), 3.80-3.75 (m, 1H), 3.70-3.68 (m, 1H), 3.25-3.16 (m, 2H), 2.93-2.80 (m, 5H), 2.59 (s, 3H), 2.41-2.15 (m, 3H), 1.93-1.81 (m, 2H), 1.18-1.09 (m, 1H). | ++++ | +++ |
| 237 | N-[(3R)-7-[(4aR,7aR)-4,4-difluoro-octahydro-1H-pyrrolo[3,4-b]pyridin-6-yl]-3,4-dihydro-2H-1-benzopyran-3-yl]-3-amino-6-methylthieno[2,3-b]pyridine-2-carboxamide | 500 | (DMSO-d6, 400 MHz) δ (ppm): 8.33 (d, J = 8.0 Hz, 1H), 7.49 (br s, 1H), 7.32 (d, J = 8.4 Hz, 1H), 7.22 (br s, 2H), 6.88 (d, J = 8.0 Hz, 1H), 6.10 (d, J = 8.4 Hz, 1H), 5.91 (s, 1H), 4.27-4.25 (m, 1H), 4.16-4.13 (m, 1H), 3.82-3.77 (m, 1H), 3.45-3.40 (m, 2H), 3.39-3.33 (m, 1H), 3.11-3.08 (m, 1H), 2.97-2.90 (m, 1H), 2.86-2.82 (m, 2H), 2.79-2.74 (m, 1H), 2.68-2.64 (m, 1H), 2.59 (s, 3H), 2.40-2.25 (m, 1H), 2.06-1.81 (m, 3H). | ++++ | ++ |

TABLE 24-continued

| | | | | | |
|---|---|---|---|---|---|
| 238 | N-[(3R)-7-[(4aS,7aS)-4,4-difluoro-octahydro-1H-pyrrolo[3,4-b]pyridin-6-yl]-3,4-dihydro-2H-1-benzopyran-3-yl]-3-amino-6-methylthieno[2,3-b]pyridine-2-carboxamide | 500 | (DMSO-d6, 400 MHz) δ (ppm): 8.33 (d, J = 8.0 Hz, 1H), 7.49 (br s, 1H), 7.32 (d, J = 8.4 Hz, 1H), 7.22 (br s, 2H), 6.88 (d, J = 8.0 Hz, 1H), 6.10 (d, J = 6.8 Hz, 1H), 5.91 (s, 1H), 4.28-4.26 (m, 1H), 4.16-4.14 (m, 1H), 3.81-3.76 (m, 1H), 3.45-3.40 (m, 2H), 3.39-3.28 (m, 1H), 3.11-3.08 (m, 1H), 2.97-2.90 (m, 1H), 2.86-2.80 (m, 2H), 2.78-2.72 (m, 1H), 2.67-2.64 (m, 1H), 2.59 (s, 3H), 2.43-2.33 (m, 1H), 2.08-1.87 (m, 3H). | ++++ | ++ |
| 239 | 3-amino-N-[(6S)-2-[(3S,4S)-3-amino-4-methoxy-3-methylpyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.56 (br s, 1H), 7.31 (d, J = 8.4 Hz, 1H), 7.19-7.16 (m, 3H), 6.20 (d, J = 8.4 Hz, 1H), 4.15-4.12 (m, 1H), 3.69-3.65 (m, 1H), 3.48-3.46 (m, 1H), 3.35-3.32 (m, 1H), 3.28-3.25 (m, 3H), 3.19-3.17 (m, 2H), 2.81-2.67 (m, 4H), 2.59 (s, 3H), 2.01-1.98 (m, 1H), 1.89-1.79 (m, 1H), 1.68 (br s, 2H), 1.17 (s, 3H). | ++ | + |
| 240 | 3-amino-N-[(6S)-2-[(3R,4R)-3-amino-4-methoxy-3-methylpyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.57(br s, 1H), 7.31 (d, J = 8.4 Hz, 1H), 7.19-7.16 (m, 3H), 6.20 (d, J = 8.4 Hz, 1H), 4.16-4.12 (m, 1H), 3.68-3.64 (m, 1H), 3.48-3.46 (m, 1H), 3.38-3.31 (m, 1H), 3.28-3.25 (m, 3H), 3.20-3.16 (m, 2H), 2.81-2.67 (m, 4H), 2.59 (s, 3H), 2.01-1.98 (m, 1H), 1.95-1.88 (m, 1H), 1.73 (br s, 2H), 1.17 (s, 3H). | ++ | + |
| 241 | 3-amino-N-[(3R)-6-cyano-7-{3,8-diazabicyclo[3.2.1]octan-3-yl}-5-fluoro-3,4-dihydro-2H-1-benzopyran-3-yl]-4,6-dimethylthieno[2,3-b]pyridine-2-carboxamide | 507 | (DMSO-d6, 400 MHz) δ (ppm): 7.70 (d, J = 6.8 Hz, 1H), 7.05 (s, 1H), 6.89 (br s, 2H), 6.29 (s, 1H), 4.34-4.25 (m, 2H), 4.06-4.01 (m, 1H), 3.48-3.46 (m, 2H), 3.35-3.28 (m, 5H), 2.96-2.88 (m, 3H), 2.82-2.76 (m, 1H), 2.73 (s, 3H), 1.90-1.85 (m, 2H), 1.68-1.67 (m, 2H). | ++++ | +++ |
| 242 | N-[(3R)-7-[(4aR,7aR)-octahydro-1H-pyrrolo[3,4-b]pyridin-1-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.31 (d, J = 8.0 Hz, 1H), 7.54 (br s, 1H), 7.31 (d, J = 8.0 Hz, 1H), 7.22 (br s, 2H), 6.94-6.89 (m, 1H), 6.53-6.51 (m, 1H), 6.36-6.30 (m, 1H), 4.32-4.28 (m, 1H), 4.16-4.11 (m, 2H), 3.82-3.77 (m, 1H), 3.28-3.10 (m, 2H), 3.00-2.95(m, 1H), 2.88-2.75 (m, 4H), 2.64-2.55 (m, 4H), 2.27-2.07 (m, 1H), 1.78-1.60 (m, 2H), 1.48-1.40 (m, 2H). | ++++ | +++ |
| 243 | N-[(3R)-7-[(4aS,7aS)-octahydro-1H-pyrrolo[3,4-b]pyridin-1-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.31 (d, J = 8.0 Hz, 1H), 7.56 (br s, 1H), 7.31 (d, J = 8.8 Hz, 1H), 7.22 (br s, 2H), 6.94-6.88 (m, 1H), 6.59-6.51 (m, 1H), 6.37-6.30 (m, 1H), 4.36-4.14 (m, 3H), 3.82-3.78 (m, 1H), 3.32-2.95 (m, 3H), 2.88-2.68 (m, 4H), 2.63-2.51 (m, 4H), 2.30-2.03 (m, 1H), 1.77-1.60 (m, 2H), 1.50-1.30 (m, 2H). | ++++ | ++++ |

TABLE 24-continued

| | | | | | |
|---|---|---|---|---|---|
| 244 | 3-amino-N-[(3R)-7-[(2R,5R)-5-amino-2-(trifluoromethyl)piperidin-1-yl]-3,4-dihydro-2H-1-benzopyran-3-yl]-6-methylthieno[2,3-b]pyridine-2-carboxamide | 506 | (MeOH-d4, 400 MHz) δ (ppm): 8.22 (d, J = 8.0 Hz, 1H), 7.32 (d, J = 8.4 Hz, 1H), 6.96 (d, J = 8.4 Hz, 1H), 6.57 (d, J = 8.4 Hz, 1H), 6.45 (s, 1H), 4.47-4.38 (m, 2H), 4.27-4.25 (m, 1H), 3.96-3.91 (m, 1H), 3.62-3.60 (m, 1H), 3.03-2.84 (m, 4H), 2.65 (s, 3H), 2.15-2.12 (m, 1H), 2.02-1.89 (m, 2H), 1.60-1.50 (m, 1H). | ++++ | ++++ |
| 245 | 3-amino-N-[(3R)-7-[(2S,5S)-5-amino-2-(trifluoromethyl)piperidin-1-yl]-3,4-dihydro-2H-1-benzopyran-3-yl]-6-methylthieno[2,3-b]pyridine-2-carboxamide | 506 | (MeOH-d4, 400 MHz) δ (ppm): 8.22 (d, J = 8.4 Hz, 1H), 7.32 (d, J = 8.4 Hz, 1H), 6.97 (d, J = 8.4 Hz, 1H), 6.57 (d, J = 8.8 Hz, 1H), 6.45 (s, 1H), 4.96-4.40 (m, 2H), 4.27-4.24 (m, 1H), 3.97-3.92 (m, 1H), 3.63-3.60 (m, 1H), 3.03-2.81 (m, 4H), 2.65 (s, 3H), 2.15-2.12 (m, 1H), 2.02-1.88 (m, 2H), 1.57-1.50 (m, 1H). | ++++ | +++ |
| 246 | 3-amino-N-[(3R)-7-[(2R,5S)-5-amino-2-(trifluoromethyl)piperidin-1-yl]-3,4-dihydro-2H-1-benzopyran-3-yl]-6-methylthieno[2,3-b]pyridine-2-carboxamide | 506 | (MeOH-d4, 400 MHz) δ (ppm): 8.22 (d, J = 8.4 Hz, 1H), 7.32 (d, J = 8.4 Hz, 1H), 6.98 (d, J = 8.4 Hz, 1H), 6.64 (d, J = 8.4 Hz, 1H), 6.50 (s, 1H), 4.48-4.46 (m, 2H), 4.27-4.25 (m, 1H), 3.97-3.93 (m, 1H), 3.45-3.37 (m, 2H), 3.18 (m, 1H), 3.04-2.99 (m, 1H), 2.91-2.85 (m, 1H), 2.68 (s, 3H), 2.33-2.26 (m, 1H), 2.06-1.99 (m, 1H), 1.92-1.89 (m, 1H), 1.67-1.62 (m, 1H). | ++++ | ++++ |
| 247 | 3-amino-N-[(3R)-7-[(2S,5R)-5-amino-2-(trifluoromethyl)piperidin-1-yl]-3,4-dihydro-2H-1-benzopyran-3-yl]-6-methylthieno[2,3-b]pyridine-2-carboxamide | 506 | (MeOH-d4, 400 MHz) δ (ppm): 8.22 (d, J = 8.4 Hz, 1H), 7.32 (d, J = 8.4 Hz, 1H), 6.98 (d, J = 8.8 Hz, 1H), 6.64 (d, J = 7.2 Hz, 1H), 6.51 (s, 1H), 4.52-4.45 (m, 2H), 4.28-4.25 (m, 1H), 3.96-3.91 (m, 1H), 3.50-3.38 (m, 2H), 3.28-3.24 (m, 1H), 3.04-2.99 (m, 1H), 2.91-2.85 (m, 1H), 2.79 (s, 3H), 2.33-2.26 (m, 1H), 2.12-2.01 (m, 1H), 1.98-1.91 (m, 1H), 1.74-1.66 (m, 1H). | ++++ | +++ |
| 248 | N-[(3R)-7-[(3aS)-3a-amino-octahydrocyclopenta[c]pyrrol-2-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.33 (d, J = 8.4 Hz, 1H), 7.49 (br s, 1H), 7.32 (d, J = 8.0 Hz, 1H), 7.21 (br s, 2H), 6.89 (d, J = 8.0 Hz, 1H), 6.20-6.18 (m, 1H), 6.00 (d, J = 2.4 Hz, 1H), 4.30-4.27 (m, 1H), 4.16-4.13 (m, 1H), 3.82-3.77 (m, 1H), 3.50-3.45 (m, 1H), 3.27-3.25 (m, 1H), 3.17-3.15 (m, 1H), 2.96-2.92 (m, 1H), 2.86-2.83 (m, 2H), 2.58 (s, 3H), 2.42-2.41 (m, 1H), 2.02-1.98 (m, 1H), 1.82-1.68 (m, 5H), 1.50-1.45 (m, 1H). | ++++ | ++ |
| 249 | N-[(3R)-7-[(3aR)-3a-amino-octahydrocyclopenta[c]pyrrol-2-yl]-3,4-dihydro-2H-1-benzopyran-3-yl]-3-amino-6-methylthieno[2,3-b]pyridine-2-carboxamide | 464 | (DMSO-d6, 400 MHz) δ (ppm): 8.33 (d, J = 8.4 Hz, 1H), 7.49 (br s, 1H), 7.32 (d, J = 8.4 Hz, 1H), 7.21 (br s, 2H), 6.89 (d, J = 8.4 Hz, 1H), 6.22-6.19 (m, 1H), 6.01 (d, J = 2.0 Hz, 1H), 4.30-4.27 (m, 1H), 4.16-4.13 (m, 1H), 3.82-3.77 (m, 1H), 3.52-3.48 (m, 1H), 3.27-3.18 (m, 2H), 2.95-2.92 (m, 1H), 2.86-2.83 (m, 2H), 2.58 (s, 3H), 2.50-2.44 (m, 1H), 1.99-1.98 (m, 1H), 1.86-1.68 (m, 4H), 1.46-1.45 (m, 1H). | ++++ | +++ |

TABLE 24-continued

| | | | | | |
|---|---|---|---|---|---|
| 250 | 3-amino-N-[(3R)-7-[(3R,4R)-3-amino-4-(methoxymethyl)pyrrolidin-1-yl]-5-fluoro-3,4-dihydro-2H-1-benzopyran-3-yl]-6-methylthieno[2,3-b]pyridine-2-carboxamide | 486 | (DMSO-d6, 400 MHz) δ (ppm): 8.32 (d, J = 8.0 Hz, 1H), 7.56 (br s, 1H), 7.32 (d, J = 8.4 Hz, 1H), 7.23 (br s, 2H), 5.94-5.91 (m, 1H), 5.75 (s, 1H), 4.27-4.21 (m, 1H), 4.17-4.14 (m, 1H), 3.85-3.80 (m, 1H), 3.59-3.55 (m, 2H), 3.40-3.20 (m, 6H), 3.09-3.05 (m, 1H), 2.97-2.94 (m, 1H), 2.83-2.81 (m, 1H), 2.75-2.68 (m, 1H), 2.59 (s, 3H), 2.43-2.41 (m, 1H), 1.90 (br s, 2H). | ++++ | ++ |
| 251 | 3-amino-N-[(3R)-7-[(3S,4S)-3-amino-4-(methoxymethyl)pyrrolidin-1-yl]-5-fluoro-3,4-dihydro-2H-1-benzopyran-3-yl]-6-methylthieno[2,3-b]pyridine-2-carboxamide | 486 | (DMSO-d6, 400 MHz) δ (ppm): 8.32 (d, J = 8.0 Hz, 1H), 7.55 (br s, 1H), 7.31 (d, J = 8.0 Hz, 1H), 7.23 (br s, 2H), 5.95-5.91 (m, 1H), 5.75 (s, 1H), 4.28-4.21 (m, 1H), 4.17-4.14 (m, 1H), 3.85-3.81 (m, 1H), 3.59-3.55 (m, 2H), 3.41-3.21 (m, 6H), 3.10-3.05 (m, 1H), 2.98-2.95 (m, 1H), 2.83-2.82 (m, 1H), 2.75-2.69 (m, 1H), 2.59 (s, 3H), 2.46-2.43 (m, 1H), 2.11 (br s, 2H). | ++++ | +++ |
| 252 | 3-amino-N-[(2S)-6-[(3R,4R)-3-amino-4-(methoxymethyl)pyrrolidin-1-yl]-1,2,3,4-tetrahydronaphthalen-2-yl]-6-methylthieno[2,3-b]pyridine-2-carboxamide | 466 | (DMSO-d6, 400 MHz) δ (ppm): 8.30 (d, J = 8.4 Hz, 1H), 7.51 (d, J = 7.6 Hz, 1H), 7.30 (d, J = 8.4 Hz, 1H), 7.14 (br s, 2H), 6.85 (d, J = 8.0 Hz, 1H), 6.29 (dd, J = 8.4, 2.4 Hz, 1H), 6.19 (s, 1H), 4.13-4.07 (m, 1H), 3.60-3.54 (m, 2H), 3.41-3.31 (m, 1H), 3.28 (s, 3H), 3.26-3.22 (m, 1H), 3.11-3.06 (m, 1H), 2.97-2.94 (m, 1H), 2.80-2.72 (m, 5H), 2.58 (s, 3H), 2.50-2.41 (m, 1H), 1.98-1.94 (m, 1H), 1.79-1.62 (m, 3H). | +++ | ++ |
| 253 | 3-amino-N-[(2S)-6-[(3S,4S)-3-amino-4-(methoxymethyl)pyrrolidin-1-yl]-1,2,3,4-tetrahydronaphthalen-2-yl]-6-methylthieno[2,3-b]pyridine-2-carboxamide | 466 | (DMSO-d6, 400 MHz) δ (ppm): 8.30 (d, J = 8.4 Hz, 1H), 7.53 (d, J = 7.6 Hz, 1H), 7.31 (d, J = 7.6 Hz, 1H), 7.15 (br s, 2H), 6.86 (d, J = 8.0 Hz, 1H), 6.29 (dd, J = 8.4, 2.4 Hz, 1H), 6.20 (s, 1H), 4.13-4.07 (m, 1H), 3.61-3.55 (m, 2H), 3.41-3.33 (m, 2H), 3.28 (s, 3H), 3.25-3.23 (m, 1H), 3.11-3.06 (m, 1H), 2.97-2.95 (m, 1H), 2.81-2.72 (m, 5H), 2.59 (s, 3H), 2.50-2.41 (m, 1H), 1.98-1.94 (m, 1H), 1.79-1.62 (m, 2H). | ++++ | ++ |
| 254 | 3-amino-N-[(6S)-2-[(3S,4R)-3-amino-4-ethoxypyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.30 (d, J = 8.4 Hz, 1H), 7.54 (d, J = 8.0 Hz, 1H), 7.30 (d, J = 8.0 Hz, 1H), 7.19-7.14 (m, 3 H), 6.20 (d, J = 8.4 Hz, 1H), 4.12 (br s, 1H), 3.84 (s, 1H), 3.60-3.42 (m, 6H), 3.03-2.98 (m, 1H), 2.78-2.67 (m, 4H), 2.58 (s, 3H), 2.01-1.97 (m, 1H), 1.89-1.80 (m, 1H), 1.62 (br s, 2H), 1.17-1.12 (m, 3H). | +++ | + |
| 255 | 3-amino-N-[(6S)-2-[(3R,4S)-3-amino-4-ethoxypyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.30 (d, J = 8.4 Hz, 1H), 7.54 (d, J = 7.6 Hz, 1H), 7.30 (d, J = 8.4 Hz, 1H), 7.19-7.14 (m, 3 H), 6.20 (d, J = 8.4 Hz, 1H), 4.12 (br s, 1H), 3.84 (s, 1H), 3.60-3.43 (m, 6H), 2.99-2.97 (m, 1H), 2.77-2.67 (m, 4H), 2.58 (s, 3H), 2.01-1.98 (m, 1H), 1.87-1.82 (m, 1H), 1.62 (br s, 2H), 1.16-1.13 (m, 3H). | +++ | + |

TABLE 24-continued

| | | | | | |
|---|---|---|---|---|---|
| 256 | 3-amino-N-[(3R)-7-[(4S)-4-amino-3,3-difluoropyrrolidin-1-yl]-3,4-dihydro-2H-1-benzopyran-3-yl]-6-methylthieno[2,3-b]pyridine-2-carboxamide | 460 | (DMSO-d6, 400 MHz) δ (ppm): 8.33 (d, J = 8.4 Hz, 1H), 7.50 (br s, 1H), 7.32 (d, J = 8.4 Hz, 1H), 7.22 (br s, 2H), 6.93 (d, J = 8.4 Hz, 1H), 6.16 (d, J = 6.4 Hz, 1H), 5.99 (s, 1H), 4.29-4.27 (m, 1H), 4.17-4.14 (m, 1H), 3.83-3.81 (m, 1H), 3.69-3.58 (m, 4H), 2.99-2.95 (m, 1H), 2.87-2.85 (m, 2H), 2.59 (s, 3H), 1.93 (br s, 2H). | ++++ | ++ |
| 257 | 3-amino-N-[(3R)-7-[(4R)-4-amino-3,3-difluoropyrrolidin-1-yl]-3,4-dihydro-2H-1-benzopyran-3-yl]-6-methylthieno[2,3-b]pyridine-2-carboxamide | 460 | (DMSO-d6, 400 MHz) δ (ppm): 8.33 (d, J = 8.4 Hz, 1H), 7.50 (br s, 1H), 7.32 (d, J = 8.4 Hz, 1H), 7.22 (br s, 2H), 6.93 (d, J = 8.0 Hz, 1H), 6.16 (d, J = 8.0 Hz, 1H), 5.99 (s, 1H), 4.29-4.27 (m, 1H), 4.18-4.15 (m, 1H), 3.84-3.81 (m, 1H), 3.69-3.58 (m, 4H), 2.97-2.95 (m, 1H), 2.87-2.85 (m, 2H), 2.59 (s, 3H), 1.94 (br s, 2H). | ++++ | +++ |
| 258 | 3-amino-N-[(3R)-7-[(8R)-8-amino-2-oxa-6-azaspiro[3.4]octan-6-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.48 (br s, 1H), 7.32 (d, J = 8.0 Hz, 1H), 7.21 (br s, 2H), 6.87 (d, J = 8.4 Hz, 1H), 6.01 (d, J = 8.0 Hz, 1H), 5.91 (s, 1H), 4.83-4.81 (m, 1H), 4.48-4.37 (m, 3H), 4.31-4.21 (m, 1H), 4.16-4.13 (m, 1H), 3.82-3.77 (m, 1H), 3.56-3.43 (m, 3H), 3.34-3.32 (m, 1H), 2.89-2.79 (m, 3H), 2.59 (s, 3H), 2.18 (br s, 2H). | ++++ | ++ |
| 259 | 3-amino-N-[(3R)-7-[(8S)-8-amino-2-oxa-6-azaspiro[3.4]octan-6-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.48 (br s, 1H), 7.32 (d, J = 8.0 Hz, 1H), 7.21 (br s, 2H), 6.87 (d, J = 8.8 Hz, 1H), 6.10 (d, J = 8.0 Hz, 1H), 5.91 (s, 1H), 4.82-4.81 (m, 1H), 4.47-4.37 (m, 3H), 4.28-4.25 (m, 1H), 4.15-4.13 (m, 1H), 3.81-3.77 (m, 1H), 3.56-3.43 (m, 3H), 3.34-3.32 (m, 1H), 2.87-2.83 (m, 3H), 2.59 (s, 3H), 2.11 (br s, 2H). | ++++ | ++ |
| 260 | 3-amino-N-[(3R)-7-[(2S,4R)-4-amino-2-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.49 (br s, 1H), 7.31 (d, J = 8.0 Hz, 1H), 7.22 (br s, 2H), 6.87 (d, J = 8.0 Hz, 1H), 6.16 (d, J = 8.4 Hz, 1H), 5.96 (s, 1H), 4.32-4.25 (m, 1H), 4.16-4.13 (m, 1H), 3.82-3.77 (m, 2H), 3.62-3.52 (m, 1H), 3.48-3.44 (m, 1H), 3.38-3.20 (m, 5H), 2.89-2.78 (m, 2H), 2.66-2.62 (m, 1H), 2.59 (s, 3H), 2.10-1.90 (m, 3H), 1.73-1.65 (m, 1H). | ++++ | ++++ |
| 261 | 3-amino-N-[(3R)-7-[(2R,4S)-4-amino-2-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.51 (br s, 1H), 7.32 (d, J = 8.0 Hz, 1H), 7.22 (br s, 2H), 6.88 (d, J = 8.4 Hz, 1H), 6.17-6.14 (m, 1H), 5.96 (d, J = 1.6 Hz, 1H), 4.30-4.25 (m, 1H), 4.15-4.12 (m, 1H), 3.82-3.77 (m, 2H), 3.62-3.58 (m, 1H), 3.47-3.43 (m, 1H), 3.38-3.35 (m, 1H), 3.27 (s, 3H), 3.23-3.19 (m, 1H), 2.86-2.81 (m, 2H), 2.65-2.51 (m, 4H), 2.06-2.01 (m, 1H), 1.73-1.64 (m, 3H). | ++++ | +++ |

TABLE 24-continued

| | | | | | |
|---|---|---|---|---|---|
| 262 | 3-amino-N-[(3R)-7-[(2R,4R)-4-amino-2-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.4 Hz, 1H), 7.49 (br s, 1H), 7.31 (d, J = 8.0 Hz, 1H), 7.21 (br s, 2H), 6.87 (d, J = 8.4 Hz, 1H), 6.19-6.17 (m, 1H), 5.99 (s, 1H), 4.28-4.25 (m, 1H), 4.15-4.12 (m, 1H), 3.82-3.75 (m, 2H), 3.53-3.51 (m, 3H), 3.27-3.24 (m, 4H), 3.04-3.01 (m, 1H), 2.85-2.81 (m, 2H), 2.58 (s, 3H), 2.20-2.17 (m, 1H), 2.10-1.90 (br s, 1H), 1.74-1.69 (m, 1H). | ++++ | ++ |
| 263 | 3-amino-N-[(3R)-7-[(2S,4S)-4-amino-2-(methoxymethyl)pyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.50 (br s, 1H), 7.32 (d, J = 8.0 Hz, 1H), 7.21 (br s, 2H), 6.87 (d, J = 8.4 Hz, 1H), 6.19 (d, J = 8.4 Hz, 1H), 6.02 (s, 1H), 4.32-4.21 (m, 1H), 4.16-4.13 (m, 1H), 3.81-3.76 (m, 2H), 3.52-3.48 (m, 3H), 3.32-3.25 (m, 4H), 3.05-3.03 (m, 1H), 2.89-2.78 (m, 2H), 2.59 (s, 3H), 2.23-2.16 (m, 2H), 1.73-1.70 (m, 1H). | ++++ | +++ |
| 264 | (6aS,7aR)-N-[(3R)-6-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide | 475 | (DMSO-d6, 400 MHz) δ (ppm): 8.27 (d, J = 2.4 Hz, 1H), 8.14 (d, J = 6.4 Hz, 1H), 7.84 (d, J = 2.4 Hz, 1H), 6.63 (br s, 1H), 6.32 (s, 1H), 4.31-4.24 (m, 2H), 4.10-4.06 (m, 1H), 3.63-3.60 (m 2H), 3.38-3.30 (m, 4H), 3.00-2.68 (m, 3H), 2.77-2.68 (m, 1H), 1.98-1.91(m, 3H), 1.76-1.67 (m, 3H), 0.96-0.90 (m, 2H). | ++++ | ++++ |
| 265 | (6aR,7aS)-N-[(3R)-6-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide | 475 | (DMSO-d6, 400 MHz) δ (ppm): 8.27 (d, J = 2.0 Hz, 1H), 8.14 (d, J = 6.4 Hz, 1H), 7.84 (d, J = 2.0 Hz, 1H), 6.63 (br s, 1H), 6.28 (s, 1H), 4.29-4.23 (m, 2H), 4.10-4.05 (m, 1H), 3.46-3.42 (m, 2H), 3.38-3.26 (m, 4H), 2.99-2.87 (m, 3H), 2.76-2.70 (m, 1H), 1.96-1.85 (m, 3H), 1.74-1.63 (m, 3H), 0.96-0.90 (m, 2H). | +++ | ++ |
| 266 | 7-amino-N-[(6S)-2-[(3S,4S)-3-acetamido-4-methoxypyrrolidin-1-yl]-5,6,7,8-tetrahydroquinolin-6-yl]-3-methylthieno[2,3-b]pyrazine-6-carboxamide | 496 | (DMSO-d6, 400 MHz) δ (ppm): 8.65 (s, 1H), 8.13 (d, J = 7.2 Hz, 1H), 7.81 (d, J = 7.6 Hz, 1H), 7.22 (d, J = 8.4 Hz, 1H), 6.92 (s, 2H), 6.28 (d, J = 8.4 Hz, 1H), 4.26 (br s, 1H), 4.15 (br s, 1H), 3.81-3.80 (m, 1H), 3.60-3.54 (m, 2H), 3.39-3.28(m, 5 H), 2.86-2.70 (m, 4 H), 2.66 (s, 3 H), 2.04-2.00 (m, 1 H), 1.90-1.83 (m, 1H), 1.82 (s, 3H). | ++ | + |
| 267 | 3-amino-N-[(2S)-6-[(3S,4R)-3-amino-4-ethoxypyrrolidin-1-yl]-1,2,3,4-tetrahydronaphthalen-2-yl]-6-methylthieno[2,3-b]pyridine-2-carboxamide | 466 | (DMSO-d6, 400 MHz) δ (ppm): 8.30 (d, J = 8.4 Hz, 1H), 7.53 (d, J = 8.0 Hz, 1H), 7.31 (d, J = 8.0 Hz, 1H), 7.15 (br s, 2H), 6.86 (d, J = 8.4 Hz, 1H), 6.29 (dd, J = 8.4, 2.0 Hz, 1H), 6.20 (s, 1H), 4.14-4.07 (m, 1H), 3.87-3.85 (m, 1H), 3.60-3.47 (m, 3H), 3.38-3.33 (m, 2H), 3.24-3.21 (m, 1H), 2.89-2.72 (m, 5H), 2.59 (s, 3H), 1.97-1.95 (m, 1H), 1.77 (br s, 2H), 1.74-1.68 (m, 1H), 1.15 (t, J = 7.2 Hz, 3H). | +++ | ++ |

TABLE 24-continued

| | | | | | |
|---|---|---|---|---|---|
| 268 | 3-amino-N-[(2S)-6-[(3R,4S)-3-amino-4-ethoxypyrrolidin-1-yl]-1,2,3,4-tetrahydronaphthalen-2-yl]-6-methylthieno[2,3-b]pyridine-2-carboxamide | 466 | (DMSO-d6, 400 MHz) δ (ppm): 8.30 (d, J = 8.4 Hz, 1H), 7.52 (d, J = 8.0 Hz, 1H), 7.31 (d, J = 8.0 Hz, 1H), 7.15 (br s, 2H), 6.86 (d, J = 8.4 Hz, 1H), 6.29 (dd, J = 8.8, 2.0 Hz, 1H), 6.20 (s, 1H), 4.13-4.07 (m, 1H), 3.86-3.85 (m, 1H), 3.60-3.47 (m, 3H), 3.38-3.33 (m, 2H), 3.24-3.21 (m, 1H), 2.88-2.68 (m, 5H), 2.59 (s, 3H), 1.97-1.95 (m, 1H), 1.76-1.74 (m, 1H), 1.58 (br s, 2H), 1.15 (t, J = 7.2 Hz, 3H). | +++ | + |
| 269 | 3-amino-N-[(6S)-2-[(3S,4R)-3-amino-4-methoxypyrrolidin-1-yl]-5,6,7,8-tetrahydroquinolin-6-yl]-6-methylthieno[2,3-b]pyridine-2-carboxamide | 453 | (DMSO-d6, 400 MHz) δ (ppm): 8.31 (d, J = 8.0 Hz, 1H), 7.57 (br s, 1H), 7.31 (d, J = 8.0 Hz, 1H), 7.20-7.16 (m, 3H), 6.21 (d, J = 8.4 Hz, 1H), 4.15-4.11 (m, 1H), 3.73-3.72 (m, 1H), 3.53-3.33 (m, 7H), 3.00-2.94 (m, 1H), 2.82-2.68 (m, 4H), 2.59 (s, 3H), 2.02-1.98 (m, 1H), 1.90-1.82 (m, 1H), 1.62 (br s, 2H). | +++ | + |
| 270 | 3-amino-N-[(6S)-2-[(3R,4S)-3-amino-4-methoxypyrrolidin-1-yl]-5,6,7,8-tetrahydroquinolin-6-yl]-6-methylthieno[2,3-b]pyridine-2-carboxamide | 453 | (DMSO-d6, 400 MHz) δ (ppm): 8.31 (d, J = 8.4 Hz, 1H), 7.57 (br s, 1H), 7.31 (d, J = 8.4 Hz, 1H), 7.20-7.16 (m, 3H), 6.21 (d, J = 8.8 Hz, 1H), 4.16-4.11 (m, 1H), 3.75-3.74 (m, 1H), 3.52-3.34 (m, 7H), 3.02-2.96 (m, 1H), 2.82-2.68 (m, 4H), 2.59 (s, 3H), 2.08-1.79 (m, 4H). | +++ | + |
| 271 | 3-amino-N-[(6S)-2-[(3S,4S)-3-amino-4-(propan-2-yloxy)pyrrolidin-1-yl]-5,6,7,8-tetrahydroquinazolin-6-yl]-6-methylthieno[2,3-b]pyridine-2-carboxamide | 482 | (DMSO-d6, 400 MHz) δ (ppm): 8.30 (d, J = 8.0 Hz, 1H), 8.06 (s, 1H), 7.61 (d, J = 7.6 Hz, 1H), 7.31 (d, J = 8.4 Hz, 1H), 7.16 (s, 2H), 4.12 (br s, 1H), 3.77-3.69 (m, 3H), 3.56-3.52 (m, 1 H), 3.37-3.32 (m, 2H), 3.25-3.22 (m, 1H), 2.84-2.64 (m, 4H), 2.59 (s, 3 H), 2.04-1.98 (m, 1 H), 1.88-1.83 (m, 1H), 1.68 (br s, 2H), 1.11-1.10 (m, 6H). | + | |
| 272 | 3-amino-N-[(6R)-2-[(3S,4S)-3-amino-4-(propan-2-yloxy)pyrrolidin-1-yl]-5,6,7,8-tetrahydroquinazolin-6-yl]-6-methylthieno[2,3-b]pyridine-2-carboxamide | 482 | (DMSO-d6, 400 MHz) δ (ppm): 8.30 (d, J = 8.0 Hz, 1H), 8.06 (s, 1H), 7.61 (d, J = 8.0 Hz, 1H), 7.31 (d, J = 8.8 Hz, 1H), 7.16 (s, 2H), 4.12 (br, 1H), 3.79-3.70 (m, 3H), 3.57-3.53 (m, 1 H), 3.37-3.32 (m, 2H), 3.25-3.22 (m, 1H), 2.84-2.61 (m, 4H), 2.59 (s, 3 H), 2.01-1.83 (m, 4 H), 1.12-1.08 (m, 6H). | ++ | |
| 273 | 3-amino-N-[(6S)-2-[(3S,4S)-3-amino-4-methoxypyrrolidin-1-yl]-5,6,7,8-tetrahydroquinazolin-6-yl]-4,6-dimethylthieno[2,3-b]pyridine-2-carboxamide | 468 | (DMSO-d6, 400 MHz) δ (ppm): 8.07 (s, 1H), 7.65 (br s, 1H), 7.04 (s, 1H), 6.83 (br s, 2H), 4.15-4.12 (m, 1H), 3.69-3.61 (m, 2H), 3.54-3.43 (m, 3H), 3.29-3.27 (m, 5H), 2.83-2.62 (m, 7H), 2.03-1.97 (m, 1H), 1.95-1.82 (m, 1H), 1.75-1.65 (m, 2H). | + | |
| 274 | 3-amino-N-[(6R)-2-[(3S,4S)-3-amino-4-methoxypyrrolidin-1-yl]-5,6,7,8-tetrahydroquinazolin-6-yl]-4,6-dimethylthieno[2,3-b]pyridine-2-carboxamide | 468 | (DMSO-d6, 400 MHz) δ (ppm): 8.06 (s, 1H), 7.65 (br s, 1H), 7.04 (s, 1H), 6.82 (br s, 2H), 4.16-4.12 (m, 1H), 3.69-3.61 (m, 2H), 3.54-3.42 (m, 3H), 3.29-3.26 (m, 5H), 2.83-2.72 (m, 6H), 2.68-2.61 (m, 1H), 2.03-1.97 (m, 1H), 1.95-1.82 (m, 1H), 1.75-1.65 (m, 2H). | ++ | |

TABLE 24-continued

| 275 | 3-amino-N-[(3R)-7-[(3R,4R)-3-amino-4-(methoxymethyl)pyrrolidin-1-yl]-3,4-dihydro-2H-1-benzopyran-3-yl]-4,6-dimethylthieno[2,3-b]pyridine-2-carboxamide | 482 | (DMSO-d6, 400 MHz) δ (ppm): 7.52 (d, J = 7.6 Hz, 1H), 7.05 (s, 1H), 6.94-6.86 (m, 2H), 6.07 (d, J = 6.4 Hz, 1H), 5.87 (s, 1H), 4.27 (br s, 1H), 4.15-4.12 (m, 1H), 3.81-3.78 (m, 1H), 3.62-3.49 (m, 2H), 3.40-3.33 (m, 2H), 3.28 (s, 3H), 3.25-3.20 (m, 1H), 3.09-3.05 (m, 1H), 2.96-2.93 (m, 1H), 2.89-2.81 (m, 2H), 2.73 (s, 3H), 2.51 (s, 3H), 2.44-2.37 (m, 1H), 1.53 (br s, 2H). | ++++ | ++ |
|---|---|---|---|---|---|
| 276 | 3-amino-N-[(3R)-7-[(3S,4S)-3-amino-4-(methoxymethyl)pyrrolidin-1-yl]-3,4-dihydro-2H-1-benzopyran-3-yl]-4,6-dimethylthieno[2,3-b]pyridine-2-carboxamide | 482 | (DMSO-d6, 400 MHz) δ (ppm): 7.52 (d, J = 7.6 Hz, 1H), 7.07 (s, 1H), 6.86 (s, 3H), 6.07 (d, J = 6.8 Hz, 1H), 5.87 (s, 1H), 4.27 (br s, 1H), 4.15-4.12 (m, 1H), 3.81-3.76 (m, 1H), 3.60-3.50 (m, 2H), 3.40-3.33 (m, 2H), 3.28 (s, 3H), 3.25-3.21 (m, 1H), 3.09-3.04 (m, 1H), 2.98-2.93 (m, 1H), 2.89-2.77 (m, 2H), 2.73 (s, 3H), 2.51 (s, 3H), 2.46-2.42 (m, 1H), 1.54 (br s, 2H). | ++++ | +++ |
| 277 | 3-amino-N-[(3R)-7-[(3R,4R)-3-amino-4-(methoxymethyl)pyrrolidin-1-yl]-5,8-difluoro-3,4-dihydro-2H-1-benzopyran-3-yl]-4,6-dimethylthieno[2,3-b]pyridine-2-carboxamide | 518 | (DMSO-d6, 400 MHz) δ (ppm): 7.66 (br s, 1H), 7.04 (s, 1H), 6.87 (br s, 2H), 6.10-6.06 (m, 1H), 4.29-4.26 (m, 2H), 3.93-3.91 (m, 1H), 3.55-3.50 (m, 5H), 3.32-3.27 (m, 4H), 3.12-3.08 (m, 1H), 2.89-2.87 (m, 1H), 2.79-2.62 (m, 4H), 2.54-2.52 (m, 3H), 2.38-2.36 (m, 1H), 2.15-2.07 (m, 1H), 1.88-1.70 (m, 2H). | ++++ | ++ |
| 278 | 3-amino-N-[(3R)-7-[(3S,4S)-3-amino-4-(methoxymethyl)pyrrolidin-1-yl]-5,8-difluoro-3,4-dihydro-2H-1-benzopyran-3-yl]-4,6-dimethylthieno[2,3-b]pyridine-2-carboxamide | 518 | (DMSO-d6, 400 MHz) δ (ppm): 7.65 (br s, 1H), 7.04 (s, 1H), 6.87 (br s, 2H), 6.10-6.06 (m, 1H), 4.29-4.24 (m, 2H), 3.93-3.89 (m, 1H), 3.58-3.49 (m, 3H), 3.40-3.36 (m, 2H), 3.29-3.23 (m, 4H), 3.08-3.06 (m, 1H), 2.89-2.87 (m, 1H), 2.79-2.67 (m, 4H), 2.54-2.52 (m, 3H), 2.39-2.33 (m, 1H), 1.88-1.70 (m, 1H). | ++++ | +++ |
| 279 | 7-amino-N-[(6S)-2-[(3S,4S)-4-amino-3-methoxy-3-methylpyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.82 (br s, 1H), 7.18 (d, J = 8.0 Hz, 1H), 6.92 (br s, 2H), 6.19 (d, J = 8.4 Hz, 1H), 4.18-4.14 (m, 1H), 3.59-3.55 (m, 1H), 3.50-3.47 (m, 1H), 3.32-3.29 (m, 2H), 3.17 (s, 3H), 3.07-3.04 (m, 1H), 2.84-2.73 (m, 4H), 2.66 (s, 3H), 2.03-2.00 (m, 1H), 1.89-1.83 (m, 1H), 1.65 (br s, 2H), 1.23 (s, 3H). | ++ | + |
| 280 | 7-amino-N-[(6S)-2-[(3R,4R)-4-amino-3-methoxy-3-methylpyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.81 (br s, 1H), 7.18 (d, J = 8.4 Hz, 1H), 6.92 (br s, 2H), 6.19 (d, J = 8.4 Hz, 1H), 4.17-4.13 (m, 1H), 3.60-3.56 (m, 1H), 3.47-3.45 (m, 1H), 3.32-3.29 (m, 2H), 3.17 (s, 3H), 3.07-3.03 (m, 1H), 2.84-2.68 (m, 4H), 2.66 (s, 3H), 2.03-2.00 (m, 1H), 1.88-1.83 (m, 1H), 1.61 (br s, 2H), 1.23 (s, 3H). | ++ | + |
| 281 | 3-amino-N-[(3R)-7-[(3S,4S)-4-amino-3-methoxy-3-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.0 Hz, 1H), 7.48 (br s, 1H), 7.31 (d, J = 8.4 Hz, 1H), 7.21 (br s, 2H), 6.86 (d, J = 8.4 Hz, 1H), 6.06 (d, J = 8.4 Hz, 1H), 5.87 (s, 1H), 4.30-4.26 (m, 1H), 4.15-4.13 (m, 1H), 3.81-3.76 (m, | | ++ |

TABLE 24-continued

| # | Name | MS | NMR | Act1 | Act2 |
|---|---|---|---|---|---|
| | | | 1H), 3.47-3.43 (m, 1H), 3.32-3.24 (m, 2H), 3.17-3.15 (m, 4H), 2.89-2.78 (m, 3H), 2.59 (s, 3H), 1.63 (br s, 2H), 1.23 (s, 3H). | | |
| 282 | 3-amino-N-[(3R)-7-[(3R,4R)-4-amino-3-methoxy-3-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.0 Hz, 1H), 7.48 (br s, 1H), 7.31 (d, J = 8.0 Hz, 1H), 7.21 (br s, 2H), 6.86 (d, J = 8.4 Hz, 1H), 6.08-6.05 (m, 1H), 5.87 (s, 1H), 4.30-4.26 (m, 1H), 4.15-4.12 (m, 1H), 3.81-3.76 (m, 1H), 3.47-3.43 (m, 1H), 3.32-3.24 (m, 2H), 3.17-3.15 (m, 4H), 2.89-2.77 (m, 3H), 2.59 (s, 3H), 1.58 (br s, 2H), 1.23 (s, 3H). | ++ | ++ |
| 283 | 3-amino-N-[(3R)-7-[(2S,3R,4S)-4-amino-3-methoxy-2-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.49 (d, J = 7.6 Hz, 1H), 7.32 (d, J = 8.4 Hz, 1H), 7.21 (br s, 2H), 6.87 (d, J = 8.0 Hz, 1H), 6.14 (d, J = 8.4 Hz, 1H), 5.95 (s, 1H), 4.31-4.26 (m, 1H), 4.16-4.12 (m, 1H), 3.81-3.77 (m, 1H), 3.66-3.61 (m, 1H), 3.37-3.32 (m, 6H), 3.09-3.05 (m, 1H), 2.89-2.78 (m, 2H), 2.59 (s, 3H), 1.83 (br s, 2H), 1.29 (d, J = 8.0 Hz, 3H). | ++++ | +++ |
| 284 | 3-amino-N-[(3R)-7-[(2R,3S,4R)-4-amino-3-methoxy-2-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.0 Hz, 1H), 7.50 (d, J = 7.6 Hz, 1H), 7.32 (d, J = 8.0 Hz, 1H), 7.21 (br s, 2H), 6.87 (d, J = 8.4 Hz, 1H), 6.14 (d, J = 8.4 Hz, 1H), 5.95 (s, 1H), 4.30-4.26 (m, 1H), 4.16-4.13 (m, 1H), 3.82-3.77 (m, 1H), 3.66-3.61 (m, 1H), 3.42-3.32 (m, 6H), 3.09-3.06 (m, 1H), 2.90-2.78 (m, 2H), 2.59 (s, 3H), 1.88 (br s, 2H), 1.29 (d, J = 8.0 Hz, 3H). | ++++ | +++ |
| 285 | 3-amino-N-[(6S)-2-[(3S,4S)-3-amino-4-cyclobutoxypyrrolidin-1-yl]-5,6,7,8-tetrahydroquinolin-6-yl]-6-methylthieno[2,3-b]pyridine-2-carboxamide | 493 | (DMSO-d6, 400 MHz) δ (ppm): 8.31 (d, J = 8.4 Hz, 1H), 7.56 (br s, 1H), 7.31 (d, J = 8.0 Hz, 1H), 7.20-7.15 (m, 3H), 6.22 (d, J = 8.4 Hz, 1H), 4.14-4.03 (m, 2H), 3.72-3.69 (m, 1H), 3.62-3.58 (m, 1H), 3.50-3.46 (m, 1H), 3.30-3.28 (m, 2H), 3.11-3.09 (m, 1H), 2.81-2.68 (m, 4H), 2.58 (s, 3H), 2.23-2.16 (m, 2H), 2.02-1.99 (m, 1H), 1.90-1.82 (m, 3H), 1.65-1.55 (m, 1H), 1.51-1.41 (m, 1H). | +++ | + |
| 286 | 3-amino-N-[(3R)-7-[(3S,4S)-3-amino-4-methoxypyrrolidin-1-yl]-2H,3H,4H-pyrano[2,3-b]pyridin-3-yl]-4,6-dimethylthieno[2,3-b]pyridine-2-carboxamide | 469 | (DMSO-d6, 400 MHz) δ (ppm): 7.56 (d, J = 7.6 Hz, 1H), 7.25 (d, J = 8.0 Hz, 1H), 7.05 (s, 1H), 6.86 (br s, 2H), 6.02 (d, J = 8.4 Hz, 1H), 4.30-4.26 (m, 1H), 4.22-4.19 (m, 1H), 3.97-3.92 (m, 1H), 3.62-3.55 (m, 2H), 3.42-3.40 (m, 2H), 3.32 (s, 3H), 3.30-3.29 (m, 4H), 3.11-3.09 (m, 1H), 2.84-2.81 (m, 2H), 2.73 (s, 3H), 1.68 (br s, 2H). | +++ | + |
| 287 | 3-amino-N-[(3R)-7-[(3S,4S)-3-amino-4-(propan-2-yloxy)pyrrolidin-1-yl]-2H,3H,4H-pyrano[2,3-b]pyridin-3-yl]-6-methylthieno[2,3-b]pyridine-2-carboxamide | 483 | (DMSO-d6, 400 MHz) δ (ppm): 8.31 (d, J = 8.4 Hz, 1H), 7.56 (d, J = 8.0 Hz, 1H), 7.31 (d, J = 8.0 Hz, 1H), 7.20-7.15 (m, 3H), 6.22 (d, J = 8.4 Hz, 1H), 4.14-4.03 (m, 2H), 3.71-3.69 (m, 1H), 3.62-3.59 (m, 1H), 3.50-3.45 (m, 1H), 3.30-3.28 (m, 2H), 3.14-3.10 (m, 1H), 2.81-2.68 (m, 4H), | ++ | + |

TABLE 24-continued

| # | Name | MW | NMR | A | B |
|---|------|----|-----|---|---|
| 288 | 3-amino-N-[(3R)-7-[(3R)-3-aminopyrrolidin-1-yl]-3,4-dihydro-2H-1-benzopyran-3-yl]-6-methylthieno[2,3-b]pyridine-2-carboxamide | 424 | (DMSO-d6, 400 MHz) δ (ppm): 8.33 (d, J = 8.4 Hz, 1H), 7.48 (br s, 1H), 7.32 (d, J = 8.4 Hz, 1H), 7.21 (br s, 2H), 6.86 (d, J = 8.4 Hz, 1H), 6.10 (d, J = 8.0 Hz, 1H), 5.90 (s, 1H), 4.30-4.26 (m, 1H), 4.16-4.12 (m, 1H), 3.82-3.77 (m, 1H), 3.55-3.53 (m, 1H), 3.30-3.25 (m, 2H), 3.19-3.13 (m, 1H), 2.89-2.80 (m, 3H), 2.59 (s, 3H), 2.58 (s, 3H), 2.21-2.17 (m, 2H), 2.07-1.95(m, 1H), 1.90-1.82 (m, 4H), 1.68-1.60 (m, 1H), 1.51-1.44 (m, 1H), 2.10-1.90 (m, 2H), 1.72-1.64 (m, 2H). | ++++ | ++ |
| 289 | N-[(3R)-7-[(3aR,6aS)-3a-methoxy-octahydropyrrolo[2,3-c]pyrrol-5-yl]-3,4-dihydro-2H-1-benzopyran-3-yl]-3-amino-6-methylthieno[2,3-b]pyridine-2-carboxamide | 480 | (DMSO-d6, 400 MHz) δ (ppm): 8.33 (d, J = 8.0 Hz, 1H), 7.52 (br s, 1H), 7.32 (d, J = 8.4 Hz, 1H), 7.23 (br s, 2H), 6.89 (d, J = 8.4 Hz, 1H), 6.24-6.21 (m, 1H), 6.05 (s, 1H), 4.32-4.28 (m, 1H), 4.16-4.13 (m, 1H), 3.82-3.77 (m, 1H), 3.63-3.61 (m, 1H), 3.43-3.23 (m, 6H), 2.98-2.83 (m, 5H), 2.59 (s, 3H), 2.04-2.00 (m, 1H), 1.85-1.81 (m, 1H). | ++++ | |
| 290 | N-[(3R)-7-[(3aS,6aR)-3a-methoxy-octahydropyrrolo[2,3-c]pyrrol-5-yl]-3,4-dihydro-2H-1-benzopyran-3-yl]-3-amino-6-methylthieno[2,3-b]pyridine-2-carboxamide | 480 | (DMSO-d6, 400 MHz) δ (ppm): 8.33 (d, J = 8.0 Hz, 1H), 7.52 (br s, 1H), 7.32 (d, J = 8.4 Hz, 1H), 7.23 (br s, 2H), 6.89 (d, J = 8.4 Hz, 1H), 6.24-6.21 (m, 1H), 6.05 (s, 1H), 4.32-4.28 (m, 1H), 4.16-4.14 (m, 1H), 3.82-3.77 (m, 1H), 3.62-3.61 (m, 1H), 3.44-3.23 (m, 6H), 3.00-2.83 (m, 5H), 2.59 (s, 3H), 2.03-2.00 (m, 1H), 1.84-1.81 (m, 1H). | ++++ | |
| 291 | N-[(3R)-7-[(3aS,6aS)-3a-methoxy-octahydropyrrolo[3,4-c]pyrrol-2-yl]-3,4-dihydro-2H-1-benzopyran-3-yl]-3-amino-6-methylthieno[2,3-b]pyridine-2-carboxamide | 480 | (DMSO-d6, 400 MHz) δ (ppm): 8.32 (d, J = 8.0 Hz, 1H), 7.50 (d, J = 7.6 Hz, 1H), 7.31 (d, J = 8.0 Hz, 1H), 7.22 (s, 2H), 6.90 (d, J = 8.4 Hz, 1H), 6.27-6.25 (m, 1H), 6.07 (s, 1H), 4.29 (br s, 1H), 4.16-4.14 (m, 1H), 3.83-3.78 (m, 1H), 3.52-3.44 (m, 2H), 3.22-3.20 (m, 4H), 3.14-3.10 (m, 1H), 3.02-2.93 (m, 1H), 2.92-2.80 (m, 4H), 2.68-2.63 (m, 2H), 2.59 (s, 3H). | ++++ | ++ |
| 292 | N-[(3R)-7-[(3aR,6aR)-3a-methoxy-octahydropyrrolo[3,4-c]pyrrol-2-yl]-3,4-dihydro-2H-1-benzopyran-3-yl]-3-amino-6-methylthieno[2,3-b]pyridine-2-carboxamide | 480 | (DMSO-d6, 400 MHz) δ (ppm): 8.32 (d, J = 8.0 Hz, 1H), 7.50 (d, J = 7.6 Hz, 1H), 7.31 (d, J = 8.4 Hz, 1H), 7.22 (m, 2H), 6.90 (d, J = 8.4 Hz, 1H), 6.27-6.25 (m, 1H), 6.07 (s, 1H), 4.28 (m, 1H), 4.16-4.13 (m, 1H), 3.82-3.78 (m, 1H), 3.52-3.44 (m, 2H), 3.22-3.20 (m, 4H), 3.14-3.09 (m, 1H), 3.01-2.98 (m, 1H), 2.94-2.80 (s, 4H), 2.68-2.58 (m, 5H). | ++++ | ++ |
| 293 | 3-amino-N-[(6S)-2-[(3S,4S)-3-acetamido-4-methoxypyrrolidin-1-yl]-5,6,7,8-tetrahydroquinolin-6-yl]-4,6-dimethylthieno[2,3-b]pyridine-2-carboxamide | 509 | (DMSO-d6, 400 MHz) δ (ppm): 8.14 (d, J = 6.8 Hz, 1H), 7.60 (br s, 1H), 7.22 (d, J = 8.4 Hz, 1H), 7.04 (br s, 1H), 6.82 (br s, 2H), 6.28 (d, J = 8.4 Hz, 1H), 4.28-4.24 (m, 1H), 4.15-4.11 (m, 1H), 3.83-3.79 (m, 1H), 3.60-3.54 (m, 2H), 3.39-3.27 (m, 5H), 2.83-2.73 (m, 7H), 2.51 (s, 3H), 2.02-1.91 (m, 1H), 1.88-1.82 (m, 4H). | +++ | + |

TABLE 24-continued

| | | | | | |
|---|---|---|---|---|---|
| 294 | 3-amino-N-[(3R)-7-[(3R,4S)-3-amino-4-(difluoromethyl)pyrrolidin-1-yl]-3,4-dihydro-2H-1-benzopyran-3-yl]-6-methylthieno[2,3-b]pyridine-2-carboxamide | 474 | (DMSO-d6, 400 MHz) δ (ppm): 8.32 (d, J = 8.4 Hz, 1H), 7.49 (br s, 1H), 7.31 (d, J = 8.0 Hz, 1H), 7.21 (br s, 2H), 6.89 (d, J = 8.0 Hz, 1H), 6.20-6.13 (m, 2H), 5.94 (d, J = 2.4 Hz, 1H), 4.30-4.26 (m, 1H), 4.16-4.13 (m, 1H), 3.82-3.77 (m, 1H), 3.51-3.47 (m, 2H), 3.41-3.33 (m, 2H), 3.25-3.20 (m, 1H), 2.90-2.82 (m, 3H), 2.58 (s, 3H), 1.88 (br s, 2H). | ++++ | +++ |
| 295 | 3-amino-N-[(3R)-7-[(3S,4R)-3-amino-4-(difluoromethyl)pyrrolidin-1-yl]-3,4-dihydro-2H-1-benzopyran-3-yl]-6-methylthieno[2,3-b]pyridine-2-carboxamide | 474 | (DMSO-d6, 400 MHz) δ (ppm): 8.32 (d, J = 8.4 Hz, 1H), 7.49 (br s, 1H), 7.31 (d, J = 8.4 Hz, 1H), 7.21 (br s, 2H), 6.90 (d, J = 8.0 Hz, 1H), 6.20-6.04 (m, 2H), 5.94 (d, J = 2.0 Hz, 1H), 4.30-4.26 (m, 1H), 4.16-4.13 (m, 1H), 3.82-3.77 (m, 1H), 3.51-3.32 (m, 4H), 3.24-3.20 (m, 1H), 2.90-2.83 (m, 3H), 2.58 (s, 3H), 1.91 (br s, 2H). | ++++ | +++ |
| 296 | 3-amino-N-[(6S)-2-[(3R,4R)-3-amino-4-(methoxymethyl)pyrrolidin-1-yl]-5,6,7,8-tetrahydroquinolin-6-yl]-4,6-dimethylthieno[2,3-b]pyridine-2-carboxamide | 481 | (MeOH-d4, 400 MHz) δ (ppm): 7.25 (d, J = 8.4 Hz, 1H), 7.07 (s, 1H), 6.32 (d, J = 8.4 Hz, 1H), 4.29-4.24 (m, 1H), 3.69-3.55 (m, 5H), 3.43-3.34 (m, 5H), 2.97-2.92 (m, 3H), 2.81-2.61 (m, 5H), 2.59 (s, 3H), 2.18-2.15 (m, 1H), 1.99-1.90 (m, 1H). | +++ | + |
| 297 | 3-amino-N-[(6S)-2-[(3S,4S)-3-amino-4-(methoxymethyl)pyrrolidin-1-yl]-5,6,7,8-tetrahydroquinolin-6-yl]-4,6-dimethylthieno[2,3-b]pyridine-2-carboxamide | 481 | (MeOH-d4, 400 MHz) δ (ppm): 7.26 (d, J = 8.4 Hz, 1H), 7.07 (s, 1H), 6.32 (d, J = 8.8 Hz, 1H), 4.30-4.24 (m, 1H), 3.69-3.63 (m, 3H), 3.60-3.55 (m, 2H), 3.43-3.35 (m, 5H), 2.97-2.92 (m, 3H), 2.81-2.72 (m, 4H), 2.66-2.61 (m, 1H), 2.58 (s, 3H), 2.18-2.15 (m, 1H), 1.97-1.89 (m, 1H). | ++++ | ++ |
| 298 | 7-amino-N-[(6S)-2-[(3R,4R)-3-amino-4-(methoxymethyl)pyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.81 (br s, 1H), 7.18 (d, J = 8.8 Hz, 1H), 6.92 (br s, 2H), 6.20 (d, J = 8.4 Hz, 1H), 4.16-4.11 (m, 1H), 3.60-3.37 (m, 5H), 3.28 (s, 3H), 3.22-3.17 (m, 2H), 2.83-2.72 (m, 4H), 2.65 (s, 3H), 2.42-2.38 (m, 1H), 2.02-1.87 (m, 2H), 1.58 (br s, 2H). | ++ | + |
| 299 | 7-amino-N-[(6S)-2-[(3S,4S)-3-amino-4-(methoxymethyl)pyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.81 (br s, 1H), 7.18 (d, J = 8.4 Hz, 1H), 6.92 (br s, 2H), 6.20 (d, J = 8.4 Hz, 1H), 4.16-4.14 (m, 1H), 3.60-3.37 (m, 5H), 3.28 (s, 3H), 3.21-3.16 (m, 2H), 2.83-2.72 (m, 4H), 2.65 (s, 3H), 2.43-2.38 (m, 1H), 2.02-1.80 (m, 2H), 1.56 (br s, 2H). | +++ | ++ |
| 300 | 3-amino-N-[(6S)-2-[(3R,4R)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide | 485 | (MeOH-d4, 400 MHz) δ (ppm): 8.22 (d, J = 8.4 Hz, 1H), 7.32 (d, J = 8.4 Hz, 1H), 7.05 (d, J = 13.6 Hz, 1H), 4.29-4.24 (m, 1H), 3.86-3.64 (m, 7H), 3.42 (s, 3H), 2.98-2.87 (m, 3H), 2.80-2.67 (m, 2H), 2.66 (s, 3H), 2.20-2.14 (m, 1H), 1.98-1.90 (m, 1H). | ++ | + |
| 301 | 3-amino-N-[(6S)-2-[(3S,4S)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide | 485 | (DMSO-d6, 400 MHz) δ (ppm): 8.31 (d, J = 8.4 Hz, 1H), 7.58 (d, J = 7.6 Hz, 1H), 7.31 (d, J = 8.4 Hz, 1H), 7.16-7.10 (m, 3H), 4.15-4.13 (m, 1H), 3.67-3.52 (m, 4H), 3.42-3.36 (m, 3H), 3.28 (s, 3H), 2.84-2.73 (m, 4H), 2.59 (s, | + | + |

TABLE 24-continued

| | | | | | |
|---|---|---|---|---|---|
| 302 | 3-amino-N-[(6R)-2-[(3R,4R)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide | 485 | (DMSO-d6, 400 MHz) δ (ppm): 8.31 (d, J = 8.0 Hz, 1H), 7.57 (d, J = 7.6 Hz, 1H), 7.31 (d, J = 8.4 Hz, 1H), 7.16-7.10 (m, 3H), 4.15-4.12 (m, 1H), 3.65-3.52 (m, 4H), 3.41-3.35 (m, 3H), 3.28 (s, 3H), 2.83-2.73 (m, 4H), 2.59 (s, 3H), 2.40-2.33 (m. 1H), 2.03-1.72 (m, 4H). | +++ | ++ |
| 303 | 3-amino-N-[(6R)-2-[(3S,4S)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide | 485 | (DMSO-d6, 400 MHz) δ (ppm): 8.31 (d, J = 8.4 Hz, 1H), 7.57 (d, J = 7.6 Hz, 1H), 7.31 (d, J = 8.4 Hz, 1H), 7.16-7.10 (m, 3H), 4.15-4.12 (m, 1H), 3.66-3.54 (m, 4H), 3.42-3.35 (m, 3H), 3.28 (s, 3H), 2.83-2.72 (m, 4H), 2.59 (s, 3H), 2.40-2.34 (m. 1H), 2.00-1.84 (m, 4H). | ++ | + |
| 304 | N-[(3R)-7-[(3aS,6aS)-octahydropyrrolo[3,4-b]pyrrol-5-yl]-3,4-dihydro-2H-1-benzopyran-3-yl]-3-amino-6-methylthieno[2,3-b]pyridine-2-carboxamide | 450 | (DMSO-d6, 400 MHz) δ (ppm): 8.32 (d, J = 8.4 Hz, 1H), 7.49 (br s, 1H), 7.32 (d, J = 8.0 Hz, 1H), 7.21 (br s, 2H), 6.87 (d, J = 8.0 Hz, 1H), 6.20-6.18 (m, 1H), 6.00 (s, 1H), 4.30-4.25 (m, 1H), 4.15-4.13 (m, 1H), 3.81-3.76 (m, 2H), 3.28-3.26 (m, 2H), 3.01-2.93 (m, 2H), 2.86-2.79 (m, 5H), 2.59 (s, 3H), 1.85-1.80 (m, 1H), 1.58-1.56 (m, 1H). | ++++ | ++ |
| 305 | N-[(3R)-7-[(3aR,6aR)-octahydropyrrolo[3,4-b]pyrrol-5-yl]-3,4-dihydro-2H-1-benzopyran-3-yl]-3-amino-6-methylthieno[2,3-b]pyridine-2-carboxamide | 450 | (DMSO-d6, 400 MHz) δ (ppm): 8.33 (d, J = 8.0 Hz, 1H), 7.50 (br s, 1H), 7.32 (d, J = 8.0 Hz, 1H), 7.22 (br s, 2H), 6.87 (d, J = 8.4 Hz, 1H), 6.19 (d, J = 6.8 Hz, 1H), 6.00 (s, 1H), 4.29-4.25 (m, 1H), 4.15-4.13 (m, 1H), 3.83-3.76 (m, 2H), 3.29-3.26 (m, 2H), 3.02-2.93 (m, 2H), 2.86-2.79 (m, 5H), 2.59 (s, 3H), 1.86-1.80 (m, 1H), 1.59-1.56 (m, 1H). | ++++ | +++ |
| 306 | 3-amino-N-[(3R)-7-{2,6-diazaspiro[3.4]octan-6-yl}-3,4-dihydro-2H-1-benzopyran-3-yl]-6-methylthieno[2,3-b]pyridine-2-carboxamide | 450 | (DMSO-d6, 400 MHz) δ (ppm): 8.32 (d, J = 8.4 Hz, 1H), 7.48 (br s, 1H), 7.31 (d, J = 8.4 Hz, 1H), 7.21 (br s, 2H), 6.87 (d, J = 8.0 Hz, 1H), 6.13-6.10 (m, 1H), 5.93 (s, 1H), 4.32-4.23 (m, 1H), 4.15-4.12 (m, 1H), 3.81-3.76 (m, 2H), 3.48-3.38 (m, 3H), 3.31-3.27 (m, 2H), 3.19-3.13 (m, 2H), 2.89-2.78 (m, 2H), 2.58 (s, 3H), 2.12-2.08 (s, 2H). | ++++ | ++ |
| 307 | 3-amino-N-[(3R)-7-[(5S,9S)-9-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.0 Hz, 1H), 7.48 (d, J = 7.6 Hz, 1H), 7.32 (d, J = 8.4 Hz, 1H), 7.21 (s, 2H), 6.86 (d, J = 8.4 Hz, 1H), 6.07 (d, J = 1.6 Hz, 1H), 5.86 (s, 1H), 4.27-4.25 (m, 1H), 4.15-4.13 (m, 1H), 3.81-3.72 (m, 3H), 3.43-3.40 (m, 1H), 3.19 (s, 1H), 3.09 (d, J = 9.6 Hz, 1H), 2.94 (d, J = 2.0 Hz, 1H), 2.92-2.79 (m, 2H), 2.59 (s, 3H), 2.22-2.15 (m, 1H), 1.92-1.85 (m, 2H), 1.70-1.63 (m, 3H). | ++++ | ++ |
| 308 | 3-amino-N-[(3R)-7-[(5R,9R)-9-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.0 Hz, 1H), 7.48 (d, J = 7.6 Hz, 1H), 7.32 (d, J = 8.4 Hz, 1H), 7.21 (s, 2H), 6.86 (d, J = 8.0 Hz, 1H), 6.07 (d, J = 1.6 Hz, 1H), 5.86 (s, 1H), 4.27-4.25 (m, 1H), 4.15-4.12 (m, 1H), 3.81-3.72 (m, | +++ | ++ |

TABLE 24-continued

| | | | | | |
|---|---|---|---|---|---|
| | | | 3H), 3.43-3.40 (m, 1H), 3.19 (s, 1H), 3.09 (d, J = 9.6 Hz, 1H), 2.94 (d, J = 2.8 Hz, 1H), 2.92-2.79 (m, 2H), 2.59 (s, 3H), 2.22-2.15 (m, 1H), 1.92-1.85 (m, 2H), 1.70-1.63 (m, 3H). | | |
| 309 | 3-amino-N-[(3R)-7-[(5S,9R)-9-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.4 Hz, 1H), 7.48 (d, J = 7.6 Hz, 1H), 7.32 (d, J = 8.0 Hz, 1H), 7.21 (s, 2H), 6.86 (d, J = 8.4 Hz, 1H), 6.06-6.04 (m, 1H), 5.85 (d, J = 1.6 Hz, 1H), 4.27-4.25 (m, 1H), 4.15-4.12 (m, 1H), 3.84-3.76 (m, 3H), 3.39-3.32 (m, 1H), 3.27-3.18 (m, 3H), 2.82-2.77 (m, 3H), 2.59 (s, 3H), 1.98-1.89 (m, 4H), 2.56 (br,s, 2H). | ++++ | +++ |
| 310 | 3-amino-N-[(3R)-7-[(5R,9S)-9-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.4 Hz, 1H), 7.48 (d, J = 7.6 Hz, 1H), 7.32 (d, J = 8.4 Hz, 1H), 7.21 (s, 2H), 6.86 (d, J = 8.4 Hz, 1H), 6.06-6.03(m, 1H), 5.85 (s, 1H), 4.29-4.27 (m, 1H), 4.15-4.12 (m, 1H), 3.85-3.76 (m, 3H), 3.39-3.32 (m, 1H), 3.28-3.17 (m, 3H), 2.85-2.77 (m, 3H), 2.59 (s, 3H), 1.98-1.89 (m, 4H), 2.56 (br,s, 1H). | ++++ | ++ |
| 311 | 3-amino-N-[(6S)-2-[(3S,4S)-3-methoxy-4-(methylamino)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.4 Hz, 1H), 7.56 (br s, 1H), 7.31 (d, J = 8.0 Hz, 1H), 7.20-7.13 (m, 3H), 6.24 (d, J = 7.6 Hz, 1H), 4.15-4.12 (m, 1H), 3.79-3.75 (m, 1H), 3.55-3.22 (m, 7H), 3.15-3.13 (m, 1H), 2.82-2.68 (m, 4H), 2.59 (s, 3H), 2.33 (s, 3H), 2.01-1.90 (m, 1H), 1.87-1.82 (m, 1H). | +++ | + |
| 312 | 3-amino-N-[(6S)-2-[(3S,4S)-3-methoxy-4-(methylamino)pyrrolidin-1-yl]-5,6,7,8-tetrahydroquinolin-6-yl]-4,6-dimethylthieno[2,3-b]pyridine-2-carboxamide | 481 | (CDCl3, 400 MHz) δ (ppm): 7.18 (d, J = 8.4 Hz, 1H), 6.90 (s, 1H), 6.36 (br s, 2H), 6.23 (d, J = 8.4 Hz, 1H), 5.48 (d, J = 7.2 Hz, 1H), 4.44-4.39 (m, 1H), 3.88-3.74 (m, 3H), 3.51-3.45 (m, 1H), 3.44 (s, 3H), 3.37-3.30 (m, 2H), 3.12-3.07 (m, 1H), 2.98-2.93 (m, 2H), 2.77 (s, 3H), 2.70-2.63 (m, 1H), 2.61 (s, 3H), 2.55 (s, 3H), 2.25-2.23 (m, 1H), 1.94-1.90 (m, 1H). | +++ | + |
| 313 | 3-amino-N-[(3R)-7-[(3R,4R)-3-amino-4-(ethoxymethyl)pyrrolidin-1-yl]-3,4-dihydro-2H-1-benzopyran-3-yl]-6-methylthieno[2,3-b]pyridine-2-carboxamide | 482 | (DMSO-d6, 400 MHz) δ (ppm): 8.32 (d, J = 8.4 Hz, 1H), 7.48 (br s, 1H), 7.31 (d, J = 8.4 Hz, 1H), 7.21 (br s, 2H), 6.86 (d, J = 8.4 Hz, 1H), 6.08 (d, J = 8.4 Hz, 1H), 5.88 (s, 1H), 4.30-4.26 (m, 1H), 4.15-4.13 (m, 1H), 3.81-3.76 (m, 1H), 3.64-3.55 (m, 1H), 3.52-3.50 (m, 1H), 3.46-3.35 (m, 4H), 3.25-3.21 (m, 1H), 3.09-3.05 (m, 1H), 2.96-2.93 (m, 1H), 2.89-2.77 (m, 2H), 2.59 (s, 3H), 2.45-2.38 (m, 1H), 1.60 (br s, 2H), 1.15-1.11 (m, 3H). | ++++ | ++ |
| 314 | 3-amino-N-[(3R)-7-[(3S,4S)-3-amino-4-(ethoxymethyl)pyrrolidin-1-yl]-3,4-dihydro-2H-1-benzopyran-3-yl]-6-methylthieno[2,3-b]pyridine-2-carboxamide | 482 | (DMSO-d6, 400 MHz) δ (ppm): 8.32 (d, J = 8.4 Hz, 1H), 7.48 (br s, 1H), 7.31 (d, J = 8.4 Hz, 1H), 7.21 (br s, 2H), 6.86 (d, J = 8.4 Hz, 1H), 6.08 (d, J = 8.8 Hz, 1H), 5.88 (s, 1H), 4.30-4.26 (m, 1H), 4.15-4.13 (m, 1H), 3.82-3.77 (m, 1H), 3.64-3.55 (m, 2H), 3.47- | ++++ | +++ |

TABLE 24-continued

| | | | |  | |
|---|---|---|---|---|---|
| | | | 3.35 (m, 4H), 3.25-3.21 (m, 1H), 3.09-3.05 (m, 1H), 2.96-2.94 (m, 1H), 2.89-2.79 (m, 2H), 2.59 (s, 3H), 2.44-2.39 (m, 1H), 1.79 (br s, 2H), 1.15-1.11 (m, 3H). | | |
| 315 | 3-amino-N-[(6S)-2-[(3S,4S)-3-amino-4-methoxypiperidin-1-yl]-5,6,7,8-tetrahydroquinolin-6-yl]-6-methylthieno[2,3-b]pyridine-2-carboxamide | 467 | (CDCl3, 400 MHz) δ (ppm): 7.82 (d, J = 8.4 Hz, 1H), 7.20 (d, J = 8.4 Hz, 2H), 6.53 (d, J = 8.8 Hz, 1H), 6.05 (br s, 2H), 5.52 (d, J = 7.6 Hz, 1H), 4.46-4.42 (m, 1H), 4.31-4.23 (m, 2H), 3.49 (s, 3H), 3.13-3.08 (m, 2H), 2.98-2.89 (m, 4H), 2.77-2.61 (m, 5H), 2.26-2.14 (m, 2H), 1.97-1.85 (m, 1H), 1.84 (br s, 2H), 1.55-1.46 (m, 1H). | +++ | ++ |
| 316 | 3-amino-N-[(6S)-2-[(3R,4R)-3-amino-4-methoxypiperidin-1-yl]-5,6,7,8-tetrahydroquinolin-6-yl]-6-methylthieno[2,3-b]pyridine-2-carboxamide | 467 | (CDCl3, 400 MHz) δ (ppm): 7.82 (d, J = 8.4 Hz, 1H), 7.20 (d, J = 8.4 Hz, 2H), 6.53 (d, J = 8.4 Hz, 1H), 6.06 (br s, 2H), 5.52 (d, J = 7.6 Hz, 1H), 4.46-4.41 (m, 1H), 4.31-4.23 (m, 2H), 3.45 (s, 3H), 3.13-3.04 (m, 2H), 2.99-2.89 (m, 4H), 2.74-2.64 (m, 5H), 2.23-2.15 (m, 2H), 1.98-1.89 (m, 1H), 1.69 (br s, 2H), 1.54-1.46 (m, 1H). | +++ | + |
| 317 | 3-amino-N-[(3R)-7-[(3S,4S)-3-amino-4-methoxypiperidin-1-yl]-3,4-dihydro-2H-1-benzopyran-3-yl]-4,6-dimethylthieno[2,3-b]pyridine-2-carboxamide | 482 | (CDCl3, 400 MHz) δ (ppm): 6.95 (d, J = 8.4 Hz, 1H), 6.88 (s, 1H), 6.56 (d, J = 8.4 Hz, 1H), 6.45 (s, 1H), 6.34 (br s, 2H), 5.69 (d, J = 7.6 Hz, 1H), 4.62-4.58 (m, 1H), 4.23-4.15 (m, 2H), 3.67-3.60 (m, 2H), 3.44 (s, 3H), 3.15-3.09 (m, 1H), 3.03-2.91 (m, 2H), 2.83-2.78 (m, 2H), 2.76 (s, 3H), 2.63-2.43 (m, 4H), 2.18-2.14 (m, 1H). | ++++ | ++ |
| 318 | 3-amino-N-[(3R)-7-[(3R,4R)-3-amino-4-methoxypiperidin-1-yl]-3,4-dihydro-2H-1-benzopyran-3-yl]-4,6-dimethylthieno[2,3-b]pyridine-2-carboxamide | 482 | (CDCl3, 400 MHz) δ (ppm): 6.95 (d, J = 8.4 Hz, 1H), 6.88 (s, 1H), 6.56 (d, J = 8.4 Hz, 1H), 6.45 (s, 1H), 6.34 (br s, 2H), 5.71-5.69 (m, 1H), 4.62-4.58 (m, 1H), 4.23-4.15 (m, 2H), 3.68-3.59 (m, 2H), 3.44 (s, 3H), 3.15-3.09 (m, 1H), 3.03-2.96 (m, 2H), 2.83-2.78 (m, 2H), 2.75 (s, 3H), 2.65-2.61 (m, 1H), 2.59 (s, 3H), 2.18-2.14 (m, 1H), 1.61-1.58 (m, 1H). | ++++ | ++ |
| 319 | 7-amino-N-[(2S)-6-[(3S,4S)-3-amino-4-(propan-2-yloxy)pyrrolidin-1-yl]-1,2,3,4-tetrahydronaphthalen-2-yl]-3-methylthieno[2,3-b]pyrazine-6-carboxamide | 481 | (DMSO-d6, 400 MHz) δ (ppm): 8.65 (s, 1H), 7.78 (br s, 1H), 6.91 (br s, 2H), 6.87 (d, J = 8.4 Hz, 1H), 6.31 (d, J = 8.4 Hz, 1H), 6.22 (s, 1H), 4.13-4.09 (m, 1H), 3.81-3.80 (m, 1H), 3.77-3.70 (m, 1H), 3.56-3.52 (m, 1H), 3.40-3.32 (m, 2H), 3.03-3.01 (m, 1H), 2.90-2.69 (m, 5H), 2.65 (s, 3H), 2.04-1.73 (m, 4H), 1.13-1.11 (m, 6H). | +++ | + |
| 320 | 3-amino-N-[(6S)-2-[(3S,4S)-3-amino-4-(propan-2-yloxy)pyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.56 (br s, 1H), 7.31 (d, J = 8.0 Hz, 1H), 7.19-7.15 (m, 3H), 6.22 (d, J = 8.4 Hz, 1H), 4.16-4.11 (m, 1H), 3.79-3.63 (m, 3H), 3.51-3.47 (m, 1H), 3.34-3.32 (m, 1H), 3.22-3.19 (m, 1H), 3.11-3.08 (m, 1H), 2.82-2.68 (m, 4H), 2.59 (s, 3H), 2.01-1.99 (m, 1H), 1.90-1.75 (m, 3H), 1.13-1.07 (m, 6H) | +++ | + |

| | | | | | |
|---|---|---|---|---|---|
| 321 | 3-amino-N-[(6S)-2-[(3S,4R)-3-amino-4-(propan-2-yloxy)pyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.0 Hz, 1H), 7.56 (br s, 1H), 7.31 (d, J = 8.0 Hz, 1H), 7.19-7.15 (m, 3H), 6.20 (d, J = 8.4 Hz, 1H), 4.13-4.12 (m, 1H), 3.95-3.92 (m, 1H), 3.75-3.70 (m, 1H), 3.50-3.42 (m, 3H), 3.36-3.30 (m, 1H), 3.01-2.98 (m, 1H), 2.78-2.68 (m, 4 H), 2.59 (s, 3H), 2.01-1.98 (m, 1H), 1.88-1.80 (m, 1 H), 1.65 (br s, 2H), 1.16-1.11 (m, 6 H). | ++ | + |
| 322 | 3-amino-N-[(6S)-2-[(3R,4S)-3-amino-4-(propan-2-yloxy)pyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.0 Hz, 1H), 7.56 (d, J = 7.6 Hz, 1H), 7.31 (d, J = 8.0 Hz, 1H), 7.19-7.15 (m, 3H), 6.20 (d, J = 8.4 Hz, 1H), 4.12 (br s, 1H), 3.94-3.93 (m, 1H), 3.76-3.70 (m, 1H), 3.50-3.42 (m, 3H), 3.37-3.30 (m, 1H), 3.00-2.96 (m, 1H), 2.82-2.68 (m, 4 H), 2.59 (s, 3H), 2.01-1.98 (m, 1H), 1.89-1.84 (m, 1 H), 1.65 (br s, 2H), 1.18-1.12 (m, 6 H). | ++ | + |
| 323 | 3-amino-N-[(3R)-7-[(3S,4R)-3-amino-4-ethoxypyrrolidin-1-yl]-3,4-dihydro-2H-1-benzopyran-3-yl]-4,6-dimethylthieno[2,3-b]pyridine-2-carboxamide | 482 | (DMSO-d6, 400 MHz) δ (ppm): 7.52 (br s, 1H), 7.05 (s, 1H), 6.88-6.82 (m, 3H), 6.09-6.06 (m, 1H), 5.89 (s, 1H), 4.30-4.27 (m, 1H), 4.15-4.12 (m, 1H), 3.86-3.76 (m, 2H), 3.60-3.47 (m, 3H), 3.36-3.30 (m, 5H), 3.23-3.19 (m, 1H), 2.89-2.79 (m, 3H), 2.73 (s, 3H), 1.82 (br s, 2H), 1.17-1.13 (m, 3 H). | ++++ | +++ |
| 324 | 3-amino-N-[(3R)-7-[(3R,4S)-3-amino-4-ethoxypyrrolidin-1-yl]-3,4-dihydro-2H-1-benzopyran-3-yl]-4,6-dimethylthieno[2,3-b]pyridine-2-carboxamide | 482 | (DMSO-d6, 400 MHz) δ (ppm): 7.51 (br s, 1H), 7.05 (s, 1H), 6,88-6.82 (m, 3H), 6.08-6.06 (m, 1H), 5.89 (s, 1H), 4.30-4.26 (m, 1H), 4.15-4.12 (m, 1H), 3.85-3.77 (m, 2H), 3.62-3.45 (m, 3H), 3.36-3.32 (m, 5H), 3.23-3.19 (m, 1H), 2.89-2.78 (m, 3H), 2.73 (s, 3H), 162 (br s, 2H), 1.17-1.13 (m, 3 H). | +++ | ++ |
| 325 | 3-amino-N-[(3R)-7-[(3S,4S)-4-amino-3-methoxy-3-methylpyrrolidin-1-yl]-2H,3H,4H-pyrano[2,3-b]pyridin-3-yl]-6-methylthieno[2,3-b]pyridine-2-carboxamide | 469 | (DMSO-d6, 400 MHz) δ (ppm): 8.33 (d, J = 8.4 Hz, 1H), 7.54 (d, J = 7.2 Hz, 1H), 7.32 (d, J = 8.4 Hz, 1H), 7.25-7.20 (m, 3H), 5.99 (d, J = 8.0 Hz, 1H), 4.27-4.22 (m, 1H), 4.21-4.19 (m, 1H), 3.94 (t, J = 10 Hz, 1H), 3.55-3.51 (m, 1H), 3.44-3.41 (m, 1H), 3.31-3.25 (m, 2H), 3.16 (s, 3H), 3.04-3.01 (m, 1H), 2.87-2.80 (m, 2H), 2.59 (s, 3H), 1.66 (br s, 2H), 1.23 (s, 3H). | +++ | + |
| 326 | 3-amino-N-[(3R)-7-[(3R,4R)-4-amino-3-methoxy-3-methylpyrrolidin-1-yl]-2H,3H,4H-pyrano[2,3-b]pyridin-3-yl]-6-methylthieno[2,3-b]pyridine-2-carboxamide | 469 | (DMSO-d6, 400 MHz) δ (ppm): 8.33 (d, J = 8.4 Hz, 1H), 7.54 (d, J = 7.6 Hz, 1H), 7.32 (d, J = 8.4 Hz, 1H), 7.25-7.22 (m, 3H), 5.99 (d, J = 8.4 Hz, 1H), 4.27-4.22 (m, 1H), 4.21-4.19 (m, 1H), 3.94 (t, J = 10 Hz, 1H), 3.55-3.51 (m, 1H), 3.44-3.41 (m, 1H), 3.31-3.25 (m, 2H), 3.16 (s, 3H), 3.04-3.01 (m, 1H), 2.87-2.80 (m, 2H), 2.59 (s, 3H), 1.66 (br s, 2H), 1.23 (s, 3H). | +++ | + |

TABLE 24-continued

| | | | | | |
|---|---|---|---|---|---|
| 327 | 3-amino-N-[(6S)-2-[(3R,4S)-3-amino-4-(methoxymethyl)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.28 (d, J = 8.0 Hz, 1H), 7.56 (br s, 1H), 7.31 (d, J = 8.4 Hz, 1H), 7.19-7.16 (m, 3H), 6.21 (d, J = 8.4 Hz, 1H), 4.16-4.10 (m, 1H), 3.63-3.55 (m, 2H), 3.52-3.48 (m, 1H), 3.32 (s, 3H), 3.27-3.17 (m, 1H), 3.15-3.08 (m, 1H), 2.99-2.95 (m, 1H), 2.80-2.67 (m, 5H), 2.58 (s, 3H), 2.17-2.12 (m, 1H), 2.00-1.98 (m, 1H), 1.87-1.82 (m, 1H). | +++ | ++ |
| 328 | 3-amino-N-[(6S)-2-[(3S,4R)-3-amino-4-(methoxymethyl)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.30 (d, J = 8.4 Hz, 1H), 7.55 (br s, 1H), 7.31 (d, J = 8.4 Hz, 1H), 7.19-7.15 (m, 3H), 6.21 (d, J = 8.4 Hz, 1H), 4.13-4.10 (m, 1H), 3.64-3.57 (m, 2H), 3.51-3.45 (m, 1H), 3.34-3.23 (m, 1H), 3.21 (s, 3H), 3.20-3.12 (m, 1H), 3.10-3.08 (m, 1H), 2.99-2.97 (m, 1H), 2.81-2.67 (m, 4H), 2.58 (s, 3H), 2.20-2.15 (m, 1H), 2.01-1.89 (m, 1H), 1.86-1.79 (m, 1H). | ++ | + |
| 329 | N-[(6S)-2-[(4aS,7aS)-4,4-difluoro-octahydro-1H-pyrrolo[3,4-b]pyridin-6-yl]-5,6,7,8-tetrahydroquinolin-6-yl]-3-amino-6-methylthieno[2,3-b]pyridine-2-carboxamide | 499 | (DMSO-d6, 400 MHz) δ (ppm): 8.31 (d, J = 8.4 Hz, 1H), 7.57 (br s, 1H), 7.31 (d, J = 8.4 Hz, 1H), 7.22-7.16 (m, 3H), 6.25 (d, J = 8.4 Hz, 1H), 4.17-4.13 (m, 1H), 3.58-3.33 (m, 5H), 2.98-2.94 (m, 1H), 2.82-2.65 (m, 6H), 2.59 (s, 3H), 2.08-1.85 (m, 4 H). | +++ | ++ |
| 330 | N-[(6S)-2-[(4aR,7aR)-4,4-difluoro-octahydro-1H-pyrrolo[3,4-b]pyridin-6-yl]-5,6,7,8-tetrahydroquinolin-6-yl]-3-amino-6-methylthieno[2,3-b]pyridine-2-carboxamide | 499 | (DMSO-d6, 400 MHz) δ (ppm): 8.31 (d, J = 8.4 Hz, 1H), 7.57 (br s, 1H), 7.31 (d, J = 8.4 Hz, 1H), 7.22-7.16 (m, 2H), 6.25 (d, J = 8.4 Hz, 1H), 4.17-4.13 (m, 1H), 3.58-3.33 (m, 5H), 2.98-2.94 (m, 1H), 2.82-2.65 (m, 6H), 2.59 (s, 3H), 2.08-1.85 (m, 4 H). | +++ | + |
| 331 | 3-amino-N-[(6S)-2-[(3R,4S)-3-hydroxy-3-methyl-4-(methylamino)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.4 Hz, 1H), 7.56 (br s, 1H), 7.31 (d, J = 8.4 Hz, 1H), 7.18-7.16 (m, 3H), 6.18 (d, J = 8.4 Hz, 1H), 4.82-4.78 (m, 1H), 4.14-4.11 (m, 1H), 3.60-3.53 (m, 1H), 3.29-3.24 (m, 2H), 3.17-3.13 (m, 1H), 2.90-2.87 (m, 1H), 2.81-2.68 (m, 4H), 2.59 (s, 3H), 2.33 (s, 3H), 2.01-1.97 (m, 1H), 1.90-1.81 (m, 1H), 1.68 (br s, 1H), 1.21 (s, 3H). | +++ | + |
| 332 | 3-amino-N-[(6S)-2-[(3S,4R)-3-hydroxy-3-methyl-4-(methylamino)pyrrolidin-1-yi]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.4 Hz, 1H), 7.56 (br s, 1H), 7.31 (d, J = 8.4 Hz, 1H), 7.18-7.16 (m, 3H), 6.18 (d, J = 8.8 Hz, 1H), 4.82-4.78 (m, 1H), 4.13-4.12 (m, 1H), 3.61-3.57 (m, 1H), 3.30-3.23 (m, 2H), 3.15-3.12 (m, 1H), 2.90-2.87 (m, 1H), 2.81-2.67 (m, 4H), 2.59 (s, 3H), 2.34 (s, 3H), 2.01-1.98 (m, 1H), 1.89-1.81 (m, 1H), 1.70 (br s, 1H), 1.21 (s, 3H). | +++ | + |
| 333 | 3-amino-N-[(3R)-7-[(2S,3S,4S)-3-amino-4-methoxy-2-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.48 (br s, 1H), 7.31 (d, J = 8.4 Hz, 1H), 7.21 (br s, 2H), 6.87 (d, J = 8.4 Hz, 1H), 6.13 (d, J = 8.4 Hz, 1H), 5.93 (s, 1H), 4.33-4.24 (m, 1H), 4.16-4.13 (m, 1H), 3.82-3.77 (m, 1H), 3.59-3.57 (m, 1H), 3.47- | ++++ | +++ |

TABLE 24-continued

| | | | | | |
|---|---|---|---|---|---|
| | | | 3.28 (m, 5H), 3.17-3.16 (m, 1H), 2.89-2.78 (m, 2H), 2.59 (s, 3H), 2.08 (br s, 2H), 1.20-1.18 (m, 3H). | | |
| 334 | 3-amino-N-[(3R)-7-[(2S,3S,4R)-4-amino-3-methoxy-2-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.4 Hz, 1H), 7.49 (br s, 1H), 7.31 (d, J = 8.4 Hz, 1H), 7.21 (s, 2H), 6.87 (d, J = 8.8 Hz, 1H), 6.12 (d, J = 6.8 Hz, 1H), 5.93 (s, 1H), 4.30-4.26 (m, 1H), 4.15-4.13 (m, 1H), 4.04-3.97 (m, 1H), 3.82-3.77 (m, 1H), 3.46-3.30 (m, 6H), 2.90-2.68 (m, 3H), 2.59 (s, 3H), 1.79 (br s, 2H), 0.99-0.96 (m, 3H). | ++++ | ++++ |
| 335 | 3-amino-N-[(3R)-7-[(2R,3R,4R)-3-amino-4-methoxy-2-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.33 (d, J = 8.0 Hz, 1H), 7.50 (br s, 1H), 7.32 (d, J = 8.0 Hz, 1H), 7.21 (s, 2H), 6.87 (d, J = 8.4 Hz, 1H), 6.12 (d, J = 7.6 Hz, 1H), 5.93 (s, 1H), 4.30-4.26 (m, 1H), 4.15-4.13 (m, 1H), 3.82-3.77 (m, 1H), 3.58-3.56 (m, 1H), 3.47-3.31 (m, 6H), 3.17-3.15 (m, 1H), 2.90-2.77 (m, 2H), 2.59 (s, 3H), 1.71 (brs, 2H), 1.18 (d, J = 6.4 Hz, 3H). | ++++ | ++ |
| 336 | 3-amino-N-[(3R)-7-[(2R,3R,4S)-4-amino-3-methoxy-2-methylpyrrolidin-1-yl]-3,4-dihydro-2H-1-benzopyran-3-yl]-6-methylthieno[2,3-b]pyridine-2-carboxamide | 468 | (DMSO-d6, 400 MHz) δ (ppm): 8.32 (d, J = 8.0 Hz, 1H), 7.50 (br s, 1H), 7.31 (d, J = 8.4 Hz, 1H), 7.22 (s, 2H), 6.87 (d, J = 8.4 Hz, 1H), 6.15-6.12 (m, 1H), 5.92 (s, 1H), 4.30-4.26 (m, 1H), 4.15-4.12 (m, 1H), 4.04-4.00 (m, 1H), 3.81-3.76 (m, 1H), 3.42-3.35 (m, 6H), 2.85-2.72 (m, 3H), 2.59 (s, 3H), 0.99-0.96 (m, 3H). | ++++ | ++ |
| 337 | 3-amino-N-[(3R)-7-[(8R)-8-amino-5-oxa-2-azaspiro[3.4]octan-2-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.52 (d, J = 7.2 Hz, 1H), 7.32 (d, J = 8.0 Hz, 1H), 7.22 (s, 2H), 6.89 (d, J = 8.0 Hz, 1H), 6.03 (d, J = 8.0 Hz, 1H), 5.86 (s, 1H), 4.30-4.26 (m, 1H), 4.16-4.09 (m, 2H), 3.87-3.69 (m, 4H), 3.53-3.48 (m, 2H), 3.32-3.30 (m, 1H), 2.90-2.79 (m, 2H), 2.58 (s, 3H), 2.10-2.01 (m, 1H), 1.89-1.80 (m, 2H), 1.66-1.60 (m, 1H). | ++++ | ++ |
| 338 | 3-amino-N-[(3R)-7-[(8S)-8-amino-5-oxa-2-azaspiro[3.4]octan-2-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.52 (d, J = 7.2 Hz, 1H), 7.32 (d, J = 8.0 Hz, 1H), 7.22 (s, 2H), 6.89 (d, J = 8.0 Hz, 1H), 6.03 (d, J = 8.0 Hz, 1H), 5.86 (s, 1H), 4.30-4.26 (m, 1H), 4.16-4.09 (m, 2H), 3.87-3.69 (m, 4H), 3.53-3.48 (m, 2H), 3.32-3.30 (m, 1H), 2.90-2.79 (m, 2H), 2.58 (s, 3H), 2.10-2.01 (m, 1H), 1.89-1.80 (m, 2H), 1.66-1.60 (m, 1H). | +++ | ++ |
| 339 | 3-amino-N-[(3R)-7-[(4R,8R)-8-amino-1-oxa-6-azaspiro[3.4]octan-6-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.51 (d, J = 7.6 Hz, 1H), 7.32 (d, J = 8.4 Hz, 1H), 7.23 (s, 2H), 6.87 (d, J = 8.4 Hz, 1H), 6.07 (d, J = 8.4 Hz, 1H), 5.87 (s, 1H), 4.44-4.34 (m, 2H), 4.29-4.25 (m, 1H), 4.15-4.12 (m, 1H), 3.80-3.75 (m, | ++++ | ++ |

TABLE 24-continued

| | | | | | |
|---|---|---|---|---|---|
| 340 | 3-amino-N-[(3R)-7-[(4S,8S)-8-amino-1-oxa-6-azaspiro[3.4]octan-6-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.51 (br s, 1H), 7.32 (d, J = 8.0 Hz, 1H), 7.22 (s, 2H), 6.87 (d, J = 7.6 Hz, 1H), 6.07 (d, J = 8.4 Hz, 1H), 5.87 (s, 1H), 4.42-4.36 (m, 2H), 4.27-4.25 (m, 1H), 4.15-4.12 (m, 1H), 3.81-3.76 (m, 1H), 3.59-3.57 (m, 1H), 3.40-3.38 (m, 1H), 3.24-3.20 (m, 1H), 2.89-2.81 (m, 2H), 2.74-2.67 (m, 2H), 2.63-2.56 (m, 5H), 2.12 (br s, 2H). [The preceding entry begins: 1H), 3.59-3.56 (m, 1H), 3.40-3.38 (m, 1H), 3.23-3.20 (m, 1H), 2.89-2.81 (m, 2H), 2.79-2.67 (m, 2H), 2.63-2.56 (m, 5H), 1.95 (brs, 2H).] | ++++ | ++ |
| 341 | 3-amino-N-[(6S)-2-[(3S,4R)-4-amino-3-(methoxymethyl)-3-methylpyrrolidin-1-yl]-5,6,7,8-tetrahydroquinolin-6-yl]-6-methylthieno[2,3-b]pyridine-2-carboxamide | 481 | (MeOH-d4, 400 MHz) δ (ppm): 8.22 (d, J = 8.4 Hz, 1H), 7.33 (d, J = 8.4 Hz, 1H), 7.28 (d, J = 8.8 Hz, 1H), 6.32 (d, J = 8.4 Hz, 1H), 4.28-4.25 (m, 1H), 3.88-3.84 (m, 1H), 3.64-3.60 (m, 1H), 3.42-3.37 (m, 6H), 3.36-3.33 (m, 2H), 2.98-2.90 (m, 3H), 2.79-2.73 (m, 1H), 2.66 (s, 3H), 2.19-2.16 (m, 1H), 1.97-1.91 (m, 1H), 1.15 (s, 3H). | +++ | ++ |
| 342 | 3-amino-N-[(6S)-2-[(3R,4R)-4-amino-3-(methoxymethyl)-3-methylpyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.57 (d, J = 8.0 Hz, 1H), 7.31 (d, J = 8.4 Hz, 1H), 7.19-7.16 (m, 3H), 6.19 (d, J = 8.4 Hz, 1H), 4.28-4.23 (m, 1H), 3.65-3.57 (m, 1H), 3.46-3.43 (m, 1H), 3.32-3.27 (m, 5H), 3.20-3.15 (m, 2H), 3.04-3.01 (m, 1H), 2.77-2.71 (m, 4H), 2.59 (s, 3H), 2.09-1.98 (m, 2H), 1.95-1.79 (m, 2H), 1.04 (s, 3H). | +++ | ++ |
| 343 | 3-amino-N-[(6S)-2-[(3S,4S)-4-amino-3-(methoxymethyl)-3-methylpyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.30 (d, J = 8.4 Hz, 1H), 7.57 (d, J = 7.6 Hz, 1H), 7.31 (d, J = 8.4 Hz, 1H), 7.18-7.14 (m, 3H), 6.18 (d, J = 8.4 Hz, 1H), 4.13-4.06 (m, 1H), 3.62-3.58 (m, 1H), 3.47-3.45 (m, 1H), 3.36-3.27 (m, 5H), 3.18-3.14 (m, 1H), 3.10-3.06 (m, 1H), 3.02-2.99 (m, 1H), 2.81-2.71 (m, 5H), 2.51 (s, 3H), 2.05-1.98 (m, 1H), 1.88-1.82 (m, 1H), 1.70-1.68 (m, 1H), 1.04 (s, 3H). | +++ | ++ |
| 344 | 3-amino-N-[(6S)-2-[(3R,4S)-4-amino-3-(methoxymethyl)-3-methylpyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.29 (d, J = 8.4 Hz, 1H), 7.57 (d, J = 7.6 Hz, 1H), 7.31 (d, J = 8.0 Hz, 1H), 7.18-7.14 (m, 3H), 6.18 (d, J = 8.4 Hz, 1H), 4.14-4.12 (m, 1H), 3.62-3.58 (m, 1H), 3.33-3.27 (m, 4H), 3.25-3.22 (m, 4H), 3.02-2.97 (m, 1H), 2.81-2.67 (m, 4H), 2.59 (s, 3H), 2.01-1.98 (m, 1H), 1.88-1.76 (m, 3H), 0.93 (s, 3H). | +++ | ++ |
| 345 | 3-amino-N-[(6S)-2-[(3R,4R)-3-amino-4-(difluoromethyl)pyrrolidin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.30 (d, J = 8.4 Hz, 1H), 7.56 (br s, 1H), 7.31 (d, J = 8.4 Hz, 1H), 7.21 (d, J = 8.0 Hz, 1H), 7.15 (br s, 2H), 6.26 (d, J = 8.4 Hz,, 2H), 4.14-4.11 (m, 1H), 3.68-3.64 (m, 1H), 3.54-3.45 (m, 3H), 3.29-3.23 (m, 1H), 2.83-2.67 (m, 5H), 2.58 (s, 3H), 2.02-1.90 (m, 2H), 1.87-1.82 (m, 1H). | +++ | ++ |

| | | | | | |
|---|---|---|---|---|---|
| 346 | 3-amino-N-[(6S)-2-[(3S,4S)-3-amino-4-(difluoromethyl)pyrrolidin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.30 (d, J = 8.8 Hz, 1H), 7.56 (br s, 1H), 7.31 (d, J = 8.4 Hz, 1H), 7.21 (d, J = 8.4 Hz, 1H), 7.15 (s, 2H), 6.26 (d, J = 7.6 Hz, 2H), 4.15-4.12 (m, 1H), 3.67-3.64 (m, 1H), 3.54-3.48 (m, 3H), 3.29-3.23 (m, 1H), 2.81-2.67 (m, 5H), 2.58 (s, 3H), 1.98-1.90 (m, 1H), 1.87-1.82 (m, 2H). | +++ | ++ |
| 347 | 3-amino-N-[(6S)-2-[(3R,4S)-3-amino-4-(difluoromethyl)pyrrolidin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.31 (d, J = 8.4 Hz, 1H), 7.57 (br s, 1H), 7.31 (d, J = 8.4 Hz, 1H), 7.22 (d, J = 8.0 Hz, 1H), 7.16 (br s, 2H), 6.34-6.05 (m, 2H), 4.16-4.12 (m, 1H), 3.67-3.30 (m, 4H), 3.05-3.01 (m, 1H), 2.83-2.73 (m, 4H), 2.59 (s, 3H), 2.50-2.43 (m, 1H), 2.02-1.81 (m, 4H). | +++ | ++ |
| 348 | 3-amino-N-[(3R)-7-[(3R,4R)-3-amino-4-(methoxymethyl)pyrrolidin-1-yl]-2H,3H,4H-pyrano[2,3-b]pyridin-3-yl]-4,6-dimethylthieno[2,3-b]pyridine-2-carboxamide | 483 | (DMSO-d6, 400 MHz) δ (ppm): 7.56 (d, J = 6.8 Hz, 1H), 7.24 (d, J = 8.0 Hz, 1H), 7.05 (s, 1H), 6.86 (br s, 2H), 6.00 (d, J = 8.8 Hz, 1H), 4.28-4.26 (m, 1H), 4.21-4.18 (m, 1H), 3.94 (t, J = 10.0 Hz, 1H), 3.59-3.51 (m, 2H), 3.48-3.37 (m, 3H), 3.28 (s, 3H), 3.19-3.15 (m, 2H), 2.87-2.81 (m, 2H), 2.73 (s, 3H), 2.51 (s, 3H), 2.45-2.39 (m, 1H), 1.69 (br s, 2H). | +++ | + |
| 349 | 3-amino-N-[(3R)-7-[(3S,4S)-3-amino-4-(methoxymethyl)pyrrolidin-1-yl]-2H,3H,4H-pyrano[2,3-b]pyridin-3-yl]-4,6-dimethylthieno[2,3-b]pyridine-2-carboxamide | 483 | (DMSO-d6, 400 MHz) δ (ppm): 7.56 (d, J = 6.8 Hz, 1H), 7.24 (d, J = 8.0 Hz, 1H), 7.05 (s, 1H), 6.86 (br s, 2H), 6.00 (d, J = 8.0 Hz, 1H), 4.28-4.26 (m, 1H), 4.21-4.18 (m, 1H), 3.94 (t, J = 9.6 Hz, 1H), 3.59-3.51 (m, 2H), 3.48-3.37 (m, 3H), 3.28 (s, 3H), 3.19-3.15 (m, 2H), 2.87-2.81 (m, 2H), 2.73 (s, 3H), 2.51 (s, 3H), 2.45-2.38 (m, 1H), 1.69 (br s, 2H). | +++ | ++ |
| 350 | 3-amino-N-[(3R)-7-[(3S,4S)-3-hydroxy-4-(methylamino)pyrrolidin-1-yl]-3,4-dihydro-2H-1-benzopyran-3-yl]-6-methylthieno[2,3-b]pyridine-2-carboxamide | 454 | (DMSO-d6, 400 MHz) δ (ppm): 8.32 (d, J = 8.4 Hz, 1H), 7.49 (br s, 1H), 7.31 (d, J = 8.0 Hz, 1H), 7.22 (br s, 2H), 6.86 (d, J = 8.4 Hz, 1H), 6.10-6.08 (m, 1H), 5.89 (s, 1H), 5.06-5.05 (m, 1H), 4.29-4.23 (m, 1H), 4.15-4.12 (m, 1H), 4.07-4.05 (m, 1H), 3.81-3.76 (m, 1H), 3.43-3.39 (m, 2H), 3.01-2.96 (m, 3H), 2.85-2.82 (m, 2H), 2.59 (s, 3H), 2.33 (s, 3H). | +++ | ++ |
| 351 | 3-amino-N-[(3R)-7-[(7R)-7-amino-2-oxa-5-azaspiro[3.4]octan-5-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.4 Hz, 1H), 7.53 (br s, 1H), 7.32 (d, J = 8.4 Hz, 1H), 7.22 (br s, 2H), 6.96 (d, J = 8.4 Hz, 1H), 6.61-6.59 (m, 1H), 6.47 (s, 1H), 5.16-5.12 (m, 2H), 4.65-4.63 (m, 1H), 4.56-4.54 (m, 1H), 4.33-4.28 (m, 1H), 4.17-4.15 (m, 1H), 3.85-3.80 (m, 1H), 3.42-3.38 (m, 2H), 2.93-2.81 (m, 3H), 2.59 (s, 3H), 2.35-2.30 (m, 1H), 2.20-2.16 (m, 1H), 1.69 (br s, 2H). | ++++ | ++++ |

TABLE 24-continued

| | | | | | |
|---|---|---|---|---|---|
| 352 | 3-amino-N-[(3R)-7-[(7S)-7-amino-2-oxa-5-azaspiro[3.4]octan-5-yl]-3,4-dihydro-2H-1-benzopyran-3-yl]-6-methylthieno[2,3-b]pyridine-2-carboxamide | 466 | (DMSO-d6, 400 MHz) δ (ppm): 8.33 (d, J = 8.0 Hz, 1H), 7.53 (br s, 1H), 7.32 (d, J = 8.4 Hz, 1H), 7.22 (br s, 2H), 6.96 (d, J = 8.4 Hz, 1H), 6.60 (d, J = 8.4 Hz, 1H), 6.48 (s, 1H), 5.15-5.13 (m, 2H), 4.65-4.63 (m, 1H), 4.56-4.54 (m, 1H), 4.35-4.29 (m, 1H), 4.18-4.16 (m, 1H), 3.84-3.82 (m, 1H), 3.40-3.37 (m, 2H), 2.93-2.83 (m, 3H), 2.59 (s, 3H), 2.34-2.30 (m, 1H), 2.21-2.17 (m, 1H), 1.75 (br s, 2H). | ++++ | +++ |
| 353 | N-[(6S)-2-[(3S,4S)-3-amino-4-methoxypyrrolidin-1-yl]-5,6,7,8-tetrahydroquinolin-6-yl]-1-ethyl-1H-pyrrolo[2,3-b]pyridine-5-carboxamide | 435 | (DMSO-d6, 400 MHz) δ (ppm): 8.76 (s, 1H), 8.47-8.44 (m, 2H), 7.68 (d, J = 3.6 Hz, 1H), 7.21 (d, J = 8.4 Hz, 1H), 6.59 (d, J = 3.6 Hz, 1H), 6.23 (d, J = 8.4 Hz, 1H), 4.36-4.30 (m, 2 H), 4.17 (br s, 1H), 3.62-3.59 (m, 2H), 3.48-3.41 (m, 2H), 3.37-3.30 (m, 4H), 3.14-3.12 (m, 1H), 2.92-2.87 (m, 1H), 2.81-2.78 (m, 2H), 2.72-2.65 (m, 1H), 2.10-2.06 (m, 1H), 1.88-1.80 (m, 2H), 1.41-1.38 (m, 3H). | ++ | + |
| 354 | 3-amino-N-[(6S)-2-(3,8-diazabicyclo[3.2.1]octan-3-yl}-5,6,7,8-tetrahydroquinolin-6-yl]-4,6-dimethylthieno[2,3-b]pyridine-2-carboxamide | 463 | (DMSO-d6, 400 MHz) δ (ppm): 7.61 (br s, 1H), 7.21 (d, J = 8.8 Hz, 1H), 7.04 (s, 1H), 6.82 (br s, 2H), 6.45 (d, J = 8.8 Hz, 1H), 4.17-4.13 (m, 1H), 3.77-3.73 (m, 2H), 3.48-3.47 (m, 2H), 2.82-2.68 (m, 10H), 2.49 (s, 3H), 2.00-1.80 (m, 2 H), 1.66-1.58 (m, 4 H). | ++++ | ++ |
| 355 | 5-chloro-N-[(3R)-7-{3,8-diazabicyclo[3.2.1]octan-3-yl]-5,8-difluoro-3,4-dihydro-2H-1-benzopyran-3-yl]-7-ethyl-7H-pyrrolo[2,3-c]pyridazine-3-carboxamide | 503 | (DMSO-d6, 400 MHz) δ (ppm): 9.14 (br s, 1H), 8.39 (s, 1H), 8.36 (s, 1H), 6.38-6.34 (m, 1H), 4.55-4.50 (m, 3H), 4.31-4.26 (m, 1H), 4.20-4.15 (m, 1H), 3.42-3.40 (m, 2H), 3.08-3.04 (m, 2H), 3.02-2.99 (m, 2H), 2.82-2.80 (m, 2H), 1.81-1.74 (m, 2H), 1.67-1.66 (m, 2H), 1.50-1.47 (m, 3H). | +++ | ++ |
| 356 | 5-chloro-N-[(3R)-8-cyano-7-{3,8-diazabicyclo[3.2.1]octan-3-yl}-5-fluoro-3,4-dihydro-2H-1-benzopyran-3-yl]-7-ethyl-7H-pyrrolo[2,3-c]pyridazine-3-carboxamide | 510 | (DMSO-d6, 400 MHz) δ (ppm): 9.19 (br s, 1H), 8.40 (s, 1H), 8.36 (s, 1H), 6.50 (d, J = 9.6 Hz, 1H), 4.55-4.50 (m, 3H), 4.41-4.38 (m, 1H), 4.31-4.27 (m, 1H), 3.46-3.44 (m, 2H), 3.32-3.28 (m, 2H), 2.98-2.89 (m, 4H), 1.90-1.89 (m, 2H), 1.65-1.63 (m, 2H), 1.51-1.47 (m, 3H). | ++ | ++ |
| 357 | 3-amino-N-[(6S)-2-[(3S,4R)-3-amino-4-(1,1-difluoroethoxy)pyrrolidin-1-yl]-5,6,7,8-tetrahydroquinolin-6-yl]-6-methylthieno[2,3-b]pyridine-2-carboxamide | 503 | (DMSO-d6, 400 MHz) δ (ppm): 8.31 (d, J = 8.4 Hz, 1H), 7.59 (br s, 1H), 7.31 (d, J = 8.0 Hz, 1H), 7.22-7.17 (m, 3H), 6.24 (d, J = 8.4 Hz, 1H), 4.69-4.65 (m, 1H), 4.15-4.13 (m, 1H), 3.60-3.49 (m, 4H), 3.00-2.94 (m, 1H), 2.78-2.68 (m, 4H), 2.59 (s, 3H), 2.02-1.95 (m, 1H), 1.85-1.78 (m, 4H), 1.70 (br s, 2H). | +++ | ++ |
| 358 | 3-amino-N-[(6S)-2-[(3R,4S)-3-amino-4-(1,1-difluoroethoxy)pyrrolidin-1-yl]-5,6,7,8-tetrahydroquinolin-6-yl]-6-methylthieno[2,3-b]pyridine-2-carboxamide | 503 | (DMSO-d6, 400 MHz) δ (ppm): 8.31 (d, J = 8.0 Hz, 1H), 7.59 (br s, 1H), 7.31 (d, J = 8.4 Hz, 1H), 7.22-7.17 (m, 3H), 6.24 (d, J = 8.4 Hz, 1H), 4.69-4.64 (m, 1H), 4.15-4.12 (m, 1H), 3.62-3.51 (m, 4H), 3.00-2.94 (m, 1H), 2.82-2.68 (m, 4H), 2.59 (s, 3H), 2.01-1.98 (m, 1H), 1.87-1.78 (m, 6H). | ++ | + |

TABLE 24-continued

| | | | | | |
|---|---|---|---|---|---|
| 359 | (6aS,7aR)-N-[(2S)-6-{3,8-diazabicyclo[3.2.1]octan-3-yl}-5-(difluoromethyl)-8-fluoro-1,2,3,4-tetrahydronaphthalen-2-yl]-5H,6H,6aH,7H,7aH-cyclopropa[c]1,8-naphthyridine-2-carboxamide | 498 | (DMSO-d6, 400 MHz) δ (ppm): 8.29 (s, 1H), 8.18 (d, J = 7.2 Hz, 1H), 7.86 (s, 1H), 7.49-7.22 (m, 1H), 7.05 (d, J = 10.8 Hz, 1H), 6.57 (s, 1H), 4.18-4.10 (br s, 1H), 3.59-3.50 (m, 5H), 3.24-3.16 (m, 1H), 3.07-2.86 (m, 4H), 2.67-2.58 (m, 3H), 2.08-1.93 (m, 2H), 1.88-1.86 (m, 2H), 1.80-1.68 (m, 4H), 0.96-0.90 (m, 2H) | + | + |
| 360 | (6aR,7aS)-N-[(2S)-6-{3,8-diazabicyclo[3.2.1]octan-3-yl}-5-(difluoromethyl)-8-fluoro-1,2,3,4-tetrahydronaphthalen-2-yl]-5H,6H,6aH,7H,7aH-cyclopropa[c]1,8-naphthyridine-2-carboxamide | 498 | (DMSO-d6, 400 MHz) δ (ppm): 8.29 (s, 1H), 8.18 (d, J = 7.2 Hz, 1H), 7.87 (s, 1H), 7.50-7.22 (m, 1H), 7.05 (d, J = 10.8 Hz, 1H), 6.57 (s, 1H), 4.18-4.10 (br s, 1H), 3.50-3.40 (m, 5H), 3.21-3.16 (m, 1H), 3.07-2.88 (m, 4H), 2.68-2.58 (m, 3H), 2.04-1.93 (m, 2H), 1.89-1.87 (m, 2H), 1.80-1.70 (m, 4H), 0.96-0.90 (m, 2H) | ++++ | ++ |
| 361 | (6aS,7aR)-N-[(2R)-6-{3,8-diazabicyclo[3.2.1]octan-3-yl}-5-(difluoromethyl)-8-fluoro-1,2,3,4-tetrahydronaphthalen-2-yl]-5H,6H,6aH,7H,7aH-cyclopropa[c]1,8-naphthyridine-2-carboxamide | 498 | (DMSO-d6, 400 MHz) δ (ppm): 8.29 (s, 1H), 8.18 (d, J = 6.8 Hz, 1H), 7.87 (s, 1H), 7.50-7.22 (m, 1H), 7.05 (d, J = 11.2 Hz, 1H), 6.59 (s, 1H), 4.18-4.10 (br s, 1H), 3.55-3.35 (m, 5H), 3.23-3.16 (m, 1H), 3.07-2.88 (m, 4H), 2.68-2.58 (m, 3H), 2.10-1.88 (m, 4H), 1.82-1.71 (m, 4H), 0.95-0.92 (m, 2H) | + | + |
| 362 | (6aR,7aS)-N-[(2R)-6-(3,8-diazabicyclo[3.2.1]octan-3-yl)-5-(difluoromethyl)-8-fluoro-1,2,3,4-tetrahydronaphthalen-2-yl]-5H,6H,6aH,7H,7aH-cyclopropa[c]1,8-naphthyridine-2-carboxamide | 498 | (DMSO-d6, 400 MHz) δ (ppm): 8.29 (m, 1H), 8.19 (d, J = 6.8 Hz, 1H), 7.86 (s, 1H), 7.49-7.22 (m, 1H), 7.05 (d, J = 11.2 Hz, 1H), 6.58 (s, 1H), 4.18-4.10 (br s, 1H), 3.53-3.43 (m, 5H), 3.21-3.17 (m, 1H), 3.07-2.90 (m, 4H), 2.65-2.62 (m, 3H), 2.04-1.88 (m, 4H), 1.76-1.71 (m, 4H), 0.96-0.92 (m, 2H) | ++ | ++ |
| 363 | 3-amino-N-[(6S)-2-[(3R,4S)-3-amino-4-(trifluoromethyl)pyrrolidin-1-yl]-5,6,7,8-tetrahydroquinolin-6-yl]-6-methylthieno[2,3-b]pyridine-2-carboxamide | 491 | (DMSO-d6, 400 MHz) δ (ppm): 8.29 (d, J = 8.0 Hz, 1H), 7.57 (br s, 1H), 7.31 (d, J = 8.0 Hz, 1H), 7.24 (d, J = 8.4 Hz, 1H), 7.16 (br s, 2H), 6.31 (d, J = 8.4 Hz, 1H), 4.15-4.12 (m, 1H), 3.77-3.67 (m, 3H), 3.49-3.45 (m, 1H), 3.11-3.05 (m, 1H), 2.96-2.92 (m, 1H), 2.83-2.68 (m, 4H), 2.59 (s, 3H), 2.17-1.80 (m, 4H). | +++ | ++ |
| 364 | 3-amino-N-[(6S)-2-[(3S,4R)-3-amino-4-(trifluoromethyl)pyrrolidin-1-yl]-5,6,7,8-tetrahydroquinolin-6-yl]-6-methylthieno[2,3-b]pyridine-2-carboxamide | 491 | (DMSO-d6, 400 MHz) δ (ppm): 8.30 (d, J = 8.4 Hz, 1H), 7.57 (br s, 1H), 7.31 (d, J = 8.4 Hz, 1H), 7.24 (d, J = 8.4 Hz, 1H), 7.16 (br s, 2H), 6.31 (d, J = 8.4 Hz, 1H), 4.16-4.12 (m, 1H), 3.77-3.65 (m, 3H), 3.48-3.43 (m, 1H), 3.11-3.05 (m, 1H), 3.01-2.89 (m, 1H), 2.84-2.70 (m, 4H), 2.59 (s, 3H), 2.08-1.83 (m, 4H). | +++ | + |
| 365 | 7-amino-N-[(6S)-2-[(8R)-8-amino-2-oxa-6-azaspiro[3.4]octan-6-yl]-5,6,7,8-tetrahydroquinolin-6-yl]-3-methylthieno[2,3-b]pyrazine-6-carboxamide | 466 | (DMSO-d6, 400 MHz) δ (ppm): 8.65 (s, 1H), 7.81 (br s, 1H), 7.20 (d, J = 8.0 Hz, 1H), 6.92 (br s, 2H), 6.23 (d, J = 8.4 Hz, 1H), 4.82-4.80 (m, 1H), 4.47-4.38 (m, 3H), 4.16-4.14 (m, 1H), 3.73-3.69 (m, 1H), 3.63-3.60 (m, 1H), 3.50-3.42 (m, 2H), 3.06-3.03 (m, 1H), 2.84-2.73 (m, 4H), 2.66 (s, 3H), 2.03-1.83 (m, 4 H). | ++++ | ++ |

TABLE 24-continued

| 366 | 7-amino-N-[(6S)-2-[(8S)-8-amino-2-oxa-6-azaspiro[3.4]octan-6-yl]-5,6,7,8-tetrahydroquinolin-6-yl]-3-methylthieno[2,3-b]pyrazine-6-carboxamide | 466 | (DMSO-d6, 400 MHz) δ (ppm): 8.65 (s, 1H), 7.81 (br s, 1H), 7.20 (d, J = 8.8 Hz, 1H), 6.92 (br s, 2H), 6.23 (d, J = 8.4 Hz, 1H), 4.82-4.80 (m, 1H), 4.47-4.38 (m, 3H), 4.16-4.14 (m, 1H), 3.73-3.70 (m, 1H), 3.63-3.61 (m, 1H), 3.50-3.42 (m, 2H), 3.06-3.03 (m, 1H), 2.84-2.73 (m, 4H), 2.66 (s, 3H), 2.05-1.83 (m, 4H). | ++ | + |
| --- | --- | --- | --- | --- | --- |
| 367 | 3-amino-N-[(6S)-2-[(1R,5S)-9,9-difluoro-2,7-diazabicyclo[3.3.1]nonan-7-yl]-5,6,7,8-tetrahydroquinolin-6-yl]-6-methylthieno[2,3-b]pyridine-2-carboxamide | 499 | (DMSO-d6, 400 MHz) δ (ppm): 8.31 (d, J = 8.0 Hz, 1H), 7.62 (br s, 1H), 7.32-7.28 (m, 2H), 7.18 (br s, 2H), 6.64 (d, J = 8.4 Hz, 1H), 4.43-4.32 (m, 2H), 4.18-4.12 (m, 1H), 3.18-3.15 (m, 4H), 2.86-2.80 (m, 4H), 2.59 (s, 3H), 2.42-2.40 (m, 1H), 2.08-2.00 (m, 2H), 1.89-1.86 (m, 2H). | ++++ | +++ |
| 368 | 3-amino-N-[(6S)-2-[(1S,5R)-9,9-difluoro-2,7-diazabicyclo[3.3.1]nonan-7-yl]-5,6,7,8-tetrahydroquinolin-6-yl]-6-methylthieno[2,3-b]pyridine-2-carboxamide | 499 | (DMSO-d6, 400 MHz) δ (ppm): 8.31 (d, J = 8.4 Hz, 1H), 7.62 (br s, 1H), 7.32-7.27 (m, 2H), 7.18 (br s, 2H), 6.64 (d, J = 8.8 Hz, 1H), 4.38-4.35 (m, 2H), 4.18-4.13 (m, 1H), 3.19-3.14 (m, 4H), 2.82-2.74 (m, 4H), 2.59 (s, 3H), 2.42-2.39 (m, 1H), 2.08-2.00 (m, 2H), 1.89-1.81 (m, 2H). | ++++ | +++ |
| 369 | 3-amino-N-[(3R)-7-[(3S)-3-aminopyrrolidin-1-yl]-3,4-dihydro-2H-1-benzopyran-3-yl]-6-methylthieno[2,3-b]pyridine-2-carboxamide | 424 | (DMSO-d6, 400 MHz) δ (ppm): 8.33 (d, J = 8.4 Hz, 1H), 7.48 (br s, 1H), 7.32 (d, J = 8.4 Hz, 1H), 7.21 (br s, 2H), 6.86 (d, J = 8.8 Hz, 1H), 6.10 (d, J = 6.4 Hz, 1H), 5.90 (s, 1H), 4.30-4.27 (m, 1H), 4.15-4.13 (m, 1H), 3.82-3.77 (m, 1H), 3.57-3.51 (m, 1H), 3.29-3.25 (m, 2H), 3.19-3.13 (m, 1H), 2.89-2.78 (m, 3H), 2.59 (s, 3H), 2.08-2.01 (m, 1H), 1.86 (br s, 2H), 1.71-1.68 (m, 1H). | ++++ | +++ |
| 370 | N-[(6S)-2-[(3R,4S)-3-amino-4-(difluoromethyl)pyrrolidin-1-yl]-5,6,7,8-tetrahydroquinolin-6-yl]-1-ethyl-1H-pyrrolo[2,3-b]pyridine-5-carboxamide | 455 | (DMSO-d6, 400 MHz) δ (ppm): 8.77 (s, 1H), 8.47-8.45 (m, 2H), 7.69 (s, 1H), 7.24 (d, J = 8.4 Hz, 1H), 6.59 (s, 1H), 6.32-6.07 (m, 2H), 4.36-4.30 (m, 2H), 4.23-4.17 (m, 1H), 3.66-3.58 (m, 2H), 3.51-3.42 (m, 1H), 3.40-3.30 (m, 1H), 3.06-3.02 (m, 1H), 2.90-2.88 (m, 1H), 2.82-2.79 (m, 2H), 2.72-2.68 (m, 1H), 2.50-2.46 (m, 1H), 2.08-1.93 (m, 3H), 1.90-1.84 (m, 1H), 1.41-1.38 (m, 3H) | ++ | ++ |
| 371 | N-[(6S)-2-[(3S,4R)-3-amino-4-(difluoromethyl)pyrrolidin-1-yl]-5,6,7,8-tetrahydroquinolin-6-yl]-1-ethyl-1H-pyrrolo[2,3-b]pyridine-5-carboxamide | 455 | (DMSO-d6, 400 MHz) δ (ppm): 8.77 (s, 1H), 8.47-8.45 (m, 2H), 7.64 (s, 1H), 7.24 (d, J = 8.4 Hz, 1H), 6.59 (s, 1H), 6.31-6.10 (m, 2H), 4.36-4.30 (m, 2H), 4.23-4.17 (m, 1H), 3.69-3.60 (m, 2H), 3.51-3.49 (m, 1H), 3.39-3.34 (m, 1H), 3.06-3.02 (m, 1H), 2.90-2.88 (m, 1H), 2.81-2.79 (m, 2H), 2.72-2.68 (m, 1H), 2.52-2.50 (m, 1H), 2.06-1.85 (m, 4H), 1.41-1.38 (m, 3H) | ++ | + |
| 372 | 3-amino-N-[(6S)-2-[(3R,4S)-3-(difluoromethyl)-4-acetamidopyrrolidin-1-yl]-5,6,7,8-tetrahydroquinolin-6-yl]-6-methylthieno[2,3-b]pyridine-2-carboxamide | 515 | (DMSO-d6, 400 MHz) δ (ppm): 8.32-8.29 (m, 2H), 7.59 (d, J = 7.6 Hz, 1H), 7.31 (d, J = 8.4 Hz, 1H), 7.17 (br s, 2H), 6.36-6.07 (m, 2H), 4.45-4.41 (m, 1H), 4.16-4.10 (m, 1H), 3.73-3.63 (m, 2H), 3.43-3.38 (m, | +++ | + |

TABLE 24-continued

| | | | | |
|---|---|---|---|---|
| | | | 1H), 3.21-3.17 (m, 1H), 2.83-2.69 (m, 5H), 2.59 (s, 3H), 2.02-1.99 (m, 1H), 1.90-1.85 (m, 4H) | | |
| 373 | 3-amino-N-[(3R)-7-[3-amino-3-(methoxymethyl)azetidin-1-yl]-3,4-dihydro-2H-1-benzopyran-3-yl]-6-methylthieno[2,3-b]pyridine-2-carboxamide | 454 | (DMSO-d6, 400 MHz) δ (ppm): 8.33 (d, J = 8.4 Hz, 1H), 7.52 (br s, 1H), 7.31 (d, J = 8.4 Hz, 1H), 7.23 (br s, 2H), 6.87 (d, J = 8.0 Hz, 1H), 6.01 (dd, J = 8.4, 2.4 Hz, 1H), 5.84 (s, 1H), 4.32-4.25 (m, 1H), 4.15-4.12 (m, 1H), 3.81-3.76 (m, 1H), 3.72-3.70 (m, 2H), 3.42 (s, 2H), 3.38-3.36 (m, 2H), 3.34 (s, 3H), 2.90-2.80 (m, 2H), 2.52 (s, 3H), 2.17 (br s, 2H) | ++++ | |
| 374 | 3-amino-N-[(6S)-2-[(3S)-3-(difluoromethyl)piperazin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.31 (d, J = 8.4 Hz, 1H), 7.60 (d, J = 7.6 Hz, 1H), 7.32-7.28 (m, 2H), 7.17 (br s, 2H), 6.67 (d, J = 8.4 Hz, 1H), 6.20-5.91 (m, 1H), 4.22-4.10 (m, 2H), 3.95-3.92 (m, 1H), 3.14-3.04 (m, 2H), 2.86-2.69 (m, 7H), 2.59 (s, 3H), 2.02-1.99 (m, 1H), 1.91-1.84 (m, 1H) | +++ | + |
| 375 | 3-amino-N-[(6S)-2-[(3R)-3-(difluoromethyl)piperazin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.31 (d, J = 8.4 Hz, 1H), 7.60 (d, J = 7.6 Hz, 1H), 7.32-7.26 (m, 2H), 7.17 (br s, 2H), 6.65 (d, J = 8.4 Hz, 1H), 6.12-5.84 (m, 1H), 4.16-4.12 (m, 2H), 3.90-3.87 (m, 1H), 3.00-2.97 (m, 2H), 2.85-2.61 (m, 7H), 2.59 (s, 3H), 2.02-1.99 (m, 1H), 1.91-1.80 (m, 1H) | +++ | + |
| 376 | 3-amino-N-[(6S)-2-[(3S,4R)-3-(difluoromethyl)-4-(methylamino)pyrrolidin-1-yl]-5,6,7,8-tetrahydroquinolin-6-yl]-6-methylthieno[2,3-b]pyridine-2-carboxamide | 487 | (DMSO-d6, 400 MHz) δ (ppm): 8.31 (d, J = 8.0 Hz, 1H), 7.60 (d, J = 7.6 Hz, 1H), 7.31 (d, J = 8.4 Hz, 1H), 7.23-7.17 (m, 3H), 6.32-6.17 (m, 2H), 4.17-4.10 (m, 1H), 3.64-3.61(m, 1H), 3.55-3.53 (m, 1H), 3.46-3.43 (m, 1H), 3.26-3.18 (m, 2H), 2.83-2.70 (m, 5H), 2.59 (s, 3H), 2.31 (s, 3H), 2.10-1.99 (m, 2H), 1.90-1.80 (m, 1H) | +++ | + |
| 377 | 3-amino-N-[(6S)-2-[(3R,4S)-3-(difluoromethyl)-4-(methylamino)pyrrolidin-1-yl]-5,6,7,8-tetrahydroquinolin-6-yl]-6-methylthieno[2,3-b]pyridine-2-carboxamide | 487 | (DMSO-d6, 400 MHz) δ (ppm): 8.31 (d, J = 8.0 Hz, 1H), 7.59 (d, J = 8.0 Hz, 1H), 7.31 (d, J = 8.4 Hz, 1H), 7.24-7.17 (m, 3H), 6.32-6.18 (m, 2H), 4.17-4.10 (m, 1H), 3.66-3.62 (m, 1H), 3.59-3.54 (m, 1H), 3.45-3.41 (m, 1H), 3.27-3.16 (m, 2H), 2.83-2.69 (m, 5H), 2.59 (s, 3H), 2.31 (s, 3H), 2.10-1.99 (m, 2H), 1.90-1.80 (m, 1H) | +++ | + |
| 378 | 3-amino-N-[(3R)-7-[(3R,4S)-3-amino-4-(difluoromethyl)pyrrolidin-1-yl]-2H,3H,4H-pyrano[2,3-b]pyridin-3-yl]-6-methylthieno[2,3-b]pyridine-2-carboxamide | 475 | (DMSO-d6, 400 MHz) δ (ppm): 8.33 (d, J = 8.0 Hz, 1H), 7.55 (d, J = 7.2 Hz, 1H), 7.29-7.27 (m, 2H), 7.23 (br s, 2H), 6.34-6.05 (m, 2H), 4.30-4.20 (m, 2H), 3.98-3.93 (m, 1H), 3.64-3.46 (m, 3H), 3.37-3.34 (m, 1H), 3.02-2.98 (m, 1H), 2.88-2.79 (m, 2H), 2.59 (s, 3H), 2.51-2.44 (m, 1H), 1.86 (br s, 2H) | +++ | |
| 379 | 3-amino-N-[(3R)-7-[(3S,4R)-3-amino-4-(difluoromethyl)pyrrolidin-1-yl]-2H,3H,4H-pyrano[2,3-b]pyridin-3-yl]-6-methylthieno[2,3-b]pyridine-2-carboxamide | 475 | (DMSO-d6, 400 MHz) δ (ppm): 8.33 (d, J = 8.4 Hz, 1H), 7.55 (d, J = 7.6 Hz, 1H), 7.33-7.23 (m, 4H), 6.34-6.05 (m, 2H), 4.30-4.20 (m, 2H), 3.98-3.93 (m, 1H), 3.64-3.47 (m, 3H), 3.37-3.34 (m, 1H), 3.02-2.98 (m, 1H), 2.88-2.79 (m, 2H), 2.59 (s, 3H), 2.51-2.44 (m, 1H), 1.86 (br s, 2H) | ++ | |

TABLE 24-continued

| | | | | | |
|---|---|---|---|---|---|
| 380 | 3-amino-N-[(6S)-2-[(3R,4S)-3-amino-4-(difluoromethyl)pyrrolidin-1-yl]-5,6,7,8-tetrahydroquinazolin-6-yl]-6-methylthieno[2,3-b]pyridine-2-carboxamide | 474 | (DMSO-d6, 400 MHz) δ (ppm): 8.31 (d, J = 8.4 Hz, 1H), 8.09 (s, 1H), 7.64 (d, J = 7.6 Hz, 1H), 7.31 (d, J = 8.4 Hz, 1H), 7.18 (br s, 2H), 6.34-6.06 (m, 1H), 4.15-4.10 (m, 1H), 3.79-3.67 (m, 2H), 3.52-3.46 (m, 2H), 3.17-3.13 (m, 1H), 2.84-2.62 (m, 4H), 2.59 (s, 3H), 2.00-1.83 (m, 4H). | +++ | + |
| 381 | 3-amino-N-[(6S)-2-[(3S,4R)-3-amino-4-(difluoromethyl)pyrrolidin-1-yl]-5,6,7,8-tetrahydroquinazolin-6-yl]-6-methylthieno[2,3-b]pyridine-2-carboxamide | 474 | (DMSO-d6, 400 MHz) δ (ppm): 8.31 (d, J = 8.4 Hz, 1H), 8.09 (s, 1H), 7.64 (d, J = 7.6 Hz, 1H), 7.31 (d, J = 8.4 Hz, 1H), 7.18 (br s, 2H), 6.34-6.06 (m, 1H), 4.15-4.10 (m, 1H), 3.79-3.67 (m, 2H), 3.52-3.47 (m, 2H), 3.16-3.12 (m, 1H), 2.84-2.62 (m, 4H), 2.59 (s, 3H), 2.00-1.83 (m, 4H). | ++ | + |
| 382 | 3-amino-N-[(6R)-2-[(3S,4R)-3-amino-4-(difluoromethyl)pyrrolidin-1-yl]-5,6,7,8-tetrahydroquinazolin-6-yl]-6-methylthieno[2,3-b]pyridine-2-carboxamide | 474 | (DMSO-d6, 400 MHz) δ (ppm): 8.31 (d, J = 8.4 Hz, 1H), 8.09 (s, 1H), 7.64 (d, J = 7.6 Hz, 1H), 7.31 (d, J = 8.4 Hz, 1H), 7.18 (br s, 2H), 6.34-6.05 (m, 1H), 4.14-4.10 (m, 1H), 3.80-3.67 (m, 2H), 3.52-3.45 (m, 2H), 3.16-3.12 (m, 1H), 2.85-2.62 (m, 4H), 2.59 (s, 3H), 2.01-1.83 (m, 4H) | ++ | + |
| 383 | 3-amino-N-[(6R)-2-[(3R,4S)-3-amino-4-(difluoromethyl)pyrrolidin-1-yl]-5,6,7,8-tetrahydroquinazolin-6-yl]-6-methylthieno[2,3-b]pyridine-2-carboxamide | 474 | (DMSO-d6, 400 MHz) δ (ppm): 8.31 (d, J = 8.4 Hz, 1H), 8.10 (s, 1H), 7.64 (d, J = 7.6 Hz, 1H), 7.31 (d, J = 8.4 Hz, 1H), 7.18 (br s, 2H), 6.35-6.06 (m, 1H), 4.13-4.10 (m, 1H), 3.80-3.67 (m, 2H), 3.52-3.47 (m, 2H), 3.17-3.13 (m, 1H), 2.85-2.62 (m, 4H), 2.59 (s, 3H), 2.01-1.81 (m, 4H) | + | + |
| 384 | 3-amino-N-[(6S)-2-[(3R,4S)-3-amino-4-(fluoromethyl)pyrrolidin-1-yl]-5,6,7,8-tetrahydroquinolin-6-yl]-6-methylthieno[2,3-b]pyridine-2-carboxamide | 455 | (DMSO-d6, 400 MHz) δ (ppm): 8.31 (d, J = 8.4 Hz, 1H), 7.58 (d, J = 7.6 Hz, 1H), 7.31(d, J = 8.0 Hz, 1H), 7.21-7.17 (m, 3H), 6.24 (d, J = 8.4 Hz, 1H), 4.65-4.46 (m, 2H), 4.14-4.11 (m, 1H), 3.65-3.61 (m, 2H), 3.30-3.18 (m, 2H), 3.04-3.00 (m, 1H), 2.81-2.68 (m, 4H), 2.59 (s, 3H), 2.33-2.25 (m, 2H), 2.01-1.99 (m, 1H), 1.87-1.82 (m, 1H) | +++ | ++ |
| 385 | 3-amino-N-[(6S)-2-[(3S,4R)-3-amino-4-(fluoromethyl)pyrrolidin-1-yl]-5,6,7,8-tetrahydroquinolin-6-yl]-6-methylthieno[2,3-b]pyridine-2-carboxamide | 455 | (DMSO-d6, 400 MHz) δ (ppm): 8.31 (d, J = 8.4 Hz, 1H), 7.58 (d, J = 7.6 Hz, 1H), 7.31(d, J = 8.4 Hz, 1H), 7.21-7.17 (m, 3H), 6.24 (d, J = 8.8 Hz, 1H), 4.67-4.47 (m, 2H), 4.13-4.12 (m, 1H), 3.64-3.62 (m, 2H), 3.30-3.17 (m, 2H), 3.04-3.00 (m, 1H), 2.81-2.68 (m, 4H), 2.59 (s, 3H), 2.33-2.28 (m, 2H), 2.01-1.99 (m, 1H), 1.87-1.82 (m, 1H) | +++ | + |
| 386 | 3-amino-N-[(6S)-2-[(3R)-3-amino-3-(hydroxymethyl)pyrrolidin-1-yl]-5,6,7,8-tetrahydroquinolin-6-yl]-6-methylthieno[2,3-b]pyridine-2-carboxamide | 453 | (DMSO-d6, 400 MHz) δ (ppm): 8.31 (d, J = 8.4 Hz, 1H), 7.58 (d, J = 8.0 Hz, 1H), 7.31 (d, J = 8.4 Hz, 1H), 7.19-7.17 (m, 3H), 6.20 (d, J = 8.4 Hz, 1H), 4.84-4.83 (m, 1H), 4.14-4.11 (m, 1H), 3.46-3.37 (m, 3H), 3.10-3.07 (m, 1H), 2.80-2.68 (m, 6H), 2.59 (s, 3H), 1.98-1.77 (m, 5H), 1.70-1.63 (m, 1H) | +++ | ++ |

TABLE 24-continued

| | | | | | |
|---|---|---|---|---|---|
| 387 | 3-amino-N-[(6S)-2-[(3S)-3-amino-3-(hydroxymethyl)pyrrolidin-1-yl]-5,6,7,8-tetrahydroquinolin-6-yl]-6-methylthieno[2,3-b]pyridine-2-carboxamide | 453 | (DMSO-d6, 400 MHz) δ (ppm): 8.31 (d, J = 7.6 Hz, 1H), 7.58 (d, J = 7.6 Hz, 1H), 7.31 (d, J = 8.4 Hz, 1H), 7.19-7.17 (m, 3H), 6.20 (d, J = 8.4 Hz, 1H), 4.85-4.83 (m, 1H), 4.14-4.11 (m, 1H), 3.45-3.38 (m, 3H), 3.10-3.07 (m, 1H), 2.80-2.68 (m, 6H), 2.59 (s, 3H), 1.98-1.82 (m, 5H), 1.70-1.63 (m, 1H) | +++ | + |
| 388 | 3-amino-N-[(6S)-2-[(3R)-3-amino-3-(methoxymethyl)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.65 (d, J = 7.6 Hz, 1H), 7.42 (d, J = 8.4 Hz, 1H), 7.31 (d, J = 8.4 Hz, 1H), 7.17 (br s, 2H), 6.61 (d, J = 8.0 Hz, 1H), 4.15-4.11 (m, 1H), 4.06 (s, 2H), 3.70-3.60 (m, 3H), 2.90-2.74 (m, 4H), 2.60-2.50 (m, 5H), 2.27-2.22 (m, 4H), 2.06-1.99 (m, 1H), 1.91-1.84 (m, 2H), 1.61-1.57 (m, 1H) | +++ | ++ |
| 389 | 3-amino-N-[(6S)-2-[(3S)-3-amino-3-(methoxymethyl)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.4 Hz, 1H), 7.64 (d, J = 8.0 Hz, 1H), 7.42 (d, J = 8.0 Hz, 1H), 7.31 (d, J = 8.0 Hz, 1H), 7.18 (br s, 2H), 6.61 (d, J = 8.0 Hz, 1H), 4.16-4.08 (m, 1H), 4.06-4.02 (m, 2H), 3.70-3.60 (m, 3H), 2.91-2.74 (m, 4H), 2.59-2.51 (m, 5H), 2.26-2.22 (m, 4H), 2.08-2.01 (m, 1H), 1.93-1.82 (m, 2H), 1.61-1.57 (m, 1H) | +++ | ++ |
| 390 | 3-amino-N-[(6S)-2-[(5S,9S)-9-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.30 (d, J = 8.4 Hz, 1H), 7.57 (br s, 1H), 7.31 (d, J = 8.0 Hz, 1H), 7.19-7.16 (m, 3H), 6.18 (d, J = 8.4 Hz, 1H), 4.14-4.09 (m, 1H), 3.79-3.70 (m, 2H), 3.54-3.50 (m, 1H), 3.45-3.42 (m, 1H), 3.30-3.28 (m, 1H), 3.20-3.14 (m, 2H), 2.81-2.68 (m, 4H), 2.59 (s, 3H), 2.21-2.14 (m, 1H), 2.01-1.82 (m, 5H), 1.72-1.65 (m, 1H). | ++ | + |
| 391 | 3-amino-N-[(6S)-2-[(5S,9R)-9-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.4 Hz, 1H), 7.56 (br s, 1H), 7.31 (d, J = 8.0 Hz, 1H), 7.19-7.16 (m, 3H), 6.18 (d, J = 8.4 Hz, 1H), 4.16-4.12 (m, 1H), 3.86-3.80 (m, 2H), 3.59-3.52 (m, 2H), 3.28-3.21 (m, 2H), 2.97-2.92 (m, 1H), 2.81-2.68 (m, 4H), 2.59 (m, 3H), 2.00-1.80 (m, 8H). | +++ | ++ |
| 392 | 3-amino-N-[(6S)-2-[(5R,9R)-9-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.4 Hz, 1H), 7.57 (br s, 1H), 7.31 (d, J = 8.0 Hz, 1H), 7.19-7.16 (m, 3H), 6.19 (d, J = 8.4 Hz, 1H), 4.16-4.12 (m, 1H), 3.77-3.72 (m, 2H), 3.53-3.49 (m, 1H), 3.44-3.41 (m, 1H), 3.30-3.28 (m, 1H), 3.20-3.16 (m, 2H), 2.81-2.68 (m, 4H), 2.59 (m, 3H), 2.21-2.15 (m, 2H), 2.01-1.98 (m, 1H), 1.92-1.82 (m, 3H), 1.72-1.68 (m, 1H). | ++ | + |
| 393 | 3-amino-N-[(6S)-2-[(5R,9S)-9-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.30 (d, J = 8.0 Hz, 1H), 7.57 (br s, 1H), 7.31 (d, J = 8.4 Hz, 1H), 7.19-7.16 (m, 3H), 6.18 (d, J = 8.4 Hz, 1H), 4.14-4.11 (m, 1H), 3.82-3.78 (m, 2H), 3.57-3.53 (m, 2H), 3.27-3.23 (m, 2H), 2.98-2.93 | +++ | + |

TABLE 24-continued

| | | | | | |
|---|---|---|---|---|---|
| | | | (m, 1H), 2.77-2.71 (m, 4H), 2.59 (m, 3H), 1.98-1.86 (m, 8H). | | |
| 394 | N-[(6S)-2-[(3aR,6aS)-3a-amino-hexahydro-1H-furo[3,4-c]pyrrol-5-yl]-5,6,7,8-tetrahydroquinolin-6-yl]-3-amino-6-methylthieno[2,3-b]pyridine-2-carboxamide | 465 | (DMSO-d6, 400 MHz) δ (ppm): 8.31 (d, J = 8.0 Hz, 1H), 7.58 (d, J = 8.0 Hz, 1H), 7.31 (d, J = 8.4 Hz, 1H), 7.22 (d, J = 8.4 Hz, 1H), 7.17 (br s, 2H), 6.28 (d, J = 8.4 Hz, 1H), 4.14-4.08 (m, 1H), 4.06-4.02 (m, 1H), 3.66-3.55 (m, 5H), 3.30-3.24 (m, 3H), 2.88-2.69 (m, 4H), 2.59 (s, 3H), 2.01-1.99 (m, 1H), 1.91-1.80 (m, 1H) | +++ | + |
| 395 | N-[(6S)-2-[(3aS,6aR)-3a-amino-hexahydro-1H-furo[3,4-c]pyrrol-5-yl]-5,6,7,8-tetrahydroquinolin-6-yl]-3-amino-6-methylthieno[2,3-b]pyridine-2-carboxamide | 465 | (DMSO-d6, 400 MHz) δ (ppm): 8.31 (d, J = 8.4 Hz, 1H), 7.58 (d, J = 7.6 Hz, 1H), 7.31 (d, J = 8.0 Hz, 1H), 7.21 (d, J = 8.4 Hz, 1H), 7.17 (br s, 2H), 6.28 (d, J = 8.4 Hz, 1H), 4.14-4.08 (m, 1H), 4.06-4.02 (m, 1H), 3.66-3.54 (m, 5H), 3.31-3.23 (m, 3H), 2.84-2.69 (m, 4H), 2.59 (s, 3H), 2.09-1.94 (m, 3H), 1.91-1.80 (m, 1H) | +++ | ++ |
| 396 | 3-amino-6-methyl-N-[(6S)-2-[(1R,5S,9r)-9-amino-3-oxa-7-azabicyclo[3.3.1]nonan-7-yl]-5,6,7,8-tetrahydroquinolin-6-yl]thieno[2,3-b]pyridine-2-carboxamide | 479 | (DMSO-d6, 400 MHz) δ (ppm): 8.31 (d, J = 8.0 Hz, 1H), 7.60 (d, J = 7.6 Hz, 1H), 7.31 (d, J = 8.4 Hz, 1H), 7.19-7.17 (m, 3H), 6.51 (d, J = 8.8 Hz, 1H), 4.29-4.22 (m, 2H), 4.19-4.06 (m, 3H), 3.51 (d, J = 11.2 Hz, 2H), 3.14-3.05 (m, 3H), 2.83-2.68 (m, 4H), 2.59 (s, 3H), 2.17 (br s, 2H), 2.01-1.99 (m, 1H), 1.89-1.82 (m, 1H), 1.61-1.59 (m, 2H) | +++ | ++ |
| 397 | 3-amino-6-methyl-N-[(6S)-2-[(1R,5S,9s)-9-amino-3-oxa-7-azabicyclo[3.3.1]nonan-7-yl]-5,6,7,8-tetrahydroquinolin-6-yl]thieno[2,3-b]pyridine-2-carboxamide | 479 | (DMSO-d6, 400 MHz) δ (ppm): 8.31 (d, J = 8.4 Hz, 1H), 7.60 (d, J = 8.0 Hz, 1H), 7.31 (d, J = 8.0 Hz, 1H), 7.22-7.17 (m, 3H), 6.48 (d, J = 8.8 Hz, 1H), 4.16-4.03 (m, 1H), 3.92-3.87 (m, 4H), 3.60-3.57 (m, 2H), 3.34-3.33 (m, 2H), 3.16 (s, 1H), 2.83-2.68 (m, 4H), 2.59 (s, 3H), 2.01-1.99 (m, 1H), 1.89-1.82 (m, 1H), 1.76-1.74 (m, 2H) | +++ | ++ |
| 398 | 3-amino-N-[(6S)-2-[(7R)-7-amino-5-oxa-2-azaspiro[3.4]octan-2-yl]-5,6,7,8-tetrahydroquinolin-6-yl]-6-methylthieno[2,3-b]pyridine-2-carboxamide | 465 | (DMSO-d6, 400 MHz) δ (ppm): 8.31 (d, J = 8.0 Hz, 1H), 7.60 (d, J = 6.8 Hz, 1H), 7.31 (d, J = 8.0 Hz, 1H), 7.24-7.17 (m, 3H), 6.20 (d, J = 8.4 Hz, 1H), 4.14-4.07 (m, 1H), 3.99-3.81 (m, 4H), 3.52-3.40 (m, 3H), 2.82-2.69 (m, 4H), 2.59 (s, 3H), 2.25-2.20 (m, 1H), 1.98-1.79 (m, 4H) | +++ | ++ |
| 399 | 3-amino-N-[(6S)-2-[(7S)-7-amino-5-oxa-2-azaspiro[3.4]octan-2-yl]-5,6,7,8-tetrahydroquinolin-6-yl]-6-methylthieno[2,3-b]pyridine-2-carboxamide | 465 | (DMSO-d6, 400 MHz) δ (ppm): 8.31 (d, J = 8.0 Hz, 1H), 7.60 (d, J = 8.0 Hz, 1H), 7.31 (d, J = 8.4 Hz, 1H), 7.23 (d, J = 8.0 Hz, 1H), 7.18 (br s, 2H), 6.20 (d, J = 8.0 Hz, 1H), 4.18-4.09 (m, 1H), 4.02-4.00 (m, 1H), 3.91-3.81 (m, 4H), 3.53-3.40 (m, 2H), 2.82-2.69 (m, 4H), 2.59 (s, 3H), 2.24-2.20 (m, 1H), 1.98-1.80 (m, 3H), 1.70 (br s, 2H) | ++++ | ++ |
| 400 | N-[(6S)-2-[(3R,4R)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide | 449 | (DMSO-d6, 400 MHz) δ (ppm): 8.77 (s, 1H), 8.47-8.45 (m, 2H), 7.69 (d, J = 3.6 Hz, 1H), 7.20 (d, J = 8.4 Hz, 1H), 6.59 (d, J = 3.6 Hz, 1H), 6.21 (d, J = 8.4 Hz, 1H), 4.36-4.30 (m, 2H), 4.22-4.17 (m, 1H), 3.60-3.33 (m, 5H), 3.28 (s, 3H), 3.23-3.18 (m, 2H), 2.88-2.81 | ++ | + |

TABLE 24-continued

| | | | | | |
|---|---|---|---|---|---|
| | | | (m, 1H), 2.80-2.77 (m, 2H), 2.71-2.67 (m, 1H), 2.41-2.38 (m, 1H), 2.10-2.05 (m, 1H), 1.88-1.82 (m, 1H), 1.59 (br s, 2H), 1.41-1.38 (m, 4H) | | |
| 401 | N-[(6S)-2-[(3S,4S)-3-amino-4-(methoxymethyl)pyrrolidin-1-yl]-5,6,7,8-tetrahydroquinolin-6-yl]-1-ethyl-1H-pyrrolo[2,3-b]pyridine-5-carboxamide | 449 | (DMSO-d6, 400 MHz) δ (ppm): 8.77 (d, J = 2.0 Hz, 1H), 8.47-8.45 (m, 2H), 7.68 (d, J = 3.6 Hz, 1H), 7.19 (d, J = 8.4 Hz, 1H), 6.59 (d, J = 3.2 Hz, 1H), 6.21 (d, J = 8.4 Hz, 1H), 4.36-4.30 (m, 2H), 4.18-4.13 (m, 1H), 3.60-3.35 (m, 5H), 3.28 (s, 3H), 3.22-3.17 (m, 2H), 2.88-2.86 (m, 1H), 2.78-2.77 (m, 2H), 2.71-2.67 (m, 1H), 2.41-2.37 (m, 1H), 2.11-2.04 (m, 1H), 1.90-1.80 (m, 1H), 1.55 (br s, 2H), 1.41-1.38 (m, 3H) | ++ | + |
| 402 | 1-ethyl-N-[(6S)-2-[(3S,4S)-3-methoxy-4-(methylamino)pyrrolidin-1-yl]-5,6,7,8-tetrahydroquinolin-6-yl]-1H-pyrrolo[2,3-b]pyridine-5-carboxamide | 449 | (DMSO-d6, 400 MHz) δ (ppm): 8.77 (d, J = 2.0 Hz, 1H), 8.47-8.45 (m, 2H), 7.69 (d, J = 3.6 Hz, 1H), 7.21 (d, J = 8.4 Hz, 1H), 6.59 (d, J = 3.6 Hz, 1H), 6.25 (d, J = 8.4 Hz, 1H), 4.36-4.30 (m, 2H), 4.22-4.18 (m, 1H), 3.78-3.77 (m, 1H), 3.54-3.22 (m, 7H), 3.13-3.11 (m, 1H), 2.88-2.87 (m, 1H), 2.81-2.78 (m, 2H), 2.72-2.68 (m, 1H), 2.32 (s, 3H), 2.11-2.06 (m, 1H), 1.90-1.80 (m, 2H), 1.41-1.38 (m, 3H) | ++ | + |
| 403 | N-[(6S)-2-[(8R)-8-amino-2-oxa-6-azaspiro[3.4]octan-6-yl]-5,6,7,8-tetrahydroquinolin-6-yl]-1-ethyl-1H-pyrrolo[2,3-b]pyridine-5-carboxamide | 447 | (DMSO-d6, 400 MHz) δ (ppm): 8.77 (s, 1H), 8.47-8.45 (m, 2H), 7.68 (d, J = 3.2 Hz, 1H), 7.21 (d, J = 8.4 Hz, 1H), 6.59 (d, J = 3.6 Hz, 1H), 6.23 (d, J = 8.4 Hz, 1H), 4.81 (d, J = 6.0 Hz, 1H), 4.47-4.30 (m, 5H), 4.22-4.13 (m, 1H), 3.72-3.60 (m, 2H), 3.48-3.36 (m, 3H), 3.06-3.04 (m, 1H), 2.92-2.73 (m, 4H), 2.08-2.02 (m, 2H), 1.88-1.82 (m, 1H), 1.41-1.38 (m, 3H) | + | |
| 404 | N-[(6S)-2-[(8S)-8-amino-2-oxa-6-azaspiro[3.4]octan-6-yl]-5,6,7,8-tetrahydroquinolin-6-yl]-1-ethyl-1H-pyrrolo[2,3-b]pyridine-5-carboxamide | 447 | (DMSO-d6, 400 MHz) δ (ppm): 8.76 (s, 1H), 8.47-8.45 (m, 2H), 7.68 (d, J = 3.6 Hz, 1H), 7.22 (d, J = 8.4 Hz, 1H), 6.59 (d, J = 3.6 Hz, 1H), 6.23 (d, J = 8.4 Hz, 1H), 4.81 (d, J = 6.0 Hz, 1H), 4.48-4.30 (m, 5H), 4.22-4.13 (m, 1H), 3.73-3.57 (m, 2H), 3.50-3.37 (m, 3H), 3.06-3.04 (m, 1H), 2.92-2.68 (m, 4H), 2.08-2.02 (m, 2H), 1.88-1.82 (m, 1H), 1.41-1.38 (m, 3H) | ++ | + |
| 405 | 3-amino-N-[(6S)-2-[(4R,5S)-4-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.30 (d, J = 8.4 Hz, 1H), 7.58 (d, J = 8.0 Hz, 1H), 7.31 (d, J = 8.0 Hz, 1H), 7.21-7.16 (m, 3H), 6.23 (d, J = 8.4 Hz, 1H), 4.15-4.09 (m, 1H), 3.85-3.49 (m, 4H), 3.30-3.28 (m, 3H), 2.77-2.70 (m, 4H), 2.59 (s, 3H), 2.23-2.15 (m, 2H), 2.08-1.84 (m, 5H), 1.76-1.68 (m, 1H) | +++ | ++ |
| 406 | 3-amino-N-[(6S)-2-[(4S,5R)-4-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.0 Hz, 1H), 7.58 (d, J = 8.0 Hz, 1H), 7.31 (d, J = 8.4 Hz, 1H), 7.21-7.17 (m, 3H), 6.23 (d, J = 8.4 Hz, 1H), 4.15-4.09 (m, 1H), 3.83-3.47 (m, 4H), 3.31-3.22 (m, 3H), 2.81-2.69 (m, 4H), 2.59 (s, 3H), 2.23-2.17 (m, 2H), 2.01- | ++ | + |

TABLE 24-continued

| | | | 1.81 (m, 5H), 1.73-1.68 (m, 1H) | | |
|---|---|---|---|---|---|
| 407 | 3-amino-N-[(6S)-2-[(4S,5S)-4-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.0 Hz, 1H), 7.58 (d, J = 8.4 Hz, 1H), 7.31 (d, J = 8.4 Hz, 1H), 7.20-7.17 (m, 3H), 6.22 (d, J = 8.0 Hz, 1H), 4.18-4.09 (m, 1H), 3.82-3.79 (m, 1H), 3.71-3.66 (m, 1H), 3.53-3.48 (m, 1H), 3.34-3.25 (m, 4H), 2.80-2.64 (m, 4H), 2.59 (s, 3H), 2.20-2.07 (m, 3H), 2.03-1.97 (m, 1H), 1.89-1.76 (m, 3H), 1.70-1.62(m, 1H) | +++ | + |
| 408 | 3-amino-N-[(6S)-2-[(4R,5R)-4-amino-1-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.4 Hz, 1H), 7.58 (d, J = 7.6 Hz, 1H), 7.31 (d, J = 8.0 Hz, 1H), 7.20-7.17 (m, 3H), 6.22 (d, J = 8.8 Hz, 1H), 4.18-4.09 (m, 1H), 3.84-3.79 (m, 1H), 3.71-3.66 (m, 1H), 3.54-3.50 (m, 1H), 3.34-3.25 (m, 4H), 2.76-2.68 (m, 4H), 2.59 (s, 3H), 2.18-2.07 (m, 2H), 2.03-1.98 (m, 2H), 1.86-1.76 (m, 2H), 1.70-1.64 (m, 1H) | +++ | + |
| 409 | 3-amino-N-[(3R)-7-[(4R,5S)-4-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.4 Hz, 1H), 7.51 (d, J = 7.6 Hz, 1H), 7.32 (d, J = 8.0 Hz, 1H), 7.23-7.17 (m, 2H), 6.87 (d, J = 8.0 Hz, 1H), 6.11 (d, J = 6.8 Hz, 1H), 5.92 (s, 1H), 4.28-4.26 (m, 1H), 4.15-4.13 (m, 1H), 3.82-3.68 (m, 3H), 3.54-3.52 (m, 1H), 3.27-3.21 (m, 3H), 2.99-2.96 (m, 1H), 2.86-2.83 (m, 2H), 2.59 (s, 3H), 2.19-2.12 (m, 1H), 2.03-1.96 (m, 1H), 1.86-1.82 (m, 1H), 1.70-1.64 (m, 1H) | ++++ | |
| 410 | 3-amino-N-[(3R)-7-[(4R,5R)-4-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.4 Hz, 1H), 7.51 (d, J = 7.2 Hz, 1H), 7.32 (d, J = 8.4 Hz, 1H), 7.22 (br s, 2H), 6.87 (d, J = 8.0 Hz, 1H), 6.09 (d, J = 6.8 Hz, 1H), 5.91 (s, 1H), 4.28-4.26 (m, 1H), 4.15-4.13 (m, 1H), 3.84-3.78 (m, 2H), 3.69-3.67 (m, 1H), 3.27-3.21 (m, 3H), 3.05-3.02 (m, 1H), 2.89-2.83 (m, 2H), 2.59 (s, 3H), 2.17-2.12 (m, 2H), 1.93-1.79 (m, 3H), 1.70-1.63 (m, 1H) | ++++ | |
| 411 | 3-amino-N-[(3R)-7-[(4S,5S)-4-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.32 (d, J = 8.0 Hz, 1H), 7.52 (d, J = 7.6 Hz, 1H), 7.32 (d, J = 8.4 Hz, 1H), 7.22 (br s, 2H), 6.86 (d, J = 8.4 Hz, 1H), 6.11-6.08 (m, 1H), 5.90 (s, 1H), 4.31-4.23 (m, 1H), 4.15-4.12 (m, 1H), 3.84-3.76 (m, 2H), 3.71-3.65 (m, 2H), 3.41-3.20 (m, 3H), 3.04-3.02 (m, 1H), 2.85-2.81 (m, 2H), 2.58 (s, 3H), 2.17-2.11 (m, 2H), 1.81-1.63 (m, 2H) | ++++ | |
| 412 | 3-amino-N-[(3R)-7-[(4S,5R)-4-amino-1-oxa-7-azaspiro[4.4]nonan-7-yl]-3,4-dihydro-2H-1-benzopyran-3-yl]-6-methylthieno[2,3-b]pyridine-2-carboxamide | 480 | (MeOH-d4, 400 MHz) δ (ppm): 8.22 (d, J = 8.4 Hz, 1H), 7.32 (d, J = 8.4 Hz, 1H), 6.92 (d, J = 8.4 Hz, 1H), 6.24-6.22 (m, 1H), 6.07 (s, 1H), 4.46-4.44 (m, 1H), 4.25-4.22 (m, 1H), 4.05-3.95 (m, 1H), 3.94-3.90 (m, 2H), 3.61 (d, J = 10.4 Hz, 1H), 3.54-3.52 (m, 1H), 3.41-3.33 (m, 2H), 3.24 (d, J = 10.4 | | |

TABLE 24-continued

| | | | |
|---|---|---|---|
| | | | Hz, 1H), 2.97-2.95 (m, 1H), 2.88-2.86 (m, 1H), 2.65 (s, 3H), 2.49-2.41 (m, 1H), 2.07-2.02 (m, 2H), 1.99-1.90 (m, 1H) |
| 413 | 3-amino-N-[(3R)-5-fluoro-7-[(1R)-1-methyl-9-oxa-3,7-diazabicyclo[3.3.1]nonan-3-yl]-3,4-dihydro-2H-1-benzopyran-3-yl]-6-methylthieno[2,3-b]pyridine-2-carboxamide | 498 | (DMSO-d6, 400 MHz) δ (ppm): 8.33 (d, J = 8.4 Hz, 1H), 7.59 (br s, 1H), 7.32 (d, J = 8.0 Hz, 1H), 7.24 (br s, 1H), 6.46 (d, J = 14.8 Hz, 1H), 6.24 (s, 1H), 4.32-4.28 (m, 1H), 4.20-4.17 (m, 1H), 3.89-3.84 (m, 1H), 3.79-3.63 (m, 3H), 3.00-2.85 (m, 5H), 2.79-2.61 (m, 3H), 2.55 (s, 3H), 0.99 (s, 3H). | ++++ | ++ |
| 414 | 3-amino-N-[(3R)-5-fluoro-7-[(1S)-1-methyl-9-oxa-3,7-diazabicyclo[3.3.1]nonan-3-yl]-3,4-dihydro-2H-1-benzopyran-3-yl]-6-methylthieno[2,3-b]pyridine-2-carboxamide | 498 | (DMSO-d6, 400 MHz) δ (ppm): 8.33 (d, J = 8.4 Hz, 1H), 7.59 (br s, 1H), 7.32 (d, J = 8.0 Hz, 1H), 7.24 (br s, 2H), 6.46 (d, J = 14.8 Hz, 1H), 6.24 (s, 1H), 4.29-4.27 (m, 1H), 4.20-4.17 (m, 1H), 3.89-3.84 (m, 1H), 3.78-3.64 (m, 3H), 3.00-2.85 (m, 5H), 2.79-2.61 (m, 3H), 2.59 (s, 3H), 2.20-2.10 (m, 1H), 0.99 (s, 3H). | +++ | ++ |
| 415 | 3-amino-N-[(3R)-7-[(3R,4R)-3-amino-4-methoxypyrrolidin-1-yl]-5,6-difluoro-3,4-dihydro-2H-1-benzopyran-3-yl]-6-methylthieno[2,3-b]pyridine-2-carboxamide | 490 | (DMSO-d6, 400 MHz) δ (ppm): 8.32 (d, J = 8.0 Hz, 1H), 7.58 (br s, 1H), 7.32 (d, J = 8.0 Hz, 1H), 7.23 (s, 2H), 6.03 (d, J = 6.4 Hz, 1H), 4.30-4.26 (m, 1H), 4.17-4.15 (m, 1H), 3.88-3.83 (m, 2H), 3.77-3.73 (m, 1H), 3.68-3.57 (m, 2H), 3.32-3.20 (m, 5H), 2.81-2.78 (m, 1H), 2.72-2.66 (m, 1H), 2.59 (s, 3H). | ++++ | ++ |
| 416 | 3-amino-N-[(3R)-7-[(3S,4S)-3-amino-4-methoxypyrrolidin-1-yl]-5,6-difluoro-3,4-dihydro-2H-1-benzopyran-3-yl]-6-methylthieno[2,3-b]pyridine-2-carboxamide | 490 | (DMSO-d6, 400 MHz) δ (ppm): 8.32 (d, J = 8.0 Hz, 1H), 7.58 (br s, 1H), 7.31 (d, J = 8.0 Hz, 1H), 7.23 (s, 2H), 5.97 (d, J = 7.6 Hz, 1H), 4.30-4.26 (m, 1H), 4.16-4.14 (m, 1H), 3.87-3.82 (m, 1H), 3.72-3.67 (m, 2H), 3.57-3.53 (m, 2H), 3.42-3.15(m, 5H), 2.81-2.78 (m, 1H), 2.72-2.66 (m, 1H), 2.59 (s, 3H). | ++++ | ++ |
| 417 | 3-amino-N-[(2S)-7,8-difluoro-6-(piperazin-1-yl)-1,2,3,4-tetrahydronaphthalen-2-yl]-6-methylthieno[2,3-b]pyridine-2-carboxamide | 458 | (DMSO-d6, 400 MHz) δ (ppm): 8.32 (d, J = 8.0 Hz, 1H), 7.64 (d, J = 7.6 Hz, 1H), 7.32 (d, J = 8.0 Hz, 1H), 7.24 (br, 2H), 6.59 (d, J = 7.6 Hz, 1H), 4.17-4.11 (m, 1H), 3.00-2.75 (m, 11H), 2.68-2.59 (m, 1H), 2.43 (s, 3H) 2.41 (br s, 1H) 1.98-1.96 (m, 1H), 1.81-1.71 (s, 1H). | ++ | + |
| 418 | 3-amino-N-[(2R)-7,8-difluoro-6-(piperazin-1-yl)-1,2,3,4-tetrahydronaphthalen-2-yl]-6-methylthieno[2,3-b]pyridine-2-carboxamide | 458 | (DMSO-d6, 400 MHz) δ (ppm): 8.32 (d, J = 8.0 Hz, 1H), 7.64 (d, J = 7.6 Hz, 1H), 7.32 (d, J = 8.0 Hz, 1H), 7.24 (br, 2H), 6.59 (d, J = 7.6 Hz, 1H), 4.17-4.11 (m, 1H), 3.00-2.75 (m, 11H), 2.68-2.60 (m, 1H), 2.59 (s, 3H) 1.98-1.96 (m, 1H), 1.81-1.71 (s, 1H). | +++ | ++ |
| 419 | 3-amino-N-[(6S)-2-[(2R,3R)-3-amino-2-(methoxymethyl)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.60 (br s, 1H), 7.31 (d, J = 8.0 Hz, 1H), 7.20 (d, J = 8.8 Hz, 1H),7.17 (br s, 2H), 6.27 (d, J = 8.4 Hz, 1H), 4.16-4.10 (m, 1H), 3.81-3.78 (m, 1H), 3.52-3.40 (m, 4H),3.34(s, 3H), 3.28-3.22 (m, 1H), 2.82-2.73 (m, 4H), 2.59 (s, 3H), 2.15-2.10 (m, 1H), 2.08-2.02 (m, 1H), | +++ | + |

TABLE 24-continued

| | | | | | |
|---|---|---|---|---|---|
| 420 | 3-amino-N-[(6S)-2-[(2S,3S)-3-amino-2-(methoxymethyl)pyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.58 (br s, 1H), 7.31 (d, J = 8.4 Hz, 1H), 7.20 (d, J = 8.8 Hz, 1H), 7.17 (br s, 2H), 6.28 (d, J = 8.4 Hz, 1H), 4.18-4.12 (m, 1H), 3.81-3.77 (m, 1H), 3.50-3.40 (m, 4H), 3.28 (s, 3H), 3.23-3.21 (m, 1H), 2.83-2.71 (m, 4H), 2.59 (s, 3H), 2.15-2.10 (m, 1H), 2.06-2.02 (m, 1H), 1.94-1.84 (m, 1H), 1.68-1.65 (m, 1H) 1.92-1.86 (m, 1H), 1.68-1.65 (m, 1H) | ++++ | +++ |
| 421 | N-[(6S)-2-[(3R,4S)-3-amino-4-(trifluoromethyl)pyrrolidin-1-yl]-5,6,7,8-tetrahydroquinolin-6-yl]-1-ethyl-1H-pyrrolo[2,3-b]pyridine-5-carboxamide | 473 | (DMSO-d6, 400 MHz) δ (ppm): 8.76 (s, 1H), 8.46-8.45 (m, 2H), 7.68 (br s, 1H), 7.25 (d, J = 8.0 Hz, 1H),6.59 (d, J = 3.6 Hz, 1H), 6.31 (d, J = 8.4 Hz, 1H), 4.32 (dd, J = 14.4, 3.2 Hz, 2H), 4.22-4.18 (m, 1H), 3.77-3.67 (m, 3H), 3.49-3.45 (m, 1H), 3.11-3.07 (m, 1H), 3.06-2.89 (m, 2H), 2.82-2.78 (m, 2H), 2.72-2.66 (m, 1H),2.12-1.98 (m, 3H), 1.93-1.83 (m, 1H), 1.39 (t, J = 8.4 Hz, 3H) | +++ | ++ |
| 422 | N-[(6S)-2-[(3S,4R)-3-amino-4-(trifluoromethyl)pyrrolidin-1-yl]-5,6,7,8-tetrahydroquinolin-6-yl]-1-ethyl-1H-pyrrolo[2,3-b]pyridine-5-carboxamide | 473 | (DMSO-d6, 400 MHz) δ (ppm): 8.76 (s, 1H), 8.46-8.45 (m, 2H), 7.68 (br s, 1H), 7.25 (d, J = 8.4 Hz, 1H),6.58 (d, J = 3.6 Hz, 1H), 6.31 (d, J = 8.4 Hz, 1H), 4.32 (dd, J = 14.4, 3.2 Hz, 2H), 4.22-4.18 (m, 1H), 3.77-3.68 (m, 3H), 3.47-3.43 (m, 1H),3.11-3.07 (m, 1H), 3.01-2.89 (m, 2H), 2.82-2.78 (m, 2H), 2.72-2.70 (m, 1H),2.12-2.06 (m, 1H), 1.96-1.82 (m, 3H), 1.39(t, J = 8.4 Hz, 3H) | ++ | + |
| 423 | 3-amino-N-[(3R)-7-[(3R,4R)-3-amino-4-(fluoromethyl)pyrrolidin-1-yl]-3,4-dihydro-2H-1-benzopyran-3-yl]-6-methylthieno[2,3-b]pyridine-2-carboxamide | 456 | (DMSO-d6, 400 MHz) δ (ppm): 8.32 (d, J = 8.0 Hz, 1H),7.50 (br s, 1H), 7.31 (d, J = 8.4 Hz, 1H), 7.22 (br s, 2H), 6.87 (d, J = 8.4 Hz, 1H), 6.09 (d, J = 8.4 Hz, 1H), 5.90 (s, 1H), 4.80-4.45 (m, 2H), 4.27-4.21 (m, 1H), 4.15-4.10 (m, 1H), 3.81-3.76 (m,1H), 3.61-3.60 (m, 1H), 3.34-3.32 (m, 1H), 3.28-3.26 (m, 1H), 3.16-3.12 (m, 1H), 2.97-2.95 (m, 1H), 2.89-2.82 (m, 2H), 2.59-2.57 (m, 4H), 1.89 (br s, 2H) | ++++ | |
| 424 | 3-amino-N-[(3R)-7-[(3S,4S)-3-amino-4-(fluoromethyl)pyrrolidin-1-yl]-3,4-dihydro-2H-1-benzopyran-3-yl]-6-methylthieno[2,3-b]pyridine-2-carboxamide | 456 | (DMSO-d6, 400 MHz) δ (ppm): 8.32 (d, J = 8.0 Hz, 1H),7.50 (br s, 1H), 7.31 (d, J = 8.0 Hz, 1H), 7.22 (br s, 2H), 6.87 (d, J = 8.4 Hz, 1H), 6.09 (d, J = 6.8 Hz, 1H), 5.90 (s, 1H), 4.81-4.46 (m, 2H), 4.29-4.23 (m, 1H), 4.15-4.12 (m, 1H), 3.81-3.76 (m, 1H), 3.61-3.60 (m, 1H), 3.42-3.34 (m, 1H), 3.28-3.26 (m, 1H), 3.16-3.12 (m, 1H), 2.97-2.95 (m, 1H), 2.89-2.83 (m, 2H), 2.59-2.57 (m, 4H), 1.86 (br s, 2H) | ++++ | ++ |
| 425 | N-[(3R)-7-[(3aS,6R,6aS)-6-amino-hexahydro-2H-furo[3,2-b]pyrrol-4-yl]-3,4-dihydro-2H-1-benzopyran-3-yl]-3-amino-6-methylthieno[2,3-b]pyridine-2-carboxamide | 466 | (DMSO-d6, 400 MHz) δ (ppm): 8.33 (d, J = 8.0 Hz, 1H), 7.51 (br s, 1H), 7.32 (d, J = 8.4 Hz, 1H), 7.22 (br s, 2H), 6.89 (d, J = 8.0 Hz, 1H), 6.18 (dd, J = 8.0, 2.0 Hz, 1H), 5.98 (s, 1H), 4.36-4.25 (m, 2H), 4.16-4.15 (m, 2H), 3.83-3.78 (m, 1H), 3.74-3.70 (m, 1H), 3.61-3.57 (m, 1H), 3.04-3.01 (m, | ++++ | |

TABLE 24-continued

| | | | | | |
|---|---|---|---|---|---|
| 426 | N-[(3R)-7-[(3aR,6S,6aR)-6-amino-hexahydro-2H-furo[3,2-b]pyrrol-4-yl]-3,4-dihydro-2H-1-benzopyran-3-yl]-3-amino-6-methylthieno[2,3-b]pyridine-2-carboxamide | 466 | (DMSO-d6, 400 MHz) δ (ppm): 8.33 (d, J = 8.4 Hz, 1H), 7.52 (br s, 1H), 7.31 (d, J = 8.0 Hz, 1H), 7.22 (br s, 2H), 6.89 (d, J = 8.4 Hz, 1H), 6.18 (dd, J = 8.0, 2.0 Hz, 1H), 5.98 (s, 1H), 4.36-4.25 (m, 2H), 4.16-4.13 (m, 2H), 3.83-3.78 (m, 1H), 3.74-3.70 (m, 1H), 3.61-3.57 (m, 1H), 3.04-3.01 (m, 1H), 2.87-2.82 (m, 3H), 2.59 (s, 3H), 2.08-2.02 (m, 1H), 1.88-1.84 (m, 1H), 1.76(br s, 2H) | ++++ | |
| 427 | 3-amino-N-[(6S)-2-[(3R,4S)-4-amino-3-methoxy-3-methylpyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.57 (br s, 1H), 7.31 (d, J = 8.4 Hz, 1H), 7.18 (d, J = 8.8 Hz, 1H), 7.16 (br s, 2H), 6.21 (d, J = 8.4 Hz, 1H), 4.17-4.10 (m, 1H), 3.78-3.75 (m, 1H), 3.52-3.48 (m, 1H), 3.17-3.13 (m, 4H), 3.09-3.06 (m, 1H), 2.99-2.95 (m, 1H), 2.82-2.68 (m, 4H), 2.59 (s, 3H), 2.03-2.00 (m, 1H), 1.92-1.84 (m, 1H), 1.61 (br s, 2H), 1.25 (s, 3H) | +++ | ++ |
| 428 | 3-amino-N-[(6S)-2-[(3S,4R)-4-amino-3-methoxy-3-methylpyrrolidin-1-yl]-5,6,7,8-tetrahydroquinolin-6-yl]-6-methylthieno[2,3-b]pyridine-2-carboxamide | 467 | (DMSO-d6, 400 MHz) δ (ppm): 8.31 (d, J = 8.0 Hz, 1H), 7.58 (br s, 1H), 7.31 (d, J = 8.4 Hz, 1H), 7.18 (d, J = 8.4 Hz, 1H), 7.16 (br s, 2H), 6.21 (d, J = 8.4 Hz, 1H), 4.17-4.10 (m, 1H), 3.80-3.77 (m, 1H), 3.53-3.49 (m, 1H), 3.18-3.14 (m, 4H), 3.08-3.05 (m, 1H), 2.98-2.93 (m, 1H), 2.82-2.68 (m, 4H), 2.59 (s, 3H), 2.03-2.00 (m, 1H), 1.92-1.84 (m, 1H), 1.61 (br s, 2H), 1.25 (s, 3H) | +++ | ++ |
| 429 | 3-amino-N-[(6S)-2-{7-amino-3,3-dioxo-3λ-thia-9-azabicyclo[3.3.1]nonan-9-yl}-5,6,7,8-tetrahydroquinolin-6-yl]-6-methylthieno[2,3-b]pyridine-2-carboxamide | 527 | (DMSO-d6, 400 MHz) δ (ppm): 8.31 (d, J = 8.4 Hz, 1H), 7.62 (br s, 1H), 7.36-7.30 (m, 2H), 7.17 (br s, 2H), 6.82 (d, J = 8.0 Hz, 1H), 5.31-5.25 (m, 2H), 4.19-4.12 (m, 1H), 3.24-3.21 (m, 3H), 3.11-3.06 (m, 2H), 2.88-2.63 (m, 6H), 2.59 (s, 3H), 2.27-2.18 (m, 2H), 2.05-1.99 (m, 1H), 1.93-1.86 (m, 3H) | ++++ | +++ |
| 430 | 3-amino-N-[(6S)-2-[(5S,9R)-9-amino-2-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.30 (d, J = 8.0 Hz, 1H), 7.56 (br s, 1H), 7.31 (d, J = 8.0 Hz, 1H), 7.18 (d, J = 8.4 Hz, 1H), 7.15 (br s, 2H), 6.21 (d, J = 8.4 Hz, 1H), 4.16-4.10 (m, 1H), 3.81-3.75 (m, 2H), 3.56-3.45 (m, 4H), 3.34-3.23 (m, 2H), 3.10-3.07 (m, 1H), 2.80-2.71 (m, 4H), 2.58 (s, 3H), 2.18-2.14 (m, 1H), 2.03-1.96 (m, 1H), 1.86-1.78 (m, 1H), 1.72 (br s, 2H), 1.58-1.54 (m, 1H) | +++ | + |
| 431 | 3-amino-N-[(6S)-2-[(5R,9S)-9-amino-2-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.30 (d, J = 8.0 Hz, 1H), 7.56 (br s, 1H), 7.31 (d, J = 8.0 Hz, 1H), 7.18 (d, J = 8.4 Hz, 1H), 7.15 (br s, 2H), 6.21 (d, J = 8.4 Hz, 1H), 4.16-4.10 (m, 1H), 3.81-3.75 (m, 2H), 3.56-3.45 (m, 4H), 3.34-3.23 (m, 2H), 3.10-3.07 (m, 1H), 2.80- | +++ | + |

TABLE 24-continued

| | | | | | |
|---|---|---|---|---|---|
| | | | 2.71 (m, 4H), 2.58 (s, 3H), 2.18-2.14 (m, 1H), 2.03-1.96 (m, 1H), 1.87-1.80 (m, 1H), 1.71 (br s, 2H), 1.61-1.57 (m, 1H) | | |
| 432 | 3-amino-N-[(3R)-7-[(5S,9S)-9-amino-2-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.0 Hz, 1H), 7.49 (br s, 1H), 7.32 (d, J = 8.4 Hz, 1H), 7.22 (br s, 2H), 6.88 (d, J = 8.4 Hz, 1H), 6.10 (dd, J = 8.4, 2.0 Hz, 1H), 5.91 (s, 1H), 4.32-4.26 (m, 1H), 4.16-4.13 (m, 1H), 3.81-3.77 (m, 3H), 3.58 (d, J = 8.4 Hz, 1H), 3.48 (d, J = 8.4 Hz, 1H), 3.43-3.40 (m, 1H), 3.34-3.30 (m, 2H), 3.17-3.15 (m, 1H), 3.03-3.01 (m, 1H), 2.89-2.81 (m, 2H), 2.59 (m, 3H), 2.21-2.17 (m, 1H), 1.68-1.61 (m, 1H) | ++++ | |
| 433 | 3-amino-N-[(3R)-7-[(5R,9S)-9-amino-2-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.0 Hz, 1H), 7.50 (br s, 1H), 7.32 (d, J = 8.4 Hz, 1H), 7.22 (br s, 2H), 6.87 (d, J = 8.0 Hz, 1H), 6.09 (d, J = 8.4 Hz, 1H), 5.89 (s, 1H), 4.31-4.27 (m, 1H), 4.15-4.12 (m, 1H), 3.93 (d, J = 8.8 Hz, 1H), 3.81-3.73 (m, 3H), 3.44-3.40 (m, 2H), 3.34-3.25 (m, 2H), 3.12-3.10 (m, 1H), 2.92-2.81 (m, 1H), 2.85-2.78 (m, 2H), 2.59 (s, 3H), 1.88-1.83 (m, 1H), 1.74-1.68 (m, 3H) | ++++ | |
| 434 | N-[(6S)-2-[(3aR,6aS)-3a-methoxy-octahydropyrrolo[2,3-c]pyrrol-5-yl]-5,6,7,8-tetrahydroquinolin-6-yl]-3-amino-6-methylthieno[2,3-b]pyridine-2-carboxamide | 479 | (DMSO-d6, 400 MHz) δ (ppm): 8.30 (d, J = 8.4 Hz, 1H), 7.57 (br s, 1H), 7.31 (d, J = 8.0 Hz, 1H), 7.21 (d, J = 8.4 Hz, 1H), 7.15 (br s, 2H), 6.31 (d, J = 8.4 Hz, 1H), 4.14-4.08 (m, 1H), 3.65-3.53 (m, 3H), 3.46-3.43 (m, 1H), 3.27-3.18 (m, 5H), 2.99-2.91 (m, 2H), 2.82-2.69 (m, 4H), 2.58 (s, 3H), 2.04-1.99 (m, 2H), 1.90-1.82 (m, 2H) | +++ | + |
| 435 | N-[(6S)-2-[(3aS,6aR)-3a-methoxy-octahydropyrrolo[2,3-c]pyrrol-5-yl]-5,6,7,8-tetrahydroquinolin-6-yl]-3-amino-6-methylthieno[2,3-b]pyridine-2-carboxamide | 479 | (DMSO-d6, 400 MHz) δ (ppm): 8.29 (d, J = 8.4 Hz, 1H), 7.57 (br s, 1H), 7.31 (d, J = 8.0 Hz, 1H), 7.21 (d, J = 8.4 Hz, 1H), 7.15 (br s, 2H), 6.31 (d, J = 8.4 Hz, 1H), 4.14-4.08 (m, 1H), 3.65-3.53 (m, 3H), 3.46-3.43 (m, 1H), 3.27-3.18 (m, 5H), 2.99-2.91 (m, 2H), 2.82-2.69 (m, 4H), 2.58 (s, 3H), 2.04-1.99 (m, 2H), 1.90-1.82 (m, 2H) | +++ | ++ |
| 436 | 3-amino-N-[(2S)-6-[(3R,4R)-3-amino-4-(fluoromethyl)pyrrolidin-1-yl]-1,2,3,4-tetrahydronaphthalen-2-yl]-6-methylthieno[2,3-b]pyridine-2-carboxamide | 454 | (MeOH-d4, 400 MHz) δ (ppm): 8.21 (d, J = 8.0 Hz, 1H), 7.32 (d, J = 8.4 Hz, 1H), 6.43 (dd, J = 8.4, 2.4 Hz, 1H), 6.35 (s, 1H), 4.81-4.61 (m, 3H), 4.26-4.21 (m, 1H), 3.81-3.79 (m, 1H), 3.57-3.53 (m, 3H), 3.45-3.41 (m, 1H), 3.24-3.21 (m, 1H), 3.01-2.89 (m, 3H), 2.79-2.73 (m, 2H), 2.66 (s, 3H), 2.14-2.11 (m, 1H), 1.89-1.81 (m, 1H) | ++++ | |
| 437 | 3-amino-N-[(6S)-2-[(5R,9R)-9-amino-2-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.4 Hz, 1H), 7.58 (br s, 1H), 7.31 (d, J = 8.0 Hz, 1H), 7.19 (d, J = 8.4 Hz, 1H), 7.17 (br s, 2H), 6.22 (d, J = 8.8 Hz, 1H), 4.15-4.10 (m, 1H), 3.93 (d, J = 8.8 Hz, 1H), 3.83-3.75 (m, 2H), 3.54-3.51 (m, 1H), 3.49-3.42 (m, 2H), 3.34-3.26 (m, 2H), 3.12-3.10 | +++ | + |

TABLE 24-continued

| | | | (m, 1H), 2.81-2.70 (m, 4H), 2.59 (s, 3H), 2.03-1.98 (m, 1H), 1.89-1.82 (m, 2H), 1.76-1.68 (m, 3H) | | |
|---|---|---|---|---|---|
| 438 | 3-amino-N-[(6S)-2-[(5S, 9S)-9-amino-2-oxa-7-azaspiro[4.4]nonan-7-yl]-5,6,7,8-tetrahydroquinolin-6-yl]-6-methylthieno[2,3-b]pyridine-2-carboxamide | 479 | (DMSO-d6, 400 MHz) δ (ppm): 8.31 (d, J = 8.4 Hz, 1H), 7.58 (br s, 1H), 7.31 (d, J = 8.4 Hz, 1H), 7.19 (d, J = 8.8 Hz, 1H), 7.16 (br s, 2H), 6.22 (d, J = 8.4 Hz, 1H), 4.15-4.10 (m, 1H), 3.93 (d, J = 8.8 Hz, 1H), 3.81-3.73 (m, 2H), 3.58-3.55 (m, 1H), 3.53-3.50 (m, 1H), 3.48-3.41 (m, 1H), 3.30-3.27 (m, 2H), 3.12-3.10 (m, 1H), 2.81-2.70 (m, 4H), 2.59 (s, 3H), 2.03-1.98 (m, 1H), 1.89-1.82 (m, 2H), 1.76-1.68 (m, 3H) | +++ | + |
| 439 | 3-amino-N-[(3R)-7-[(5R,9R)-9-amino-2-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.32 (d, J = 8.4 Hz, 1H), 7.48 (br s, 1H), 7.31 (d, J = 8.4 Hz, 1H), 7.21 (br s, 2H), 6.86 (d, J = 8.4 Hz, 1H), 6.08 (d, J = 6.8 Hz, 1H), 5.88 (s, 1H), 4.27-4.24 (m, 1H), 4.15-4.12 (m, 1H), 3.81-3.77 (m,3H), 3.55 (d, J = 8.4 Hz, 1H), 3.48 (d, J = 8.4 Hz, 1H),3.39-3.36 (m, 1H), 3.32-3.23 (m, 2H), 3.14-3.11 (m, 1H), 2.92-2.90 (m, 1H), 2.89-2.81 (m, 2H), 2.58 (s, 3H), 2.10-2.06 (m, 1H), 1.72 (br s, 2H), 1.61-1.57 (m, 1H) | ++++ | ++ |
| 440 | 3-amino-N-[(3R)-7-[(5S,9R)-9-amino-2-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.4 Hz, 1H), 7.49 (br s, 1H), 7.32 (d, J = 8.4 Hz, 1H), 7.21 (br s, 2H), 6.87 (d, J = 8.4 Hz, 1H), 6.09 (d, J = 6.8 Hz, 1H), 5.89 (s, 1H), 4.28-4.24 (m, 1H), 4.16-4.13 (m, 1H), 3.93 (d, J = 8.8 Hz, 1H), 3.82-3.71 (m, 3H), 3.44-3.40 (m, 2H),3.33-3.27 (m, 2H), 3.12-3.10 (m, 1H), 2.93-2.89 (m, 1H), 2.85-2.78 (m, 2H), 2.59 (s, 3H), 1.91-1.85 (m, 3H), 1.74-1.71 (m, 1H) | | |
| 441 | 3-amino-N-[(6S)-2-[(3R,4R)-3-(fluoromethyl)-4-(methylamino)pyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.0 Hz, 1H),7.57 (br s, 1H), 7.31 (d, J = 8.0 Hz, 1H), 7.20 (d, J = 8.4 Hz, 1H) 7.17 (br s, 2H), 6.26 (d, J = 8.8 Hz, 1H), 4.76-4.61 (m, 1H), 4.53-4.37 (m, 1H), 4.15-4.11 (m, 1H), 3.53-3.51 (m, 1H), 3.44-3.42 (m, 2H), 3.23-3.20 (m, 1H), 2.82-2.68 (m, 6H), 2.59 (s, 3H), 2.31 (s, 3H), 2.04-1.98 (m, 1H), 1.88-1.82 (m, 2H) | +++ | + |
| 442 | 3-amino-N-[(6S)-2-[(3S,4S)-3-(fluoromethyl)-4-(methylamino)pyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.30 (d, J = 8.0 Hz, 1H),7.58 (br s, 1H), 7.31 (d, J = 8.4 Hz, 1H), 7.20 (d, J = 8.4 Hz, 1H) 7.16 (br s, 2H), 6.26 (d, J = 8.4 Hz, 1H), 4.76-4.61 (m, 1H), 4.53-4.37 (m, 1H), 4.15-4.11 (m, 1H), 3.51-3.48 (m, 2H), 3.38-3.21 (m, 2H), 2.82-2.75 (m, 6H), 2.59 (s, 3H), 2.31 (s, 3H), 2.04-1.98 (m, 1H), 1.90-1.82 (m, 2H) | +++ | + |
| 443 | 3-amino-N-[(3R)-7-[(3R,4R)-3-(fluoromethyl)-4-(methylamino)pyrrolidin-1-yl]-3,4-dihydro-2H-1-benzopyran-3-yl]-6-methylthieno[2,3-b]pyridine-2-carboxamide | 470 | (DMSO-d6, 400 MHz) δ (ppm): 8.32 (d, J = 8.0 Hz, 1H), 7.51 (br s, 1H), 7.32 (d, J = 8.4 Hz, 1H), 7.21 (br s, 2H), 6.88 (d, J = 8.4 Hz, 1H), 6.12 (d, J = 7.6 Hz, 1H), 5.93 (s, 1H), 4.78-4.60 (m, 1H), 4.52-4.36 (m, | | |

TABLE 24-continued

| | | | |
|---|---|---|---|
| 444 | 3-amino-N-[(3R)-7-[(3S,4S)-3-(fluoromethyl)-4-(methylamino)pyrrolidin-1-yl]-3,4-dihydro-2H-1-benzopyran-3-yl]-6-methylthieno[2,3-b]pyridine-2-carboxamide | 470 | 1H), 4.32-4.25 (m, 1H), 4.15-4.13 (m, 1H), 3.82-3.77 (m, 1H), 3.40-3.37 (m, 3H), 3.23-3.21 (m, 1H), 3.08-3.06 (m, 1H), 2.87-2.83 (m, 2H), 2.78-2.69 (m, 1H), 2.59 (s, 3H), 2.30 (s, 3H), 1.91-1.84 (m, 1H), 1.83 (br s, 1H) (DMSO-d6, 400 MHz) δ (ppm): 8.33 (d, J = 8.0 Hz, 1H), 7.50 (br s, 1H), 7.32 (d, J = 8.4 Hz, 1H), 7.22 (br s, 2H), 6.88 (d, J = 8.4 Hz, 1H), 6.12 (dd, J = 8.4, 2.4 Hz, 1H), 5.93 (s, 1H), 4.75-4.61 (m, 1H), 4.51-4.36 (m, 1H), 4.32-4.25 (m, 1H), 4.15-4.13 (m, 1H), 3.82-3.77 (m, 1H), 3.40-3.37 (m, 3H), 3.23-3.21 (m, 1H), 3.08-3.06 (m, 1H), 2.87-2.83 (m, 2H), 2.78-2.69 (m, 1H), 2.59 (s, 3H), 2.30 (s, 3H), 1.91-1.84 (m, 1H), 1.82 (br s, 1H) | | | |
| 445 | 3-amino-N-[(6R)-2-[(3R,4R)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.4 Hz, 1H), 8.07 (s, 1H), 7.63 (br s, 1H), 7.31 (d, J = 8.4 Hz, 1H), 7.17 (br s, 2H), 4.80-4.47 (m, 2H), 4.14-4.08 (m, 1H), 3.61-3.57 (m, 5H), 2.84-2.64 (m, 4H), 2.60-2.57 (m, 4H), 2.04-1.98 (m, 1H), 1.91-1.84 (m, 1H), 1.72 (br s, 2H) | ++ | + |
| 446 | 3-amino-N-[(6R)-2-[(3S,4S)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.0 Hz, 1H), 8.07 (s, 1H), 7.63 (br s, 1H), 7.31 (d, J = 8.4 Hz, 1H), 7.17 (br s, 2H), 4.80-4.47 (m, 2H), 4.12-4.10 (m, 1H), 3.61-3.57 (m, 5H), 2.84-2.64 (m, 4H), 2.60-2.57 (m, 4H), 2.04-1.98 (m, 1H), 1.91-1.84 (m, 1H), 1.75 (br s, 2H) | ++ | + |
| 447 | 3-amino-N-[(2S)-6-[(3S,4S)-3-amino-4-(fluoromethyl)pyrrolidin-1-yl]-1,2,3,4-tetrahydronaphthalen-2-yl]-6-methylthieno[2,3-b]pyridine-2-carboxamide | 454 | (DMSO-d6, 400 MHz) δ (ppm): 8.30 (d, J = 8.4 Hz, 1H), 7.54 (br s, 1H), 7.31 (d, J = 8.0 Hz, 1H), 7.15 (br s, 2H), 6.89 (d, J = 8.4 Hz, 1H), 6.34 (d, J = 8.8 Hz, 1H), 6.25 (s, 1H), 4.80-4.52 (m, 2H), 4.13-4.07 (m, 1H), 3.77-3.74 (m, 1H), 3.27-3.22 (m, 3H), 3.14-3.12 (m, 1H), 2.86-2.68 (m, 6H), 2.59-2.57 (m, 4H), 1.99-1.93 (m, 1H), 1.82-1.71 (m, 1H) | | |
| 448 | N-((2S)-6-(9-oxa-3,7-diazabicyclo[3.3.1]nonan-3-yl)-1,2,3,4-tetrahydronaphthalen-2-yl)-7-amino-3-methylthieno[2,3-b]pyrazine-6-carboxamide | 465 | Library format synthesis, 1H NMR not taken. | ++++ | ++ | ++ |
| 449 | N-((2S)-6-(9-oxa-3,7-diazabicyclo[3.3.1]nonan-3-yl)-1,2,3,4-tetrahydronaphthalen-2-yl)-3-amino-6-methylthieno[2,3-b]pyridine-2-carboxamide | 464 | Library format synthesis, 1H NMR not taken. | | ++ | |
| 450 | N-((2R)-6-(9-oxa-3,7-diazabicyclo[3.3.1]nonan-3-yl)-1,2,3,4-tetrahydronaphthalen-2-yl)-7-amino-3-methylthieno[2,3-b]pyrazine-6-carboxamide | 465 | Library format synthesis, 1H NMR not taken. | ++ | + | + |
| 451 | N-((2R)-6-(9-oxa-3,7-diazabicyclo[3.3.1]nonan-3-yl)-1,2,3,4-tetrahydronaphthalen-2-yl)-3-amino-6-methylthieno[2,3-b]pyridine-2-carboxamide | 464 | Library format synthesis, 1H NMR not taken. | +++ | ++ | ++ |
| 452 | (R)-N-(6-(1,4-diazepan-1-yl)-1,2,3,4-tetrahydronaphthalen-2-yl)-7-amino-3-methylthieno[2,3-b]pyrazine-6-carboxamide | 437 | Library format synthesis, 1H NMR not taken. | ++ | + | + |

TABLE 24-continued

| # | Name | MW | Notes | | | |
|---|---|---|---|---|---|---|
| 453 | 7-amino-N-((R)-6-((S)-6-fluoro-1,4-diazepan-1-yl)-1,2,3,4-tetrahydronaphthalen-2-yl)-3-methylthieno[2,3-b]pyrazine-6-carboxamide | 455 | Library format synthesis, 1H NMR not taken. | +++ | ++ | ++ |
| 454 | (S)-7-amino-N-(6-(6,6-difluoro-1,4-diazepan-1-yl)-1,2,3,4-tetrahydronaphthalen-2-yl)-3-methylthieno[2,3-b]pyrazine-6-carboxamide | 473 | Library format synthesis, 1H NMR not taken. | | +++ | |
| 455 | (S)-N-(6-(1,4-diazepan-1-yl)-1,2,3,4-tetrahydronaphthalen-2-yl)-7-amino-3-methylthieno[2,3-b]pyrazine-6-carboxamide | 437 | Library format synthesis, 1H NMR not taken. | +++ | ++ | ++ |
| 456 | N-((2S)-6-(3-oxa-7,9-diazabicyclo[3.3.1]nonan-7-yl)-1,2,3,4-tetrahydronaphthalen-2-yl)-7-amino-3-methylthieno[2,3-b]pyrazine-6-carboxamide | 465 | Library format synthesis, 1H NMR not taken. | +++ | ++ | + |
| 457 | (R)-7-bromo-N-(7-(piperazin-1-yl)chroman-3-yl)pyrazolo[1,5-a]pyridine-3-carboxamide | 457 | Library format synthesis, 1H NMR not taken. | | ++ | |
| 458 | (R)-7-methyl-N-(7-(piperazin-1-yl)chroman-3-yl)pyrazolo[1,5-a]pyridine-3-carboxamide | 392 | Library format synthesis, 1H NMR not taken. | ++++ | | ++ |
| 459 | (R)-1-acetyl-N-(7-(piperazin-1-yl)chroman-3-yl)-1,2,3,4-tetrahydroquinoline-6-carboxamide | 435 | Library format synthesis, 1H NMR not taken. | + | + | + |
| 460 | (R)-N-(7-(piperazin-1-yl)chroman-3-yl)pyrazolo[1,5-a]pyridine-3-carboxamide | 378 | Library format synthesis, 1H NMR not taken. | + | + | + |
| 461 | (R)-5-methoxy-N-(7-(piperazin-1-yl)chroman-3-yl)pyrazolo[1,5-a]pyridine-3-carboxamide | 408 | Library format synthesis, 1H NMR not taken. | + | | + |
| 462 | (R)-6-chloro-N-(7-(piperazin-1-yl)chroman-3-yl)pyrazolo[1,5-a]pyridine-3-carboxamide | 412 | Library format synthesis, 1H NMR not taken. | + | + | + |
| 463 | (R)-5,7-dimethyl-N-(7-(piperazin-1-yl)chroman-3-yl)pyrazolo[1,5-a]pyrimidine-3-carboxamide | 407 | Library format synthesis, 1H NMR not taken. | + | + | + |
| 464 | (R)-6-chloro-N-(7-(piperazin-1-yl)chroman-3-yl)imidazo[1,2-b]pyridazine-2-carboxamide | 413 | Library format synthesis, 1H NMR not taken. | + | | + |
| 465 | (R)-5-methyl-N-(7-(piperazin-1-yl)chroman-3-yl)pyrazolo[1,5-a]pyridine-3-carboxamide | 392 | Library format synthesis, 1H NMR not taken. | + | | + |
| 466 | (R)-N-(7-(piperazin-1-yl)chroman-3-yl)pyrazolo[1,5-a]pyrimidine-3-carboxamide | 379 | Library format synthesis, 1H NMR not taken. | + | | + |
| 467 | (R)-6-((3-chlorobenzyl)amino)-N-(7-(piperazin-1-yl)chroman-3-yl)nicotinamide | 477 | Library format synthesis, 1H NMR not taken. | ++ | ++ | |
| 468 | (R)-N-(7-(piperazin-1-yl)chroman-3-yl)-6-((pyridin-3-ylmethyl)amino)nicotinamide | 445 | Library format synthesis, 1H NMR not taken. | ++ | + | + |
| 469 | (R)-N-(7-(piperazin-1-yl)chroman-3-yl)-6-((3-(trifluoromethyl)benzyl)amino)nicotinamide | 512 | Library format synthesis, 1H NMR not taken. | +++ | ++ | +++ |
| 470 | (R)-N-(7-(piperazin-1-yl)chroman-3-yl)-6-((pyridin-2-ylmethyl)amino)nicotinamide | 445 | Library format synthesis, 1H NMR not taken. | + | + | + |
| 471 | (R)-6-(((2,3-dihydrobenzo[b][1,4]dioxin-6-yl)methyl)amino)-N-(7-(piperazin-1-yl)chroman-3-yl)nicotinamide | 502 | Library format synthesis, 1H NMR not taken. | ++ | + | ++ |
| 472 | (R)-6-(((2,3-dihydrobenzofuran-5-yl)methyl)amino)-N-(7-(piperazin-1-yl)chroman-3-yl)nicotinamide | 486 | Library format synthesis, 1H NMR not taken. | ++ | ++ | ++ |
| 473 | (R)-6-((3-acetamidobenzyl)amino)-N-(7-(piperazin-1-yl)chroman-3-yl)nicotinamide | 501 | Library format synthesis, 1H NMR not taken. | ++ | + | + |
| 474 | 7-ethyl-N-[(3R)-7-(piperazin-1-yl)-3,4-dihydro-2H-1-benzopyran-3-yl]pyrazolo[1,5-a]pyridine-3-carboxamide | 406 | Library format synthesis, 1H NMR not taken. | ++++ | | ++ |
| 475 | 7-(hydroxymethyl)-N-[(3R)-7-(piperazin-1-yl)-3,4-dihydro-2H-1-benzopyran-3-yl]pyrazolo[1,5-a]pyridine-3-carboxamide | 408 | Library format synthesis, 1H NMR not taken. | ++ | | + |

TABLE 24-continued

| | | | | | |
|---|---|---|---|---|---|
| 525 | (R)-3-amino-6-methyl-N-(7-(piperazin-1-yl)-3,4-dihydro-2H-pyrano[2,3-b]pyridin-3-yl)thieno[2,3-b]pyridine-2-carboxamide | See above | See above | +++ | ++ |
| 526 | (R)-3-amino-N-(6-fluoro-7-(piperazin-1-yl)-3,4-dihydro-2H-pyrano[2,3-b]pyridin-3-yl)-6-methylthieno[2,3-b]pyridine-2-carboxamide | See above | See above | +++ | ++ |
| 539 | 3-amino-N-[(3R)-7-[(3R,4R)-3-amino-4-(fluoromethyl)pyrrolidin-1-yl]-2H,3H,4H-pyrano[2,3-b]pyridin-3-yl]-6-methylthieno[2,3-b]pyridine-2-carboxamide | | 457 | (MeOH-d4, 400 MHz) δ (ppm): 8.22 (d, J = 8.4 Hz, 1H), 7.32 (dd, J = 8.4, 4.8 Hz, 2H), 6.13 (d, J = 8.4 Hz, 1H), 4.81-4.60 (m, 2H), 4.60-4.50 (m, 1H), 4.50-4.40 (m, 1H), 4.15-4.05 (m, 1H), 3.75-3.70 (m, 1H), 3.70-3.60 (m, 1H), 3.60-3.51 (m, 1H), 3.45-3.35 (m, 2H), 3.00-2.92 (m, 1H), 2.90-2.82 (m, 1H), 2.77-2.70 (m, 1H), 2.65 (s, 3H) | +++ |
| 540 | 3-amino-N-[(3R)-7-[(3S,4S)-3-amino-4-(fluoromethyl)pyrrolidin-1-yl]-2H,3H,4H-pyrano[2,3-b]pyridin-3-yl]-6-methylthieno[2,3-b]pyridine-2-carboxamide | | 457 | (DMSO-d6, 400 MHz) δ (ppm): 8.33 (d, J = 8.4 Hz, 1H), 7.54 (br s, 1H), 7.35-7.20 (m, 4H), 6.02 (d, J = 8.4 Hz), 4.82-4.45 (m, 2H), 4.30-4.15 (m, 2H), 4.01-3.90 (m, 1H), 3.60-3.50 (m, 1H), 3.40-3.39 (m, 1H), 3.30-3.22 (m, 1H), 3.20-3.10 (m, 1H), 2.90-2.79 (m, 1H), 2.61-2.51 (m, 4H), 1.92 (br s, 2H) | +++ |
| 541 | 3-amino-N-[(3R)-7-[(3R,4S)-3-amino-4-(fluoromethyl)pyrrolidin-1-yl]-2H,3H,4H-pyrano[2,3-b]pyridin-3-yl]-6-methylthieno[2,3-b]pyridine-2-carboxamide | | 457 | (DMSO-d6, 400 MHz) δ (ppm): 8.33 (d, J = 8.4 Hz, 1H), 7.55 (br s, 1H), 7.33-7.23 (m, 4H), 6.02 (d, J = 8.0 Hz, 1H), 4.65-4.51 (m, 2H), 4.47-4.20 (m, 2H), 3.97-3.92 (m, 1H), 3.63-3.57 (m, 2H), 3.29-2.19 (m, 1H), 3.17-3.14 (m, 1H), 3.00-2.95 (m, 1H), 2.83-2.78 (m, 2H), 2.56 (s, 3H), 2.31-2.24 (m, 1H), 2.07 (br s, 2H) | ++ |

TABLE 24-continued

| | | | | |
|---|---|---|---|---|
| 542 | 3-amino-N-[(3R)-7-[(3S,4R)-3-amino-4-(fluoromethyl)pyrrolidin-1-yl]-2H,3H,4H-pyrano[2,3-b]pyridin-3-yl]-6-methylthieno[2,3-b]pyridine-2-carboxamide | 457 | (DMSO-d6, 400 MHz) δ (ppm): 8.33 (d, J = 8.4 Hz, 1H), 7.55 (br s, 1H), 7.33-7.23 (m, 4H), 6.02 (d, J = 8.0 Hz, 1H), 4.65-4.51 (m, 2H), 4.47-4.20 (m, 2H), 3.97-3.92 (m, 1H), 3.63-3.57 (m, 2H), 3.29-2.19 (m, 1H), 3.17-3.14 (m, 1H), 3.00-2.95 (m, 1H), 2.83-2.78 (m, 2H), 2.56 (s, 3H), 2.33-2.23 (m, 3H) | +++ |
| 543 | 3-amino-N-[(3R)-7-[(9S)-9-amino-1,4-dioxa-7-azaspiro[4.4]nonan-7-yl]-2H,3H,4H-pyrano[2,3-b]pyridin-3-yl]-6-methylthieno[2,3-b]pyridine-2-carboxamide | 483 | (DMSO-d6, 400 MHz) δ (ppm): 8.32 (d, J = 8.0 Hz, 1H), 7.54 (d, J = 7.6 Hz, 1H), 7.33-7.22 (m, 4H), 6.00 (d, J = 8.0 Hz, 1H), 4.35-4.22 (m, 2H), 4.01-3.95 (m, 5H), 3.55-3.45 (m, 2H), 3.30-3.28 (m, 2H), 3.07-2.98 (m, 1H), 2.84-2.79 (m, 2H), 2.59 (s, 3H), 1.62 (br s, 2H) | ++ |
| 544 | 3-amino-N-[(3R)-7-[(9R)-9-amino-1,4-dioxa-7-azaspiro[4.4]nonan-7-yl]-2H,3H,4H-pyrano[2,3-b]pyridin-3-yl]-6-methylthieno[2,3-b]pyridine-2-carboxamide | 483 | (DMSO-d6, 400 MHz) δ (ppm): 8.32 (d, J = 8.0 Hz, 1H), 7.54 (d, J = 7.6 Hz, 1H), 7.33-7.22 (m, 4H), 6.00 (d, J = 8.0 Hz, 1H), 4.35-4.22 (m, 2H), 4.04-3.90 (m, 5H), 3.58-3.45 (m, 2H), 3.30-3.27 (m, 2H), 3.03-2.97 (m, 1H), 2.84-2.79 (m, 2H), 2.59 (s, 3H), 1.62 (br s, 2H) | ++ |
| 601 | 6-amino-N-[(3R)-7-{3,8-diazabicyclo[3.2.1]octan-3-yl}-5,8-difluoro-3,4-dihydro-2H-1-benzopyran-3-yl]-2-methylthieno[2,3-d][1,3]thiazole-5-carboxamide | See above | See above | ++++ | +++ |
| 602 | 3-amino-N-[(2S)-5-cyano-6-{3,8-diazabicyclo[3.2.1]octan-3-y]}-8-fluoro-1,2,3,4-tetrahydronaphthalen-2-yl]-6-methylthieno [2,3-b]pyridine-2-carboxamide | See above | See above | ++++ | ++++ |
| 603 | 3-amino-N-[(2S)-6-{3,8-diazabicyclo[3.2.1]octan-3-yl}-5,8-difluoro-1,2,3,4-tetrahydronaphthalen-2-yl]-6-methylthieno[2,3-b]pyridine-2-carboxamide | See above | See above | ++++ | ++++ |
| 604 | 3-amino-N-((R)-5-fluoro-7-((3aS,6aS)-hexahydropyrrolo[3,4-b]pyrrol-1(2H)-yl)chroman-3-yl)-6-methylthieno[2,3-b]pyridine-2-carboxamide | See above | See above | ++++ | +++ |
| 606 | 5-chloro-N-[(3R)-8-cyano-7-{3,8-diazabicyclo[3.2.1]octan-3-yl}-5-fluoro-3,4-dihydro-2H-1-benzopyran-3-yl]-7-ethyl-7Hpyrrolo[2,3-c]pyridazine-3-carboxamide | See above | See above | ++ | ++ |

TABLE 24-continued

| | | | | |
|---|---|---|---|---|
| 611-1 | 3-amino-N-[(3R)-7-[(4S,5R)-4-amino-6-oxa-2-azaspiro[4.5]decan-2-yl]-3,4-dihydro-2H-1-benzopyran-3-yl]-6-methylthieno[2,3-b]pyridine-2-carboxamide | See above | See above | ++++ |
| 611-2 | 3-amino-N-[(3R)-7-[(4R,5S)-4-amino-6-oxa-2-azaspiro[4.5]decan-2-yl]-3,4-dihydro-2H-1-benzopyran-3-yl]-6-methylthieno [2,3-b]pyridine-2-carboxamide | See above | See above | ++++ |
| 612-1 | 3-amino-N-[(3R)-7-[(4S,5R,9S)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide | See above | See above | ++++ |
| 612-2 | 3-amino-N-[(3R)-7-[(4R,5R,9S)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide | See above | See above | ++++ |
| 612-3 | 3-amino-N-[(3R)-7-[(4S,5S,9R)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide | See above | See above | ++++ |
| 612-4 | 3-amino-N-[(3R)-7-[(4R,5S,9R)-9-amino-4-methyl-1-oxa-7-azaspiro[4.4]nonan-7-yl]-3,4-dihydro-2H-1-benzopyran-3-yl]-6-methylthieno[2,3-b]pyridine-2-carboxamide | See above | See above | ++++ |
| 652 | 3-amino-N-[(3R)-7-[(4S,5S)-4-amino-6-oxa-2-azaspiro[4.5]decan-2-yl]-3,4-dihydro-2H-1-benzopyran-3-yl]-6-methylthieno[2,3-b]pyridine-2-carboxamide | 494 | (DMSO-d6, 400 MHz) δ (ppm): 8.33 (d, J = 8.4 Hz, 1H), 7.49 (br s, 1H), 7.31 (d, J = 8.4 Hz, 1H), 7.21 (br s, 2H), 6.86 (d, J = 8.4 Hz, 1H), 6.10-6.07 (m, 1H), 5.89 (s, 1H), 4.31-4.21 (m, 1H), 4.15-4.12 (m, 1H), 3.81-3.76 (m, 1H), 3.67-3.64 (m, 1H), 3.56-3.54 (m, 1H), 3.44-3.40 (m, 1H), 3.28-3.23 (m, 3H), 2.91-2.81 (m, 3H), 2.59 (s, 3H), 1.71-1.66 (m, 2H), 1.60-1.53 (m, 4H), 1.48-1.47 (m, 2H) | ++++ |
| 653 | 3-amino-N-[(3R)-7-[(4R,5R)-4-amino-6-oxa-2-azaspiro[4.5]decan-2-yl]-3,4-dihydro-2H-1-benzopyran-3-yl]-6-methylthieno[2,3-b]pyridine-2-carboxamide | 494 | (DMSO-d6, 400 MHz) δ (ppm): 8.33 (d, J = 8.4 Hz, 1H), 7.48 (br s, 1H), 7.31 (d, J = 8.0 Hz, 1H), 7.21 (br s, 2H), 6.86 (d, J = 8.4 Hz, 1H), 6.09-6.07 (m, 1H), 5.89 (s, 1H), 4.31-4.21 (m, 1H), 4.15-4.12 (m, 1H), 3.81-3.76 (m, 1H), 3.67-3.64 (m, 1H), 3.55-3.54(m, 1H), 3.44-3.40 (m, 1H), 3.28-3.23 (m, 3H), 2.91-2.81 (m, 3H), 2.59 (s, 3H), 1.71-1.67 (m, 2H), 1.59-1.51 (m, 4H), 1.48-1.47 (m, 2H) | ++++ |
| 654 | N-[(3R)-7-[(3aS,6aS)-3,3-difluorooctahydropyrrolo[3,4-b]pyrrol-5-yl]-3,4-dihydro-2H-1-benzopyran-3-yl]-3-amino-6-methylthieno[2,3-b]pyridine-2-carboxamide | 486 | (DMSO-d6, 400 MHz) δ (ppm): 8.33 (d, J = 8.0 Hz, 1H), 7.52 (br s, 1H), 7.32 (d, J = 8.4 Hz, 1H), 7.23 (br s, 2H), 6.90 (d, J = 8.4 Hz, 1H), 6.27 (dd, J = 8.4, 2.0 Hz, 1H), 6.08 (s, 1H), 4.40-4.20 (m, 1H), 4.20-4.05 (m, 2H), 3.82-3.80 (m, 1H), 3.49-3.45 (m, 1H), 3.22-3.20 (m, 5H), 3.16-3.14 (m, 1H), 2.87-2.85 (m, 2H), 2.59 (s, 3H). | ++++ |

TABLE 24-continued

| 655 | N-[(3R)-7-[(6aR)-3,3-difluorooctahydropyrrolo[3,4-b]pyrrol-5-yl]-3,4-dihydro-2H-1-benzopyran-3-yl]-3-amino-6-methylthieno[2,3-b]pyridine-2-carboxamide | 486 | (DMSO-d6, 400 MHz) δ (ppm): 8.33 (d, J = 8.4 Hz, 1H), 7.52 (br s, 1H), 7.32 (d, J = 8.4 Hz, 1H), 7.23 (br s, 2H), 6.90 (d, J = 8.4 Hz, 1H), 6.27 (dd, J = 8.4, 2.0 Hz, 1H), 6.08 (s, 1H), 4.30-4.26 (m, 1H), .17-4.09 (m, 2H), 3.82-3.80 (m, 1H), 3.48-3.45 (m, 1H), 3.34-3.17 (m, 5H), 3.15-3.02 (m, 1H), 2.87-2.84 (m, 2H), 2.59 (s, 3H). | ++++ | |
| --- | --- | --- | --- | --- | --- |
| 656 | 3-amino-N-[(3R)-7-[(5S,9R)-9-amino-2-oxa-7-azaspiro[4.4]nonan-7-yl]-3,4-dihydro-2H-1-benzopyran-3-yl]-6-methylthieno[2,3-b]pyridine-2-carboxamide | 480 | (DMSO-d6, 400 MHz) δ (ppm): 8.33 (d, J = 8.4 Hz, 1H), 7.49 (br s, 1H), 7.32 (d, J = 8.4 Hz, 1H), 7.21 (br s, 2H), 6.87 (d, J = 8.4 Hz, 1H), 6.09 (d, J = 6.8 Hz, 1H), 5.89 (s, 1H), 4.28-4.24 (m, 1H), 4.16-4.13 (m, 1H), 3.93 (d, J = 8.8 Hz., 1H), 3.82-3.71 (m, 3H), 3.44-3.40 (m, 2H),3.33-3.27 (m, 2H), 3.12-3.10 (m, 1H), 2.93-2.89 (m, 1H), 2.85-2.78 (m, 2H), 2.59 (s, 3H), 1.91-1.85 (m, 3H), 1.74-1.71 (m, 1H) | ++++ | ++ |
| 657 | 3-amino-N-[(2S)-6-[(3S,4S)-3-amino-4-(fluoromethyl)pyrrolidin-1-yl]-1,2,3,4-tetrahydronaphthalen-2-yl]-6-methylthieno[2,3-b]pyridine-2-carboxamide | 454 | (DMSO-d6, 400 MHz) δ (ppm): 8.30 (d, J = 8.4 Hz, 1H), 7.54 (br s, 1H), 7.31 (d, J = 8.0 Hz, 1H), 7.15 (br s, 2H), 6.89 (d, J = 8.4 Hz, 1H), 6.34 (d, J = 8.8 Hz, 1H), 6.25 (s, 1H), 4.80-4.52 (m, 2H), 4.13-4.07 (m, 1H), 3.77-3.74 (m, 1H), 3.27-3.22 (m, 3H), 3.14-3.12 (m, 1H), 2.86-2.68 (m, 6H), 2.59-2.57 (m, 4H), 1.99-1.93 (m, 1H), 1.82-1.71 (m, 1H) | +++ | ++ |
| 658 | 3-amino-N-[(3R)-7-[(3R,4R)-4-amino-3-(fluoromethyl)-3-methylpyrrolidin-1-yl]-3,4-dihydro-2H-1-benzopyran-3-yl]-6-methylthieno[2,3-b]pyridine-2-carboxamide | 470 | (DMSO-d6, 400 MHz) v (ppm): 8.33 (d, J = 8.4 Hz, 1H), 7.50 (br s, 1H), 7.31 (d, J = 8.4 Hz, 1H), 7.22 (br s, 2H), 6.89 (d, J = 8.4 Hz, 1H), 6.10 (d, J = 8.0 Hz, 1H), 5.91 (s, 1H), 4.43-4.41 (m, 1H), 4.31-4.25 (m, 2H), 4.16-4.13 (m, 1H), 3.82-3.77 (m, 1H), 3.56-3.52 (m, 2H), 3.23-3.21 (m, 1H), 3.13-3.11 (m, 2H), 2.86-2.83 (m, 2H), 2.58 (s, 3H), 1.06 (m,3H). | ++++ | +++ |
| 659 | 3-amino-N-[(3R)-7-[(3S,4R)-4-amino-3-(fluoromethyl)-3-methylpyrrolidin-1-yl]-3,4-dihydro-2H-1-benzopyran-3-yl]-6-methylthieno[2,3-b]pyridine-2-carboxamide | 470 | (DMSO-d6, 400 MHz) δ (ppm): 8.33 (d, J = 8.4 Hz, 1H), 7.50 (br s, 1H), 7.32 (d, J = 8.4 Hz, 1H), 7.22 (br s, 2H), 6.88 (d, J = 8.4 Hz, 1H), 6.11-6.08 (m, 1H), 5.89 (s, 1H), 4.54-4.52 (m, 1H), 4.42-4.40 (m, 1H), 4.30-4.26 (m, 1H), 4.16-4.13 (m, 1H), 3.82-3.77 (m, 1H), 3.52-3.48 (m, 1H), 3.23-3.21 (m, 2H), 3.03-2.94 (m, 2H), 2.86-2.82 (m, 2H), 2.58 (s, 3H), 1.12 (m, 3H). | ++++ | +++ |
| 660 | 3-amino-N-[(3R)-7-[(3S,4S)-4-amino-3-(fluoromethyl)-3-methylpyrrolidin-1-yl]-3,4-dihydro-2H-1-benzopyran-3-yl]-6-methylthieno[2,3-b]pyridine-2-carboxamide | 470 | (DMSO-d6, 400 MHz) δ (ppm): 8.33 (d, J = 8.4 Hz, 1H), 7.50 (br s, 1H), 7.32 (d, J = 8.0 Hz, 1H), 7.22 (br s, 2H), 6.87 (d, J = 8.4 Hz, 1H), 6.09-6.06 (m, 1H), 5.87 (s, 1H), 4.41-4.40 (m, 2H), 4.29-4.25 (m, 2H), 4.15-4.13 (m, 1H), 3.82-3.77 (m, 1H), 3.46-3.42 (m, 1H), 3.30-3.28 (m, 1H), 3.22-3.19 (m, 1H), 3.06-3.04 (m, 1H), 2.94-2.90 (m, | ++++ | ++++ |

TABLE 24-continued

| | | | | | |
|---|---|---|---|---|---|
| | | | 1H), 2.85-2.82 (m, 2H), 2.59 (s, 3H), 1.72 (br s, 2H), 0.99 (s, 3H). | | |
| 661 | 3-amino-N-[(3R)-7-[(3R,4S)-4-amino-3-(fluoromethyl)-3-methylpyrrolidin-1-yl]-3,4-dihydro-2H-1-benzopyran-3-yl]-6-methylthieno[2,3-b]pyridine-2-carboxamide | 470 | (DMSO-d6, 400 MHz) δ (ppm): 8.33 (d, J = 8.4 Hz., 1H), 7.50 (br s, 1H), 7.32 (d, J = 8.4 Hz, 1H), 7.22 (br s, 2H), 6.87 (d, J = 8.4 Hz, 1H), 6.10-6.07 (m, 1H), 5.87 (s, 1H), 4.52-4.50 (m, 1H), 4.40-4.38 (m, 1H), 4.29-4.27 (m, 1H), 4.16-4.12 (m, 1H), 3.82-3.77 (m, 1H), 3.49-3.45 (m, 1H), 3.33-3.31 (m, 1H), 3.26-3.23 (m, 1H), 2.96-2.91 (m, 2H), 2.85-2.82 (m, 2H), 2.59 (s, 3H), 1.72 (br s, 2H), 1.12 (s, 3H). | ++++ | +++ |
| 662 | 3-amino-N-[(3R)-7-[(3S,4R)-3-(fluoromethyl)-4-(methylamino)pyrrolidin-1-yl]-3,4-dihydro-2H-1-benzopyran-3-yl]-6-methylthieno[2,3-b]pyridine-2-carboxamide | 470 | (DMSO-d6, 400 MHz) δ (ppm): 8.33 (d, J = 8.0 Hz, 1H), 7.51 (br s, 1H), 7.32 (d, J = 8.4 Hz, 1H), 7.22 (br s, 2H), 6.88 (d, J = 8.4 Hz, 1H), 6.15 (d, J = 7.6 Hz, 1H), 6.14 (s, 1H), 4.59-4.13 (m,4H), 3.81-3.77 (m, 1H), 3.50-3.41 (m, 2H), 3.08-2.82 (m, 5H), 2.59 (s, 3H), 2.45-2.39 (m, 1H), 2.32 (s, 3H). | ++++ | ++++ |
| 663 | 3-amino-N-[(3R)-7-[(3R,4S)-3-(fluoromethyl)-4-(methylamino)pyrrolidin-1-yl]-3,4-dihydro-2H-1-benzopyran-3-yl]-6-methylthieno[2,3-b]pyridine-2-carboxamide | 470 | (DMSO-d6, 400 MHz) δ (ppm): 8.33 (d, J = 8.0 Hz, 1H), 7.52 (br s, 1H), 7.32 (d, J = 8.4 Hz, 1H), 7.22 (br s, 2H), 6.88 (d, J = 8.4 Hz, 1H), 6.15 (dd, d, J = 8.4, 2.4 Hz, 1H), 6.14 (s, 1H), 4.59-4.13 (m, 4H), 3.81-3.77 (m, 1H), 3.50-3.41 (m, 2H), 3.08-2.82 (m, 5H), 2.59 (s, 3H), 2.45-2.39 (m, 1H), 2.32 (s, 3H), 2.10 (br s, 1H). | ++++ | +++ |
| 664 | 3-amino-N-[(3R)-7-[(1S,6R)-3,8-diazabicyclo[4.2.0]octan-8-yl]-5-fluoro-3,4-dihydro-2H-1-benzopyran-3-yl]-6-methylthieno[2,3-b]pyridine-2-carboxamide | 468 | (CDCl3, 400 MHz) δ (ppm): 7.81 (d, J = 8.0 Hz, 1H), 7.20 (br s, 1H), 6.06 (br s, 2H), 5.95-5.89 (m, 2 H), 5.71 (d, J = 7.6 Hz, 1H), 4.62-4.61 (m, 1H), 4.20-4.18 (m, 2H), 3.89-3.87 (m, 1H), 3.71-3.68 (m, 1H), 3.57-3.55 (m, 1H), 3.34-3.31 (m, 1H), 3.15-3.12 (m, 1H), 3.04-2.95 (m, 2H), 2.84-2.80 (m, 1H), 2.69 (s, 3H), 2.63-2.56 (m,2H), 2.11-2.07 (m, 1H), 1.81-1.78 (m, 1H). | ++++ | |
| 665 | 3-amino-N-[(3R)-7-[(1R,6S)-3,8-diazabicyclo[4.2.0]octan-8-yl]-5-fluoro-3,4-dihydro-2H-1-benzopyran-3-yl]-6-methylthieno[2,3-b]pyridine-2-carboxamide | 468 | (CDCl3, 400 MHz) δ (ppm): 7.81 (d, J = 8.4 Hz, 1H), 7.20 (br s, 1H), 6.06 (br s, 2H), 5.95-5.90 (m, 2H), 5.71 (d, J = 7.6 Hz, 1H), 4.63-4.61 (m, 1H), 4.49-4.48 (m, 2H), 3.90-3.88 (m, 1H), 3.71-3.68 (m, 1H), 3.57-3.55 (m, 1H), 3.34-3.31 (m, 1H), 3.16-3.12 (m, 1H), 3.05-2.95 (m, 2H), 2.84-2.78 (m, 1H), 2.69 (s, 3H), 2.63-2.57 (m, 2H), 2.11-2.07 (m, 1H), 1.81-1.78 (m, 1H). | ++++ | +++ |
| 666 | N-[(3R)-7-[(3aS,6aS)-3a-methoxyoctahydropyrrolo[2,3-c]pyrrol-5-yl]-3,4-dihydro-2H-1-benzopyran-3-yl]-3-amino-6-methylthieno[2,3-b]pyridine-2-carboxamide | 480 | (DMSO-d6, 400 MHz) δ (ppm): 8.33 (d, J = 8.4 Hz, 1H), 7.49 (br s, 1H), 7.32 (d, J = 8.4 Hz, 1H), 7.22 (br s, 2H), 6.86 (d, J = 8.4 Hz, 1H), 6.09 (dd, J = 8.4, 1.6 Hz, 1H), 5.91 (s, 1H), 4.30-4.26 (m, 1H), 4.15-4.12 (m, 1H), 3.81-3.76 (m, 1H), 3.50-3.47 (m, 1H), 3.37-3.35 (m, 1H), 3.24-3.11 (m, 6H), 3.03-2.95 (m, 2H), 2.85-2.79 (m, 2H), 2.59 (s, | ++++ | |

TABLE 24-continued

| | | | | |
|---|---|---|---|---|
| 667 | N-[(3R)-7-[(3aR,6aR)-3a-methoxyoctahydropyrrolo[2,3-c]pyrrol-5-yl]-3,4-dihydro-2H-1-benzopyran-3-yl]-3-amino-6-methylthieno[2,3-b]pyridine-2-carboxamide | 480 | (DMSO-d6, 400 MHz) δ (ppm): 8.33 (d, J = 8.4 Hz, 1H), 7.49 (br s, 1H), 7.32 (d, J = 8.4 Hz, 1H), 7.22 (br s, 2H), 6.86 (d, J = 8.0 Hz, 1H), 6.09 (dd, J = 8.4, 2.0 Hz, 1H), 5.91 (s, 1H), 4.30-4.26 (m, 1H), 4.15-4.12 (m, 1H), 3.82-3.77 (m, 1H), 3.50-3.47 (m, 1H), 3.37-3.35 (m, 1H), 3.24-3.11 (m, 6H), 3.03-2.95 (m, 2H), 2.85-2.79 (m, 2H), 2.59 (s, 3H), 2.18 (br s, 1H), 2.04-1.99 (m, 2H), 1.57-1.50 (m, 1H). | ++++ |
| 668 | 3-amino-N-[(3R)-7-[(3R,4S)-3-(ethylamino)-4-(methoxymethyl)pyrrolidin-1-yl]-3,4-dihydro-2H-1-benzopyran-3-yl]-6-methylthieno[2,3-b]pyridine-2-carboxamide | 496 | (DMSO-d6, 400 MHz) δ (ppm): 8.31 (d, J = 8.0 Hz, 1H), 7.50 (d, J = 7.6 Hz, 1H), 7.31 (d, J = 8.0 Hz, 1H), 7.22 (br s, 2H), 6.86 (d, J = 8.4 Hz, 1H), 6.13-6.10 (m, 1H), 5.91 (s, 1H), 4.32-4.23 (m, 1H), 4.15-4.12 (m, 1H), 3.81-3.76 (m, 1H), 3.47-3.43 (m, 2H), 3.36-3.34 (m, 1H), 3.32-3.29 (m, 1H), 3.27 (s, 3H), 3.11-3.08 (m, 1H), 2.99-2.96 (m, 1H), 2.94-2.90 (m, 1H), 2.85-2.82 (m, 2H), 2.59-2.50 (m, 5H), 2.31-2.29 (m, 1H), 1.76 (br s, 1H), 1.04-1.00 (m, 3H). | ++++ |
| 669 | 3-amino-N-[(3R)-7-[(3S,4R)-3-(ethylamino)-4-(methoxymethyl)pyrrolidin-1-yl]-3,4-dihydro-2H-1-benzopyran-3-yl]-6-methylthieno[2,3-b]pyridine-2-carboxamide | 496 | (DMSO-d6, 400 MHz) δ (ppm 8.33 (d, J = 8.0 Hz, 1H), 7.50 (d, J = 7.6 Hz, 1H), 7.31 (d, J = 8.0 Hz, 1H), 7.22 (br s, 2H), 6.86 (d, J = 8.4 Hz, 1H), 6.13-6.10 (m, 1H), 5.91 (s, 1H), 4.32-4.24 (m, 1H), 4.15-4.12 (m, 1H), 3.81-3.76 (m, 1H), 3.47-3.43 (m, 2H), 3.36-3.34 (m, 1H), 3.32-3.29 (m, 1H), 3.27 (s, 3H), 3.09-3.05 (m, 1H), 3.00-2.98 (m, 1H), 2.96-2.90 (m, 1H), 2.85-2.82 (m, 2H), 2.59-2.50 (m, 5H), 2.31-2.29 (m, 1H), 1.76 (br s, 1H), 1.04-1.00 (m, 3H). | |
| 670 | 3-amino-N-[(3R)-7-[(3S,4R)-3-(methoxymethyl)-4-[($^2$H$_\square$)methylamino]pyrrolidin-1-yl]-3,4-dihydro-2H-1-benzopyran-3-yl]-6-methylthieno[2,3-b]pyridine-2-carboxamide | 485 | (DMSO-d6, 400 MHz) δ (ppm): 8.33 (d, J = 8.4 Hz, 1H), 7.50 (d, J = 7.6 Hz, 1H), 7.32 (d, J = 8.4 Hz, 1H), 7.22 (br s, 2H), 6.87 (d, J = 8.4 Hz, 1H), 6.13-6.11 (m, 1H), 5.92 (s, 1H), 4.30-4.21 (m, 1H), 4.15-4.11 (m, 1H), 3.81-3.78 (m, 1H), 3.45-3.42 (m, 2H), 3.34-3.29 (m, 2H), 3.27 (s, 3H), 3.01-2.89 (m, 3H), 2.84-2.82 (m, 2H), 2.59 (s, 3H), 2.33-2.28 (m, 1H), 1.94-1.87 (m, 1H) | ++++ |
| 671 | 3-amino-N-[(3R)-7-[(3R,4S)-3-(methoxymethyl)-4-[($^2$H$_\square$)methylamino]pyrrolidin-1-yl]-3,4-dihydro-2H-1-benzopyran-3-yl]-6-methylthieno[2,3-b]pyridine-2-carboxamide | 485 | (DMSO-d6, 400 MHz) δ (ppm): 8.33 (d, J = 8.4 Hz., 1H), 7.50 (d, J = 7.6 Hz, 1H), 7.32 (d, J = 8.0 Hz, 1H), 7.22 (br s, 2H), 6.87 (d, J = 8.4 Hz, 1H) , 6.13-6.11 (m, 1H), 5.92 (s, 1H), 4.30-4.21 (m, 1H), 4.15-4.11 (m, 1H), 3.81-3.78 (m, 1H), 3.45-3.42 (m, 2H), 3.34-3.29 (m, 2H), 3.27 (s, 3H), 3.01-2.89 (m, 3H), 2.84-2.82 (m, 2H), 2.59 (s, 3H), 2.33-2.28 (m, 1H), 1.94-1.87 (m, 1H). | ++++ |

TABLE 24-continued

| | | | | |
|---|---|---|---|---|
| 672 | 3-amino-N-[(3R)-7-[(3R,4R)-3-amino-4-[(trifluoromethoxy)methyl]pyrrolidin-1-yl]-3,4-dihydro-2H-1-benzopyran-3-yl]-6-methylthieno[2,3-b]pyridine-2-carboxamide | 522 | (DMSO-d6, 400 MHz) δ (ppm): 8.33 (d, J = 8.0 Hz, 1H), 7.51 (d, J = 7.6 Hz, 1H), 7.32 (d, J = 8.4 Hz, 1H), 7.22 (br s, 2H), 6.88 (d, J = 8.4 Hz, 1H), 6.12 (d, J = 7.6 Hz, 1H), 5.90 (s, 1H), 4.41-4.38 (m, 1H), 4.35-4.23 (m, 1H), 4.17-4.11 (m, 2H), 3.81-3.77 (m, 1H), 3.63-3.59 (m, 1H), 3.43-3.29 (m, 2H), 3.19-3.13 (m, 1H), 3.02-2.97 (m, 1H), 2.89-2.79 (m, 2H), 2.59-2.55 (m, 4H), 2.10 (br s, 2H). | +++ |
| 673 | 3-amino-N-[(3R)-7-[(3S,4S)-3-amino-4-[(trifluoromethoxy)methyl]pyrrolidin-1-yl]-3,4-dihydro-2H-1-benzopyran-3-yl]-6-methylthieno[2,3-b]pyridine-2-carboxamide | 522 | (DMSO-d6, 400 MHz) δ (ppm): 8.32 (d, J = 8.4 Hz, 1H), 7.51 (d, J = 7.6 Hz, 1H), 7.32 (d, J = 8.4 Hz, 1H), 7.22 (br s, 2H), 6.88 (d, J = 8.4 Hz, 1H), 6.12-6.09 (m, 1H), 5.91 (s, 1H), 4.40-4.36 (m, 1H), 4.31-4.23 (m, 1H), 4.15-4.11 (m, 2H), 3.82-3.77 (m, 1H), 3.62-3.60 (m, 1H), 3.43-3.30 (m, 2H), 3.17-3.13 (m, 1H), 3.01-2.98 (m, 1H), 2.86-2.79 (m, 2H), 2.59-2.55 (m, 4H), 1.92 (br s, 2H). | ++++ |
| 674 | 4-(methylamino)-N-[(3R)-7-(piperazin-1-yl)-3,4-dihydro-2H-1-benzopyran-3-yl]-1Hpyrrolo[3,2-c]pyridine-7-carboxamide | 407 | (DMSO-d6, 400 MHz) δ (ppm): 11.13 (brs, 1H), 8.31-8.32 (m, 1H), 8.09 (d, J = 7.2 Hz, 1H), 7.15-7.12 (m, 1H), 7.07-7.8 (m, 1H), 6.95 (d, J = 8.4 Hz, 1H), 6.61-6.60 (m, 1H), 6.52 (dd, J = 8.4, 2.4 Hz, 1H), 6.33 (s, 1H), 4.36-4.32 (m, 1H), 4.25-4.21 (m, 1H), 3.83-3.78 (m, 1H), 3.04-3.01 (m, 4H), 2.97 (s, 3H), 2.91-2.83 (m, 6H). | ++ |
| 675 | 3-chloro-4-(methylamino)-N-[(3R)-7-(piperazin-1-yl)-3,4-dihydro-2H-1-benzopyran-3-yl]-1H-pyrrolo[3,2-c]pyridine-7-carboxamide | 441, 443 | (DMSO-d6, 400 MHz) δ (ppm): 11.39 (br s, 1H), 8.34-8.33 (m, 1H), 8.18 (d, J = 6.4 Hz, 1H), 7.18-7.16 (m, 1H), 6.94 (d, J = 8.4 Hz, 1H), 6.52-6.48 (m, 2H), 6.31 (s, 1H), 4.35-4.30 (m, 1H), 4.25-4.21 (m, 1H), 3.83-3.78 (m, 1H), 3.01-2.96 (m, 7H), 2.91-2.51 (m, 6H). | ++ |
| 676 | 4-ethoxy-N-[(3R)-7-(piperazin-1-yl)-3,4-dihydro-2H-1-benzopyran-3-yl]-1Hpyrrolo[3,2-c]pyridine-7-carboxamide | 422 | (DMSO-d6, 400 MHz) δ (ppm): 11.52 (br s, 1H), 8.43 (d, J = 8.8 Hz, 1H), 8.35 (s, 1H), 7.26 (d, J = 2.4 Hz, 1H), 6.95 (d, J = 8.4 Hz, 1H), 6.53-6.50 (m, 2H), 6.32 (s, 1H), 4.53-4.50 (m, 2H), 4.48-4.35 (m, 1H), 4.26-4.23 (m, 1H), 3.87-3.82 (m, 1H), 2.99-2.90 (m, 5H), 2.88-2.812 (m, 1H), 2.81-2.79 (m, 4H). | ++ |
| 677 | 5-(methylamino)-N-[(3R)-7-(piperazin-1-yl)-3,4-dihydro-2H-1-benzopyran-3-yl]-1,2,3,4-tetrahydro-1,6-naphthyridine-8-carboxamide | 423 | (MeOH-d4, 400 MHz) δ (ppm): 7.97 (s, 1H), 6.98 (d, J = 8.4 Hz, 1H), 6.57 (d, J = 8.0 Hz, 1H), 6.43 (s, 1H), 4.40-4.38 (m, 1H), 4.25-4.22 (m, 1H), 3.95-3.90 (m, 1H), 3.35-3.33 (m, 2H), 3.12-3.08 (m, 4H), 3.02-2.98 (m, 5 H), 2.92 (s, 3H), 2.86-2.80 (m, 1H), 2.39-2.36 (m, 2H), 1.95-1.92 (m, 2H) | ++ |
| 678 | 5-ethoxy-N-[(3R)-7-(piperazin-1-yl)-3,4-dihydro-2H-1-benzopyran-3-yl]-1,2,3,4-tetrahydro-1,6-naphthyridine-8-carboxamide | 438 | (CD3OD-d4, 400 MHz) δ (ppm): 7.97 (s, 1H), 6.98 (d, J = 8.4 Hz, 1H), 6.58 (dd, J = 8.4 Hz, 2.4 Hz, 1H), 6.43 (d, J = 2.4 Hz, 1H), 4.40-4.38 (m, 1H), 4.32-4.23 (m, 3H), 3.96-3.91 (m, 1H), 3.35-3.33 (m, 2H), 3.13-3.11 (m, 4H), 3.02- | ++++ |

TABLE 24-continued

| | | | | |
|---|---|---|---|---|
| | | | 2.99 (m, 5 H), 2.86-2.80 (m, 1H), 2.60 (t, J = 6.4 Hz, 2H), 1.89-1.86 (m, 2H), 1.36 (t, J = 7.2 Hz, 3H). | |
| 679 | 3-amino-N-[(3R)-7-[(3R,4R)-3-(methoxymethyl)-4-(methylamino)pyrrolidin-1-yl]-3,4-dihydro-2H-1-benzopyran-3-yl]-6-methylthieno[2,3-b]pyridine-2-carboxamide | 482 | (DMSO-d6, 400 MHz) δ (ppm): 8.33 (d, J = 8.0 Hz, 1H), 7.50 (d, J = 7.6 Hz, 1H), 7.32 (d, J = 8.4 Hz, 1H), 7.22 (br s, 2H), 6.87 (d, J = 8.4 Hz, 1H), 6.11-6.08 (m, 1H), 5.90 (s, 1H), 4.32-4.19 (m, 1H), 4.15-4.12 (m, 1H), 3.81-3.76 (m, 1H), 3.56-3.52 (m, 1H), 3.32-3.21 (m, 7H), 3.16-3.12 (m, 1H), 3.07-3.02 (m, 1H), 2.89-2.74 (m, 2H), 2.61-2.56 (m, 4H), 2.31 (s, 3H). | ++++ |
| 680 | 3-amino-N-[(3R)-7-[(3S,4S)-3-(methoxymethyl)-4-(methylamino)pyrrolidin-1-yl]-3,4-dihydro-2H-1-benzopyran-3-yl]-6-methylthieno[2,3-b]pyridine-2-carboxamide | 482 | (DMSO-d6, 400 MHz) δ (ppm): 8.33 (d, J = 8.4 Hz, 1H), 7.49 (d, J = 7.6 Hz, 1H), 7.31 (d, J = 8.4 Hz, 1H), 7.22 (br s, 2H), 6.86 (d, J = 8.4 Hz, 1H), 6.11-6.08 (m, 1H), 5.89 (s, 1H), 4.31-4.25 (m, 1H), 4.14-4.11 (m, 1H), 3.81-3.77 (m, 1H), 3.54-3.52 (m, 1H), 3.34-3.21 (m, 8H), 3.18-3.11 (m, 1H), 3.09-3.05 (m, 1H), 2.85-2.81 (m, 2H), 2.59 (s, 3H), 2.30 (s, 3H), 1.75 (br s, 1H). | ++++ |
| 681 | 3-amino-N-[(3R)-7-[(9S)-9-amino-1,4-dioxa-7-azaspiro[4.4]nonan-7-yl]-3,4-dihydro-2H-1-benzopyran-3-yl]-6-methylthieno[2,3-b]pyridine-2-carboxamide | 482 | (DMSO-d6, 400 MHz) δ (ppm): 8.33 (d, J = 8.0 Hz, 1H), 7.48 (d, J = 7.6 Hz, 1H), 7.31 (d, J = 8.4 Hz, 1H), 7.20 (br s, 2H), 6.88 (d, J = 8.0 Hz, 1H), 6.09-6.06 (m, 1H), 5.89 (s, 1H), 4.31-4.23 (m, 1H), 4.16-4.13 (m, 1H), 4.04-3.93 (m, 4H), 3.82-3.77 (m, 1H), 3.45-3.41 (m, 1H), 3.35-3.33 (m, 2H), 3.23-3.21 (m, 1H), 2.89-2.81 (m, 3H), 2.59 (s, 3H), 1.62 (br s, 2H). | ++++ |
| 682 | 3-amino-N-[(3R)-7-[(9R)-9-amino-1,4-dioxa-7-azaspiro[4.4]nonan-7-yl]-3,4-dihydro-2H-1-benzopyran-3-yl]-6-methylthieno[2,3-b]pyridine-2-carboxamide | 482 | (DMSO-d6, 400 MHz) δ (ppm): 8.33 (d, J = 8.0 Hz, 1H), 7.48 (d, J = 7.6 Hz, 1H), 7.31 (d, J = 8.4 Hz, 1H), 7.21 (br s, 2H), 6.88 (d, J = 8.4 Hz, 1H), 6.09-6.07 (m, 1H), 5.89 (s, 1H), 4.31-4.23 (m, 1H), 4.16-4.13 (m, 1H), 4.04-3.93 (m, 4H), 3.82-3.77 (m, 1H), 3.45-3.41 (m, 1H), 3.35-3.32 (m, 2H), 3.23-3.21 (m, 1H), 2.90-2.82 (m, 3H), 2.59 (s, 3H), 1.90 (br s, 2H). | +++ |
| 683 | 3-amino-N-[(3R)-7-[(5R)-1,7-diazaspiro[4.4]nonan-7-yl]-5-fluoro-3,4-dihydro-2H-1-benzopyran-3-yl]-6-methylthieno [2,3-b]pyridine-2-carboxamide | 482 | (DMSO-d6, 400 MHz) δ (ppm): 8.33 (d, J = 7.6 Hz, 1H), 7.55 (d, J = 7.2 Hz, 1H), 7.31 (d, J = 7.6 Hz, 1H), 7.22 (br s, 2H), 5.94-5.51 (m, 1H), 5.75 (s, 1H), 4.34-4.19 (m, 1H), 4.18-4.11 (m, 1H), 3.87-3.69 (m, 1H), 3.32-3.19 (m, 2H), 3.18-3.03 (m, 2H), 2.91-2.78 (m, 3H), 2.68-2.66 (m, 1H), 2.59 (s, 3H), 1.95-1.82 (m, 2H), 1.80-1.60 (m, 4H). | ++++ |
| 684 | 3-amino-N-[(3R)-7-[(5S)-1,7-diazaspiro[4.4]nonan-7-yl]-5-fluoro-3,4-dihydro-2H-1-benzopyran-3-yl]-6-methylthieno [2,3-b]pyridine-2-carboxamide | 482 | (DMSO-d6, 400 MHz) δ (ppm): 8.33 (d, J = 8.4 Hz, 1H), 7.55 (d, J = 7.2 Hz, 1H), 7.31 (d, J = 8.4 Hz, 1H), 7.22 (br s, 2H), 5.94-5.91 (m, 1H), 5.75 (s, 1H), 4.31-4.21 (m, 1H), 4.17-4.15 (m, 1H), 3.85-3.80 (m, 1H), 3.32-3.20 (m, 2H), 3.13-3.04 (m, 2H), 2.88-2.82 (m, 3H), 2.75-2.68 (m, 1H), 2.59 (s, 3H), 1.90- | ++++ |

TABLE 24-continued

| | | | 1.86 (m, 2H), 1.76-1.62 (m, 4H). | |
|---|---|---|---|---|
| 685 | 3-amino-N-[(3R)-7-{[(3S)-4,4-difluoropyrrolidin-3-yl]methoxy}-3,4-dihydro-2H-1-benzopyran-3-yl]-6-methylthieno[2,3-b]pyridine-2-carboxamide | 475 | (DMSO-d6, 400 MHz) δ (ppm): 8.31 (d, J = 8.0 Hz, 1H), 7.54 (d, J = 7.2 Hz, 1H), 7.32 (d, J = 8.4 Hz, 1H), 7.22 (br s, 2H), 7.01 (d, J = 8.4 Hz, 1H), 6.52-6.49 (m, 1H), 6.39 (s, 1H), 4.32-4.29 (m, 1H), 4.20-4.17 (m, 1H), 4.10-4.06 (m, 1H), 3.97-3.93 (m, 1H), 3.87-3.82 (m, 1H), 3.26-3.13 (m, 2H), 3.07-2.94 (m, 1H), 2.91-2.85 (m, 3H), 2.79-2.68 (m, 2H), 2.59 (s, 3H). | ++++ |
| 686 | 3-amino-N-[(3R)-7-{[(3R)-4,4-difluoropyrrolidin-3-yl]methoxy}-3,4-dihydro-2H-1-benzopyran-3-yl]-6-methylthieno[2,3-b]pyridine-2-carboxamide | 475 | (DMSO-d6, 400 MHz) δ (ppm): 8.32 (d, J = 8.0 Hz, 1H), 7.54 (d, J = 7.6 Hz, 1H), 7.32 (d, J = 8.4 Hz, 1H), 7.22 (br s, 2H), 7.01 (d, J = 8.4 Hz, 1H), 6.52-6.49 (m, 1H), 6.40 (s, 1H), 4.31-4.28 (m, 1H), 4.20-4.17 (m, 1H), 4.10-4.06 (m, 1H), 3.98-3.93 (m, 1H), 3.87-3.82 (m, 1H), 3.26-3.16 (m, 2H), 3.07-3.00 (m, 1H), 2.91-2.87 (m, 3H), 2.79-2.68 (m, 2H), 2.59 (s, 3H). | ++++ |
| 687 | 3-amino-6-methyl-N-[(3R)-7-{[(3S,4S)-4-(trifluoromethyl)pyrrolidin-3-yl]methoxy}-3,4-dihydro-2H-1-benzopyran-3-yl]thieno[2,3-b]pyridine-2-carboxamide | 507 | (DMSO-d6, 400 MHz) δ (ppm): 8.33 (d, J = 8.0 Hz, 1H), 7.54 (br s, 1H), 7.32 (d, J = 8.4 Hz, 1H), 7.22 (br s, 2H), 7.01 (d, J = 8.4 Hz, 1H), 6.51-6.48 (m, 1H), 6.39 (s, 1H), 4.31-4.28 (m, 1H), 4.21-4.17 (m, 1H), 3.93-3.91 (m, 2H), 3.87-3.82 (m, 1H), 3.17-3.12 (m, 1H), 2.96-2.89 (m, 3H), 2.83-2.69 (m, 3H), 2.59 (s, 3H), 2.52-2.47 (m, 2H) | ++++ |
| 688 | 3-amino-6-methyl-N-[(3R)-7-{[(3R,4R)-4-(trifluoromethyl)pyrrolidin-3-yl]methoxy}-3,4-dihydro-2H-1-benzopyran-3-yl]thieno[2,3-b]pyridine-2-carboxamide | 507 | (DMSO-d6, 400 MHz) δ (ppm): 8.33 (d, J = 8.4 Hz, 1H), 7.54 (br s, 1H), 7.32 (d, J = 8.4 Hz, 1H), 7.22 (br s, 2H), 7.01 (d, J = 8.4 Hz, 1H), 6.50-6.48 (m, 1H), 6.39 (s, 1H), 4.35-4.28 (m, 1H), 4.22-4.17 (m, 1H), 3.95-3.91 (m, 2H), 3.86-3.81 (m, 1H), 3.16-3.11 (m, 1H), 2.95-2.89 (m, 3H), 2.82-2.67 (m, 4H), 2.59-2.51 (m, 4H) | ++++ |
| 689 | 3-amino-N-[(3R)-7-[(3R,4R)-3-amino-4-methoxyazepan-1-yl]-5-fluoro-3,4-dihydro-2H-1-benzopyran-3-yl]-6-methylthieno[2,3-b]pyridine-2-carboxamide | 500 | (DMSO-d6, 400 MHz) δ (ppm): 8.32 (d, J = 8.4 Hz, 1H), 7.56 (br s, 1H), 7.31 (d, J = 8.4 Hz, 1H), 7.22 (br s, 2H), 6.22-6.18 (m, 1H), 6.01 (s, 1H), 4.27-4.26 (m, 1H), 4.17-4.14 (m, 1H), 3.86-3.81 (m, 1H), 3.49-3.41 (m, 2H), 3.26-3.24 (m, 4H), 3.14-3.05 (m, 2H), 2.97-2.94 (m, 1H), 2.83-2.81 (m, 1H), 2.75-2.68 (m, 1H), 2.59 (s, 3H), 1.94-1.89 (m, 1H), 1.76-1.73 (m, 3H), 1.27-1.24 (m, 1H). | ++++ |
| 690 | 3-amino-N-[(3R)-7-[(3S,4S)-3-amino-4-methoxyazepan-1-yl]-5-fluoro-3,4-dihydro-2H-1-benzopyran-3-yl]-6-methylthieno[2,3-b]pyridine-2-carboxamide | 500 | (DMSO-d6, 400 MHz) δ (ppm): 8.32 (d, J = 8.4 Hz, 1H), 7.56 (br s, 1H), 7.31 (d, J = 8.4 Hz, 1H), 7.22 (br s, 2H), 6.22-6.18 (m, 1H), 6.01 (s, 1H), 4.28-4.27 (m, 1H), 4.18-4.15 (m, 1H), 3.86-3.81 (m, 1H), 3.48-3.41 (m, 2H), 3.26-3.24 (m, 4H), 3.14-3.05 (m, 2H), 2.97-2.94 (m, 1H), 2.83-2.81 (m, 1H), 2.75-2.68 (m, 1H), 2.59 (s, 3H), 1.96-1.73 (m, 5H), 1.27-1.24 (m, 1H). | ++++ |

TABLE 24-continued

| | | | | |
|---|---|---|---|---|
| 691 | 3-amino-N-[(3R)-7-[(3R,4S)-3-amino-4-methoxyazepan-1-yl]-5-fluoro-3,4-dihydro-2H-1-benzopyran-3-yl]-6-methylthieno[2,3-b]pyridine-2-carboxamide | 500 | (DMSO-d6, 400 MHz) δ (ppm): 8.32 (d, J = 8.4 Hz, 1H), 7.56 (br s, 1H), 7.31 (d, J = 8.4 Hz, 1H), 7.22 (br s, 2H), 6.25-6.21 (m, 1H), 6.03 (s, 1H), 4.27-4.26 (m, 1H), 4.17-4.14 (m, 1H), 3.86-3.81 (m, 1H), 3.37-3.32 (m, 1H), 3.27-3.26 (m, 4H), 3.15-3.02 (m, 2H), 2.90-2.82 (m, 2H), 2.75-2.68 (m, 2H), 2.59 (s, 3H), 1.93-1.88 (m, 2H), 1.71-1.62 (m, 3H), 1.26-1.24 (m, 1H). | +++ |
| 692 | 3-amino-N-[(3R)-7-[(3S,4R)-3-amino-4-methoxyazepan-1-yl]-5-fluoro-3,4-dihydro-2H-1-benzopyran-3-yl]-6-methylthieno[2,3-b]pyridine-2-carboxamide | 500 | (DMSO-d6, 400 MHz) δ (ppm): 8.32 (d, J = 8.4 Hz, 1H), 7.56 (br s, 1H), 7.31 (d, J = 8.4 Hz, 1H), 7.22 (br s, 2H), 6.24-6.21 (m, 1H), 6.03 (s, 1H), 4.27-4.26 (m, 1H), 4.17-4.14 (m, 1H), 3.86-3.81 (m, 1H), 3.37-3.32 (m, 1H), 3.27-3.26 (m, 4H), 3.15-3.02 (m, 2H), 2.90-2.82 (m, 2H), 2.75-2.68 (m, 2H), 2.59 (s, 3H), 1.93-1.88 (m, 2H), 1.72-1.62 (m, 3H), 1.25-1.22 (m, 1H). | ++++ |
| 693 | 5-amino-N-[(3R)-7-[(3S,4S)-3-amino-4-methoxypyrrolidin-1-yl]-5-fluoro-3,4-dihydro-2H-1-benzopyran-3-yl]-2-methylthieno[2,3-d]pyrimidine-6-carboxamide | 473 | (DMSO-d6, 400 MHz) δ (ppm): 9.36 (s, 1H), 7.73 (br s, 1H), 7.43 (br s, 2H), 5.98-5.94 (m, 1H), 5.78 (s, 1H), 4.29-4.25 (m, 1H), 4.18-4.15 (m, 1H), 3.85-3.80 (m, 1H), 3.63-3.62 (m, 1H), 3.50-3.42 (m, 2H), 3.36-3.29 (m, 4H), 3.14-3.11 (m, 1H), 2.91-2.83 (m, 2H), 2.74-2.68 (m, 4H), 1.87 (br s, 2H) | ++ |
| 694 | 5-amino-N-[(3R)-7-[(3R,4R)-3-amino-4-(methoxymethyl)pyrrolidin-1-yl]-5-fluoro-3,4-dihydro-2H-1-benzopyran-3-yl]-2-methylthieno[2,3-d]pyrimidine-6-carboxamide | 487 | (DMSO-d6, 400 MHz) δ (ppm): 9.36 (s, 1H), 7.73 (br s, 1H), 7.43 (br s, 2H), 5.94-5.91 (m, 1H), 5.74 (s, 1H), 4.30-4.20 (m, 1H), 4.18-4.15 (m, 1H), 3.85-3.80 (m, 1H), 3.59-3.55 (m, 2H), 3.40-3.29 (m, 2H), 3.28 (s, 3H), 3.25-3.21 (m, 1H), 3.09-3.05 (m, 1H), 2.96-2.93 (m, 1H), 2.88-2.82 (m, 1H), 2.74-2.68 (m, 4H), 2.46-2.39 (m, 1H), 1.50 (br s, 1H) | ++ |
| 695 | 5-amino-N-[(3R)-5-fluoro-7-[(3R,4S)-3-(methoxymethyl)-4-(methylamino)pyrrolidin-1-yl]-3,4-dihydro-2H-1-benzopyran-3-yl]-2-methylthieno[2,3-d]pyrimidine-6-carboxamide | 501 | (DMSO-d6, 400 MHz) δ (ppm): 9.36 (s, 1H), 7.73 (br s, 1H), 7.43 (br s, 2H), 5.99-5.95 (m, 1H), 5.78 (s, 1H), 4.29-4.21 (m, 1H), 4.18-4.15 (m, 1H), 3.85-3.81 (m, 1H), 3.44-3.40 (m, 2H), 3.36-3.27 (m, 5H), 3.00-2.92 (m, 3H), 2.88-2.83 (m, 1H), 2.74-2.68 (m, 4H), 2.33-2.28 (m, 4H), 1.85 (br s, 1H) | ++ |
| 696 | N-[(3R)-7-[(3S,4S)-3-amino-4-methoxypyrrolidin-1-yl]-3,4-dihydro-2H-1-benzopyran-3-yl]-5-chloro-7-ethyl-7Hpyrrolo[2,3-c]pyridazine-3-carboxamide | 471, 473 | (DMSO-d6, 400 MHz) δ (ppm): 8.94 (d, J = 8.0 Hz, 1H), 8.39 (s, 1H), 8.36 (s, 1H), 6.89 (d, J = 8.4 Hz, 1H), 6.12 (d, J = 8.4 Hz, 1H), 5.95 (s, 1H), 4.54-4.47 (m, 3H), 4.20-4.17 (m, 1H), 4.08-4.04 (m, 1H), 3.63-3.62 (m, 1H), 3.53-3.48 (m, 1H), 3.42-3.30 (m, 5H), 3.14-3.11 (m, 1H), 2.98-2.89 (m, 3H), 1.81 (br s, 2H), 1.50-1.46 (m, 3H) | ++ |
| 697 | 6-{[(2,4-dichlorophenyl)methyl]amino}-N-[(3R)-7-(piperazin-1-yl)-3,4-dihydro-2H-1-benzopyran-3-yl]pyridine-3-carboxamide | 513 | | ++++ ++++ |

TABLE 24-continued

| | | | | | |
|---|---|---|---|---|---|
| 698 | 6-{[(1H-indazol-7-yl)methyl]amino}-N-[(3R)-7-(piperazin-1-yl)-3,4-dihydro-2H-1-benzopyran-3-yl]pyridine-3-carboxamide | 484 | | ++ | ++ |
| 699 | 6-{[(2,3-dichlorophenyl)methyl]amino}-N-[(3R)-7-(piperazin-1-yl)-3,4-dihydro-2H-1-benzopyran-3-yl]pyridine-3-carboxamide | 513 | | ++++ | ++++ |
| 701 | N-[(3R)-7-[(3S,4S)-3-amino-4-methoxypyrrolidin-1-yl]-3,4-dihydro-2H-1-benzopyran-3-yl]-7-ethyl-5-fluoro-7Hpyrrolo[2,3-c]pyridazine-3-carboxamide | | | | |
| 702 | 3-amino-N-[7-(3-amino-4 methoxypyrrolidin-1-yl)-4,4-difluoro-3,4-dihydro-2H-1-benzopyran-3-yl]-6-methylthieno[2,3-b]pyridine-2-carboxamide | | | | |

| Ex. # | Chemical Name | MS m/z [M + H]⁺ | 1H NMR | USP28 A-1(a) | USP25 A-2 |
|---|---|---|---|---|---|
| 447 | 3-amino-N-[(6S)-2-[(3S,4R)-3-amino-4-(1,1-difluoro-2-methoxyethyl)pyrrolidin-1-yl]-5,6,7,8-tetrahydroquinolin-6-yl]-6-methylthieno[2,3-b]pyridine-2-carboxamide | 517 | (DMSO-d6, 400 MHz) δ (ppm): 8.31 (d, J = 8.0 Hz, 1H), 7.59 (br s, 1H), 7.31 (d, J = 8.0 Hz, 1H), 7.22 (d, J = 8.4 Hz, 1H), 7.17 (br s, 2H), 6.27 (d, J = 8.4 Hz, 1H), 4.13-4.11 (m, 1H), 3.82-3.79 (m, 2H), 3.75-3.54 (m, 3H), 3.43-3.39 (m, 4 H), 3.05-3.01 (m, 1H), 2.78-2.60 (m, 5H), 2.59 (s, 3H), 2.03-1.85 (m, 3H) | +++ | |
| 448 | 3-amino-N-[(6S)-2-[(3S,4S)-3-amino-4-{[(2S)-1-methoxypropan-2-yl]oxy}pyrrolidin-1-yl]-5,6,7,8-tetrahydroquinolin-6-yl]-6-methylthieno[2,3-b]pyridine-2-carboxamide | 511 | (DMSO-d6, 400 MHz) δ (ppm): 8.31 (d, J = 8.0 Hz, 1H), 7.57 (d, J = 7.6 Hz, 1H), 7.31 (d, J = 8.0 Hz, 1H), 7.20-7.16 (m, 3H), 6.22 (d, J = 8.4 Hz, 1H), 4.13-4.10 (m, 1H), 3.85-3.83 (m, 1H), 3.76-3.70 (m, 1H), 3.67-3.63 (m, 1 H), 3.50-3.46 (m, 1H), 3.27-3.22 (m, 7H), 3.11-3.08 (m, 1H), 2.82-2.68 (m ,4H), 2.59 (s, 3H), 2.01-1.98 (m, 1H), 1.90-1.79 (m, 1H), 1.69 (br s, 2 H), 1.05 (d, J = 6.0 Hz, 3H) | ++ | |
| 449 | 3-amino-N-[(6S)-2-[(4R,5S)-4-amino-6-oxa-2-azaspiro[4.5]decan-2-yl]-5,6,7,8-tetrahydroquinolin-6-yl]-6-methylthieno[2,3-b]pyridine-2-carboxamide | 493 | (DMSO-d6, 400 MHz) δ (ppm): 8.29 (d, J = 8.0 Hz, 1H), 7.56 (d, J = 7.6 Hz, 1H), 7.31 (d, J = 8.4 Hz, 1H), 7.20-7.15 (m, 3H), 6.23 (d, J = 8.4 Hz, 1H), 4.15-4.09 (m, 1H), 3.96 (d, J = 8.0 Hz, 1H), 3.73-3.70 (m, 1H), 3.59-3.52 (m, 2H), 3.31-3.06 (m, 2H), 2.96-2.91 (m, 1H), 2.81-2.72 (m, 4H), 2.59 (s, 3H), 2.03-1.98 (m, 1H), 1.91-1.68 (m, 3H), 1.63-1.41 (m, 6H) | ++++ | |
| 450 | 3-amino-N-[(6R)-2-[(3S,4S)-3-amino-4-methoxypyrrolidin-1-yl]-5,6,7,8-tetrahydroquinolin-6-yl]-6-methylfuro[2,3-b]pyridine-2-carboxamide | 437 | (DMSO-d6, 400 MHz) δ (ppm): 8.18 (d, J = 8.0 Hz, 1H), 7.94 (br s, 1H), 7.23-7.18 (m, 2H), 6.23 (d, J = 8.8 HZ, 1H), 6.11 (br s, 2H), 4.18-4.11 (m, 1H), 3.62-3.59 (m, 2H), 3.46-3.30 (m, 5H), 3.14-3.12 (m, 1H), 2.79-2.75 (m, 4H), 2.55 (s, 3H), 2.03-1.60 (m, 3H) | + | + |
| 451 | 3-amino-N-[(6S)-2-[(3S,4S)-3-amino-4-methoxypyrrolidin-1-yl]-5,6,7,8-tetrahydroquinolin-6-yl]-6-methylfuro[2,3-b]pyridine-2-carboxamide | 437 | (DMSO-d6, 400 MHz) δ (ppm): 8.18 (d, J = 7.6 Hz, 1H), 7.94 (br s, 1H), 7.24-7.18 (m, 2H), 6.23 (d, J = 8.4 Hz, 1H), 6.12 (br s, 2H), 4.19-4.11 (m, 1H), 3.62-3.61 (m, 2H), 3.48-3.43 (m, 2H), 3.36-3.33 (m, 1H), 3.30 (s, 3H), 3.14-3.12 (m, 1H), 2.82-2.76 (m, 4H), 2.55 (s, 3H), 2.02-1.99 (m, 1H), 1.92-1.86 (m, 1H), 1.84-1.78 (br s, 2H) | + | + |
| 452 | 3-amino-N-[(6S)-2-[(2S,4R)-4-amino-2-ethylpyrrolidin-1-yl]-5,6,7,8-tetrahydroquinolin-6-yl]-6-methylthieno[2,3-b]pyridine-2-carboxamide | 451 | (DMSO-d6, 400 MHz) δ (ppm): 8.29 (d, J = 8.0 Hz, 1H), 7.58 (br s, 1H), 7.31 (d, J = 8.4 Hz, 1H), 7.18-7.16 (m, 3H), 6.21 (d, J = 8.4 Hz, 1H), 4.18-4.15 (m, 1H), 3.79-3.71 (m, 1H), 3.70-3.67 (m, 1H), 2.99-2.95 (m, 1H), 2.78-2.72 (m, 4H), | +++ | ++ |

TABLE 24-continued

| | | | 2.68 (s, 3H), 2.59-2.56 (m, 1H), 2.25-2.21 (m, 1H), 1.98-1.82 (m, 3H), 1.53-1.46 (m, 2H), 0.85-0.82 (m, 3H) | | |
|---|---|---|---|---|---|
| 453 | 3-amino-N-[(6S)-2-[(3R,4R)-3-amino-4-(fluoromethyl)pyrrolidin-1-yl]-5,6,7,8-tetrahydroquinolin-6-yl]-5-fluoro-6-methylthieno[2,3-b]pyridine-2-carboxamide | 473 | (DMSO-d6, 400 MHz) δ (ppm): 8.29 (d, J = 10.0 Hz, 1H), 7.67 (br s, 1H), 7.19 (d, J = 8.8 Hz, 1H), 7.13 (br s, 2H), 6.23 (d, J = 8.4 Hz, 1H), 4.82-4.78 (m, 1H), 4.67-4.49 (m, 1H), 4.18-4.08 (m, 1H), 3.61-3.50 (m, 3H), 3.30-3.28 (m, 1H), 3.20-3.17 (m, 1H), 2.78-2.71 (m, 4H), 2.68-2.54 (m, 4H), 2.04-1.96 (m, 1H), 1.93-1.80 (m, 1H), 1.79-1.54 (br s, 2H) | +++ | |
| 454 | 3-amino-N-[(6S)-2-[(3S,4S)-3-amino-4-(fluoromethyl)pyrrolidin-1-yl]-5,6,7,8-tetrahydroquinolin-6-yl]-5-fluoro-6-methylthieno[2,3-b]pyridine-2-carboxamide | 473 | (DMSO-d6, 400 MHz) δ (ppm): 8.30 (d, J = 10.4 Hz, 1H), 7.68 (br s, 1H), 7.20 (d, J = 8.4 Hz, 1H), 7.14 (br s, 2H), 6.23 (d, J = 8.4 Hz, 1H), 4.68-4.50 (m, 2H), 4.14-4.06 (m, 1H), 3.61-3.47 (m, 3H), 3.31-3.27 (m, 1H), 3.21-3.18 (m, 1H), 2.79-2.75 (m, 4H), 2.72-2.57 (m, 4H), 2.04-1.97 (m, 1H), 1.90-1.81 (m, 1H), 1.78-1.59 (br s, 2H) | ++++ | ++ |
| 455 | 3-amino-N-[(6S)-2-[(3R,4R)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.4 Hz, 1H), 8.07 (s, 1H), 7.63 (br s, 1H), 7.31 (d, J = 8.4 Hz, 1H), 7.17 (br s, 2H), 4.80-4.47 (m, 2H), 4.14-4.10 (m, 1H), 3.62-3.58 (m, 3H), 3.40-3.36 (m, 2H), 2.84-2.67 (m, 4H), 2.65-2.58 (m, 4H), 2.00-1.83 (m, 3H) | + | |
| 456 | 3-amino-N-[(6S)-2-[(3S,4S)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.4 Hz, 1H), 8.07 (s, 1H), 7.63 (br s, 1H), 7.31 (d, J = 8.4 Hz, 1H), 7.17 (br s, 2H), 4.80-4.47 (m, 2H), 4.14-4.10 (m, 1H), 3.61-3.56 (m, 3H), 3.40-3.35 (m, 2H), 2.84-2.73 (m, 3H), 2.67-2.59 (m, 5H), 2.00-1.98 (m, 1H), 1.88-1.82 (m, 1H), 1.76 (br s, 2H) | + | |
| 457 | 3-amino-N-[(6S)-2-[(3S,4S)-3-amino-4-(2-methoxyethoxy)pyrrolidin-1-yl]-5,6,7,8-tetrahydroquinolin-6-yl]-4,6-dimethylthieno[2,3-b]pyridine-2-carboxamide | 511 | (DMSO-d6, 400 MHz) δ (ppm): 7.61 (br s, 1H), 7.19 (d, J = 8.0 Hz, 1H), 7.04 (s, 1H), 6.89-6.78 (m, 2H), 6.22 (d, J = 8.0 Hz, 1H), 4.20-4.10 (m, 1H), 3.80-3.70 (m, 1H), 3.65-3.55 (m, 3H), 3.50-3.42 (m, 4H), 3.30-3.25 (m, 1H), 3.25-3.20 (m, 3H), 3.20-3.10 (m, 1H), 2.85-2.70 (m, 7H), 2.51-2.50 (m, 3H), 2.05-1.95 (m, 1H), 1.95-1.71 | +++ | |
| 458 | 3-amino-N-[(6S)-2-[(3R,4R)-3-amino-4-(2-methoxyethoxy)pyrrolidin-1-yl]-5,6,7,8-tetrahydroquinolin-6-yl]-4,6-dimethylthieno[2,3-b]pyridine-2-carboxamide | 511 | (DMSO-d6, 400 MHz) δ (ppm): 7.61 (br s, 1H), 7.19 (d, J = 8.0 Hz, 1H), 7.00 (s, 1H), 6.82-6.81 (m, 2H), 6.23 (d, J = 8.0 Hz, 1H), 4.20-4.10 (m, 1H), 3.80-3.70 (m, 1H), 3.65-3.55 (m, 3H), 3.50-3.40 (m, 4H), 3.40-3.30 (m, 1H), 3.29-3.22 (m, 3H), 3.19-3.04 (m, 1H), 2.90-2.65 (m, 7H), 2.50 (m, 3H), 2.10-1.90 (m, 1H), 1.90-1.60 (m, 3H) | +++ | |
| 459 | 3-amino-N-[(6S)-2-[(3S)-3-amino-3-(difluoromethyl)pyrrolidin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.31 (d, J = 8.4 Hz, 1H), 7.59 (br s, 1H), 7.31 (d, J = 8.4 Hz, 1H), 7.21 (d, J = 8.4 Hz, 1H), 7.17 (br s, 2H), 6.26 (d, J = 8.4 Hz, 1H), 6.02 (t, J = 16.8 Hz, 1H), 4.18-4.11 (m, 1H), 3.52-3.48 (m, 3H), 3.25-3.22 (m, 1H), 2.82-2.73 (m, 4H), 2.59 (s, 3H), 2.10-2.00 (m, 2H), 1.93-1.83 (m, 3H), 1.82-1.77 (m, 1H) | +++ | |
| 460 | 3-amino-N-[(6S)-2-[(3R)-3-amino-3-(difluoromethyl)pyrrolidin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.31 (d, J = 8.4 Hz, 1H), 7.59 (br s, 1H), 7.31 (d, J = 8.4 Hz, 1H), 7.21 (d, J = 8.4 Hz, 1H), 7.17 (br s, 2H), 6.26 (d, J = 8.4 Hz, 1H), 6.02 (t, J = 16.8 Hz, 1H), 4.18-4.11 (m, 1H), 3.52-3.45 (m, 3H), 3.25-3.22 (m, 1H), 2.80-2.73 (m, 4H), 2.59 (s, | +++ | |

TABLE 24-continued

| | | | | |
|---|---|---|---|---|
| | | | 3H), 2.10-1.99 (m, 2H), 1.92-1.84 (m, 3H), 1.82-1.77 (m, 1H) | |
| 461 | N-[(6S)-2-[(3aS,6aS)-3,3-difluoro-octahydropyrrolo[3,4-b]pyrrol-5-yl]-5,6,7,8-tetrahydroquinolin-6-yl]-3-amino-6-methylthieno[2,3-b]pyridine-2-carboxamide | 485 | (DMSO-d6, 400 MHz) δ (ppm): 8.31 (d, J = 8.0 Hz, 1H), 7.59 (br s, 1H), 7.31 (d, J = 8.0 Hz, 1H), 7.24 (d, J = 8.4 Hz, 1H), 7.17 (br s, 2H), 6.37 (d, J = 8.4 Hz, 1H), 4.19-4.07 (m, 2H), 3.68-3.61 (m, 1H), 3.40-3.38 (m, 3H), 3.20-2.95 (m, 3H), 2.80-2.76 (m, 4H), 2.59 (s, 3H), 2.04-1.92 (m, 1H), 1.90-1.76 (m, 1H) | +++ |
| 462 | N-[(6S)-2-[(3aR,6aR)-3,3-difluoro-octahydropyrrolo[3,4-b]pyrrol-5-yl]-5,6,7,8-tetrahydroquinolin-6-yl]-3-amino-6-methylthieno[2,3-b]pyridine-2-carboxamide | 485 | (DMSO-d6, 400 MHz) δ (ppm): 8.31 (d, J = 8.0 Hz, 1H), 7.59 (br s, 1H), 7.31 (d, J = 8.0 Hz, 1H), 7.24 (d, J = 8.4 Hz, 1H), 7.17 (br s, 2H), 6.37 (d, J = 8.4 Hz, 1H), 4.19-4.07 (m, 2H), 3.68-3.61 (m, 1H), 3.40-3.38 (m, 3H), 3.20-2.95 (m, 3H), 2.80-2.76 (m, 4H), 2.59 (s, 3H), 2.04-1.92 (m, 1H), 1.90-1.76 (m, 1H) | +++ |
| 463 | 3-amino-N-[(6S)-2-[(1R,6S)-3,8-diazabicyclo[4.2.0]octan-8-yl]-5,6,7,8-tetrahydroquinolin-6-yl]-4,6-dimethylthieno[2,3-b]pyridine-2-carboxamide | 463 | (DMSO-d6, 400 MHz) δ (ppm): 7.30 (d, J = 8.4 Hz, 1H), 7.07 (s, 1H), 6.33 (d, J = 8.4 Hz, 1H), 4.28-4.19 (m, 2H), 3.89-3.86 (m, 1H), 3.70-3.67 (m, 1H), 3.49-3.46 (m, 1 H), 3.20-3.18 (m, 1H), 3.07-2.90 (m, 4H), 2.81 (s, 3H), 2.78-2.68 (m, 3H), 2.58 (s, 3H), 2.17-2.15 (m, 2H), 1.95-1.88 (m, 2H) | ++++ |
| 464 | 3-amino-N-[(6S)-2-[(3R,4S)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.4 Hz, 1H), 8.08 (s, 1H), 7.63 (br s, 1H), 7.31 (d, J = 8.4 Hz, 1H), 7.17 (s, 2H), 4.64-4.45 (m, 2H), 4.12-4.08 (m, 1H), 3.78-3.72 (m, 2H), 3.30-3.24 (m, 3H), 3.11-3.07 (m, 1H), 2.84-2.73 (m, 3H), 2.68-2.61 (m, 1H), 2.59 (s, 3H), 2.30-2.22 (m, 1H), 2.05-1.95 (m, 2H), 1.92-1.78 (m, 1H) | ++ |
| 465 | 3-amino-N-[(6R)-2-[(3R,4S)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.0 Hz, 1H), 8.08 (s, 1H), 7.63 (br s, 1H), 7.31 (d, J = 8.4 Hz, 1H), 7.17 (s, 2H), 4.64-4.45 (m, 2H), 4.12-4.08 (m, 1H), 3.76-3.74 (m, 2H), 3.34-3.25 (m, 3H), 3.11-3.09 (m, 1H), 2.83-2.79 (m, 1H), 2.78-2.72 (m, 2H), 2.67-2.61 (m, 1H), 2.59 (s, 3H), 2.32-2.20 (m, 1H), 2.00-1.80 (m, 3H) | +++ |
| 466 | 3-amino-N-[(6S)-2-[(1S,6R)-3,8-diazabicyclo[4.2.0]octan-8-yl]-5,6,7,8-tetrahydroquinolin-6-yl]-4,6-dimethylthieno[2,3-b]pyridine-2-carboxamide | 463 | (DMSO-d6, 400 MHz) δ (ppm): 7.30 (d, J = 8.4 Hz, 1H), 7.07 (s, 1H), 6.33 (d, J = 8.4 Hz, 1H), 4.30-4.20 (m, 1H), 4.19-4.17 (m, 1H), 3.89-3.85 (m, 1H), 3.70-3.68 (m, 1H), 3.49-3.46 (m, 1 H), 3.19-3.16 (m, 1H), 3.05-2.89 (m, 4H), 2.81 (s, 3H), 2.77-2.67(m, 3H), 2.58 (s, 3H), 2.18-2.15 (m, 2H), 1.97-1.83 (m, 2H) | ++++ |
| 467 | 3-amino-N-[(6S)-2-[(3S,4R)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.4 Hz, 1H), 8.08 (s, 1H), 7.63 (br s, 1H), 7.31 (d, J = 8.0 Hz, 1H), 7.17 (br s, 2H), 4.64-4.45 (m, 2H), 4.12-4.08 (m, 1H), 3.79-3.71 (m, 2H), 3.34-3.24 (m, 3H), 3.12-3.08 (m, 1H), 2.84-2.73 (m, 3H), 2.68-2.61 (m, 1H), 2.59 (s, 3H), 2.32-2.18 (m, 2H), 2.01-1.95 (m, 1H), 1.90-1.80 (m, 1H) | + |
| 468 | 3-amino-N-[(6R)-2-[(3S,4R)-3-amino-4-(fluoromethyl)pyrrolidin-1-yl]-5,6,7,8-tetrahydroquinazolin-6-yl]-6-methylthieno[2,3-b]pyridine-2-carboxamide | 456 | (DMSO-d6, 400 MHz) δ (ppm): 8.31 (d, J = 8.4 Hz, 1H), 8.08 (s, 1H), 7.63 (br s, 1H), 7.31 (d, J = 8.0 Hz, 1H), 7.17 (br s, 2H), 4.64-4.45 (m, 2H), 4.12-4.08 (m, 1H), 3.77-3.74 (m, 2H), 3.34-3.25 (m, 3H), 3.11-3.08 (m, 1H), 2.80-2.72 (m, 3H), 2.67-2.61 (m, 1H), 2.59 (s, | ++ |

TABLE 24-continued

| | | | | | |
|---|---|---|---|---|---|
| | | | 3H), 2.38-2.21 (m, 1H), 2.01-1.95 (m, 1H), 1.90-1.80 (m, 2H) | | |
| 469 | 3-amino-N-[(6S)-2-[(3R,4R)-4-amino-3-(fluoromethyl)-3-methylpyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.4 Hz, 1H), 7.58 (br s, 1H), 7.31 (d, J = 8.4 Hz, 1H), 7.20-7.17 (m, 3H), 6.21 (d, J = 8.4 Hz, 1H), 4.55-4.48 (m, 1H), 4.48-4.36 (m, 1H), 4.13 (s, 1H), 3.71-3.61 (m 1H), 3.54-3.51 (m 1H), 3.34-3.26 (m, 1H), 3.18-3.09 (m, 2H), 2.82-2.68 (m, 4H), 2.59 (s, 3H), 2.08-1.75 (m, 4H), 1.09 (s, 3H) | ++++ | ++ |
| 470 | 3-amino-N-[(6S)-2-[(3R,4S)-4-amino-3-(fluoromethyl)-3-methylpyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.4 Hz, 1H), 7.58 (br s, 1H), 7.31 (d, J = 8.0 Hz, 1H), 7.20-7.17 (m, 3H), 6.21 (d, J = 8.4 Hz, 1H), 4.43-4.40 (m, 1H), 4.40-4.27 (m, 1H), 4.12 (s, 1H), 3.66-3.60 (m 1H), 3.34-3.28 (m 3H), 3.05-3.01 (m, 1H), 2.82-2.68 (m, 4H), 2.59 (s, 3H), 2.05-1.95 (m, 1H), 1.95-1.78 (m, 1H), 1.66 (br s, 2H), 0.98 (s, 3H) | +++ | ++ |
| 471 | 3-amino-N-[(6S)-2-[(3S,4R)-4-amino-3-(fluoromethyl)-3-methylpyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.4 Hz, 1H), 7.58 (br s, 1H), 7.31 (d, J = 8.4 Hz, 1H), 7.20-7.17 (m, 3H), 6.21 (d, J = 8.4 Hz, 1H), 4.42-4.40 (m, 1H), 4.40-4.28 (m, 1H), 4.12 (s, 1H), 3.65-3.60 (m 1H), 3.34-3.28 (m 3H), 3.06-3.01 (m, 1H), 2.82-2.68 (m, 4H), 2.59 (s, 3H), 2.04-1.95 (m, 1H), 1.95-1.78 (m, 1H), 1.66 (br s, 2H), 0.97 (s, 3H) | ++++ | ++ |
| 472 | 3-amino-N-[(6S)-2-[(3S,4S)-4-amino-3-(fluoromethyl)-3-methylpyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.0 Hz, 1H), 7.58 (br s, 1H), 7.31 (d, J = 8.0 Hz, 1H), 7.20-7.17 (m, 3H), 6.21 (d, J = 8.4 Hz, 1H), 4.52-4.49 (m, 1H), 4.49-4.38 (m, 1H), 4.13 (s, 1H), 3.64-3.62 (m 1H), 3.56-3.53 (m 1H), 3.24-3.22 (m, 1H), 3.10-3.05 (m, 2H), 2.78-2.68 (m, 4H), 2.59 (s, 3H), 2.08-1.98 (m, 1H), 1.98-1.75 (m, 1H), 1.66 (br s, 2H), 1.09 (s, 3H) | ++++ | ++ |
| 473 | 3-amino-N-[(6S)-2-[(3S,4R)-3-(fluoromethyl)-4-(methylamino)pyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.0 Hz, 1H), 7.58 (br s, 1H), 7.31 (d, J = 8.4 Hz, 1H), 7.21 (d, J = 8.8 Hz, 1H), 7.16 (br s, 2H), 6.27 (d, J = 8.4 Hz, 1H), 4.59-4.42 (m, 2H), 4.15-4.10 (m, 1H), 3.68-3.55 (m, 2H), 3.26-3.06 (m, 3H), 2.80-2.72 (m, 4H), 2.59 (s, 3H), 2.45-2.40 (m, 1H), 2.31 (s, 3H), 2.05-1.94 (m, 1H), 1.90-1.78 (m, 1H) | ++++ | ++ |
| 474 | 3-amino-N-[(6S)-2-[(3R,4S)-3-(fluoromethyl)-4-(methylamino)pyrrolidin-1-yl]-5,6,7,8-tetrahydroquinolin-6-yl]-6-methylthieno[2,3-b]pyridine-2-carboxamide | 469 | (DMSO-d6, 400 MHz) δ (ppm): 8.31 (d, J = 8.0 Hz, 1H), 7.58 (br s, 1H), 7.31 (d, J = 8.0 Hz, 1H), 7.21 (d, J = 8.4 Hz, 1H), 7.17 (br s, 2H), 6.27 (d, J = 8.4 Hz, 1H), 4.59-4.42 (m, 2H), 4.15-4.10 (m, 1H), 3.68-3.55 (m, 2H), 3.26-3.06 (m, 3H), 2.80-2.72 (m, 4H), 2.59 (s, 3H), 2.45-2.40 (m, 1H), 2.31(s, 3H), 2.05-1.94 (m, 1H), 1.90-1.78 (m, 1H) | +++ | ++ |
| 475 | 3-amino-N-[(6S)-2-[(3R,4S)-3-amino-4-(fluoromethyl)pyrrolidin-1-yl]-5,6,7,8-tetrahydroquinolin-6-yl]-5-fluoro-6-methylthieno[2,3-b]pyridine-2-carboxamide | 473 | (DMSO-d6, 400 MHz) δ (ppm): 8.29 (d, J = 6.4 Hz, 1H), 7.67 (br s, 1H), 7.20 (d, J = 8.4 Hz, 1H), 7.13 (br, s 2H), 6.23 (d, J = 8.4 Hz, 1H), 4.65-4.46 (m, 2H), 4.15-4.09 (m, 1H), 3.66-3.61 (m, 2H), 3.34-3.18 (m, 2H), 3.02-2.98 (m, 1H), 2.78-2.68 (m, 4H), 2.57 (s, 3H), 2.35-2.16 (m, 1H), 2.05-1.70 (m, 4H) | +++ | |

| | | | | | |
|---|---|---|---|---|---|
| 476 | 3-amino-N-[(6S)-2-[(3R,4S)-3-(ethylamino)-4-(methoxymethyl)pyrrolidin-1-yl]-5,6,7,8-tetrahydroquinolin-6-yl]-6-methylthieno[2,3-b]pyridine-2-carboxamide | 495 | (DMSO-d6, 400 MHz) δ (ppm): 8.31 (d, J = 8.4 Hz, 1H), 7.58 (d, J = 8.0 Hz, 1H), 7.31 (d, J = 8.0 Hz, 1H), 7.20-7.16 (m, 3H), 6.24 (d, J = 8.4 Hz, 1H), 4.13-4.10 (m, 1H), 3.65-3.61 (m, 1H), 3.56-3.49 (m, 1H), 3.47-3.44 (m, 1 H), 3.34-3.27 (m, 4H), 3.14-3.07 (m, 3H), 2.81-2.69 (m, 4H), 2.59-2.50 (m, 5H), 2.32-2.27 (m, 1H), 2.02-1.97 (m, 1H), 1.90-1.70 (m, 2H), 1.04-1.00 (m, 3H) | +++ | + |
| 477 | 3-amino-N-[(6S)-2-[(3S,4R)-3-(ethylamino)-4-(methoxymethyl)pyrrolidin-1-yl]-5,6,7,8-tetrahydroquinolin-6-yl]-6-methylthieno[2,3-b]pyridine-2-carboxamide | 495 | (DMSO-d6, 400 MHz) δ (ppm): 8.31 (d, J = 8.4 Hz, 1H), 7.58 (d, J = 8.0 Hz, 1H), 7.31 (d, J = 8.4 Hz, 1H), 7.20-7.16 (m, 3H), 6.24 (d, J = 8.4 Hz, 1H), 4.13-4.09 (m, 1H), 3.64-3.61 (m, 1H), 3.55-3.48 (m, 1H), 3.46-3.44 (m, 1 H), 3.33-3.27 (m, 4H), 3.16-3.08 (m, 3H), 2.78-2.72 (m, 4H), 2.59-2.50 (m, 5H), 2.32-2.27 (m, 1H), 2.02-1.97 (m, 1H), 1.90-1.70 (m, 2H), 1.04-1.00 (m, 3H) | +++ | + |
| 478 | 3-amino-N-[(6S)-2-[(2R,3R)-3-amino-2-(difluoromethyl)pyrrolidin-1-yl]-5,6,7,8-tetrahydroquinolin-6-yl]-6-methylthieno[2,3-b]pyridine-2-carboxamide | 473 | (DMSO-d6, 400 MHz) δ (ppm): 8.31 (d, J = 8.0 Hz, 1H), 7.62 (br s, 1H), 7.31 (d, J = 8.4 Hz, 1H), 7.28 (d, J = 8.4 Hz, 1H), 7.17 (br s, 2H), 6.40 (d, J = 8.4 Hz, 1H), 6.26 (t, J = 18.0 Hz, 1H), 4.16-4.13 (m, 1H), 4.09-4.02 (m, 1H), 3.71-3.69 (m, 1H), 3.46-3.43 (m, 2H), 2.85-2.67 (m, 4H), 2.59 (s, 3H), 2.15-2.00 (m, 2H), 1.91-1.81 (m, 1H), 1.76-1.72 (m, 3H) | +++ | + |
| 479 | 3-amino-N-[(6S)-2-[(2S,3S)-3-amino-2-(difluoromethyl)pyrrolidin-1-yl]-5,6, 7,8-tetrahydroquinolin-6-yl]-6-methylthieno[2,3-b]pyridine-2-carboxamide | 473 | (DMSO-d6, 400 MHz) δ (ppm): 8.31 (d, J = 8.0 Hz, 1H), 7.60 (br s, 1H), 7.31 (d, J = 8.4 Hz, 1H), 7.28 (d, J = 8.4 Hz, 1H), 7.17 (br s, 2H), 6.41 (d, J = 8.4 Hz, 1H), 6.23 (t, J = 18.0 Hz, 1H), 4.15-4.14 (m, 1H), 4.09-4.02 (m, 1H), 3.70-3.69 (m, 1H), 3.49-3.42 (m, 2H), 2.86-2.71 (m, 4H), 2.59 (s, 3H), 2.12-2.00 (m, 2H), 1.91-1.80 (m, 1H), 1.75-1.72 (m, 3H) | ++++ | +++ |
| 480 | 3-amino-N-[(6S)-2-[(3R,4S)-3-amino-4-(1,1-difluoro-2-methoxyethyl)pyrrolidin-1-yl]-5,6,7,8-tetrahydroquinolin-6-yl]-6-methylthieno[2,3-b]pyridine-2-carboxamide | 517 | (DMSO-d6, 400 MHz) δ (ppm): 8.31 (d, J = 8.4 Hz, 1H), 7.59 (br s, 1H), 7.31 (d, J = 8.4 Hz, 1H), 7.22 (d, J = 8.4 Hz, 1H), 7.16 (br s, 2H), 6.27 (d, J = 8.4 Hz, 1H) , 4.13-4.11 (m, 1H), 3.82-3.79 (m, 2H), 3.75-3.54 (m, 3H), 3.45-3.35 (m, 4 H), 3.05-3.01 (m, 1H), 2.78-2.60 (m, 5H), 2.59 (s, 3H), 2.03-1.85 (m, 3H) | +++ | |
| 481 | 3-amino-N-[(6S)-2-[(3S,4S)-3-amino-4-[(2S)-2-methoxypropoxy]pyrrolidin-1-yl]-5,6,7,8-tetrahydroquinolin-6-yl]-6-methylthieno[2,3-b]pyridine-2-carboxamide | 511 | (DMSO-d6, 400 MHz) δ (ppm): 8.31 (d, J = 8.0 Hz, 1H), 7.58 (d, J = 8.0 Hz, 1H), 7.31 (d, J = 8.4 Hz, 1H), 7.20-7.17 (m, 3H), 6.23 (d, J = 8.4 Hz, 1H), 4.14-4.10 (m, 1H), 3.74-3.73 (m, 1H), 3.64-3.60 (m, 1H), 3.49-3.38 (m, 5 H), 3.34-3.30 (m, 1H), 3.25 (s, 3H), 3.14-3.12 (m, 1H), 2.80-2.68 (m ,4H), 2.59 (s, 3H), 2.01-1.99 (m, 1H), 1.87-1.82(m, 1H), 1.68 (br s, 2 H), 1.04 (d, J = 6.0 Hz, 3H) | +++ | |
| 482 | 3-amino-N-[(6S)-2-[(3S,4S)-3-amino-4-[(2R)-2-methoxypropoxy]pyrrolidin-1-yl]-5,6,7,8-tetrahydroquinolin-6-yl]-6-methylthieno[2,3-b]pyridine-2-carboxamide | 511 | (DMSO-d6, 400 MHz) δ (ppm): 8.31 (d, J = 8.4 Hz, 1H), 7.58 (d, J = 8.0 Hz, 1H), 7.31 (d, J = 8.4 Hz, 1H), 7.20-7.17 (m, 3H), 6.23 (d, J = 8.8 Hz, 1H), 4.14-4.10 (m, 1H), 3.74-3.73 (m, 1H), 3.64-3.60 (m, 1H), 3.49-3.38 (m, 5 H), 3.34-3.30 (m, 1H), 3.25 (s, 3H), 3.14-3.12 (m, 1H), 2.80-2.68 (m, 4H), 2.59 (s, 3H), 2.03-1.99 (m, 1H), 1.87-1.82 (m, 1H), 1.68 (br s, 2 H), 1.04 (d, J = 6.0 Hz, 3H) | +++ | |

TABLE 24-continued

| | | | | |
|---|---|---|---|---|
| 483 | 3-amino-N-[(6S)-2-[(3R,4R)-3-amino-4-{[(2R)-1-methoxypropan-2-yl]oxy}pyrrolidin-1-yl]-5,6,7,8-tetrahydroquinolin-6-yl]-6-methylthieno[2,3-b]pyridine-2-carboxamide | 511 | (DMSO-d6, 400 MHz) δ (ppm): 8.31 (d, J = 8.0 Hz, 1H), 7.58 (d, J = 7.6 Hz, 1H), 7.31 (d, J = 8.4 Hz, 1H), 7.20-7.17 (m, 3H), 6.21 (d, J = 8.4 Hz, 1H), 4.13-4.10 (m, 1H), 3.85-3.84 (m, 1H), 3.74-3.70 (m, 1H), 3.65-3.61 (m, 1 H), 3.49-3.46 (m, 1H), 3.27-3.21 (m, 7H), 3.12-3.09 (m, 1H), 2.78-2.72 (m ,4H), 2.59 (s, 3H), 2.02-1.98 (m, 1H), 1.90-1.79 (m, 1H), 1.70 (br s, 2 H), 1.08 (d, J = 6.4 Hz, 3H) | +++ |
| 484 | 3-amino-N-[(6S)-2-[(3R,4R)-3-amino-4-[(trifluoromethoxy)methyl]pyrrolidin-1-yl]-5,6,7,8-tetrahydroquinolin-6-yl]-6-methylthieno[2,3-b]pyridine-2-carboxamide | 521 | (DMSO-d6, 400 MHz) δ (ppm): 8.31 (d, J = 8.4 Hz, 1H), 7.58 (d, J = 8.0 Hz, 1H), 7.31 (d, J = 8.0 Hz, 1H), 7.20 (d, J = 8.4 Hz, 1H), 7.17 (br s, 2H), 6.23 (d, J = 8.4 Hz, 1H), 4.40-4.36 (m, 1H), 4.17-4.12 (m, 2H), 3.62-3.59 (m, 1H), 3.54-3.49 (m, 2H), 3.32-3.22 (m, 2H), 2.83-2.69 (m, 4H), 2.59 (s, 3H), 2.58-2.50 (m, 1H), 2.01-1.94 (m, 2H), 1.91-1.79 (m, 2H) | ++ |
| 485 | 3-amino-N-[(6S)-2-[(3S,4S)-3-amino-4-[(trifluoromethoxy)methyl]pyrrolidin-1-yl]-5,6,7,8-tetrahydroquinolin-6-yl]-6-methylthieno[2,3-b]pyridine-2-carboxamide | 521 | (DMSO-d6, 400 MHz) δ (ppm): 8.31 (d, J = 8.4 Hz, 1H), 7.58 (d, J = 8.0 Hz, 1H), 7.31 (d, J = 8.4 Hz, 1H), 7.20 (d, J = 8.4 Hz, 1H), 7.17 (br s, 2H), 6.23 (d, J = 8.4 Hz, 1H), 4.40-4.36 (m, 1H), 4.17-4.12 (m, 2H), 3.62-3.60 (m, 2H), 3.55-3.50 (m, 2H), 3.32-3.22 (m, 2H), 2.84-2.69 (m, 4H), 2.59-2.50 (m, 4H), 2.03-1.97 (m, 1H), 1.92-1.68 (m, 3H) | +++ |
| 486 | 3-amino-N-[(6S)-2-[(3S,4R)-3-(methoxymethyl)-4-[($^{2}H_3$)methylamino]pyrrolidin-1-yl]-5,6,7,8-tetrahydroquinolin-6-yl]-6-methylthieno[2,3-b]pyridine-2-carboxamide | 484 | (DMSO-d6, 400 MHz) δ (ppm): 8.31 (d, J = 8.0 Hz, 1H), 7.58 (d, J = 7.6 Hz, 1H), 7.31 (d, J = 8.4 Hz, 1H), 7.21-7.16 (m, 3H), 6.25 (d, J = 8.4 Hz, 1H), 4.13-4.08 (m, 1H), 3.64-3.60 (m, 1H), 3.55-3.51 (m, 1H), 3.46-3.26 (m, 5 H), 3.17-3.13 (m, 2H), 3.07-3.04 (m, 1H), 2.81-2.71 (m ,4H), 2.59 (s, 3H), 2.38-2.33 (m, 1H), 2.01-1.97 (m, 1H), 1.87-1.79 (m, 1H) | +++ |
| 487 | 3-amino-N-[(6S)-2-[(3R,4S)-3-(methoxymethyl)-4-[($^{2}H_3$)methylamino]pyrrolidin-1-yl]-5,6,7,8-tetrahydroquinolin-6-yl]-6-methylthieno[2,3-b]pyridine-2-carboxamide | 484 | (DMSO-d6, 400 MHz) δ (ppm): 8.31 (d, J = 8.0 Hz, 1H), 7.58 (d, J = 7.6 Hz, 1H), 7.31 (d, J = 8.4 Hz, 1H), 7.21-7.16 (m, 3H), 6.25 (d, J = 8.4 Hz, 1H), 4.13-4.08 (m, 1H), 3.64-3.60 (m, 1H), 3.55-3.51 (m, 1H), 3.46-3.26 (m, 5 H), 3.17-3.13 (m, 2H), 3.07-3.04 (m, 1H), 2.81-2.71 (m, 4H), 2.59 (s, 3H), 2.33-2.28 (m, 1H), 2.01-1.97 (m, 1H), 1.87-1.79 (m, 1H) | ++ |
| 488 | 3-amino-N-[(6S)-2-[(3R,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.0 Hz, 1H), 7.57 (d, J = 8.0 Hz, 1H), 7.31 (d, J = 8.4 Hz, 1H), 7.18 (d, J = 8.4 Hz, 1H), 7.17 (br s, 2H), 6.23 (d, J = 8.4 Hz, 1H), 4.16-4.09 (m, 1H), 3.56-3.52 (m, 1H), 3.49-3.41 (m, 1H), 3.39-3.35 (m, 2H), 3.32-3.30 (m, 1H), 3.28-3.22 (m, 5H), 2.82-2.64 (m, 4H), 2.59 (s, 3H), 2.30 (s, 3H), 2.04-1.96 (m, 1H), 1.90-1.64 (m, 3H) | +++ |
| 489 | 3-amino-N-[(6S)-2-[(3S,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.58 (d, J = 8.0 Hz, 1H), 7.31 (d, J = 8.4 Hz, 1H), 7.19-7.17 (m, 3H), 6.22 (d, J = 8.4 Hz, 1H), 4.14-4.09 (m, 1H), 3.56-3.52 (m, 1H), 3.45-3.41 (m, 1H), 3.39-3.34 (m, 1H), 3.32-3.30 (m, 2H), 3.26-3.22 (m, 5H), 2.79-2.70 (m, 4H), 2.59 (s, 3H), 2.52-2.50 (m, 1H), 2.30 (s, 3H), 2.03-1.95 (m, 1H), 1.90-1.80 (m, 1H), 1.70 (br s, 1H) | +++ |

TABLE 24-continued

| | | | | |
|---|---|---|---|---|
| 490 | 7-amino-N-[(6S)-2-[(3S,4S)-3-methoxy-4-(methylamino)pyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.82 (d, J = 7.6 Hz, 1H), 7.20 (d, J = 8.8 Hz, 1H), 6.93 (br s, 2H), 6.24 (d, J = 8.4 Hz, 1H), 4.17-4.13 (m, 1H), 3.78-3.76 (m, 1H), 3.54-3.50 (m, 1H), 3.48-3.44 (m, 1H), 3.40-3.37 (m, 1H), 3.30 (s, 3H), 3.24-3.22 (m, 1H), 3.12-3.11 (m, 1H), 2.84-2.72 (m, 4H), 2.65 (s, 3H), 2.32 (s, 3H), 2.08-1.97 (m, 1H), 1.90-1.83 (m, 2H) | +++ |
| 491 | 7-amino-N-[(6S)-2-[(3S,4R)-3-amino-4-methoxypyrrolidin-1-yl]-5,6,7,8-tetrahydroquinolin-6-yl]-3-methylthieno[2,3-b]pyrazine-6-carboxamide | 454 | (DMSO-d6, 400 MHz) δ (ppm): 8.65 (s, 1H), 7.82 (d, J = 7.6 Hz, 1H), 7.19 (d, J = 8.4 Hz, 1H), 6.92 (br s, 2H), 6.21 (d, J = 8.4 Hz, 1H), 4.17-4.11 (m, 1H), 3.73-3.72 (m, 1H), 3.51-3.40 (m, 4H), 3.01-2.96 (m, 1H), 2.84-2.69 (m ,4H), 2.65 (s, 3H), 2.04-1.98 (m, 1H), 1.90-1.80 (m, 1H), 1.60 (br s, 2H) | +++ |
| 492 | 7-amino-N-[(6S)-2-[(3R,4S)-3-amino-4-methoxypyrrolidin-1-yl]-5,6,7,8-tetrahydroquinolin-6-yl]-3-methylthieno[2,3-b]pyrazine-6-carboxamide | 454 | (DMSO-d6, 400 MHz) δ (ppm): 8.65 (s, 1H), 7.82 (d, J = 7.6 Hz, 1H), 7.19 (d, J = 8.4 Hz, 1H), 6.93 (br s, 2H), 6.22 (d, J = 8.4 Hz, 1H), 4.17-4.11 (m, 1H), 3.73-3.72 (m, 1H), 3.53-3.39 (m, 4H), 2.97-2.92 (m, 1H), 2.79-2.72 (m, 4H), 2.66 (s, 3H), 2.06-1.98 (m, 1H), 1.90-1.80 (m, 1H), 1.65 (br s, 2H) | +++ |
| 493 | 3-amino-N-[(6S)-2-[(3R,4R)-3-amino-4-methoxyazepan-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.56 (d, J = 7.6 Hz, 1H), 7.31 (d, J = 8.4 Hz, 1H), 7.20-7.16 (m, 3H), 6.47 (d, J = 8.8 Hz, 1H), 4.18-4.09 (m, 1H), 3.91-3.84 (m, 1H), 3.81-3.76 (m, 1H), 3.28 (s, 3H), 3.26-3.05 (m, 4H), 2.82-2.68 (m, 4H), 2.59 (s, 3H), 2.01-1.73 (m, 5H), 1.30-1.24 (m, 1H) | ++++ |
| 494 | 3-amino-N-[(6S)-2-[(3S,4S)-3-amino-4-methoxyazepan-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.56 (d, J = 7.6 Hz, 1H), 7.31 (d, J = 8.0 Hz, 1H), 7.20-7.15 (m, 3H), 6.47 (d, J = 8.8 Hz, 1H), 4.18-4.09 (m, 1H), 3.90-3.86 (m, 1H), 3.81-3.77 (m, 1H), 3.27 (s, 3H), 3.24-3.05 (m, 4H), 2.80-2.68 (m, 4H), 2.59 (s, 3H), 2.01-1.74 (m, 5H), 1.31-1.24 (m, 1H) | ++++ |
| 495 | 3-amino-N-[(6S)-2-[(3S,4R)-3-amino-4-methoxyazepan-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.56 (d, J = 7.6 Hz, 1H), 7.31 (d, J = 8.4 Hz, 1H), 7.20-7.15 (m, 3H), 6.50 (d, J = 8.4 Hz, 1H), 4.15-4.10 (m, 1H), 3.75-3.65 (m, 2H), 3.27-3.22 (m, 5H), 2.90-2.86 (m, 1H), 2.78-2.72 (m, 5H), 2.59 (s, 3H), 2.08-1.98 (m, 2H), 1.92-1.83 (m, 3H), 1.62-1.56 (m, 1H), 1.30-1.23 (m, 1H) | +++ |
| 496 | 7-amino-N-[(6S)-2-[(3R,4S)-3-methoxy-4-(methylamino)pyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.81 (d, J = 7.6 Hz, 1H), 7.20 (d, J = 8.4 Hz, 1H), 6.92 (br s, 2H), 6.23 (d, J = 8.4 Hz, 1H), 4.17-4.11 (m, 1H), 3.95-3.94 (m, 1H), 3.56-3.50 (m, 2H), 3.42-3.38 (m, 1H), 3.32 (s, 3H), 3.23-3.19 (m, 1H), 3.05-3.01 (m, 1H), 2.81-2.73 (m, 4H), 2.66 (s, 3H), 2.34 (s, 3H), 2.04-1.98 (m, 1H), 1.92-1.82 (m, 1H), 1.63 (br s, 1H) | ++ |
| 497 | 7-amino-N-[(6S)-2-[(3S,4R)-3-methoxy-4-(methylamino)pyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.82 (d, J = 8.0 Hz, 1H), 7.20 (d, J = 8.4 Hz, 1H), 6.92 (br s, 2H), 6.23 (d, J = 8.4 Hz, 1H), 4.17-4.11 (m, 1H), 3.95-3.94 (m, 1H), 3.58-3.51 (m, 2H), 3.41-3.37 (m, 1H), 3.32 (s, 3H), 3.23-3.19 (m, 1H), 3.04-2.99 (m, 1H), 2.84-2.73 (m, 4H), 2.66 (s, 3H), 2.34 (s, 3H), | ++ |

TABLE 24-continued

| | | | | |
|---|---|---|---|---|
| | | | 2.04-1.98 (m, 1H), 1.92-1.82 (m, 1H), 1.61 (br s, 1H) | |
| 498 | 7-amino-N-[(6S)-2-[(9S)-9-amino-1,4-dioxa-7-azaspiro[4.4]nonan-7-yl]-5,6,7,8-tetrahydroquinolin-6-yl]-3-methylthieno[2,3-b]pyrazine-6-carboxamide | 482 | (DMSO-d6, 400 MHz) δ (ppm): 8.66 (s, 1H), 7.81 (d, J = 7.6 Hz, 1H), 7.21 (d, J = 8.4 Hz, 1H), 6.92 (br s, 2H), 6.22 (d, J = 8.4 Hz, 1H), 4.17-4.15 (m, 1H), 4.03-3.94 (m, 4H), 3.60-3.50 (m, 2H), 3.35-3.33 (m, 2H), 3.06-3.02 (m, 1H), 2.85-2.72 (m, 4H), 2.66 (s, 3H), 2.05-1.98 (m, 1H), 1.93-1.87 (m, 1H), 1.60 (br s, 2H) | ++ |
| 499 | 7-amino-N-[(6S)-2-[(9R)-9-amino-1,4-dioxa-7-azaspiro[4.4]nonan-7-yl]-5,6,7,8-tetrahydroquinolin-6-yl]-3-methylthieno[2,3-b]pyrazine-6-carboxamide | 482 | (DMSO-d6, 400 MHz) δ (ppm): 8.65 (s, 1H), 7.81 (d, J = 7.6 Hz, 1H), 7.21 (d, J = 8.4 Hz, 1H), 6.92 (br s, 2H), 6.22 (d, J = 8.8 Hz, 1H), 4.17-4.10 (m, 1H), 4.04-3.94 (m, 4H), 3.61-3.51 (m, 2H), 3.35-3.33 (m, 2H), 3.05-3.01 (m, 1H), 2.84-2.73 (m, 4H), 2.66 (s, 3H), 2.05-1.98 (m, 1H), 1.91-1.83 (m, 1H), 1.60 (br s, 2H) | ++ |
| 500 | 3-amino-N-[(6S)-2-[(3R,4R)-3-amino-4-(methoxymethyl)pyrrolidin-1-yl]-5,6,7,8-tetrahydroquinolin-6-yl]thieno[2,3-c]pyridine-2-carboxamide | 453 | (DMSO-d6, 400 MHz) δ (ppm): 9.14 (s, 1H), 8.50 (d, J = 5.2 Hz, 1H), 8.01 (d, J = 5.6 Hz, 1H), 7.82 (d, J = 8.0 Hz, 1H), 7.21-7.14 (m, 3H), 6.24-6.19 (m, 1H), 4.22-4.10 (m, 1H), 3.59-3.18 (m, 10H), 2.83-2.68 (m, 4H), 2.45-2.34 (m, 1H), 2.03-2.00 (m, 1H), 1.92-1.85 (m, 1H) | + |
| 501 | 3-amino-N-[(6S)-2-[(3R,4S)-3-amino-4-methoxyazepan-1-yl]-5,6,7,8-tetrahydroquinolin-6-yl]-6-methylthieno[2,3-b]pyridine-2-carboxamide | 481 | (DMSO-d6, 400 MHz) δ (ppm): 8.31 (d, J = 8.4 Hz, 1H), 7.58 (d, J = 7.6 Hz, 1H), 7.31 (d, J = 8.4 Hz, 1H), 7.20-7.15 (m, 3H), 6.50 (d, J = 8.4 Hz, 1H), 4.15-4.10 (m, 1H), 3.76-3.72 (m, 1H), 3.66-3.62 (m, 1H), 3.28-3.24 (m, 5H), 2.89-2.87 (m, 1H), 2.78-2.70 (m, 5H), 2.59 (s, 3H), 2.01-1.98 (m, 1H), 1.94-1.79 (m, 3H), 1.65-1.56 (m, 1H), 1.30-1.22 (m, 1H) | ++ |
| 502 | 3-amino-6-methyl-N-[(6S)-2-[(4S,5R)-4-(methylamino)-6-oxa-2-azaspiro[4.5]decan-2-yl]-5,6,7,8-tetrahydroquinolin-6-yl]thieno[2,3-b]pyridine-2-carboxamide | 507 | (DMSO-d6, 400 MHz) δ (ppm): 8.30 (d, J = 8.4 Hz, 1H), 7.57 (d, J = 8.0 Hz, 1H), 7.31 (d, J = 8.4 Hz, 1H), 7.19 (d, J = 8.4 Hz, 1H), 7.16 (br s, 2H), 6.26 (d, J = 8.4 Hz, 1H), 4.15-4.09 (m, 1H), 3.77 (d, J = 7.2 Hz, 1H), 3.68-3.53 (m, 3H), 3.23 (d, J = 11.2 Hz, 1H), 3.13-3.09 (m, 1H), 2.96-2.93 (m, 1H), 2.81-2.68 (m, 4H), 2.59 (s, 3H), 2.39 (s, 3H), 2.02-1.98 (m, 1H), 1.87-1.81 (m, 2H), 1.78-1.70 (m, 1H), 1.61-1.46 (m, 4H) | +++ |
| 503 | 3-amino-6-methyl-N-[(6S)-2-[(4R,5S)-4-(methylamino)-6-oxa-2-azaspiro[4.5]decan-2-yl]-5,6,7,8-tetrahydroquinolin-6-yl]thieno[2,3-b]pyridine-2-carboxamide | 507 | (DMSO-d6, 400 MHz) δ (ppm): 8.30 (d, J = 8.4 Hz, 1H), 7.57 (d, J = 7.6 Hz, 1H), 7.31 (d, J = 8.4 Hz, 1H), 7.19 (d, J = 8.8 Hz, 1H), 7.16 (br s, 2H), 6.26 (d, J = 8.4 Hz, 1H), 4.15-4.09 (m, 1H), 3.79 (d, J = 6.8 Hz, 1H), 3.68-3.55 (m, 3H), 3.22 (d, J = 11.2 Hz, 1H), 3.10-3.06 (m, 1H), 2.96-2.93 (m, 1H), 2.81-2.68 (m, 4H), 2.59 (s, 3H), 2.38 (s, 3H), 2.02-1.98 (m, 1H), 1.87-1.79 (m, 2H), 1.76-1.67 (m, 1H), 1.61-1.44 (m, 5H) | +++ |
| 504 | 3-amino-N-[(6S)-2-[(3S,4S)-3-amino-4-methoxypyrrolidin-1-yl]-5,6,7,8-tetrahydroquinolin-6-yl]thieno[2,3-c]pyridine-2-carboxamide | 439 | (DMSO-d6, 400 MHz) δ (ppm): 9.14 (s, 1H), 8.50 (d, J = 5.6 Hz, 1H), 8.01 (d, J = 5.2 Hz, 1H), 7.81 (d, J = 7.6 Hz, 1H), 7.20 (d, J = 8.4 Hz, 1H), 7.13 (br s, 2H), 6.23 (d, J = 8.4 Hz, 1H), 4.15-4.10 (m, 1H), 3.62-3.60 (m, 2H), 3.44-3.43 (m, 2H), 3.35-3.30 (m, 4H), 3.13-3.10 (m, 1H), 2.79-2.70 (m, 4H), 2.02-1.97 (m, 1H), 1.90-1.70 (m, 2H) | + |

TABLE 24-continued

| No. | Name | MW | NMR | A | B |
|---|---|---|---|---|---|
| 505 | 3-amino-N-[(6S)-2-[(5R)-1,7-diazaspiro[4.4]nonan-7-yl]-5,6,7,8-tetrahydroquinolin-6-yl]-6-methylthieno[2,3-b]pyridine-2-carboxamide | 463 | (DMSO-d6, 400 MHz) δ (ppm): 8.30 (d, J = 8.4 Hz, 1H), 7.55 (d, J = 8.0 Hz, 1H), 7.31 (d, J = 8.0 Hz, 1H), 7.18 (d, J = 8.8 Hz, 1H), 7.15 (br s, 2H), 6.20 (d, J = 8.8 Hz, 1H), 4.20-4.08 (m, 1H), 3.42-3.38 (m, 2H), 3.32-3.25 (m, 2H), 2.88-2.68 (m, 6H), 2.59 (s, 3H), 2.40-2.10 (br, 1H), 2.04-1.99 (m, 1H), 1.93-1.81 (m, 3H), 1.79-1.59 (m, 4H) | +++ | |
| 506 | 3-amino-N-[(6S)-2-[(5S)-1,7-diazaspiro[4.4]nonan-7-yl]-5,6,7,8-tetrahydroquinolin-6-yl]-6-methylthieno[2,3-b]pyridine-2-carboxamide | 463 | (DMSO-d6, 400 MHz) δ (ppm): 8.30 (d, J = 8.4 Hz, 1H), 7.55 (d, J = 8.0 Hz, 1H), 7.31 (d, J = 8.4 Hz, 1H), 7.18 (d, J = 8.4 Hz, 1H), 7.15 (br s, 2H), 6.20 (d, J = 8.4 Hz, 1H), 4.20-4.08 (m, 1H), 3.44-3.36 (m, 2H), 3.32-3.26 (m, 2H), 2.87-2.72 (m, 6H), 2.59 (s, 3H), 2.40-2.10 (br s, 1H), 2.04-1.96 (m, 1H), 1.91-1.81 (m, 3H), 1.79-1.58 (m, 4H) | | |
| 507 | 3-amino-N-[(6S)-2-[(3S,4R)-3-amino-4-(fluoromethyl)pyrrolidin-1-yl]-5,6,7,8-tetrahydroquinolin-6-yl]-5-fluoro-6-methylthieno[2,3-b]pyridine-2-carboxamide | 473 | (DMSO-d6, 400 MHz) δ (ppm): 8.31 (d, J = 8.0 Hz, 1H), 7.59 (br s, 1H), 7.31 (d, J = 8.0 Hz, 1H), 7.22 (d, J = 8.4 Hz, 1H), 7.17 (br s, 2H), 6.27 (d, J = 8.4 Hz, 1H), 4.13-4.11 (m, 1H), 3.82-3.79 (m, 2H), 3.75-3.54 (m, 3H), 3.43-3.39 (m, 4H), 3.05-3.01 (m, 1H), 2.78-2.60 (m, 5H), 2.59 (s, 3H), 2.03-1.85 (m, 3H) | +++ | ++ |
| 508 | 3-amino-N-[(6S)-2-[(4S,5R)-4-amino-6-oxa-2-azaspiro[4.5]decan-2-yl]-5,6,7,8-tetrahydroquinolin-6-yl]-6-methylthieno[2,3-b]pyridine-2-carboxamide | 493 | (DMSO-d6, 400 MHz) δ (ppm): 8.29 (d, J = 8.0 Hz, 1H), 7.55 (d, J = 7.6 Hz, 1H), 7.31 (d, J = 8.0 Hz, 1H), 7.20-7.15 (m, 3H), 6.23 (d, J = 8.4 Hz, 1H), 4.15-4.09 (m, 1H), 3.93 (d, J = 8.0 Hz, 1H), 3.73-3.69 (m, 1H), 3.60-3.51 (m, 2H), 3.32-3.06 (m, 2H), 2.97-2.92 (m, 1H), 2.82-2.70 (m, 4H), 2.59 (s, 3H), 2.03-1.97 (m, 1H), 1.91-1.68 (m, 3H), 1.61-1.41 (m, 6H) | +++ | |
| 509 | 3-amino-N-[(6S)-2-[(4S,5R,9S)-9-amino-4-methyl-1-oxa-7-azaspiro[4.4]nonan-7-yl]-5,6,7,8-tetrahydroquinolin-6-yl]-6-methylthieno[2,3-b]pyridine-2-carboxamide | 493 | (DMSO-d6, 400 MHz) δ (ppm): 8.31 (d, J = 8.0 Hz, 1H), 7.55 (d, J = 7.6 Hz, 1H), 7.31 (d, J = 8.4 Hz, 1H), 7.19-7.16 (m, 3H), 6.20 (d, J = 8.4 Hz, 1H), 4.15-4.09 (m, 1H), 3.84-3.79 (m, 1H), 3.76-3.72 (m, 1H), 3.61-3.57 (m, 1H), 3.38-3.22 (m, 3H), 2.93-2.89 (m, 1H), 2.82-2.78 (m, 4H), 2.59 (s, 3H), 2.31-2.25 (m, 1H), 2.20-2.12 (m, 1H), 2.02-1.98 (m, 1H), 1.91-1.79 (m, 1H), 1.65-1.59 (m, 1H), 1.03 (d, J = 6.8 Hz, 3H) | +++ | |
| 510 | 3-amino-N-[(6S)-2-[(4R,5R,9S)-9-amino-4-methyl-1-oxa-7-azaspiro[4.4]nonan-7-yl]-5,6,7,8-tetrahydroquinolin-6-yl]-6-methylthieno[2,3-b]pyridine-2-carboxamide | 493 | (DMSO-d6, 400 MHz) δ (ppm): 8.31 (d, J = 8.4 Hz, 1H), 7.55 (d, J = 7.6 Hz, 1H), 7.31 (d, J = 8.4 Hz, 1H), 7.19-7.15 (m, 3H), 6.17 (d, J = 8.4 Hz, 1H), 4.15-4.09 (m, 1H), 3.98-3.94 (m, 1H), 3.71-3.58 (m, 2H), 3.39-3.27 (m, 3H), 2.91-2.86 (m, 1H), 2.82-2.74 (m, 4H), 2.59 (s, 3H), 2.20-2.12 (m, 1H), 2.02-1.98 (m, 2H), 1.88-1.78 (m, 2H), 1.59 (m, 2H), 1.14 (d, J = 6.8 Hz, 3H) | +++ | |
| 511 | 3-amino-N-[(6S)-2-[(4S,5S,9R)-9-amino-4-methyl-1-oxa-7-azaspiro[4.4]nonan-7-yl]-5,6,7,8-tetrahydroquinolin-6-yl]-6-methylthieno[2,3-b]pyridine-2-carboxamide | 493 | (DMSO-d6, 400 MHz) δ (ppm): 8.31 (d, J = 8.4 Hz, 1H), 7.55 (d, J = 7.6 Hz, 1H), 7.31 (d, J = 8.4 Hz, 1H), 7.19-7.15 (m, 3H), 6.17 (d, J = 8.4 Hz, 1H), 4.15-4.09 (m, 1H), 3.98-3.94 (m, 1H), 3.71-3.58 (m, 2H), 3.39-3.27 (m, 3H), 2.91-2.86 (m, 1H), 2.82-2.74 (m, 4H), 2.59 (s, 3H), 2.22-2.14 (m, 1H), 2.02-1.96 (m, 2H), 1.90-1.78 (m, 2H), 1.59 (m, 2H), 1.14 (d, J = 6.8 Hz, 3H) | ++ | |

TABLE 24-continued

| | | | | |
|---|---|---|---|---|
| 512 | 3-amino-N-[(6S)-2-[(4R,5S,9R)-9-amino-4-methyl-1-oxa-7-azaspiro[4.4]nonan-7-yl]-5,6,7,8-tetrahydroquinolin-6-yl]-6-methylthieno[2,3-b]pyridine-2-carboxamide | 493 | (DMSO-d6, 400 MHz) δ (ppm): 8.31 (d, J = 8.0 Hz, 1H), 7.55 (d, J = 8.0 Hz, 1H), 7.31 (d, J = 8.4 Hz, 1H), 7.19-7.15 (m, 3H), 6.21 (d, J = 8.4 Hz, 1H), 4.15-4.09 (m, 1H), 3.84-3.82 (m, 1H), 3.74-3.58 (m, 1H), 3.61-3.58 (m, 1H), 3.38-3.22 (m, 3H), 2.94-2.88 (m, 1H), 2.82-2.78 (m, 4H), 2.59 (s, 3H), 2.32-2.25 (m, 1H), 2.21-2.12 (m, 1H), 2.02-1.97 (m, 1H), 1.91-1.79 (m, 1H), 1.65-1.59 (m, 1H), 1.03 (d, J = 6.8 Hz, 3H) | +++ |
| 513 | 3-amino-N-[(6S)-2-[(3R,4R)-3-amino-4-(methoxymethyl)pyrrolidin-1-yl]-5,6,7,8-tetrahydroquinolin-6-yl]-5-fluoro-6-methylthieno[2,3-b]pyridine-2-carboxamide | 485 | (DMSO-d6, 400 MHz) δ (ppm): 8.29 (d, J = 10.4 Hz, 1H), 7.65 (d, J = 7.6 Hz, 1H), 7.17 (d, J = 8.4 Hz, 1H), 7.12 (br s, 2H), 6.20 (d, J = 8.4 Hz, 1H), 4.15-4.09 (m, 1H), 3.60-3.52 (m, 2H), 3.49-3.37 (m, 3H), 3.28 (s, 3H), 3.26-3.17 (m, 2H), 2.82-2.67 (m, 4H), 2.56 (s, 3H), 2.42-2.35 (m, 1H), 2.02-1.98 (m, 1H), 1.89-1.79 (m, 1H), 1.55 (br s, 2H) | +++ |
| 514 | 3-amino-5-fluoro-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide | 499 | (DMSO-d6, 400 MHz) δ (ppm): 8.29 (d, J = 10.0 Hz, 1H), 7.65 (d, J = 7.6 Hz, 1H), 7.19 (d, J = 8.4 Hz, 1H), 7.12 (br s, 2H), 6.24 (d, J = 8.4 Hz, 1H), 4.15-4.09 (m, 1H), 3.62-3.59 (m, 1H), 3.54-3.50 (m, 1H), 3.46-3.42 (m, 1H), 3.33-3.26 (m, 4H), 3.18-3.09 (m, 2H), 3.00-2.98 (m, 1H), 2.81-2.68 (m, 4H), 2.59 (s, 3H), 2.34-2.31 (m, 4H), 2.02-1.98 (m, 1H), 1.91-1.79 (m, 1H) | +++ |
| 515 | 3-amino-5-fluoro-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide | 499 | (DMSO-d6, 400 MHz) δ (ppm): 8.29 (d, J = 10.0 Hz, 1H), 7.65 (d, J = 7.6 Hz, 1H), 7.19 (d, J = 8.4 Hz, 1H), 7.12 (br s, 2H), 6.24 (d, J = 8.4 Hz, 1H), 4.15-4.09 (m, 1H), 3.64-3.60 (m, 1H), 3.55-3.50 (m, 1H), 3.46-3.42 (m, 1H), 3.33-3.27 (m, 4H), 3.17-3.08 (m, 2H), 3.00-2.97 (m, 1H), 2.81-2.68 (m, 4H), 2.57 (s, 3H), 2.34-2.31 (m, 4H), 2.02-1.79 (m, 3H) | +++ |
| 516 | 3-amino-N-[(6S)-2-[(3R,4R)-3-amino-4-[(difluoromethoxy)methyl]pyrrolidin-1-yl]-5,6,7,8-tetrahydroquinolin-6-yl]-6-methylthieno[2,3-b]pyridine-2-carboxamide | 503 | (DMSO-d6, 400 MHz) δ (ppm): 8.31 (d, J = 8.0 Hz, 1H), 7.55 (d, J = 8.0 Hz, 1H), 7.31 (d, J = 8.4 Hz, 1H), 7.19 (d, J = 8.4 Hz, 1H), 7.15 (br s, 2H), 6.90-6.52 (m, 1H), 6.22 (d, J = 8.4 Hz, 1H), 4.18-4.09 (m, 2H), 3.93-3.88 (m, 1H), 3.58-3.47 (m, 3H), 3.33-3.20 (m, 2H), 2.81-2.68 (m, 4H), 2.59 (s, 3H), 2.50-2.47 (m, 1H), 2.02-1.99 (m, 1H), 1.91-1.79 (m, 1H), 1.60 (br s, 2H) | +++ |
| 517 | 3-amino-N-[(6S)-2-[(3S,4S)-3-amino-4-[(difluoromethoxy)methyl]pyrrolidin-1-yl]-5,6,7,8-tetrahydroquinolin-6-yl]-6-methylthieno[2,3-b]pyridine-2-carboxamide | 503 | (DMSO-d6, 400 MHz) δ (ppm): 8.31 (d, J = 8.0 Hz, 1H), 7.55 (d, J = 7.6 Hz, 1H), 7.31 (d, J = 8.0 Hz, 1H), 7.19 (d, J = 8.4 Hz, 1H), 7.15 (br s, 2H), 6.90-6.52 (m, 1H), 6.22 (d, J = 8.4 Hz, 1H), 4.18-4.09 (m, 2H), 3.93-3.89 (m, 1H), 3.58-3.49 (m, 3H), 3.31-3.21 (m, 2H), 2.81-2.68 (m, 4H), 2.59 (s, 3H), 2.50-2.46 (m, 1H), 2.01-1.97 (m, 1H), 1.91-1.65 (m, 3H) | +++ |
| 518 | 3-amino-N-[(6S)-2-[(5S)-5-amino-3,3-difluoropiperidin-1-yl]-5,6,7,8-tetrahydroquinolin-6-yl]-6-methylthieno[2,3-b]pyridine-2-carboxamide | 473 | | ++++ |
| 519 | 3-amino-N-[(6S)-2-[(5R)-5-amino-3,3-difluoropiperidin-1-yl]-5,6,7,8-tetrahydroquinolin-6-yl]-6-methylthieno[2,3-b]pyridine-2-carboxamide | 473 | | ++++ |

TABLE 24-continued

| 520 | 7-amino-N-[(6S)-2-[(3S,4S)-3-amino-4-ethoxypyrrolidin-1-yl]-5,6,7,8-tetrahydroquinolin-6-yl]-3-methylthieno[2,3-b]pyrazine-6-carboxamide | 468 | (DMSO-d6, 400 MHz) δ (ppm): 8.65 (s, 1H), 7.82 (d, J = 7.6 Hz, 1H), 7.19 (d, J = 8.4 Hz, 1H), 6.92 (br s, 2H), 6.23 (d, J = 8.4 Hz, 1H), 4.17-4.11 (m, 1H), 3.71-3.70 (m, 1H), 3.64-3.60 (m, 1H), 3.54-3.46 (m, 3H), 3.40-3.39 (m, 1H), 3.32-3.29 (m, 1H), 3.13-3.10 (m, 1H), 2.84-2.68 (m, 4H), 2.66 (s, 3H), 2.03-1.97 (m, 1H), 1.88-1.77 (m, 3H), 1.13-1.09 (m, 3H) | ++ |
| --- | --- | --- | --- | --- |
| 521 | N-[(6S)-2-[(3aS,7aR)-octahydro-1H-pyrrolo[3,2-c]pyridin-1-yl]-5,6,7,8-tetrahydroquinolin-6-yl]-3-amino-6-methylthieno[2,3-b]pyridine-2-carboxamide | 463 | | |
| 522 | N-[(6S)-2-[(3aR,7aS)-octahydro-1H-pyrrolo[3,2-c]pyridin-1-yl]-5,6,7,8-tetrahydroquinolin-6-yl]-3-amino-6-methylthieno[2,3-b]pyridine-2-carboxamide | 463 | | |
| 523 | 3-amino-N-[(6S)-2-[(3R)-3-amino-4,4-difluoropiperidin-1-yl]-5,6,7,8-tetrahydroquinolin-6-yl]-6-methylthieno[2,3-b]pyridine-2-carboxamide | 473 | | |
| 524 | 3-amino-N-[(6S)-2-[(3S)-3-amino-4,4-difluoropiperidin-1-yl]-5,6,7,8-tetrahydroquinolin-6-yl]-6-methylthieno[2,3-b]pyridine-2-carboxamide | 473 | | |

TABLE 25

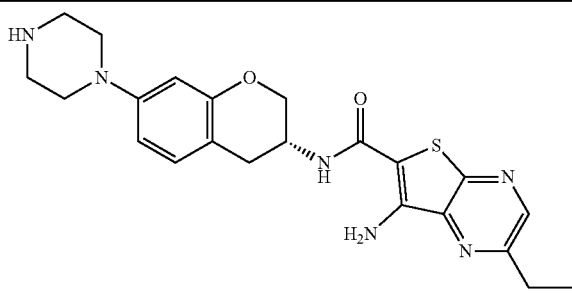

36. (R)-7-amino-2-ethyl-N-(7-(piperazin-1-yl)chroman-3-yl)thieno[2,3-b]pyrazine-6-carboxamide

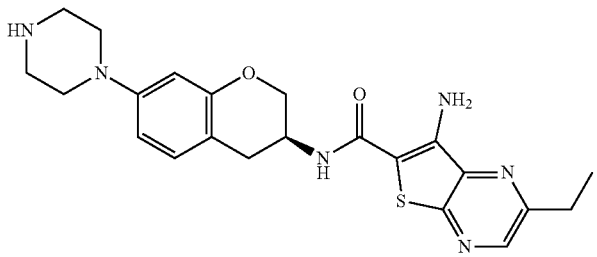 [SMILES: CCc1cnc2sc(C(=O)N[C@@H]3COc4cc(N5CCNCC5)ccc4C3)c(N)c2n1]

37. (S)-7-amino-2-ethyl-N-(7-(piperazin-1-yl)chroman-3-yl)thieno[2,3-b]pyrazine-6-carboxamide TABLE 25-continued
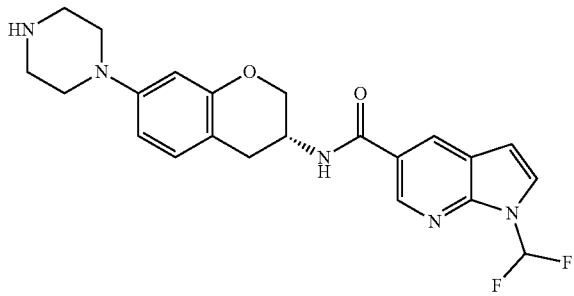 [SMILES: O=C(N[C@H]1COc2cc(N3CCNCC3)ccc2C1)c1cnc2c(ccn2C(F)F)c1]
38. (R)-1-(difluoromethyl)-N-(7-(piperazin-1-yl)chroman-3-yl)-1H-pyrrolo[2,3-b]pyridine-5-carboxamide
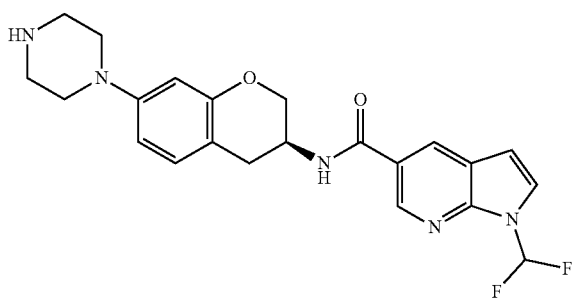 [SMILES: O=C(N[C@@H]1COc2cc(N3CCNCC3)ccc2C1)c1cnc2c(ccn2C(F)F)c1]
39. (S)-1-(difluoromethyl)-N-(7-(piperazin-1-yl)chroman-3-yl)-1H-pyrrolo[2,3-b]pyridine-5-carboxamide
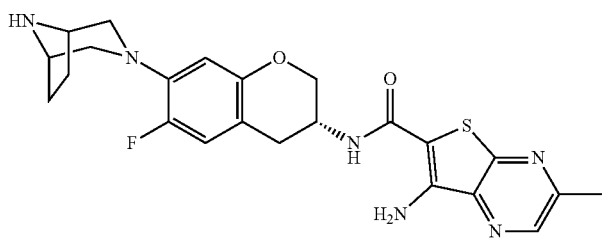 [SMILES: Cc1cnc2c(N)c(C(=O)N[C@H]3COc4cc(N5CC6CCC(C5)N6)c(F)cc4C3)sc2n1]
40. N-((3R)-7-(3,8-diazabicyclo[3.2.1]octan-3-yl)-6-fluorochroman-3-yl)-7-amino-3-methylthieno[2,3-b]pyrazine-6-carboxamide
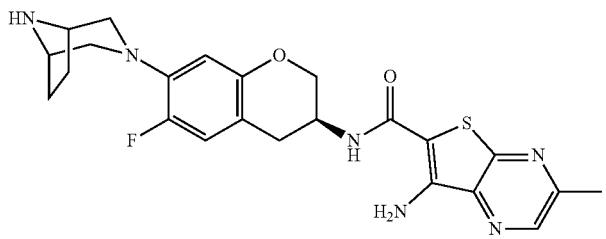 [SMILES: Cc1cnc2c(N)c(C(=O)N[C@@H]3COc4cc(N5CC6CCC(C5)N6)c(F)cc4C3)sc2n1]
41. N-((3S)-7-(3,8-diazabicyclo[3.2.1]octan-3-yl)-6-fluorochroman-3-yl)-7-amino-3-methylthieno[2,3-b]pyrazine-6-carboxamide TABLE 25-continued

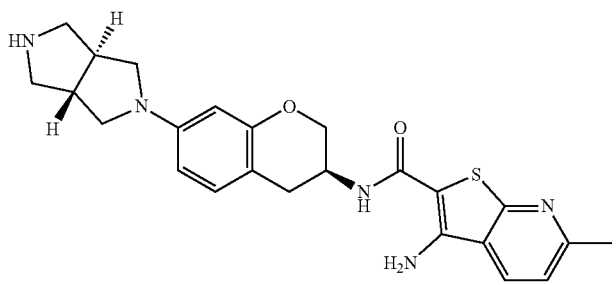 [SMILES: Cc1ccc2c(N)c(C(=O)N[C@@H]3COc4cc(N5C[C@@H]6CNC[C@H]6C5)ccc4C3)sc2n1]

42. 3-amino-N-((S)-7-((3aS,6aS)-hexahydropyrrolo[3,4-c]pyrrol-2(1H)-yl)chroman-3-yl)-6-methylthieno[2,3-b]pyridine-2-carboxamide

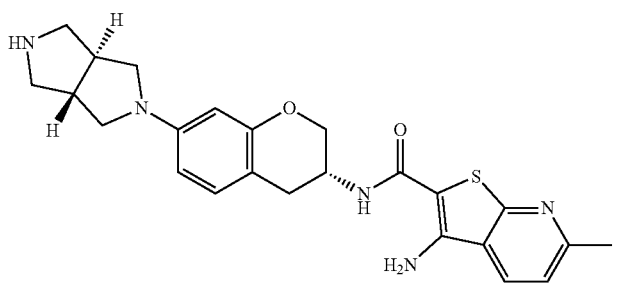 [SMILES: Cc1ccc2c(N)c(C(=O)N[C@H]3COc4cc(N5C[C@@H]6CNC[C@H]6C5)ccc4C3)sc2n1]

43. 3-amino-N-((R)-7-((3aR,6aR)-hexahydropyrrolo[3,4-c]pyrrol-2(1H)-yl)chroman-3-yl)-6-methylthieno[2,3-b]pyridine-2-carboxamide

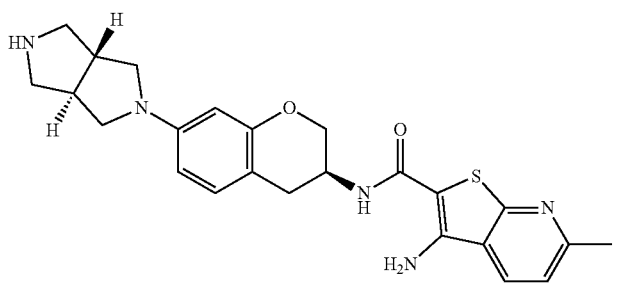 [SMILES: Cc1ccc2c(N)c(C(=O)N[C@@H]3COc4cc(N5C[C@H]6CNC[C@@H]6C5)ccc4C3)sc2n1]

44. 3-amino-N-((S)-7-((3aR,6aR)-hexahydropyrrolo[3,4-c]pyrrol-2(1H)-yl)chroman-3-yl)-6-methylthieno[2,3-b]pyridine-2-carboxamide

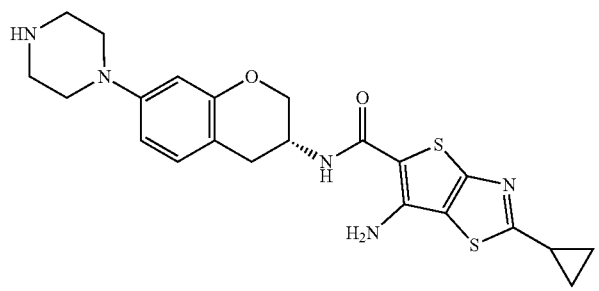 [SMILES: Nc1c(C(=O)N[C@H]2COc3cc(N4CCNCC4)ccc3C2)sc2nc(C3CC3)sc12]

45. (R)-6-amino-2-cyclopropyl-N-(7-(piperazin-1-yl)chroman-3-yl)thieno[2,3-d]thiazole-5-carboxamide

TABLE 25-continued
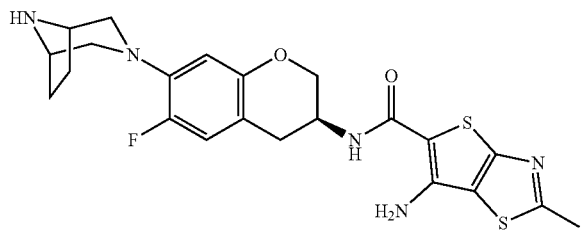 [SMILES: Cc1nc2sc(C(=O)N[C@@H]3COc4cc(N5CC6CCC(C5)N6)c(F)cc4C3)c(N)c2s1]
46. N-((3S)-7-(3,8-diazabicyclo[3.2.1]octan-3-yl)-6-fluorochroman-3-yl)-6-amino-2-methylthieno[2,3-d]thiazole-5-carboxamide
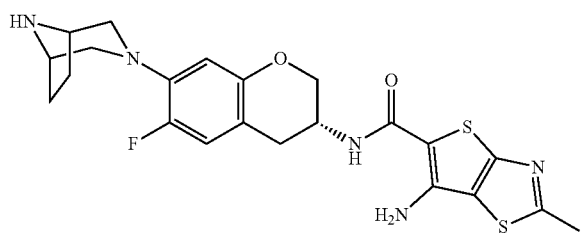 [SMILES: Cc1nc2sc(C(=O)N[C@H]3COc4cc(N5CC6CCC(C5)N6)c(F)cc4C3)c(N)c2s1]
47. N-((3R)-7-(3,8-diazabicyclo[3.2.1]octan-3-yl)-6-fluorochroman-3-yl)-6-amino-2-methylthieno[2,3-d]thiazole-5-carboxamide
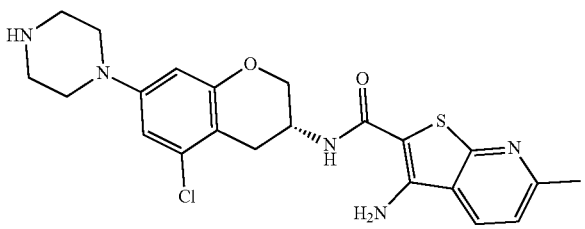 [SMILES: Cc1ccc2c(N)c(C(=O)N[C@H]3COc4cc(N5CCNCC5)cc(Cl)c4C3)sc2n1]
48. (R)-3-amino-N-(5-chloro-7-(piperazin-1-yl)chroman-3-yl)-6-methylthieno[2,3-b]pyridine-2-carboxamide
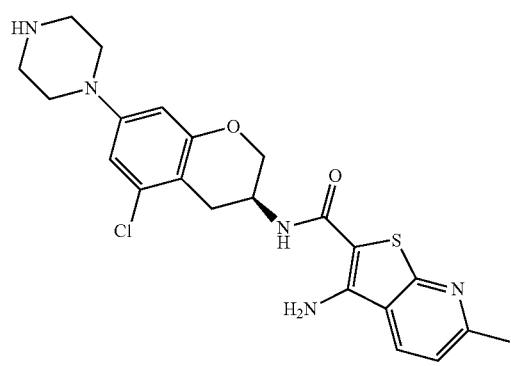 [SMILES: Cc1ccc2c(N)c(C(=O)N[C@@H]3COc4cc(N5CCNCC5)cc(Cl)c4C3)sc2n1]
49. (S)-3-amino-N-(5-chloro-7-(piperazin-1-yl)chroman-3-yl)-6-methylthieno[2,3-b]pyridine-2-carboxamide

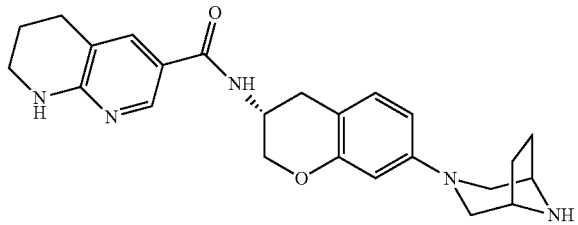 [SMILES: O=C(N[C@H]1COc2cc(N3CC4CCC(C3)N4)ccc2C1)c1cnc2c(c1)CCCN2]
50. N-((3R)-7-(3,8-diazabicyclo[3.2.1]octan-3-yl)chroman-3-yl)-5,6,7,8-tetrahydro-1,8-naphthyridine-3-carboxamide
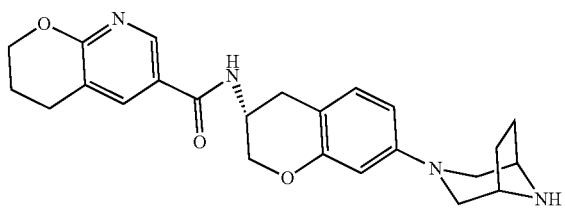 [SMILES: O=C(N[C@H]1COc2cc(N3CC4CCC(C3)N4)ccc2C1)c1cnc2c(c1)CCCO2]
51. N-((3R)-7-(3,8-diazabicyclo[3.2.1]octan-3-yl)chroman-3-yl)-3,4-dihydro-2H-pyrano[2,3-b]pyridine-6-carboxamide
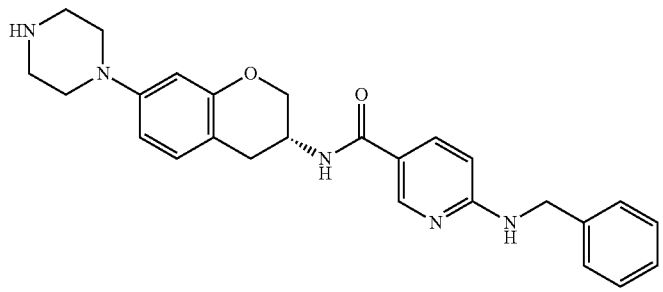 [SMILES: O=C(N[C@H]1COc2cc(N3CCNCC3)ccc2C1)c1ccc(NCc2ccccc2)nc1]
52. (R)-6-(benzylamino)-N-(7-(piperazin-1-yl)chroman-3-yl)nicotinamide
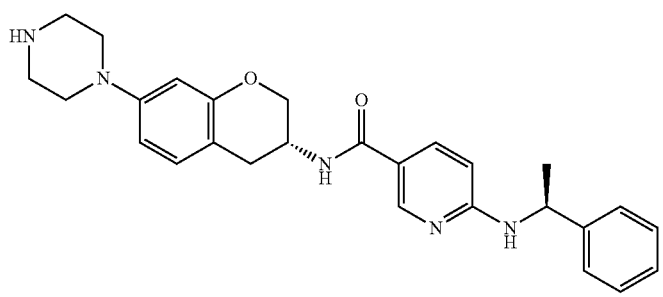 [SMILES: C[C@H](Nc1ccc(C(=O)N[C@H]2COc3cc(N4CCNCC4)ccc3C2)cn1)c1ccccc1]
53. 6-(((S)-1-phenylethyl)amino)-N-((R)-7-(piperazin-1-yl)chroman-3-yl)nicotinamide TABLE 25-continued
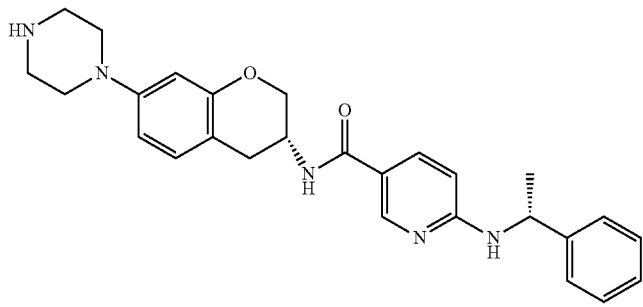 [SMILES: C[C@@H](Nc1ccc(C(=O)N[C@H]2COc3cc(N4CCNCC4)ccc3C2)cn1)c1ccccc1]
54. 6-(((R)-1-phenylethyl)amino)-N-((R)-7-(piperazin-1-yl)chroman-3-yl)nicotinamide
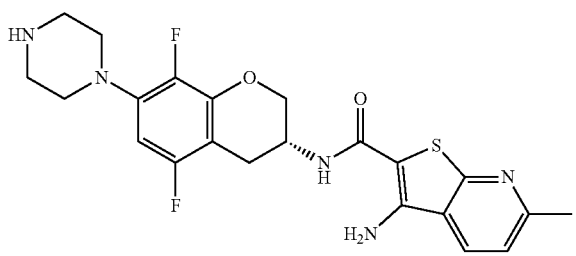 [SMILES: Cc1ccc2c(N)c(C(=O)N[C@H]3COc4c(F)c(N5CCNCC5)cc(F)c4C3)sc2n1]
55. (R)-3-amino-N-(5,8-difluoro-7-(piperazin-1-yl)chroman-3-yl)-6-methylthieno[2,3-b]pyridine-2-carboxamide
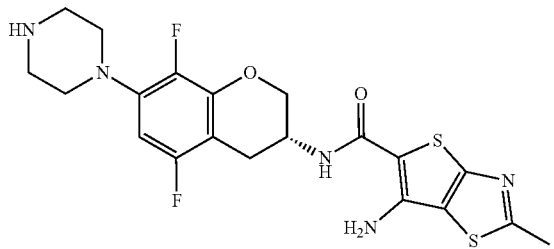 [SMILES: Cc1nc2sc(C(=O)N[C@H]3COc4c(F)c(N5CCNCC5)cc(F)c4C3)c(N)c2s1]
56. (R)-6-amino-N-(5,8-difluoro-7-(piperazin-1-yl)chroman-3-yl)-2-methylthieno[2,3-d]thiazole-5-carboxamide
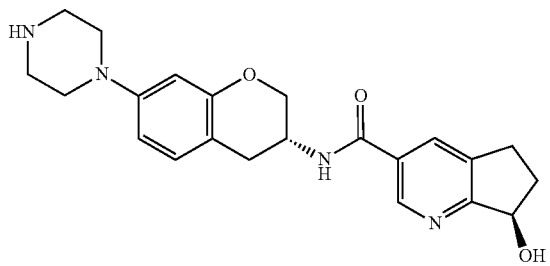 [SMILES: O=C(N[C@H]1COc2cc(N3CCNCC3)ccc2C1)c1cnc2c(c1)CC[C@H]2O]
57. (R)-7-hydroxy-N-((R)-7-(piperazin-1-yl)chroman-3-yl)-6,7-dihydro-5H-cyclopenta[b]pyridine-3-carboxamide

TABLE 25-continued
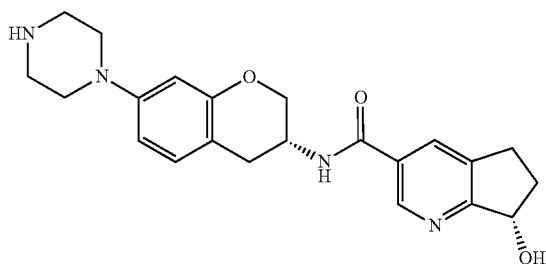 [SMILES: O=C(N[C@H]1COc2cc(N3CCNCC3)ccc2C1)c1cnc2c(c1)CC[C@@H]2O]
58. (S)-7-hydroxy-N-((R)-7-(piperazin-1-yl)chroman-3-yl)-6,7-dihydro-5H-cyclopenta[b]pyridine-3-carboxamide
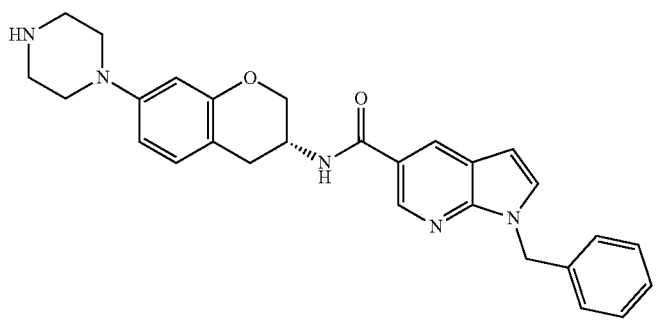 [SMILES: O=C(N[C@H]1COc2cc(N3CCNCC3)ccc2C1)c1cnc2c(ccn2Cc2ccccc2)c1]
59. (R)-1-benzyl-N-(7-(piperazin-1-yl)chroman-3-yl)-1H-pyrrolo[2,3-b]pyridine-5-carboxamide
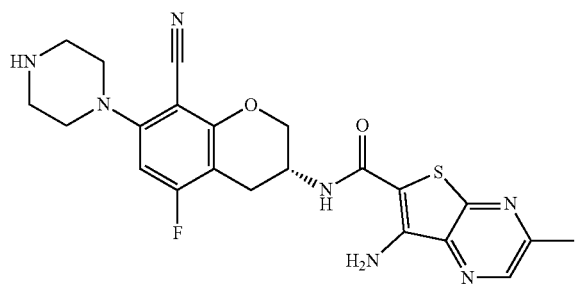 [SMILES: Cc1cnc2c(N)c(C(=O)N[C@H]3COc4c(C#N)c(N5CCNCC5)cc(F)c4C3)sc2n1]
60. (R)-7-amino-N-(8-cyano-5-fluoro-7-(piperazin-1-yl)chroman-3-yl)-3-methylthieno[2,3-b]pyrazine-6-carboxamide
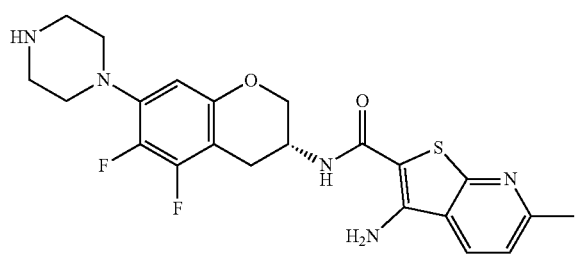 [SMILES: Cc1ccc2c(N)c(C(=O)N[C@H]3COc4cc(N5CCNCC5)c(F)c(F)c4C3)sc2n1]
61. (R)-3-amino-N-(5,6-difluoro-7-(piperazin-1-yl)chroman-3-yl)-6-methylthieno[2,3-b]pyridine-2-carboxamide TABLE 25-continued
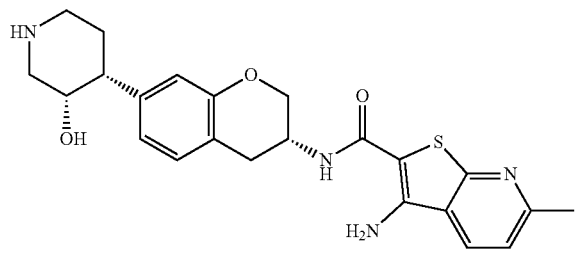 [SMILES: Cc1ccc2c(N)c(C(=O)N[C@H]3COc4cc([C@H]5CCNC[C@H]5O)ccc4C3)sc2n1]
62. 3-amino-N-((R)-7-((3S,4R)-3-
hydroxypiperidin-4-yl)chroman-3-yl)-6-
methylthieno[2,3-b]pyridine-2-carboxamide
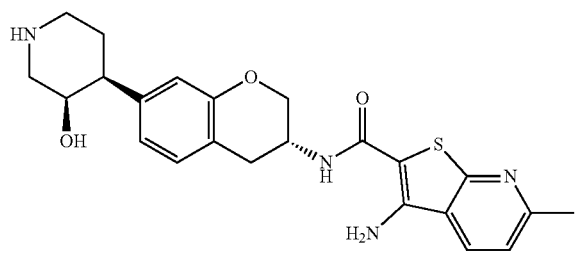 [SMILES: Cc1ccc2c(N)c(C(=O)N[C@H]3COc4cc([C@@H]5CCNC[C@@H]5O)ccc4C3)sc2n1]
63. 3-amino-N-((R)-7-((3R,4S)-3-
hydroxypiperidin-4-yl)chroman-3-yl)-6-
methylthieno[2,3-b]pyridine-2-carboxamide
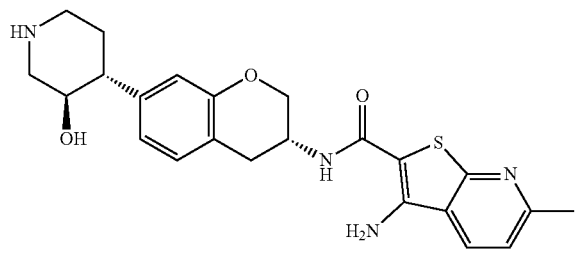 [SMILES: Cc1ccc2c(N)c(C(=O)N[C@H]3COc4cc([C@H]5CCNC[C@@H]5O)ccc4C3)sc2n1]
64. 3-amino-N-((R)-7-((3R,4R)-3-
hydroxypiperidin-4-yl)chroman-3-yl)-6-
methylthieno[2,3-b]pyridine-2-carboxamide
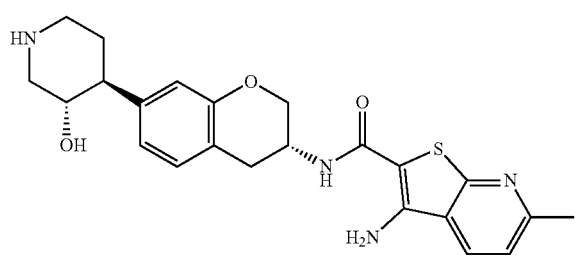 [SMILES: Cc1ccc2c(N)c(C(=O)N[C@H]3COc4cc([C@@H]5CCNC[C@H]5O)ccc4C3)sc2n1]
65. 3-amino-N-((R)-7-((3S,4S)-3-
hydroxypiperidin-4-yl)chroman-3-yl)-6-
methylthieno[2,3-b]pyridine-2-carboxamide TABLE 25-continued
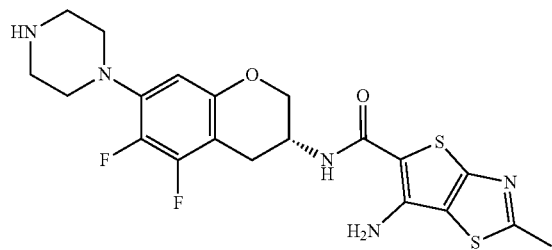 [SMILES: Cc1nc2sc(C(=O)N[C@H]3COc4cc(N5CCNCC5)c(F)c(F)c4C3)c(N)c2s1]
66. (R)-6-amino-N-(5,6-difluoro-7-
(piperazin-1-yl)chroman-3-yl)-2-
methylthieno[2,3-d]thiazole-5-carboxamide
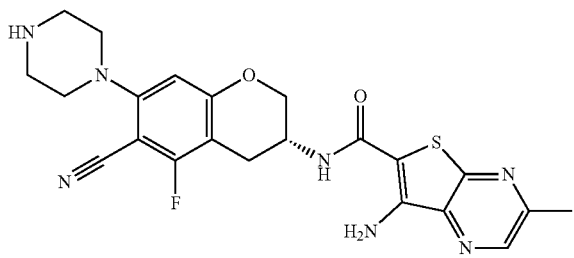 [SMILES: Cc1cnc2c(N)c(C(=O)N[C@H]3COc4cc(N5CCNCC5)c(C#N)c(F)c4C3)sc2n1]
67. (R)-7-amino-N-(6-cyano-5-fluoro-7-
(piperazin-1-yl)chroman-3-yl)-3-
methylthieno[2,3-b]pyrazine-6-carboxamide
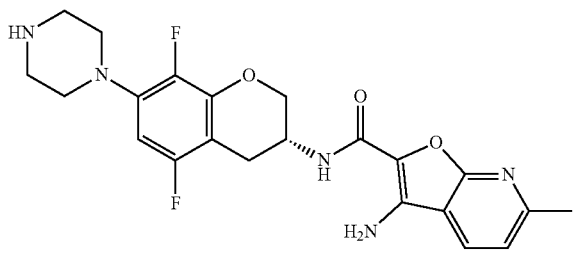 [SMILES: Cc1ccc2c(N)c(C(=O)N[C@H]3COc4c(F)c(N5CCNCC5)cc(F)c4C3)oc2n1]
68. (R)-3-amino-N-(5,8-difluoro-7-
(piperazin-1-yl)chroman-3-yl)-6-
methylfuro[2,3-b]pyridine-2-carboxamide
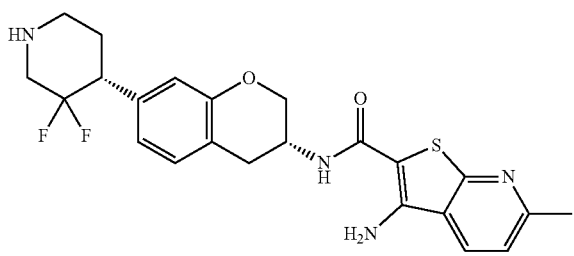 [SMILES: Cc1ccc2c(N)c(C(=O)N[C@H]3COc4cc([C@H]5CCNCC5(F)F)ccc4C3)sc2n1]
69. 3-amino-N-((R)-7-((R)-3,3-
difluoropiperidin-4-yl)chroman-3-yl)-6-
methylthieno[2,3-b]pyridine-2-carboxamide TABLE 25-continued

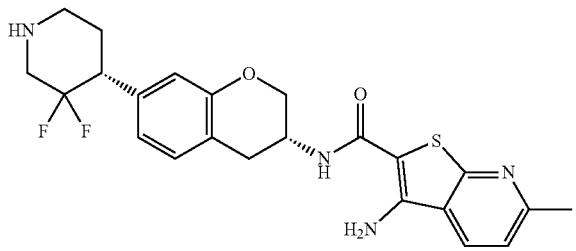 [SMILES: Cc1ccc2c(N)c(C(=O)N[C@H]3COc4cc([C@H]5CCNCC5(F)F)ccc4C3)sc2n1]

70. 3-amino-N-((R)-7-((S)-3,3-
difluoropiperidin-4-yl)chroman-3-yl)-6-
methylthieno[2,3-b]pyridine-2-carboxamide

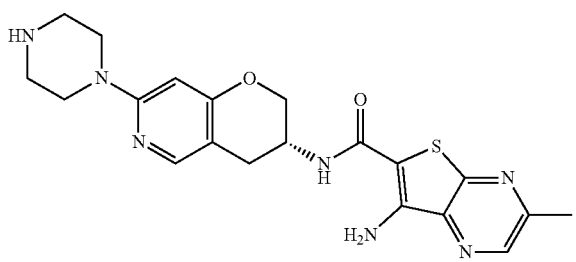 [SMILES: Cc1cnc2c(N)c(C(=O)N[C@H]3COc4cc(N5CCNCC5)ncc4C3)sc2n1]

71. (R)-7-amino-3-methyl-N-(7-(piperazin-1-
yl)-3,4-dihydro-2H-pyrano[3,2-c]pyridin-3-
yl)thieno[2,3-b]pyrazine-6-carboxamide

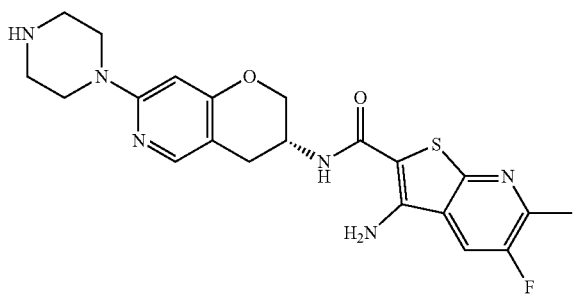 [SMILES: Cc1nc2sc(C(=O)N[C@H]3COc4cc(N5CCNCC5)ncc4C3)c(N)c2cc1F]

72. (R)-3-amino-5-fluoro-6-methyl-N-(7-
(piperazin-1-yl)-3,4-dihydro-2H-pyrano[3,2-
c]pyridin-3-yl)thieno[2,3-b]pyridine-2-
carboxamide

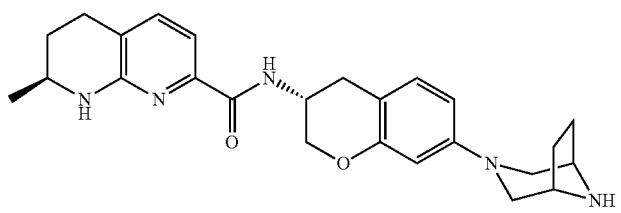 [SMILES: C[C@H]1CCc2ccc(C(=O)N[C@H]3COc4cc(N5CC6CCC(C5)N6)ccc4C3)nc2N1]

73. (7S)-N-((3R)-7-(3,8-
diazabicyclo[3.2.1]octan-3-yl)chroman-3-yl)-
7-methyl-5,6,7,8-tetrahydro-1,8-naphthyridine-
3-carboxamide

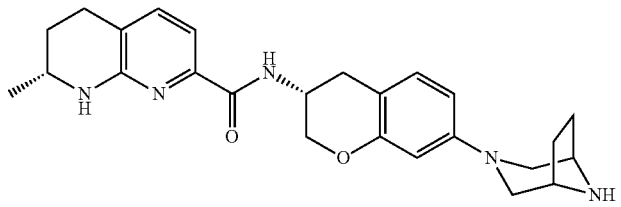 [SMILES: C[C@@H]1CCc2ccc(C(=O)N[C@H]3COc4cc(N5CC6CCC(C5)N6)ccc4C3)nc2N1]

74. (7R)-N-((3R)-7-(3,8-diazabicyclo[3.2.1]octan-3-yl)chroman-3-yl)-7-methyl-5,6,7,8-tetrahydro-1,8-naphthyridine-3-carboxamide

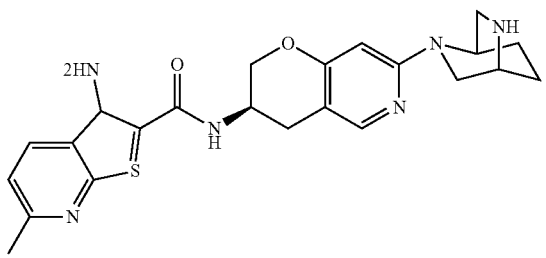

75. N-((R)-7-((1S,4S)-2,5-diazabicyclo[2.2.2]octan-2-yl)-3,4-dihydro-2H-pyrano[3,2-c]pyridin-3-yl)-3-amino-6-methylthieno[2,3-b]pyridine-2-carboxamide

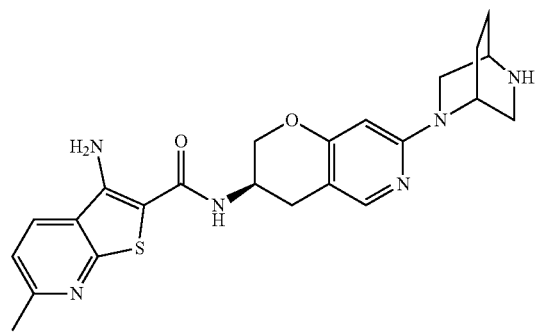 [SMILES: Cc1ccc2c(N)c(C(=O)N[C@H]3COc4cc(N5CC6CCC5CN6)ncc4C3)sc2n1]

76. N-((R)-7-((1R,4R)-2,5-diazabicyclo[2.2.2]octan-2-yl)-3,4-dihydro-2H-pyrano[3,2-c]pyridin-3-yl)-3-amino-6-methylthieno[2,3-b]pyridine-2-carboxamide

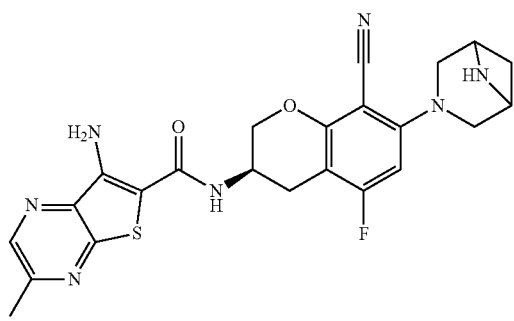 [SMILES: Cc1cnc2c(N)c(C(=O)N[C@H]3COc4c(C#N)c(N5CC6CC(C5)N6)cc(F)c4C3)sc2n1]

77. N-((3R)-7-(3,6-diazabicyclo[3.1.1]heptan-3-yl)-8-cyano-5-fluorochroman-3-yl)-7-amino-3-methylthieno[2,3-b]pyrazine-6-carboxamide

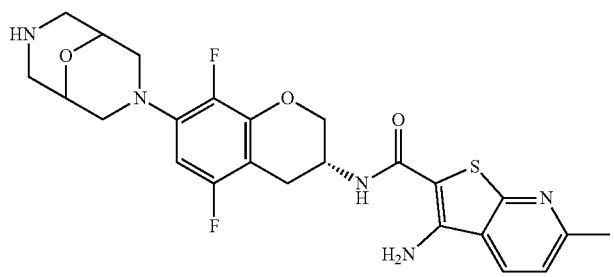 [SMILES: Cc1ccc2c(N)c(C(=O)N[C@H]3COc4c(F)c(N5CC6CNCC(C5)O6)cc(F)c4C3)sc2n1]
78. N-((3R)-7-(9-oxa-3,7-diazabicyclo[3.3.1]nonan-3-yl)-5,8-difluorochroman-3-yl)-3-amino-6-methylthieno[2,3-b]pyridine-2-carboxamide
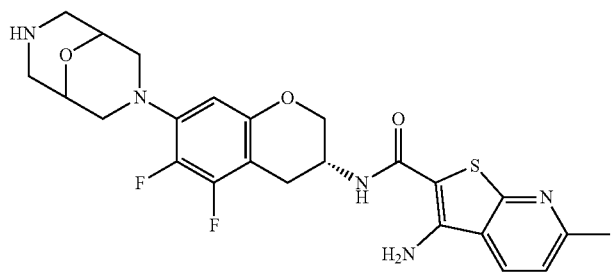 [SMILES: Cc1ccc2c(N)c(C(=O)N[C@H]3COc4cc(N5CC6CNCC(C5)O6)c(F)c(F)c4C3)sc2n1]
79. N-((3R)-7-(9-oxa-3,7-diazabicyclo[3.3.1]nonan-3-yl)-5,6-difluorochroman-3-yl)-3-amino-6-methylthieno[2,3-b]pyridine-2-carboxamide
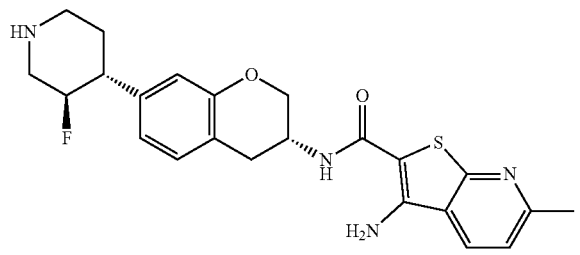 [SMILES: Cc1ccc2c(N)c(C(=O)N[C@H]3COc4cc([C@H]5CCNC[C@@H]5F)ccc4C3)sc2n1]
80. 3-amino-N-((R)-7-((3R,4R)-3-fluoropiperidin-4-yl)chroman-3-yl)-6-methylthieno[2,3-b]pyridine-2-carboxamide
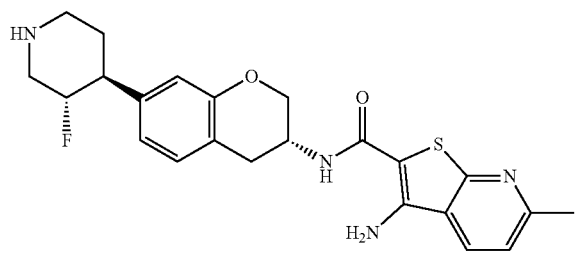 [SMILES: Cc1ccc2c(N)c(C(=O)N[C@H]3COc4cc([C@@H]5CCNC[C@H]5F)ccc4C3)sc2n1]
81. 3-amino-N-((R)-7-((3S,4S)-3-fluoropiperidin-4-yl)chroman-3-yl)-6-methylthieno[2,3-b]pyridine-2-carboxamide TABLE 25-continued
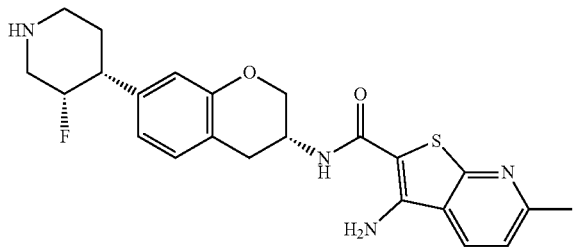 [SMILES: Cc1ccc2c(N)c(C(=O)N[C@H]3COc4cc([C@H]5CCNC[C@H]5F)ccc4C3)sc2n1]
82. 3-amino-N-((R)-7-((3S,4R)-3-fluoropiperidin-4-yl)chroman-3-yl)-6-methylthieno[2,3-b]pyridine-2-carboxamide
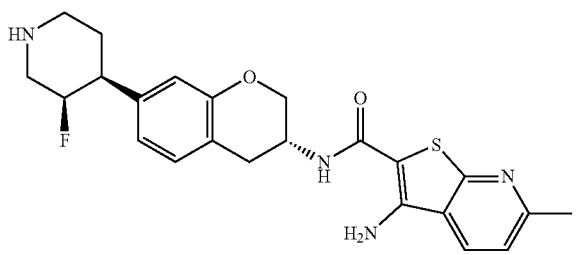 [SMILES: Cc1ccc2c(N)c(C(=O)N[C@H]3COc4cc([C@@H]5CCNC[C@@H]5F)ccc4C3)sc2n1]
83. 3-amino-N-((R)-7-((3R,4S)-3-fluoropiperidin-4-yl)chroman-3-yl)-6-methylthieno[2,3-b]pyridine-2-carboxamide
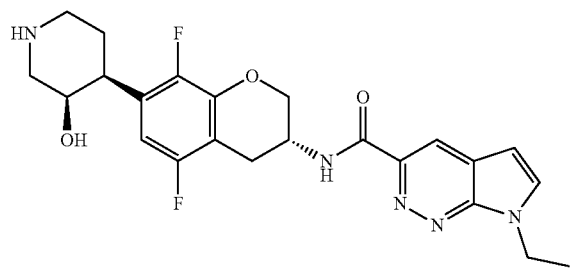 [SMILES: CCn1ccc2cc(C(=O)N[C@H]3COc4c(F)c([C@@H]5CCNC[C@@H]5O)cc(F)c4C3)nnc21]
84. N-((R)-5,8-difluoro-7-((3R,4S)-3-hydroxypiperidin-4-yl)chroman-3-yl)-7-ethyl-7H-pyrrolo[2,3-c]pyridazine-3-carboxamide
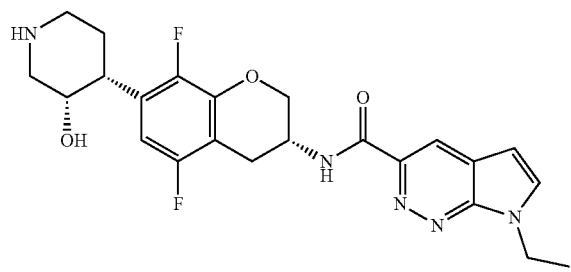 [SMILES: CCn1ccc2cc(C(=O)N[C@H]3COc4c(F)c([C@H]5CCNC[C@H]5O)cc(F)c4C3)nnc21]
85. N-((R)-5,8-difluoro-7-((3S,4R)-3-hydroxypiperidin-4-yl)chroman-3-yl)-7-ethyl-7H-pyrrolo[2,3-c]pyridazine-3-carboxamide TABLE 25-continued

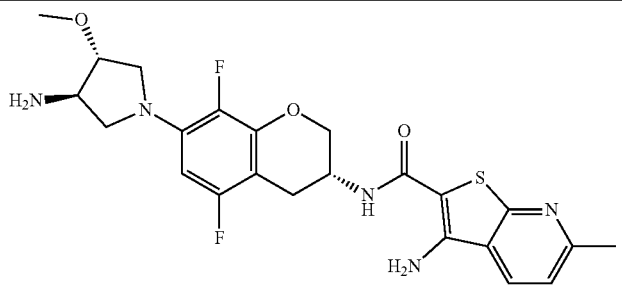

86. 3-amino-N-((R)-7-((3R,4R)-3-amino-4-
methoxypyrrolidin-1-yl)-5,8-
difluorochroman-3-yl)-6-methylthieno[2,3-
b]pyridine-2-carboxamide

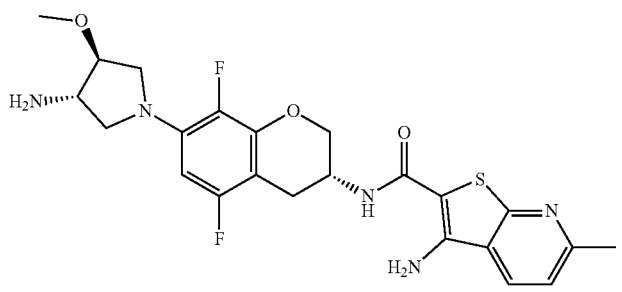 [SMILES: CO[C@H]1CN(c2cc(F)c3c(c2F)OC[C@H](NC(=O)c2sc4nc(C)ccc4c2N)C3)C[C@@H]1N]

87. 3-amino-N-((R)-7-((3S,4S)-3-amino-4-
methoxypyrrolidin-1-yl)-5,8-difluorochroman-
3-yl)-6-methylthieno[2,3-b]pyridine-2-
carboxamide

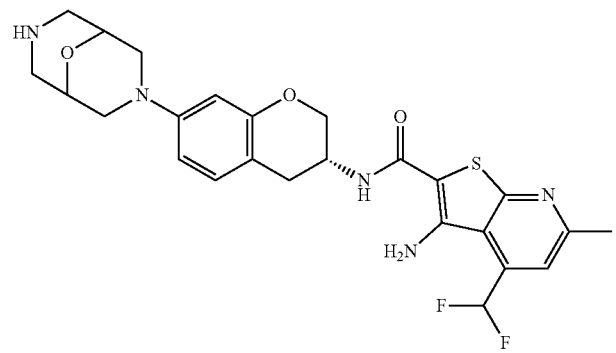 [SMILES: Cc1cc(C(F)F)c2c(N)c(C(=O)N[C@H]3COc4cc(N5CC6CNCC(C5)O6)ccc4C3)sc2n1]

88. N-((3R)-7-(9-oxa-3,7-
diazabicyclo[3.3.1]nonan-3-yl)chroman-3-
yl)-3-amino-4-(difluoromethyl)-6-
methylthieno[2,3-b]pyridine-2-carboxamide

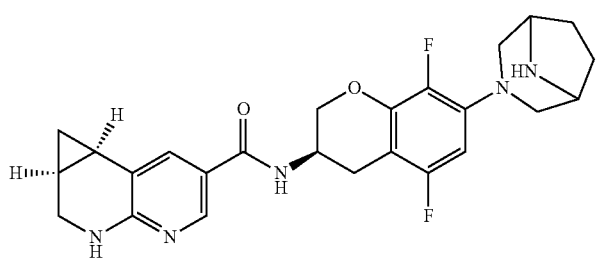 [SMILES: O=C(N[C@H]1COc2c(F)c(N3CC4CCC(C3)N4)cc(F)c2C1)c1cnc2c(c1)[C@@H]1C[C@@H]1CN2]

89. (1aS,7bR)-N-((3R)-7-(3,8-
diazabicyclo[3.2.1]octan-3-yl)-5,8-
difluorochroman-3-yl)-1a,2,3,7b-tetrahydro-
1H-cyclopropa[c][1,8]naphthyridine-6-
carboxamide TABLE 25-continued

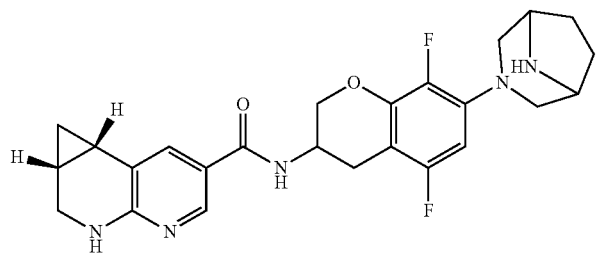 [SMILES: O=C(NC1COc2c(F)c(N3CC4CCC(C3)N4)cc(F)c2C1)c1cnc2c(c1)[C@H]1C[C@H]1CN2]

90. 1aR,7bS)-N-((3R)-7-(3,8-
diazabicyclo[3.2.1]octan-3-yl)-5,8-
difluorochroman-3-yl)-1a,2,3,7b-tetrahydro-
1H-cyclopropa[c][1,8]naphthyridine-6-
carboxamide

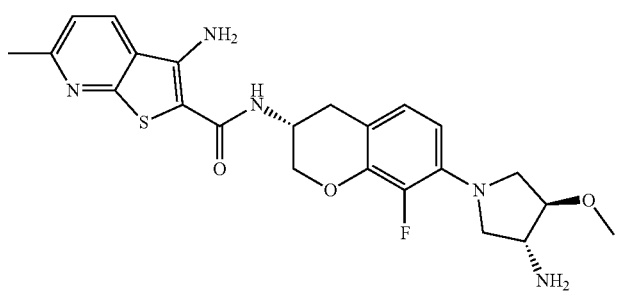

91. 3-amino-N-[(3R)-7-[(3R,4R)-3-amino-4-
methoxypyrrolidin-1-yl]-8-fluoro-3,4-dihydro-
2H-1-benzopyran-3-yl]-6-methylthieno[2,3-
b]pyridine-2-carboxamide

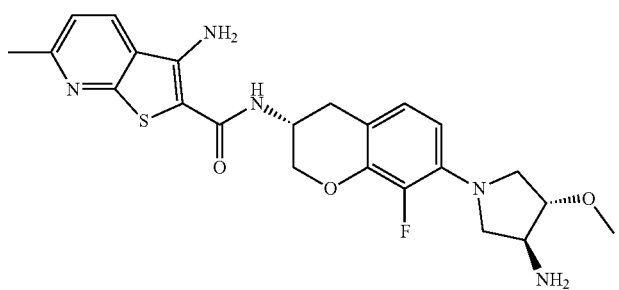

92. 3-amino-N-[(3R)-7-[(3S,4S)-3-amino-4-
methoxypyrrolidin-1-yl]-8-fluoro-3,4-
dihydro-2H-1-benzopyran-3-yl]-6-
methylthieno[2,3-b]pyridine-2-carboxamide

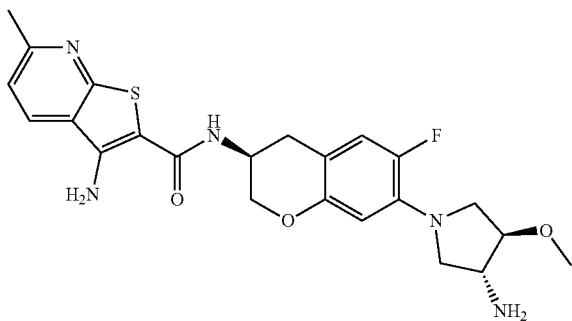 [SMILES: CO[C@@H]1CN(c2cc3c(cc2F)C[C@H](NC(=O)c2sc4nc(C)ccc4c2N)CO3)C[C@H]1N]

93. 3-amino-N-[(3R)-7-[(3R,4R)-3-amino-4-
methoxypyrrolidin-1-yl]-6-fluoro-3,4-dihydro-
2H-1-benzopyran-3-yl]-6-methylthieno[2,3-
b]pyridine-2-carboxamide TABLE 25-continued
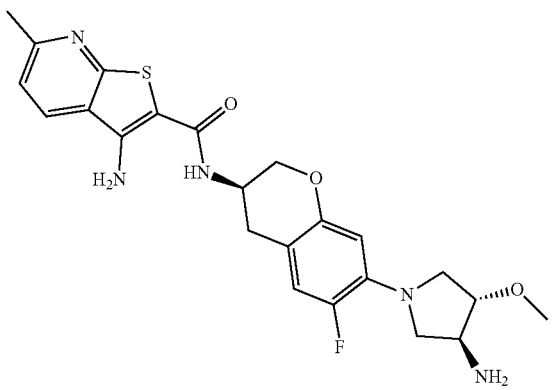
94. 3-amino-N-[(3R)-7-[(3S,4S)-3-amino-4-
methoxypyrrolidin-1-yl]-6-fluoro-3,4-
dihydro-2H-1-benzopyran-3-yl]-6-
methylthieno[2,3-b]pyridine-2-carboxamide
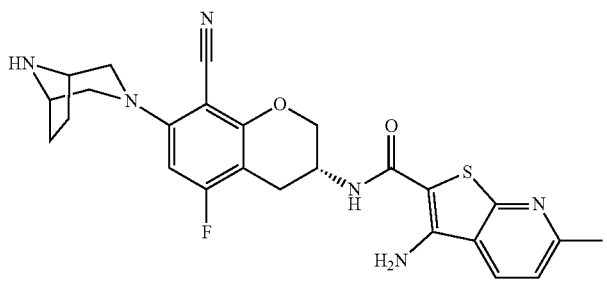 [SMILES: Cc1ccc2c(N)c(C(=O)N[C@H]3COc4c(C#N)c(N5CC6CCC(C5)N6)cc(F)c4C3)sc2n1]
95. 3-amino-N-[(3R)-8-cyano-7-{3,8-
diazabicyclo[3.2.1]octan-3-yl}-5-fluoro-3,4-
dihydro-2H-1-benzopyran-3-yl]-6-
methylthieno[2,3-b]pyridine-2-carboxamide
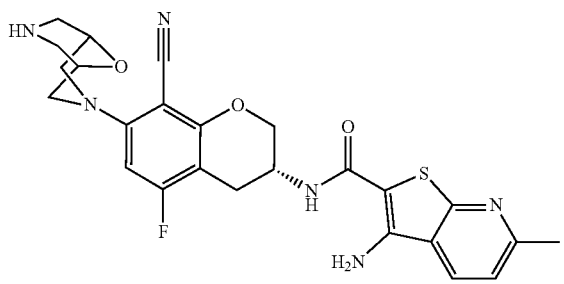 [SMILES: Cc1ccc2c(N)c(C(=O)N[C@H]3COc4c(C#N)c(N5CC6CNCC(C5)O6)cc(F)c4C3)sc2n1]
96. 3-amino-N-[(3R)-8-cyano-5-fluoro-7-{9-
oxa-3,7-diazabicyclo[3.3.1]nonan-3-yl}-3,4-
dihydro-2H-1-benzopyran-3-yl]-6-
methylthieno[2,3-b]pyridine-2-carboxamide

TABLE 25-continued
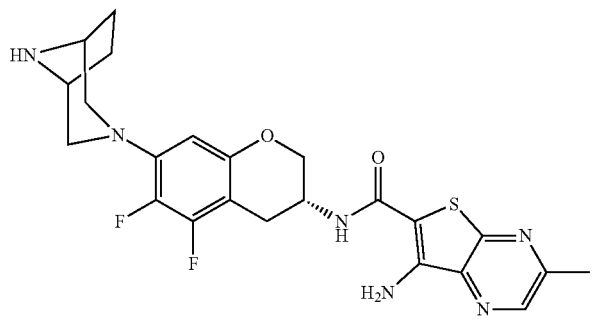 [SMILES: Cc1cnc2c(N)c(C(=O)N[C@H]3COc4cc(N5CC6CCC(C5)N6)c(F)c(F)c4C3)sc2n1]
97. 7-amino-N-[(3R)-7-{3,8-diazabicyclo[3.2.1]octan-3-yl}-5,6-difluoro-3,4-dihydro-2H-1-benzopyran-3-yl]-3-methylthieno[2,3-b]pyrazine-6-carboxamide
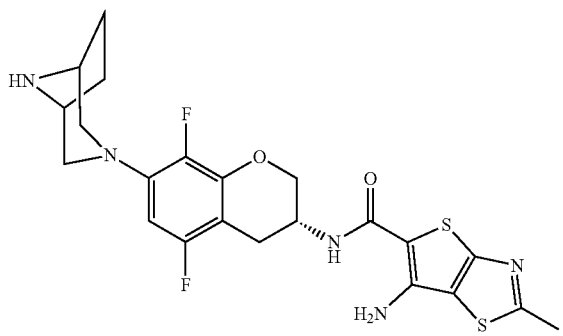 [SMILES: Cc1nc2sc(C(=O)N[C@H]3COc4c(F)c(N5CC6CCC(C5)N6)cc(F)c4C3)c(N)c2s1]
98. 6-amino-N-[(3R)-7-{3,8-diazabicyclo[3.2.1]octan-3-yl}-5,8-difluoro-3,4-dihydro-2H-1-benzopyran-3-yl]-2-methylthieno[2,3-d][1,3]thiazole-5-carboxamide
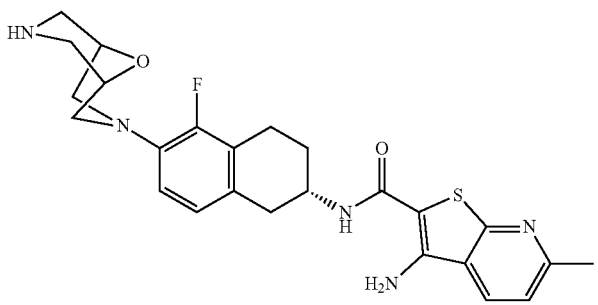 [SMILES: Cc1ccc2c(N)c(C(=O)N[C@H]3CCc4c(ccc(N5CC6CNCC(C5)O6)c4F)C3)sc2n1]
99. 3-amino-N-[(2S)-5-fluoro-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide TABLE 25-continued

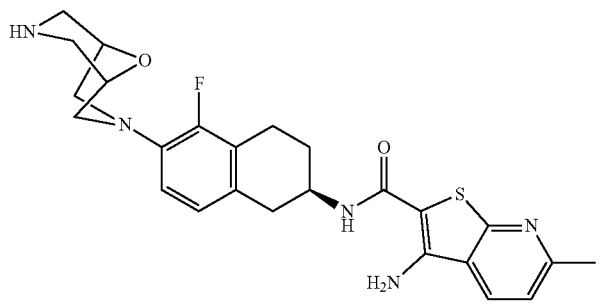 [SMILES: Cc1ccc2c(N)c(C(=O)N[C@@H]3CCc4c(ccc(N5CC6CNCC(C5)O6)c4F)C3)sc2n1]

100. 3-amino-N-[(2R)-5-fluoro-6-{9-oxa-
3,7-diazabicyclo[3.3.1]nonan-3-yl}-1,2,3,4-
tetrahydronaphthalen-2-yl]-6-
methylthieno[2,3-b]pyridine-2-carboxamide

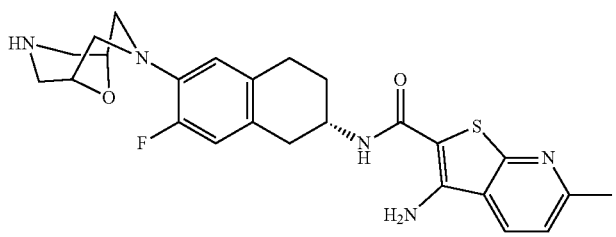 [SMILES: Cc1ccc2c(N)c(C(=O)N[C@H]3CCc4cc(N5CC6CNCC(C5)O6)c(F)cc4C3)sc2n1]

101. 3-amino-N-[(2S)-7-fluoro-6-{9-oxa-3,7-
diazabicyclo[3.3.1]nonan-3-yl}-1,2,3,4-
tetrahydronaphthalen-2-yl]-6-
methylthieno[2,3-b]pyridine-2-carboxamide

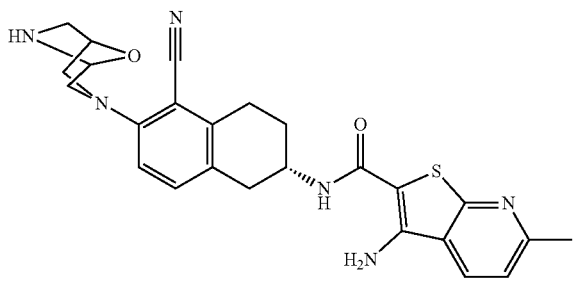 [SMILES: Cc1ccc2c(N)c(C(=O)N[C@H]3CCc4c(ccc(N5CC6CNC(C5)O6)c4C#N)C3)sc2n1]

102. 3-amino-N-[(2S)-5-cyano-6-{9-oxa-3,7-
diazabicyclo[3.3.1]nonan-3-yl}-1,2,3,4-
tetrahydronaphthalen-2-yl]-6-
methylthieno[2,3-b]pyridine-2-carboxamide

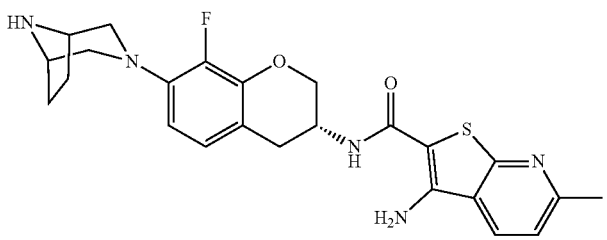 [SMILES: Cc1ccc2c(N)c(C(=O)N[C@H]3COc4c(ccc(N5CC6CCC(C5)N6)c4F)C3)sc2n1]

103. 3-amino-N-[(3R)-7-{3,8-
diazabicyclo[3.2.1]octan-3-yl}-8-fluoro-3,4-
dihydro-2H-1-benzopyran-3-yl]-6-
methylthieno[2,3-b]pyridine-2-carboxamide TABLE 25-continued

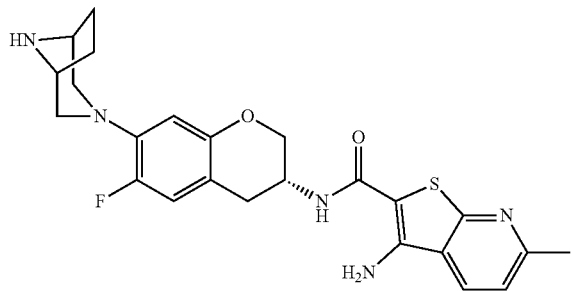 [SMILES: Cc1ccc2c(N)c(C(=O)N[C@H]3COc4cc(N5CC6CCC(C5)N6)c(F)cc4C3)sc2n1]

104. 3-amino-N-[(3R)-7-{3,8-diazabicyclo[3.2.1]octan-3-yl}-6-fluoro-3,4-dihydro-2H-1-benzopyran-3-yl]-6-methylthieno[2,3-b]pyridine-2-carboxamide

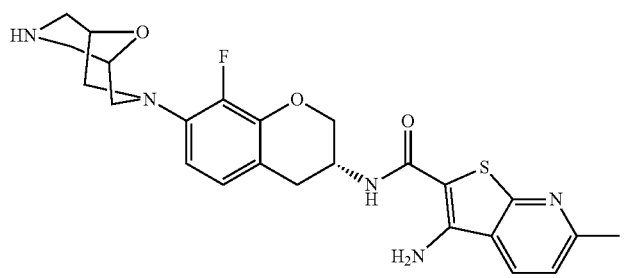 [SMILES: Cc1ccc2c(N)c(C(=O)N[C@H]3COc4c(ccc(N5CC6CNCC(C5)O6)c4F)C3)sc2n1]

105. 3-amino-N-[(3R)-8-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide

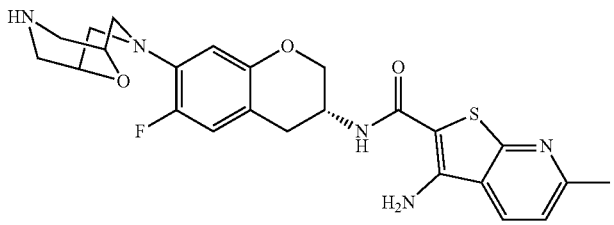 [SMILES: Cc1ccc2c(N)c(C(=O)N[C@H]3COc4cc(N5CC6CNCC(C5)O6)c(F)cc4C3)sc2n1]

106. 3-amino-N-[(3R)-6-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide

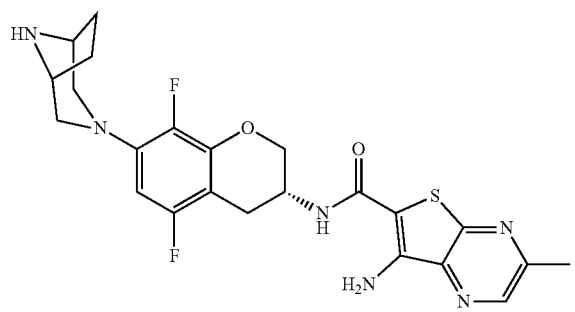 [SMILES: Cc1cnc2c(N)c(C(=O)N[C@H]3COc4c(F)c(N5CC6CCC(C5)N6)cc(F)c4C3)sc2n1]

107. 7-amino-N-[(3R)-7-{3,8-diazabicyclo[3.2.1]octan-3-yl}-5,8-difluoro-3,4-dihydro-2H-1-benzopyran-3-yl]-3-methylthieno[2,3-b]pyrazine-6-carboxamide TABLE 25-continued

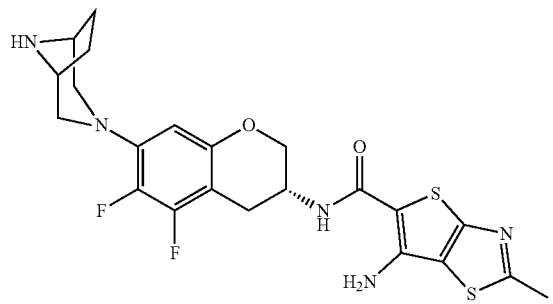 [SMILES: Cc1nc2sc(C(=O)N[C@H]3COc4cc(N5CC6CCC(C5)N6)c(F)c(F)c4C3)c(N)c2s1]

108. 6-amino-N-[(3R)-7-{3,8-diazabicyclo[3.2.1]octan-3-yl}-5,6-difluoro-3,4-dihydro-2H-1-benzopyran-3-yl]-2-methylthieno[2,3-d][1,3]thiazole-5-carboxamide

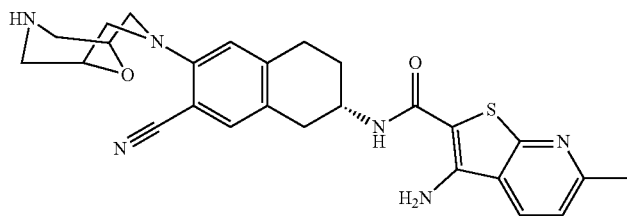 [SMILES: Cc1ccc2c(N)c(C(=O)N[C@H]3CCc4cc(N5CC6CNCC(C5)O6)c(C#N)cc4C3)sc2n1]

109. 3-amino-N-[(2S)-7-cyano-6-{9-oxa-3,7-diazabicyclo[3.3.1]nonan-3-yl}-1,2,3,4-tetrahydronaphthalen-2-yl]-6-methylthieno[2,3-b]pyridine-2-carboxamide

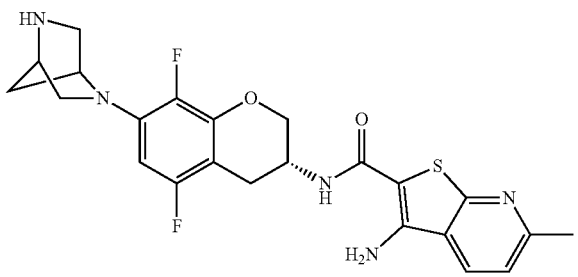 [SMILES: Cc1ccc2c(N)c(C(=O)N[C@H]3COc4c(F)c(N5CC6CC5CN6)cc(F)c4C3)sc2n1]

110. 3-amino-N-[(3R)-7-[(1S,4S)-2,5-diazabicyclo[2.2.1]heptan-2-yl]-5,8-difluoro-3,4-dihydro-2H-1-benzopyran-3-yl]-6-methylthieno[2,3-b]pyridine-2-carboxamide

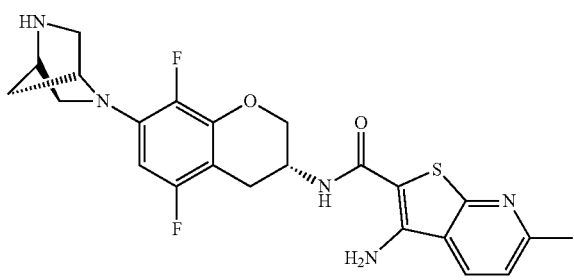

111. 3-amino-N-[(3R)-7-[(1R,4R)-2,5-diazabicyclo[2.2.1]heptan-2-yl]-5,8-difluoro-3,4-dihydro-2H-1-benzopyran-3-yl]-6-methylthieno[2,3-b]pyridine-2-carboxamide TABLE 25-continued

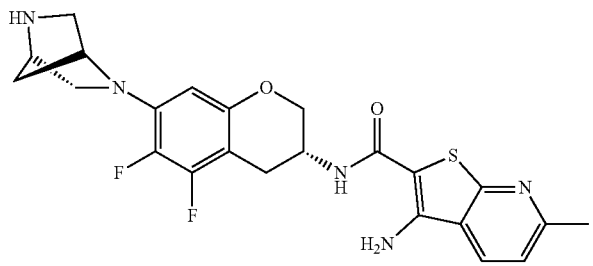

112. 3-amino-N-[(3R)-7-[(1S,4S)-2,5-
diazabicyclo[2.2.1]heptan-2-yl]-5,6-difluoro-
3,4-dihydro-2H-1-benzopyran-3-yl]-6-
methylthieno[2,3-b]pyridine-2-carboxamide

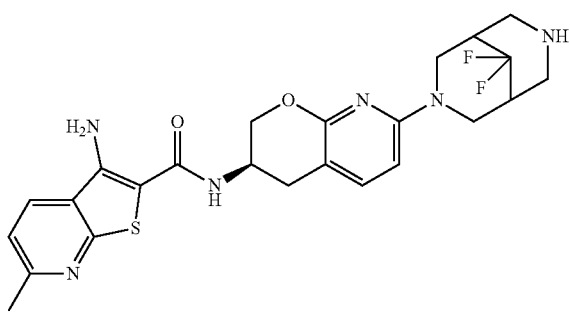 [SMILES: Cc1ccc2c(N)c(C(=O)N[C@H]3COc4nc(N5CC6CNCC(C5)C6(F)F)ccc4C3)sc2n1]

113. 3-amino-N-[(3R)-7-{9,9-difluoro-3,7-
diazabicyclo[3.3.1]nonan-3-yl}-2H,3H,4H-
pyrano[2,3-b]pyridin-3-yl]-6-
methylthieno[2,3-b]pyridine-2-carboxamide

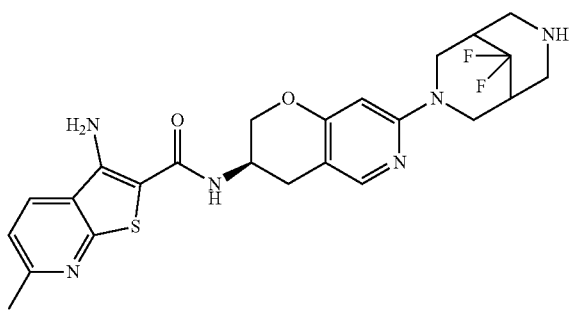 [SMILES: Cc1ccc2c(N)c(C(=O)N[C@H]3COc4cc(N5CC6CNCC(C5)C6(F)F)ncc4C3)sc2n1]

114. 3-amino-N-[(3R)-7-{9,9-difluoro-3,7-
diazabicyclo[3.3.1]nonan-3-yl}-2H,3H,4H-
pyrano[3,2-c]pyridin-3-yl]-6-
methylthieno[2,3-b]pyridine-2-carboxamide

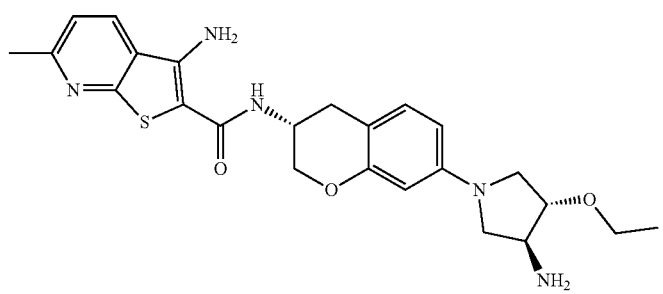 [SMILES: CCO[C@H]1CN(c2ccc3c(c2)OC[C@H](NC(=O)c2sc4nc(C)ccc4c2N)C3)C[C@@H]1N]

115. 3-amino-N-[(3R)-7-[(3S,4S)-3-amino-4-
ethoxypyrrolidin-1-yl]-3,4-dihydro-2H-1-
benzopyran-3-yl]-6-methylthieno[2,3-
b]pyridine-2-carboxamide TABLE 25-continued

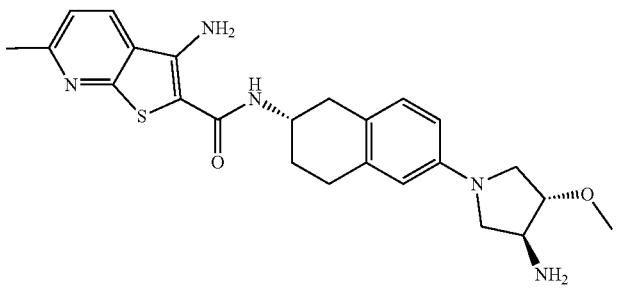

116. 3-amino-N-[(2S)-6-[(3S,4S)-3-amino-4-
methoxypyrrolidin-1-yl]-1,2,3,4-
tetrahydronaphthalen-2-yl]-6-
methylthieno[2,3-b]pyridine-2-carboxamide

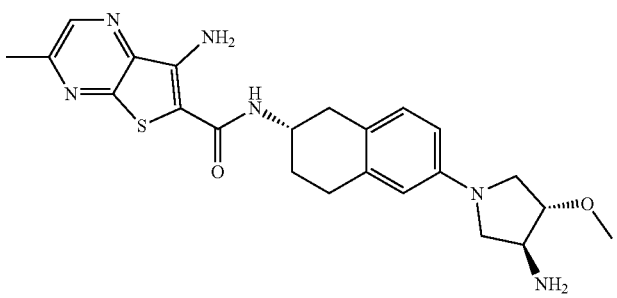

117. 7-amino-N-[(3R)-7-[(3S,4S)-3-amino-4-
methoxypyrrolidin-1-yl]-3,4-dihydro-2H-1-
benzopyran-3-yl]-3-methylthieno[2,3-
b]pyrazine-6-carboxamide

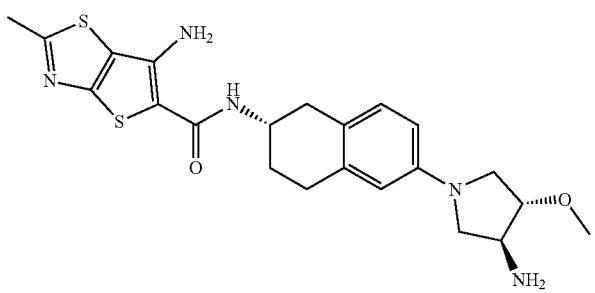

118. 6-amino-N-[(3R)-7-[(3S,4S)-3-amino-
4-methoxypyrrolidin-1-yl]-3,4-dihydro-2H-
1-benzopyran-3-yl]-2-methylthieno[2,3-
d][1,3]thiazole-5-carboxamide

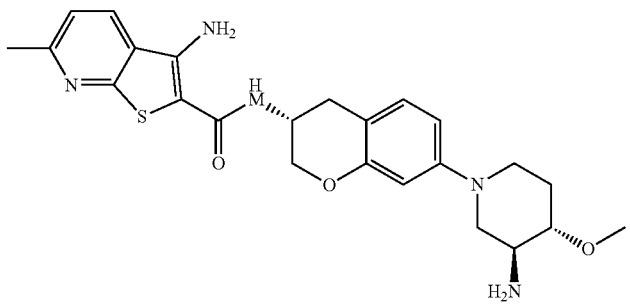

119. 3-amino-N-[(3R)-7-[(3S,4S)-3-amino-4-
methoxypiperidin-1-yl]-3,4-dihydro-2H-1-
benzopyran-3-yl]-6-methylthieno[2,3-
b]pyridine-2-carboxamide TABLE 25-continued

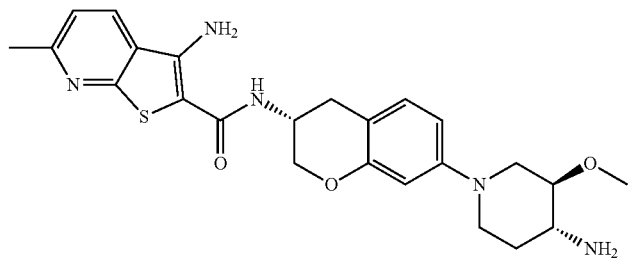

120. 3-amino-N-[(3R)-7-[(3R,4R)-3-amino-
4-methoxypiperidin-1-yl]-3,4-dihydro-2H-1-
benzopyran-3-yl]-6-methylthieno[2,3-
b]pyridine-2-carboxamide

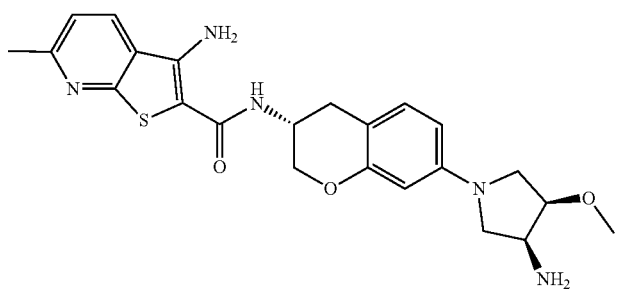

121. 3-amino-N-[(3R)-7-[(3S,4R)-3-amino-4-
methoxypyrrolidin-1-yl]-3,4-dihydro-2H-1-
benzopyran-3-yl]-6-methylthieno[2,3-
b]pyridine-2-carboxamide

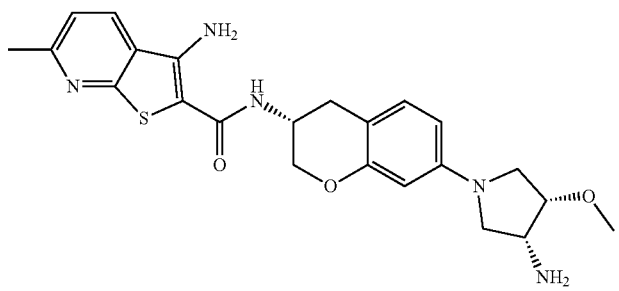

122. 3-amino-N-[(3R)-7-[(3R,4S)-3-amino-
4-methoxypyrrolidin-1-yl]-3,4-dihydro-2H-
1-benzopyran-3-yl]-6-methylthieno[2,3-
b]pyridine-2-carboxamide

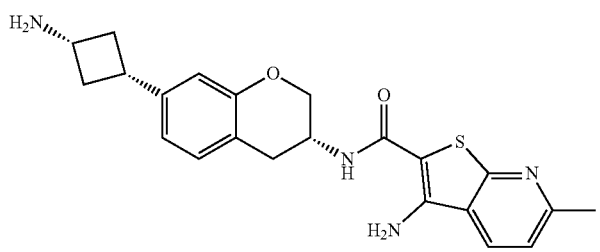 [SMILES: Cc1ccc2c(N)c(C(=O)N[C@H]3COc4cc([C@H]5C[C@@H](N)C5)ccc4C3)sc2n1]

123. 3-amino-6-methyl-N-[(3R)-7-[(1s,3S)-3-
aminocyclobutyl]-3,4-dihydro-2H-1-
benzopyran-3-yl]thieno[2,3-b]pyridine-2-
carboxamide TABLE 25-continued

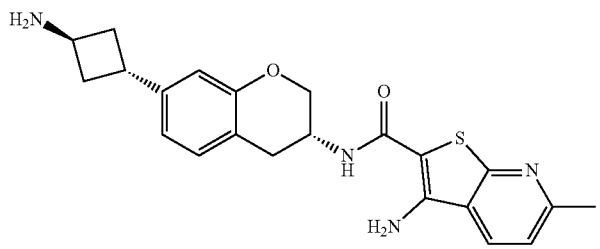 [SMILES: Cc1ccc2c(N)c(C(=O)N[C@H]3COc4cc([C@H]5C[C@H](N)C5)ccc4C3)sc2n1]

124. 3-amino-6-methyl-N-[(3R)-7-[(1r,3r)-3-aminocyclobutyl]-3,4-dihydro-2H-1-benzopyran-3-yl]thieno[2,3-b]pyridine-2-carboxamide

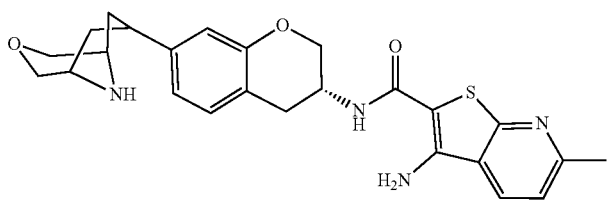 [SMILES: Cc1ccc2c(N)c(C(=O)N[C@H]3COc4cc(C5CC6COCC(C5)N6)ccc4C3)sc2n1]

125. 3-amino-6-methyl-N-[(3R)-7-{3-oxa-9-azabicyclo[3.3.1]nonan-7-yl}-3,4-dihydro-2H-1-benzopyran-3-yl]thieno[2,3-b]pyridine-2-carboxamide

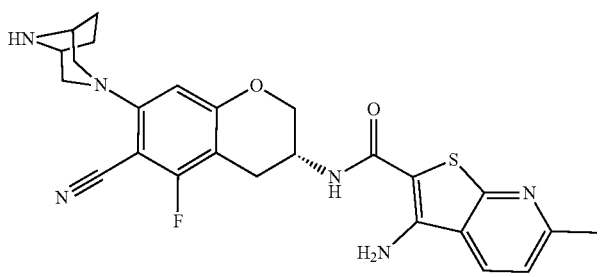 [SMILES: Cc1ccc2c(N)c(C(=O)N[C@H]3COc4cc(N5CC6CCC(C5)N6)c(C#N)c(F)c4C3)sc2n1]

126. 3-amino-N-[(3R)-6-cyano-7-{3,8-diazabicyclo[3.2.1]octan-3-yl}-5-fluoro-3,4-dihydro-2H-1-benzopyran-3-yl]-6-methylthieno[2,3-b]pyridine-2-carboxamide

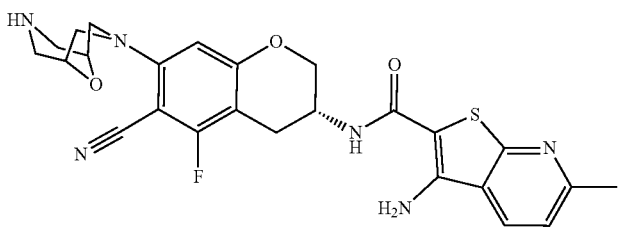 [SMILES: Cc1ccc2c(N)c(C(=O)N[C@H]3COc4cc(N5CC6CNCC(C5)O6)c(C#N)c(F)c4C3)sc2n1]

127. 3-amino-N-[(3R)-6-cyano-5-fluoro-7-{9-oxa-3,7-diazabicyclo[3.3.1]nonan-3-yl}-3,4-dihydro-2H-1-benzopyran-3-yl]-6-methylthieno[2,3-b]pyridine-2-carboxamide TABLE 25-continued

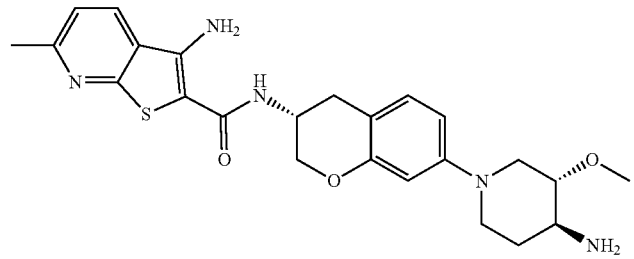

128. 3-amino-N-[(3R)-7-[(3S,4S)-4-amino-3-methoxypiperidin-1-yl]-3,4-dihydro-2H-1-benzopyran-3-yl]-6-methylthieno[2,3-b]pyridine-2-carboxamide

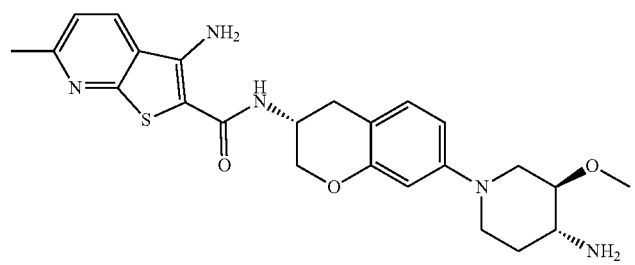

129. 3-amino-N-[(3R)-7-[(3R,4R)-4-amino-3-methoxypiperidin-1-yl]-3,4-dihydro-2H-1-benzopyran-3-yl]-6-methylthieno[2,3-b]pyridine-2-carboxamide

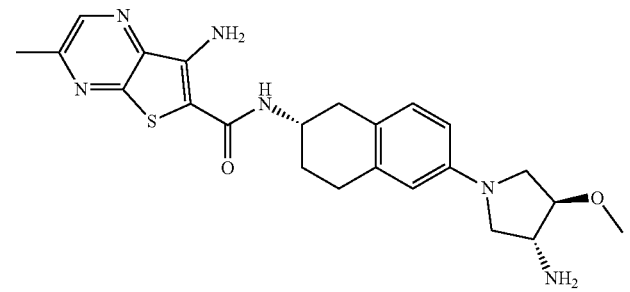

130. 7-amino-N-[(2S)-6-[(3S,4S)-3-amino-4-methoxypyrrolidin-1-yl]-1,2,3,4-tetrahydronaphthalen-2-yl]-3-methylthieno[2,3-b]pyrazine-6-carboxamide

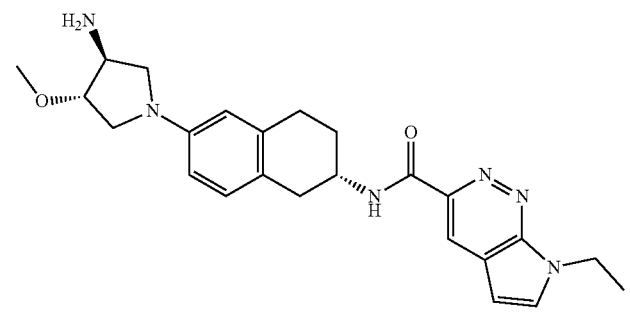 [SMILES: CCn1ccc2cc(C(=O)N[C@H]3CCc4cc(N5C[C@H](OC)[C@@H](N)C5)ccc4C3)nnc21]

131. N-[(2S)-6-[(3S,4S)-3-amino-4-methoxypyrrolidin-1-yl]-1,2,3,4-tetrahydronaphthalen-2-yl]-7-ethyl-7H-pyrrolo[2,3-c]pyridazine-3-carboxamide TABLE 25-continued
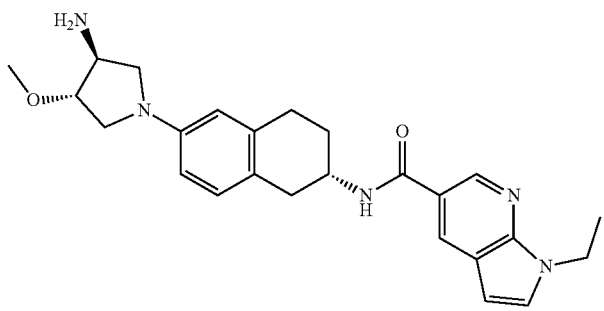 [SMILES: CCn1ccc2cc(C(=O)N[C@H]3CCc4cc(N5C[C@H](OC)[C@@H](N)C5)ccc4C3)cnc21]
132. N-[(2S)-6-[(3S,4S)-3-amino-4-
methoxypyrrolidin-1-yl]-1,2,3,4-
tetrahydronaphthalen-2-yl]-1-ethyl-1H-
pyrrolo[2,3-b]pyridine-5-carboxamide
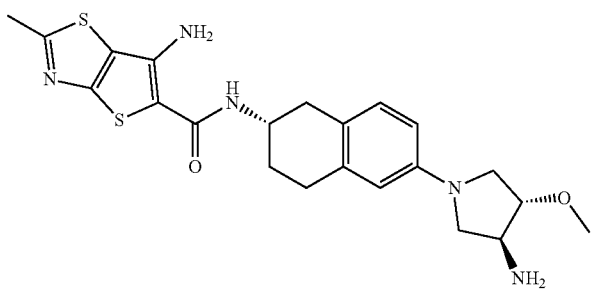
133. 6-amino-N-[(2S)-6-[(3S,4S)-3-amino-4-
methoxypyrrolidin-1-yl]-1,2,3,4-
tetrahydronaphthalen-2-yl]-2-
methylthieno[2,3-d][1,3]thiazole-5-
carboxamide
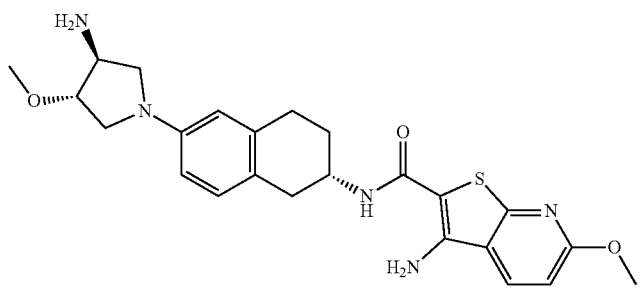
134. 3-amino-N-[(2S)-6-[(3S,4S)-3-amino-4-
methoxypyrrolidin-1-yl]-1,2,3,4-
tetrahydronaphthalen-2-yl]-6-
methoxythieno[2,3-b]pyridine-2-
carboxamide TABLE 25-continued

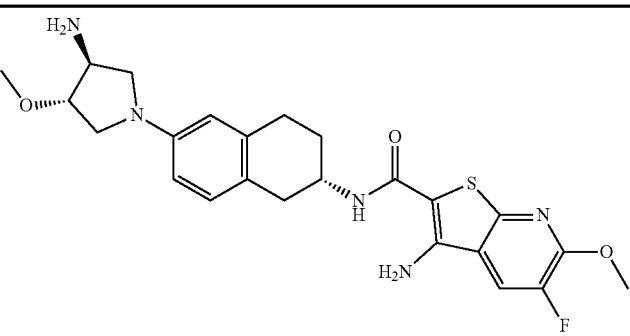

135. 3-amino-N-[(2S)-6-[(3S,4S)-3-amino-4-
methoxypyrrolidin-1-yl]-1,2,3,4-
tetrahydronaphthalen-2-yl]-5-fluoro-6-
methoxythieno[2,3-b]pyridine-2-carboxamide

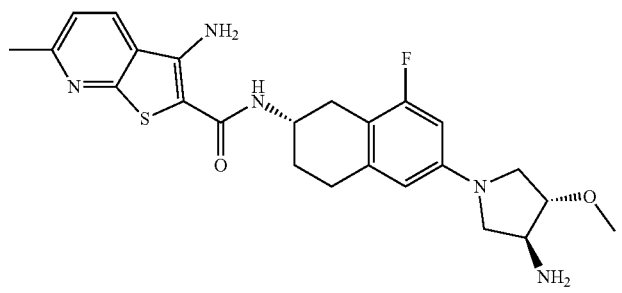

136. 3-amino-N-[(2S)-6-[(3S,4S)-3-amino-4-
methoxypyrrolidin-1-yl]-8-fluoro-1,2,3,4-
tetrahydronaphthalen-2-yl]-6-
methylthieno[2,3-b]pyridine-2-carboxamide

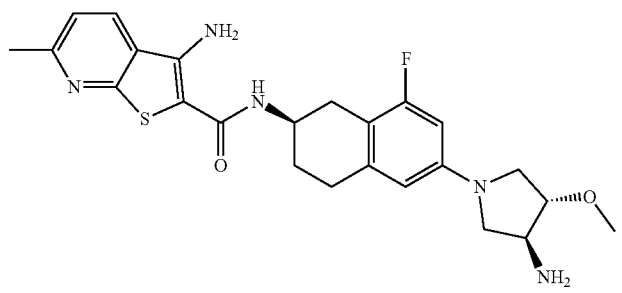

137. 3-amino-N-[(2R)-6-[(3S,4S)-3-amino-4-
methoxypyrrolidin-1-yl]-8-fluoro-1,2,3,4-
tetrahydronaphthalen-2-yl]-6-
methylthieno[2,3-b]pyridine-2-carboxamide

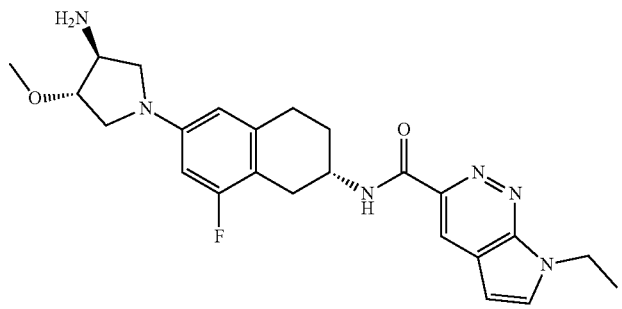 [SMILES: CCn1ccc2cc(C(=O)N[C@H]3CCc4cc(N5C[C@H](OC)[C@@H](N)C5)cc(F)c4C3)nnc21]

138. N-[(2S)-6-[(3S,4S)-3-amino-4-
methoxypyrrolidin-1-yl]-8-fluoro-1,2,3,4-
tetrahydronaphthalen-2-yl]-7-ethyl-7H-
pyrrolo[2,3-c]pyridazine-3-carboxamide TABLE 25-continued

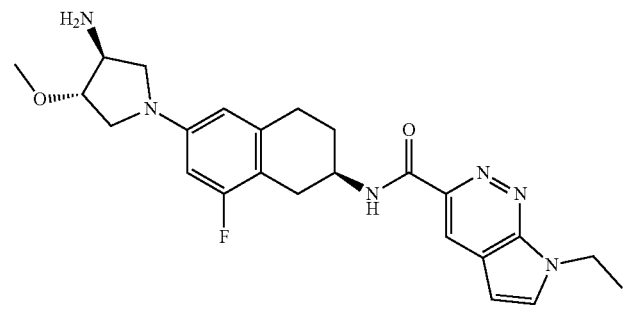 [SMILES: CCn1ccc2cc(C(=O)N[C@@H]3CCc4cc(N5C[C@H](OC)[C@@H](N)C5)cc(F)c4C3)nnc21]

139. N-[(2R)-6-[(3S,4S)-3-amino-4-
methoxypyrrolidin-1-yl]-8-fluoro-1,2,3,4-
tetrahydronaphthalen-2-yl]-7-ethyl-7H-
pyrrolo[2,3-c]pyridazine-3-carboxamide

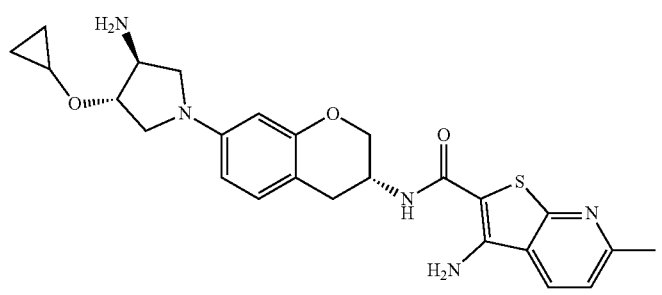 [SMILES: Cc1ccc2c(N)c(C(=O)N[C@H]3COc4cc(N5C[C@H](OC6CC6)[C@@H](N)C5)ccc4C3)sc2n1]

140. 3-amino-N-[(3R)-7-[(3S,4S)-3-amino-
4-cyclopropoxypyrrolidin-1-yl]-3,4-dihydro-
2H-1-benzopyran-3-yl]-6-methylthieno[2,3-
b]pyridine-2-carboxamide


141. 3-amino-N-[(3R)-7-[(3S,4S)-3-amino-4-
cyclobutoxypyrrolidin-1-yl]-3,4-dihydro-2H-
1-benzopyran-3-yl]-6-methylthieno[2,3-
b]pyridine-2-carboxamide

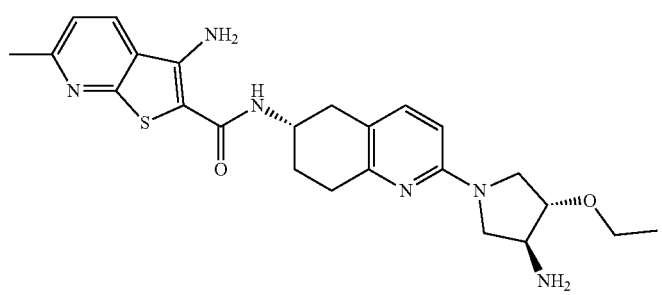 [SMILES: CCO[C@H]1CN(c2ccc3c(n2)CC[C@H](NC(=O)c2sc4nc(C)ccc4c2N)C3)C[C@@H]1N]

142. 3-amino-N-[(6S)-2-[(3S,4S)-3-amino-4-
ethoxypyrrolidin-1-yl]-5,6,7,8-
tetrahydroquinolin-6-yl]-6-methylthieno[2,3-
b]pyridine-2-carboxamide

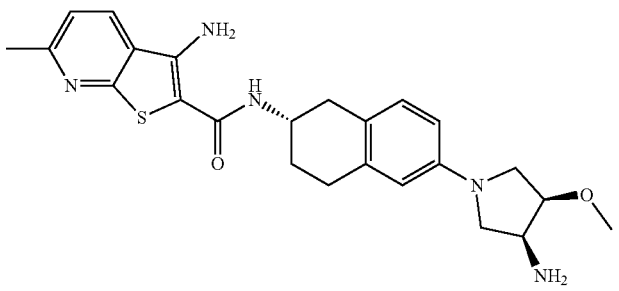

143. 3-amino-N-[(2S)-6-[(3S,4R)-3-amino-4-methoxypyrrolidin-1-yl]-1,2,3,4-tetrahydronaphthalen-2-yl]-6-methylthieno[2,3-b]pyridine-2-carboxamide

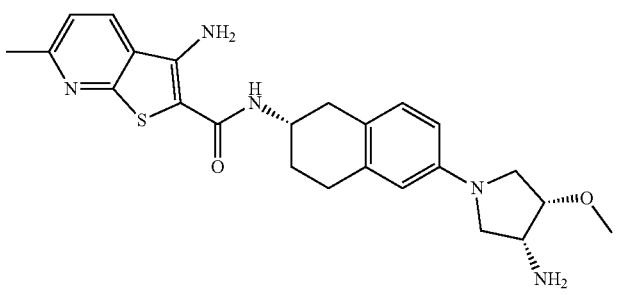

144. 3-amino-N-[(2S)-6-[(3R,4S)-3-amino-4-methoxypyrrolidin-1-yl]-1,2,3,4-tetrahydronaphthalen-2-yl]-6-methylthieno[2,3-b]pyridine-2-carboxamide

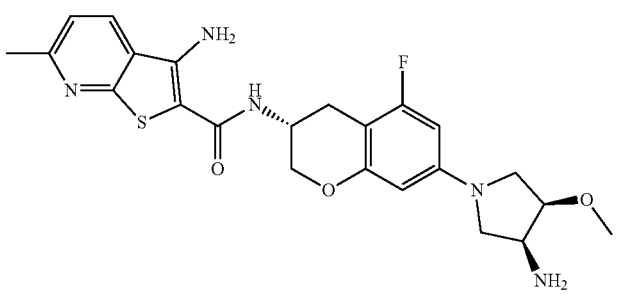

145. 3-amino-N-[(3R)-7-[(3S,4R)-3-amino-4-methoxypyrrolidin-1-yl]-5-fluoro-3,4-dihydro-2H-1-benzopyran-3-yl]-6-methylthieno[2,3-b]pyridine-2-carboxamide

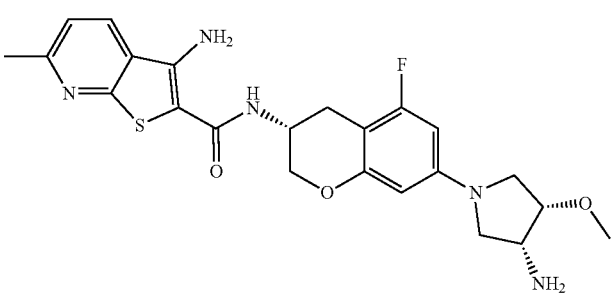

146. 3-amino-N-[(3R)-7-[(3R,4S)-3-amino-4-methoxypyrrolidin-1-yl]-5-fluoro-3,4-dihydro-2H-1-benzopyran-3-yl]-6-methylthieno[2,3-b]pyridine-2-carboxamide

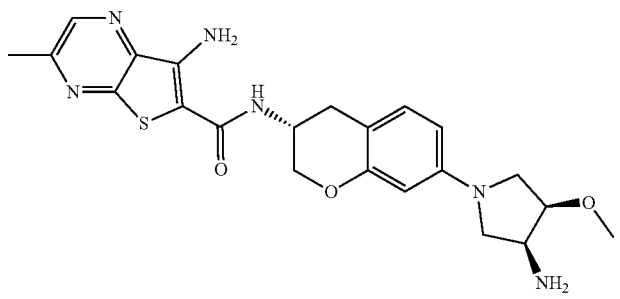

147. 7-amino-N-[(3R)-7-[(3S,4R)-3-amino-4-methoxypyrrolidin-1-yl]-3,4-dihydro-2H-1-benzopyran-3-yl]-3-methylthieno[2,3-b]pyrazine-6-carboxamide

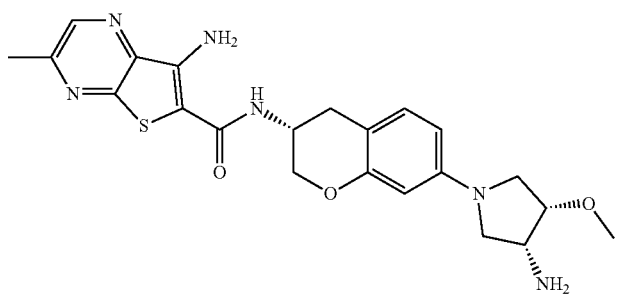

148. 7-amino-N-[(3R)-7-[(3R,4S)-3-amino-4-methoxypyrrolidin-1-yl]-3,4-dihydro-2H-1-benzopyran-3-yl]-3-methylthieno[2,3-b]pyrazine-6-carboxamide

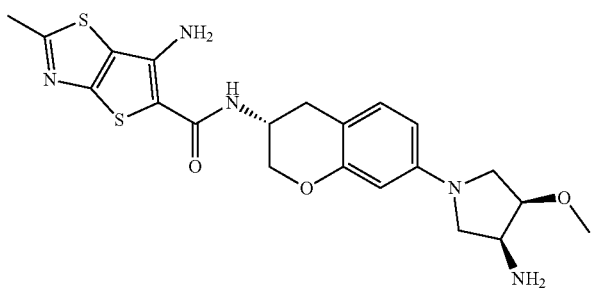

149. 6-amino-N-[(3R)-7-[(3S,4R)-3-amino-4-methoxypyrrolidin-1-yl]-3,4-dihydro-2H-1-benzopyran-3-yl]-2-methylthieno[2,3-d][1,3]thiazole-5-carboxamide

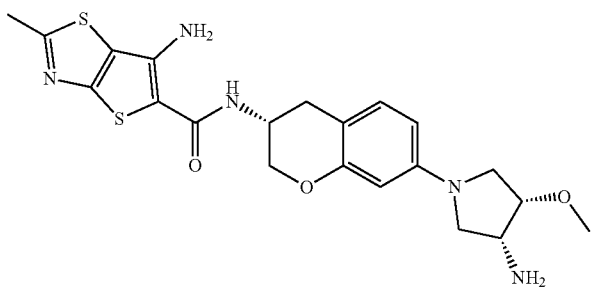

150. 6-amino-N-[(3R)-7-[(3R,4S)-3-amino-4-methoxypyrrolidin-1-yl]-3,4-dihydro-2H-1-benzopyran-3-yl]-2-methylthieno[2,3-d][1,3]thiazole-5-carboxamide TABLE 25-continued

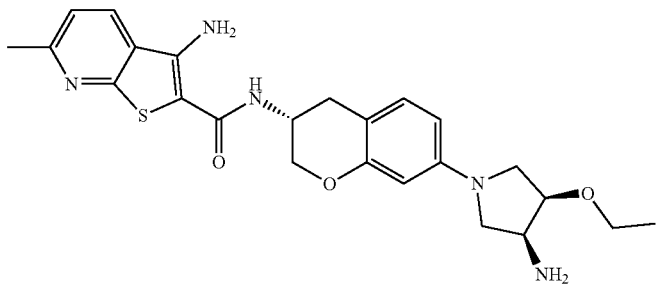 [SMILES: CCO[C@@H]1CN(c2ccc3c(c2)OC[C@H](NC(=O)c2sc4nc(C)ccc4c2N)C3)C[C@@H]1N]

151. 3-amino-N-[(3R)-7-[(3S,4R)-3-amino-4-
ethoxypyrrolidin-1-yl]-3,4-dihydro-2H-1-
benzopyran-3-yl]-6-methylthieno[2,3-
b]pyridine-2-carboxamide

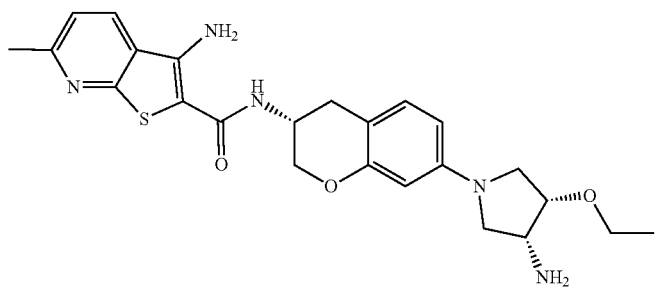 [SMILES: CCO[C@H]1CN(c2ccc3c(c2)OC[C@H](NC(=O)c2sc4nc(C)ccc4c2N)C3)C[C@H]1N]

152. 3-amino-N-[(3R)-7-[(3R,4S)-3-amino-
4-ethoxypyrrolidin-1-yl]-3,4-dihydro-2H-1-
benzopyran-3-yl]-6-methylthieno[2,3-
b]pyridine-2-carboxamide

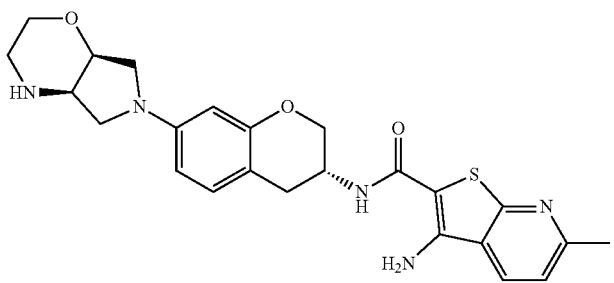 [SMILES: Cc1ccc2c(N)c(C(=O)N[C@H]3COc4cc(N5C[C@@H]6OCCN[C@@H]6C5)ccc4C3)sc2n1]

153. N-[(3R)-7-[(4aS,7aR)-
octahydropyrrolo[3,4-b]morpholin-6-yl]-3,4-
dihydro-2H-1-benzopyran-3-yl]-3-amino-6-
methylthieno[2,3-b]pyridine-2-carboxamide

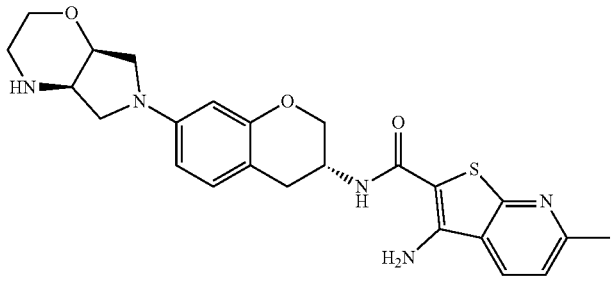 [SMILES: Cc1ccc2c(N)c(C(=O)N[C@H]3COc4cc(N5C[C@@H]6OCCN[C@@H]6C5)ccc4C3)sc2n1]

154. N-[(3R)-7-[(4aR,7aS)-
octahydropyrrolo[3,4-b]morpholin-6-yl]-3,4-
dihydro-2H-1-benzopyran-3-yl]-3-amino-6-
methylthieno[2,3-b]pyridine-2-carboxamide TABLE 25-continued

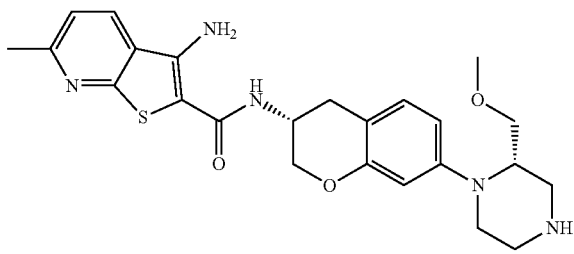 [SMILES: COC[C@@H]1CNCCN1c1ccc2c(c1)OC[C@H](NC(=O)c1sc3nc(C)ccc3c1N)C2]

155. 3-amino-N-[(3R)-7-[(2S)-2-(methoxymethyl)piperazin-1-yl]-3,4-dihydro-2H-1-benzopyran-3-yl]-6-methylthieno[2,3-b]pyridine-2-carboxamide

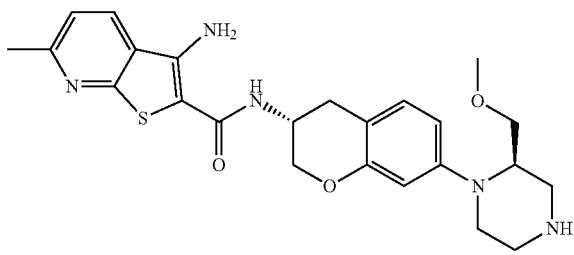 [SMILES: COC[C@H]1CNCCN1c1ccc2c(c1)OC[C@H](NC(=O)c1sc3nc(C)ccc3c1N)C2]

156. 3-amino-N-[(3R)-7-[(2R)-2-(methoxymethyl)piperazin-1-yl]-3,4-dihydro-2H-1-benzopyran-3-yl]-6-methylthieno[2,3-b]pyridine-2-carboxamide

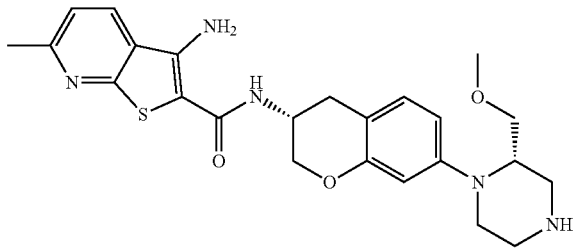 [SMILES: COC[C@@H]1CNCCN1c1ccc2c(c1)OC[C@H](NC(=O)c1sc3nc(C)ccc3c1N)C2]

157. 3-amino-N-[(3R)-7-[(3R)-3-(methoxymethyl)piperazin-1-yl]-3,4-dihydro-2H-1-benzopyran-3-yl]-6-methylthieno[2,3-b]pyridine-2-carboxamide

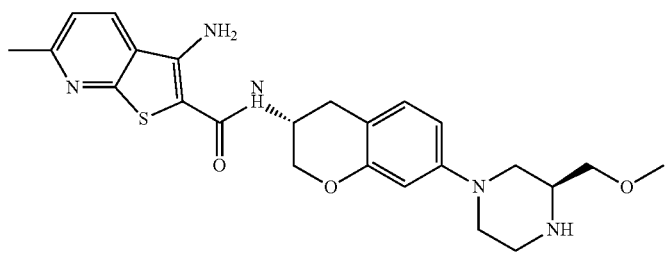

158. 3-amino-N-[(3R)-7-[(3S)-3-(methoxymethyl)piperazin-1-yl]-3,4-dihydro-2H-1-benzopyran-3-yl]-6-methylthieno[2,3-b]pyridine-2-carboxamide

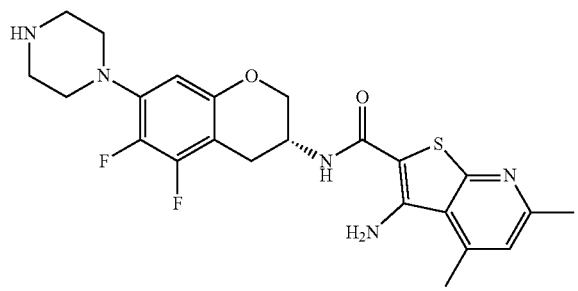 [SMILES: Cc1cc(C)c2c(N)c(C(=O)N[C@H]3COc4cc(N5CCNCC5)c(F)c(F)c4C3)sc2n1]

159. 3-amino-N-[(3R)-5,6-difluoro-7-
(piperazin-1-yl)-3,4-dihydro-2H-1-
benzopyran-3-yl]-4,6-dimethylthieno[2,3-
b]pyridine-2-carboxamide

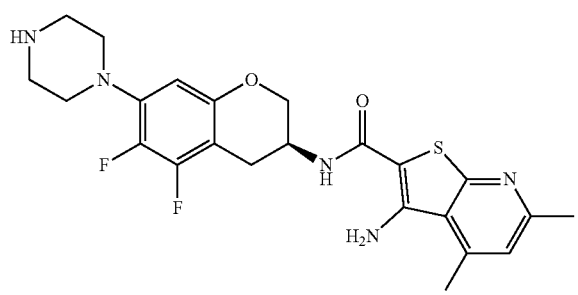 [SMILES: Cc1cc(C)c2c(N)c(C(=O)N[C@@H]3COc4cc(N5CCNCC5)c(F)c(F)c4C3)sc2n1]

160. 3-amino-N-[(3S)-5,6-difluoro-7-
(piperazin-1-yl)-3,4-dihydro-2H-1-
benzopyran-3-yl]-4,6-dimethylthieno[2,3-
b]pyridine-2-carboxamide

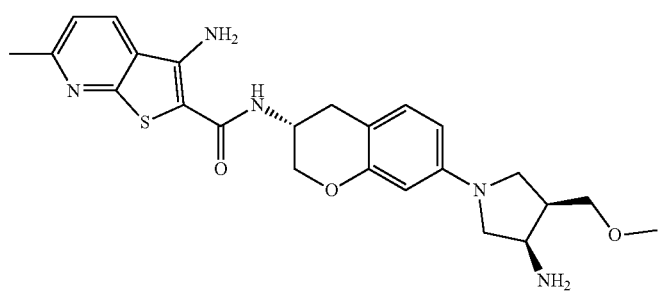

161. 3-amino-N-[(3R)-7-[(3R,4R)-3-amino-4-
(methoxymethyl)pyrrolidin-1-yl]-3,4-dihydro-
2H-1-benzopyran-3-yl]-6-methylthieno[2,3-
b]pyridine-2-carboxamide

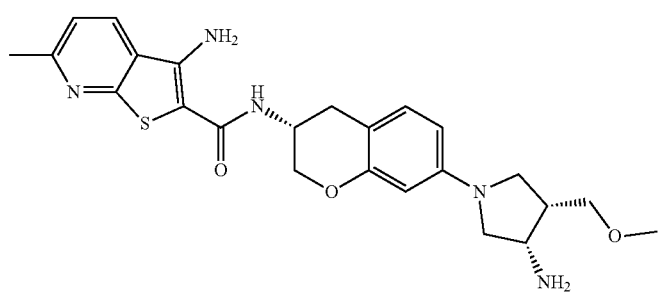

162. 3-amino-N-[(3R)-7-[(3S,4S)-3-amino-
4-(methoxymethyl)pyrrolidin-1-yl]-3,4-
dihydro-2H-1-benzopyran-3-yl]-6-
methylthieno[2,3-b]pyridine-2-carboxamide TABLE 25-continued

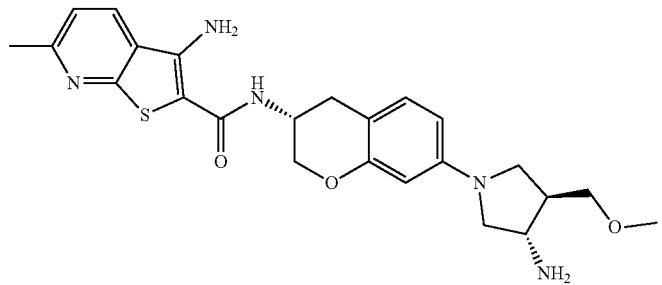

163. 3-amino-N-[(3R)-7-[(3S,4R)-3-amino-4-
(methoxymethyl)pyrrolidin-1-yl]-3,4-dihydro-
2H-1-benzopyran-3-yl]-6-methylthieno[2,3-
b]pyridine-2-carboxamide

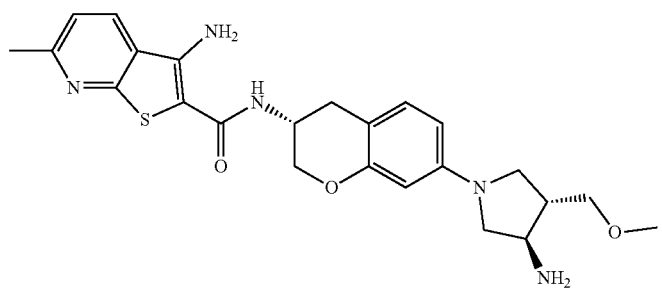

164. 3-amino-N-[(3R)-7-[(3R,4S)-3-amino-
4-(methoxymethyl)pyrrolidin-1-yl]-3,4-
dihydro-2H-1-benzopyran-3-yl]-6-
methylthieno[2,3-b]pyridine-2-carboxamide

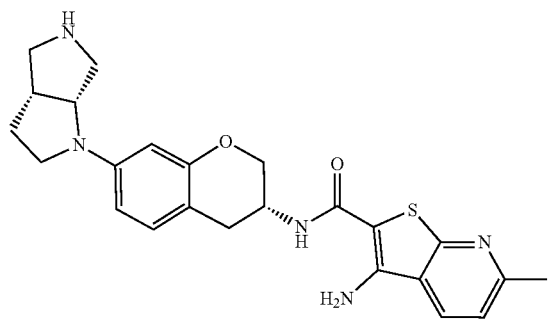 [SMILES: Cc1ccc2c(N)c(C(=O)N[C@H]3COc4cc(N5CC[C@@H]6CNC[C@@H]65)ccc4C3)sc2n1]

165. N-[(3R)-7-[(3aR,6aR)-
octahydropyrrolo[2,3-c]pyrrol-1-yl]-3,4-
dihydro-2H-1-benzopyran-3-yl]-3-amino-6-
methylthieno[2,3-b]pyridine-2-carboxamide

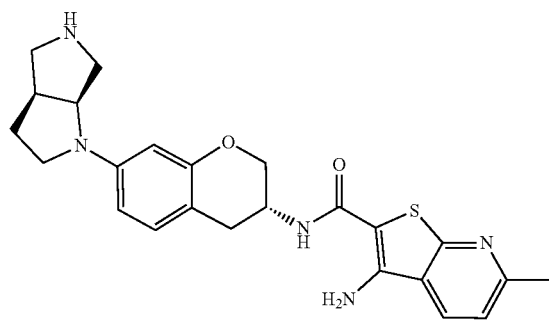 [SMILES: Cc1ccc2c(N)c(C(=O)N[C@H]3COc4cc(N5CC[C@H]6CNC[C@H]65)ccc4C3)sc2n1]

166. N-[(3R)-7-[(3aS,6aS)-
octahydropyrrolo[2,3-c]pyrrol-1-yl]-3,4-
dihydro-2H-1-benzopyran-3-yl]-3-amino-6-
methylthieno[2,3-b]pyridine-2-carboxamide TABLE 25-continued
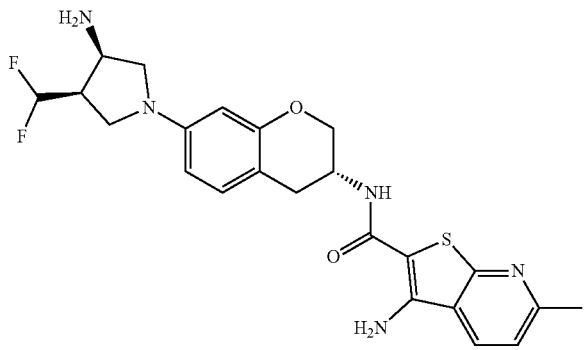 [SMILES: Cc1ccc2c(N)c(C(=O)N[C@H]3COc4cc(N5C[C@H](N)[C@H](C(F)F)C5)ccc4C3)sc2n1]
167. 3-amino-N-[(3R)-7-[(3R,4R)-3-amino-4-(difluoromethyl)pyrrolidin-1-yl]-3,4-dihydro-2H-1-benzopyran-3-yl]-6-methylthieno[2,3-b]pyridine-2-carboxamide
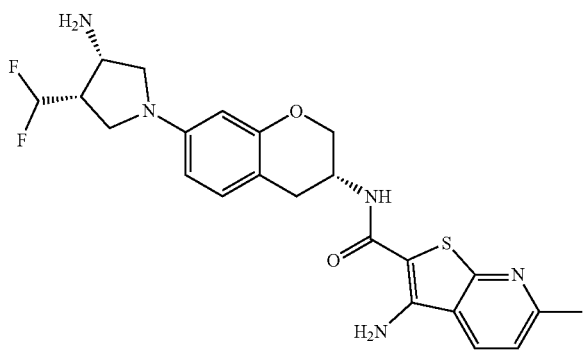 [SMILES: Cc1ccc2c(N)c(C(=O)N[C@H]3COc4cc(N5C[C@@H](N)[C@@H](C(F)F)C5)ccc4C3)sc2n1]
168. 3-amino-N-[(3R)-7-[(3S,4S)-3-amino-4-(difluoromethyl)pyrrolidin-1-yl]-3,4-dihydro-2H-1-benzopyran-3-yl]-6-methylthieno[2,3-b]pyridine-2-carboxamide
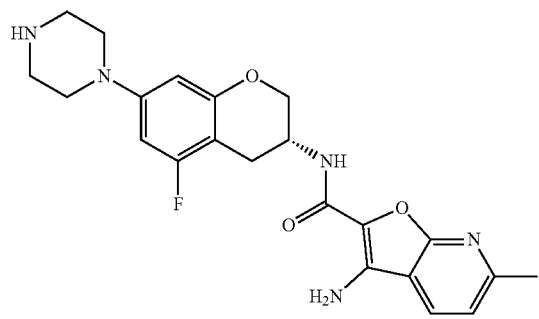 [SMILES: Cc1ccc2c(N)c(C(=O)N[C@H]3COc4cc(N5CCNCC5)cc(F)c4C3)oc2n1]
169. 3-amino-N-[(3R)-5-fluoro-7-(piperazin-1-yl)-3,4-dihydro-2H-1-benzopyran-3-yl]-6-methylfuro[2,3-b]pyridine-2-carboxamide TABLE 25-continued
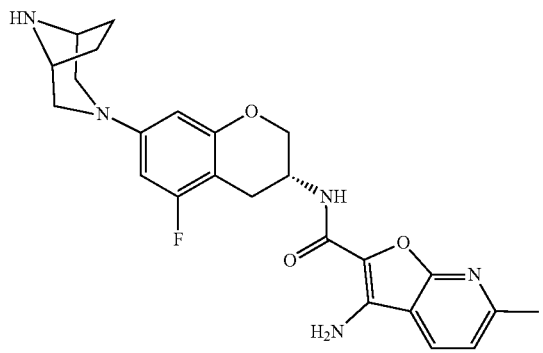 [SMILES: Cc1ccc2c(N)c(C(=O)N[C@H]3COc4cc(N5CC6CCC(C5)N6)cc(F)c4C3)oc2n1]
170. 3-amino-N-[(3R)-7-{3,8-diazabicyclo[3.2.1]octan-3-yl}-5-fluoro-3,4-dihydro-2H-1-benzopyran-3-yl]-6-methylfuro[2,3-b]pyridine-2-carboxamide
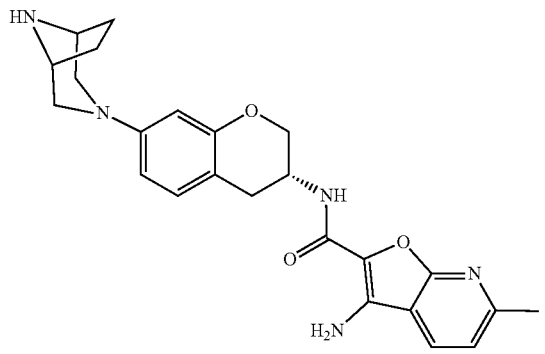
171. 3-amino-N-[(2S)-6-{3,8-diazabicyclo[3.2.1]octan-3-yl}-1,2,3,4-tetrahydronaphthalen-2-yl]-6-methylfuro[2,3-b]pyridine-2-carboxamide
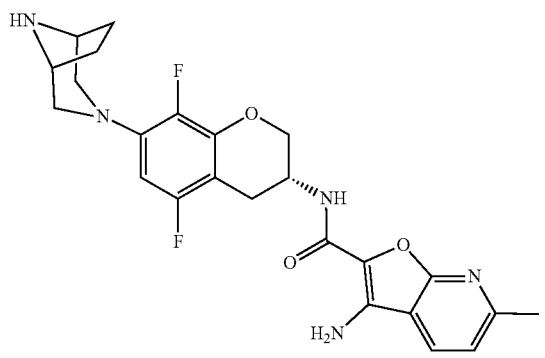 [SMILES: Cc1ccc2c(N)c(C(=O)N[C@H]3COc4c(F)c(N5CC6CCC(C5)N6)cc(F)c4C3)oc2n1]
172. 3-amino-N-[(3R)-7-{3,8-diazabicyclo[3.2.1]octan-3-yl}-5,8-difluoro-3,4-dihydro-2H-1-benzopyran-3-yl]-6-methylfuro[2,3-b]pyridine-2-carboxamide TABLE 25-continued
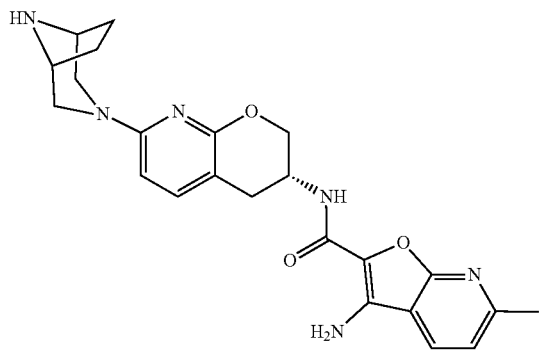 [SMILES: Cc1ccc2c(N)c(C(=O)N[C@H]3COc4nc(N5CC6CCC(C5)N6)ccc4C3)oc2n1]
173. 3-amino-N-[(3R)-7-{3,8-
diazabicyclo[3.2.1]octan-3-yl}-2H,3H,4H-
pyrano[2,3-b]pyridin-3-yl]-6-
methylthieno[2,3-b]pyridine-2-carboxamide
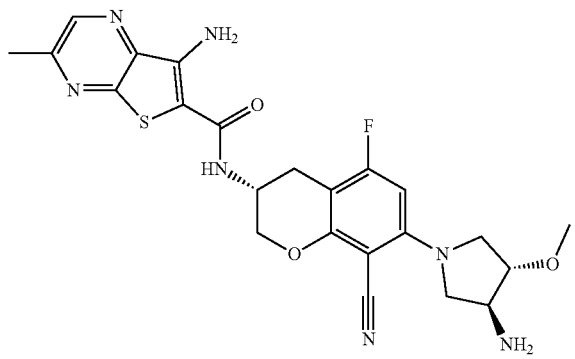
174. 7-amino-N-[(3R)-7-[(3S,4S)-3-amino-
4-methoxypyrrolidin-1-yl]-8-cyano-5-fluoro-
3,4-dihydro-2H-1-benzopyran-3-yl]-3-
methylthieno[2,3-b]pyrazine-6-carboxamide
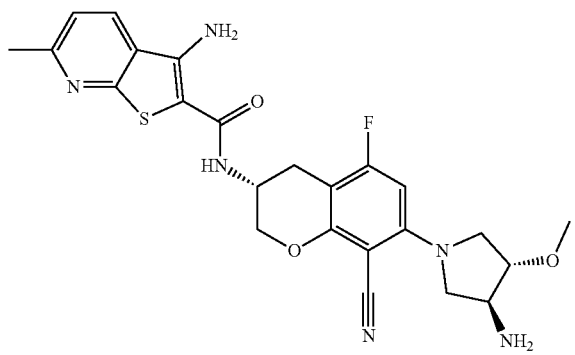
175. 3-amino-N-[(3R)-7-[(3S,4S)-3-amino-4-
methoxypyrrolidin-1-yl]-8-cyano-5-fluoro-3,4-
dihydro-2H-1-benzopyran-3-yl]-6-
methylthieno[2,3-b]pyridine-2-carboxamide

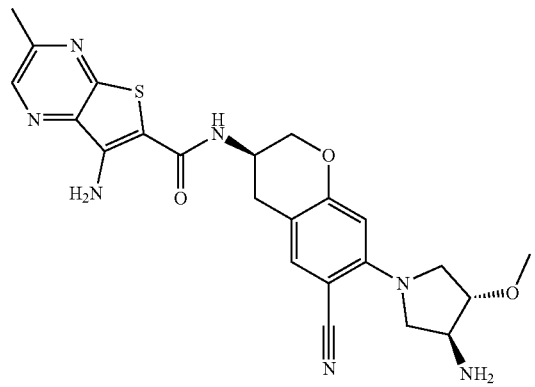
176. 7-amino-N-[(3R)-7-[(3S,4S)-3-amino-4-methoxypyrrolidin-1-yl]-6-cyano-3,4-dihydro-2H-1-benzopyran-3-yl]-3-methylthieno[2,3-b]pyrazine-6-carboxamide
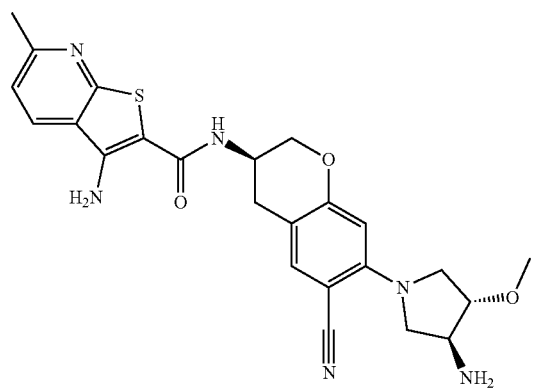 [SMILES: CO[C@H]1CN(c2cc3c(cc2C#N)C[C@@H](NC(=O)c2sc4nc(C)cnc4c2N)CO3)C[C@@H]1N]
177. 3-amino-N-[(3R)-7-[(3S,4S)-3-amino-4-methoxypyrrolidin-1-yl]-6-cyano-3,4-dihydro-2H-1-benzopyran-3-yl]-6-methylthieno[2,3-b]pyridine-2-carboxamide
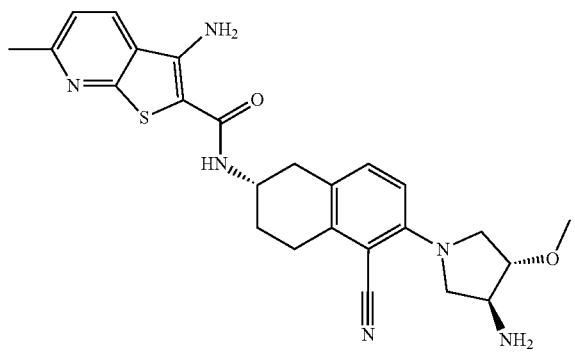
178. 3-amino-N-[(2S)-6-[(3S,4S)-3-amino-4-methoxypyrrolidin-1-yl]-5-cyano-1,2,3,4-tetrahydronaphthalen-2-yl]-6-methylthieno[2,3-b]pyridine-2-carboxamide TABLE 25-continued
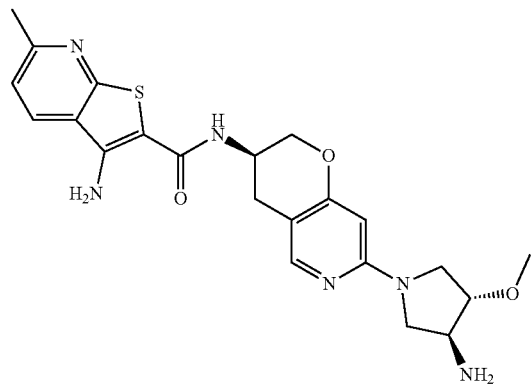 [SMILES: CO[C@H]1CN(c2cc3c(cn2)C[C@@H](NC(=O)c2sc4nc(C)ccc4c2N)CO3)C[C@@H]1N]
179. 3-amino-N-[(3R)-7-[(3S,4S)-3-amino-4-
methoxypyrrolidin-1-yl]-2H,3H,4H-
pyrano[3,2-c]pyridin-3-yl]-6-
methylthieno[2,3-b]pyridine-2-carboxamide
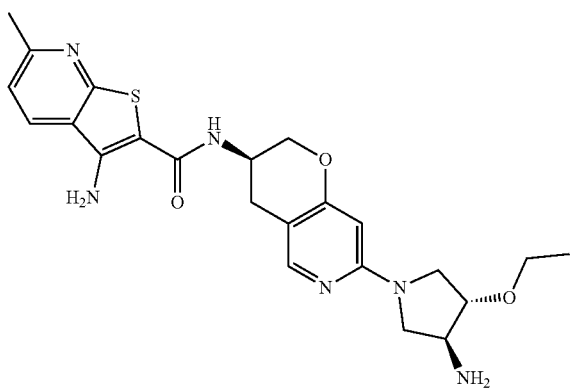 [SMILES: CCO[C@H]1CN(c2cc3c(cn2)C[C@@H](NC(=O)c2sc4nc(C)ccc4c2N)CO3)C[C@@H]1N]
180. 3-amino-N-[(3R)-7-[(3S,4S)-3-amino-
4-ethoxypyrrolidin-1-yl]-2H,3H,4H-
pyrano[3,2-c]pyridin-3-yl]-6-
methylthieno[2,3-b]pyridine-2-carboxamide
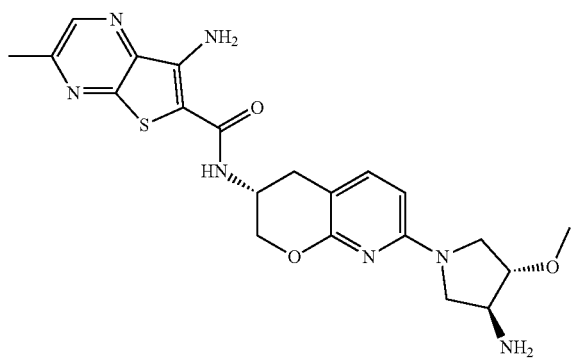
181. 7-amino-N-[(3R)-7-[(3S,4S)-3-amino-4-
methoxypyrrolidin-1-yl]-2H,3H,4H-
pyrano[2,3-b]pyridin-3-yl]-3-
methylthieno[2,3-b]pyrazine-6-carboxamide TABLE 25-continued
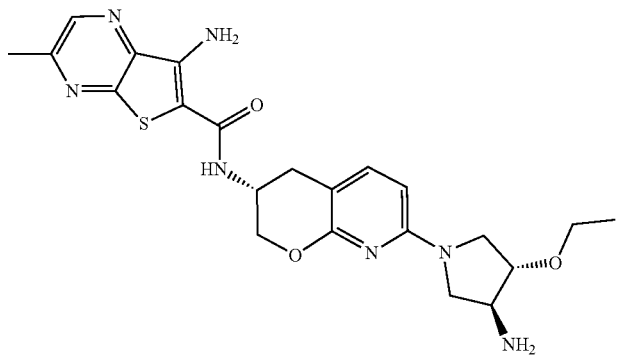 [SMILES: CCO[C@H]1CN(c2ccc3c(n2)OC[C@H](NC(=O)c2sc4c(c2N)=NCC=C(C)N=4)C3)C[C@@H]1N]
182. 7-amino-N-[(3R)-7-[(3S,4S)-3-amino-
4-ethoxypyrrolidin-1-yl]-2H,3H,4H-
pyrano[2,3-b]pyridin-3-yl]-3-
methylthieno[2,3-b]pyrazine-6-carboxamide
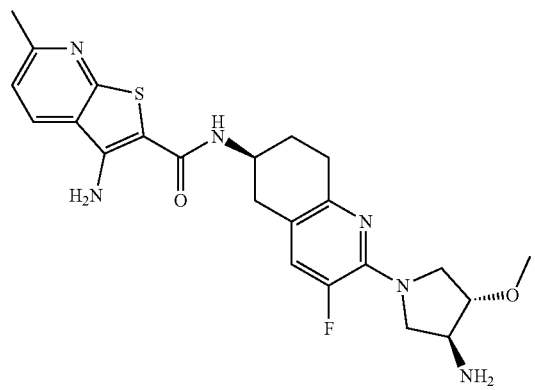 [SMILES: CO[C@H]1CN(c2nc3c(cc2F)C[C@@H](NC(=O)c2sc4nc(C)ccc4c2N)CC3)C[C@@H]1N]
183. 3-amino-N-[(6S)-2-[(3S,4S)-3-amino-4-
methoxypyrrolidin-1-yl]-3-fluoro-5,6,7,8-
tetrahydroquinolin-6-yl]-6-methylthieno[2,3-
b]pyridine-2-carboxamide
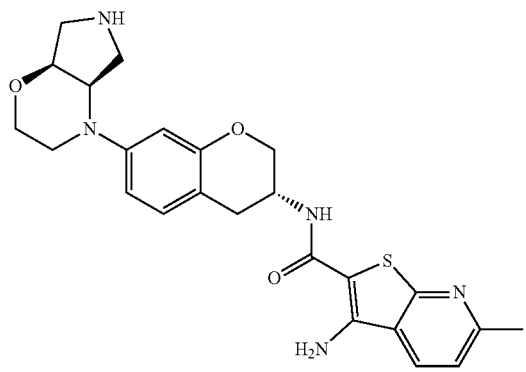 [SMILES: Cc1ccc2c(N)c(C(=O)N[C@H]3COc4cc(N5CCO[C@H]6CNC[C@H]65)ccc4C3)sc2n1]
184. N-[(3R)-7-[(4aR,7aS)-
octahydropyrrolo[3,4-b]morpholin-4-yl]-3,4-
dihydro-2H-1-benzopyran-3-yl]-3-amino-6-
methylthieno[2,3-b]pyridine-2-carboxamide TABLE 25-continued
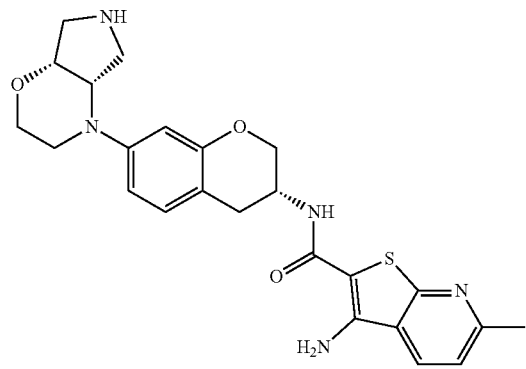 [SMILES: Cc1ccc2c(N)c(C(=O)N[C@H]3COc4cc(N5CCO[C@@H]6CNC[C@@H]65)ccc4C3)sc2n1]
185. N-[(3R)-7-[(4aS,7aR)-
octahydropyrrolo[3,4-b]morpholin-4-yl]-3,4-
dihydro-2H-1-benzopyran-3-yl]-3-amino-6-
methylthieno[2,3-b]pyridine-2-carboxamide
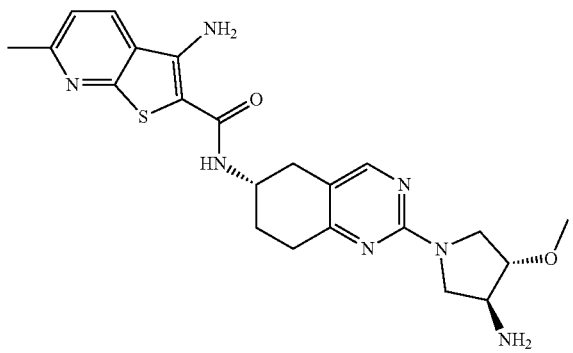
186. 3-amino-N-[(6S)-2-[(3S,4S)-3-amino-4-
methoxypyrrolidin-1-yl]-5,6,7,8-
tetrahydroquinazolin-6-yl]-6-
methylthieno[2,3-b]pyridine-2-carboxamide
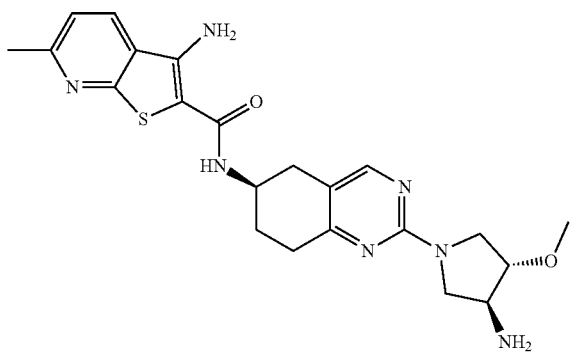
187. 3-amino-N-[(6R)-2-[(3S,4S)-3-amino-4-
methoxypyrrolidin-1-yl]-5,6,7,8-
tetrahydroquinazolin-6-yl]-6-
methylthieno[2,3-b]pyridine-2-carboxamide

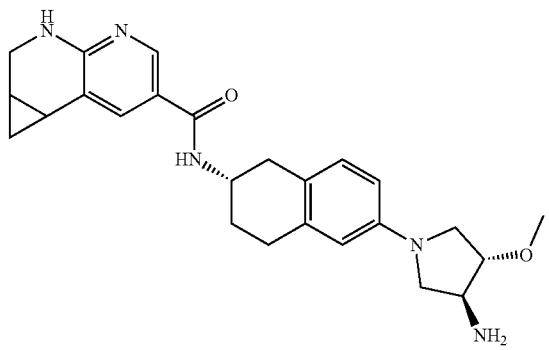 [SMILES: CO[C@H]1CN(c2ccc3c(c2)CC[C@H](NC(=O)c2cnc4c(c2)C2CC2CN4)C3)C[C@@H]1N]
188. N-[(2S)-6-[(3S,4S)-3-amino-4-methoxypyrrolidin-1-yl]-1,2,3,4-tetrahydronaphthalen-2-yl]-5H,6H,6aH,7H,7aH-cyclopropa[c]1,8-naphthyridine-2-carboxamide
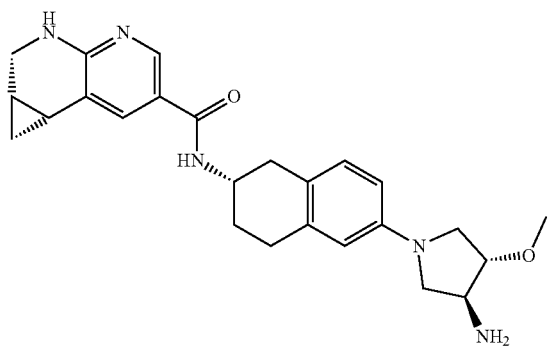
189. (6aS,7aR)-N-[(2S)-6-[(3S,4S)-3-amino-4-methoxypyrrolidin-1-yl]-1,2,3,4-tetrahydronaphthalen-2-yl]-5H,6H,6aH,7H,7aH-cyclopropa[c]1,8-naphthyridine-2-carboxamide
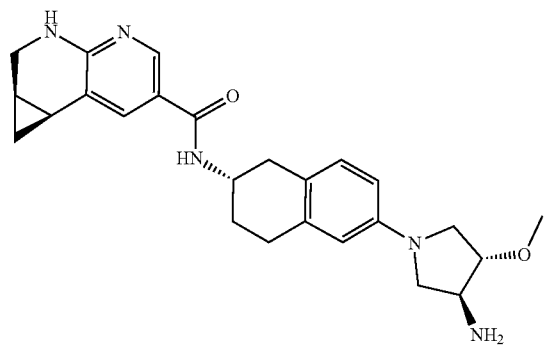 [SMILES: CO[C@H]1CN(c2ccc3c(c2)CC[C@H](NC(=O)c2cnc4c(c2)[C@H]2C[C@H]2CN4)C3)C[C@@H]1N]
190. (6aR,7aS)-N-[(2S)-6-[(3S,4S)-3-amino-4-methoxypyrrolidin-1-yl]-1,2,3,4-tetrahydronaphthalen-2-yl]-5H,6H,6aH,7H,7aH-cyclopropa[c]1,8-naphthyridine-2-carboxamide TABLE 25-continued

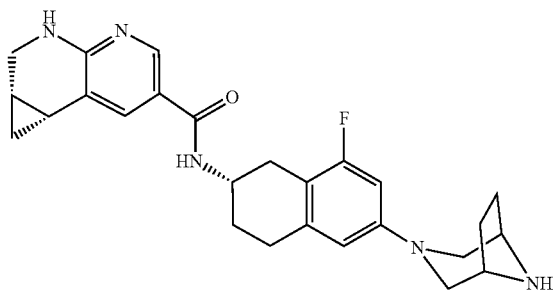 [SMILES: O=C(N[C@H]1CCc2cc(N3CC4CCC(C3)N4)cc(F)c2C1)c1cnc2c(c1)[C@@H]1C[C@@H]1CN2]

191. (6aS,7aR)-N-[(2S)-6-{3,8-
diazabicyclo[3.2.1]octan-3-yl}-8-fluoro-
1,2,3,4-tetrahydronaphthalen-2-yl]-
5H,6H,6aH,7H,7aH-cyclopropa[c]1,8-
naphthyridine-2-carboxamide

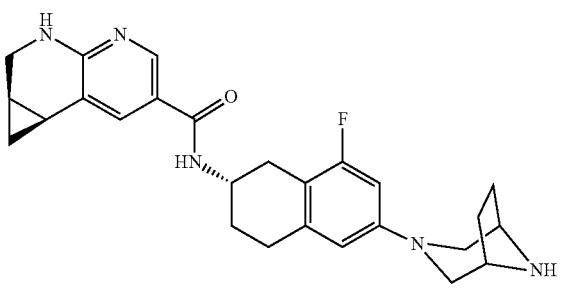 [SMILES: O=C(N[C@H]1CCc2cc(N3CC4CCC(C3)N4)cc(F)c2C1)c1cnc2c(c1)[C@H]1C[C@H]1CN2]

192. (6aR,7aS)-N-[(2S)-6-{3,8-
diazabicyclo[3.2.1]octan-3-yl}-8-fluoro-
1,2,3,4-tetrahydronaphthalen-2-yl]-
5H,6H,6aH,7H,7aH-cyclopropa[c]1,8-
naphthyridine-2-carboxamide

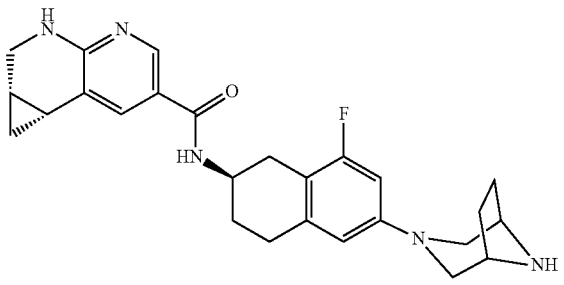 [SMILES: O=C(N[C@@H]1CCc2cc(N3CC4CCC(C3)N4)cc(F)c2C1)c1cnc2c(c1)[C@@H]1C[C@@H]1CN2]

193. (6aS,7aR)-N-[(2R)-6-{3,8-
diazabicyclo[3.2.1]octan-3-yl}-8-fluoro-
1,2,3,4-tetrahydronaphthalen-2-yl]-
5H,6H,6aH,7H,7aH-cyclopropa[c]1,8-
naphthyridine-2-carboxamide

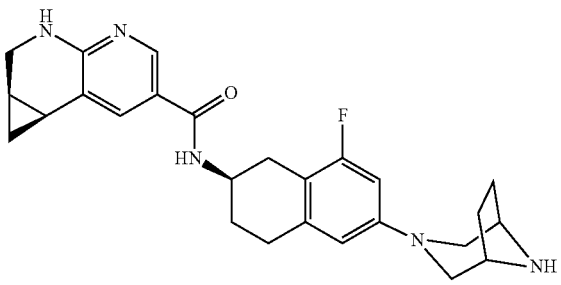 [SMILES: O=C(N[C@@H]1CCc2cc(N3CC4CCC(C3)N4)cc(F)c2C1)c1cnc2c(c1)[C@H]1C[C@H]1CN2]

194. (6aR,7aS)-N-[(2R)-6-{3,8-
diazabicyclo[3.2.1]octan-3-yl}-8-fluoro-
1,2,3,4-tetrahydronaphthalen-2-yl]-
5H,6H,6aH,7H,7aH-cyclopropa[c]1,8-
naphthyridine-2-carboxamide TABLE 25-continued

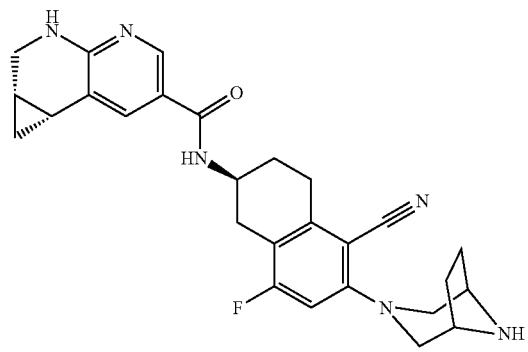 [SMILES: N#Cc1c(N2CC3CCC(C2)N3)cc(F)c2c1CC[C@H](NC(=O)c1cnc3c(c1)[C@@H]1C[C@@H]1CN3)C2]

195. (6aS,7aR)-N-[(2S)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide

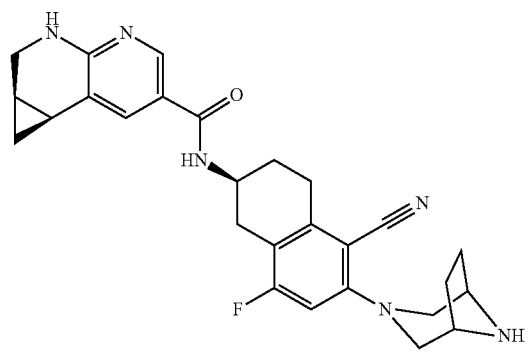 [SMILES: N#Cc1c(N2CC3CCC(C2)N3)cc(F)c2c1CC[C@H](NC(=O)c1cnc3c(c1)[C@H]1C[C@H]1CN3)C2]

196. (6aR,7aS)-N-[(2S)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide

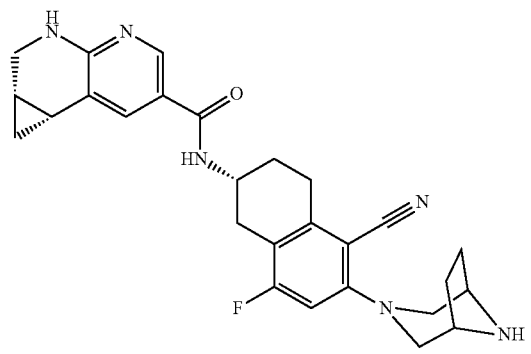 [SMILES: N#Cc1c(N2CC3CCC(C2)N3)cc(F)c2c1CC[C@@H](NC(=O)c1cnc3c(c1)[C@@H]1C[C@@H]1CN3)C2]

197. (6aS,7aR)-N-[(2R)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide TABLE 25-continued

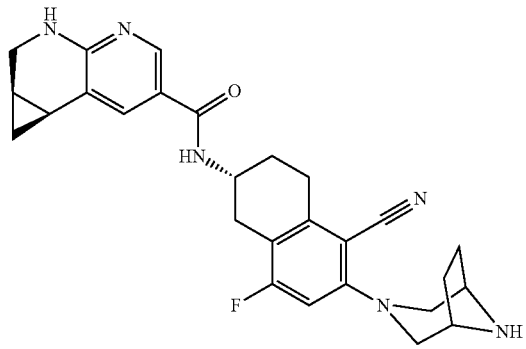 [SMILES: N#Cc1c(N2CC3CCC(C2)N3)cc(F)c2c1CC[C@@H](NC(=O)c1cnc3c(c1)[C@H]1C[C@H]1CN3)C2]

198. (6aR,7aS)-N-[(2R)-5-cyano-6-{3,8-diazabicyclo[3.2.1]octan-3-yl}-8-fluoro-1,2,3,4-tetrahydronaphthalen-2-yl]-5H,6H,6aH,7H,7aH-cyclopropa[c]1,8-naphthyridine-2-carboxamide

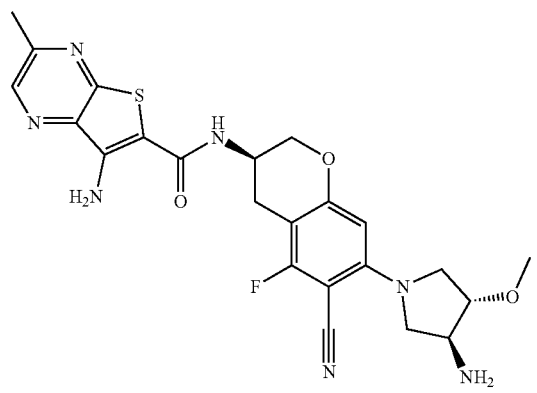

199. 7-amino-N-[(3R)-7-[(3S,4S)-3-amino-4-methoxypyrrolidin-1-yl]-6-cyano-5-fluoro-3,4-dihydro-2H-1-benzopyran-3-yl]-3-methylthieno[2,3-b]pyrazine-6-carboxamide

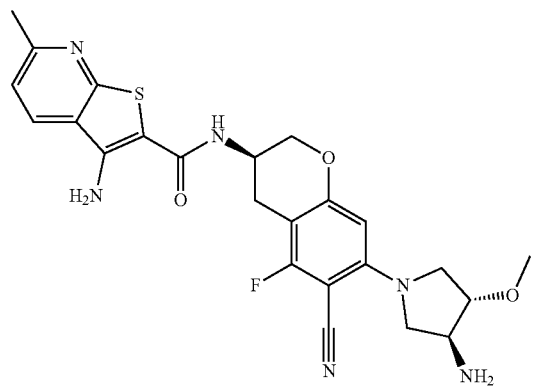 [SMILES: CO[C@H]1CN(c2cc3c(c(F)c2C#N)C[C@@H](NC(=O)c2sc4nc(C)ccc4c2N)CO3)C[C@@H]1N]

200. 3-amino-N-[(3R)-7-[(3S,4S)-3-amino-4-methoxypyrrolidin-1-yl]-6-cyano-5-fluoro-3,4-dihydro-2H-1-benzopyran-3-yl]-6-methylthieno[2,3-b]pyridine-2-carboxamide

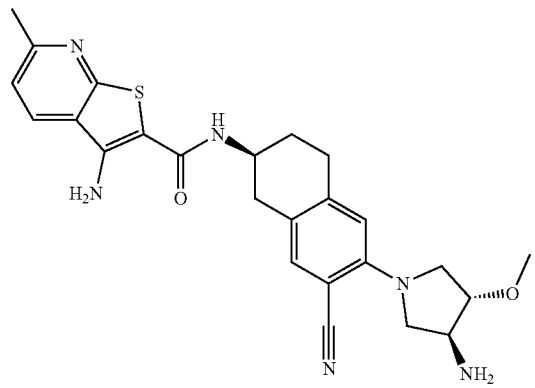
201. 3-amino-N-[(2S)-6-[(3S,4S)-3-amino-4-
methoxypyrrolidin-1-yl]-7-cyano-1,2,3,4-
tetrahydronaphthalen-2-yl]-6-
methylthieno[2,3-b]pyridine-2-carboxamide
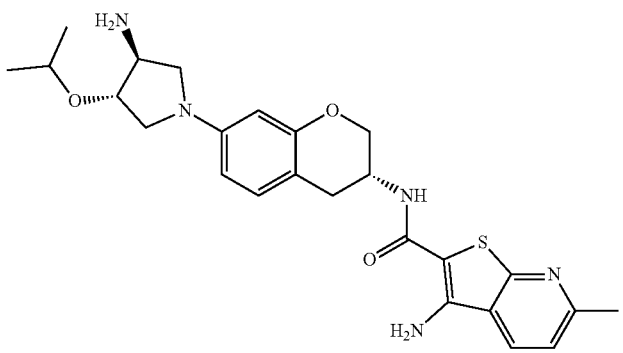 [SMILES: Cc1ccc2c(N)c(C(=O)N[C@H]3COc4cc(N5C[C@H](OC(C)C)[C@@H](N)C5)ccc4C3)sc2n1]
202. 3-amino-N-[(3R)-7-[(3S,4S)-3-amino-
4-(propan-2-yloxy)pyrrolidin-1-yl]-3,4-
dihydro-2H-1-benzopyran-3-yl]-6-
methylthieno[2,3-b]pyridine-2-carboxamide
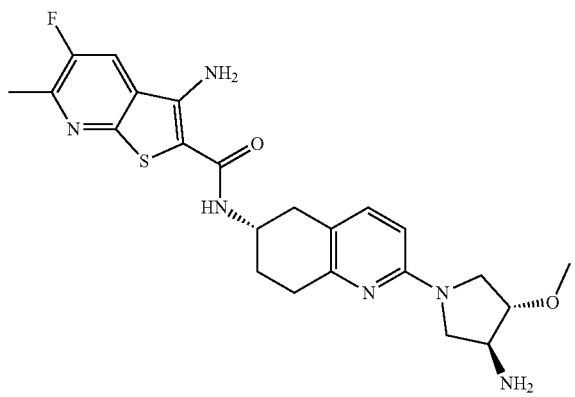
203. 3-amino-N-[(6S)-2-[(3S,4S)-3-amino-4-
methoxypyrrolidin-1-yl]-5,6,7,8-
tetrahydroquinolin-6-yl]-5-fluoro-6-
methylthieno[2,3-b]pyridine-2-carboxamide TABLE 25-continued
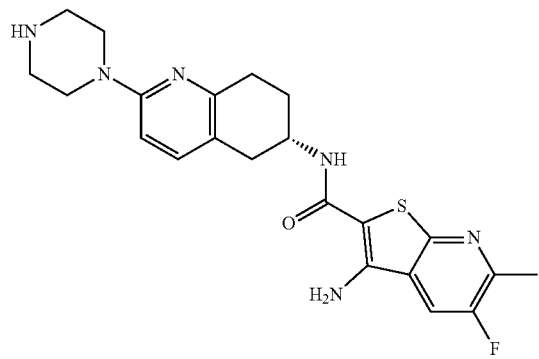 [SMILES: Cc1nc2sc(C(=O)N[C@H]3CCc4nc(N5CCNCC5)ccc4C3)c(N)c2cc1F]
204. 3-amino-5-fluoro-6-methyl-N-[(6S)-2-
(piperazin-1-yl)-5,6,7,8-tetrahydroquinolin-
6-yl]thieno[2,3-b]pyridine-2-carboxamide
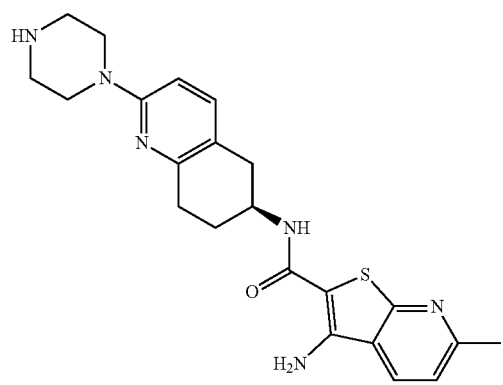 [SMILES: Cc1ccc2c(N)c(C(=O)N[C@H]3CCc4nc(N5CCNCC5)ccc4C3)sc2n1]
205. 3-amino-6-methyl-N-[(6S,8S)-8-methyl-
2-(piperazin-1-yl)-5,6,7,8-tetrahydroquinolin-
6-yl]thieno[2,3-b]pyridine-2-carboxamide
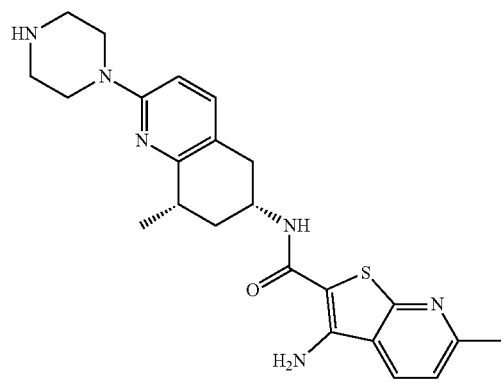 [SMILES: Cc1ccc2c(N)c(C(=O)N[C@H]3Cc4ccc(N5CCNCC5)nc4[C@@H](C)C3)sc2n1]
206. 3-amino-6-methyl-N-[(6R,8S)-8-
methyl-2-(piperazin-1-yl)-5,6,7,8-
tetrahydroquinolin-6-yl]thieno[2,3-
b]pyridine-2-carboxamide TABLE 25-continued
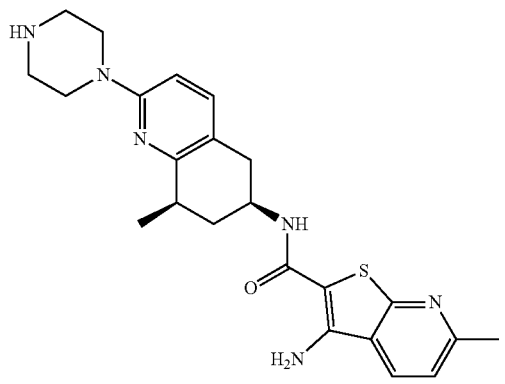 [SMILES: Cc1ccc2c(N)c(C(=O)N[C@@H]3Cc4ccc(N5CCNCC5)nc4[C@H](C)C3)sc2n1]
207. 3-amino-6-methyl-N-[(6S,8R)-8-methyl-
2-(piperazin-1-yl)-5,6,7,8-tetrahydroquinolin-
6-yl]thieno[2,3-b]pyridine-2-carboxamide
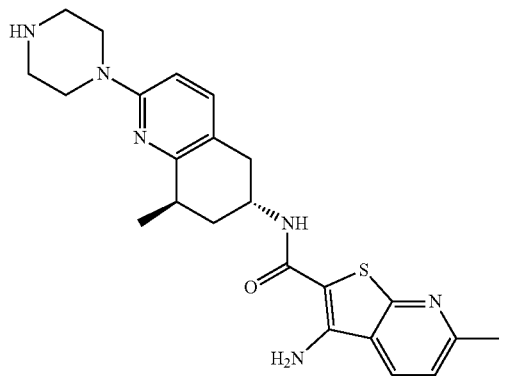 [SMILES: Cc1ccc2c(N)c(C(=O)N[C@H]3Cc4ccc(N5CCNCC5)nc4[C@H](C)C3)sc2n1]
208. 3-amino-6-methyl-N-[(6R,8R)-8-
methyl-2-(piperazin-1-yl)-5,6,7,8-
tetrahydroquinolin-6-yl]thieno[2,3-
b]pyridine-2-carboxamide
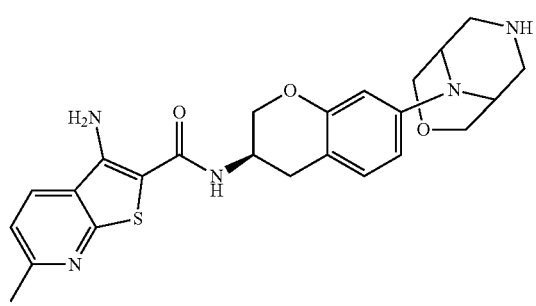 [SMILES: Cc1ccc2c(N)c(C(=O)N[C@H]3COc4cc(N5C6CNCC5COC6)ccc4C3)sc2n1]
209. 3-amino-6-methyl-N-[(3R)-7-{3-oxa-7,9-
diazabicyclo[3.3.1]nonan-9-yl}-3,4-dihydro-
2H-1-benzopyran-3-yl]thieno[2,3-b]pyridine-
2-carboxamide

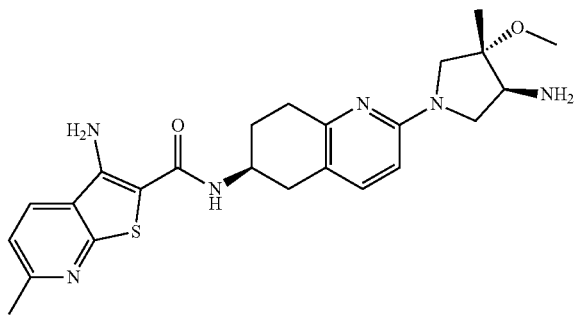 [SMILES: CO[C@@]1(C)CN(c2ccc3c(n2)CC[C@H](NC(=O)c2sc4nc(C)ccc4c2N)C3)C[C@@H]1N]
210. 3-amino-N-[(6S)-2-[(3S,4S)-4-amino-3-methoxy-3-methylpyrrolidin-1-yl]-5,6,7,8-tetrahydroquinolin-6-yl]-6-methylthieno[2,3-b]pyridine-2-carboxamide
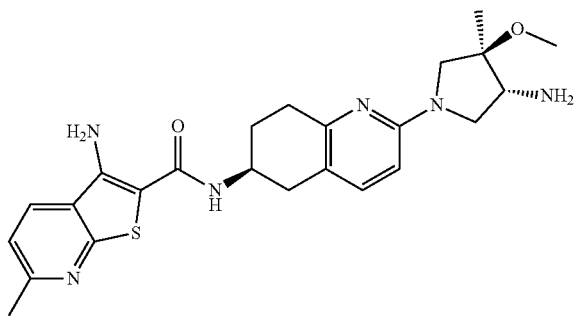
211. 3-amino-N-[(6S)-2-[(3R,4R)-4-amino-3-methoxy-3-methylpyrrolidin-1-yl]-5,6,7,8-tetrahydroquinolin-6-yl]-6-methylthieno[2,3-b]pyridine-2-carboxamide
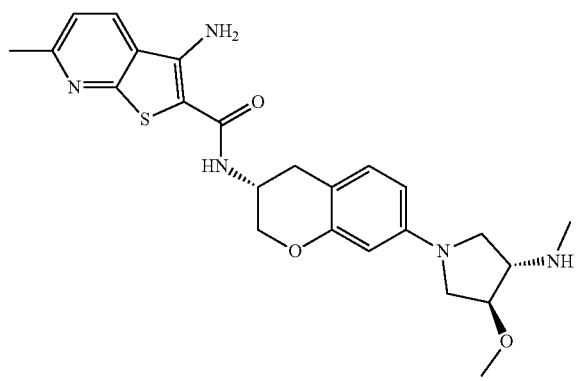
212. 3-amino-N-[(3R)-7-[(3S,4S)-3-methoxy-4-(methylamino)pyrrolidin-1-yl]-3,4-dihydro-2H-1-benzopyran-3-yl]-6-methylthieno[2,3-b]pyridine-2-carboxamide TABLE 25-continued
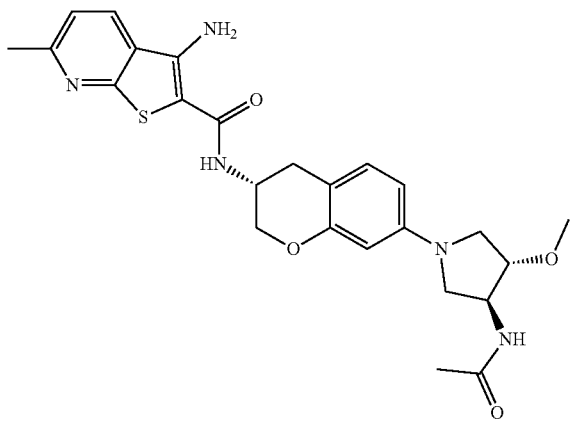
213. 3-amino-N-[(3R)-7-[(3S,4S)-3-
acetamido-4-methoxypyrrolidin-1-yl]-3,4-
dihydro-2H-1-benzopyran-3-yl]-6-
methylthieno[2,3-b]pyridine-2-carboxamide
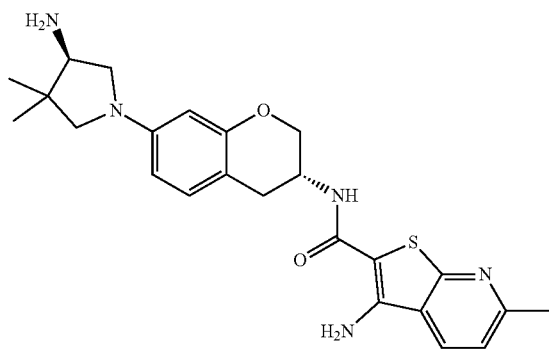
214. 3-amino-N-[(3R)-7-[(4R)-4-amino-3,3-
dimethylpyrrolidin-1-yl]-3,4-dihydro-2H-1-
benzopyran-3-yl]-6-methylthieno[2,3-
b]pyridine-2-carboxamide
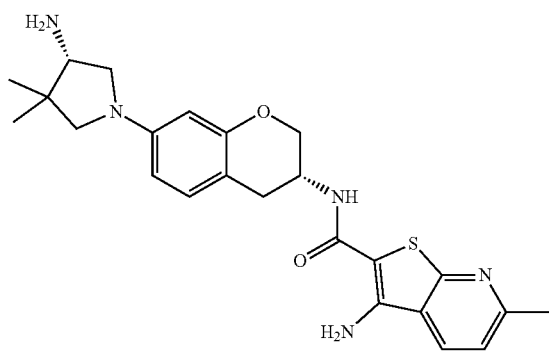
215. 3-amino-N-[(3R)-7-[(4S)-4-amino-3,3-
dimethylpyrrolidin-1-yl]-3,4-dihydro-2H-1-
benzopyran-3-yl]-6-methylthieno[2,3-
b]pyridine-2-carboxamide TABLE 25-continued
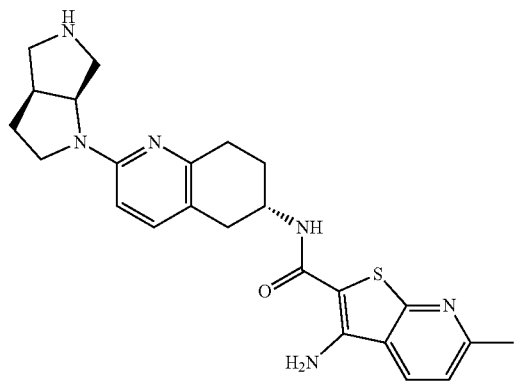 [SMILES: Cc1ccc2c(N)c(C(=O)N[C@H]3CCc4nc(N5CC[C@H]6CNC[C@H]65)ccc4C3)sc2n1]
216. N-[(6S)-2-[(3aS,6aS)-octahydropyrrolo[2,3-c]pyrrol-1-yl]-5,6,7,8-tetrahydroquinolin-6-yl]-3-amino-6-methylthieno[2,3-b]pyridine-2-carboxamide
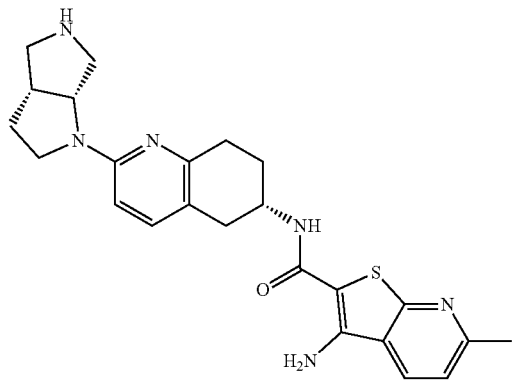 [SMILES: Cc1ccc2c(N)c(C(=O)N[C@H]3CCc4nc(N5CC[C@@H]6CNC[C@@H]65)ccc4C3)sc2n1]
217. N-[(6S)-2-[(3aR,6aR)-octahydropyrrolo[2,3-c]pyrrol-1-yl]-5,6,7,8-tetrahydroquinolin-6-yl]-3-amino-6-methylthieno[2,3-b]pyridine-2-carboxamide
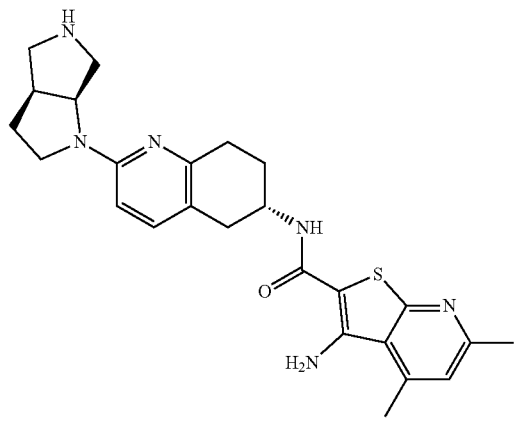 [SMILES: Cc1cc(C)c2c(N)c(C(=O)N[C@H]3CCc4nc(N5CC[C@H]6CNC[C@H]65)ccc4C3)sc2n1]
218. N-[(6S)-2-[(3aS,6aS)-octahydropyrrolo[2,3-c]pyrrol-1-yl]-5,6,7,8-tetrahydroquinolin-6-yl]-3-amino-4,6-dimethylthieno[2,3-b]pyridine-2-carboxamide TABLE 25-continued
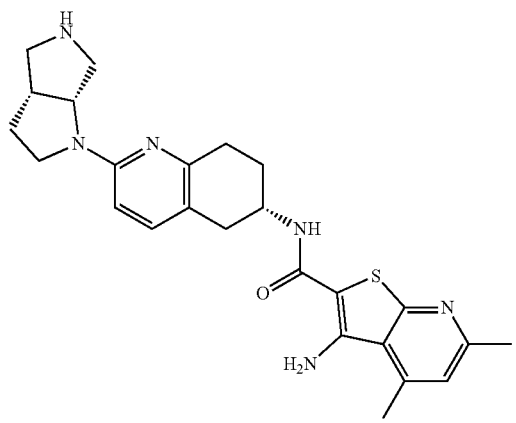 [SMILES: Cc1cc(C)c2c(N)c(C(=O)N[C@H]3CCc4nc(N5CC[C@@H]6CNC[C@@H]65)ccc4C3)sc2n1]
219. N-[(6S)-2-[(3aR,6aR)-
octahydropyrrolo[2,3-c]pyrrol-1-yl]-5,6,7,8-
tetrahydroquinolin-6-yl]-3-amino-4,6-
dimethylthieno[2,3-b]pyridine-2-carboxamide
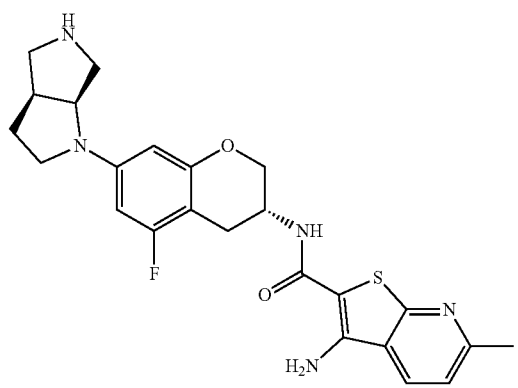 [SMILES: Cc1ccc2c(N)c(C(=O)N[C@H]3COc4cc(N5CC[C@H]6CNC[C@H]65)cc(F)c4C3)sc2n1]
220. N-[(3R)-7-[(3aS,6aS)-
octahydropyrrolo[2,3-c]pyrrol-1-yl]-5-
fluoro-3,4-dihydro-2H-1-benzopyran-3-yl]-
3-amino-6-methylthieno[2,3-b]pyridine-2-
carboxamide
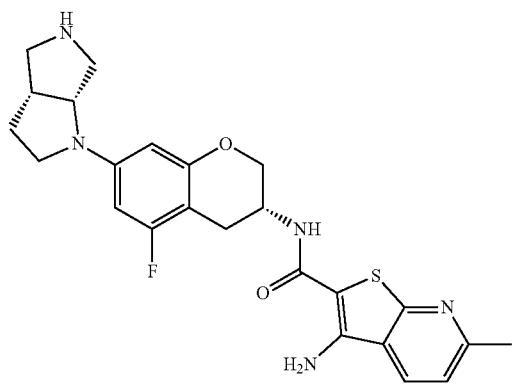 [SMILES: Cc1ccc2c(N)c(C(=O)N[C@H]3COc4cc(N5CC[C@@H]6CNC[C@@H]65)cc(F)c4C3)sc2n1]
221. N-[(3R)-7-[(3aR,6aR)-
octahydropyrrolo[2,3-c]pyrrol-1-yl]-5-fluoro-
3,4-dihydro-2H-1-benzopyran-3-yl]-3-amino-
6-methylthieno[2,3-b]pyridine-2-carboxamide TABLE 25-continued
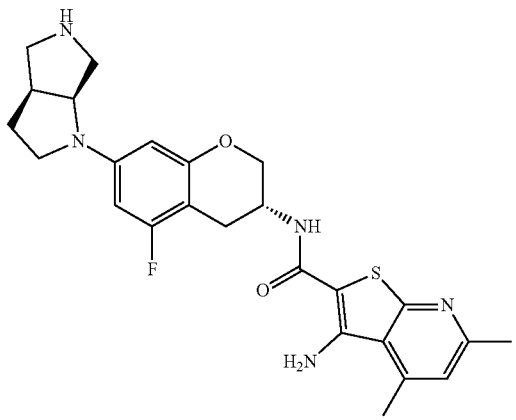 [SMILES: Cc1cc(C)c2c(N)c(C(=O)N[C@H]3COc4cc(N5CC[C@H]6CNC[C@H]65)cc(F)c4C3)sc2n1]
222. N-[(3R)-7-[(3aS,6aS)-
octahydropyrrolo[2,3-c]pyrrol-1-yl]-5-
fluoro-3,4-dihydro-2H-1-benzopyran-3-yl]-
3-amino-4,6-dimethylthieno[2,3-b]pyridine-
2-carboxamide
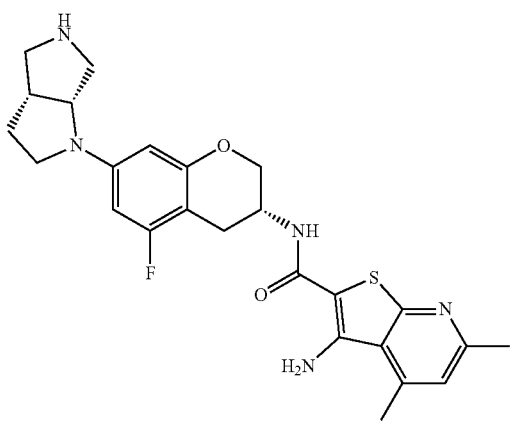 [SMILES: Cc1cc(C)c2c(N)c(C(=O)N[C@H]3COc4cc(N5CC[C@@H]6CNC[C@@H]65)cc(F)c4C3)sc2n1]
223. N-[(3R)-7-[(3aR,6aR)-
octahydropyrrolo[2,3-c]pyrrol-1-yl]-5-fluoro-
3,4-dihydro-2H-1-benzopyran-3-yl]-3-amino-
4,6-dimethylthieno[2,3-b]pyridine-2-
carboxamide
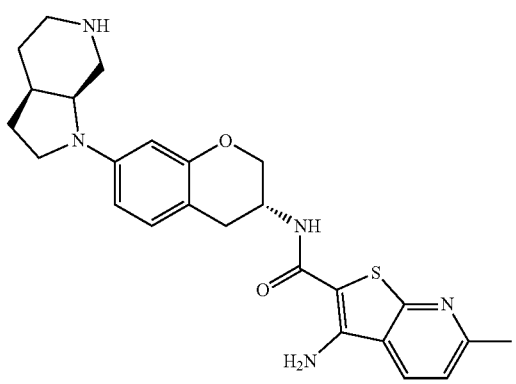 [SMILES: Cc1ccc2c(N)c(C(=O)N[C@H]3COc4cc(N5CC[C@H]6CCNC[C@H]65)ccc4C3)sc2n1]
224. N-[(3R)-7-[(3aR,7aS)-octahydro-1H-
pyrrolo[2,3-c]pyridin-1-yl]-3,4-dihydro-2H-
1-benzopyran-3-yl]-3-amino-6-
methylthieno[2,3-b]pyridine-2-carboxamide TABLE 25-continued
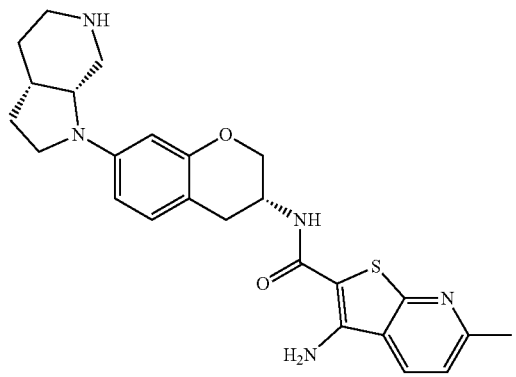 [SMILES: Cc1ccc2c(N)c(C(=O)N[C@H]3COc4cc(N5CC[C@@H]6CCNC[C@@H]65)ccc4C3)sc2n1]
225. N-[(3R)-7-[(3aS,7aR)-octahydro-1H-
pyrrolo[2,3-c]pyridin-1-yl]-3,4-dihydro-2H-1-
benzopyran-3-yl]-3-amino-6-
methylthieno[2,3-b]pyridine-2-carboxamide
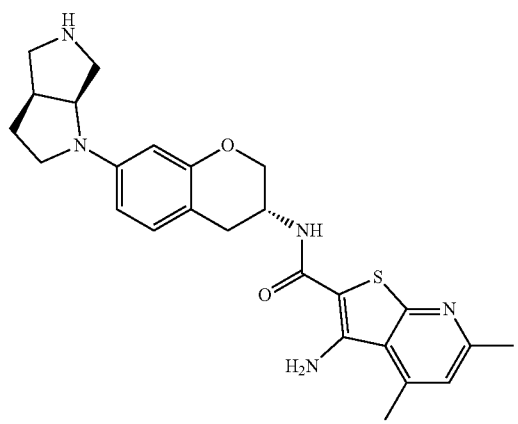 [SMILES: Cc1cc(C)c2c(N)c(C(=O)N[C@H]3COc4cc(N5CC[C@H]6CNC[C@H]65)ccc4C3)sc2n1]
226. N-[(3R)-7-[(3aS,6aS)-
octahydropyrrolo[2,3-c]pyrrol-1-yl]-3,4-
dihydro-2H-1-benzopyran-3-yl]-3-amino-
4,6-dimethylthieno[2,3-b]pyridine-2-
carboxamide
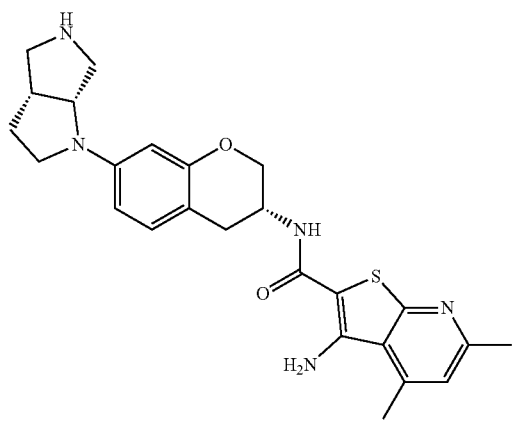 [SMILES: Cc1cc(C)c2c(N)c(C(=O)N[C@H]3COc4cc(N5CC[C@@H]6CNC[C@@H]65)ccc4C3)sc2n1]
227. N-[(3R)-7-[(3aR,6aR)-
octahydropyrrolo[2,3-c]pyrrol-1-yl]-3,4-
dihydro-2H-1-benzopyran-3-yl]-3-amino-4,6-
dimethylthieno[2,3-b]pyridine-2-carboxamide TABLE 25-continued

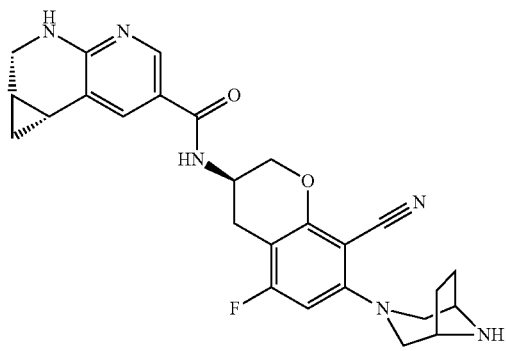

228. (6aS,7aR)-N-[(3R)-8-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide

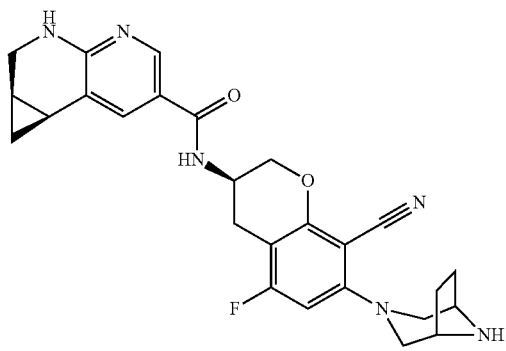 [SMILES: N#Cc1c(N2CC3CCC(C2)N3)cc(F)c2c1OC[C@H](NC(=O)c1cnc3c(c1)[C@H]1C[C@H]1CN3)C2]

229. (6aR,7aS)-N-[(3R)-8-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide

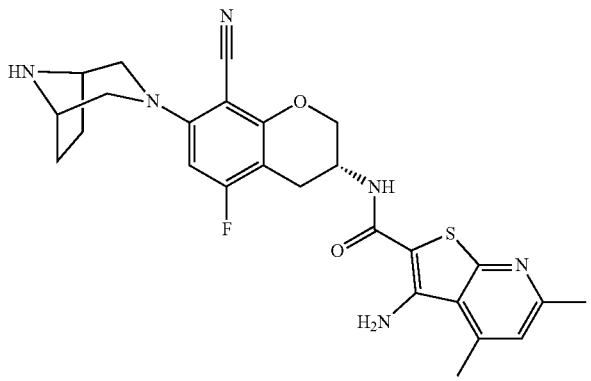 [SMILES: Cc1cc(C)c2c(N)c(C(=O)N[C@H]3COc4c(C#N)c(N5CC6CCC(C5)N6)cc(F)c4C3)sc2n1]

230. 3-amino-N-[(3R)-8-cyano-7-{3,8-diazabicyclo[3.2.1]octan-3-yl}-5-fluoro-3,4-dihydro-2H-1-benzopyran-3-yl]-4,6-dimethylthieno[2,3-b]pyridine-2-carboxamide TABLE 25-continued
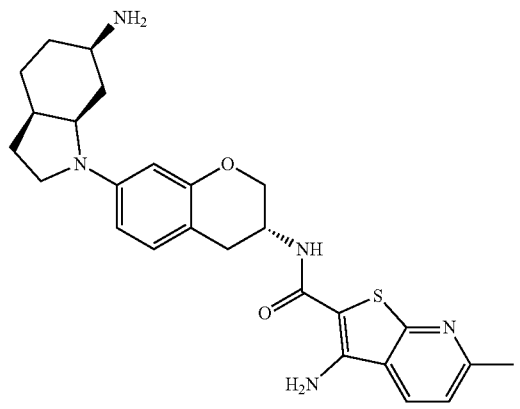 [SMILES: Cc1ccc2c(N)c(C(=O)N[C@H]3COc4cc(N5CC[C@H]6CC[C@@H](N)C[C@H]65)ccc4C3)sc2n1]
231. N-[(3R)-7-[(3aR,6R,7aR)-6-amino-octahydro-1H-indol-1-yl]-3,4-dihydro-2H-1-benzopyran-3-yl]-3-amino-6-methylthieno[2,3-b]pyridine-2-carboxamide
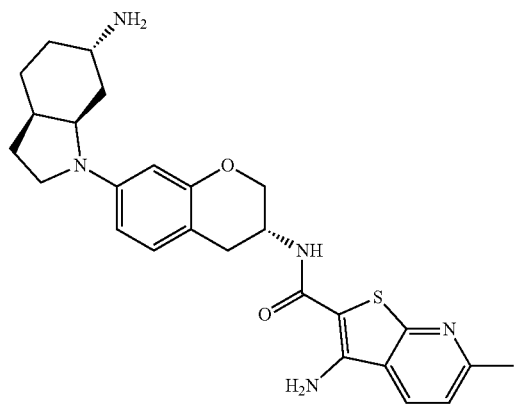 [SMILES: Cc1ccc2c(N)c(C(=O)N[C@H]3COc4cc(N5CC[C@H]6CC[C@H](N)C[C@H]65)ccc4C3)sc2n1]
232. N-[(3R)-7-[(3aR,6S,7aR)-6-amino-octahydro-1H-indol-1-yl]-3,4-dihydro-2H-1-benzopyran-3-yl]-3-amino-6-methylthieno[2,3-b]pyridine-2-carboxamide
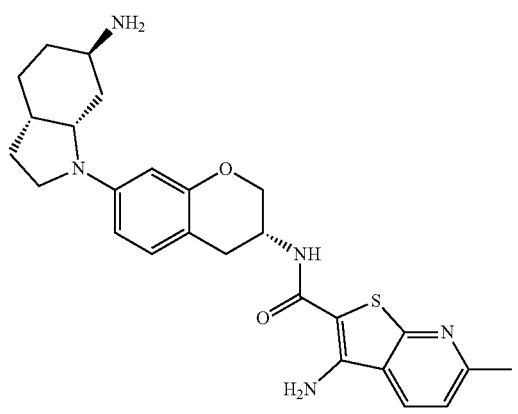 [SMILES: Cc1ccc2c(N)c(C(=O)N[C@H]3COc4cc(N5CC[C@@H]6CC[C@@H](N)C[C@@H]65)ccc4C3)sc2n1]
233. N-[(3R)-7-[(3aS,6R,7aS)-6-amino-octahydro-1H-indol-1-yl]-3,4-dihydro-2H-1-benzopyran-3-yl]-3-amino-6-methylthieno[2,3-b]pyridine-2-carboxamide TABLE 25-continued
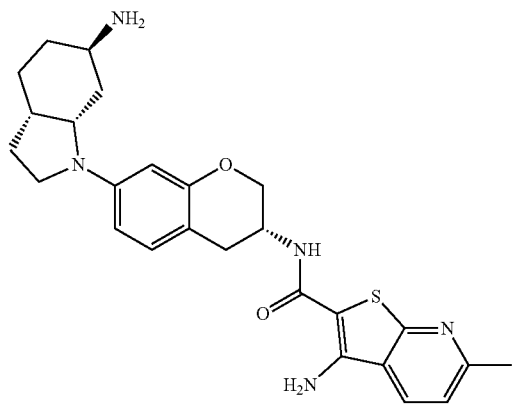 [SMILES: Cc1ccc2c(N)c(C(=O)N[C@H]3COc4cc(N5CC[C@@H]6CC[C@@H](N)C[C@@H]65)ccc4C3)sc2n1]
234. N-[(3R)-7-[(3aS,6S,7aS)-6-amino-
octahydro-1H-indol-1-yl]-3,4-dihydro-2H-1-
benzopyran-3-yl]-3-amino-6-
methylthieno[2,3-b]pyridine-2-carboxamide
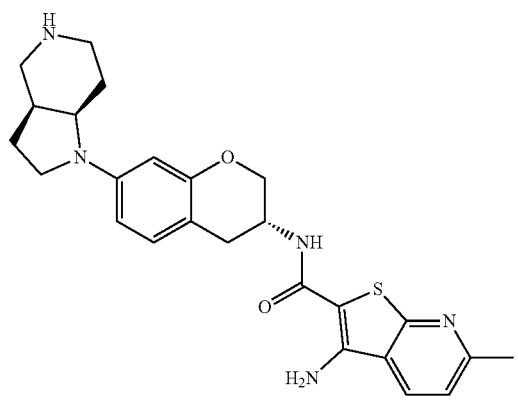 [SMILES: Cc1ccc2c(N)c(C(=O)N[C@H]3COc4cc(N5CC[C@H]6CNCC[C@H]65)ccc4C3)sc2n1]
235. N-[(3R)-7-[(3aS,7aR)-octahydro-1H-
pyrrolo[3,2-c]pyridin-1-yl]-3,4-dihydro-2H-1-
benzopyran-3-yl]-3-amino-6-
methylthieno[2,3-b]pyridine-2-carboxamide
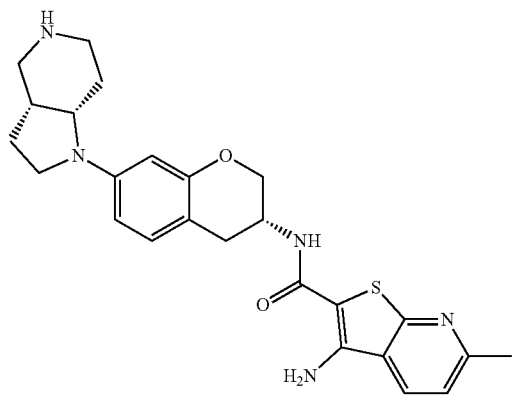 [SMILES: Cc1ccc2c(N)c(C(=O)N[C@H]3COc4cc(N5CC[C@@H]6CNCC[C@@H]65)ccc4C3)sc2n1]
236. N-[(3R)-7-[(3aR,7aS)-octahydro-1H-
pyrrolo[3,2-c]pyridin-1-yl]-3,4-dihydro-2H-
1-benzopyran-3-yl]-3-amino-6-
methylthieno[2,3-b]pyridine-2-carboxamide TABLE 25-continued

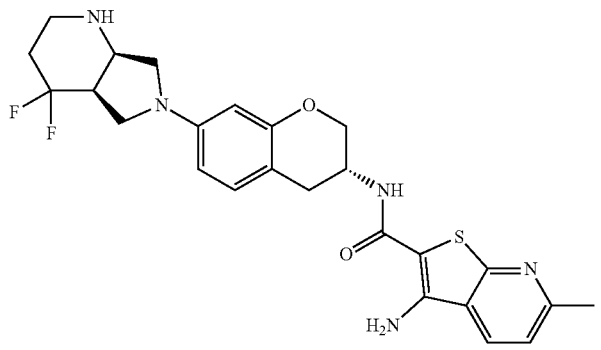 [SMILES: Cc1ccc2c(N)c(C(=O)N[C@H]3COc4cc(N5C[C@@H]6NCCC(F)(F)[C@@H]6C5)ccc4C3)sc2n1]

237. N-[(3R)-7-[(4aR,7aR)-4,4-difluoro-
octahydro-1H-pyrrolo[3,4-b]pyridin-6-yl]-3,4-
dihydro-2H-1-benzopyran-3-yl]-3-amino-6-
methylthieno[2,3-b]pyridine-2-carboxamide

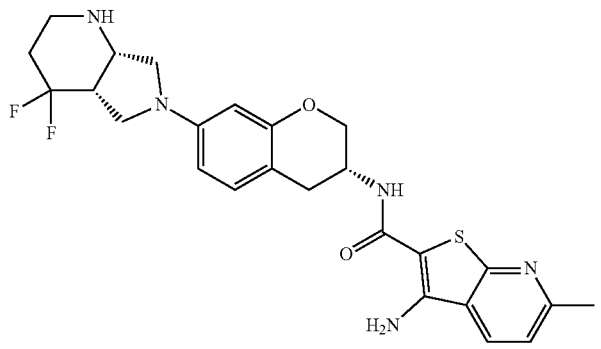 [SMILES: Cc1ccc2c(N)c(C(=O)N[C@H]3COc4cc(N5C[C@H]6NCCC(F)(F)[C@H]6C5)ccc4C3)sc2n1]

238. N-[(3R)-7-[(4aS,7aS)-4,4-difluoro-
octahydro-1H-pyrrolo[3,4-b]pyridin-6-yl]-
3,4-dihydro-2H-1-benzopyran-3-yl]-3-
amino-6-methylthieno[2,3-b]pyridine-2-
carboxamide

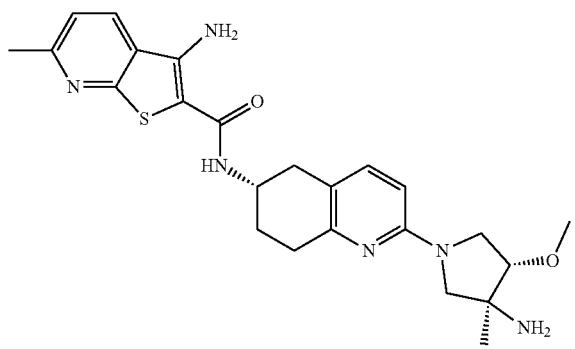

239. 3-amino-N-[(6S)-2-[(3S,4S)-3-amino-4-
methoxy-3-methylpyrrolidin-1-yl]-5,6,7,8-
tetrahydroquinolin-6-yl]-6-methylthieno[2,3-
b]pyridine-2-carboxamide TABLE 25-continued
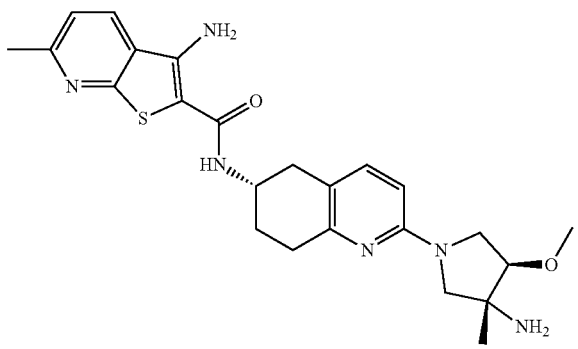
240. 3-amino-N-[(6S)-2-[(3R,4R)-3-amino-
4-methoxy-3-methylpyrrolidin-1-yl]-5,6,7,8-
tetrahydroquinolin-6-yl]-6-methylthieno[2,3-
b]pyridine-2-carboxamide
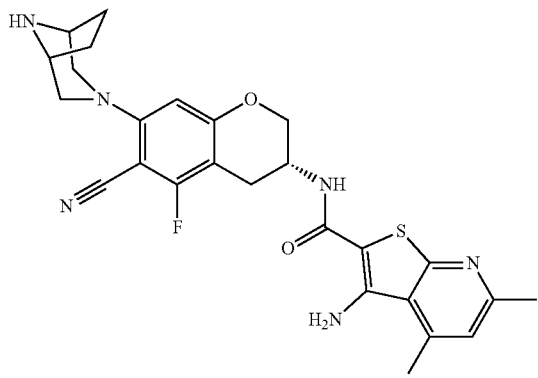 [SMILES: Cc1cc(C)c2c(N)c(C(=O)N[C@H]3COc4cc(N5CC6CCC(C5)N6)c(C#N)c(F)c4C3)sc2n1]
241. 3-amino-N-[(3R)-6-cyano-7-{3,8-
diazabicyclo[3.2.1]octan-3-yl}-5-fluoro-3,4-
dihydro-2H-1-benzopyran-3-yl]-4,6-
dimethylthieno[2,3-b]pyridine-2-carboxamide
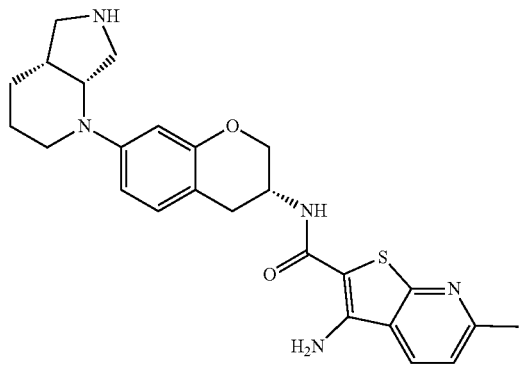 [SMILES: Cc1ccc2c(N)c(C(=O)N[C@H]3COc4cc(N5CCC[C@@H]6CNC[C@@H]65)ccc4C3)sc2n1]
242. N-[(3R)-7-[(4aR,7aR)-octahydro-1H-
pyrrolo[3,4-b]pyridin-1-yl]-3,4-dihydro-2H-
1-benzopyran-3-yl]-3-amino-6-
methylthieno[2,3-b]pyridine-2-carboxamide TABLE 25-continued
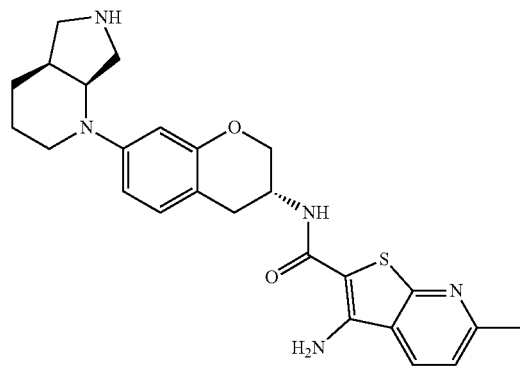 [SMILES: Cc1ccc2c(N)c(C(=O)N[C@H]3COc4cc(N5CCC[C@H]6CNC[C@H]65)ccc4C3)sc2n1]
243. N-[(3R)-7-[(4aS, 7aS)-octahydro-1H-pyrrolo[3,4-b]pyridin-1-yl]-3,4-dihydro-2H-1-benzopyran-3-yl]-3-amino-6-methylthieno[2,3-b]pyridine-2-carboxamide
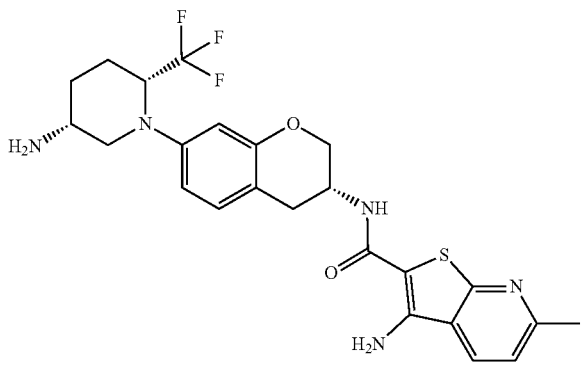 [SMILES: Cc1ccc2c(N)c(C(=O)N[C@H]3COc4cc(N5C[C@H](N)CC[C@@H]5C(F)(F)F)ccc4C3)sc2n1]
244. 3-amino-N-[(3R)-7-[(2R,5R)-5-amino-2-(trifluoromethyl)piperidin-1-yl]-3,4-dihydro-2H-1-benzopyran-3-yl]-6-methylthieno[2,3-b]pyridine-2-carboxamide
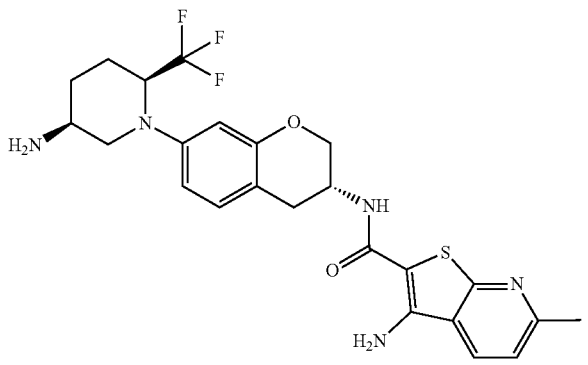 [SMILES: Cc1ccc2c(N)c(C(=O)N[C@H]3COc4cc(N5C[C@@H](N)CC[C@H]5C(F)(F)F)ccc4C3)sc2n1]
245. 3-amino-N-[(3R)-7-[(2S,5S)-5-amino-2-(trifluoromethyl)piperidin-1-yl]-3,4-dihydro-2H-1-benzopyran-3-yl]-6-methylthieno[2,3-b]pyridine-2-carboxamide TABLE 25-continued
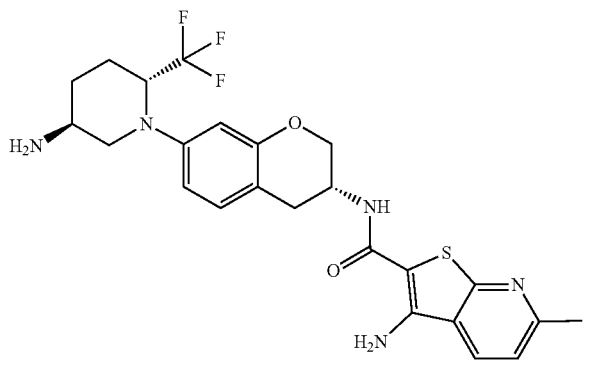 [SMILES: Cc1ccc2c(N)c(C(=O)N[C@H]3COc4cc(N5C[C@@H](N)CC[C@@H]5C(F)(F)F)ccc4C3)sc2n1]
246. 3-amino-N-[(3R)-7-[(2R,5S)-5-amino-
2-(trifluoromethyl)piperidin-1-yl]-3,4-
dihydro-2H-1-benzopyran-3-yl]-6-
methylthieno[2,3-b]pyridine-2-carboxamide
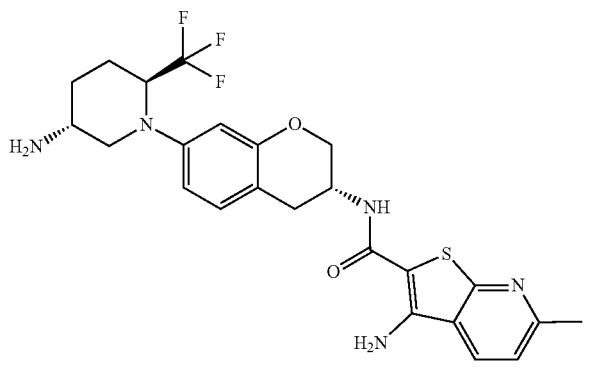 [SMILES: Cc1ccc2c(N)c(C(=O)N[C@H]3COc4cc(N5C[C@H](N)CC[C@H]5C(F)(F)F)ccc4C3)sc2n1]
247. 3-amino-N-[(3R)-7-[(2S,5R)-5-amino-2-
(trifluoromethyl)piperidin-1-yl]-3,4-dihydro-
2H-1-benzopyran-3-yl]-6-methylthieno[2,3-
b]pyridine-2-carboxamide
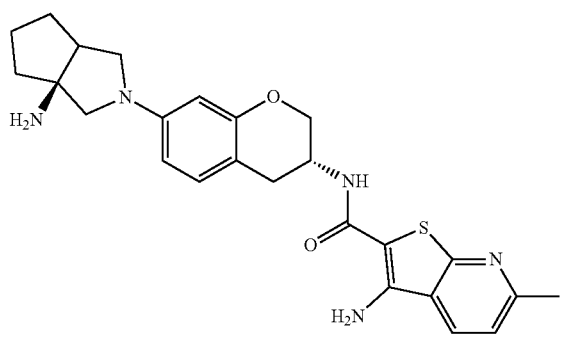 [SMILES: Cc1ccc2c(N)c(C(=O)N[C@H]3COc4cc(N5CC6CCC[C@@]6(N)C5)ccc4C3)sc2n1]
248. N-[(3R)-7-[(3aS)-3a-amino-
octahydrocyclopenta[c]pyrrol-2-yl]-3,4-
dihydro-2H-1-benzopyran-3-yl]-3-amino-6-
methylthieno[2,3-b]pyridine-2-carboxamide

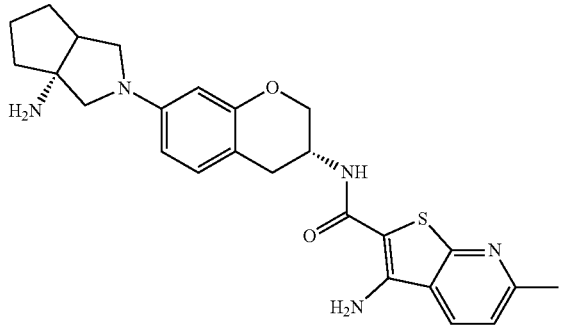 [SMILES: Cc1ccc2c(N)c(C(=O)N[C@H]3COc4cc(N5CC6CCC[C@]6(N)C5)ccc4C3)sc2n1]
249. N-[(3R)-7-[(3aR)-3a-amino-octahydrocyclopenta[c]pyrrol-2-yl]-3,4-dihydro-2H-1-benzopyran-3-yl]-3-amino-6-methylthieno[2,3-b]pyridine-2-carboxamide
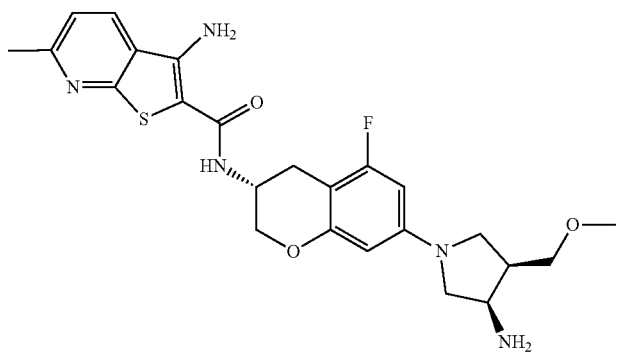
250. 3-amino-N-[(3R)-7-[(3R,4R)-3-amino-4-(methoxymethyl)pyrrolidin-1-yl]-5-fluoro-3,4-dihydro-2H-1-benzopyran-3-yl]-6-methylthieno[2,3-b]pyridine-2-carboxamide
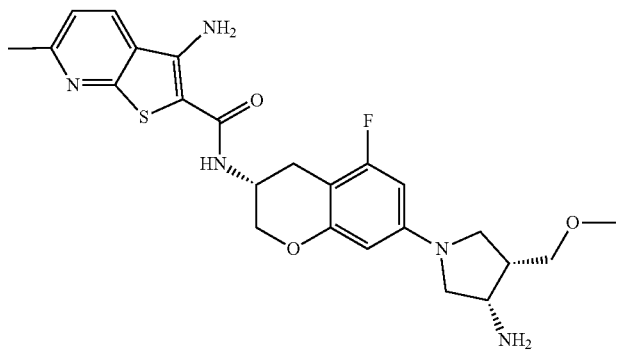
251. 3-amino-N-[(3R)-7-[(3S,4S)-3-amino-4-(methoxymethyl)pyrrolidin-1-yl]-5-fluoro-3,4-dihydro-2H-1-benzopyran-3-yl]-6-methylthieno[2,3-b]pyridine-2-carboxamide

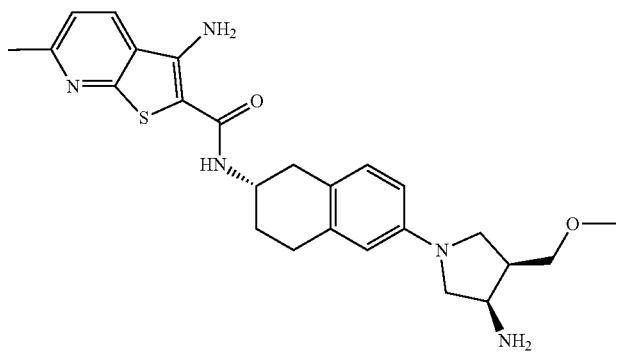
252. 3-amino-N-[(2S)-6-[(3R,4R)-3-amino-
4-(methoxymethyl)pyrrolidin-1-yl]-1,2,3,4-
tetrahydronaphthalen-2-yl]-6-
methylthieno[2,3-b]pyridine-2-carboxamide
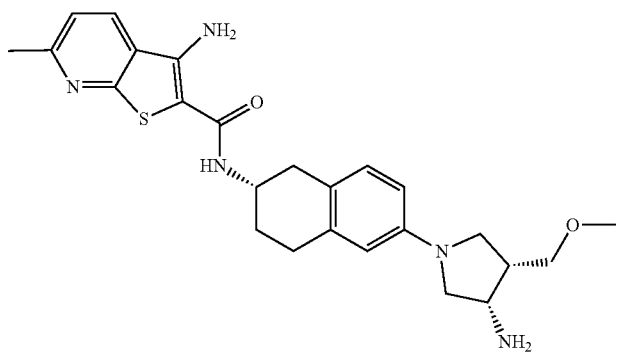
253. 3-amino-N-[(2S)-6-[(3S,4S)-3-amino-4-
(methoxymethyl)pyrrolidin-1-yl]-1,2,3,4-
tetrahydronaphthalen-2-yl]-6-
methylthieno[2,3-b]pyridine-2-carboxamide
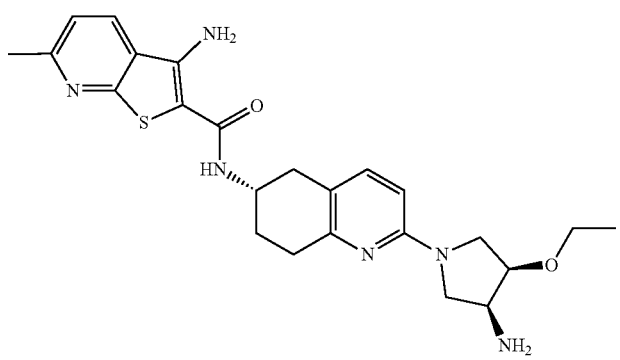 [SMILES: CCO[C@@H]1CN(c2ccc3c(n2)CC[C@H](NC(=O)c2sc4nc(C)ccc4c2N)C3)C[C@@H]1N]
254. 3-amino-N-[(6S)-2-[(3S,4R)-3-amino-
4-ethoxypyrrolidin-1-yl]-5,6,7,8-
tetrahydroquinolin-6-yl]-6-methylthieno[2,3-
b]pyridine-2-carboxamide

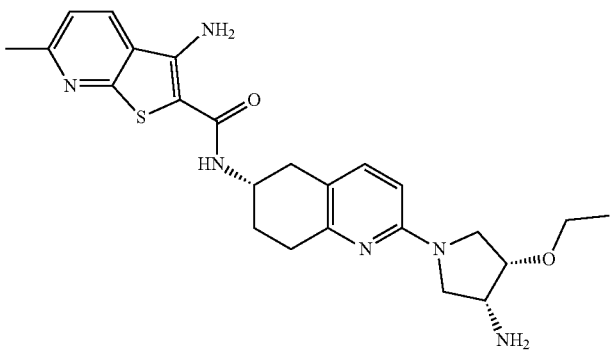 [SMILES: CCO[C@H]1CN(c2ccc3c(n2)CC[C@H](NC(=O)c2sc4nc(C)ccc4c2N)C3)C[C@H]1N]
255. 3-amino-N-[(6S)-2-[(3R,4S)-3-amino-4-
ethoxypyrrolidin-1-yl]-5,6,7,8-
tetrahydroquinolin-6-yl]-6-methylthieno[2,3-
b]pyridine-2-carboxamide
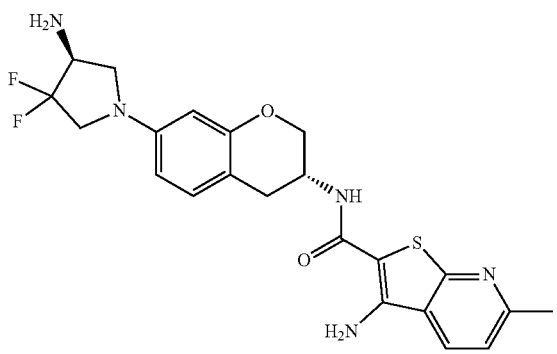 [SMILES: Cc1ccc2c(N)c(C(=O)N[C@H]3COc4cc(N5C[C@H](N)C(F)(F)C5)ccc4C3)sc2n1]
256. 3-amino-N-[(3R)-7-[(4S)-4-amino-3,3-
difluoropyrrolidin-1-yl]-3,4-dihydro-2H-1-
benzopyran-3-yl]-6-methylthieno[2,3-
b]pyridine-2-carboxamide
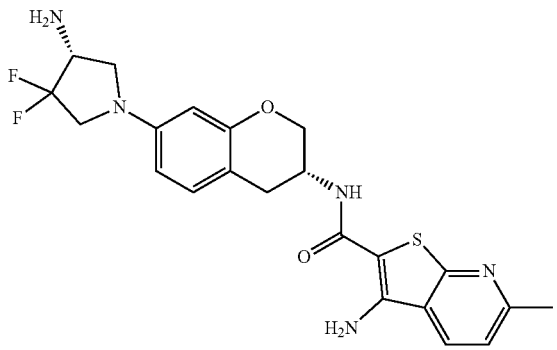 [SMILES: Cc1ccc2c(N)c(C(=O)N[C@H]3COc4cc(N5C[C@@H](N)C(F)(F)C5)ccc4C3)sc2n1]
257. 3-amino-N-[(3R)-7-[(4R)-4-amino-3,3-
difluoropyrrolidin-1-yl]-3,4-dihydro-2H-1-
benzopyran-3-yl]-6-methylthieno[2,3-
b]pyridine-2-carboxamide

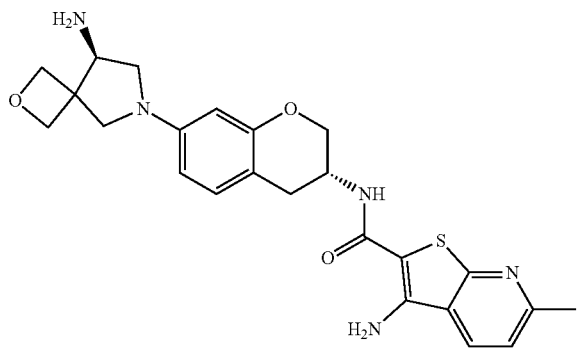 [SMILES: Cc1ccc2c(N)c(C(=O)N[C@H]3COc4cc(N5C[C@H](N)C6(COC6)C5)ccc4C3)sc2n1]
258. 3-amino-N-[(3R)-7-[(8R)-8-amino-2-oxa-6-azaspiro[3.4]octan-6-yl]-3,4-dihydro-2H-1-benzopyran-3-yl]-6-methylthieno[2,3-b]pyridine-2-carboxamide
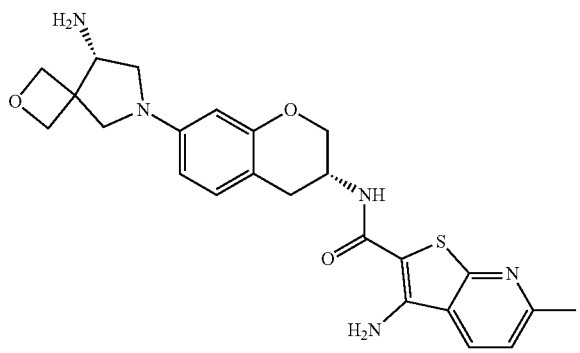 [SMILES: Cc1ccc2c(N)c(C(=O)N[C@H]3COc4cc(N5C[C@@H](N)C6(COC6)C5)ccc4C3)sc2n1]
259. 3-amino-N-[(3R)-7-[(8S)-8-amino-2-oxa-6-azaspiro[3.4]octan-6-yl]-3,4-dihydro-2H-1-benzopyran-3-yl]-6-methylthieno[2,3-b]pyridine-2-carboxamide
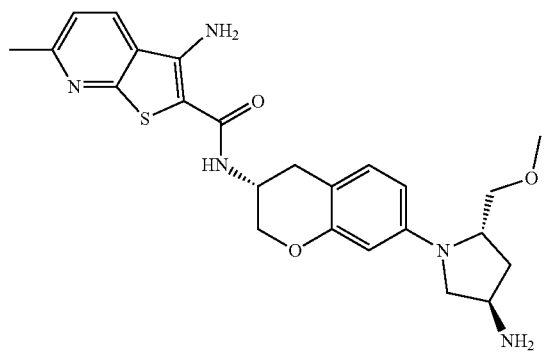
260. 3-amino-N-[(3R)-7-[(2S,4R)-4-amino-2-(methoxymethyl)pyrrolidin-1-yl]-3,4-dihydro-2H-1-benzopyran-3-yl]-6-methylthieno[2,3-b]pyridine-2-carboxamide TABLE 25-continued
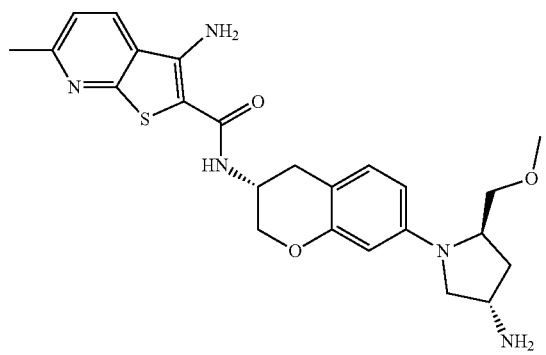
261. 3-amino-N-[(3R)-7-[(2R,4S)-4-amino-2-
(methoxymethyl)pyrrolidin-1-yl]-3,4-dihydro-
2H-1-benzopyran-3-yl]-6-methylthieno[2,3-
b]pyridine-2-carboxamide
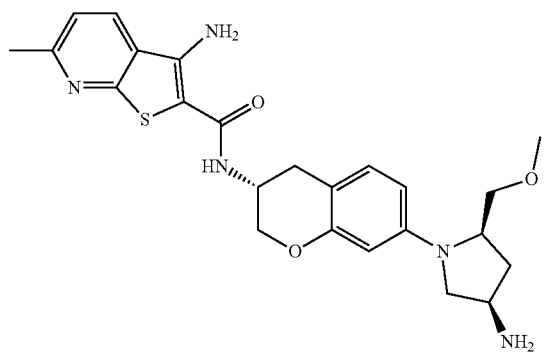
262. 3-amino-N-[(3R)-7-[(2R,4R)-4-amino-
2-(methoxymethyl)pyrrolidin-1-yl]-3,4-
dihydro-2H-1-benzopyran-3-yl]-6-
methylthieno[2,3-b]pyridine-2-carboxamide
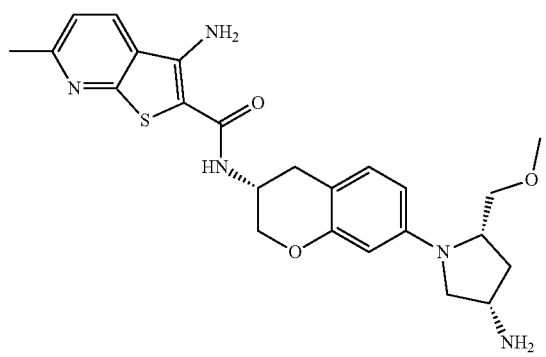
263. 3-amino-N-[(3R)-7-[(2S,4S)-4-amino-2-
(methoxymethyl)pyrrolidin-1-yl]-3,4-dihydro-
2H-1-benzopyran-3-yl]-6-methylthieno[2,3-
b]pyridine-2-carboxamide

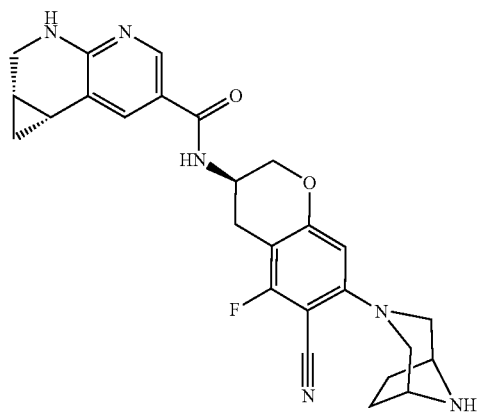 [SMILES: N#Cc1c(N2CC3CCC(C2)N3)cc2c(c1F)C[C@@H](NC(=O)c1cnc3c(c1)[C@@H]1C[C@@H]1CN3)CO2]
264. (6aS,7aR)-N-[(3R)-6-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide
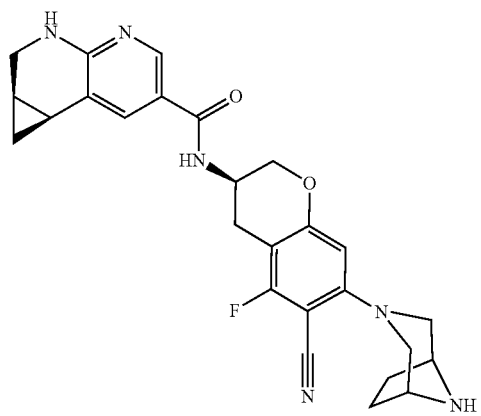 [SMILES: N#Cc1c(N2CC3CCC(C2)N3)cc2c(c1F)C[C@@H](NC(=O)c1cnc3c(c1)[C@H]1C[C@H]1CN3)CO2]
265. (6aR,7aS)-N-[(3R)-6-cyano-7-{3,8-diazabicyclo[3.2.1]octan-3-yl}-5-fluoro-3,4-dihydro-2H-1-benzopyran-3-yl]-5H,6H,6aH,7H,7aH-cyclopropa[c]1,8-naphthyridine-2-carboxamide
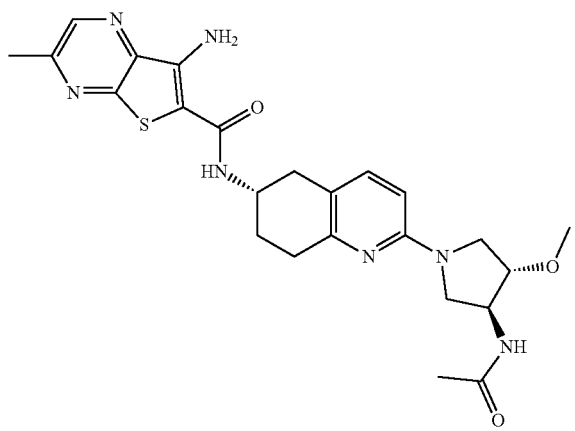
266. 7-amino-N-[(6S)-2-[(3S,4S)-3-acetamido-4-methoxypyrrolidin-1-yl]-5,6,7,8-tetrahydroquinolin-6-yl]-3-methylthieno[2,3-b]pyrazine-6-carboxamide TABLE 25-continued
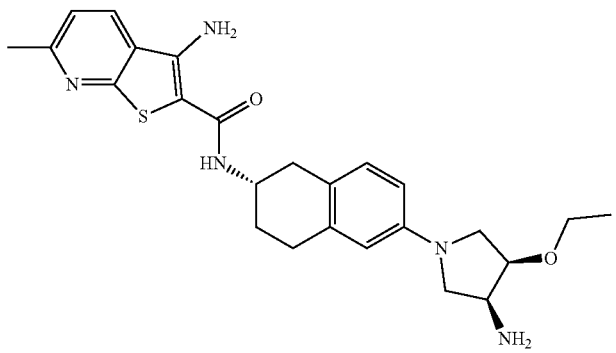 [SMILES: CCO[C@@H]1CN(c2ccc3c(c2)CC[C@H](NC(=O)c2sc4nc(C)ccc4c2N)C3)C[C@@H]1N]
267. 3-amino-N-[(2S)-6-[(3S,4R)-3-amino-4-
ethoxypyrrolidin-1-yl]-1,2,3,4-
tetrahydronaphthalen-2-yl]-6-
methylthieno[2,3-b]pyridine-2-carboxamide
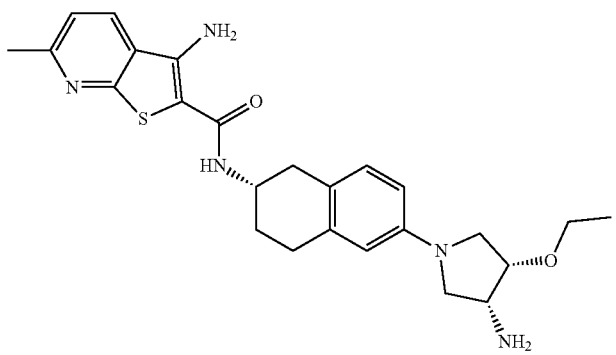 [SMILES: CCO[C@H]1CN(c2ccc3c(c2)CC[C@H](NC(=O)c2sc4nc(C)ccc4c2N)C3)C[C@H]1N]
268. 3-amino-N-[(2S)-6-[(3R,4S)-3-amino-
4-ethoxypyrrolidin-1-yl]-1,2,3,4-
tetrahydronaphthalen-2-yl]-6-
methylthieno[2,3-b]pyridine-2-carboxamide
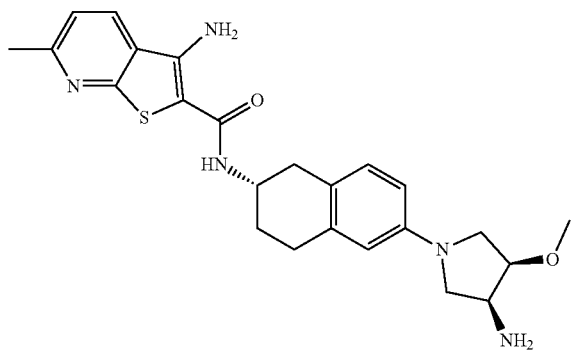
269. 3-amino-N-[(6S)-2-[(3S,4R)-3-amino-4-
methoxypyrrolidin-1-yl]-5,6,7,8-
tetrahydroquinolin-6-yl]-6-methylthieno[2,3-
b]pyridine-2-carboxamide TABLE 25-continued
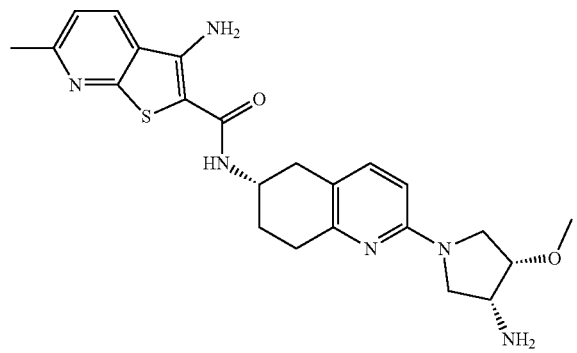
270. 3-amino-N-[(6S)-2-[(3R,4S)-3-amino-
4-methoxypyrrolidin-1-yl]-5,6,7,8-
tetrahydroquinolin-6-yl]-6-methylthieno[2,3-
b]pyridine-2-carboxamide
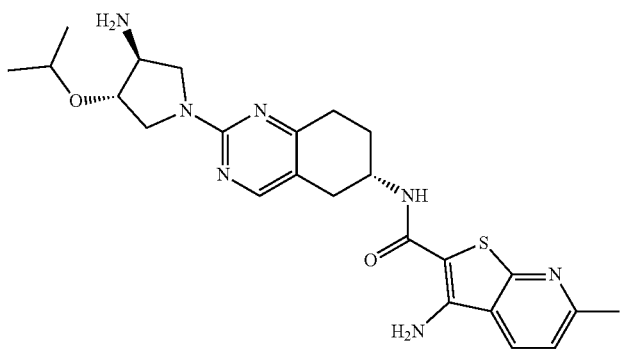 [SMILES: Cc1ccc2c(N)c(C(=O)N[C@H]3CCc4nc(N5C[C@H](OC(C)C)[C@@H](N)C5)ncc4C3)sc2n1]
271. 3-amino-N-[(6S)-2-[(3S,4S)-3-amino-4-
(propan-2-yloxy)pyrrolidin-1-yl]-5,6,7,8-
tetrahydroquinazolin-6-yl]-6-
methylthieno[2,3-b]pyridine-2-carboxamide
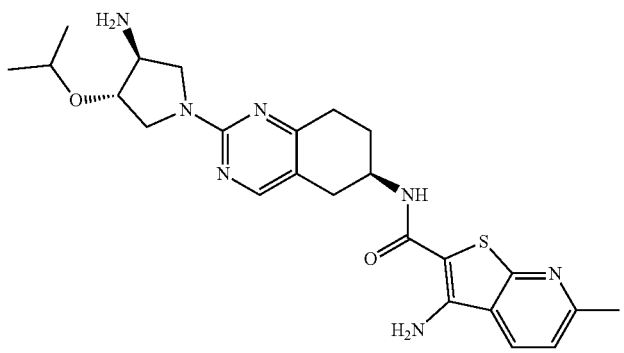 [SMILES: Cc1ccc2c(N)c(C(=O)N[C@@H]3CCc4nc(N5C[C@H](OC(C)C)[C@@H](N)C5)ncc4C3)sc2n1]
272. 3-amino-N-[(6R)-2-[(3S,4S)-3-amino-
4-(propan-2-yloxy)pyrrolidin-1-yl]-5,6,7,8-
tetrahydroquinazolin-6-yl]-6-
methylthieno[2,3-b]pyridine-2-carboxamide TABLE 25-continued
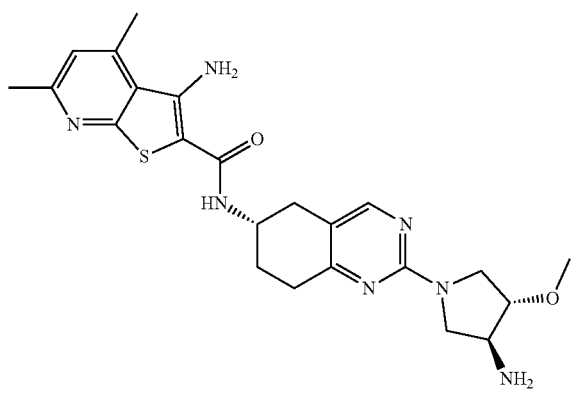
273. 3-amino-N-[(6S)-2-[(3S,4S)-3-amino-4-
methoxypyrrolidin-1-yl]-5,6,7,8-
tetrahydroquinazolin-6-yl]-4,6-
dimethylthieno[2,3-b]pyridine-2-carboxamide
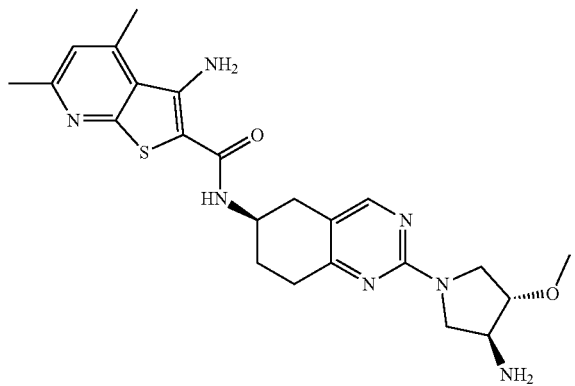
274. 3-amino-N-[(6R)-2-[(3S,4S)-3-amino-
4-methoxypyrrolidin-1-yl]-5,6,7,8-
tetrahydroquinazolin-6-yl]-4,6-
dimethylthieno[2,3-b]pyridine-2-
carboxamide
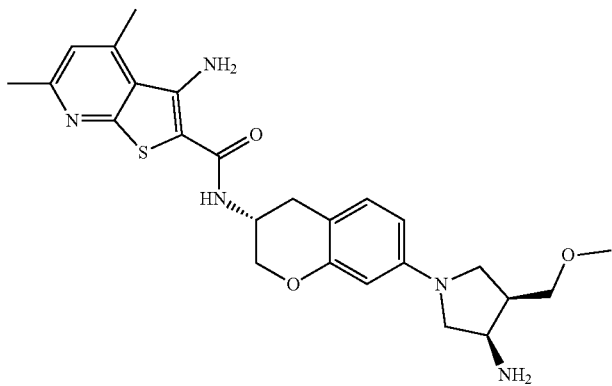
275. 3-amino-N-[(3R)-7-[(3R,4R)-3-amino-4-
(methoxymethyl)pyrrolidin-1-yl]-3,4-dihydro-
2H-1-benzopyran-3-yl]-4,6-
dimethylthieno[2,3-b]pyridine-2-carboxamide TABLE 25-continued

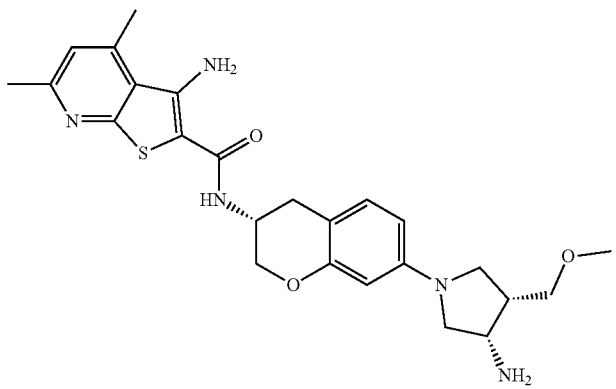

276. 3-amino-N-[(3R)-7-[(3S,4S)-3-amino-
4-(methoxymethyl)pyrrolidin-1-yl]-3,4-
dihydro-2H-1-benzopyran-3-yl]-4,6-
dimethylthieno[2,3-b]pyridine-2-
carboxamide

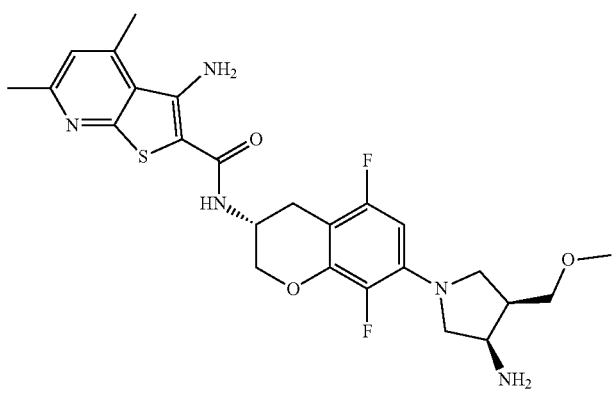

277. 3-amino-N-[(3R)-7-[(3R,4R)-3-amino-4-
(methoxymethyl)pyrrolidin-1-yl]-5,8-difluoro-
3,4-dihydro-2H-1-benzopyran-3-yl]-4,6-
dimethylthieno[2,3-b]pyridine-2-carboxamide

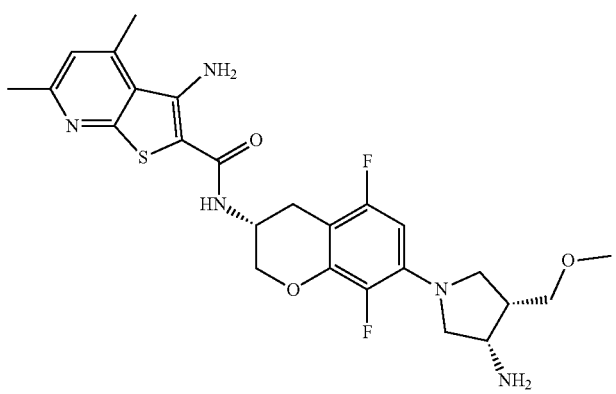

278. 3-amino-N-[(3R)-7-[(3S,4S)-3-amino-
4-(methoxymethyl)pyrrolidin-1-yl]-5,8-
difluoro-3,4-dihydro-2H-1-benzopyran-3-
yl]-4,6-dimethylthieno[2,3-b]pyridine-2-
carboxamide TABLE 25-continued
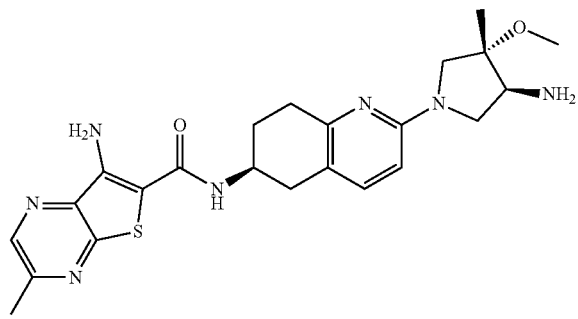 [SMILES: CO[C@@]1(C)CN(c2ccc3c(n2)CC[C@H](NC(=O)c2sc4nc(C)cnc4c2N)C3)C[C@@H]1N]
279. 7-amino-N-[(6S)-2-[(3S,4S)-4-amino-3-
methoxy-3-methylpyrrolidin-1-yl]-5,6,7,8-
tetrahydroquinolin-6-yl]-3-methylthieno[2,3-
b]pyrazine-6-carboxamide
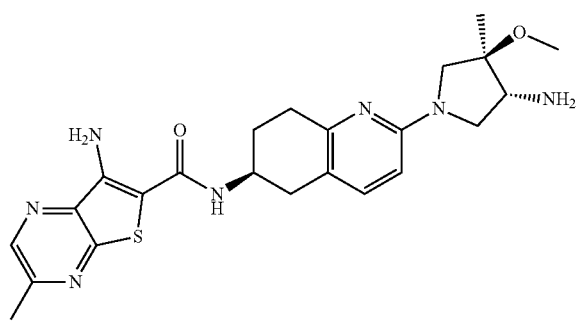 [SMILES: CO[C@]1(C)CN(c2ccc3c(n2)CC[C@H](NC(=O)c2sc4nc(C)cnc4c2N)C3)C[C@H]1N]
280. 7-amino-N-[(6S)-2-[(3R,4R)-4-amino-
3-methoxy-3-methylpyrrolidin-1-yl]-5,6,7,8-
tetrahydroquinolin-6-yl]-3-methylthieno[2,3-
b]pyrazine-6-carboxamide
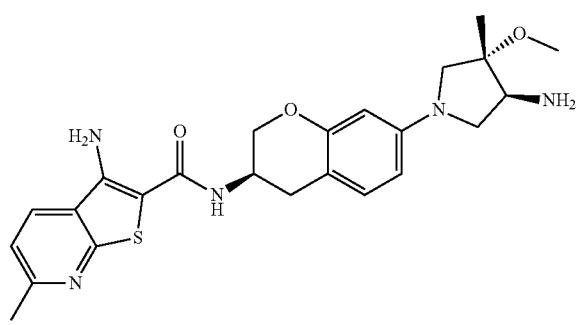 [SMILES: CO[C@@]1(C)CN(c2ccc3c(c2)OC[C@H](NC(=O)c2sc4nc(C)ccc4c2N)C3)C[C@@H]1N]
281. 3-amino-N-[(3R)-7-[(3S,4S)-4-amino-3-
methoxy-3-methylpyrrolidin-1-yl]-3,4-
dihydro-2H-1-benzopyran-3-yl]-6-
methylthieno[2,3-b]pyridine-2-carboxamide

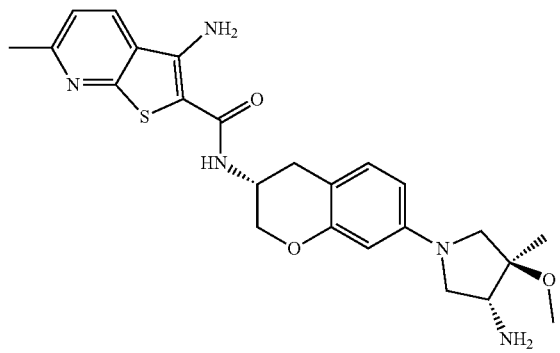
282. 3-amino-N-[(3R)-7-[(3R,4R)-4-amino-3-methoxy-3-methylpyrrolidin-1-yl]-3,4-dihydro-2H-1-benzopyran-3-yl]-6-methylthieno[2,3-b]pyridine-2-carboxamide
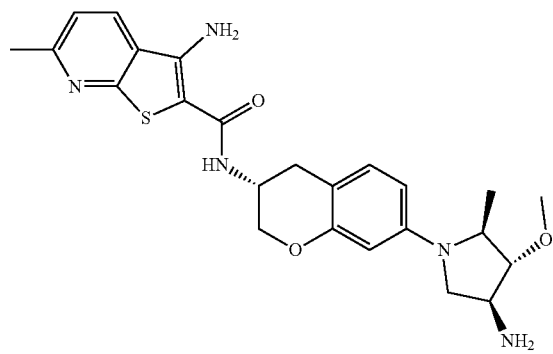 [SMILES: CO[C@@H]1[C@@H](N)CN(c2ccc3c(c2)OC[C@H](NC(=O)c2sc4nc(C)ccc4c2N)C3)[C@H]1C]
283. 3-amino-N-[(3R)-7-[(2S,3R,4S)-4-amino-3-methoxy-2-methylpyrrolidin-1-yl]-3,4-dihydro-2H-1-benzopyran-3-yl]-6-methylthieno[2,3-b]pyridine-2-carboxamide
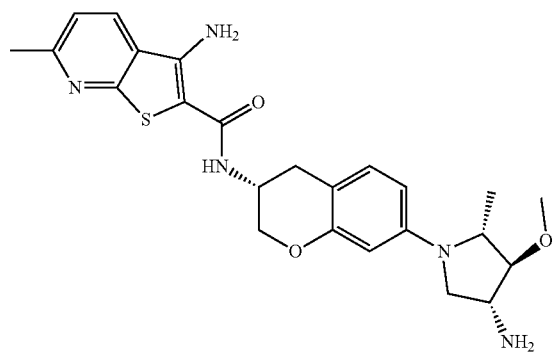 [SMILES: CO[C@H]1[C@H](N)CN(c2ccc3c(c2)OC[C@H](NC(=O)c2sc4nc(C)ccc4c2N)C3)[C@@H]1C]
284. 3-amino-N-[(3R)-7-[(2R,3S,4R)-4-amino-3-methoxy-2-methylpyrrolidin-1-yl]-3,4-dihydro-2H-1-benzopyran-3-yl]-6-methylthieno[2,3-b]pyridine-2-carboxamide

TABLE 25-continued
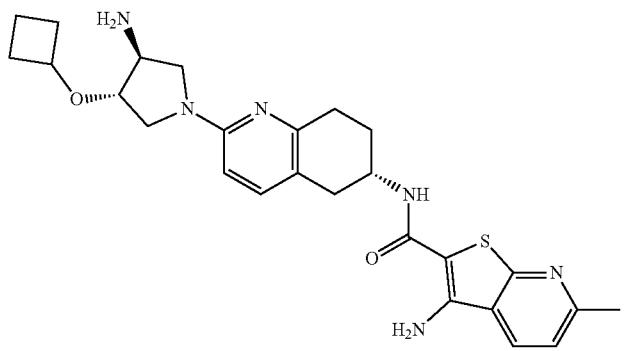 [SMILES: Cc1ccc2c(N)c(C(=O)N[C@H]3CCc4nc(N5C[C@H](OC6CCC6)[C@@H](N)C5)ccc4C3)sc2n1]
285. 3-amino-N-[(6S)-2-[(3S,4S)-3-amino-4-
cyclobutoxypyrrolidin-1-yl]-5,6,7,8-
tetrahydroquinolin-6-yl]-6-methylthieno[2,3-
b]pyridine-2-carboxamide
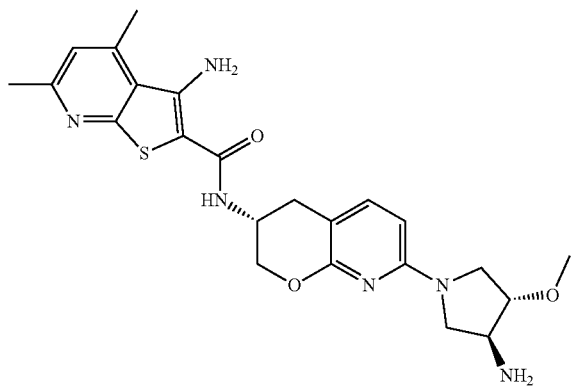
286. 3-amino-N-[(3R)-7-[(3S,4S)-3-amino-
4-methoxypyrrolidin-1-yl]-2H,3H,4H-
pyrano[2,3-b]pyridin-3-yl]-4,6-
dimethylthieno[2,3-b]pyridine-2-
carboxamide
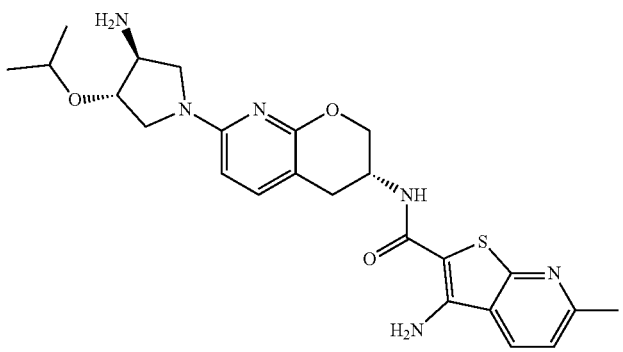
287. 3-amino-N-[(3R)-7-[(3S,4S)-3-amino-4-
(propan-2-yloxy)pyrrolidin-1-yl]-2H,3H,4H-
pyrano[2,3-b]pyridin-3-yl]-6-
methylthieno[2,3-b]pyridine-2-carboxamide

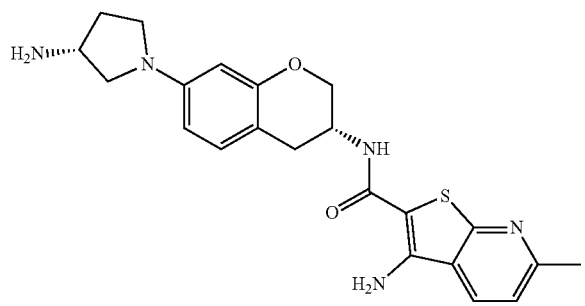 [SMILES: Cc1ccc2c(N)c(C(=O)N[C@H]3COc4cc(N5CC[C@@H](N)C5)ccc4C3)sc2n1]
288. 3-amino-N-[(3R)-7-[(3R)-3-
aminopyrrolidin-1-yl]-3,4-dihydro-2H-1-
benzopyran-3-yl]-6-methylthieno[2,3-
b]pyridine-2-carboxamide
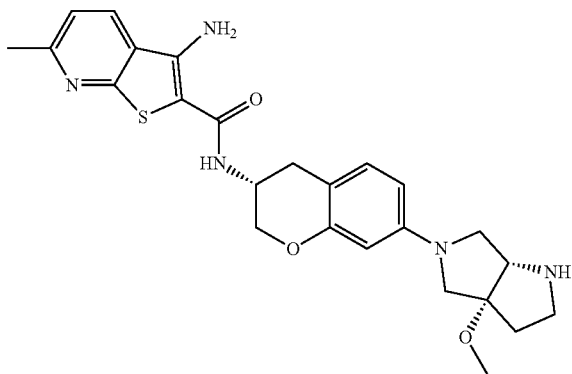 [SMILES: CO[C@@]12CCN[C@H]1CN(c1ccc3c(c1)OC[C@H](NC(=O)c1sc4nc(C)ccc4c1N)C3)C2]
289. N-[(3R)-7-[(3aR,6aS)-3a-methoxy-
octahydropyrrolo[2,3-c]pyrrol-5-yl]-3,4-
dihydro-2H-1-benzopyran-3-yl]-3-amino-6-
methylthieno[2,3-b]pyridine-2-carboxamide
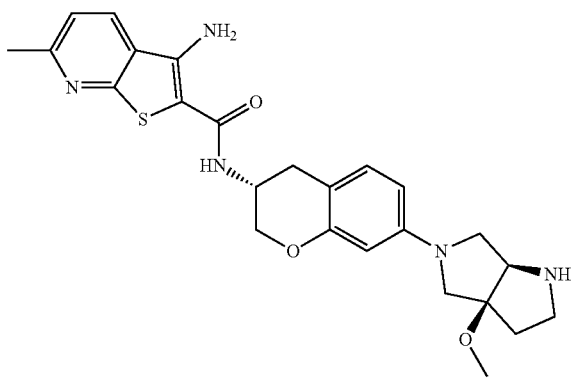 [SMILES: CO[C@]12CCN[C@@H]1CN(c1ccc3c(c1)OC[C@H](NC(=O)c1sc4nc(C)ccc4c1N)C3)C2]
290. N-[(3R)-7-[(3aS,6aR)-3a-methoxy-
octahydropyrrolo[2,3-c]pyrrol-5-yl]-3,4-
dihydro-2H-1-benzopyran-3-yl]-3-amino-6-
methylthieno[2,3-b]pyridine-2-carboxamide TABLE 25-continued
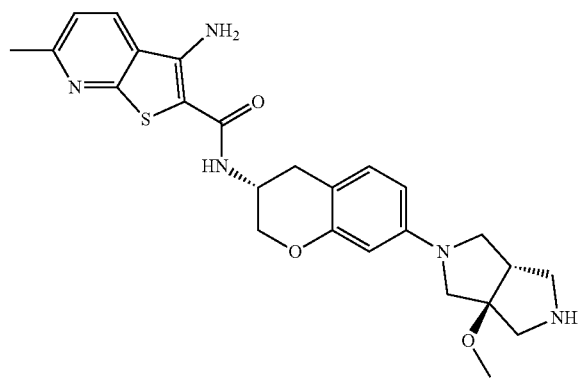 [SMILES: CO[C@]12CNC[C@H]1CN(c1ccc3c(c1)OC[C@H](NC(=O)c1sc4nc(C)ccc4c1N)C3)C2]
291. N-[(3R)-7-[(3aS,6aS)-3a-methoxy-
octahydropyrrolo[3,4-c]pyrrol-2-yl]-3,4-
dihydro-2H-1-benzopyran-3-yl]-3-amino-6-
methylthieno[2,3-b]pyridine-2-carboxamide
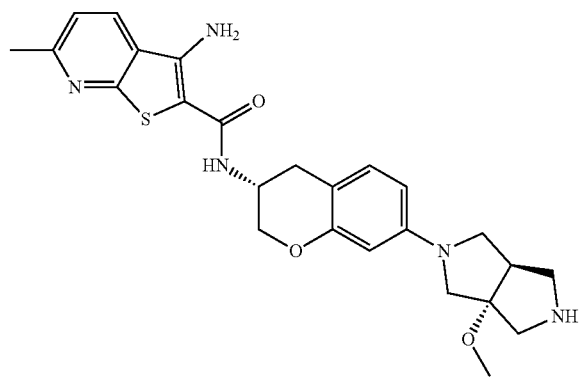 [SMILES: CO[C@@]12CNC[C@@H]1CN(c1ccc3c(c1)OC[C@H](NC(=O)c1sc4nc(C)ccc4c1N)C3)C2]
292. N-[(3R)-7-[(3aR,6aR)-3a-methoxy-
octahydropyrrolo[3,4-c]pyrrol-2-yl]-3,4-
dihydro-2H-1-benzopyran-3-yl]-3-amino-6-
methylthieno[2,3-b]pyridine-2-carboxamide
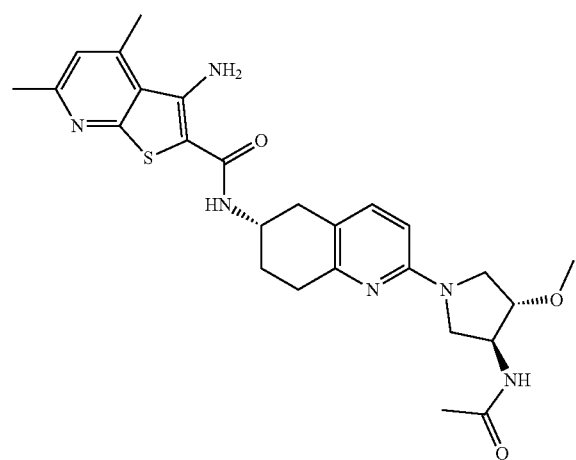
293. 3-amino-N-[(6S)-2-[(3S,4S)-3-acetamido-
4-methoxypyrrolidin-1-yl]-5,6,7,8-
tetrahydroquinolin-6-yl]-4,6-
dimethylthieno[2,3-b]pyridine-2-carboxamide

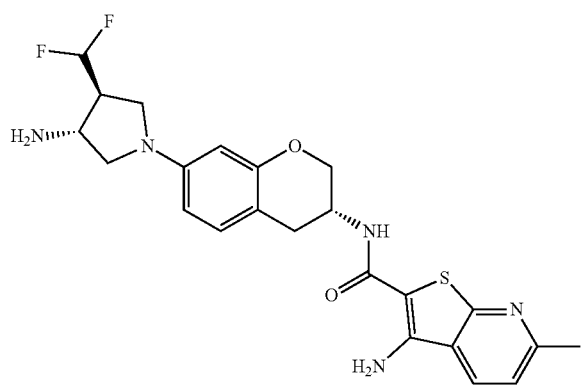 [SMILES: Cc1ccc2c(N)c(C(=O)N[C@H]3COc4cc(N5C[C@H](C(F)F)[C@@H](N)C5)ccc4C3)sc2n1]
294. 3-amino-N-[(3R)-7-[(3R,4S)-3-amino-
4-(difluoromethyl)pyrrolidin-1-yl]-3,4-
dihydro-2H-1-benzopyran-3-yl]-6-
methylthieno[2,3-b]pyridine-2-carboxamide
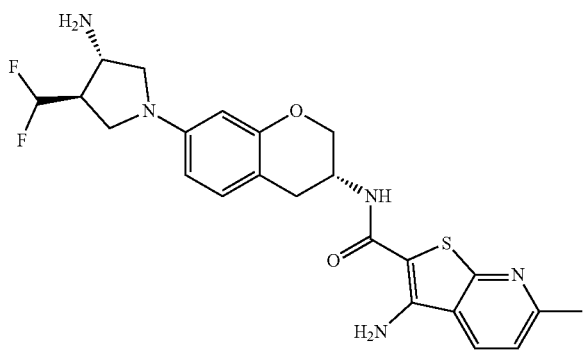
295. 3-amino-N-[(3R)-7-[(3S,4R)-3-amino-4-
(difluoromethyl)pyrrolidin-1-yl]-3,4-dihydro-
2H-1-benzopyran-3-yl]-6-methylthieno[2,3-
b]pyridine-2-carboxamide
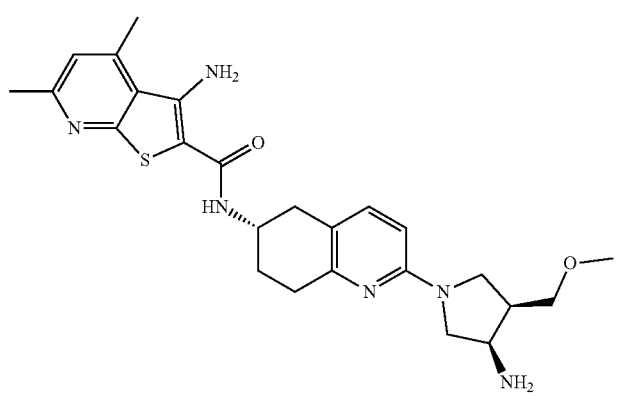
296. 3-amino-N-[(6S)-2-[(3R,4R)-3-amino-
4-(methoxymethyl)pyrrolidin-1-yl]-5,6,7,8-
tetrahydroquinolin-6-yl]-4,6-
dimethylthieno[2,3-b]pyridine-2-
carboxamide TABLE 25-continued
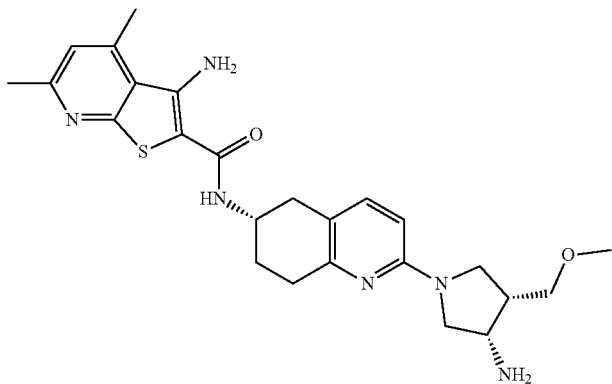
297. 3-amino-N-[(6S)-2-[(3S,4S)-3-amino-4-
(methoxymethyl)pyrrolidin-1-yl]-5,6,7,8-
tetrahydroquinolin-6-yl]-4,6-
dimethylthieno[2,3-b]pyridine-2-carboxamide
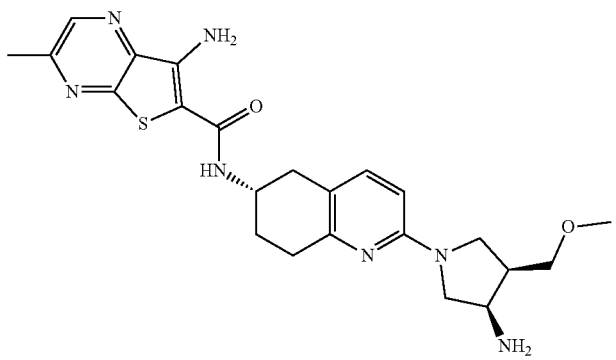
298. 7-amino-N-[(6S)-2-[(3R,4R)-3-amino-
4-(methoxymethyl)pyrrolidin-1-yl]-5,6,7,8-
tetrahydroquinolin-6-yl]-3-methylthieno[2,3-
b]pyrazine-6-carboxamide
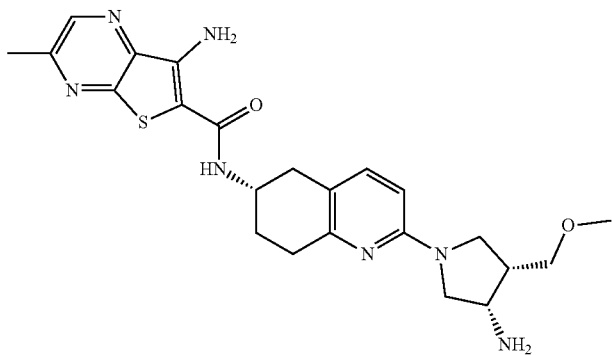
299. 7-amino-N-[(6S)-2-[(3S,4S)-3-amino-4-
(methoxymethyl)pyrrolidin-1-yl]-5,6,7,8-
tetrahydroquinolin-6-yl]-3-methylthieno[2,3-
b]pyrazine-6-carboxamide

TABLE 25-continued

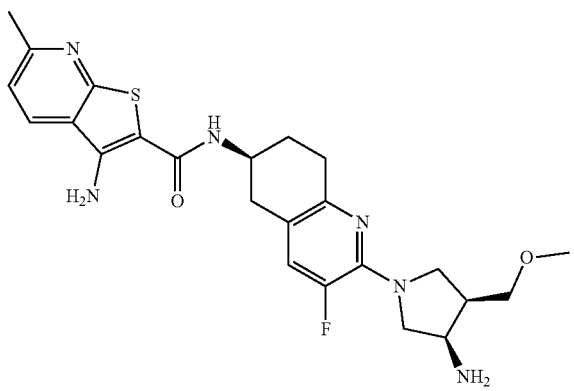 [SMILES: COC[C@@H]1CN(c2nc3c(cc2F)C[C@@H](NC(=O)c2sc4nc(C)ccc4c2N)CC3)C[C@@H]1N]

300. 3-amino-N-[(6S)-2-[(3R,4R)-3-amino-
4-(methoxymethyl)pyrrolidin-1-yl]-3-fluoro-
5,6,7,8-tetrahydroquinolin-6-yl]-6-
methylthieno[2,3-b]pyridine-2-carboxamide

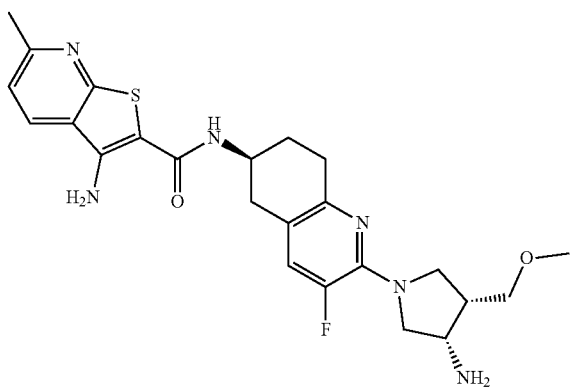 [SMILES: COC[C@H]1CN(c2nc3c(cc2F)C[C@@H](NC(=O)c2sc4nc(C)ccc4c2N)CC3)C[C@H]1N]

301. 3-amino-N-[(6S)-2-[(3S,4S)-3-amino-4-
(methoxymethyl)pyrrolidin-1-yl]-3-fluoro-
5,6,7,8-tetrahydroquinolin-6-yl]-6-
methylthieno[2,3-b]pyridine-2-carboxamide

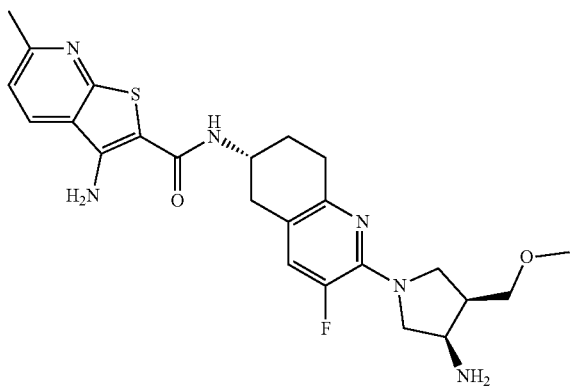 [SMILES: COC[C@@H]1CN(c2nc3c(cc2F)C[C@H](NC(=O)c2sc4nc(C)ccc4c2N)CC3)C[C@@H]1N]

302. 3-amino-N-[(6R)-2-[(3R,4R)-3-amino-
4-(methoxymethyl)pyrrolidin-1-yl]-3-fluoro-
5,6,7,8-tetrahydroquinolin-6-yl]-6-
methylthieno[2,3-b]pyridine-2-carboxamide TABLE 25-continued
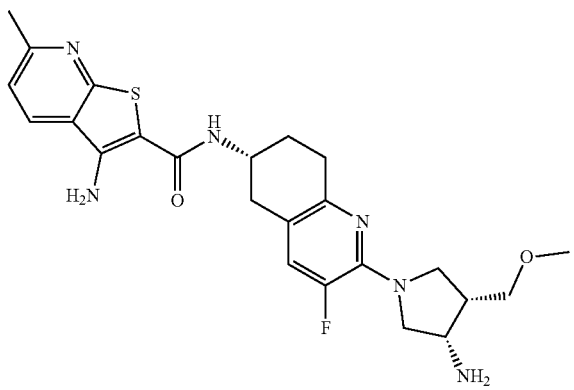 [SMILES: COC[C@H]1CN(c2nc3c(cc2F)C[C@H](NC(=O)c2sc4nc(C)ccc4c2N)CC3)C[C@H]1N]
303. 3-amino-N-[(6R)-2-[(3S,4S)-3-amino-4-
(methoxymethyl)pyrrolidin-1-yl]-3-fluoro-
5,6,7,8-tetrahydroquinolin-6-yl]-6-
methylthieno[2,3-b]pyridine-2-carboxamide
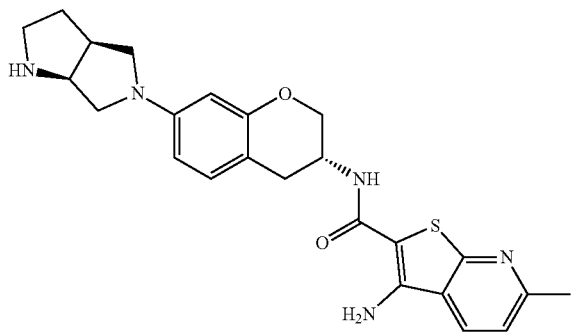 [SMILES: Cc1ccc2c(N)c(C(=O)N[C@H]3COc4cc(N5C[C@@H]6CCN[C@@H]6C5)ccc4C3)sc2n1]
304. N-[(3R)-7-[(3aS,6aS)-
octahydropyrrolo[3,4-b]pyrrol-5-yl]-3,4-
dihydro-2H-1-benzopyran-3-yl]-3-amino-6-
methylthieno[2,3-b]pyridine-2-carboxamide
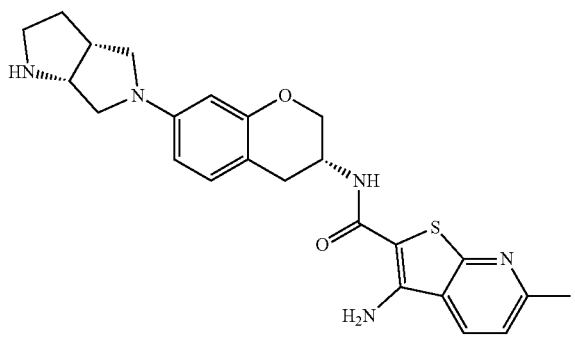 [SMILES: Cc1ccc2c(N)c(C(=O)N[C@H]3COc4cc(N5C[C@H]6CCN[C@H]6C5)ccc4C3)sc2n1]
305. N-[(3R)-7-[(3aR,6aR)-
octahydropyrrolo[3,4-b]pyrrol-5-yl]-3,4-
dihydro-2H-1-benzopyran-3-yl]-3-amino-6-
methylthieno[2,3-b]pyridine-2-carboxamide TABLE 25-continued
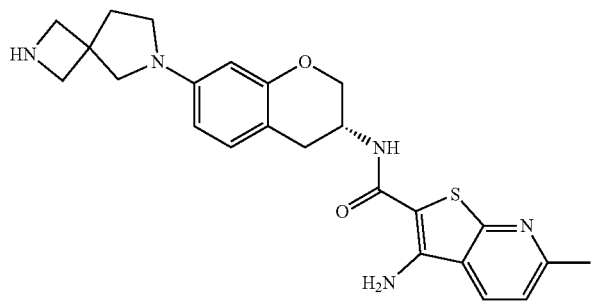 [SMILES: Cc1ccc2c(N)c(C(=O)N[C@H]3COc4cc(N5CCC6(CNC6)C5)ccc4C3)sc2n1]
306. 3-amino-N-[(3R)-7-{2,6-diazaspiro[3.4]octan-6-yl}-3,4-dihydro-2H-1-benzopyran-3-yl]-6-methylthieno[2,3-b]pyridine-2-carboxamide
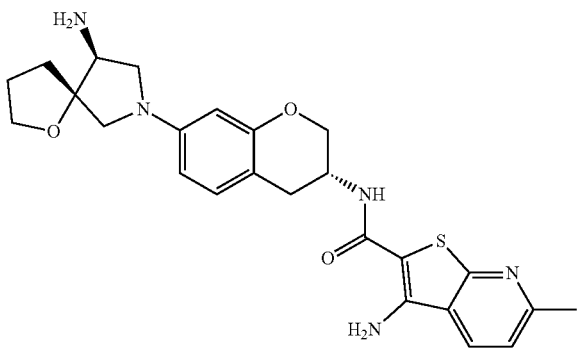 [SMILES: Cc1ccc2c(N)c(C(=O)N[C@H]3COc4cc(N5C[C@H](N)[C@]6(CCCO6)C5)ccc4C3)sc2n1]
307. 3-amino-N-[(3R)-7-[(5S,9S)-9-amino-1-oxa-7-azaspiro[4.4]nonan-7-yl]-3,4-dihydro-2H-1-benzopyran-3-yl]-6-methylthieno[2,3-b]pyridine-2-carboxamide
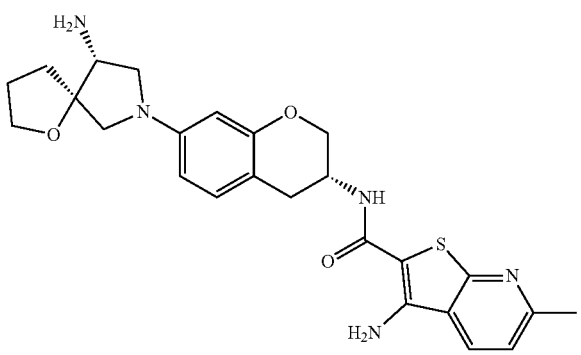 [SMILES: Cc1ccc2c(N)c(C(=O)N[C@H]3COc4cc(N5C[C@@H](N)[C@@]6(CCCO6)C5)ccc4C3)sc2n1]
308. 3-amino-N-[(3R)-7-[(5R,9R)-9-amino-1-oxa-7-azaspiro[4.4]nonan-7-yl]-3,4-dihydro-2H-1-benzopyran-3-yl]-6-methylthieno[2,3-b]pyridine-2-carboxamide

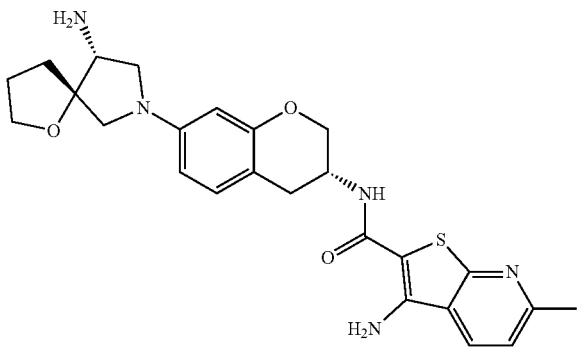 [SMILES: Cc1ccc2c(N)c(C(=O)N[C@H]3COc4cc(N5C[C@@H](N)[C@]6(CCCO6)C5)ccc4C3)sc2n1]
309. 3-amino-N-[(3R)-7-[(5S,9R)-9-amino-1-
oxa-7-azaspiro[4.4]nonan-7-yl]-3,4-dihydro-
2H-1-benzopyran-3-yl]-6-methylthieno[2,3-
b]pyridine-2-carboxamide
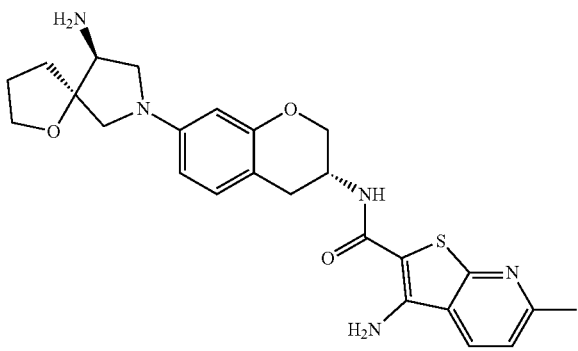 [SMILES: Cc1ccc2c(N)c(C(=O)N[C@H]3COc4cc(N5C[C@H](N)[C@@]6(CCCO6)C5)ccc4C3)sc2n1]
310. 3-amino-N-[(3R)-7-[(5R,9S)-9-amino-
1-oxa-7-azaspiro[4.4]nonan-7-yl]-3,4-
dihydro-2H-1-benzopyran-3-yl]-6-
methylthieno[2,3-b]pyridine-2-carboxamide
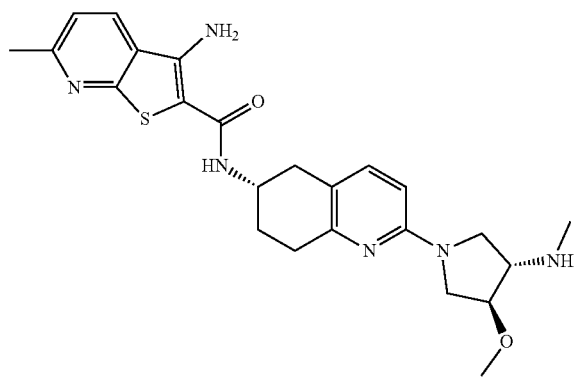
311. 3-amino-N-[(6S)-2-[(3S,4S)-3-methoxy-
4-(methylamino)pyrrolidin-1-yl]-5,6,7,8-
tetrahydroquinolin-6-yl]-6-methylthieno[2,3-
b]pyridine-2-carboxamide TABLE 25-continued
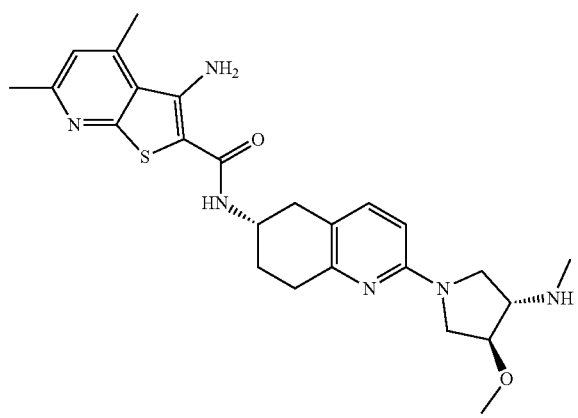
312. 3-amino-N-[(6S)-2-[(3S,4S)-3-
methoxy-4-(methylamino)pyrrolidin-1-yl]-
5,6,7,8-tetrahydroquinolin-6-yl]-4,6-
dimethylthieno[2,3-b]pyridine-2-
carboxamide
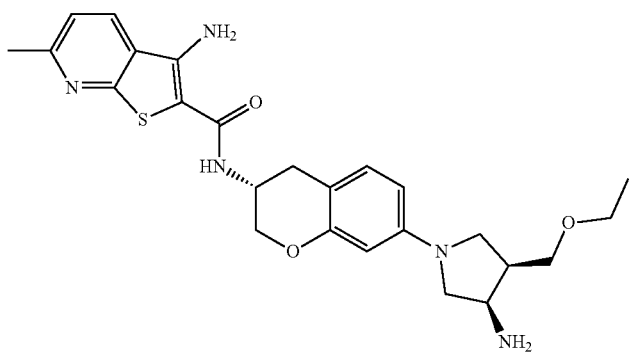 [SMILES: CCOC[C@@H]1CN(c2ccc3c(c2)OC[C@H](NC(=O)c2sc4nc(C)ccc4c2N)C3)C[C@@H]1N]
313. 3-amino-N-[(3R)-7-[(3R,4R)-3-amino-4-
(ethoxymethyl)pyrrolidin-1-yl]-3,4-dihydro-
2H-1-benzopyran-3-yl]-6-methylthieno[2,3-
b]pyridine-2-carboxamide
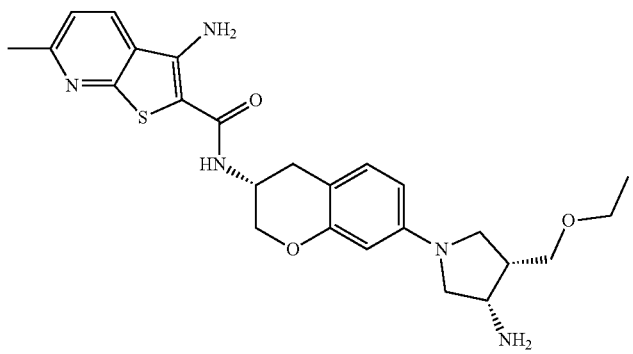 [SMILES: CCOC[C@H]1CN(c2ccc3c(c2)OC[C@H](NC(=O)c2sc4nc(C)ccc4c2N)C3)C[C@H]1N]
314. 3-amino-N-[(3R)-7-[(3S,4S)-3-amino-
4-(ethoxymethyl)pyrrolidin-1-yl]-3,4-
dihydro-2H-1-benzopyran-3-yl]-6-
methylthieno[2,3-b]pyridine-2-carboxamide TABLE 25-continued
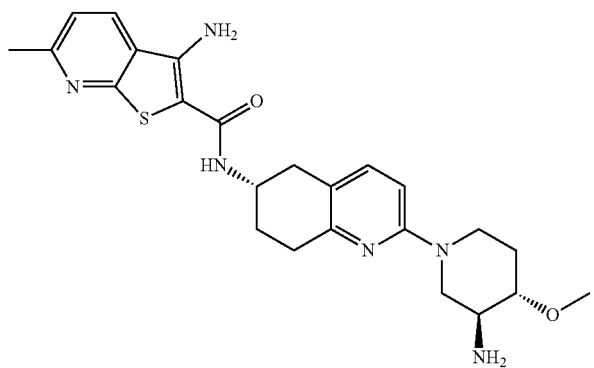
315. 3-amino-N-[(6S)-2-[(3S,4S)-3-amino-4-
methoxypiperidin-1-yl]-5,6,7,8-
tetrahydroquinolin-6-yl]-6-methylthieno[2,3-
b]pyridine-2-carboxamide
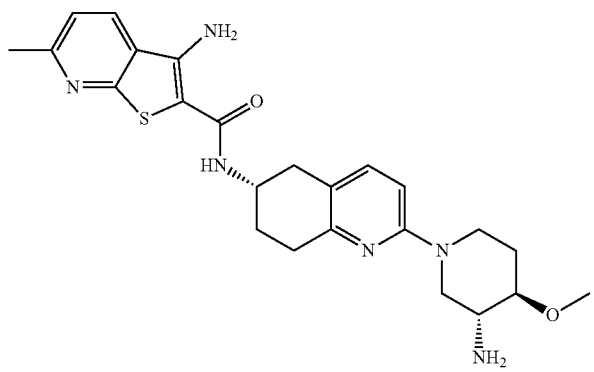
316. 3-amino-N-[(6S)-2-[(3R,4R)-3-amino-
4-methoxypiperidin-1-yl]-5,6,7,8-
tetrahydroquinolin-6-yl]-6-methylthieno[2,3-
b]pyridine-2-carboxamide
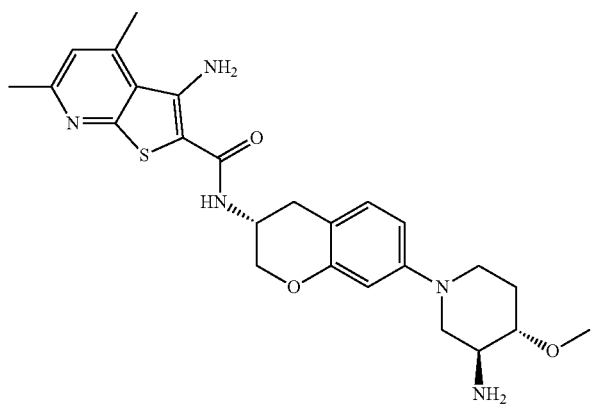
317. 3-amino-N-[(3R)-7-[(3S,4S)-3-amino-4-
methoxypiperidin-1-yl]-3,4-dihydro-2H-1-
benzopyran-3-yl]-4,6-dimethylthieno[2,3-
b]pyridine-2-carboxamide TABLE 25-continued
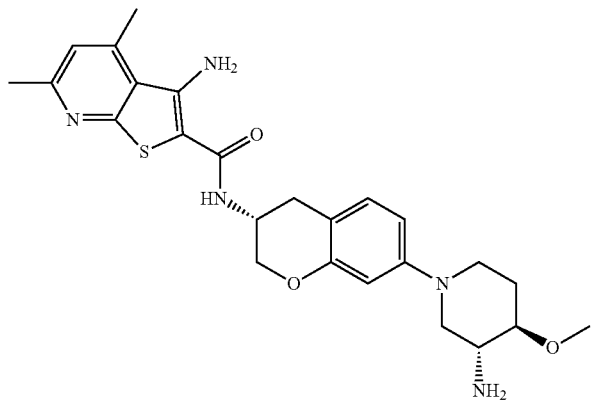
318. 3-amino-N-[(3R)-7-[(3R,4R)-3-amino-
4-methoxypiperidin-1-yl]-3,4-dihydro-2H-1-
benzopyran-3-yl]-4,6-dimethylthieno[2,3-
b]pyridine-2-carboxamide
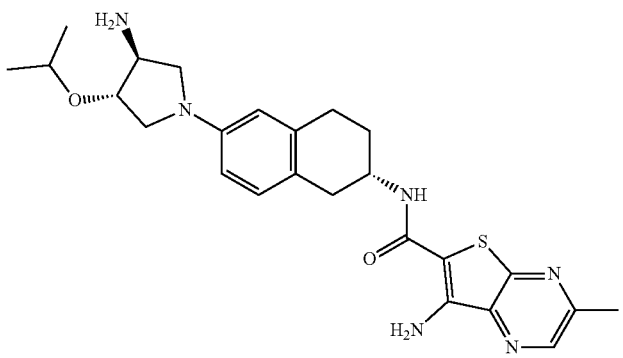 [SMILES: Cc1cnc2c(N)c(C(=O)N[C@H]3CCc4cc(N5C[C@H](OC(C)C)[C@@H](N)C5)ccc4C3)sc2n1]
319. 7-amino-N-[(2S)-6-[(3S,4S)-3-amino-4-
(propan-2-yloxy)pyrrolidin-1-yl]-1,2,3,4-
tetrahydronaphthalen-2-yl]-3-
methylthieno[2,3-b]pyrazine-6-carboxamide
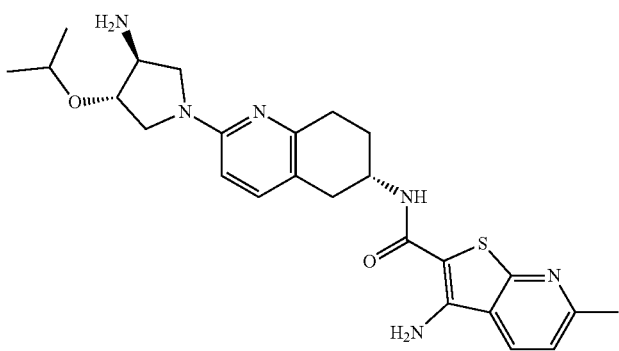 [SMILES: Cc1ccc2c(N)c(C(=O)N[C@H]3CCc4nc(N5C[C@H](OC(C)C)[C@@H](N)C5)ccc4C3)sc2n1]
320. 3-amino-N-[(6S)-2-[(3S,4S)-3-amino-4-
(propan-2-yloxy)pyrrolidin-1-yl]-5,6,7,8-
tetrahydroquinolin-6-yl]-6-methylthieno[2,3-
b]pyridine-2-carboxamide

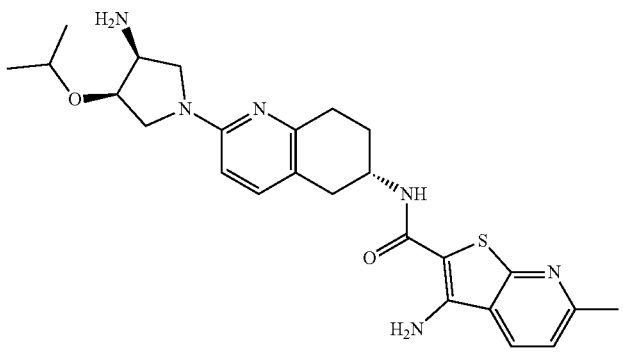 [SMILES: Cc1ccc2c(N)c(C(=O)N[C@H]3CCc4nc(N5C[C@H](N)[C@H](OC(C)C)C5)ccc4C3)sc2n1]
321. 3-amino-N-[(6S)-2-[(3S,4R)-3-amino-4-(propan-2-yloxy)pyrrolidin-1-yl]-5,6,7,8-tetrahydroquinolin-6-yl]-6-methylthieno[2,3-b]pyridine-2-carboxamide
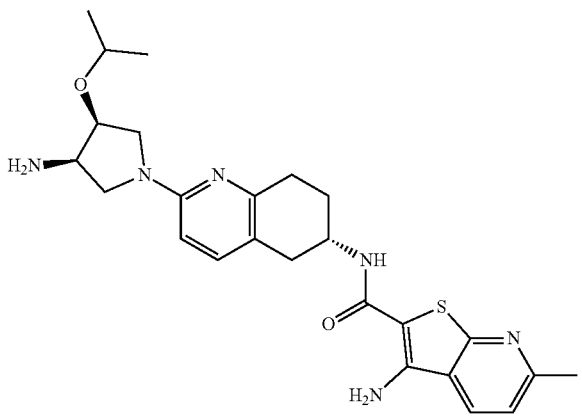 [SMILES: Cc1ccc2c(N)c(C(=O)N[C@H]3CCc4nc(N5C[C@@H](N)[C@@H](OC(C)C)C5)ccc4C3)sc2n1]
322. 3-amino-N-[(6S)-2-[(3R,4S)-3-amino-4-(propan-2-yloxy)pyrrolidin-1-yl]-5,6,7,8-tetrahydroquinolin-6-yl]-6-methylthieno[2,3-b]pyridine-2-carboxamide
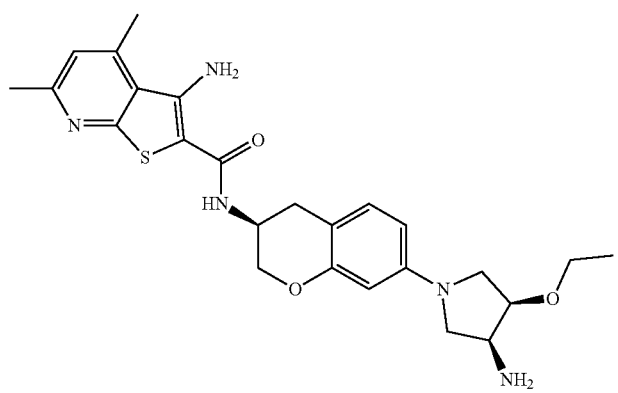 [SMILES: CCO[C@@H]1CN(c2ccc3c(c2)OC[C@@H](NC(=O)c2sc4nc(C)cc(C)c4c2N)C3)C[C@@H]1N]
323. 3-amino-N-[(3R)-7-[(3S,4R)-3-amino-4-ethoxypyrrolidin-1-yl]-3,4-dihydro-2H-1-benzopyran-3-yl]-4,6-dimethylthieno[2,3-b]pyridine-2-carboxamide TABLE 25-continued
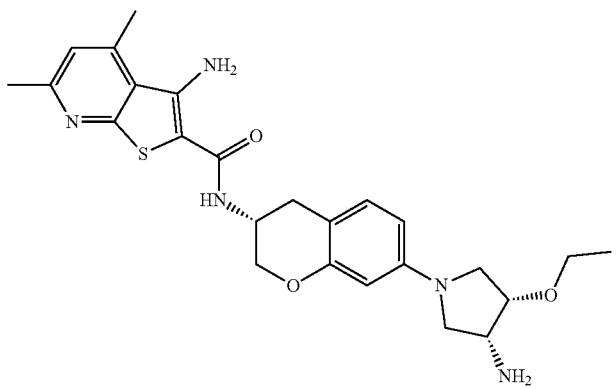
324. 3-amino-N-[(3R)-7-[(3R,4S)-3-amino-
4-ethoxypyrrolidin-1-yl]-3,4-dihydro-2H-1-
benzopyran-3-yl]-4,6-dimethylthieno[2,3-
b]pyridine-2-carboxamide
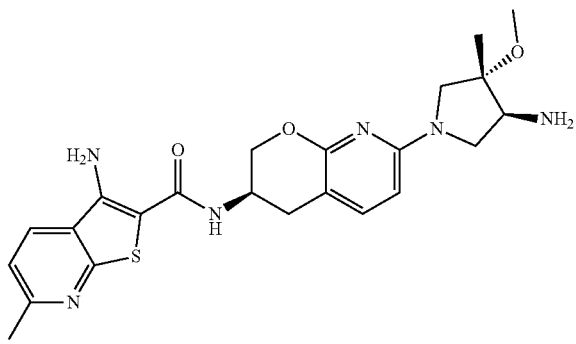 [SMILES: CO[C@@]1(C)CN(c2ccc3c(n2)OC[C@H](NC(=O)c2sc4nc(C)ccc4c2N)C3)C[C@@H]1N]
325. 3-amino-N-[(3R)-7-[(3S,4S)-4-amino-3-
methoxy-3-methylpyrrolidin-1-yl]-2H,3H,4H-
pyrano[2,3-b]pyridin-3-yl]-6-
methylthieno[2,3-b]pyridine-2-carboxamide
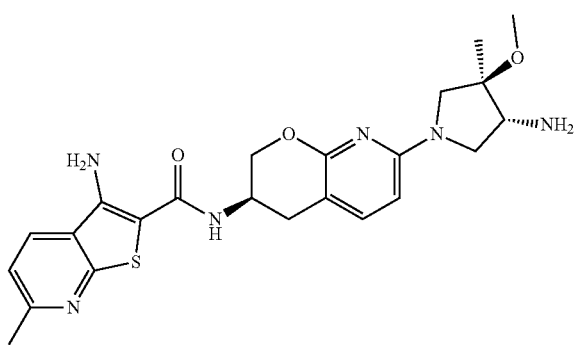 [SMILES: CO[C@]1(C)CN(c2ccc3c(n2)OC[C@H](NC(=O)c2sc4nc(C)ccc4c2N)C3)C[C@H]1N]
326. 3-amino-N-[(3R)-7-[(3R,4R)-4-amino-
3-methoxy-3-methylpyrrolidin-1-yl]-
2H,3H,4H-pyrano[2,3-b]pyridin-3-yl]-6-
methylthieno[2,3-b]pyridine-2-carboxamide

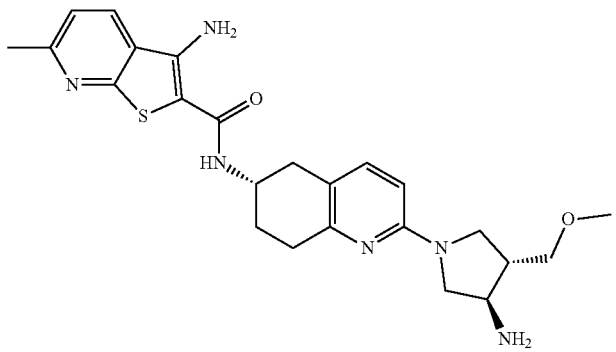
327. 3-amino-N-[(6S)-2-[(3R,4S)-3-amino-4-
(methoxymethyl)pyrrolidin-1-yl]-5,6,7,8-
tetrahydroquinolin-6-yl]-6-methylthieno[2,3-
b]pyridine-2-carboxamide
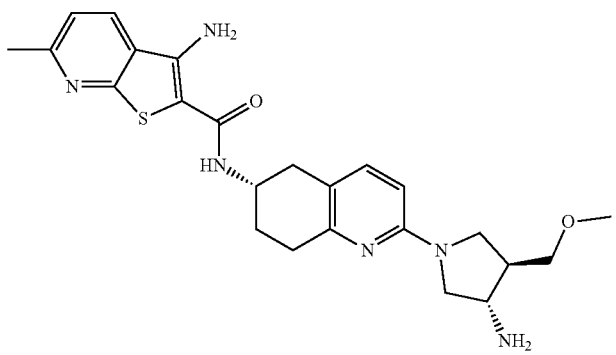
328. 3-amino-N-[(6S)-2-[(3S,4R)-3-amino-
4-(methoxymethyl)pyrrolidin-1-yl]-5,6,7,8-
tetrahydroquinolin-6-yl]-6-methylthieno[2,3-
b]pyridine-2-carboxamide
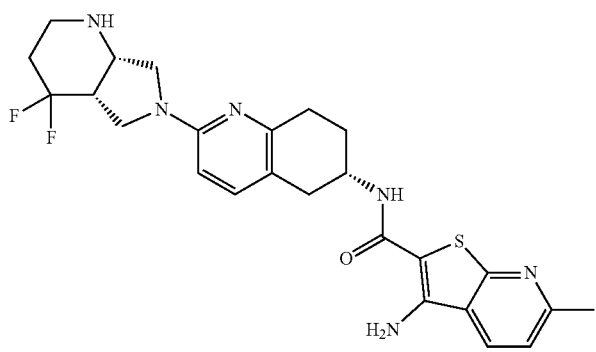 [SMILES: Cc1ccc2c(N)c(C(=O)N[C@H]3CCc4nc(N5C[C@H]6NCCC(F)(F)[C@H]6C5)ccc4C3)sc2n1]
329. N-[(6S)-2-[(4aS,7aS)-4,4-difluoro-
octahydro-1H-pyrrolo[3,4-b]pyridin-6-yl]-
5,6,7,8-tetrahydroquinolin-6-yl]-3-amino-6-
methylthieno[2,3-b]pyridine-2-carboxamide TABLE 25-continued

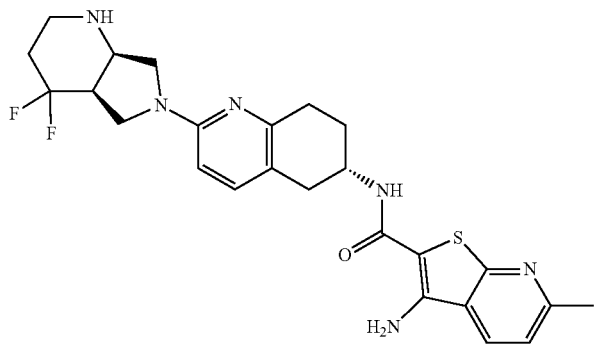 [SMILES: Cc1ccc2c(N)c(C(=O)N[C@H]3CCc4nc(N5C[C@@H]6NCCC(F)(F)[C@@H]6C5)ccc4C3)sc2n1]

330. N-[(6S)-2-[(4aR,7aR)-4,4-difluoro-octahydro-1H-pyrrolo[3,4-b]pyridin-6-yl]-5,6,7,8-tetrahydroquinolin-6-yl]-3-amino-6-methylthieno[2,3-b]pyridine-2-carboxamide

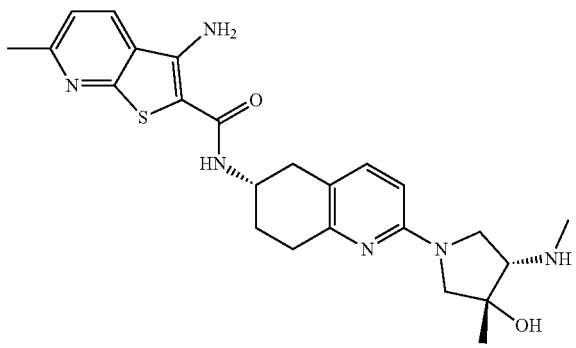

331. 3-amino-N-[(6S)-2-[(3R,4S)-3-hydroxy-3-methyl-4-(methylamino)pyrrolidin-1-yl]-5,6,7,8-tetrahydroquinolin-6-yl]-6-methylthieno[2,3-b]pyridine-2-carboxamide

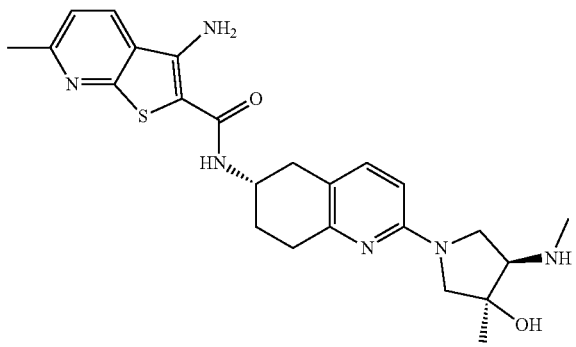

332. 3-amino-N-[(6S)-2-[(3S,4R)-3-hydroxy-3-methyl-4-(methylamino)pyrrolidin-1-yl]-5,6,7,8-tetrahydroquinolin-6-yl]-6-methylthieno[2,3-b]pyridine-2-carboxamide TABLE 25-continued
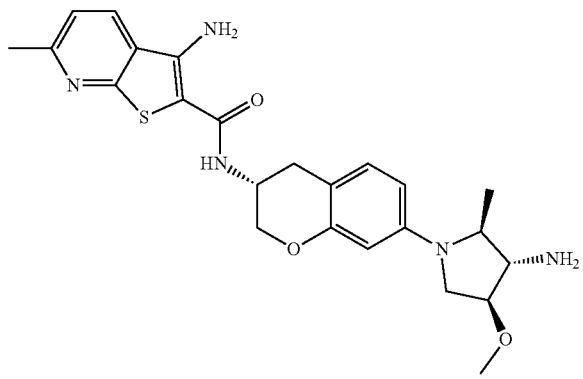 [SMILES: CO[C@H]1CN(c2ccc3c(c2)OC[C@H](NC(=O)c2sc4nc(C)ccc4c2N)C3)[C@@H](C)[C@@H]1N]
333. 3-amino-N-[(3R)-7-[(2S,3S,4S)-3-amino-
4-methoxy-2-methylpyrrolidin-1-yl]-3,4-
dihydro-2H-1-benzopyran-3-yl]-6-
methylthieno[2,3-b]pyridine-2-carboxamide
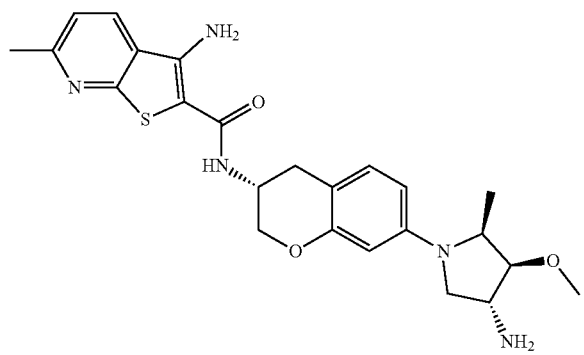
334. 3-amino-N-[(3R)-7-[(2S,3S,4R)-4-
amino-3-methoxy-2-methylpyrrolidin-1-yl]-
3,4-dihydro-2H-1-benzopyran-3-yl]-6-
methylthieno[2,3-b]pyridine-2-carboxamide
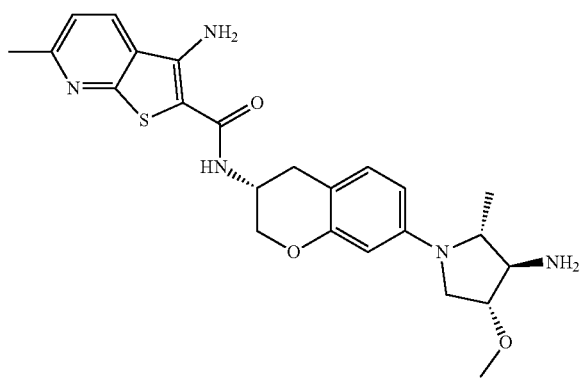 [SMILES: CO[C@@H]1CN(c2ccc3c(c2)OC[C@H](NC(=O)c2sc4nc(C)ccc4c2N)C3)[C@H](C)[C@H]1N]
335. 3-amino-N-[(3R)-7-[(2R,3R,4R)-3-
amino-4-methoxy-2-methylpyrrolidin-1-yl]-
3,4-dihydro-2H-1-benzopyran-3-yl]-6-
methylthieno[2,3-b]pyridine-2-carboxamide TABLE 25-continued
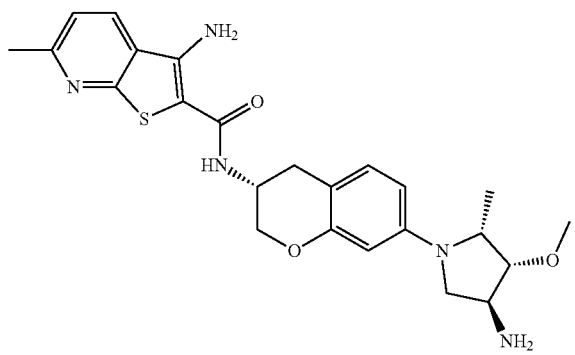
336. 3-amino-N-[(3R)-7-[(2R,3R,4S)-4-
amino-3-methoxy-2-methylpyrrolidin-1-yl]-
3,4-dihydro-2H-1-benzopyran-3-yl]-6-
methylthieno[2,3-b]pyridine-2-carboxamide
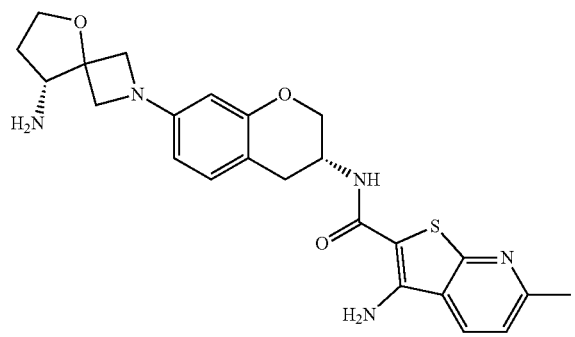 [SMILES: Cc1ccc2c(N)c(C(=O)N[C@H]3COc4cc(N5CC6(C5)OCC[C@H]6N)ccc4C3)sc2n1]
337. 3-amino-N-[(3R)-7-[(8R)-8-amino-5-oxa-
2-azaspiro[3.4]octan-2-yl]-3,4-dihydro-2H-1-
benzopyran-3-yl]-6-methylthieno[2,3-
b]pyridine-2-carboxamide
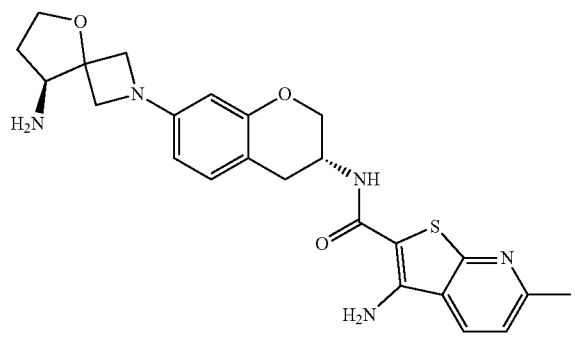 [SMILES: Cc1ccc2c(N)c(C(=O)N[C@H]3COc4cc(N5CC6(C5)OCC[C@@H]6N)ccc4C3)sc2n1]
338. 3-amino-N-[(3R)-7-[(8S)-8-amino-5-
oxa-2-azaspiro[3.4]octan-2-yl]-3,4-dihydro-
2H-1-benzopyran-3-yl]-6-methylthieno[2,3-
b]pyridine-2-carboxamide TABLE 25-continued
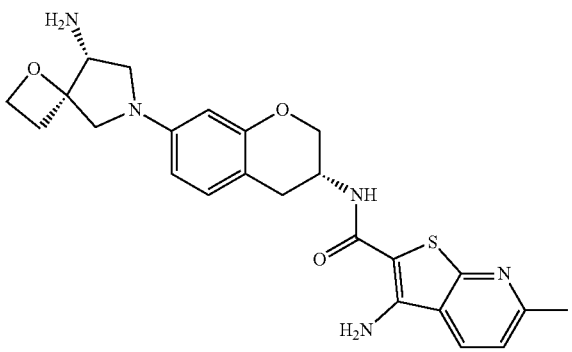 [SMILES: Cc1ccc2c(N)c(C(=O)N[C@H]3COc4cc(N5C[C@@H](N)[C@@]6(CCO6)C5)ccc4C3)sc2n1]
339. 3-amino-N-[(3R)-7-[(4R,8R)-8-amino-1-
oxa-6-azaspiro[3.4]octan-6-yl]-3,4-dihydro-
2H-1-benzopyran-3-yl]-6-methylthieno[2,3-
b]pyridine-2-carboxamide
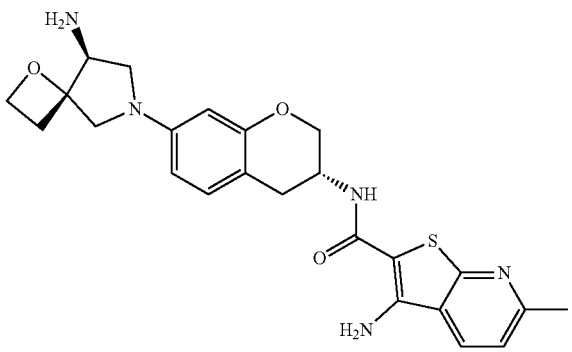 [SMILES: Cc1ccc2c(N)c(C(=O)N[C@H]3COc4cc(N5C[C@H](N)[C@]6(CCO6)C5)ccc4C3)sc2n1]
340. 3-amino-N-[(3R)-7-[(4S,8S)-8-amino-
1-oxa-6-azaspiro[3.4]octan-6-yl]-3,4-
dihydro-2H-1-benzopyran-3-yl]-6-
methylthieno[2,3-b]pyridine-2-carboxamide
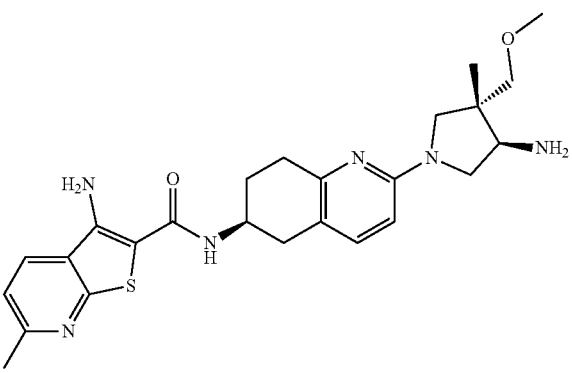 [SMILES: COC[C@@]1(C)CN(c2ccc3c(n2)CC[C@H](NC(=O)c2sc4nc(C)ccc4c2N)C3)C[C@@H]1N]
341. 3-amino-N-[(6S)-2-[(3S,4R)-4-amino-3-
(methoxymethyl)-3-methylpyrrolidin-1-yl]-
5,6,7,8-tetrahydroquinolin-6-yl]-6-
methylthieno[2,3-b]pyridine-2-carboxamide TABLE 25-continued

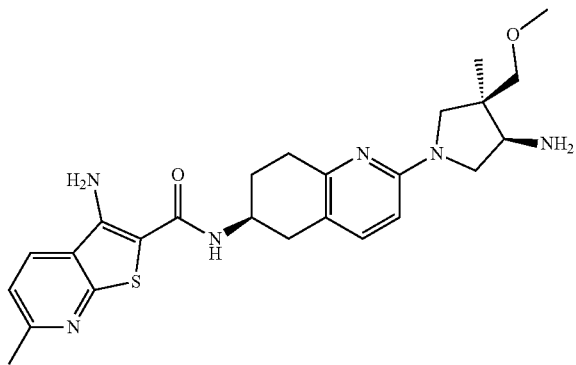 [SMILES: COC[C@]1(C)CN(c2ccc3c(n2)CC[C@H](NC(=O)c2sc4nc(C)ccc4c2N)C3)C[C@@H]1N]

342. 3-amino-N-[(6S)-2-[(3R,4R)-4-amino-
3-(methoxymethyl)-3-methylpyrrolidin-1-
yl]-5,6,7,8-tetrahydroquinolin-6-yl]-6-
methylthieno[2,3-b]pyridine-2-carboxamide

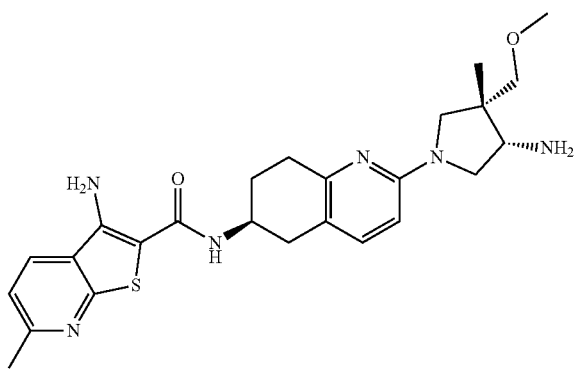 [SMILES: COC[C@@]1(C)CN(c2ccc3c(n2)CC[C@H](NC(=O)c2sc4nc(C)ccc4c2N)C3)C[C@H]1N]

343. 3-amino-N-[(6S)-2-[(3S,4S)-4-amino-3-
(methoxymethyl)-3-methylpyrrolidin-1-yl]-
5,6,7,8-tetrahydroquinolin-6-yl]-6-
methylthieno[2,3-b]pyridine-2-carboxamide

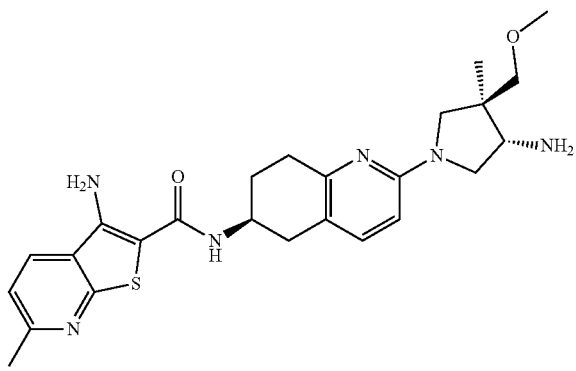 [SMILES: COC[C@]1(C)CN(c2ccc3c(n2)CC[C@H](NC(=O)c2sc4nc(C)ccc4c2N)C3)C[C@H]1N]

344. 3-amino-N-[(6S)-2-[(3R,4S)-4-amino-
3-(methoxymethyl)-3-methylpyrrolidin-1-
yl]-5,6,7,8-tetrahydroquinolin-6-yl]-6-
methylthieno[2,3-b]pyridine-2-carboxamide

TABLE 25-continued
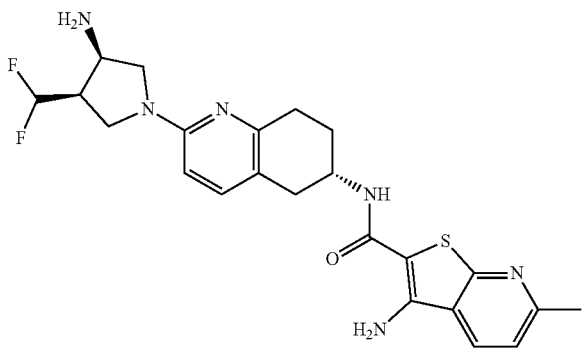 [SMILES: Cc1ccc2c(N)c(C(=O)N[C@H]3CCc4nc(N5C[C@H](N)[C@H](C(F)F)C5)ccc4C3)sc2n1]
345. 3-amino-N-[(6S)-2-[(3R,4R)-3-amino-4-
(difluoromethyl)pyrrolidin-1-yl]-5,6,7,8-
tetrahydroquinolin-6-yl]-6-methylthieno[2,3-
b]pyridine-2-carboxamide
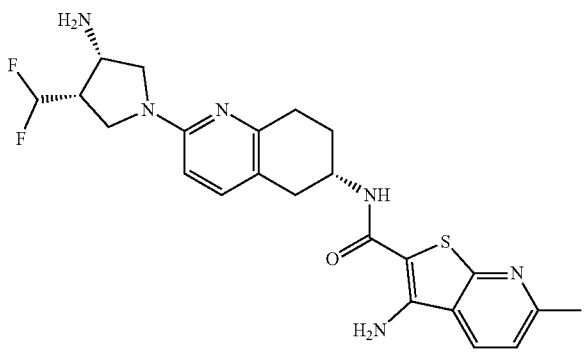 [SMILES: Cc1ccc2c(N)c(C(=O)N[C@H]3CCc4nc(N5C[C@@H](N)[C@@H](C(F)F)C5)ccc4C3)sc2n1]
346. 3-amino-N-[(6S)-2-[(3S,4S)-3-amino-4-
(difluoromethyl)pyrrolidin-1-yl]-5,6,7,8-
tetrahydroquinolin-6-yl]-6-methylthieno[2,3-
b]pyridine-2-carboxamide
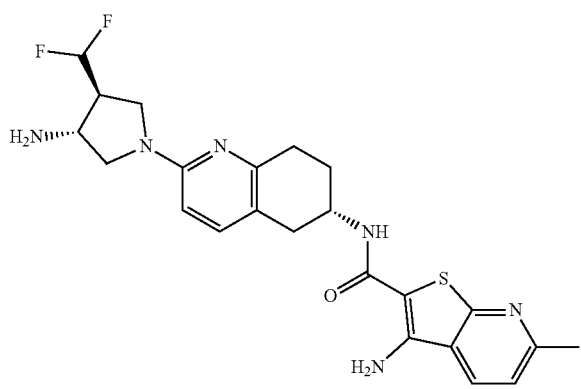 [SMILES: Cc1ccc2c(N)c(C(=O)N[C@H]3CCc4nc(N5C[C@H](C(F)F)[C@@H](N)C5)ccc4C3)sc2n1]
347. 3-amino-N-[(6S)-2-[(3R,4S)-3-amino-4-
(difluoromethyl)pyrrolidin-1-yl]-5,6,7,8-
tetrahydroquinolin-6-yl]-6-methylthieno[2,3-
b]pyridine-2-carboxamide TABLE 25-continued
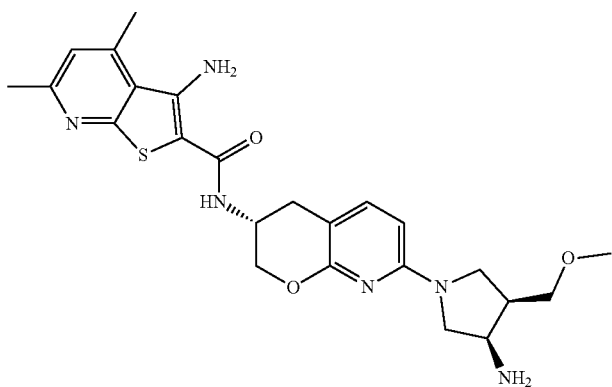
348. 3-amino-N-[(3R)-7-[(3R,4R)-3-amino-
4-(methoxymethyl)pyrrolidin-1-yl]-
2H,3H,4H-pyrano[2,3-b]pyridin-3-yl]-4,6-
dimethylthieno[2,3-b]pyridine-2-
carboxamide
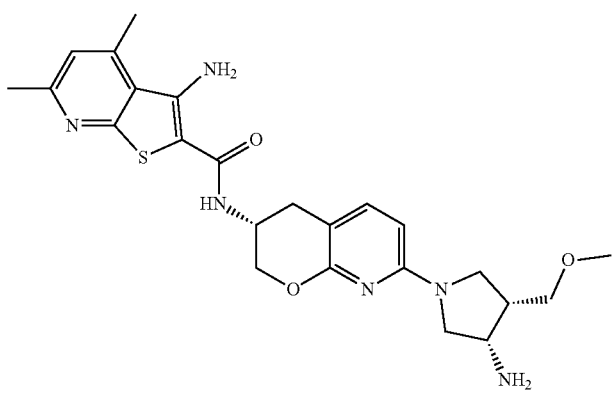
349. 3-amino-N-[(3R)-7-[(3S,4S)-3-amino-4-
(methoxymethyl)pyrrolidin-1-yl]-2H,3H,4H-
pyrano[2,3-b]pyridin-3-yl]-4,6-
dimethylthieno[2,3-b]pyridine-2-carboxamide
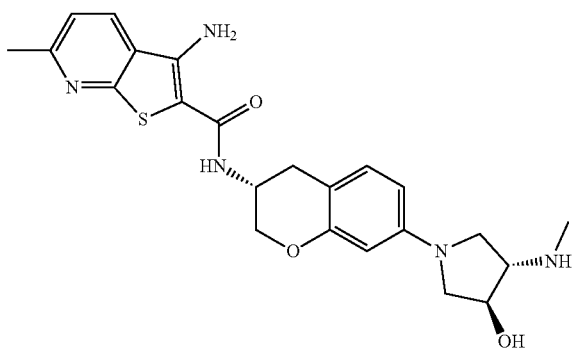
350. 3-amino-N-[(3R)-7-[(3S,4S)-3-
hydroxy-4-(methylamino)pyrrolidin-1-yl]-
3,4-dihydro-2H-1-benzopyran-3-yl]-6-
methylthieno[2,3-b]pyridine-2-carboxamide TABLE 25-continued
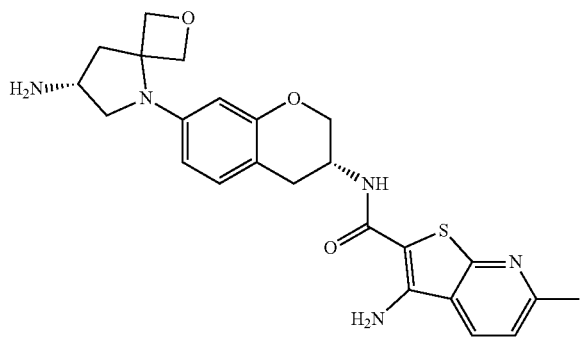 [SMILES: Cc1ccc2c(N)c(C(=O)N[C@H]3COc4cc(N5C[C@H](N)CC56COC6)ccc4C3)sc2n1]
351. 3-amino-N-[(3R)-7-[(7R)-7-amino-2-oxa-
5-azaspiro[3.4]octan-5-yl]-3,4-dihydro-2H-1-
benzopyran-3-yl]-6-methylthieno[2,3-
b]pyridine-2-carboxamide
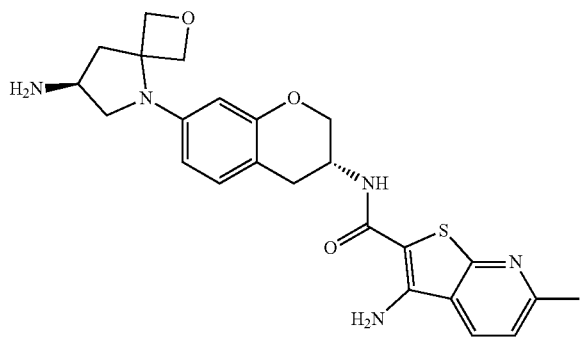 [SMILES: Cc1ccc2c(N)c(C(=O)N[C@H]3COc4cc(N5C[C@@H](N)CC56COC6)ccc4C3)sc2n1]
352. 3-amino-N-[(3R)-7-[(7S)-7-amino-2-
oxa-5-azaspiro[3.4]octan-5-yl]-3,4-dihydro-
2H-1-benzopyran-3-yl]-6-methylthieno[2,3-
b]pyridine-2-carboxamide
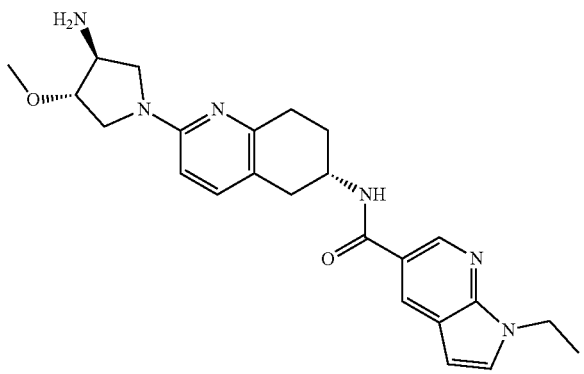 [SMILES: CCn1ccc2cc(C(=O)N[C@H]3CCc4nc(N5C[C@H](OC)[C@@H](N)C5)ccc4C3)cnc21]
353. N-[(6S)-2-[(3S,4S)-3-amino-4-
methoxypyrrolidin-1-yl]-5,6,7,8-
tetrahydroquinolin-6-yl]-1-ethyl-1H-
pyrrolo[2,3-b]pyridine-5-carboxamide

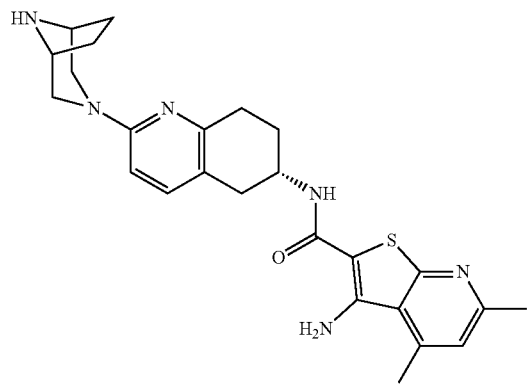 [SMILES: Cc1cc(C)c2c(N)c(C(=O)N[C@H]3CCc4nc(N5CC6CCC(C5)N6)ccc4C3)sc2n1]
354. 3-amino-N-[(6S)-2-{3,8-diazabicyclo[3.2.1]octan-3-yl}-5,6,7,8-tetrahydroquinolin-6-yl]-4,6-dimethylthieno[2,3-b]pyridine-2-carboxamide
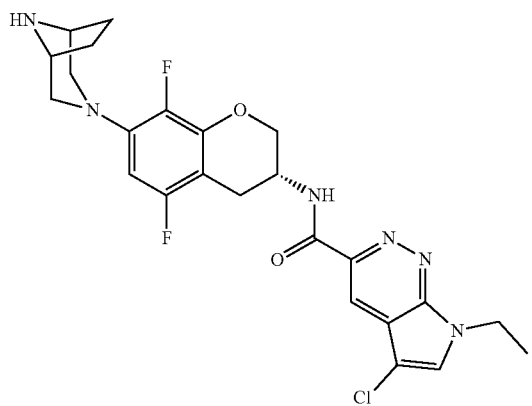 [SMILES: CCn1cc(Cl)c2cc(C(=O)N[C@H]3COc4c(F)c(N5CC6CCC(C5)N6)cc(F)c4C3)nnc21]
355. 5-chloro-N-[(3R)-7-{3,8-diazabicyclo[3.2.1]octan-3-yl}-5,8-difluoro-3,4-dihydro-2H-1-benzopyran-3-yl]-7-ethyl-7H-pyrrolo[2,3-c]pyridazine-3-carboxamide
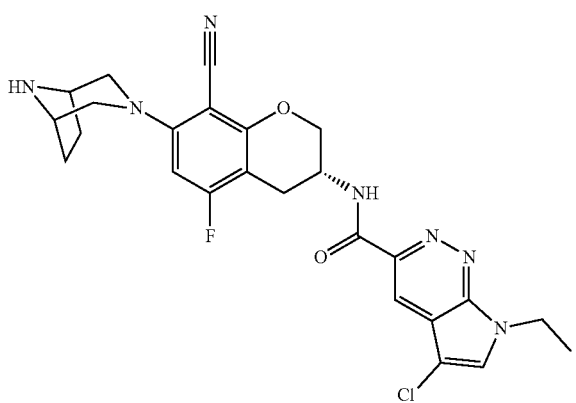 [SMILES: CCn1cc(Cl)c2cc(C(=O)N[C@H]3COc4c(C#N)c(N5CC6CCC(C5)N6)cc(F)c4C3)nnc21]
356. 5-chloro-N-[(3R)-8-cyano-7-{3,8-diazabicyclo[3.2.1]octan-3-yl}-5-fluoro-3,4-dihydro-2H-1-benzopyran-3-yl]-7-ethyl-7H-pyrrolo[2,3-c]pyridazine-3-carboxamide TABLE 25-continued

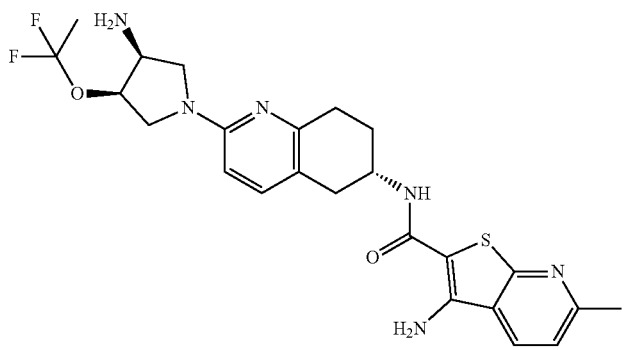 [SMILES: Cc1ccc2c(N)c(C(=O)N[C@H]3CCc4nc(N5C[C@H](N)[C@H](OC(C)(F)F)C5)ccc4C3)sc2n1]

357. 3-amino-N-[(6S)-2-[(3S,4R)-3-amino-4-
(1,1-difluoroethoxy)pyrrolidin-1-yl]-5,6,7,8-
tetrahydroquinolin-6-yl]-6-methylthieno[2,3-
b]pyridine-2-carboxamide

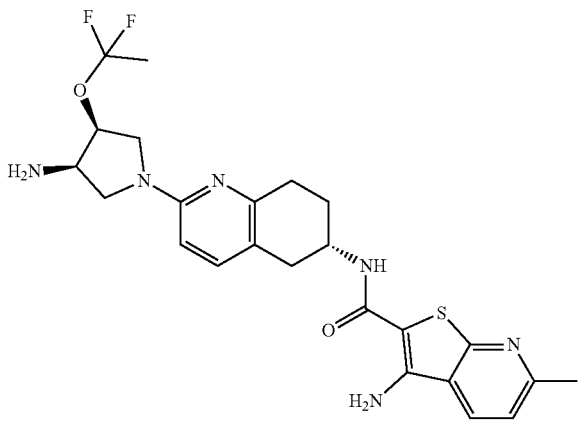 [SMILES: Cc1ccc2c(N)c(C(=O)N[C@H]3CCc4nc(N5C[C@@H](N)[C@@H](OC(C)(F)F)C5)ccc4C3)sc2n1]

358. 3-amino-N-[(6S)-2-[(3R,4S)-3-amino-
4-(1,1-difluoroethoxy)pyrrolidin-1-yl]-
5,6,7,8-tetrahydroquinolin-6-yl]-6-
methylthieno[2,3-b]pyridine-2-carboxamide 359. (6aS,7aR)-N-[(2S)-6-{3,8-

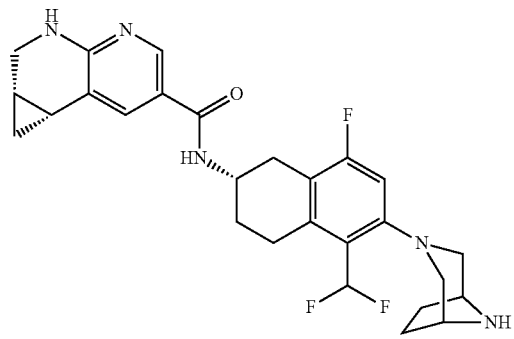 [SMILES: O=C(N[C@H]1CCc2c(c(F)cc(N3CC4CCC(C3)N4)c2C(F)F)C1)c1cnc2c(c1)[C@@H]1C[C@@H]1CN2]

359. diazabicyclo[3.2.1]octan-3-yl}-5-
(difluoromethyl)-8-fluoro-1,2,3,4-
tetrahydronaphthalen-2-yl]-
5H,6H,6aH,7H,7aH-cyclopropa[c]1,8-
naphthyridine-2-carboxamide TABLE 25-continued

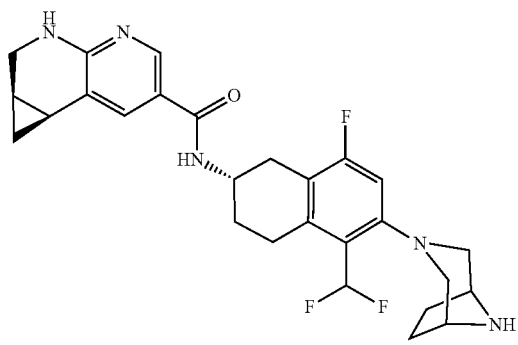 [SMILES: O=C(N[C@H]1CCc2c(c(F)cc(N3CC4CCC(C3)N4)c2C(F)F)C1)c1cnc2c(c1)[C@H]1C[C@H]1CN2]

360. (6aR,7aS)-N-[(2S)-6-{3,8-
diazabicyclo[3.2.1]octan-3-yl}-5-
(difluoromethyl)-8-fluoro-1,2,3,4-
tetrahydronaphthalen-2-yl]-
5H,6H,6aH,7H,7aH-cyclopropa[c]1,8-
naphthyridine-2-carboxamide

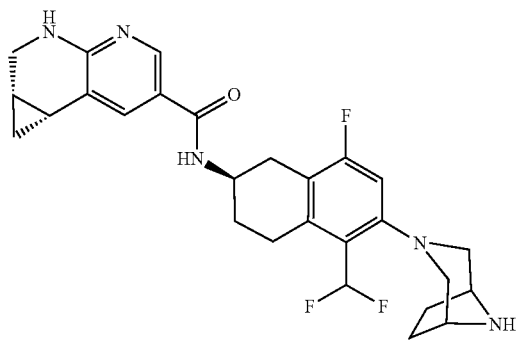 [SMILES: O=C(N[C@@H]1CCc2c(c(F)cc(N3CC4CCC(C3)N4)c2C(F)F)C1)c1cnc2c(c1)[C@@H]1C[C@@H]1CN2]

361. (6aS,7aR)-N-[(2R)-6-{3,8-
diazabicyclo[3.2.1]octan-3-yl}-5-
(difluoromethyl)-8-fluoro-1,2,3,4-
tetrahydronaphthalen-2-yl]-
5H,6H,6aH,7H,7aH-cyclopropa[c]1,8-
naphthyridine-2-carboxamide

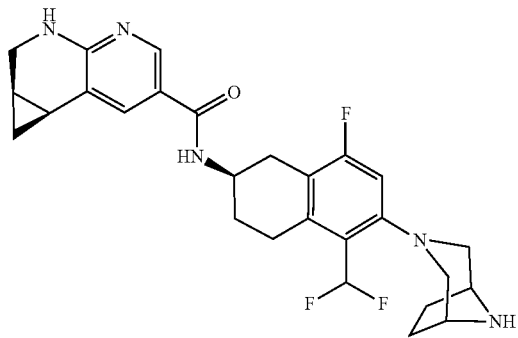 [SMILES: O=C(N[C@@H]1CCc2c(c(F)cc(N3CC4CCC(C3)N4)c2C(F)F)C1)c1cnc2c(c1)[C@H]1C[C@H]1CN2]

362. (6aR,7aS)-N-[(2R)-6-{3,8-
diazabicyclo[3.2.1]octan-3-yl}-5-
(difluoromethyl)-8-fluoro-1,2,3,4-
tetrahydronaphthalen-2-yl]-
5H,6H,6aH,7H,7aH-cyclopropa[c]1,8-
naphthyridine-2-carboxamide TABLE 25-continued
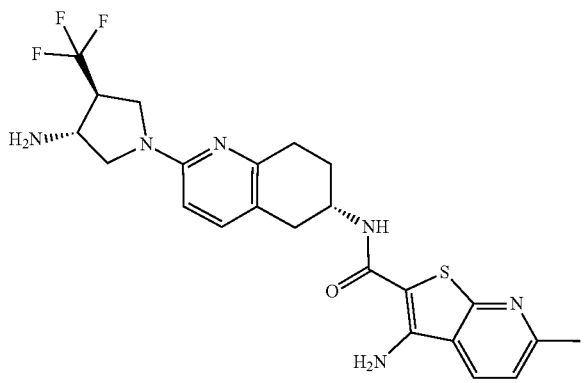 [SMILES: Cc1ccc2c(N)c(C(=O)N[C@H]3CCc4nc(N5C[C@H](N)[C@@H](C(F)(F)F)C5)ccc4C3)sc2n1]
363. 3-amino-N-[(6S)-2-[(3R,4S)-3-amino-4-
(trifluoromethyl)pyrrolidin-1-yl]-5,6,7,8-
tetrahydroquinolin-6-yl]-6-methylthieno[2,3-
b]pyridine-2-carboxamide
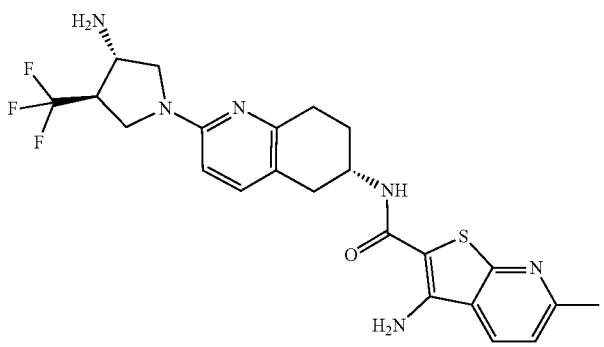 [SMILES: Cc1ccc2c(N)c(C(=O)N[C@H]3CCc4nc(N5C[C@@H](N)[C@H](C(F)(F)F)C5)ccc4C3)sc2n1]
364. 3-amino-N-[(6S)-2-[(3S,4R)-3-amino-
4-(trifluoromethyl)pyrrolidin-1-yl]-5,6,7,8-
tetrahydroquinolin-6-yl]-6-methylthieno[2,3-
b]pyridine-2-carboxamide
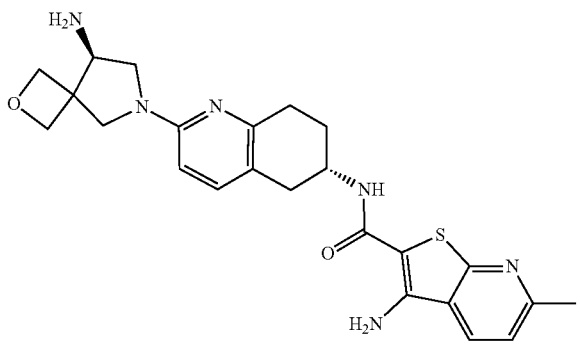 [SMILES: Cc1ccc2c(N)c(C(=O)N[C@H]3CCc4nc(N5C[C@H](N)C6(COC6)C5)ccc4C3)sc2n1]
365. 7-amino-N-[(6S)-2-[(8R)-8-amino-2-oxa-
6-azaspiro[3.4]octan-6-yl]-5,6,7,8-
tetrahydroquinolin-6-yl]-3-methylthieno[2,3-
b]pyrazine-6-carboxamide TABLE 25-continued
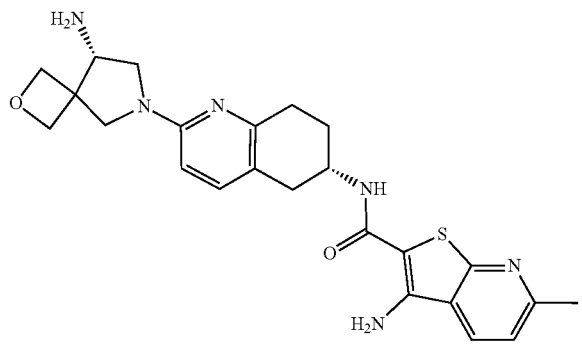 [SMILES: Cc1ccc2c(N)c(C(=O)N[C@H]3CCc4nc(N5C[C@@H](N)C6(COC6)C5)ccc4C3)sc2n1]
366. 7-amino-N-[(6S)-2-[(8S)-8-amino-2-
oxa-6-azaspiro[3.4]octan-6-yl]-5,6,7,8-
tetrahydroquinolin-6-yl]-3-methylthieno[2,3-
b]pyrazine-6-carboxamide
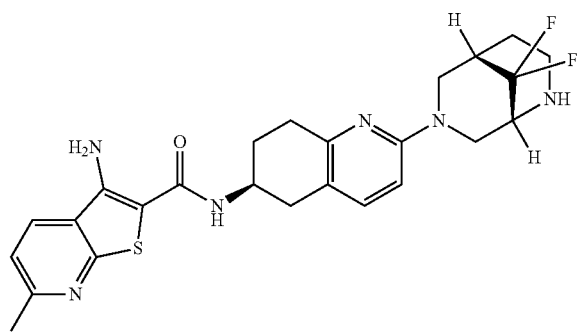 [SMILES: Cc1ccc2c(N)c(C(=O)N[C@H]3CCc4nc(N5C[C@@H]6CCN[C@H](C5)C6(F)F)ccc4C3)sc2n1]
367. 3-amino-N-[(6S)-2-[(1R,5S)-9,9-difluoro-
2,7-diazabicyclo[3.3.1]nonan-7-yl]-5,6,7,8-
tetrahydroquinolin-6-yl]-6-methylthieno[2,3-
b]pyridine-2-carboxamide
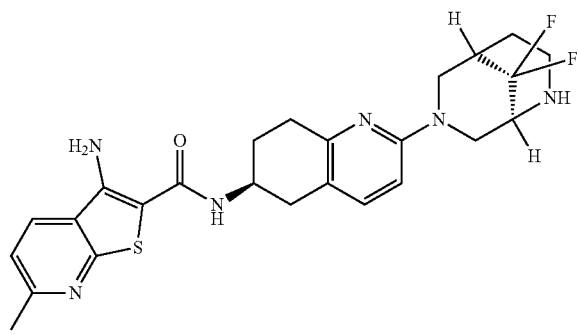
368. 3-amino-N-[(6S)-2-[(1S,5R)-9,9-
difluoro-2, 7-diazabicyclo[3.3.1]nonan-7-yl]-
5,6,7,8-tetrahydroquinolin-6-yl]-6-
methylthieno[2,3-b]pyridine-2-carboxamide TABLE 25-continued
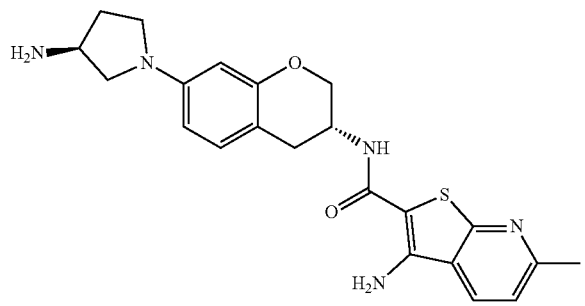 [SMILES: Cc1ccc2c(N)c(C(=O)N[C@H]3COc4cc(N5CC[C@H](N)C5)ccc4C3)sc2n1]
369. 3-amino-N-[(3R)-7-[(3S)-3-
aminopyrrolidin-1-yl]-3,4-dihydro-2H-1-
benzopyran-3-yl]-6-methylthieno[2,3-
b]pyridine-2-carboxamide
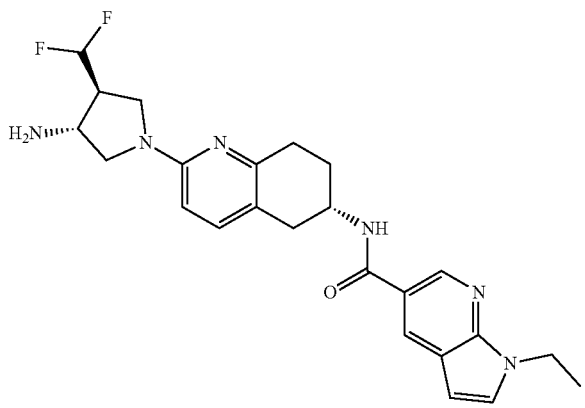 [SMILES: CCn1ccc2cc(C(=O)N[C@H]3CCc4nc(N5C[C@H](C(F)F)[C@@H](N)C5)ccc4C3)cnc21]
370. N-[(6S)-2-[(3R,4S)-3-amino-4-
(difluoromethyl)pyrrolidin-1-yl]-5,6,7,8-
tetrahydroquinolin-6-yl]-1-ethyl-1H-
pyrrolo[2,3-b]pyridine-5-carboxamide
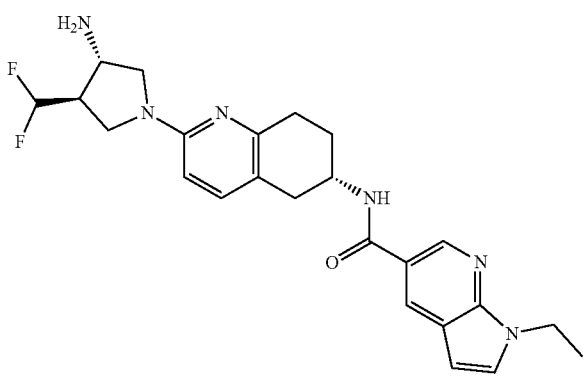 [SMILES: CCn1ccc2cc(C(=O)N[C@H]3CCc4nc(N5C[C@@H](N)[C@H](C(F)F)C5)ccc4C3)cnc21]
371. N-[(6S)-2-[(3S,4R)-3-amino-4-
(difluoromethyl)pyrrolidin-1-yl]-5,6,7,8-
tetrahydroquinolin-6-yl]-1-ethyl-1H-
pyrrolo[2,3-b]pyridine-5-carboxamide

TABLE 25-continued
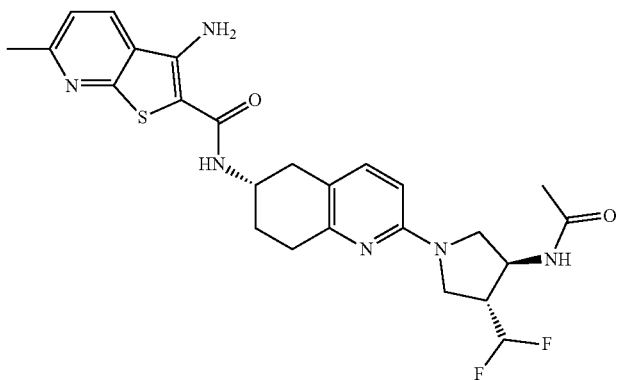 [SMILES: CC(=O)N[C@@H]1CN(c2ccc3c(n2)CC[C@H](NC(=O)c2sc4nc(C)ccc4c2N)C3)C[C@H]1C(F)F]
372. 3-amino-N-[(6S)-2-[(3R,4S)-3-
(difluoromethyl)-4-acetamidopyrrolidin-1-
yl]-5,6,7,8-tetrahydroquinolin-6-yl]-6-
methylthieno[2,3-b]pyridine-2-carboxamide
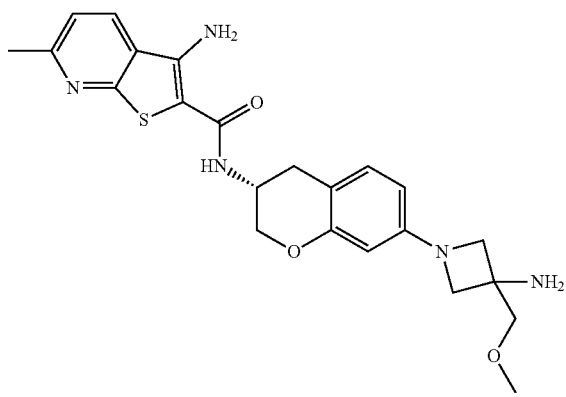 [SMILES: COCC1(N)CN(c2ccc3c(c2)OC[C@H](NC(=O)c2sc4nc(C)ccc4c2N)C3)C1]
373. 3-amino-N-[(3R)-7-[3-amino-3-
(methoxymethyl)azetidin-1-yl]-3,4-dihydro-
2H-1-benzopyran-3-yl]-6-methylthieno[2,3-
b]pyridine-2-carboxamide
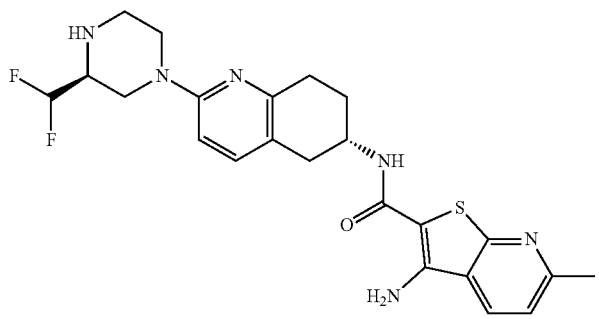 [SMILES: Cc1ccc2c(N)c(C(=O)N[C@H]3CCc4nc(N5CCN[C@H](C(F)F)C5)ccc4C3)sc2n1]
374. 3-amino-N-[(6S)-2-[(3S)-3-
(difluoromethyl)piperazin-1-yl]-5,6,7,8-
tetrahydroquinolin-6-yl]-6-methylthieno[2,3-
b]pyridine-2-carboxamide TABLE 25-continued
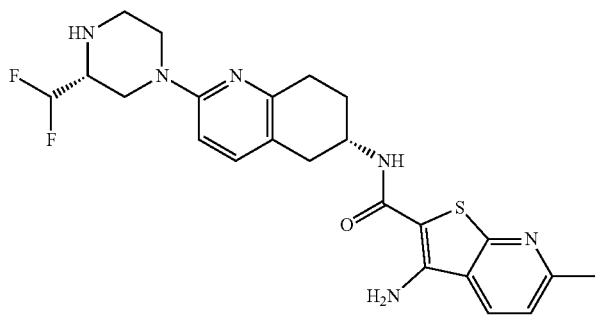 [SMILES: Cc1ccc2c(N)c(C(=O)N[C@H]3CCc4nc(N5CCN[C@@H](C(F)F)C5)ccc4C3)sc2n1]
375. 3-amino-N-[(6S)-2-[(3R)-3-
(difluoromethyl)piperazin-1-yl]-5,6,7,8-
tetrahydroquinolin-6-yl]-6-methylthieno[2,3-
b]pyridine-2-carboxamide
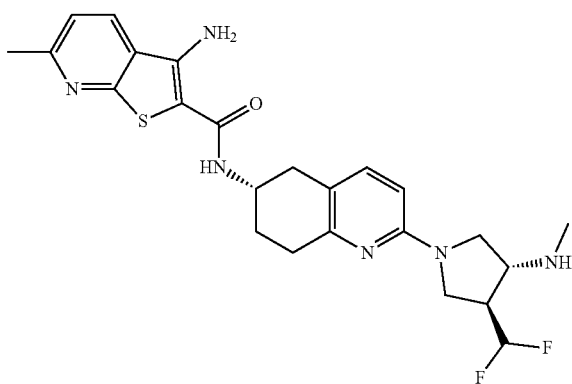
376. 3-amino-N-[(6S)-2-[(3S,4R)-3-
(difluoromethyl)-4-(methylamino)pyrrolidin-
1-yl]-5,6,7,8-tetrahydroquinolin-6-yl]-6-
methylthieno[2,3-b]pyridine-2-carboxamide
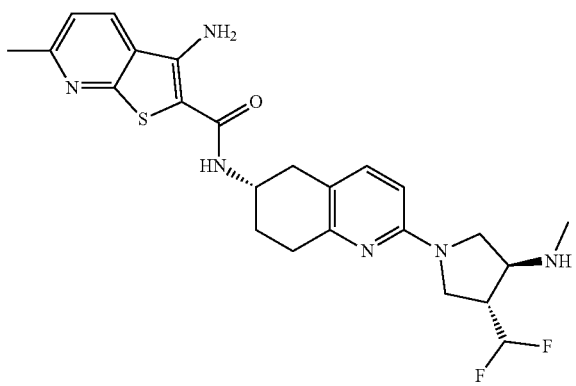
377. 3-amino-N-[(6S)-2-[(3R,4S)-3-
(difluoromethyl)-4-(methylamino)pyrrolidin-1-
yl]-5,6,7,8-tetrahydroquinolin-6-yl]-6-
methylthieno[2,3-b]pyridine-2-carboxamide

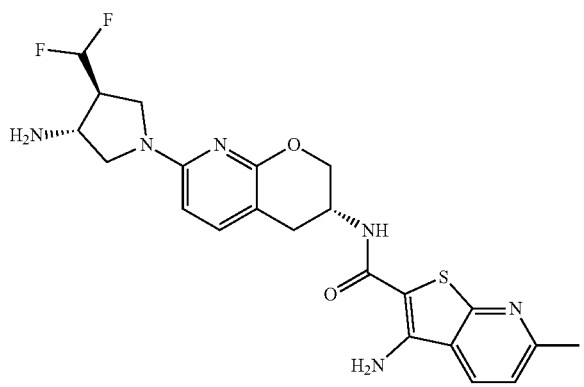 [SMILES: Cc1ccc2c(N)c(C(=O)N[C@H]3COc4nc(N5C[C@H](C(F)F)[C@@H](N)C5)ccc4C3)sc2n1]
378. 3-amino-N-[(3R)-7-[(3R,4S)-3-amino-
4-(difluoromethyl)pyrrolidin-1-yl]-
2H,3H,4H-pyrano[2,3-b]pyridin-3-yl]-6-
methylthieno[2,3-b]pyridine-2-carboxamide
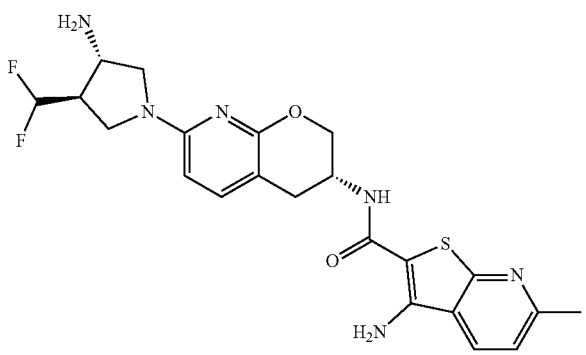 [SMILES: Cc1ccc2c(N)c(C(=O)N[C@H]3COc4nc(N5C[C@@H](N)[C@H](C(F)F)C5)ccc4C3)sc2n1]
379. 3-amino-N-[(3R)-7-[(3S,4R)-3-amino-4-
(difluoromethyl)pyrrolidin-1-yl]-2H,3H,4H-
pyrano[2,3-b]pyridin-3-yl]-6-
methylthieno[2,3-b]pyridine-2-carboxamide
380. 3-amino-N-[(6S)-2-[(3R,4S)-3-amino-
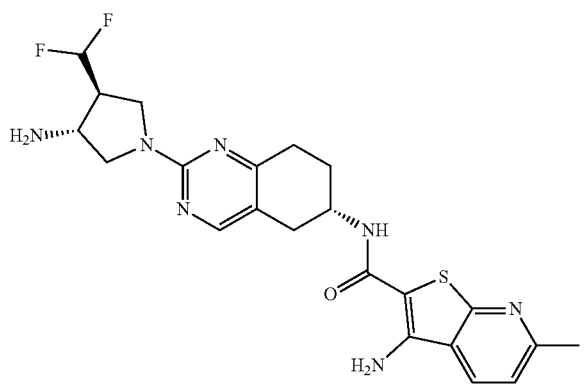 [SMILES: Cc1ccc2c(N)c(C(=O)N[C@H]3CCc4nc(N5C[C@H](C(F)F)[C@@H](N)C5)ncc4C3)sc2n1]
380. 4-(difluoromethyl)pyrrolidin-1-yl]-5,6,7,8-
tetrahydroquinazolin-6-yl]-6-
methylthieno[2,3-b]pyridine-2-carboxamide TABLE 25-continued
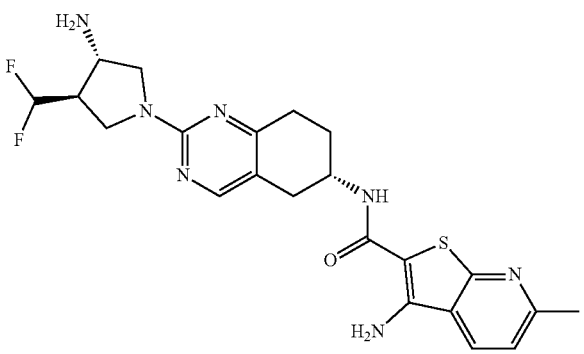 [SMILES: Cc1ccc2c(N)c(C(=O)N[C@H]3CCc4nc(N5C[C@@H](N)[C@H](C(F)F)C5)ncc4C3)sc2n1]
381. 3-amino-N-[(6S)-2-[(3S,4R)-3-amino-4-
(difluoromethyl)pyrrolidin-1-yl]-5,6,7,8-
tetrahydroquinazolin-6-yl]-6-
methylthieno[2,3-b]pyridine-2-carboxamide
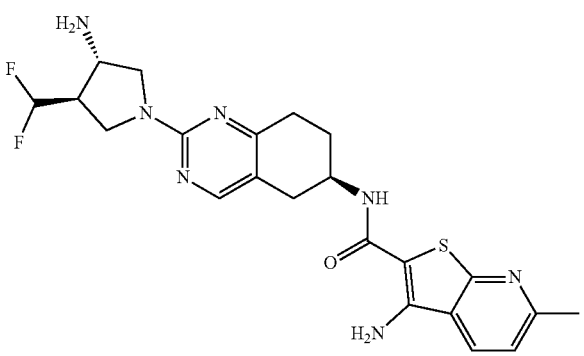 [SMILES: Cc1ccc2c(N)c(C(=O)N[C@@H]3CCc4nc(N5C[C@@H](N)[C@H](C(F)F)C5)ncc4C3)sc2n1]
382. 3-amino-N-[(6R)-2-[(3S,4R)-3-amino-
4-(difluoromethyl)pyrrolidin-1-yl]-5,6,7,8-
tetrahydroquinazolin-6-yl]-6-
methylthieno[2,3-b]pyridine-2-carboxamide
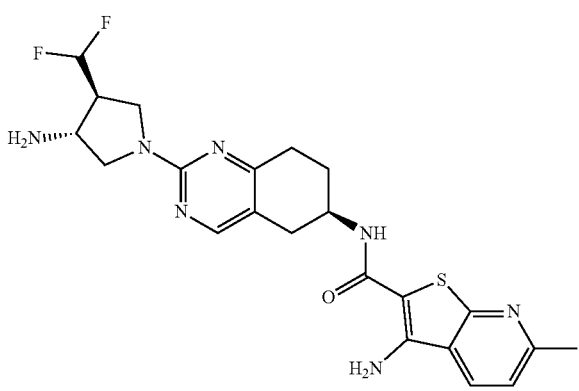 [SMILES: Cc1ccc2c(N)c(C(=O)N[C@@H]3CCc4nc(N5C[C@H](C(F)F)[C@@H](N)C5)ncc4C3)sc2n1]
383. 3-amino-N-[(6R)-2-[(3R,4S)-3-amino-4-
(difluoromethyl)pyrrolidin-1-yl]-5,6,7,8-
tetrahydroquinazolin-6-yl]-6-
methylthieno[2,3-b]pyridine-2-carboxamide TABLE 25-continued
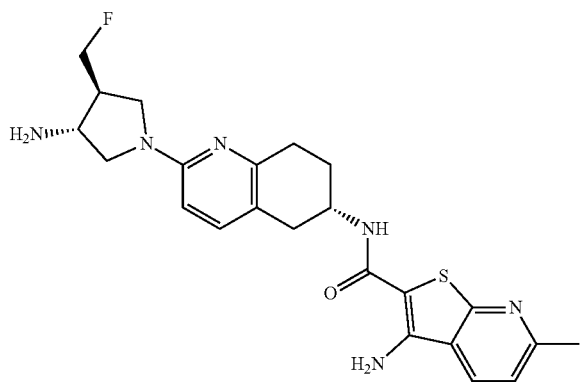 [SMILES: Cc1ccc2c(N)c(C(=O)N[C@H]3CCc4nc(N5C[C@H](CF)[C@@H](N)C5)ccc4C3)sc2n1]
384. 3-amino-N-[(6S)-2-[(3R,4S)-3-amino-
4-(fluoromethyl)pyrrolidin-1-yl]-5,6,7,8-
tetrahydroquinolin-6-yl]-6-methylthieno[2,3-
b]pyridine-2-carboxamide
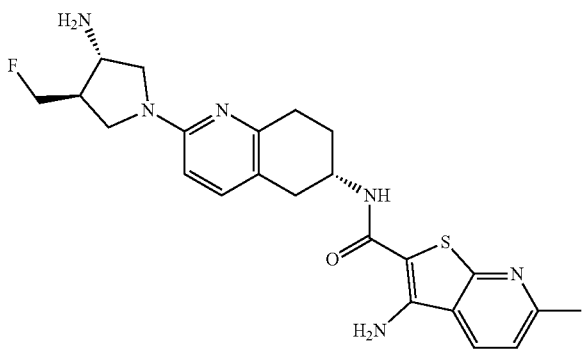 [SMILES: Cc1ccc2c(N)c(C(=O)N[C@H]3CCc4nc(N5C[C@@H](CF)[C@H](N)C5)ccc4C3)sc2n1]
385. 3-amino-N-[(6S)-2-[(3S,4R)-3-amino-4-
(fluoromethyl)pyrrolidin-1-yl]-5,6,7,8-
tetrahydroquinolin-6-yl]-6-methylthieno[2,3-
b]pyridine-2-carboxamide
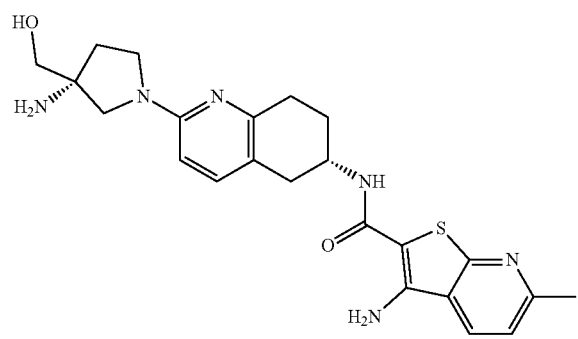 [SMILES: Cc1ccc2c(N)c(C(=O)N[C@H]3CCc4nc(N5CC[C@](N)(CO)C5)ccc4C3)sc2n1]
386. 3-amino-N-[(6S)-2-[(3R)-3-amino-3-
(hydroxymethyl)pyrrolidin-1-yl]-5,6,7,8-
tetrahydroquinolin-6-yl]-6-methylthieno[2,3-
b]pyridine-2-carboxamide TABLE 25-continued
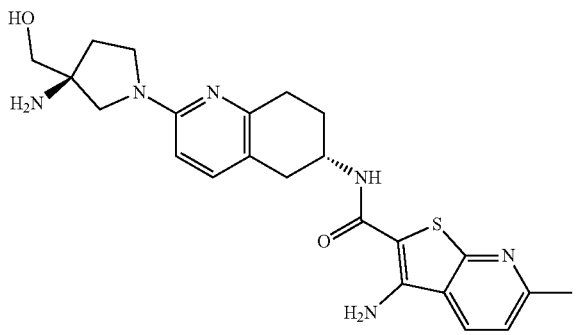 [SMILES: Cc1ccc2c(N)c(C(=O)N[C@H]3CCc4nc(N5CC[C@@](N)(CO)C5)ccc4C3)sc2n1]
387. 3-amino-N-[(6S)-2-[(3S)-3-amino-3-
(hydroxymethyl)pyrrolidin-1-yl]-5,6,7,8-
tetrahydroquinolin-6-yl]-6-methylthieno[2,3-
b]pyridine-2-carboxamide
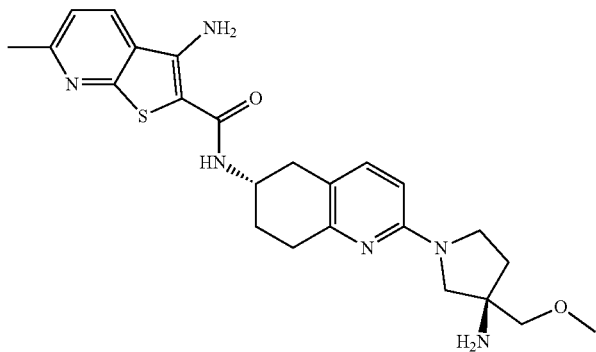
388. 3-amino-N-[(6S)-2-[(3R)-3-amino-3-
(methoxymethyl)pyrrolidin-1-yl]-5,6,7,8-
tetrahydroquinolin-6-yl]-6-methylthieno[2,3-
b]pyridine-2-carboxamide
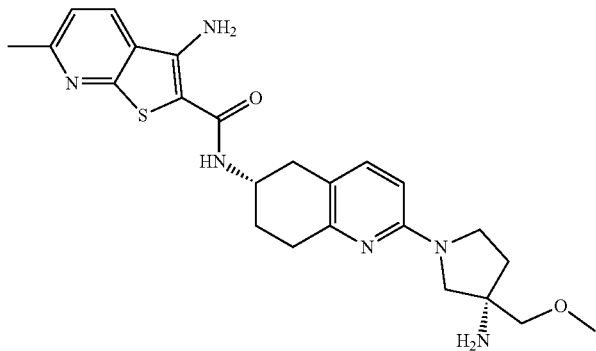
389. 3-amino-N-[(6S)-2-[(3S)-3-amino-3-
(methoxymethyl)pyrrolidin-1-yl]-5,6,7,8-
tetrahydroquinolin-6-yl]-6-methylthieno[2,3-
b]pyridine-2-carboxamide TABLE 25-continued
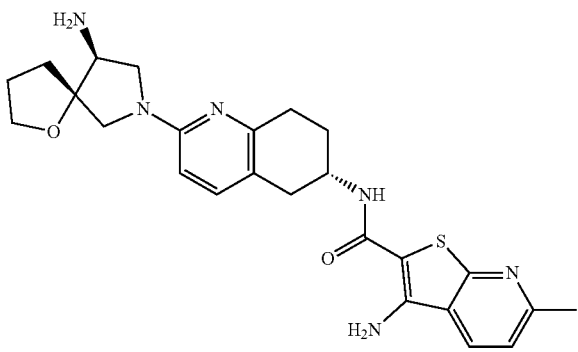
390. 3-amino-N-[(6S)-2-[(5S,9S)-9-amino-1-
oxa-7-azaspiro[4.4]nonan-7-yl]-5,6,7,8-
tetrahydroquinolin-6-yl]-6-methylthieno[2,3-
b]pyridine-2-carboxamide
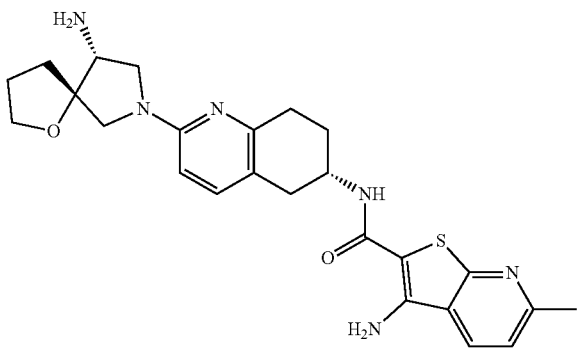 [SMILES: Cc1ccc2c(N)c(C(=O)N[C@H]3CCc4nc(N5C[C@@H](N)[C@]6(CCCO6)C5)ccc4C3)sc2n1]
391. 3-amino-N-[(6S)-2-[(5S,9R)-9-amino-1-
oxa-7-azaspiro[4.4]nonan-7-yl]-5,6,7,8-
tetrahydroquinolin-6-yl]-6-methylthieno[2,3-
b]pyridine-2-carboxamide
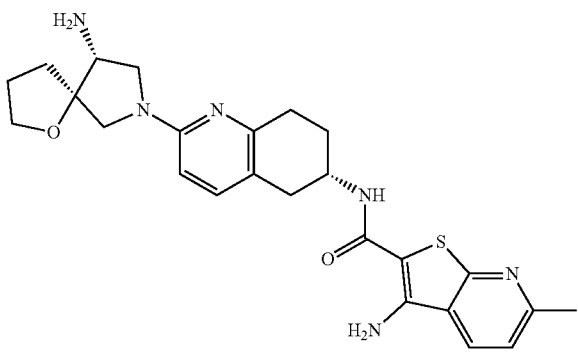 [SMILES: Cc1ccc2c(N)c(C(=O)N[C@H]3CCc4nc(N5C[C@@H](N)[C@@]6(CCCO6)C5)ccc4C3)sc2n1]
392. 3-amino-N-[(6S)-2-[(5R,9R)-9-amino-
1-oxa-7-azaspiro[4.4]nonan-7-yl]-5,6,7,8-
tetrahydroquinolin-6-yl]-6-methylthieno[2,3-
b]pyridine-2-carboxamide

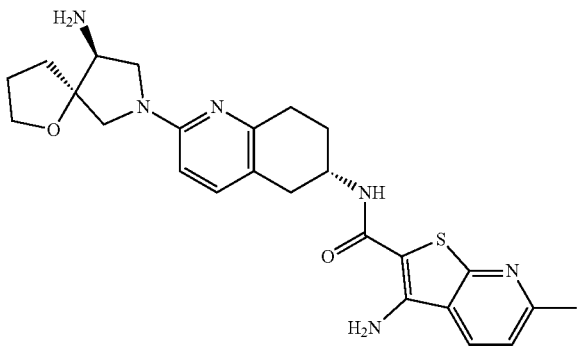 [SMILES: Cc1ccc2c(N)c(C(=O)N[C@H]3CCc4nc(N5C[C@H](N)[C@@]6(CCCO6)C5)ccc4C3)sc2n1]
393. 3-amino-N-[(6S)-2-[(5R,9S)-9-amino-1-oxa-7-azaspiro[4.4]nonan-7-yl]-5,6,7,8-tetrahydroquinolin-6-yl]-6-methylthieno[2,3-b]pyridine-2-carboxamide
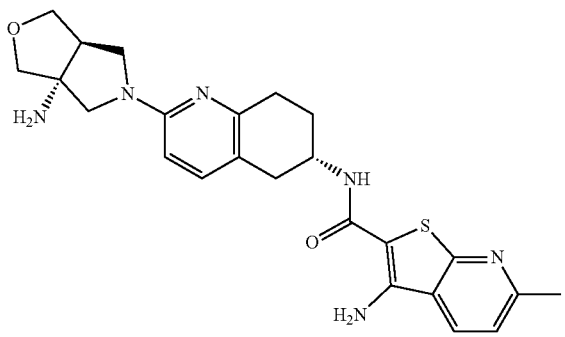 [SMILES: Cc1ccc2c(N)c(C(=O)N[C@H]3CCc4nc(N5C[C@@H]6COC[C@]6(N)C5)ccc4C3)sc2n1]
394. N-[(6S)-2-[(3aR,6aS)-3a-amino-hexahydro-1H-furo[3,4-c]pyrrol-5-yl]-5,6,7,8-tetrahydroquinolin-6-yl]-3-amino-6-methylthieno[2,3-b]pyridine-2-carboxamide
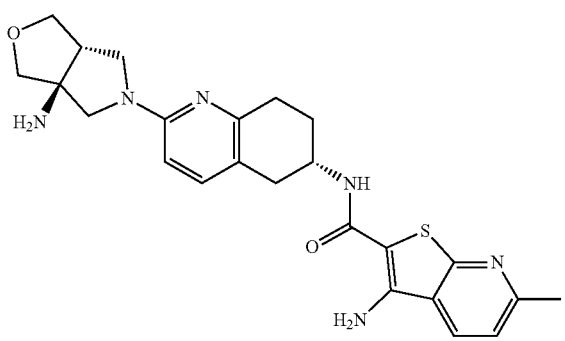 [SMILES: Cc1ccc2c(N)c(C(=O)N[C@H]3CCc4nc(N5C[C@H]6COC[C@@]6(N)C5)ccc4C3)sc2n1]
395. N-[(6S)-2-[(3aS,6aR)-3a-amino-hexahydro-1H-furo[3,4-c]pyrrol-5-yl]-5,6,7,8-tetrahydroquinolin-6-yl]-3-amino-6-methylthieno[2,3-b]pyridine-2-carboxamide TABLE 25-continued
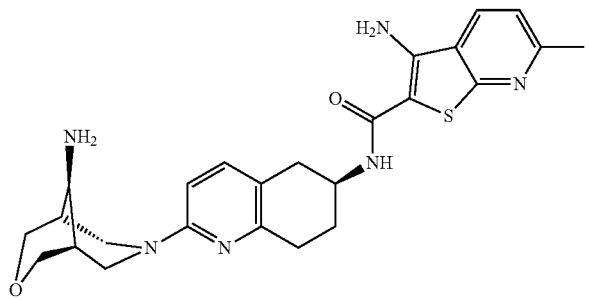
396. 3-amino-6-methyl-N-[(6S)-2-
[(1R,5S,9r)-9-amino-3-oxa-7-
azabicyclo[3.3.1]nonan-7-yl]-5,6,7,8-
tetrahydroquinolin-6-yl]thieno[2,3-
b]pyridine-2-carboxamide
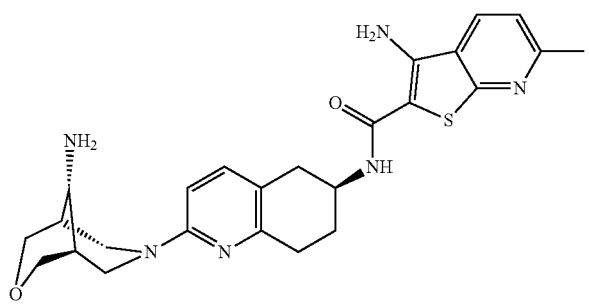
397. 3-amino-6-methyl-N-[(6S)-2-[(1R,5S,9s)-
9-amino-3-oxa-7-azabicyclo[3.3.1]nonan-7-
yl]-5,6,7,8-tetrahydroquinolin-6-yl]thieno[2,3-
b]pyridine-2-carboxamide
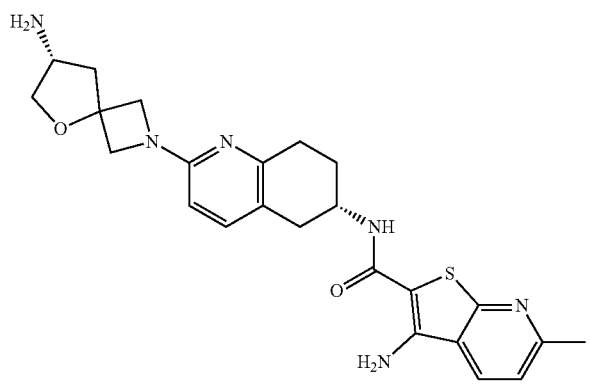 [SMILES: Cc1ccc2c(N)c(C(=O)N[C@H]3CCc4nc(N5CC6(C[C@@H](N)CO6)C5)ccc4C3)sc2n1]
398. 3-amino-N-[(6S)-2-[(7R)-7-amino-5-
oxa-2-azaspiro[3.4]octan-2-yl]-5,6,7,8-
tetrahydroquinolin-6-yl]-6-methylthieno[2,3-
b]pyridine-2-carboxamide TABLE 25-continued
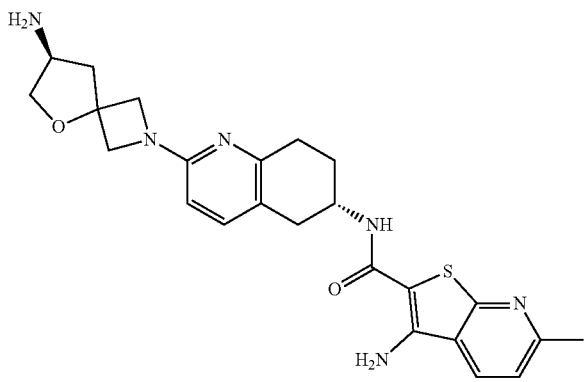 [SMILES: Cc1ccc2c(N)c(C(=O)N[C@H]3CCc4nc(N5CC6(C[C@H](N)CO6)C5)ccc4C3)sc2n1]
399. 3-amino-N-[(6S)-2-[(7S)-7-amino-5-oxa-
2-azaspiro[3.4]octan-2-yl]-5,6,7,8-
tetrahydroquinolin-6-yl]-6-methylthieno[2,3-
b]pyridine-2-carboxamide
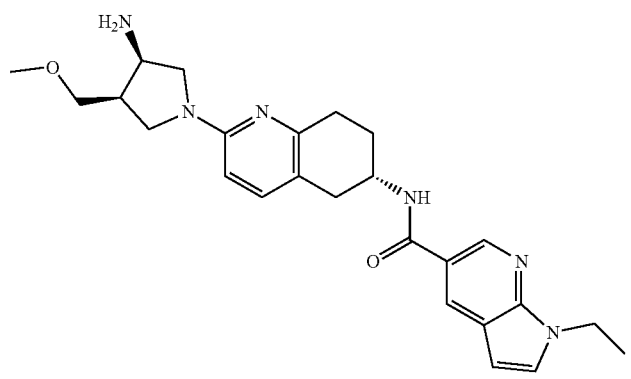 [SMILES: CCn1ccc2cc(C(=O)N[C@H]3CCc4nc(N5C[C@@H](COC)[C@@H](N)C5)ccc4C3)cnc21]
400. N-[(6S)-2-[(3R,4R)-3-amino-4-
(methoxymethyl)pyrrolidin-1-yl]-5,6,7,8-
tetrahydroquinolin-6-yl]-1-ethyl-1H-
pyrrolo[2,3-b]pyridine-5-carboxamide
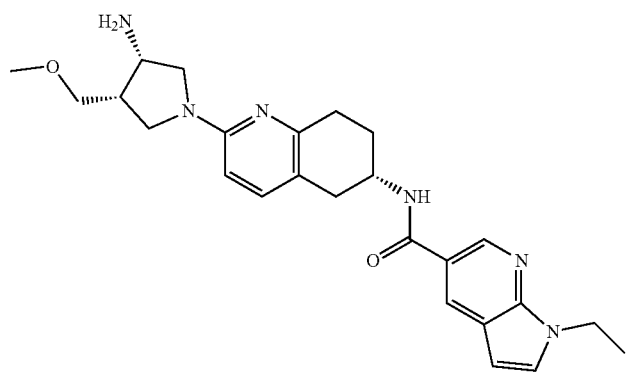 [SMILES: CCn1ccc2cc(C(=O)N[C@H]3CCc4nc(N5C[C@H](COC)[C@H](N)C5)ccc4C3)cnc21]
401. N-[(6S)-2-[(3S,4S)-3-amino-4-
(methoxymethyl)pyrrolidin-1-yl]-5,6,7,8-
tetrahydroquinolin-6-yl]-1-ethyl-1H-
pyrrolo[2,3-b]pyridine-5-carboxamide TABLE 25-continued
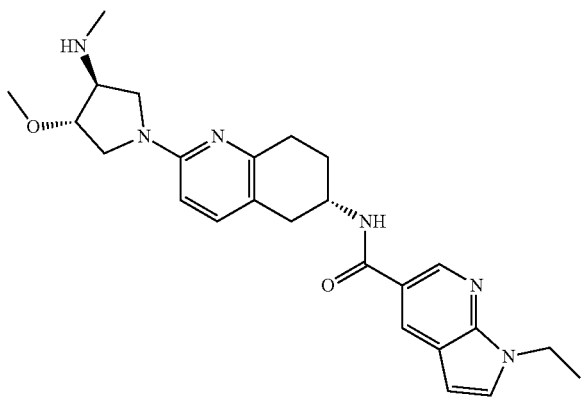 [SMILES: CCn1ccc2cc(C(=O)N[C@H]3CCc4nc(N5C[C@H](NC)[C@@H](OC)C5)ccc4C3)cnc21]
402. 1-ethyl-N-[(6S)-2-[(3S,4S)-3-methoxy-
4-(methylamino)pyrrolidin-1-yl]-5,6,7,8-
tetrahydroquinolin-6-yl]-1H-pyrrolo[2,3-
b]pyridine-5-carboxamide
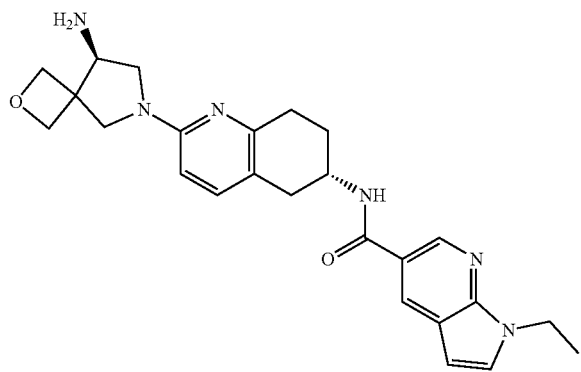 [SMILES: CCn1ccc2cc(C(=O)N[C@H]3CCc4nc(N5C[C@H](N)C6(COC6)C5)ccc4C3)cnc21]
403. N-[(6S)-2-[(8R)-8-amino-2-oxa-6-
azaspiro[3.4]octan-6-yl]-5,6,7,8-
tetrahydroquinolin-6-yl]-1-ethyl-1H-
pyrrolo[2,3-b]pyridine-5-carboxamide
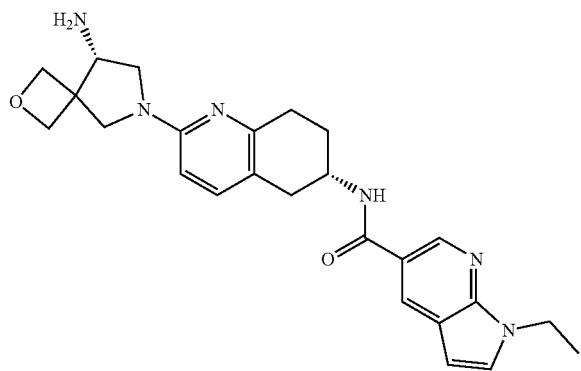 [SMILES: CCn1ccc2cc(C(=O)N[C@H]3CCc4nc(N5C[C@@H](N)C6(COC6)C5)ccc4C3)cnc21]
404. N-[(6S)-2-[(8S)-8-amino-2-oxa-6-
azaspiro[3.4]octan-6-yl]-5,6,7,8-
tetrahydroquinolin-6-yl]-1-ethyl-1H-
pyrrolo[2,3-b]pyridine-5-carboxamide TABLE 25-continued

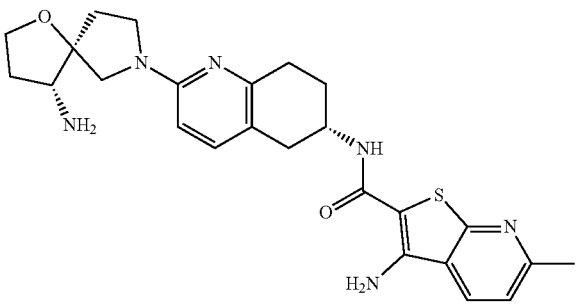 [SMILES: Cc1ccc2c(N)c(C(=O)N[C@H]3CCc4nc(N5CC[C@@]6(C5)OCC[C@H]6N)ccc4C3)sc2n1]

405. 3-amino-N-[(6S)-2-[(4R,5S)-4-amino-1-
oxa-7-azaspiro[4.4]nonan-7-yl]-5,6,7,8-
tetrahydroquinolin-6-yl]-6-methylthieno[2,3-
b]pyridine-2-carboxamide

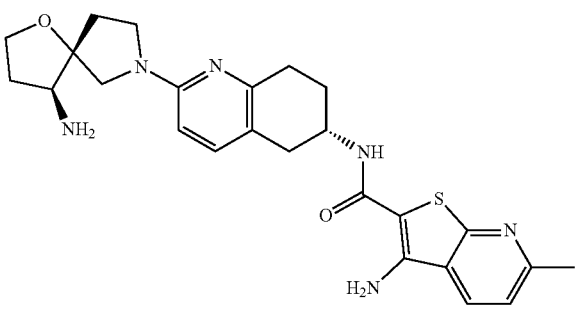 [SMILES: Cc1ccc2c(N)c(C(=O)N[C@H]3CCc4nc(N5CC[C@]6(C5)OCC[C@@H]6N)ccc4C3)sc2n1]

406. 3-amino-N-[(6S)-2-[(4S,5R)-4-amino-
1-oxa-7-azaspiro[4.4]nonan-7-yl]-5,6,7,8-
tetrahydroquinolin-6-yl]-6-methylthieno[2,3-
b]pyridine-2-carboxamide

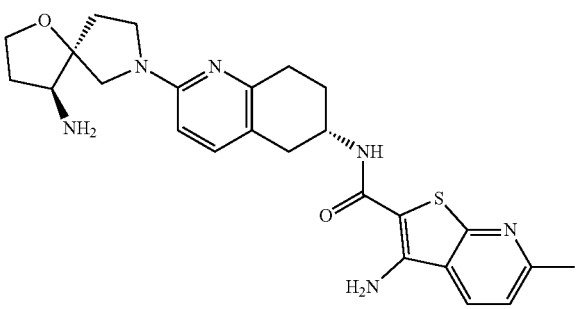 [SMILES: Cc1ccc2c(N)c(C(=O)N[C@H]3CCc4nc(N5CC[C@@]6(C5)OCC[C@@H]6N)ccc4C3)sc2n1]

407. 3-amino-N-[(6S)-2-[(4S,5S)-4-amino-1-
oxa-7-azaspiro[4.4]nonan-7-yl]-5,6,7,8-
tetrahydroquinolin-6-yl]-6-methylthieno[2,3-
b]pyridine-2-carboxamide

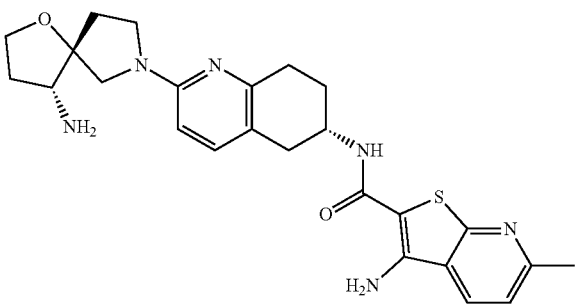 [SMILES: Cc1ccc2c(N)c(C(=O)N[C@H]3CCc4nc(N5CC[C@]6(C5)OCC[C@H]6N)ccc4C3)sc2n1]

408. 3-amino-N-[(6S)-2-[(4R,5R)-4-amino-
1-oxa-7-azaspiro[4.4]nonan-7-yl]-5,6,7,8-
tetrahydroquinolin-6-yl]-6-methylthieno[2,3-
b]pyridine-2-carboxamide TABLE 25-continued

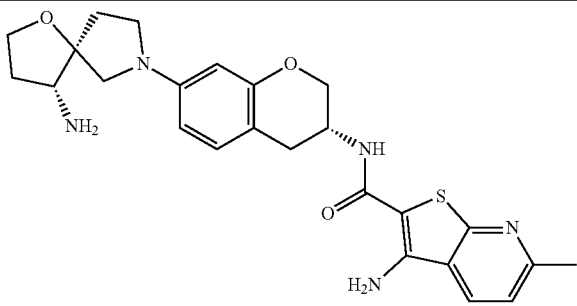

409. 3-amino-N-[(3R)-7-[(4R,5S)-4-amino-1-
oxa-7-azaspiro[4.4]nonan-7-yl]-3,4-dihydro-
2H-1-benzopyran-3-yl]-6-methylthieno[2,3-
b]pyridine-2-carboxamide

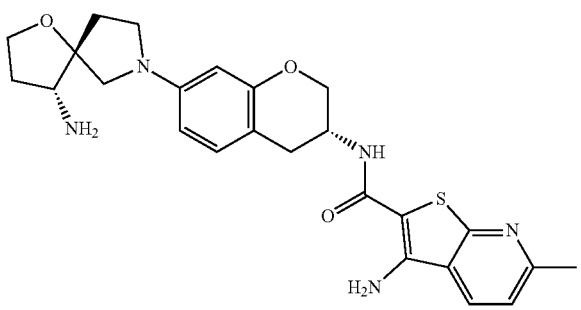 [SMILES: Cc1ccc2c(N)c(C(=O)N[C@H]3COc4cc(N5CC[C@]6(C5)OCC[C@H]6N)ccc4C3)sc2n1]

410. 3-amino-N-[(3R)-7-[(4R,5R)-4-amino-
1-oxa-7-azaspiro[4.4]nonan-7-yl]-3,4-
dihydro-2H-1-benzopyran-3-yl]-6-
methylthieno[2,3-b]pyridine-2-carboxamide

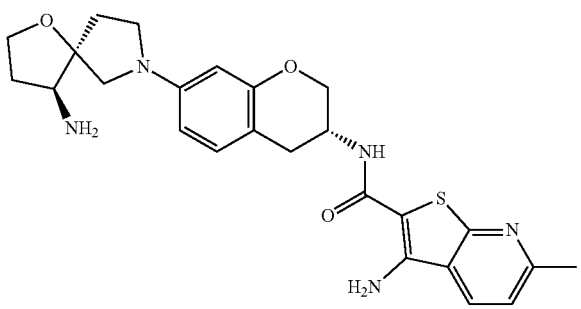 [SMILES: Cc1ccc2c(N)c(C(=O)N[C@H]3COc4cc(N5CC[C@@]6(C5)OCC[C@@H]6N)ccc4C3)sc2n1]

411. 3-amino-N-[(3R)-7-[(4S,5S)-4-amino-1-
oxa-7-azaspiro[4.4]nonan-7-yl]-3,4-dihydro-
2H-1-benzopyran-3-yl]-6-methylthieno[2,3-
b]pyridine-2-carboxamide

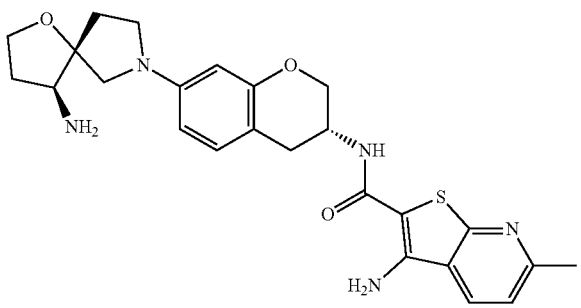 [SMILES: Cc1ccc2c(N)c(C(=O)N[C@H]3COc4cc(N5CC[C@]6(C5)OCC[C@@H]6N)ccc4C3)sc2n1]

412. 3-amino-N-[(3R)-7-[(4S,5R)-4-amino-
1-oxa-7-azaspiro[4.4]nonan-7-yl]-3,4-
dihydro-2H-1-benzopyran-3-yl]-6-
methylthieno[2,3-b]pyridine-2-carboxamide

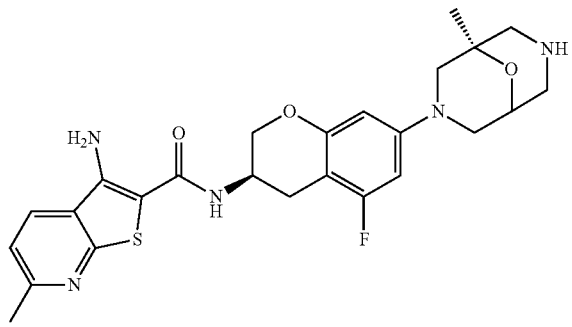 [SMILES: Cc1ccc2c(N)c(C(=O)N[C@H]3COc4cc(N5CC6CNC[C@](C)(C5)O6)cc(F)c4C3)sc2n1]
413. 3-amino-N-[(3R)-5-fluoro-7-[(1R)-1-methyl-9-oxa-3,7-diazabicyclo[3.3.1]nonan-3-yl]-3,4-dihydro-2H-1-benzopyran-3-yl]-6-methylthieno[2,3-b]pyridine-2-carboxamide
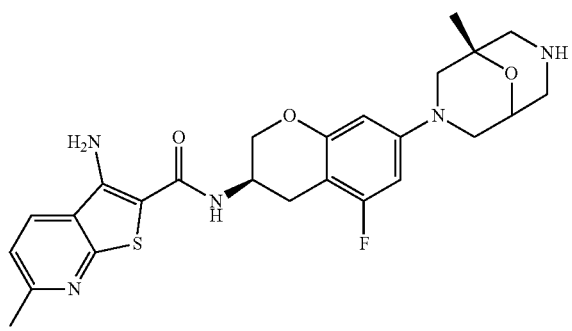 [SMILES: Cc1ccc2c(N)c(C(=O)N[C@H]3COc4cc(N5CC6CNC[C@@](C)(C5)O6)cc(F)c4C3)sc2n1]
414. 3-amino-N-[(3R)-5-fluoro-7-[(1S)-1-methyl-9-oxa-3,7-diazabicyclo[3.3.1]nonan-3-yl]-3,4-dihydro-2H-1-benzopyran-3-yl]-6-methylthieno[2,3-b]pyridine-2-carboxamide
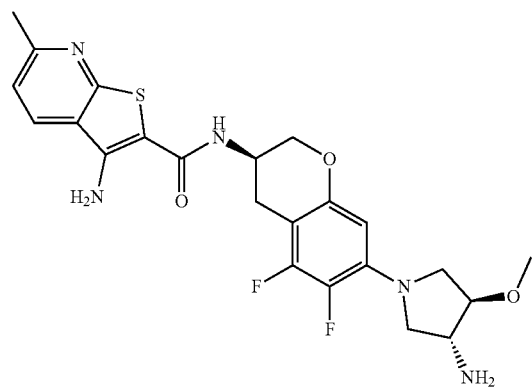 [SMILES: CO[C@@H]1CN(c2cc3c(c(F)c2F)C[C@@H](NC(=O)c2sc4nc(C)ccc4c2N)CO3)C[C@H]1N]
415. 3-amino-N-[(3R)-7-[(3R,4R)-3-amino-4-methoxypyrrolidin-1-yl]-5,6-difluoro-3,4-dihydro-2H-1-benzopyran-3-yl]-6-methylthieno[2,3-b]pyridine-2-carboxamide

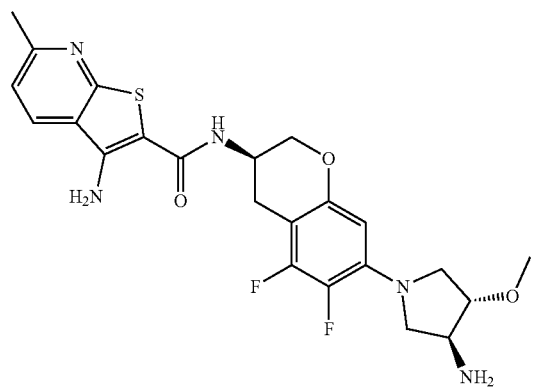 [SMILES: CO[C@H]1CN(c2cc3c(c(F)c2F)C[C@@H](NC(=O)c2sc4nc(C)ccc4c2N)CO3)C[C@@H]1N]
416. 3-amino-N-[(3R)-7-[(3S,4S)-3-amino-4-methoxypyrrolidin-1-yl]-5,6-difluoro-3,4-dihydro-2H-1-benzopyran-3-yl]-6-methylthieno[2,3-b]pyridine-2-carboxamide
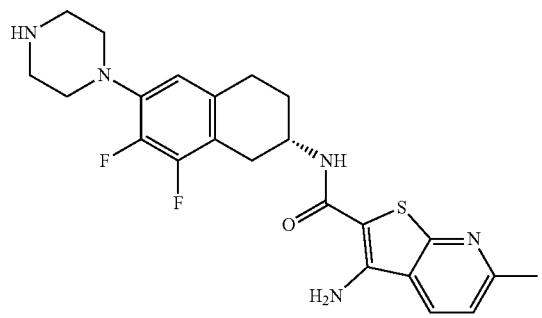 [SMILES: Cc1ccc2c(N)c(C(=O)N[C@H]3CCc4cc(N5CCNCC5)c(F)c(F)c4C3)sc2n1]
417. 3-amino-N-[(2S)-7,8-difluoro-6-(piperazin-1-yl)-1,2,3,4-tetrahydronaphthalen-2-yl]-6-methylthieno[2,3-b]pyridine-2-carboxamide
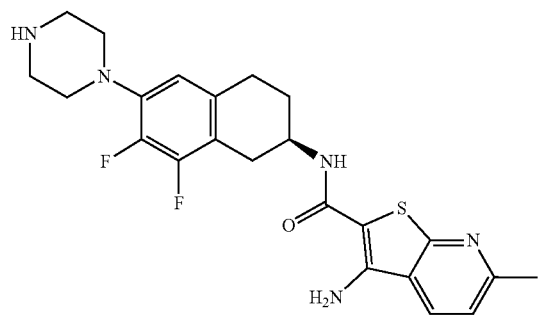 [SMILES: Cc1ccc2c(N)c(C(=O)N[C@@H]3CCc4cc(N5CCNCC5)c(F)c(F)c4C3)sc2n1]
418. 3-amino-N-[(2R)-7,8-difluoro-6-(piperazin-1-yl)-1,2,3,4-tetrahydronaphthalen-2-yl]-6-methylthieno[2,3-b]pyridine-2-carboxamide

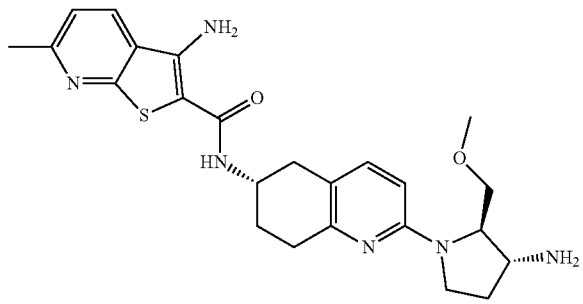 [SMILES: COC[C@H]1[C@H](N)CCN1c1ccc2c(n1)CC[C@H](NC(=O)c1sc3nc(C)ccc3c1N)C2]
419. 3-amino-N-[(6S)-2-[(2R,3R)-3-amino-2-(methoxymethyl)pyrrolidin-1-yl]-5,6,7,8-tetrahydroquinolin-6-yl]-6-methylthieno[2,3-b]pyridine-2-carboxamide
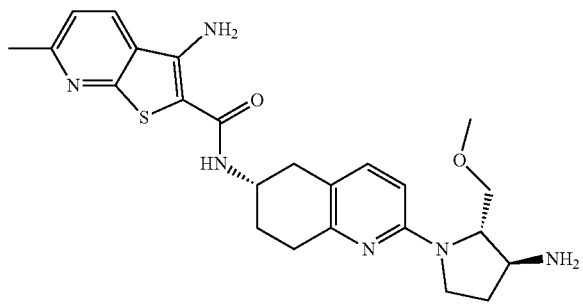 [SMILES: COC[C@@H]1[C@@H](N)CCN1c1ccc2c(n1)CC[C@H](NC(=O)c1sc3nc(C)ccc3c1N)C2]
420. 3-amino-N-[(6S)-2-[(2S,3S)-3-amino-2-(methoxymethyl)pyrrolidin-1-yl]-5,6,7,8-tetrahydroquinolin-6-yl]-6-methylthieno[2,3-b]pyridine-2-carboxamide
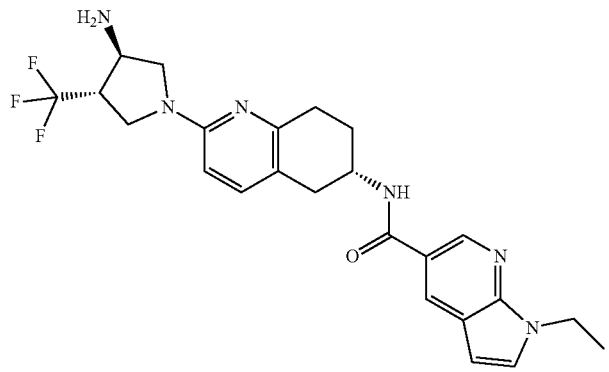 [SMILES: CCn1ccc2cc(C(=O)N[C@H]3CCc4nc(N5C[C@H](N)[C@@H](C(F)(F)F)C5)ccc4C3)cnc21]
421. N-[(6S)-2-[(3R,4S)-3-amino-4-(trifluoromethyl)pyrrolidin-1-yl]-5,6,7,8-tetrahydroquinolin-6-yl]-1-ethyl-1H-pyrrolo[2,3-b]pyridine-5-carboxamide

TABLE 25-continued
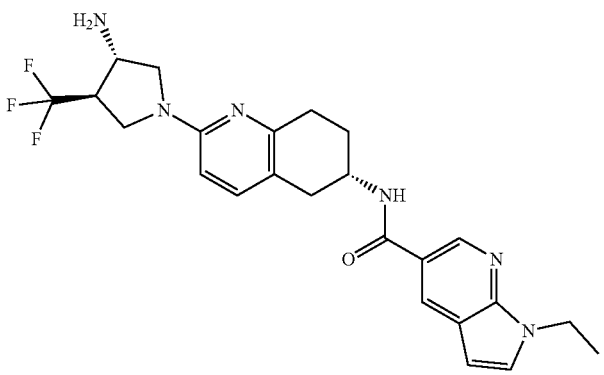 [SMILES: CCn1ccc2cc(C(=O)N[C@H]3CCc4nc(N5C[C@@H](N)[C@H](C(F)(F)F)C5)ccc4C3)cnc21]
422. N-[(6S)-2-[(3S,4R)-3-amino-4-
(trifluoromethyl)pyrrolidin-1-yl]-5,6,7,8-
tetrahydroquinolin-6-yl]-1-ethyl-1H-
pyrrolo[2,3-b]pyridine-5-carboxamide
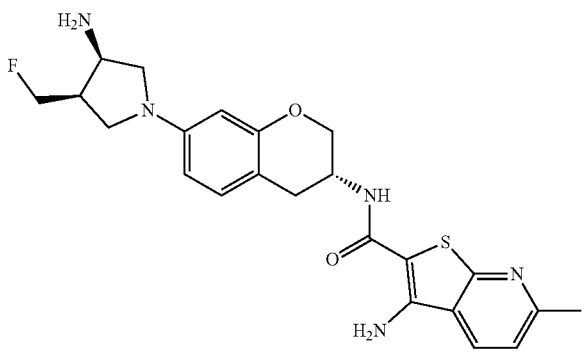 [SMILES: Cc1ccc2c(N)c(C(=O)N[C@H]3COc4cc(N5C[C@@H](CF)[C@@H](N)C5)ccc4C3)sc2n1]
423. 3-amino-N-[(3R)-7-[(3R,4R)-3-amino-4-
(fluoromethyl)pyrrolidin-1-yl]-3,4-dihydro-
2H-1-benzopyran-3-yl]-6-methylthieno[2,3-
b]pyridine-2-carboxamide
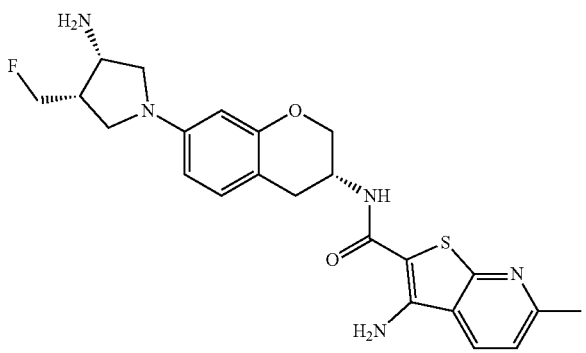
424. 3-amino-N-[(3R)-7-[(3S,4S)-3-amino-
4-(fluoromethyl)pyrrolidin-1-yl]-3,4-
dihydro-2H-1-benzopyran-3-yl]-6-
methylthieno[2,3-b]pyridine-2-carboxamide TABLE 25-continued
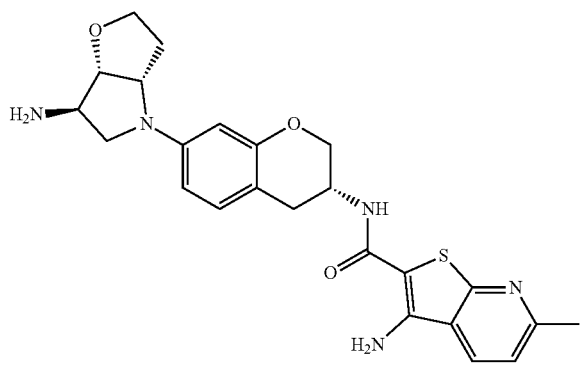 [SMILES: Cc1ccc2c(N)c(C(=O)N[C@H]3COc4cc(N5C[C@@H](N)[C@@H]6OCC[C@@H]65)ccc4C3)sc2n1]
425. N-[(3R)-7-[(3aS,6R,6aS)-6-amino-
hexahydro-2H-furo[3,2-b]pyrrol-4-yl]-3,4-
dihydro-2H-1-benzopyran-3-yl]-3-amino-6-
methylthieno[2,3-b]pyridine-2-carboxamide
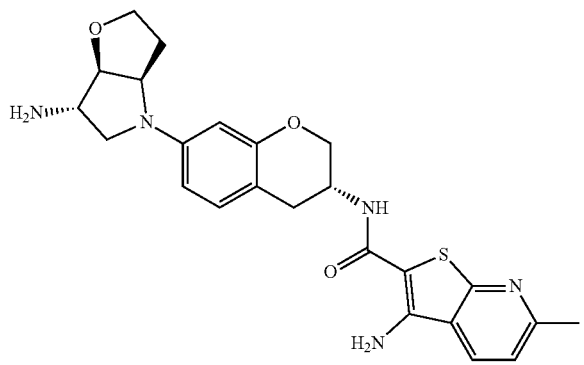 [SMILES: Cc1ccc2c(N)c(C(=O)N[C@H]3COc4cc(N5C[C@H](N)[C@H]6OCC[C@H]65)ccc4C3)sc2n1]
426. N-[(3R)-7-[(3aR,6S,6aR)-6-amino-
hexahydro-2H-furo[3,2-b]pyrrol-4-yl]-3,4-
dihydro-2H-1-benzopyran-3-yl]-3-amino-6-
methylthieno[2,3-b]pyridine-2-carboxamide
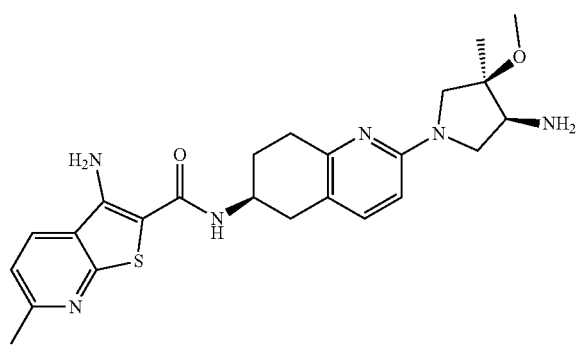 [SMILES: CO[C@]1(C)CN(c2ccc3c(n2)CC[C@H](NC(=O)c2sc4nc(C)ccc4c2N)C3)C[C@@H]1N]
427. 3-amino-N-[(6S)-2-[(3R,4S)-4-amino-3-
methoxy-3-methylpyrrolidin-1-yl]-5,6,7,8-
tetrahydroquinolin-6-yl]-6-methylthieno[2,3-
b]pyridine-2-carboxamide TABLE 25-continued
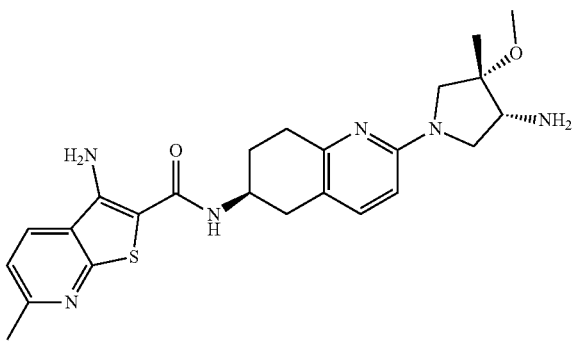 [SMILES: CO[C@@]1(C)CN(c2ccc3c(n2)CC[C@H](NC(=O)c2sc4nc(C)ccc4c2N)C3)C[C@H]1N]
428. 3-amino-N-[(6S)-2-[(3S,4R)-4-amino-
3-methoxy-3-methylpyrrolidin-1-yl]-5,6,7,8-
tetrahydroquinolin-6-yl]-6-methylthieno[2,3-
b]pyridine-2-carboxamide
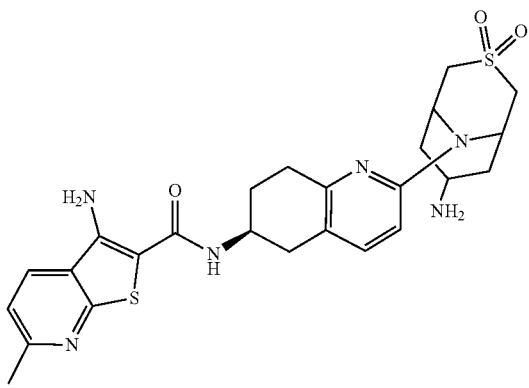 [SMILES: Cc1ccc2c(N)c(C(=O)N[C@H]3CCc4nc(N5C6CC(N)CC5CS(=O)(=O)C6)ccc4C3)sc2n1]
429. 3-amino-N-[(6S)-2-{7-amino-3,3-dioxo-
3λ6-thia-9-azabicyclo[3.3.1]nonan-9-yl}-
5,6,7,8-tetrahydroquinolin-6-yl]-6-
methylthieno[2,3-b]pyridine-2-carboxamide
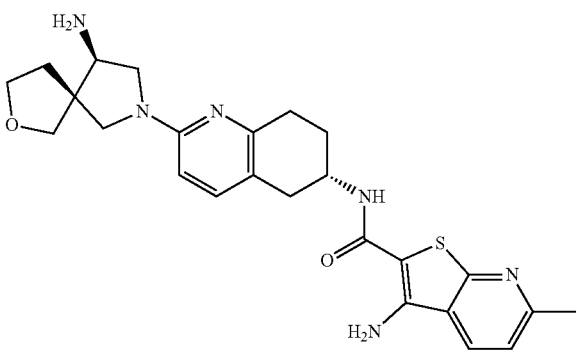 [SMILES: Cc1ccc2c(N)c(C(=O)N[C@H]3CCc4nc(N5C[C@H](N)[C@]6(CCOC6)C5)ccc4C3)sc2n1]
430. 3-amino-N-[(6S)-2-[(5S,9R)-9-amino-
2-oxa-7-azaspiro[4.4]nonan-7-yl]-5,6,7,8-
tetrahydroquinolin-6-yl]-6-methylthieno[2,3-
b]pyridine-2-carboxamide TABLE 25-continued
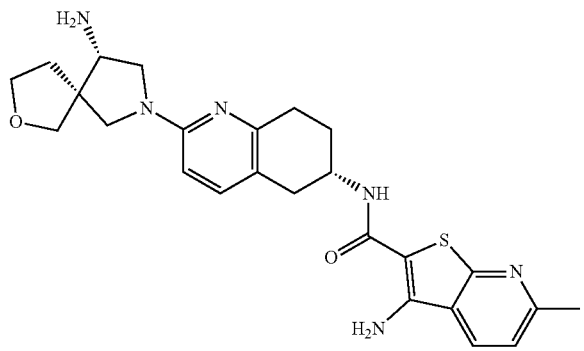 [SMILES: Cc1ccc2c(N)c(C(=O)N[C@H]3CCc4nc(N5C[C@@H](N)[C@@]6(CCOC6)C5)ccc4C3)sc2n1]
431. 3-amino-N-[(6S)-2-[(5R,9S)-9-amino-2-
oxa-7-azaspiro[4.4]nonan-7-yl]-5,6,7,8-
tetrahydroquinolin-6-yl]-6-methylthieno[2,3-
b]pyridine-2-carboxamide
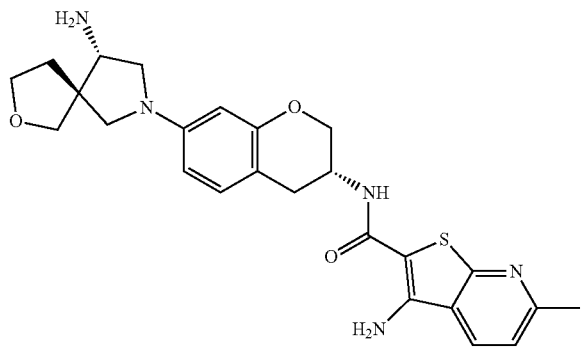 [SMILES: Cc1ccc2c(N)c(C(=O)N[C@H]3COc4cc(N5C[C@@H](N)[C@]6(CCOC6)C5)ccc4C3)sc2n1]
432. 3-amino-N-[(3R)-7-[(5S,9S)-9-amino-
2-oxa-7-azaspiro[4.4]nonan-7-yl]-3,4-
dihydro-2H-1-benzopyran-3-yl]-6-
methylthieno[2,3-b]pyridine-2-carboxamide
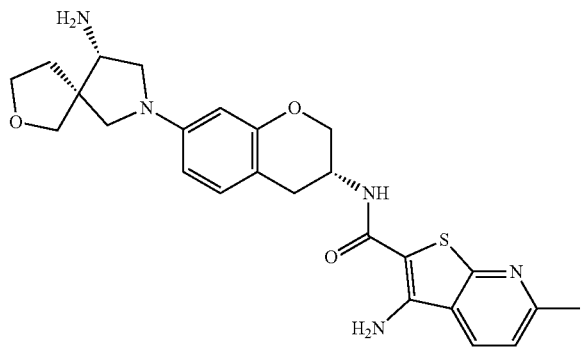 [SMILES: Cc1ccc2c(N)c(C(=O)N[C@H]3COc4cc(N5C[C@@H](N)[C@@]6(CCOC6)C5)ccc4C3)sc2n1]
433. 3-amino-N-[(3R)-7-[(5R,9S)-9-amino-2-
oxa-7-azaspiro[4.4]nonan-7-yl]-3,4-dihydro-
2H-1-benzopyran-3-yl]-6-methylthieno[2,3-
b]pyridine-2-carboxamide TABLE 25-continued
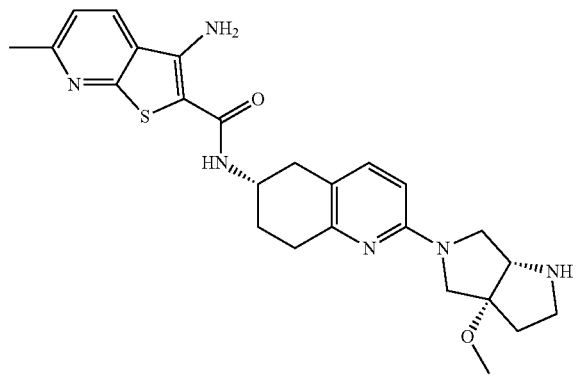 [SMILES: CO[C@@]12CCN[C@H]1CN(c1ccc3c(n1)CC[C@H](NC(=O)c1sc4nc(C)ccc4c1N)C3)C2]
434. N-[(6S)-2-[(3aR,6aS)-3a-methoxy-
octahydropyrrolo[2,3-c]pyrrol-5-yl]-5,6,7,8-
tetrahydroquinolin-6-yl]-3-amino-6-
methylthieno[2,3-b]pyridine-2-carboxamide
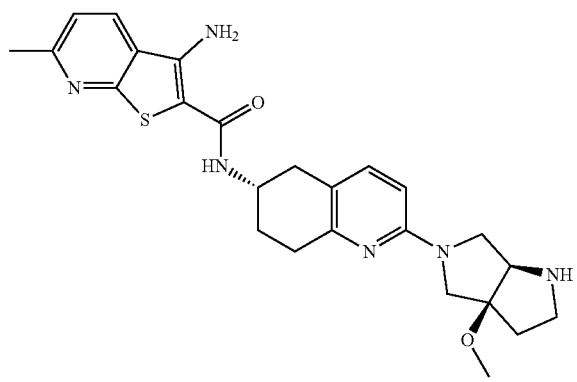 [SMILES: CO[C@]12CCN[C@@H]1CN(c1ccc3c(n1)CC[C@H](NC(=O)c1sc4nc(C)ccc4c1N)C3)C2]
435. N-[(6S)-2-[(3aS,6aR)-3a-methoxy-
octahydropyrrolo[2,3-c]pyrrol-5-yl]-5,6,7,8-
tetrahydroquinolin-6-yl]-3-amino-6-
methylthieno[2,3-b]pyridine-2-carboxamide
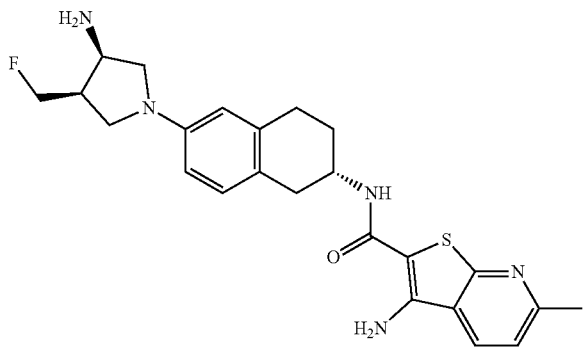 [SMILES: Cc1ccc2c(N)c(C(=O)N[C@H]3CCc4cc(N5C[C@@H](CF)[C@@H](N)C5)ccc4C3)sc2n1]
436. 3-amino-N-[(2S)-6-[(3R,4R)-3-amino-
4-(fluoromethyl)pyrrolidin-1-yl]-1,2,3,4-
tetrahydronaphthalen-2-yl]-6-
methylthieno[2,3-b]pyridine-2-carboxamide TABLE 25-continued
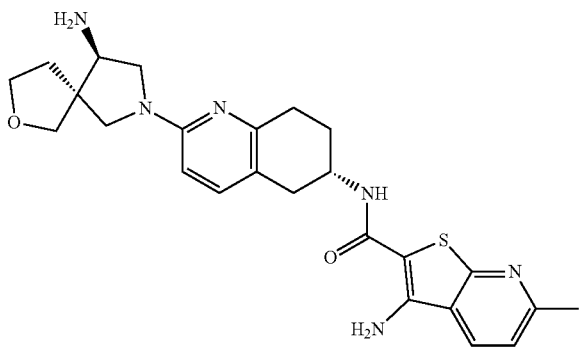 [SMILES: Cc1ccc2c(N)c(C(=O)N[C@H]3CCc4nc(N5C[C@H](N)[C@@]6(CCOC6)C5)ccc4C3)sc2n1]
437. 3-amino-N-[(6S)-2-[(5R,9R)-9-amino-2-
oxa-7-azaspiro[4.4]nonan-7-yl]-5,6,7,8-
tetrahydroquinolin-6-yl]-6-methylthieno[2,3-
b]pyridine-2-carboxamide
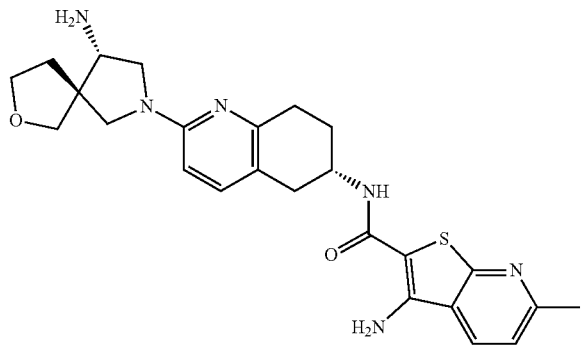 [SMILES: Cc1ccc2c(N)c(C(=O)N[C@H]3CCc4nc(N5C[C@@H](N)[C@]6(CCOC6)C5)ccc4C3)sc2n1]
438. 3-amino-N-[(6S)-2-[(5S,9S)-9-amino-2-
oxa-7-azaspiro[4.4]nonan-7-yl]-5,6,7,8-
tetrahydroquinolin-6-yl]-6-methylthieno[2,3-
b]pyridine-2-carboxamide
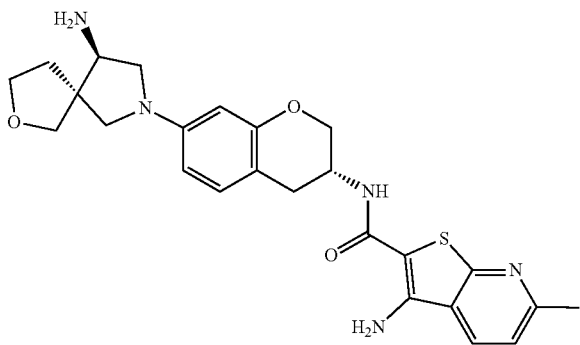 [SMILES: Cc1ccc2c(N)c(C(=O)N[C@H]3COc4cc(N5C[C@H](N)[C@@]6(CCOC6)C5)ccc4C3)sc2n1]
439. 3-amino-N-[(3R)-7-[(5R,9R)-9-amino-2-
oxa-7-azaspiro[4.4]nonan-7-yl]-3,4-dihydro-
2H-1-benzopyran-3-yl]-6-methylthieno[2,3-
b]pyridine-2-carboxamide TABLE 25-continued
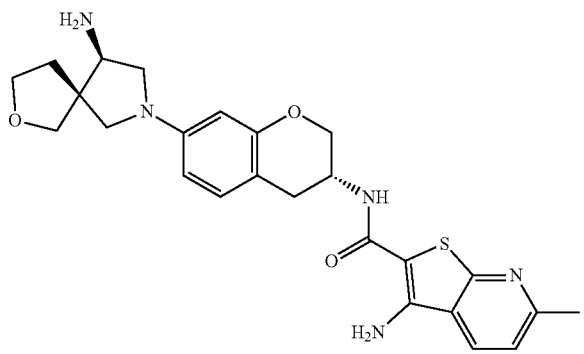 [SMILES: Cc1ccc2c(N)c(C(=O)N[C@H]3COc4cc(N5C[C@H](N)[C@]6(CCOC6)C5)ccc4C3)sc2n1]
440. 3-amino-N-[(3R)-7-[(5S,9R)-9-amino-
2-oxa-7-azaspiro[4.4]nonan-7-yl]-3,4-
dihydro-2H-1-benzopyran-3-yl]-6-
methylthieno[2,3-b]pyridine-2-carboxamide
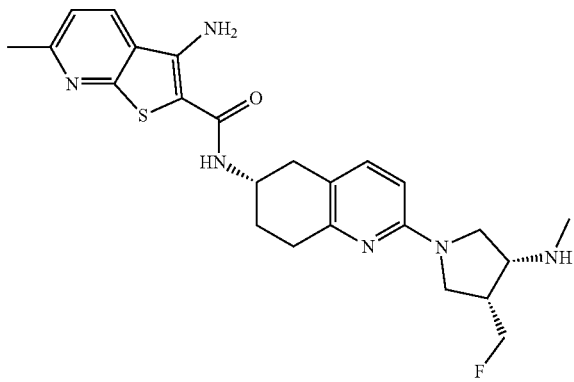
441. 3-amino-N-[(6S)-2-[(3R,4R)-3-
(fluoromethyl)-4-(methylamino)pyrrolidin-1-
yl]-5,6,7,8-tetrahydroquinolin-6-yl]-6-
methylthieno[2,3-b]pyridine-2-carboxamide
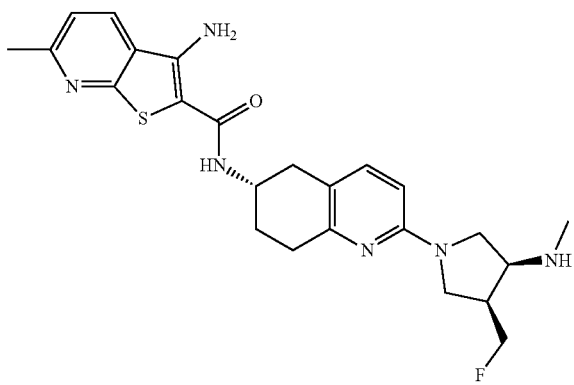
442. 3-amino-N-[(6S)-2-[(3S,4S)-3-
(fluoromethyl)-4-(methylamino)pyrrolidin-1-
yl]-5,6,7,8-tetrahydroquinolin-6-yl]-6-
methylthieno[2,3-b]pyridine-2-carboxamide TABLE 25-continued
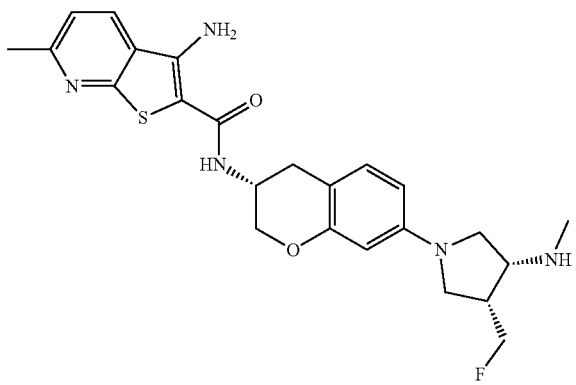
443. 3-amino-N-[(3R)-7-[(3R,4R)-3-
(fluoromethyl)-4-(methylamino)pyrrolidin-1-
yl]-3,4-dihydro-2H-1-benzopyran-3-yl]-6-
methylthieno[2,3-b]pyridine-2-carboxamide
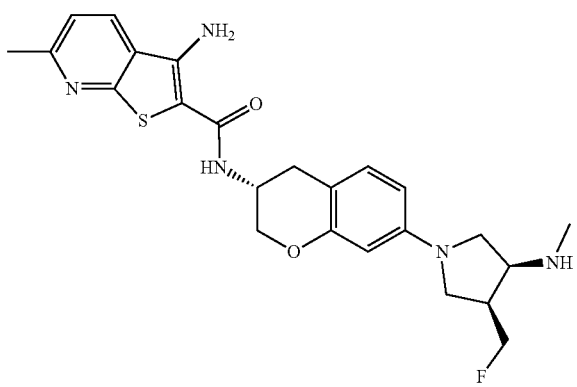
444. 3-amino-N-[(3R)-7-[(3S,4S)-3-
(fluoromethyl)-4-(methylamino)pyrrolidin-1-
yl]-3,4-dihydro-2H-1-benzopyran-3-yl]-6-
methylthieno[2,3-b]pyridine-2-carboxamide
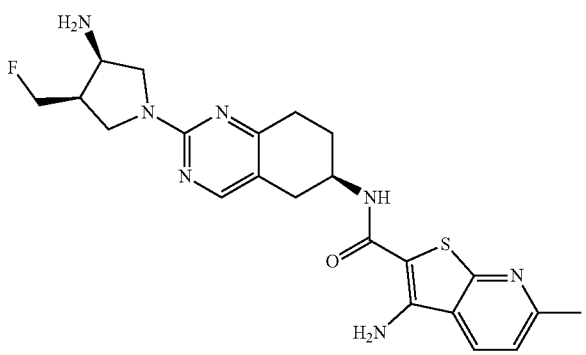 [SMILES: Cc1ccc2c(N)c(C(=O)N[C@@H]3CCc4nc(N5C[C@@H](CF)[C@@H](N)C5)ncc4C3)sc2n1]
445. 3-amino-N-[(6R)-2-[(3R,4R)-3-amino-4-
(fluoromethyl)pyrrolidin-1-yl]-5,6,7,8-
tetrahydroquinazolin-6-yl]-6-
methylthieno[2,3-b]pyridine-2-carboxamide

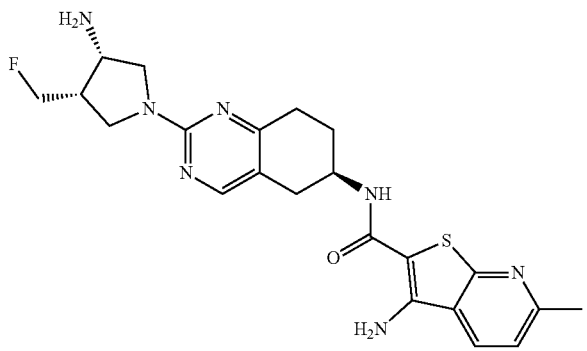 [SMILES: Cc1ccc2c(N)c(C(=O)N[C@@H]3CCc4nc(N5C[C@H](CF)[C@H](N)C5)ncc4C3)sc2n1]
446. 3-amino-N-[(6R)-2-[(3S,4S)-3-amino-
4-(fluoromethyl)pyrrolidin-1-yl]-5,6,7,8-
tetrahydroquinazolin-6-yl]-6-
methylthieno[2,3-b]pyridine-2-carboxamide
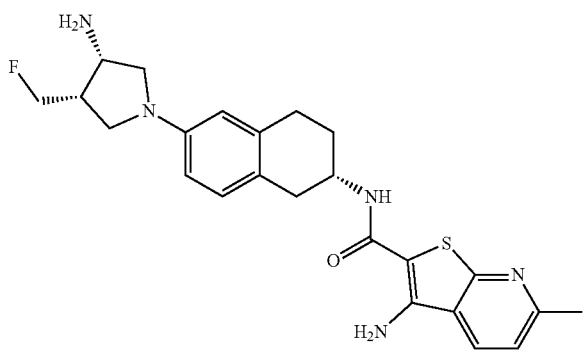 [SMILES: Cc1ccc2c(N)c(C(=O)N[C@H]3CCc4cc(N5C[C@H](CF)[C@H](N)C5)ccc4C3)sc2n1]
447. 3-amino-N-[(2S)-6-[(3S,4S)-3-amino-4-
(fluoromethyl)pyrrolidin-1-yl]-1,2,3,4-
tetrahydronaphthalen-2-yl]-6-
methylthieno[2,3-b]pyridine-2-carboxamide
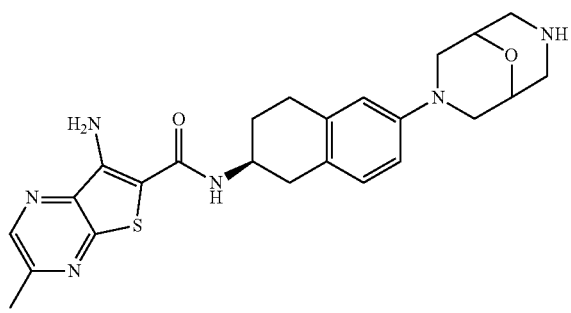
448. N-((2S)-6-(9-oxa-3,7-
diazabicyclo[3.3.1]nonan-3-yl)-1,2,3,4-
tetrahydronaphthalen-2-yl)-7-amino-3-
methylthieno[2,3-b]pyrazine-6-carboxamide TABLE 25-continued
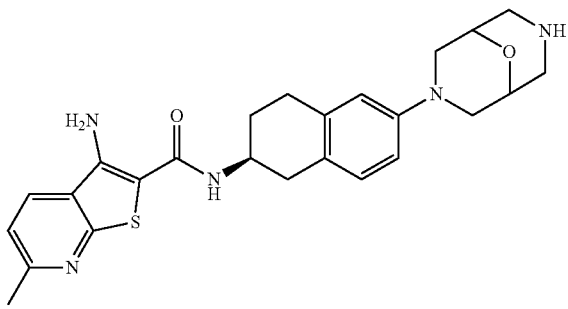 [SMILES: Cc1ccc2c(N)c(C(=O)N[C@H]3CCc4cc(N5CC6CNCC(C5)O6)ccc4C3)sc2n1]
449. N-((2S)-6-(9-oxa-3,7-
diazabicyclo[3.3.1]nonan-3-yl)-1,2,3,4-
tetrahydronaphthalen-2-yl)-3-amino-6-
methylthieno[2,3-b]pyridine-2-carboxamide
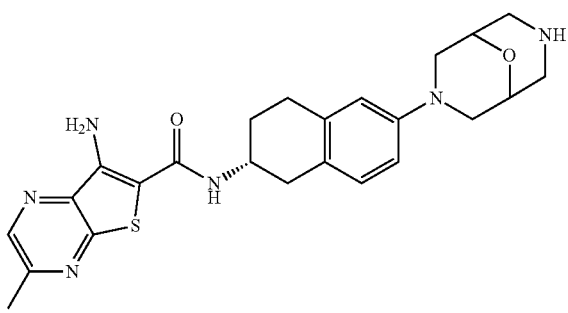 [SMILES: Cc1cnc2c(N)c(C(=O)N[C@@H]3CCc4cc(N5CC6CNCC(C5)O6)ccc4C3)sc2n1]
450. N-((2R)-6-(9-oxa-3,7-
diazabicyclo[3.3.1]nonan-3-yl)-1,2,3,4-
tetrahydronaphthalen-2-yl)-7-amino-3-
methylthieno[2,3-b]pyrazine-6-carboxamide
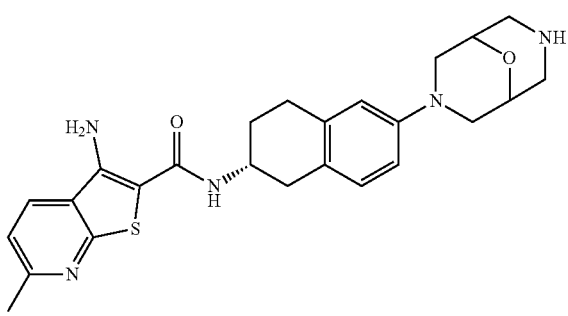 [SMILES: Cc1ccc2c(N)c(C(=O)N[C@@H]3CCc4cc(N5CC6CNCC(C5)O6)ccc4C3)sc2n1]
451. N-((2R)-6-(9-oxa-3,7-
diazabicyclo[3.3.1]nonan-3-yl)-1,2,3,4-
tetrahydronaphthalen-2-yl)-3-amino-6-
methylthieno[2,3-b]pyridine-2-carboxamide TABLE 25-continued
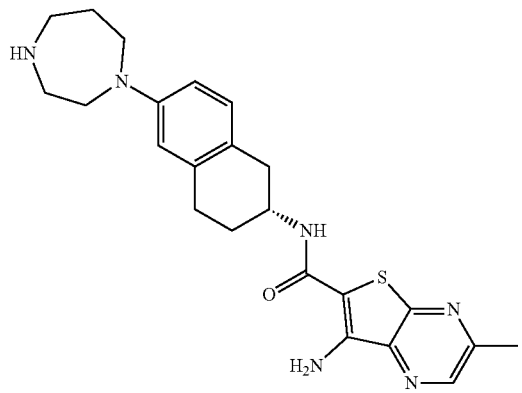 [SMILES: Cc1cnc2c(N)c(C(=O)N[C@@H]3CCc4cc(N5CCCNCC5)ccc4C3)sc2n1]
452. (R)- N-(6-(1,4-diazepan-1-yl)-1,2,3,4-tetrahydronaphthalen-2-yl)-7-amino-3-methylthieno[2,3-b]pyrazine-6-carboxamide
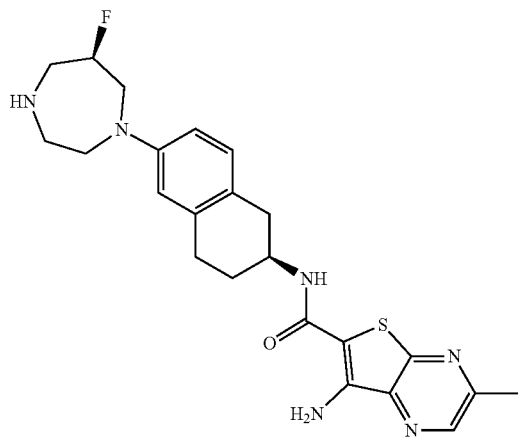 [SMILES: Cc1cnc2c(N)c(C(=O)N[C@H]3CCc4cc(N5CCNC[C@@H](F)C5)ccc4C3)sc2n1]
453. 7-amino-N-((R)-6-((S)-6-fluoro-1,4-diazepan-1-yl)-1,2,3,4-tetrahydronaphthalen-2-yl)-3-methylthieno[2,3-b]pyrazine-6-carboxamide
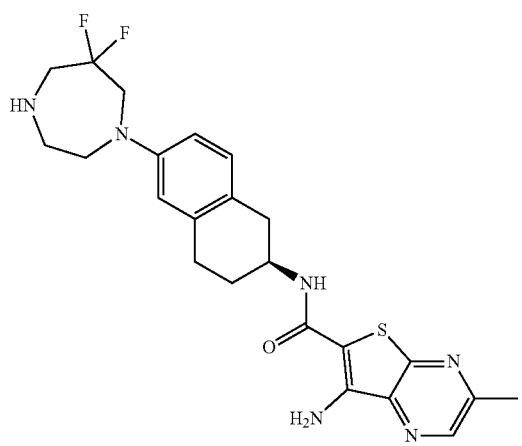 [SMILES: Cc1cnc2c(N)c(C(=O)N[C@H]3CCc4cc(N5CCNCC(F)(F)C5)ccc4C3)sc2n1]
454. (S)-7-amino-N-(6-(6,6-difluoro-1,4-diazepan-1-yl)-1,2,3,4-tetrahydronaphthalen-2-yl)-3-methylthieno[2,3-b]pyrazine-6-carboxamide TABLE 25-continued
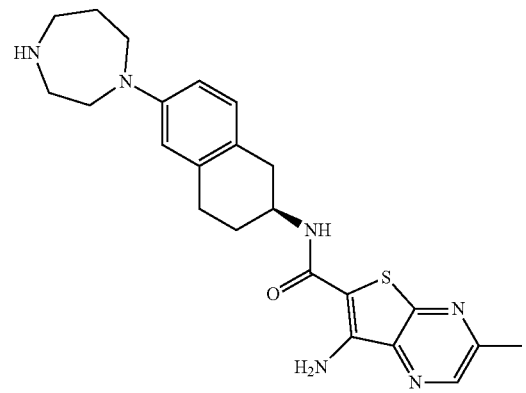 [SMILES: Cc1cnc2c(N)c(C(=O)N[C@H]3CCc4cc(N5CCCNCC5)ccc4C3)sc2n1]
455. (S)-N-(6-(1,4-diazepan-1-yl)-1,2,3,4-
tetrahydronaphthalen-2-yl)-7-amino-3-
methylthieno[2,3-b]pyrazine-6-carboxamide
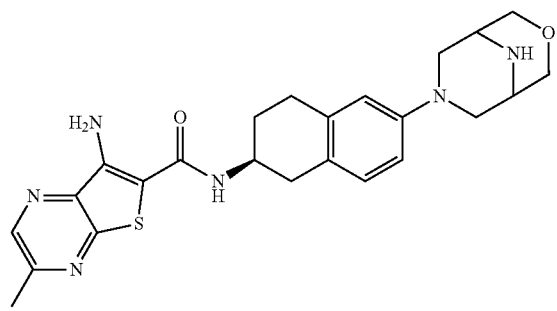 [SMILES: Cc1cnc2c(N)c(C(=O)N[C@H]3CCc4cc(N5CC6COCC(C5)N6)ccc4C3)sc2n1]
456. N-((2S)-6-(3-oxa-7,9-
diazabicyclo[3.3.1]nonan-7-yl)-1,2,3,4-
tetrahydronaphthalen-2-yl)-7-amino-3-
methylthieno[2,3-b]pyrazine-6-carboxamide
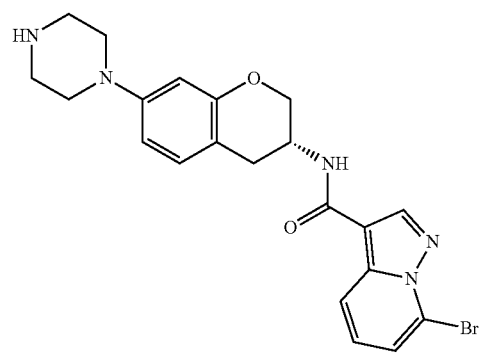 [SMILES: O=C(N[C@H]1COc2cc(N3CCNCC3)ccc2C1)c1cnn2c(Br)cccc12]
457. (R)-7-bromo-N-(7-(piperazin-1-
yl)chroman-3-yl)pyrazolo[1,5-a]pyridine-3-
carboxamide TABLE 25-continued
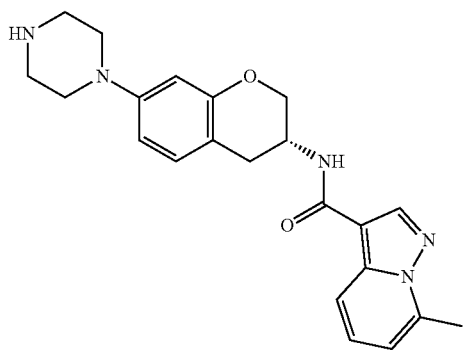 [SMILES: Cc1cccc2c(C(=O)N[C@H]3COc4cc(N5CCNCC5)ccc4C3)cnn12]
458. (R)-7-methyl-N-(7-(piperazin-1-yl)chroman-3-yl)pyrazolo[1,5-a]pyridine-3-carboxamide
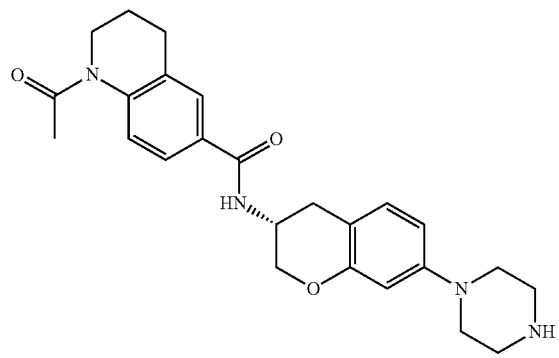 [SMILES: CC(=O)N1CCCc2cc(C(=O)N[C@H]3COc4cc(N5CCNCC5)ccc4C3)ccc21]
459. (R)-1-acetyl-N-(7-(piperazin-1-yl)chroman-3-yl)-1,2,3,4-tetrahydroquinoline-6-carboxamide
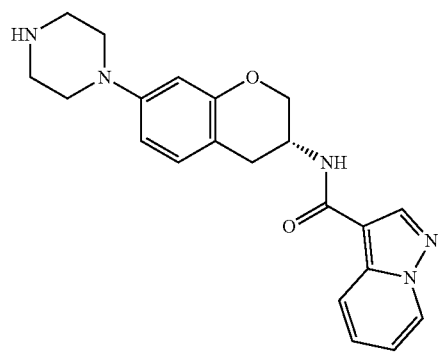 [SMILES: O=C(N[C@H]1COc2cc(N3CCNCC3)ccc2C1)c1cnn2ccccc12]
460. (R)-N-(7-(piperazin-1-yl)chroman-3-yl)pyrazolo[1,5-a]pyridine-3-carboxamide TABLE 25-continued
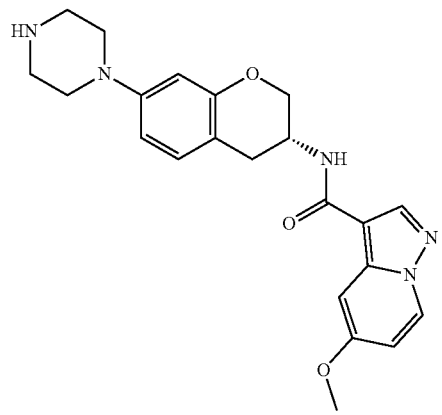 [SMILES: COc1ccn2ncc(C(=O)N[C@H]3COc4cc(N5CCNCC5)ccc4C3)c2c1]
461. (R)-5-methoxy-N-(7-(piperazin-1-yl)chroman-3-yl)pyrazolo[1,5-a]pyridine-3-carboxamide
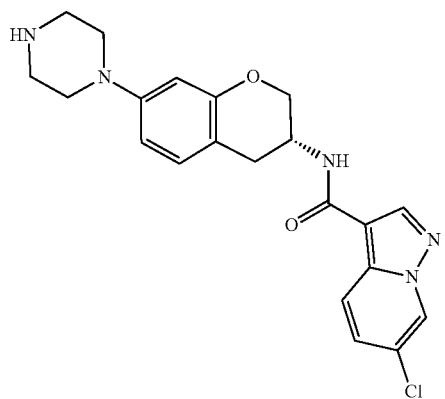 [SMILES: O=C(N[C@H]1COC2=C(C=CCC(N3CCNCC3)=C2)C1)c1cnn2cc(Cl)ccc12]
462. (R)-6-chloro-N-(7-(piperazin-1-yl)chroman-3-yl)pyrazolo[1,5-a]pyridine-3-carboxamide
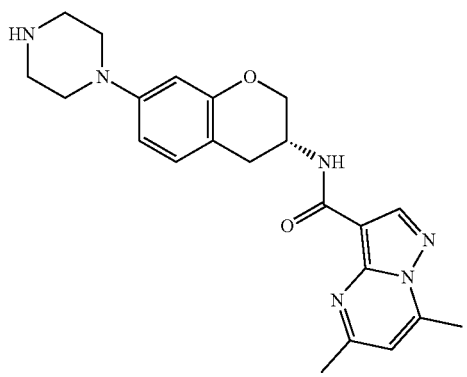 [SMILES: Cc1cc(C)n2ncc(C(=O)N[C@H]3COc4cc(N5CCNCC5)ccc4C3)c2n1]
463. (R)-5,7-dimethyl-N-(7-(piperazin-1-yl)chroman-3-yl)pyrazolo[1,5-a]pyrimidine-3-carboxamide TABLE 25-continued
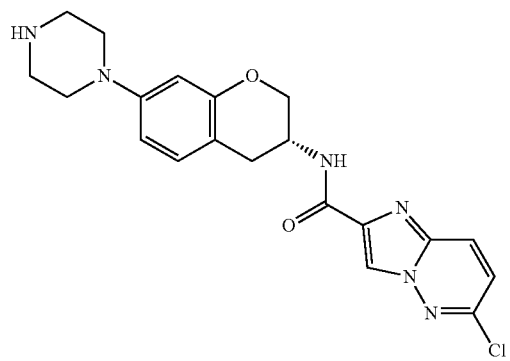 [SMILES: O=C(N[C@H]1COc2cc(N3CCNCC3)ccc2C1)c1cn2nc(Cl)ccc2n1]
464. (R)-6-chloro-N-(7-(piperazin-1-
yl)chroman-3-yl)imidazo[1,2-b]pyridazine-
2-carboxamide
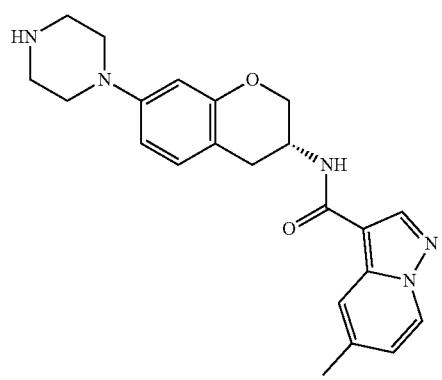 [SMILES: Cc1ccn2ncc(C(=O)N[C@H]3COc4cc(N5CCNCC5)ccc4C3)c2c1]
465. (R)-5-methyl-N-(7-(piperazin-1-
yl)chroman-3-yl)pyrazolo[1,5-a]pyridine-3-
carboxamide
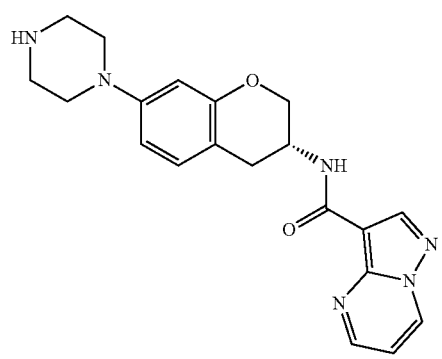 [SMILES: O=C(N[C@H]1COc2cc(N3CCNCC3)ccc2C1)c1cnn2cccnc12]
466. (R)-N-(7-(piperazin-1-yl)chroman-3-
yl)pyrazolo[1,5-a]pyrimidine-3-carboxamide TABLE 25-continued
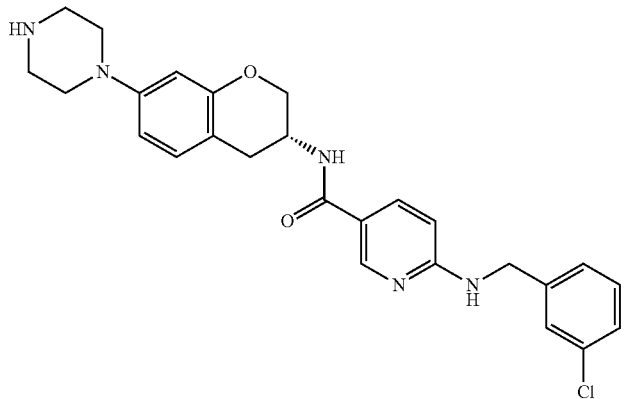 [SMILES: O=C(N[C@H]1COc2cc(N3CCNCC3)ccc2C1)c1ccc(NCc2cccc(Cl)c2)nc1]
467. (R)-6-((3-chlorobenzyl)amino)-N-(7-(piperazin-1-yl)chroman-3-yl)nicotinamide
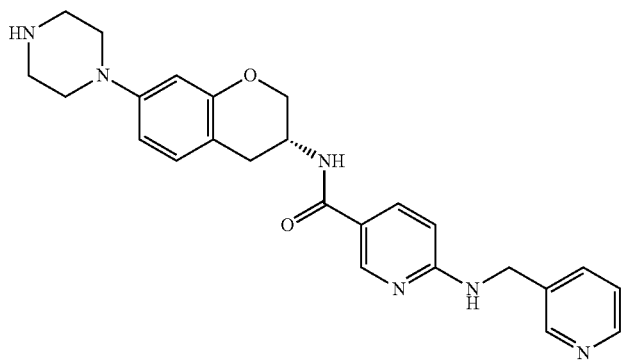 [SMILES: O=C(N[C@H]1COc2cc(N3CCNCC3)ccc2C1)c1ccc(NCc2cccnc2)nc1]
468. (R)-N-(7-(piperazin-1-yl)chroman-3-yl)-6-((pyridin-3-ylmethyl)amino)nicotinamide
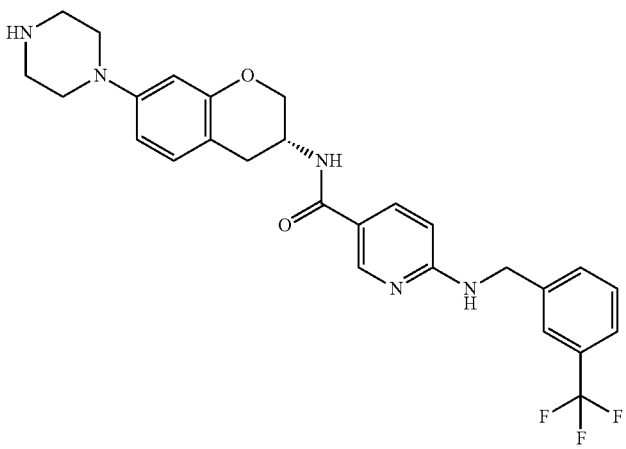 [SMILES: O=C(N[C@H]1COc2cc(N3CCNCC3)ccc2C1)c1ccc(NCc2cccc(C(F)(F)F)c2)nc1]
469. (R)-N-(7-(piperazin-1-yl)chroman-3-yl)-6-((3-(trifluoromethyl)benzyl)amino)nicotinamide TABLE 25-continued
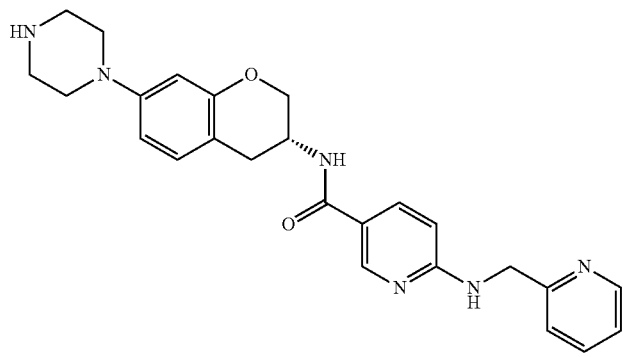 [SMILES: O=C(N[C@H]1COc2cc(N3CCNCC3)ccc2C1)c1ccc(NCc2ccccn2)nc1]
470. (R)-N-(7-(piperazin-1-yl)chroman-3-
yl)-6-((pyridin-2-
ylmethyl)amino)nicotinamide
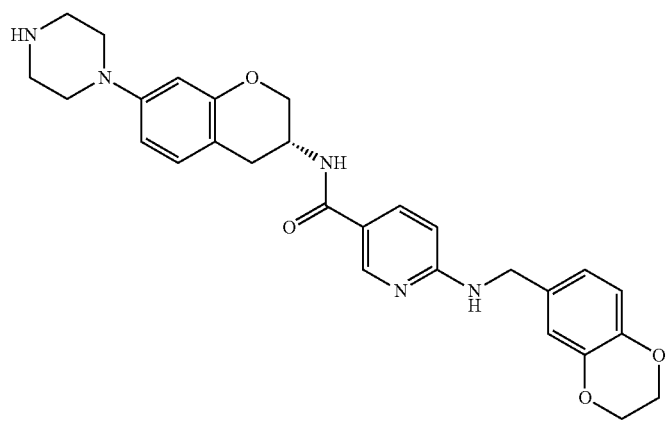 [SMILES: O=C(N[C@H]1COc2cc(N3CCNCC3)ccc2C1)c1ccc(NCc2ccc3c(c2)OCCO3)nc1]
471. (R)-6-(((2,3-dihydrobenzo[b][1,4]dioxin-
6-yl)methyl)amino)-N-(7-(piperazin-1-
yl)chroman-3-yl)nicotinamide
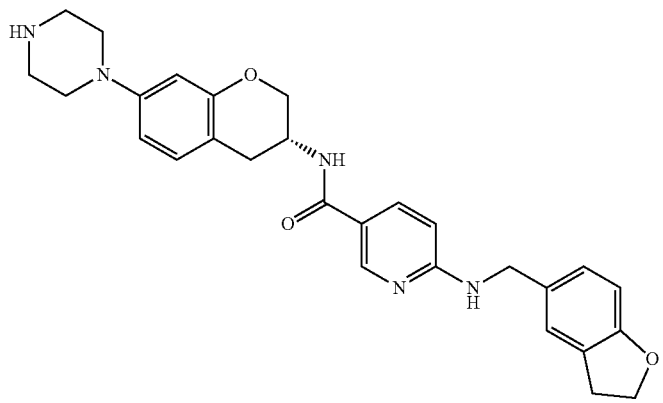 [SMILES: O=C(N[C@H]1COc2cc(N3CCNCC3)ccc2C1)c1ccc(NCc2ccc3c(c2)CCO3)nc1]
472. (R)-6-(((2,3-dihydrobenzofuran-5-
yl)methyl)amino)-N-(7-(piperazin-1-
yl)chroman-3-yl)nicotinamide TABLE 25-continued
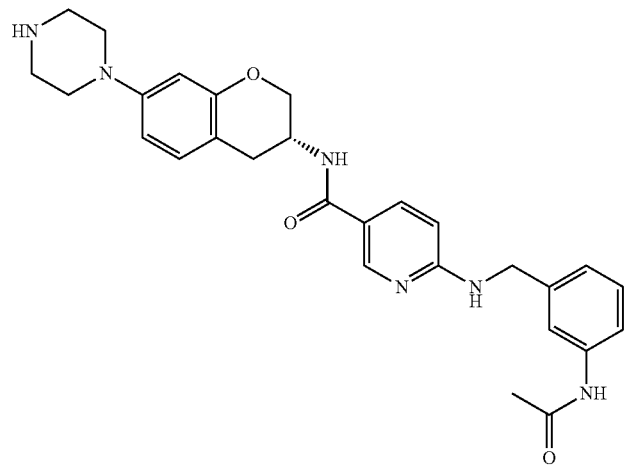 [SMILES: CC(=O)Nc1cccc(CNc2ccc(C(=O)N[C@H]3COc4cc(N5CCNCC5)ccc4C3)cn2)c1]
473. (R)-6-((3-acetamidobenzyl)amino)-N-(7-(piperazin-1-yl)chroman-3-yl)nicotinamide
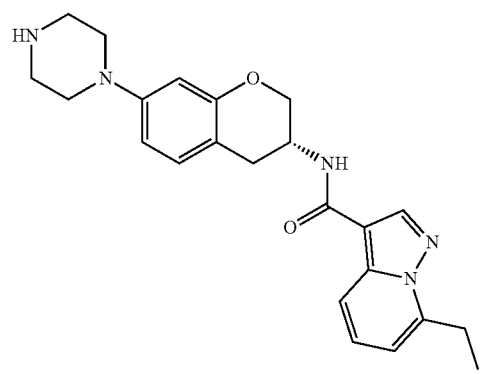 [SMILES: CCc1cccc2c(C(=O)N[C@H]3COc4cc(N5CCNCC5)ccc4C3)cnn12]
474. 7-ethyl-N-[(3R)-7-(piperazin-1-yl)-3,4-dihydro-2H-1-benzopyran-3-yl]pyrazolo[1,5-a]pyridine-3-carboxamide
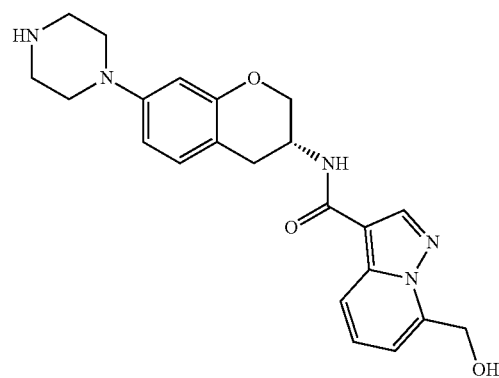 [SMILES: O=C(N[C@H]1COc2cc(N3CCNCC3)ccc2C1)c1cnn2c(CO)cccc12]
475. 7-(hydroxymethyl)-N-[(3R)-7-(piperazin-1-yl)-3,4-dihydro-2H-1-benzopyran-3-yl]pyrazolo[1,5-a]pyridine-3-carboxamide TABLE 26
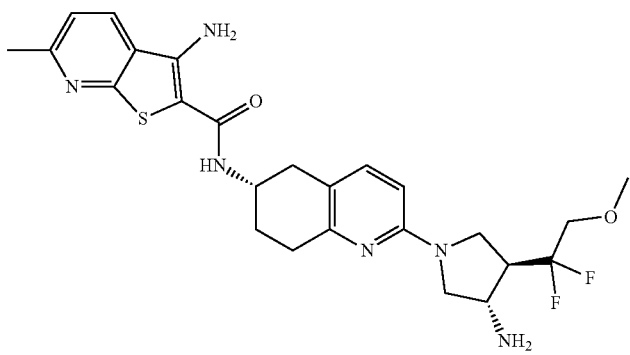
547. 3-amino-N-[(6S)-2-[(3S,4R)-3-amino-4-(1,1-difluoro-2-methoxyethyl)pyrrolidin-1-yl]-5,6,7,8-tetrahydroquinolin-6-yl]-6-methylthieno[2,3-b]pyridine-2-carboxamide
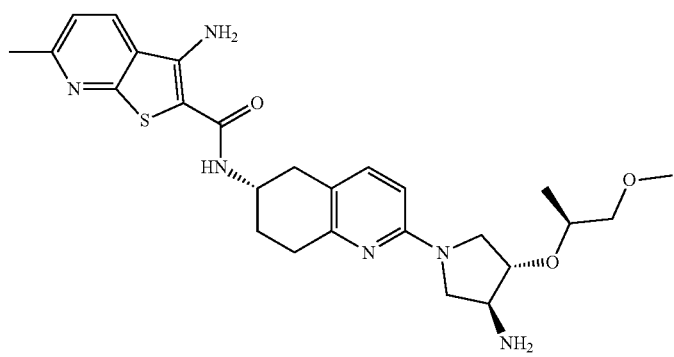
548. 3-amino-N-[(6S)-2-[(3S,4S)-3-amino-4-{[(2S)-1-methoxypropan-2-yl]oxy}pyrrolidin-1-yl]-5,6,7,8-tetrahydroquinolin-6-yl]-6-methylthieno[2,3-b]pyridine-2-carboxamide
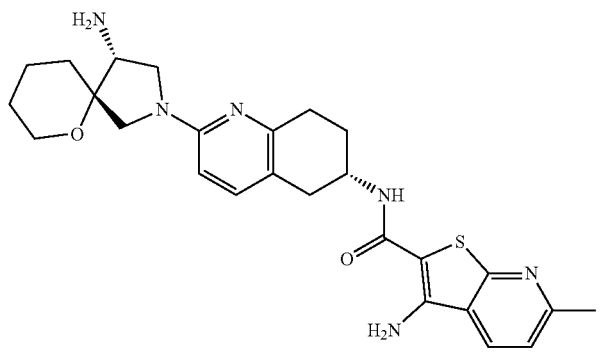 [SMILES: Cc1ccc2c(N)c(C(=O)N[C@H]3CCc4nc(N5C[C@@H](N)[C@]6(CCCCO6)C5)ccc4C3)sc2n1]
549. 3-amino-N-[(6S)-2-[(4R,5S)-4-amino-6-oxa-2-azaspiro[4.5]decan-2-yl]-5,6,7,8-tetrahydroquinolin-6-yl]-6-methylthieno[2,3-b]pyridine-2-carboxamide TABLE 26-continued
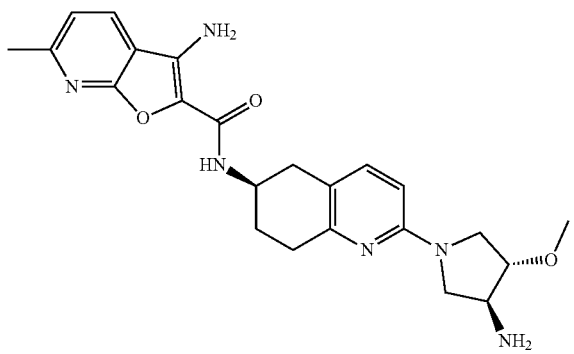
550. 3-amino-N-[(6R)-2-[(3S,4S)-3-amino-4-methoxypyrrolidin-1-yl]-5,6,7,8-tetrahydroquinolin-6-yl]-6-methylfuro[2,3-b]pyridine-2-carboxamide
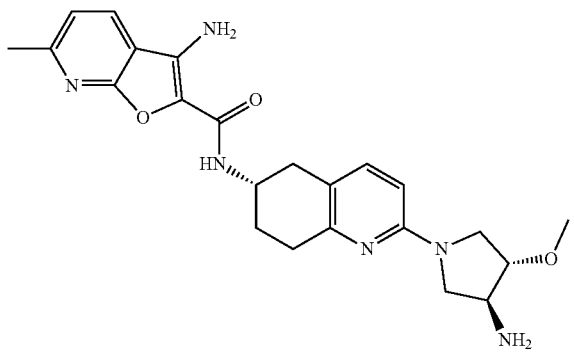
551. 3-amino-N-[(6S)-2-[(3S,4S)-3-amino-4-methoxypyrrolidin-1-yl]-5,6,7,8-tetrahydroquinolin-6-yl]-6-methylfuro[2,3-b]pyridine-2-carboxamide
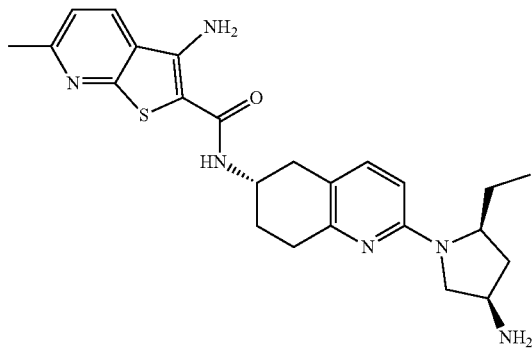 [SMILES: CC[C@H]1C[C@@H](N)CN1c1ccc2c(n1)CC[C@H](NC(=O)c1sc3nc(C)ccc3c1N)C2]
552. 3-amino-N-[(6S)-2-[(2S,4R)-4-amino-2-ethylpyrrolidin-1-yl]-5,6,7,8-tetrahydroquinolin-6-yl]-6-methylthieno[2,3-b]pyridine-2-carboxamide TABLE 26-continued
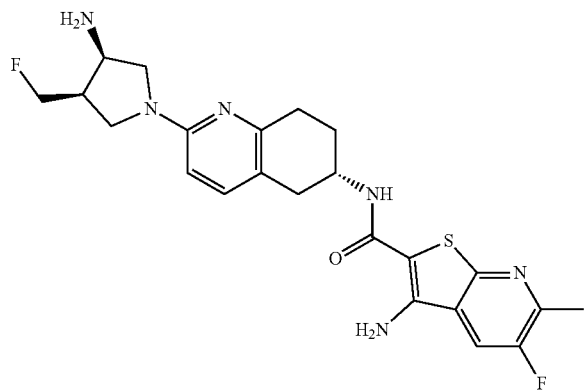 [SMILES: Cc1nc2sc(C(=O)N[C@H]3CCc4nc(N5C[C@@H](CF)[C@@H](N)C5)ccc4C3)c(N)c2cc1F]
553. 3-amino-N-[(6S)-2-[(3R,4R)-3-amino-
4-(fluoromethyl)pyrrolidin-1-yl]-5,6,7,8-
tetrahydroquinolin-6-yl]-5-fluoro-6-
methylthieno[2,3-b]pyridine-2-carboxamide
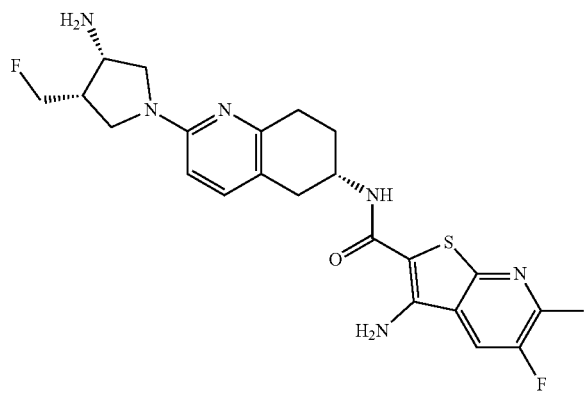 [SMILES: Cc1nc2sc(C(=O)N[C@H]3CCc4nc(N5C[C@H](CF)[C@H](N)C5)ccc4C3)c(N)c2cc1F]
554. 3-amino-N-[(6S)-2-[(3S,4S)-3-amino-4-
(fluoromethyl)pyrrolidin-1-yl]-5,6,7,8-
tetrahydroquinolin-6-yl]-5-fluoro-6-
methylthieno[2,3-b]pyridine-2-carboxamide
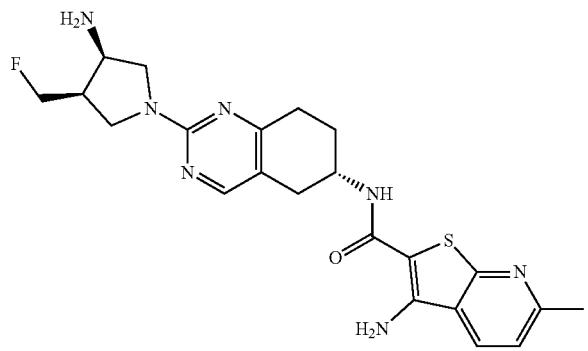
555. 3-amino-N-[(6S)-2-[(3R,4R)-3-amino-
4-(fluoromethyl)pyrrolidin-1-yl]-5,6,7,8-
tetrahydroquinazolin-6-yl]-6-
methylthieno[2,3-b]pyridine-2-carboxamide

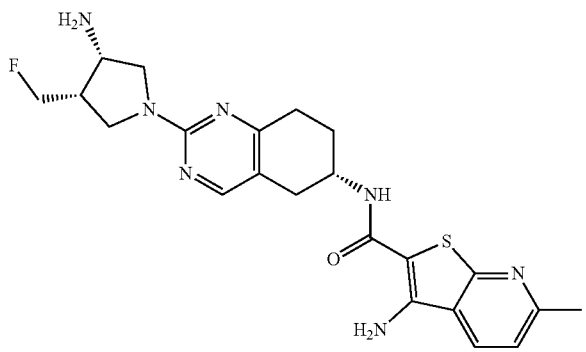 [SMILES: Cc1ccc2c(N)c(C(=O)N[C@H]3CCc4nc(N5C[C@H](CF)[C@H](N)C5)ncc4C3)sc2n1]
556. 3-amino-N-[(6S)-2-[(3S,4S)-3-amino-4-
(fluoromethyl)pyrrolidin-1-yl]-5,6,7,8-
tetrahydroquinazolin-6-yl]-6-
methylthieno[2,3-b]pyridine-2-carboxamide
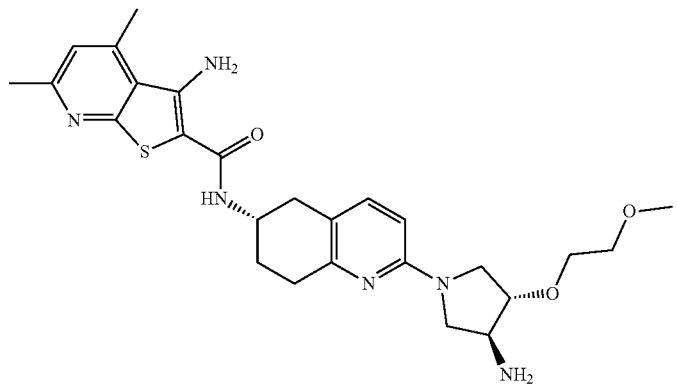
557. 3-amino-N-[(6S)-2-[(3S,4S)-3-amino-4-
(2-methoxyethoxy)pyrrolidin-1-yl]-5,6,7,8-
tetrahydroquinolin-6-yl]-4,6-
dimethylthieno[2,3-b]pyridine-2-
carboxamide
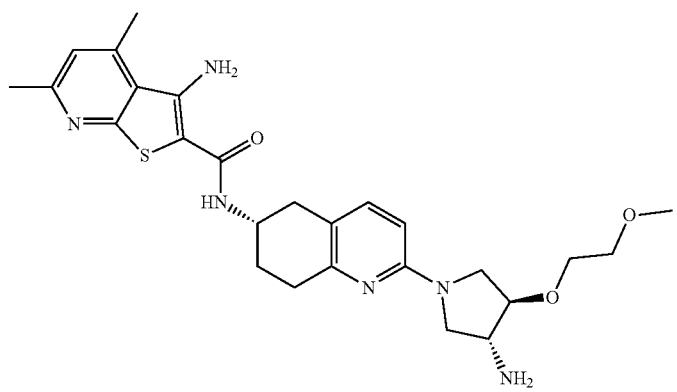
558. 3-amino-N-[(6S)-2-[(3R,4R)-3-amino-4-
(2-methoxyethoxy)pyrrolidin-1-yl]-5,6,7,8-
tetrahydroquinolin-6-yl]-4,6-
dimethylthieno[2,3-b]pyridine-2-carboxamide

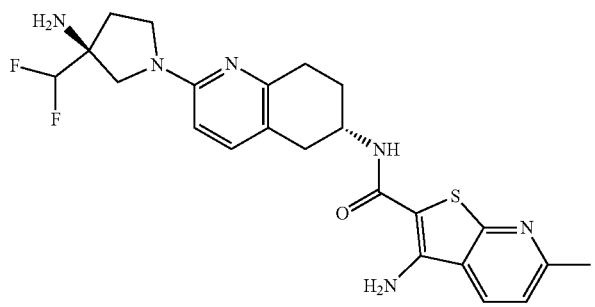 [SMILES: Cc1ccc2c(N)c(C(=O)N[C@H]3CCc4nc(N5CC[C@@](N)(C(F)F)C5)ccc4C3)sc2n1]
559. 3-amino-N-[(6S)-2-[(3S)-3-amino-3-(difluoromethyl)pyrrolidin-1-yl]-5,6,7,8-tetrahydroquinolin-6-yl]-6-methylthieno[2,3-b]pyridine-2-carboxamide
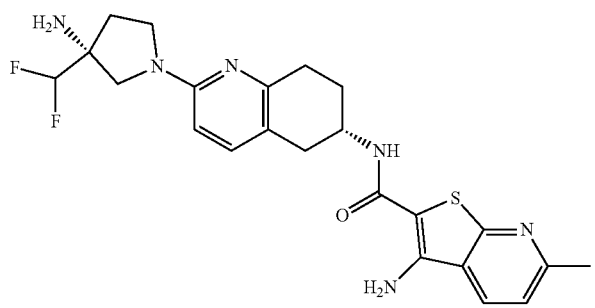 [SMILES: Cc1ccc2c(N)c(C(=O)N[C@H]3CCc4nc(N5CC[C@](N)(C(F)F)C5)ccc4C3)sc2n1]
560. 3-amino-N-[(6S)-2-[(3R)-3-amino-3-(difluoromethyl)pyrrolidin-1-yl]-5,6,7,8-tetrahydroquinolin-6-yl]-6-methylthieno[2,3-b]pyridine-2-carboxamide
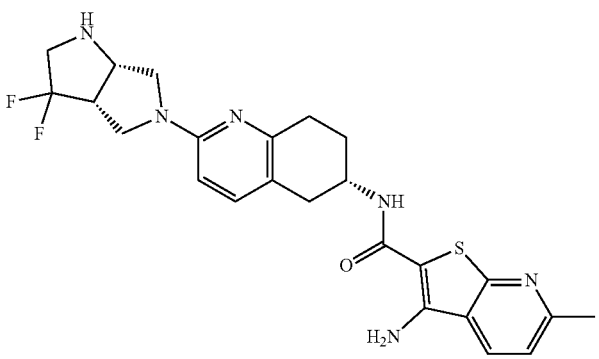 [SMILES: Cc1ccc2c(N)c(C(=O)N[C@H]3CCc4nc(N5C[C@H]6NCC(F)(F)[C@H]6C5)ccc4C3)sc2n1]
561. N-[(6S)-2-[(3aS,6aS)-3,3-difluoro-octahydropyrrolo[3,4-b]pyrrol-5-yl]-5,6,7,8-tetrahydroquinolin-6-yl]-3-amino-6-methylthieno[2,3-b]pyridine-2-carboxamide TABLE 26-continued
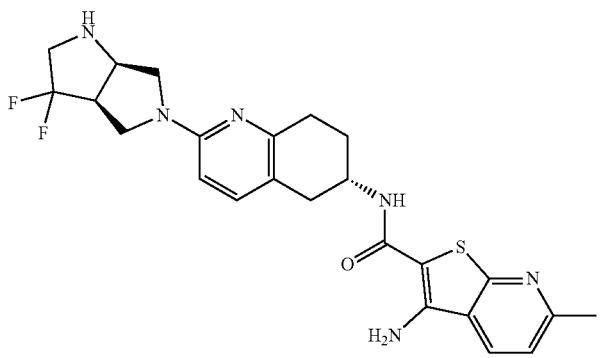 [SMILES: Cc1ccc2c(N)c(C(=O)N[C@H]3CCc4nc(N5C[C@@H]6NCC(F)(F)[C@@H]6C5)ccc4C3)sc2n1]
562. N-[(6S)-2-[(3aR,6aR)-3,3-difluoro-
octahydropyrrolo[3,4-b]pyrrol-5-yl]-5,6,7,8-
tetrahydroquinolin-6-yl]-3-amino-6-
methylthieno[2,3-b]pyridine-2-carboxamide
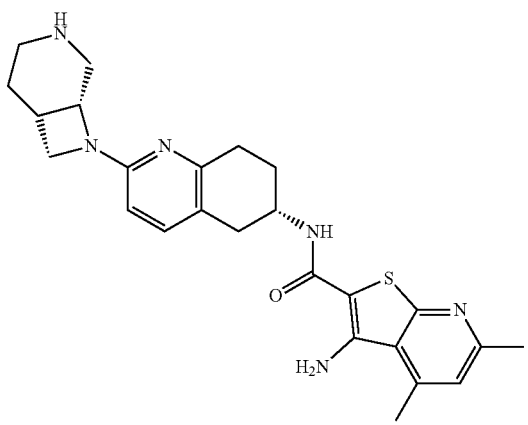
563. 3-amino-N-[(6S)-2-[(1R,6S)-3,8-
diazabicyclo[4.2.0]octan-8-yl]-5,6,7,8-
tetrahydroquinolin-6-yl]-4,6-
dimethylthieno[2,3-b]pyridine-2-
carboxamide
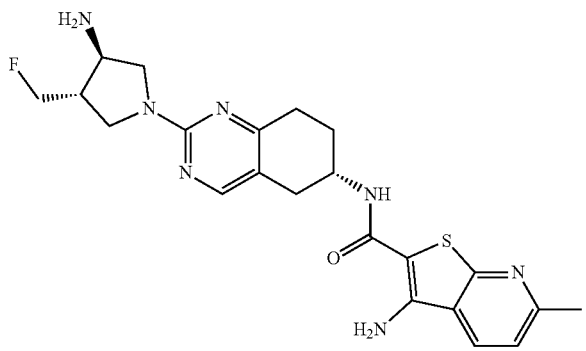 [SMILES: Cc1ccc2c(N)c(C(=O)N[C@H]3CCc4nc(N5C[C@H](CF)[C@@H](N)C5)ncc4C3)sc2n1]
564. 3-amino-N-[(6S)-2-[(3R,4S)-3-amino-4-
(fluoromethyl)pyrrolidin-1-yl]-5,6,7,8-
tetrahydroquinazolin-6-yl]-6-
methylthieno[2,3-b]pyridine-2-carboxamide TABLE 26-continued
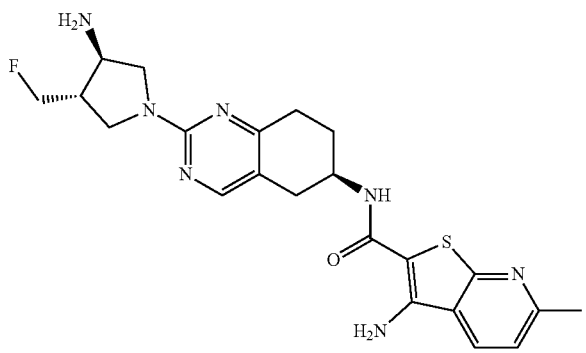 [SMILES: Cc1ccc2c(N)c(C(=O)N[C@@H]3CCc4nc(N5C[C@H](CF)[C@@H](N)C5)ncc4C3)sc2n1]
565. 3-amino-N-[(6R)-2-[(3R,4S)-3-amino-4-(fluoromethyl)pyrrolidin-1-yl]-5,6,7,8-tetrahydroquinazolin-6-yl]-6-methylthieno[2,3-b]pyridine-2-carboxamide
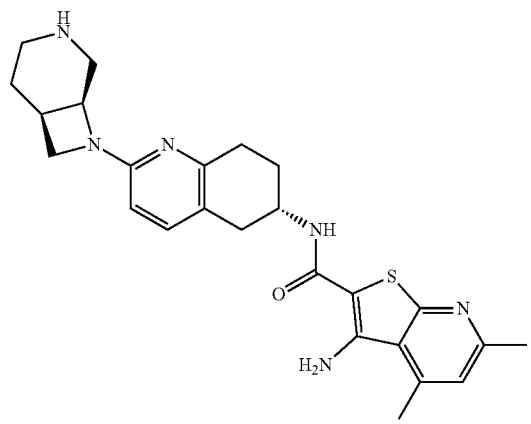 [SMILES: Cc1cc(C)c2c(N)c(C(=O)N[C@H]3CCc4nc(N5C[C@H]6CCNC[C@H]65)ccc4C3)sc2n1]
566. 3-amino-N-[(6S)-2-[(1S,6R)-3,8-diazabicyclo[4.2.0]octan-8-yl]-5,6,7,8-tetrahydroquinolin-6-yl]-4,6-dimethylthieno[2,3-b]pyridine-2-carboxamide
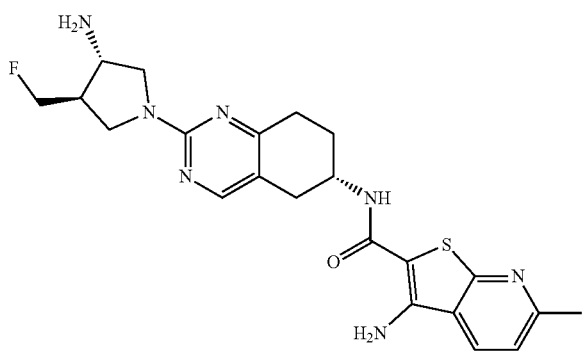 [SMILES: Cc1ccc2c(N)c(C(=O)N[C@H]3CCc4nc(N5C[C@@H](CF)[C@H](N)C5)ncc4C3)sc2n1]
567. 3-amino-N-[(6S)-2-[(3S,4R)-3-amino-4-(fluoromethyl)pyrrolidin-1-yl]-5,6,7,8-tetrahydroquinazolin-6-yl]-6-methylthieno[2,3-b]pyridine-2-carboxamide TABLE 26-continued

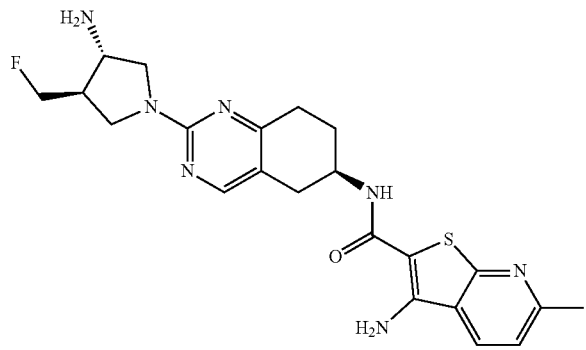 [SMILES: Cc1ccc2c(N)c(C(=O)N[C@@H]3CCc4nc(N5C[C@@H](CF)[C@H](N)C5)ncc4C3)sc2n1]

568. 3-amino-N-[(6R)-2-[(3S,4R)-3-amino-4-
(fluoromethyl)pyrrolidin-1-yl]-5,6,7,8-
tetrahydroquinazolin-6-yl]-6-
methylthieno[2,3-b]pyridine-2-carboxamide

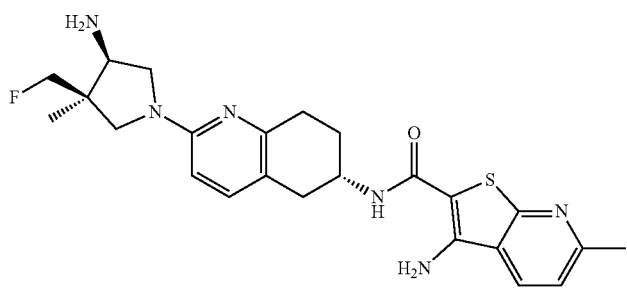 [SMILES: Cc1ccc2c(N)c(C(=O)N[C@H]3CCc4nc(N5C[C@H](N)[C@](C)(CF)C5)ccc4C3)sc2n1]

569. 3-amino-N-[(6S)-2-[(3R,4R)-4-amino-
3-(fluoromethyl)-3-methylpyrrolidin-1-yl]-
5,6,7,8-tetrahydroquinolin-6-yl]-6-
methylthieno[2,3-b]pyridine-2-carboxamide

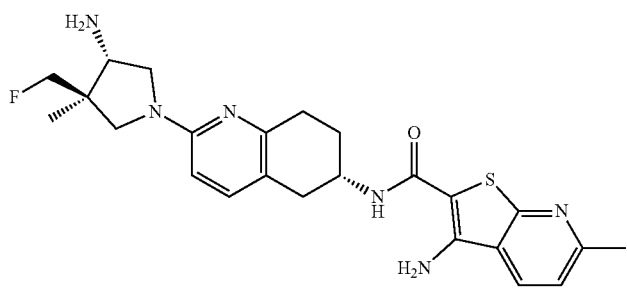 [SMILES: Cc1ccc2c(N)c(C(=O)N[C@H]3CCc4nc(N5C[C@@H](N)[C@](C)(CF)C5)ccc4C3)sc2n1]

570. 3-amino-N-[(6S)-2-[(3R,4S)-4-amino-3-
(fluoromethyl)-3-methylpyrrolidin-1-yl]-
5,6,7,8-tetrahydroquinolin-6-yl]-6-
methylthieno[2,3-b]pyridine-2-carboxamide

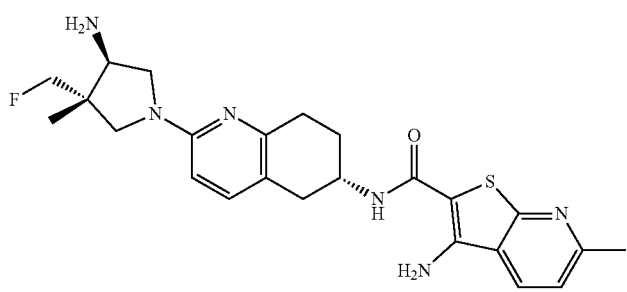 [SMILES: Cc1ccc2c(N)c(C(=O)N[C@H]3CCc4nc(N5C[C@H](N)[C@@](C)(CF)C5)ccc4C3)sc2n1]

571. 3-amino-N-[(6S)-2-[(3S,4R)-4-amino-
3-(fluoromethyl)-3-methylpyrrolidin-1-yl]-
5,6,7,8-tetrahydroquinolin-6-yl]-6-
methylthieno[2,3-b]pyridine-2-carboxamide TABLE 26-continued

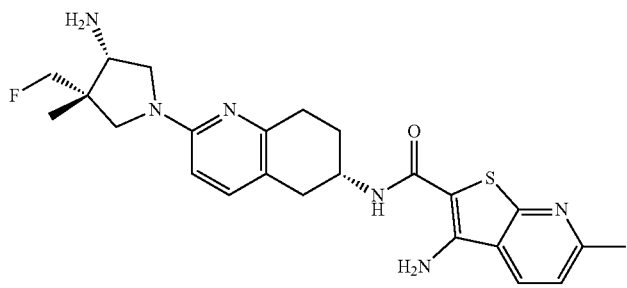 [SMILES: Cc1ccc2c(N)c(C(=O)N[C@H]3CCc4nc(N5C[C@@H](N)[C@@](C)(CF)C5)ccc4C3)sc2n1]

572. 3-amino-N-[(6S)-2-[(3S,4S)-4-amino-3-
(fluoromethyl)-3-methylpyrrolidin-1-yl]-
5,6,7,8-tetrahydroquinolin-6-yl]-6-
methylthieno[2,3-b]pyridine-2-carboxamide

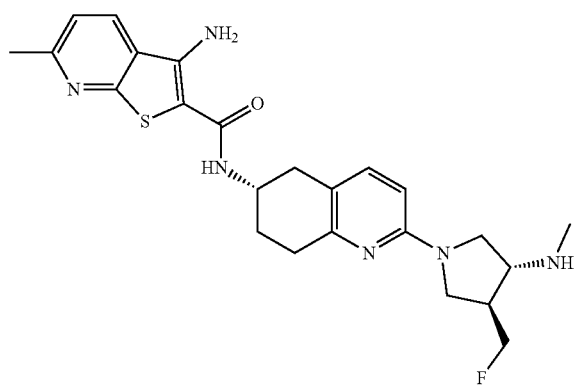

573. 3-amino-N-[(6S)-2-[(3S,4R)-3-
(fluoromethyl)-4-(methylamino)pyrrolidin-1-
yl]-5,6,7,8-tetrahydroquinolin-6-yl]-6-
methylthieno[2,3-b]pyridine-2-carboxamide

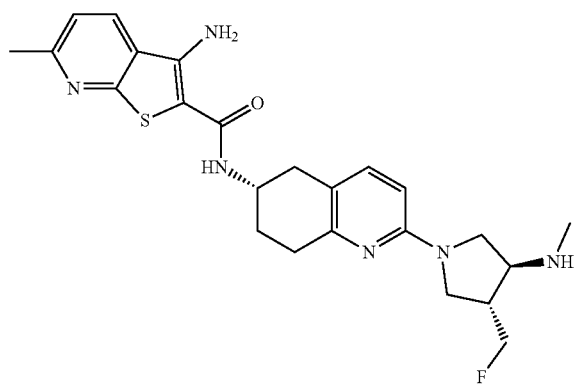

574. 3-amino-N-[(6S)-2-[(3R,4S)-3-
(fluoromethyl)-4-(methylamino)pyrrolidin-1-
yl]-5,6,7,8-tetrahydroquinolin-6-yl]-6-
methylthieno[2,3-b]pyridine-2-carboxamide

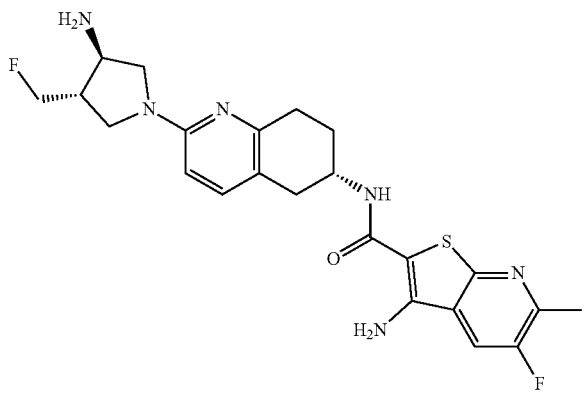 [SMILES: Cc1nc2sc(C(=O)N[C@H]3CCc4nc(N5C[C@H](CF)[C@@H](N)C5)ccc4C3)c(N)c2cc1F]
575. 3-amino-N-[(6S)-2-[(3R,4S)-3-amino-
4-(fluoromethyl)pyrrolidin-1-yl]-5,6,7,8-
tetrahydroquinolin-6-yl]-5-fluoro-6-
methylthieno[2,3-b]pyridine-2-carboxamide
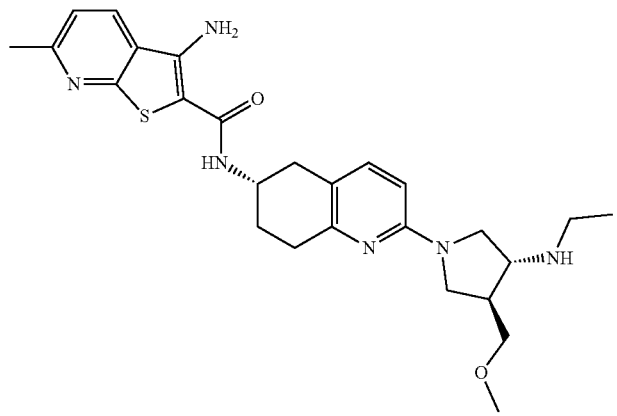 [SMILES: CCN[C@H]1CN(c2ccc3c(n2)CC[C@H](NC(=O)c2sc4nc(C)ccc4c2N)C3)C[C@@H]1COC]
576. 3-amino-N-[(6S)-2-[(3R,4S)-3-
(ethylamino)-4-(methoxymethyl)pyrrolidin-1-
yl]-5,6,7,8-tetrahydroquinolin-6-yl]-6-
methylthieno[2,3-b]pyridine-2-carboxamide
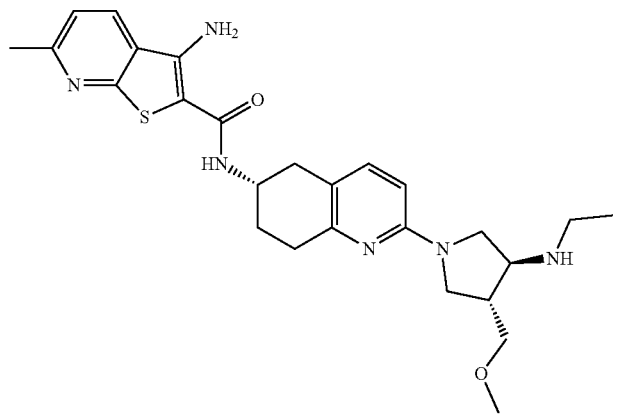 [SMILES: CCN[C@@H]1CN(c2ccc3c(n2)CC[C@H](NC(=O)c2sc4nc(C)ccc4c2N)C3)C[C@H]1COC]
577. 3-amino-N-[(6S)-2-[(3S,4R)-3-
(ethylamino)-4-(methoxymethyl)pyrrolidin-
1-yl]-5,6,7,8-tetrahydroquinolin-6-yl]-6-
methylthieno[2,3-b]pyridine-2-carboxamide

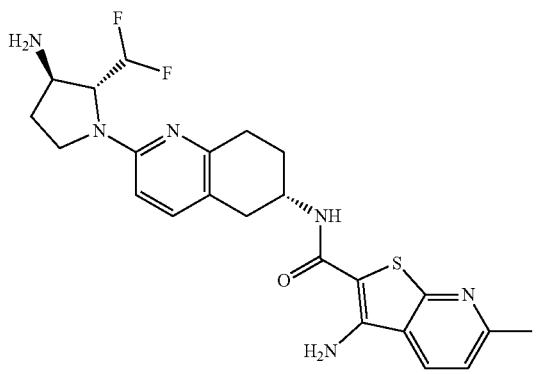 [SMILES: Cc1ccc2c(N)c(C(=O)N[C@H]3CCc4nc(N5CC[C@@H](N)[C@@H]5C(F)F)ccc4C3)sc2n1]
578. 3-amino-N-[(6S)-2-[(2R,3R)-3-amino-2-
(difluoromethyl)pyrrolidin-1-yl]-5,6,7,8-
tetrahydroquinolin-6-yl]-6-methylthieno[2,3-
b]pyridine-2-carboxamide
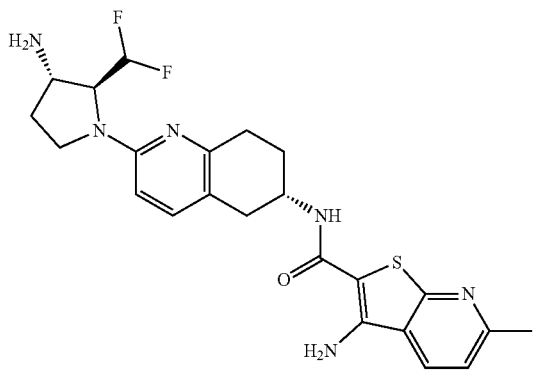 [SMILES: Cc1ccc2c(N)c(C(=O)N[C@H]3CCc4nc(N5CC[C@H](N)[C@H]5C(F)F)ccc4C3)sc2n1]
579. 3-amino-N-[(6S)-2-[(2S,3S)-3-amino-2-
(difluoromethyl)pyrrolidin-1-yl]-5,6,7,8-
tetrahydroquinolin-6-yl]-6-methylthieno[2,3-
b]pyridine-2-carboxamide
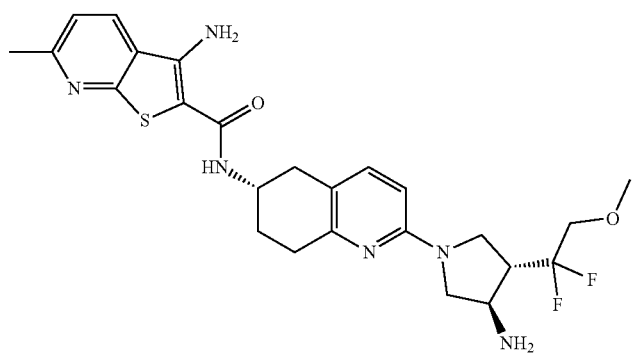
580. 3-amino-N-[(6S)-2-[(3R,4S)-3-amino-4-
(1,1-difluoro-2-methoxyethyl)pyrrolidin-1-yl]-
5,6,7,8-tetrahydroquinolin-6-yl]-6-
methylthieno[2,3-b]pyridine-2-carboxamide TABLE 26-continued
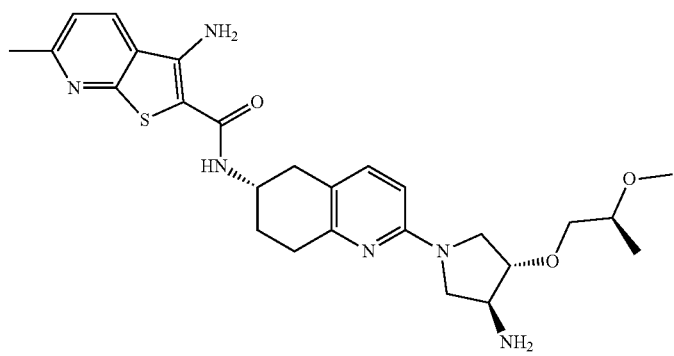
581. 3-amino-N-[(6S)-2-[(3S,4S)-3-amino-4-
[(2S)-2-methoxypropoxy]pyrrolidin-1-yl]-
5,6,7,8-tetrahydroquinolin-6-yl]-6-
methylthieno[2,3-b]pyridine-2-carboxamide
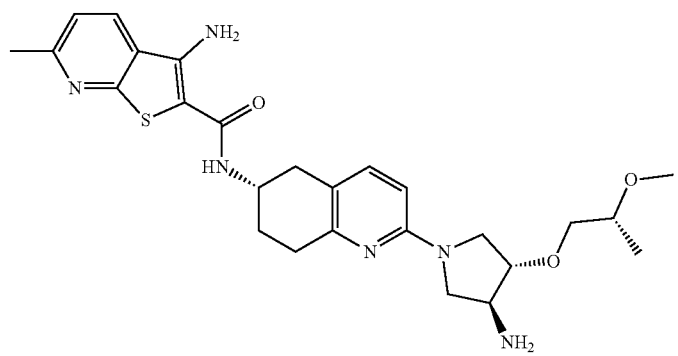
582. 3-amino-N-[(6S)-2-[(3S,4S)-3-amino-4-
[(2R)-2-methoxypropoxy]pyrrolidin-1-yl]-
5,6,7,8-tetrahydroquinolin-6-yl]-6-
methylthieno[2,3-b]pyridine-2-carboxamide
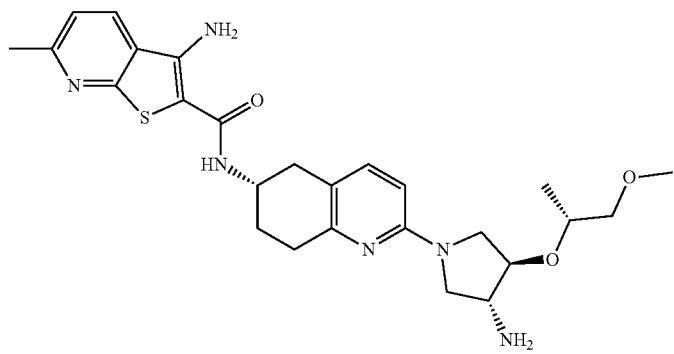
583. 3-amino-N-[(6S)-2-[(3R,4R)-3-amino-
4-{[(2R)-1-methoxypropan-2-
yl]oxy} pyrrolidin-1-yl]-5,6,7,8-
tetrahydroquinolin-6-yl]-6-methylthieno[2,3-
b]pyridine-2-carboxamide

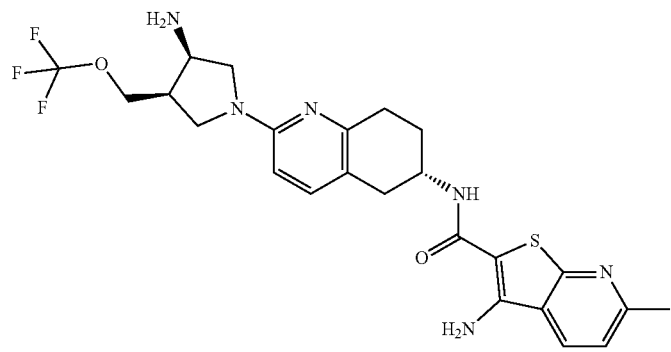 [SMILES: Cc1ccc2c(N)c(C(=O)N[C@H]3CCc4nc(N5C[C@@H](COC(F)(F)F)[C@@H](N)C5)ccc4C3)sc2n1]

584. 3-amino-N-[(6S)-2-[(3R,4R)-3-amino-4-
[(trifluoromethoxy)methyl]pyrrolidin-1-yl]-
5,6,7,8-tetrahydroquinolin-6-yl]-6-
methylthieno[2,3-b]pyridine-2-carboxamide

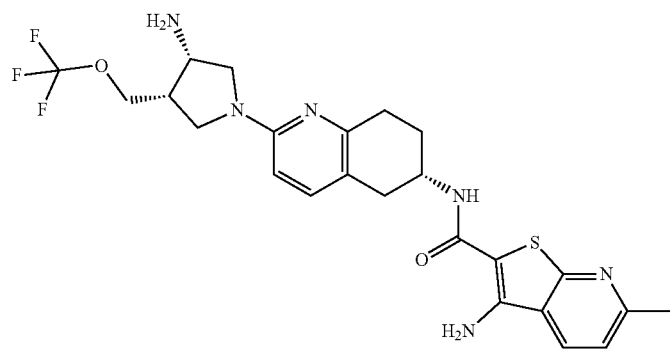 [SMILES: Cc1ccc2c(N)c(C(=O)N[C@H]3CCc4nc(N5C[C@H](COC(F)(F)F)[C@H](N)C5)ccc4C3)sc2n1]

585. 3-amino-N-[(6S)-2-[(3S,4S)-3-amino-4-
[(trifluoromethoxy)methyl]pyrrolidin-1-yl]-
5,6,7,8-tetrahydroquinolin-6-yl]-6-
methylthieno[2,3-b]pyridine-2-carboxamide

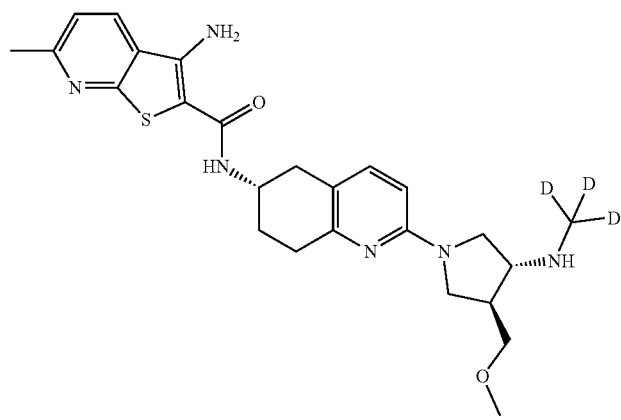 [SMILES: [2H]C([2H])([2H])N[C@H]1CN(c2ccc3c(n2)CC[C@H](NC(=O)c2sc4nc(C)ccc4c2N)C3)C[C@@H]1COC]

586. 3-amino-N-[(6S)-2-[(3S,4R)-3-
(methoxymethyl)-4-
[($^2$H$_3$)methylamino]pyrrolidin-1-yl]-5,6,7,8-
tetrahydroquinolin-6-yl]-6-methylthieno[2,3-
b]pyridine-2-carboxamide TABLE 26-continued

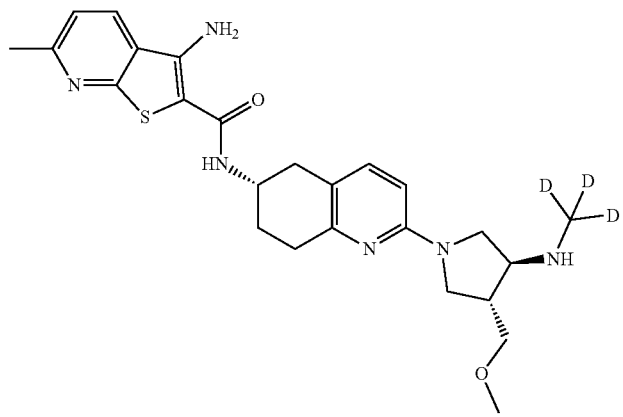 [SMILES: [2H]C([2H])([2H])N[C@@H]1CN(c2ccc3c(n2)CC[C@H](NC(=O)c2sc4nc(C)ccc4c2N)C3)C[C@H]1COC]

587. 3-amino-N-[(6S)-2-[(3R,4S)-3-
(methoxymethyl)-4-
[(²H₃)methylamino]pyrrolidin-1-yl]-5,6,7,8-
tetrahydroquinolin-6-yl]-6-methylthieno[2,3-
b]pyridine-2-carboxamide

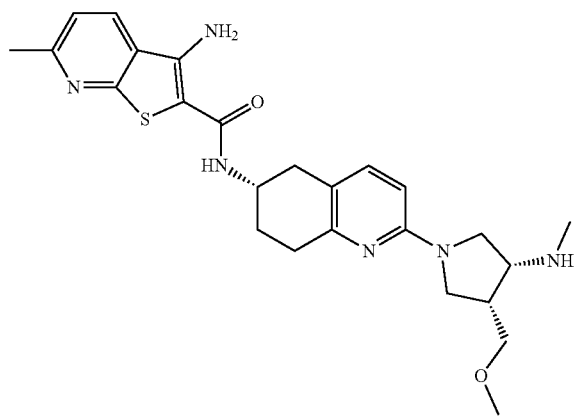

588. 3-amino-N-[(6S)-2-[(3R,4R)-3-
(methoxymethyl)-4-(methylamino)pyrrolidin-
1-yl]-5,6,7,8-tetrahydroquinolin-6-yl]-6-
methylthieno[2,3-b]pyridine-2-carboxamide

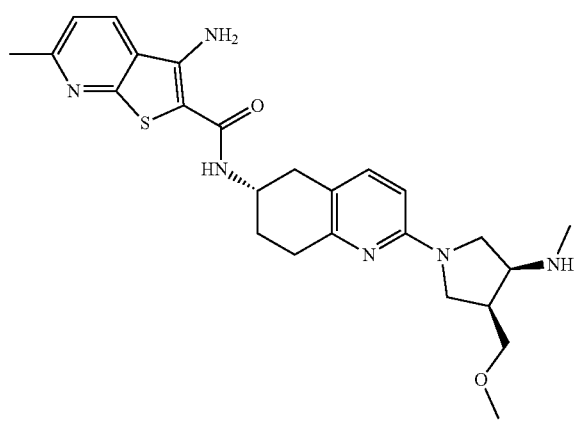

589. 3-amino-N-[(6S)-2-[(3S,4S)-3-
(methoxymethyl)-4-
(methylamino)pyrrolidin-1-yl]-5,6,7,8-
tetrahydroquinolin-6-yl]-6-methylthieno[2,3-
b]pyridine-2-carboxamide

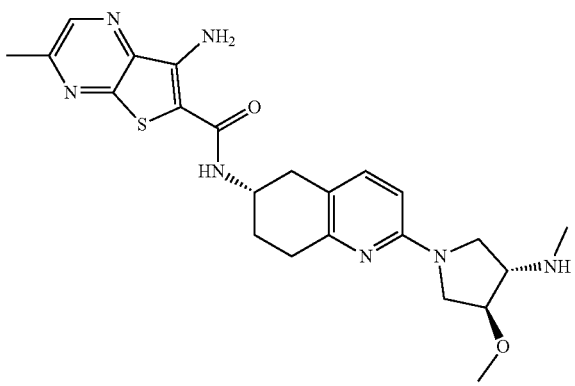
590. 7-amino-N-[(6S)-2-[(3S,4S)-3-methoxy-4-(methylamino)pyrrolidin-1-yl]-5,6,7,8-tetrahydroquinolin-6-yl]-3-methylthieno[2,3-b]pyrazine-6-carboxamide
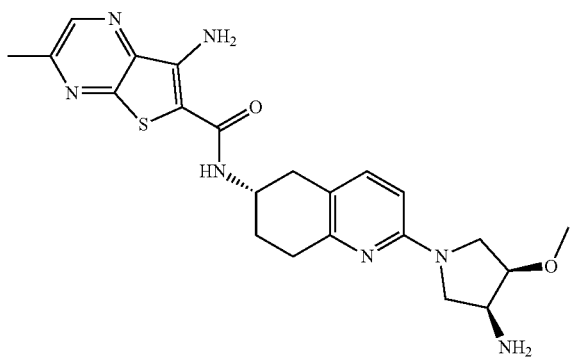
591. 7-amino-N-[(6S)-2-[(3S,4R)-3-amino-4-methoxypyrrolidin-1-yl]-5,6,7,8-tetrahydroquinolin-6-yl]-3-methylthieno[2,3-b]pyrazine-6-carboxamide
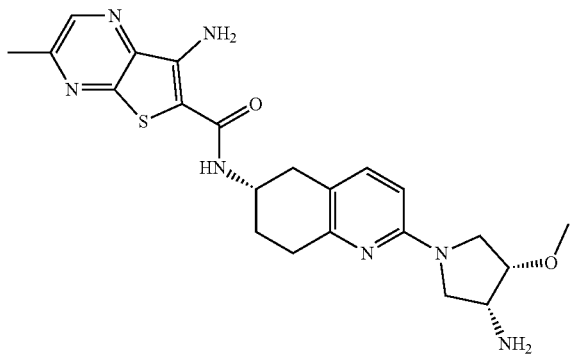
592. 7-amino-N-[(6S)-2-[(3R,4S)-3-amino-4-methoxypyrrolidin-1-yl]-5,6,7,8-tetrahydroquinolin-6-yl]-3-methylthieno[2,3-b]pyrazine-6-carboxamide

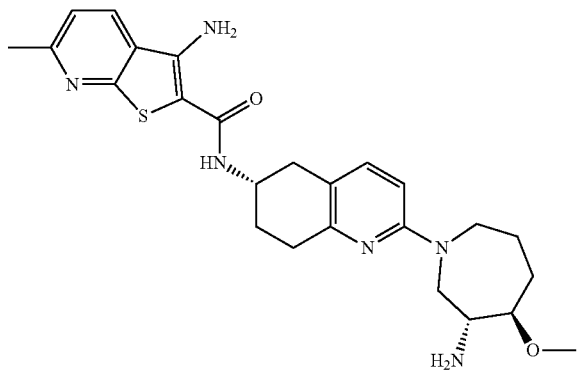
593. 3-amino-N-[(6S)-2-[(3R,4R)-3-amino-4-methoxyazepan-1-yl]-5,6,7,8-tetrahydroquinolin-6-yl]-6-methylthieno[2,3-b]pyridine-2-carboxamide
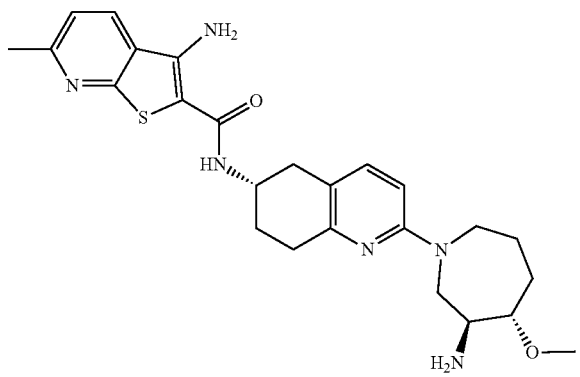
594. 3-amino-N-[(6S)-2-[(3S,4S)-3-amino-4-methoxyazepan-1-yl]-5,6,7,8-tetrahydroquinolin-6-yl]-6-methylthieno[2,3-b]pyridine-2-carboxamide
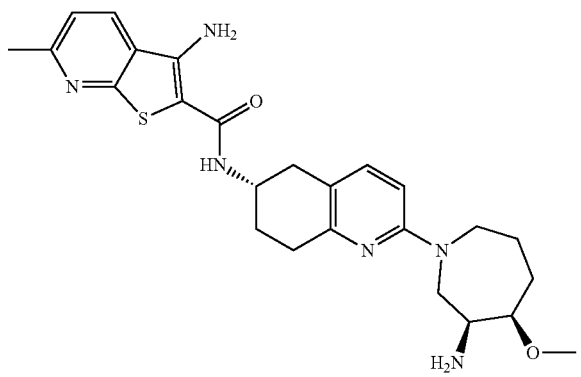
595. 3-amino-N-[(6S)-2-[(3S,4R)-3-amino-4-methoxyazepan-1-yl]-5,6,7,8-tetrahydroquinolin-6-yl]-6-methylthieno[2,3-b]pyridine-2-carboxamide TABLE 26-continued
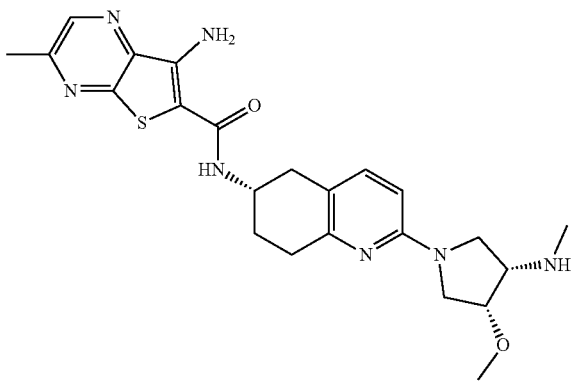
596. 7-amino-N-[(6S)-2-[(3R,4S)-3-methoxy-
4-(methylamino)pyrrolidin-1-yl]-5,6,7,8-
tetrahydroquinolin-6-yl]-3-methylthieno[2,3-
b]pyrazine-6-carboxamide
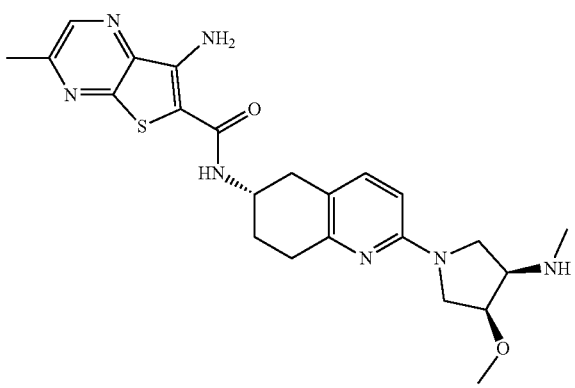
597. 7-amino-N-[(6S)-2-[(3S,4R)-3-
methoxy-4-(methylamino)pyrrolidin-1-yl]-
5,6,7,8-tetrahydroquinolin-6-yl]-3-
methylthieno[2,3-b]pyrazine-6-carboxamide
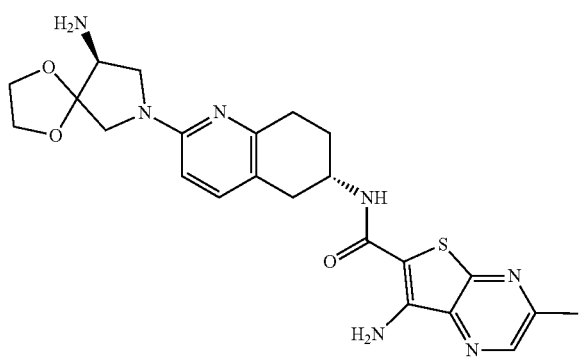 [SMILES: Cc1cnc2c(N)c(C(=O)N[C@H]3CCc4nc(N5C[C@H](N)C6(C5)OCCO6)ccc4C3)sc2n1]
598. 7-amino-N-[(6S)-2-[(9S)-9-amino-1,4-
dioxa-7-azaspiro[4.4]nonan-7-yl]-5,6,7,8-
tetrahydroquinolin-6-yl]-3-methylthieno[2,3-
b]pyrazine-6-carboxamide TABLE 26-continued
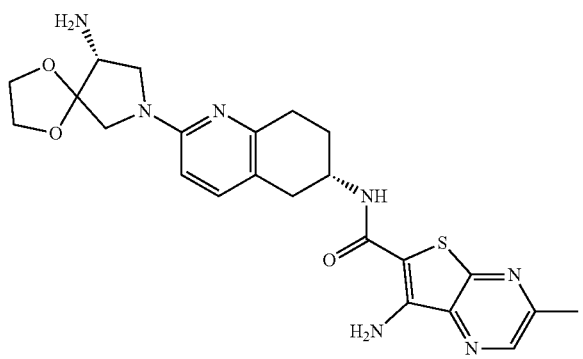 [SMILES: Cc1cnc2c(N)c(C(=O)N[C@H]3CCc4nc(N5C[C@@H](N)C6(C5)OCCO6)ccc4C3)sc2n1]
599. 7-amino-N-[(6S)-2-[(9R)-9-amino-1,4-
dioxa-7-azaspiro[4.4]nonan-7-yl]-5,6,7,8-
tetrahydroquinolin-6-yl]-3-methylthieno[2,3-
b]pyrazine-6-carboxamide
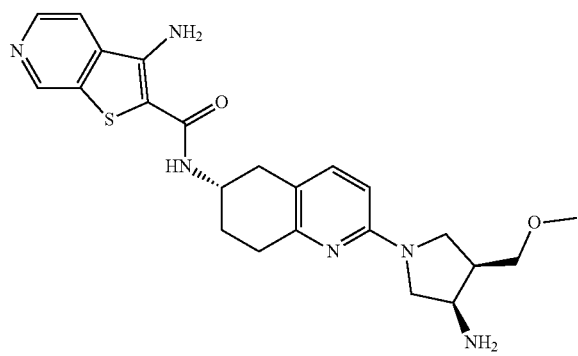 [SMILES: COC[C@@H]1CN(c2ccc3c(n2)CC[C@H](NC(=O)c2sc4cnccc4c2N)C3)C[C@@H]1N]
600. 3-amino-N-[(6S)-2-[(3R,4R)-3-amino-4-
(methoxymethyl)pyrrolidin-1-yl]-5,6,7,8-
tetrahydroquinolin-6-yl]thieno[2,3-c]pyridine-
2-carboxamide
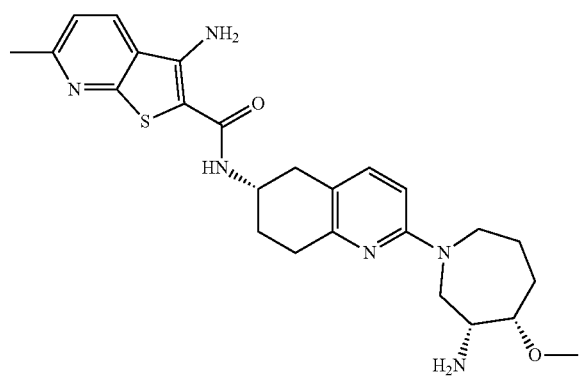
601. 3-amino-N-[(6S)-2-[(3R,4S)-3-amino-
4-methoxyazepan-1-yl]-5,6,7,8-
tetrahydroquinolin-6-yl]-6-methylthieno[2,3-
b]pyridine-2-carboxamide

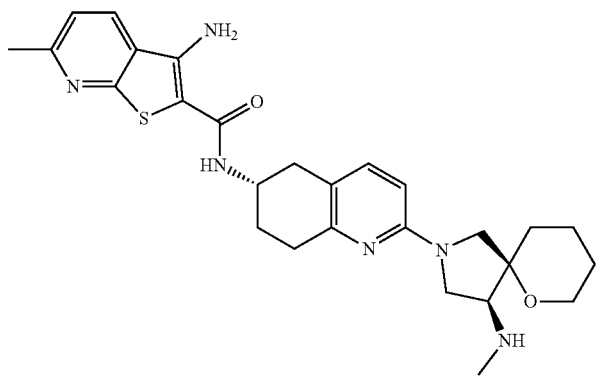 [SMILES: CN[C@H]1CN(c2ccc3c(n2)CC[C@H](NC(=O)c2sc4nc(C)ccc4c2N)C3)C[C@]12CCCCO2]
602. 3-amino-6-methyl-N-[(6S)-2-[(4S,5R)-4-(methylamino)-6-oxa-2-azaspiro[4.5]decan-2-yl]-5,6,7,8-tetrahydroquinolin-6-yl]thieno[2,3-b]pyridine-2-carboxamide
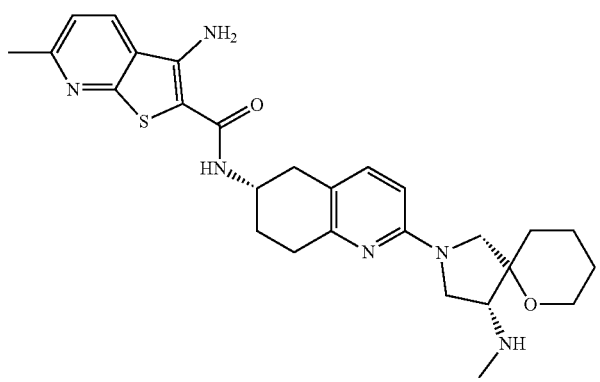
603. 3-amino-6-methyl-N-[(6S)-2-[(4R,5S)-4-(methylamino)-6-oxa-2-azaspiro[4.5]decan-2-yl]-5,6,7,8-tetrahydroquinolin-6-yl]thieno[2,3-b]pyridine-2-carboxamide
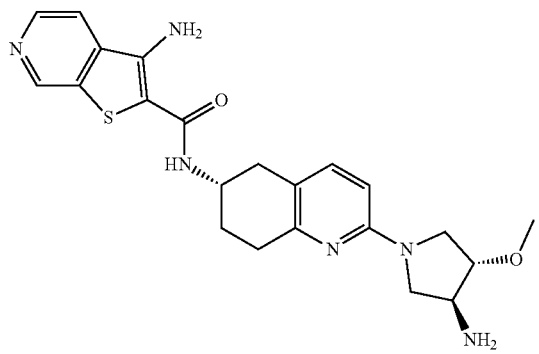 [SMILES: CO[C@H]1CN(c2ccc3c(n2)CC[C@H](NC(=O)c2sc4cnccc4c2N)C3)C[C@@H]1N]
604. 3-amino-N-[(6S)-2-[(3S,4S)-3-amino-4-methoxypyrrolidin-1-yl]-5,6,7,8-tetrahydroquinolin-6-yl]thieno[2,3-c]pyridine-2-carboxamide TABLE 26-continued
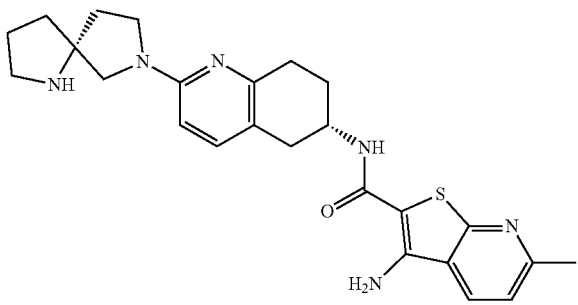 [SMILES: Cc1ccc2c(N)c(C(=O)N[C@H]3CCc4nc(N5CC[C@]6(CCCN6)C5)ccc4C3)sc2n1]
605. 3-amino-N-[(6S)-2-[(5R)-1,7-
diazaspiro[4.4]nonan-7-yl]-5,6,7,8-
tetrahydroquinolin-6-yl]-6-methylthieno[2,3-
b]pyridine-2-carboxamide
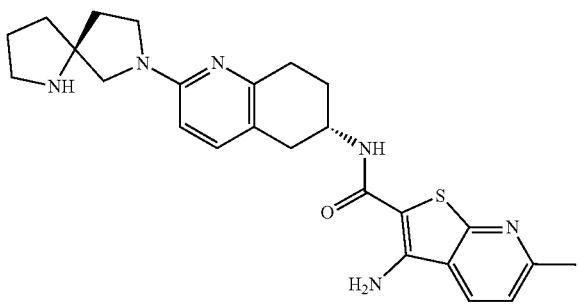 [SMILES: Cc1ccc2c(N)c(C(=O)N[C@H]3CCc4nc(N5CC[C@@]6(CCCN6)C5)ccc4C3)sc2n1]
606. 3-amino-N-[(6S)-2-[(5S)-1,7-
diazaspiro[4.4]nonan-7-yl]-5,6,7,8-
tetrahydroquinolin-6-yl]-6-methylthieno[2,3-
b]pyridine-2-carboxamide
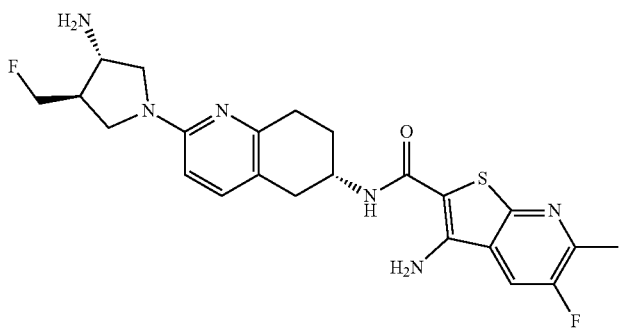 [SMILES: Cc1nc2sc(C(=O)N[C@H]3CCc4nc(N5C[C@@H](CF)[C@H](N)C5)ccc4C3)c(N)c2cc1F]
607. 3-amino-N-[(6S)-2-[(3S,4R)-3-amino-
4-(fluoromethyl)pyrrolidin-1-yl]-5,6,7,8-
tetrahydroquinolin-6-yl]-5-fluoro-6-
methylthieno[2,3-b]pyridine-2-
carboxamide TABLE 26-continued
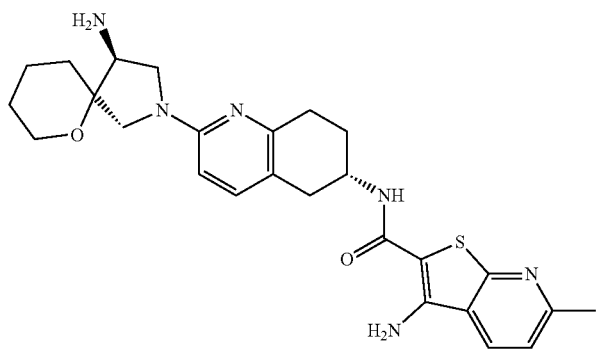
608. 3-amino-N-[(6S)-2-[(4S,5R)-4-amino-6-
oxa-2-azaspiro[4.5]decan-2-yl]-5,6,7,8-
tetrahydroquinolin-6-yl]-6-methylthieno[2,3-
b]pyridine-2-carboxamide
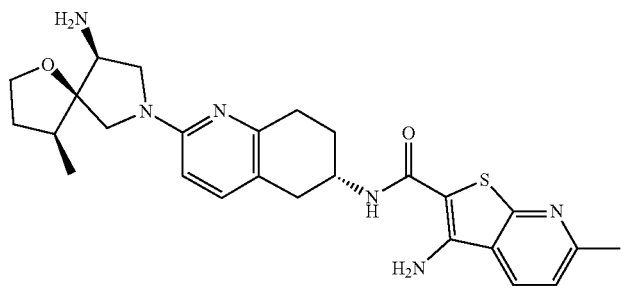 [SMILES: Cc1ccc2c(N)c(C(=O)N[C@H]3CCc4nc(N5CC[C@H](N)[C@@]6(C5)OCC[C@@H]6C)ccc4C3)sc2n1]
609. 3-amino-N-[(6S)-2-[(4S,5R,9S)-9-
amino-4-methyl-1-oxa-7-
azaspiro[4.4]nonan-7-yl]-5,6,7,8-
tetrahydroquinolin-6-yl]-6-methylthieno[2,3-
b]pyridine-2-carboxamide
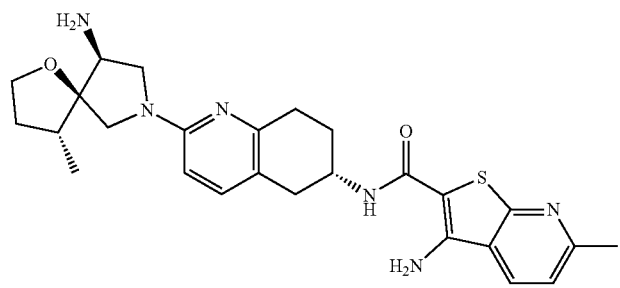 [SMILES: Cc1ccc2c(N)c(C(=O)N[C@H]3CCc4nc(N5C[C@H](N)[C@@]6(C5)OCC[C@H]6C)ccc4C3)sc2n1]
610. 3-amino-N-[(6S)-2-[(4R,5R,9S)-9-amino-
4-methyl-1-oxa-7-azaspiro[4.4]nonan-7-yl]-
5,6,7,8-tetrahydroquinolin-6-yl]-6-
methylthieno[2,3-b]pyridine-2-carboxamide TABLE 26-continued
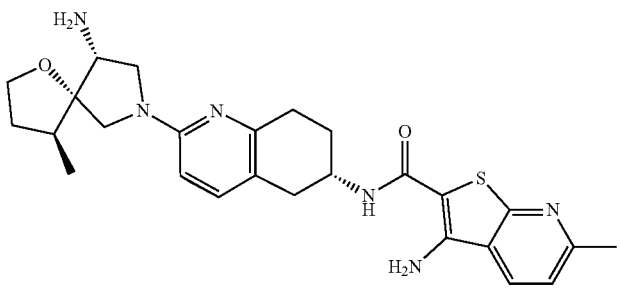 [SMILES: Cc1ccc2c(N)c(C(=O)N[C@H]3CCc4nc(N5CC[C@]6(OCC[C@@H]6C)[C@H](N)C5)c5c(c4C3)C5)sc2n1]
611. 3-amino-N-[(6S)-2-[(4S,5S,9R)-9-
amino-4-methyl-1-oxa-7-
azaspiro[4.4]nonan-7-yl]-5,6,7,8-
tetrahydroquinolin-6-yl]-6-methylthieno[2,3-
b]pyridine-2-carboxamide
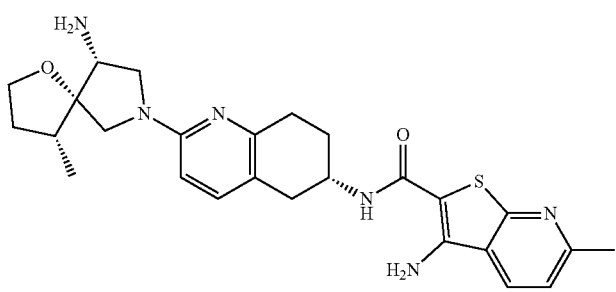 [SMILES: Cc1ccc2c(N)c(C(=O)N[C@H]3CCc4nc(N5C[C@@H](N)[C@]6(C5)OCC[C@H]6C)ccc4C3)sc2n1]
612. 3-amino-N-[(6S)-2-[(4R,5S,9R)-9-amino-
4-methyl-1-oxa-7-azaspiro[4.4]nonan-7-yl]-
5,6,7,8-tetrahydroquinolin-6-yl]-6-
methylthieno[2,3-b]pyridine-2-carboxamide
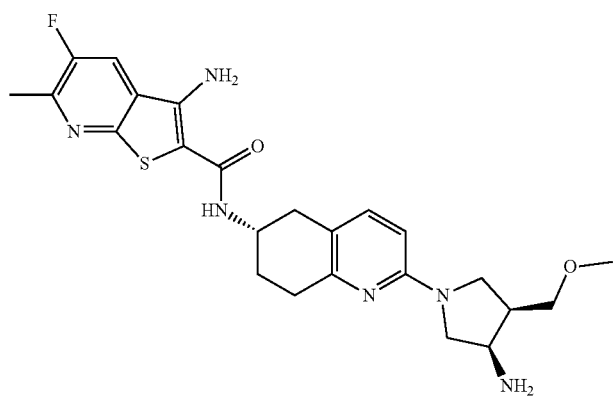
613. 3-amino-N-[(6S)-2-[(3R,4R)-3-amino-
4-(methoxymethyl)pyrrolidin-1-yl]-5,6,7,8-
tetrahydroquinolin-6-yl]-5-fluoro-6-
methylthieno[2,3-b]pyridine-2-carboxamide

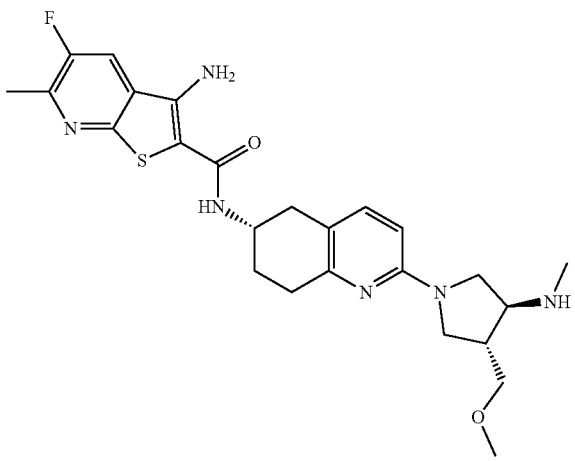

614. 3-amino-5-fluoro-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide

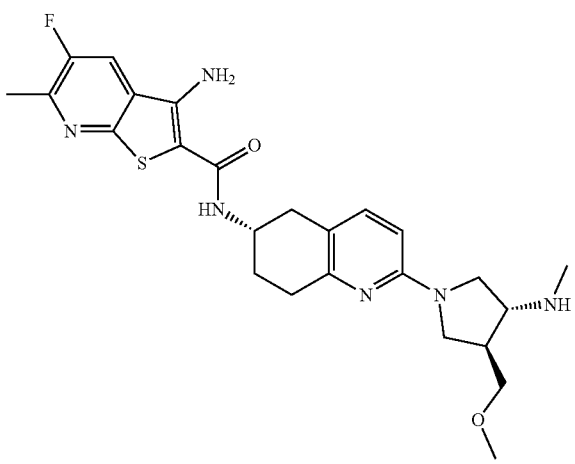

615. 3-amino-5-fluoro-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide

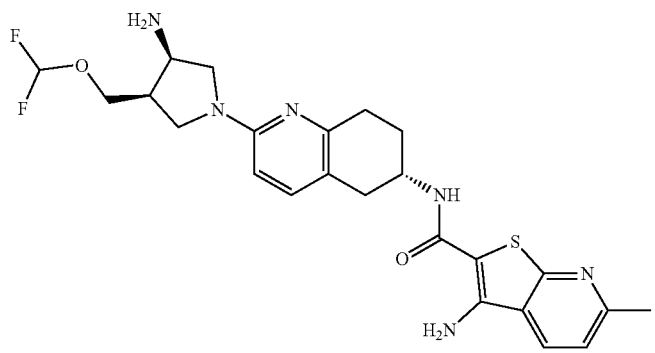 [SMILES: Cc1ccc2c(N)c(C(=O)N[C@H]3CCc4nc(N5C[C@@H](COC(F)F)[C@@H](N)C5)ccc4C3)sc2n1]

616. 3-amino-N-[(6S)-2-[(3R,4R)-3-amino-4-[(difluoromethoxy)methyl]pyrrolidin-1-yl]-5,6,7,8-tetrahydroquinolin-6-yl]-6-methylthieno[2,3-b]pyridine-2-carboxamide

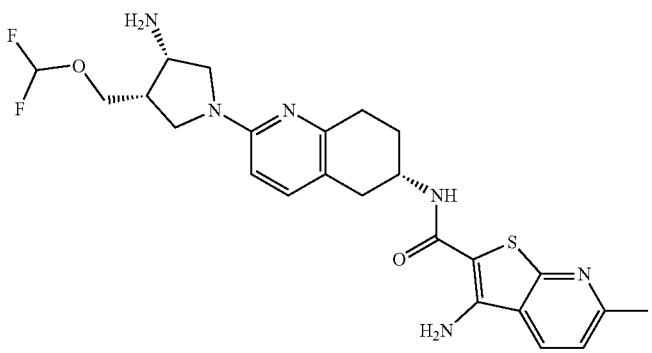 [SMILES: Cc1ccc2c(N)c(C(=O)N[C@H]3CCc4nc(N5C[C@H](COC(F)F)[C@H](N)C5)ccc4C3)sc2n1]
617. 3-amino-N-[(6S)-2-[(3S,4S)-3-amino-4-[(difluoromethoxy)methyl]pyrrolidin-1-yl]-5,6,7,8-tetrahydroquinolin-6-yl]-6-methylthieno[2,3-b]pyridine-2-carboxamide
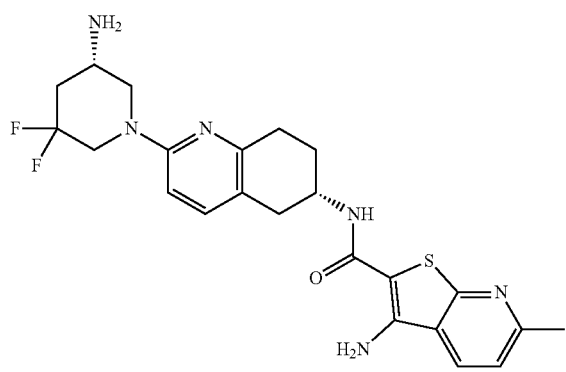 [SMILES: Cc1ccc2c(N)c(C(=O)N[C@H]3CCc4nc(N5C[C@@H](N)CC(F)(F)C5)ccc4C3)sc2n1]
618. 3-amino-N-[(6S)-2-[(5S)-5-amino-3,3-difluoropiperidin-1-yl]-5,6,7,8-tetrahydroquinolin-6-yl]-6-methylthieno[2,3-b]pyridine-2-carboxamide
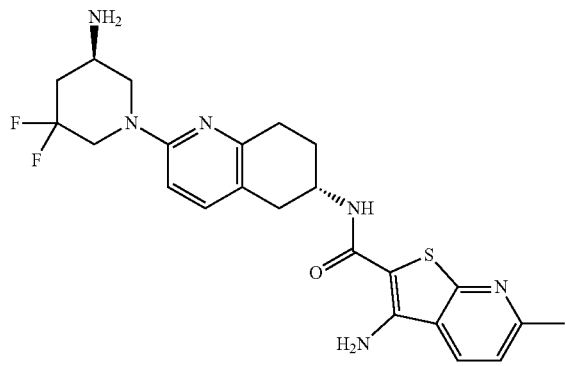 [SMILES: Cc1ccc2c(N)c(C(=O)N[C@H]3CCc4nc(N5C[C@H](N)CC(F)(F)C5)ccc4C3)sc2n1]
619. 3-amino-N-[(6S)-2-[(5R)-5-amino-3,3-difluoropiperidin-1-yl]-5,6,7,8-tetrahydroquinolin-6-yl]-6-methylthieno[2,3-b]pyridine-2-carboxamide

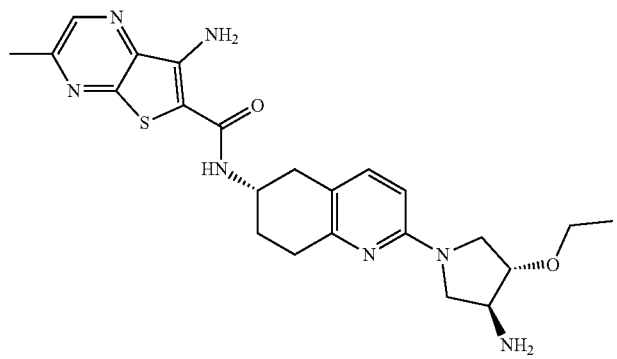 [SMILES: CCO[C@H]1CN(c2ccc3c(n2)CC[C@H](NC(=O)c2sc4nc(C)cnc4c2N)C3)C[C@@H]1N]
620. 7-amino-N-[(6S)-2-[(3S,4S)-3-amino-4-
ethoxypyrrolidin-1-yl]-5,6,7,8-
tetrahydroquinolin-6-yl]-3-methylthieno[2,3-
b]pyrazine-6-carboxamide
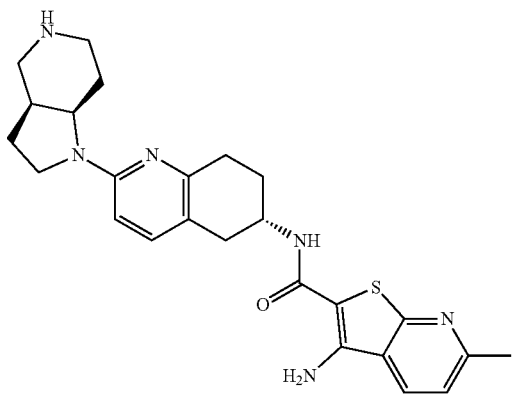 [SMILES: Cc1ccc2c(N)c(C(=O)N[C@H]3CCc4nc(N5CC[C@H]6CNCC[C@H]65)ccc4C3)sc2n1]
621. N-[(6S)-2-[(3aS,7aR)-octahydro-1H-
pyrrolo[3,2-c]pyridin-1-yl]-5,6,7,8-
tetrahydroquinolin-6-yl]-3-amino-6-
methylthieno[2,3-b]pyridine-2-carboxamide
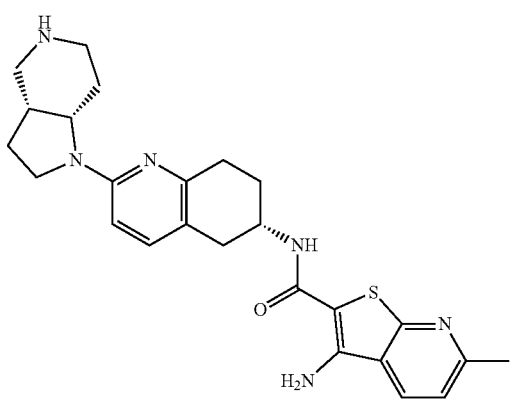 [SMILES: Cc1ccc2c(N)c(C(=O)N[C@H]3CCc4nc(N5CC[C@@H]6CNCC[C@@H]65)ccc4C3)sc2n1]
622. N-[(6S)-2-[(3aR,7aS)-octahydro-1H-
pyrrolo[3,2-c]pyridin-1-yl]-5,6,7,8-
tetrahydroquinolin-6-yl]-3-amino-6-
methylthieno[2,3-b]pyridine-2-carboxamide

TABLE 26-continued

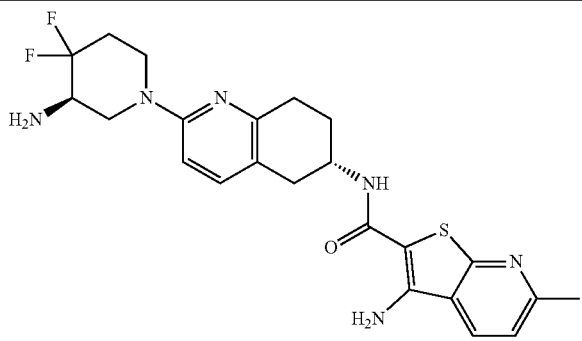

623. 3-amino-N-[(6S)-2-[(3R)-3-amino-4,4-difluoropiperidin-1-yl]-5,6,7,8-tetrahydroquinolin-6-yl]-6-methylthieno[2,3-b]pyridine-2-carboxamide

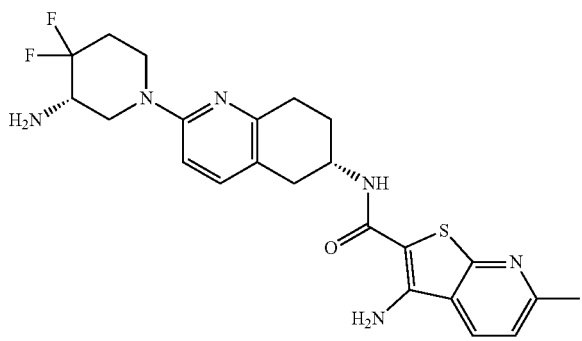 [SMILES: Cc1ccc2c(N)c(C(=O)N[C@H]3CCc4nc(N5CCC(F)(F)[C@@H](N)C5)ccc4C3)sc2n1]

624. 3-amino-N-[(6S)-2-[(3S)-3-amino-4,4-difluoropiperidin-1-yl]-5,6,7,8-tetrahydroquinolin-6-yl]-6-methylthieno[2,3-b]pyridine-2-carboxamide

TABLE 27

| Structure | Chemical Name |
|---|---|
| 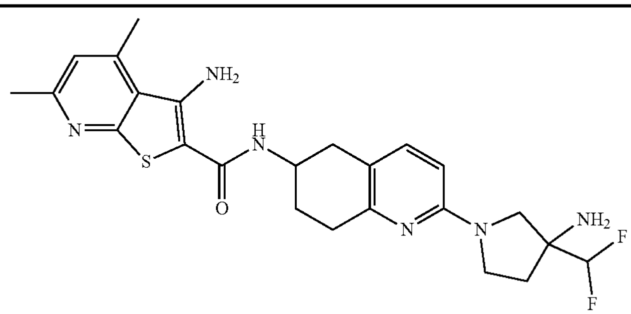 | 3-amino-N-{2-[3-amino-3-(difluoromethyl)pyrrolidin-1-yl]-5,6,7,8-tetrahydroquinolin-6-yl}-4,6-dimethylthieno[2,3-b]pyridine-2-carboxamide |
| 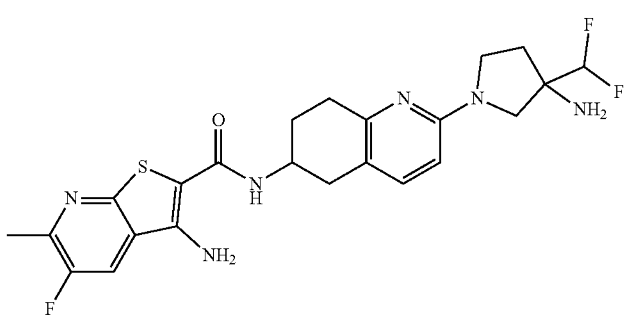 [SMILES: Cc1nc2sc(C(=O)NC3CCc4nc(N5CCC(N)(C(F)F)C5)ccc4C3)c(N)c2cc1F] | 3-amino-N-{2-[3-amino-3-(difluoromethyl)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 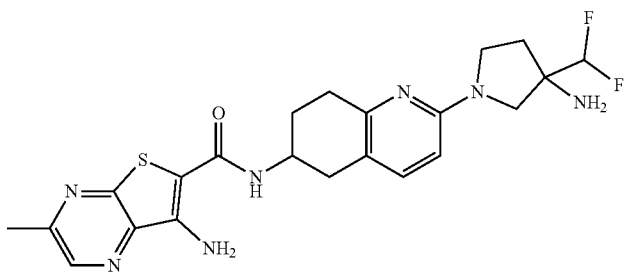 [SMILES: Cc1cnc2c(N)c(C(=O)NC3CCc4nc(N5CCC(N)(C(F)F)C5)ccc4C3)sc2n1] | 7-amino-N-{2-[3-amino-3-(difluoromethyl)pyrrolidin-1-yl]-5,6,7,8-tetrahydroquinolin-6-yl}-3-methylthieno[2,3-b]pyrazine-6-carboxamide |
| 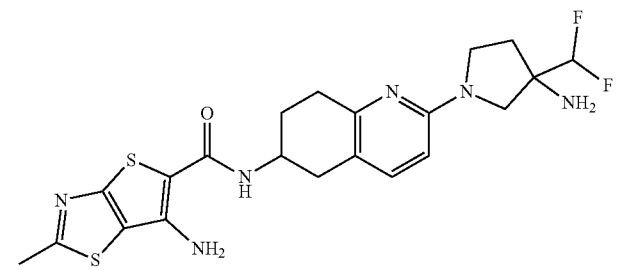 [SMILES: Cc1nc2sc(C(=O)NC3CCc4nc(N5CCC(N)(C(F)F)C5)ccc4C3)c(N)c2s1] | 6-amino-N-{2-[3-amino-3-(difluoromethyl)pyrrolidin-1-yl]-5,6,7,8-tetrahydroquinolin-6-yl}-2-methylthieno[2,3-d][1,3]thiazole-5-carboxamide |
| 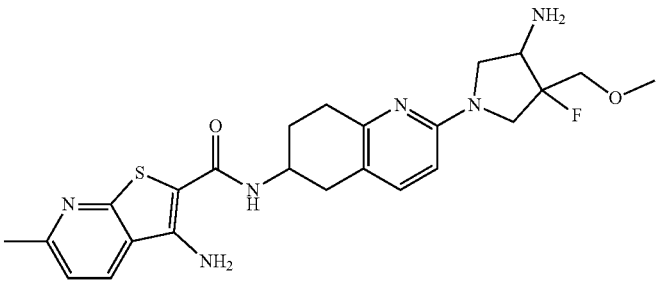 | 3-amino-N-{2-[4-amino-3-fluoro-3-(methoxymethyl)pyrrolidin-1-yl]-5,6,7,8-tetrahydroquinolin-6-yl}-6-methylthieno[2,3-b]pyridine-2-carboxamide |
| 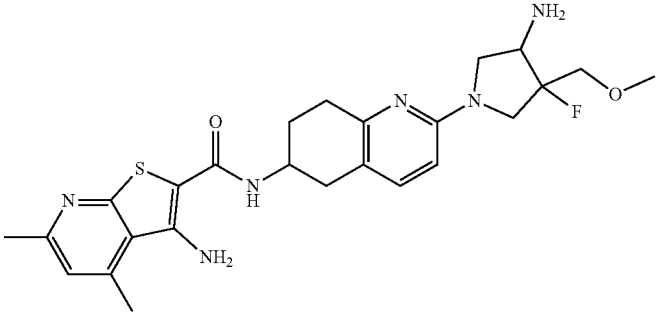 | 3-amino-N-{2-[4-amino-3-fluoro-3-(methoxymethyl)pyrrolidin-1-yl]-5,6,7,8-tetrahydroquinolin-6-yl}-4,6-dimethylthieno[2,3-b]pyridine-2-carboxamide |
| 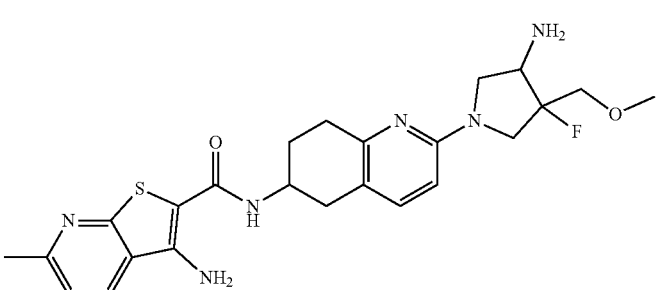 | 3-amino-N-{2-[4-amino-3-fluoro-3-(methoxymethyl)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 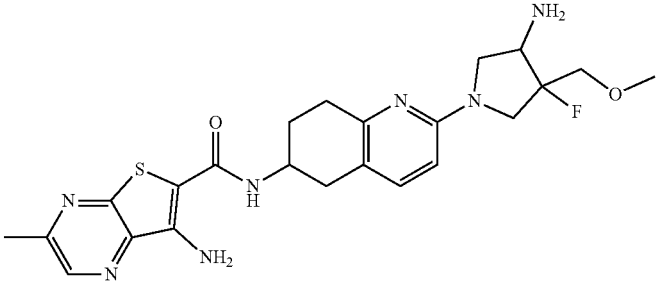 | 7-amino-N-{2-[4-amino-3-fluoro-3-(methoxymethyl)pyrrolidin-1-yl]-5,6,7,8-tetrahydroquinolin-6-yl}-3-methylthieno[2,3-b]pyrazine-6-carboxamide |
| 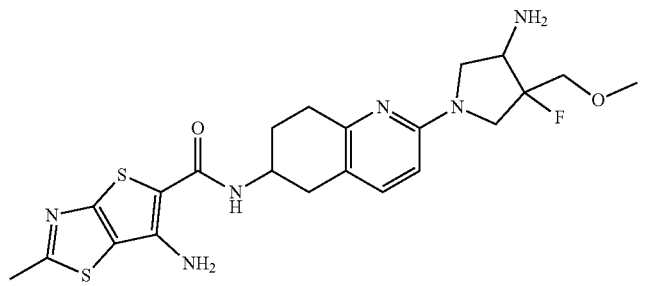 | 6-amino-N-{2-[4-amino-3-fluoro-3-(methoxymethyl)pyrrolidin-1-yl]-5,6,7,8-tetrahydroquinolin-6-yl}-2-methylthieno[2,3-d][1,3]thiazole-5-carboxamide |
| 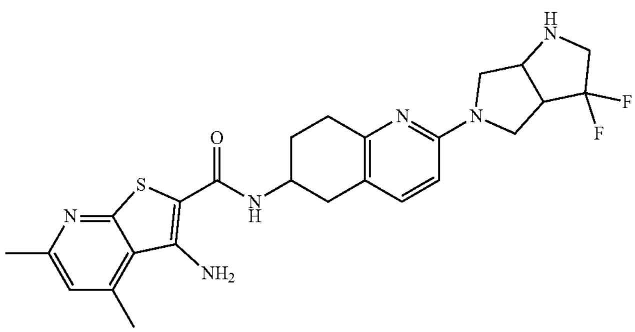 [SMILES: Cc1cc(C)c2c(N)c(C(=O)NC3CCc4nc(N5CC6NCC(F)(F)C6C5)ccc4C3)sc2n1] | 3-amino-N-(2-{3,3-difluoro-octahydropyrrolo[2,3-c]pyrrol-5-yl}-5,6,7,8-tetrahydroquinolin-6-yl)-4,6-dimethylthieno[2,3-b]pyridine-2-carboxamide |
| 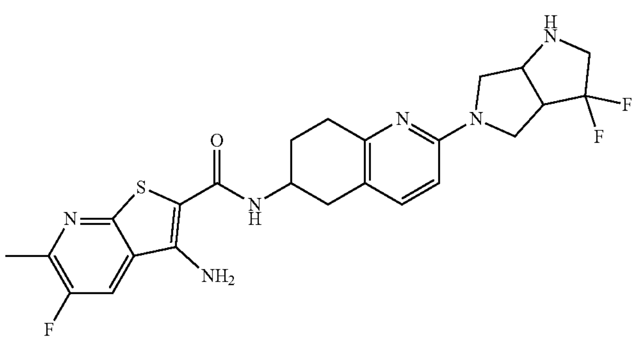 [SMILES: Cc1nc2sc(C(=O)NC3CCc4nc(N5CC6NCC(F)(F)C6C5)ccc4C3)c(N)c2cc1F] | 3-amino-N-(2-{3,3-difluoro-octahydropyrrolo[2,3-c]pyrrol-5-yl}-5,6,7,8-tetrahydroquinolin-6-yl)-5-fluoro-6-methylthieno[2,3-b]pyridine-2-carboxamide |
|  | 7-amino-N-(2-{3,3-difluoro-octahydropyrrolo[2,3-c]pyrrol-5-yl}-5,6,7,8-tetrahydroquinolin-6-yl)-3-methylthieno[2,3-b]pyrazine-6-carboxamide |

TABLE 27-continued

| Structure | Chemical Name |
|---|---|
| 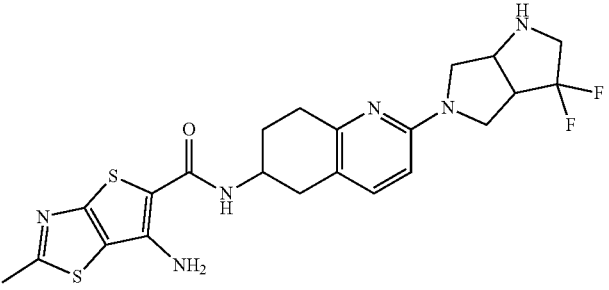 [SMILES: Cc1nc2sc(C(=O)NC3CCc4nc(N5CC6NCC(F)(F)C6C5)ccc4C3)c(N)c2s1] | 6-amino-N-(2-{3,3-difluoro-octahydropyrrolo[2,3-c]pyrrol-5-yl}-5,6,7,8-tetrahydroquinolin-6-yl)-2-methylthieno[2,3-d][1,3]thiazole-5-carboxamide |
| 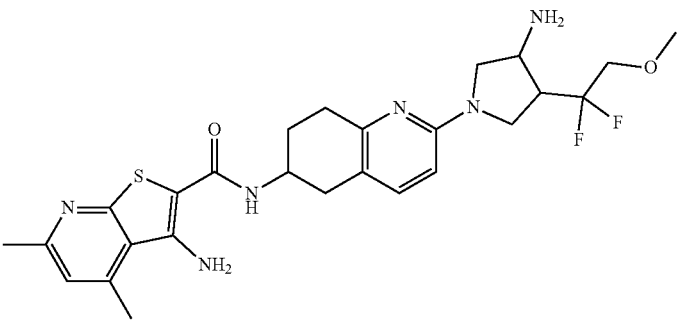 | 3-amino-N-{2-[3-amino-4-(1,1-difluoro-2-methoxyethyl)pyrrolidin-1-yl]-5,6,7,8-tetrahydroquinolin-6-yl}-4,6-dimethylthieno[2,3-b]pyridine-2-carboxamide |
| 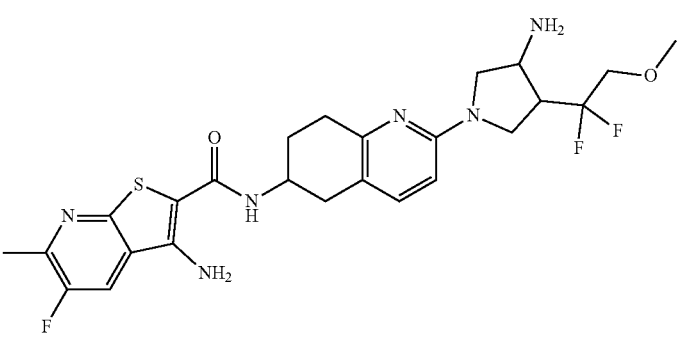 | 3-amino-N-{2-[3-amino-4-(1,1-difluoro-2-methoxyethyl)pyrrolidin-1-yl]-5,6,7,8-tetrahydroquinolin-6-yl}-5-fluoro-6-methylthieno[2,3-b]pyridine-2-carboxamide |
| 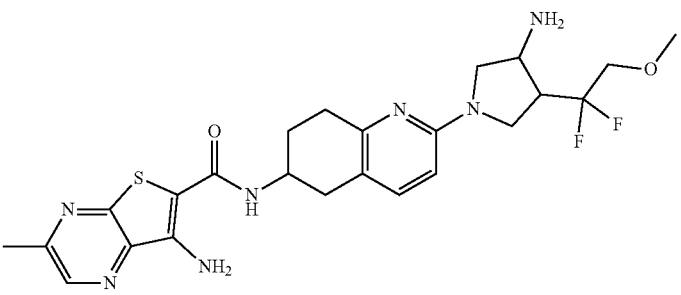 | 7-amino-N-{2-[3-amino-4-(1,1-difluoro-2-methoxyethyl)pyrrolidin-1-yl]-5,6,7,8-tetrahydroquinolin-6-yl}-3-methylthieno[2,3-b]pyrazine-6-carboxamide |
| 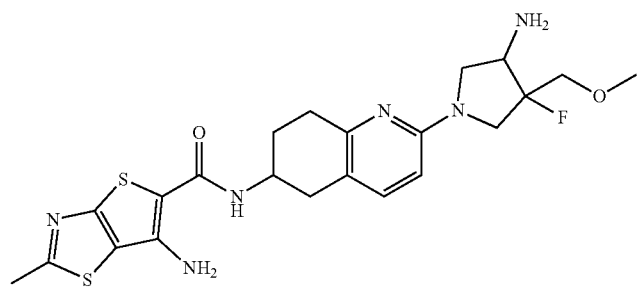 | 6-amino-N-{2-[3-amino-4-(1,1-difluoro-2-methoxyethyl)pyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 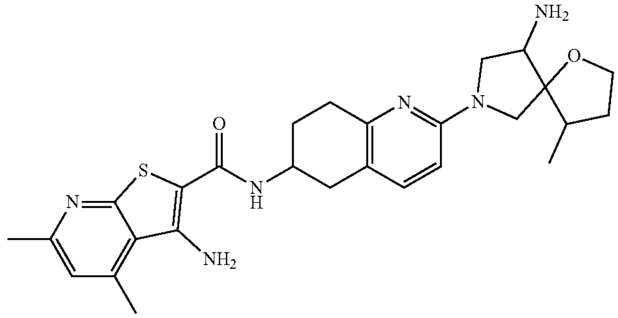 [SMILES: Cc1cc(C)c2c(N)c(C(=O)NC3CCc4nc(N5CC(N)C6(C5)OCCC6C)ccc4C3)sc2n1] | 3-amino-N-(2-{9-amino-4-methyl-1-oxa-7-azaspiro[4.4]nonan-7-yl}-5,6,7,8-tetrahydroquinolin-6-yl)-4,6-dimethylthieno[2,3-b]pyridine-2-carboxamide |
| 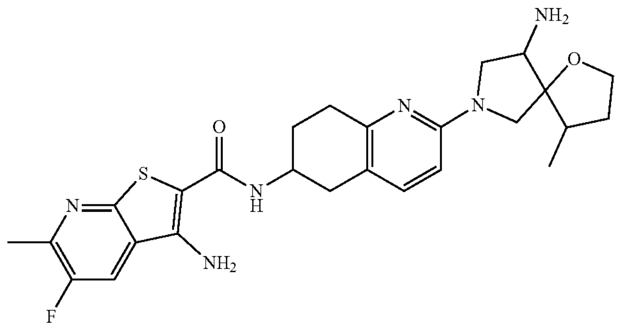 [SMILES: Cc1nc2sc(C(=O)NC3CCc4nc(N5CC(N)C6(C5)OCCC6C)ccc4C3)c(N)c2cc1F] | 3-amino-N-(2-{9-amino-4-methyl-1-oxa-7-azaspiro[4.4]nonan-7-yl}-5,6,7,8-tetrahydroquinolin-6-yl)-5-fluoro-6-methylthieno[2,3-b]pyridine-2-carboxamide |
| 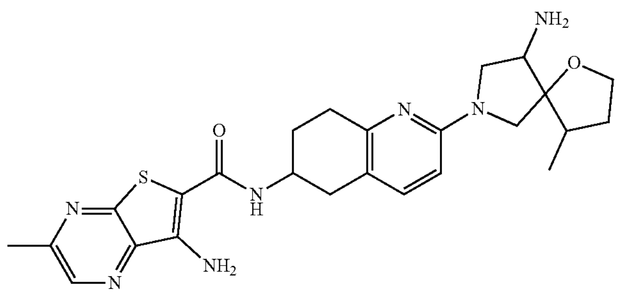 [SMILES: Cc1cnc2c(N)c(C(=O)NC3CCc4nc(N5CC(N)C6(C5)OCCC6C)ccc4C3)sc2n1] | 7-amino-N-(2-{9-amino-4-methyl-1-oxa-7-azaspiro[4.4]nonan-7-yl}-5,6,7,8-tetrahydroquinolin-6-yl)-3-methylthieno[2,3-b]pyrazine-6-carboxamide |
| 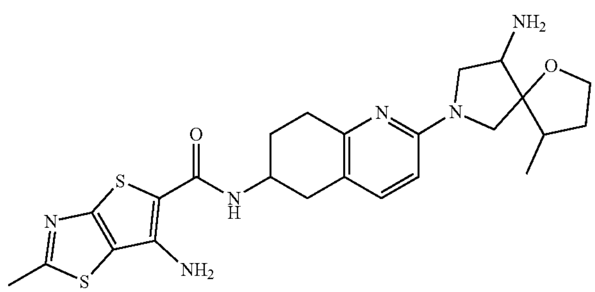 [SMILES: Cc1nc2sc(C(=O)NC3CCc4nc(N5CC(N)C6(C5)OCCC6C)ccc4C3)c(N)c2s1] | 6-amino-N-(2-{9-amino-4-methyl-1-oxa-7-azaspiro[4.4]nonan-7-yl}-5,6,7,8-tetrahydroquinolin-6-yl)-2-methylthieno[2,3-d][1,3]thiazole-5-carboxamide |
| 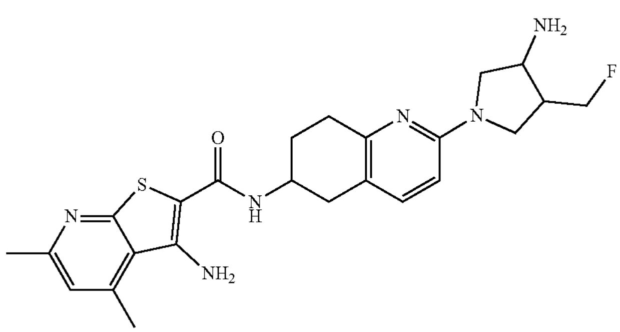 [SMILES: Cc1cc(C)c2c(N)c(C(=O)NC3CCc4nc(N5CC(N)C(CF)C5)ccc4C3)sc2n1] | 3-amino-N-{2-[3-amino-4-(fluoromethyl)pyrrolidin-1-yl]-5,6,7,8-tetrahydroquinolin-6-yl}-4,6-dimethylthieno[2,3-b]pyridine-2-carboxamide |

TABLE 27-continued

| Structure | Chemical Name |
|---|---|
| 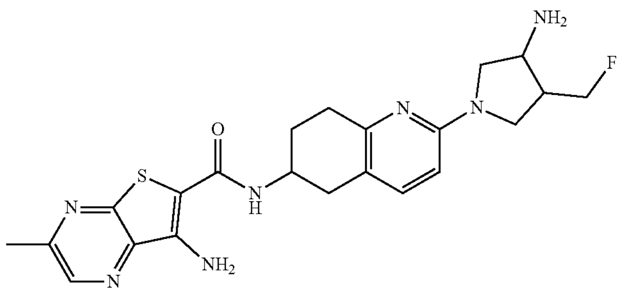 | 7-amino-N-{2-[3-amino-4-(fluoromethyl)pyrrolidin-1-yl]-5,6,7,8-tetrahydroquinolin-6-yl}-3-methylthieno[2,3-b]pyrazine-6-carboxamide |
| 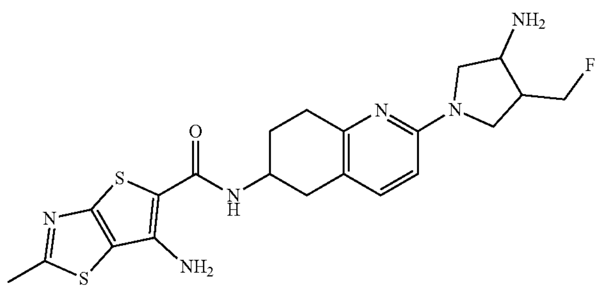 [SMILES: Cc1nc2sc(C(=O)NC3CCc4nc(N5CC(N)C(CF)C5)ccc4C3)c(N)c2s1] | 6-amino-N-{2-[3-amino-4-(fluoromethyl)pyrrolidin-1-yl]-5,6,7,8-tetrahydroquinolin-6-yl}-2-methylthieno[2,3-d][1,3]thiazole-5-carboxamide |
| 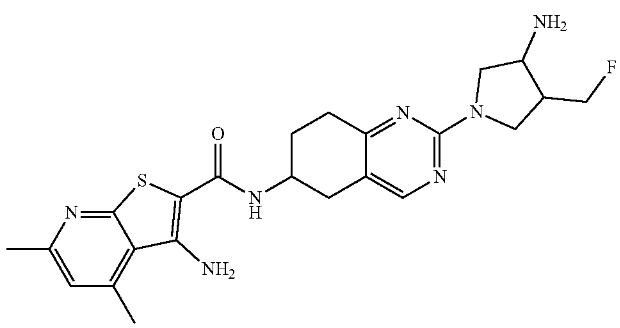 [SMILES: Cc1cc(C)c2c(N)c(C(=O)NC3CCc4nc(N5CC(N)C(CF)C5)ncc4C3)sc2n1] | 3-amino-N-{2-[3-amino-4-(fluoromethyl)pyrrolidin-1-yl]-5,6,7,8-tetrahydroquinazolin-6-yl}-4,6-dimethylthieno[2,3-b]pyridine-2-carboxamide |
| 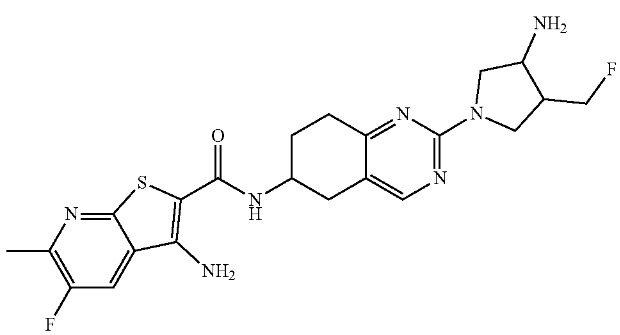 [SMILES: Cc1nc2sc(C(=O)NC3CCc4nc(N5CC(N)C(CF)C5)ncc4C3)c(N)c2cc1F] | 3-amino-N-{2-[3-amino-4-(fluoromethyl)pyrrolidin-1-yl]-5,6,7,8-tetrahydroquinazolin-6-yl}-5-fluoro-6-methylthieno[2,3-b]pyridine-2-carboxamide |
| 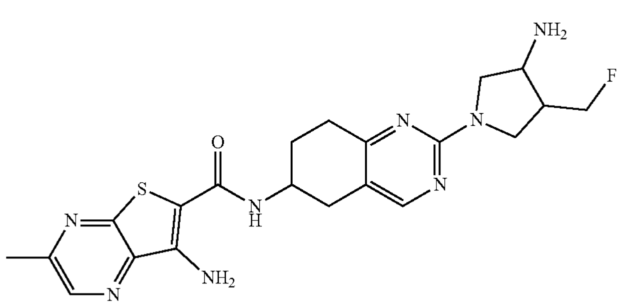 [SMILES: Cc1cnc2c(N)c(C(=O)NC3CCc4nc(N5CC(N)C(CF)C5)ncc4C3)sc2n1] | 7-amino-N-{2-[3-amino-4-(fluoromethyl)pyrrolidin-1-yl]-5,6,7,8-tetrahydroquinazolin-6-yl}-3-methylthieno[2,3-b]pyrazine-6-carboxamide |

TABLE 27-continued

| Structure | Chemical Name |
|---|---|
| 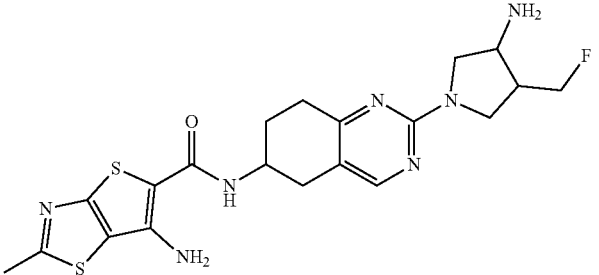 [SMILES: Cc1nc2sc(C(=O)NC3CCc4nc(N5CC(N)C(CF)C5)ncc4C3)c(N)c2s1] | 6-amino-N-{2-[3-amino-4-(fluoromethyl)pyrrolidin-1-yl]-5,6,7,8-tetrahydroquinazolin-6-yl}-2-methylthieno[2,3-d][1,3]thiazole-5-carboxamide |
| 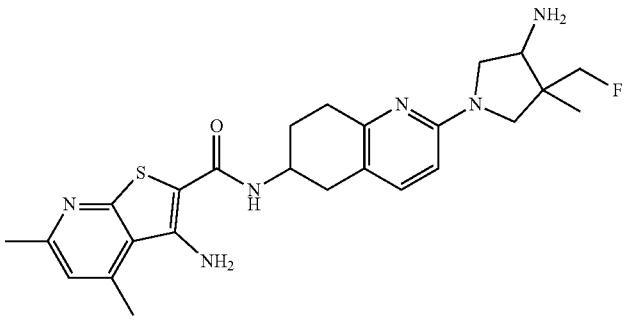 [SMILES: Cc1cc(C)c2c(N)c(C(=O)NC3CCc4nc(N5CC(N)C(C)(CF)C5)ccc4C3)sc2n1] | 3-amino-N-{2-[4-amino-3-(fluoromethyl)-3-methylpyrrolidin-1-yl]-5,6,7,8-tetrahydroquinolin-6-yl}-4,6-dimethylthieno[2,3-b]pyridine-2-carboxamide |
| 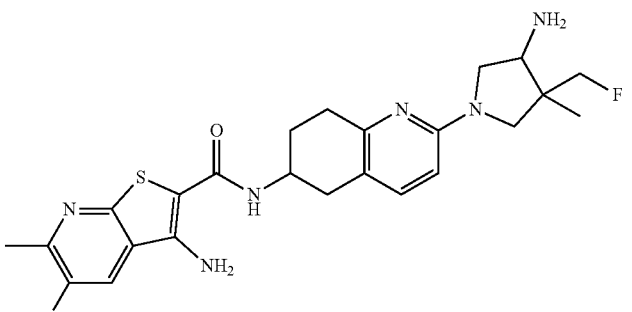 | 3-amino-N-{2-[4-amino-3-(fluoromethyl)-3-methylpyrrolidin-1-yl]-5,6,7,8-tetrahydroquinolin-6-yl}-5-fluoro-6-methylthieno[2,3-b]pyridine-2-carboxamide |
| 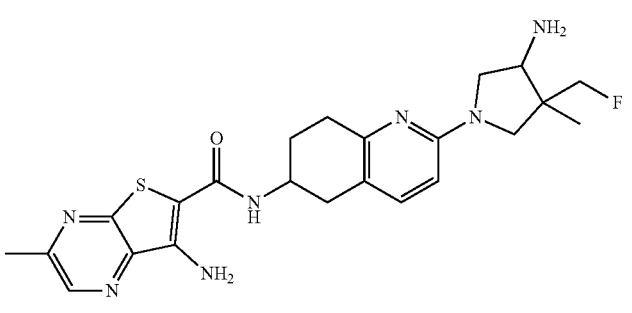 [SMILES: Cc1cnc2c(N)c(C(=O)NC3CCc4nc(N5CC(N)C(C)(CF)C5)ccc4C3)sc2n1] | 7-amino-N-{2-[4-amino-3-(fluoromethyl)-3-methylpyrrolidin-1-yl]-5,6,7,8-tetrahydroquinolin-6-yl}-3-methylthieno[2,3-b]pyrazine-6-carboxamide |
| 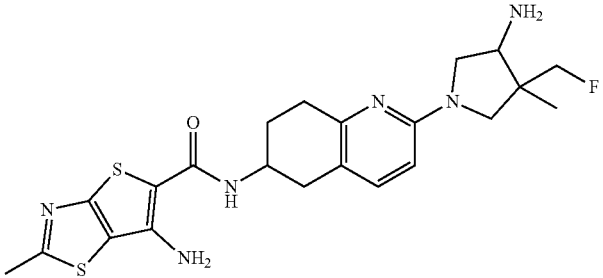 [SMILES: Cc1nc2sc(C(=O)NC3CCc4nc(N5CC(N)C(C)(CF)C5)ccc4C3)c(N)c2s1] | 6-amino-N-{2-[4-amino-3-(fluoromethyl)-3-methylpyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 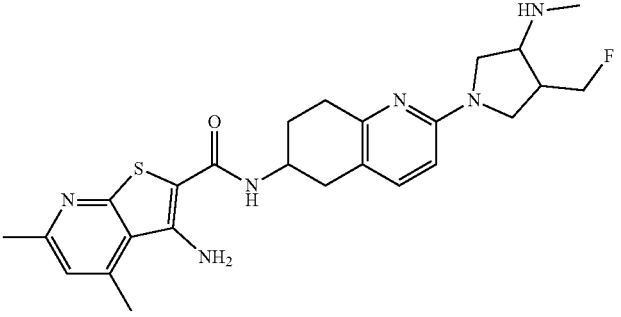 | 3-amino-N-{2-[3-(fluoromethyl)-4-(methylamino)pyrrolidin-1-yl]-5,6,7,8-tetrahydroquinolin-6-yl}-4,6-dimethylthieno[2,3-b]pyridine-2-carboxamide |
| 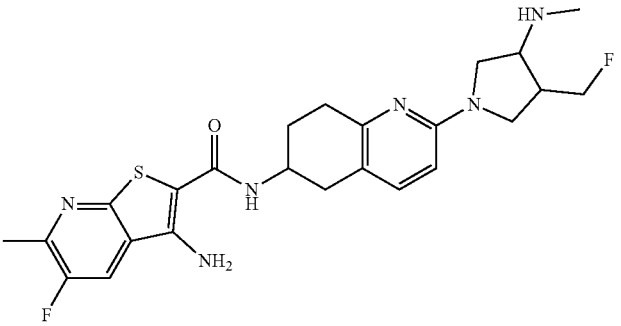 [SMILES: CNC1CN(c2ccc3c(n2)CCC(NC(=O)c2sc4nc(C)c(F)cc4c2N)C3)CC1CF] | 3-amino-5-fluoro-N-{2-[3-(fluoromethyl)-4-(methylamino)pyrrolidin-1-yl]-5,6,7,8-tetrahydroquinolin-6-yl}-6-methylthieno[2,3-b]pyridine-2-carboxamide |
| 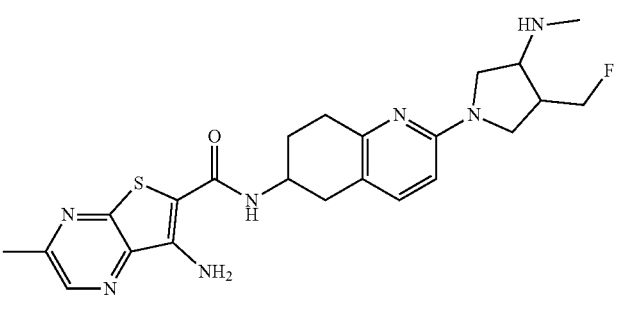 [SMILES: CNC1CN(c2ccc3c(n2)CCC(NC(=O)c2sc4nc(C)cnc4c2N)C3)CC1CF] | 7-amino-N-{2-[3-(fluoromethyl)-4-(methylamino)pyrrolidin-1-yl]-5,6,7,8-tetrahydroquinolin-6-yl}-3-methylthieno[2,3-b]pyrazine-6-carboxamide |
| 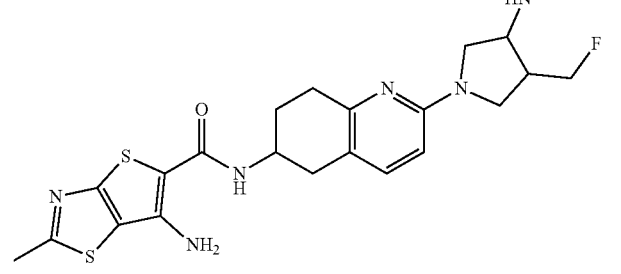 | 6-amino-N-{2-[3-(fluoromethyl)-4-(methylamino)pyrrolidin-1-yl]-5,6,7,8-tetrahydroquinolin-6-yl}-2-methylthieno[2,3-d][1,3]thiazole-5-carboxamide |
| 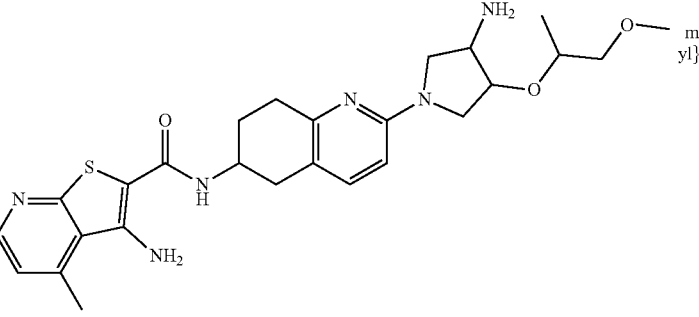 | 3-amino-N-(2-{3-amino-4-[(1-methoxypropan-2-yl)oxy]pyrrolidin-1-yl}-5,6,7,8-tetrahydroquinolin-6-yl)-4,6-dimethylthieno[2,3-b]pyridine-2-carboxamide |

TABLE 27-continued

| Structure | Chemical Name |
|---|---|
| 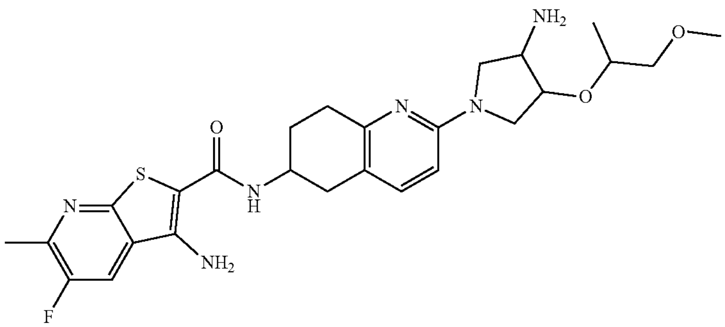 | 3-amino-N-(2-{3-amino-4-[(1-methoxypropan-2-yl)oxy]pyrrolidin-1-yl}-5,6,7,8-tetrahydroquinolin-6-yl)-5-fluoro-6-methylthieno[2,3-b]pyridine-2-carboxamide |
| 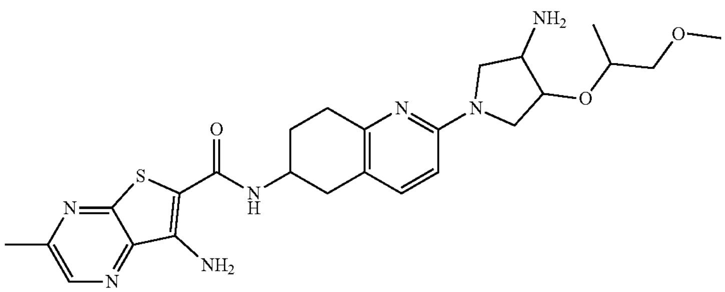 | 7-amino-N-(2-{3-amino-4-[(1-methoxypropan-2-yl)oxy]pyrrolidin-1-yl}-5,6,7,8-tetrahydroquinolin-6-yl)-3-methylthieno[2,3-b]pyrazine-6-carboxamide |
| 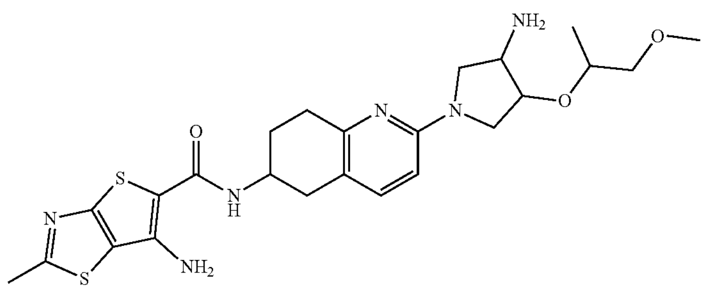 | 6-amino-N-(2-{3-amino-4-[(1-methoxypropan-2-yl)oxy]pyrrolidin-1-yl}-5,6,7,8-tetrahydroquinolin-6-yl)-2-methylthieno[2,3-d][1,3]thiazole-5-carboxamide |
| 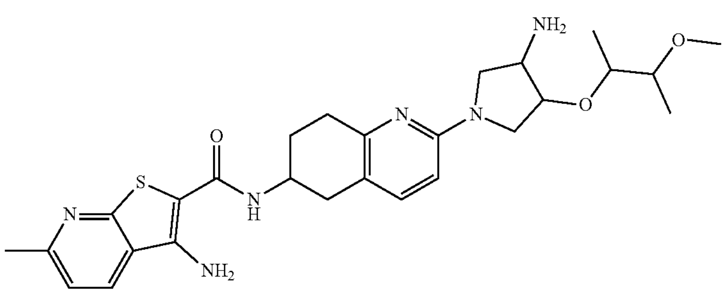 | 3-amino-N-(2-{3-amino-4-[(3-methoxybutan-2-yl)oxy]pyrrolidin-1-yl}-5,6,7,8-tetrahydroquinolin-6-yl)-6-methylthieno[2,3-b]pyridine-2-carboxamide |
| 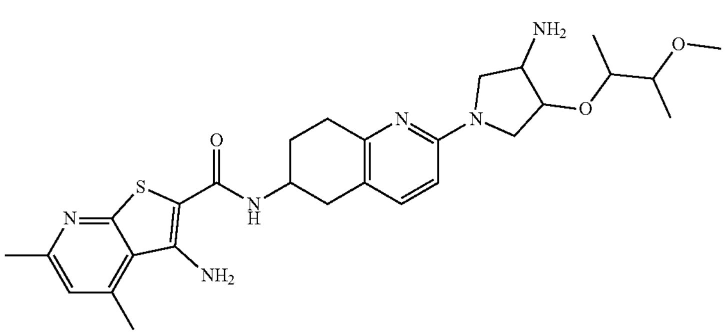 | 3-amino-N-(2-{3-amino-4-[(3-methoxybutan-2-yl)oxy]pyrrolidin-1-yl}-5,6,7,8-tetrahydroquinolin-6-yl)-4,6-dimethylthieno[2,3-b]pyridine-2-carboxamide |

TABLE 27-continued

| Structure | Chemical Name |
|---|---|
| 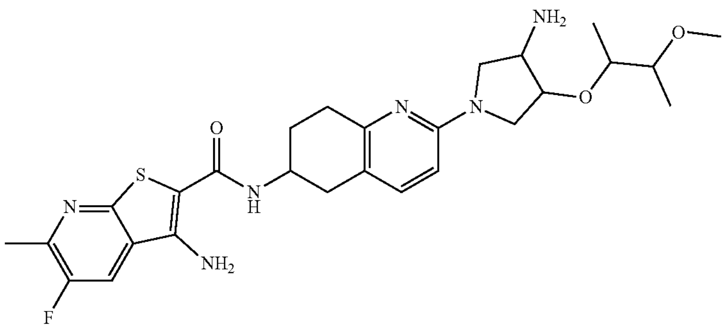 | 3-amino-N-(2-{3-amino-4-[(3-methoxybutan-2-yl)oxy]pyrrolidin-1-yl}-5,6,7,8-tetrahydroquinolin-6-yl)-5-fluoro-6-methylthieno[2,3-b]pyridine-2-carboxamide |
| 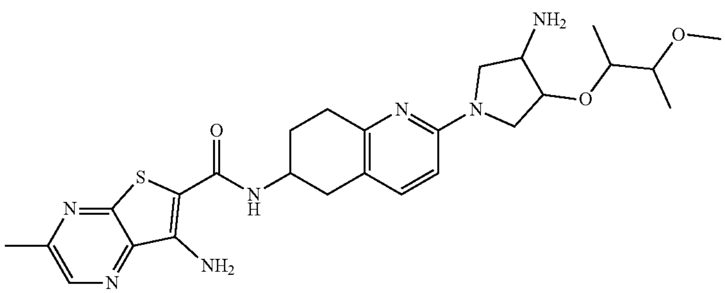 | 7-amino-N-(2-{3-amino-4-[(3-methoxybutan-2-yl)oxy]pyrrolidin-1-yl}-5,6,7,8-tetrahydroquinolin-6-yl)-3-methylthieno[2,3-b]pyrazine-6-carboxamide |
| 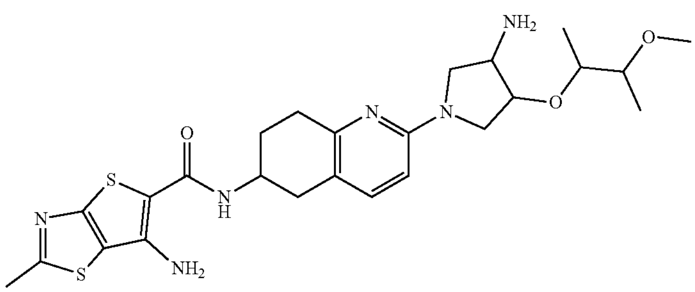 | 6-amino-N-(2-{3-amino-4-[(3-methoxybutan-2-yl)oxy]pyrrolidin-1-yl}-5,6,7,8-tetrahydroquinolin-6-yl)-2-methylthieno[2,3-d][1,3]thiazole-5-carboxamide |
| 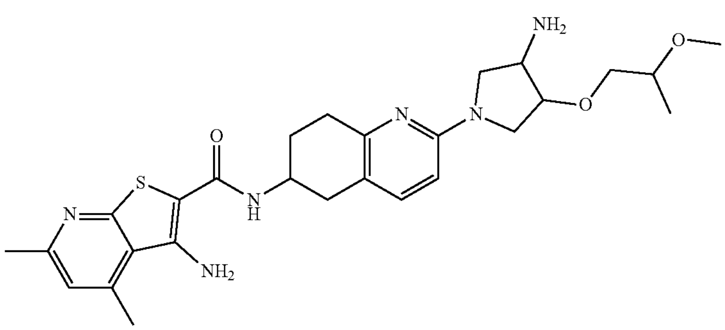 | 3-amino-N-{2-[3-amino-4-(2-methoxypropoxy)pyrrolidin-1-yl]-5,6,7,8-tetrahydroquinolin-6-yl}-4,6-dimethylthieno[2,3-b]pyridine-2-carboxamide |
| 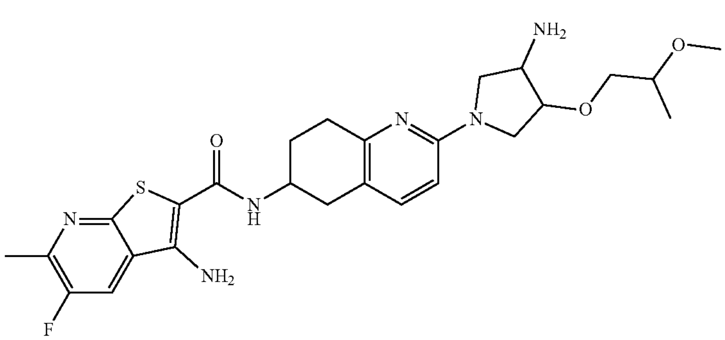 | 3-amino-N-{2-[3-amino-4-(2-methoxypropoxy)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 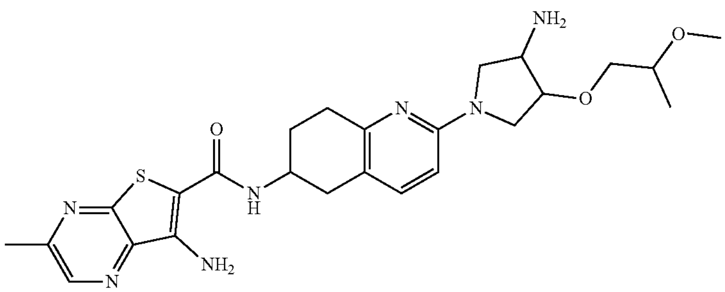 | 7-amino-N-{2-[3-amino-4-(2-methoxypropoxy)pyrrolidin-1-yl]-5,6,7,8-tetrahydroquinolin-6-yl}-3-methylthieno[2,3-b]pyrazine-6-carboxamide |
| 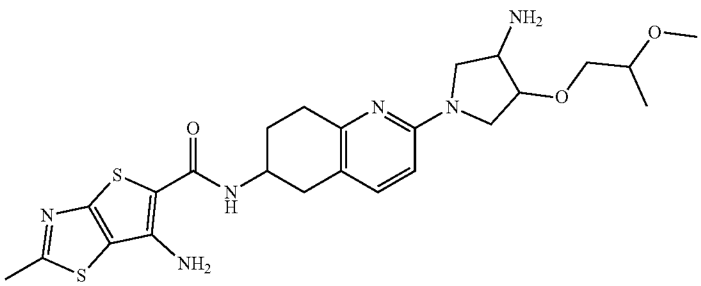 | 6-amino-N-{2-[3-amino-4-(2-methoxypropoxy)pyrrolidin-1-yl]-5,6,7,8-tetrahydroquinolin-6-yl}-2-methylthieno[2,3-d][1,3]thiazole-5-carboxamide |
| 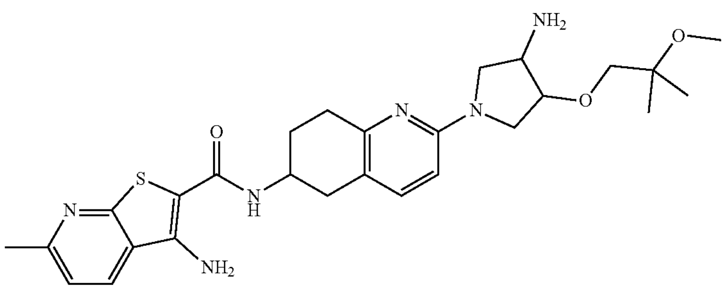 | 3-amino-N-{2-[3-amino-4-(2-methoxy-2-methylpropoxy)pyrrolidin-1-yl]-5,6,7,8-tetrahydroquinolin-6-yl}-6-methylthieno[2,3-b]pyridine-2-carboxamide |
| 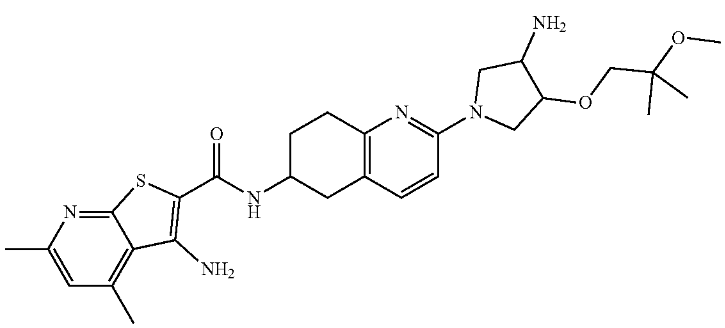 | 3-amino-N-{2-[3-amino-4-(2-methoxy-2-methylpropoxy)pyrrolidin-1-yl]-5,6,7,8-tetrahydroquinolin-6-yl}-4,6-dimethylthieno[2,3-b]pyridine-2-carboxamide |
| 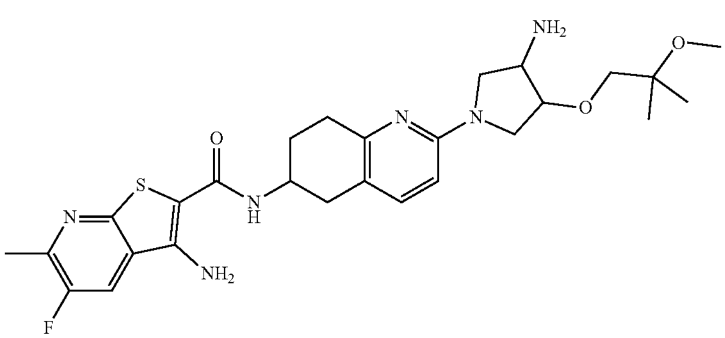 | 3-amino-N-{2-[3-amino-4-(2-methoxy-2-methylpropoxy)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 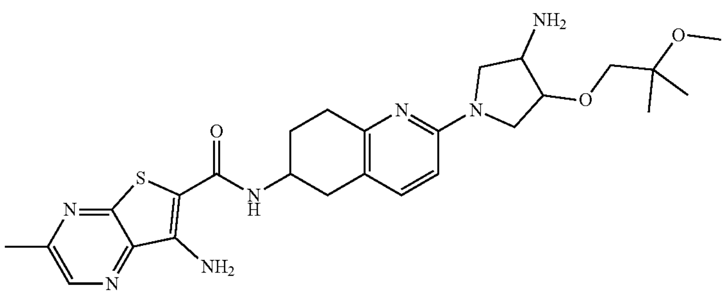 | 7-amino-N-{2-[3-amino-4-(2-methoxy-2-methylpropoxy)pyrrolidin-1-yl]-5,6,7,8-tetrahydroquinolin-6-yl}-3-methylthieno[2,3-b]pyrazine-6-carboxamide |
| 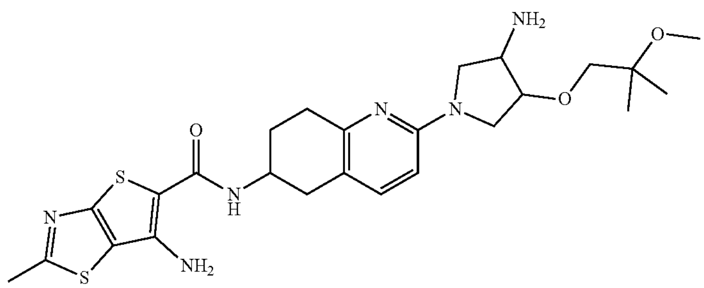 | 6-amino-N-{2-[3-amino-4-(2-methoxy-2-methylpropoxy)pyrrolidin-1-yl]-5,6,7,8-tetrahydroquinolin-6-yl}-2-methylthieno[2,3-d][1,3]thiazole-5-carboxamide |
| 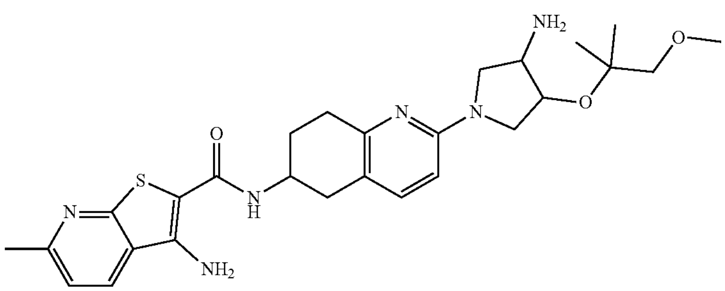 | 3-amino-N-(2-{3-amino-4-[(1-methoxy-2-methylpropan-2-yl)oxy]pyrrolidin-1-yl}-5,6,7,8-tetrahydroquinolin-6-yl)-6-methylthieno[2,3-b]pyridine-2-carboxamide |
| 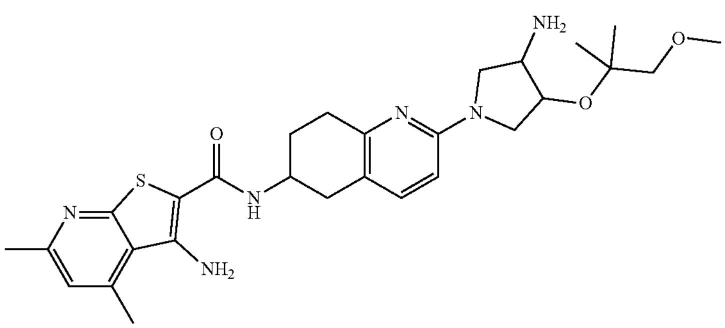 | 3-amino-N-(2-{3-amino-4-[(1-methoxy-2-methylpropan-2-yl)oxy]pyrrolidin-1-yl}-5,6,7,8-tetrahydroquinolin-6-yl)-4,6-dimethylthieno[2,3-b]pyridine-2-carboxamide |
| 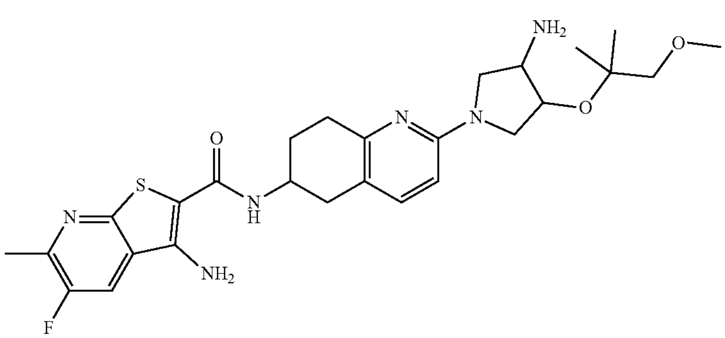 | 3-amino-N-(2-{3-amino-4-[(1-methoxy-2-methylpropan-2-yl)oxy]pyrrolidin-1-yl}-5,6,7,8-tetrahydroquinolin-6-yl)-5-fluoro-6-methylthieno[2,3-b]pyridine-2-carboxamide |

TABLE 27-continued

| Structure | Chemical Name |
|---|---|
| 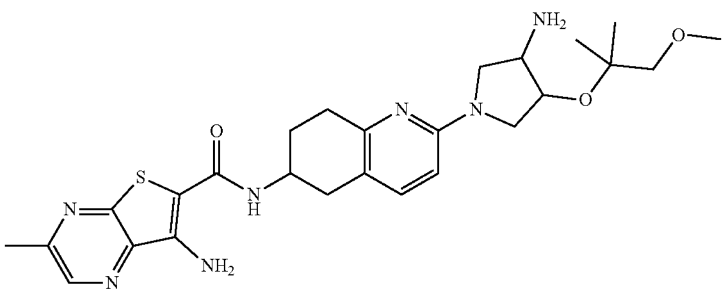 | 7-amino-N-(2-{3-amino-4-[(1-methoxy-2-methylpropan-2-yl)oxy]pyrrolidin-1-yl}-5,6,7,8-tetrahydroquinolin-6-yl)-3-methylthieno[2,3-b]pyrazine-6-carboxamide |
| 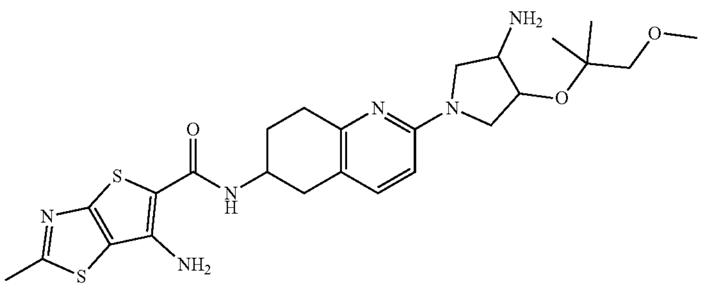 | 6-amino-N-(2-{3-amino-4-[(1-methoxy-2-methylpropan-2-yl)oxy]pyrrolidin-1-yl}-5,6,7,8-tetrahydroquinolin-6-yl)-2-methylthieno[2,3-d][1,3]thiazole-5-carboxamide |
| 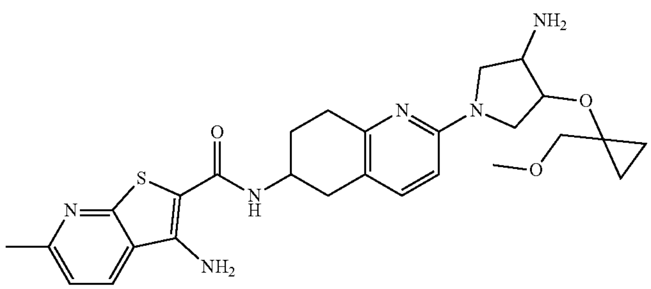 [SMILES: COCC1(OC2CN(c3ccc4c(n3)CCC(NC(=O)c3sc5nc(C)ccc5c3N)C4)CC2N)CC1] | 3-amino-N-(2-{3-amino-4-[1-(methoxymethyl)cyclopropoxy]pyrrolidin-1-yl}-5,6,7,8-tetrahydroquinolin-6-yl)-6-methylthieno[2,3-b]pyridine-2-carboxamide |
| 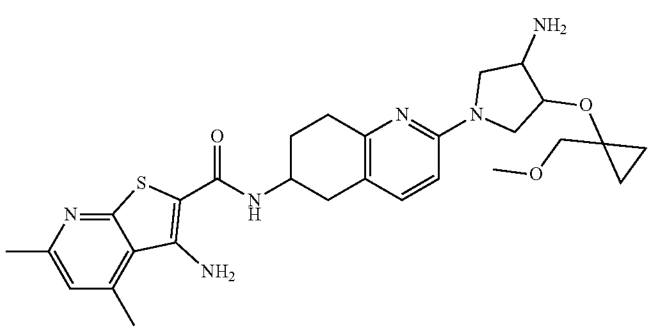 | 3-amino-N-(2-{3-amino-4-[1-(methoxymethyl)cyclopropoxy]pyrrolidin-1-yl}-5,6,7,8-tetrahydroquinolin-6-yl)-4,6-dimethylthieno[2,3-b]pyridine-2-carboxamide |
| 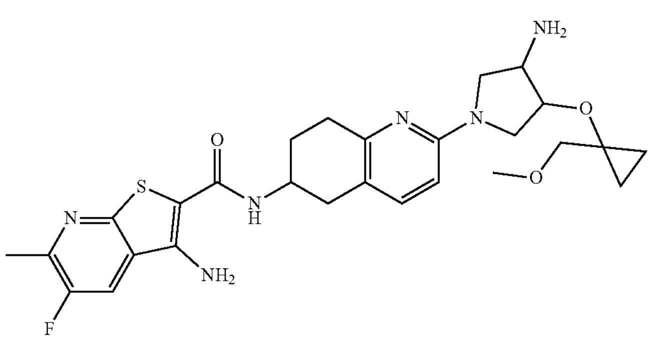 [SMILES: COCC1(OC2CN(c3ccc4c(n3)CCC(NC(=O)c3sc5nc(C)c(F)cc5c3N)C4)CC2N)CC1] | 3-amino-N-(2-{3-amino-4-[1-(methoxymethyl)cyclopropoxy]pyrrolidin-1-yl}-5,6,7,8-tetrahydroquinolin-6-yl)-5-fluoro-6-methylthieno[2,3-b]pyridine-2-carboxamide |

TABLE 27-continued

| Structure | Chemical Name |
|---|---|
| 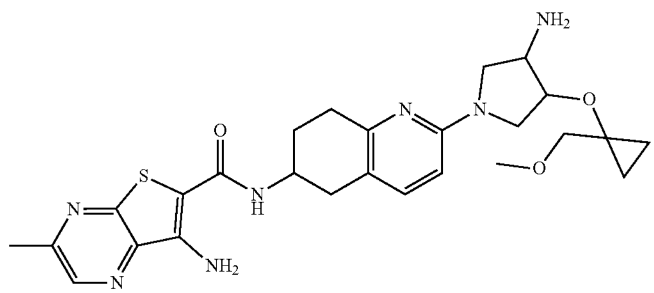 [SMILES: COCC1(OC2CN(c3ccc4c(n3)CCC(NC(=O)c3sc5nc(C)cnc5c3N)C4)CC2N)CC1] | 7-amino-N-(2-{3-amino-4-[1-(methoxymethyl)cyclopropoxy]pyrrolidin-1-yl}-5,6,7,8-tetrahydroquinolin-6-yl)-3-methylthieno[2,3-b]pyrazine-6-carboxamide |
| 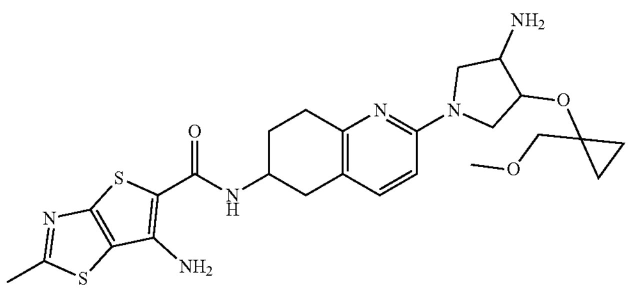 [SMILES: COCC1(OC2CN(c3ccc4c(n3)CCC(NC(=O)c3sc5nc(C)sc5c3N)C4)CC2N)CC1] | 6-amino-N-(2-{3-amino-4-[1-(methoxymethyl)cyclopropoxy]pyrrolidin-1-yl}-5,6,7,8-tetrahydroquinolin-6-yl)-2-methylthieno[2,3-d][1,3]thiazole-5-carboxamide |
| 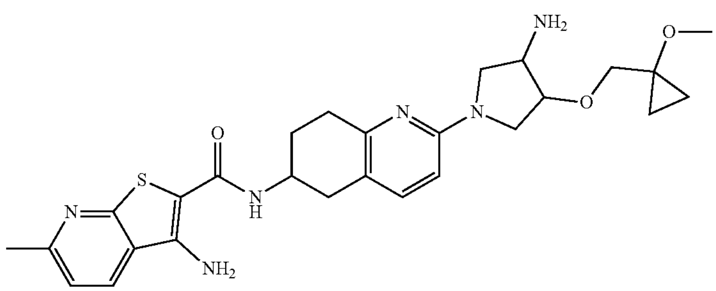 | 3-amino-N-(2-{3-amino-4-[(1-methoxycyclopropyl)methoxy]pyrrolidin-1-yl}-5,6,7,8-tetrahydroquinolin-6-yl)-6-methylthieno[2,3-b]pyridine-2-carboxamide |
| 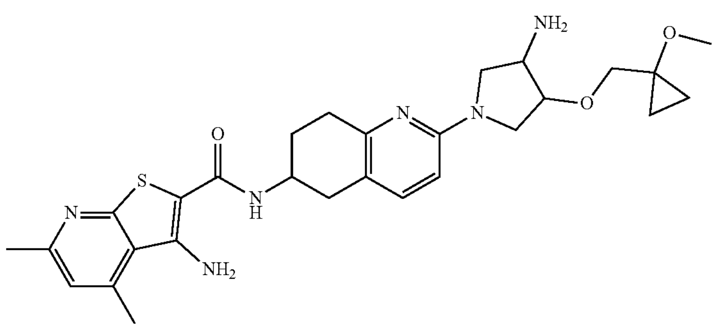 | 3-amino-N-(2-{3-amino-4-[(1-methoxycyclopropyl)methoxy]pyrrolidin-1-yl}-5,6,7,8-tetrahydroquinolin-6-yl)-4,6-dimethylthieno[2,3-b]pyridine-2-carboxamide |
| 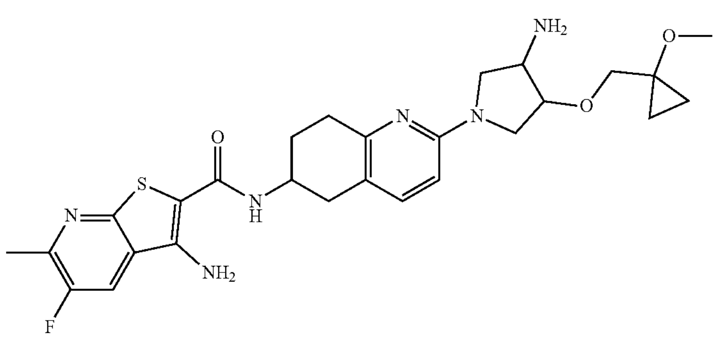 | 3-amino-N-(2-{3-amino-4-[(1-methoxycyclopropyl)methoxy]pyrrolidin-1-yl}-5,6,7,8-tetrahydroquinolin-6-yl)-5-fluoro-6-methylthieno[2,3-b]pyridine-2-carboxamide |

TABLE 27-continued

| Structure | Chemical Name |
|---|---|
| 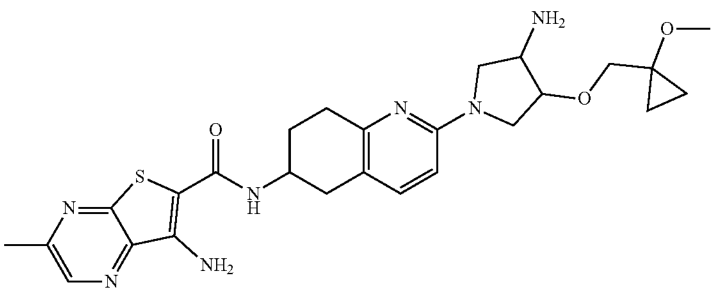 | 7-amino-N-(2-{3-amino-4-[(1-methoxycyclopropyl)methoxy]pyrrolidin-1-yl}-5,6,7,8-tetrahydroquinolin-6-yl)-3-methylthieno[2,3-b]pyrazine-6-carboxamide |
| 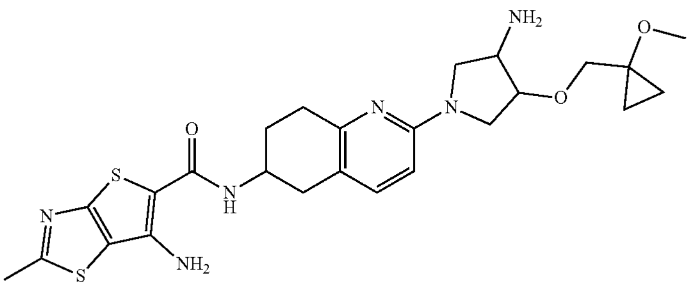 | 6-amino-N-(2-{3-amino-4-[(1-methoxycyclopropyl)methoxy]pyrrolidin-1-yl}-5,6,7,8-tetrahydroquinolin-6-yl)-2-methylthieno[2,3-d][1,3]thiazole-5-carboxamide |
| 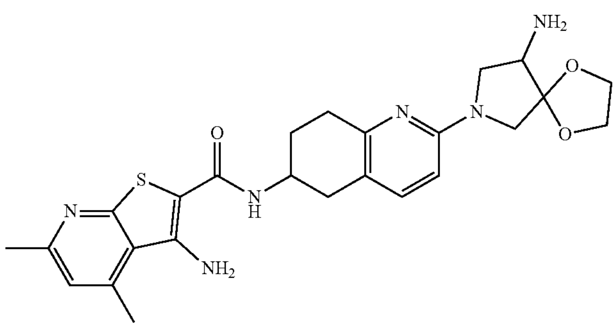 [SMILES: Cc1cc(C)c2c(N)c(C(=O)NC3CCc4nc(N5CC(N)C6(C5)OCCO6)ccc4C3)sc2n1] | 3-amino-N-(2-{9-amino-1,4-dioxa-7-azaspiro[4.4]nonan-7-yl}-5,6,7,8-tetrahydroquinolin-6-yl)-4,6-dimethylthieno[2,3-b]pyridine-2-carboxamide |
| 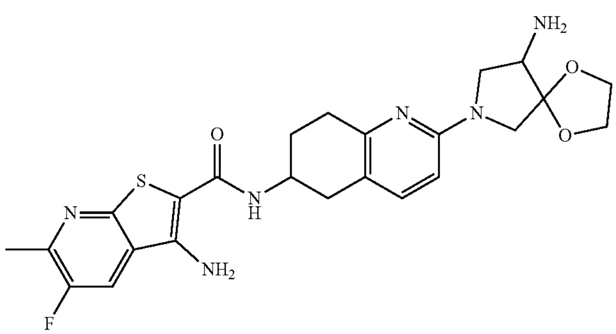 | 3-amino-N-(2-{9-amino-1,4-dioxa-7-azaspiro[4.4]nonan-7-yl}-5,6,7,8-tetrahydroquinolin-6-yl)-5-fluoro-6-methylthieno[2,3-b]pyridine-2-carboxamide |
| 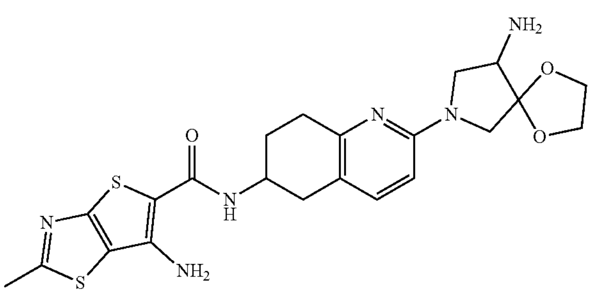 [SMILES: Cc1nc2sc(C(=O)NC3CCc4nc(N5CC(N)C6(C5)OCCO6)ccc4C3)c(N)c2s1] | 6-amino-N-(2-{9-amino-1,4-dioxa-7-azaspiro[4.4]nonan-7-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
|  | 3-amino-N-(2-{9-amino-2,3-dimethyl-1,4-dioxa-7-azaspiro[4.4]nonan-7-yl}-5,6,7,8-tetrahydroquinolin-6-yl)-6-methylthieno[2,3-b]pyridine-2-carboxamide |
| 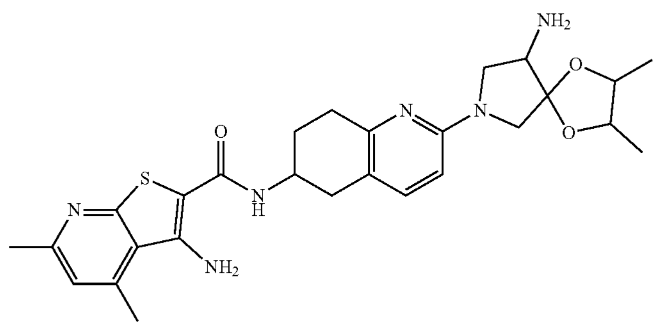 | 3-amino-N-(2-{9-amino-2,3-dimethyl-1,4-dioxa-7-azaspiro[4.4]nonan-7-yl}-5,6,7,8-tetrahydroquinolin-6-yl)-4,6-dimethylthieno[2,3-b]pyridine-2-carboxamide |
| 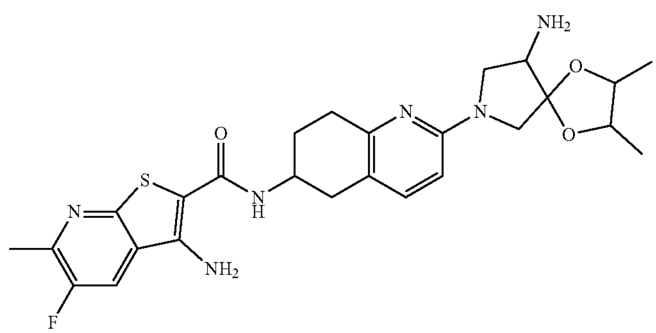 | 3-amino-N-(2-{9-amino-2,3-dimethyl-1,4-dioxa-7-azaspiro[4.4]nonan-7-yl}-5,6,7,8-tetrahydroquinolin-6-yl)-5-fluoro-6-methylthieno[2,3-b]pyridine-2-carboxamide |
| 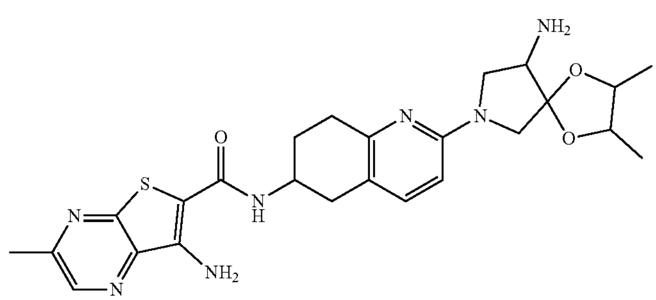 | 7-amino-N-(2-{9-amino-2,3-dimethyl-1,4-dioxa-7-azaspiro[4.4]nonan-7-yl}-5,6,7,8-tetrahydroquinolin-6-yl)-3-methylthieno[2,3-b]pyrazine-6-carboxamide |
| 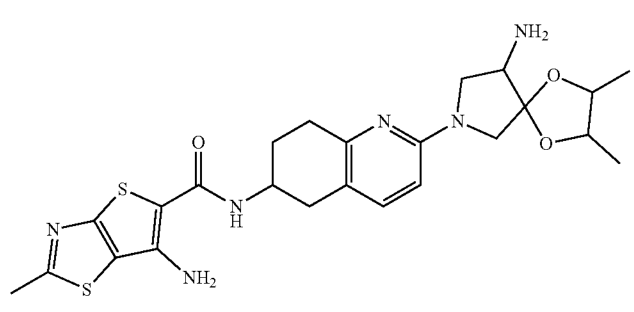 | 6-amino-N-(2-{9-amino-2,3-dimethyl-1,4-dioxa-7-azaspiro[4.4]nonan-7-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 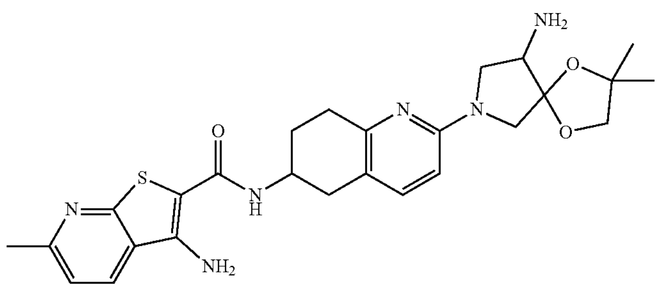 | 3-amino-N-(2-{9-amino-2,2-dimethyl-1,4-dioxa-7-azaspiro[4.4]nonan-7-yl}-5,6,7,8-tetrahydroquinolin-6-yl)-6-methylthieno[2,3-b]pyridine-2-carboxamide |
| 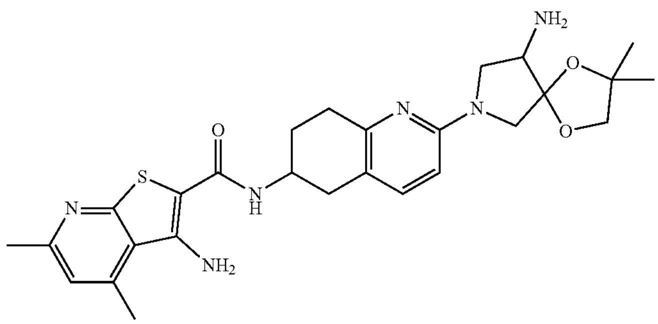 | 3-amino-N-(2-{9-amino-2,2-dimethyl-1,4-dioxa-7-azaspiro[4.4]nonan-7-yl}-5,6,7,8-tetrahydroquinolin-6-yl)-4,6-dimethylthieno[2,3-b]pyridine-2-carboxamide |
| 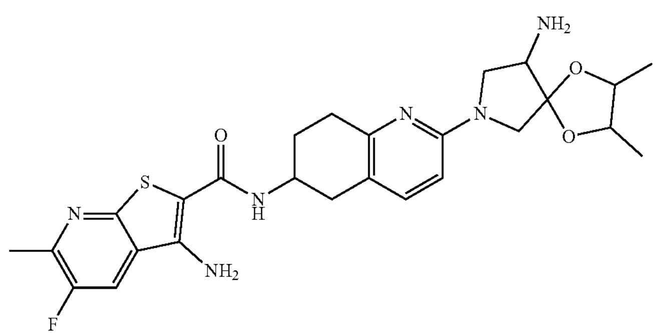 | 3-amino-N-(2-{9-amino-2,2-dimethyl-1,4-dioxa-7-azaspiro[4.4]nonan-7-yl}-5,6,7,8-tetrahydroquinolin-6-yl)-5-fluoro-6-methylthieno[2,3-b]pyridine-2-carboxamide |
| 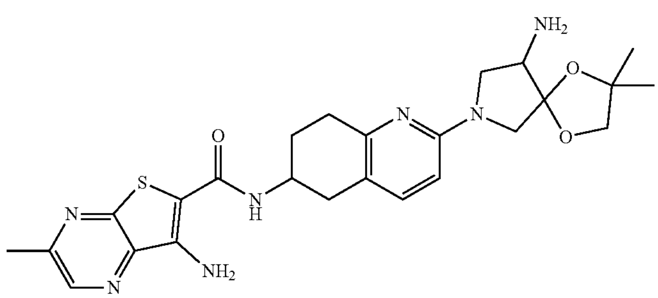 | 7-amino-N-(2-{9-amino-2,2-dimethyl-1,4-dioxa-7-azaspiro[4.4]nonan-7-yl}-5,6,7,8-tetrahydroquinolin-6-yl)-3-methylthieno[2,3-b]pyrazine-6-carboxamide |
| 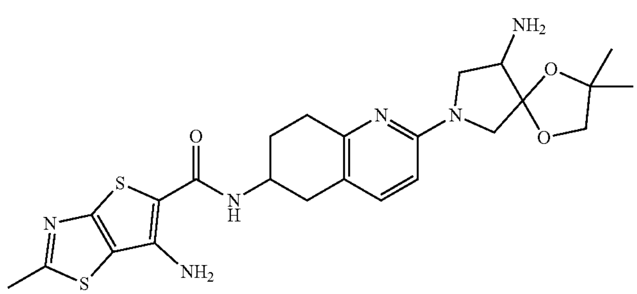 | 6-amino-N-(2-{9-amino-2,2-dimethyl-1,4-dioxa-7-azaspiro[4.4]nonan-7-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 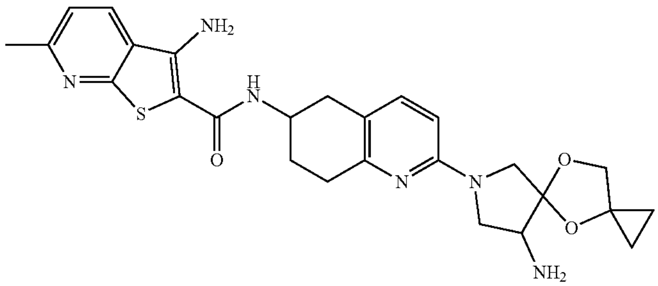 [SMILES: Cc1ccc2c(N)c(C(=O)NC3CCc4nc(N5CC(N)C6(C5)OCC5(CC5)O6)ccc4C3)sc2n1] | 3-amino-N-(2-{9-amino-4,10-dioxa-7-azadispiro[2.1.4$^5$.2$^3$]undecan-7-yl}-5,6,7,8-tetrahydroquinolin-6-yl)-6-methylthieno[2,3-b]pyridine-2-carboxamide |
| 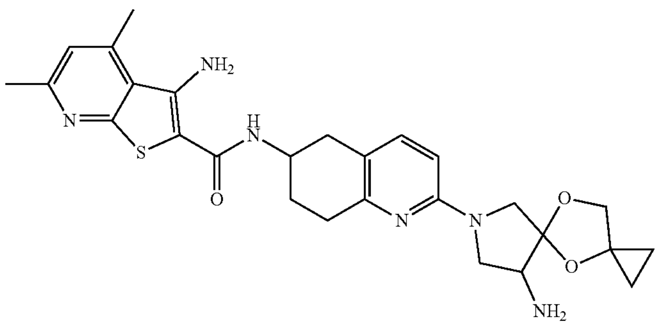 [SMILES: Cc1cc(C)c2c(N)c(C(=O)NC3CCc4nc(N5CC(N)C6(C5)OCC5(CC5)O6)ccc4C3)sc2n1] | 3-amino-N-(2-{9-amino-4,10-dioxa-7-azadispiro[2.1.4$^5$.2$^3$]undecan-7-yl}-5,6,7,8-tetrahydroquinolin-6-yl)-4,6-dimethylthieno[2,3-b]pyridine-2-carboxamide |
| 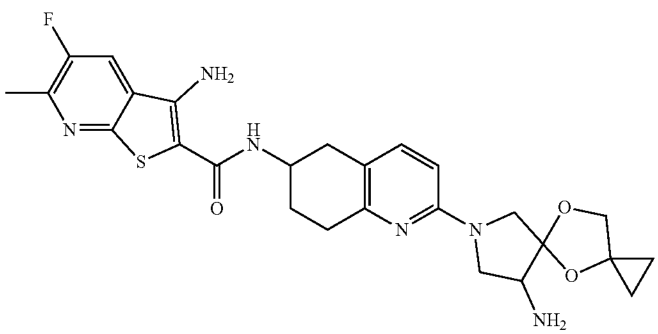 [SMILES: Cc1nc2sc(C(=O)NC3CCc4nc(N5CC(N)C6(C5)OCC5(CC5)O6)ccc4C3)c(N)c2cc1F] | 3-amino-N-(2-{9-amino-4,10-dioxa-7-azadispiro[2.1.4$^5$.2$^3$]undecan-7-yl}-5,6,7,8-tetrahydroquinolin-6-yl)-5-fluoro-6-methylthieno[2,3-b]pyridine-2-carboxamide |
| 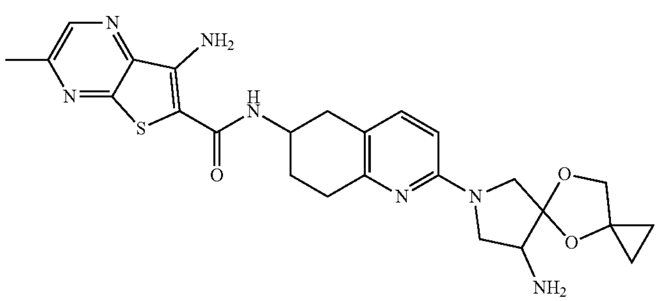 [SMILES: Cc1cnc2c(N)c(C(=O)NC3CCc4nc(N5CC(N)C6(C5)OCC5(CC5)O6)ccc4C3)sc2n1] | 7-amino-N-(2-{9-amino-4,10-dioxa-7-azadispiro[2.1.4$^5$.2$^3$]undecan-7-yl}-5,6,7,8-tetrahydroquinolin-6-yl)-3-methylthieno[2,3-b]pyrazine-6-carboxamide |
| 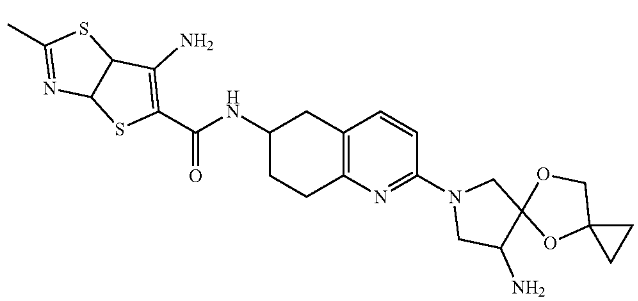 [SMILES: CC1=NC2SC(C(=O)NC3CCc4nc(N5CC(N)C6(C5)OCC5(CC5)O6)ccc4C3)=C(N)C2S1] | 6-amino-N-(2-{9-amino-4,10-dioxa-7-azadispiro[2.1.4$^5$.2$^3$]undecan-7-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 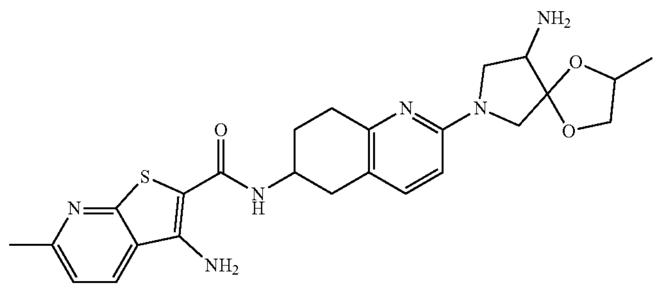 | 3-amino-N-(2-{9-amino-2-methyl-1,4-dioxa-7-azaspiro[4.4]nonan-7-yl}-5,6,7,8-tetrahydroquinolin-6-yl)-6-methylthieno[2,3-b]pyridine-2-carboxamide |
| 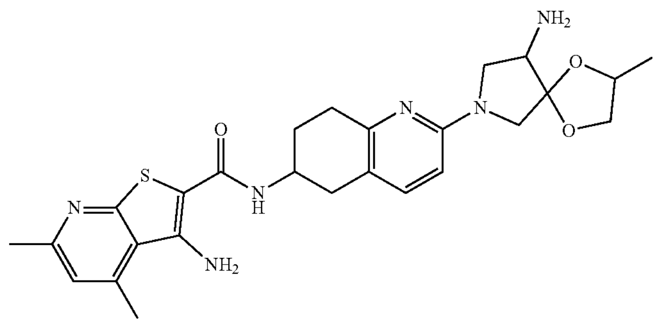 | 3-amino-N-(2-{9-amino-2-methyl-1,4-dioxa-7-azaspiro[4.4]nonan-7-yl}-5,6,7,8-tetrahydroquinolin-6-yl)-4,6-dimethylthieno[2,3-b]pyridine-2-carboxamide |
| 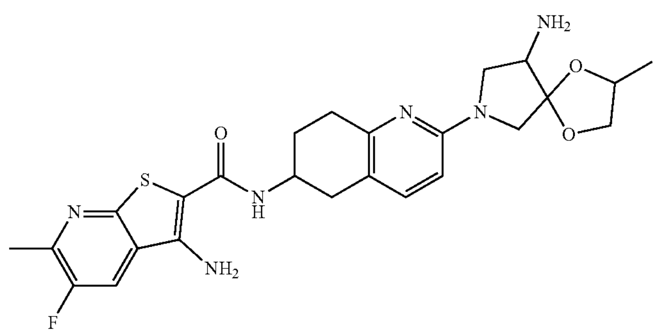 | 3-amino-N-(2-{9-amino-2-methyl-1,4-dioxa-7-azaspiro[4.4]nonan-7-yl}-5,6,7,8-tetrahydroquinolin-6-yl)-5-fluoro-6-methylthieno[2,3-b]pyridine-2-carboxamide |
| 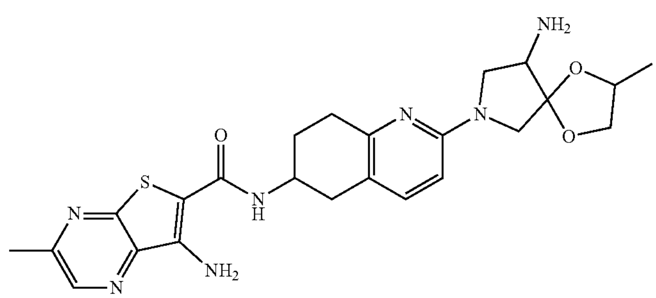 | 7-amino-N-(2-{9-amino-2-methyl-1,4-dioxa-7-azaspiro[4.4]nonan-7-yl}-5,6,7,8-tetrahydroquinolin-6-yl)-3-methylthieno[2,3-b]pyrazine-6-carboxamide |
| 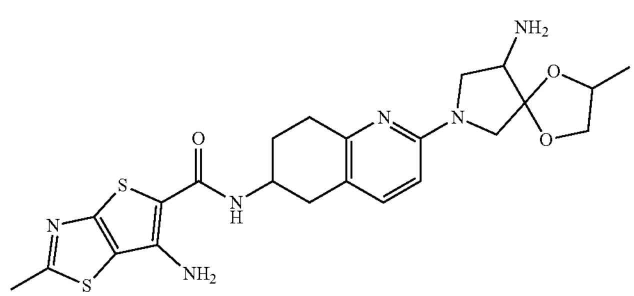 | 6-amino-N-(2-{9-amino-2-methyl-1,4-dioxa-7-azaspiro[4.4]nonan-7-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 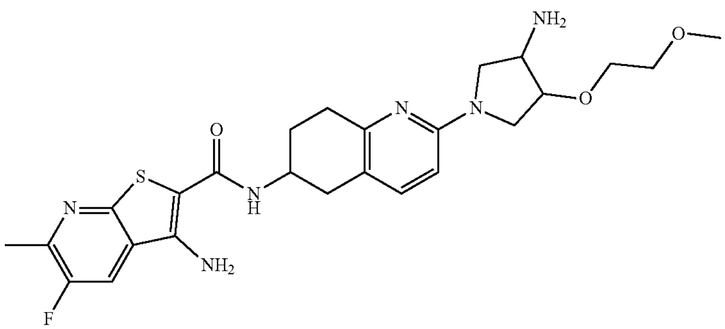 | 3-amino-N-{2-[3-amino-4-(2-methoxyethoxy)pyrrolidin-1-yl]-5,6,7,8-tetrahydroquinolin-6-yl}-5-fluoro-6-methylthieno[2,3-b]pyridine-2-carboxamide |
| 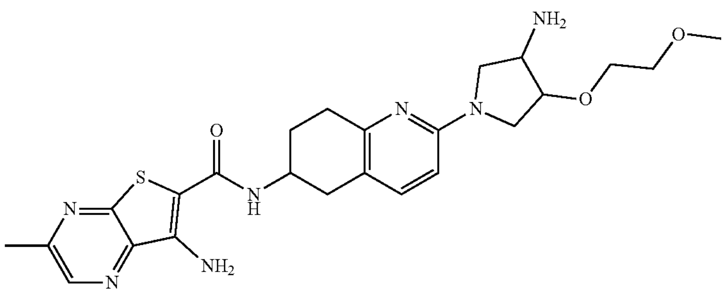 | 7-amino-N-{2-[3-amino-4-(2-methoxyethoxy)pyrrolidin-1-yl]-5,6,7,8-tetrahydroquinolin-6-yl}-3-methylthieno[2,3-b]pyrazine-6-carboxamide |
| 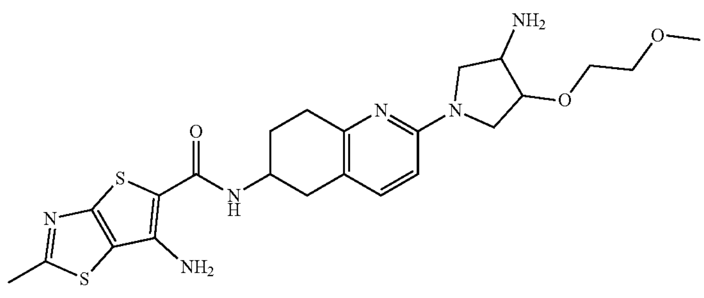 | 6-amino-N-{2-[3-amino-4-(2-methoxyethoxy)pyrrolidin-1-yl]-5,6,7,8-tetrahydroquinolin-6-yl}-2-methylthieno[2,3-d][1,3]thiazole-5-carboxamide |
| 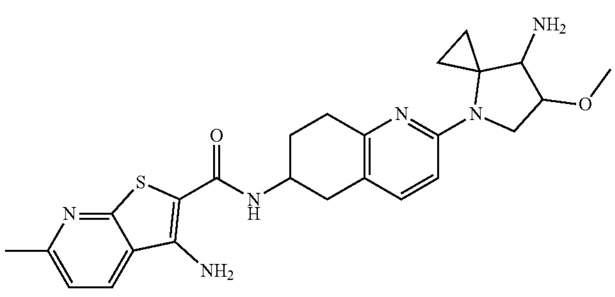 | 3-amino-N-(2-{7-amino-6-methoxy-4-azaspiro[2.4]heptan-4-yl}-5,6,7,8-tetrahydroquinolin-6-yl)-6-methylthieno[2,3-b]pyridine-2-carboxamide |
| 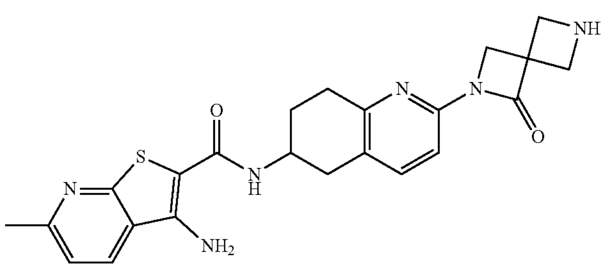 [SMILES: Cc1ccc2c(N)c(C(=O)NC3CCc4nc(N5CC6(CNC6)C5=O)ccc4C3)sc2n1] | 3-amino-6-methyl-N-(2-{1-oxo-2,6-diazaspiro[3.3]heptan-2-yl}-5,6,7,8-tetrahydroquinolin-6-yl)thieno[2,3-b]pyridine-2-carboxamide |

TABLE 27-continued

| Structure | Chemical Name |
|---|---|
| 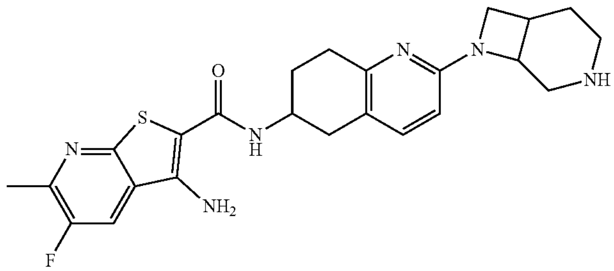 [SMILES: Cc1nc2sc(C(=O)NC3CCc4nc(N5CC6CCNCC65)ccc4C3)c(N)c2cc1F] | 3-amino-N-(2-{3,8-diazabicyclo[4.2.0]octan-8-yl}-5,6,7,8-tetrahydroquinolin-6-yl)-5-fluoro-6-methylthieno[2,3-b]pyridine-2-carboxamide |
| 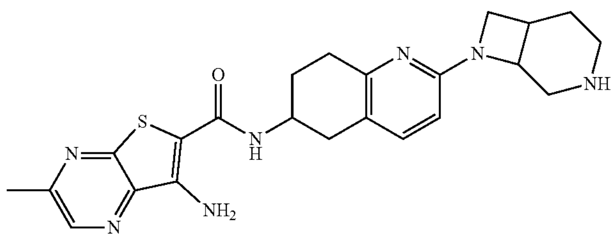 [SMILES: Cc1cnc2c(N)c(C(=O)NC3CCc4nc(N5CC6CCNCC65)ccc4C3)sc2n1] | 7-amino-N-(2-{3,8-diazabicyclo[4.2.0]octan-8-yl}-5,6,7,8-tetrahydroquinolin-6-yl)-3-methylthieno[2,3-b]pyrazine-6-carboxamide |
| 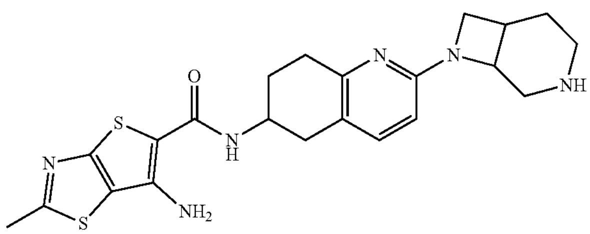 [SMILES: Cc1nc2sc(C(=O)NC3CCc4nc(N5CC6CCNCC65)ccc4C3)c(N)c2s1] | 6-amino-N-(2-{3,8-diazabicyclo[4.2.0]octan-8-yl}-5,6,7,8-tetrahydroquinolin-6-yl)-2-methylthieno[2,3-d][1,3]thiazole-5-carboxamide |
| 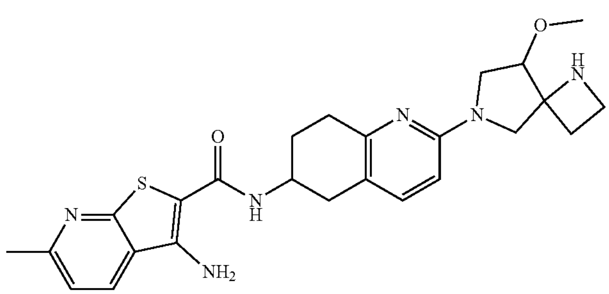 [SMILES: COC1CN(c2ccc3c(n2)CCC(NC(=O)c2sc4nc(C)ccc4c2N)C3)CC12CCN2] | 3-amino-N-(2-{8-methoxy-1,6-diazaspiro[3.4]octan-6-yl}-5,6,7,8-tetrahydroquinolin-6-yl)-6-methylthieno[2,3-b]pyridine-2-carboxamide |
| 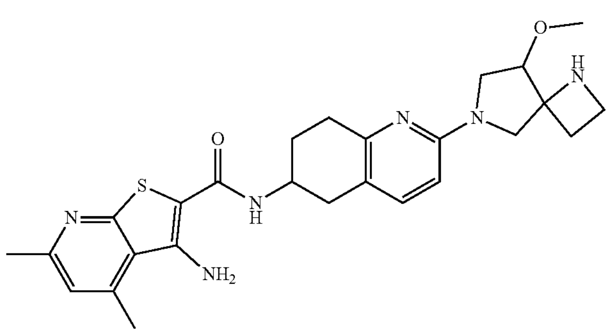 [SMILES: COC1CN(c2ccc3c(n2)CCC(NC(=O)c2sc4nc(C)cc(C)c4c2N)C3)CC12CCN2] | 3-amino-N-(2-{8-methoxy-1,6-diazaspiro[3.4]octan-6-yl}-5,6,7,8-tetrahydroquinolin-6-yl)-4,6-dimethylthieno[2,3-b]pyridine-2-carboxamide |

TABLE 27-continued

| Structure | Chemical Name |
|---|---|
| 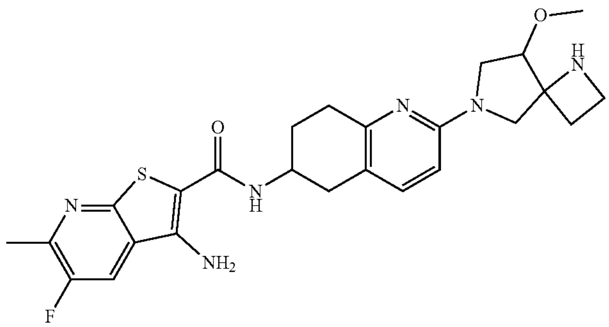 [SMILES: COC1CN(c2ccc3c(n2)CCC(NC(=O)c2sc4nc(C)c(F)cc4c2N)C3)CC12CCN2] | 3-amino-5-fluoro-N-(2-{8-methoxy-1,6-diazaspiro[3.4]octan-6-yl}-5,6,7,8-tetrahydroquinolin-6-yl)-6-methylthieno[2,3-b]pyridine-2-carboxamide |
| 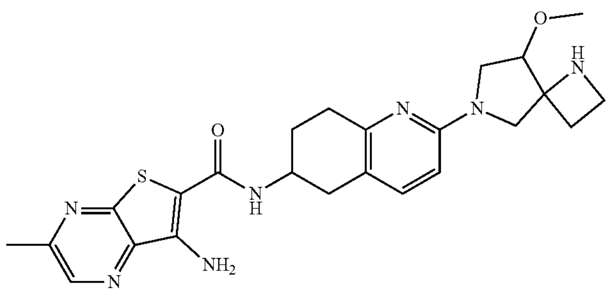 [SMILES: COC1CN(c2ccc3c(n2)CCC(NC(=O)c2sc4nc(C)cnc4c2N)C3)CC12CCN2] | 7-amino-N-(2-{8-methoxy-1,6-diazaspiro[3.4]octan-6-yl}-5,6,7,8-tetrahydroquinolin-6-yl)-3-methylthieno[2,3-b]pyrazine-6-carboxamide |
| 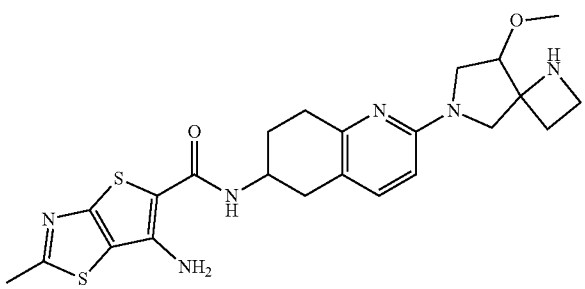 [SMILES: COC1CN(c2ccc3c(n2)CCC(NC(=O)c2sc4nc(C)sc4c2N)C3)CC12CCN2] | 6-amino-N-(2-{8-methoxy-1,6-diazaspiro[3.4]octan-6-yl}-5,6,7,8-tetrahydroquinolin-6-yl)-2-methylthieno[2,3-d][1,3]thiazole-5-carboxamide |
| 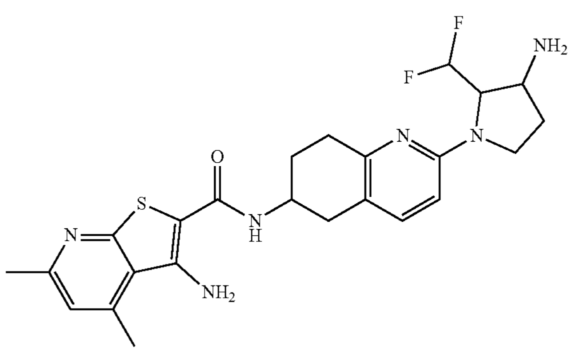 [SMILES: Cc1cc(C)c2c(N)c(C(=O)NC3CCc4nc(N5CCC(N)C5C(F)F)ccc4C3)sc2n1] | 3-amino-N-{2-[3-amino-2-(difluoromethyl)pyrrolidin-1-yl]-5,6,7,8-tetrahydroquinolin-6-yl}-4,6-dimethylthieno[2,3-b]pyridine-2-carboxamide |
| 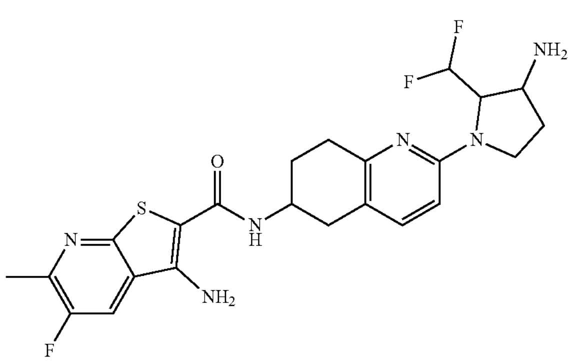 [SMILES: Cc1nc2sc(C(=O)NC3CCc4nc(N5CCC(N)C5C(F)F)ccc4C3)c(N)c2cc1F] | 3-amino-N-{2-[3-amino-2-(difluoromethyl)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 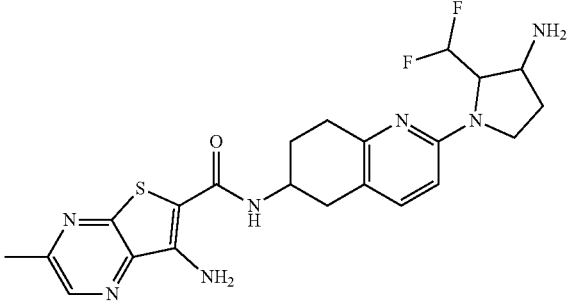 [SMILES: Cc1cnc2c(N)c(C(=O)NC3CCc4nc(N5CCC(N)C5C(F)F)ccc4C3)sc2n1] | 7-amino-N-{2-[3-amino-2-(difluoromethyl)pyrrolidin-1-yl]-5,6,7,8-tetrahydroquinolin-6-yl}-3-methylthieno[2,3-b]pyrazine-6-carboxamide |
| 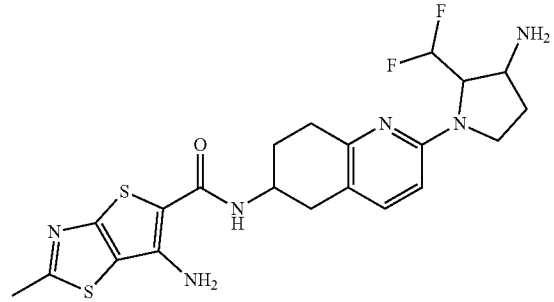 [SMILES: Cc1nc2sc(C(=O)NC3CCc4nc(N5CCC(N)C5C(F)F)ccc4C3)c(N)c2s1] | 6-amino-N-{2-[3-amino-2-(difluoromethyl)pyrrolidin-1-yl]-5,6,7,8-tetrahydroquinolin-6-yl}-2-methylthieno[2,3-d][1,3]thiazole-5-carboxamide |
| 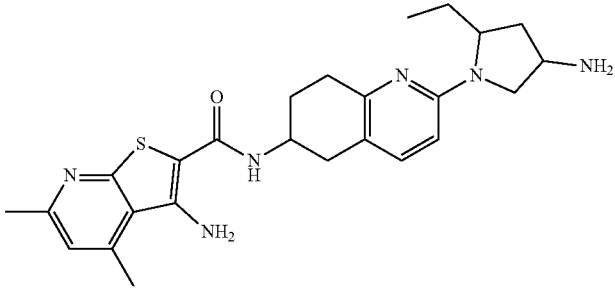 [SMILES: CCC1CC(N)CN1c1ccc2c(n1)CCC(NC(=O)c1sc3nc(C)cc(C)c3c1N)C2] | 3-amino-N-[2-(4-amino-2-ethylpyrrolidin-1-yl)-5,6,7,8-tetrahydroquinolin-6-yl]-4,6-dimethylthieno[2,3-b]pyridine-2-carboxamide |
| 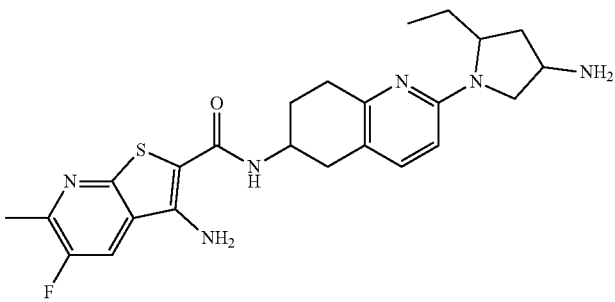 [SMILES: CCC1CC(N)CN1c1ccc2c(n1)CCC(NC(=O)c1sc3nc(C)c(F)cc3c1N)C2] | 3-amino-N-[2-(4-amino-2-ethylpyrrolidin-1-yl)-5,6,7,8-tetrahydroquinolin-6-yl]-5-fluoro-6-methylthieno[2,3-b]pyridine-2-carboxamide |
| 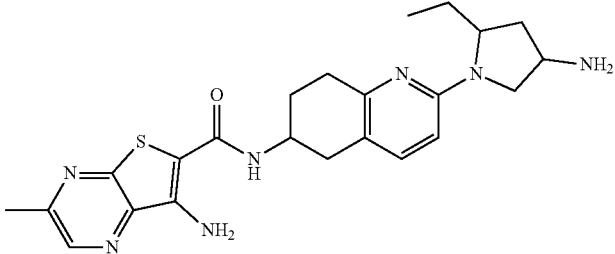 [SMILES: CCC1CC(N)CN1c1ccc2c(n1)CCC(NC(=O)c1sc3nc(C)cnc3c1N)C2] | 7-amino-N-[2-(4-amino-2-ethylpyrrolidin-1-yl)-5,6,7,8-tetrahydroquinolin-6-yl]-3-methylthieno[2,3-b]pyrazine-6-carboxamide |

TABLE 27-continued

| Structure | Chemical Name |
|---|---|
| 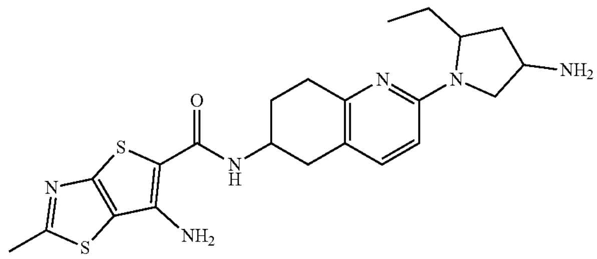 [SMILES: CCC1CC(N)CN1c1ccc2c(n1)CCC(NC(=O)c1sc3nc(C)sc3c1N)C2] | 6-amino-N-[2-(4-amino-2-ethylpyrrolidin-1-yl)-5,6,7,8-tetrahydroquinolin-6-yl]-2-methylthieno[2,3-d][1,3]thiazole-5-carboxamide |
| 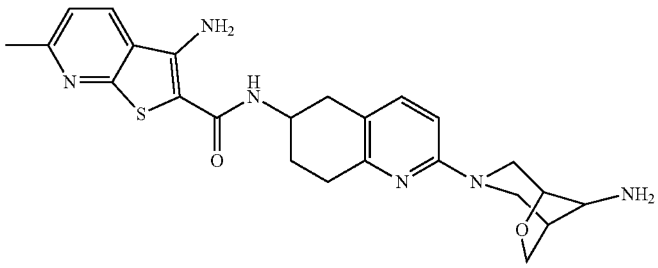 [SMILES: Cc1ccc2c(N)c(C(=O)NC3CCc4nc(N5CC6COC(C5)C6N)ccc4C3)sc2n1] | 3-amino-N-(2-{8-amino-6-oxa-3-azabicyclo[3.2.1]octan-3-yl}-5,6,7,8-tetrahydroquinolin-6-yl)-6-methylthieno[2,3-b]pyridine-2-carboxamide |
| 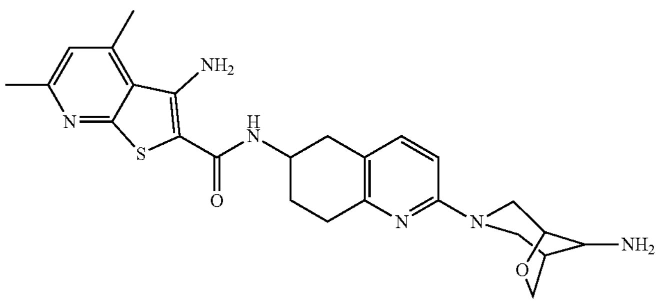 [SMILES: Cc1cc(C)c2c(N)c(C(=O)NC3CCc4nc(N5CC6COC(C5)C6N)ccc4C3)sc2n1] | 3-amino-N-(2-{8-amino-6-oxa-3-azabicyclo[3.2.1]octan-3-yl}-5,6,7,8-tetrahydroquinolin-6-yl)-4,6-dimethylthieno[2,3-b]pyridine-2-carboxamide |
| 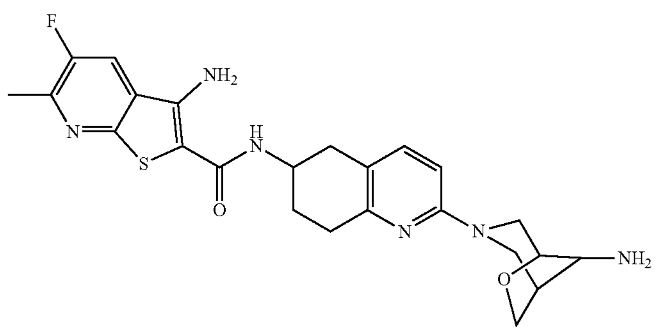 [SMILES: Cc1nc2sc(C(=O)NC3CCc4nc(N5CC6COC(C5)C6N)ccc4C3)c(N)c2cc1F] | 3-amino-N-(2-{8-amino-6-oxa-3-azabicyclo[3.2.1]octan-3-yl}-5,6,7,8-tetrahydroquinolin-6-yl)-5-fluoro-6-methylthieno[2,3-b]pyridine-2-carboxamide |
| 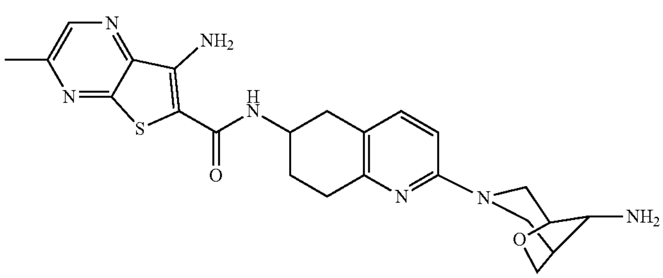 [SMILES: Cc1cnc2c(N)c(C(=O)NC3CCc4nc(N5CC6COC(C5)C6N)ccc4C3)sc2n1] | 7-amino-N-(2-{8-amino-6-oxa-3-azabicyclo[3.2.1]octan-3-yl}-5,6,7,8-tetrahydroquinolin-6-yl)-3-methylthieno[2,3-b]pyrazine-6-carboxamide |

TABLE 27-continued

| Structure | Chemical Name |
|---|---|
| 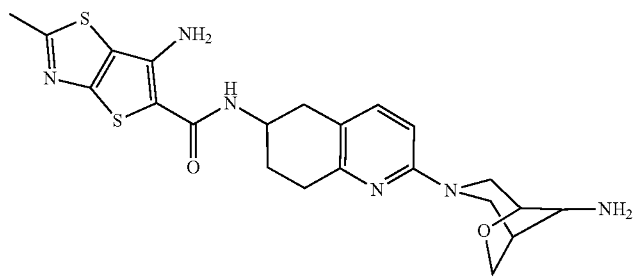 [SMILES: Cc1nc2sc(C(=O)NC3CCc4nc(N5CC6COC(C5)C6N)ccc4C3)c(N)c2s1] | 6-amino-N-(2-{8-amino-6-oxa-3-azabicyclo[3.2.1]octan-3-yl}-5,6,7,8-tetrahydroquinolin-6-yl)-2-methylthieno[2,3-d][1,3]thiazole-5-carboxamide |
| 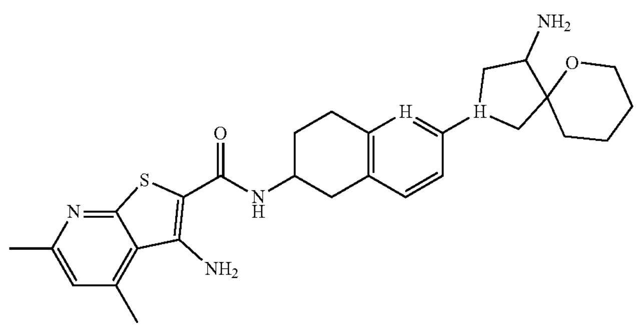 | 3-amino-N-(2-{4-amino-6-oxa-2-azaspiro[4.5]decan-2-yl}-5,6,7,8-tetrahydroquinolin-6-yl)-4,6-dimethylthieno[2,3-b]pyridine-2-carboxamide |
| 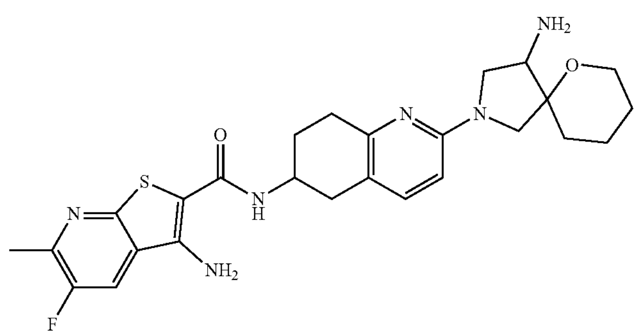 [SMILES: Cc1nc2sc(C(=O)NC3CCc4nc(N5CC(N)C6(CCCCO6)C5)ccc4C3)c(N)c2cc1F] | 3-amino-N-(2-{4-amino-6-oxa-2-azaspiro[4.5]decan-2-yl}-5,6,7,8-tetrahydroquinolin-6-yl)-5-fluoro-6-methylthieno[2,3-b]pyridine-2-carboxamide |
| 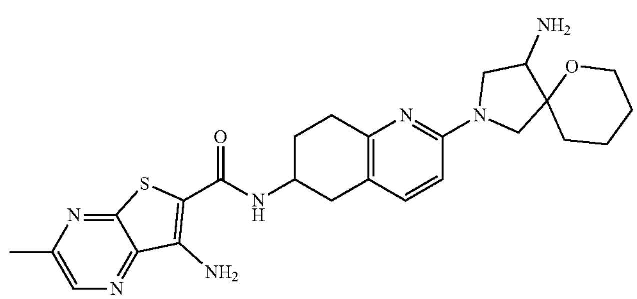 [SMILES: Cc1cnc2c(N)c(C(=O)NC3CCc4nc(N5CC(N)C6(CCCCO6)C5)ccc4C3)sc2n1] | 7-amino-N-(2-{4-amino-6-oxa-2-azaspiro[4.5]decan-2-yl}-5,6,7,8-tetrahydroquinolin-6-yl)-3-methylthieno[2,3-b]pyrazine-6-carboxamide |
| 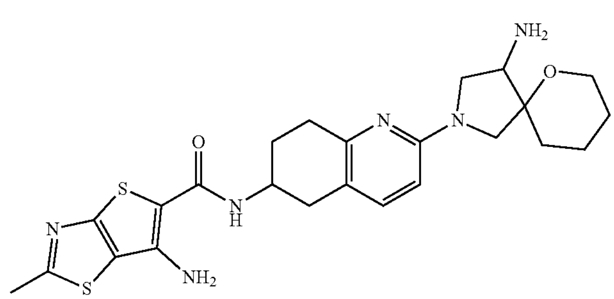 [SMILES: Cc1nc2sc(C(=O)NC3CCc4nc(N5CC(N)C6(CCCCO6)C5)ccc4C3)c(N)c2s1] | 6-amino-N-(2-{4-amino-6-oxa-2-azaspiro[4.5]decan-2-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 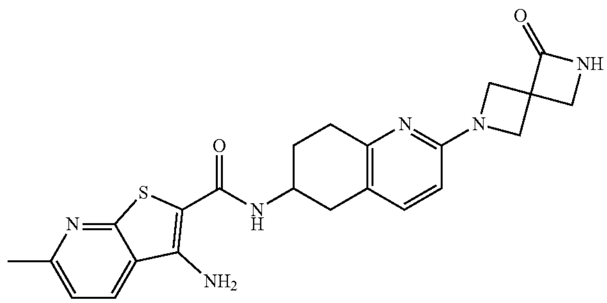 [SMILES: Cc1ccc2c(N)c(C(=O)NC3CCc4nc(N5CC6(CNC6=O)C5)ccc4C3)sc2n1] | 3-amino-6-methyl-N-(2-{5-oxo-2,6-diazaspiro[3.3]heptan-2-yl}-5,6,7,8-tetrahydroquinolin-6-yl)thieno[2,3-b]pyridine-2-carboxamide |
| 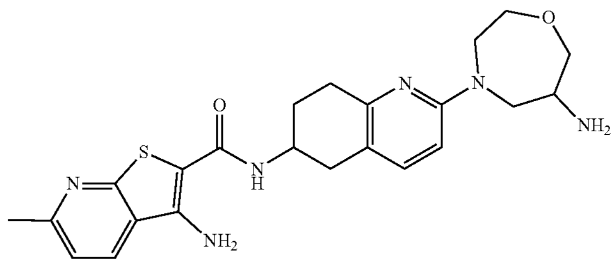 [SMILES: Cc1ccc2c(N)c(C(=O)NC3CCc4nc(N5CCOCC(N)C5)ccc4C3)sc2n1] | 3-amino-N-[2-(6-amino-1,4-oxazepan-4-yl)-5,6,7,8-tetrahydroquinolin-6-yl]-6-methylthieno[2,3-b]pyridine-2-carboxamide |
| 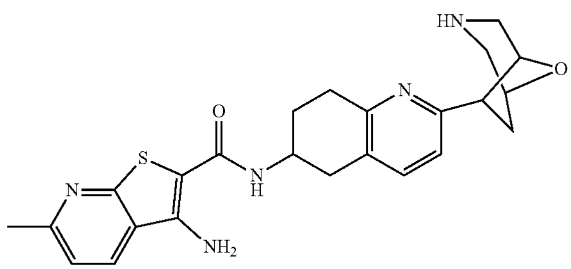 [SMILES: Cc1ccc2c(N)c(C(=O)NC3CCc4nc(C5CC6CNCC5O6)ccc4C3)sc2n1] | 3-amino-6-methyl-N-(2-{8-oxa-3-azabicyclo[3.2.1]octan-1-yl}-5,6,7,8-tetrahydroquinolin-6-yl)thieno[2,3-b]pyridine-2-carboxamide |
| 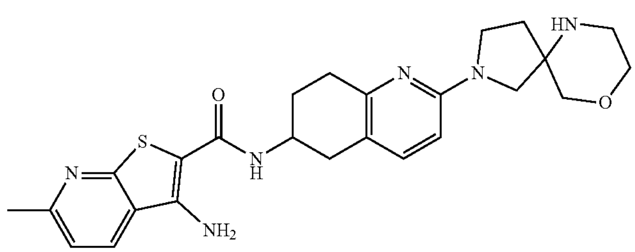 [SMILES: Cc1ccc2c(N)c(C(=O)NC3CCc4nc(N5CCC6(COCCN6)C5)ccc4C3)sc2n1] | 3-amino-6-methyl-N-(2-{9-oxa-2,6-diazaspiro[4.5]decan-2-yl}-5,6,7,8-tetrahydroquinolin-6-yl)thieno[2,3-b]pyridine-2-carboxamide |
| 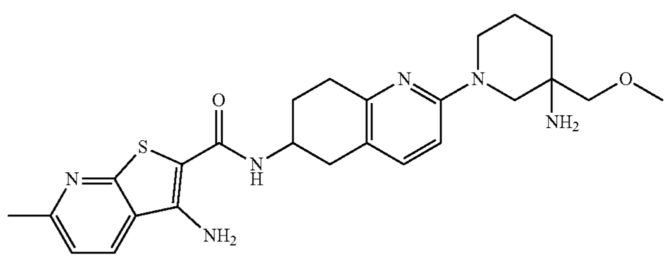 | 3-amino-N-{2-[3-amino-3-(methoxymethyl)piperidin-1-yl]-5,6,7,8-tetrahydroquinolin-6-yl}-6-methylthieno[2,3-b]pyridine-2-carboxamide |
| 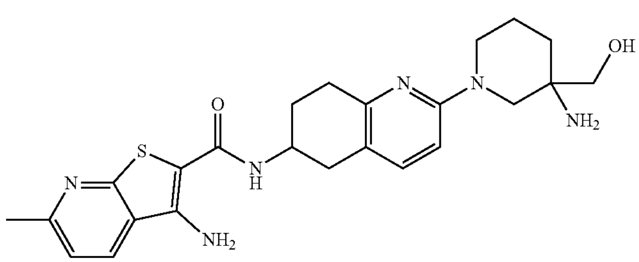 [SMILES: Cc1ccc2c(N)c(C(=O)NC3CCc4nc(N5CCCC(N)(CO)C5)ccc4C3)sc2n1] | 3-amino-N-{2-[3-amino-3-(hydroxymethyl)piperidin-1-yl]-5,6,7,8-tetrahydroquinolin-6-yl}-6-methylthieno[2,3-b]pyridine-2-carboxamide |

TABLE 27-continued

| Structure | Chemical Name |
|---|---|
| 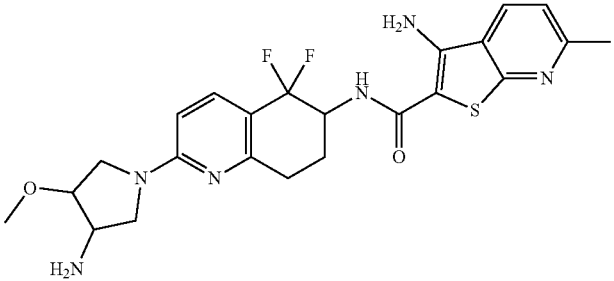 | 3-amino-N-[2-(3-amino-4-methoxypyrrolidin-1-yl)-5,5-difluoro-5,6,7,8-tetrahydroquinolin-6-yl]-6-methylthieno[2,3-b]pyridine-2-carboxamide |
| 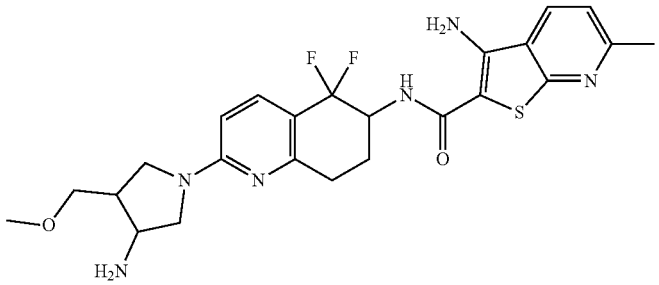 | 7-amino-N-[2-(3-amino-4-methoxypyrrolidin-1-yl)-5,5-difluoro-5,6,7,8-tetrahydroquinolin-6-yl]-3-methylthieno[2,3-b]pyrazine-6-carboxamide |
| 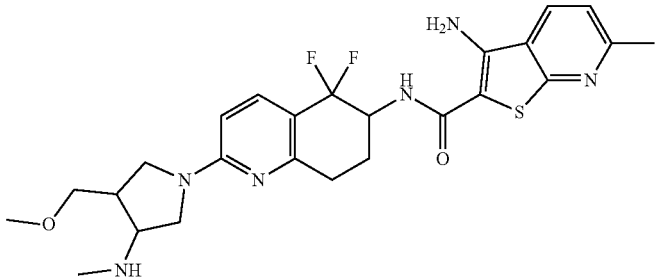 | 3-amino-N-{2-[3-amino-4-(methoxymethyl)pyrrolidin-1-yl]-5,5-difluoro-5,6,7,8-tetrahydroquinolin-6-yl}-6-methylthieno[2,3-b]pyridine-2-carboxamide |
| 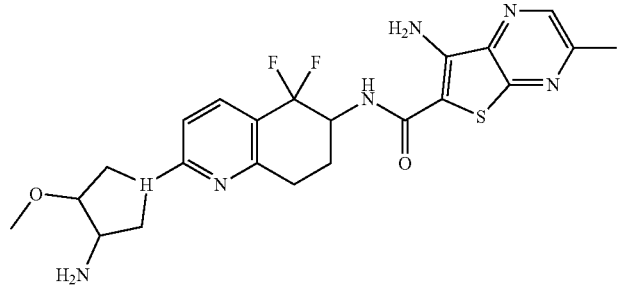 | 7-amino-N-[2-(3-amino-4-methoxypyrrolidin-1-yl)-5,5-difluoro-5,6,7,8-tetrahydroquinolin-6-yl]-3-methylthieno[2,3-b]pyrazine-6-carboxamide |
| 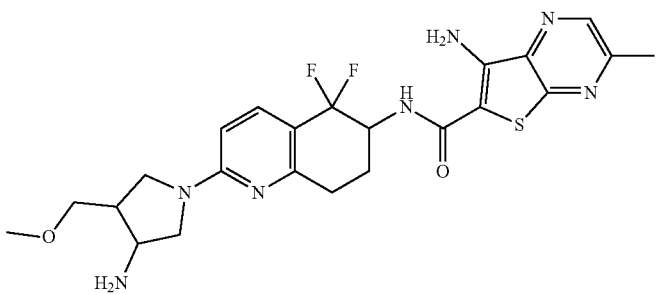 | 7-amino-N-{2-[3-amino-4-(methoxymethyl)pyrrolidin-1-yl]-5,5-difluoro-5,6,7,8-tetrahydroquinolin-6-yl}-3-methylthieno[2,3-b]pyrazine-6-carboxamide |

TABLE 27-continued

| Structure | Chemical Name |
|---|---|
| 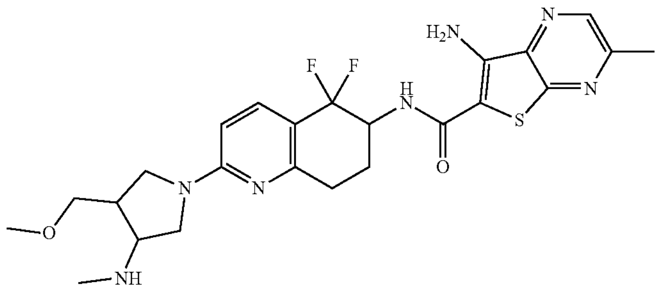 | 7-amino-N-{5,5-difluoro-2-[3-(methoxymethyl)-4-(methylamino)pyrrolidin-1-yl]-5,6,7,8-tetrahydroquinolin-6-yl}-3-methylthieno[2,3-b]pyrazine-6-carboxamide |
| 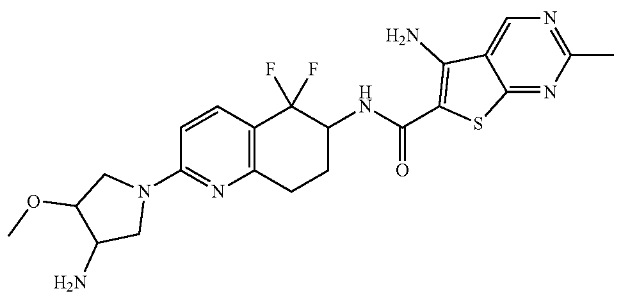 | 5-amino-N-[2-(3-amino-4-methoxypyrrolidin-1-yl)-5,5-difluoro-5,6,7,8-tetrahydroquinolin-6-yl]-2-methylthieno[2,3-d]pyrimidine-6-carboxamide |
| 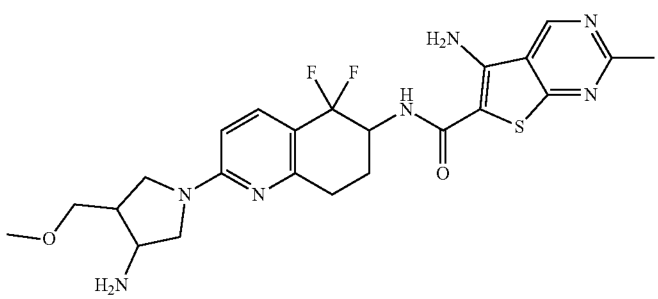 | 5-amino-N-{2-[3-amino-4-(methoxymethyl)pyrrolidin-1-yl]-5,5-difluoro-5,6,7,8-tetrahydroquinolin-6-yl}-2-methylthieno[2,3-d]pyrimidine-6-carboxamide |
| 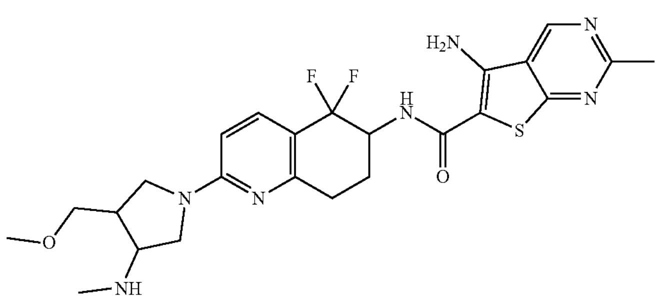 | 5-amino-N-{5,5-difluoro-2-[3-(methoxymethyl)-4-(methylamino)pyrrolidin-1-yl]-5,6,7,8-tetrahydroquinolin-6-yl}-2-methylthieno[2,3-d]pyrimidine-6-carboxamide |
| 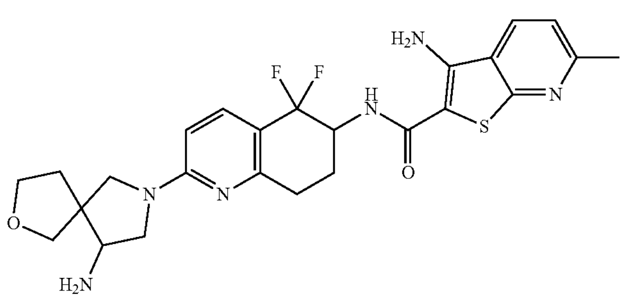 [SMILES: Cc1ccc2c(N)c(C(=O)NC3CCc4nc(N5CC(N)C6(CCOC6)C5)ccc4C3(F)F)sc2n1] | 3-amino-N-(2-{9-amino-2-oxa-7-azaspiro[4.4]nonan-7-yl}-5,5-difluoro-5,6,7,8-tetrahydroquinolin-6-yl)-6-methylthieno[2,3-b]pyridine-2-carboxamide |

TABLE 27-continued

| Structure | Chemical Name |
|---|---|
| 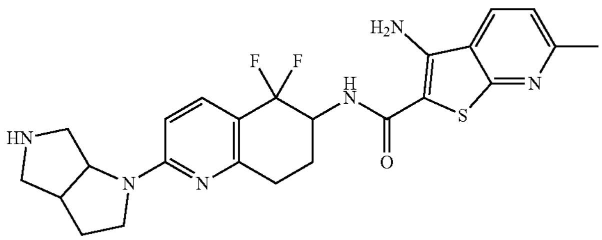 [SMILES: Cc1ccc2c(N)c(C(=O)NC3CCc4nc(N5CCC6CNCC65)ccc4C3(F)F)sc2n1] | 3-amino-N-(5,5-difluoro-2-{octahydropyrrolo[2,3-c]pyrrol-1-yl}-5,6,7,8-tetrahydroquinolin-6-yl)-6-methylthieno[2,3-b]pyridine-2-carboxamide |
| 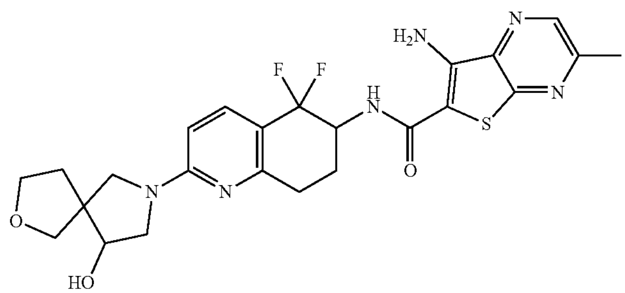 [SMILES: Cc1cnc2c(N)c(C(=O)NC3CCc4nc(N5CC(O)C6(CCOC6)C5)ccc4C3(F)F)sc2n1] | 7-amino-N-(5,5-difluoro-2-{9-hydroxy-2-oxa-7-azaspiro[4.4]nonan-7-yl}-5,6,7,8-tetrahydroquinolin-6-yl)-3-methylthieno[2,3-b]pyrazine-6-carboxamide |
| 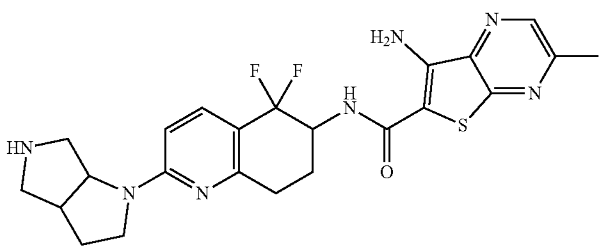 [SMILES: Cc1cnc2c(N)c(C(=O)NC3CCc4nc(N5CCC6CNCC65)ccc4C3(F)F)sc2n1] | 7-amino-N-(5,5-difluoro-2-{octahydropyrrolo[2,3-c]pyrrol-1-yl}-5,6,7,8-tetrahydroquinolin-6-yl)-3-methylthieno[2,3-b]pyrazine-6-carboxamide |
| 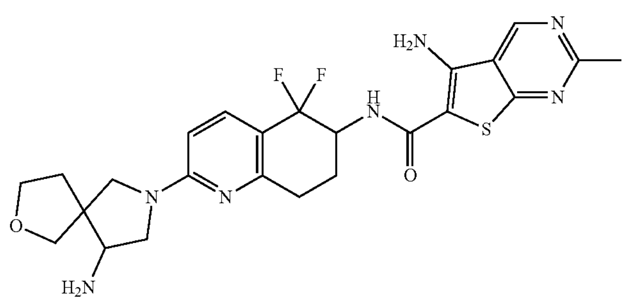 [SMILES: Cc1ncc2c(N)c(C(=O)NC3CCc4nc(N5CC(N)C6(CCOC6)C5)ccc4C3(F)F)sc2n1] | 5-amino-N-(2-{9-amino-2-oxa-7-azaspiro[4.4]nonan-7-yl}-5,5-difluoro-5,6,7,8-tetrahydroquinolin-6-yl)-2-methylthieno[2,3-d]pyrimidine-6-carboxamide |
| 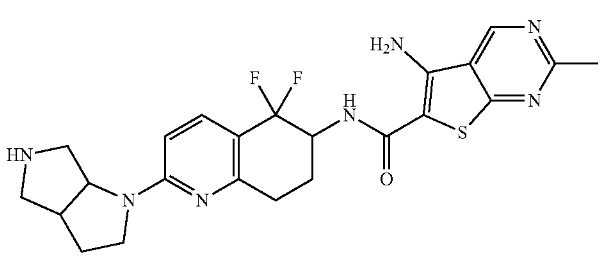 [SMILES: Cc1ncc2c(N)c(C(=O)NC3CCc4nc(N5CCC6CNCC65)ccc4C3(F)F)sc2n1] | 5-amino-N-(5,5-difluoro-2-{octahydropyrrolo[2,3-c]pyrrol-1-yl}-5,6,7,8-tetrahydroquinolin-6-yl)-2-methylthieno[2,3-d]pyrimidine-6-carboxamide |

TABLE 27-continued

| Structure | Chemical Name |
|---|---|
| 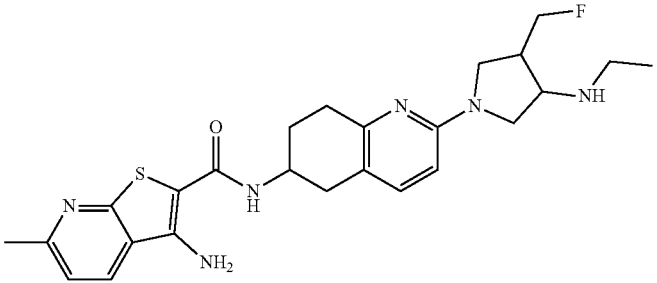 [SMILES: CCNC1CN(c2ccc3c(n2)CCC(NC(=O)c2sc4nc(C)ccc4c2N)C3)CC1CF] | 3-amino-N-{2-[3-(ethylamino)-4-(fluoromethyl)pyrrolidin-1-yl]-5,6,7,8-tetrahydroquinolin-6-yl}-6-methylthieno[2,3-b]pyridine-2-carboxamide |
| 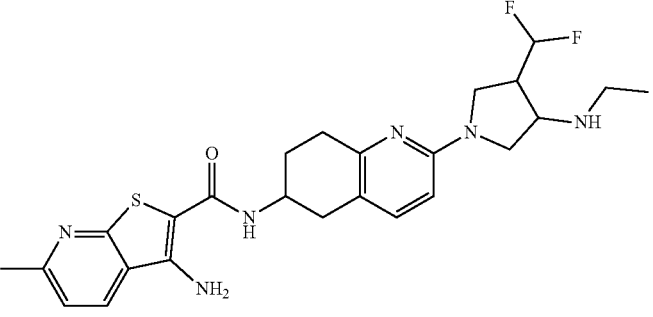 [SMILES: CCNC1CN(c2ccc3c(n2)CCC(NC(=O)c2sc4nc(C)ccc4c2N)C3)CC1C(F)F] | 3-amino-N-{2-[3-(difluoromethyl)-4-(ethylamino)pyrrolidin-1-yl]-5,6,7,8-tetrahydroquinolin-6-yl}-6-methylthieno[2,3-b]pyridine-2-carboxamide |
| 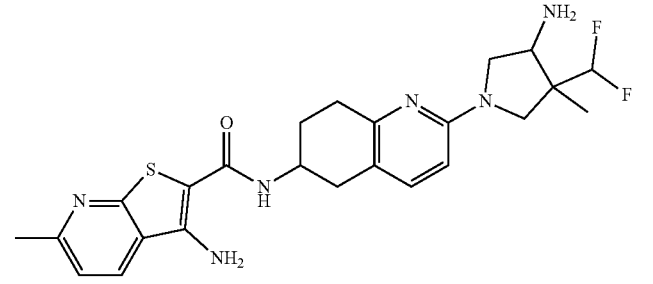 [SMILES: Cc1ccc2c(N)c(C(=O)NC3CCc4nc(N5CC(N)C(C)(C(F)F)C5)ccc4C3)sc2n1] | 3-amino-N-{2-[4-amino-3-(difluoromethyl)-3-methylpyrrolidin-1-yl]-5,6,7,8-tetrahydroquinolin-6-yl}-6-methylthieno[2,3-b]pyridine-2-carboxamide |
| 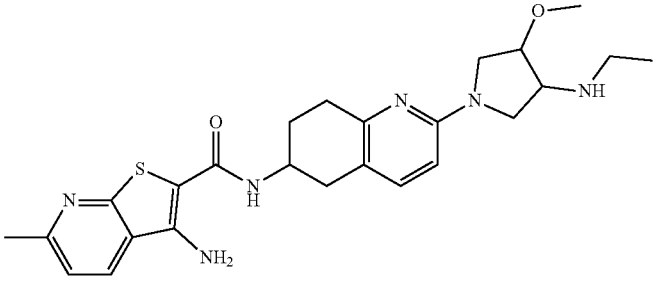 [SMILES: CCNC1CN(c2ccc3c(n2)CCC(NC(=O)c2sc4nc(C)ccc4c2N)C3)CC1OC] | 3-amino-N-{2-[3-(ethylamino)-4-methoxypyrrolidin-1-yl]-5,6,7,8-tetrahydroquinolin-6-yl}-6-methylthieno[2,3-b]pyridine-2-carboxamide |
| 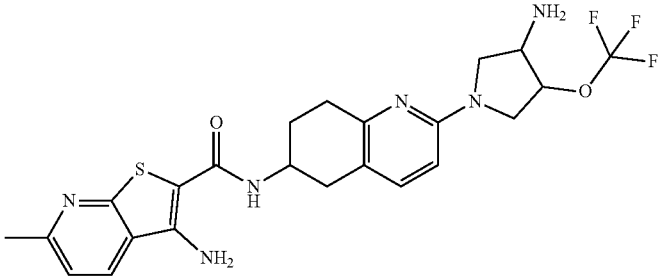 [SMILES: Cc1ccc2c(N)c(C(=O)NC3CCc4nc(N5CC(N)C(OC(F)(F)F)C5)ccc4C3)sc2n1] | 3-amino-N-{2-[3-amino-4-(trifluoromethoxy)pyrrolidin-1-yl]-5,6,7,8-tetrahydroquinolin-6-yl}-6-methylthieno[2,3-b]pyridine-2-carboxamide |

TABLE 27-continued

| Structure | Chemical Name |
| --- | --- |
| 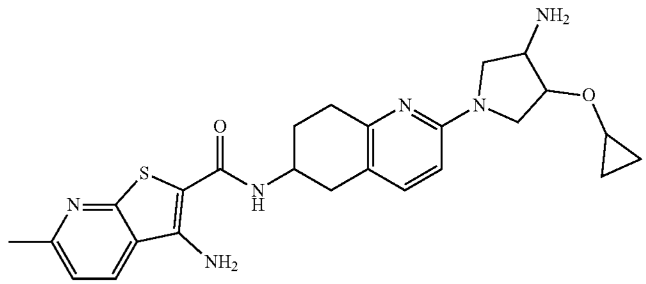 [SMILES: Cc1ccc2c(N)c(C(=O)NC3CCc4nc(N5CC(N)C(OC6CC6)C5)ccc4C3)sc2n1] | 3-amino-N-[2-(3-amino-4-cyclopropoxypyrrolidin-1-yl)-5,6,7,8-tetrahydroquinolin-6-yl]-6-methylthieno[2,3-b]pyridine-2-carboxamide |
| 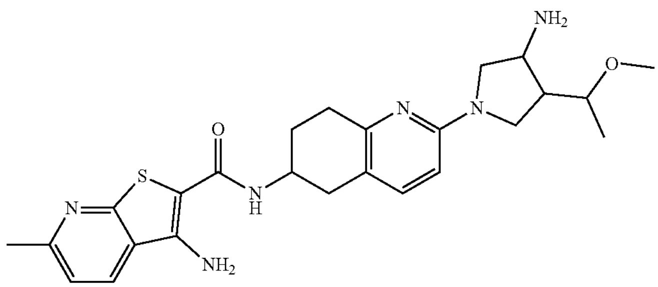 | 3-amino-N-{2-[3-amino-4-(1-methoxyethyl)pyrrolidin-1-yl]-5,6,7,8-tetrahydroquinolin-6-yl}-6-methylthieno[2,3-b]pyridine-2-carboxamide |
| 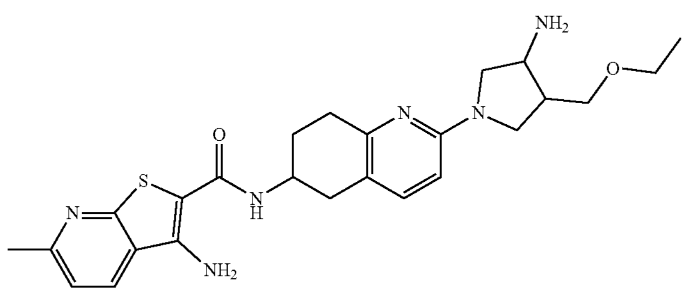 [SMILES: CCOCC1CN(c2ccc3c(n2)CCC(NC(=O)c2sc4nc(C)ccc4c2N)C3)CC1N] | 3-amino-N-{2-[3-amino-4-(ethoxymethyl)pyrrolidin-1-yl]-5,6,7,8-tetrahydroquinolin-6-yl}-6-methylthieno[2,3-b]pyridine-2-carboxamide |
| 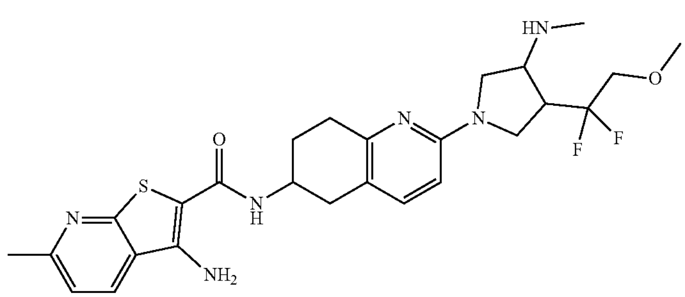 | 3-amino-N-{2-[3-(1,1-difluoro-2-methoxyethyl)-4-(methylamino)pyrrolidin-1-yl]-5,6,7,8-tetrahydroquinolin-6-yl}-6-methylthieno[2,3-b]pyridine-2-carboxamide |
| 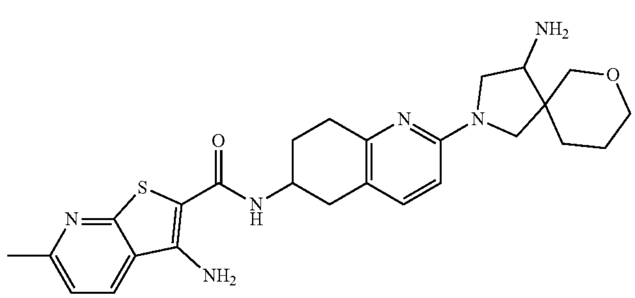 [SMILES: Cc1ccc2c(N)c(C(=O)NC3CCc4nc(N5CC(N)C6(CCCOC6)C5)ccc4C3)sc2n1] | 3-amino-N-(2-{4-amino-7-oxa-2-azaspiro[4.5]decan-2-yl}-5,6,7,8-tetrahydroquinolin-6-yl)-6-methylthieno[2,3-b]pyridine-2-carboxamide |

TABLE 27-continued

| Structure | Chemical Name |
|---|---|
| 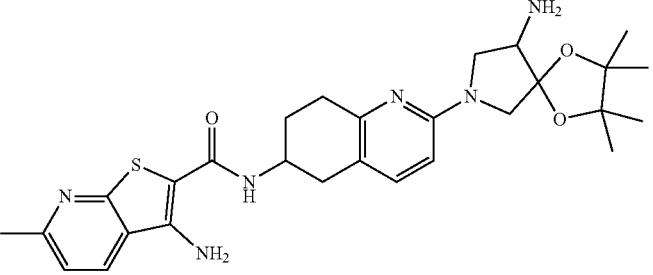 | 3-amino-N-(2-{9-amino-2,2,3,3-tetramethyl-1,4-dioxa-7-azaspiro[4.4]nonan-7-yl}-5,6,7,8-tetrahydroquinolin-6-yl)-6-methylthieno[2,3-b]pyridine-2-carboxamide |
| 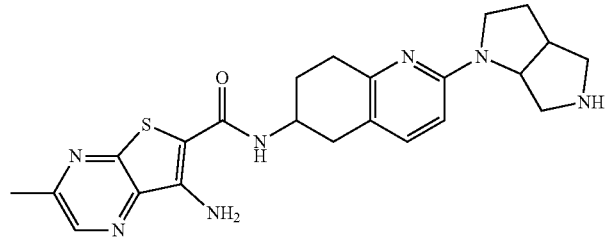 [SMILES: Cc1cnc2c(N)c(C(=O)NC3CCc4nc(N5CCC6CNCC65)ccc4C3)sc2n1] | 7-amino-3-methyl-N-(2-{octahydropyrrolo[2,3-c]pyrrol-1-yl}-5,6,7,8-tetrahydroquinolin-6-yl)thieno[2,3-b]pyrazine-6-carboxamide |
| 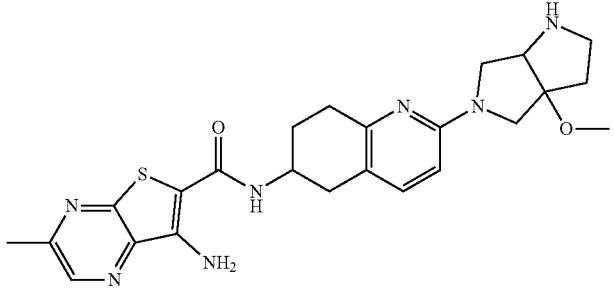 | N-(2-{3a-methoxy-octahydropyrrolo[3,4-b]pyrrol-5-yl}-5,6,7,8-tetrahydroquinolin-6-yl)-7-amino-3-methylthieno[2,3-b]pyrazine-6-carboxamide |
| 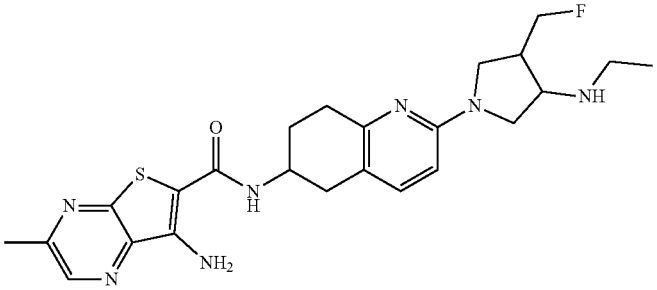 [SMILES: CCNC1CN(c2ccc3c(n2)CCC(NC(=O)c2sc4nc(C)cnc4c2N)C3)CC1CF] | 7-amino-N-{2-[3-(ethylamino)-4-(fluoromethyl)pyrrolidin-1-yl]-5,6,7,8-tetrahydroquinolin-6-yl}-3-methylthieno[2,3-b]pyrazine-6-carboxamide |
| 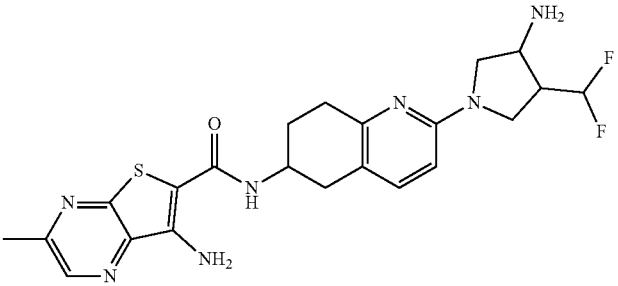 [SMILES: Cc1cnc2c(N)c(C(=O)NC3CCc4nc(N5CC(N)C(C(F)F)C5)ccc4C3)sc2n1] | 7-amino-N-{2-[3-amino-4-(difluoromethyl)pyrrolidin-1-yl]-5,6,7,8-tetrahydroquinolin-6-yl}-3-methylthieno[2,3-b]pyrazine-6-carboxamide |

TABLE 27-continued

| Structure | Chemical Name |
|---|---|
| 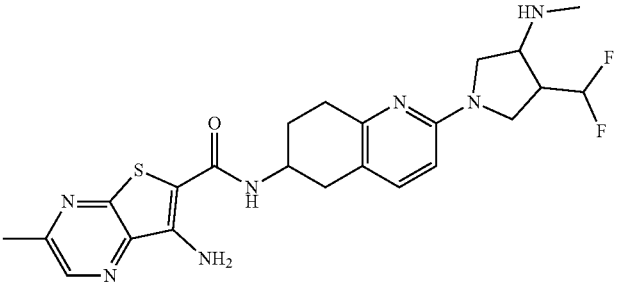 [SMILES: CNC1CN(c2ccc3c(n2)CCC(NC(=O)c2sc4nc(C)cnc4c2N)C3)CC1C(F)F] | 7-amino-N-{2-[3-(difluoromethyl)-4-(methylamino)pyrrolidin-1-yl]-5,6,7,8-tetrahydroquinolin-6-yl}-3-methylthieno[2,3-b]pyrazine-6-carboxamide |
| 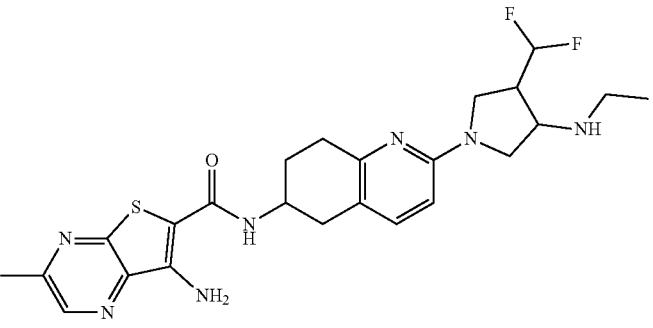 | 7-amino-N-{2-[3-(difluoromethyl)-4-(ethylamino)pyrrolidin-1-yl]-5,6,7,8-tetrahydroquinolin-6-yl}-3-methylthieno[2,3-b]pyrazine-6-carboxamide |
| 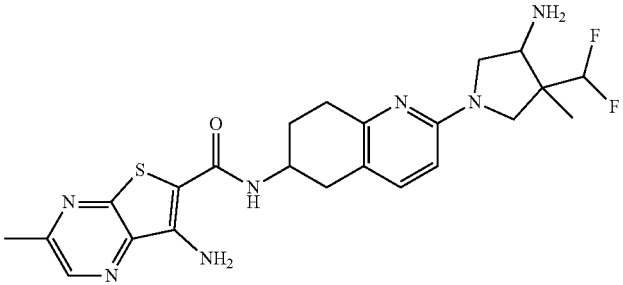 [SMILES: Cc1cnc2c(N)c(C(=O)NC3CCc4nc(N5CC(N)C(C)(C(F)F)C5)ccc4C3)sc2n1] | 7-amino-N-{2-[4-amino-3-(difluoromethyl)-3-methylpyrrolidin-1-yl]-5,6,7,8-tetrahydroquinolin-6-yl}-3-methylthieno[2,3-b]pyrazine-6-carboxamide |
| 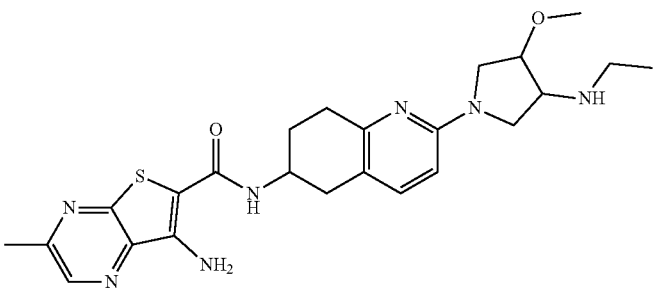 [SMILES: CCNC1CN(c2ccc3c(n2)CCC(NC(=O)c2sc4nc(C)cnc4c2N)C3)CC1OC] | 7-amino-N-{2-[3-(ethylamino)-4-methoxypyrrolidin-1-yl]-5,6,7,8-tetrahydroquinolin-6-yl}-3-methylthieno[2,3-b]pyrazine-6-carboxamide |
| 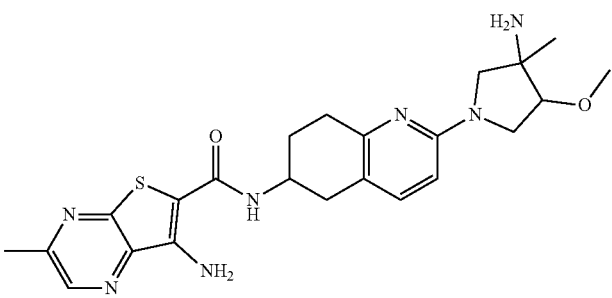 | 7-amino-N-[2-(3-amino-4-methoxy-3-methylpyrrolidin-1-yl)-5,6,7,8-tetrahydroquinolin-6-yl]-3-methylthieno[2,3-b]pyrazine-6-carboxamide |

TABLE 27-continued

| Structure | Chemical Name |
|---|---|
| 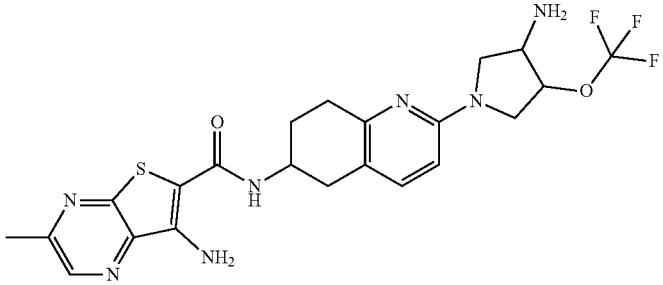 | 7-amino-N-{2-[3-amino-4-(trifluoromethoxy)pyrrolidin-1-yl]-5,6,7,8-tetrahydroquinolin-6-yl}-3-methylthieno[2,3-b]pyrazine-6-carboxamide |
| 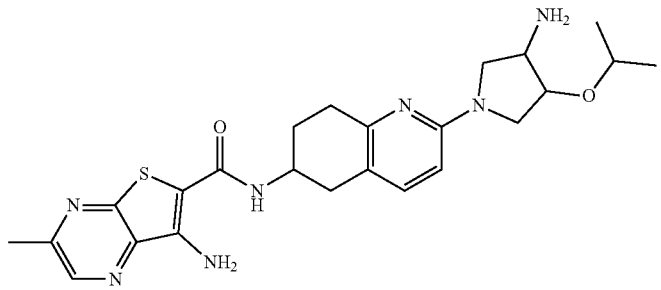 | 7-amino-N-{2-[3-amino-4-(propan-2-yloxy)pyrrolidin-1-yl]-5,6,7,8-tetrahydroquinolin-6-yl}-3-methylthieno[2,3-b]pyrazine-6-carboxamide |
| 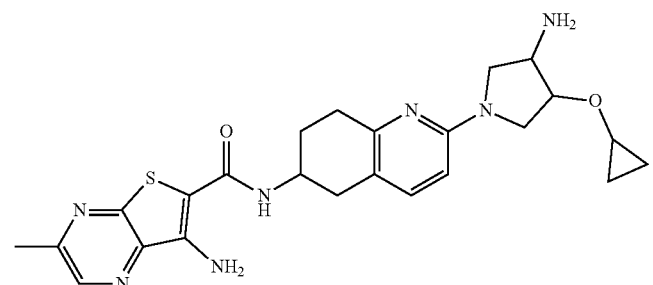 | 7-amino-N-[2-(3-amino-4-cyclopropoxypyrrolidin-1-yl)-5,6,7,8-tetrahydroquinolin-6-yl]-3-methylthieno[2,3-b]pyrazine-6-carboxamide |
| 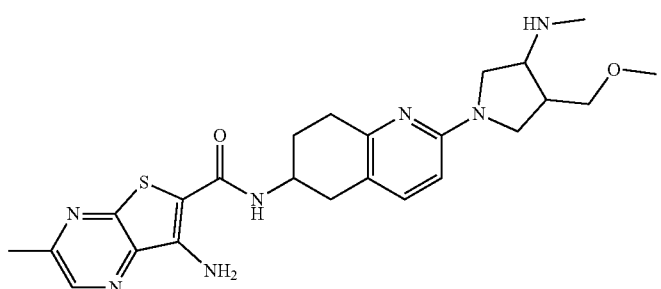 | 7-amino-N-{2-[3-(methoxymethyl)-4-(methylamino)pyrrolidin-1-yl]-5,6,7,8-tetrahydroquinolin-6-yl}-3-methylthieno[2,3-b]pyrazine-6-carboxamide |
| 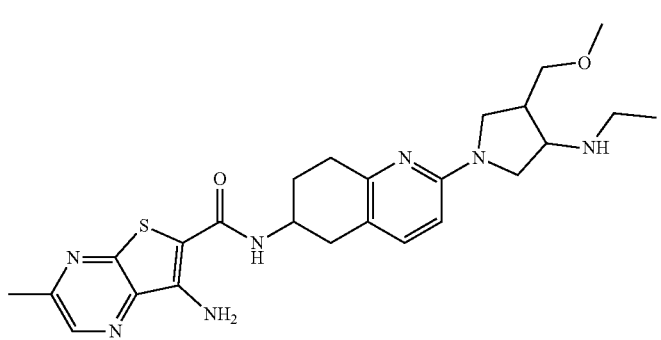 [SMILES: CCNC1CN(c2ccc3c(n2)CCC(NC(=O)c2sc4nc(C)cnc4c2N)C3)CC1COC] | 7-amino-N-{2-[3-(ethylamino)-4-(methoxymethyl)pyrrolidin-1-yl]-5,6,7,8-tetrahydroquinolin-6-yl}-3-methylthieno[2,3-b]pyrazine-6-carboxamide |

TABLE 27-continued

| Structure | Chemical Name |
|---|---|
| 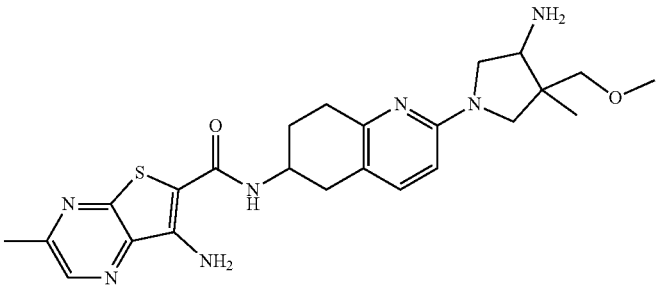 | 7-amino-N-{2-[4-amino-3-(methoxymethyl)-3-methylpyrrolidin-1-yl]-5,6,7,8-tetrahydroquinolin-6-yl}-3-methylthieno[2,3-b]pyrazine-6-carboxamide |
| 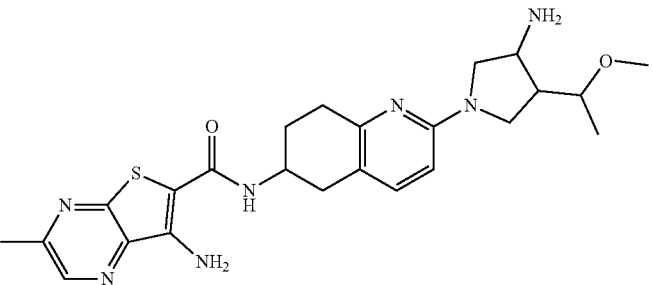 | 7-amino-N-{2-[3-amino-4-(1-methoxyethyl)pyrrolidin-1-yl]-5,6,7,8-tetrahydroquinolin-6-yl}-3-methylthieno[2,3-b]pyrazine-6-carboxamide |
| 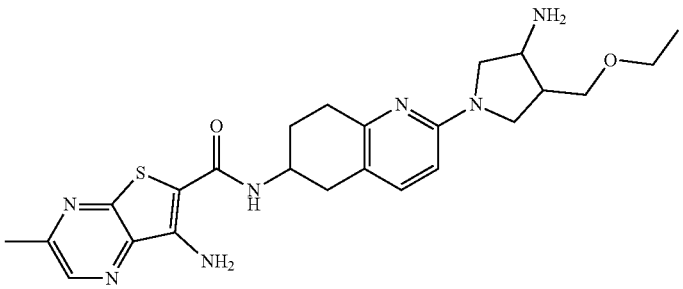 [SMILES: CCOCC1CN(c2ccc3c(n2)CCC(NC(=O)c2sc4nc(C)cnc4c2N)C3)CC1N] | 7-amino-N-{2-[3-amino-4-(ethoxymethyl)pyrrolidin-1-yl]-5,6,7,8-tetrahydroquinolin-6-yl}-3-methylthieno[2,3-b]pyrazine-6-carboxamide |
| 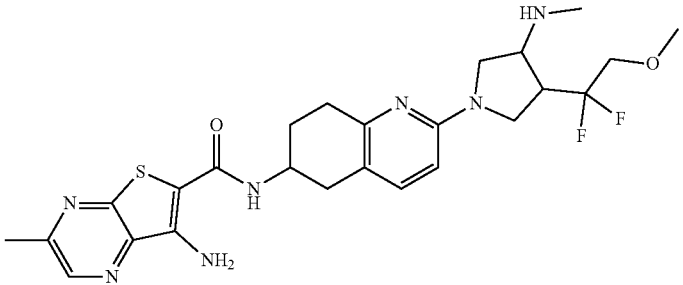 | 7-amino-N-{2-[3-(1,1-difluoro-2-methoxyethyl)-4-(methylamino)pyrrolidin-1-yl]-5,6,7,8-tetrahydroquinolin-6-yl}-3-methylthieno[2,3-b]pyrazine-6-carboxamide |
| 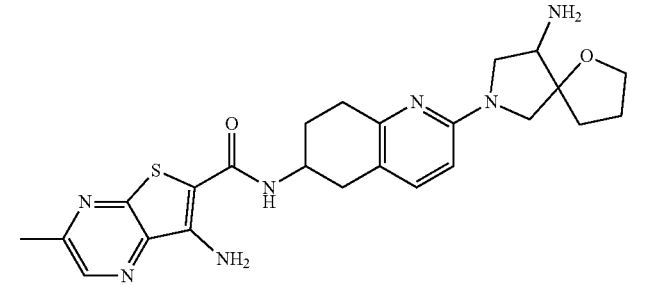 [SMILES: Cc1cnc2c(N)c(C(=O)NC3CCc4nc(N5CC(N)C6(CCCO6)C5)ccc4C3)sc2n1] | 7-amino-N-(2-{9-amino-1-oxa-7-azaspiro[4.4]nonan-7-yl}-5,6,7,8-tetrahydroquinolin-6-yl)-3-methylthieno[2,3-b]pyrazine-6-carboxamide |

TABLE 27-continued

| Structure | Chemical Name |
|---|---|
| 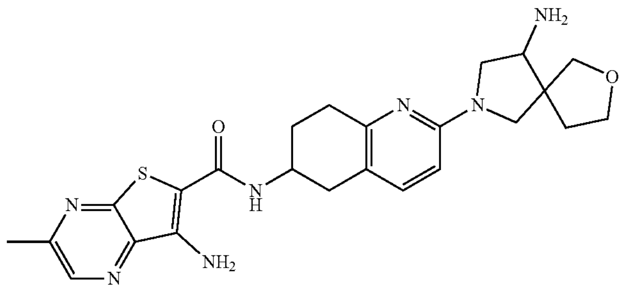 [SMILES: Cc1cnc2c(N)c(C(=O)NC3CCc4nc(N5CC(N)C6(CCOC6)C5)ccc4C3)sc2n1] | 7-amino-N-(2-{9-amino-2-oxa-7-azaspiro[4.4]nonan-7-yl}-5,6,7,8-tetrahydroquinolin-6-yl)-3-methylthieno[2,3-b]pyrazine-6-carboxamide |
| 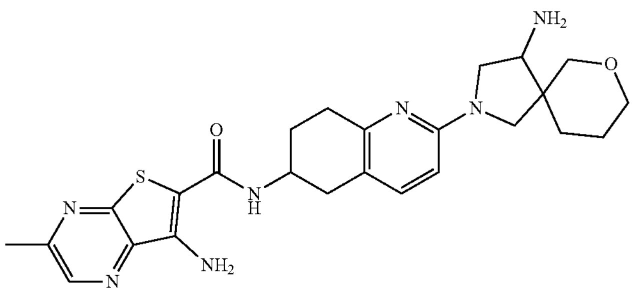 [SMILES: Cc1cnc2c(N)c(C(=O)NC3CCc4nc(N5CC(N)C6(CCCOC6)C5)ccc4C3)sc2n1] | 7-amino-N-(2-{4-amino-7-oxa-2-azaspiro[4.5]decan-2-yl}-5,6,7,8-tetrahydroquinolin-6-yl)-3-methylthieno[2,3-b]pyrazine-6-carboxamide |
| 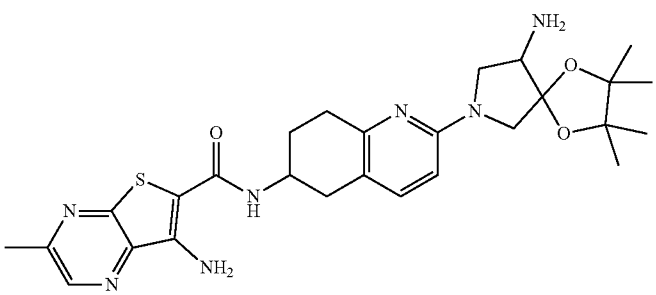 | 7-amino-N-(2-{9-amino-2,2,3,3-tetramethyl-1,4-dioxa-7-azaspiro[4.4]nonan-7-yl}-5,6,7,8-tetrahydroquinolin-6-yl)-3-methylthieno[2,3-b]pyrazine-6-carboxamide |
| 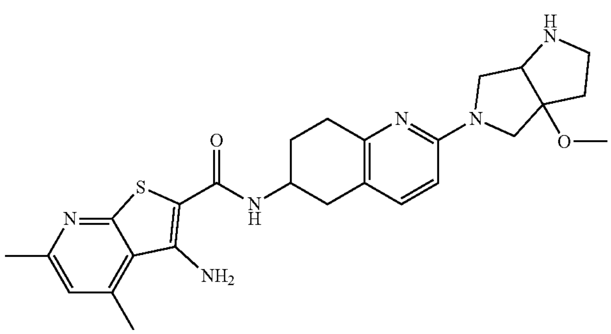 | N-(2-{3a-methoxy-octahydropyrrolo[3,4-b]pyrrol-5-yl}-5,6,7,8-tetrahydroquinolin-6-yl)-3-amino-4,6-dimethylthieno[2,3-b]pyridine-2-carboxamide |
| 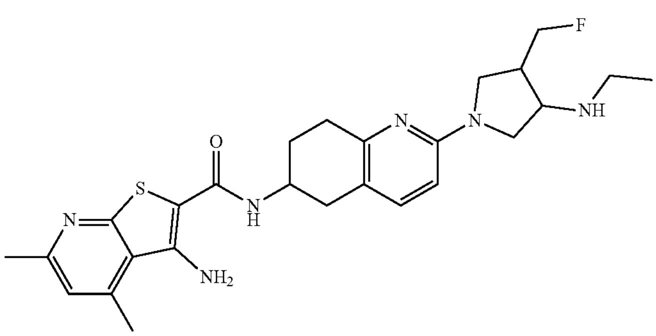 [SMILES: CCNC1CN(c2ccc3c(n2)CCC(NC(=O)c2sc4nc(C)cc(C)c4c2N)C3)CC1CF] | 3-amino-N-{2-[3-(ethylamino)-4-(fluoromethyl)pyrrolidin-1-yl]-5,6,7,8-tetrahydroquinolin-6-yl}-4,6-dimethylthieno[2,3-b]pyridine-2-carboxamide |

TABLE 27-continued

| Structure | Chemical Name |
|---|---|
| 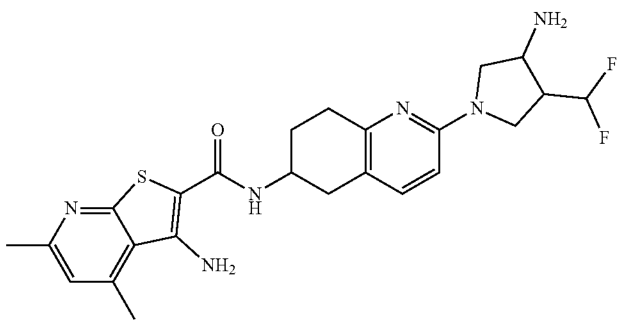 [SMILES: Cc1cc(C)c2c(N)c(C(=O)NC3CCc4nc(N5CC(N)C(C(F)F)C5)ccc4C3)sc2n1] | 3-amino-N-{2-[3-amino-4-(difluoromethyl)pyrrolidin-1-yl]-5,6,7,8-tetrahydroquinolin-6-yl}-4,6-dimethylthieno[2,3-b]pyridine-2-carboxamide |
| 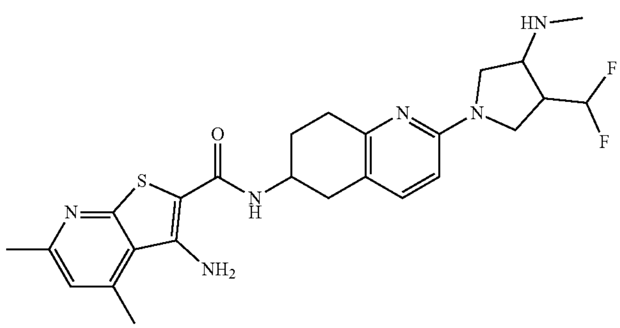 | 3-amino-N-{2-[3-(difluoromethyl)-4-(methylamino)pyrrolidin-1-yl]-5,6,7,8-tetrahydroquinolin-6-yl}-4,6-dimethylthieno[2,3-b]pyridine-2-carboxamide |
| 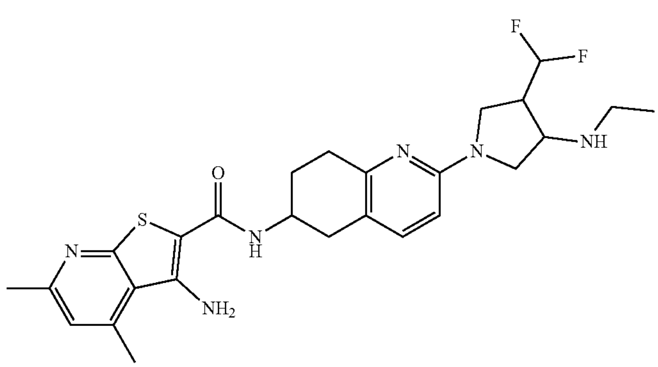 [SMILES: CCNC1CN(c2ccc3c(n2)CCC(NC(=O)c2sc4nc(C)cc(C)c4c2N)C3)CC1C(F)F] | 3-amino-N-{2-[3-(difluoromethyl)-4-(ethylamino)pyrrolidin-1-yl]-5,6,7,8-tetrahydroquinolin-6-yl}-4,6-dimethylthieno[2,3-b]pyridine-2-carboxamide |
| 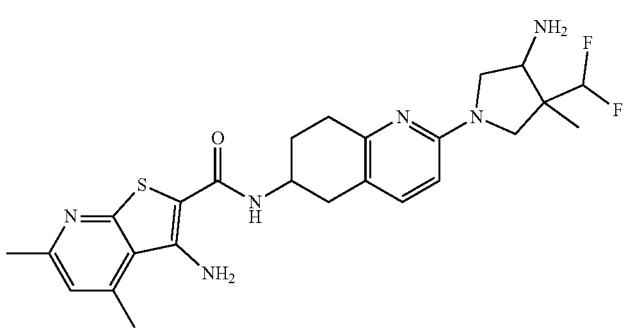 [SMILES: Cc1cc(C)c2c(N)c(C(=O)NC3CCc4nc(N5CC(N)C(C)(C(F)F)C5)ccc4C3)sc2n1] | 3-amino-N-{2-[4-amino-3-(difluoromethyl)-3-methylpyrrolidin-1-yl]-5,6,7,8-tetrahydroquinolin-6-yl}-4,6-dimethylthieno[2,3-b]pyridine-2-carboxamide |

TABLE 27-continued

| Structure | Chemical Name |
|---|---|
| 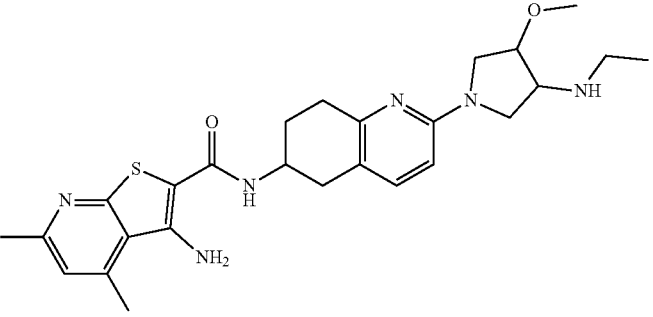 | 3-amino-N-{2-[3-(ethylamino)-4-methoxypyrrolidin-1-yl]-5,6,7,8-tetrahydroquinolin-6-yl}-4,6-dimethylthieno[2,3-b]pyridine-2-carboxamide |
| 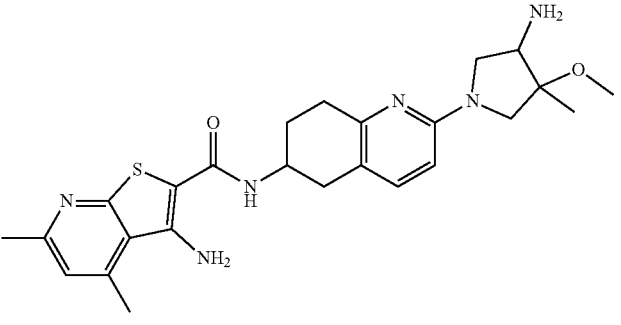 | 3-amino-N-[2-(4-amino-3-methoxy-3-methylpyrrolidin-1-yl)-5,6,7,8-tetrahydroquinolin-6-yl]-4,6-dimethylthieno[2,3-b]pyridine-2-carboxamide |
| 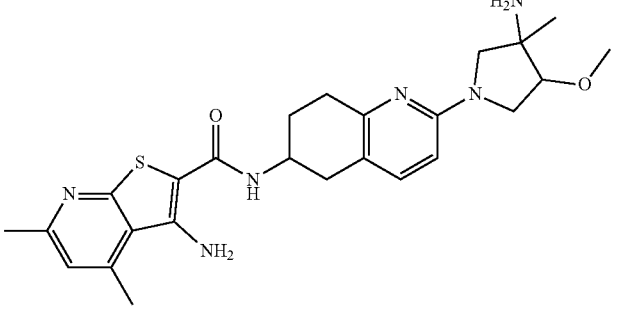 | 3-amino-N-[2-(3-amino-4-methoxy-3-methylpyrrolidin-1-yl)-5,6,7,8-tetrahydroquinolin-6-yl]-4,6-dimethylthieno[2,3-b]pyridine-2-carboxamide |
| 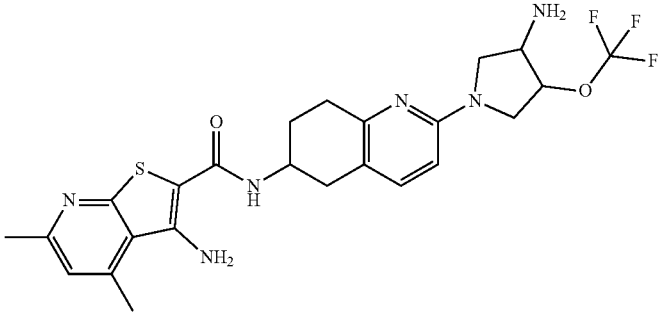 [SMILES: Cc1cc(C)c2c(N)c(C(=O)NC3CCc4nc(N5CC(N)C(OC(F)(F)F)C5)ccc4C3)sc2n1] | 3-amino-N-{2-[3-amino-4-(trifluoromethoxy)pyrrolidin-1-yl]-5,6,7,8-tetrahydroquinolin-6-yl}-4,6-dimethylthieno[2,3-b]pyridine-2-carboxamide |

TABLE 27-continued

| Structure | Chemical Name |
|---|---|
| 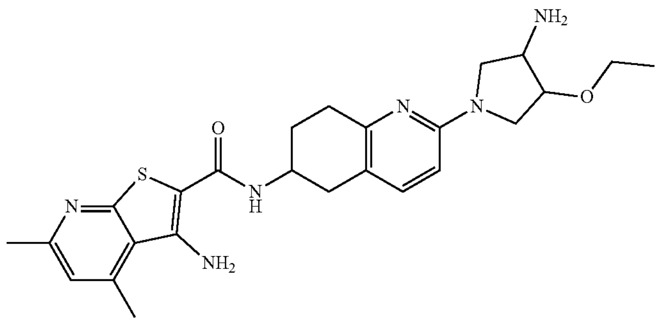 [SMILES: CCOC1CN(c2ccc3c(n2)CCC(NC(=O)c2sc4nc(C)cc(C)c4c2N)C3)CC1N] | 3-amino-N-[2-(3-amino-4-ethoxypyrrolidin-1-yl)-5,6,7,8-tetrahydroquinolin-6-yl]-4,6-dimethylthieno[2,3-b]pyridine-2-carboxamide |
| 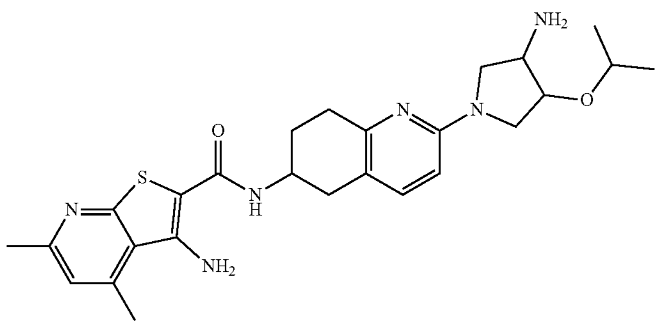 [SMILES: Cc1cc(C)c2c(N)c(C(=O)NC3CCc4nc(N5CC(N)C(OC(C)C)C5)ccc4C3)sc2n1] | 3-amino-N-{2-[3-amino-4-(propan-2-yloxy)pyrrolidin-1-yl]-5,6,7,8-tetrahydroquinolin-6-yl}-4,6-dimethylthieno[2,3-b]pyridine-2-carboxamide |
| 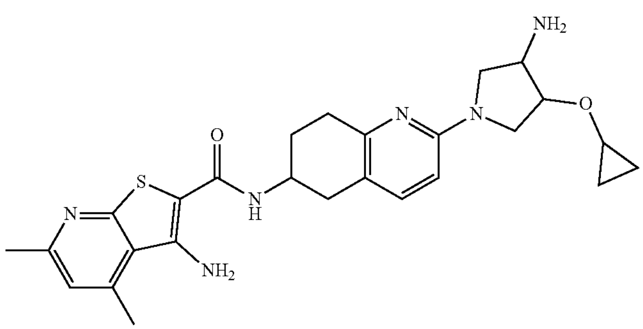 [SMILES: Cc1cc(C)c2c(N)c(C(=O)NC3CCc4nc(N5CC(N)C(OC6CC6)C5)ccc4C3)sc2n1] | 3-amino-N-[2-(3-amino-4-cyclopropoxypyrrolidin-1-yl)-5,6,7,8-tetrahydroquinolin-6-yl]-4,6-dimethylthieno[2,3-b]pyridine-2-carboxamide |
| 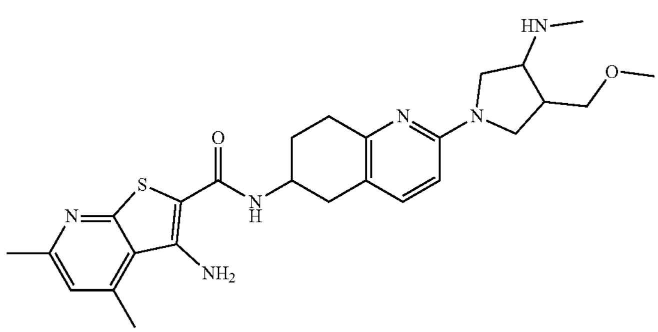 | 3-amino-N-{2-[3-(methoxymethyl)-4-(methylamino)pyrrolidin-1-yl]-5,6,7,8-tetrahydroquinolin-6-yl}-4,6-dimethylthieno[2,3-b]pyridine-2-carboxamide |

TABLE 27-continued

| Structure | Chemical Name |
|---|---|
| 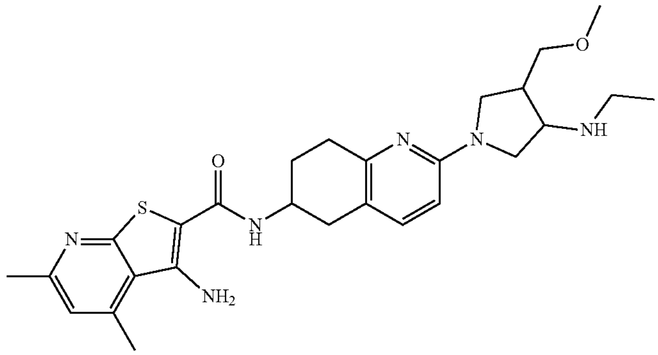 [SMILES: CCNC1CN(c2ccc3c(n2)CCC(NC(=O)c2sc4nc(C)cc(C)c4c2N)C3)CC1COC] | 3-amino-N-{2-[3-(ethylamino)-4-(methoxymethyl)pyrrolidin-1-yl]-5,6,7,8-tetrahydroquinolin-6-yl}-4,6-dimethylthieno[2,3-b]pyridine-2-carboxamide |
| 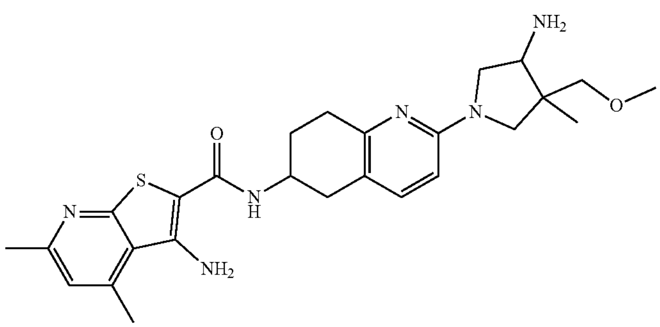 | 3-amino-N-{2-[4-amino-3-(methoxymethyl)-3-methylpyrrolidin-1-yl]-5,6,7,8-tetrahydroquinolin-6-yl}-4,6-dimethylthieno[2,3-b]pyridine-2-carboxamide |
| 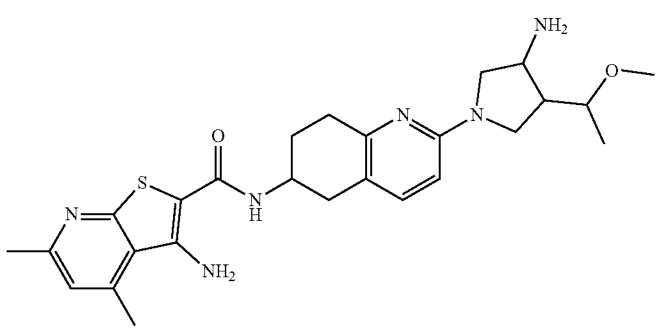 | 3-amino-N-{2-[3-amino-4-(1-methoxyethyl)pyrrolidin-1-yl]-5,6,7,8-tetrahydroquinolin-6-yl}-4,6-dimethylthieno[2,3-b]pyridine-2-carboxamide |
| 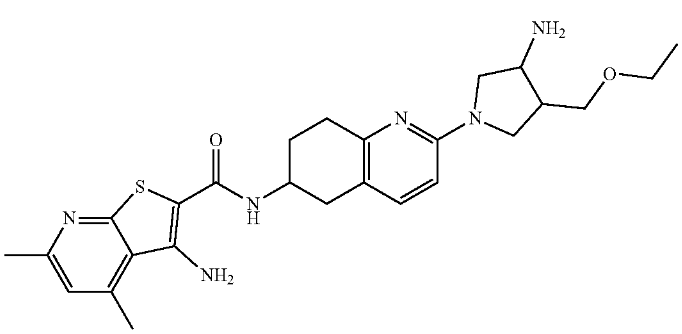 | 3-amino-N-{2-[3-amino-4-(ethoxymethyl)pyrrolidin-1-yl]-5,6,7,8-tetrahydroquinolin-6-yl}-4,6-dimethylthieno[2,3-b]pyridine-2-carboxamide |

TABLE 27-continued

| Structure | Chemical Name |
|---|---|
| 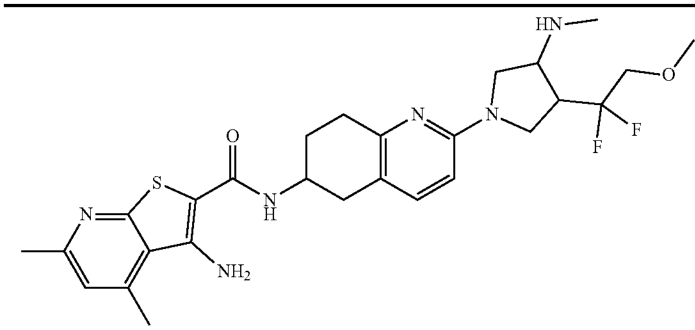 | 3-amino-N-{2-[3-(1,1-difluoro-2-methoxyethyl)-4-(methylamino)pyrrolidin-1-yl]-5,6,7,8-tetrahydroquinolin-6-yl}-4,6-dimethylthieno[2,3-b]pyridine-2-carboxamide |
| 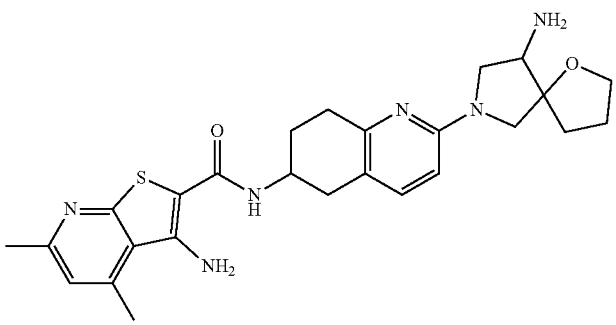 | 3-amino-N-(2-{9-amino-1-oxa-7-azaspiro[4.4]nonan-7-yl}-5,6,7,8-tetrahydroquinolin-6-yl)-4,6-dimethylthieno[2,3-b]pyridine-2-carboxamide |
| 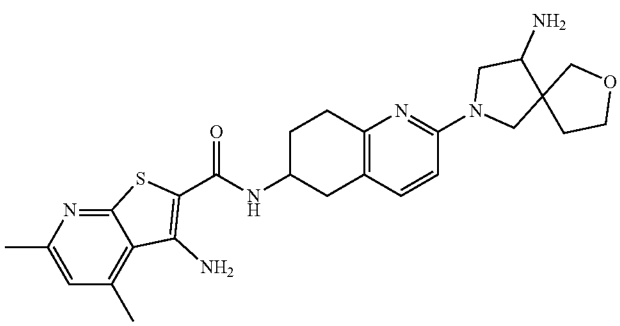 [SMILES: Cc1cc(C)c2c(N)c(C(=O)NC3CCc4nc(N5CC(N)C6(CCOC6)C5)ccc4C3)sc2n1] | 3-amino-N-(2-{9-amino-2-oxa-7-azaspiro[4.4]nonan-7-yl}-5,6,7,8-tetrahydroquinolin-6-yl)-4,6-dimethylthieno[2,3-b]pyridine-2-carboxamide |
| 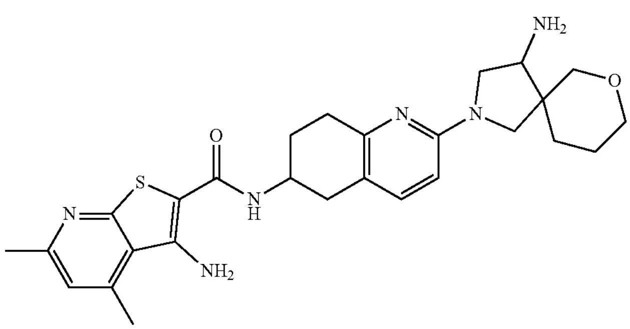 [SMILES: Cc1cc(C)c2c(N)c(C(=O)NC3CCc4nc(N5CC(N)C6(CCCOC6)C5)ccc4C3)sc2n1] | 3-amino-N-(2-{4-amino-7-oxa-2-azaspiro[4.5]decan-2-yl}-5,6,7,8-tetrahydroquinolin-6-yl)-4,6-dimethylthieno[2,3-b]pyridine-2-carboxamide |
| 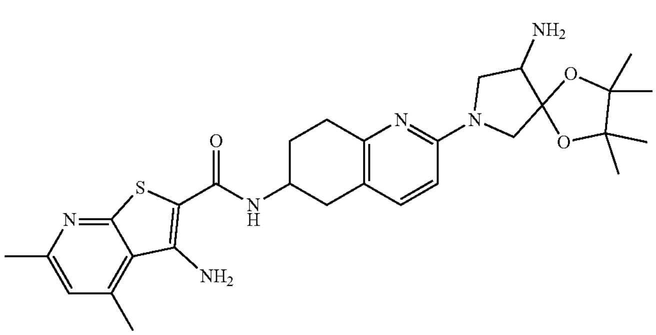 | 3-amino-N-(2-{9-amino-2,2,3,3-tetramethyl-1,4-dioxa-7-azaspiro[4.4]nonan-7-yl}-5,6,7,8-tetrahydroquinolin-6-yl)-4,6-dimethylthieno[2,3-b]pyridine-2-carboxamide |

TABLE 27-continued

| Structure | Chemical Name |
|---|---|
| 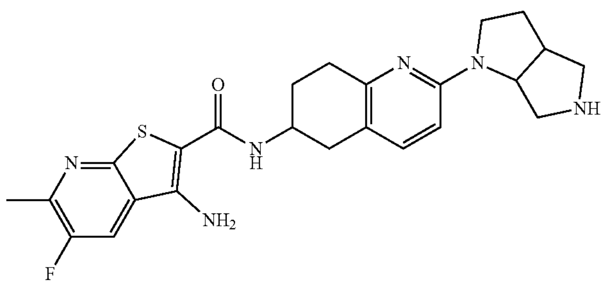 [SMILES: Cc1nc2sc(C(=O)NC3CCc4nc(N5CCC6CNCC65)ccc4C3)c(N)c2cc1F] | 3-amino-5-fluoro-6-methyl-N-(2-{octahydropyrrolo[2,3-c]pyrrol-1-yl}-5,6,7,8-tetrahydroquinolin-6-yl)thieno[2,3-b]pyridine-2-carboxamide |
| 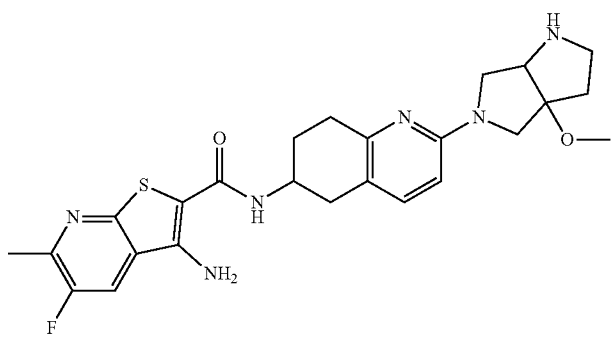 | N-(2-{3a-methoxy-octahydropyrrolo[3,4-b]pyrrol-5-yl}-5,6,7,8-tetrahydroquinolin-6-yl)-3-amino-5-fluoro-6-methylthieno[2,3-b]pyridine-2-carboxamide |
| 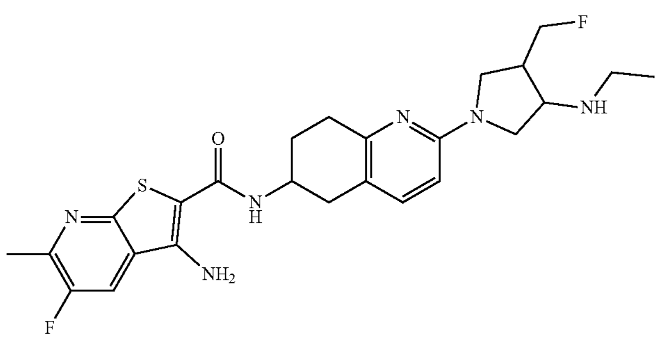 [SMILES: CCNC1CN(c2ccc3c(n2)CCC(NC(=O)c2sc4nc(C)c(F)cc4c2N)C3)CC1CF] | 3-amino-N-{2-[3-(ethylamino)-4-(fluoromethyl)pyrrolidin-1-yl]-5,6,7,8-tetrahydroquinolin-6-yl}-5-fluoro-6-methylthieno[2,3-b]pyridine-2-carboxamide |
| 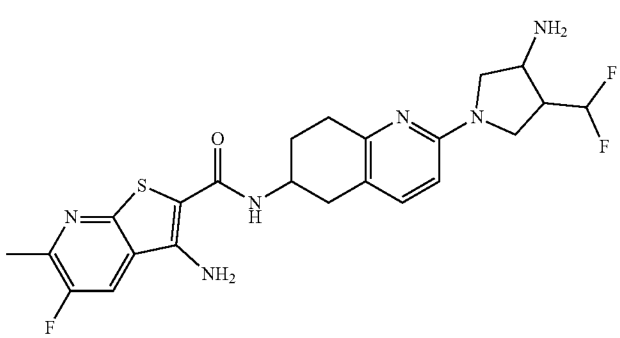 [SMILES: Cc1nc2sc(C(=O)NC3CCc4nc(N5CC(N)C(C(F)F)C5)ccc4C3)c(N)c2cc1F] | 3-amino-N-{2-[3-amino-4-(difluoromethyl)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 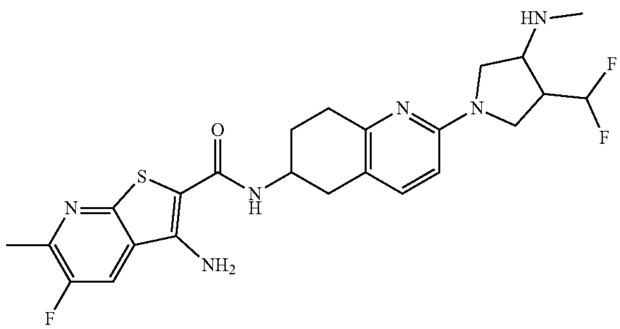 [SMILES: CNC1CN(c2ccc3c(n2)CCC(NC(=O)c2sc4nc(C)c(F)cc4c2N)C3)CC1C(F)F] | 3-amino-N-{2-[3-(difluoromethyl)-4-(methylamino)pyrrolidin-1-yl]-5,6,7,8-tetrahydroquinolin-6-yl}-5-fluoro-6-methylthieno[2,3-b]pyridine-2-carboxamide |
| 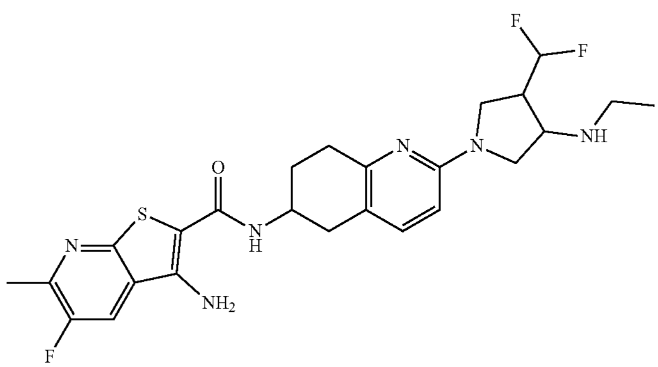 [SMILES: CCNC1CN(c2ccc3c(n2)CCC(NC(=O)c2sc4nc(C)c(F)cc4c2N)C3)CC1C(F)F] | 3-amino-N-{2-[3-(difluoromethyl)-4-(ethylamino)pyrrolidin-1-yl]-5,6,7,8-tetrahydroquinolin-6-yl}-5-fluoro-6-methylthieno[2,3-b]pyridine-2-carboxamide |
| 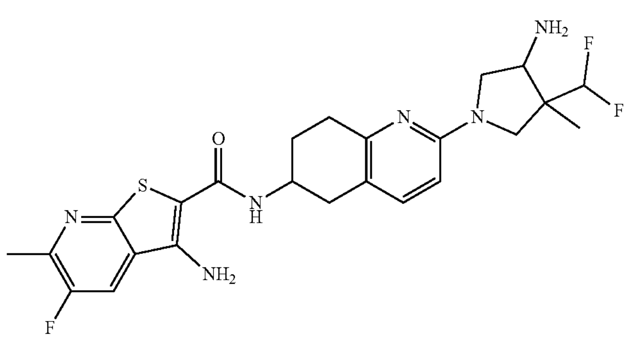 [SMILES: Cc1nc2sc(C(=O)NC3CCc4nc(N5CC(N)C(C)(C(F)F)C5)ccc4C3)c(N)c2cc1F] | 3-amino-N-{2-[4-amino-3-(difluoromethyl)-3-methylpyrrolidin-1-yl]-5,6,7,8-tetrahydroquinolin-6-yl}-5-fluoro-6-methylthieno[2,3-b]pyridine-2-carboxamide |
| 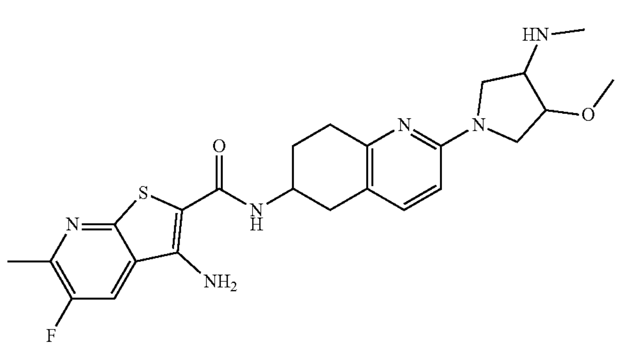 | 3-amino-5-fluoro-N-{2-[3-methoxy-4-(methylamino)pyrrolidin-1-yl]-5,6,7,8-tetrahydroquinolin-6-yl}-6-methylthieno[2,3-b]pyridine-2-carboxamide |

TABLE 27-continued

| Structure | Chemical Name |
|---|---|
| 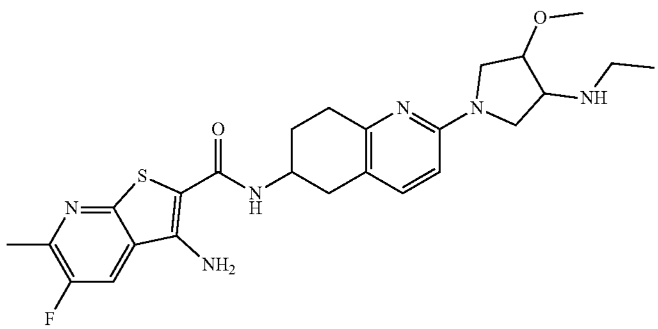 [SMILES: CCNC1CN(c2ccc3c(n2)CCC(NC(=O)c2sc4nc(C)c(F)cc4c2N)C3)CC1OC] | 3-amino-N-{2-[3-(ethylamino)-4-methoxypyrrolidin-1-yl]-5,6,7,8-tetrahydroquinolin-6-yl}-5-fluoro-6-methylthieno[2,3-b]pyridine-2-carboxamide |
| 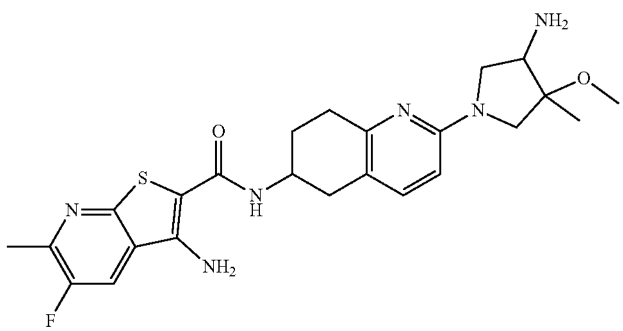 | 3-amino-N-[2-(4-amino-3-methoxy-3-methylpyrrolidin-1-yl)-5,6,7,8-tetrahydroquinolin-6-yl]-5-fluoro-6-methylthieno[2,3-b]pyridine-2-carboxamide |
| 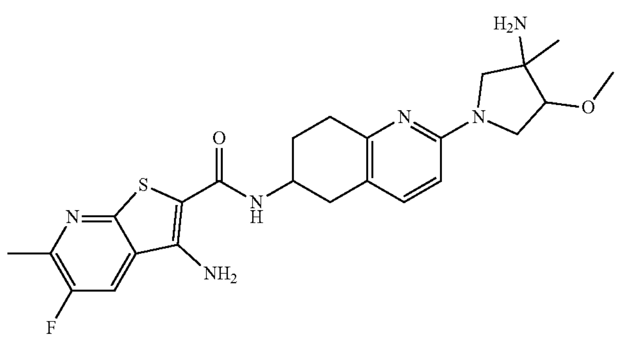 | 3-amino-N-[2-(3-amino-4-methoxy-3-methylpyrrolidin-1-yl)-5,6,7,8-tetrahydroquinolin-6-yl]-5-fluoro-6-methylthieno[2,3-b]pyridine-2-carboxamide |
| 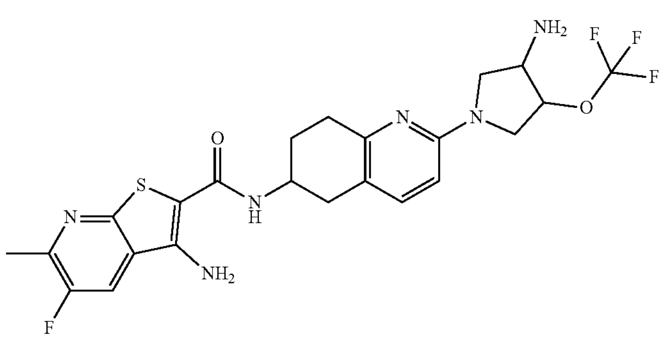 [SMILES: Cc1nc2sc(C(=O)NC3CCc4nc(N5CC(N)C(OC(F)(F)F)C5)ccc4C3)c(N)c2cc1F] | 3-amino-N-{2-[3-amino-4-(trifluoromethoxy)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 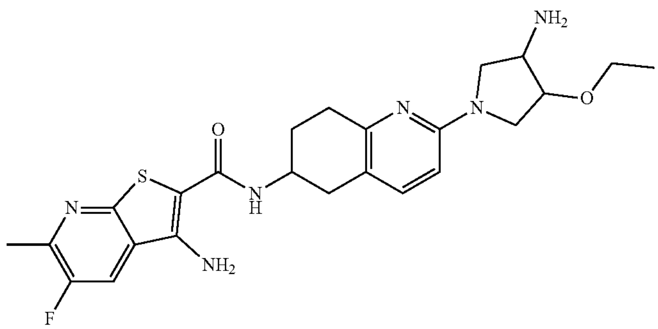 [SMILES: CCOC1CN(c2ccc3c(n2)CCC(NC(=O)c2sc4nc(C)c(F)cc4c2N)C3)CC1N] | 3-amino-N-[2-(3-amino-4-ethoxypyrrolidin-1-yl)-5,6,7,8-tetrahydroquinolin-6-yl]-5-fluoro-6-methylthieno[2,3-b]pyridine-2-carboxamide |
| 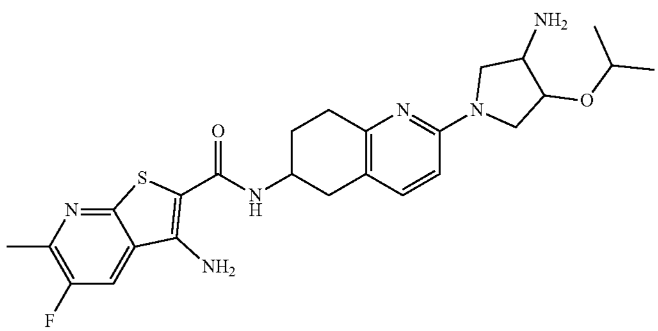 [SMILES: Cc1nc2sc(C(=O)NC3CCc4nc(N5CC(N)C(OC(C)C)C5)ccc4C3)c(N)c2cc1F] | 3-amino-N-{2-[3-amino-4-(propan-2-yloxy)pyrrolidin-1-yl]-5,6,7,8-tetrahydroquinolin-6-yl}-5-fluoro-6-methylthieno[2,3-b]pyridine-2-carboxamide |
| 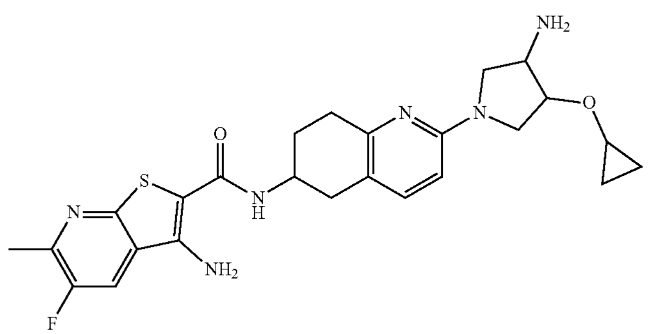 [SMILES: Cc1nc2sc(C(=O)NC3CCc4nc(N5CC(N)C(OC6CC6)C5)ccc4C3)c(N)c2cc1F] | 3-amino-N-[2-(3-amino-4-cyclopropoxypyrrolidin-1-yl)-5,6,7,8-tetrahydroquinolin-6-yl]-5-fluoro-6-methylthieno[2,3-b]pyridine-2-carboxamide |
| 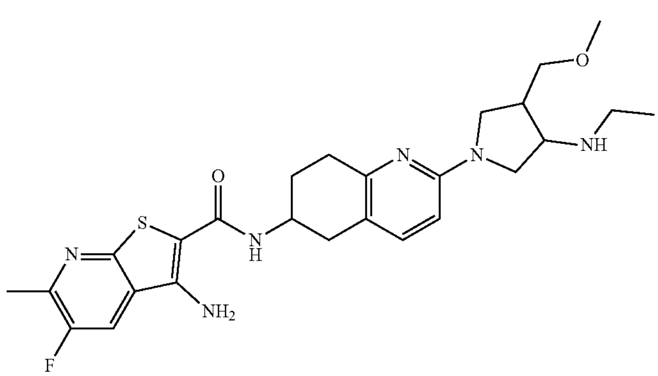 [SMILES: CCNC1CN(c2ccc3c(n2)CCC(NC(=O)c2sc4nc(C)c(F)cc4c2N)C3)CC1COC] | 3-amino-N-{2-[3-(ethylamino)-4-(methoxymethyl)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 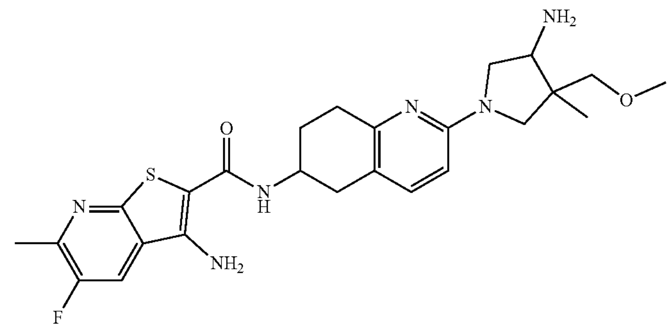 | 3-amino-N-{2-[4-amino-3-(methoxymethyl)-3-methylpyrrolidin-1-yl]-5,6,7,8-tetrahydroquinolin-6-yl}-5-fluoro-6-methylthieno[2,3-b]pyridine-2-carboxamide |
| 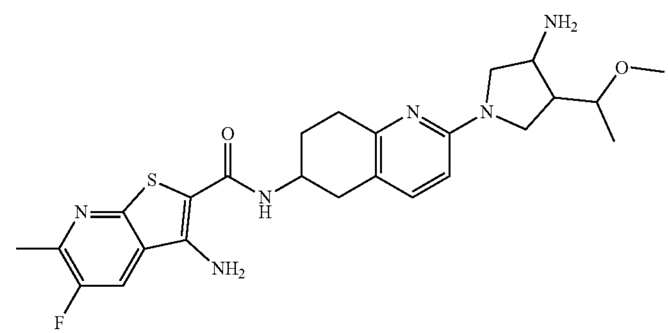 | 3-amino-N-{2-[3-amino-4-(1-methoxyethyl)pyrrolidin-1-yl]-5,6,7,8-tetrahydroquinolin-6-yl}-5-fluoro-6-methylthieno[2,3-b]pyridine-2-carboxamide |
| 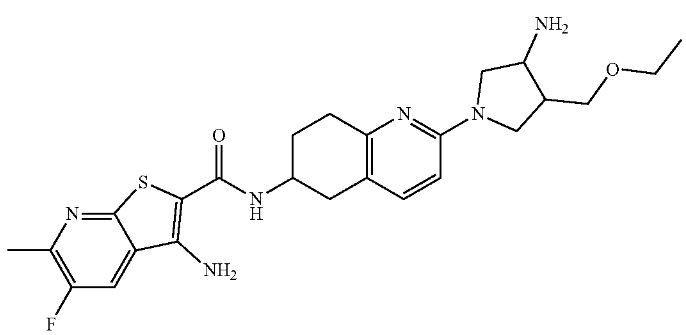 [SMILES: CCOCC1CN(c2ccc3c(n2)CCC(NC(=O)c2sc4nc(C)c(F)cc4c2N)C3)CC1N] | 3-amino-N-{2-[3-amino-4-(ethoxymethyl)pyrrolidin-1-yl]-5,6,7,8-tetrahydroquinolin-6-yl}-5-fluoro-6-methylthieno[2,3-b]pyridine-2-carboxamide |
| 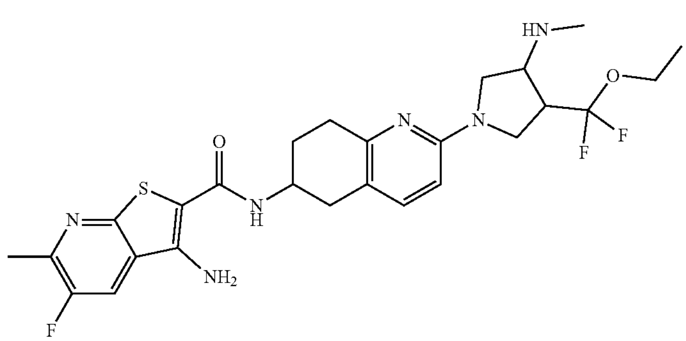 [SMILES: CCOC(F)(F)C1CN(c2ccc3c(n2)CCC(NC(=O)c2sc4nc(C)c(F)cc4c2N)C3)CC1NC] | 3-amino-N-{2-[3-(1,1-difluoro-2-methoxyethyl)-4-(methylamino)pyrrolidin-1-yl]-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 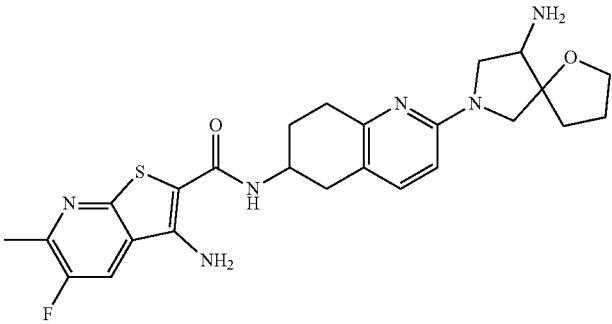 [SMILES: Cc1nc2sc(C(=O)NC3CCc4nc(N5CC(N)C6(CCCO6)C5)ccc4C3)c(N)c2cc1F] | 3-amino-N-(2-{9-amino-1-oxa-7-azaspiro[4.4]nonan-7-yl}-5,6,7,8-tetrahydroquinolin-6-yl)-5-fluoro-6-methylthieno[2,3-b]pyridine-2-carboxamide |
| 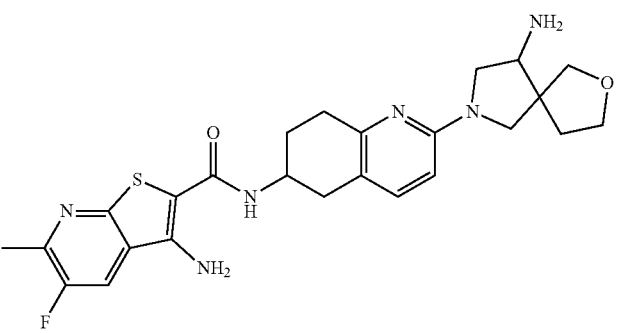 [SMILES: Cc1nc2sc(C(=O)NC3CCc4nc(N5CC(N)C6(CCOC6)C5)ccc4C3)c(N)c2cc1F] | 3-amino-N-(2-{9-amino-2-oxa-7-azaspiro[4.4]nonan-7-yl}-5,6,7,8-tetrahydroquinolin-6-yl)-5-fluoro-6-methylthieno[2,3-b]pyridine-2-carboxamide |
| 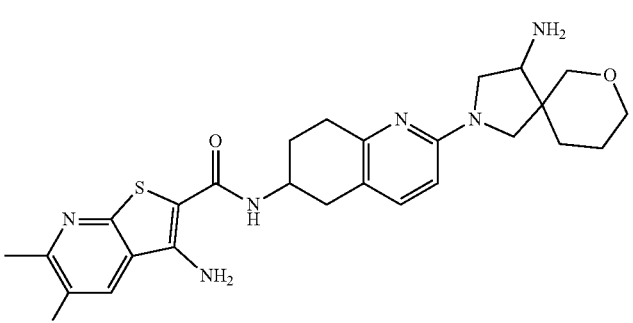 | 3-amino-N-(2-{4-amino-7-oxa-2-azaspiro[4.5]decan-2-yl}-5,6,7,8-tetrahydroquinolin-6-yl)-5-fluoro-6-methylthieno[2,3-b]pyridine-2-carboxamide |
| 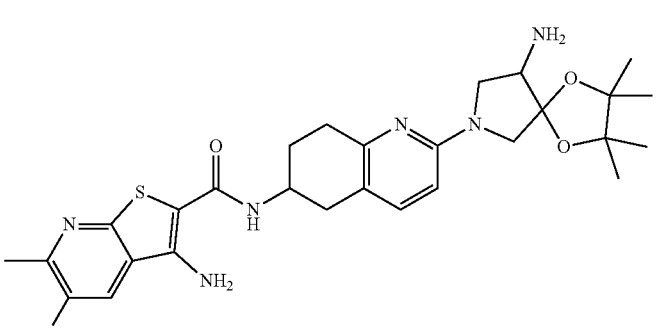 | 3-amino-N-(2-{9-amino-2,2,3,3-tetramethyl-1,4-dioxa-7-azaspiro[4.4]nonan-7-yl}-5,6,7,8-tetrahydroquinolin-6-yl)-5-fluoro-6-methylthieno[2,3-b]pyridine-2-carboxamide |
| 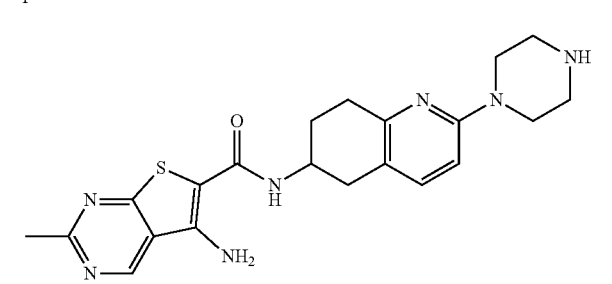 | 5-amino-2-methyl-N-[2-(piperazin-1-yl)-5,6,7,8-tetrahydroquinolin-6-yl]thieno[2,3-d]pyrimidine-6-carboxamide |

| Structure | Chemical Name |
|---|---|
| 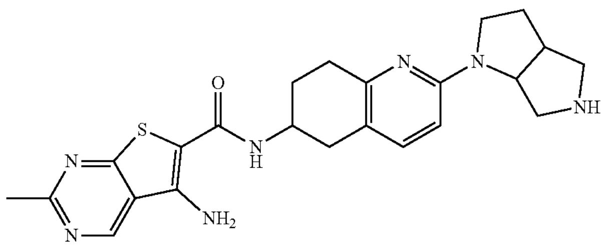 [SMILES: Cc1ncc2c(N)c(C(=O)NC3CCc4nc(N5CCC6CNCC65)ccc4C3)sc2n1] | 5-amino-2-methyl-N-(2-{octahydropyrrolo[2,3-c]pyrrol-1-yl}-5,6,7,8-tetrahydroquinolin-6-yl)thieno[2,3-d]pyrimidine-6-carboxamide |
| 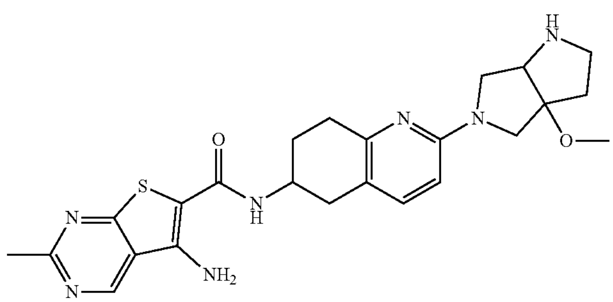 | N-(2-{3a-methoxy-octahydropyrrolo[3,4-b]pyrrol-5-yl}-5,6,7,8-tetrahydroquinolin-6-yl)-5-amino-2-methylthieno[2,3-d]pyrimidine-6-carboxamide |
| 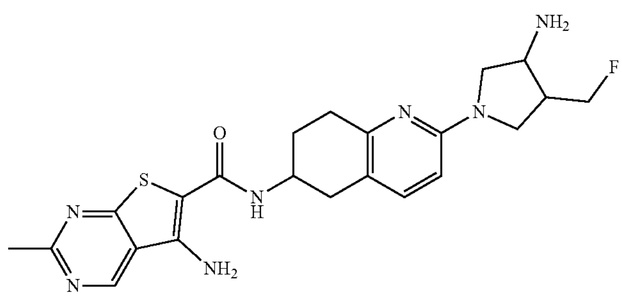 [SMILES: Cc1ncc2c(N)c(C(=O)NC3CCc4nc(N5CC(N)C(CF)C5)ccc4C3)sc2n1] | 5-amino-N-{2-[3-amino-4-(fluoromethyl)pyrrolidin-1-yl]-5,6,7,8-tetrahydroquinolin-6-yl}-2-methylthieno[2,3-d]pyrimidine-6-carboxamide |
| 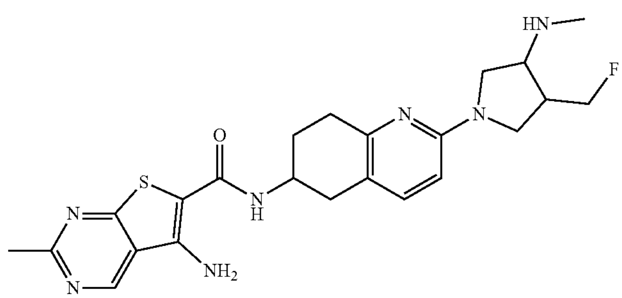 [SMILES: CNC1CN(c2ccc3c(n2)CCC(NC(=O)c2sc4nc(C)ncc4c2N)C3)CC1CF] | 5-amino-N-{2-[3-(fluoromethyl)-4-(methylamino)pyrrolidin-1-yl]-5,6,7,8-tetrahydroquinolin-6-yl}-2-methylthieno[2,3-d]pyrimidine-6-carboxamide |
| 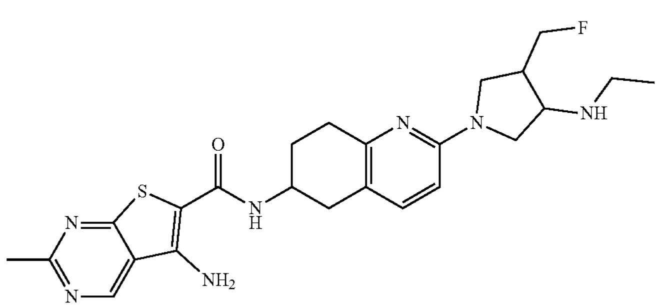 [SMILES: CCNC1CN(c2ccc3c(n2)CCC(NC(=O)c2sc4nc(C)ncc4c2N)C3)CC1CF] | 5-amino-N-{2-[3-(ethylamino)-4-(fluoromethyl)pyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 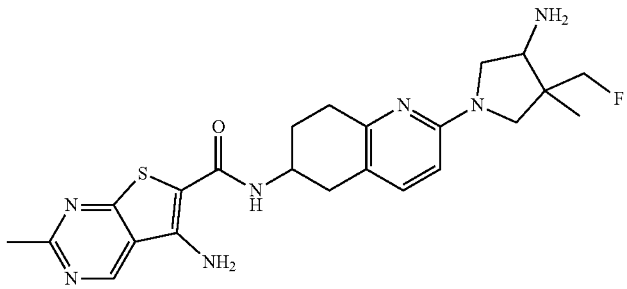 [SMILES: Cc1ncc2c(N)c(C(=O)NC3CCc4nc(N5CC(N)C(C)(CF)C5)ccc4C3)sc2n1] | 5-amino-N-{2-[4-amino-3-(fluoromethyl)-3-methylpyrrolidin-1-yl]-5,6,7,8-tetrahydroquinolin-6-yl}-2-methylthieno[2,3-d]pyrimidine-6-carboxamide |
| 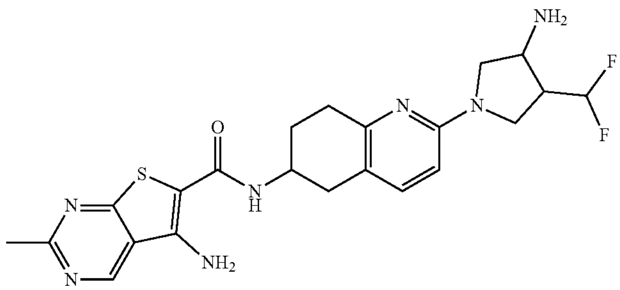 | 5-amino-N-{2-[3-amino-4-(difluoromethyl)pyrrolidin-1-yl]-5,6,7,8-tetrahydroquinolin-6-yl}-2-methylthieno[2,3-d]pyrimidine-6-carboxamide |
| 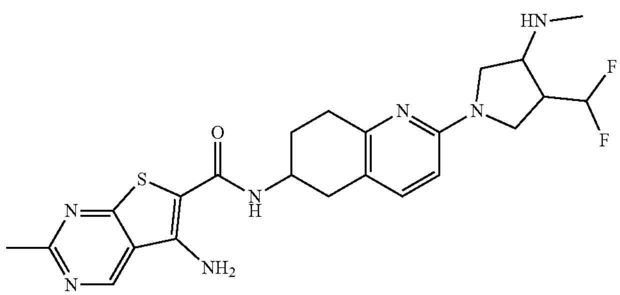 | 5-amino-N-{2-[3-(difluoromethyl)-4-(methylamino)pyrrolidin-1-yl]-5,6,7,8-tetrahydroquinolin-6-yl}-2-methylthieno[2,3-d]pyrimidine-6-carboxamide |
| 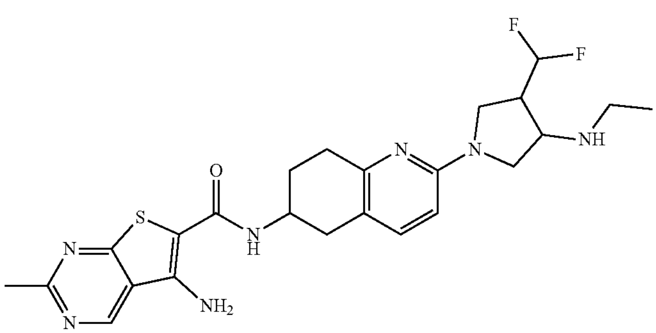 [SMILES: CCNC1CN(c2ccc3c(n2)CCC(NC(=O)c2sc4nc(C)ncc4c2N)C3)CC1C(F)F] | 5-amino-N-{2-[3-(difluoromethyl)-4-(ethylamino)pyrrolidin-1-yl]-5,6,7,8-tetrahydroquinolin-6-yl}-2-methylthieno[2,3-d]pyrimidine-6-carboxamide |
| 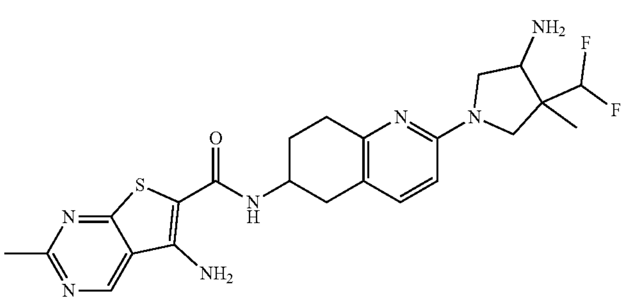 [SMILES: Cc1ncc2c(N)c(C(=O)NC3CCc4nc(N5CC(N)C(C)(C(F)F)C5)ccc4C3)sc2n1] | 5-amino-N-{2-[4-amino-3-(difluoromethyl)-3-methylpyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 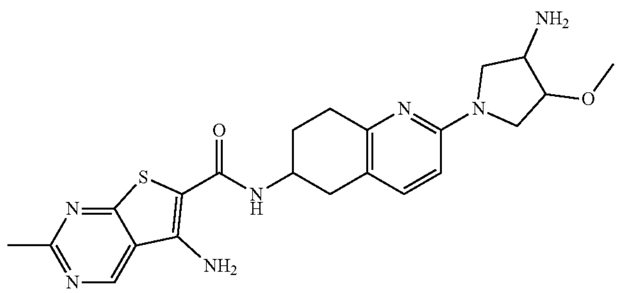 | 5-amino-N-[2-(3-amino-4-methoxypyrrolidin-1-yl)-5,6,7,8-tetrahydroquinolin-6-yl]-2-methylthieno[2,3-d]pyrimidine-6-carboxamide |
| 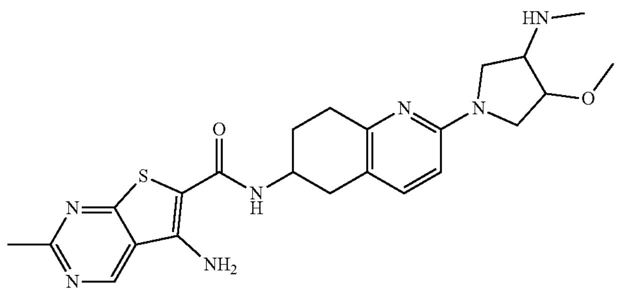 | 5-amino-N-{2-[3-methoxy-4-(methylamino)pyrrolidin-1-yl]-5,6,7,8-tetrahydroquinolin-6-yl}-2-methylthieno[2,3-d]pyrimidine-6-carboxamide |
| 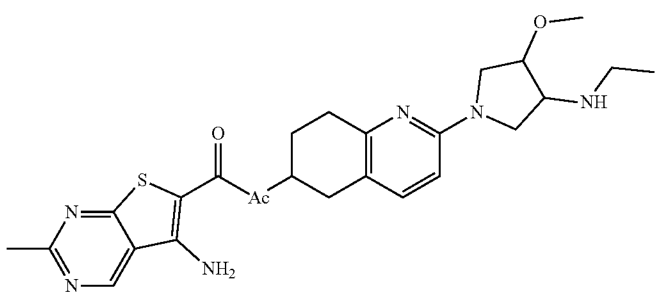 | 5-amino-N-{2-[3-(ethylamino)-4-methoxypyrrolidin-1-yl]-5,6,7,8-tetrahydroquinolin-6-yl}-2-methylthieno[2,3-d]pyrimidine-6-carboxamide |
| 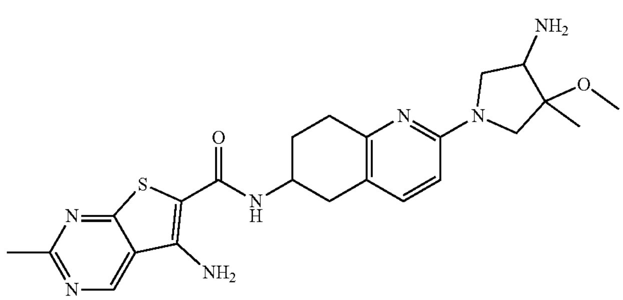 | 5-amino-N-[2-(4-amino-3-methoxy-3-methylpyrrolidin-1-yl)-5,6,7,8-tetrahydroquinolin-6-yl]-2-methylthieno[2,3-d]pyrimidine-6-carboxamide |
| 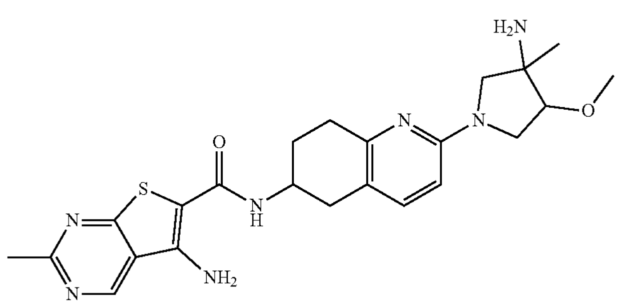 | 5-amino-N-[2-(3-amino-4-methoxy-3-methylpyrrolidin-1-yl)-5,6,7,8-tetrahydroquinolin-6-yl]-2-methylthieno[2,3-d]pyrimidine-6-carboxamide |

TABLE 27-continued

| Structure | Chemical Name |
|---|---|
| 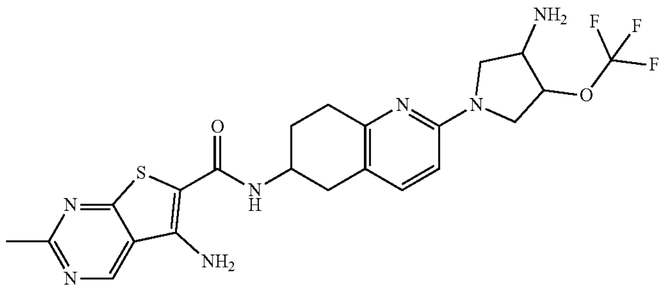 [SMILES: Cc1ncc2c(N)c(C(=O)NC3CCc4nc(N5CC(N)C(OC(F)(F)F)C5)ccc4C3)sc2n1] | 5-amino-N-{2-[3-amino-4-(trifluoromethoxy)pyrrolidin-1-yl]-5,6,7,8-tetrahydroquinolin-6-yl}-2-methylthieno[2,3-d]pyrimidine-6-carboxamide |
| 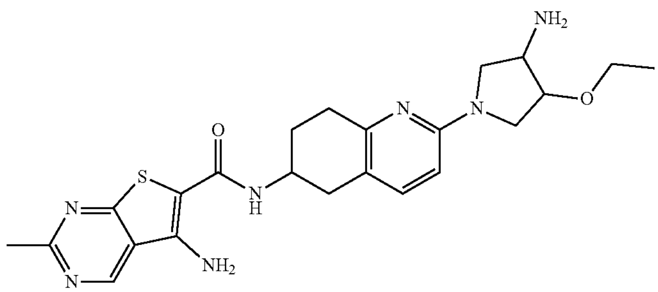 [SMILES: CCOC1CN(c2ccc3c(n2)CCC(NC(=O)c2sc4nc(C)ncc4c2N)C3)CC1N] | 5-amino-N-[2-(3-amino-4-ethoxypyrrolidin-1-yl)-5,6,7,8-tetrahydroquinolin-6-yl]-2-methylthieno[2,3-d]pyrimidine-6-carboxamide |
| 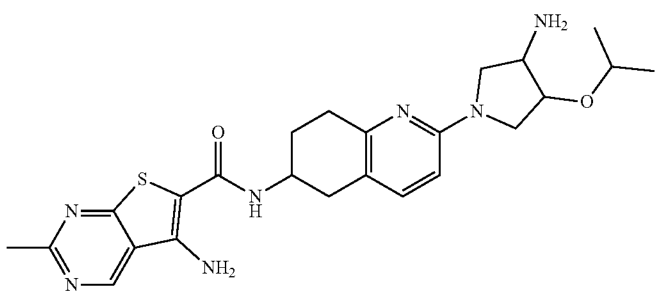 [SMILES: Cc1ncc2c(N)c(C(=O)NC3CCc4nc(N5CC(N)C(OC(C)C)C5)ccc4C3)sc2n1] | 5-amino-N-{2-[3-amino-4-(propan-2-yloxy)pyrrolidin-1-yl]-5,6,7,8-tetrahydroquinolin-6-yl}-2-methylthieno[2,3-d]pyrimidine-6-carboxamide |
| 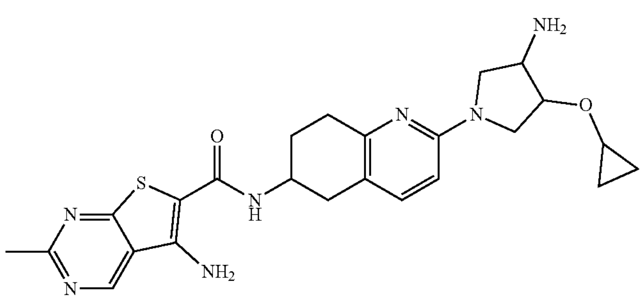 [SMILES: Cc1ncc2c(N)c(C(=O)NC3CCc4nc(N5CC(N)C(OC6CC6)C5)ccc4C3)sc2n1] | 5-amino-N-[2-(3-amino-4-cyclopropoxypyrrolidin-1-yl)-5,6,7,8-tetrahydroquinolin-6-yl]-2-methylthieno[2,3-d]pyrimidine-6-carboxamide |
| 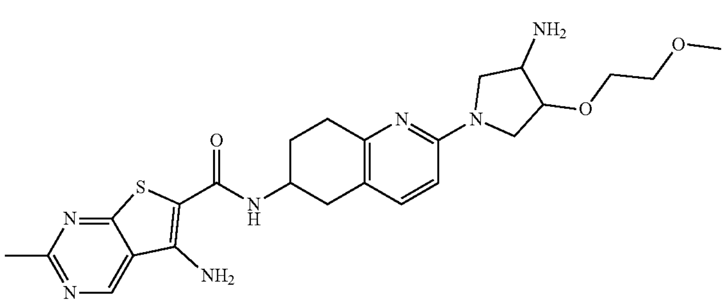 | 5-amino-N-{2-[3-amino-4-(2-methoxyethoxy)pyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 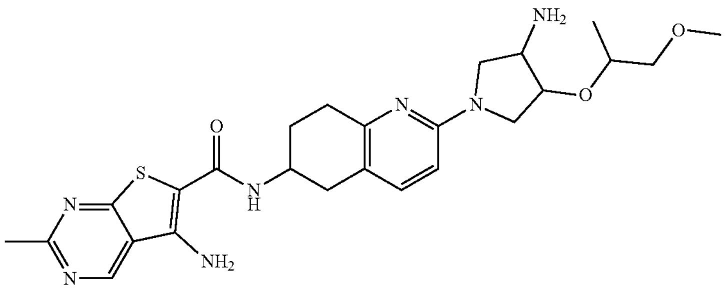 | 5-amino-N-(2-{3-amino-4-[(1-methoxypropan-2-yl)oxy]pyrrolidin-1-yl}-5,6,7,8-tetrahydroquinolin-6-yl)-2-methylthieno[2,3-d]pyrimidine-6-carboxamide |
| 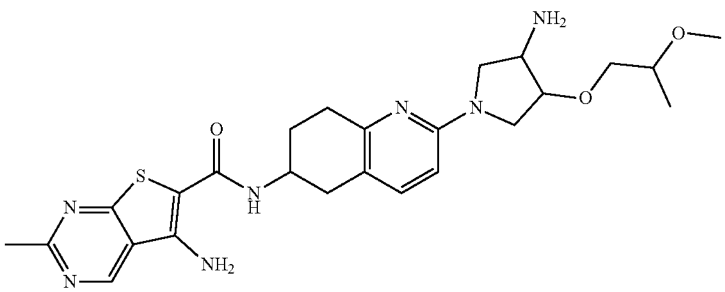 | 5-amino-N-{2-[3-amino-4-(2-methoxypropoxy)pyrrolidin-1-yl]-5,6,7,8-tetrahydroquinolin-6-yl}-2-methylthieno[2,3-d]pyrimidine-6-carboxamide |
| 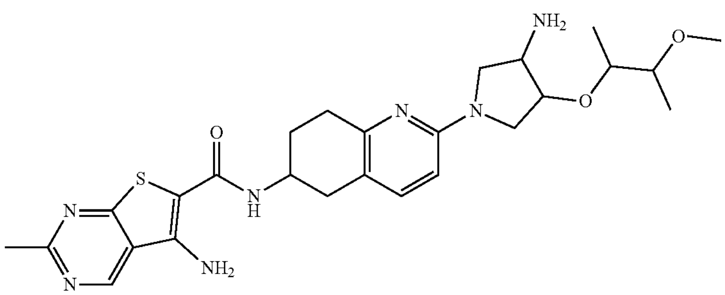 | 5-amino-N-(2-{3-amino-4-[(3-methoxybutan-2-yl)oxy]pyrrolidin-1-yl}-5,6,7,8-tetrahydroquinolin-6-yl)-2-methylthieno[2,3-d]pyrimidine-6-carboxamide |
| 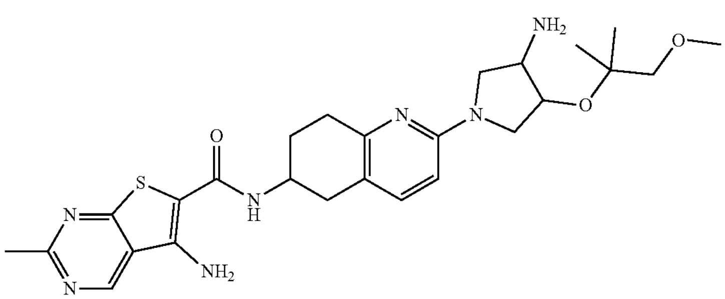 | 5-amino-N-(2-{3-amino-4-[(1-methoxy-2-methylpropan-2-yl)oxy]pyrrolidin-1-yl}-5,6,7,8-tetrahydroquinolin-6-yl)-2-methylthieno[2,3-d]pyrimidine-6-carboxamide |
| 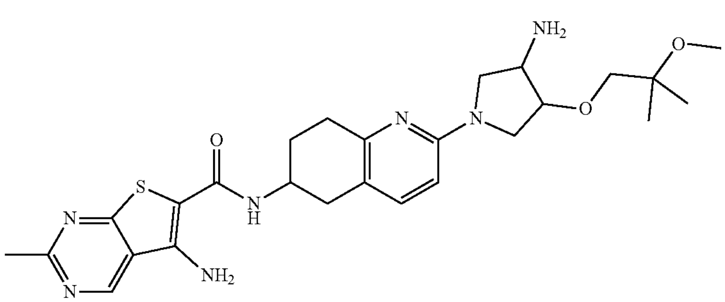 | 5-amino-N-{2-[3-amino-4-(2-methoxy-2-methylpropoxy)pyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 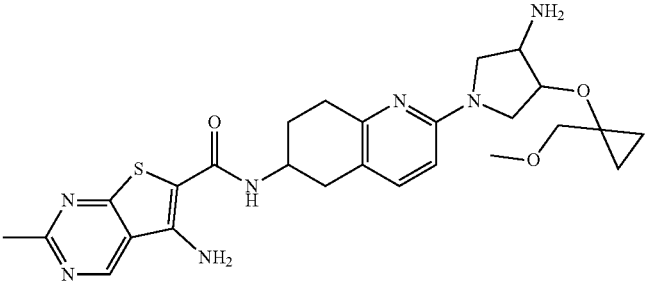 [SMILES: COCC1(OC2CN(c3ccc4c(n3)CCC(NC(=O)c3sc5nc(C)ncc5c3N)C4)CC2N)CC1] | 5-amino-N-(2-{3-amino-4-[1-(methoxymethyl)cyclopropoxy]pyrrolidin-1-yl}-5,6,7,8-tetrahydroquinolin-6-yl)-2-methylthieno[2,3-d]pyrimidine-6-carboxamide |
| 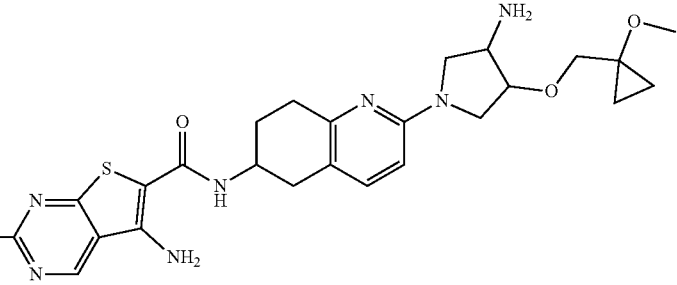 | 5-amino-N-(2-{3-amino-4-[(1-methoxycyclopropyl)methoxy]pyrrolidin-1-yl}-5,6,7,8-tetrahydroquinolin-6-yl)-2-methylthieno[2,3-d]pyrimidine-6-carboxamide |
| 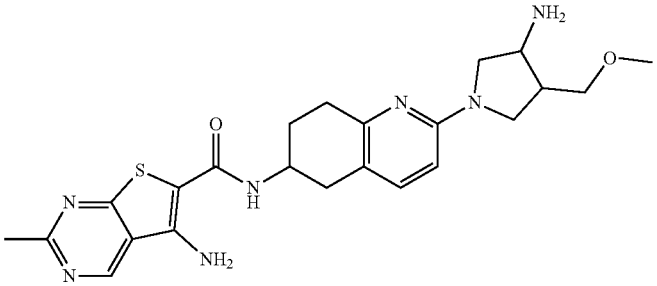 | 5-amino-N-{2-[3-amino-4-(methoxymethyl)pyrrolidin-1-yl]-5,6,7,8-tetrahydroquinolin-6-yl}-2-methylthieno[2,3-d]pyrimidine-6-carboxamide |
| 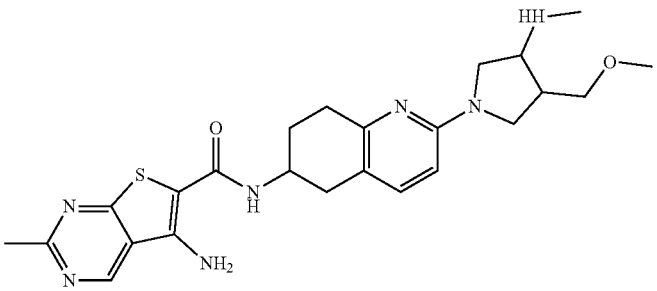 | 5-amino-N-{2-[3-(methoxymethyl)-4-(methylamino)pyrrolidin-1-yl]-5,6,7,8-tetrahydroquinolin-6-yl}-2-methylthieno[2,3-d]pyrimidine-6-carboxamide |
| 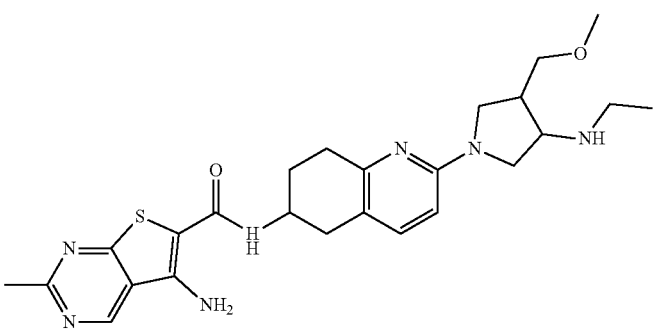 | 5-amino-N-{2-[3-(ethylamino)-4-(methoxymethyl)pyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 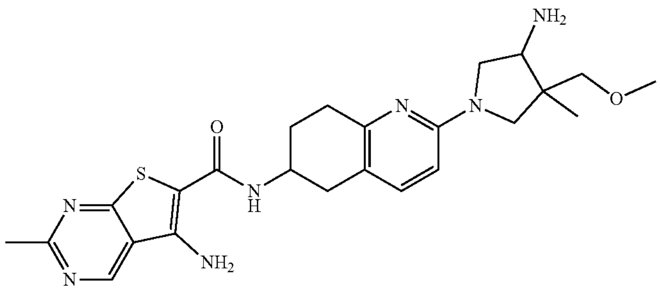 | 5-amino-N-{2-[4-amino-3-(methoxymethyl)-3-methylpyrrolidin-1-yl]-5,6,7,8-tetrahydroquinolin-6-yl}-2-methylthieno[2,3-d]pyrimidine-6-carboxamide |
| 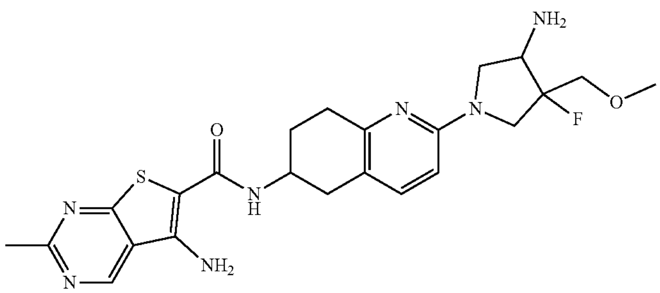 | 5-amino-N-{2-[4-amino-3-fluoro-3-(methoxymethyl)pyrrolidin-1-yl]-5,6,7,8-tetrahydroquinolin-6-yl}-2-methylthieno[2,3-d]pyrimidine-6-carboxamide |
| 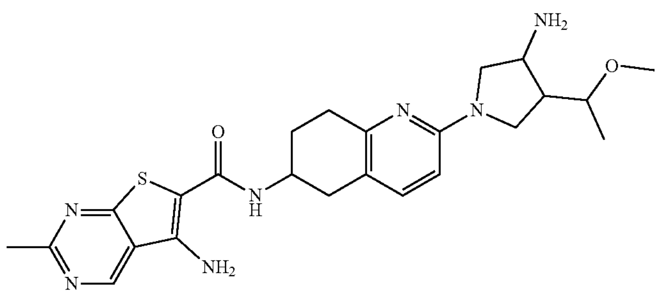 | 5-amino-N-{2-[3-amino-4-(1-methoxyethyl)pyrrolidin-1-yl]-5,6,7,8-tetrahydroquinolin-6-yl}-2-methylthieno[2,3-d]pyrimidine-6-carboxamide |
| 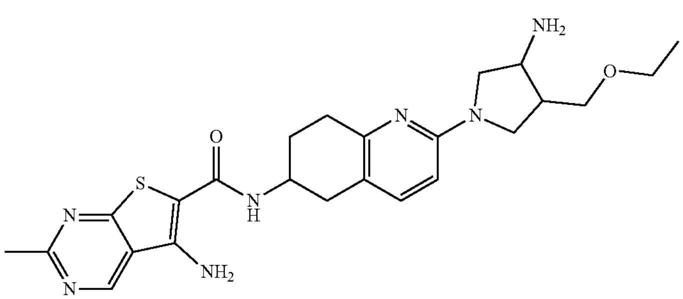 [SMILES: CCOCC1CN(c2ccc3c(n2)CCC(NC(=O)c2sc4nc(C)ncc4c2N)C3)CC1N] | 5-amino-N-{2-[3-amino-4-(ethoxymethyl)pyrrolidin-1-yl]-5,6,7,8-tetrahydroquinolin-6-yl}-2-methylthieno[2,3-d]pyrimidine-6-carboxamide |
| 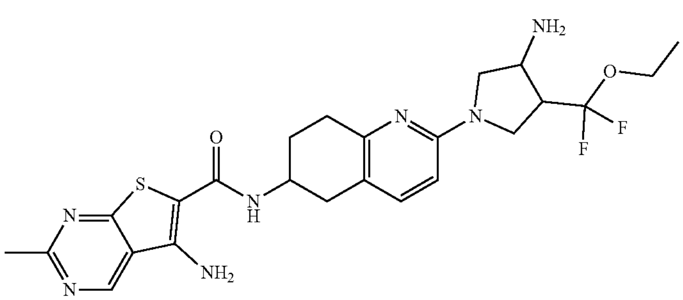 [SMILES: CCOC(F)(F)C1CN(c2ccc3c(n2)CCC(NC(=O)c2sc4nc(C)ncc4c2N)C3)CC1N] | 5-amino-N-{2-[3-amino-4-(1,1-difluoro-2-methoxyethyl)pyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 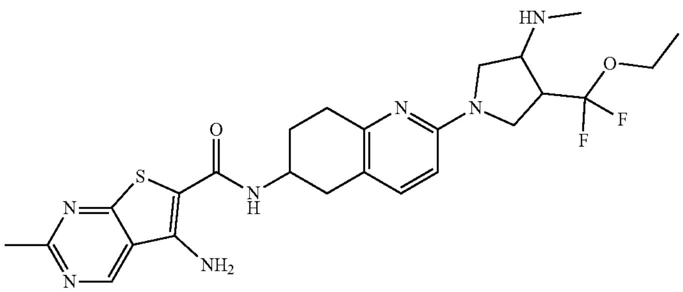 [SMILES: CCOC(F)(F)C1CN(c2ccc3c(n2)CCC(NC(=O)c2sc4nc(C)ncc4c2N)C3)CC1NC] | 5-amino-N-{2-[3-(1,1-difluoro-2-methoxyethyl)-4-(methylamino)pyrrolidin-1-yl]-5,6,7,8-tetrahydroquinolin-6-yl}-2-methylthieno[2,3-d]pyrimidine-6-carboxamide |
| 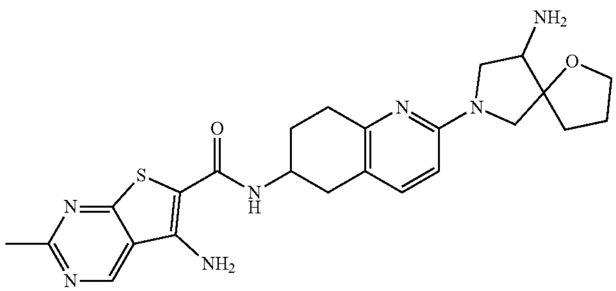 [SMILES: Cc1ncc2c(N)c(C(=O)NC3CCc4nc(N5CC(N)C6(CCCO6)C5)ccc4C3)sc2n1] | 5-amino-N-(2-{9-amino-1-oxa-7-azaspiro[4.4]nonan-7-yl}-5,6,7,8-tetrahydroquinolin-6-yl)-2-methylthieno[2,3-d]pyrimidine-6-carboxamide |
| 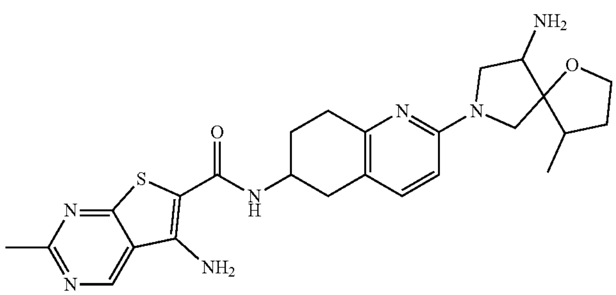 [SMILES: Cc1ncc2c(N)c(C(=O)NC3CCc4nc(N5CC(N)C6(C5)OCCC6C)ccc4C3)sc2n1] | 5-amino-N-(2-{9-amino-4-methyl-1-oxa-7-azaspiro[4.4]nonan-7-yl}-5,6,7,8-tetrahydroquinolin-6-yl)-2-methylthieno[2,3-d]pyrimidine-6-carboxamide |
| 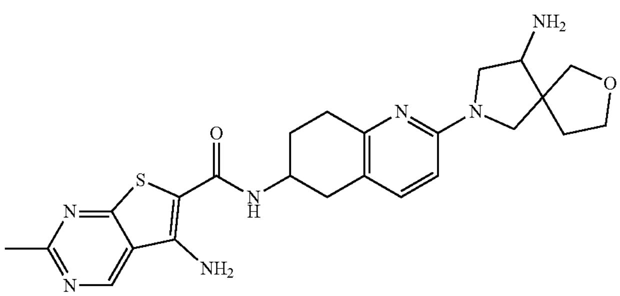 [SMILES: Cc1ncc2c(N)c(C(=O)NC3CCc4nc(N5CC(N)C6(CCOC6)C5)ccc4C3)sc2n1] | 5-amino-N-(2-{9-amino-2-oxa-7-azaspiro[4.4]nonan-7-yl}-5,6,7,8-tetrahydroquinolin-6-yl)-2-methylthieno[2,3-d]pyrimidine-6-carboxamide |
| 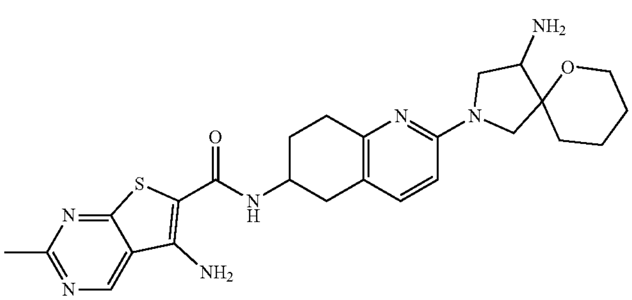 [SMILES: Cc1ncc2c(N)c(C(=O)NC3CCc4nc(N5CC(N)C6(CCCCO6)C5)ccc4C3)sc2n1] | 5-amino-N-(2-{4-amino-6-oxa-2-azaspiro[4.5]decan-2-yl}-5,6,7,8-tetrahydroquinolin-6-yl)-2-methylthieno[2,3-d]pyrimidine-6-carboxamide |

TABLE 27-continued

| Structure | Chemical Name |
|---|---|
| 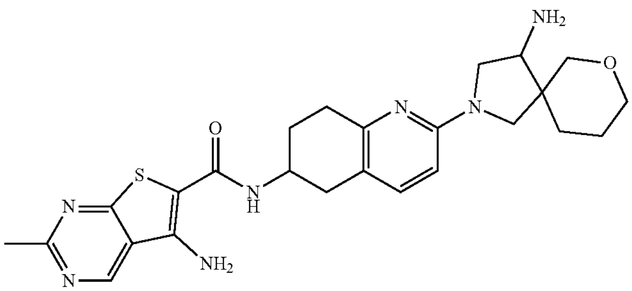 [SMILES: Cc1ncc2c(N)c(C(=O)NC3CCc4nc(N5CC(N)C6(CCCOC6)C5)ccc4C3)sc2n1] | 5-amino-N-(2-{4-amino-7-oxa-2-azaspiro[4.5]decan-2-yl}-5,6,7,8-tetrahydroquinolin-6-yl)-2-methylthieno[2,3-d]pyrimidine-6-carboxamide |
| 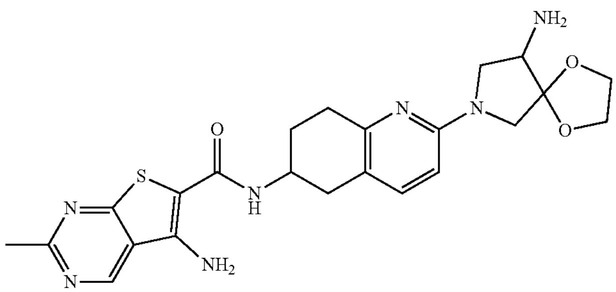 [SMILES: Cc1ncc2c(N)c(C(=O)NC3CCc4nc(N5CC(N)C6(C5)OCCO6)ccc4C3)sc2n1] | 5-amino-N-(2-{9-amino-1,4-dioxa-7-azaspiro[4.4]nonan-7-yl}-5,6,7,8-tetrahydroquinolin-6-yl)-2-methylthieno[2,3-d]pyrimidine-6-carboxamide |
| 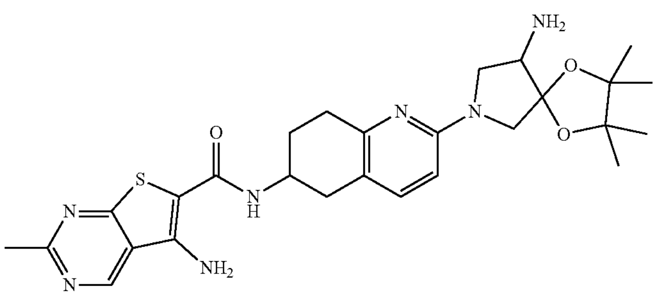 | 5-amino-N-(2-{9-amino-2,2,3,3-tetramethyl-1,4-dioxa-7-azaspiro[4.4]nonan-7-yl}-5,6,7,8-tetrahydroquinolin-6-yl)-2-methylthieno[2,3-d]pyrimidine-6-carboxamide |
| 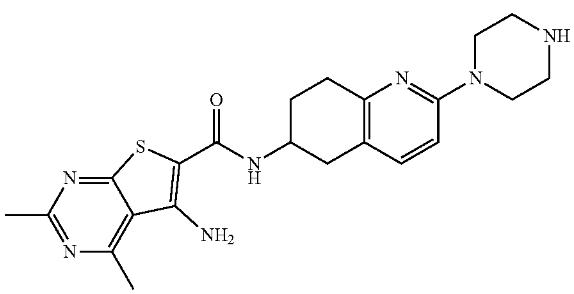 [SMILES: Cc1nc(C)c2c(N)c(C(=O)NC3CCc4nc(N5CCNCC5)ccc4C3)sc2n1] | 5-amino-2,4-dimethyl-N-[2-(piperazin-1-yl)-5,6,7,8-tetrahydroquinolin-6-yl]thieno[2,3-d]pyrimidine-6-carboxamide |
| 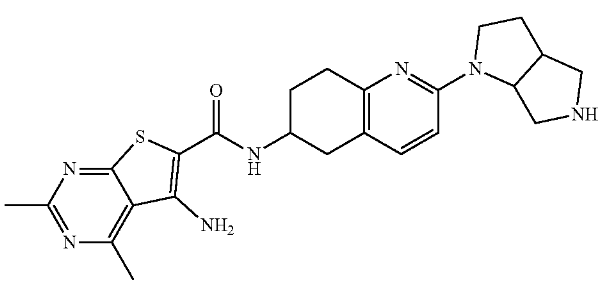 [SMILES: Cc1nc(C)c2c(N)c(C(=O)NC3CCc4nc(N5CCC6CNCC65)ccc4C3)sc2n1] | 5-amino-2,4-dimethyl-N-(2-{octahydropyrrolo[2,3-c]pyrrol-1-yl}-5,6,7,8-tetrahydroquinolin-6-yl)thieno[2,3-d]pyrimidine-6-carboxamide |

TABLE 27-continued

| Structure | Chemical Name |
|---|---|
| 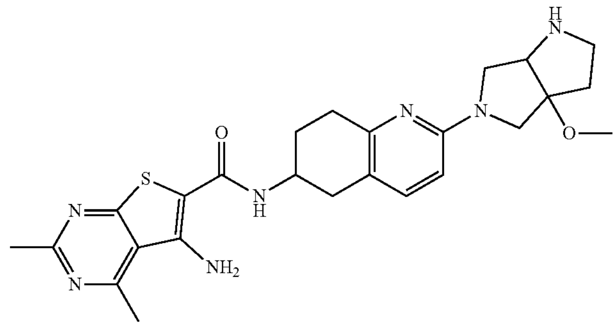 | N-(2-{3a-methoxy-octahydropyrrolo[3,4-b]pyrrol-5-yl}-5,6,7,8-tetrahydroquinolin-6-yl)-5-amino-2,4-dimethylthieno[2,3-d]pyrimidine-6-carboxamide |
| 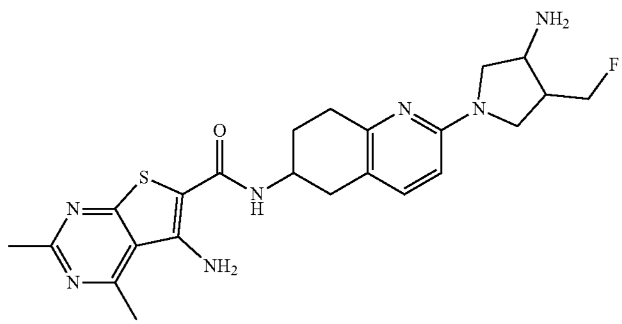 [SMILES: Cc1nc(C)c2c(N)c(C(=O)NC3CCc4nc(N5CC(N)C(CF)C5)ccc4C3)sc2n1] | 5-amino-N-{2-[3-amino-4-(fluoromethyl)pyrrolidin-1-yl]-5,6,7,8-tetrahydroquinolin-6-yl}-2,4-dimethylthieno[2,3-d]pyrimidine-6-carboxamide |
| 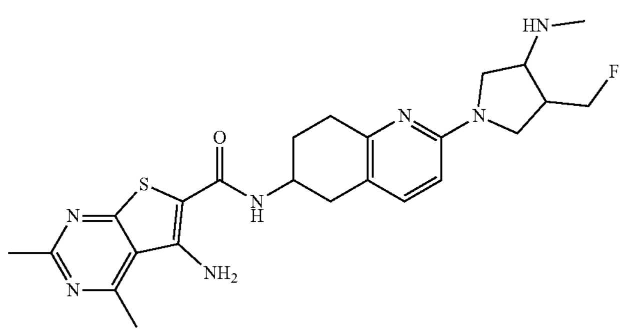 [SMILES: CNC1CN(c2ccc3c(n2)CCC(NC(=O)c2sc4nc(C)nc(C)c4c2N)C3)CC1CF] | 5-amino-N-{2-[3-(fluoromethyl)-4-(methylamino)pyrrolidin-1-yl]-5,6,7,8-tetrahydroquinolin-6-yl}-2,4-dimethylthieno[2,3-d]pyrimidine-6-carboxamide |
| 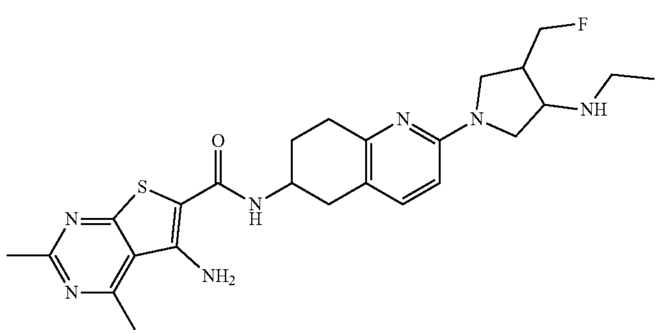 [SMILES: CCNC1CN(c2ccc3c(n2)CCC(NC(=O)c2sc4nc(C)nc(C)c4c2N)C3)CC1CF] | 5-amino-N-{2-[3-(ethylamino)-4-(fluoromethyl)pyrrolidin-1-yl]-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 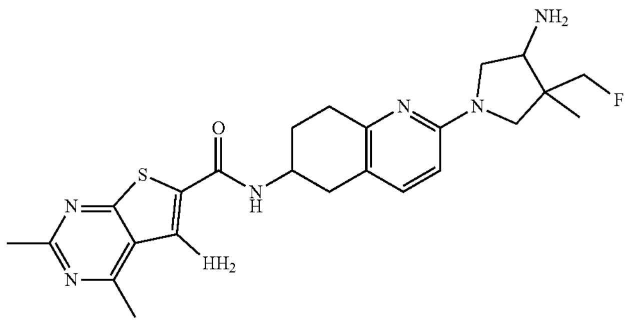 | 5-amino-N-{2-[4-amino-3-(fluoromethyl)-3-methylpyrrolidin-1-yl]-5,6,7,8-tetrahydroquinolin-6-yl}-2,4-dimethylthieno[2,3-d]pyrimidine-6-carboxamide |
| 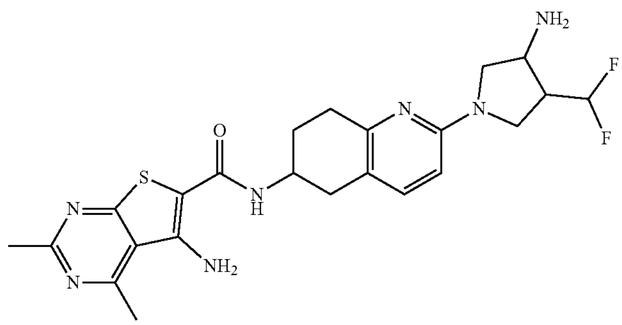 [SMILES: Cc1nc(C)c2c(N)c(C(=O)NC3CCc4nc(N5CC(N)C(C(F)F)C5)ccc4C3)sc2n1] | 5-amino-N-{2-[3-amino-4-(difluoromethyl)pyrrolidin-1-yl]-5,6,7,8-tetrahydroquinolin-6-yl}-2,4-dimethylthieno[2,3-d]pyrimidine-6-carboxamide |
| 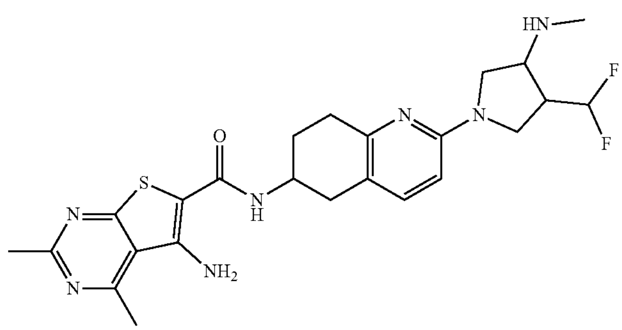 [SMILES: CNC1CN(c2ccc3c(n2)CCC(NC(=O)c2sc4nc(C)nc(C)c4c2N)C3)CC1C(F)F] | 5-amino-N-{2-[3-(difluoromethyl)-4-(methylamino)pyrrolidin-1-yl]-5,6,7,8-tetrahydroquinolin-6-yl}-2,4-dimethylthieno[2,3-d]pyrimidine-6-carboxamide |
| 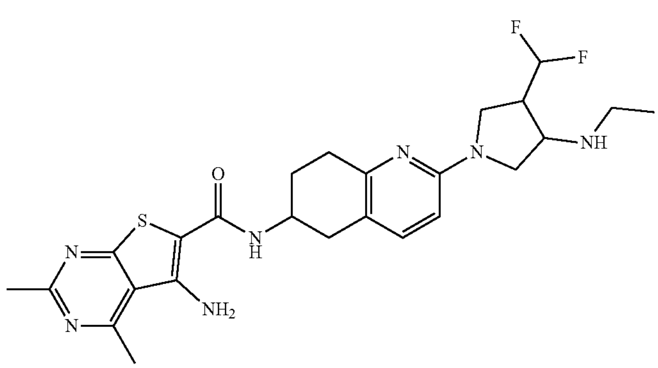 [SMILES: CCNC1CN(c2ccc3c(n2)CCC(NC(=O)c2sc4nc(C)nc(C)c4c2N)C3)CC1C(F)F] | 5-amino-N-{2-[3-(difluoromethyl)-4-(ethylamino)pyrrolidin-1-yl]-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 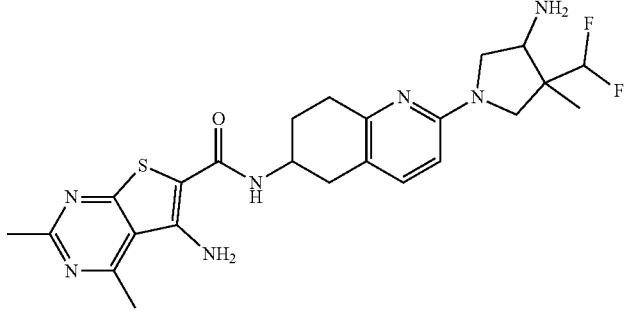 [SMILES: Cc1nc(C)c2c(N)c(C(=O)NC3CCc4nc(N5CC(N)C(C)(C(F)F)C5)ccc4C3)sc2n1] | 5-amino-N-{2-[4-amino-3-(difluoromethyl)-3-methylpyrrolidin-1-yl]-5,6,7,8-tetrahydroquinolin-6-yl}-2,4-dimethylthieno[2,3-d]pyrimidine-6-carboxamide |
| 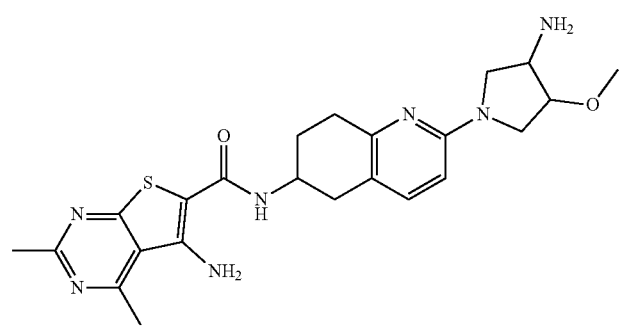 | 5-amino-N-[2-(3-amino-4-methoxypyrrolidin-1-yl)-5,6,7,8-tetrahydroquinolin-6-yl]-2,4-dimethylthieno[2,3-d]pyrimidine-6-carboxamide |
| 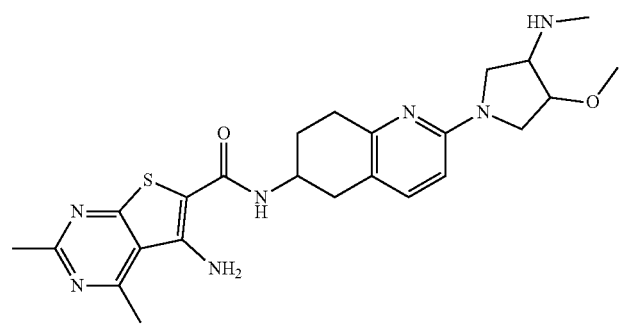 | 5-amino-N-{2-[3-methoxy-4-(methylamino)pyrrolidin-1-yl]-5,6,7,8-tetrahydroquinolin-6-yl}-2,4-dimethylthieno[2,3-d]pyrimidine-6-carboxamide |
| 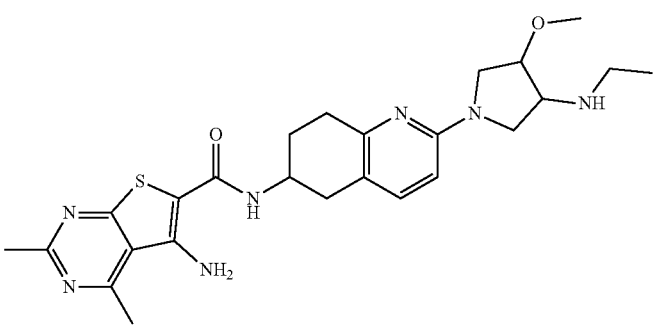 [SMILES: CCNC1CN(c2ccc3c(n2)CCC(NC(=O)c2sc4nc(C)nc(C)c4c2N)C3)CC1OC] | 5-amino-N-{2-[3-(ethylamino)-4-methoxypyrrolidin-1-yl]-5,6,7,8-tetrahydroquinolin-6-yl}-2,4-dimethylthieno[2,3-d]pyrimidine-6-carboxamide |
| 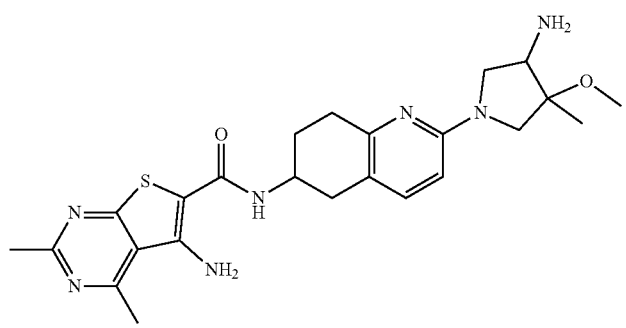 | 5-amino-N-[2-(4-amino-3-methoxy-3-methylpyrrolidin-1-yl)-5,6,7,8-tetrahydroquinolin-6-yl]-2,4-dimethylthieno[2,3-d]pyrimidine-6-carboxamide |

TABLE 27-continued

| Structure | Chemical Name |
|---|---|
| 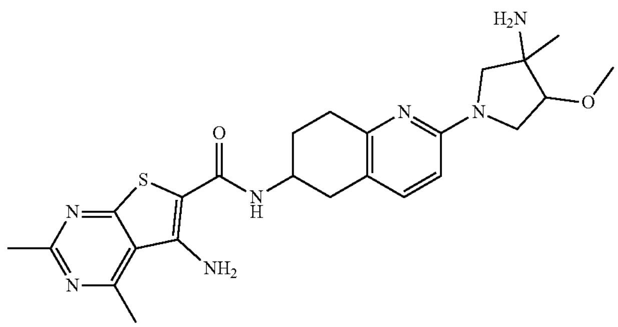 | 5-amino-N-[2-(3-amino-4-methoxy-3-methylpyrrolidin-1-yl)-5,6,7,8-tetrahydroquinolin-6-yl]-2,4-dimethylthieno[2,3-d]pyrimidine-6-carboxamide |
| 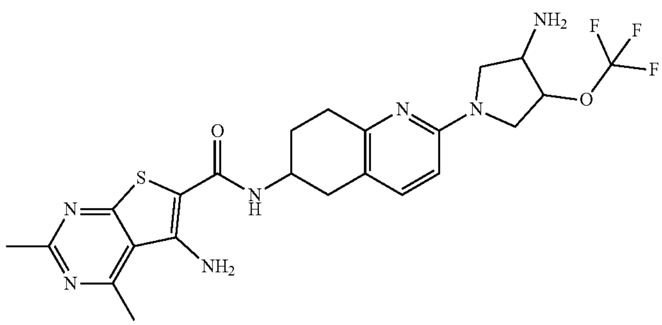 | 5-amino-N-{2-[3-amino-4-(trifluoromethoxy)pyrrolidin-1-yl]-5,6,7,8-tetrahydroquinolin-6-yl}-2,4-dimethylthieno[2,3-d]pyrimidine-6-carboxamide |
| 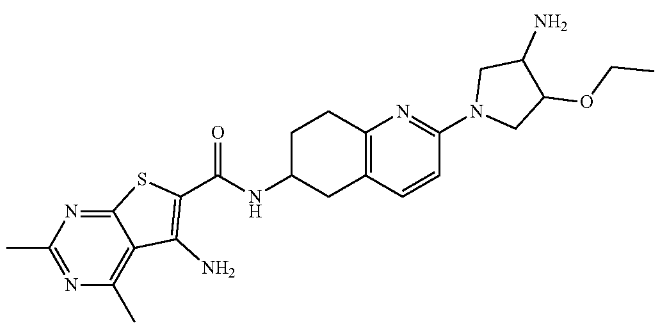 | 5-amino-N-[2-(3-amino-4-ethoxypyrrolidin-1-yl)-5,6,7,8-tetrahydroquinolin-6-yl]-2,4-dimethylthieno[2,3-d]pyrimidine-6-carboxamide |
| 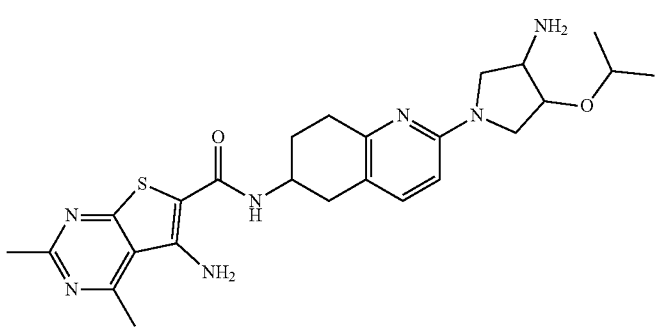 | 5-amino-N-{2-[3-amino-4-(propan-2-yloxy)pyrrolidin-1-yl]-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 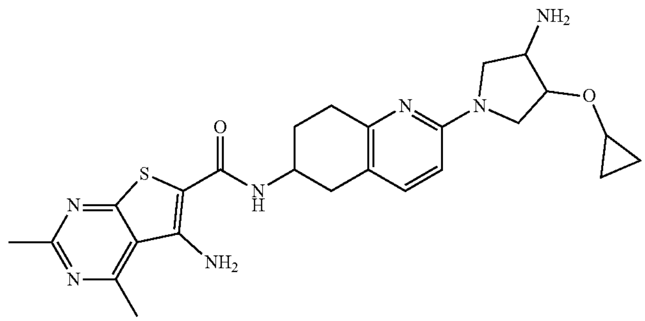 [SMILES: Cc1nc(C)c2c(N)c(C(=O)NC3CCc4nc(N5CC(N)C(OC6CC6)C5)ccc4C3)sc2n1] | 5-amino-N-[2-(3-amino-4-cyclopropoxypyrrolidin-1-yl)-5,6,7,8-tetrahydroquinolin-6-yl]-2,4-dimethylthieno[2,3-d]pyrimidine-6-carboxamide |
| 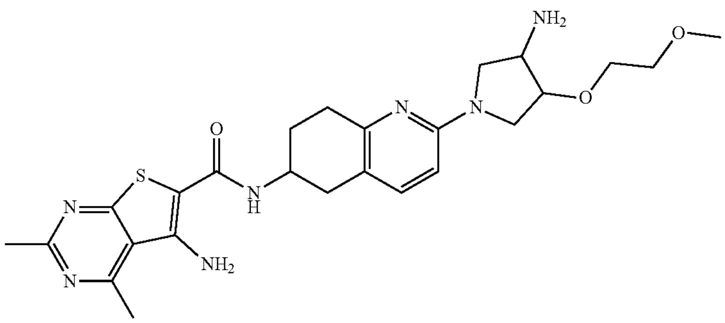 | 5-amino-N-{2-[3-amino-4-(2-methoxyethoxy)pyrrolidin-1-yl]-5,6,7,8-tetrahydroquinolin-6-yl}-2,4-dimethylthieno[2,3-d]pyrimidine-6-carboxamide |
| 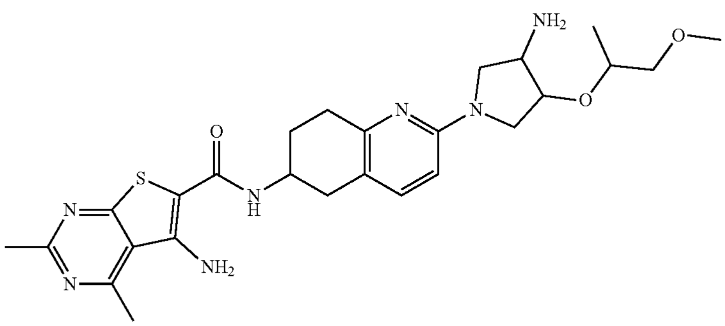 | 5-amino-N-(2-{3-amino-4-[(1-methoxypropan-2-yl)oxy]pyrrolidin-1-yl}-5,6,7,8-tetrahydroquinolin-6-yl)-2,4-dimethylthieno[2,3-d]pyrimidine-6-carboxamide |
| 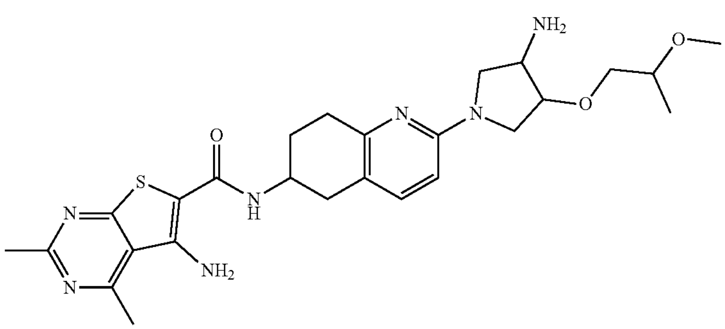 | 5-amino-N-{2-[3-amino-4-(2-methoxypropoxy)pyrrolidin-1-yl]-5,6,7,8-tetrahydroquinolin-6-yl}-2,4-dimethylthieno[2,3-d]pyrimidine-6-carboxamide |
| 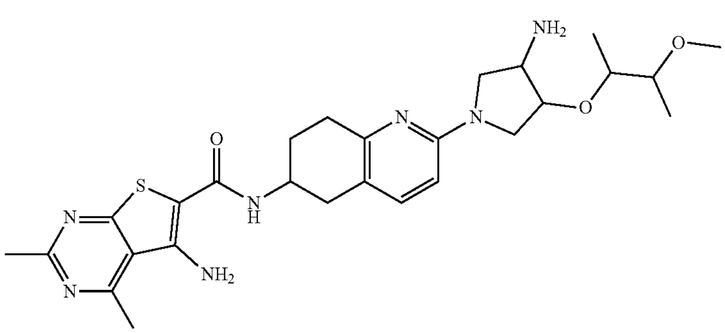 | 5-amino-N-(2-{3-amino-4-[(3-methoxybutan-2-yl)oxy]pyrrolidin-1-yl}-5,6,7,8-tetrahydroquinolin-6-yl)-2,4-dimethylthieno[2,3-d]pyrimidine-6-carboxamide |

TABLE 27-continued

| Structure | Chemical Name |
|---|---|
| 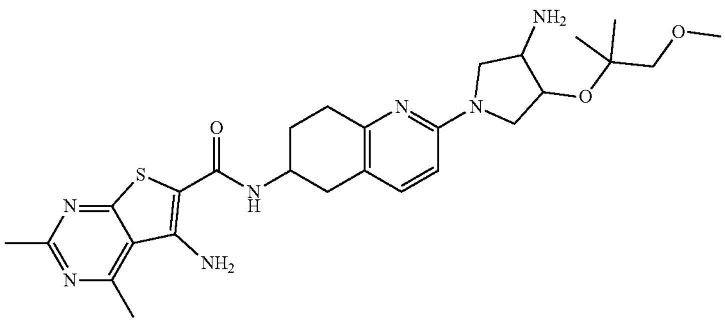 | 5-amino-N-(2-{3-amino-4-[(1-methoxy-2-methylpropan-2-yl)oxy]pyrrolidin-1-yl}-5,6,7,8-tetrahydroquinolin-6-yl)-2,4-dimethylthieno[2,3-d]pyrimidine-6-carboxamide |
| 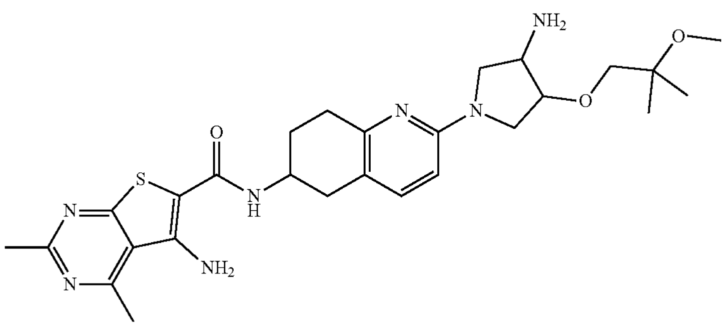 | 5-amino-N-{2-[3-amino-4-(2-methoxy-2-methylpropoxy)pyrrolidin-1-yl]-5,6,7,8-tetrahydroquinolin-6-yl}-2,4-dimethylthieno[2,3-d]pyrimidine-6-carboxamide |
| 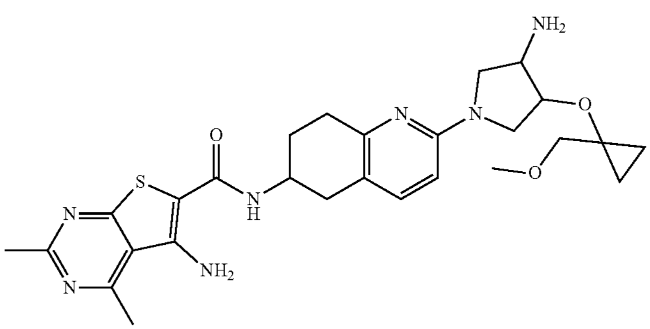 [SMILES: COCC1(OC2CN(c3ccc4c(n3)CCC(NC(=O)c3sc5nc(C)nc(C)c5c3N)C4)CC2N)CC1] | 5-amino-N-(2-{3-amino-4-[1-(methoxymethyl)cyclopropoxy]pyrrolidin-1-yl}-5,6,7,8-tetrahydroquinolin-6-yl)-2,4-dimethylthieno[2,3-d]pyrimidine-6-carboxamide |
| 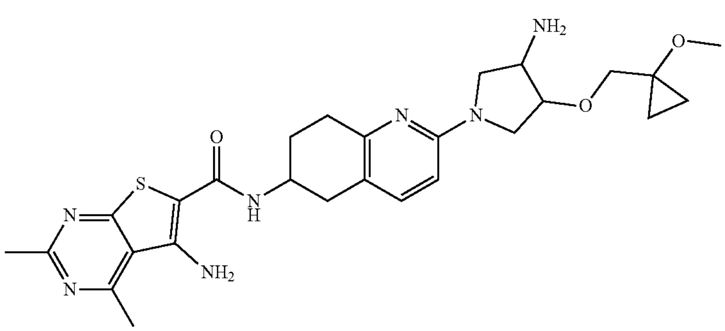 | 5-amino-N-[2-(3-amino-4-ethoxypyrrolidin-1-yl)-5,6,7,8-tetrahydroquinolin-6-yl]-2,4-dimethylthieno[2,3-d]pyrimidine-6-carboxamide |

TABLE 27-continued

| Structure | Chemical Name |
|---|---|
| 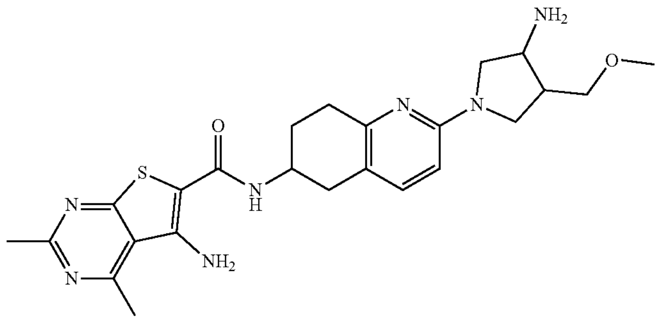 | 5-amino-N-{2-[3-amino-4-(methoxymethyl)pyrrolidin-1-yl]-5,6,7,8-tetrahydroquinolin-6-yl}-2,4-dimethylthieno[2,3-d]pyrimidine-6-carboxamide |
| 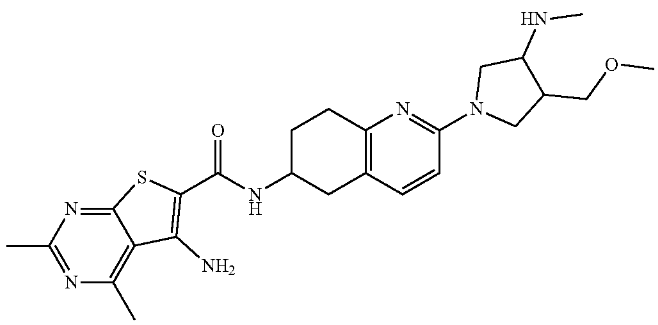 | 5-amino-N-{2-[3-(methoxymethyl)-4-(methylamino)pyrrolidin-1-yl]-5,6,7,8-tetrahydroquinolin-6-yl}-2,4-dimethylthieno[2,3-d]pyrimidine-6-carboxamide |
| 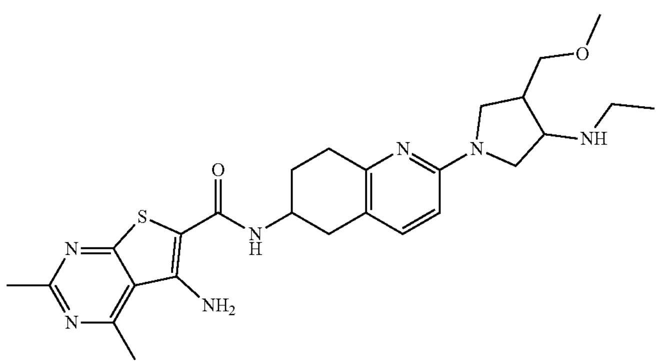 | 5-amino-N-{2-[3-(ethylamino)-4-(methoxymethyl)pyrrolidin-1-yl]-5,6,7,8-tetrahydroquinolin-6-yl}-2,4-dimethylthieno[2,3-d]pyrimidine-6-carboxamide |
| 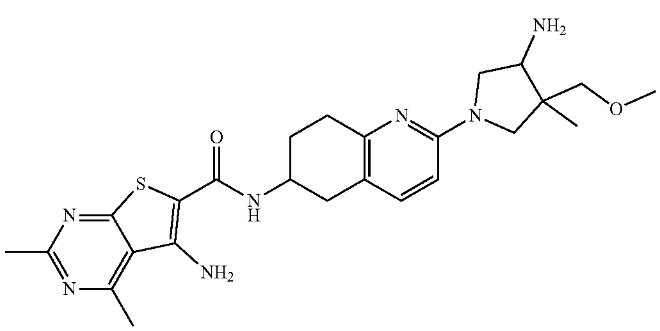 | 5-amino-N-{2-[4-amino-3-(methoxymethyl)-3-methylpyrrolidin-1-yl]-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 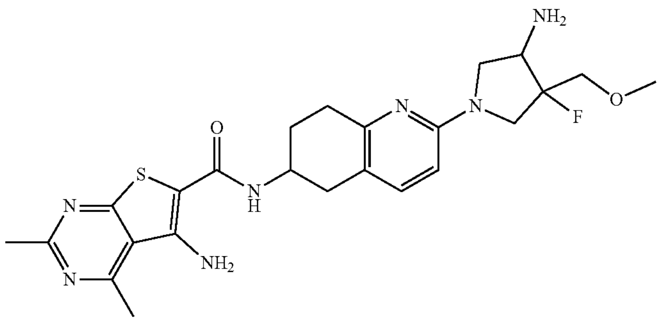 | 5-amino-N-{2-[4-amino-3-fluoro-3-(methoxymethyl)pyrrolidin-1-yl]-5,6,7,8-tetrahydroquinolin-6-yl}-2,4-dimethylthieno[2,3-d]pyrimidine-6-carboxamide |
| 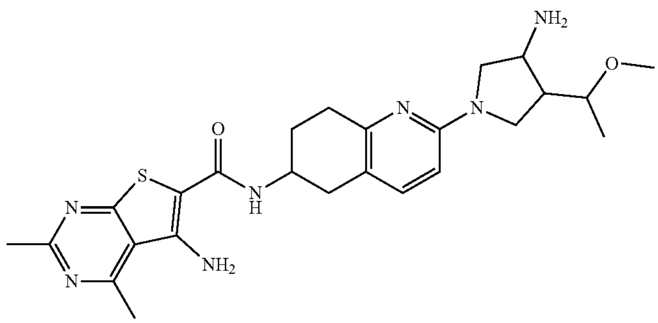 | 5-amino-N-{2-[3-amino-4-(1-methoxyethyl)pyrrolidin-1-yl]-5,6,7,8-tetrahydroquinolin-6-yl}-2,4-dimethylthieno[2,3-d]pyrimidine-6-carboxamide |
| 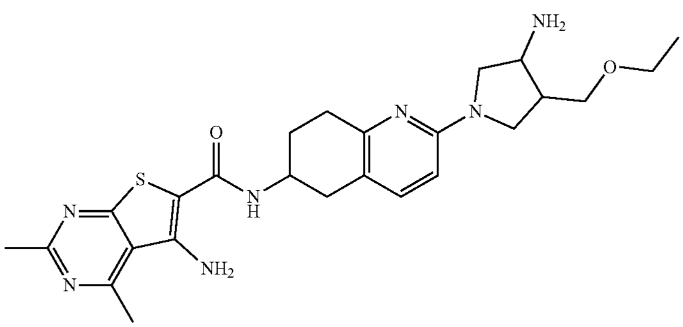 [SMILES: CCOCC1CN(c2ccc3c(n2)CCC(NC(=O)c2sc4nc(C)nc(C)c4c2N)C3)CC1N] | 5-amino-N-{2-[3-amino-4-(ethoxymethyl)pyrrolidin-1-yl]-5,6,7,8-tetrahydroquinolin-6-yl}-2,4-dimethylthieno[2,3-d]pyrimidine-6-carboxamide |
| 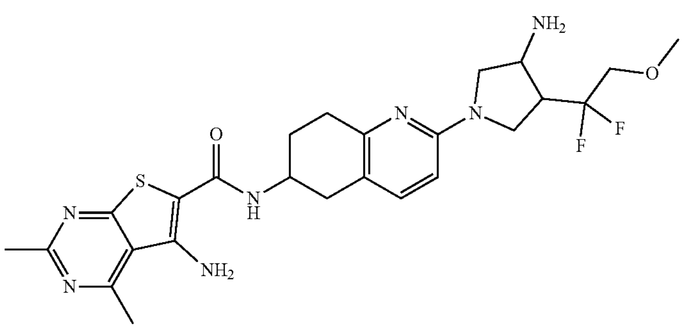 | 5-amino-N-{2-[3-amino-4-(1,1-difluoro-2-methoxyethyl)pyrrolidin-1-yl]-5,6,7,8-tetrahydroquinolin-6-yl}-2,4-dimethylthieno[2,3-d]pyrimidine-6-carboxamide |
| 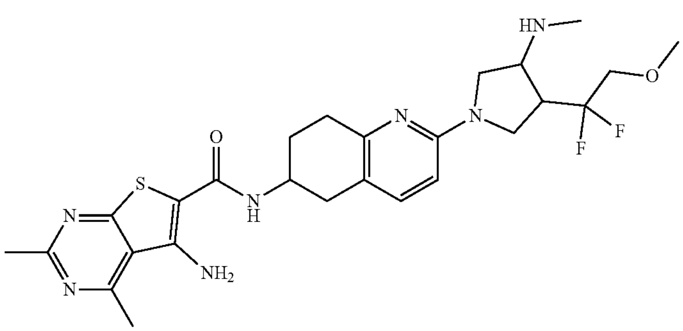 | 5-amino-N-{2-[3-(1,1-difluoro-2-methoxyethyl)-4-(methylamino)pyrrolidin-1-yl]-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 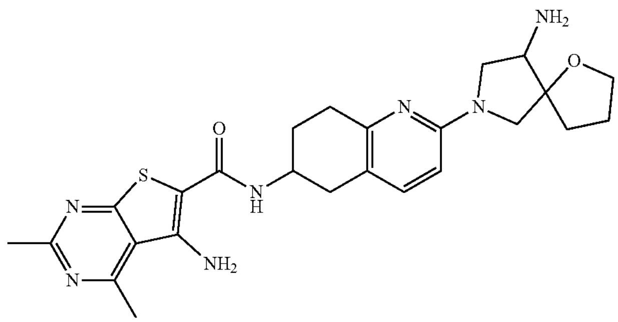 [SMILES: Cc1nc(C)c2c(N)c(C(=O)NC3CCc4nc(N5CC(N)C6(CCCO6)C5)ccc4C3)sc2n1] | 5-amino-N-(2-{9-amino-1-oxa-7-azaspiro[4.4]nonan-7-yl}-5,6,7,8-tetrahydroquinolin-6-yl)-2,4-dimethylthieno[2,3-d]pyrimidine-6-carboxamide |
| 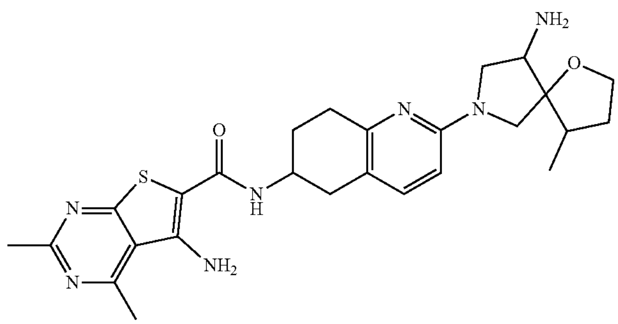 [SMILES: Cc1nc(C)c2c(N)c(C(=O)NC3CCc4nc(N5CC(N)C6(C5)OCCC6C)ccc4C3)sc2n1] | 5-amino-N-(2-{9-amino-4-methyl-1-oxa-7-azaspiro[4.4]nonan-7-yl}-5,6,7,8-tetrahydroquinolin-6-yl)-2,4-dimethylthieno[2,3-d]pyrimidine-6-carboxamide |
| 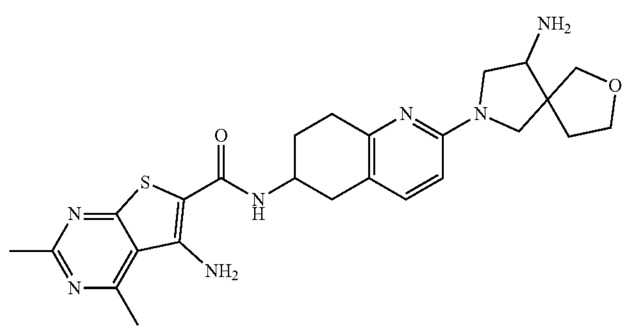 [SMILES: Cc1nc(C)c2c(N)c(C(=O)NC3CCc4nc(N5CC(N)C6(CCOC6)C5)ccc4C3)sc2n1] | 5-amino-N-(2-{9-amino-2-oxa-7-azaspiro[4.4]nonan-7-yl}-5,6,7,8-tetrahydroquinolin-6-yl)-2,4-dimethylthieno[2,3-d]pyrimidine-6-carboxamide |
| 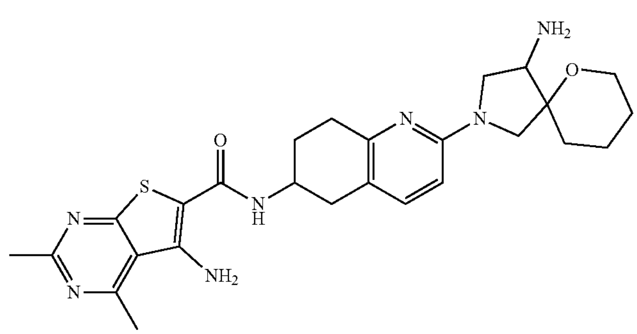 [SMILES: Cc1nc(C)c2c(N)c(C(=O)NC3CCc4nc(N5CC(N)C6(CCCCO6)C5)ccc4C3)sc2n1] | 5-amino-N-(2-{4-amino-6-oxa-2-azaspiro[4.5]decan-2-yl}-5,6,7,8-tetrahydroquinolin-6-yl)-2,4-dimethylthieno[2,3-d]pyrimidine-6-carboxamide |

TABLE 27-continued

| Structure | Chemical Name |
|---|---|
| 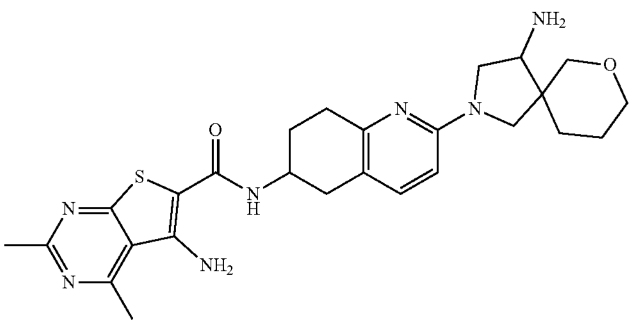 | 5-amino-N-(2-{4-amino-7-oxa-2-azaspiro[4.5]decan-2-yl}-5,6,7,8-tetrahydroquinolin-6-yl)-2,4-dimethylthieno[2,3-d]pyrimidine-6-carboxamide |
| 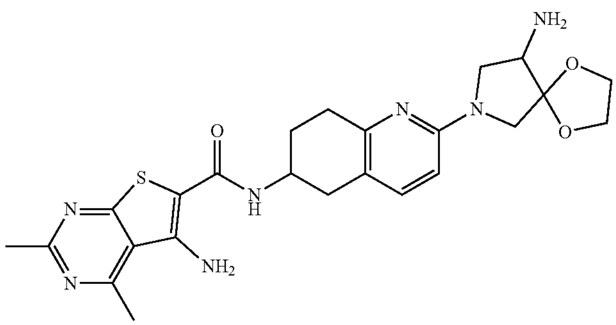 [SMILES: Cc1nc(C)c2c(N)c(C(=O)NC3CCc4nc(N5CC(N)C6(C5)OCCO6)ccc4C3)sc2n1] | 5-amino-N-(2-{9-amino-1,4-dioxa-7-azaspiro[4.4]nonan-7-yl}-5,6,7,8-tetrahydroquinolin-6-yl)-2,4-dimethylthieno[2,3-d]pyrimidine-6-carboxamide |
| 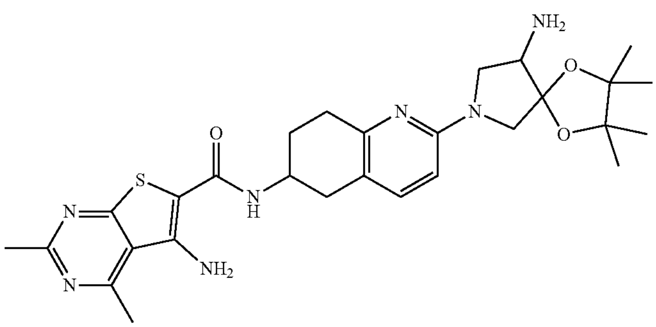 | 5-amino-N-(2-{9-amino-2,2,3,3-tetramethyl-1,4-dioxa-7-azaspiro[4.4]nonan-7-yl}-5,6,7,8-tetrahydroquinolin-6-yl)-2,4-dimethylthieno[2,3-d]pyrimidine-6-carboxamide |
| 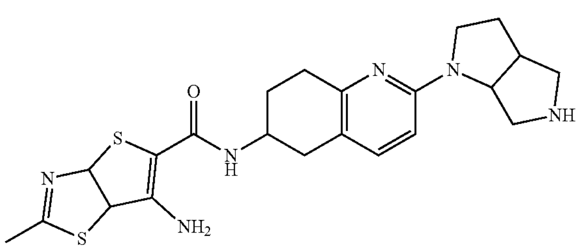 [SMILES: CC1=NC2SC(C(=O)NC3CCc4nc(N5CCC6CNCC65)ccc4C3)=C(N)C2S1] | 6-amino-2-methyl-N-(2-{octahydropyrrolo[2,3-c]pyrrol-1-yl}-5,6,7,8-tetrahydroquinolin-6-yl)thieno[2,3-d][1,3]thiazole-5-carboxamide |
| 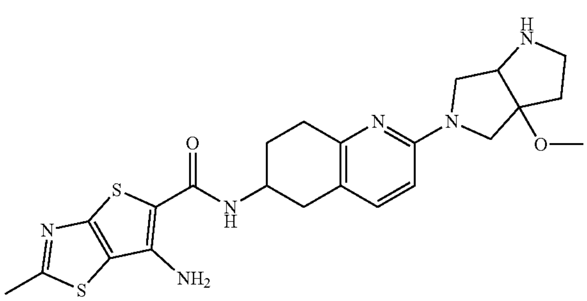 | N-(2-{3a-methoxy-octahydropyrrolo[3,4-b]pyrrol-5-yl}-5,6,7,8-tetrahydroquinolin-6-yl)-6-amino-2-methylthieno[2,3-d][1,3]thiazole-5-carboxamide |

TABLE 27-continued

| Structure | Chemical Name |
|---|---|
| 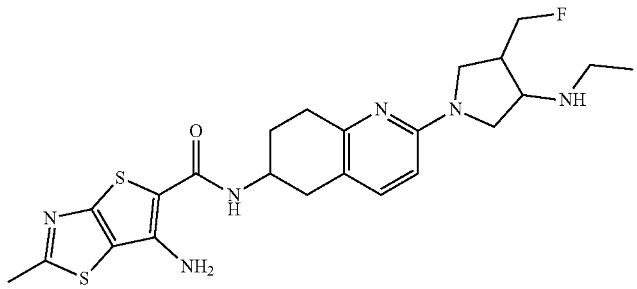 [SMILES: CCNC1CN(c2ccc3c(n2)CCC(NC(=O)c2sc4nc(C)sc4c2N)C3)CC1CF] | 6-amino-N-{2-[3-(ethylamino)-4-(fluoromethyl)pyrrolidin-1-yl]-5,6,7,8-tetrahydroquinolin-6-yl}-2-methylthieno[2,3-d][1,3]thiazole-5-carboxamide |
| 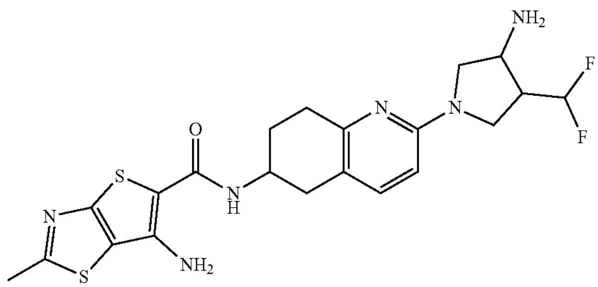 [SMILES: Cc1nc2sc(C(=O)NC3CCc4nc(N5CC(N)C(C(F)F)C5)ccc4C3)c(N)c2s1] | 6-amino-N-{2-[3-amino-4-(difluoromethyl)pyrrolidin-1-yl]-5,6,7,8-tetrahydroquinolin-6-yl}-2-methylthieno[2,3-d][1,3]thiazole-5-carboxamide |
| 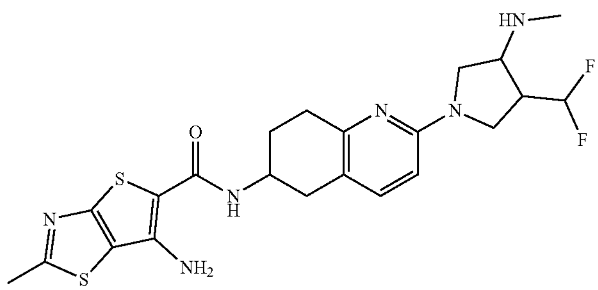 [SMILES: CNC1CN(c2ccc3c(n2)CCC(NC(=O)c2sc4nc(C)sc4c2N)C3)CC1C(F)F] | 6-amino-N-{2-[3-(difluoromethyl)-4-(methylamino)pyrrolidin-1-yl]-5,6,7,8-tetrahydroquinolin-6-yl}-2-methylthieno[2,3-d][1,3]thiazole-5-carboxamide |
| 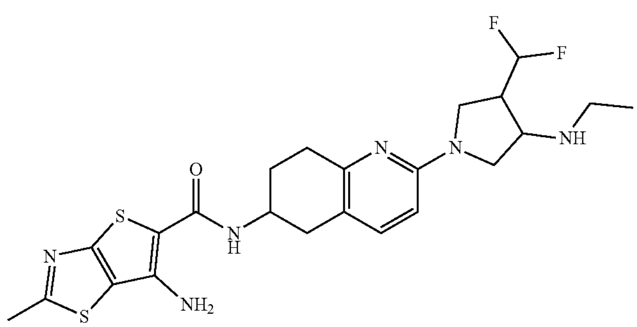 [SMILES: CCNC1CN(c2ccc3c(n2)CCC(NC(=O)c2sc4nc(C)sc4c2N)C3)CC1C(F)F] | 6-amino-N-{2-[3-(difluoromethyl)-4-(ethylamino)pyrrolidin-1-yl]-5,6,7,8-tetrahydroquinolin-6-yl}-2-methylthieno[2,3-d][1,3]thiazole-5-carboxamide |
| 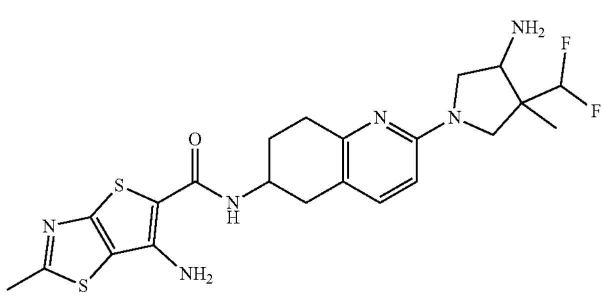 [SMILES: Cc1nc2sc(C(=O)NC3CCc4nc(N5CC(N)C(C)(C(F)F)C5)ccc4C3)c(N)c2s1] | 6-amino-N-{2-[4-amino-3-(difluoromethyl)-3-methylpyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 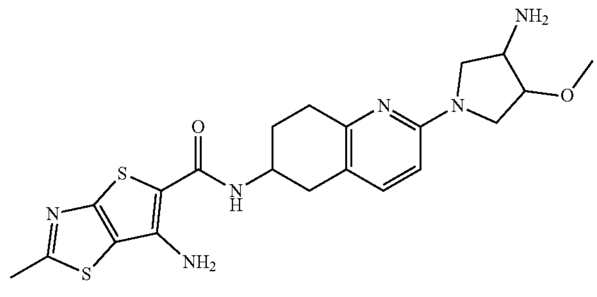 | 6-amino-N-[2-(3-amino-4-methoxypyrrolidin-1-yl)-5,6,7,8-tetrahydroquinolin-6-yl]-2-methylthieno[2,3-d][1,3]thiazole-5-carboxamide |
| 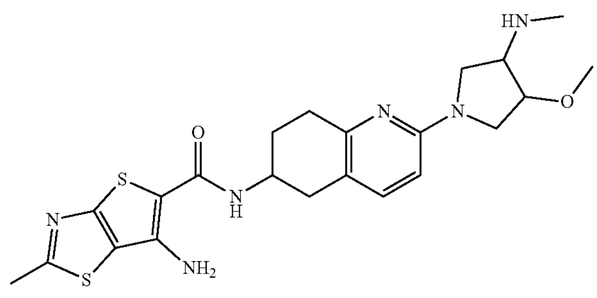 | 6-amino-N-{2-[3-methoxy-4-(methylamino)pyrrolidin-1-yl]-5,6,7,8-tetrahydroquinolin-6-yl}-2-methylthieno[2,3-d][1,3]thiazole-5-carboxamide |
| 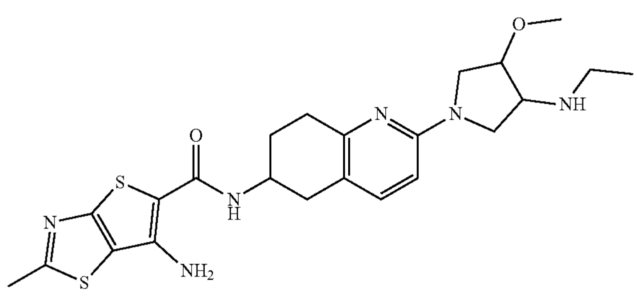 [SMILES: CCNC1CN(c2ccc3c(n2)CCC(NC(=O)c2sc4nc(C)sc4c2N)C3)CC1OC] | 6-amino-N-{2-[3-(ethylamino)-4-methoxypyrrolidin-1-yl]-5,6,7,8-tetrahydroquinolin-6-yl}-2-methylthieno[2,3-d][1,3]thiazole-5-carboxamide |
| 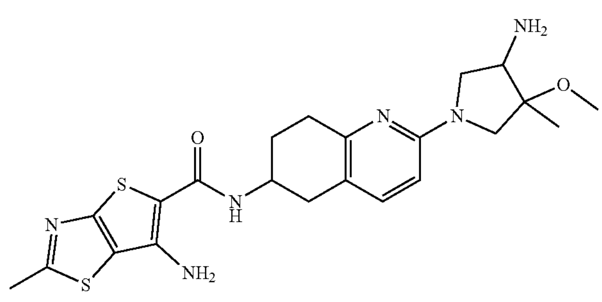 | 6-amino-N-[2-(4-amino-3-methoxy-3-methylpyrrolidin-1-yl)-5,6,7,8-tetrahydroquinolin-6-yl]-2-methylthieno[2,3-d][1,3]thiazole-5-carboxamide |
| 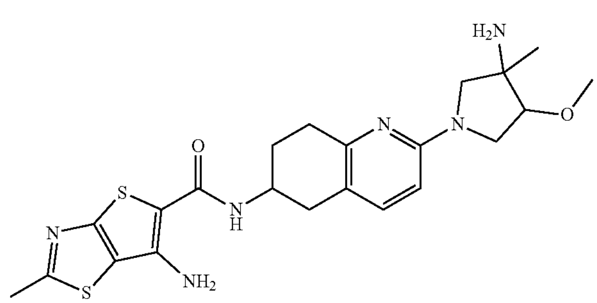 | 6-amino-N-[2-(3-amino-4-methoxy-3-methylpyrrolidin-1-yl)-5,6,7,8-tetrahydroquinolin-6-yl]-2-methylthieno[2,3-d][1,3]thiazole-5-carboxamide |

TABLE 27-continued

| Structure | Chemical Name |
|---|---|
| 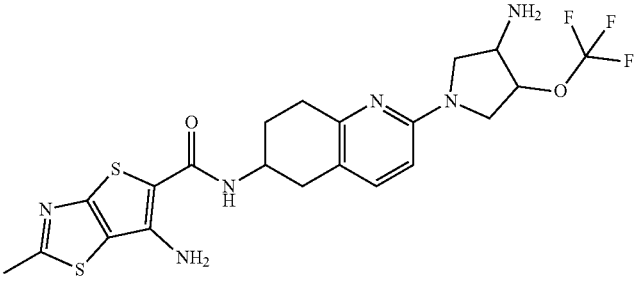 [SMILES: Cc1nc2sc(C(=O)NC3CCc4nc(N5CC(N)C(OC(F)(F)F)C5)ccc4C3)c(N)c2s1] | 6-amino-N-{2-[3-amino-4-(trifluoromethoxy)pyrrolidin-1-yl]-5,6,7,8-tetrahydroquinolin-6-yl}-2-methylthieno[2,3-d][1,3]thiazole-5-carboxamide |
| 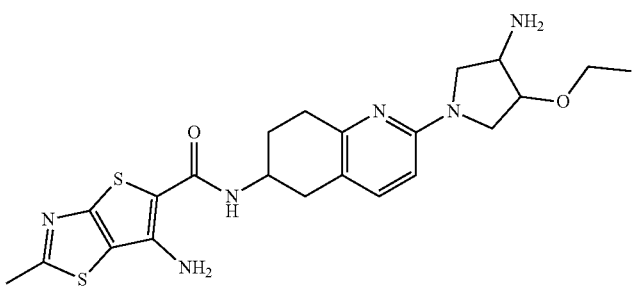 [SMILES: CCOC1CN(c2ccc3c(n2)CCC(NC(=O)c2sc4nc(C)sc4c2N)C3)CC1N] | 6-amino-N-[2-(3-amino-4-ethoxypyrrolidin-1-yl)-5,6,7,8-tetrahydroquinolin-6-yl]-2-methylthieno[2,3-d][1,3]thiazole-5-carboxamide |
| 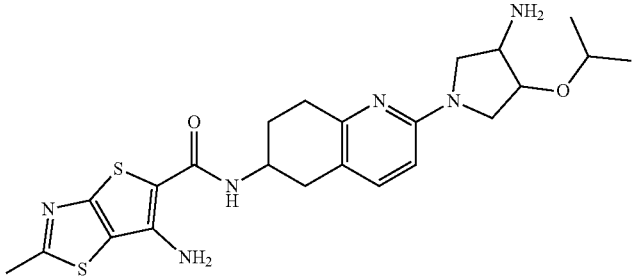 [SMILES: Cc1nc2sc(C(=O)NC3CCc4nc(N5CC(N)C(OC(C)C)C5)ccc4C3)c(N)c2s1] | 6-amino-N-{2-[3-amino-4-(propan-2-yloxy)pyrrolidin-1-yl]-5,6,7,8-tetrahydroquinolin-6-yl}-2-methylthieno[2,3-d][1,3]thiazole-5-carboxamide |
| 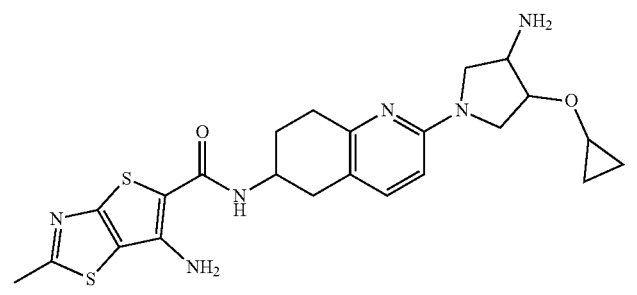 [SMILES: Cc1nc2sc(C(=O)NC3CCc4nc(N5CC(N)C(OC6CC6)C5)ccc4C3)c(N)c2s1] | 6-amino-N-[2-(3-amino-4-cyclopropoxypyrrolidin-1-yl)-5,6,7,8-tetrahydroquinolin-6-yl]-2-methylthieno[2,3-d][1,3]thiazole-5-carboxamide |
| 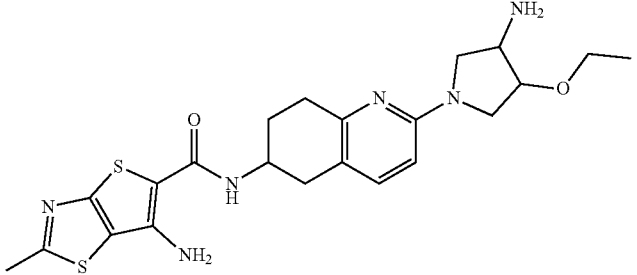 [SMILES: CCOC1CN(c2ccc3c(n2)CCC(NC(=O)c2sc4nc(C)sc4c2N)C3)CC1N] | 6-amino-N-{2-[3-amino-4-(methoxymethyl)pyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 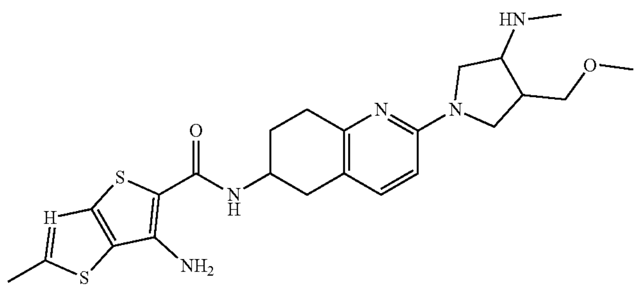 | 6-amino-N-{2-[3-(methoxymethyl)-4-(methylamino)pyrrolidin-1-yl]-5,6,7,8-tetrahydroquinolin-6-yl}-2-methylthieno[2,3-d][1,3]thiazole-5-carboxamide |
| 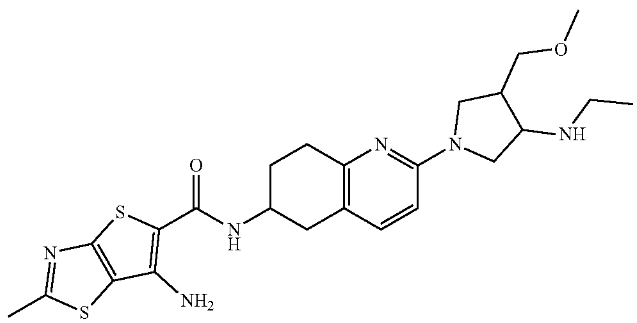 [SMILES: CCNC1CN(c2ccc3c(n2)CCC(NC(=O)c2sc4nc(C)sc4c2N)C3)CC1COC] | 6-amino-N-{2-[3-(ethylamino)-4-(methoxymethyl)pyrrolidin-1-yl]-5,6,7,8-tetrahydroquinolin-6-yl}-2-methylthieno[2,3-d][1,3]thiazole-5-carboxamide |
| 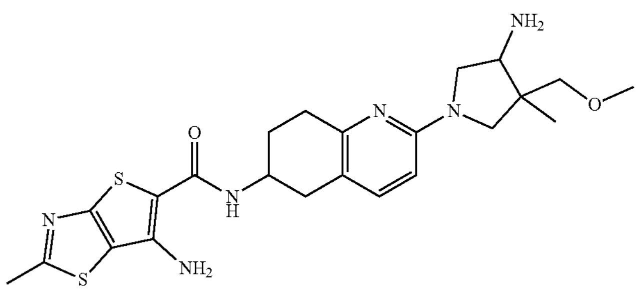 | 6-amino-N-{2-[4-amino-3-(methoxymethyl)-3-methylpyrrolidin-1-yl]-5,6,7,8-tetrahydroquinolin-6-yl}-2-methylthieno[2,3-d][1,3]thiazole-5-carboxamide |
| 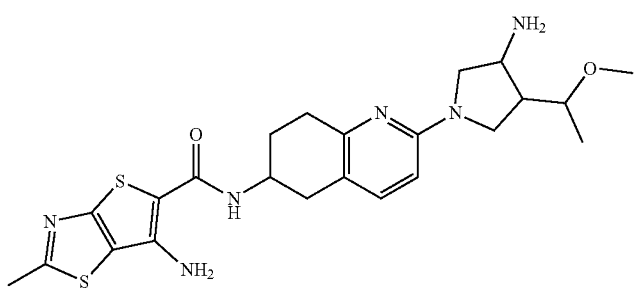 | 6-amino-N-{2-[3-amino-4-(1-methoxyethyl)pyrrolidin-1-yl]-5,6,7,8-tetrahydroquinolin-6-yl}-2-methylthieno[2,3-d][1,3]thiazole-5-carboxamide |
| 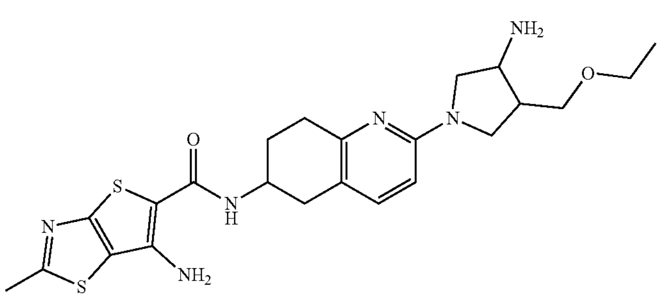 [SMILES: CCOCC1CN(c2ccc3c(n2)CCC(NC(=O)c2sc4nc(C)sc4c2N)C3)CC1N] | 6-amino-N-{2-[3-amino-4-(ethoxymethyl)pyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 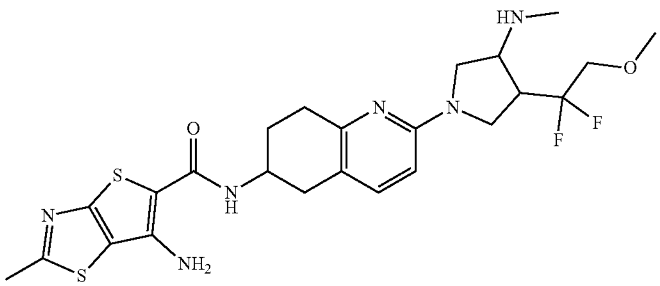 | 6-amino-N-{2-[3-(1,1-difluoro-2-methoxyethyl)-4-(methylamino)pyrrolidin-1-yl]-5,6,7,8-tetrahydroquinolin-6-yl}-2-methylthieno[2,3-d][1,3]thiazole-5-carboxamide |
| 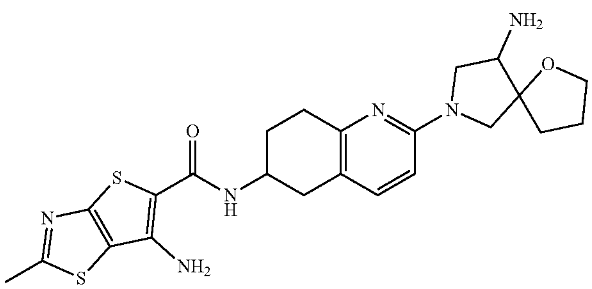 [SMILES: Cc1nc2sc(C(=O)NC3CCc4nc(N5CC(N)C6(CCCO6)C5)ccc4C3)c(N)c2s1] | 6-amino-N-(2-{9-amino-1-oxa-7-azaspiro[4.4]nonan-7-yl}-5,6,7,8-tetrahydroquinolin-6-yl)-2-methylthieno[2,3-d][1,3]thiazole-5-carboxamide |
| 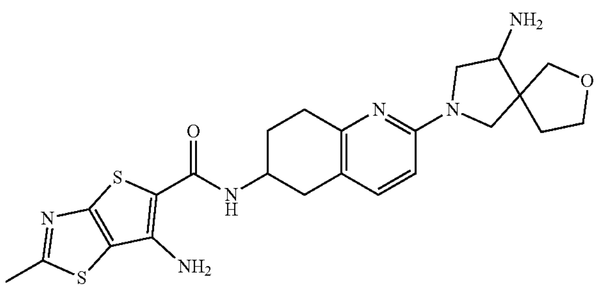 [SMILES: Cc1nc2sc(C(=O)NC3CCc4nc(N5CC(N)C6(CCOC6)C5)ccc4C3)c(N)c2s1] | 6-amino-N-(2-{9-amino-2-oxa-7-azaspiro[4.4]nonan-7-yl}-5,6,7,8-tetrahydroquinolin-6-yl)-2-methylthieno[2,3-d][1,3]thiazole-5-carboxamide |
| 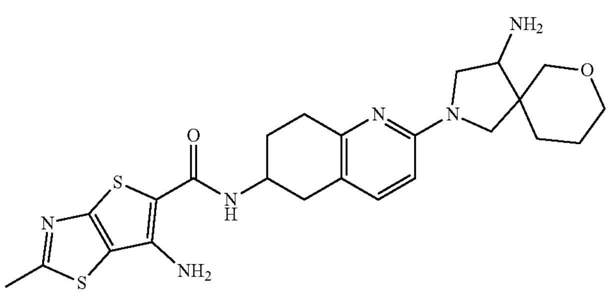 [SMILES: Cc1nc2sc(C(=O)NC3CCc4nc(N5CC(N)C6(CCCOC6)C5)ccc4C3)c(N)c2s1] | 6-amino-N-(2-{4-amino-7-oxa-2-azaspiro[4.5]decan-2-yl}-5,6,7,8-tetrahydroquinolin-6-yl)-2-methylthieno[2,3-d][1,3]thiazole-5-carboxamide |
| 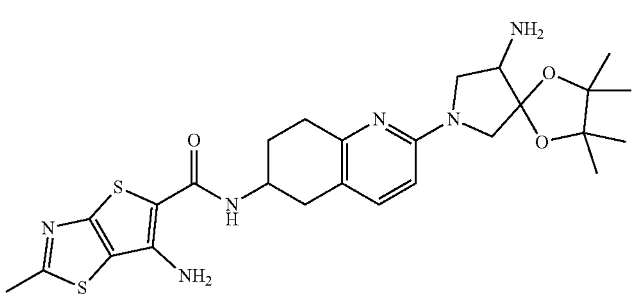 | 6-amino-N-(2-{9-amino-2,2,3,3-tetramethyl-1,4-dioxa-7-azaspiro[4.4]nonan-7-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 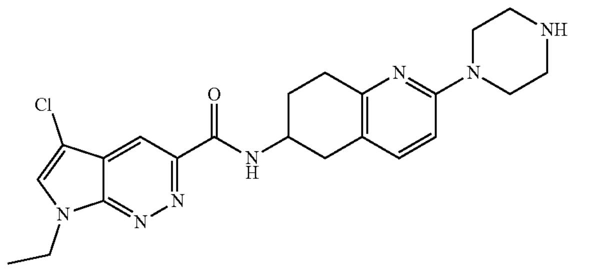 [SMILES: CCn1cc(Cl)c2cc(C(=O)NC3CCc4nc(N5CCNCC5)ccc4C3)nnc21] | 5-chloro-7-ethyl-N-[2-(piperazin-1-yl)-5,6,7,8-tetrahydroquinolin-6-yl]-7H-pyrrolo[2,3-c]pyridazine-3-carboxamide |
| 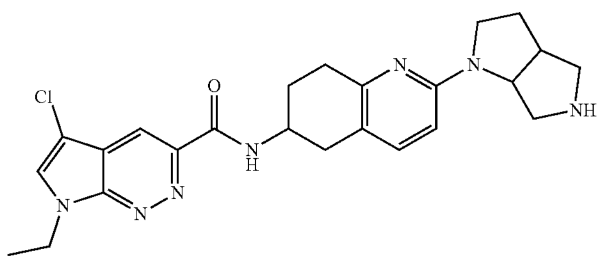 [SMILES: CCn1cc(Cl)c2cc(C(=O)NC3CCc4nc(N5CCC6CNCC65)ccc4C3)nnc21] | 5-chloro-7-ethyl-N-(2-{octahydropyrrolo[2,3-c]pyrrol-1-yl}-5,6,7,8-tetrahydroquinolin-6-yl)-7H-pyrrolo[2,3-c]pyridazine-3-carboxamide |
| 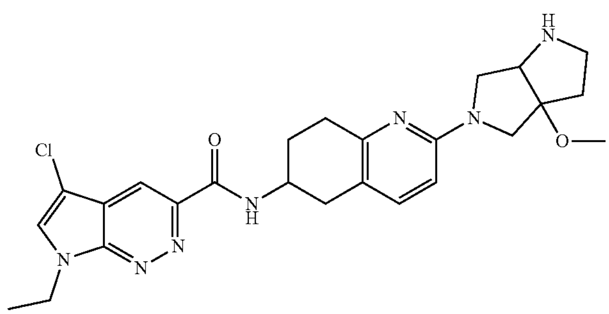 [SMILES: CCn1cc(Cl)c2cc(C(=O)NC3CCc4nc(N5CC6NCCC6(OC)C5)ccc4C3)nnc21] | N-(2-{3a-methoxy-octahydropyrrolo[3,4-b]pyrrol-5-yl}-5,6,7,8-tetrahydroquinolin-6-yl)-5-chloro-7-ethyl-7H-pyrrolo[2,3-c]pyridazine-3-carboxamide |
| 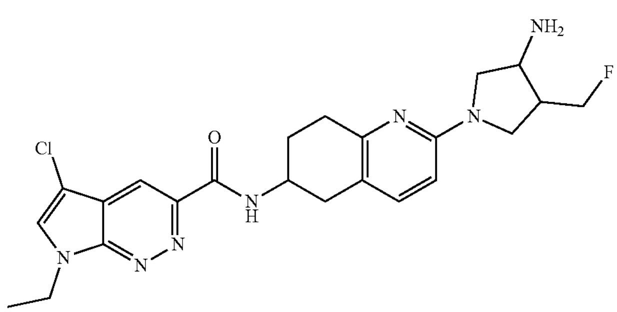 [SMILES: CCn1cc(Cl)c2cc(C(=O)NC3CCc4nc(N5CC(N)C(CF)C5)ccc4C3)nnc21] | N-{2-[3-amino-4-(fluoromethyl)pyrrolidin-1-yl]-5,6,7,8-tetrahydroquinolin-6-yl}-5-chloro-7-ethyl-7H-pyrrolo[2,3-c]pyridazine-3-carboxamide |
| 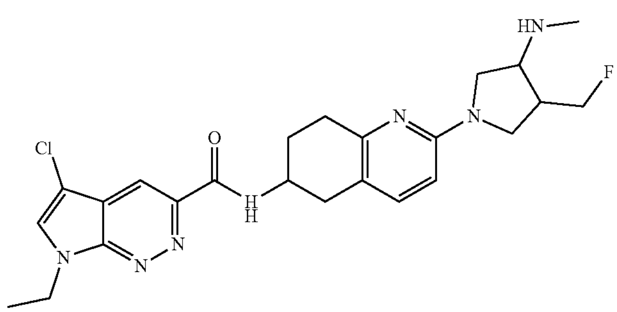 | 5-chloro-7-ethyl-N-{2-[3-(fluoromethyl)-4-(methylamino)pyrrolidin-1-yl]-5,6,7,8-tetrahydroquinolin-6-yl}-7H-pyrrolo[2,3-c]pyridazine-3-carboxamide |

TABLE 27-continued

| Structure | Chemical Name |
|---|---|
| 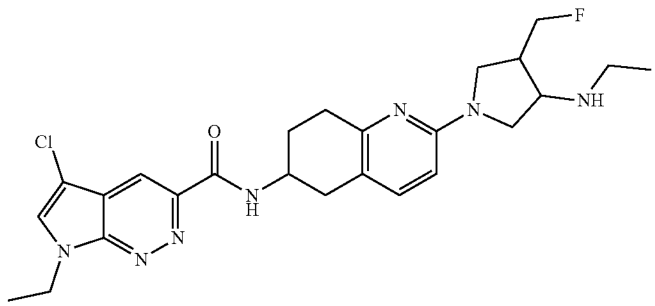 [SMILES: CCNC1CN(c2ccc3c(n2)CCC(NC(=O)c2cc4c(Cl)cn(CC)c4nn2)C3)CC1CF] | 5-chloro-7-ethyl-N-{2-[3-(ethylamino)-4-(fluoromethyl)pyrrolidin-1-yl]-5,6,7,8-tetrahydroquinolin-6-yl}-7H-pyrrolo[2,3-c]pyridazine-3-carboxamide |
| 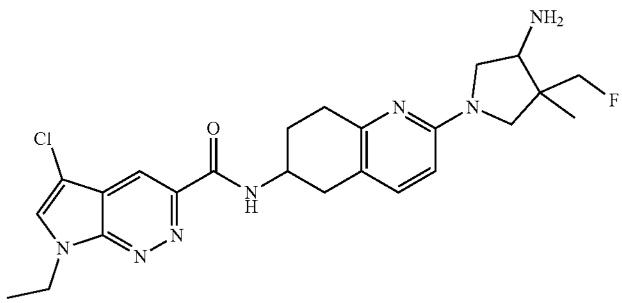 [SMILES: CCn1cc(Cl)c2cc(C(=O)NC3CCc4nc(N5CC(N)C(C)(CF)C5)ccc4C3)nnc21] | N-{2-[4-amino-3-(fluoromethyl)-3-methylpyrrolidin-1-yl]-5,6,7,8-tetrahydroquinolin-6-yl}-5-chloro-7-ethyl-7H-pyrrolo[2,3-c]pyridazine-3-carboxamide |
| 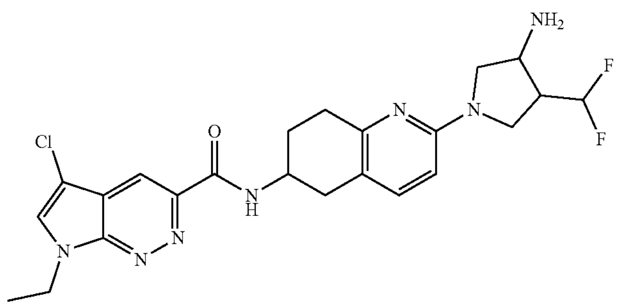 [SMILES: CCn1cc(Cl)c2cc(C(=O)NC3CCc4nc(N5CC(N)C(C(F)F)C5)ccc4C3)nnc21] | N-{2-[3-amino-4-(difluoromethyl)pyrrolidin-1-yl]-5,6,7,8-tetrahydroquinolin-6-yl}-5-chloro-7-ethyl-7H-pyrrolo[2,3-c]pyridazine-3-carboxamide |
| 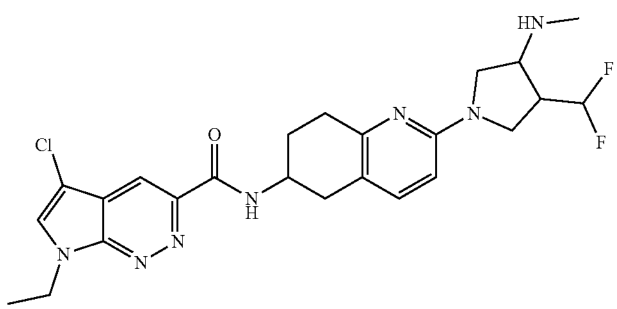 [SMILES: CCn1cc(Cl)c2cc(C(=O)NC3CCc4nc(N5CC(NC)C(C(F)F)C5)ccc4C3)nnc21] | 5-chloro-N-{2-[3-(difluoromethyl)-4-(methylamino)pyrrolidin-1-yl]-5,6,7,8-tetrahydroquinolin-6-yl}-7-ethyl-7H-pyrrolo[2,3-c]pyridazine-3-carboxamide |
| 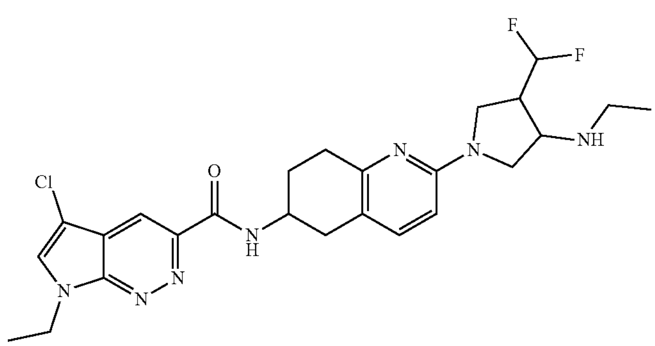 [SMILES: CCNC1CN(c2ccc3c(n2)CCC(NC(=O)c2cc4c(Cl)cn(CC)c4nn2)C3)CC1C(F)F] | 5-chloro-N-{2-[3-(difluoromethyl)-4-(ethylamino)pyrrolidin-1-yl]-5,6,7,8-tetrahydroquinolin-6-yl}-7-ethyl-7H-pyrrolo[2,3-c]pyridazine-3-carboxamide |

TABLE 27-continued

| Structure | Chemical Name |
|---|---|
| 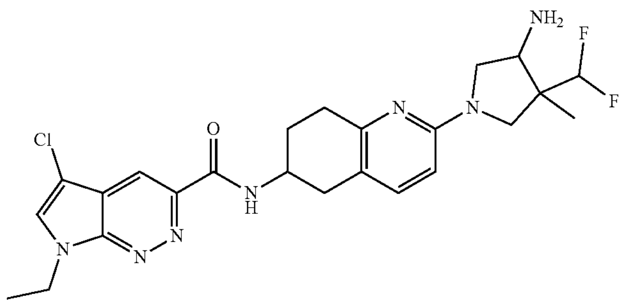 [SMILES: CCn1cc(Cl)c2cc(C(=O)NC3CCc4nc(N5CC(N)C(C)(C(F)F)C5)ccc4C3)nnc21] | N-{2-[4-amino-3-(difluoromethyl)-3-methylpyrrolidin-1-yl]-5,6,7,8-tetrahydroquinolin-6-yl}-5-chloro-7-ethyl-7H-pyrrolo[2,3-c]pyridazine-3-carboxamide |
| 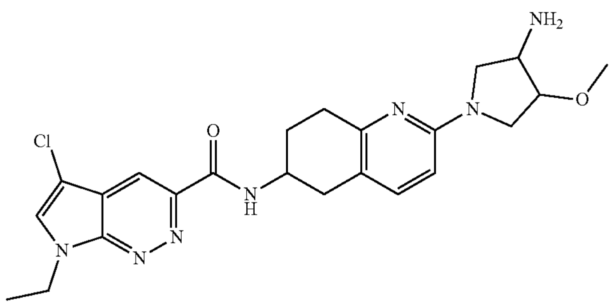 [SMILES: CCn1cc(Cl)c2cc(C(=O)NC3CCc4nc(N5CC(N)C(OC)C5)ccc4C3)nnc21] | N-[2-(3-amino-4-methoxypyrrolidin-1-yl)-5,6,7,8-tetrahydroquinolin-6-yl]-5-chloro-7-ethyl-7H-pyrrolo[2,3-c]pyridazine-3-carboxamide |
| 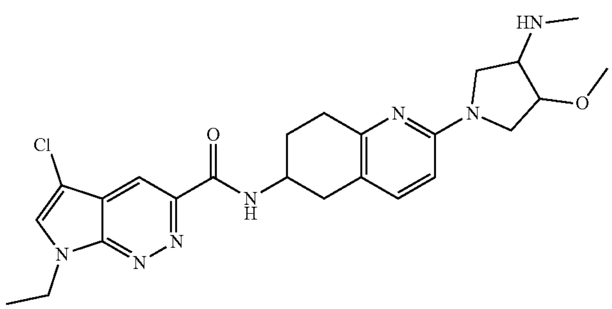 [SMILES: CCn1cc(Cl)c2cc(C(=O)NC3CCc4nc(N5CC(NC)C(OC)C5)ccc4C3)nnc21] | 5-chloro-7-ethyl-N-{2-[3-methoxy-4-(methylamino)pyrrolidin-1-yl]-5,6,7,8-tetrahydroquinolin-6-yl}-7H-pyrrolo[2,3-c]pyridazine-3-carboxamide |
| 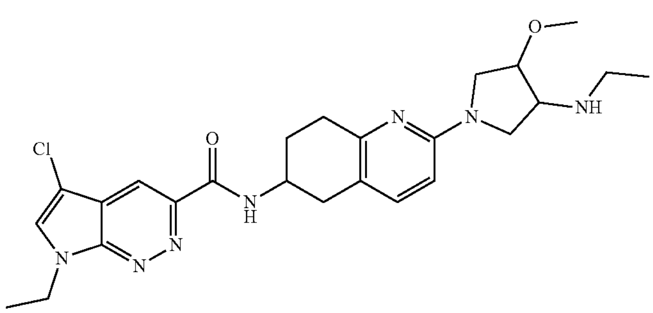 [SMILES: CCNC1CN(c2ccc3c(n2)CCC(NC(=O)c2cc4c(Cl)cn(CC)c4nn2)C3)CC1OC] | 5-chloro-7-ethyl-N-{2-[3-(ethylamino)-4-methoxypyrrolidin-1-yl]-5,6,7,8-tetrahydroquinolin-6-yl}-7H-pyrrolo[2,3-c]pyridazine-3-carboxamide |
| 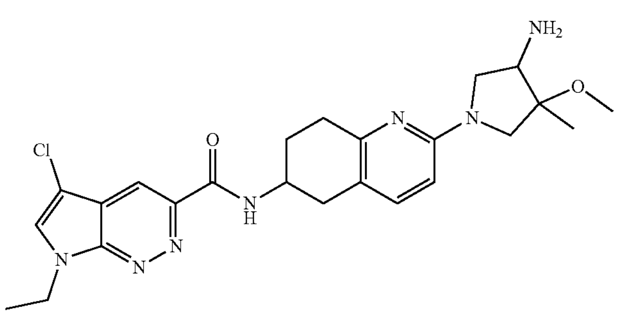 [SMILES: CCn1cc(Cl)c2cc(C(=O)NC3CCc4nc(N5CC(N)C(C)(OC)C5)ccc4C3)nnc21] | N-[2-(4-amino-3-methoxy-3-methylpyrrolidin-1-yl)-5,6,7,8-tetrahydroquinolin-6-yl]-5-chloro-7-ethyl-7H-pyrrolo[2,3-c]pyridazine-3-carboxamide |

TABLE 27-continued

| Structure | Chemical Name |
|---|---|
| 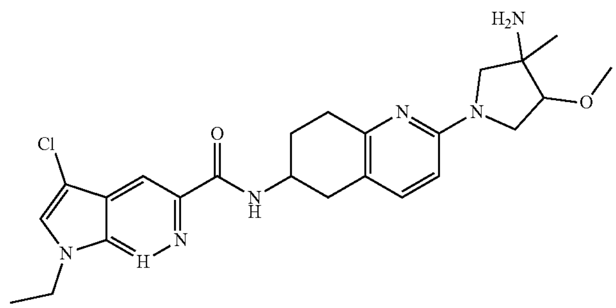 | N-[2-(3-amino-4-methoxy-3-methylpyrrolidin-1-yl)-5,6,7,8-tetrahydroquinolin-6-yl]-5-chloro-7-ethyl-7H-pyrrolo[2,3-c]pyridazine-3-carboxamide |
| 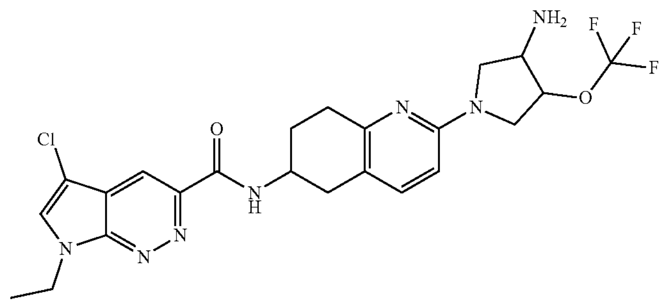 [SMILES: CCn1cc(Cl)c2cc(C(=O)NC3CCc4nc(N5CC(N)C(OC(F)(F)F)C5)ccc4C3)nnc21] | N-{2-[3-amino-4-(trifluoromethoxy)pyrrolidin-1-yl]-5,6,7,8-tetrahydroquinolin-6-yl}-5-chloro-7-ethyl-7H-pyrrolo[2,3-c]pyridazine-3-carboxamide |
| 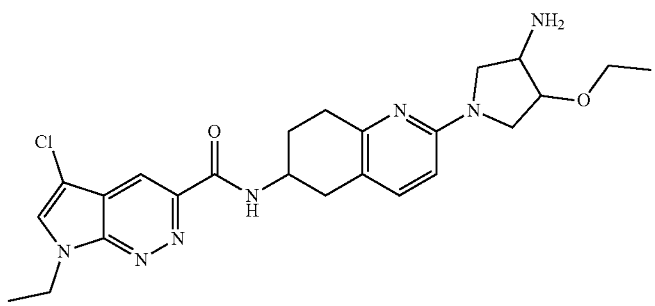 [SMILES: CCOC1CN(c2ccc3c(n2)CCC(NC(=O)c2cc4c(Cl)cn(CC)c4nn2)C3)CC1N] | N-[2-(3-amino-4-ethoxypyrrolidin-1-yl)-5,6,7,8-tetrahydroquinolin-6-yl]-5-chloro-7-ethyl-7H-pyrrolo[2,3-c]pyridazine-3-carboxamide |
| 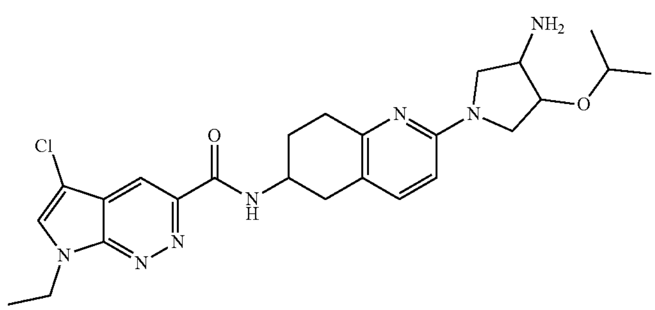 [SMILES: CCn1cc(Cl)c2cc(C(=O)NC3CCc4nc(N5CC(N)C(OC(C)C)C5)ccc4C3)nnc21] | N-{2-[3-amino-4-(propan-2-yloxy)pyrrolidin-1-yl]-5,6,7,8-tetrahydroquinolin-6-yl}-5-chloro-7-ethyl-7H-pyrrolo[2,3-c]pyridazine-3-carboxamide |
| 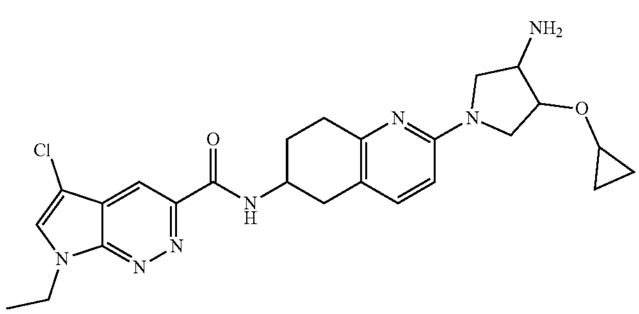 [SMILES: CCn1cc(Cl)c2cc(C(=O)NC3CCc4nc(N5CC(N)C(OC6CC6)C5)ccc4C3)nnc21] | N-[2-(3-amino-4-cyclopropoxypyrrolidin-1-yl)-5,6,7,8-tetrahydroquinolin-6-yl]-5-chloro-7-ethyl-7H-pyrrolo[2,3-c]pyridazine-3-carboxamide |

TABLE 27-continued

| Structure | Chemical Name |
|---|---|
| 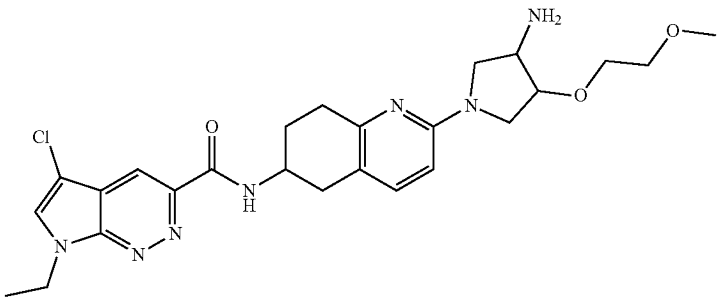 [SMILES: CCn1cc(Cl)c2cc(C(=O)NC3CCc4nc(N5CC(N)C(OCCOC)C5)ccc4C3)nnc21] | N-{2-[3-amino-4-(2-methoxyethoxy)pyrrolidin-1-yl]-5,6,7,8-tetrahydroquinolin-6-yl}-5-chloro-7-ethyl-7H-pyrrolo[2,3-c]pyridazine-3-carboxamide |
| 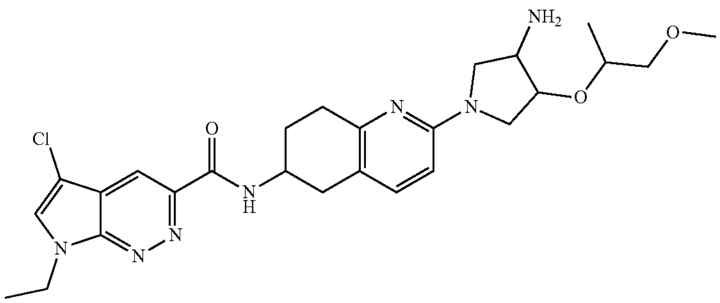 [SMILES: CCn1cc(Cl)c2cc(C(=O)NC3CCc4nc(N5CC(N)C(OC(C)COC)C5)ccc4C3)nnc21] | N-(2-{3-amino-4-[(1-methoxypropan-2-yl)oxy]pyrrolidin-1-yl}-5,6,7,8-tetrahydroquinolin-6-yl)-5-chloro-7-ethyl-7H-pyrrolo[2,3-c]pyridazine-3-carboxamide |
| 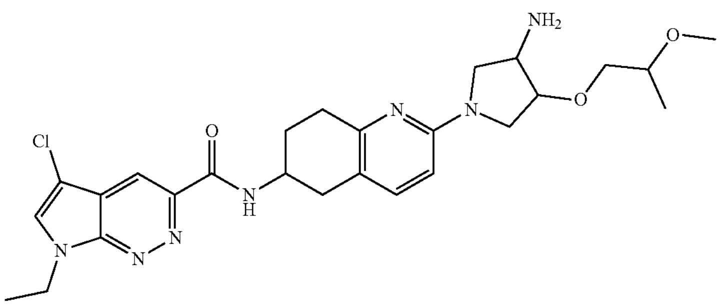 [SMILES: CCn1cc(Cl)c2cc(C(=O)NC3CCc4nc(N5CC(N)C(OCC(C)OC)C5)ccc4C3)nnc21] | N-{2-[3-amino-4-(2-methoxypropoxy)pyrrolidin-1-yl]-5,6,7,8-tetrahydroquinolin-6-yl}-5-chloro-7-ethyl-7H-pyrrolo[2,3-c]pyridazine-3-carboxamide |
| 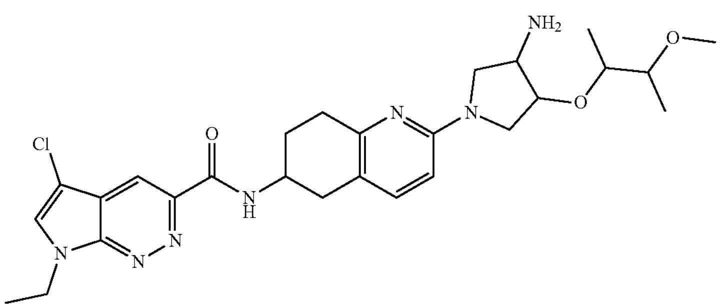 [SMILES: CCn1cc(Cl)c2cc(C(=O)NC3CCc4nc(N5CC(N)C(OC(C)C(C)OC)C5)ccc4C3)nnc21] | N-(2-{3-amino-4-[(3-methoxybutan-2-yl)oxy]pyrrolidin-1-yl}-5,6,7,8-tetrahydroquinolin-6-yl)-5-chloro-7-ethyl-7H-pyrrolo[2,3-c]pyridazine-3-carboxamide |
| 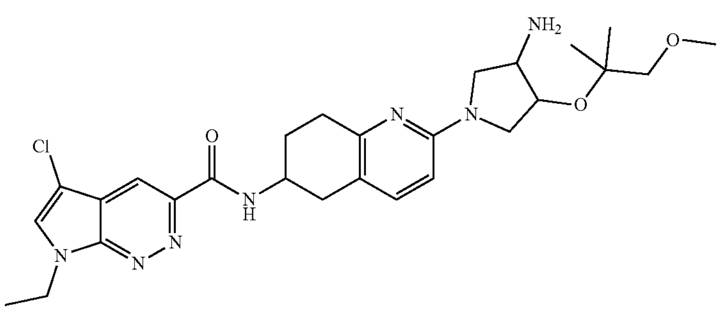 [SMILES: CCn1cc(Cl)c2cc(C(=O)NC3CCc4nc(N5CC(N)C(OC(C)(C)COC)C5)ccc4C3)nnc21] | N-(2-{3-amino-4-[(1-methoxy-2-methylpropan-2-yl)oxy]pyrrolidin-1-yl}-5,6,7,8-tetrahydroquinolin-6-yl)-5-chloro-7-ethyl-7H-pyrrolo[2,3-c]pyridazine-3-carboxamide |

TABLE 27-continued

| Structure | Chemical Name |
|---|---|
| 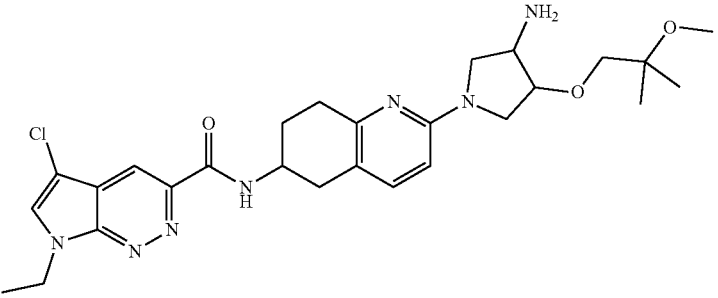 [SMILES: CCn1cc(Cl)c2cc(C(=O)NC3CCc4nc(N5CC(N)C(OCC(C)(C)OC)C5)ccc4C3)nnc21] | N-{2-[3-amino-4-(2-methoxy-2-methylpropoxy)pyrrolidin-1-yl]-5,6,7,8-tetrahydroquinolin-6-yl}-5-chloro-7-ethyl-7H-pyrrolo[2,3-c]pyridazine-3-carboxamide |
| 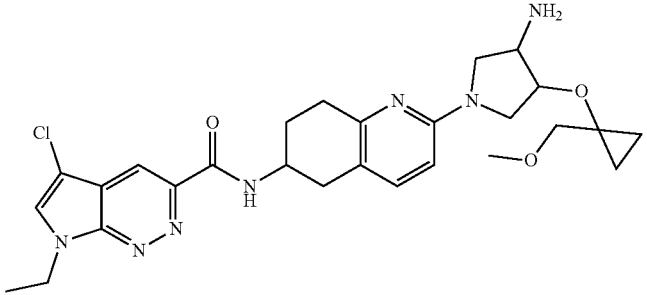 [SMILES: CCn1cc(Cl)c2cc(C(=O)NC3CCc4nc(N5CC(N)C(OC6(COC)CC6)C5)ccc4C3)nnc21] | N-(2-{3-amino-4-[1-(methoxymethyl)cyclopropoxy]pyrrolidin-1-yl}-5,6,7,8-tetrahydroquinolin-6-yl)-5-chloro-7-ethyl-7H-pyrrolo[2,3-c]pyridazine-3-carboxamide |
| 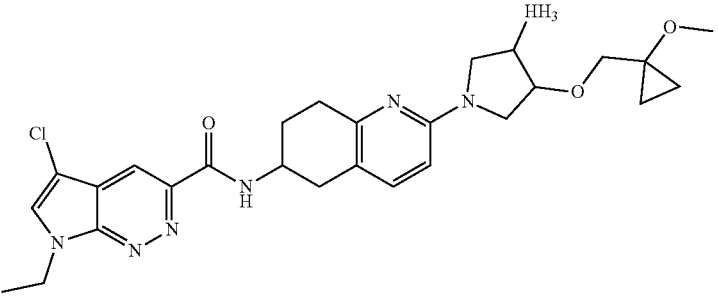 | N-(2-{3-amino-4-[(1-methoxycyclopropyl)methoxy]pyrrolidin-1-yl}-5,6,7,8-tetrahydroquinolin-6-yl)-5-chloro-7-ethyl-7H-pyrrolo[2,3-c]pyridazine-3-carboxamide |
| 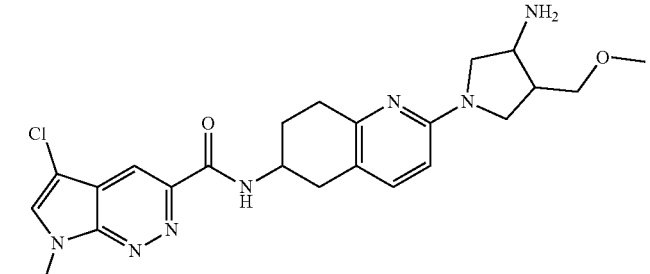 | N-{2-[3-amino-4-(methoxymethyl)pyrrolidin-1-yl]-5,6,7,8-tetrahydroquinolin-6-yl}-5-chloro-7-ethyl-7H-pyrrolo[2,3-c]pyridazine-3-carboxamide |
| 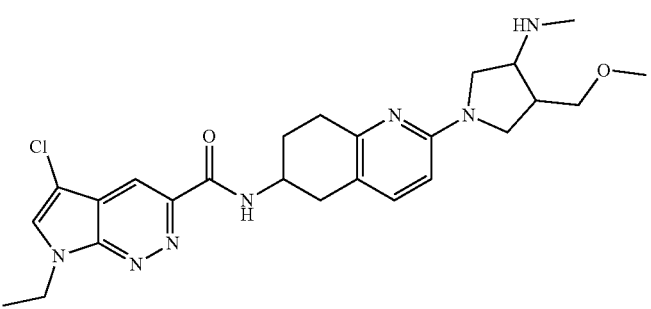 [SMILES: CCn1cc(Cl)c2cc(C(=O)NC3CCc4nc(N5CC(COC)C(NC)C5)ccc4C3)nnc21] | 5-chloro-7-ethyl-N-{2-[3-(methoxymethyl)-4-(methylamino)pyrrolidin-1-yl]-5,6,7,8-tetrahydroquinolin-6-yl}-7H-pyrrolo[2,3-c]pyridazine-3-carboxamide |

TABLE 27-continued

| Structure | Chemical Name |
|---|---|
| 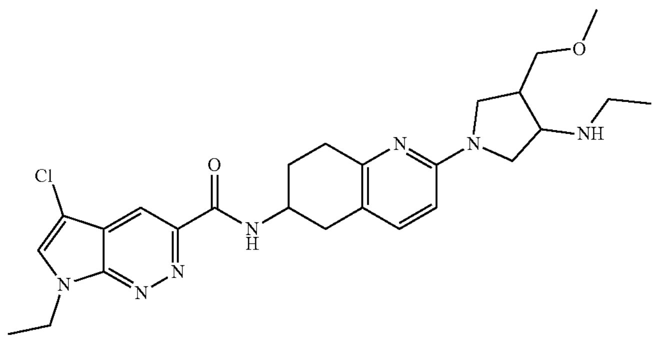 [SMILES: CCNC1CN(c2ccc3c(n2)CCC(NC(=O)c2cc4c(Cl)cn(CC)c4nn2)C3)CC1COC] | 5-chloro-7-ethyl-N-{2-[3-(ethylamino)-4-(methoxymethyl)pyrrolidin-1-yl]-5,6,7,8-tetrahydroquinolin-6-yl}-7H-pyrrolo[2,3-c]pyridazine-3-carboxamide |
| 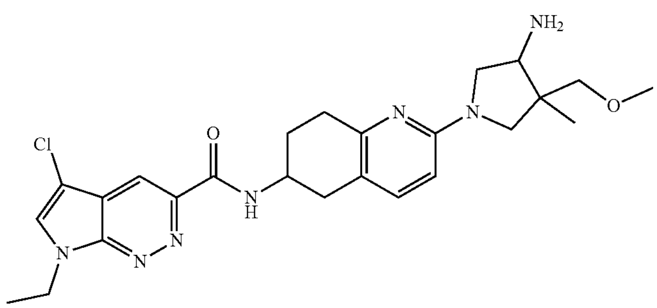 [SMILES: CCn1cc(Cl)c2cc(C(=O)NC3CCc4nc(N5CC(N)C(C)(COC)C5)ccc4C3)nnc21] | N-{2-[4-amino-3-(methoxymethyl)-3-methylpyrrolidin-1-yl]-5,6,7,8-tetrahydroquinolin-6-yl}-5-chloro-7-ethyl-7H-pyrrolo[2,3-c]pyridazine-3-carboxamide |
| 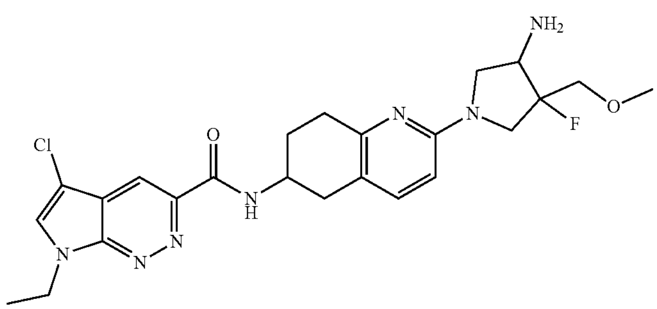 [SMILES: CCn1cc(Cl)c2cc(C(=O)NC3CCc4nc(N5CC(N)C(F)(COC)C5)ccc4C3)nnc21] | N-{2-[4-amino-3-fluoro-3-(methoxymethyl)pyrrolidin-1-yl]-5,6,7,8-tetrahydroquinolin-6-yl}-5-chloro-7-ethyl-7H-pyrrolo[2,3-c]pyridazine-3-carboxamide |
| 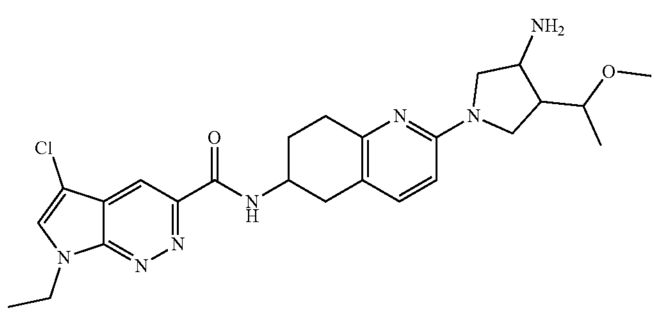 [SMILES: CCn1cc(Cl)c2cc(C(=O)NC3CCc4nc(N5CC(N)C(C(C)OC)C5)ccc4C3)nnc21] | N-{2-[3-amino-4-(1-methoxyethyl)pyrrolidin-1-yl]-5,6,7,8-tetrahydroquinolin-6-yl}-5-chloro-7-ethyl-7H-pyrrolo[2,3-c]pyridazine-3-carboxamide |
| 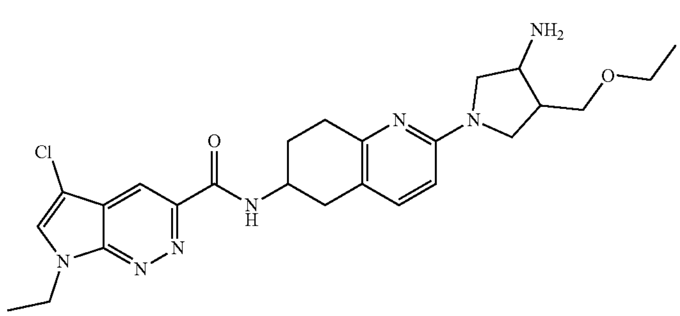 [SMILES: CCOCC1CN(c2ccc3c(n2)CCC(NC(=O)c2cc4c(Cl)cn(CC)c4nn2)C3)CC1N] | N-{2-[3-amino-4-(ethoxymethyl)pyrrolidin-1-yl]-5,6,7,8-tetrahydroquinolin-6-yl}-5-chloro-7-ethyl-7H-pyrrolo[2,3-c]pyridazine-3-carboxamide |

TABLE 27-continued

| Structure | Chemical Name |
|---|---|
| 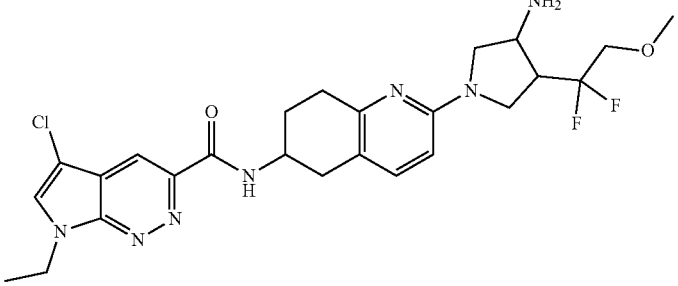 | N-{2-[3-amino-4-(1,1-difluoro-2-methoxyethyl)pyrrolidin-1-yl]-5,6,7,8-tetrahydroquinolin-6-yl}-5-chloro-7-ethyl-7H-pyrrolo[2,3-c]pyridazine-3-carboxamide |
| 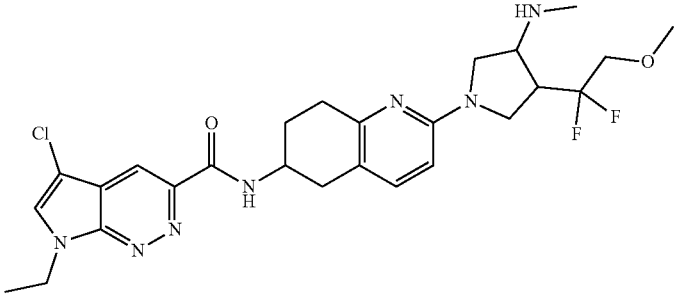 [SMILES: CCn1cc(Cl)c2cc(C(=O)NC3CCc4nc(N5CC(NC)C(C(F)(F)COC)C5)ccc4C3)nnc21] | 5-chloro-N-{2-[3-(1,1-difluoro-2-methoxyethyl)-4-(methylamino)pyrrolidin-1-yl]-5,6,7,8-tetrahydroquinolin-6-yl}-7-ethyl-7H-pyrrolo[2,3-c]pyridazine-3-carboxamide |
| 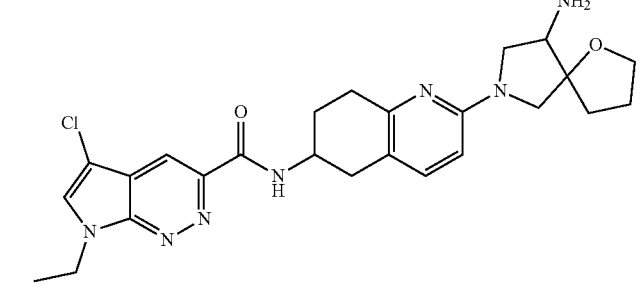 | N-(2-{9-amino-1-oxa-7-azaspiro[4.4]nonan-7-yl}-5,6,7,8-tetrahydroquinolin-6-yl)-5-chloro-7-ethyl-7H-pyrrolo[2,3-c]pyridazine-3-carboxamide |
| 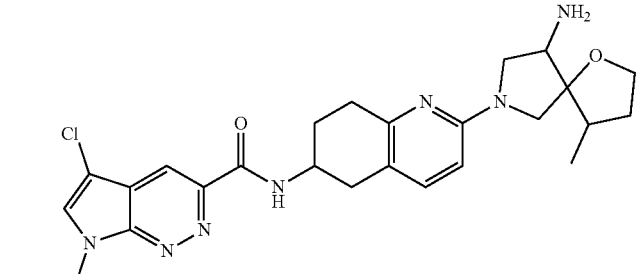 | N-(2-{9-amino-4-methyl-1-oxa-7-azaspiro[4.4]nonan-7-yl}-5,6,7,8-tetrahydroquinolin-6-yl)-5-chloro-7-ethyl-7H-pyrrolo[2,3-c]pyridazine-3-carboxamide |
| 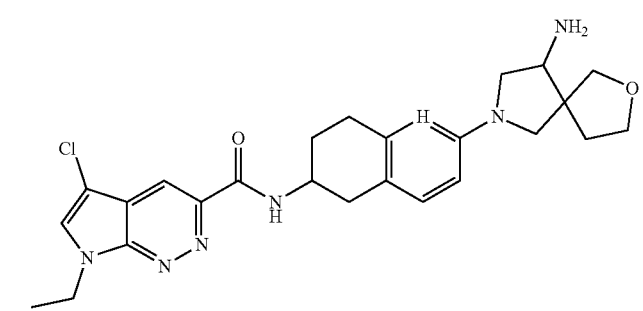 | N-(2-{9-amino-2-oxa-7-azaspiro[4.4]nonan-7-yl}-5,6,7,8-tetrahydroquinolin-6-yl)-5-chloro-7-ethyl-7H-pyrrolo[2,3-c]pyridazine-3-carboxamide |

| Structure | Chemical Name |
|---|---|
| 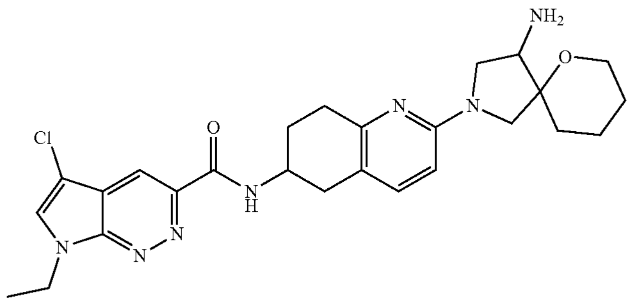 [SMILES: CCn1cc(Cl)c2cc(C(=O)NC3CCc4nc(N5CC(N)C6(CCCCO6)C5)ccc4C3)nnc21] | N-(2-{4-amino-6-oxa-2-azaspiro[4.5]decan-2-yl}-5,6,7,8-tetrahydroquinolin-6-yl)-5-chloro-7-ethyl-7H-pyrrolo[2,3-c]pyridazine-3-carboxamide |
| 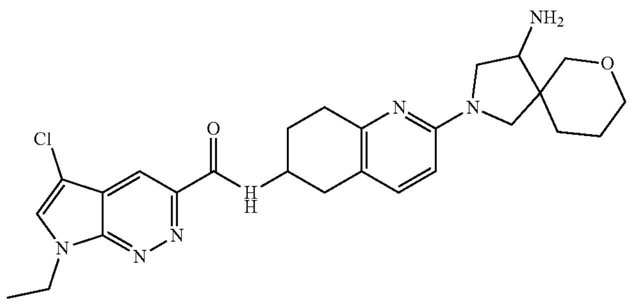 | N-(2-{4-amino-7-oxa-2-azaspiro[4.5]decan-2-yl}-5,6,7,8-tetrahydroquinolin-6-yl)-5-chloro-7-ethyl-7H-pyrrolo[2,3-c]pyridazine-3-carboxamide |
| 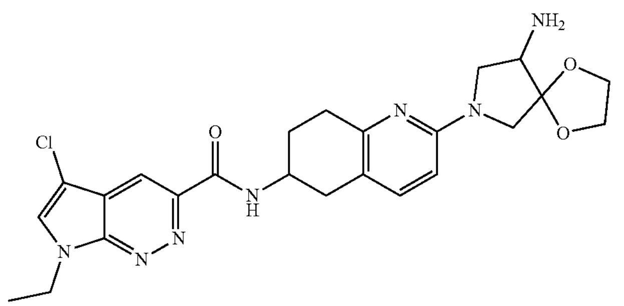 | N-(2-{9-amino-1,4-dioxa-7-azaspiro[4.4]nonan-7-yl}-5,6,7,8-tetrahydroquinolin-6-yl)-5-chloro-7-ethyl-7H-pyrrolo[2,3-c]pyridazine-3-carboxamide |
| 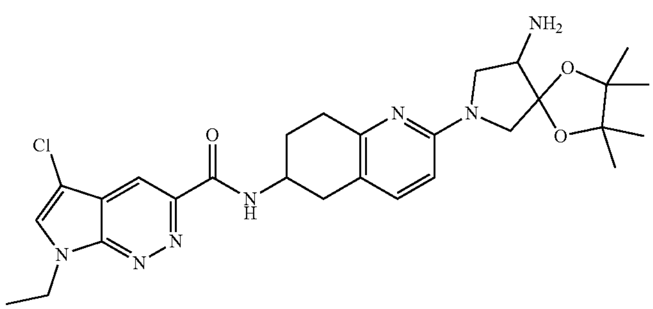 [SMILES: CCn1cc(Cl)c2cc(C(=O)NC3CCc4nc(N5CC(N)C6(C5)OC(C)(C)C(C)(C)O6)ccc4C3)nnc21] | N-(2-{9-amino-2,2,3,3-tetramethyl-1,4-dioxa-7-azaspiro[4.4]nonan-7-yl}-5,6,7,8-tetrahydroquinolin-6-yl)-5-chloro-7-ethyl-7H-pyrrolo[2,3-c]pyridazine-3-carboxamide |
| 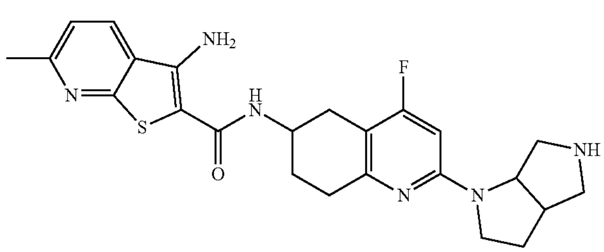 [SMILES: Cc1ccc2c(N)c(C(=O)NC3CCc4nc(N5CCC6CNCC65)cc(F)c4C3)sc2n1] | 3-amino-N-(4-fluoro-2-{octahydropyrrolo[2,3-c]pyrrol-1-yl}-5,6,7,8-tetrahydroquinolin-6-yl)-6-methylthieno[2,3-b]pyridine-2-carboxamide |

TABLE 27-continued

| Structure | Chemical Name |
|---|---|
| 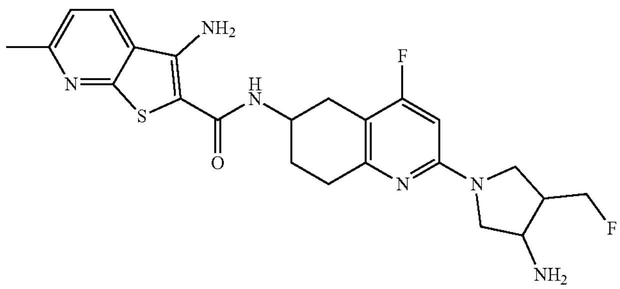 [SMILES: Cc1ccc2c(N)c(C(=O)NC3CCc4nc(N5CC(N)C(CF)C5)cc(F)c4C3)sc2n1] | 3-amino-N-{2-[3-amino-4-(fluoromethyl)pyrrolidin-1-yl]-4-fluoro-5,6,7,8-tetrahydroquinolin-6-yl}-6-methylthieno[2,3-b]pyridine-2-carboxamide |
| 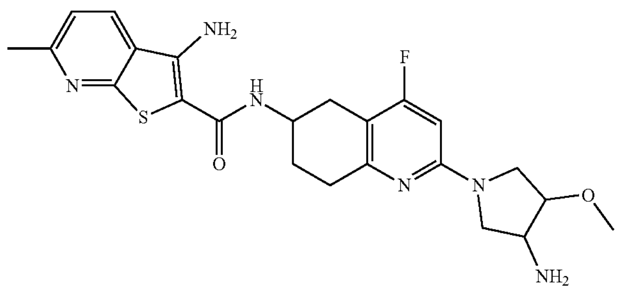 | 3-amino-N-[2-(3-amino-4-methoxypyrrolidin-1-yl)-4-fluoro-5,6,7,8-tetrahydroquinolin-6-yl]-6-methylthieno[2,3-b]pyridine-2-carboxamide |
| 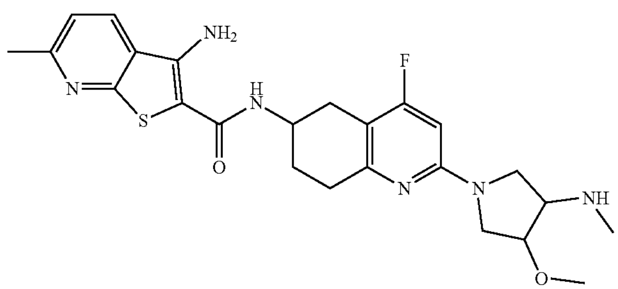 | 3-amino-N-{4-fluoro-2-[3-methoxy-4-(methylamino)pyrrolidin-1-yl]-5,6,7,8-tetrahydroquinolin-6-yl}-6-methylthieno[2,3-b]pyridine-2-carboxamide |
| 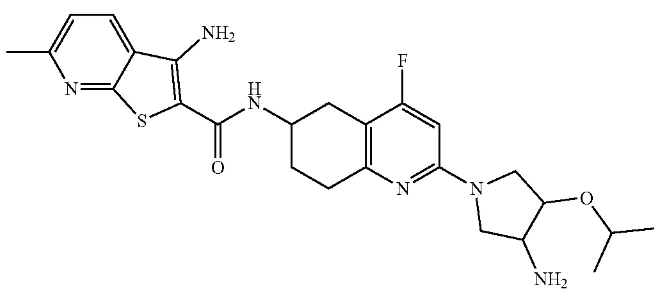 [SMILES: Cc1ccc2c(N)c(C(=O)NC3CCc4nc(N5CC(N)C(OC(C)C)C5)cc(F)c4C3)sc2n1] | 3-amino-N-{2-[3-amino-4-(propan-2-yloxy)pyrrolidin-1-yl]-4-fluoro-5,6,7,8-tetrahydroquinolin-6-yl}-6-methylthieno[2,3-b]pyridine-2-carboxamide |
| 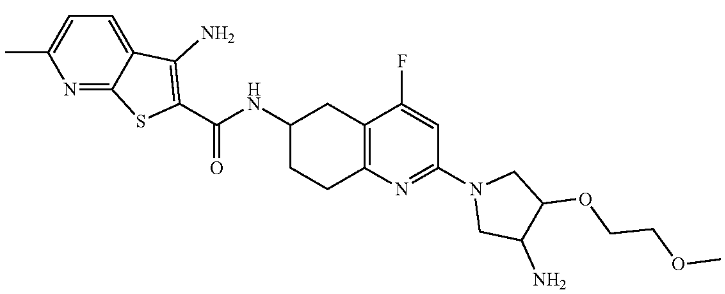 | 3-amino-N-{2-[3-amino-4-(2-methoxyethoxy)pyrrolidin-1-yl]-4-fluoro-5,6,7,8-tetrahydroquinolin-6-yl}-6-methylthieno[2,3-b]pyridine-2-carboxamide |

TABLE 27-continued

| Structure | Chemical Name |
|---|---|
| 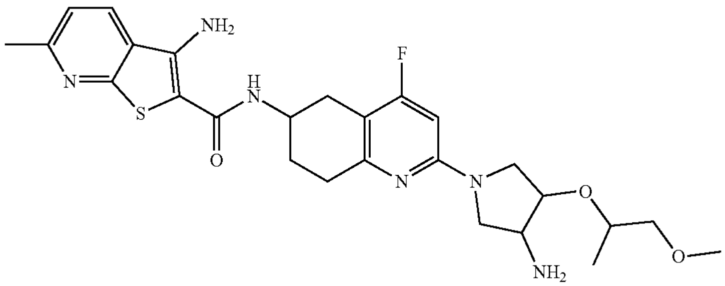 | 3-amino-N-(2-{3-amino-4-[(1-methoxypropan-2-yl)oxy]pyrrolidin-1-yl}-4-fluoro-5,6,7,8-tetrahydroquinolin-6-yl)-6-methylthieno[2,3-b]pyridine-2-carboxamide |
| 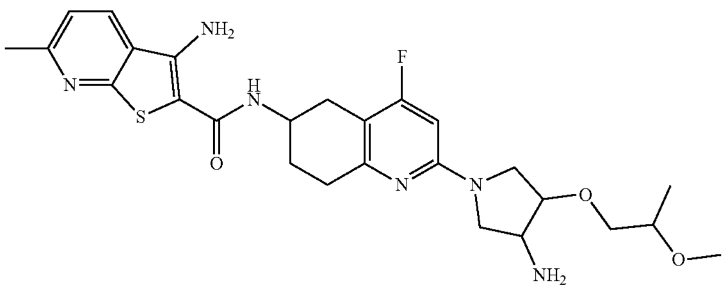 | 3-amino-N-{2-[3-amino-4-(2-methoxypropoxy)pyrrolidin-1-yl]-4-fluoro-5,6,7,8-tetrahydroquinolin-6-yl}-6-methylthieno[2,3-b]pyridine-2-carboxamide |
| 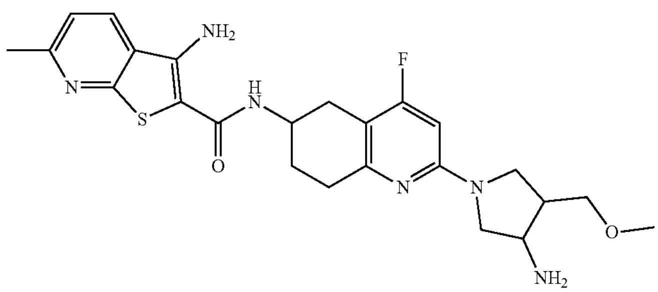 | 3-amino-N-{2-[3-amino-4-(methoxymethyl)pyrrolidin-1-yl]-4-fluoro-5,6,7,8-tetrahydroquinolin-6-yl}-6-methylthieno[2,3-b]pyridine-2-carboxamide |
| 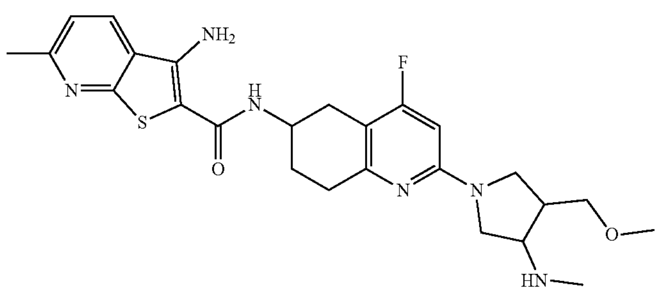 | 3-amino-N-{4-fluoro-2-[3-(methoxymethyl)-4-(methylamino)pyrrolidin-1-yl]-5,6,7,8-tetrahydroquinolin-6-yl}-6-methylthieno[2,3-b]pyridine-2-carboxamide |
| 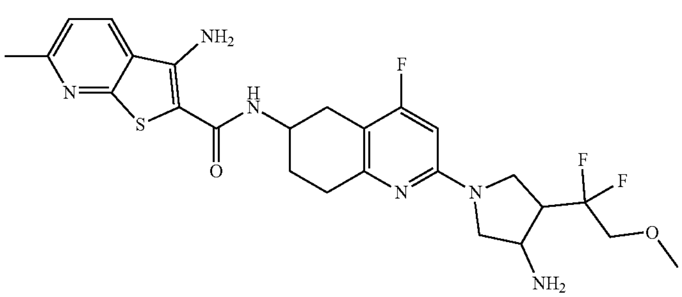 | 3-amino-N-{2-[3-amino-4-(1,1-difluoro-2-methoxyethyl)pyrrolidin-1-yl]-4-fluoro-5,6,7,8-tetrahydroquinolin-6-yl}-6-methylthieno[2,3-b]pyridine-2-carboxamide |

TABLE 27-continued

| Structure | Chemical Name |
|---|---|
| 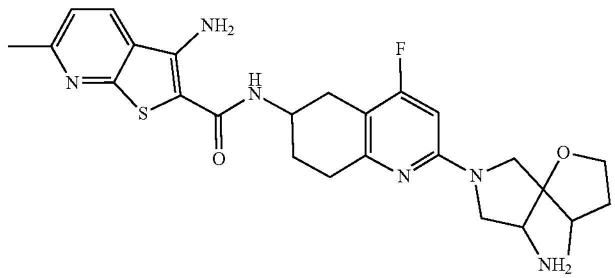 [SMILES: Cc1ccc2c(N)c(C(=O)NC3CCc4nc(N5CC6NC7CCOC76C5)cc(F)c4C3)sc2n1] | 3-amino-N-(2-{9-amino-4-methyl-1-oxa-7-azaspiro[4.4]nonan-7-yl}-4-fluoro-5,6,7,8-tetrahydroquinolin-6-yl)-6-methylthieno[2,3-b]pyridine-2-carboxamide |
| 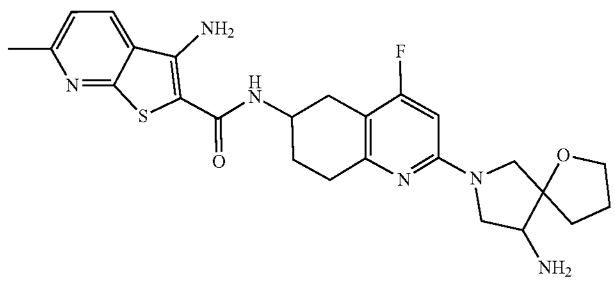 [SMILES: Cc1ccc2c(N)c(C(=O)NC3CCc4nc(N5CC(N)C6(CCCO6)C5)cc(F)c4C3)sc2n1] | 3-amino-N-(2-{9-amino-2-oxa-7-azaspiro[4.4]nonan-7-yl}-4-fluoro-5,6,7,8-tetrahydroquinolin-6-yl)-6-methylthieno[2,3-b]pyridine-2-carboxamide |
| 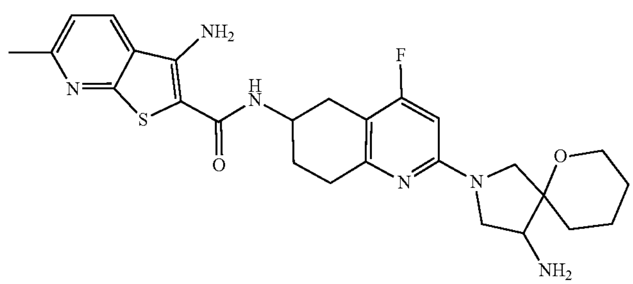 [SMILES: Cc1ccc2c(N)c(C(=O)NC3CCc4nc(N5CC(N)C6(CCCCO6)C5)cc(F)c4C3)sc2n1] | 3-amino-N-(2-{4-amino-6-oxa-2-azaspiro[4.5]decan-2-yl}-4-fluoro-5,6,7,8-tetrahydroquinolin-6-yl)-6-methylthieno[2,3-b]pyridine-2-carboxamide |
| 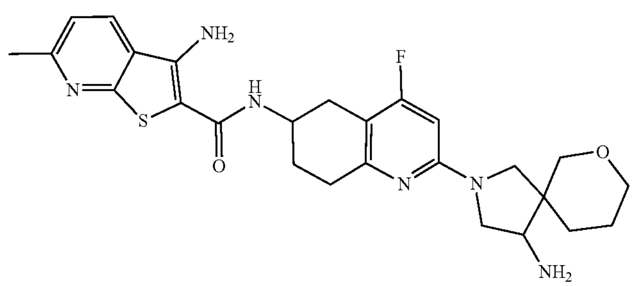 [SMILES: Cc1ccc2c(N)c(C(=O)NC3CCc4nc(N5CC(N)C6(CCCOC6)C5)cc(F)c4C3)sc2n1] | 3-amino-N-(2-{4-amino-7-oxa-2-azaspiro[4.5]decan-2-yl}-4-fluoro-5,6,7,8-tetrahydroquinolin-6-yl)-6-methylthieno[2,3-b]pyridine-2-carboxamide |
| 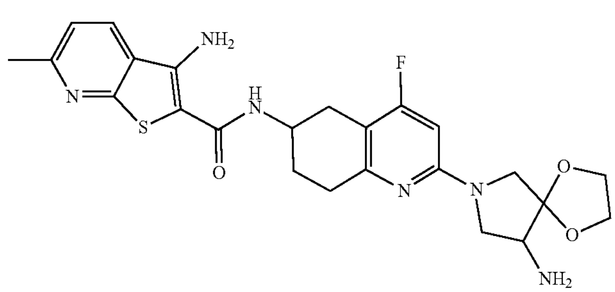 [SMILES: Cc1ccc2c(N)c(C(=O)NC3CCc4nc(N5CC(N)C6(C5)OCCO6)cc(F)c4C3)sc2n1] | 3-amino-N-(2-{9-amino-1,4-dioxa-7-azaspiro[4.4]nonan-7-yl}-4-fluoro-5,6,7,8-tetrahydroquinolin-6-yl)-6-methylthieno[2,3-b]pyridine-2-carboxamide |

TABLE 27-continued

| Structure | Chemical Name |
|---|---|
| 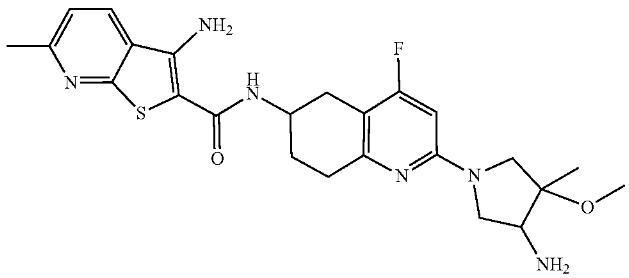 | 3-amino-N-[2-(4-amino-3-methoxy-3-methylpyrrolidin-1-yl)-4-fluoro-5,6,7,8-tetrahydroquinolin-6-yl]-6-methylthieno[2,3-b]pyridine-2-carboxamide |
| 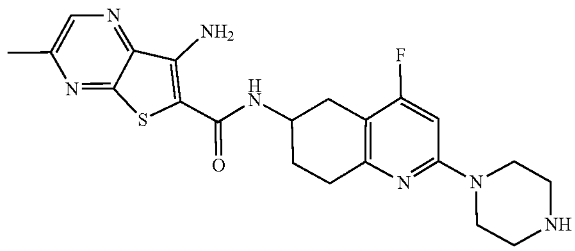 [SMILES: Cc1cnc2c(N)c(C(=O)NC3CCc4nc(N5CCNCC5)cc(F)c4C3)sc2n1] | 7-amino-N-[4-fluoro-2-(piperazin-1-yl)-5,6,7,8-tetrahydroquinolin-6-yl]-3-methylthieno[2,3-b]pyrazine-6-carboxamide |
| 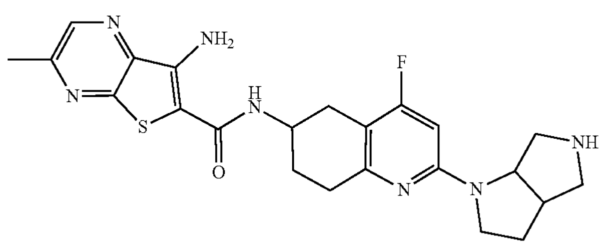 [SMILES: Cc1cnc2c(N)c(C(=O)NC3CCc4nc(N5CCC6CNCC65)cc(F)c4C3)sc2n1] | 7-amino-N-(4-fluoro-2-{octahydropyrrolo[2,3-c]pyrrol-1-yl}-5,6,7,8-tetrahydroquinolin-6-yl)-3-methylthieno[2,3-b]pyrazine-6-carboxamide |
| 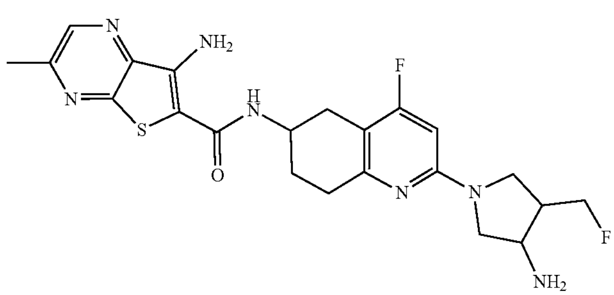 [SMILES: Cc1cnc2c(N)c(C(=O)NC3CCc4nc(N5CC(N)C(CF)C5)cc(F)c4C3)sc2n1] | 7-amino-N-{2-[3-amino-4-(fluoromethyl)pyrrolidin-1-yl]-4-fluoro-5,6,7,8-tetrahydroquinolin-6-yl}-3-methylthieno[2,3-b]pyrazine-6-carboxamide |
| 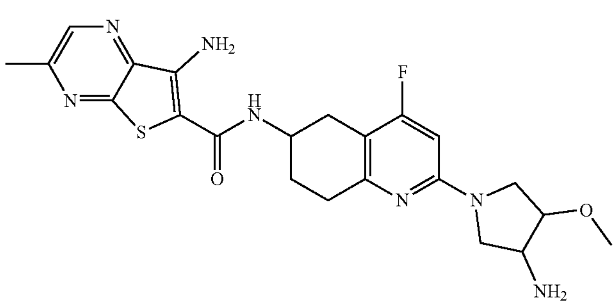 | 7-amino-N-[2-(3-amino-4-methoxypyrrolidin-1-yl)-4-fluoro-5,6,7,8-tetrahydroquinolin-6-yl]-3-methylthieno[2,3-b]pyrazine-6-carboxamide |

TABLE 27-continued

| Structure | Chemical Name |
|---|---|
| 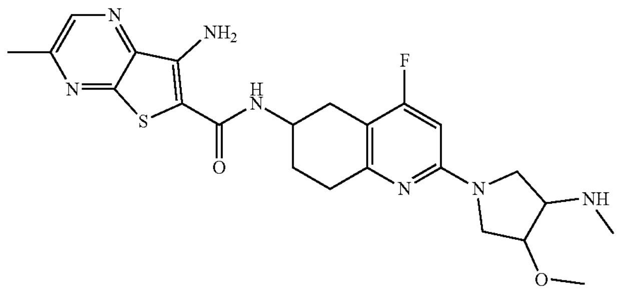 | 7-amino-N-{4-fluoro-2-[3-methoxy-4-(methylamino)pyrrolidin-1-yl]-5,6,7,8-tetrahydroquinolin-6-yl}-3-methylthieno[2,3-b]pyrazine-6-carboxamide |
| 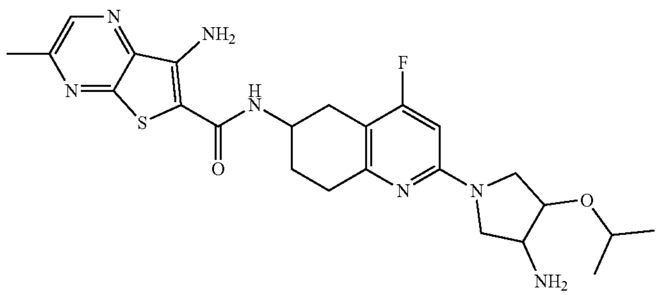 [SMILES: Cc1cnc2c(N)c(C(=O)NC3CCc4nc(N5CC(N)C(OC(C)C)C5)cc(F)c4C3)sc2n1] | 7-amino-N-{2-[3-amino-4-(propan-2-yloxy)pyrrolidin-1-yl]-4-fluoro-5,6,7,8-tetrahydroquinolin-6-yl}-3-methylthieno[2,3-b]pyrazine-6-carboxamide |
| 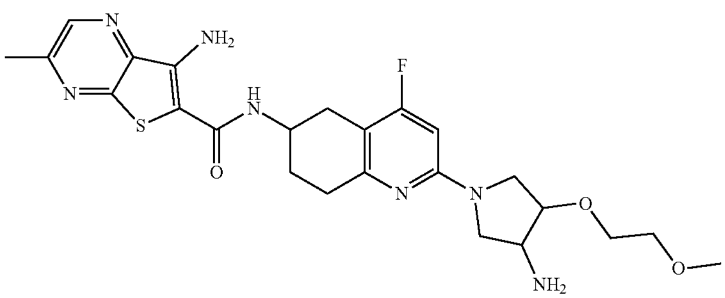 | 7-amino-N-{2-[3-amino-4-(2-methoxyethoxy)pyrrolidin-1-yl]-4-fluoro-5,6,7,8-tetrahydroquinolin-6-yl}-3-methylthieno[2,3-b]pyrazine-6-carboxamide |
| 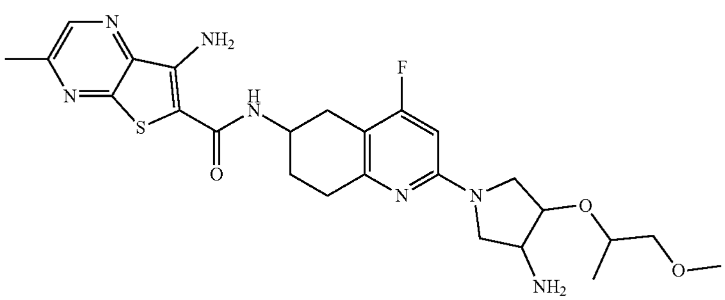 | 7-amino-N-(2-{3-amino-4-[(1-methoxypropan-2-yl)oxy]pyrrolidin-1-yl}-4-fluoro-5,6,7,8-tetrahydroquinolin-6-yl)-3-methylthieno[2,3-b]pyrazine-6-carboxamide |
| 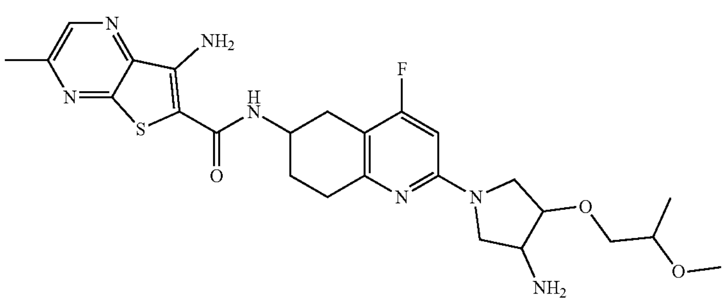 | 7-amino-N-{2-[3-amino-4-(2-methoxypropoxy)pyrrolidin-1-yl]-4-fluoro-5,6,7,8-tetrahydroquinolin-6-yl}-3-methylthieno[2,3-b]pyrazine-6-carboxamide |

TABLE 27-continued

| Structure | Chemical Name |
|---|---|
| 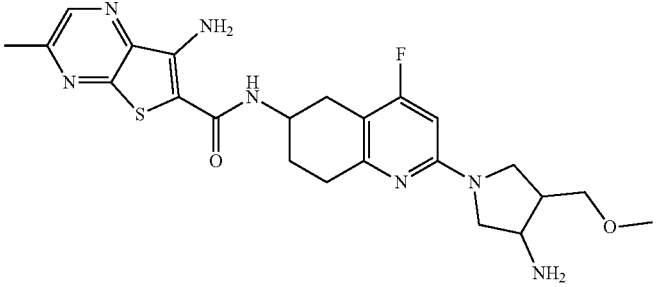 | 7-amino-N-{2-[3-amino-4-(methoxymethyl)pyrrolidin-1-yl]-4-fluoro-5,6,7,8-tetrahydroquinolin-6-yl}-3-methylthieno[2,3-b]pyrazine-6-carboxamide |
| 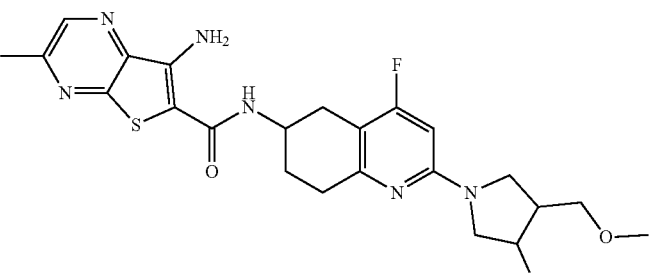 | 7-amino-N-{4-fluoro-2-[3-(methoxymethyl)-4-(methylamino)pyrrolidin-1-yl]-5,6,7,8-tetrahydroquinolin-6-yl}-3-methylthieno[2,3-b]pyrazine-6-carboxamide |
| 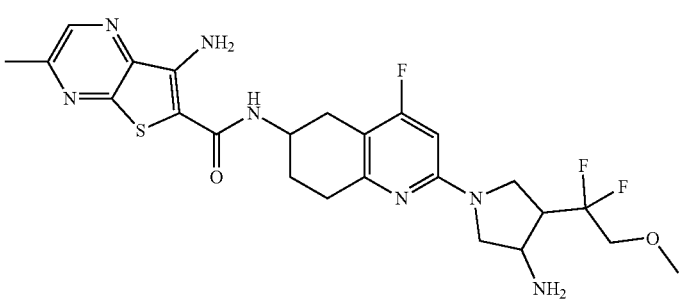 | 7-amino-N-{2-[3-amino-4-(1,1-difluoro-2-methoxyethyl)pyrrolidin-1-yl]-4-fluoro-5,6,7,8-tetrahydroquinolin-6-yl}-3-methylthieno[2,3-b]pyrazine-6-carboxamide |
| 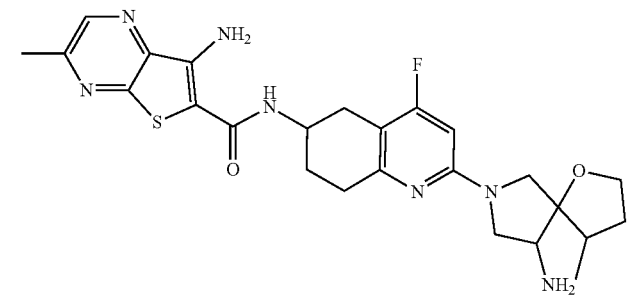 [SMILES: Cc1cnc2c(N)c(C(=O)NC3CCc4nc(N5CC(N)C6(C5)OCCC6C)cc(F)c4C3)sc2n1] | 7-amino-N-(2-{9-amino-4-methyl-1-oxa-7-azaspiro[4.4]nonan-7-yl}-4-fluoro-5,6,7,8-tetrahydroquinolin-6-yl)-3-methylthieno[2,3-b]pyrazine-6-carboxamide |
| 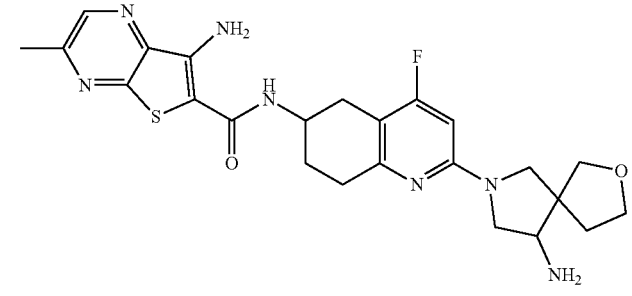 [SMILES: Cc1cnc2c(N)c(C(=O)NC3CCc4nc(N5CC(N)C6(CCOC6)C5)cc(F)c4C3)sc2n1] | 7-amino-N-(2-{9-amino-2-oxa-7-azaspiro[4.4]nonan-7-yl}-4-fluoro-5,6,7,8-tetrahydroquinolin-6-yl)-3-methylthieno[2,3-b]pyrazine-6-carboxamide |

TABLE 27-continued

| Structure | Chemical Name |
|---|---|
| 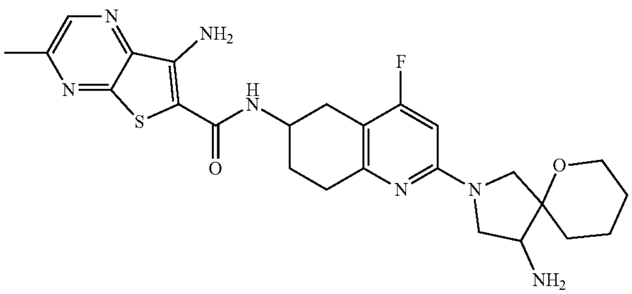 [SMILES: Cc1cnc2c(N)c(C(=O)NC3CCc4nc(N5CC(N)C6(CCCCO6)C5)cc(F)c4C3)sc2n1] | 7-amino-N-(2-{4-amino-6-oxa-2-azaspiro[4.5]decan-2-yl}-4-fluoro-5,6,7,8-tetrahydroquinolin-6-yl)-3-methylthieno[2,3-b]pyrazine-6-carboxamide |
| 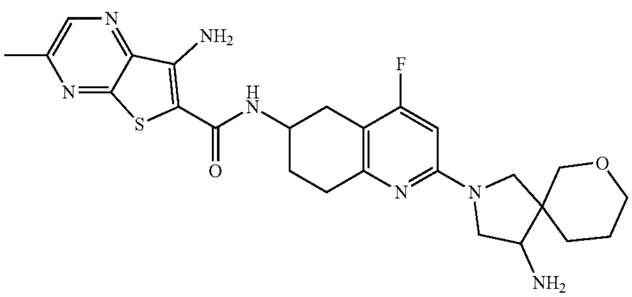 [SMILES: Cc1cnc2c(N)c(C(=O)NC3CCc4nc(N5CC(N)C6(CCCOC6)C5)cc(F)c4C3)sc2n1] | 7-amino-N-(2-{4-amino-7-oxa-2-azaspiro[4.5]decan-2-yl}-4-fluoro-5,6,7,8-tetrahydroquinolin-6-yl)-3-methylthieno[2,3-b]pyrazine-6-carboxamide |
| 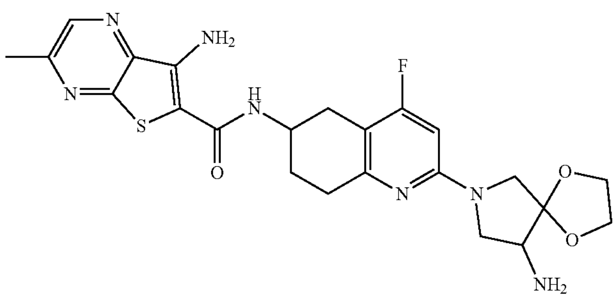 | 7-amino-N-(2-{9-amino-1,4-dioxa-7-azaspiro[4.4]nonan-7-yl}-4-fluoro-5,6,7,8-tetrahydroquinolin-6-yl)-3-methylthieno[2,3-b]pyrazine-6-carboxamide |
| 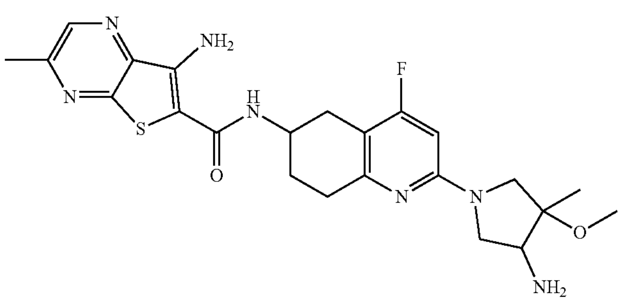 | 7-amino-N-[2-(4-amino-3-methoxy-3-methylpyrrolidin-1-yl)-4-fluoro-5,6,7,8-tetrahydroquinolin-6-yl]-3-methylthieno[2,3-b]pyrazine-6-carboxamide |
| 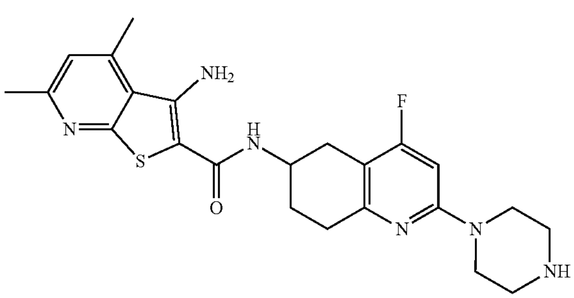 [SMILES: Cc1cc(C)c2c(N)c(C(=O)NC3CCc4nc(N5CCNCC5)cc(F)c4C3)sc2n1] | 3-amino-N-[4-fluoro-2-(piperazin-1-yl)-5,6,7,8-tetrahydroquinolin-6-yl]-4,6-dimethylthieno[2,3-b]pyridine-2-carboxamide |

TABLE 27-continued

| Structure | Chemical Name |
|---|---|
| 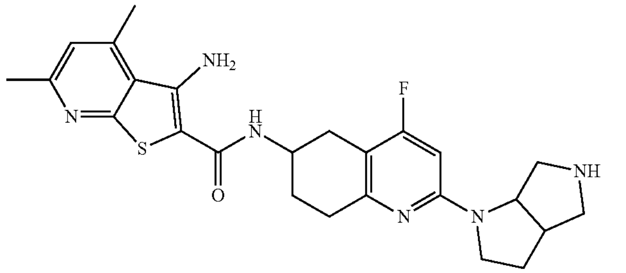 [SMILES: Cc1cc(C)c2c(N)c(C(=O)NC3CCc4nc(N5CCC6CNCC65)cc(F)c4C3)sc2n1] | 3-amino-N-(4-fluoro-2-{octahydropyrrolo[2,3-c]pyrrol-1-yl}-5,6,7,8-tetrahydroquinolin-6-yl)-4,6-dimethylthieno[2,3-b]pyridine-2-carboxamide |
| 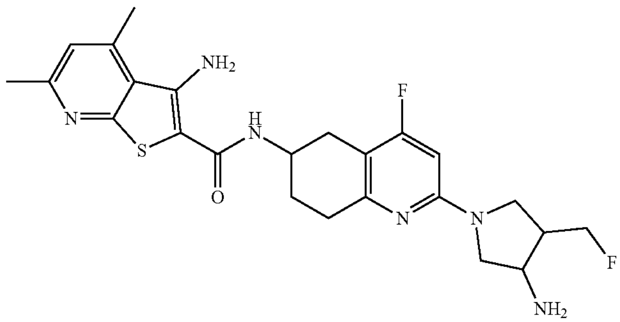 [SMILES: Cc1cc(C)c2c(N)c(C(=O)NC3CCc4nc(N5CC(N)C(CF)C5)cc(F)c4C3)sc2n1] | 3-amino-N-{2-[3-amino-4-(fluoromethyl)pyrrolidin-1-yl]-4-fluoro-5,6,7,8-tetrahydroquinolin-6-yl}-4,6-dimethylthieno[2,3-b]pyridine-2-carboxamide |
| 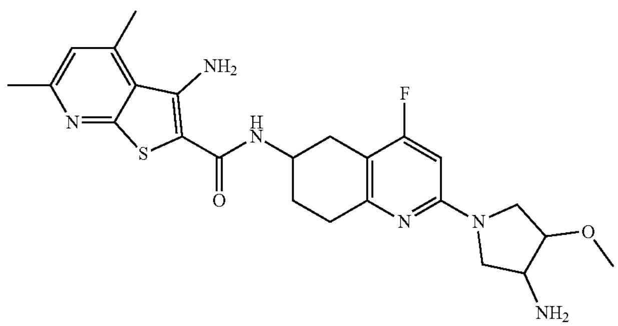 | 3-amino-N-[2-(3-amino-4-methoxypyrrolidin-1-yl)-4-fluoro-5,6,7,8-tetrahydroquinolin-6-yl]-4,6-dimethylthieno[2,3-b]pyridine-2-carboxamide |
| 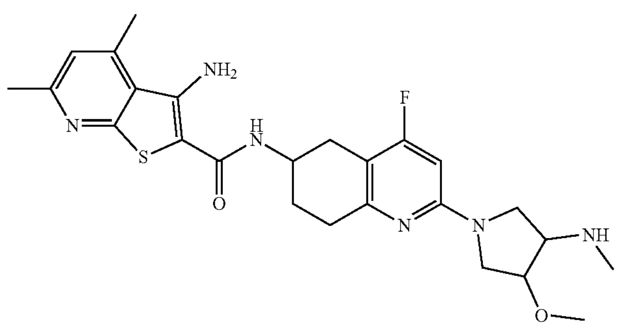 | 3-amino-N-{4-fluoro-2-[3-methoxy-4-(methylamino)pyrrolidin-1-yl]-5,6,7,8-tetrahydroquinolin-6-yl}-4,6-dimethylthieno[2,3-b]pyridine-2-carboxamide |
| 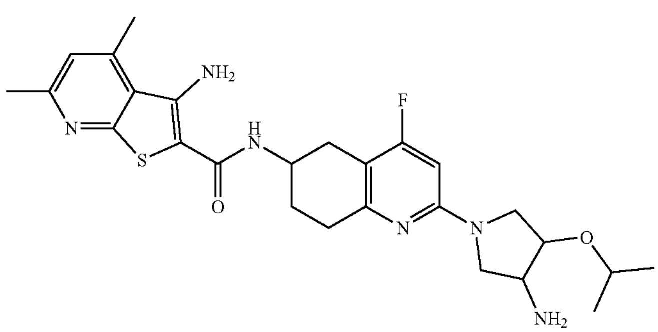 [SMILES: Cc1cc(C)c2c(N)c(C(=O)NC3CCc4nc(N5CC(N)C(OC(C)C)C5)cc(F)c4C3)sc2n1] | 3-amino-N-{2-[3-amino-4-(propan-2-yloxy)pyrrolidin-1-yl]-4-fluoro-5,6,7,8-tetrahydroquinolin-6-yl}-4,6-dimethylthieno[2,3-b]pyridine-2-carboxamide |

TABLE 27-continued

| Structure | Chemical Name |
|---|---|
| 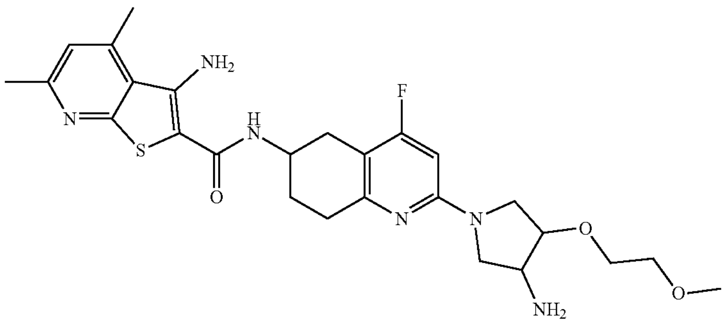 | 3-amino-N-{2-[3-amino-4-(2-methoxyethoxy)pyrrolidin-1-yl]-4-fluoro-5,6,7,8-tetrahydroquinolin-6-yl}-4,6-dimethylthieno[2,3-b]pyridine-2-carboxamide |
| 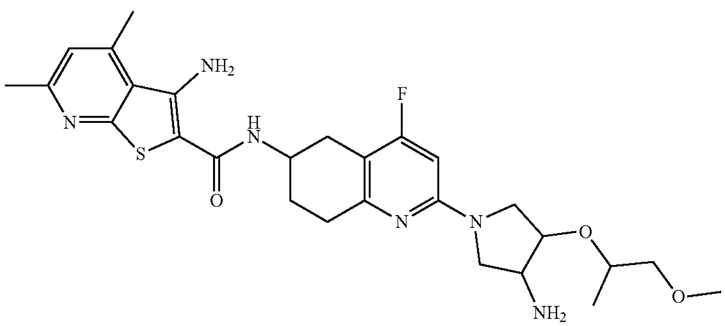 | 3-amino-N-(2-{3-amino-4-[(1-methoxypropan-2-yl)oxy]pyrrolidin-1-yl}-4-fluoro-5,6,7,8-tetrahydroquinolin-6-yl)-4,6-dimethylthieno[2,3-b]pyridine-2-carboxamide |
| 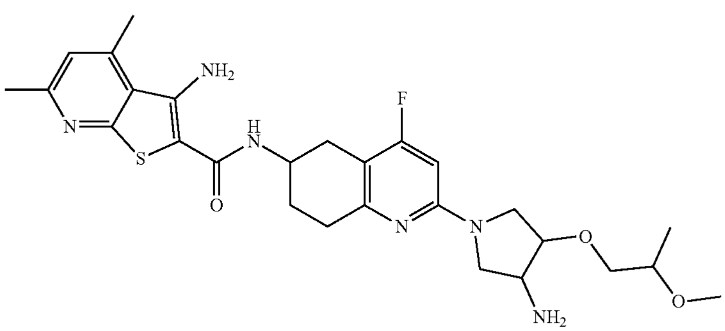 | 3-amino-N-{2-[3-amino-4-(2-methoxypropoxy)pyrrolidin-1-yl]-4-fluoro-5,6,7,8-tetrahydroquinolin-6-yl}-4,6-dimethylthieno[2,3-b]pyridine-2-carboxamide |
| 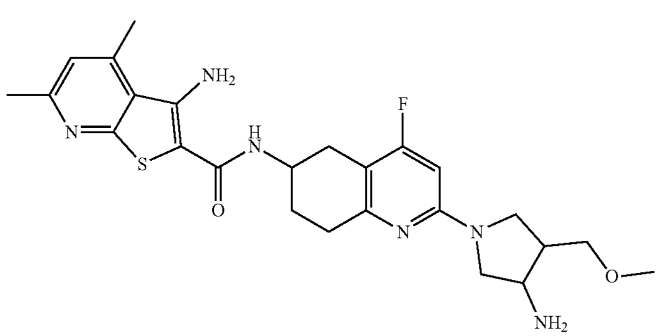 | 3-amino-N-{2-[3-amino-4-(methoxymethyl)pyrrolidin-1-yl]-4-fluoro-5,6,7,8-tetrahydroquinolin-6-yl}-4,6-dimethylthieno[2,3-b]pyridine-2-carboxamide |

TABLE 27-continued

| Structure | Chemical Name |
|---|---|
| 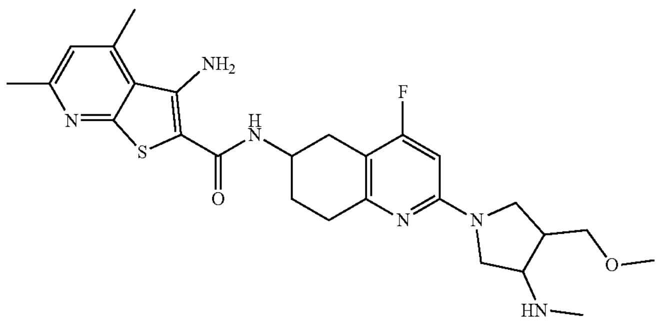 | 3-amino-N-{4-fluoro-2-[3-(methoxymethyl)-4-(methylamino)pyrrolidin-1-yl]-5,6,7,8-tetrahydroquinolin-6-yl}-4,6-dimethylthieno[2,3-b]pyridine-2-carboxamide |
| 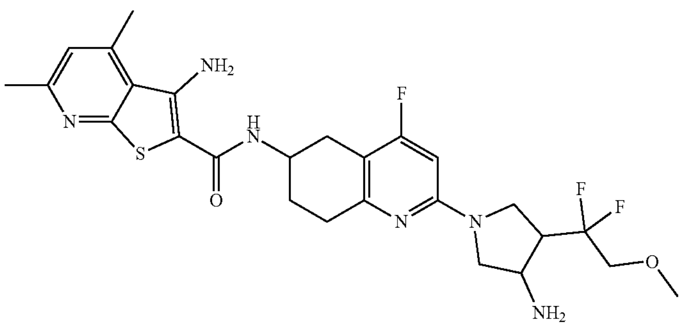 | 3-amino-N-{2-[3-amino-4-(1,1-difluoro-2-methoxyethyl)pyrrolidin-1-yl]-4-fluoro-5,6,7,8-tetrahydroquinolin-6-yl}-4,6-dimethylthieno[2,3-b]pyridine-2-carboxamide |
| 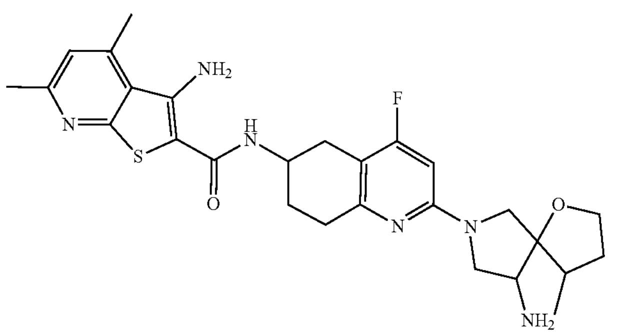 [SMILES: Cc1cc(C)c2c(N)c(C(=O)NC3CCc4nc(N5CC(N)C6(C5)OCCC6C)cc(F)c4C3)sc2n1] | 3-amino-N-(2-{9-amino-4-methyl-1-oxa-7-azaspiro[4.4]nonan-7-yl}-4-fluoro-5,6,7,8-tetrahydroquinolin-6-yl)-4,6-dimethylthieno[2,3-b]pyridine-2-carboxamide |
| 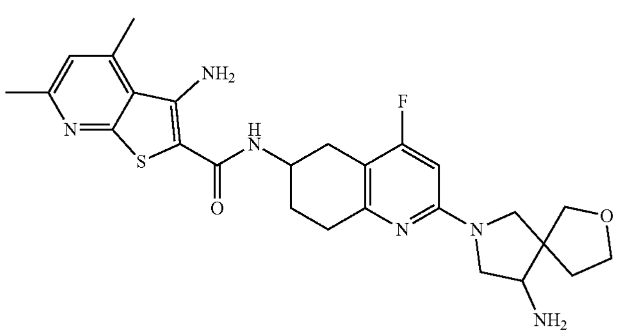 [SMILES: Cc1cc(C)c2c(N)c(C(=O)NC3CCc4nc(N5CC(N)C6(CCOC6)C5)cc(F)c4C3)sc2n1] | 3-amino-N-(2-{9-amino-2-oxa-7-azaspiro[4.4]nonan-7-yl}-4-fluoro-5,6,7,8-tetrahydroquinolin-6-yl)-4,6-dimethylthieno[2,3-b]pyridine-2-carboxamide |

TABLE 27-continued

| Structure | Chemical Name |
|---|---|
| | 3-amino-N-(2-{4-amino-6-oxa-2-azaspiro[4.5]decan-2-yl}-4-fluoro-5,6,7,8-tetrahydroquinolin-6-yl)-4,6-dimethylthieno[2,3-b]pyridine-2-carboxamide |
| 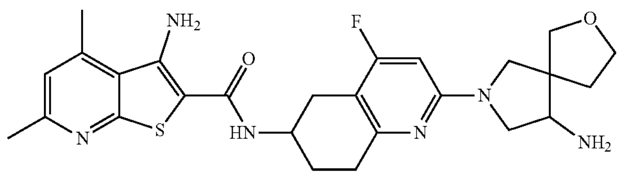 | 3-amino-N-(2-{9-amino-2-oxa-7-azaspiro[4.4]nonan-7-yl}-4-fluoro-5,6,7,8-tetrahydroquinolin-6-yl)-4,6-dimethylthieno[2,3-b]pyridine-2-carboxamide |
| | 3-amino-N-(2-{4-amino-6-oxa-2-azaspiro[4.5]decan-2-yl}-4-fluoro-5,6,7,8-tetrahydroquinolin-6-yl)-4,6-dimethylthieno[2,3-b]pyridine-2-carboxamide |
| 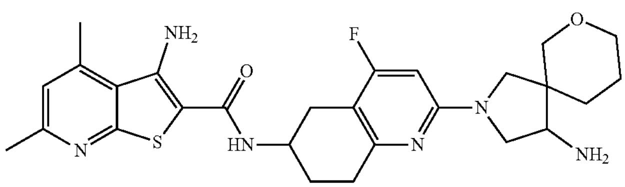 [SMILES: Cc1cc(C)c2c(N)c(C(=O)NC3CCc4nc(N5CC(N)C6(CCCOC6)C5)cc(F)c4C3)sc2n1] | 3-amino-N-(2-{4-amino-7-oxa-2-azaspiro[4.5]decan-2-yl}-4-fluoro-5,6,7,8-tetrahydroquinolin-6-yl)-4,6-dimethylthieno[2,3-b]pyridine-2-carboxamide |
| 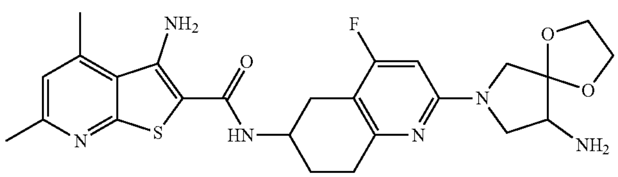 [SMILES: Cc1cc(C)c2c(N)c(C(=O)NC3CCc4nc(N5CC(N)C6(C5)OCCO6)cc(F)c4C3)sc2n1] | 3-amino-N-(2-{9-amino-1,4-dioxa-7-azaspiro[4.4]nonan-7-yl}-4-fluoro-5,6,7,8-tetrahydroquinolin-6-yl)-4,6-dimethylthieno[2,3-b]pyridine-2-carboxamide |
| 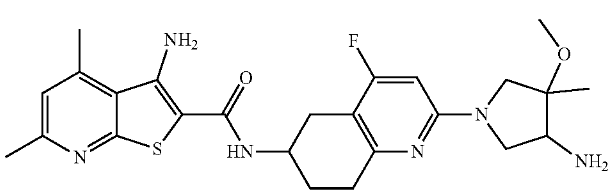 | 3-amino-N-[2-(4-amino-3-methoxy-3-methylpyrrolidin-1-yl)-4-fluoro-5,6,7,8-tetrahydroquinolin-6-yl]-4,6-dimethylthieno[2,3-b]pyridine-2-carboxamide |
| 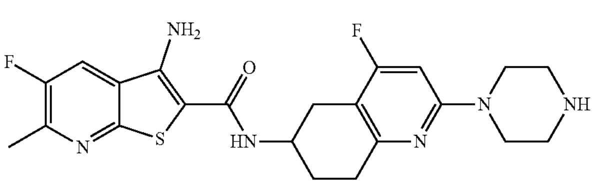 [SMILES: Cc1nc2sc(C(=O)NC3CCc4nc(N5CCNCC5)cc(F)c4C3)c(N)c2cc1F] | 3-amino-5-fluoro-N-[4-fluoro-2-(piperazin-1-yl)-5,6,7,8-tetrahydroquinolin-6-yl]-6-methylthieno[2,3-b]pyridine-2-carboxamide |

TABLE 27-continued

| Structure | Chemical Name |
|---|---|
| 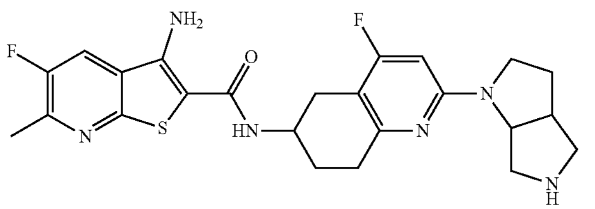 [SMILES: Cc1nc2sc(C(=O)NC3CCc4nc(N5CCC6CNCC65)cc(F)c4C3)c(N)c2cc1F] | 3-amino-5-fluoro-N-(4-fluoro-2-{octahydropyrrolo[2,3-c]pyrrol-1-yl}-5,6,7,8-tetrahydroquinolin-6-yl)-6-methylthieno[2,3-b]pyridine-2-carboxamide |
| 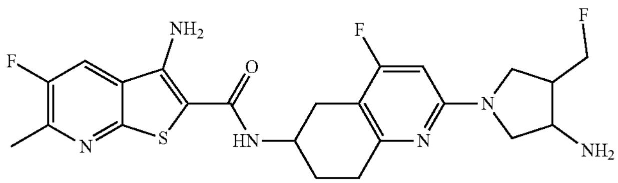 [SMILES: Cc1nc2sc(C(=O)NC3CCc4nc(N5CC(N)C(CF)C5)cc(F)c4C3)c(N)c2cc1F] | 3-amino-N-{2-[3-amino-4-(fluoromethyl)pyrrolidin-1-yl]-4-fluoro-5,6,7,8-tetrahydroquinolin-6-yl}-5-fluoro-6-methylthieno[2,3-b]pyridine-2-carboxamide |
| 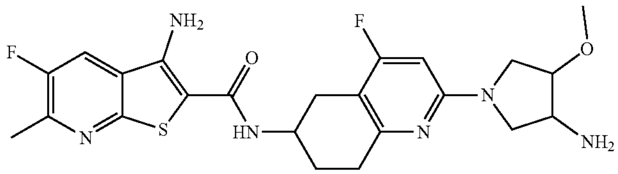 [SMILES: COC1CN(c2cc(F)c3c(n2)CCC(NC(=O)c2sc4nc(C)c(F)cc4c2N)C3)CC1N] | 3-amino-N-[2-(3-amino-4-methoxypyrrolidin-1-yl)-4-fluoro-5,6,7,8-tetrahydroquinolin-6-yl]-5-fluoro-6-methylthieno[2,3-b]pyridine-2-carboxamide |
| 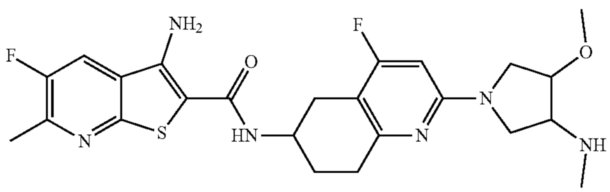 [SMILES: CNC1CN(c2cc(F)c3c(n2)CCC(NC(=O)c2sc4nc(C)c(F)cc4c2N)C3)CC1OC] | 3-amino-5-fluoro-N-{4-fluoro-2-[3-methoxy-4-(methylamino)pyrrolidin-1-yl]-5,6,7,8-tetrahydroquinolin-6-yl}-6-methylthieno[2,3-b]pyridine-2-carboxamide |
| 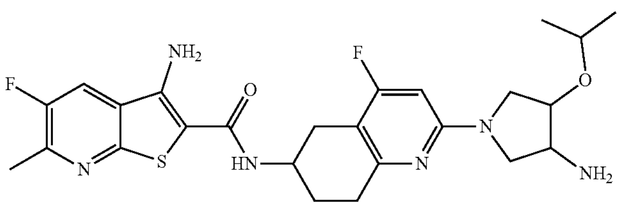 [SMILES: Cc1nc2sc(C(=O)NC3CCc4nc(N5CC(N)C(OC(C)C)C5)cc(F)c4C3)c(N)c2cc1F] | 3-amino-N-{2-[3-amino-4-(propan-2-yloxy)pyrrolidin-1-yl]-4-fluoro-5,6,7,8-tetrahydroquinolin-6-yl}-5-fluoro-6-methylthieno[2,3-b]pyridine-2-carboxamide |
| 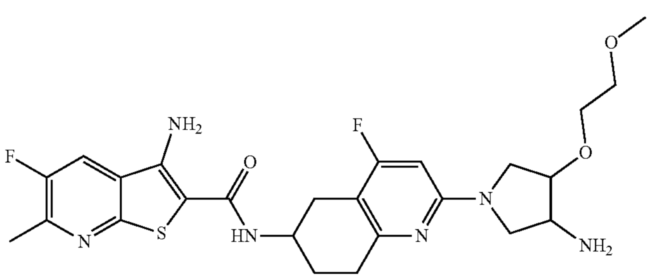 [SMILES: COCCOC1CN(c2cc(F)c3c(n2)CCC(NC(=O)c2sc4nc(C)c(F)cc4c2N)C3)CC1N] | 3-amino-N-{2-[3-amino-4-(2-methoxyethoxy)pyrrolidin-1-yl]-4-fluoro-5,6,7,8-tetrahydroquinolin-6-yl}-5-fluoro-6-methylthieno[2,3-b]pyridine-2-carboxamide |
| 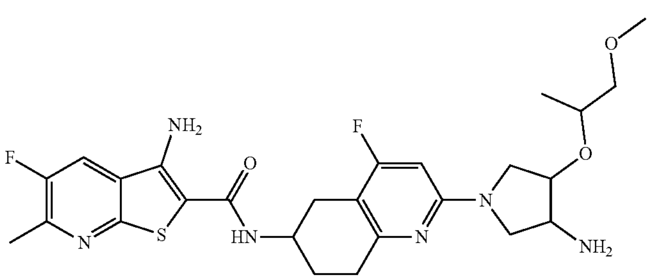 | 3-amino-N-(2-{3-amino-4-[(1-methoxypropan-2-yl)oxy]pyrrolidin-1-yl}-4-fluoro-5,6,7,8-tetrahydroquinolin-6-yl)-5-fluoro-6-methylthieno[2,3-b]pyridine-2-carboxamide |

TABLE 27-continued

| Structure | Chemical Name |
|---|---|
| 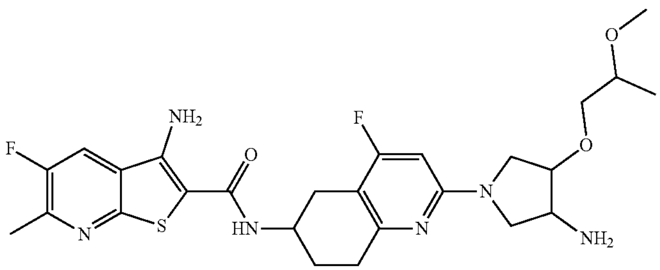 [SMILES: COC(C)COC1CN(c2cc(F)c3c(n2)CCC(NC(=O)c2sc4nc(C)c(F)cc4c2N)C3)CC1N] | 3-amino-N-{2-[3-amino-4-(2-methoxypropoxy)pyrrolidin-1-yl]-4-fluoro-5,6,7,8-tetrahydroquinolin-6-yl}-5-fluoro-6-methylthieno[2,3-b]pyridine-2-carboxamide |
| 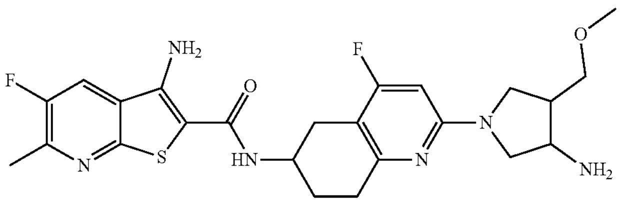 [SMILES: COCC1CN(c2cc(F)c3c(n2)CCC(NC(=O)c2sc4nc(C)c(F)cc4c2N)C3)CC1N] | 3-amino-N-{2-[3-amino-4-(methoxymethyl)pyrrolidin-1-yl]-4-fluoro-5,6,7,8-tetrahydroquinolin-6-yl}-5-fluoro-6-methylthieno[2,3-b]pyridine-2-carboxamide |
| 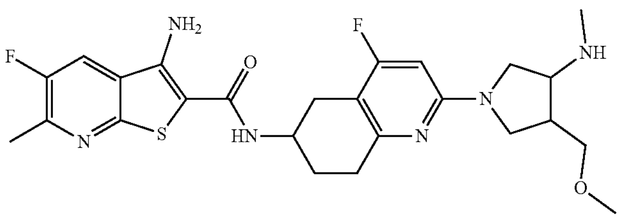 | 3-amino-5-fluoro-N-{4-fluoro-2-[3-(methoxymethyl)-4-(methylamino)pyrrolidin-1-yl]-5,6,7,8-tetrahydroquinolin-6-yl}-6-methylthieno[2,3-b]pyridine-2-carboxamide |
| 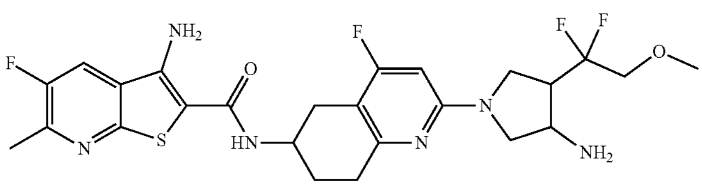 | 3-amino-N-{2-[3-amino-4-(1,1-difluoro-2-methoxyethyl)pyrrolidin-1-yl]-4-fluoro-5,6,7,8-tetrahydroquinolin-6-yl}-5-fluoro-6-methylthieno[2,3-b]pyridine-2-carboxamide |
| 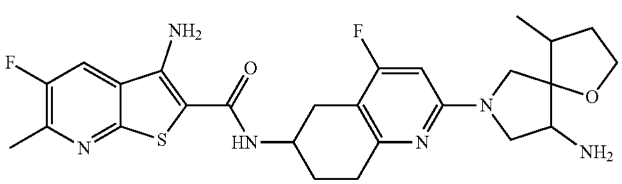 [SMILES: Cc1nc2sc(C(=O)NC3CCc4nc(N5CC(N)C6(C5)OCCC6C)cc(F)c4C3)c(N)c2cc1F] | 3-amino-N-(2-{9-amino-4-methyl-1-oxa-7-azaspiro[4.4]nonan-7-yl}-4-fluoro-5,6,7,8-tetrahydroquinolin-6-yl)-5-fluoro-6-methylthieno[2,3-b]pyridine-2-carboxamide |
| 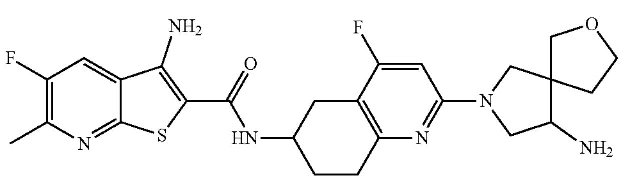 [SMILES: Cc1nc2sc(C(=O)NC3CCc4nc(N5CC(N)C6(CCOC6)C5)cc(F)c4C3)c(N)c2cc1F] | 3-amino-N-(2-{9-amino-2-oxa-7-azaspiro[4.4]nonan-7-yl}-4-fluoro-5,6,7,8-tetrahydroquinolin-6-yl)-5-fluoro-6-methylthieno[2,3-b]pyridine-2-carboxamide |
| 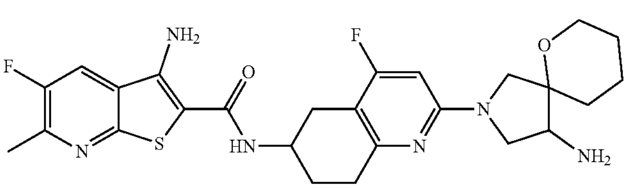 [SMILES: Cc1nc2sc(C(=O)NC3CCc4nc(N5CC(N)C6(CCCCO6)C5)cc(F)c4C3)c(N)c2cc1F] | 3-amino-N-(2-{4-amino-6-oxa-2-azaspiro[4.5]decan-2-yl}-4-fluoro-5,6,7,8-tetrahydroquinolin-6-yl)-5-fluoro-6-methylthieno[2,3-b]pyridine-2-carboxamide |

TABLE 27-continued

| Structure | Chemical Name |
|---|---|
| 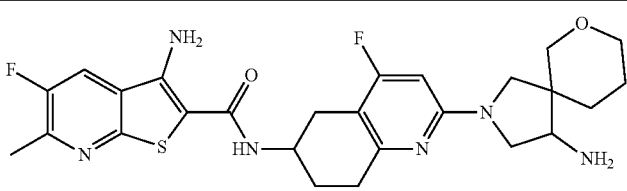 | 3-amino-N-(2-{4-amino-7-oxa-2-azaspiro[4.5]decan-2-yl}-4-fluoro-5,6,7,8-tetrahydroquinolin-6-yl)-5-fluoro-6-methylthieno[2,3-b]pyridine-2-carboxamide |
| 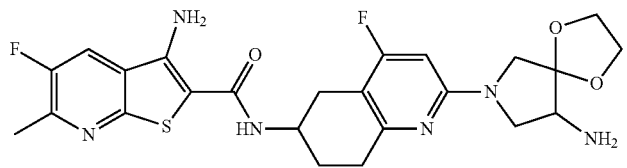 | 3-amino-N-(2-{9-amino-1,4-dioxa-7-azaspiro[4.4]nonan-7-yl}-4-fluoro-5,6,7,8-tetrahydroquinolin-6-yl)-5-fluoro-6-methylthieno[2,3-b]pyridine-2-carboxamide |
| 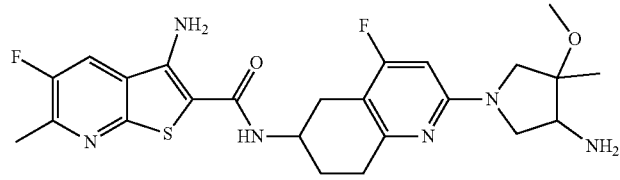 | 3-amino-N-[2-(4-amino-3-methoxy-3-methylpyrrolidin-1-yl)-4-fluoro-5,6,7,8-tetrahydroquinolin-6-yl]-5-fluoro-6-methylthieno[2,3-b]pyridine-2-carboxamide |
| 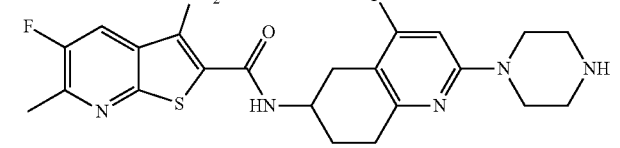 | 5-amino-N-[4-fluoro-2-(piperazin-1-yl)-5,6,7,8-tetrahydroquinolin-6-yl]-2-methylthieno[2,3-d]pyrimidine-6-carboxamide |
| 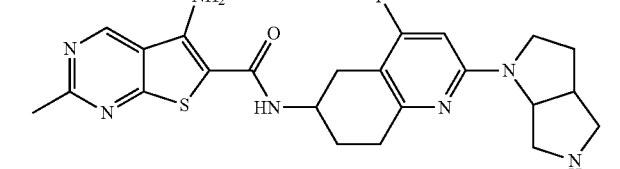 | 5-amino-N-(4-fluoro-2-{octahydropyrrolo[2,3-c]pyrrol-1-yl}-5,6,7,8-tetrahydroquinolin-6-yl)-2-methylthieno[2,3-d]pyrimidine-6-carboxamide |
| 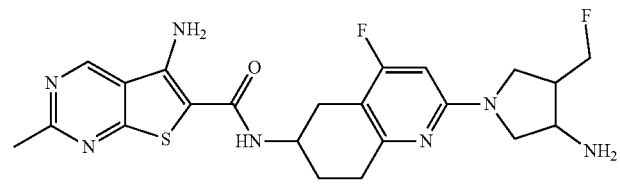 [SMILES: Cc1ncc2c(N)c(C(=O)NC3CCc4nc(N5CC(N)C(CF)C5)cc(F)c4C3)sc2n1] | 5-amino-N-{2-[3-amino-4-(fluoromethyl)pyrrolidin-1-yl]-4-fluoro-5,6,7,8-tetrahydroquinolin-6-yl}-2-methylthieno[2,3-d]pyrimidine-6-carboxamide |
| 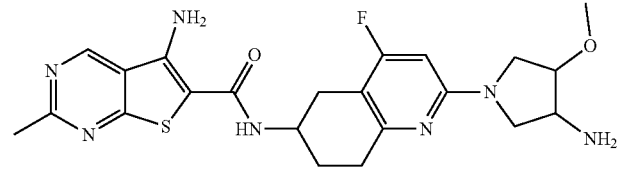 [SMILES: COC1CN(c2cc(F)c3c(n2)CCC(NC(=O)c2sc4nc(C)ncc4c2N)C3)CC1N] | 5-amino-N-[2-(3-amino-4-methoxypyrrolidin-1-yl)-4-fluoro-5,6,7,8-tetrahydroquinolin-6-yl]-2-methylthieno[2,3-d]pyrimidine-6-carboxamide |
| 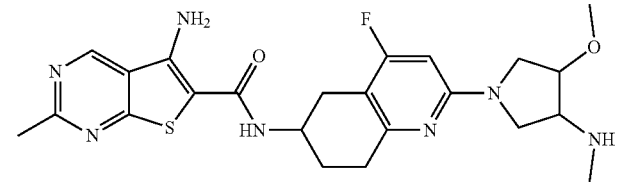 [SMILES: CNC1CN(c2cc(F)c3c(n2)CCC(NC(=O)c2sc4nc(C)ncc4c2N)C3)CC1OC] | 5-amino-N-{4-fluoro-2-[3-methoxy-4-(methylamino)pyrrolidin-1-yl]-5,6,7,8-tetrahydroquinolin-6-yl}-2-methylthieno[2,3-d]pyrimidine-6-carboxamide |

| Structure | Chemical Name |
|---|---|
| 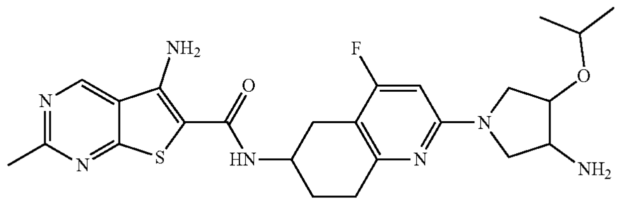 [SMILES: Cc1ncc2c(N)c(C(=O)NC3CCc4nc(N5CC(N)C(OC(C)C)C5)cc(F)c4C3)sc2n1] | 5-amino-N-{2-[3-amino-4-(propan-2-yloxy)pyrrolidin-1-yl]-4-fluoro-5,6,7,8-tetrahydroquinolin-6-yl}-2-methylthieno[2,3-d]pyrimidine-6-carboxamide |
| 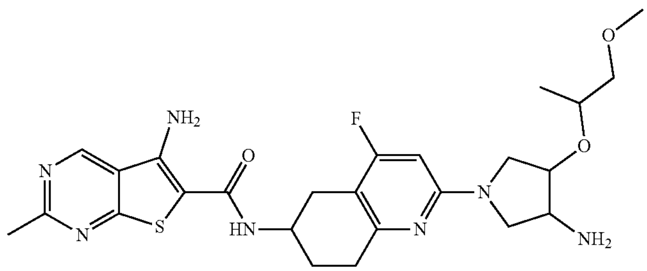 | 5-amino-N-{2-[3-amino-4-(2-methoxyethoxy)pyrrolidin-1-yl]-4-fluoro-5,6,7,8-tetrahydroquinolin-6-yl}-2-methylthieno[2,3-d]pyrimidine-6-carboxamide |
| 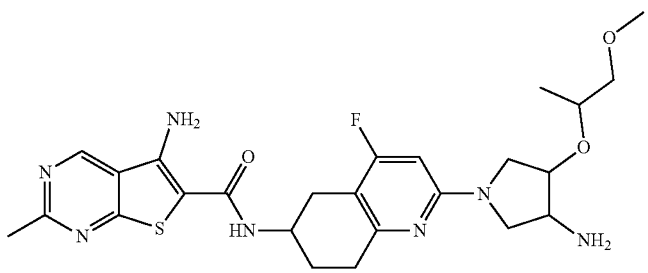 | 5-amino-N-(2-{3-amino-4-[(1-methoxypropan-2-yl)oxy]pyrrolidin-1-yl}-4-fluoro-5,6,7,8-tetrahydroquinolin-6-yl)-2-methylthieno[2,3-d]pyrimidine-6-carboxamide |
| 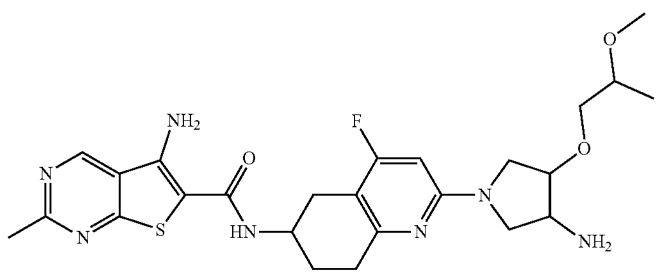 | 5-amino-N-{2-[3-amino-4-(2-methoxypropoxy)pyrrolidin-1-yl]-4-fluoro-5,6,7,8-tetrahydroquinolin-6-yl}-2-methylthieno[2,3-d]pyrimidine-6-carboxamide |
| 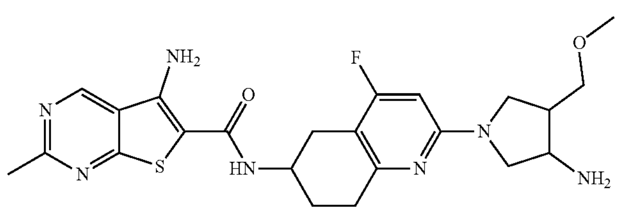 | 5-amino-N-{2-[3-amino-4-(methoxymethyl)pyrrolidin-1-yl]-4-fluoro-5,6,7,8-tetrahydroquinolin-6-yl}-2-methylthieno[2,3-d]pyrimidine-6-carboxamide |
| 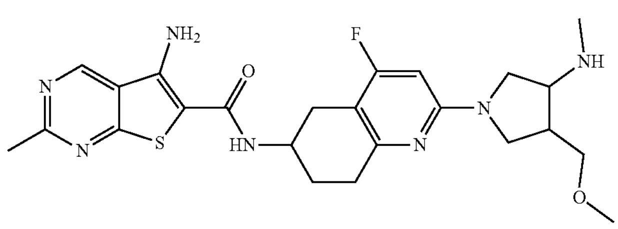 | 5-amino-N-{4-fluoro-2-[3-(methoxymethyl)-4-(methylamino)pyrrolidin-1-yl]-5,6,7,8-tetrahydroquinolin-6-yl}-2-methylthieno[2,3-d]pyrimidine-6-carboxamide |

TABLE 27-continued

| Structure | Chemical Name |
|---|---|
| 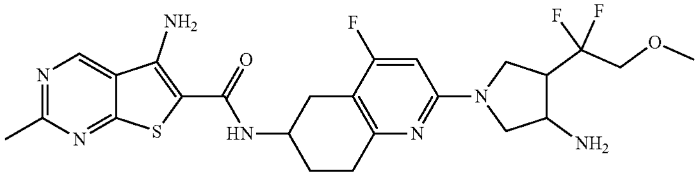 | 5-amino-N-{2-[3-amino-4-(1,1-difluoro-2-methoxyethyl)pyrrolidin-1-yl]-4-fluoro-5,6,7,8-tetrahydroquinolin-6-yl}-2-methylthieno[2,3-d]pyrimidine-6-carboxamide |
| 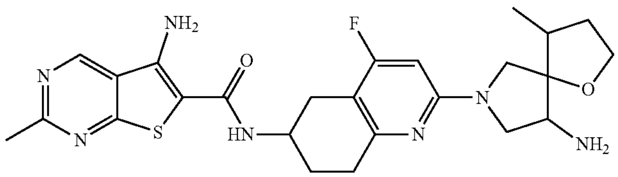 [SMILES: Cc1ncc2c(N)c(C(=O)NC3CCc4nc(N5CC(N)C6(C5)OCCC6C)cc(F)c4C3)sc2n1] | 5-amino-N-(2-{9-amino-4-methyl-1-oxa-7-azaspiro[4.4]nonan-7-yl}-4-fluoro-5,6,7,8-tetrahydroquinolin-6-yl)-2-methylthieno[2,3-d]pyrimidine-6-carboxamide |
| 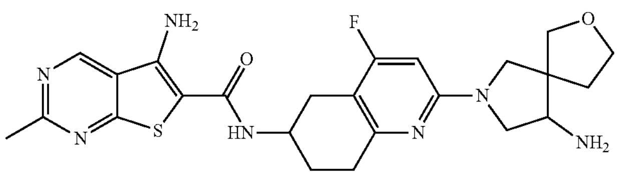 [SMILES: Cc1ncc2c(N)c(C(=O)NC3CCc4nc(N5CC(N)C6(CCOC6)C5)cc(F)c4C3)sc2n1] | 5-amino-N-(2-{9-amino-2-oxa-7-azaspiro[4.4]nonan-7-yl}-4-fluoro-5,6,7,8-tetrahydroquinolin-6-yl)-2-methylthieno[2,3-d]pyrimidine-6-carboxamide |
| 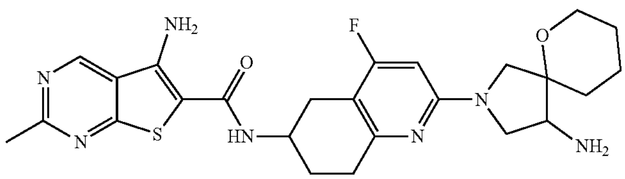 [SMILES: Cc1ncc2c(N)c(C(=O)NC3CCc4nc(N5CC(N)C6(CCCCO6)C5)cc(F)c4C3)sc2n1] | 5-amino-N-(2-{4-amino-6-oxa-2-azaspiro[4.5]decan-2-yl}-4-fluoro-5,6,7,8-tetrahydroquinolin-6-yl)-2-methylthieno[2,3-d]pyrimidine-6-carboxamide |
| 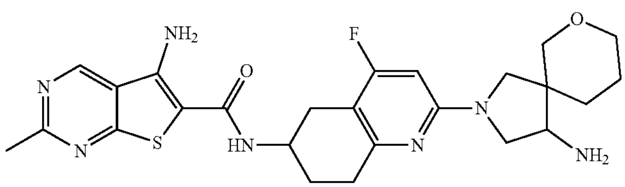 [SMILES: Cc1ncc2c(N)c(C(=O)NC3CCc4nc(N5CC(N)C6(CCCOC6)C5)cc(F)c4C3)sc2n1] | 5-amino-N-(2-{4-amino-7-oxa-2-azaspiro[4.5]decan-2-yl}-4-fluoro-5,6,7,8-tetrahydroquinolin-6-yl)-2-methylthieno[2,3-d]pyrimidine-6-carboxamide |
| 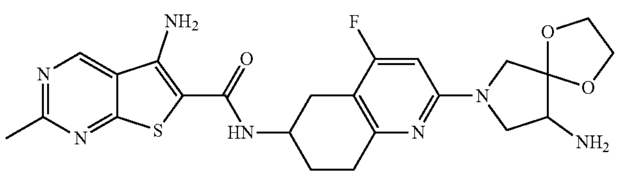 [SMILES: Cc1ncc2c(N)c(C(=O)NC3CCc4nc(N5CC(N)C6(C5)OCCO6)cc(F)c4C3)sc2n1] | 5-amino-N-(2-{9-amino-1,4-dioxa-7-azaspiro[4.4]nonan-7-yl}-4-fluoro-5,6,7,8-tetrahydroquinolin-6-yl)-2-methylthieno[2,3-d]pyrimidine-6-carboxamide |
| 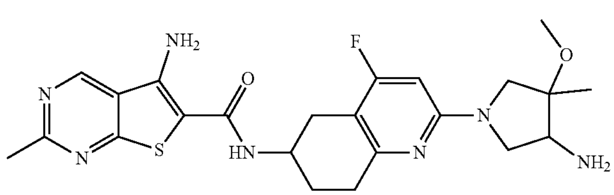 | 5-amino-N-[2-(4-amino-3-methoxy-3-methylpyrrolidin-1-yl)-4-fluoro-5,6,7,8-tetrahydroquinolin-6-yl]-2-methylthieno[2,3-d]pyrimidine-6-carboxamide |
| 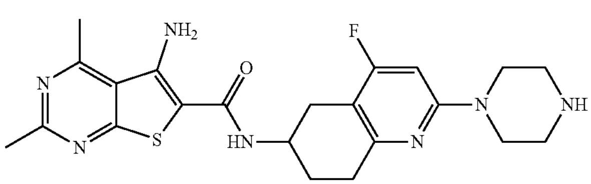 | 5-amino-N-[4-fluoro-2-(piperazin-1-yl)-5,6,7,8-tetrahydroquinolin-6-yl]-2,4-dimethylthieno[2,3-d]pyrimidine-6-carboxamide |

TABLE 27-continued

| Structure | Chemical Name |
|---|---|
| 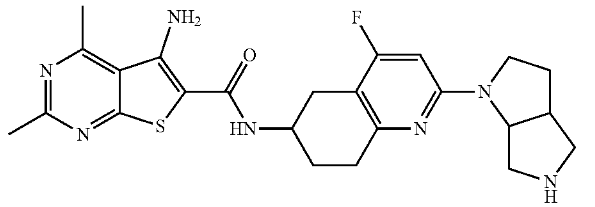 [SMILES: Cc1nc(C)c2c(N)c(C(=O)NC3CCc4nc(N5CCC6CNCC65)cc(F)c4C3)sc2n1] | 5-amino-N-(4-fluoro-2-{octahydropyrrolo[2,3-c]pyrrol-1-yl}-5,6,7,8-tetrahydroquinolin-6-yl)-2,4-dimethylthieno[2,3-d]pyrimidine-6-carboxamide |
| 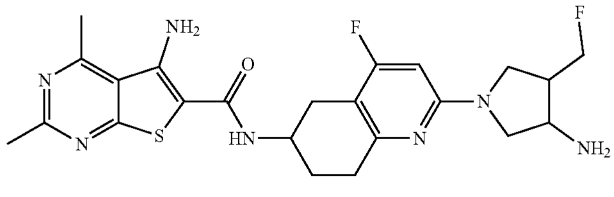 [SMILES: Cc1nc(C)c2c(N)c(C(=O)NC3CCc4nc(N5CC(N)C(CF)C5)cc(F)c4C3)sc2n1] | 5-amino-N-{2-[3-amino-4-(fluoromethyl)pyrrolidin-1-yl]-4-fluoro-5,6,7,8-tetrahydroquinolin-6-yl}-2,4-dimethylthieno[2,3-d]pyrimidine-6-carboxamide |
| 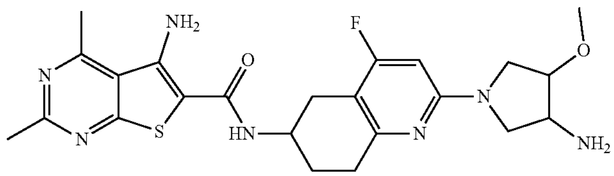 [SMILES: COC1CN(c2cc(F)c3c(n2)CCC(NC(=O)c2sc4nc(C)nc(C)c4c2N)C3)CC1N] | 5-amino-N-[2-(3-amino-4-methoxypyrrolidin-1-yl)-4-fluoro-5,6,7,8-tetrahydroquinolin-6-yl]-2,4-dimethylthieno[2,3-d]pyrimidine-6-carboxamide |
| 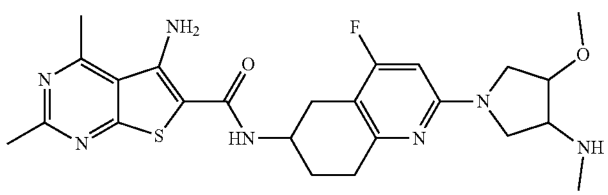 [SMILES: CNC1CN(c2cc(F)c3c(n2)CCC(NC(=O)c2sc4nc(C)nc(C)c4c2N)C3)CC1OC] | 5-amino-N-{4-fluoro-2-[3-methoxy-4-(methylamino)pyrrolidin-1-yl]-5,6,7,8-tetrahydroquinolin-6-yl}-2,4-dimethylthieno[2,3-d]pyrimidine-6-carboxamide |
| 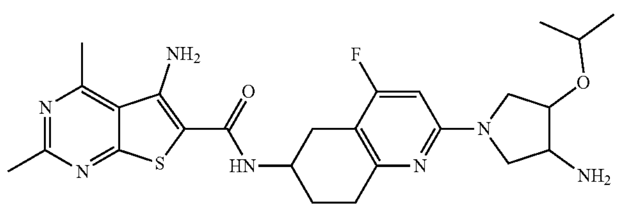 [SMILES: Cc1nc(C)c2c(N)c(C(=O)NC3CCc4nc(N5CC(N)C(OC(C)C)C5)cc(F)c4C3)sc2n1] | 5-amino-N-{2-[3-amino-4-(propan-2-yloxy)pyrrolidin-1-yl]-4-fluoro-5,6,7,8-tetrahydroquinolin-6-yl}-2,4-dimethylthieno[2,3-d]pyrimidine-6-carboxamide |
| 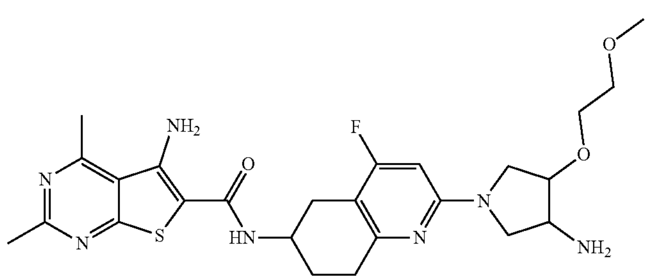 | 5-amino-N-{2-[3-amino-4-(2-methoxyethoxy)pyrrolidin-1-yl]-4-fluoro-5,6,7,8-tetrahydroquinolin-6-yl}-2,4-dimethylthieno[2,3-d]pyrimidine-6-carboxamide |
| 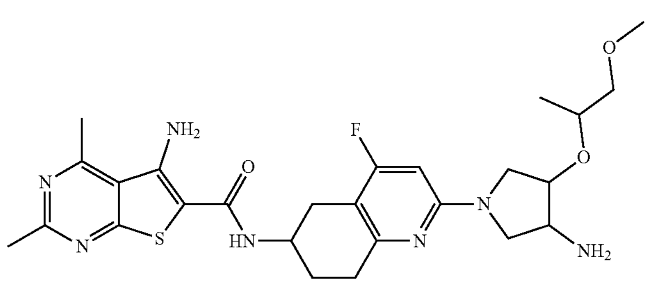 | 5-amino-N-(2-{3-amino-4-[(1-methoxypropan-2-yl)oxy]pyrrolidin-1-yl}-4-fluoro-5,6,7,8-tetrahydroquinolin-6-yl)-2,4-dimethylthieno[2,3-d]pyrimidine-6-carboxamide |

TABLE 27-continued

| Structure | Chemical Name |
|---|---|
| 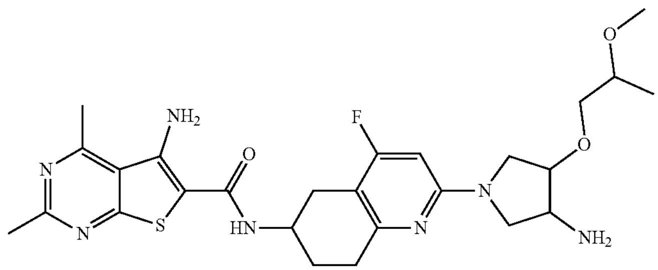 [SMILES: COC(C)COC1CN(c2cc(F)c3c(n2)CCC(NC(=O)c2sc4nc(C)nc(C)c4c2N)C3)CC1N] | 5-amino-N-{2-[3-amino-4-(2-methoxypropoxy)pyrrolidin-1-yl]-4-fluoro-5,6,7,8-tetrahydroquinolin-6-yl}-2,4-dimethylthieno[2,3-d]pyrimidine-6-carboxamide |
| 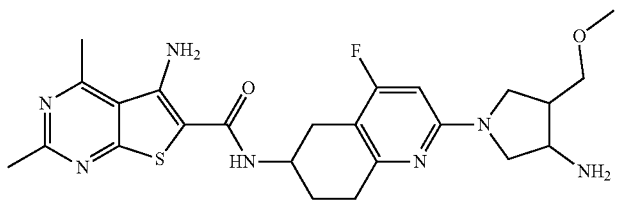 | 5-amino-N-{2-[3-amino-4-(methoxymethyl)pyrrolidin-1-yl]-4-fluoro-5,6,7,8-tetrahydroquinolin-6-yl}-2,4-dimethylthieno[2,3-d]pyrimidine-6-carboxamide |
| 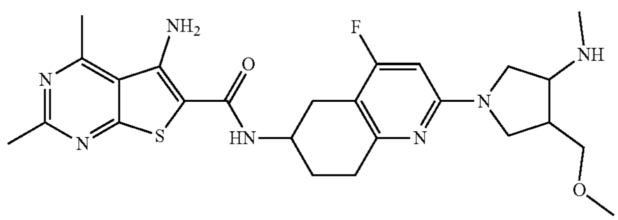 | 5-amino-N-{4-fluoro-2-[3-(methoxymethyl)-4-(methylamino)pyrrolidin-1-yl]-5,6,7,8-tetrahydroquinolin-6-yl}-2,4-dimethylthieno[2,3-d]pyrimidine-6-carboxamide |
| 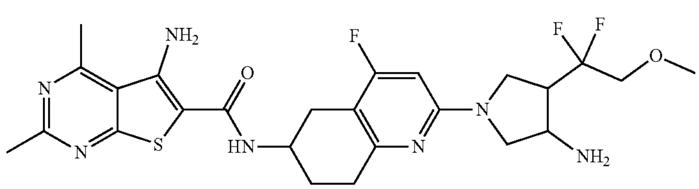 | 5-amino-N-{2-[3-amino-4-(1,1-difluoro-2-methoxyethyl)pyrrolidin-1-yl]-4-fluoro-5,6,7,8-tetrahydroquinolin-6-yl}-2,4-dimethylthieno[2,3-d]pyrimidine-6-carboxamide |
| 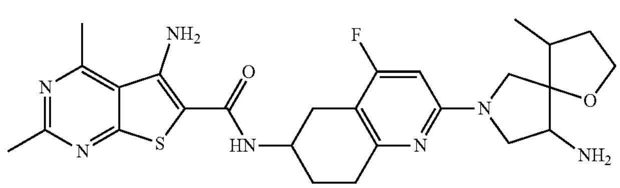 [SMILES: Cc1nc(C)c2c(N)c(C(=O)NC3CCc4nc(N5CC(N)C6(C5)OCCC6C)cc(F)c4C3)sc2n1] | 5-amino-N-(2-{9-amino-4-methyl-1-oxa-7-azaspiro[4.4]nonan-7-yl}-4-fluoro-5,6,7,8-tetrahydroquinolin-6-yl)-2,4-dimethylthieno[2,3-d]pyrimidine-6-carboxamide |
| 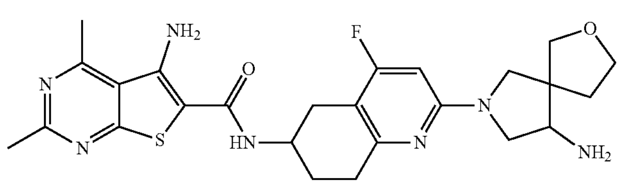 [SMILES: Cc1nc(C)c2c(N)c(C(=O)NC3CCc4nc(N5CC(N)C6(CCOC6)C5)cc(F)c4C3)sc2n1] | 5-amino-N-(2-{9-amino-2-oxa-7-azaspiro[4.4]nonan-7-yl}-4-fluoro-5,6,7,8-tetrahydroquinolin-6-yl)-2,4-dimethylthieno[2,3-d]pyrimidine-6-carboxamide |
| 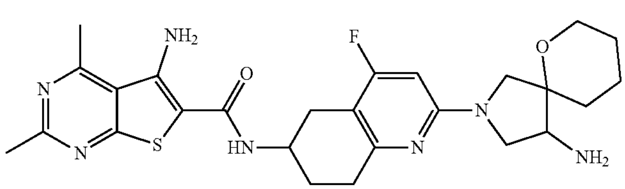 [SMILES: Cc1nc(C)c2c(N)c(C(=O)NC3CCc4nc(N5CC(N)C6(CCCCO6)C5)cc(F)c4C3)sc2n1] | 5-amino-N-(2-{4-amino-6-oxa-2-azaspiro[4.5]decan-2-yl}-4-fluoro-5,6,7,8-tetrahydroquinolin-6-yl)-2,4-dimethylthieno[2,3-d]pyrimidine-6-carboxamide |

TABLE 27-continued

| Structure | Chemical Name |
|---|---|
| 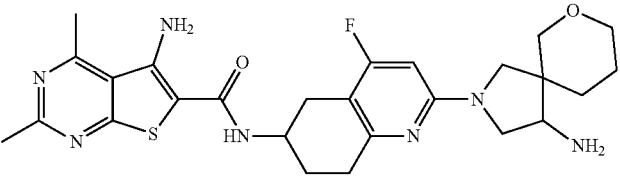 [SMILES: Cc1nc(C)c2c(N)c(C(=O)NC3CCc4nc(N5CC(N)C6(CCCOC6)C5)cc(F)c4C3)sc2n1] | 5-amino-N-(2-{4-amino-7-oxa-2-azaspiro[4.5]decan-2-yl}-4-fluoro-5,6,7,8-tetrahydroquinolin-6-yl)-2,4-dimethylthieno[2,3-d]pyrimidine-6-carboxamide |
| 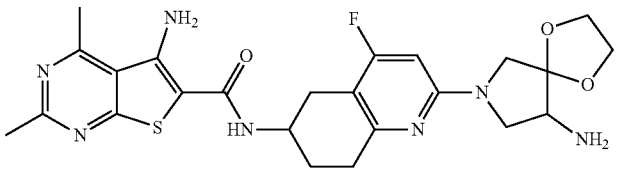 | 5-amino-N-(2-{9-amino-1,4-dioxa-7-azaspiro[4.4]nonan-7-yl}-4-fluoro-5,6,7,8-tetrahydroquinolin-6-yl)-2,4-dimethylthieno[2,3-d]pyrimidine-6-carboxamide |
| 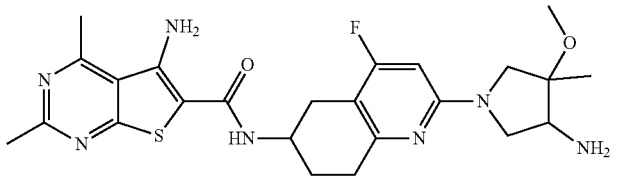 | 5-amino-N-[2-(4-amino-3-methoxy-3-methylpyrrolidin-1-yl)-4-fluoro-5,6,7,8-tetrahydroquinolin-6-yl]-2,4-dimethylthieno[2,3-d]pyrimidine-6-carboxamide |
| 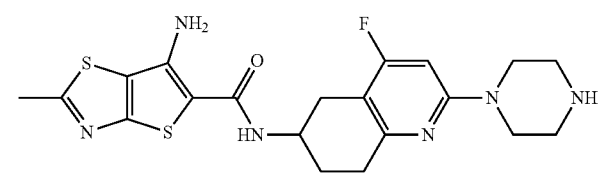 [SMILES: Cc1nc2sc(C(=O)NC3CCc4nc(N5CCNCC5)cc(F)c4C3)c(N)c2s1] | 6-amino-N-[4-fluoro-2-(piperazin-1-yl)-5,6,7,8-tetrahydroquinolin-6-yl]-2-methylthieno[2,3-d][1,3]thiazole-5-carboxamide |
| 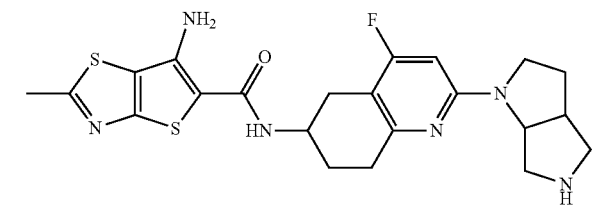 [SMILES: Cc1nc2sc(C(=O)NC3CCc4nc(N5CCC6CNCC65)cc(F)c4C3)c(N)c2s1] | 6-amino-N-(4-fluoro-2-{octahydropyrrolo[2,3-c]pyrrol-1-yl}-5,6,7,8-tetrahydroquinolin-6-yl)-2-methylthieno[2,3-d][1,3]thiazole-5-carboxamide |
| 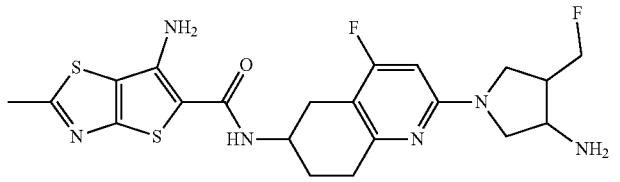 [SMILES: Cc1nc2sc(C(=O)NC3CCc4nc(N5CC(N)C(CF)C5)cc(F)c4C3)c(N)c2s1] | 6-amino-N-{2-[3-amino-4-(fluoromethyl)pyrrolidin-1-yl]-4-fluoro-5,6,7,8-tetrahydroquinolin-6-yl}-2-methylthieno[2,3-d][1,3]thiazole-5-carboxamide |
| 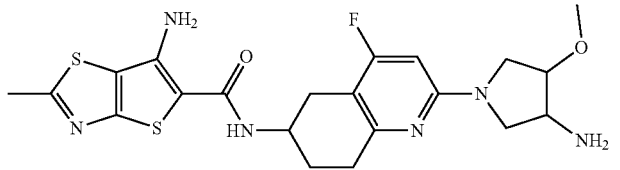 [SMILES: COC1CN(c2cc(F)c3c(n2)CCC(NC(=O)c2sc4nc(C)sc4c2N)C3)CC1N] | 6-amino-N-[2-(3-amino-4-methoxypyrrolidin-1-yl)-4-fluoro-5,6,7,8-tetrahydroquinolin-6-yl]-2-methylthieno[2,3-d][1,3]thiazole-5-carboxamide |
| 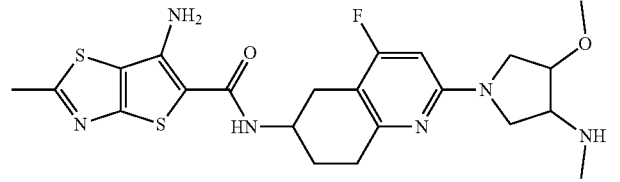 [SMILES: CNC1CN(c2cc(F)c3c(n2)CCC(NC(=O)c2sc4nc(C)sc4c2N)C3)CC1OC] | 6-amino-N-{4-fluoro-2-[3-methoxy-4-(methylamino)pyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 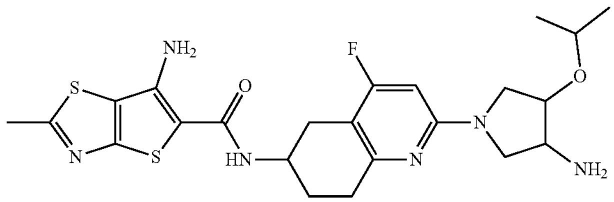 [SMILES: Cc1nc2sc(C(=O)NC3CCc4nc(N5CC(N)C(OC(C)C)C5)cc(F)c4C3)c(N)c2s1] | 6-amino-N-{2-[3-amino-4-(propan-2-yloxy)pyrrolidin-1-yl]-4-fluoro-5,6,7,8-tetrahydroquinolin-6-yl}-2-methylthieno[2,3-d][1,3]thiazole-5-carboxamide |
| 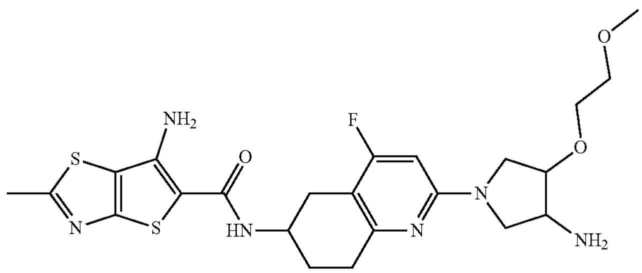 | 6-amino-N-{2-[3-amino-4-(2-methoxyethoxy)pyrrolidin-1-yl]-4-fluoro-5,6,7,8-tetrahydroquinolin-6-yl}-2-methylthieno[2,3-d][1,3]thiazole-5-carboxamide |
| 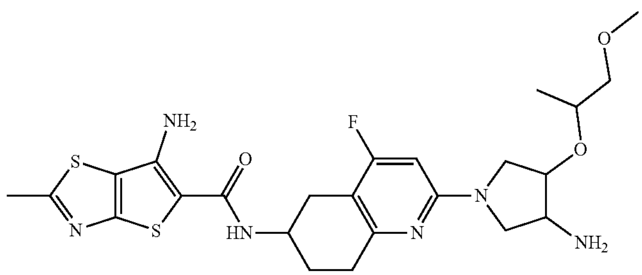 | 6-amino-N-(2-{3-amino-4-[(1-methoxypropan-2-yl)oxy]pyrrolidin-1-yl}-4-fluoro-5,6,7,8-tetrahydroquinolin-6-yl)-2-methylthieno[2,3-d][1,3]thiazole-5-carboxamide |
| 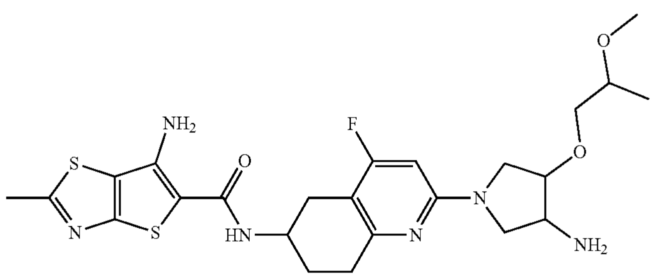 [SMILES: COC(C)COC1CN(c2cc(F)c3c(n2)CCC(NC(=O)c2sc4nc(C)sc4c2N)C3)CC1N] | 6-amino-N-{2-[3-amino-4-(2-methoxypropoxy)pyrrolidin-1-yl]-4-fluoro-5,6,7,8-tetrahydroquinolin-6-yl}-2-methylthieno[2,3-d][1,3]thiazole-5-carboxamide |
| 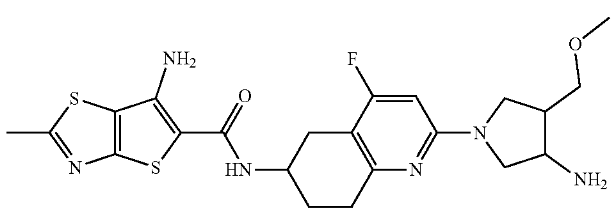 | 6-amino-N-{2-[3-amino-4-(methoxymethyl)pyrrolidin-1-yl]-4-fluoro-5,6,7,8-tetrahydroquinolin-6-yl}-2-methylthieno[2,3-d][1,3]thiazole-5-carboxamide |
| 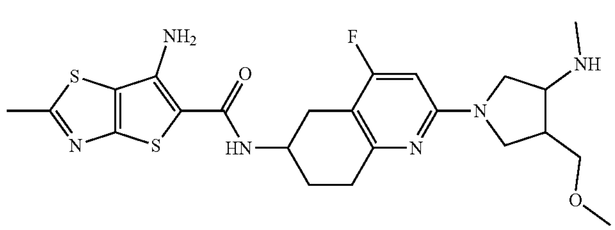 | 6-amino-N-{4-fluoro-2-[3-(methoxymethyl)-4-(methylamino)pyrrolidin-1-yl]-5,6,7,8-tetrahydroquinolin-6-yl}-2-methylthieno[2,3-d][1,3]thiazole-5-carboxamide |

TABLE 27-continued

| Structure | Chemical Name |
|---|---|
| 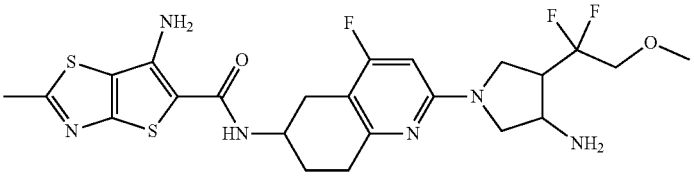 | 6-amino-N-{2-[3-amino-4-(1,1-difluoro-2-methoxyethyl)pyrrolidin-1-yl]-4-fluoro-5,6,7,8-tetrahydroquinolin-6-yl}-2-methylthieno[2,3-d][1,3]thiazole-5-carboxamide |
| 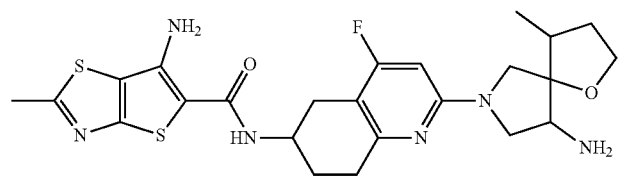 [SMILES: Cc1nc2sc(C(=O)NC3CCc4nc(N5CC(N)C6(C5)OCCC6C)cc(F)c4C3)c(N)c2s1] | 6-amino-N-(2-{9-amino-4-methyl-1-oxa-7-azaspiro[4.4]nonan-7-yl}-4-fluoro-5,6,7,8-tetrahydroquinolin-6-yl)-2-methylthieno[2,3-d][1,3]thiazole-5-carboxamide |
| 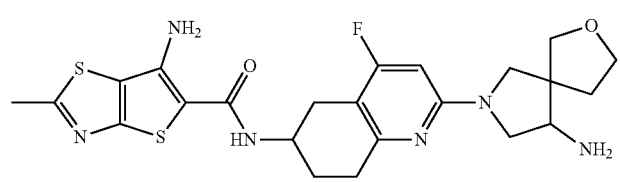 [SMILES: Cc1nc2sc(C(=O)NC3CCc4nc(N5CC(N)C6(CCOC6)C5)cc(F)c4C3)c(N)c2s1] | 6-amino-N-(2-{9-amino-2-oxa-7-azaspiro[4.4]nonan-7-yl}-4-fluoro-5,6,7,8-tetrahydroquinolin-6-yl)-2-methylthieno[2,3-d][1,3]thiazole-5-carboxamide |
| 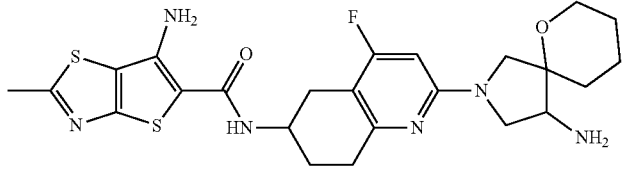 [SMILES: Cc1nc2sc(C(=O)NC3CCc4nc(N5CC(N)C6(CCCCO6)C5)cc(F)c4C3)c(N)c2s1] | 6-amino-N-(2-{4-amino-6-oxa-2-azaspiro[4.5]decan-2-yl}-4-fluoro-5,6,7,8-tetrahydroquinolin-6-yl)-2-methylthieno[2,3-d][1,3]thiazole-5-carboxamide |
| 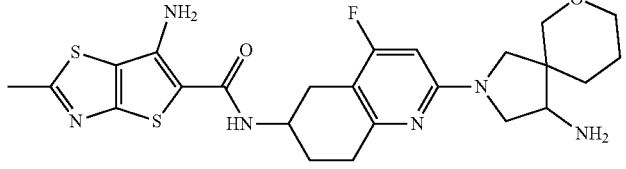 | 6-amino-N-(2-{4-amino-7-oxa-2-azaspiro[4.5]decan-2-yl}-4-fluoro-5,6,7,8-tetrahydroquinolin-6-yl)-2-methylthieno[2,3-d][1,3]thiazole-5-carboxamide |
| 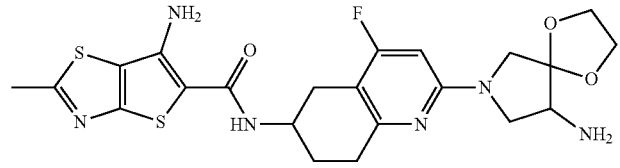 [SMILES: Cc1nc2sc(C(=O)NC3CCc4nc(N5CC(N)C6(C5)OCCO6)cc(F)c4C3)c(N)c2s1] | 6-amino-N-(2-{9-amino-1,4-dioxa-7-azaspiro[4.4]nonan-7-yl}-4-fluoro-5,6,7,8-tetrahydroquinolin-6-yl)-2-methylthieno[2,3-d][1,3]thiazole-5-carboxamide |
| 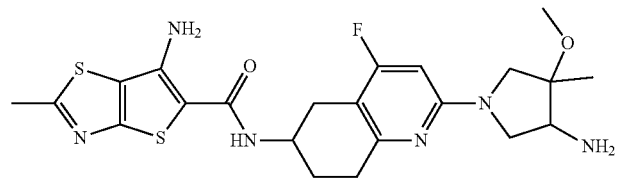 | 6-amino-N-[2-(4-amino-3-methoxy-3-methylpyrrolidin-1-yl)-4-fluoro-5,6,7,8-tetrahydroquinolin-6-yl]-2-methylthieno[2,3-d][1,3]thiazole-5-carboxamide |
| 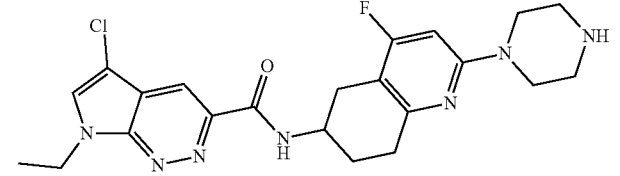 [SMILES: CCn1cc(Cl)c2cc(C(=O)NC3CCc4nc(N5CCNCC5)cc(F)c4C3)nnc21] | 5-chloro-7-ethyl-N-[4-fluoro-2-(piperazin-1-yl)-5,6,7,8-tetrahydroquinolin-6-yl]-7H-pyrrolo[2,3-c]pyridazine-3-carboxamide |

TABLE 27-continued

| Structure | Chemical Name |
|---|---|
| 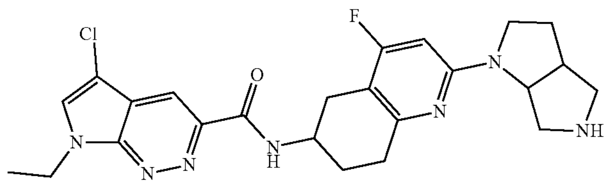 [SMILES: CCn1cc(Cl)c2cc(C(=O)NC3CCc4nc(N5CCC6CNCC65)cc(F)c4C3)nnc21] | 5-chloro-7-ethyl-N-(4-fluoro-2-{octahydropyrrolo[2,3-c]pyrrol-1-yl}-5,6,7,8-tetrahydroquinolin-6-yl)-7H-pyrrolo[2,3-c]pyridazine-3-carboxamide |
| 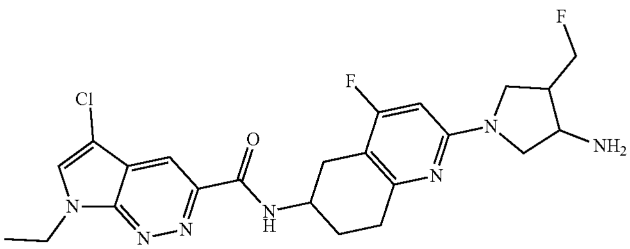 [SMILES: CCn1cc(Cl)c2cc(C(=O)NC3CCc4nc(N5CC(N)C(CF)C5)cc(F)c4C3)nnc21] | N-{2-[3-amino-4-(fluoromethyl)pyrrolidin-1-yl]-4-fluoro-5,6,7,8-tetrahydroquinolin-6-yl}-5-chloro-7-ethyl-7H-pyrrolo[2,3-c]pyridazine-3-carboxamide |
| 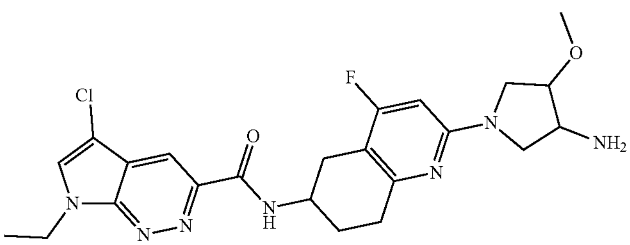 [SMILES: CCn1cc(Cl)c2cc(C(=O)NC3CCc4nc(N5CC(N)C(OC)C5)cc(F)c4C3)nnc21] | N-[2-(3-amino-4-methoxypyrrolidin-1-yl)-4-fluoro-5,6,7,8-tetrahydroquinolin-6-yl]-5-chloro-7-ethyl-7H-pyrrolo[2,3-c]pyridazine-3-carboxamide |
| 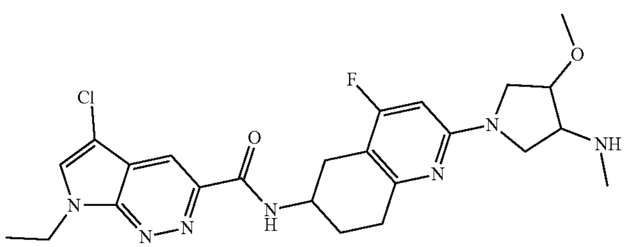 [SMILES: CCn1cc(Cl)c2cc(C(=O)NC3CCc4nc(N5CC(NC)C(OC)C5)cc(F)c4C3)nnc21] | 5-chloro-7-ethyl-N-{4-fluoro-2-[3-methoxy-4-(methylamino)pyrrolidin-1-yl]-5,6,7,8-tetrahydroquinolin-6-yl}-7H-pyrrolo[2,3-c]pyridazine-3-carboxamide |
| 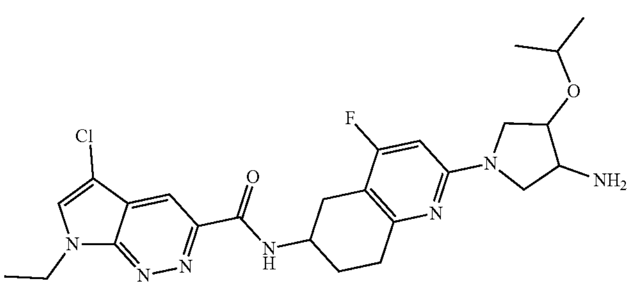 [SMILES: CCn1cc(Cl)c2cc(C(=O)NC3CCc4nc(N5CC(N)C(OC(C)C)C5)cc(F)c4C3)nnc21] | N-{2-[3-amino-4-(propan-2-yloxy)pyrrolidin-1-yl]-4-fluoro-5,6,7,8-tetrahydroquinolin-6-yl}-5-chloro-7-ethyl-7H-pyrrolo[2,3-c]pyridazine-3-carboxamide |
| 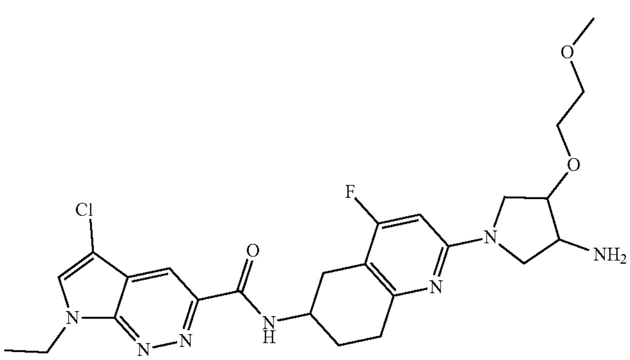 [SMILES: CCn1cc(Cl)c2cc(C(=O)NC3CCc4nc(N5CC(N)C(OCCOC)C5)cc(F)c4C3)nnc21] | N-{2-[3-amino-4-(2-methoxyethoxy)pyrrolidin-1-yl]-4-fluoro-5,6,7,8-tetrahydroquinolin-6-yl}-5-chloro-7-ethyl-7H-pyrrolo[2,3-c]pyridazine-3-carboxamide |

TABLE 27-continued

| Structure | Chemical Name |
|---|---|
| 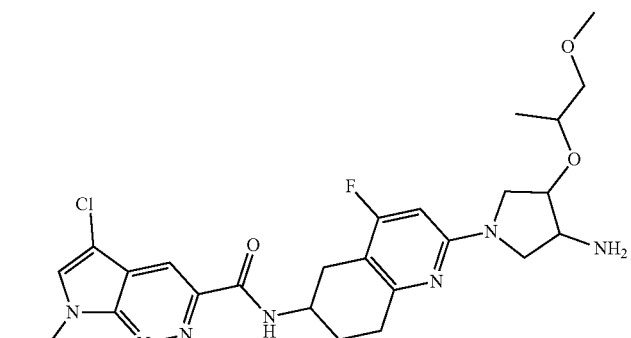 | N-(2-{3-amino-4-[(1-methoxypropan-2-yl)oxy]pyrrolidin-1-yl}-4-fluoro-5,6,7,8-tetrahydroquinolin-6-yl)-5-chloro-7-ethyl-7H-pyrrolo[2,3-c]pyridazine-3-carboxamide |
| 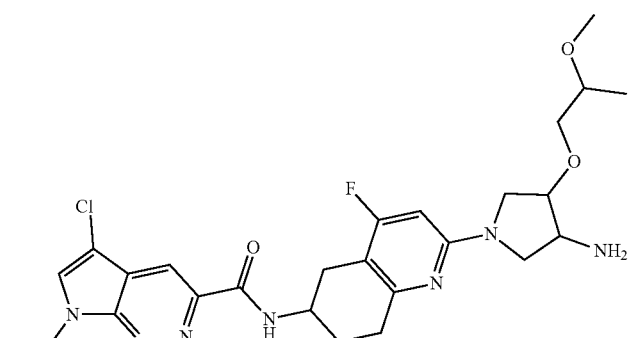 | N-{2-[3-amino-4-(2-methoxypropoxy)pyrrolidin-1-yl]-4-fluoro-5,6,7,8-tetrahydroquinolin-6-yl}-5-chloro-7-ethyl-7H-pyrrolo[2,3-c]pyridazine-3-carboxamide |
| 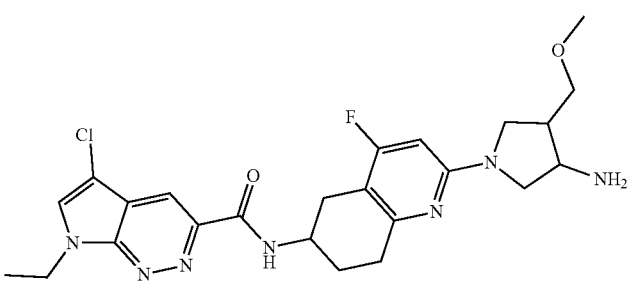 [SMILES: CCn1cc(Cl)c2cc(C(=O)NC3CCc4nc(N5CC(N)C(COC)C5)cc(F)c4C3)nnc21] | N-{2-[3-amino-4-(methoxymethyl)pyrrolidin-1-yl]-4-fluoro-5,6,7,8-tetrahydroquinolin-6-yl}-5-chloro-7-ethyl-7H-pyrrolo[2,3-c]pyridazine-3-carboxamide |
| 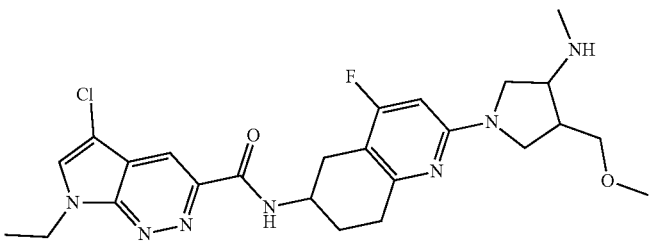 [SMILES: CCn1cc(Cl)c2cc(C(=O)NC3CCc4nc(N5CC(COC)C(NC)C5)cc(F)c4C3)nnc21] | 5-chloro-7-ethyl-N-{4-fluoro-2-[3-(methoxymethyl)-4-(methylamino)pyrrolidin-1-yl]-5,6,7,8-tetrahydroquinolin-6-yl}-7H-pyrrolo[2,3-c]pyridazine-3-carboxamide |
| 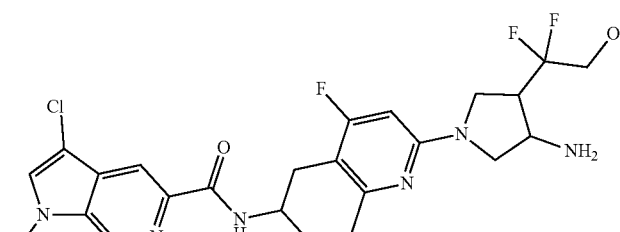 | N-{2-[3-amino-4-(1,1-difluoro-2-methoxyethyl)pyrrolidin-1-yl]-4-fluoro-5,6,7,8-tetrahydroquinolin-6-yl}-5-chloro-7-ethyl-7H-pyrrolo[2,3-c]pyridazine-3-carboxamide |

TABLE 27-continued

| Structure | Chemical Name |
|---|---|
| 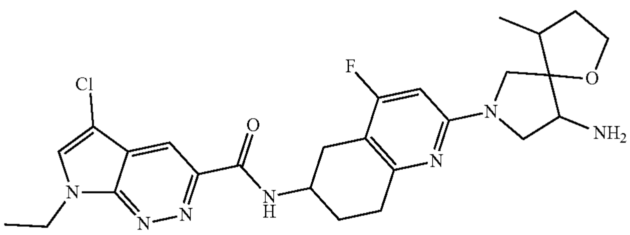 [SMILES: CCn1cc(Cl)c2cc(C(=O)NC3CCc4nc(N5CC(N)C6(C5)OCCC6C)cc(F)c4C3)nnc21] | N-(2-{9-amino-4-methyl-1-oxa-7-azaspiro[4.4]nonan-7-yl}-4-fluoro-5,6,7,8-tetrahydroquinolin-6-yl)-5-chloro-7-ethyl-7H-pyrrolo[2,3-c]pyridazine-3-carboxamide |
| 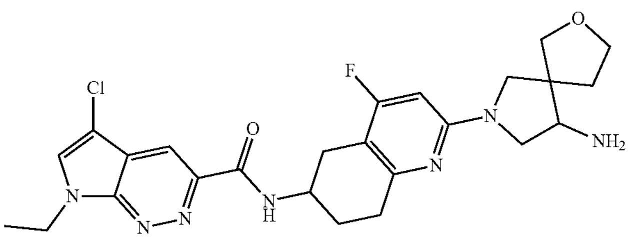 [SMILES: CCn1cc(Cl)c2cc(C(=O)NC3CCc4nc(N5CC(N)C6(CCOC6)C5)cc(F)c4C3)nnc21] | N-(2-{9-amino-2-oxa-7-azaspiro[4.4]nonan-7-yl}-4-fluoro-5,6,7,8-tetrahydroquinolin-6-yl)-5-chloro-7-ethyl-7H-pyrrolo[2,3-c]pyridazine-3-carboxamide |
| 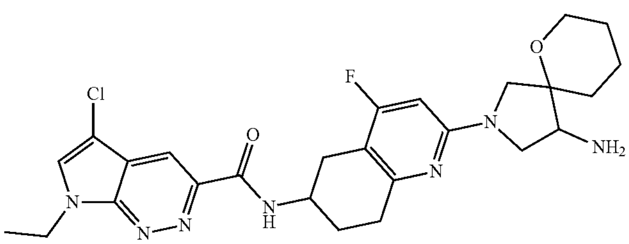 [SMILES: CCn1cc(Cl)c2cc(C(=O)NC3CCc4nc(N5CC(N)C6(CCCCO6)C5)cc(F)c4C3)nnc21] | N-(2-{4-amino-6-oxa-2-azaspiro[4.5]decan-2-yl}-4-fluoro-5,6,7,8-tetrahydroquinolin-6-yl)-5-chloro-7-ethyl-7H-pyrrolo[2,3-c]pyridazine-3-carboxamide |
| 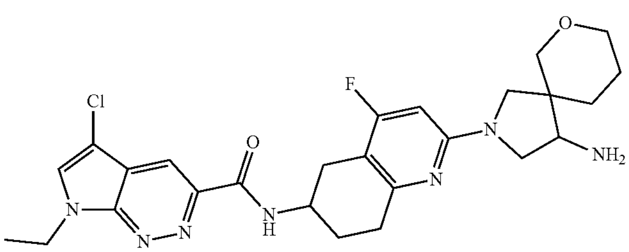 [SMILES: CCn1cc(Cl)c2cc(C(=O)NC3CCc4nc(N5CC(N)C6(CCCOC6)C5)cc(F)c4C3)nnc21] | N-(2-{4-amino-7-oxa-2-azaspiro[4.5]decan-2-yl}-4-fluoro-5,6,7,8-tetrahydroquinolin-6-yl)-5-chloro-7-ethyl-7H-pyrrolo[2,3-c]pyridazine-3-carboxamide |
| 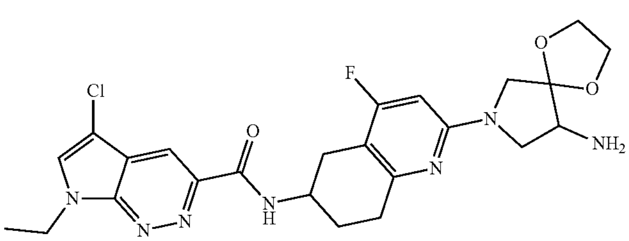 [SMILES: CCn1cc(Cl)c2cc(C(=O)NC3CCc4nc(N5CC(N)C6(C5)OCCO6)cc(F)c4C3)nnc21] | N-(2-{9-amino-1,4-dioxa-7-azaspiro[4.4]nonan-7-yl}-4-fluoro-5,6,7,8-tetrahydroquinolin-6-yl)-5-chloro-7-ethyl-7H-pyrrolo[2,3-c]pyridazine-3-carboxamide |
| 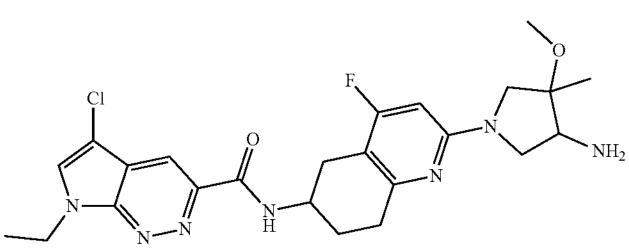 [SMILES: CCn1cc(Cl)c2cc(C(=O)NC3CCc4nc(N5CC(N)C(C)(OC)C5)cc(F)c4C3)nnc21] | N-[2-(4-amino-3-methoxy-3-methylpyrrolidin-1-yl)-4-fluoro-5,6,7,8-tetrahydroquinolin-6-yl]-5-chloro-7-ethyl-7H-pyrrolo[2,3-c]pyridazine-3-carboxamide |

TABLE 27-continued

| Structure | Chemical Name |
|---|---|
| 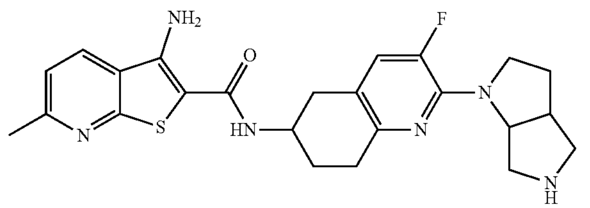 [SMILES: Cc1ccc2c(N)c(C(=O)NC3CCc4nc(N5CCC6CNCC65)c(F)cc4C3)sc2n1] | 3-amino-N-(3-fluoro-2-{octahydropyrrolo[2,3-c]pyrrol-1-yl}-5,6,7,8-tetrahydroquinolin-6-yl)-6-methylthieno[2,3-b]pyridine-2-carboxamide |
| 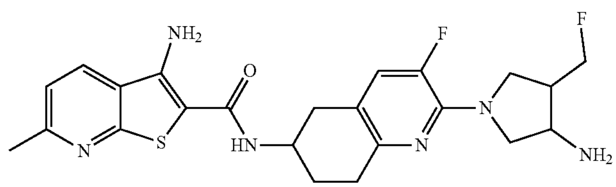 [SMILES: Cc1ccc2c(N)c(C(=O)NC3CCc4nc(N5CC(N)C(CF)C5)c(F)cc4C3)sc2n1] | 3-amino-N-{2-[3-amino-4-(fluoromethyl)pyrrolidin-1-yl]-3-fluoro-5,6,7,8-tetrahydroquinolin-6-yl}-6-methylthieno[2,3-b]pyridine-2-carboxamide |
| 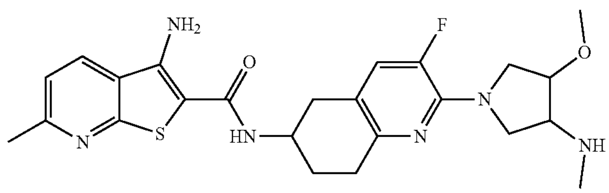 | 3-amino-N-{3-fluoro-2-[3-methoxy-4-(methylamino)pyrrolidin-1-yl]-5,6,7,8-tetrahydroquinolin-6-yl}-6-methylthieno[2,3-b]pyridine-2-carboxamide |
| 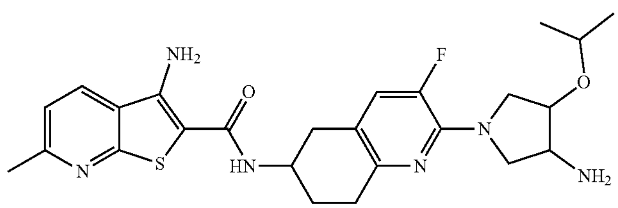 [SMILES: Cc1ccc2c(N)c(C(=O)NC3CCc4nc(N5CC(N)C(OC(C)C)C5)c(F)cc4C3)sc2n1] | 3-amino-N-{2-[3-amino-4-(propan-2-yloxy)pyrrolidin-1-yl]-3-fluoro-5,6,7,8-tetrahydroquinolin-6-yl}-6-methylthieno[2,3-b]pyridine-2-carboxamide |
| 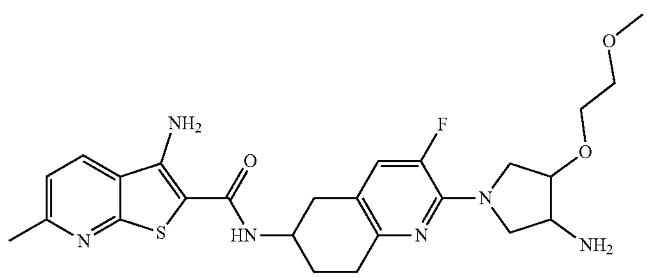 | 3-amino-N-{2-[3-amino-4-(2-methoxyethoxy)pyrrolidin-1-yl]-3-fluoro-5,6,7,8-tetrahydroquinolin-6-yl}-6-methylthieno[2,3-b]pyridine-2-carboxamide |
| 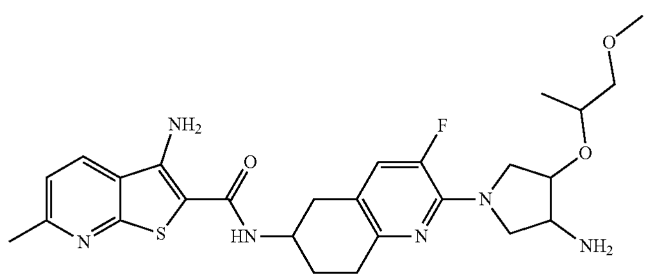 | 3-amino-N-(2-{3-amino-4-[(1-methoxypropan-2-yl)oxy]pyrrolidin-1-yl}-3-fluoro-5,6,7,8-tetrahydroquinolin-6-yl)-6-methylthieno[2,3-b]pyridine-2-carboxamide |

TABLE 27-continued

| Structure | Chemical Name |
|---|---|
| 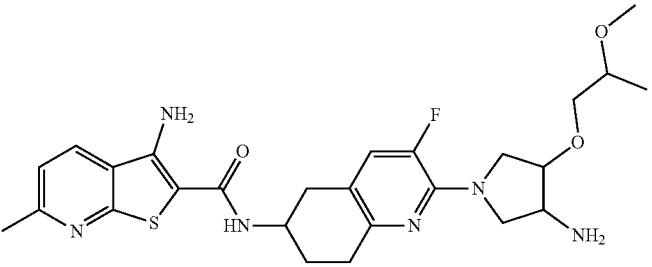 [SMILES: COC(C)COC1CN(c2nc3c(cc2F)CC(NC(=O)c2sc4nc(C)ccc4c2N)CC3)CC1N] | 3-amino-N-{2-[3-amino-4-(2-methoxypropoxy)pyrrolidin-1-yl]-3-fluoro-5,6,7,8-tetrahydroquinolin-6-yl}-6-methylthieno[2,3-b]pyridine-2-carboxamide |
| 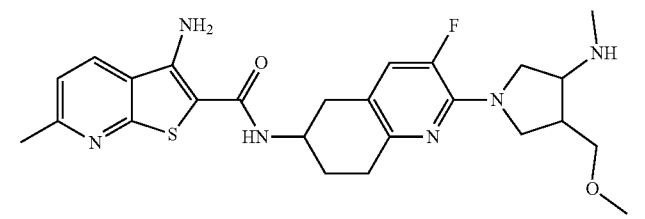 | 3-amino-N-{3-fluoro-2-[3-(methoxymethyl)-4-(methylamino)pyrrolidin-1-yl]-5,6,7,8-tetrahydroquinolin-6-yl}-6-methylthieno[2,3-b]pyridine-2-carboxamide |
| 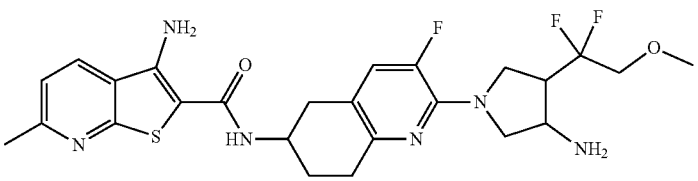 | 3-amino-N-{2-[3-amino-4-(1,1-difluoro-2-methoxyethyl)pyrrolidin-1-yl]-3-fluoro-5,6,7,8-tetrahydroquinolin-6-yl}-6-methylthieno[2,3-b]pyridine-2-carboxamide |
| 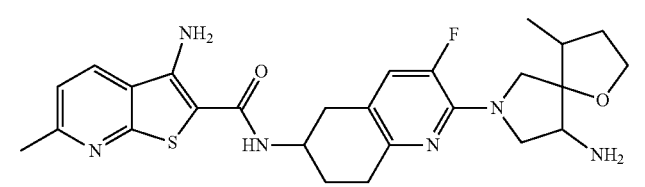 | 3-amino-N-(2-{9-amino-4-methyl-1-oxa-7-azaspiro[4.4]nonan-7-yl}-3-fluoro-5,6,7,8-tetrahydroquinolin-6-yl)-6-methylthieno[2,3-b]pyridine-2-carboxamide |
| 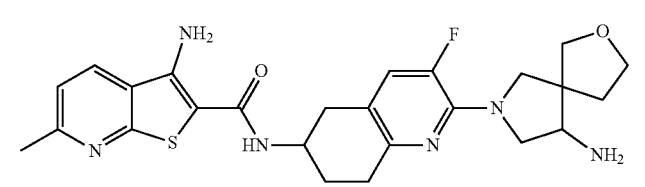 [SMILES: Cc1ccc2c(N)c(C(=O)NC3CCc4nc(N5CC(N)C6(CCOC6)C5)c(F)cc4C3)sc2n1] | 3-amino-N-(2-{9-amino-2-oxa-7-azaspiro[4.4]nonan-7-yl}-3-fluoro-5,6,7,8-tetrahydroquinolin-6-yl)-6-methylthieno[2,3-b]pyridine-2-carboxamide |
| 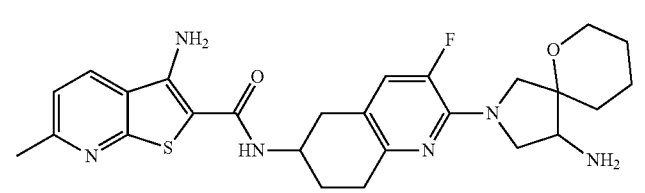 | 3-amino-N-(2-{4-amino-6-oxa-2-azaspiro[4.5]decan-2-yl}-3-fluoro-5,6,7,8-tetrahydroquinolin-6-yl)-6-methylthieno[2,3-b]pyridine-2-carboxamide |
| 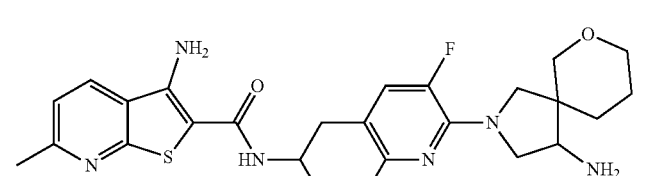 | 3-amino-N-(2-{4-amino-7-oxa-2-azaspiro[4.5]decan-2-yl}-3-fluoro-5,6,7,8-tetrahydroquinolin-6-yl)-6-methylthieno[2,3-b]pyridine-2-carboxamide |
| 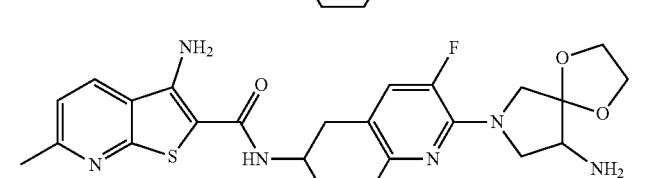 | 3-amino-N-(2-{9-amino-1,4-dioxa-7-azaspiro[4.4]nonan-7-yl}-3-fluoro-5,6,7,8-tetrahydroquinolin-6-yl)-6-methylthieno[2,3-b]pyridine-2-carboxamide |

TABLE 27-continued

| Structure | Chemical Name |
|---|---|
| 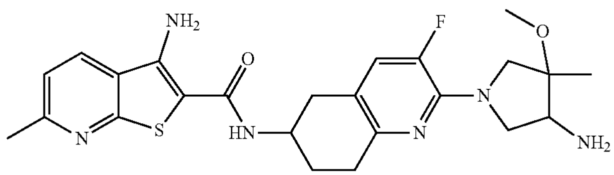 | 3-amino-N-[2-(4-amino-3-methoxy-3-methylpyrrolidin-1-yl)-3-fluoro-5,6,7,8-tetrahydroquinolin-6-yl]-6-methylthieno[2,3-b]pyridine-2-carboxamide |
| 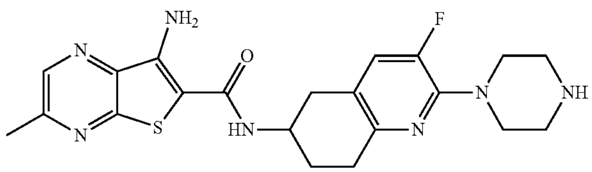 [SMILES: Cc1cnc2c(N)c(C(=O)NC3CCc4nc(N5CCNCC5)c(F)cc4C3)sc2n1] | 7-amino-N-[3-fluoro-2-(piperazin-1-yl)-5,6,7,8-tetrahydroquinolin-6-yl]-3-methylthieno[2,3-b]pyrazine-6-carboxamide |
| 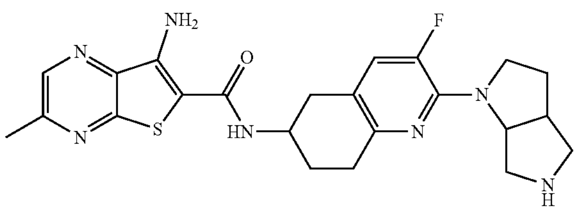 | 7-amino-N-(3-fluoro-2-{octahydropyrrolo[2,3-c]pyrrol-1-yl}-5,6,7,8-tetrahydroquinolin-6-yl)-3-methylthieno[2,3-b]pyrazine-6-carboxamide |
| 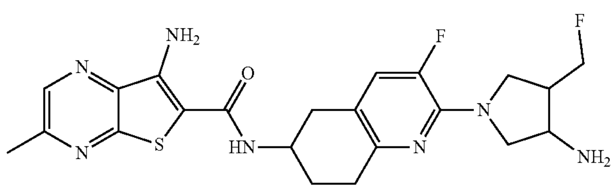 | 7-amino-N-{2-[3-amino-4-(fluoromethyl)pyrrolidin-1-yl]-3-fluoro-5,6,7,8-tetrahydroquinolin-6-yl}-3-methylthieno[2,3-b]pyrazine-6-carboxamide |
| 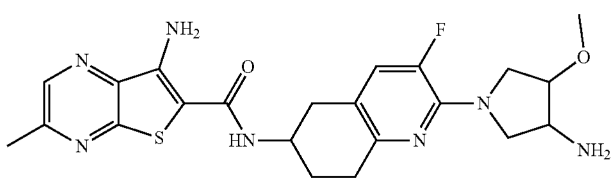 [SMILES: COC1CN(c2nc3c(cc2F)CC(NC(=O)c2sc4nc(C)cnc4c2N)CC3)CC1N] | 7-amino-N-[2-(3-amino-4-methoxypyrrolidin-1-yl)-3-fluoro-5,6,7,8-tetrahydroquinolin-6-yl]-3-methylthieno[2,3-b]pyrazine-6-carboxamide |
| 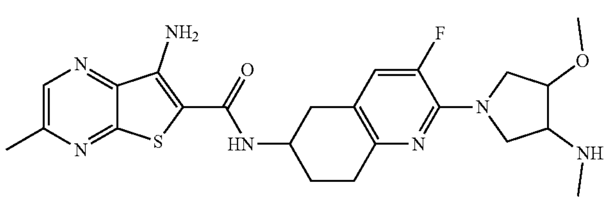 [SMILES: CNC1CN(c2nc3c(cc2F)CC(NC(=O)c2sc4nc(C)cnc4c2N)CC3)CC1OC] | 7-amino-N-{3-fluoro-2-[3-methoxy-4-(methylamino)pyrrolidin-1-yl]-5,6,7,8-tetrahydroquinolin-6-yl}-3-methylthieno[2,3-b]pyrazine-6-carboxamide |
| 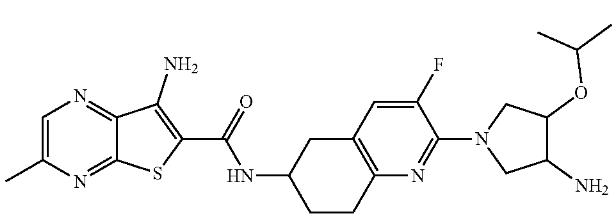 | 7-amino-N-{2-[3-amino-4-(propan-2-yloxy)pyrrolidin-1-yl]-3-fluoro-5,6,7,8-tetrahydroquinolin-6-yl}-3-methylthieno[2,3-b]pyrazine-6-carboxamide |

TABLE 27-continued

| Structure | Chemical Name |
|---|---|
| 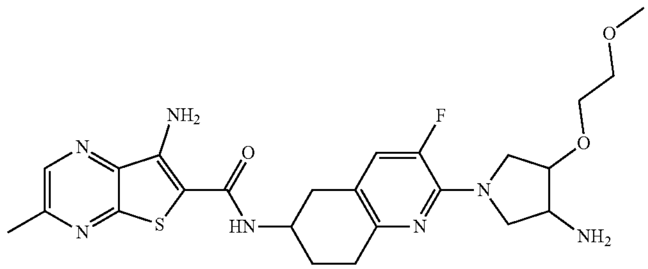 | 7-amino-N-{2-[3-amino-4-(2-methoxyethoxy)pyrrolidin-1-yl]-3-fluoro-5,6,7,8-tetrahydroquinolin-6-yl}-3-methylthieno[2,3-b]pyrazine-6-carboxamide |
| 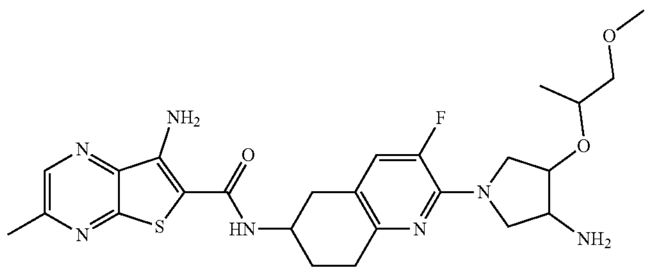 | 7-amino-N-(2-{3-amino-4-[(1-methoxypropan-2-yl)oxy]pyrrolidin-1-yl}-3-fluoro-5,6,7,8-tetrahydroquinolin-6-yl)-3-methylthieno[2,3-b]pyrazine-6-carboxamide |
| 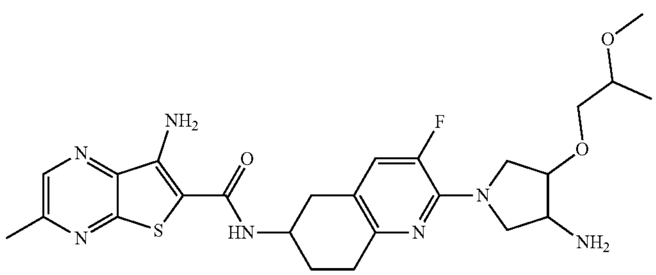 [SMILES: COC(C)COC1CN(c2nc3c(cc2F)CC(NC(=O)c2sc4nc(C)cnc4c2N)CC3)CC1N] | 7-amino-N-{2-[3-amino-4-(2-methoxypropoxy)pyrrolidin-1-yl]-3-fluoro-5,6,7,8-tetrahydroquinolin-6-yl}-3-methylthieno[2,3-b]pyrazine-6-carboxamide |
| 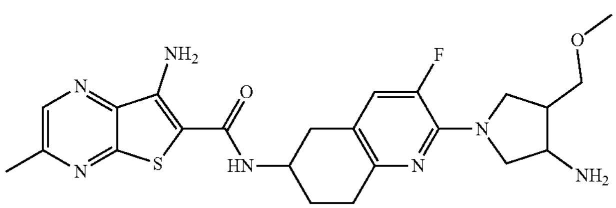 | 7-amino-N-{2-[3-amino-4-(methoxymethyl)pyrrolidin-1-yl]-3-fluoro-5,6,7,8-tetrahydroquinolin-6-yl}-3-methylthieno[2,3-b]pyrazine-6-carboxamide |
| 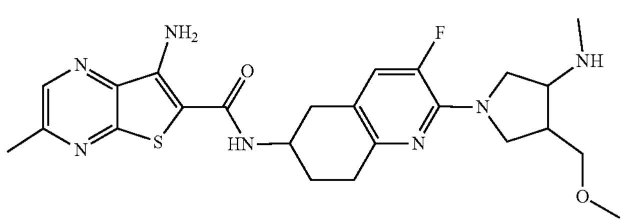 | 7-amino-N-{3-fluoro-2-[3-(methoxymethyl)-4-(methylamino)pyrrolidin-1-yl]-5,6,7,8-tetrahydroquinolin-6-yl}-3-methylthieno[2,3-b]pyrazine-6-carboxamide |
| 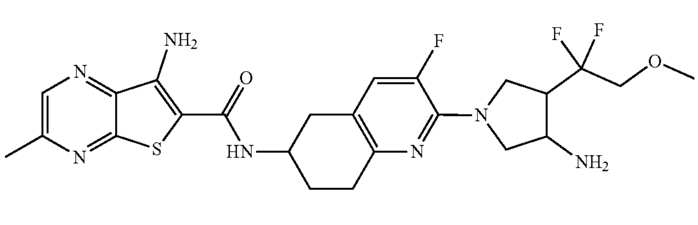 | 7-amino-N-{2-[3-amino-4-(1,1-difluoro-2-methoxyethyl)pyrrolidin-1-yl]-3-fluoro-5,6,7,8-tetrahydroquinolin-6-yl}-3-methylthieno[2,3-b]pyrazine-6-carboxamide |

TABLE 27-continued

| Structure | Chemical Name |
|---|---|
| 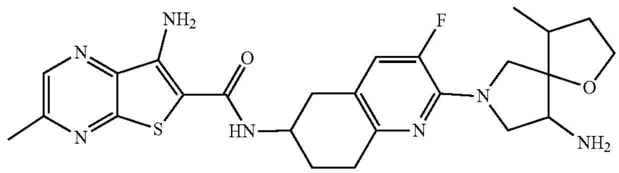 [SMILES: Cc1cnc2c(N)c(C(=O)NC3CCc4nc(N5CC(N)C6(C5)OCCC6C)c(F)cc4C3)sc2n1] | 7-amino-N-(2-{9-amino-4-methyl-1-oxa-7-azaspiro[4.4]nonan-7-yl}-3-fluoro-5,6,7,8-tetrahydroquinolin-6-yl)-3-methylthieno[2,3-b]pyrazine-6-carboxamide |
| 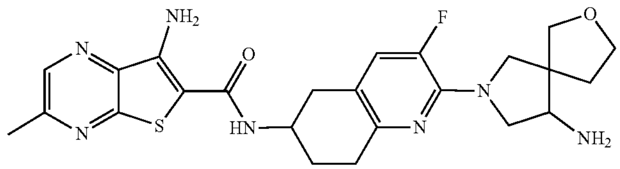 [SMILES: Cc1cnc2c(N)c(C(=O)NC3CCc4nc(N5CC(N)C6(CCOC6)C5)c(F)cc4C3)sc2n1] | 7-amino-N-(2-{9-amino-2-oxa-7-azaspiro[4.4]nonan-7-yl}-3-fluoro-5,6,7,8-tetrahydroquinolin-6-yl)-3-methylthieno[2,3-b]pyrazine-6-carboxamide |
| 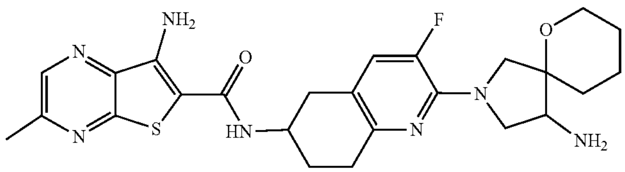 [SMILES: Cc1cnc2c(N)c(C(=O)NC3CCc4nc(N5CC(N)C6(CCCCO6)C5)c(F)cc4C3)sc2n1] | 7-amino-N-(2-{4-amino-6-oxa-2-azaspiro[4.5]decan-2-yl}-3-fluoro-5,6,7,8-tetrahydroquinolin-6-yl)-3-methylthieno[2,3-b]pyrazine-6-carboxamide |
| 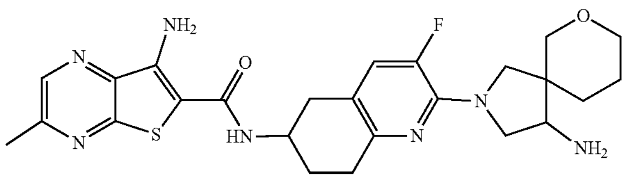 [SMILES: Cc1cnc2c(N)c(C(=O)NC3CCc4nc(N5CC(N)C6(CCCOC6)C5)c(F)cc4C3)sc2n1] | 7-amino-N-(2-{4-amino-7-oxa-2-azaspiro[4.5]decan-2-yl}-3-fluoro-5,6,7,8-tetrahydroquinolin-6-yl)-3-methylthieno[2,3-b]pyrazine-6-carboxamide |
| 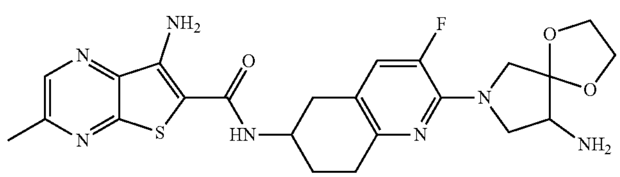 | 7-amino-N-(2-{9-amino-1,4-dioxa-7-azaspiro[4.4]nonan-7-yl}-3-fluoro-5,6,7,8-tetrahydroquinolin-6-yl)-3-methylthieno[2,3-b]pyrazine-6-carboxamide |
| 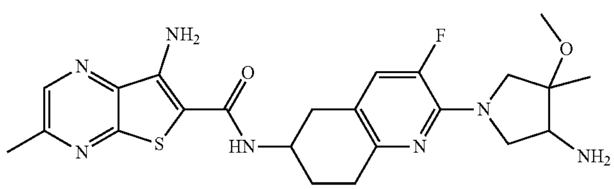 | 7-amino-N-[2-(4-amino-3-methoxy-3-methylpyrrolidin-1-yl)-3-fluoro-5,6,7,8-tetrahydroquinolin-6-yl]-3-methylthieno[2,3-b]pyrazine-6-carboxamide |
| 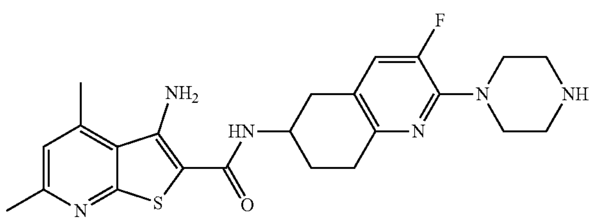 [SMILES: Cc1cc(C)c2c(N)c(C(=O)NC3CCc4nc(N5CCNCC5)c(F)cc4C3)sc2n1] | 3-amino-N-[3-fluoro-2-(piperazin-1-yl)-5,6,7,8-tetrahydroquinolin-6-yl]-4,6-dimethylthieno[2,3-b]pyridine-2-carboxamide |
| 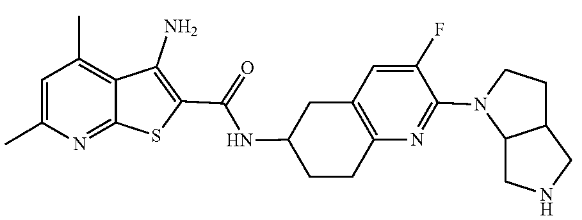 [SMILES: Cc1cc(C)c2c(N)c(C(=O)NC3CCc4nc(N5CCC6CNCC65)c(F)cc4C3)sc2n1] | 3-amino-N-(3-fluoro-2-{octahydropyrrolo[2,3-c]pyrrol-1-yl}-5,6,7,8-tetrahydroquinolin-6-yl)-4,6-dimethylthieno[2,3-b]pyridine-2-carboxamide |

TABLE 27-continued

| Structure | Chemical Name |
|---|---|
| 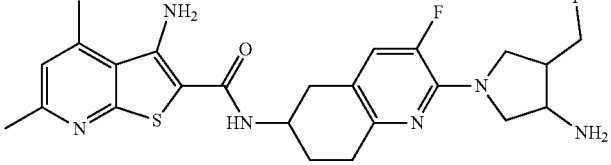 | 3-amino-N-{2-[3-amino-4-(fluoromethyl)pyrrolidin-1-yl]-3-fluoro-5,6,7,8-tetrahydroquinolin-6-yl}-4,6-dimethylthieno[2,3-b]pyridine-2-carboxamide |
| 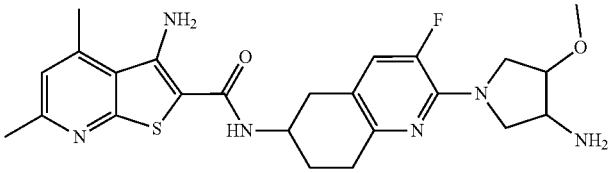 [SMILES: COC1CN(c2nc3c(cc2F)CC(NC(=O)c2sc4nc(C)cc(C)c4c2N)CC3)CC1N] | 3-amino-N-[2-(3-amino-4-methoxypyrrolidin-1-yl)-3-fluoro-5,6,7,8-tetrahydroquinolin-6-yl]-4,6-dimethylthieno[2,3-b]pyridine-2-carboxamide |
| 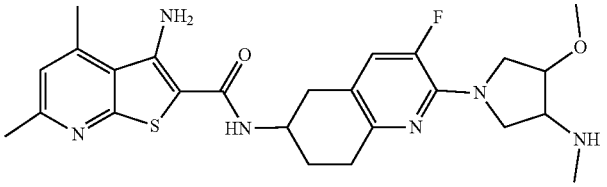 [SMILES: CNC1CN(c2nc3c(cc2F)CC(NC(=O)c2sc4nc(C)cc(C)c4c2N)CC3)CC1OC] | 3-amino-N-{3-fluoro-2-[3-methoxy-4-(methylamino)pyrrolidin-1-yl]-5,6,7,8-tetrahydroquinolin-6-yl}-4,6-dimethylthieno[2,3-b]pyridine-2-carboxamide |
| 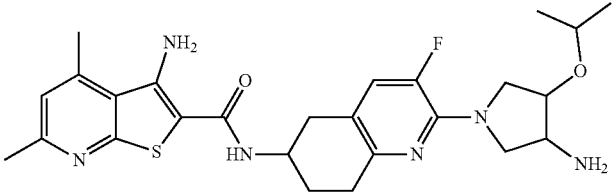 [SMILES: Cc1cc(C)c2c(N)c(C(=O)NC3CCc4nc(N5CC(N)C(OC(C)C)C5)c(F)cc4C3)sc2n1] | 3-amino-N-{2-[3-amino-4-(propan-2-yloxy)pyrrolidin-1-yl]-3-fluoro-5,6,7,8-tetrahydroquinolin-6-yl}-4,6-dimethylthieno[2,3-b]pyridine-2-carboxamide |
| 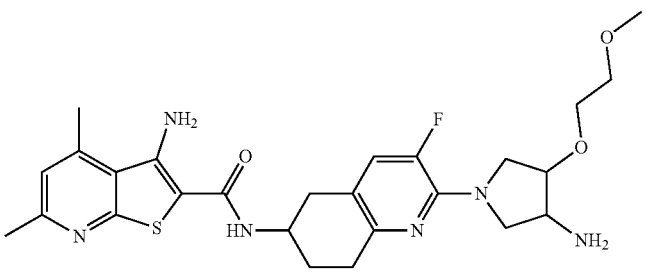 | 3-amino-N-{2-[3-amino-4-(2-methoxyethoxy)pyrrolidin-1-yl]-3-fluoro-5,6,7,8-tetrahydroquinolin-6-yl}-4,6-dimethylthieno[2,3-b]pyridine-2-carboxamide |
| 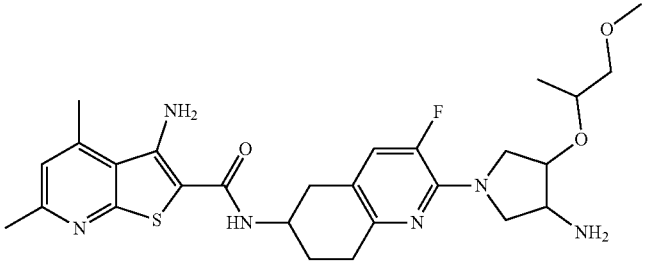 | 3-amino-N-(2-{3-amino-4-[(1-methoxypropan-2-yl)oxy]pyrrolidin-1-yl}-3-fluoro-5,6,7,8-tetrahydroquinolin-6-yl)-4,6-dimethylthieno[2,3-b]pyridine-2-carboxamide |
| 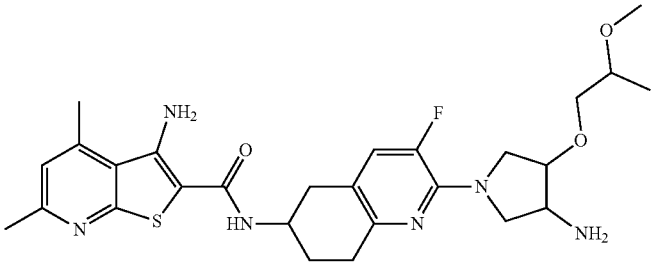 [SMILES: COC(C)COC1CN(c2nc3c(cc2F)CC(NC(=O)c2sc4nc(C)cc(C)c4c2N)CC3)CC1N] | 3-amino-N-{2-[3-amino-4-(2-methoxypropoxy)pyrrolidin-1-yl]-3-fluoro-5,6,7,8-tetrahydroquinolin-6-yl}-4,6-dimethylthieno[2,3-b]pyridine-2-carboxamide |

TABLE 27-continued

| Structure | Chemical Name |
|---|---|
| 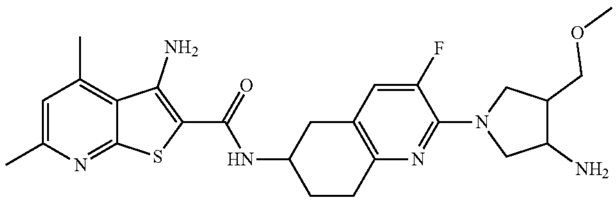 | 3-amino-N-{2-[3-amino-4-(methoxymethyl)pyrrolidin-1-yl]-3-fluoro-5,6,7,8-tetrahydroquinolin-6-yl}-4,6-dimethylthieno[2,3-b]pyridine-2-carboxamide |
| 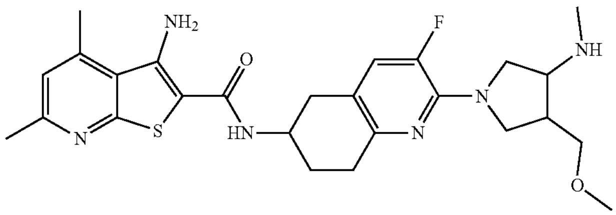 | 3-amino-N-{3-fluoro-2-[3-(methoxymethyl)-4-(methylamino)pyrrolidin-1-yl]-5,6,7,8-tetrahydroquinolin-6-yl}-4,6-dimethylthieno[2,3-b]pyridine-2-carboxamide |
| 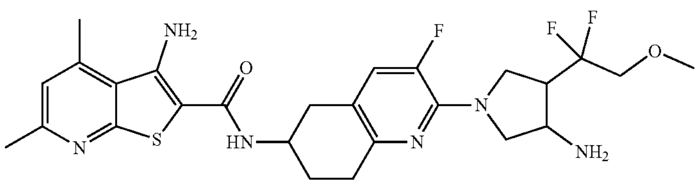 | 3-amino-N-{2-[3-amino-4-(1,1-difluoro-2-methoxyethyl)pyrrolidin-1-yl]-3-fluoro-5,6,7,8-tetrahydroquinolin-6-yl}-4,6-dimethylthieno[2,3-b]pyridine-2-carboxamide |
| 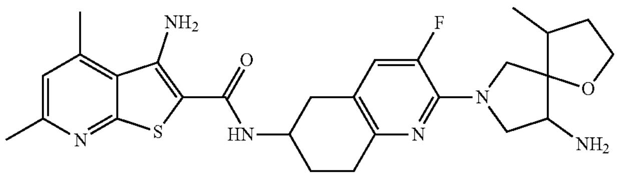 [SMILES: Cc1cc(C)c2c(N)c(C(=O)NC3CCc4nc(N5CC(N)C6(C5)OCCC6C)c(F)cc4C3)sc2n1] | 3-amino-N-(2-{9-amino-4-methyl-1-oxa-7-azaspiro[4.4]nonan-7-yl}-3-fluoro-5,6,7,8-tetrahydroquinolin-6-yl)-4,6-dimethylthieno[2,3-b]pyridine-2-carboxamide |
| 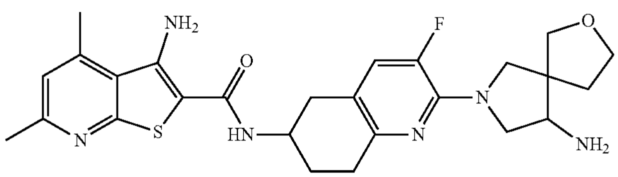 [SMILES: Cc1cc(C)c2c(N)c(C(=O)NC3CCc4nc(N5CC(N)C6(CCOC6)C5)c(F)cc4C3)sc2n1] | 3-amino-N-(2-{9-amino-2-oxa-7-azaspiro[4.4]nonan-7-yl}-3-fluoro-5,6,7,8-tetrahydroquinolin-6-yl)-4,6-dimethylthieno[2,3-b]pyridine-2-carboxamide |
| 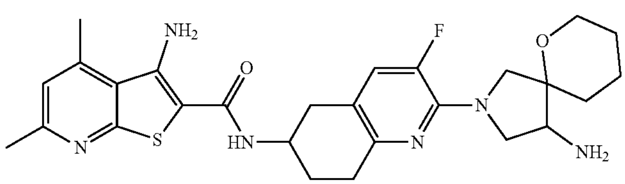 | 3-amino-N-(2-{4-amino-6-oxa-2-azaspiro[4.5]decan-2-yl}-3-fluoro-5,6,7,8-tetrahydroquinolin-6-yl)-4,6-dimethylthieno[2,3-b]pyridine-2-carboxamide |
| 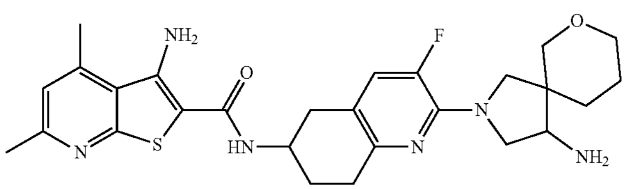 [SMILES: Cc1cc(C)c2c(N)c(C(=O)NC3CCc4nc(N5CC(N)C6(CCCOC6)C5)c(F)cc4C3)sc2n1] | 3-amino-N-(2-{4-amino-7-oxa-2-azaspiro[4.5]decan-2-yl}-3-fluoro-5,6,7,8-tetrahydroquinolin-6-yl)-4,6-dimethylthieno[2,3-b]pyridine-2-carboxamide |
| 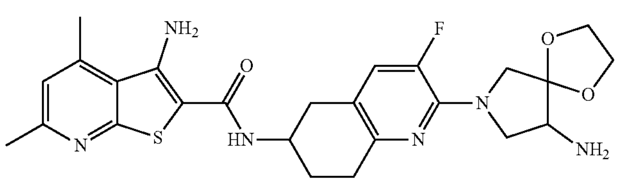 [SMILES: Cc1cc(C)c2c(N)c(C(=O)NC3CCc4nc(N5CC(N)C6(C5)OCCO6)c(F)cc4C3)sc2n1] | 3-amino-N-(2-{9-amino-1,4-dioxa-7-azaspiro[4.4]nonan-7-yl}-3-fluoro-5,6,7,8-tetrahydroquinolin-6-yl)-4,6-dimethylthieno[2,3-b]pyridine-2-carboxamide |

TABLE 27-continued

| Structure | Chemical Name |
|---|---|
| 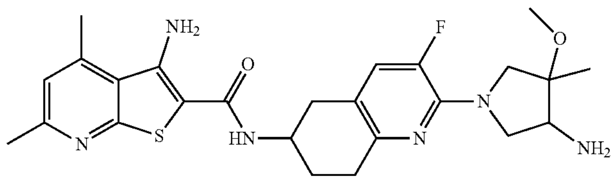 | 3-amino-N-[2-(4-amino-3-methoxy-3-methylpyrrolidin-1-yl)-3-fluoro-5,6,7,8-tetrahydroquinolin-6-yl]-4,6-dimethylthieno[2,3-b]pyridine-2-carboxamide |
| 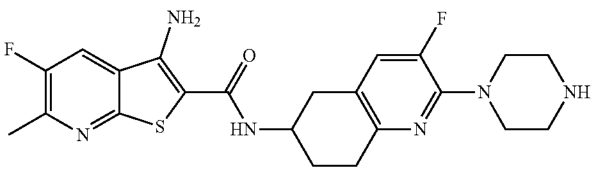 [SMILES: Cc1nc2sc(C(=O)NC3CCc4nc(N5CCNCC5)c(F)cc4C3)c(N)c2cc1F] | 3-amino-5-fluoro-N-[3-fluoro-2-(piperazin-1-yl)-5,6,7,8-tetrahydroquinolin-6-yl]-6-methylthieno[2,3-b]pyridine-2-carboxamide |
| 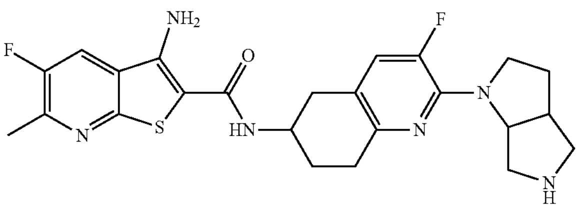 [SMILES: Cc1nc2sc(C(=O)NC3CCc4nc(N5CCC6CNCC65)c(F)cc4C3)c(N)c2cc1F] | 3-amino-5-fluoro-N-(3-fluoro-2-{octahydropyrrolo[2,3-c]pyrrol-1-yl}-5,6,7,8-tetrahydroquinolin-6-yl)-6-methylthieno[2,3-b]pyridine-2-carboxamide |
| 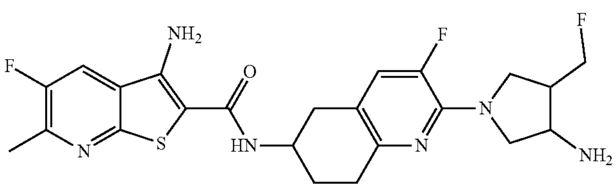 [SMILES: Cc1nc2sc(C(=O)NC3CCc4nc(N5CC(N)C(CF)C5)c(F)cc4C3)c(N)c2cc1F] | 3-amino-N-{2-[3-amino-4-(fluoromethyl)pyrrolidin-1-yl]-3-fluoro-5,6,7,8-tetrahydroquinolin-6-yl}-5-fluoro-6-methylthieno[2,3-b]pyridine-2-carboxamide |
| 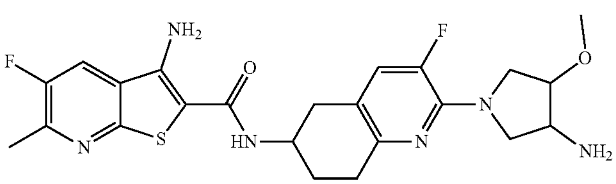 [SMILES: COC1CN(c2nc3c(cc2F)CC(NC(=O)c2sc4nc(C)c(F)cc4c2N)CC3)CC1N] | 3-amino-N-[2-(3-amino-4-methoxypyrrolidin-1-yl)-3-fluoro-5,6,7,8-tetrahydroquinolin-6-yl]-5-fluoro-6-methylthieno[2,3-b]pyridine-2-carboxamide |
| 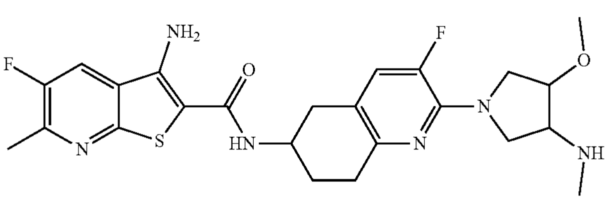 [SMILES: CNC1CN(c2nc3c(cc2F)CC(NC(=O)c2sc4nc(C)c(F)cc4c2N)CC3)CC1OC] | 3-amino-5-fluoro-N-{3-fluoro-2-[3-methoxy-4-(methylamino)pyrrolidin-1-yl]-5,6,7,8-tetrahydroquinolin-6-yl}-6-methylthieno[2,3-b]pyridine-2-carboxamide |
| 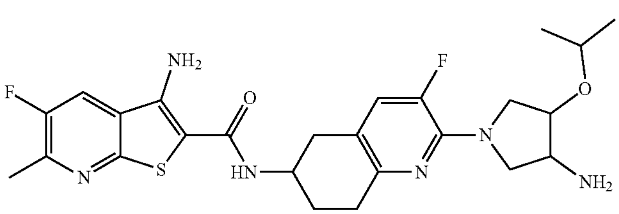 [SMILES: Cc1nc2sc(C(=O)NC3CCc4nc(N5CC(N)C(OC(C)C)C5)c(F)cc4C3)c(N)c2cc1F] | 3-amino-N-{2-[3-amino-4-(propan-2-yloxy)pyrrolidin-1-yl]-3-fluoro-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 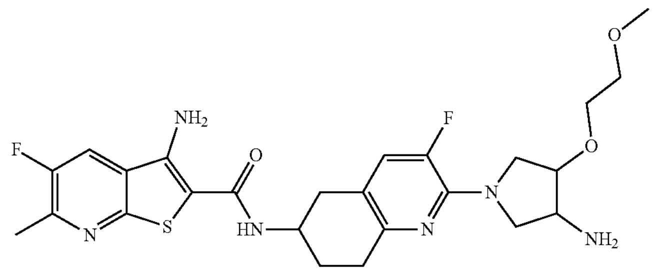 [SMILES: COCCOC1CN(c2nc3c(cc2F)CC(NC(=O)c2sc4nc(C)c(F)cc4c2N)CC3)CC1N] | 3-amino-N-{2-[3-amino-4-(2-methoxyethoxy)pyrrolidin-1-yl]-3-fluoro-5,6,7,8-tetrahydroquinolin-6-yl}-5-fluoro-6-methylthieno[2,3-b]pyridine-2-carboxamide |
| 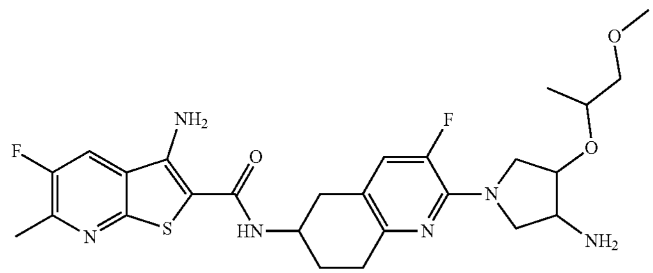 [SMILES: COCC(C)OC1CN(c2nc3c(cc2F)CC(NC(=O)c2sc4nc(C)c(F)cc4c2N)CC3)CC1N] | 3-amino-N-(2-{3-amino-4-[(1-methoxypropan-2-yl)oxy]pyrrolidin-1-yl}-3-fluoro-5,6,7,8-tetrahydroquinolin-6-yl)-5-fluoro-6-methylthieno[2,3-b]pyridine-2-carboxamide |
| 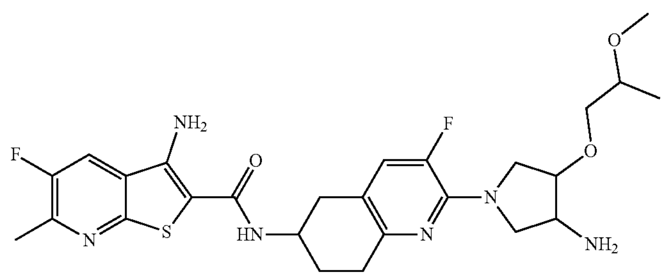 [SMILES: COC(C)COC1CN(c2nc3c(cc2F)CC(NC(=O)c2sc4nc(C)c(F)cc4c2N)CC3)CC1N] | 3-amino-N-{2-[3-amino-4-(2-methoxypropoxy)pyrrolidin-1-yl]-3-fluoro-5,6,7,8-tetrahydroquinolin-6-yl}-5-fluoro-6-methylthieno[2,3-b]pyridine-2-carboxamide |
| 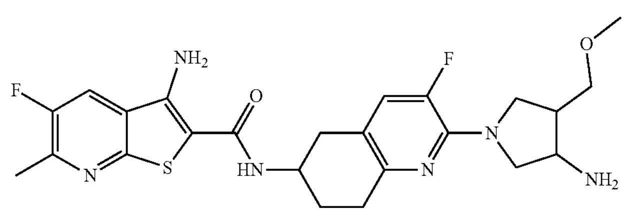 [SMILES: COCC1CN(c2nc3c(cc2F)CC(NC(=O)c2sc4nc(C)c(F)cc4c2N)CC3)CC1N] | 3-amino-N-{2-[3-amino-4-(methoxymethyl)pyrrolidin-1-yl]-3-fluoro-5,6,7,8-tetrahydroquinolin-6-yl}-5-fluoro-6-methylthieno[2,3-b]pyridine-2-carboxamide |
| 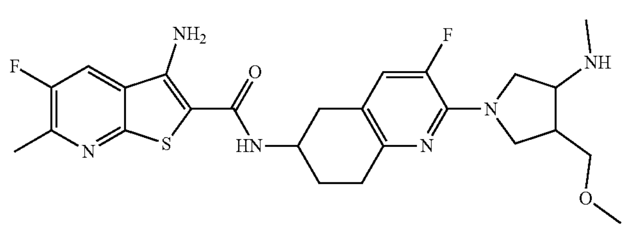 [SMILES: CNC1CN(c2nc3c(cc2F)CC(NC(=O)c2sc4nc(C)c(F)cc4c2N)CC3)CC1COC] | 3-amino-5-fluoro-N-{3-fluoro-2-[3-(methoxymethyl)-4-(methylamino)pyrrolidin-1-yl]-5,6,7,8-tetrahydroquinolin-6-yl}-6-methylthieno[2,3-b]pyridine-2-carboxamide |
| 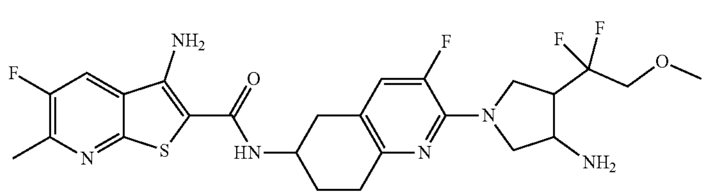 [SMILES: COCC(F)(F)C1CN(c2nc3c(cc2F)CC(NC(=O)c2sc4nc(C)c(F)cc4c2N)CC3)CC1N] | 3-amino-N-{2-[3-amino-4-(1,1-difluoro-2-methoxyethyl)pyrrolidin-1-yl]-3-fluoro-5,6,7,8-tetrahydroquinolin-6-yl}-5-fluoro-6-methylthieno[2,3-b]pyridine-2-carboxamide |

TABLE 27-continued

| Structure | Chemical Name |
|---|---|
| 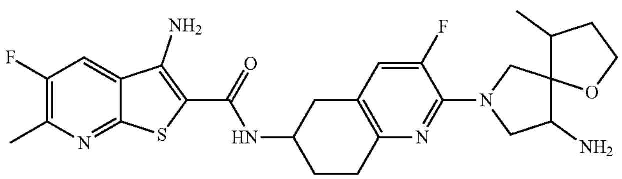 [SMILES: Cc1nc2sc(C(=O)NC3CCc4nc(N5CC(N)C6(C5)OCCC6C)c(F)cc4C3)c(N)c2cc1F] | 3-amino-N-(2-{9-amino-4-methyl-1-oxa-7-azaspiro[4.4]nonan-7-yl}-3-fluoro-5,6,7,8-tetrahydroquinolin-6-yl)-5-fluoro-6-methylthieno[2,3-b]pyridine-2-carboxamide |
| 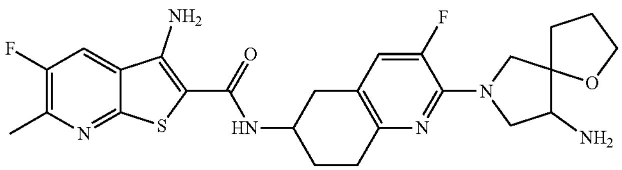 | 3-amino-N-(2-{9-amino-2-oxa-7-azaspiro[4.4]nonan-7-yl}-3-fluoro-5,6,7,8-tetrahydroquinolin-6-yl)-5-fluoro-6-methylthieno[2,3-b]pyridine-2-carboxamide |
| 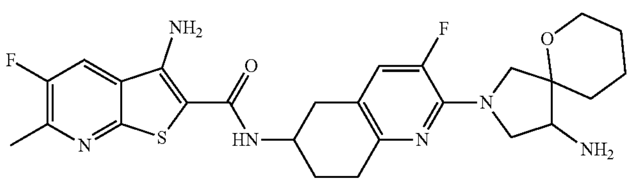 [SMILES: Cc1nc2sc(C(=O)NC3CCc4nc(N5CC(N)C6(CCCCO6)C5)c(F)cc4C3)c(N)c2cc1F] | 3-amino-N-(2-{4-amino-6-oxa-2-azaspiro[4.5]decan-2-yl}-3-fluoro-5,6,7,8-tetrahydroquinolin-6-yl)-5-fluoro-6-methylthieno[2,3-b]pyridine-2-carboxamide |
| 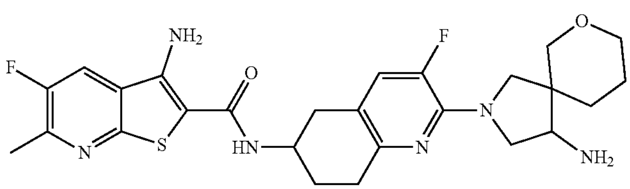 [SMILES: Cc1nc2sc(C(=O)NC3CCc4nc(N5CC(N)C6(CCCOC6)C5)c(F)cc4C3)c(N)c2cc1F] | 3-amino-N-(2-{4-amino-7-oxa-2-azaspiro[4.5]decan-2-yl}-3-fluoro-5,6,7,8-tetrahydroquinolin-6-yl)-5-fluoro-6-methylthieno[2,3-b]pyridine-2-carboxamide |
| 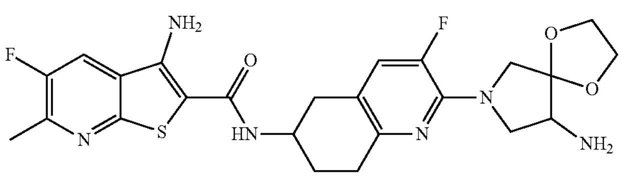 [SMILES: Cc1nc2sc(C(=O)NC3CCc4nc(N5CC(N)C6(C5)OCCO6)c(F)cc4C3)c(N)c2cc1F] | 3-amino-N-(2-{9-amino-1,4-dioxa-7-azaspiro[4.4]nonan-7-yl}-3-fluoro-5,6,7,8-tetrahydroquinolin-6-yl)-5-fluoro-6-methylthieno[2,3-b]pyridine-2-carboxamide |
| 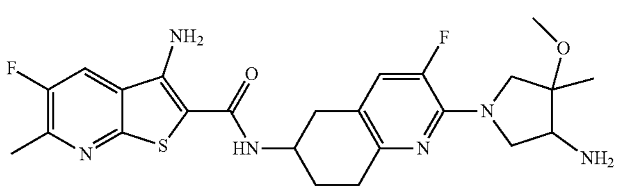 [SMILES: COC1(C)CN(c2nc3c(cc2F)CC(NC(=O)c2sc4nc(C)c(F)cc4c2N)CC3)CC1N] | 3-amino-N-[2-(4-amino-3-methoxy-3-methylpyrrolidin-1-yl)-3-fluoro-5,6,7,8-tetrahydroquinolin-6-yl]-5-fluoro-6-methylthieno[2,3-b]pyridine-2-carboxamide |
| 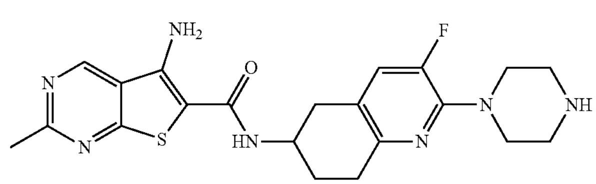 [SMILES: Cc1ncc2c(N)c(C(=O)NC3CCc4nc(N5CCNCC5)c(F)cc4C3)sc2n1] | 5-amino-N-[3-fluoro-2-(piperazin-1-yl)-5,6,7,8-tetrahydroquinolin-6-yl]-2-methylthieno[2,3-d]pyrimidine-6-carboxamide |
| 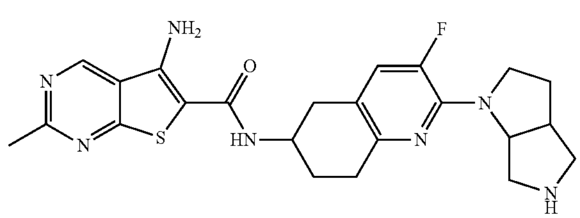 | 5-amino-N-(3-fluoro-2-{octahydropyrrolo[2,3-c]pyrrol-1-yl}-5,6,7,8-tetrahydroquinolin-6-yl)-2-methylthieno[2,3-d]pyrimidine-6-carboxamide |

TABLE 27-continued

| Structure | Chemical Name |
|---|---|
| 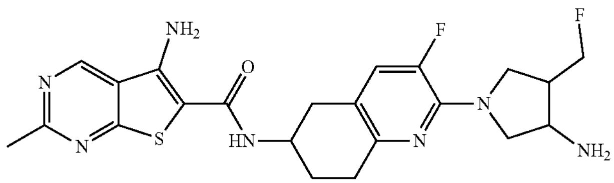 [SMILES: Cc1ncc2c(N)c(C(=O)NC3CCc4nc(N5CC(N)C(CF)C5)c(F)cc4C3)sc2n1] | 5-amino-N-{2-[3-amino-4-(fluoromethyl)pyrrolidin-1-yl]-3-fluoro-5,6,7,8-tetrahydroquinolin-6-yl}-2-methylthieno[2,3-d]pyrimidine-6-carboxamide |
| 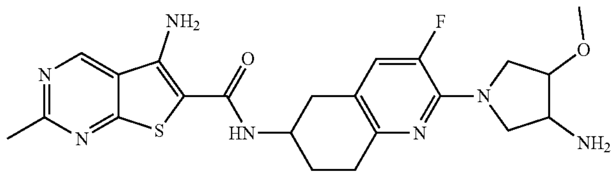 | 5-amino-N-[2-(3-amino-4-methoxypyrrolidin-1-yl)-3-fluoro-5,6,7,8-tetrahydroquinolin-6-yl]-2-methylthieno[2,3-d]pyrimidine-6-carboxamide |
| 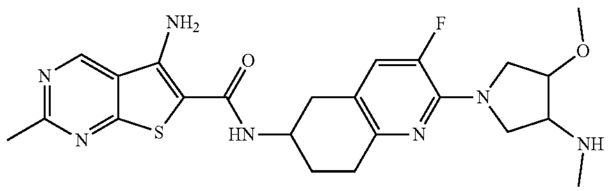 [SMILES: CNC1CN(c2nc3c(cc2F)CC(NC(=O)c2sc4nc(C)ncc4c2N)CC3)CC1OC] | 5-amino-N-{3-fluoro-2-[3-methoxy-4-(methylamino)pyrrolidin-1-yl]-5,6,7,8-tetrahydroquinolin-6-yl}-2-methylthieno[2,3-d]pyrimidine-6-carboxamide |
| 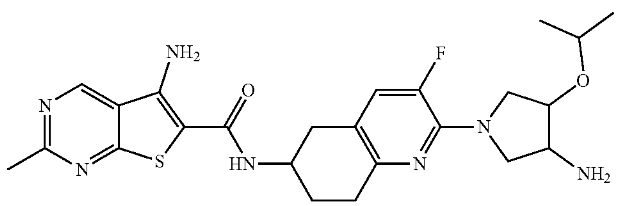 [SMILES: Cc1ncc2c(N)c(C(=O)NC3CCc4nc(N5CC(N)C(OC(C)C)C5)c(F)cc4C3)sc2n1] | 5-amino-N-{2-[3-amino-4-(propan-2-yloxy)pyrrolidin-1-yl]-3-fluoro-5,6,7,8-tetrahydroquinolin-6-yl}-2-methylthieno[2,3-d]pyrimidine-6-carboxamide |
| 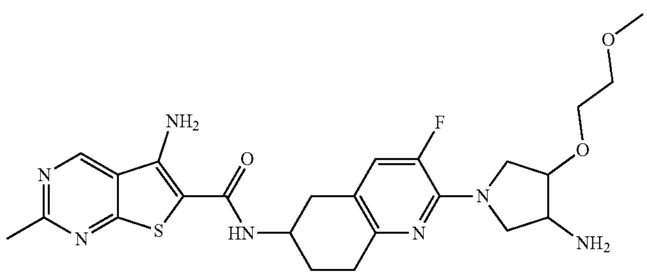 | 5-amino-N-{2-[3-amino-4-(2-methoxyethoxy)pyrrolidin-1-yl]-3-fluoro-5,6,7,8-tetrahydroquinolin-6-yl}-2-methylthieno[2,3-d]pyrimidine-6-carboxamide |
| 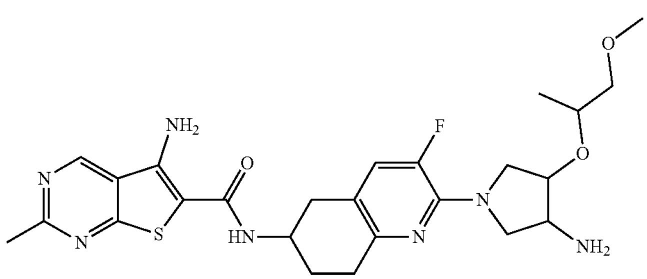 | 5-amino-N-(2-{3-amino-4-[(1-methoxypropan-2-yl)oxy]pyrrolidin-1-yl}-3-fluoro-5,6,7,8-tetrahydroquinolin-6-yl)-2-methylthieno[2,3-d]pyrimidine-6-carboxamide |
| 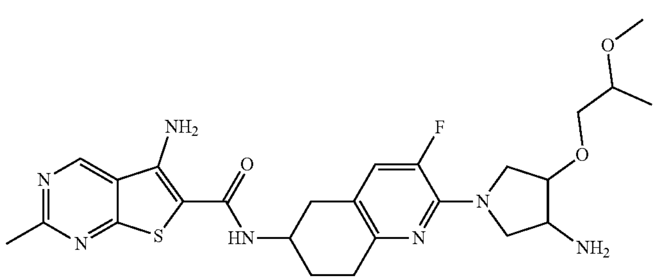 [SMILES: COC(C)COC1CN(c2nc3c(cc2F)CC(NC(=O)c2sc4nc(C)ncc4c2N)CC3)CC1N] | 5-amino-N-{2-[3-amino-4-(2-methoxypropoxy)pyrrolidin-1-yl]-3-fluoro-5,6,7,8-tetrahydroquinolin-6-yl}-2-methylthieno[2,3-d]pyrimidine-6-carboxamide |

TABLE 27-continued

| Structure | Chemical Name |
|---|---|
| 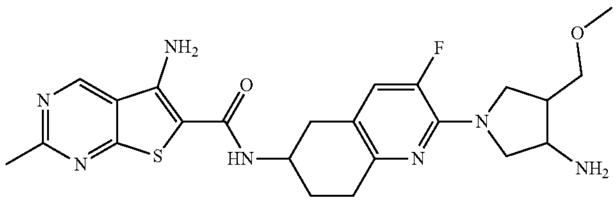 | 5-amino-N-{2-[3-amino-4-(methoxymethyl)pyrrolidin-1-yl]-3-fluoro-5,6,7,8-tetrahydroquinolin-6-yl}-2-methylthieno[2,3-d]pyrimidine-6-carboxamide |
| 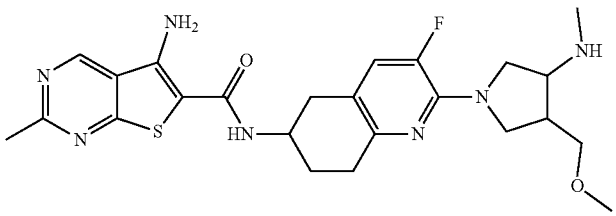 | 5-amino-N-{3-fluoro-2-[3-(methoxymethyl)-4-(methylamino)pyrrolidin-1-yl]-5,6,7,8-tetrahydroquinolin-6-yl}-2-methylthieno[2,3-d]pyrimidine-6-carboxamide |
| 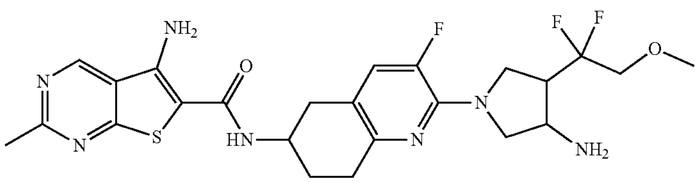 | 5-amino-N-{2-[3-amino-4-(1,1-difluoro-2-methoxyethyl)pyrrolidin-1-yl]-3-fluoro-5,6,7,8-tetrahydroquinolin-6-yl}-2-methylthieno[2,3-d]pyrimidine-6-carboxamide |
| 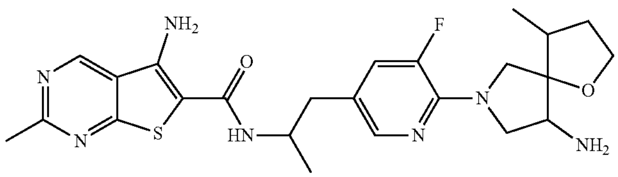 [SMILES: Cc1ncc2c(N)c(C(=O)NC(C)Cc3cnc(N4CC(N)C5(C4)OCCC5C)c(F)c3)sc2n1] | 5-amino-N-(2-{9-amino-4-methyl-1-oxa-7-azaspiro[4.4]nonan-7-yl}-3-fluoro-5,6,7,8-tetrahydroquinolin-6-yl)-2-methylthieno[2,3-d]pyrimidine-6-carboxamide |
| 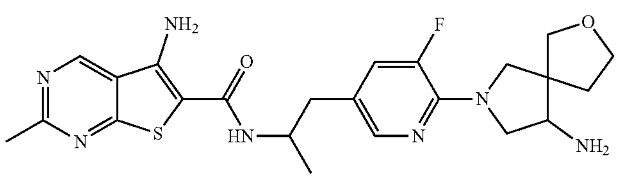 [SMILES: Cc1ncc2c(N)c(C(=O)NC(C)Cc3cnc(N4CC(N)C5(CCOC5)C4)c(F)c3)sc2n1] | 5-amino-N-(2-{9-amino-2-oxa-7-azaspiro[4.4]nonan-7-yl}-3-fluoro-5,6,7,8-tetrahydroquinolin-6-yl)-2-methylthieno[2,3-d]pyrimidine-6-carboxamide |
| 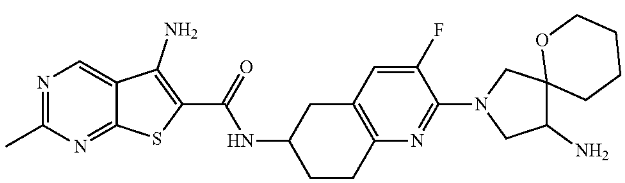 [SMILES: Cc1ncc2c(N)c(C(=O)NC3CCc4nc(N5CC(N)C6(CCCCO6)C5)c(F)cc4C3)sc2n1] | 5-amino-N-(2-{4-amino-6-oxa-2-azaspiro[4.5]decan-2-yl}-3-fluoro-5,6,7,8-tetrahydroquinolin-6-yl)-2-methylthieno[2,3-d]pyrimidine-6-carboxamide |
| 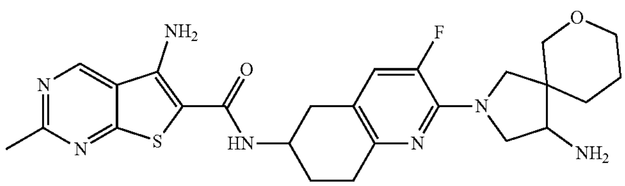 [SMILES: Cc1ncc2c(N)c(C(=O)NC3CCc4nc(N5CC(N)C6(CCCOC6)C5)c(F)cc4C3)sc2n1] | 5-amino-N-(2-{4-amino-7-oxa-2-azaspiro[4.5]decan-2-yl}-3-fluoro-5,6,7,8-tetrahydroquinolin-6-yl)-2-methylthieno[2,3-d]pyrimidine-6-carboxamide |
| 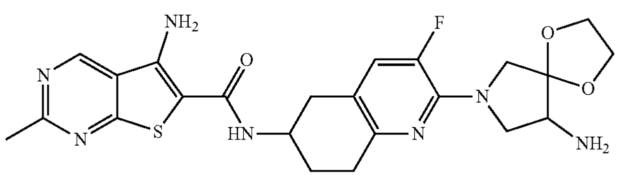 [SMILES: Cc1ncc2c(N)c(C(=O)NC3CCc4nc(N5CC(N)C6(C5)OCCO6)c(F)cc4C3)sc2n1] | 5-amino-N-(2-{9-amino-1,4-dioxa-7-azaspiro[4.4]nonan-7-yl}-3-fluoro-5,6,7,8-tetrahydroquinolin-6-yl)-2-methylthieno[2,3-d]pyrimidine-6-carboxamide |

TABLE 27-continued

| Structure | Chemical Name |
|---|---|
| 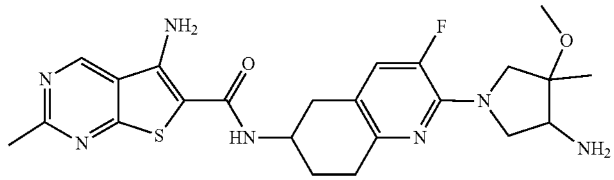 | 5-amino-N-[2-(4-amino-3-methoxy-3-methylpyrrolidin-1-yl)-3-fluoro-5,6,7,8-tetrahydroquinolin-6-yl]-2-methylthieno[2,3-d]pyrimidine-6-carboxamide |
| 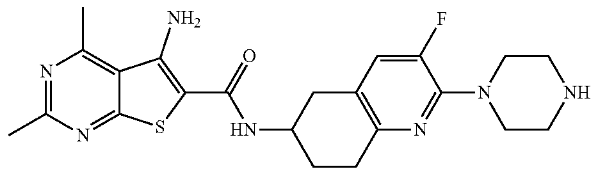 [SMILES: Cc1nc(C)c2c(N)c(C(=O)NC3CCc4nc(N5CCNCC5)c(F)cc4C3)sc2n1] | 5-amino-N-[3-fluoro-2-(piperazin-1-yl)-5,6,7,8-tetrahydroquinolin-6-yl]-2,4-dimethylthieno[2,3-d]pyrimidine-6-carboxamide |
| 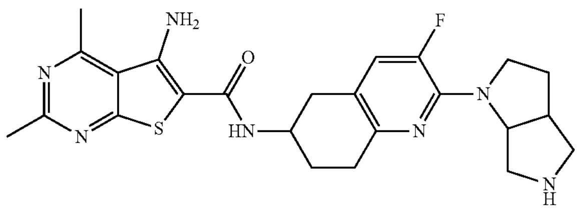 [SMILES: Cc1nc(C)c2c(N)c(C(=O)NC3CCc4nc(N5CCC6CNCC65)c(F)cc4C3)sc2n1] | 5-amino-N-(3-fluoro-2-{octahydropyrrolo[2,3-c]pyrrol-1-yl}-5,6,7,8-tetrahydroquinolin-6-yl)-2,4-dimethylthieno[2,3-d]pyrimidine-6-carboxamide |
| 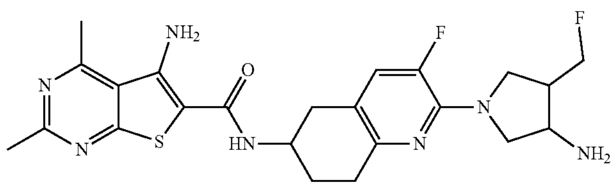 | 5-amino-N-{2-[3-amino-4-(fluoromethyl)pyrrolidin-1-yl]-3-fluoro-5,6,7,8-tetrahydroquinolin-6-yl}-2,4-dimethylthieno[2,3-d]pyrimidine-6-carboxamide |
| 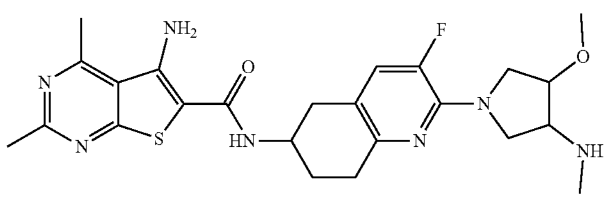 [SMILES: CNC1CN(c2nc3c(cc2F)CC(NC(=O)c2sc4nc(C)nc(C)c4c2N)CC3)CC1OC] | 5-amino-N-[2-(3-amino-4-methoxypyrrolidin-1-yl)-3-fluoro-5,6,7,8-tetrahydroquinolin-6-yl]-2,4-dimethylthieno[2,3-d]pyrimidine-6-carboxamide |
| 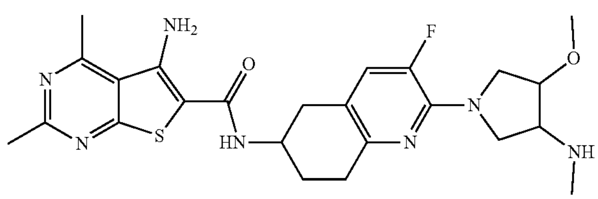 [SMILES: CNC1CN(c2nc3c(cc2F)CC(NC(=O)c2sc4nc(C)nc(C)c4c2N)CC3)CC1OC] | 5-amino-N-{3-fluoro-2-[3-methoxy-4-(methylamino)pyrrolidin-1-yl]-5,6,7,8-tetrahydroquinolin-6-yl}-2,4-dimethylthieno[2,3-d]pyrimidine-6-carboxamide |
| 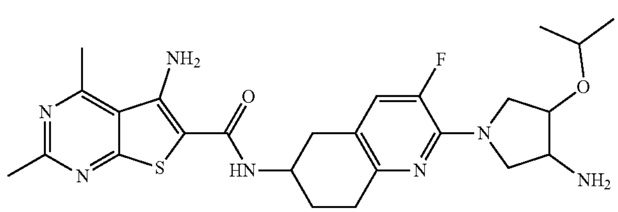 [SMILES: Cc1nc(C)c2c(N)c(C(=O)NC3CCc4nc(N5CC(N)C(OC(C)C)C5)c(F)cc4C3)sc2n1] | 5-amino-N-{2-[3-amino-4-(propan-2-yloxy)pyrrolidin-1-yl]-3-fluoro-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 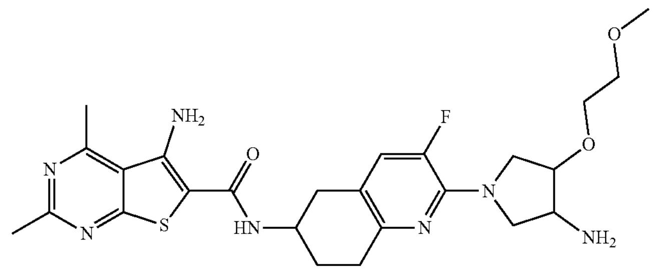 | 5-amino-N-{2-[3-amino-4-(2-methoxyethoxy)pyrrolidin-1-yl]-3-fluoro-5,6,7,8-tetrahydroquinolin-6-yl}-2,4-dimethylthieno[2,3-d]pyrimidine-6-carboxamide |
| 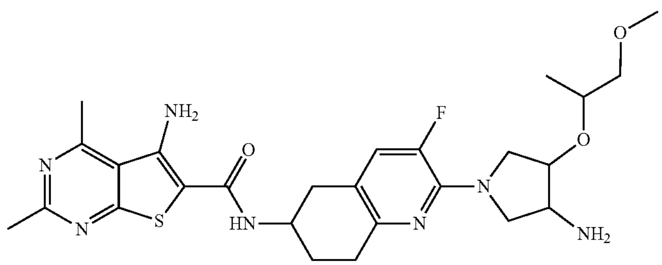 | 5-amino-N-(2-{3-amino-4-[(1-methoxypropan-2-yl)oxy]pyrrolidin-1-yl}-3-fluoro-5,6,7,8-tetrahydroquinolin-6-yl)-2,4-dimethylthieno[2,3-d]pyrimidine-6-carboxamide |
| 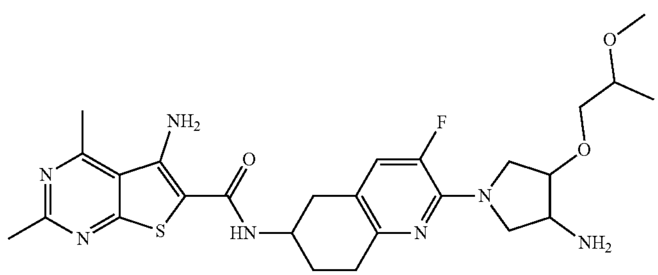 [SMILES: COC(C)COC1CN(c2nc3c(cc2F)CC(NC(=O)c2sc4nc(C)nc(C)c4c2N)CC3)CC1N] | 5-amino-N-{2-[3-amino-4-(2-methoxypropoxy)pyrrolidin-1-yl]-3-fluoro-5,6,7,8-tetrahydroquinolin-6-yl}-2,4-dimethylthieno[2,3-d]pyrimidine-6-carboxamide |
| 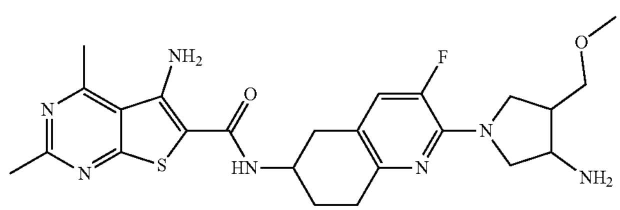 | 5-amino-N-{2-[3-amino-4-(methoxymethyl)pyrrolidin-1-yl]-3-fluoro-5,6,7,8-tetrahydroquinolin-6-yl}-2,4-dimethylthieno[2,3-d]pyrimidine-6-carboxamide |
| 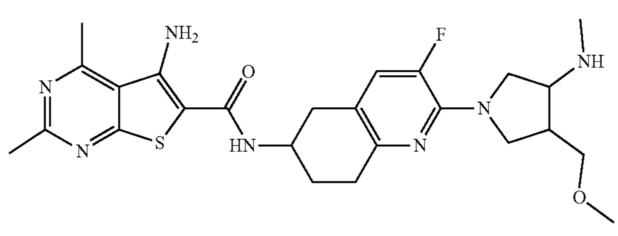 | 5-amino-N-{3-fluoro-2-[3-(methoxymethyl)-4-(methylamino)pyrrolidin-1-yl]-5,6,7,8-tetrahydroquinolin-6-yl}-2,4-dimethylthieno[2,3-d]pyrimidine-6-carboxamide |
| 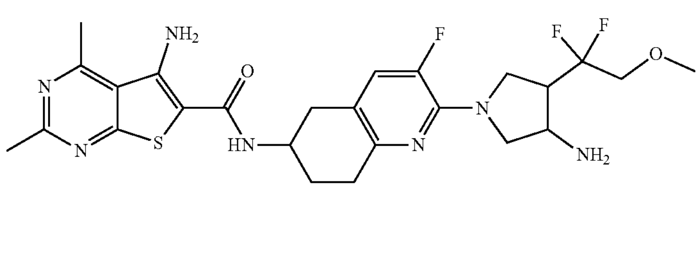 | 5-amino-N-{2-[3-amino-4-(1,1-difluoro-2-methoxyethyl)pyrrolidin-1-yl]-3-fluoro-5,6,7,8-tetrahydroquinolin-6-yl}-2,4-dimethylthieno[2,3-d]pyrimidine-6-carboxamide |

TABLE 27-continued

| Structure | Chemical Name |
|---|---|
| 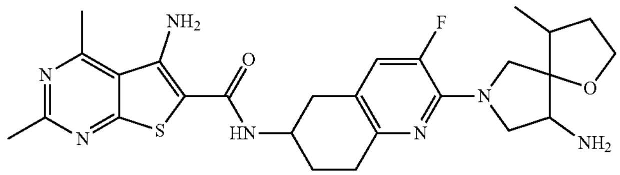 | 5-amino-N-(2-{9-amino-4-methyl-1-oxa-7-azaspiro[4.4]nonan-7-yl}-3-fluoro-5,6,7,8-tetrahydroquinolin-6-yl)-2,4-dimethylthieno[2,3-d]pyrimidine-6-carboxamide |
| 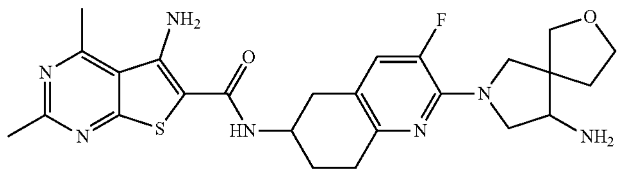 [SMILES: Cc1nc(C)c2c(N)c(C(=O)NC3CCc4nc(N5CC(N)C6(CCOC6)C5)c(F)cc4C3)sc2n1] | 5-amino-N-(2-{9-amino-2-oxa-7-azaspiro[4.4]nonan-7-yl}-3-fluoro-5,6,7,8-tetrahydroquinolin-6-yl)-2,4-dimethylthieno[2,3-d]pyrimidine-6-carboxamide |
| 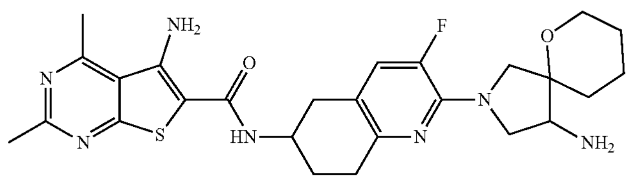 [SMILES: Cc1nc(C)c2c(N)c(C(=O)NC3CCc4nc(N5CC(N)C6(CCCCO6)C5)c(F)cc4C3)sc2n1] | 5-amino-N-(2-{4-amino-6-oxa-2-azaspiro[4.5]decan-2-yl}-3-fluoro-5,6,7,8-tetrahydroquinolin-6-yl)-2,4-dimethylthieno[2,3-d]pyrimidine-6-carboxamide |
| 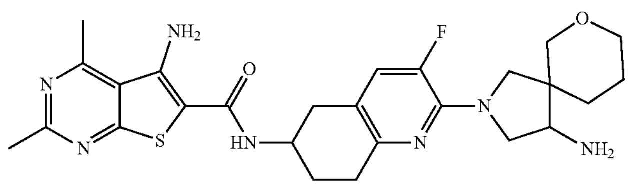 [SMILES: Cc1nc(C)c2c(N)c(C(=O)NC3CCc4nc(N5CC(N)C6(CCCOC6)C5)c(F)cc4C3)sc2n1] | 5-amino-N-(2-{4-amino-7-oxa-2-azaspiro[4.5]decan-2-yl}-3-fluoro-5,6,7,8-tetrahydroquinolin-6-yl)-2,4-dimethylthieno[2,3-d]pyrimidine-6-carboxamide |
| 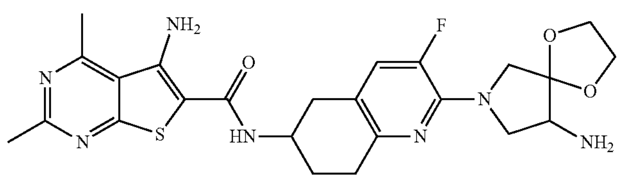 [SMILES: Cc1nc(C)c2c(N)c(C(=O)NC3CCc4nc(N5CC(N)C6(C5)OCCO6)c(F)cc4C3)sc2n1] | 5-amino-N-(2-{9-amino-1,4-dioxa-7-azaspiro[4.4]nonan-7-yl}-3-fluoro-5,6,7,8-tetrahydroquinolin-6-yl)-2,4-dimethylthieno[2,3-d]pyrimidine-6-carboxamide |
| 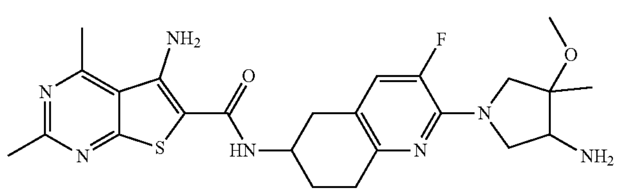 | 5-amino-N-[2-(4-amino-3-methoxy-3-methylpyrrolidin-1-yl)-3-fluoro-5,6,7,8-tetrahydroquinolin-6-yl]-2,4-dimethylthieno[2,3-d]pyrimidine-6-carboxamide |
| 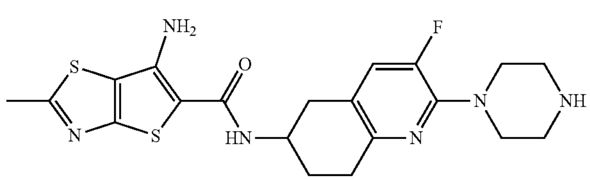 [SMILES: Cc1nc2sc(C(=O)NC3CCc4nc(N5CCNCC5)c(F)cc4C3)c(N)c2s1] | 6-amino-N-[3-fluoro-2-(piperazin-1-yl)-5,6,7,8-tetrahydroquinolin-6-yl]-2-methylthieno[2,3-d][1,3]thiazole-5-carboxamide |
| 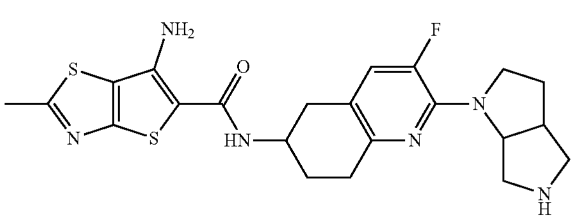 [SMILES: Cc1nc2sc(C(=O)NC3CCc4nc(N5CCC6CNCC65)c(F)cc4C3)c(N)c2s1] | 6-amino-N-(3-fluoro-2-{octahydropyrrolo[2,3-c]pyrrol-1-yl}-5,6,7,8-tetrahydroquinolin-6-yl)-2-methylthieno[2,3-d][1,3]thiazole-5-carboxamide |

TABLE 27-continued

| Structure | Chemical Name |
|---|---|
| 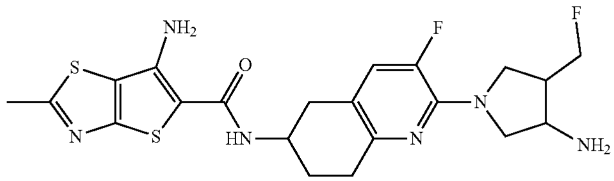 [SMILES: Cc1nc2sc(C(=O)NC3CCc4nc(N5CC(N)C(CF)C5)c(F)cc4C3)c(N)c2s1] | 6-amino-N-{2-[3-amino-4-(fluoromethyl)pyrrolidin-1-yl]-3-fluoro-5,6,7,8-tetrahydroquinolin-6-yl}-2-methylthieno[2,3-d][1,3]thiazole-5-carboxamide |
| 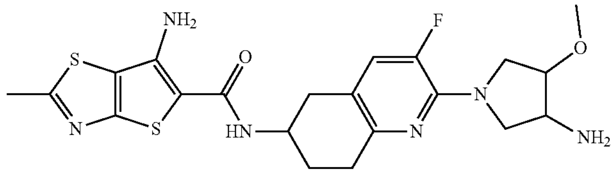 [SMILES: COC1CN(c2nc3c(cc2F)CC(NC(=O)c2sc4nc(C)sc4c2N)CC3)CC1N] | 6-amino-N-[2-(3-amino-4-methoxypyrrolidin-1-yl)-3-fluoro-5,6,7,8-tetrahydroquinolin-6-yl]-2-methylthieno[2,3-d][1,3]thiazole-5-carboxamide |
| 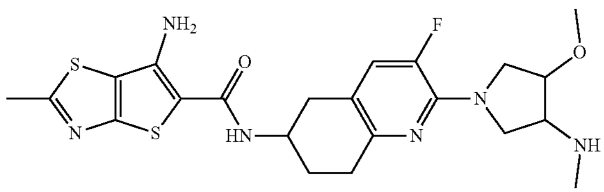 [SMILES: CNC1CN(c2nc3c(cc2F)CC(NC(=O)c2sc4nc(C)sc4c2N)CC3)CC1OC] | 6-amino-N-{3-fluoro-2-[3-methoxy-4-(methylamino)pyrrolidin-1-yl]-5,6,7,8-tetrahydroquinolin-6-yl}-2-methylthieno[2,3-d][1,3]thiazole-5-carboxamide |
| 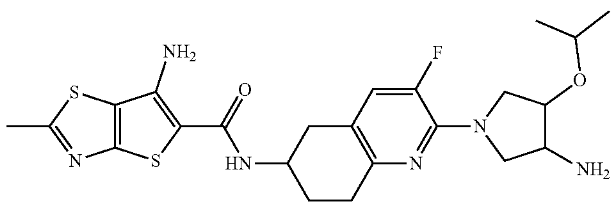 [SMILES: Cc1nc2sc(C(=O)NC3CCc4nc(N5CC(N)C(OC(C)C)C5)c(F)cc4C3)c(N)c2s1] | 6-amino-N-{2-[3-amino-4-(propan-2-yloxy)pyrrolidin-1-yl]-3-fluoro-5,6,7,8-tetrahydroquinolin-6-yl}-2-methylthieno[2,3-d][1,3]thiazole-5-carboxamide |
| 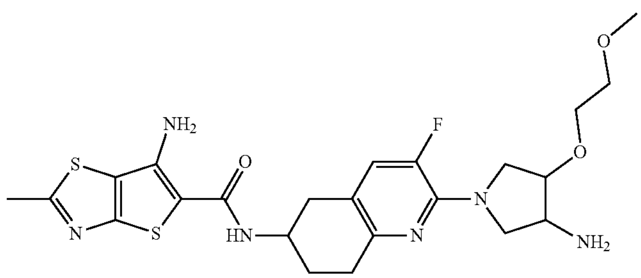 | 6-amino-N-{2-[3-amino-4-(2-methoxyethoxy)pyrrolidin-1-yl]-3-fluoro-5,6,7,8-tetrahydroquinolin-6-yl}-2-methylthieno[2,3-d][1,3]thiazole-5-carboxamide |
| 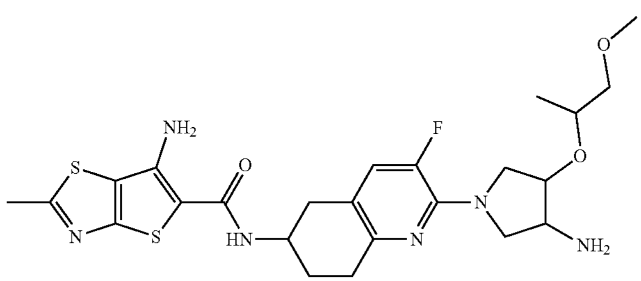 | 6-amino-N-(2-{3-amino-4-[(1-methoxypropan-2-yl)oxy]pyrrolidin-1-yl}-3-fluoro-5,6,7,8-tetrahydroquinolin-6-yl)-2-methylthieno[2,3-d][1,3]thiazole-5-carboxamide |
| 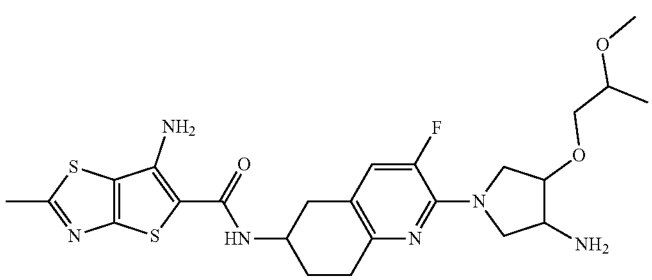 [SMILES: COC(C)COC1CN(c2nc3c(cc2F)CC(NC(=O)c2sc4nc(C)sc4c2N)CC3)CC1N] | 6-amino-N-{2-[3-amino-4-(2-methoxypropoxy)pyrrolidin-1-yl]-3-fluoro-5,6,7,8-tetrahydroquinolin-6-yl}-2-methylthieno[2,3-d][1,3]thiazole-5-carboxamide |

TABLE 27-continued

| Structure | Chemical Name |
|---|---|
| 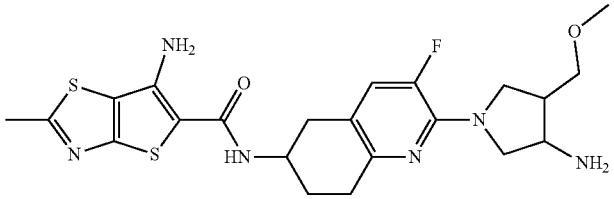 | 6-amino-N-{2-[3-amino-4-(methoxymethyl)pyrrolidin-1-yl]-3-fluoro-5,6,7,8-tetrahydroquinolin-6-yl}-2-methylthieno[2,3-d][1,3]thiazole-5-carboxamide |
| 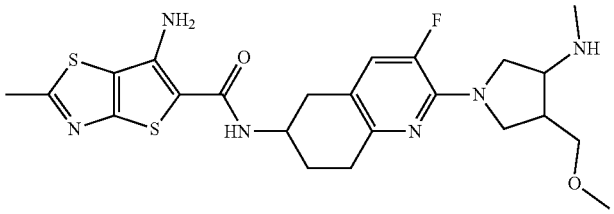 | 6-amino-N-{3-fluoro-2-[3-(methoxymethyl)-4-(methylamino)pyrrolidin-1-yl]-5,6,7,8-tetrahydroquinolin-6-yl}-2-methylthieno[2,3-d][1,3]thiazole-5-carboxamide |
| 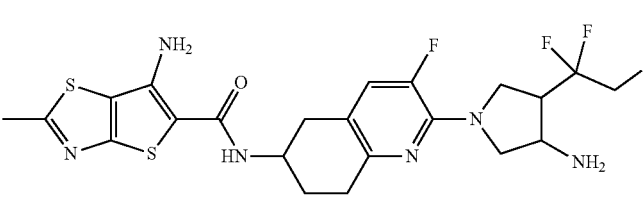 | 6-amino-N-{2-[3-amino-4-(1,1-difluoro-2-methoxyethyl)pyrrolidin-1-yl]-3-fluoro-5,6,7,8-tetrahydroquinolin-6-yl}-2-methylthieno[2,3-d][1,3]thiazole-5-carboxamide |
| 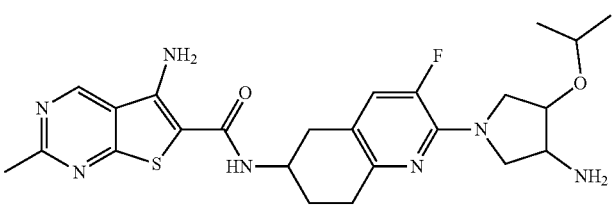 [SMILES: Cc1ncc2c(N)c(C(=O)NC3CCc4nc(N5CC(N)C(OC(C)C)C5)c(F)cc4C3)sc2n1] | 6-amino-N-(2-{9-amino-4-methyl-1-oxa-7-azaspiro[4.4]nonan-7-yl}-3-fluoro-5,6,7,8-tetrahydroquinolin-6-yl)-2-methylthieno[2,3-d][1,3]thiazole-5-carboxamide |
| 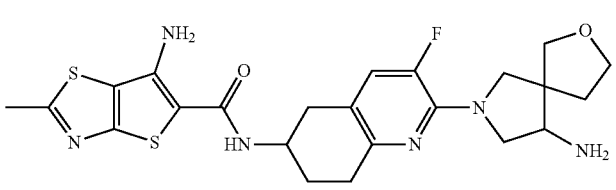 [SMILES: Cc1nc2sc(C(=O)NC3CCc4nc(N5CC(N)C6(CCOC6)C5)c(F)cc4C3)c(N)c2s1] | 6-amino-N-(2-{9-amino-2-oxa-7-azaspiro[4.4]nonan-7-yl}-3-fluoro-5,6,7,8-tetrahydroquinolin-6-yl)-2-methylthieno[2,3-d][1,3]thiazole-5-carboxamide |
| 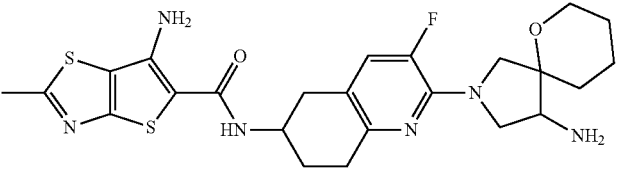 [SMILES: Cc1nc2sc(C(=O)NC3CCc4nc(N5CC(N)C6(CCCCO6)C5)c(F)cc4C3)c(N)c2s1] | 6-amino-N-(2-{4-amino-6-oxa-2-azaspiro[4.5]decan-2-yl}-3-fluoro-5,6,7,8-tetrahydroquinolin-6-yl)-2-methylthieno[2,3-d][1,3]thiazole-5-carboxamide |
| 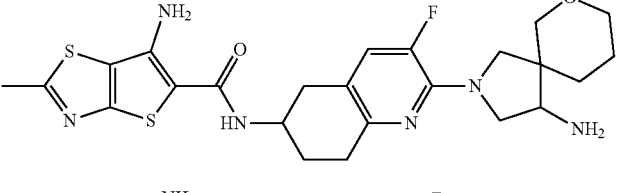 | 6-amino-N-(2-{4-amino-7-oxa-2-azaspiro[4.5]decan-2-yl}-3-fluoro-5,6,7,8-tetrahydroquinolin-6-yl)-2-methylthieno[2,3-d][1,3]thiazole-5-carboxamide |
| 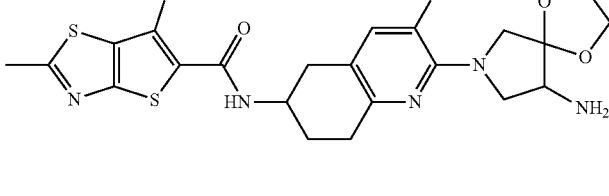 | 6-amino-N-(2-{9-amino-1,4-dioxa-7-azaspiro[4.4]nonan-7-yl}-3-fluoro-5,6,7,8-tetrahydroquinolin-6-yl)-2-methylthieno[2,3-d][1,3]thiazole-5-carboxamide |

TABLE 27-continued

| Structure | Chemical Name |
|---|---|
| 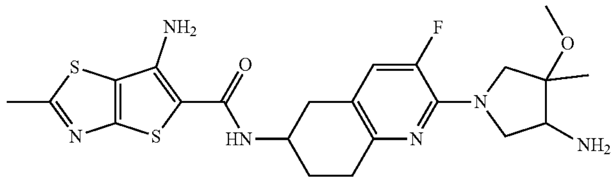 | 6-amino-N-[2-(4-amino-3-methoxy-3-methylpyrrolidin-1-yl)-3-fluoro-5,6,7,8-tetrahydroquinolin-6-yl]-2-methylthieno[2,3-d][1,3]thiazole-5-carboxamide |
| 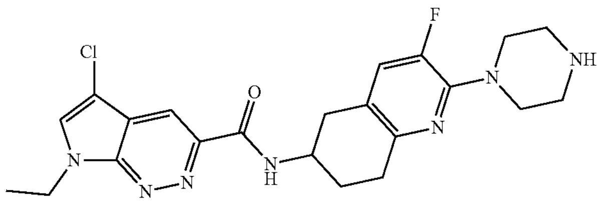 [SMILES: CCn1cc(Cl)c2cc(C(=O)NC3CCc4nc(N5CCNCC5)c(F)cc4C3)nnc21] | 5-chloro-7-ethyl-N-[3-fluoro-2-(piperazin-1-yl)-5,6,7,8-tetrahydroquinolin-6-yl]-7H-pyrrolo[2,3-c]pyridazine-3-carboxamide |
| 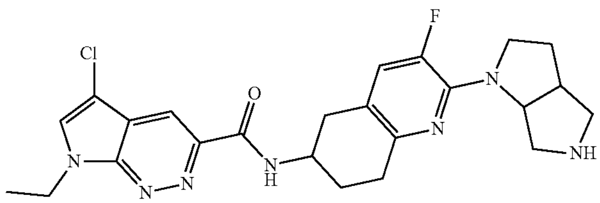 [SMILES: CCn1cc(Cl)c2cc(C(=O)NC3CCc4nc(N5CCC6CNCC65)c(F)cc4C3)nnc21] | 5-chloro-7-ethyl-N-(3-fluoro-2-{octahydropyrrolo[2,3-c]pyrrol-1-yl}-5,6,7,8-tetrahydroquinolin-6-yl)-7H-pyrrolo[2,3-c]pyridazine-3-carboxamide |
| 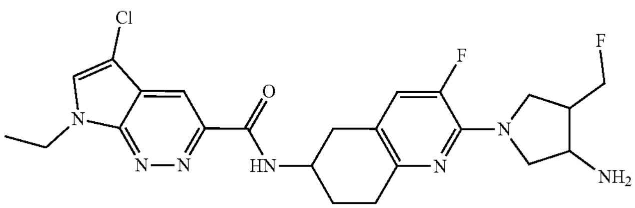 [SMILES: CCn1cc(Cl)c2cc(C(=O)NC3CCc4nc(N5CC(N)C(CF)C5)c(F)cc4C3)nnc21] | N-{2-[3-amino-4-(fluoromethyl)pyrrolidin-1-yl]-3-fluoro-5,6,7,8-tetrahydroquinolin-6-yl}-5-chloro-7-ethyl-7H-pyrrolo[2,3-c]pyridazine-3-carboxamide |
| 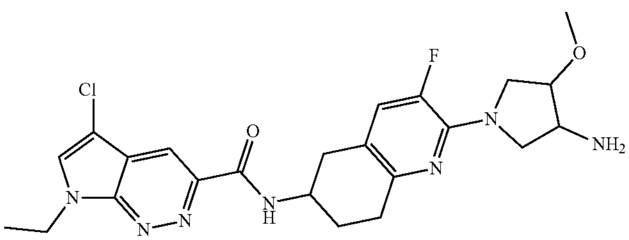 [SMILES: CCn1cc(Cl)c2cc(C(=O)NC3CCc4nc(N5CC(N)C(OC)C5)c(F)cc4C3)nnc21] | N-[2-(3-amino-4-methoxypyrrolidin-1-yl)-3-fluoro-5,6,7,8-tetrahydroquinolin-6-yl]-5-chloro-7-ethyl-7H-pyrrolo[2,3-c]pyridazine-3-carboxamide |
| 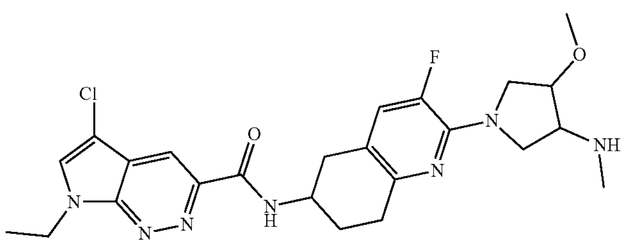 [SMILES: CCn1cc(Cl)c2cc(C(=O)NC3CCc4nc(N5CC(NC)C(OC)C5)c(F)cc4C3)nnc21] | 5-chloro-7-ethyl-N-{3-fluoro-2-[3-methoxy-4-(methylamino)pyrrolidin-1-yl]-5,6,7,8-tetrahydroquinolin-6-yl}-7H-pyrrolo[2,3-c]pyridazine-3-carboxamide |
| 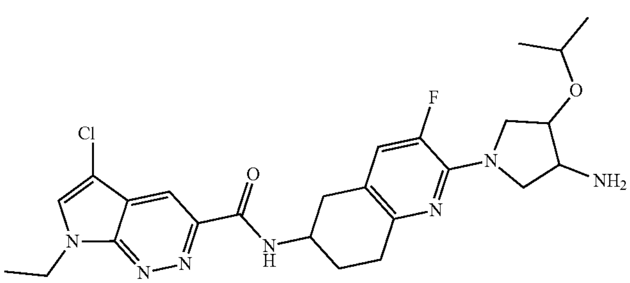 [SMILES: CCn1cc(Cl)c2cc(C(=O)NC3CCc4nc(N5CC(N)C(OC(C)C)C5)c(F)cc4C3)nnc21] | N-{2-[3-amino-4-(propan-2-yloxy)pyrrolidin-1-yl]-3-fluoro-5,6,7,8-tetrahydroquinolin-6-yl}-5-chloro-7-ethyl-7H-pyrrolo[2,3-c]pyridazine-3-carboxamide |

TABLE 27-continued

| Structure | Chemical Name |
|---|---|
| 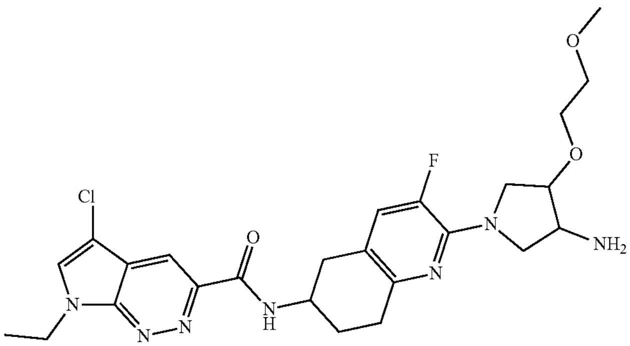 [SMILES: CCn1cc(Cl)c2cc(C(=O)NC3CCc4nc(N5CC(N)C(OCCOC)C5)c(F)cc4C3)nnc21] | N-{2-[3-amino-4-(2-methoxyethoxy)pyrrolidin-1-yl]-3-fluoro-5,6,7,8-tetrahydroquinolin-6-yl}-5-chloro-7-ethyl-7H-pyrrolo[2,3-c]pyridazine-3-carboxamide |
| 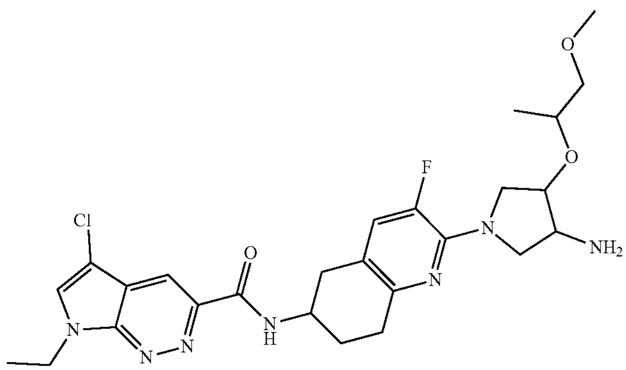 [SMILES: CCn1cc(Cl)c2cc(C(=O)NC3CCc4nc(N5CC(N)C(OC(C)COC)C5)c(F)cc4C3)nnc21] | N-(2-{3-amino-4-[(1-methoxypropan-2-yl)oxy]pyrrolidin-1-yl}-3-fluoro-5,6,7,8-tetrahydroquinolin-6-yl)-5-chloro-7-ethyl-7H-pyrrolo[2,3-c]pyridazine-3-carboxamide |
| 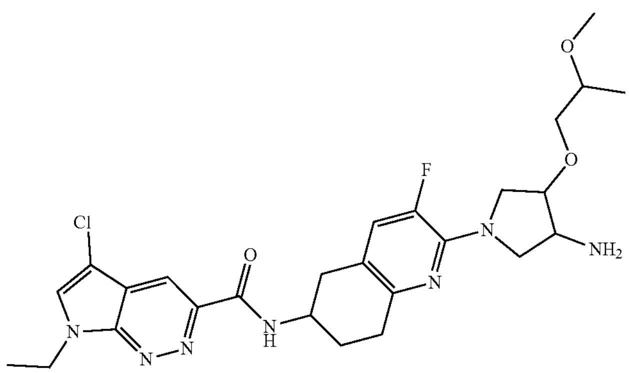 [SMILES: CCn1cc(Cl)c2cc(C(=O)NC3CCc4nc(N5CC(N)C(OCC(C)OC)C5)c(F)cc4C3)nnc21] | N-{2-[3-amino-4-(2-methoxypropoxy)pyrrolidin-1-yl]-3-fluoro-5,6,7,8-tetrahydroquinolin-6-yl}-5-chloro-7-ethyl-7H-pyrrolo[2,3-c]pyridazine-3-carboxamide |
| 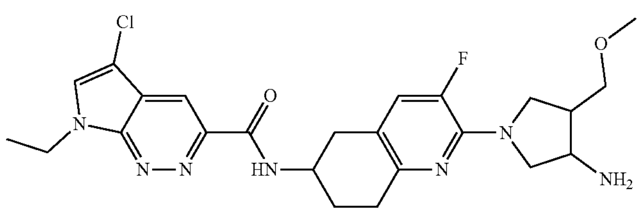 [SMILES: CCn1cc(Cl)c2cc(C(=O)NC3CCc4nc(N5CC(N)C(COC)C5)c(F)cc4C3)nnc21] | N-{2-[3-amino-4-(methoxymethyl)pyrrolidin-1-yl]-3-fluoro-5,6,7,8-tetrahydroquinolin-6-yl}-5-chloro-7-ethyl-7H-pyrrolo[2,3-c]pyridazine-3-carboxamide |
| 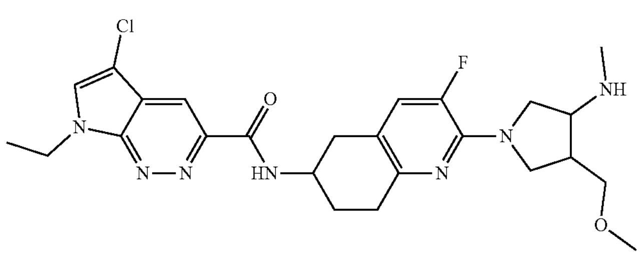 [SMILES: CCn1cc(Cl)c2cc(C(=O)NC3CCc4nc(N5CC(COC)C(NC)C5)c(F)cc4C3)nnc21] | 5-chloro-7-ethyl-N-{3-fluoro-2-[3-(methoxymethyl)-4-(methylamino)pyrrolidin-1-yl]-5,6,7,8-tetrahydroquinolin-6-yl}-7H-pyrrolo[2,3-c]pyridazine-3-carboxamide |

TABLE 27-continued

| Structure | Chemical Name |
|---|---|
| 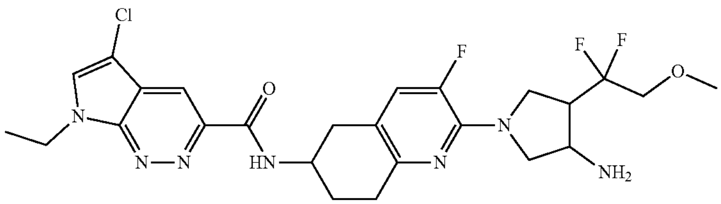 [SMILES: CCn1cc(Cl)c2cc(C(=O)NC3CCc4nc(N5CC(N)C(C(F)(F)COC)C5)c(F)cc4C3)nnc21] | N-{2-[3-amino-4-(1,1-difluoro-2-methoxyethyl)pyrrolidin-1-yl]-3-fluoro-5,6,7,8-tetrahydroquinolin-6-yl}-5-chloro-7-ethyl-7H-pyrrolo[2,3-c]pyridazine-3-carboxamide |
| 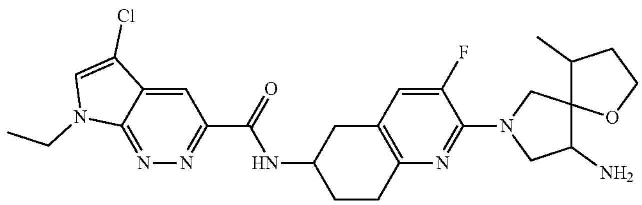 [SMILES: CCn1cc(Cl)c2cc(C(=O)NC3CCc4nc(N5CC(N)C6(C5)OCCC6C)c(F)cc4C3)nnc21] | N-(2-{9-amino-4-methyl-1-oxa-7-azaspiro[4.4]nonan-7-yl}-3-fluoro-5,6,7,8-tetrahydroquinolin-6-yl)-5-chloro-7-ethyl-7H-pyrrolo[2,3-c]pyridazine-3-carboxamide |
| 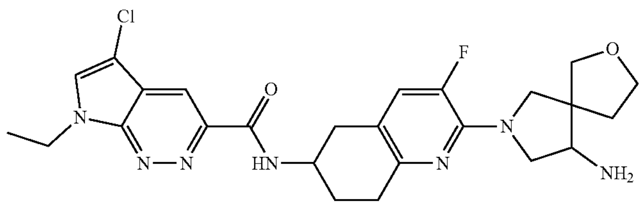 [SMILES: CCn1cc(Cl)c2cc(C(=O)NC3CCc4nc(N5CC(N)C6(CCOC6)C5)c(F)cc4C3)nnc21] | N-(2-{9-amino-2-oxa-7-azaspiro[4.4]nonan-7-yl}-3-fluoro-5,6,7,8-tetrahydroquinolin-6-yl)-5-chloro-7-ethyl-7H-pyrrolo[2,3-c]pyridazine-3-carboxamide |
| 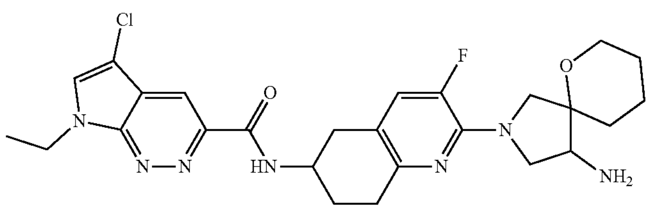 [SMILES: CCn1cc(Cl)c2cc(C(=O)NC3CCc4nc(N5CC(N)C6(CCCCO6)C5)c(F)cc4C3)nnc21] | N-(2-{4-amino-6-oxa-2-azaspiro[4.5]decan-2-yl}-3-fluoro-5,6,7,8-tetrahydroquinolin-6-yl)-5-chloro-7-ethyl-7H-pyrrolo[2,3-c]pyridazine-3-carboxamide |
| 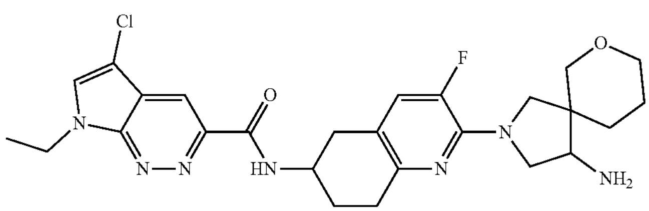 [SMILES: CCn1cc(Cl)c2cc(C(=O)NC3CCc4nc(N5CC(N)C6(CCCOC6)C5)c(F)cc4C3)nnc21] | N-(2-{4-amino-7-oxa-2-azaspiro[4.5]decan-2-yl}-3-fluoro-5,6,7,8-tetrahydroquinolin-6-yl)-5-chloro-7-ethyl-7H-pyrrolo[2,3-c]pyridazine-3-carboxamide |
| 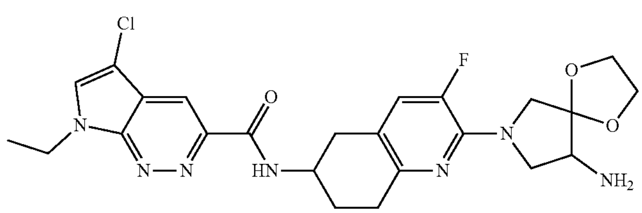 [SMILES: CCn1cc(Cl)c2cc(C(=O)NC3CCc4nc(N5CC(N)C6(C5)OCCO6)c(F)cc4C3)nnc21] | N-(2-{9-amino-1,4-dioxa-7-azaspiro[4.4]nonan-7-yl}-3-fluoro-5,6,7,8-tetrahydroquinolin-6-yl)-5-chloro-7-ethyl-7H-pyrrolo[2,3-c]pyridazine-3-carboxamide |
| 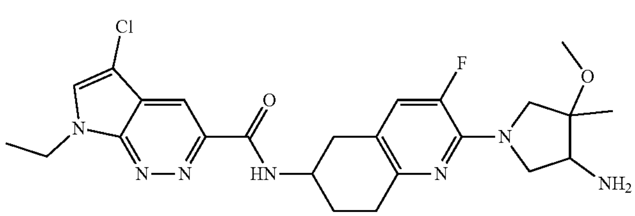 [SMILES: CCn1cc(Cl)c2cc(C(=O)NC3CCc4nc(N5CC(N)C(C)(OC)C5)c(F)cc4C3)nnc21] | N-[2-(4-amino-3-methoxy-3-methylpyrrolidin-1-yl)-3-fluoro-5,6,7,8-tetrahydroquinolin-6-yl]-5-chloro-7-ethyl-7H-pyrrolo[2,3-c]pyridazine-3-carboxamide |

TABLE 27-continued

| Structure | Chemical Name |
|---|---|
| 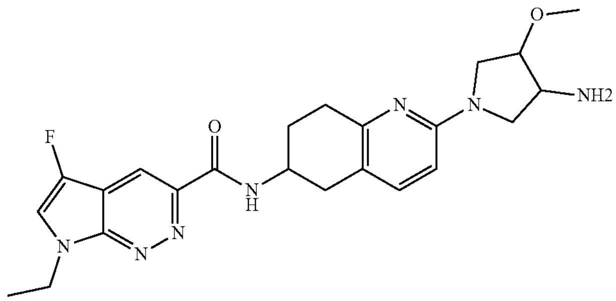 [SMILES: CCn1cc(F)c2cc(C(=O)NC3CCc4nc(N5CC(N)C(OC)C5)ccc4C3)nnc21] | N-[2-(3-amino-4-methoxypyrrolidin-1-yl)-5,6,7,8-tetrahydroquinolin-6-yl]-7-ethyl-5-fluoro-7H-pyrrolo[2,3-c]pyridazine-3-carboxamide |
| 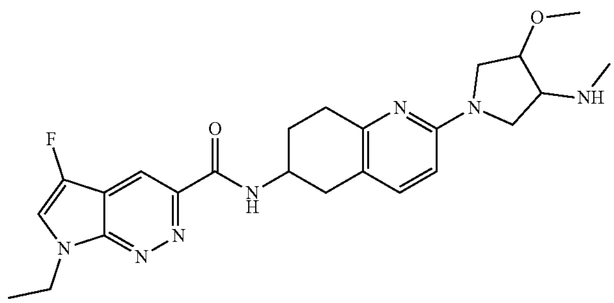 [SMILES: CCn1cc(F)c2cc(C(=O)NC3CCc4nc(N5CC(NC)C(OC)C5)ccc4C3)nnc21] | 7-ethyl-5-fluoro-N-{2-[3-methoxy-4-(methylamino)pyrrolidin-1-yl]-5,6,7,8-tetrahydroquinolin-6-yl}-7H-pyrrolo[2,3-c]pyridazine-3-carboxamide |
| 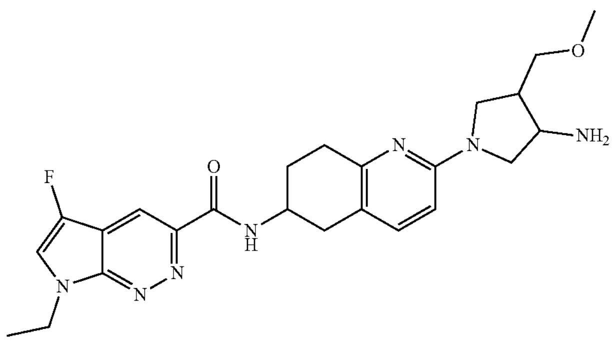 [SMILES: CCn1cc(F)c2cc(C(=O)NC3CCc4nc(N5CC(N)C(COC)C5)ccc4C3)nnc21] | N-{2-[3-amino-4-(methoxymethyl)pyrrolidin-1-yl]-5,6,7,8-tetrahydroquinolin-6-yl}-7-ethyl-5-fluoro-7H-pyrrolo[2,3-c]pyridazine-3-carboxamide |
| 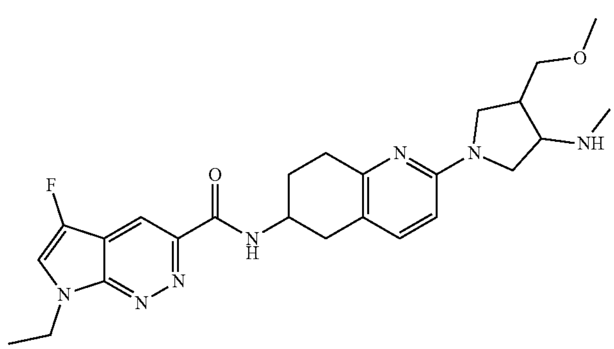 [SMILES: CCn1cc(F)c2cc(C(=O)NC3CCc4nc(N5CC(COC)C(NC)C5)ccc4C3)nnc21] | 7-ethyl-5-fluoro-N-{2-[3-(methoxymethyl)-4-(methylamino)pyrrolidin-1-yl]-5,6,7,8-tetrahydroquinolin-6-yl}-7H-pyrrolo[2,3-c]pyridazine-3-carboxamide |

TABLE 28

| Structure | Chemical Name |
|---|---|
| 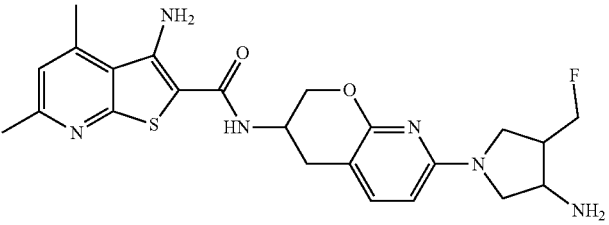 [SMILES: Cc1cc(C)c2c(N)c(C(=O)NC3COc4nc(N5CC(N)C(CF)C5)ccc4C3)sc2n1] | 3-amino-N-{7-[3-amino-4-(fluoromethyl)pyrrolidin-1-yl]-2H,3H,4H-pyrano[2,3-b]pyridin-3-yl}-4,6-dimethylthieno[2,3-b]pyridine-2-carboxamide |
| 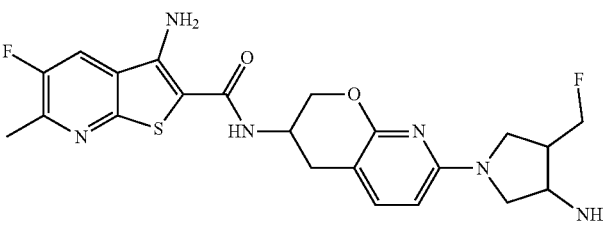 | 3-amino-N-{7-[3-amino-4-(fluoromethyl)pyrrolidin-1-yl]-2H,3H,4H-pyrano[2,3-b]pyridin-3-yl}-5-fluoro-6-methylthieno[2,3-b]pyridine-2-carboxamide |
| 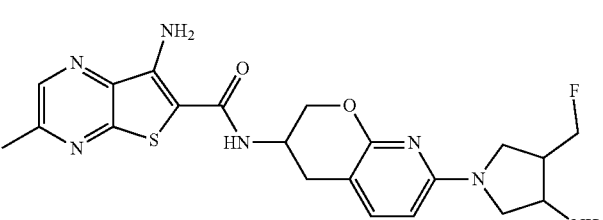 | 7-amino-N-{7-[3-amino-4-(fluoromethyl)pyrrolidin-1-yl]-2H,3H,4H-pyrano[2,3-b]pyridin-3-yl}-3-methylthieno[2,3-b]pyrazine-6-carboxamide |
| 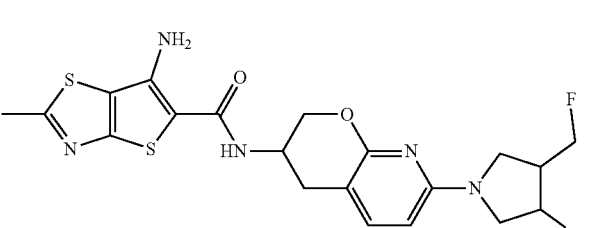 | 6-amino-N-{7-[3-amino-4-(fluoromethyl)pyrrolidin-1-yl]-2H,3H,4H-pyrano[2,3-b]pyridin-3-yl}-2-methylthieno[2,3-d][1,3]thiazole-5-carboxamide |
| 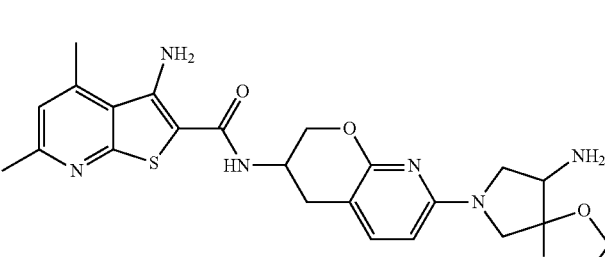 | 3-amino-N-(7-{9-amino-1,4-dioxa-7-azaspiro[4.4]nonan-7-yl}-2H,3H,4H-pyrano[2,3-b]pyridin-3-yl)-4,6-dimethylthieno[2,3-b]pyridine-2-carboxamide |
| 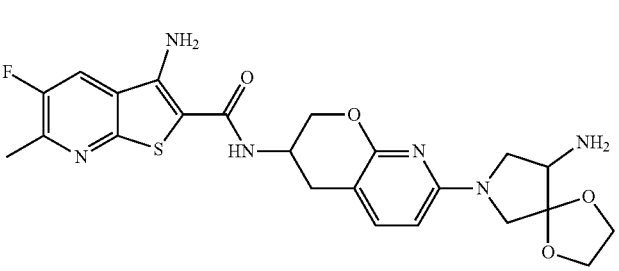 [SMILES: Cc1nc2sc(C(=O)NC3COc4nc(N5CC(N)C6(C5)OCCO6)ccc4C3)c(N)c2cc1F] | 3-amino-N-(7-{9-amino-1,4-dioxa-7-azaspiro[4.4]nonan-7-yl}-2H,3H,4H-pyrano[2,3-b]pyridin-3-yl)-5-fluoro-6-methylthieno[2,3-b]pyridine-2-carboxamide |

TABLE 28-continued

| Structure | Chemical Name |
|---|---|
| 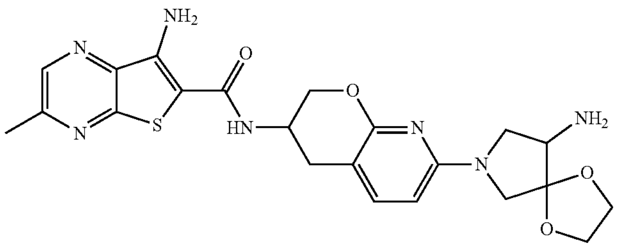 [SMILES: Cc1cnc2c(N)c(C(=O)NC3COc4nc(N5CC(N)C6(C5)OCCO6)ccc4C3)sc2n1] | 7-amino-N-(7-{9-amino-1,4-dioxa-7-azaspiro[4.4]nonan-7-yl}-2H,3H,4H-pyrano[2,3-b]pyridin-3-yl)-3-methylthieno[2,3-b]pyrazine-6-carboxamide |
| 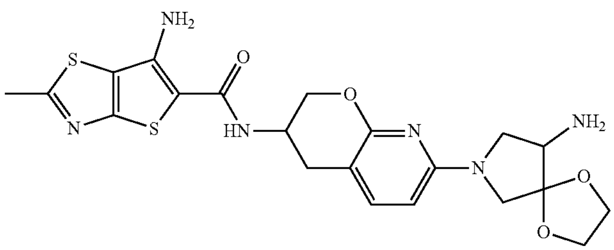 [SMILES: Cc1nc2sc(C(=O)NC3COc4nc(N5CC(N)C6(C5)OCCO6)ccc4C3)c(N)c2s1] | 6-amino-N-(7-{9-amino-1,4-dioxa-7-azaspiro[4.4]nonan-7-yl}-2H,3H,4H-pyrano[2,3-b]pyridin-3-yl)-2-methylthieno[2,3-d][1,3]thiazole-5-carboxamide |
| 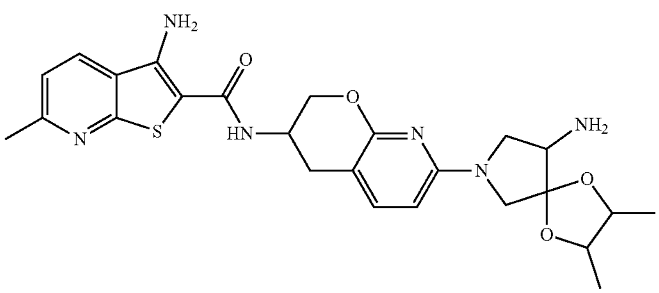 | 3-amino-N-(7-{9-amino-2,3-dimethyl-1,4-dioxa-7-azaspiro[4.4]nonan-7-yl}-2H,3H,4H-pyrano[2,3-b]pyridin-3-yl)-6-methylthieno[2,3-b]pyridine-2-carboxamide |
| 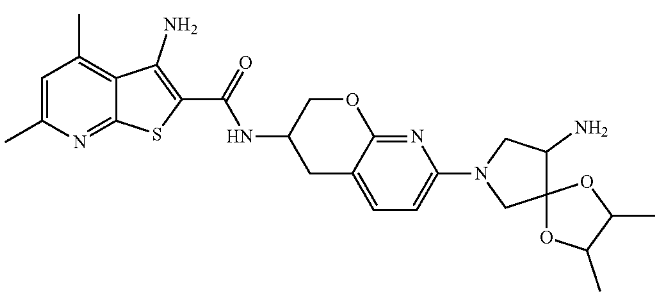 | 3-amino-N-(7-{9-amino-2,3-dimethyl-1,4-dioxa-7-azaspiro[4.4]nonan-7-yl}-2H,3H,4H-pyrano[2,3-b]pyridin-3-yl)-4,6-dimethylthieno[2,3-b]pyridine-2-carboxamide |
| 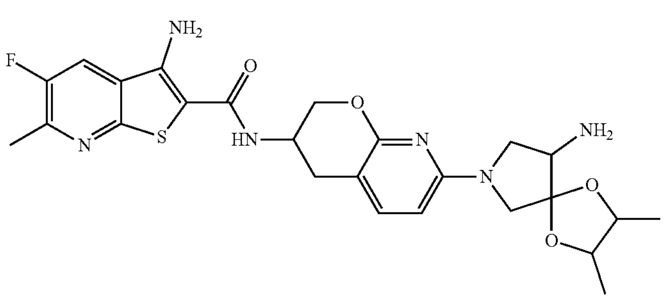 [SMILES: Cc1nc2sc(C(=O)NC3COc4nc(N5CC(N)C6(C5)OC(C)C(C)O6)ccc4C3)c(N)c2cc1F] | 3-amino-N-(7-{9-amino-2,3-dimethyl-1,4-dioxa-7-azaspiro[4.4]nonan-7-y]}-2H,3H,4H-pyrano[2,3-b]pyridin-3-yl)-5-fluoro-6-methylthieno[2,3-b]pyridine-2-carboxamide |

TABLE 28-continued

| Structure | Chemical Name |
|---|---|
| | 7-amino-N-(7-{9-amino-2,3-dimethyl-1,4-dioxa-7-azaspiro[4.4]nonan-7-yl}-2H,3H,4H-pyrano[2,3-b]pyridin-3-yl)-3-methylthieno[2,3-b]pyrazine-6-carboxamide |
| 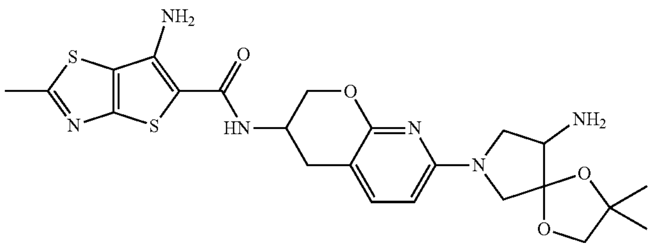 | 6-amino-N-(7-{9-amino-2,3-dimethyl-1,4-dioxa-7-azaspiro[4.4]nonan-7-yl}-2H,3H,4H-pyrano[2,3-b]pyridin-3-yl)-2-methylthieno[2,3-d][1,3]thiazole-5-carboxamide |
| 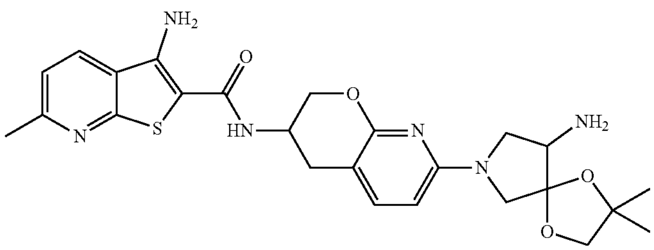 | 3-amino-N-(7-{9-amino-2,2-dimethyl-1,4-dioxa-7-azaspiro[4.4]nonan-7-yl}-2H,3H,4H-pyrano[2,3-b]pyridin-3-yl)-6-methylthieno[2,3-b]pyridine-2-carboxamide |
| 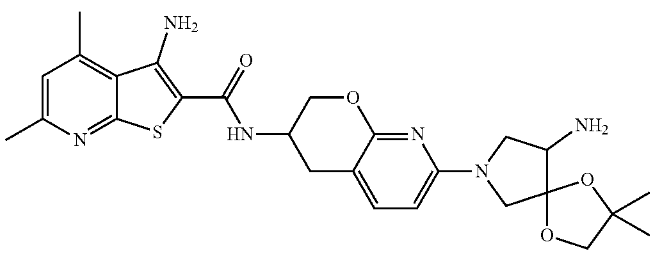 | 3-amino-N-(7-{9-amino-2,2-dimethyl-1,4-dioxa-7-azaspiro[4.4]nonan-7-yl}-2H,3H,4H-pyrano[2,3-b]pyridin-3-yl)-4,6-dimethylthieno[2,3-b]pyridine-2-carboxamide |
| 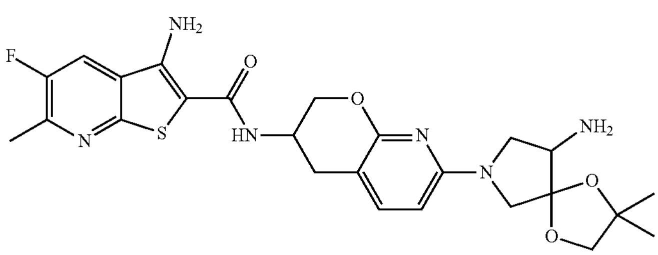 | 3-amino-N-(7-{9-amino-2,2-dimethyl-1,4-dioxa-7-azaspiro[4.4]nonan-7-yl}-2H,3H,4H-pyrano[2,3-b]pyridin-3-yl)-5-fluoro-6-methylthieno[2,3-b]pyridine-2-carboxamide |
| 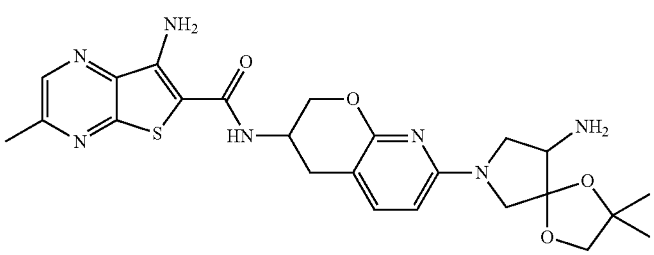 | 7-amino-N-(7-{9-amino-2,2-dimethyl-1,4-dioxa-7-azaspiro[4.4]nonan-7-yl}-2H,3H,4H-pyrano[2,3-b]pyridin-3-yl)-3-methylthieno[2,3-b]pyrazine-6-carboxamide |

TABLE 28-continued

| Structure | Chemical Name |
|---|---|
| | 6-amino-N-(7-{9-amino-2,2-dimethyl-1,4-dioxa-7-azaspiro[4.4]nonan-7-yl}-2H,3H,4H-pyrano[2,3-b]pyridin-3-yl)-2-methylthieno[2,3-d][1,3]thiazole-5-carboxamide |
| | 3-amino-N-(7-{9-amino-4,10-dioxa-7-azadispiro[2.1.4⁵.2³]undecan-7-yl}-2H,3H,4H-pyrano[2,3-b]pyridin-3-yl)-6-methylthieno[2,3-b]pyridine-2-carboxamide |
| | 3-amino-N-(7-{9-amino-4,10-dioxa-7-azadispiro[2.1.4⁵.2³]undecan-7-yl}-2H,3H,4H-pyrano[2,3-b]pyridin-3-yl)-4,6-dimethylthieno[2,3-b]pyridine-2-carboxamide |
| | 3-amino-N-(7-{9-amino-4,10-dioxa-7-azadispiro[2.1.4⁵.2³]undecan-7-yl}-2H,3H,4H-pyrano[2,3-b]pyridin-3-yl)-5-fluoro-6-methylthieno[2,3-b]pyridine-2-carboxamide |
| | 7-amino-N-(7-{9-amino-4,10-dioxa-7-azadispiro[2.1.4⁵.2³]undecan-7-yl}-2H,3H,4H-pyrano[2,3-b]pyridin-3-yl)-3-methylthieno[2,3-b]pyrazine-6-carboxamide |

TABLE 28-continued

| Structure | Chemical Name |
|---|---|
| | 6-amino-N-(7-{9-amino-4,10-dioxa-7-azadispiro[2.1.4⁵.2³]undecan-7-yl}-2H,3H,4H-pyrano[2,3-b]pyridin-3-yl)-2-methylthieno[2,3-d][1,3]thiazole-5-carboxamide |
| 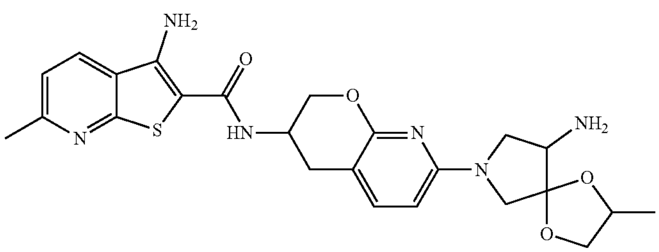 | 3-amino-N-(7-{9-amino-2-methyl-1,4-dioxa-7-azaspiro[4.4]nonan-7-yl}-2H,3H,4H-pyrano[2,3-b]pyridin-3-yl)-6-methylthieno[2,3-b]pyridine-2-carboxamide |
| 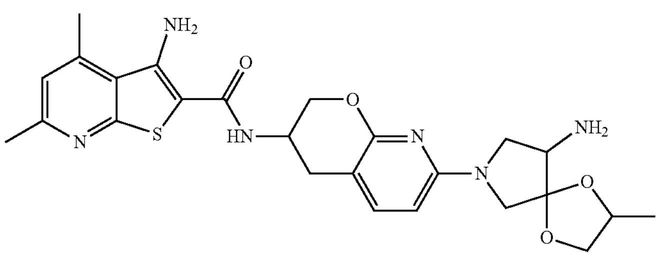 | 3-amino-N-(7-{9-amino-2-methyl-1,4-dioxa-7-azaspiro[4.4]nonan-7-yl}-2H,3H,4H-pyrano[2,3-b]pyridin-3-yl)-4,6-dimethylthieno[2,3-b]pyridine-2-carboxamide |
| 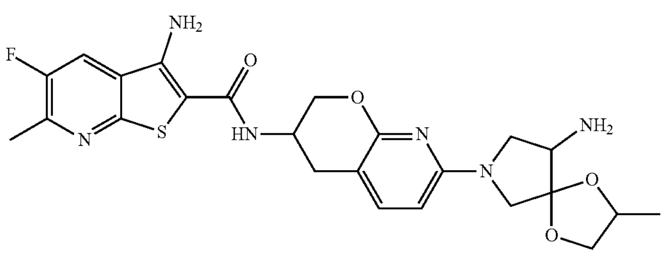 [SMILES: Cc1nc2sc(C(=O)NC3COc4nc(N5CC(N)C6(C5)OCC(C)O6)ccc4C3)c(N)c2cc1F] | 3-amino-N-(7-{9-amino-2-methyl-1,4-dioxa-7-azaspiro[4.4]nonan-7-yl}-2H,3H,4H-pyrano[2,3-b]pyridin-3-yl)-5-fluoro-6-methylthieno[2,3-b]pyridine-2-carboxamide |
| 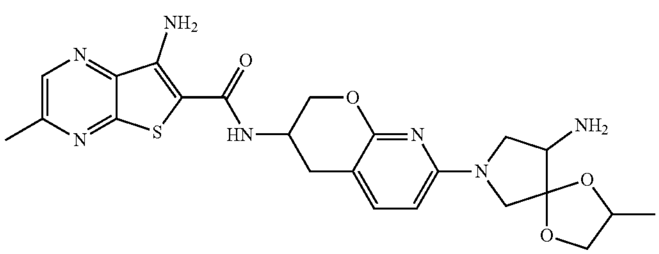 | 7-amino-N-(7-{9-amino-2-methyl-1,4-dioxa-7-azaspiro[4.4]nonan-7-yl}-2H,3H,4H-pyrano[2,3-b]pyridin-3-yl)-3-methylthieno[2,3-b]pyrazine-6-carboxamide |
| 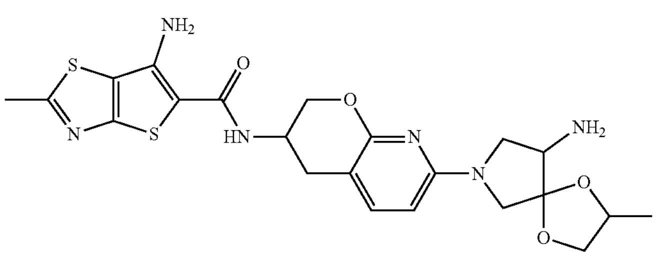 | 6-amino-N-(7-{9-amino-2-methyl-1,4-dioxa-7-azaspiro[4.4]nonan-7-yl}-2H,3H,4H-pyrano[2,3-b]pyridin-3-yl)-2-methylthieno[2,3-d][1,3]thiazole-5-carboxamide |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula (I):

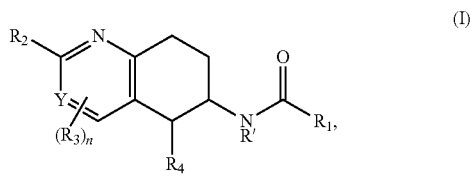

(I)

or a pharmaceutically acceptable form thereof, wherein

Y is chosen from $C(R_3)$ and N;

R' is chosen from H and $CH_3$;

$R_1$ is chosen from 6-11 membered heteroaryls optionally substituted with one or more substituents chosen from $R_5$ or $R_6$;

$R_2$ is chosen from N-linked 4-12 membered heterocyclyls and C-linked 4-12 membered heterocyclyls, wherein the heterocyclyls are optionally substituted with one or more $R_5$, and further wherein any $R_2$ group containing hydrogen can have one or more hydrogens replaced with deuterium;

each $R_3$ is independently chosen from H, deuterium, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, —OH, —CN, wherein each of $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, cycloalkyl, heterocycloalkyl, aryl, and heteroaryl groups are optionally substituted with one or more $R_7$;

$R_4$ is chosen from H, deuterium, $(C_1\text{-}C_6)$ alkyl, halogen, —OH, —CN, and further wherein any $R_4$ group containing hydrogen can have one or more hydrogens replaced with deuterium;

each $R_5$ (if present) is independently chosen from —OH, —$NH_2$, $NHC(O)CH_3$, —$C(O)NHCH_3$, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, cycloalkyl, heterocycloalkyl, and —C(O)-heterocycloalkyl groups, wherein each of —$NH_2$, —NHC(O)$CH_3$, —C(O)NH$CH_3$, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, cycloalkyl, heterocycloalkyl, and —C(O)-heterocycloalkyl are optionally substituted with one or more substituents independently chosen from $(C_1\text{-}C_6)$ alkoxy, —$NH_2$, and —OH, and wherein any $R_5$ group containing hydrogen can have one or more hydrogens replaced with deuterium;

each $R_6$ (if present) is chosen from —NH$(C_1\text{-}C_6)$alkyl-aryls, —NH$(C_1\text{-}C_6)$alkyl-heteroaryls, —NH$(C_1\text{-}C_6)$alkyl-heterocyclyl groups, and —NH$(C_1\text{-}C_6)$alkyl-heterocyclyl groups, wherein each of the $R_6$ groups are optionally substituted with one or more substituents chosen from —OH, —NH, halogens, $(C_1\text{-}C_6)$ alkyl, $(C_1\text{-}C_6)$ alkoxy, and $(C_1\text{-}C_6)$ haloalkyl groups, and further wherein any $R_6$ group containing hydrogen can have one or more hydrogens replaced with deuterium;

each $R_7$ is independently chosen from —OH, —$NH_2$, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, cycloalkyl, —C(O)-cycloalkyl, heterocycloalkyl, and —C(O)-heterocycloalkyl groups, wherein each of —$NH_2$, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, cycloalkyl, —C(O)-cycloalkyl, heterocycloalkyl, and —C(O)-heterocycloalkyl are optionally substituted with one or more substituents independently chosen from $(C_1\text{-}C_6)$ alkyl, $(C_1\text{-}C_6)$ alkoxy, and —OH; and n is 0, 1, 2, or 3.

2. The compound of claim 1, of Formula (II):

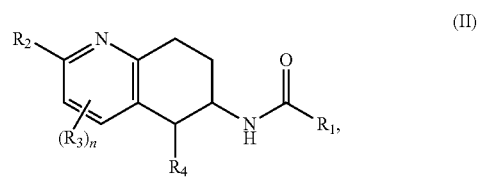

(II)

or a pharmaceutically acceptable form thereof, wherein $R_1$, $R_2$, $R_3$, $R_4$, $R_5$, $R_6$, $R_7$, and n are all as defined for Formula (I).

3. The compound of claim 1, of Formula (III):

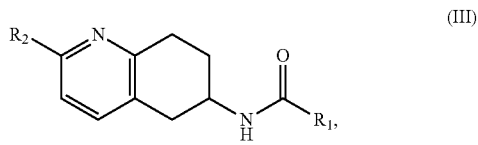

(III)

or a pharmaceutically acceptable form thereof, wherein $R_1$ is chosen from 8-11 membered heteroaryls optionally substituted with one or more $R_5$;

$R_2$ is chosen from N-linked 4-12 membered heterocyclyls and C-linked 4-12 membered heterocyclyls, optionally substituted with one or more $R_5$;

each $R_5$ (if present) is independently chosen from —OH, —$NH_2$, NHC(O)$CH_3$, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, halogen, cycloalkyl, heterocycloalkyl, and —C(O)— heterocycloalkyl groups, wherein each of —$NH_2$, —NHC(O)$CH_3$, $(C_1\text{-}C_6)$ alkyl, $(C_1\text{-}C_6)$ alkoxy, $(C_1\text{-}C_6)$ haloalkyl, $(C_1\text{-}C_6)$ haloalkoxy, cycloalkyl, heterocycloalkyl, and —C(O)-heterocycloalkyl are optionally substituted with one or more substituents independently chosen from $(C_1\text{-}C_6)$ alkoxy, —$NH_2$, and —OH; and n is 0, 1, 2, or 3.

4. The compound of claim 1, of Formula (IV):

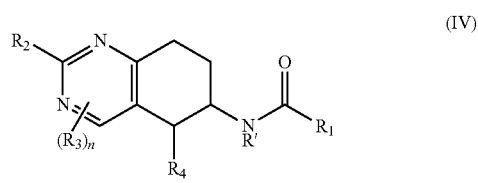

(IV)

and pharmaceutically acceptable forms thereof, wherein R', R₁, R₂, R₃, R₄, R₅, R₆, R₇, and n are all as defined for Formula (I).

5. The compound of claim 1, of Formula (V):

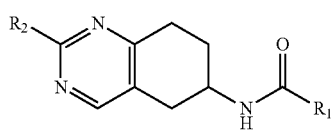

(V)

or a pharmaceutically acceptable form thereof, wherein
R₁ is chosen from 8-9 membered heteroaryls optionally substituted with one or more R₅;
R₂ is chosen from N-linked 4-12 membered heterocyclyls optionally substituted with one or more R₅;
each R₅ (if present) is independently chosen from —OH, —NH₂, NHC(O)CH₃, (C₁-C₆) alkyl, (C₁-C₆) alkoxy, (C₁-C₆) haloalkyl, (C₁-C₆) haloalkoxy, halogen, cycloalkyl, heterocycloalkyl, and —C(O)— heterocycloalkyl groups, wherein each of —NH₂, —NHC(O)CH₃, (C₁-C₆) alkyl, (C₁-C₆) alkoxy, (C₁-C₆) haloalkyl, (C₁-C₆) haloalkoxy, cycloalkyl, heterocycloalkyl, and —C(O)-heterocycloalkyl are optionally substituted with one or more substituents independently chosen from (C₁-C₆) alkoxy, —NH₂, and —OH; and
n is 0, 1, 2, or 3.

6. The compound of claim 1, wherein R₁, optionally substituted with R₅ or R₆, is chosen from

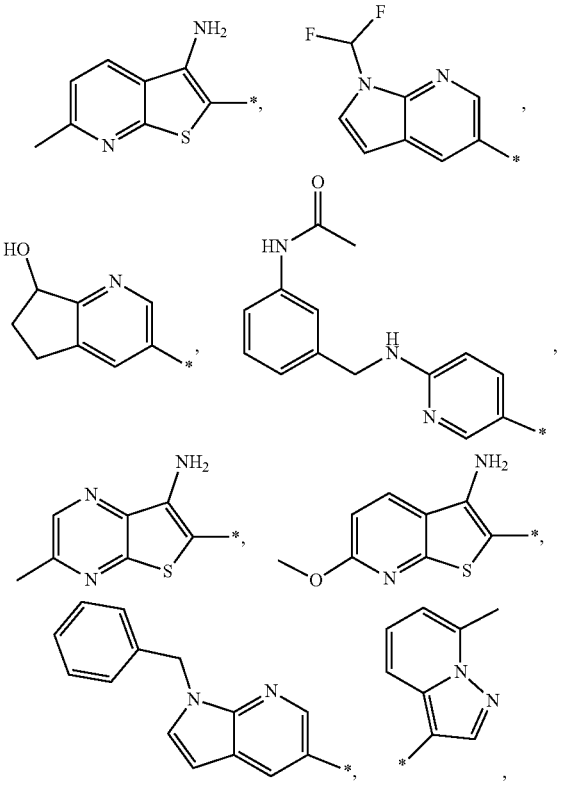

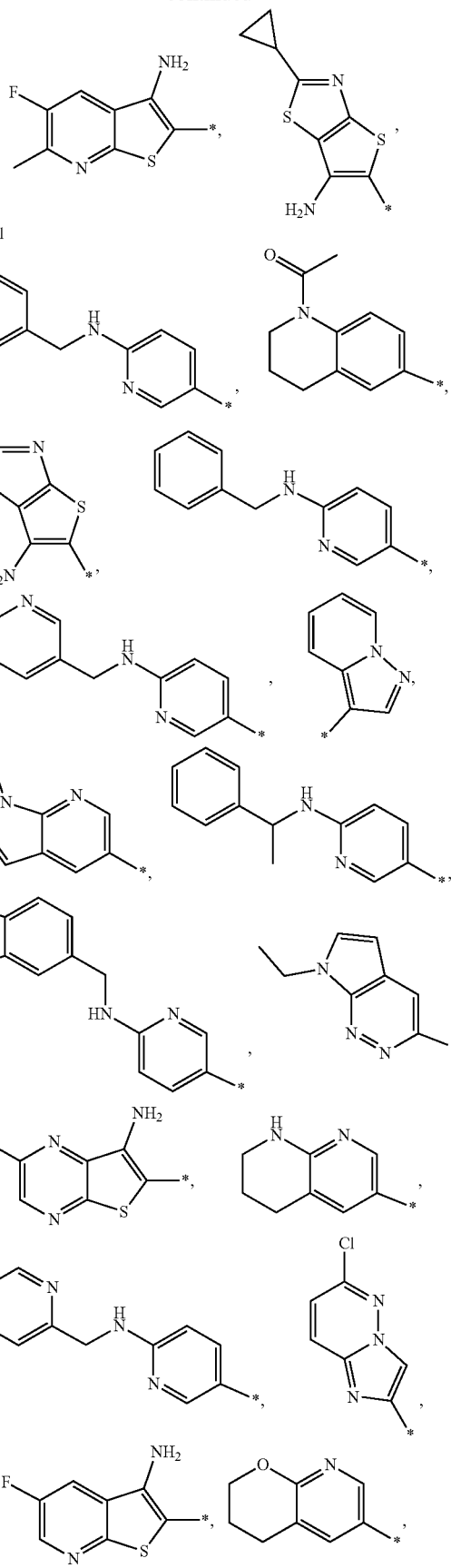

-continued
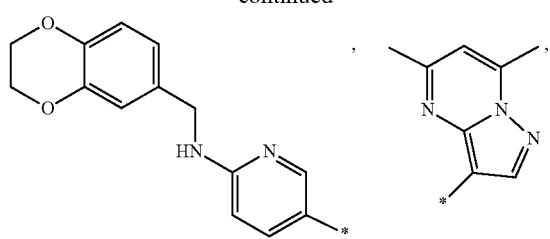
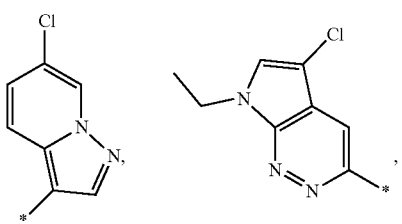
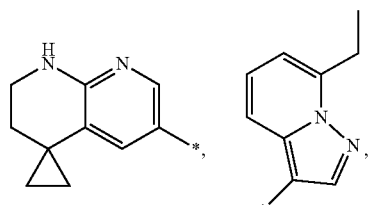
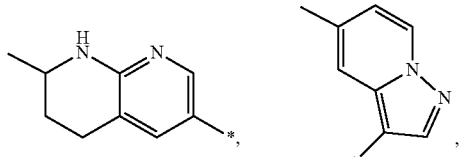
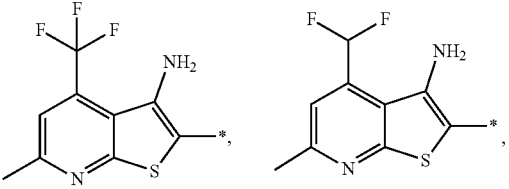
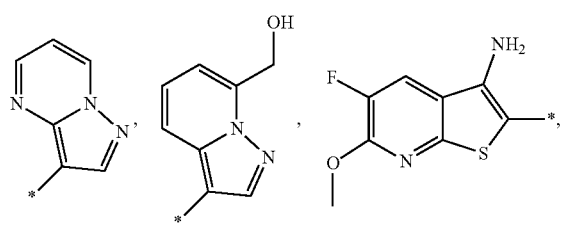
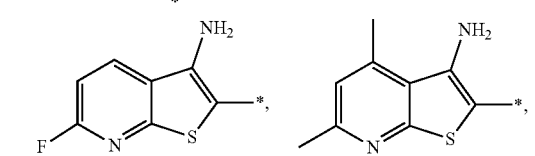
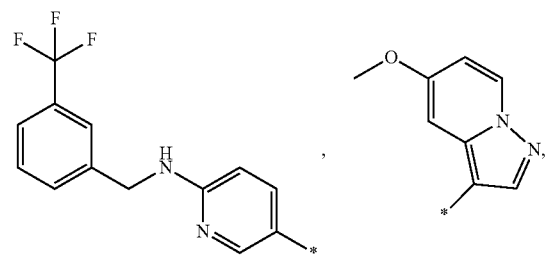
-continued
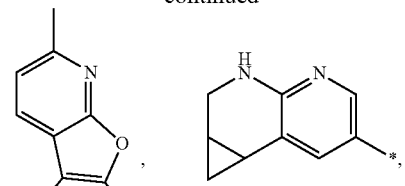
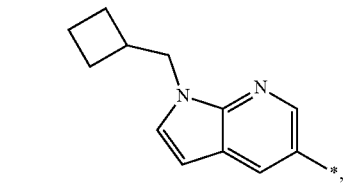
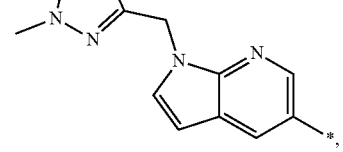
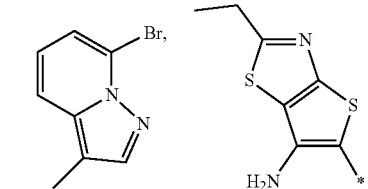
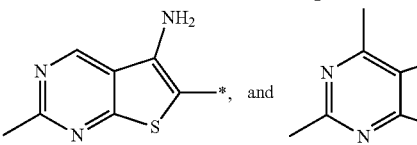, and
7. The compound of claim 1, wherein $R_2$, optionally substituted with $R_5$, is chosen from
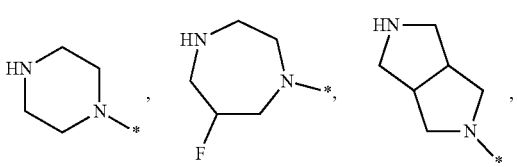
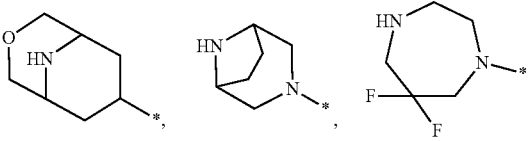
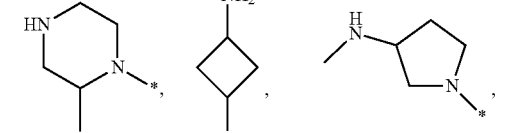
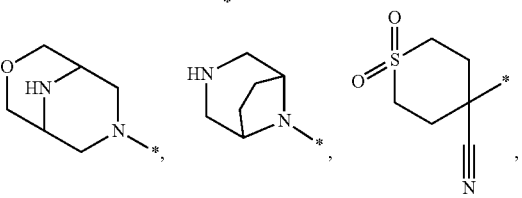

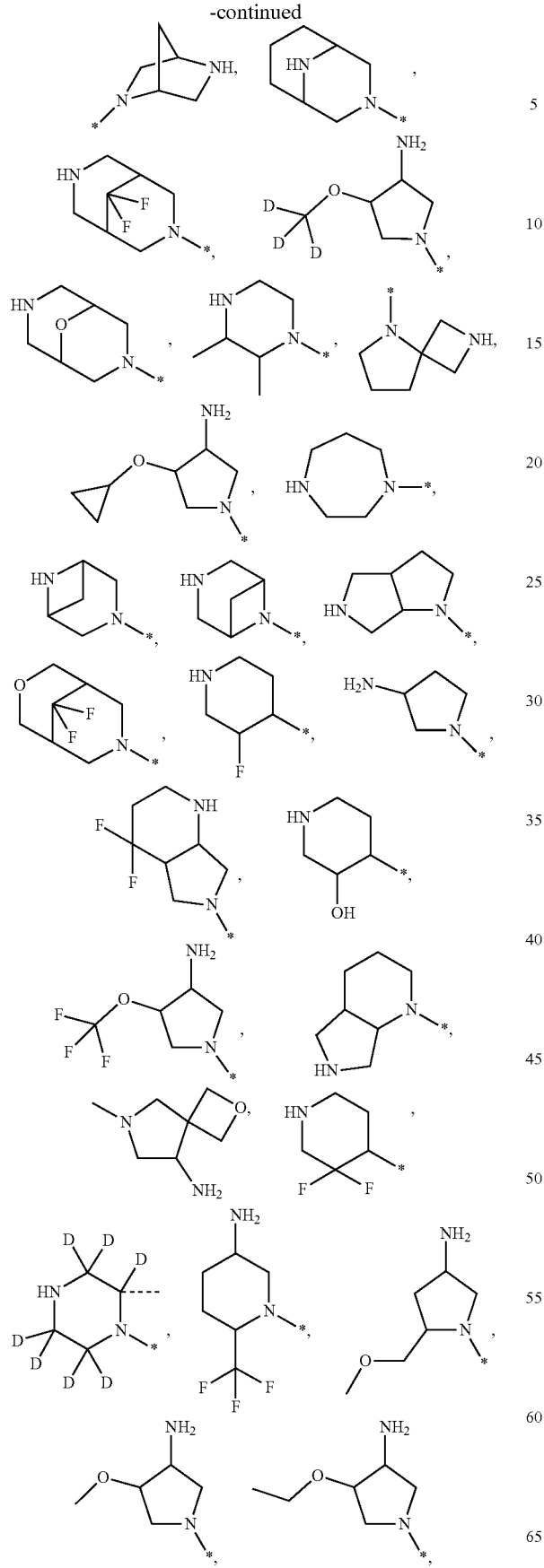
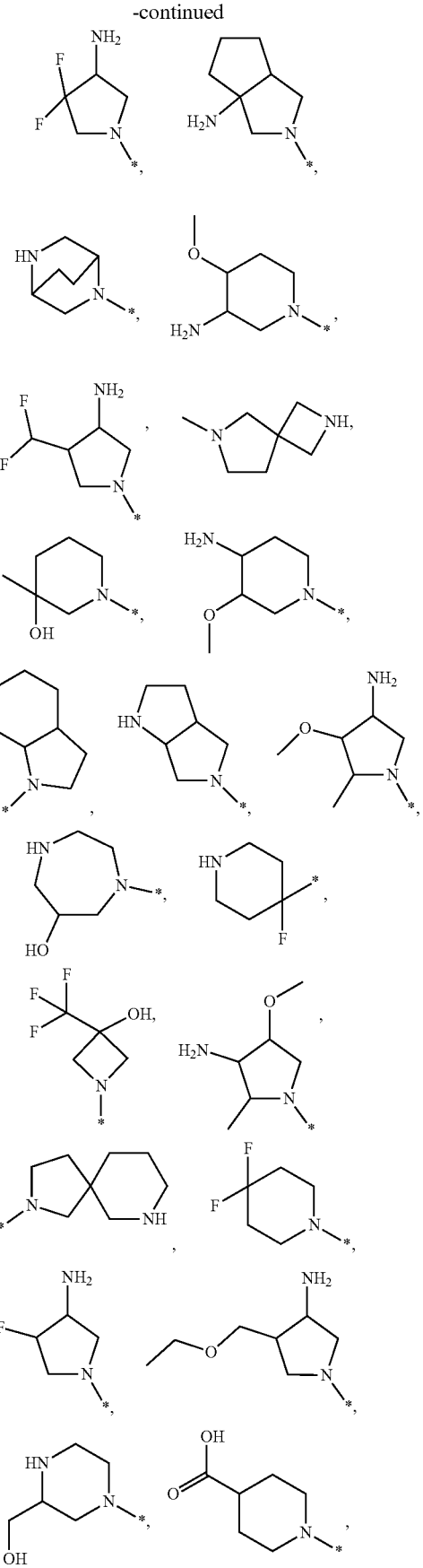

1167
-continued
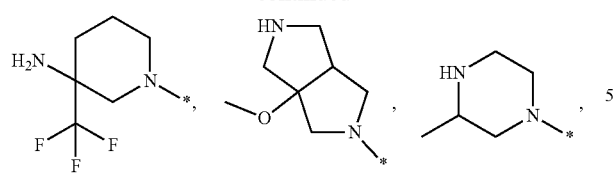
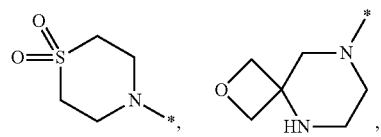
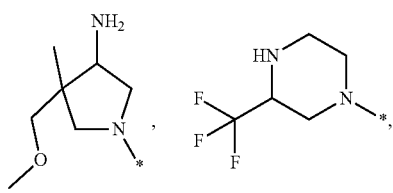
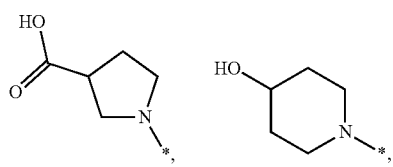
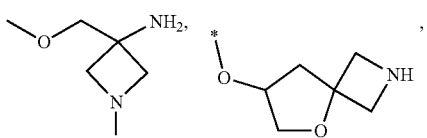
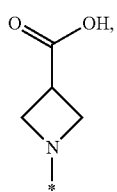
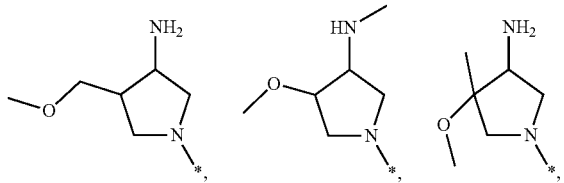
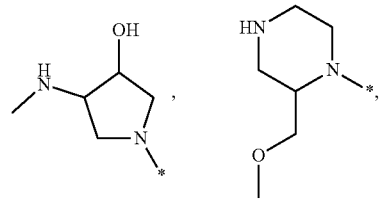
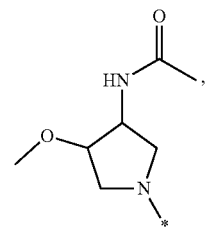
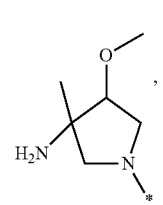
1168
-continued
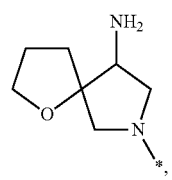
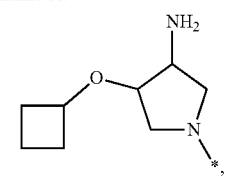
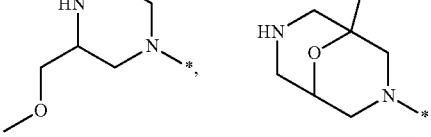
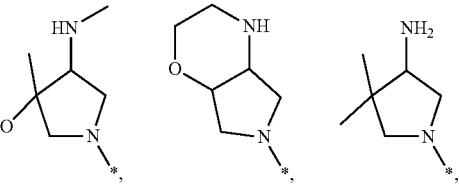
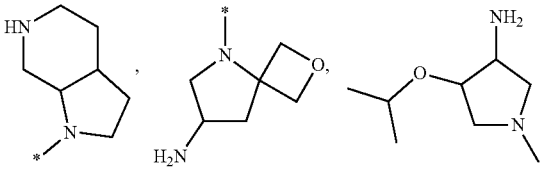
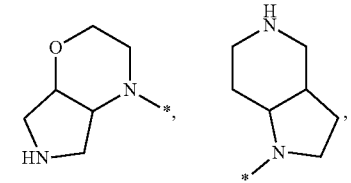
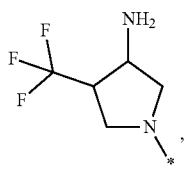
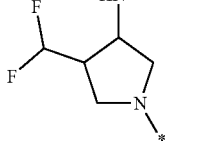
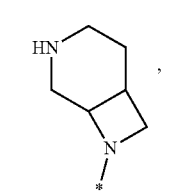
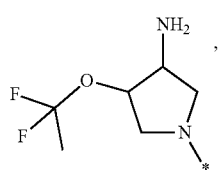
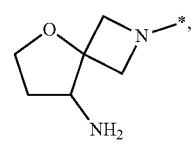
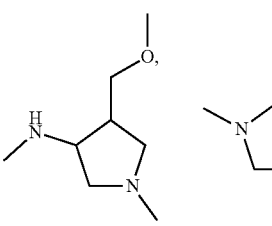
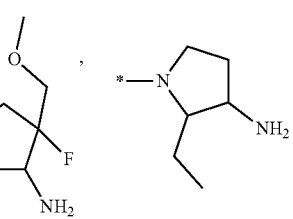

1169
-continued
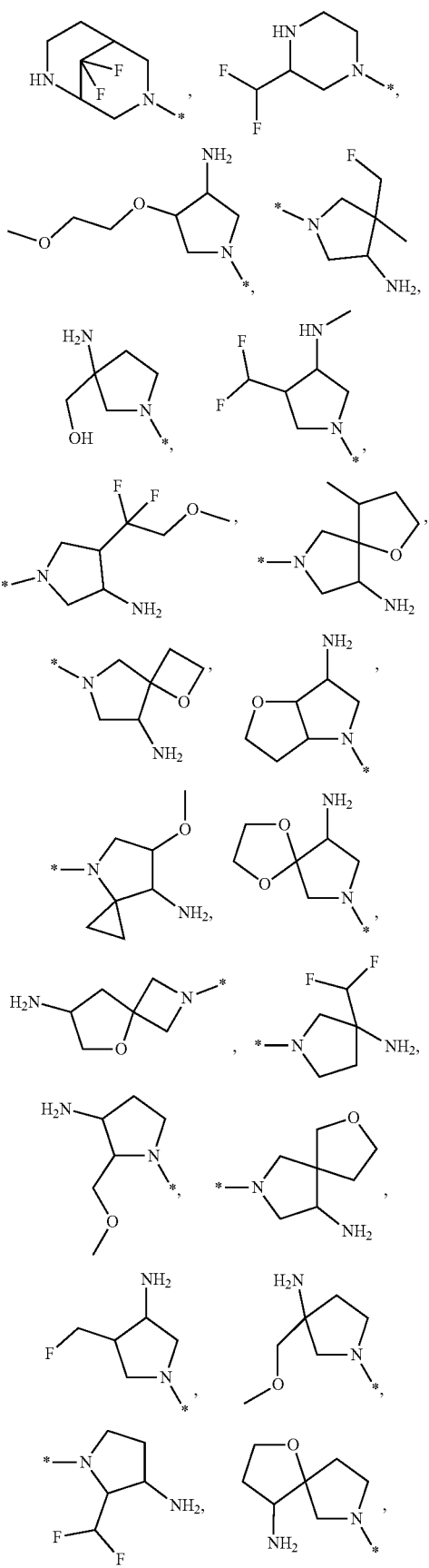
1170
-continued
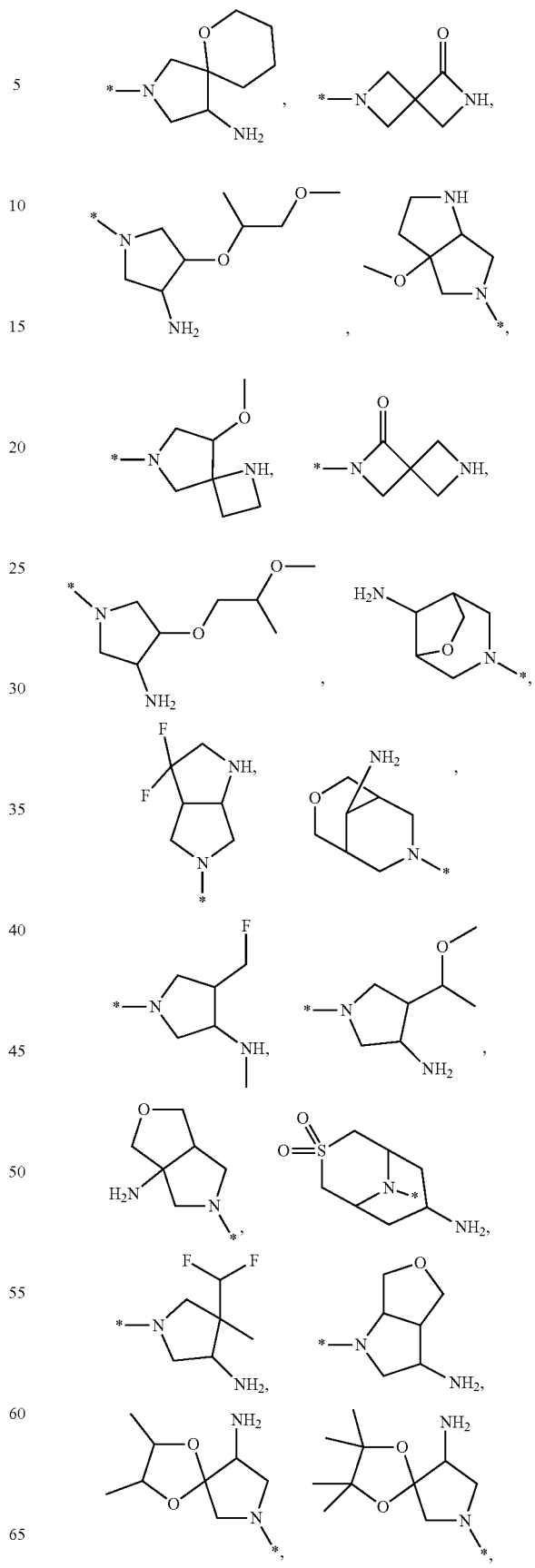

-continued
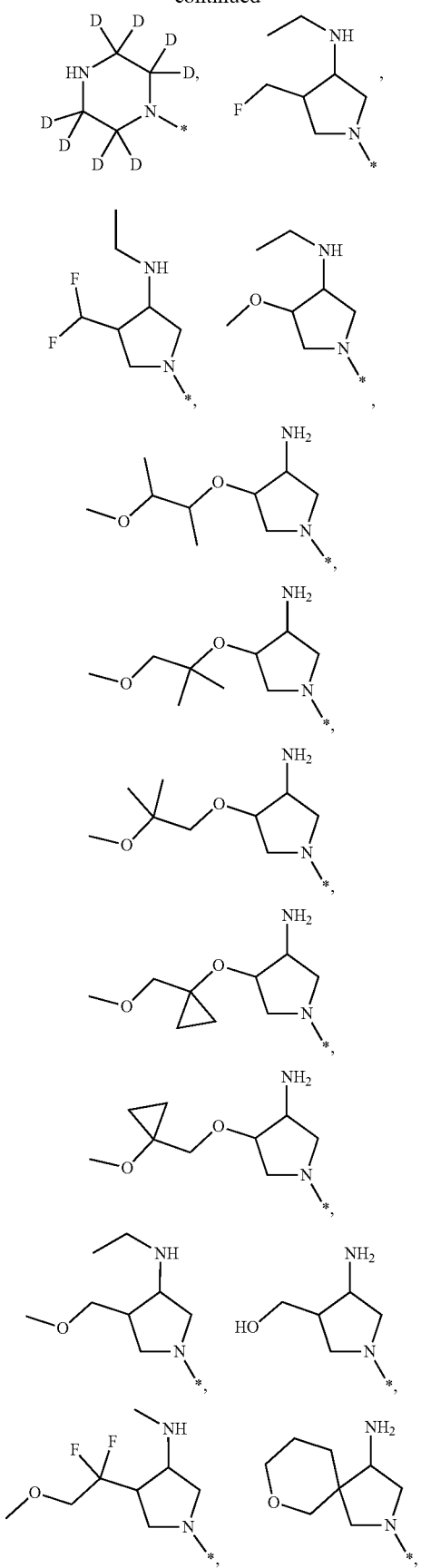
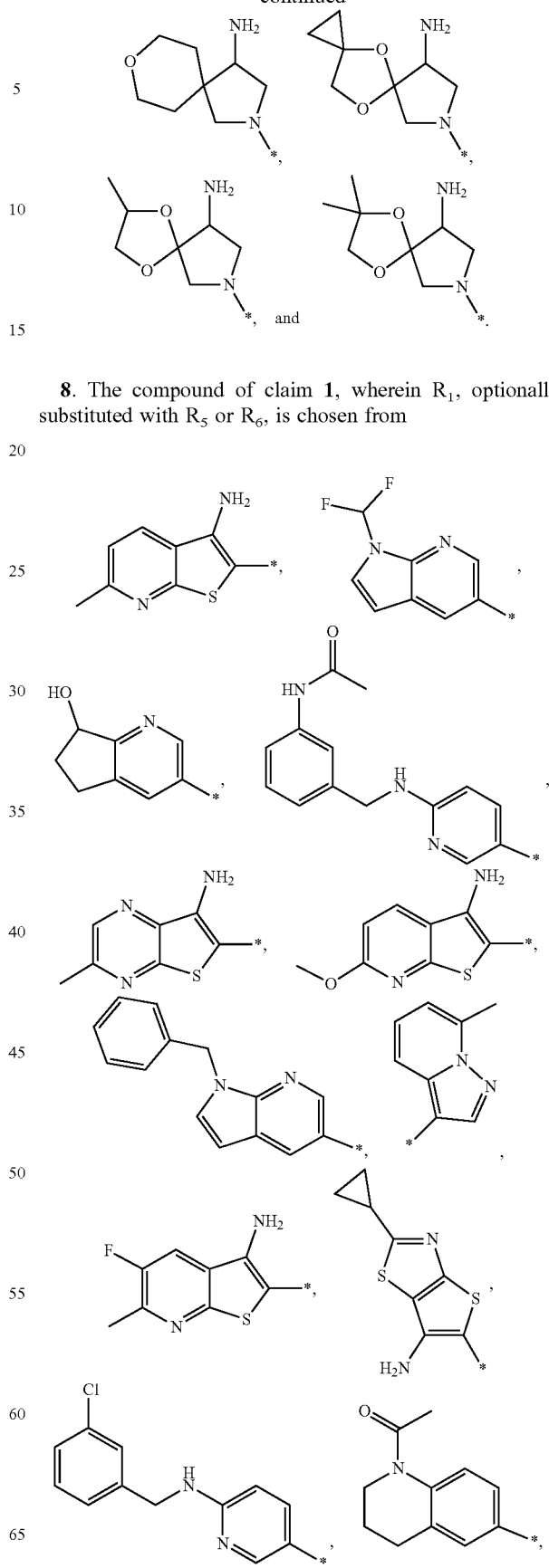
8. The compound of claim 1, wherein $R_1$, optionally substituted with $R_5$ or $R_6$, is chosen from 1173
-continued
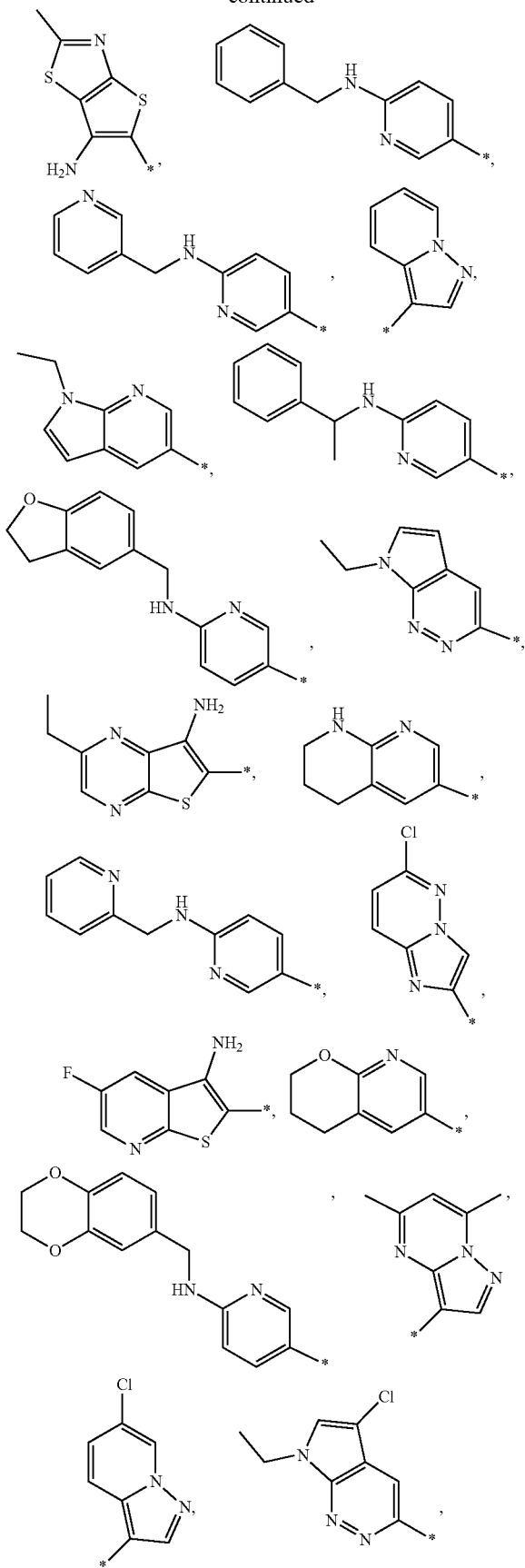
1174
-continued
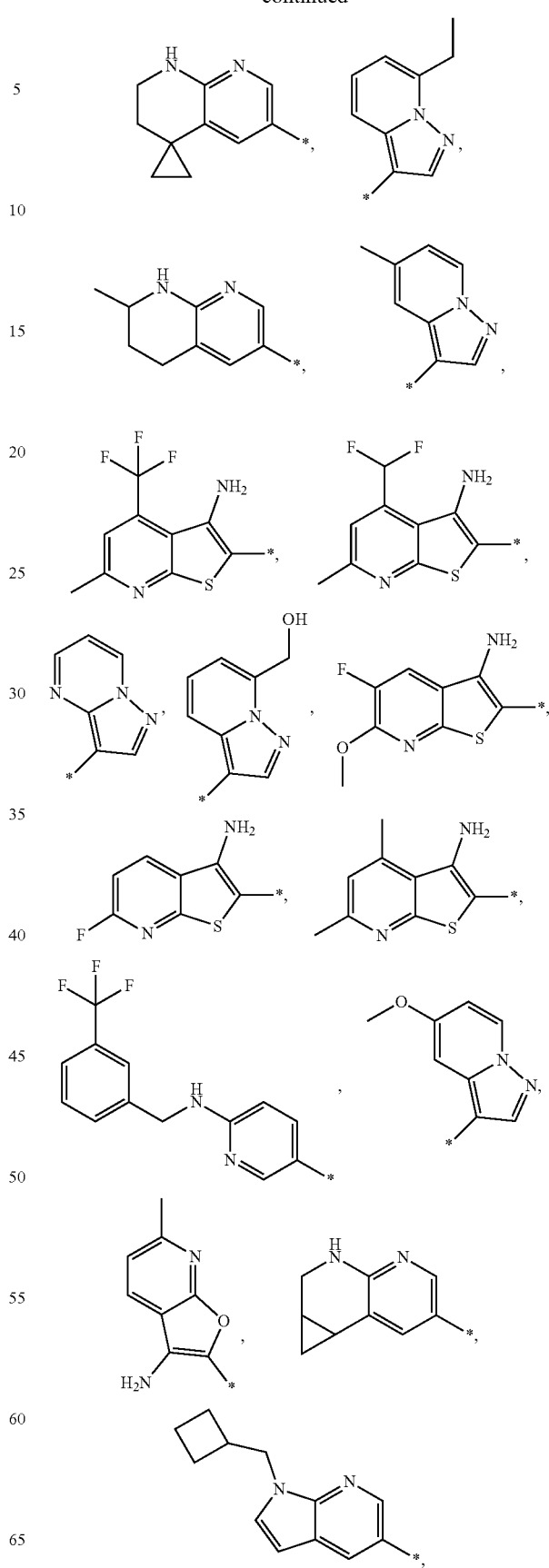

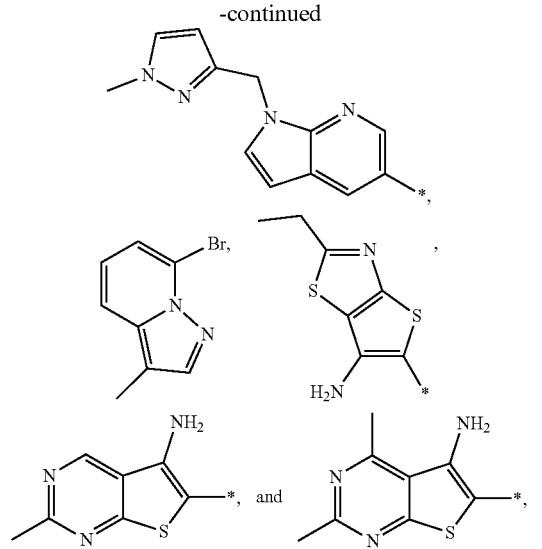
and $R_2$, optionally substituted with $R_5$, is chosen from
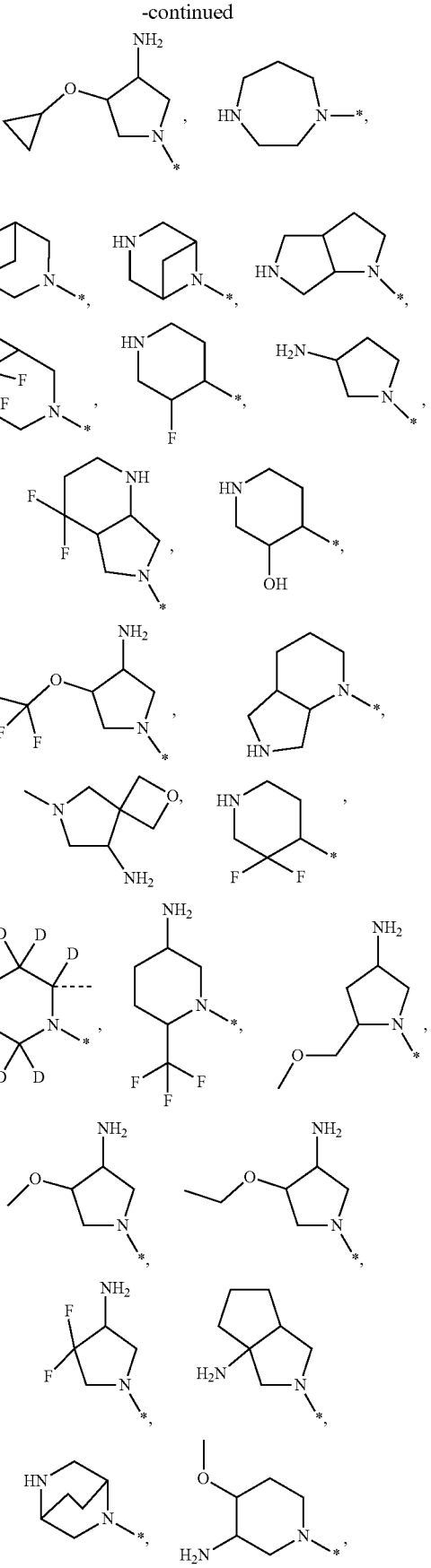

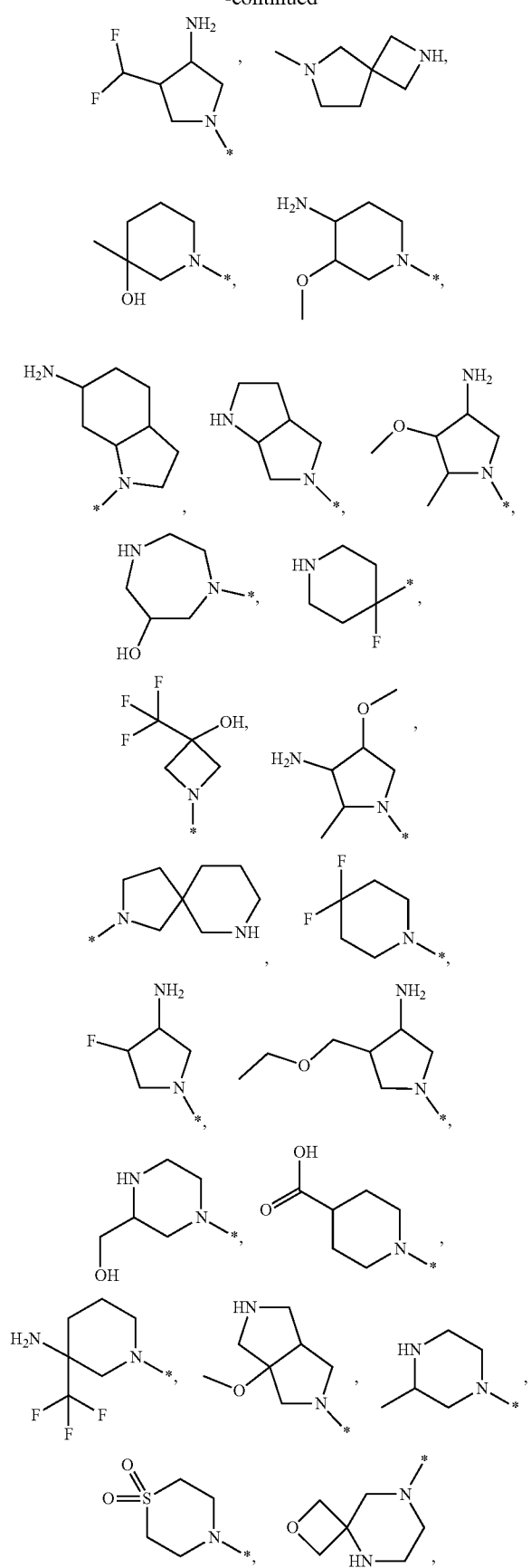
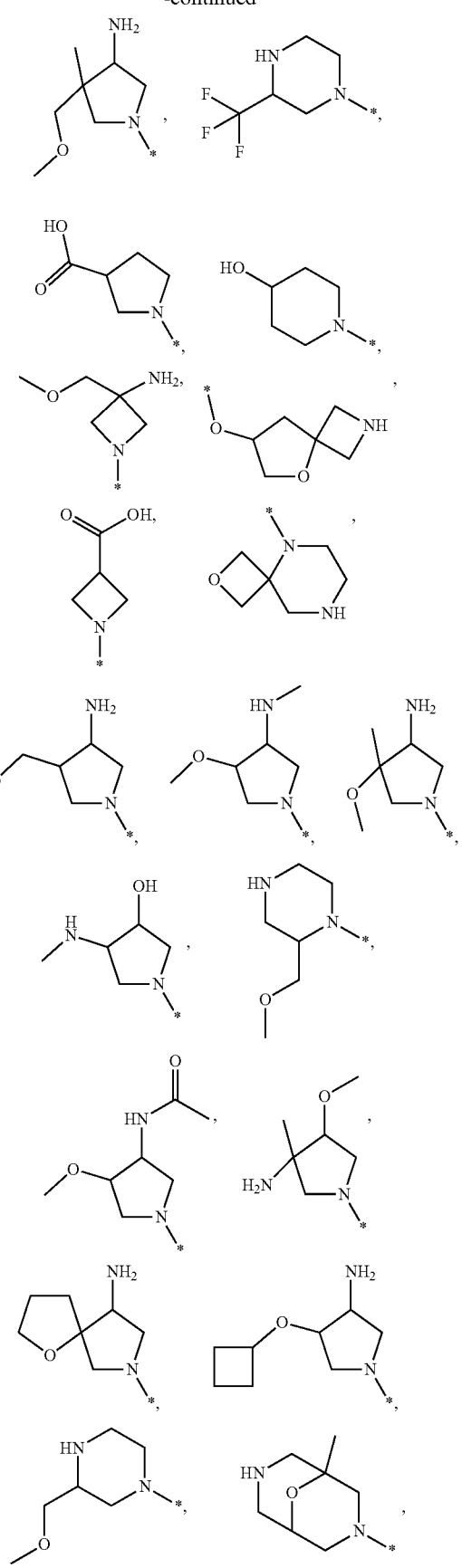

1179
-continued
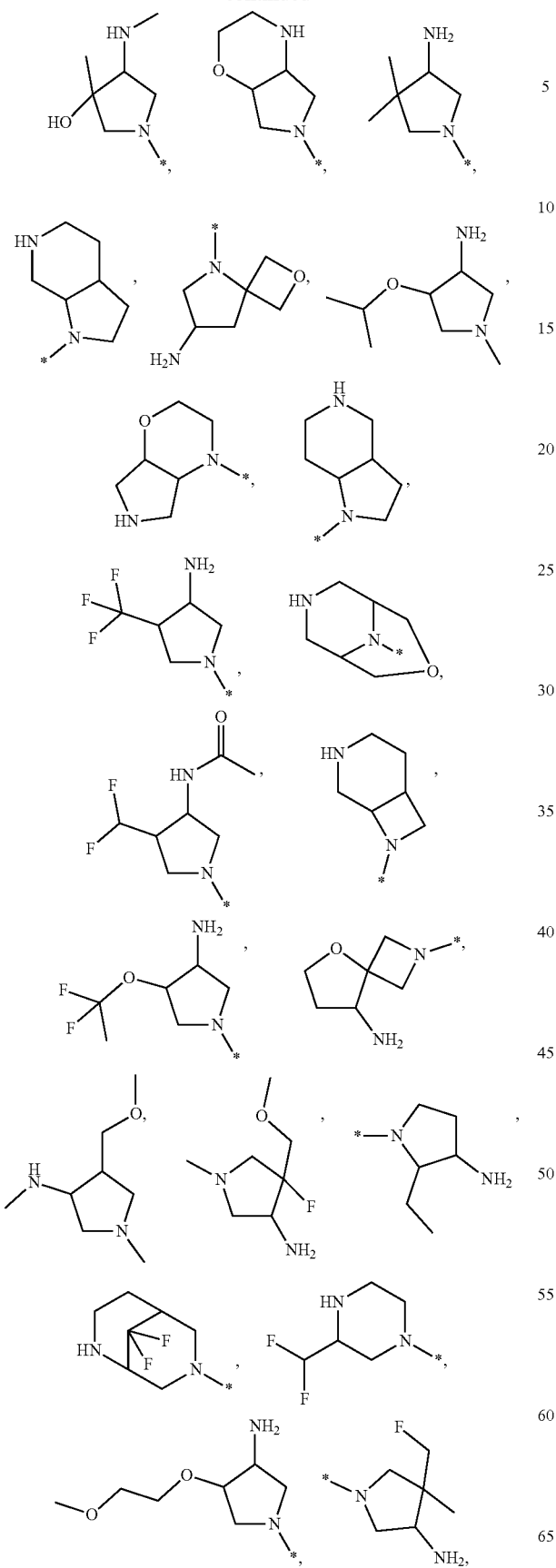
1180
-continued
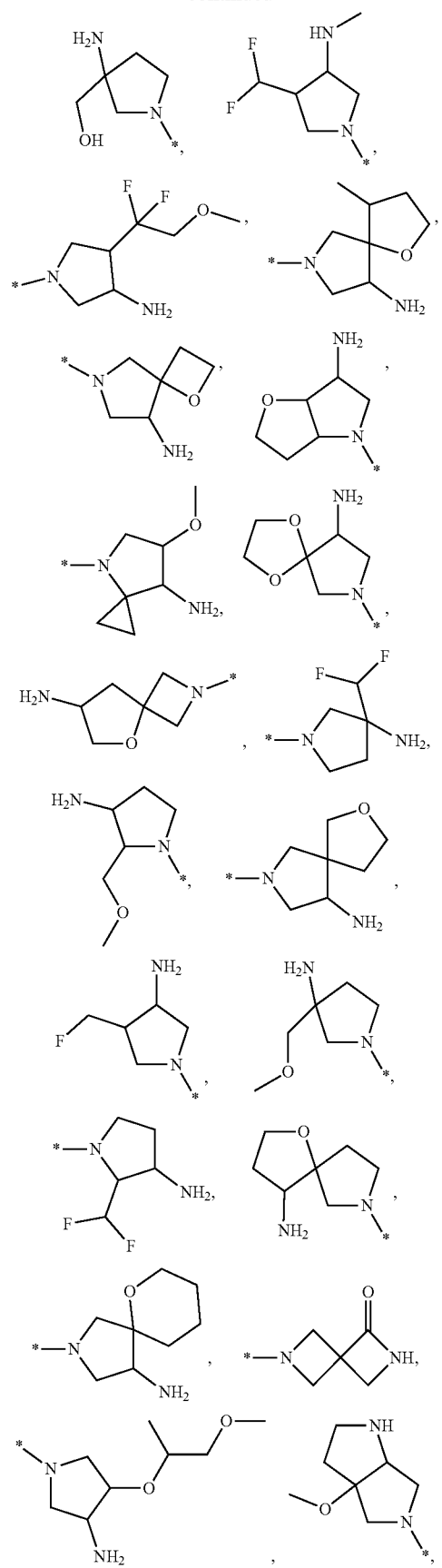

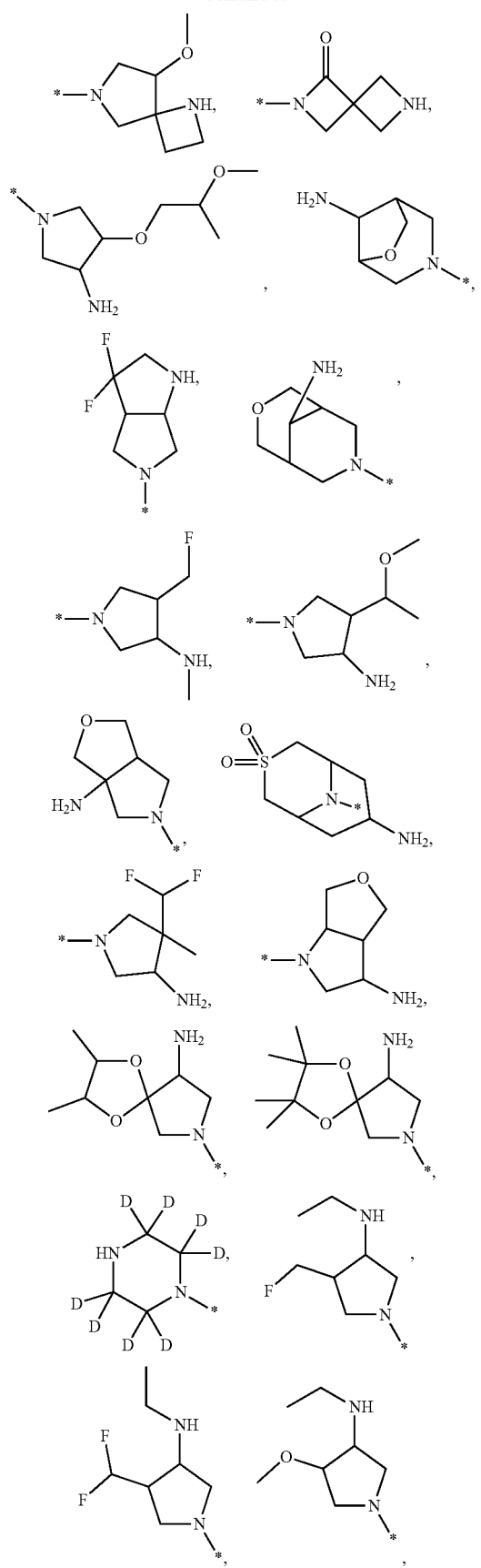
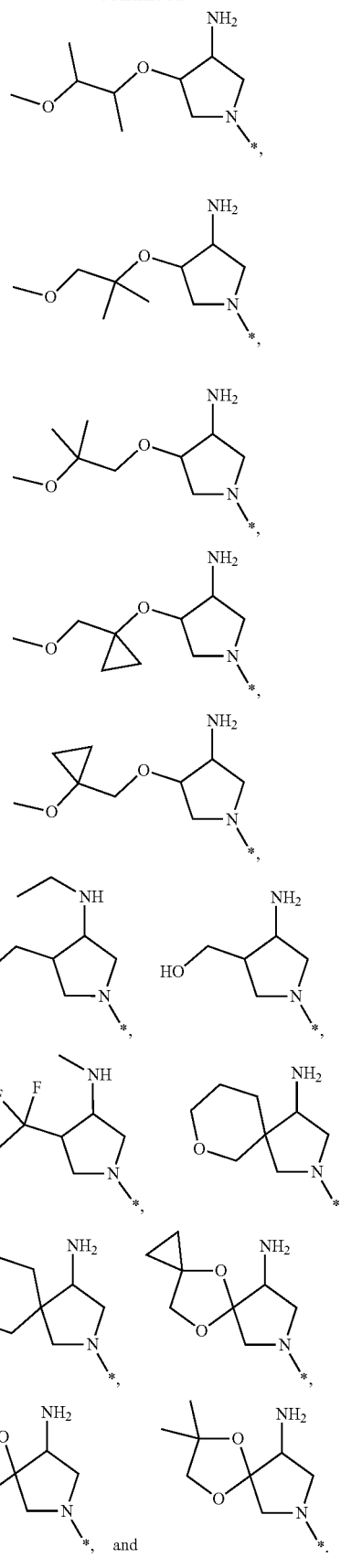

9. The compound of claim 1, wherein $R_1$ is chosen from

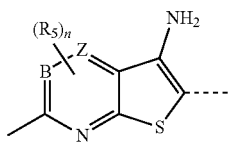

wherein B is chosen from a bond or C;
Z is chosen from N, S, and C(Rii);
Rii is chosen from H, $CH_3$ and $R_5$;
$R_2$ is chosen from N-linked 5-8 membered heterocyclyls substituted with one to three $R_5$;
each $R_5$ (if present) is independently chosen from —OH, —$NH_2$, $NHC(O)CH_3$, $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, and —C(O)— heterocycloalkyl groups, wherein each of —$NH_2$, —$NHC(O)CH_3$, $(C_1-C_6)$ alkyl, $(C_1-C_6)$ alkoxy, $(C_1-C_6)$ haloalkyl, $(C_1-C_6)$ haloalkoxy, cycloalkyl, heterocycloalkyl, and —C(O)-heterocycloalkyl are optionally substituted with one or more substituents independently chosen from $(C_1-C_6)$ alkoxy, —$NH_2$, and —OH; and
n is 0, 1, 2, or 3.

10. The compound of claim 1, wherein
$R_1$, optionally substituted with $R_5$, is chosen from

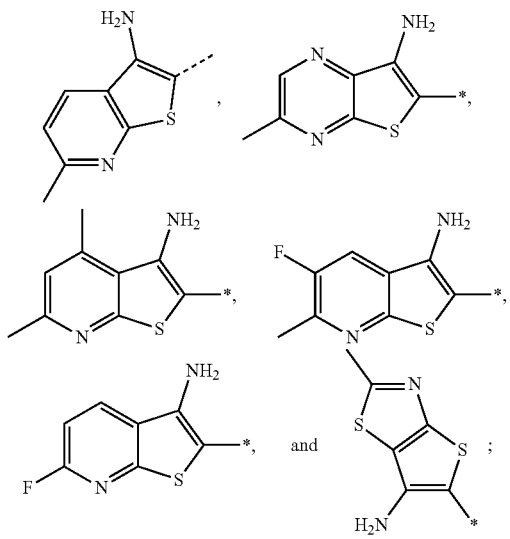

and
$R_2$, optionally substituted with $R_5$, is chosen from

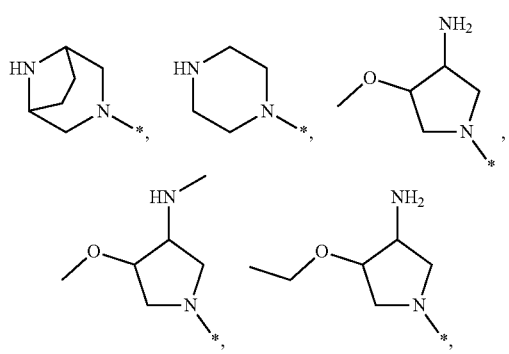

-continued

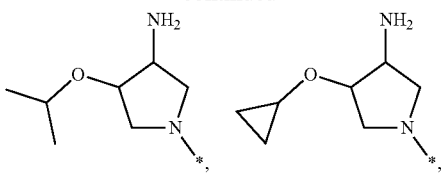

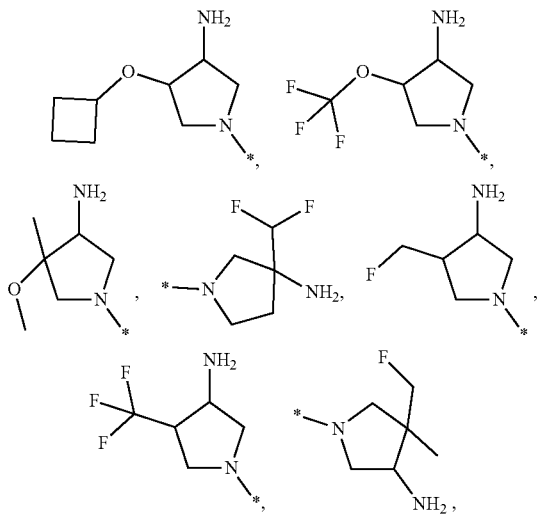

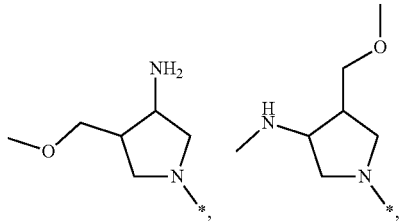

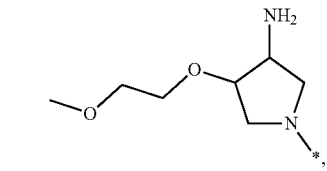

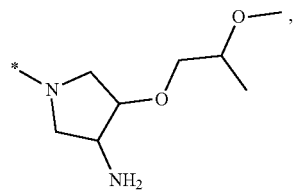

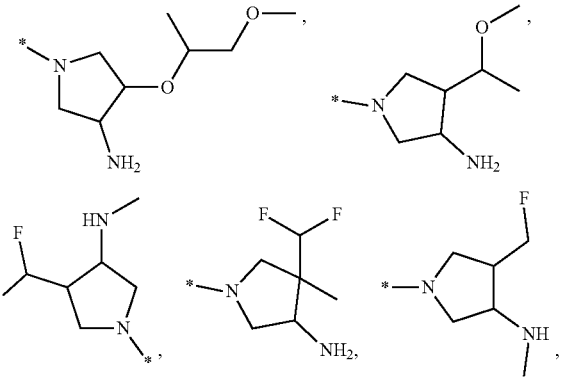

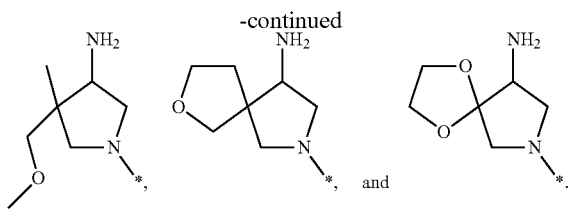

11. The compound of claim 1, wherein the compound is
a. a compound having an USP28 $IC_{50}$ of 0.001-2 micromolar or
b. a compound having an USP25 $IC_{50}$ of 0.001-2 micromolar.

12. The compound of claim 1, chosen from the following compounds:
- 23-1: 7-amino-N-[(6S)-2-[(3S,4S)-3-amino-4-methoxypyrrolidin-1-yl]-5,6,7,8-tetrahydroquinolin-6-yl]-3-methylthieno[2,3-b]pyrazine-6-carboxamide;
- 23-2: 7-amino-N-[(6R)-2-[(3S,4S)-3-amino-4-methoxypyrrolidin-1-yl]-5,6,7,8-tetrahydroquinolin-6-yl]-3-methylthieno[2,3-b]pyrazine-6-carboxamide;
- 23-3: 3-amino-N-[(6S)-2-[(3S,4S)-3-amino-4-methoxypyrrolidin-1-yl]-5,6,7,8-tetrahydroquinolin-6-yl]-4,6-dimethylthieno[2,3-b]pyridine-2-carboxamide;
- 23-4: 3-amino-N-[(6S)-2-[(3S,4S)-3-amino-4-methoxypyrrolidin-1-yl]-5,6,7,8-tetrahydroquinolin-6-yl]-6-methylthieno[2,3-b]pyridine-2-carboxamide;
- 23-5: 3-amino-N-[(6R)-2-[(3S,4S)-3-amino-4-methoxypyrrolidin-1-yl]-5,6,7,8-tetrahydroquinolin-6-yl]-6-methylthieno[2,3-b]pyridine-2-carboxamide;
- 23-6: 7-amino-3-methyl-N-[(6S)-2-(piperazin-1-yl)-5,6,7,8-tetrahydroquinolin-6-yl]thieno[2,3-b]pyrazine-6-carboxamide;
- 23-7: 3-amino-6-methyl-N-[(6S)-2-(piperazin-1-yl)-5,6,7,8-tetrahydroquinolin-6-yl]thieno[2,3-b]pyridine-2-carboxamide;
- 23-8: 3-amino-6-methyl-N-[(6R)-2-(piperazin-1-yl)-5,6,7,8-tetrahydroquinolin-6-yl]thieno[2,3-b]pyridine-2-carboxamide;
- 23-9: 6-amino-2-methyl-N-[(6S)-2-(piperazin-1-yl)-5,6,7,8-tetrahydroquinolin-6-yl]thieno[2,3-d][1,3]thiazole-5-carboxamide;
- 23-12: 3-amino-N-[(6S)-2-{3,8-diazabicyclo[3.2.1]octan-3-yl}-5,6,7,8-tetrahydroquinolin-6-yl]-6-methylthieno[2,3-b]pyridine-2-carboxamide;
- 23-13: 7-amino-N-[(6S)-2-{3,8-diazabicyclo[3.2.1]octan-3-yl}-5,6,7,8-tetrahydroquinolin-6-yl]-3-methylthieno[2,3-b]pyrazine-6-carboxamide;
- 23-14: 3-amino-4,6-dimethyl-N-[(6S)-2-(piperazin-1-yl)-5,6,7,8-tetrahydroquinolin-6-yl]thieno[2,3-b]pyridine-2-carboxamide;
- 23-17: 3-amino-N-[(6S)-4-fluoro-2-(piperazin-1-yl)-5,6,7,8-tetrahydroquinolin-6-yl]-6-methylthieno[2,3-b]pyridine-2-carboxamide;
- 23-18: 3-amino-N-[(6S)-2-{3,8-diazabicyclo[3.2.1]octan-3-yl}-4-fluoro-5,6,7,8-tetrahydroquinolin-6-yl]-6-methylthieno[2,3-b]pyridine-2-carboxamide;
- 24-1: 3-amino-N-[(6S)-2-[(3R,4R)-3-amino-4-(methoxymethyl)pyrrolidin-1-yl]-5,6,7,8-tetrahydroquinolin-6-yl]-6-methylthieno[2,3-b]pyridine-2-carboxamide;
- 24-2: 3-amino-N-[(6S)-2-[(3S,4S)-3-amino-4-(methoxymethyl)pyrrolidin-1-yl]-5,6,7,8-tetrahydroquinolin-6-yl]-6-methylthieno[2,3-b]pyridine-2-carboxamide;
- 25: 3-amino-N-[(6S)-2-[(3S,4R)-3-amino-4-(difluoromethyl)pyrrolidin-1-yl]-5,6,7,8-tetrahydroquinolin-6-yl]-6-methylthieno[2,3-b]pyridine-2-carboxamide;
- 26-1: 3-amino-N-[(6S)-2-[(3S,4R)-3-(methoxymethyl)-4-(methylamino)pyrrolidin-1-yl]-5,6,7,8-tetrahydroquinolin-6-yl]-6-methylthieno[2,3-b]pyridine-2-carboxamide;
- 26-2: 3-amino-N-[(6S)-2-[(3R,4S)-3-(methoxymethyl)-4-(methylamino)pyrrolidin-1-yl]-5,6,7,8-tetrahydroquinolin-6-yl]-6-methylthieno[2,3-b]pyridine-2-carboxamide;
- 27-1: 3-amino-N-[(6S)-2-[(3R,4R)-3-amino-4-(fluoromethyl)pyrrolidin-1-yl]-5,6,7,8-tetrahydroquinolin-6-yl]-6-methylthieno[2,3-b]pyridine-2-carboxamide;
- 27-2: 3-amino-N-[(6S)-2-[(3S,4S)-3-amino-4-(fluoromethyl)pyrrolidin-1-yl]-5,6,7,8-tetrahydroquinolin-6-yl]-6-methylthieno[2,3-b]pyridine-2-carboxamide;
- 28-1: 3-amino-N-[(6S)-2-[(3S,4S)-3-amino-4-(2-methoxyethoxy)pyrrolidin-1-yl]-5,6,7,8-tetrahydroquinolin-6-yl]-6-methylthieno[2,3-b]pyridine-2-carboxamide;
- 28-2: 3-amino-N-[(6S)-2-[(3R,4R)-3-amino-4-(2-methoxyethoxy)pyrrolidin-1-yl]-5,6,7,8-tetrahydroquinolin-6-yl]-6-methylthieno[2,3-b]pyridine-2-carboxamide;
- 29-1: 3-amino-N-[(6S)-2-[(9S)-9-amino-1,4-dioxa-7-azaspiro[4.4]nonan-7-yl]-5,6,7,8-tetrahydroquinolin-6-yl]-6-methylthieno[2,3-b]pyridine-2-carboxamide;
- 29-2: 3-amino-N-[(6S)-2-[(9R)-9-amino-1,4-dioxa-7-azaspiro[4.4]nonan-7-yl]-5,6,7,8-tetrahydroquinolin-6-yl]-6-methylthieno[2,3-b]pyridine-2-carboxamide;
- 30-1: 3-amino-N-[(6S)-3-fluoro-2-(piperazin-1-yl)-5,6,7,8-tetrahydroquinolin-6-yl]-6-methylthieno[2,3-b]pyridine-2-carboxamide;
- 30-2: 3-amino-N-[(6R)-3-fluoro-2-(piperazin-1-yl)-5,6,7,8-tetrahydroquinolin-6-yl]-6-methylthieno[2,3-b]pyridine-2-carboxamide;
- 31-3: 3-amino-6-methyl-N-[(6'S)-2'-(piperazin-1-yl)-6',7'-dihydro-5'H-spiro[cyclopropane-1,8'-quinoline]-6'-yl]thieno[2,3-b]pyridine-2-carboxamide;
- 31-4: 3-amino-6-methyl-N-[(6'R)-2'-(piperazin-1-yl)-6',7'-dihydro-5'H-spiro[cyclopropane-1,8'-quinoline]-6'-yl]thieno[2,3-b]pyridine-2-carboxamide;
- 142: 3-amino-N-[(6S)-2-[(3S,4S)-3-amino-4-ethoxypyrrolidin-1-yl]-5,6,7,8-tetrahydroquinolin-6-yl]-6-methylthieno[2,3-b]pyridine-2-carboxamide;
- 203: 3-amino-N-[(6S)-2-[(3S,4S)-3-amino-4-methoxypyrrolidin-1-yl]-5,6,7,8-tetrahydroquinolin-6-yl]-5-fluoro-6-methylthieno[2,3-b]pyridine-2-carboxamide;
- 204: 3-amino-5-fluoro-6-methyl-N-[(6S)-2-(piperazin-1-yl)-5,6,7,8-tetrahydroquinolin-6-yl]thieno[2,3-b]pyridine-2-carboxamide;
- 205: 3-amino-6-methyl-N-[(6S,8S)-8-methyl-2-(piperazin-1-yl)-5,6,7,8-tetrahydroquinolin-6-yl]thieno[2,3-b]pyridine-2-carboxamide;
- 206: 3-amino-6-methyl-N-[(6R,8S)-8-methyl-2-(piperazin-1-yl)-5,6,7,8-tetrahydroquinolin-6-yl]thieno[2,3-b]pyridine-2-carboxamide;
- 207: 3-amino-6-methyl-N-[(6S,8R)-8-methyl-2-(piperazin-1-yl)-5,6,7,8-tetrahydroquinolin-6-yl]thieno[2,3-b]pyridine-2-carboxamide;
- 208: 3-amino-6-methyl-N-[(6R,8R)-8-methyl-2-(piperazin-1-yl)-5,6,7,8-tetrahydroquinolin-6-yl]thieno[2,3-b]pyridine-2-carboxamide;
- 210: 3-amino-N-[(6S)-2-[(3S,4S)-4-amino-3-methoxy-3-methylpyrrolidin-1-yl]-5,6,7,8-tetrahydroquinolin-6-yl]-6-methylthieno[2,3-b]pyridine-2-carboxamide;

211: 3-amino-N-[(6S)-2-[(3R,4R)-4-amino-3-methoxy-3-methylpyrrolidin-1-yl]-5,6,7,8-tetrahydroquinolin-6-yl]-6-methylthieno[2,3-b]pyridine-2-carboxamide;

239: 3-amino-N-[(6S)-2-[(3S,4S)-3-amino-4-methoxy-3-methylpyrrolidin-1-yl]-5,6,7,8-tetrahydroquinolin-6-yl]-6-methylthieno[2,3-b]pyridine-2-carboxamide;

240: 3-amino-N-[(6S)-2-[(3R,4R)-3-amino-4-methoxy-3-methylpyrrolidin-1-yl]-5,6,7,8-tetrahydroquinolin-6-yl]-6-methylthieno[2,3-b]pyridine-2-carboxamide;

254: 3-amino-N-[(6S)-2-[(3S,4R)-3-amino-4-ethoxypyrrolidin-1-yl]-5,6,7,8-tetrahydroquinolin-6-yl]-6-methylthieno[2,3-b]pyridine-2-carboxamide;

255: 3-amino-N-[(6S)-2-[(3R,4S)-3-amino-4-ethoxypyrrolidin-1-yl]-5,6,7,8-tetrahydroquinolin-6-yl]-6-methylthieno[2,3-b]pyridine-2-carboxamide;

269: 3-amino-N-[(6S)-2-[(3S,4R)-3-amino-4-methoxypyrrolidin-1-yl]-5,6,7,8-tetrahydroquinolin-6-yl]-6-methylthieno[2,3-b]pyridine-2-carboxamide;

270: 3-amino-N-[(6S)-2-[(3R,4S)-3-amino-4-methoxypyrrolidin-1-yl]-5,6,7,8-tetrahydroquinolin-6-yl]-6-methylthieno[2,3-b]pyridine-2-carboxamide;

279: 7-amino-N-[(6S)-2-[(3S,4S)-4-amino-3-methoxy-3-methylpyrrolidin-1-yl]-5,6,7,8-tetrahydroquinolin-6-yl]-3-methylthieno[2,3-b]pyrazine-6-carboxamide;

280: 7-amino-N-[(6S)-2-[(3R,4R)-4-amino-3-methoxy-3-methylpyrrolidin-1-yl]-5,6,7,8-tetrahydroquinolin-6-yl]-3-methylthieno[2,3-b]pyrazine-6-carboxamide;

285: 3-amino-N-[(6S)-2-[(3S,4S)-3-amino-4-cyclobutoxypyrrolidin-1-yl]-5,6,7,8-tetrahydroquinolin-6-yl]-6-methylthieno[2,3-b]pyridine-2-carboxamide;

296: 3-amino-N-[(6S)-2-[(3R,4R)-3-amino-4-(methoxymethyl)pyrrolidin-1-yl]-5,6,7,8-tetrahydroquinolin-6-yl]-4,6-dimethylthieno[2,3-b]pyridine-2-carboxamide;

297: 3-amino-N-[(6S)-2-[(3S,4S)-3-amino-4-(methoxymethyl)pyrrolidin-1-yl]-5,6,7,8-tetrahydroquinolin-6-yl]-4,6-dimethylthieno[2,3-b]pyridine-2-carboxamide;

298: 7-amino-N-[(6S)-2-[(3R,4R)-3-amino-4-(methoxymethyl)pyrrolidin-1-yl]-5,6,7,8-tetrahydroquinolin-6-yl]-3-methylthieno[2,3-b]pyrazine-6-carboxamide;

299: 7-amino-N-[(6S)-2-[(3S,4S)-3-amino-4-(methoxymethyl)pyrrolidin-1-yl]-5,6,7,8-tetrahydroquinolin-6-yl]-3-methylthieno[2,3-b]pyrazine-6-carboxamide;

300: 3-amino-N-[(6S)-2-[(3R,4R)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide;

301: 3-amino-N-[(6S)-2-[(3S,4S)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide;

302: 3-amino-N-[(6R)-2-[(3R,4R)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide;

303: 3-amino-N-[(6R)-2-[(3S,4S)-3-amino-4-(methoxymethyl)pyrrolidin-1-yl]-3-fluoro-5,6,7,8-tetrahydroquinolin-6-yl]-6-methylthieno[2,3-b]pyridine-2-carboxamide;

311: 3-amino-N-[(6S)-2-[(3S,4S)-3-methoxy-4-(methylamino)pyrrolidin-1-yl]-5,6,7,8-tetrahydroquinolin-6-yl]-6-methylthieno[2,3-b]pyridine-2-carboxamide;

312: 3-amino-N-[(6S)-2-[(3S,4S)-3-methoxy-4-(methylamino)pyrrolidin-1-yl]-5,6,7,8-tetrahydroquinolin-6-yl]-4,6-dimethylthieno[2,3-b]pyridine-2-carboxamide;

320: 3-amino-N-[(6S)-2-[(3S,4S)-3-amino-4-(propan-2-yloxy)pyrrolidin-1-yl]-5,6,7,8-tetrahydroquinolin-6-yl]-6-methylthieno[2,3-b]pyridine-2-carboxamide;

321: 3-amino-N-[(6S)-2-[(3S,4R)-3-amino-4-(propan-2-yloxy)pyrrolidin-1-yl]-5,6,7,8-tetrahydroquinolin-6-yl]-6-methylthieno[2,3-b]pyridine-2-carboxamide;

322: 3-amino-N-[(6S)-2-[(3R,4S)-3-amino-4-(propan-2-yloxy)pyrrolidin-1-yl]-5,6,7,8-tetrahydroquinolin-6-yl]-6-methylthieno[2,3-b]pyridine-2-carboxamide;

327: 3-amino-N-[(6S)-2-[(3R,4S)-3-amino-4-(methoxymethyl)pyrrolidin-1-yl]-5,6,7,8-tetrahydroquinolin-6-yl]-6-methylthieno[2,3-b]pyridine-2-carboxamide;

328: 3-amino-N-[(6S)-2-[(3S,4R)-3-amino-4-(methoxymethyl)pyrrolidin-1-yl]-5,6,7,8-tetrahydroquinolin-6-yl]-6-methylthieno[2,3-b]pyridine-2-carboxamide;

331: 3-amino-N-[(6S)-2-[(3R,4S)-3-hydroxy-3-methyl-4-(methylamino)pyrrolidin-1-yl]-5,6,7,8-tetrahydroquinolin-6-yl]-6-methylthieno[2,3-b]pyridine-2-carboxamide;

332: 3-amino-N-[(6S)-2-[(3S,4R)-3-hydroxy-3-methyl-4-(methylamino)pyrrolidin-1-yl]-5,6,7,8-tetrahydroquinolin-6-yl]-6-methylthieno[2,3-b]pyridine-2-carboxamide;

341: 3-amino-N-[(6S)-2-[(3S,4R)-4-amino-3-(methoxymethyl)-3-methylpyrrolidin-1-yl]-5,6,7,8-tetrahydroquinolin-6-yl]-6-methylthieno[2,3-b]pyridine-2-carboxamide;

342: 3-amino-N-[(6S)-2-[(3R,4R)-4-amino-3-(methoxymethyl)-3-methylpyrrolidin-1-yl]-5,6,7,8-tetrahydroquinolin-6-yl]-6-methylthieno[2,3-b]pyridine-2-carboxamide;

343: 3-amino-N-[(6S)-2-[(3S,4S)-4-amino-3-(methoxymethyl)-3-methylpyrrolidin-1-yl]-5,6,7,8-tetrahydroquinolin-6-yl]-6-methylthieno[2,3-b]pyridine-2-carboxamide;

344: 3-amino-N-[(6S)-2-[(3R,4S)-4-amino-3-(methoxymethyl)-3-methylpyrrolidin-1-yl]-5,6,7,8-tetrahydroquinolin-6-yl]-6-methylthieno[2,3-b]pyridine-2-carboxamide;

345: 3-amino-N-[(6S)-2-[(3R,4R)-3-amino-4-(difluoromethyl)pyrrolidin-1-yl]-5,6,7,8-tetrahydroquinolin-6-yl]-6-methylthieno[2,3-b]pyridine-2-carboxamide;

346: 3-amino-N-[(6S)-2-[(3S,4S)-3-amino-4-(difluoromethyl)pyrrolidin-1-yl]-5,6,7,8-tetrahydroquinolin-6-yl]-6-methylthieno[2,3-b]pyridine-2-carboxamide;

347: 3-amino-N-[(6S)-2-[(3R,4S)-3-amino-4-(difluoromethyl)pyrrolidin-1-yl]-5,6,7,8-tetrahydroquinolin-6-yl]-6-methylthieno[2,3-b]pyridine-2-carboxamide;

354: 3-amino-N-[(6S)-2-{3,8-diazabicyclo[3.2.1]octan-3-yl}-5,6,7,8-tetrahydroquinolin-6-yl]-4,6-dimethylthieno[2,3-b]pyridine-2-carboxamide;

363: 3-amino-N-[(6S)-2-[(3R,4S)-3-amino-4-(trifluoromethyl)pyrrolidin-1-yl]-5,6,7,8-tetrahydroquinolin-6-yl]-6-methylthieno[2,3-b]pyridine-2-carboxamide;

364: 3-amino-N-[(6S)-2-[(3S,4R)-3-amino-4-(trifluoromethyl)pyrrolidin-1-yl]-5,6,7,8-tetrahydroquinolin-6-yl]-6-methylthieno[2,3-b]pyridine-2-carboxamide;

376: 3-amino-N-[(6S)-2-[(3S,4R)-3-(difluoromethyl)-4-(methylamino)pyrrolidin-1-yl]-5,6,7,8-tetrahydroquinolin-6-yl]-6-methylthieno[2,3-b]pyridine-2-carboxamide;

377: 3-amino-N-[(6S)-2-[(3R,4S)-3-(difluoromethyl)-4-(methylamino)pyrrolidin-1-yl]-5,6,7,8-tetrahydroquinolin-6-yl]-6-methylthieno[2,3-b]pyridine-2-carboxamide;
384: 3-amino-N-[(6S)-2-[(3R,4S)-3-amino-4-(fluoromethyl)pyrrolidin-1-yl]-5,6,7,8-tetrahydroquinolin-6-yl]-6-methylthieno[2,3-b]pyridine-2-carboxamide;
385: 3-amino-N-[(6S)-2-[(3S,4R)-3-amino-4-(fluoromethyl)pyrrolidin-1-yl]-5,6,7,8-tetrahydroquinolin-6-yl]-6-methylthieno[2,3-b]pyridine-2-carboxamide;
427: 3-amino-N-[(6S)-2-[(3R,4S)-4-amino-3-methoxy-3-methylpyrrolidin-1-yl]-5,6,7,8-tetrahydroquinolin-6-yl]-6-methylthieno[2,3-b]pyridine-2-carboxamide;
428: 3-amino-N-[(6S)-2-[(3S,4R)-4-amino-3-methoxy-3-methylpyrrolidin-1-yl]-5,6,7,8-tetrahydroquinolin-6-yl]-6-methylthieno[2,3-b]pyridine-2-carboxamide;
430: 3-amino-N-[(6S)-2-[(5S,9R)-9-amino-2-oxa-7-azaspiro[4.4]nonan-7-yl]-5,6,7,8-tetrahydroquinolin-6-yl]-6-methylthieno[2,3-b]pyridine-2-carboxamide;
431: 3-amino-N-[(6S)-2-[(5R,9S)-9-amino-2-oxa-7-azaspiro[4.4]nonan-7-yl]-5,6,7,8-tetrahydroquinolin-6-yl]-6-methylthieno[2,3-b]pyridine-2-carboxamide;
437: 3-amino-N-[(6S)-2-[(5R,9R)-9-amino-2-oxa-7-azaspiro[4.4]nonan-7-yl]-5,6,7,8-tetrahydroquinolin-6-yl]-6-methylthieno[2,3-b]pyridine-2-carboxamide;
441: 3-amino-N-[(6S)-2-[(3R,4R)-3-(fluoromethyl)-4-(methylamino)pyrrolidin-1-yl]-5,6,7,8-tetrahydroquinolin-6-yl]-6-methylthieno[2,3-b]pyridine-2-carboxamide; and
442: 3-amino-N-[(6S)-2-[(3S,4S)-3-(fluoromethyl)-4-(methylamino)pyrrolidin-1-yl]-5,6,7,8-tetrahydroquinolin-6-yl]-6-methylthieno[2,3-b]pyridine-2-carboxamide.

13. A composition comprising at least one compound of claim 1, and a biologically acceptable carrier.

14. The compound of claim 1, wherein $R_1$, optionally substituted with $R_5$ or $R_6$, is chosen from

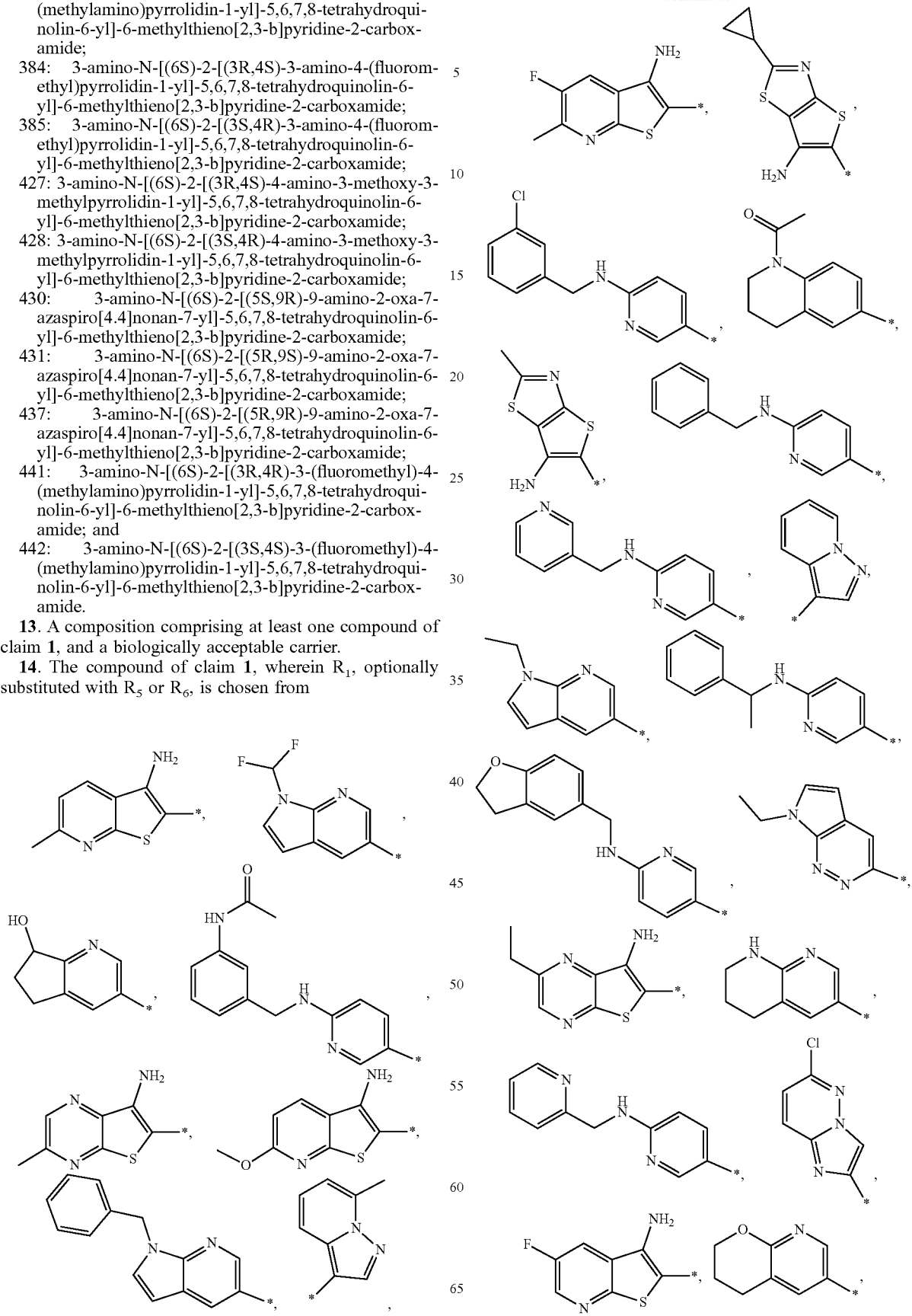

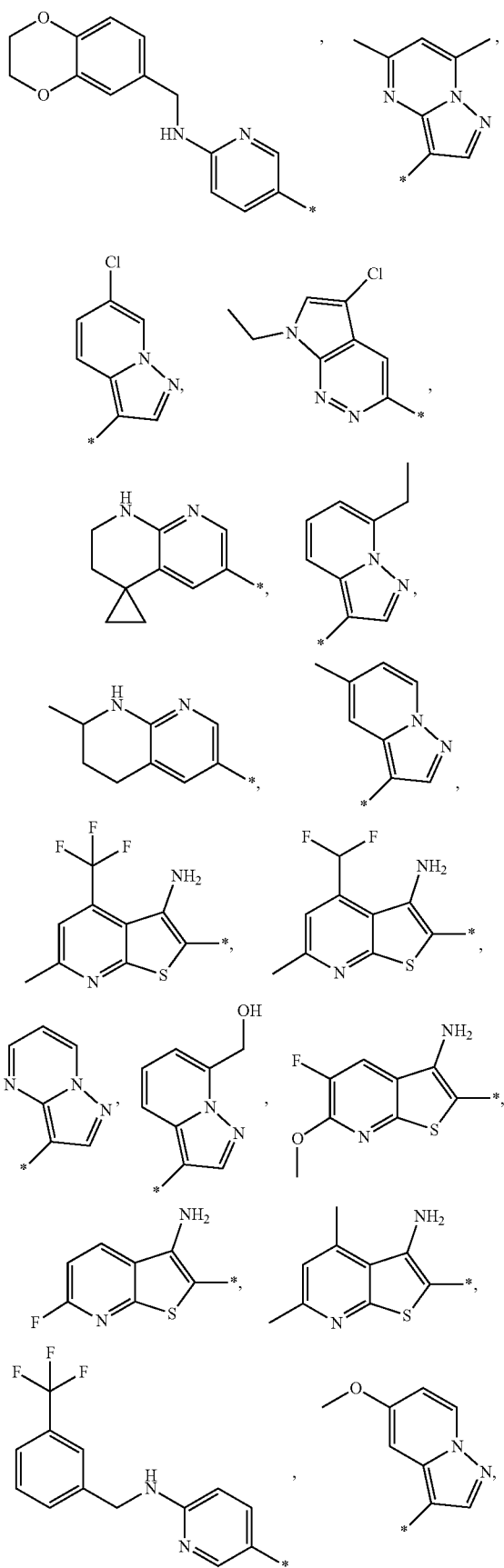
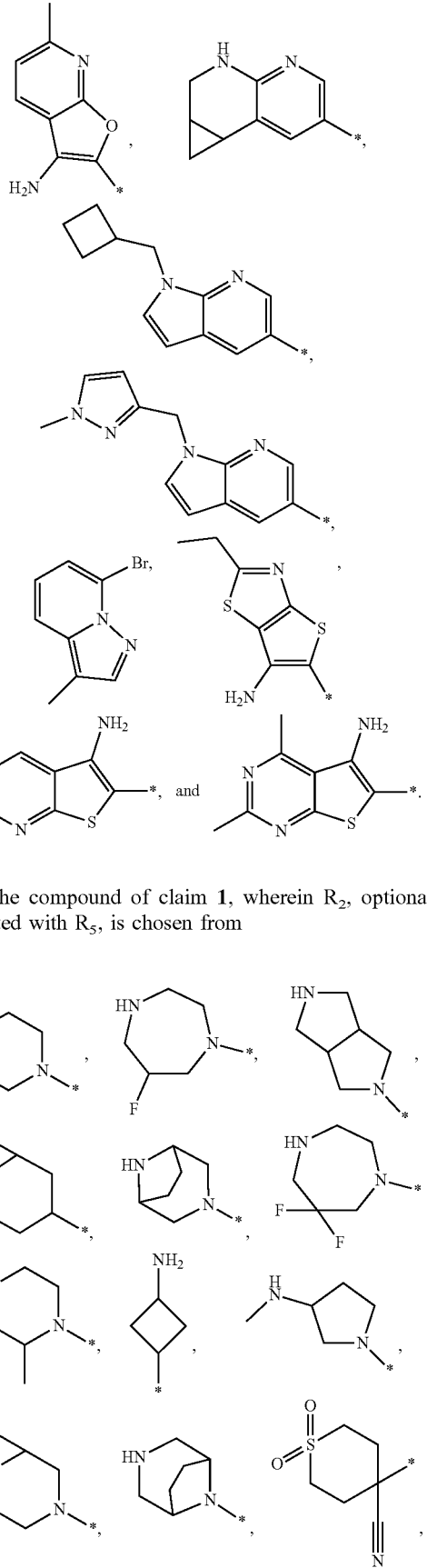
15. The compound of claim 1, wherein $R_2$, optionally substituted with $R_5$, is chosen from -continued
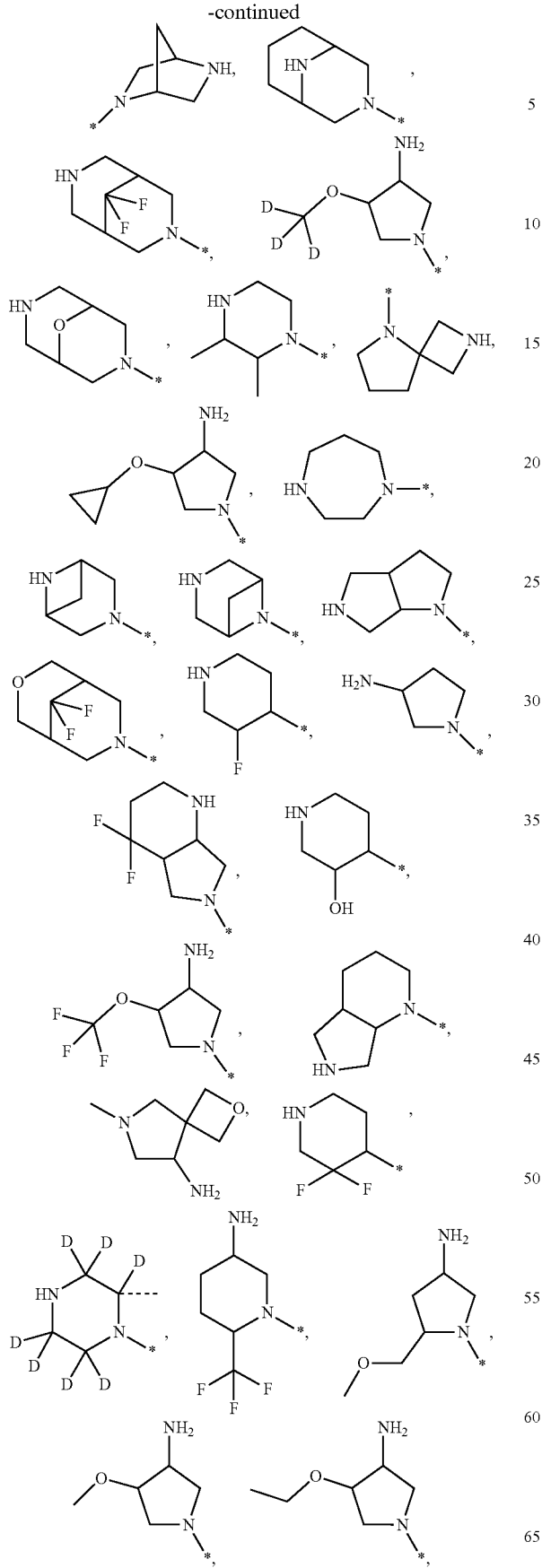
-continued
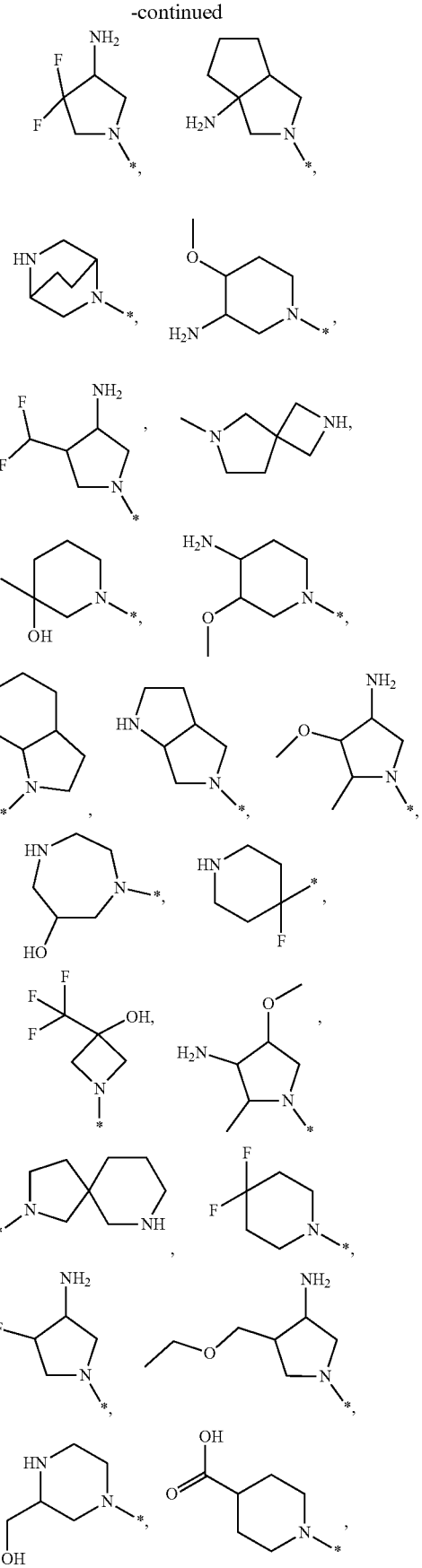

1195
-continued
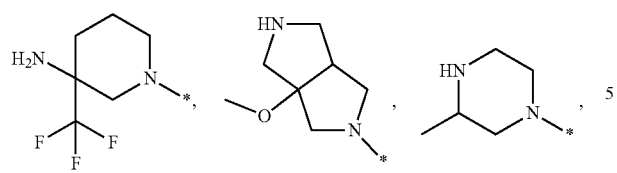
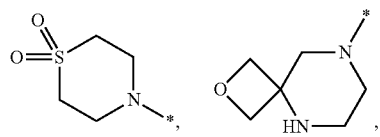
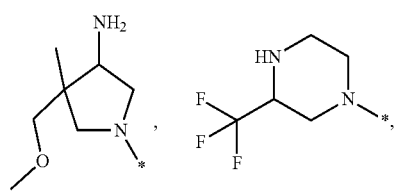
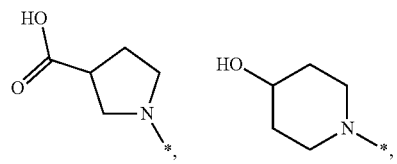
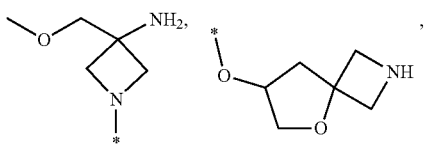
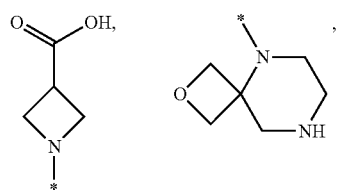
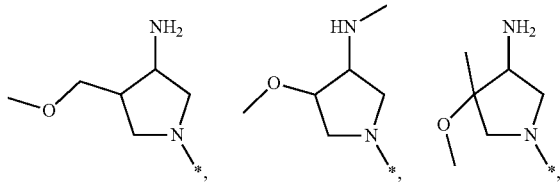
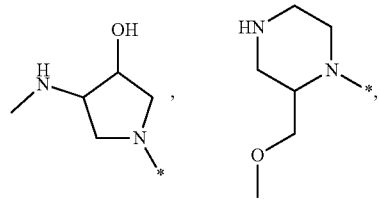
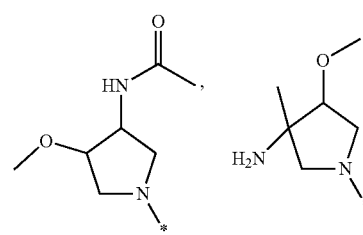
1196
-continued
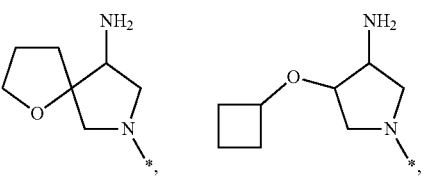
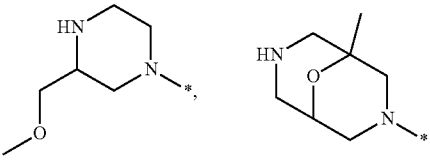
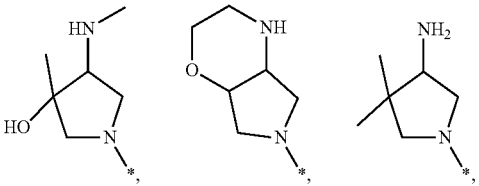
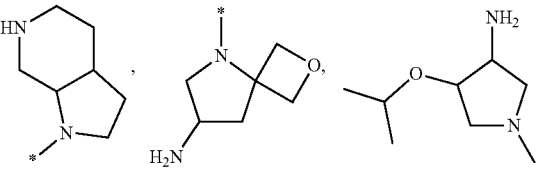
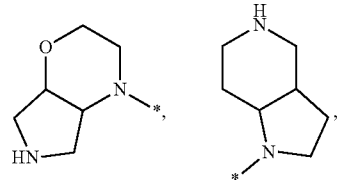
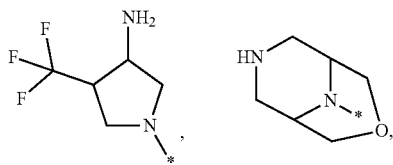
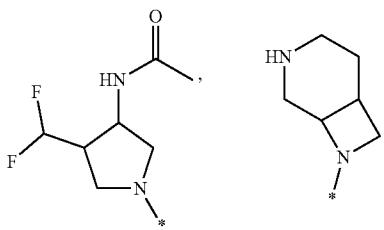
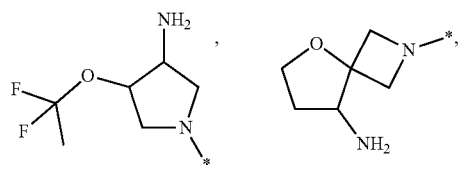
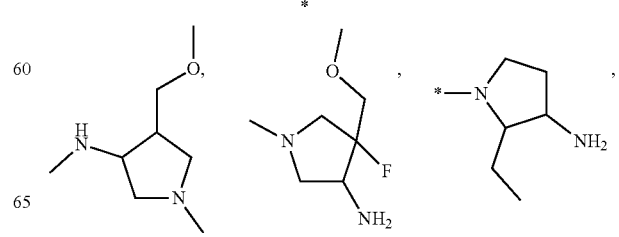

1197
-continued
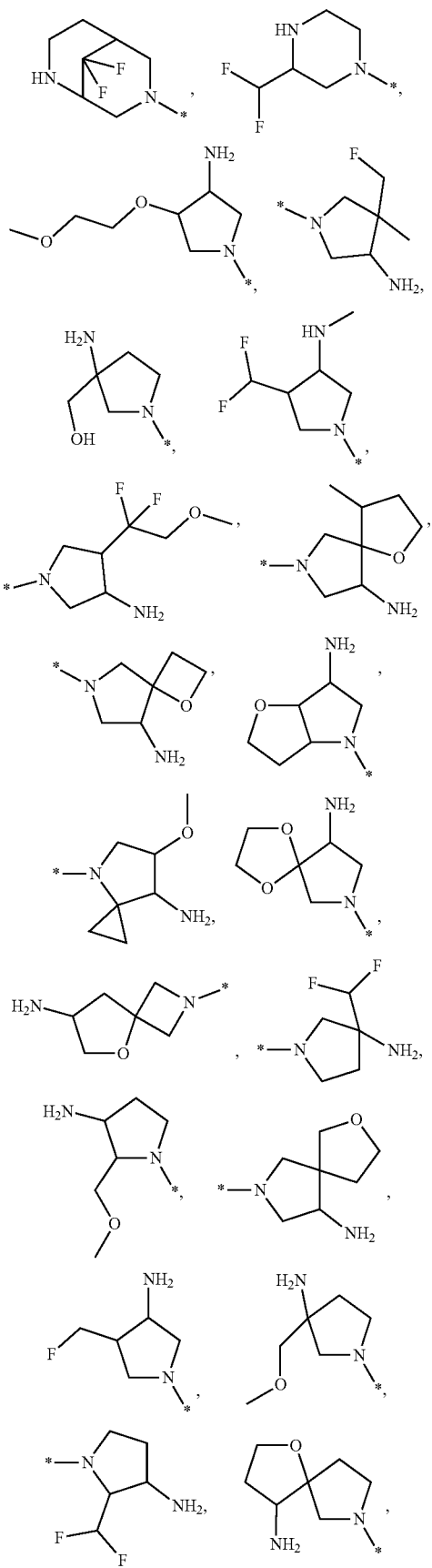
1198
-continued
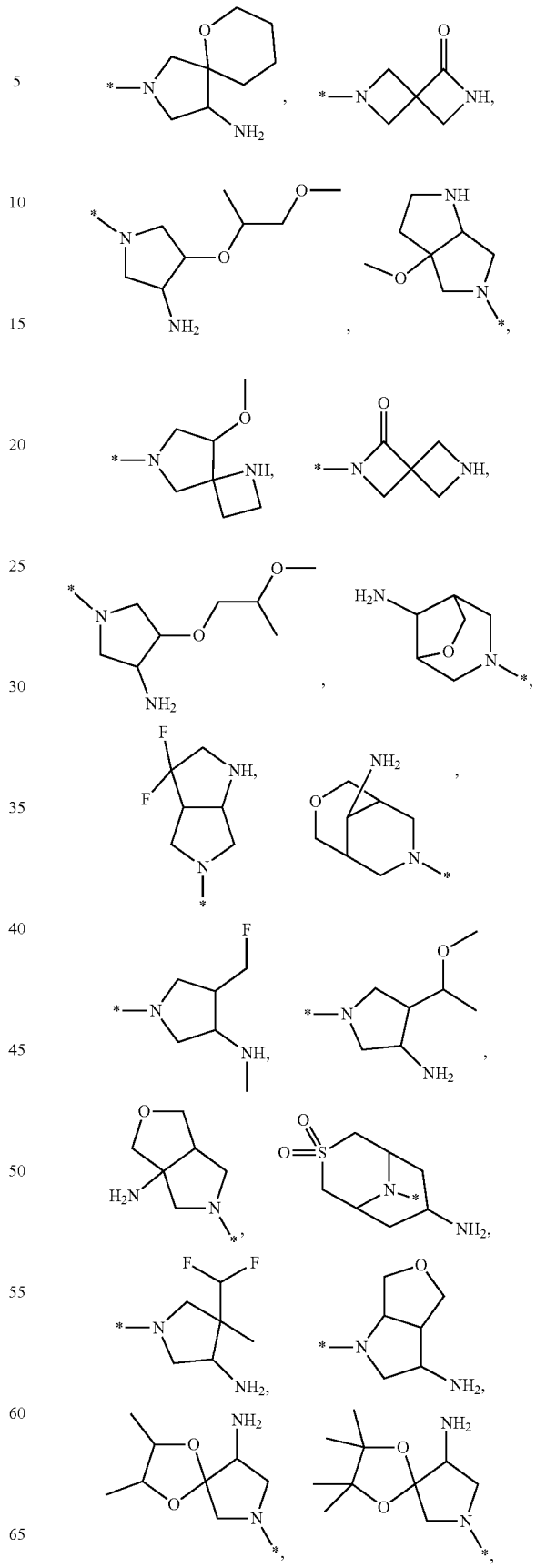

1199
-continued
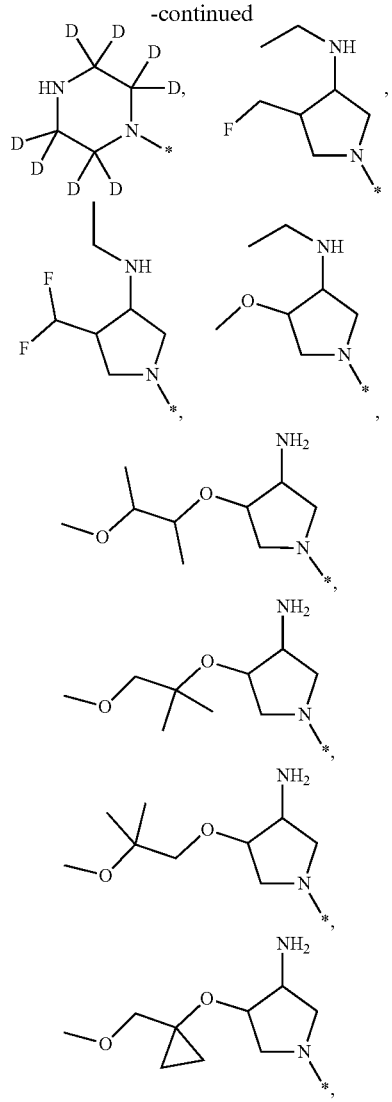
1200
-continued
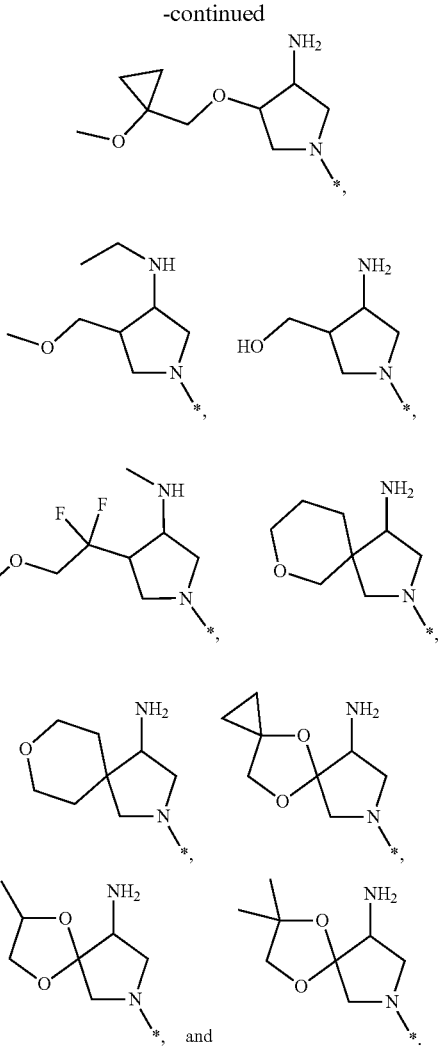
and
* * * * *